(12) United States Patent
Ji et al.

(10) Patent No.: US 11,362,282 B2
(45) Date of Patent: Jun. 14, 2022

(54) HETEROCYCLIC COMPOUND AND ORGANIC LIGHT EMITTING ELEMENT COMPRISING SAME

(71) Applicant: LT MATERIALS CO., LTD., Yongin (KR)

(72) Inventors: Hye-Su Ji, Osan-si (KR); Han-Kook Oh, Osan (KR); Yun-Ji Lee, Osan (KR); Won-Jang Jeong, Hwaseong (KR); Jin-Seok Choi, Suwon-si (KR); Dae-Hyuk Choi, Yongin-si (KR)

(73) Assignee: LT MATERIALS CO., LTD., Yongin (KR)

( * ) Notice: Subject to any disclaimer, the term of this patent is extended or adjusted under 35 U.S.C. 154(b) by 330 days.

(21) Appl. No.: 16/649,423

(22) PCT Filed: Sep. 28, 2018

(86) PCT No.: PCT/KR2018/011608
§ 371 (c)(1),
(2) Date: Mar. 20, 2020

(87) PCT Pub. No.: WO2020/067595
PCT Pub. Date: Apr. 2, 2020

(65) Prior Publication Data
US 2021/0234102 A1    Jul. 29, 2021

(51) Int. Cl.
*H01L 51/00* (2006.01)
*C07D 491/048* (2006.01)
(Continued)

(52) U.S. Cl.
CPC ...... *H01L 51/0067* (2013.01); *C07D 491/048* (2013.01); *C07D 495/04* (2013.01); *C07D 519/00* (2013.01); *H01L 51/0071* (2013.01); *H01L 51/0072* (2013.01); *H01L 51/0073* (2013.01); *H01L 51/0074* (2013.01); *H01L 51/5016* (2013.01); *H01L 51/5072* (2013.01);
(Continued)

(58) Field of Classification Search
CPC .. H01L 51/0067; H01L 51/0071–0074; C07D 49/048; C07D 49/104; C07D 495/04; C07D 519/00
USPC .......................................................... 257/40
See application file for complete search history.

(56) References Cited

U.S. PATENT DOCUMENTS 4,356,429 A     10/1982  Tang
2013/0292653 A1  11/2013  Park et al.
(Continued)

FOREIGN PATENT DOCUMENTS

KR    10-2013-0127567 A    11/2013
KR    10-2016-0001702 A     1/2016
(Continued)

OTHER PUBLICATIONS

Indu et al., "Transition-Metal-Catalyzed Selective Cyclization Strategy to 2-Substituted Benzofurans and Indoles en Route to the Oxa Analogues of Isocryptolepine", European Journal of Organic Chemistry, vol. 2014, Issue 32, 2014, pp. 7193-7202.
(Continued)

*Primary Examiner* — Sheng-Bai Zhu
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

16 Claims, 3 Drawing Sheets

(51) Int. Cl.
  *C07D 495/04* (2006.01)
  *C07D 519/00* (2006.01)
  *H01L 51/50* (2006.01)
(52) U.S. Cl.
  CPC ...... *H01L 51/5092* (2013.01); *H01L 51/5096* (2013.01)

(56) References Cited

U.S. PATENT DOCUMENTS

2016/0141515 A1  5/2016  Hayama et al.
2017/0141325 A1  5/2017  Lee et al.

FOREIGN PATENT DOCUMENTS

KR  10-2016-0018458 A  2/2016
KR  10-2016-0041822 A  4/2016
KR  10-2016-0051212 A  5/2016

OTHER PUBLICATIONS

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenylamino)triphenylamine (m-MTDATA), as Hole-Transport Materials", Advanced Materials vol. 6 No. 9 1994 pp. 677-679.

Li et al., "Palladium-Catalyzed IntramelecularC(sp2)-H Imidoylation for the Synthesis of Six-Membered N-Heterocycles", The Journal of Organic Chemistry, vol. 80, 2015, pp. 2223-2230.

【FIG. 1】
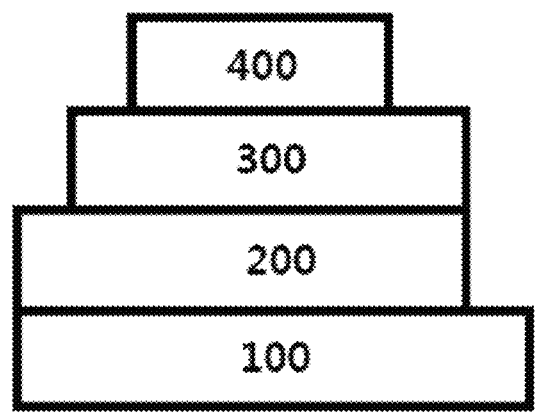
【FIG. 2】
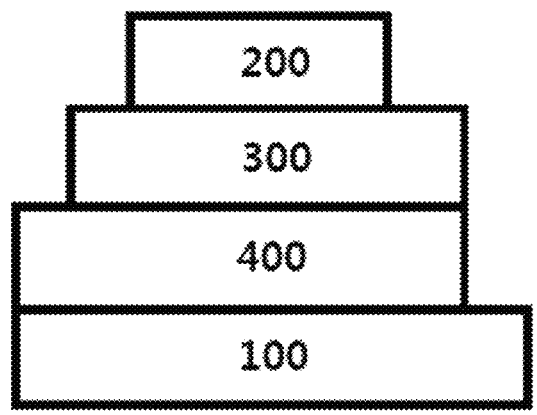

[FIG. 3]
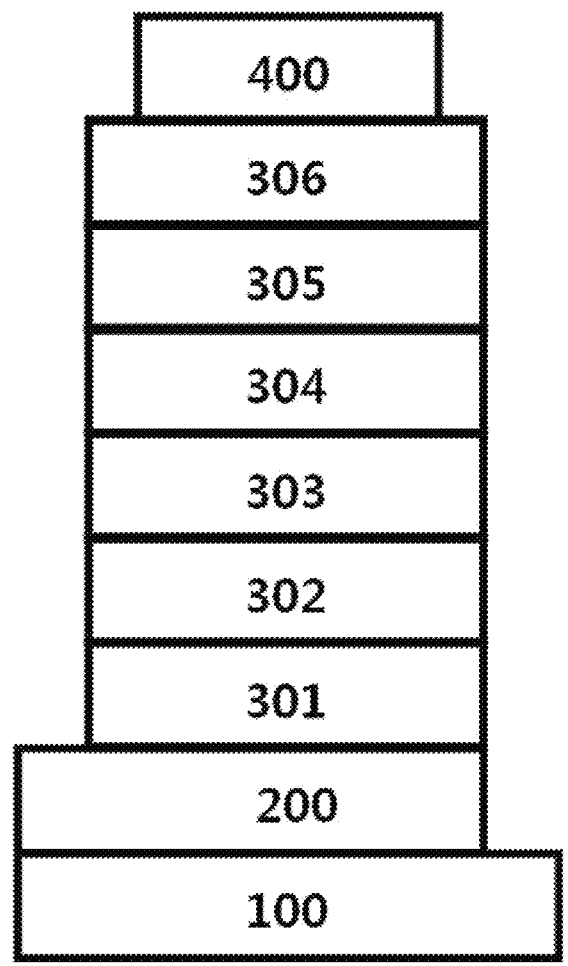

[FIG. 4]

| CATHODE |
| --- |
| ELECTRON INJECTION LAYER |
| SECOND ELECTRON TRANSFER LAYER |
| SECOND HOLE BLOCKING LAYER |
| SECOND STACK LIGHT EMITTING LAYER |
| SECOND ELECTRON BLOCKING LAYER |
| SECOND HOLE TRANSFER LAYER |
| P-TYPE CHARGE GENERATION LAYER |
| N-TYPE CHARGE GENERATION LAYER |
| FIRST ELECTRON TRANSFER LAYER |
| FIRST HOLE BLOCKING LAYER |
| FIRST STACK LIGHT EMITTING LAYER |
| FIRST ELECTRON BLOCKING LAYER |
| FIRST HOLE TRANSFER LAYER |
| FIRST HOLE INJECTION LAYER |
| ANODE |
| SUBSTRATE |

HETEROCYCLIC COMPOUND AND ORGANIC LIGHT EMITTING ELEMENT COMPRISING SAME

TECHNICAL FIELD

The present specification relates to a heterocyclic compound and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

DISCLOSURE

Technical Problem

The present disclosure is directed to providing a heterocyclic compound and an organic light emitting device comprising the same.

Technical Solution

One embodiment of the present application provides a heterocyclic compound represented by the following Chemical Formula 1.

[Chemical Formula 1]

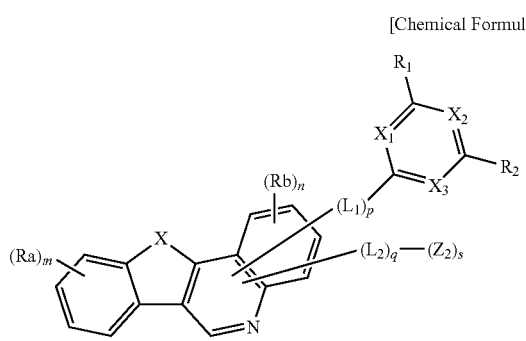

In Chemical Formula 1,
X is O or S,
$L_1$ and $L_2$ are a substituted or unsubstituted arylene group; or a substituted or unsubstituted heteroarylene group,
$Z_2$ is hydrogen; a substituted or unsubstituted alkyl group; a substituted or unsubstituted aryl group; a substituted or unsubstituted heteroaryl group; —SiRR'R"; or —P(=O)RR',
$X_1$ to $X_3$ are the same as or different from each other, and each independently N; $CR_3$; or P,
$R_1$ and $R_2$ are the same as or different from each other, and each independently hydrogen; deuterium; a substituted or unsubstituted alkyl group; a substituted or unsubstituted aryl group; a substituted or unsubstituted heteroaryl group; or P(=O)RR',
$R_3$ is hydrogen; a halogen group; a substituted or unsubstituted alkyl group; a substituted or unsubstituted aryl group; a substituted or unsubstituted heteroaryl group; or P(=O)RR',
$R_a$ and $R_b$ are the same as or different from each other, and each independently hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aliphatic or aromatic hydrocarbon ring,
R, R' and R" are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group,
m is an integer of 0 to 4,
p and n are an integer of 0 to 3,
q is an integer of 0 to 3,
s is an integer of 1 to 4, and
when q is an integer of 0 and $Z_2$ is hydrogen, n is an integer of 2 or 3, and $R_b$ is a substituted or unsubstituted aryl group; or a substituted or unsubstituted heteroaryl group, or two or more groups adjacent to each other bond to each other to form a substituted or unsubstituted aliphatic or aromatic hydrocarbon ring.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

Advantageous Effects

The compound described in the present specification can be used as an organic material layer material of an organic light emitting device. The compound is capable of performing a role of a hole injection material, a hole transfer material, a light emitting material, an electron transfer material, an electron injection material and the like in the organic light emitting device. Particularly, the heterocyclic compound represented by Chemical Formula 1 can be used as an electron transfer layer material, a hole blocking layer material or a charge generation layer material of the organic light emitting device. In addition, when using the compound represented by Chemical Formula 1 in the organic material layer, a driving voltage is lowered and light efficiency is enhanced in the device, and device lifetime properties can be enhanced by thermal stability of the compound.

In addition, the compound of Chemical Formula 1 is a bipolar-type compound having both P-type and N-type substituents in the core structure, and, when used as an organic material layer of an organic light emitting device afterword, is capable of blocking hole leakage and effectively trapping excitons in a light emitting layer. In addition, hole properties are strengthened in a specific device structure changing electron mobility relatively slowly, which balances electrons and holes in the light emitting layer properly forming a recombination region of the excitons, and as a result, efficiency and lifetime increase.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode Mode for Disclosure Hereinafter, the present application will be described in detail.

The term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylm- ethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenzyloxy and the like, but are not limited thereto.

In the present specification, the cycloalkyl group comprises monocyclic or multicyclic having 3 to 60 carbon atoms, and may be further substituted with other substituents. Herein, the multicyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or multicyclic having 2 to 60 carbon atoms, and may be further substituted with other substituents. Herein, the multicyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or multicyclic having 6 to 60 carbon atoms, and may be further substituted with other substituents. Herein, the multicyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the silyl group is a substituent comprising Si, having the Si atom directly linked as a radical, and is represented by —SiR$_{104}$R$_{105}$R$_{106}$. R$_{104}$ to R$_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted,

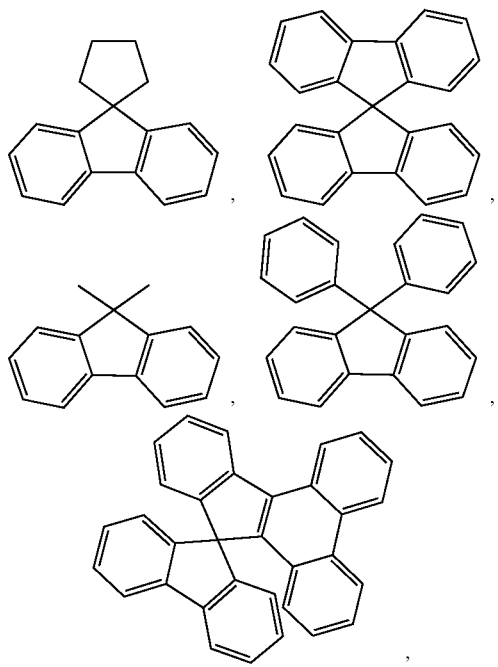

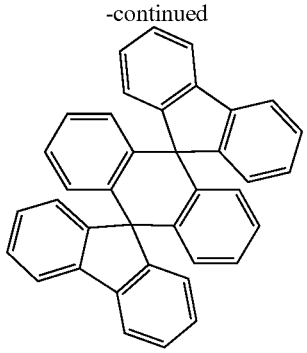

and the like may be included. However, the structure is not limited thereto.

In the present specification, the heteroaryl group comprises O, S, Se, N or Si as a heteroatom, comprises monocyclic or multicyclic having 2 to 60 carbon atoms, and may be further substituted with other substituents. Herein, the multicyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzofuran group, a benzothiophene group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for each being a divalent. In addition, the heteroarylene group means the heteroaryl group having two bonding sites, that is, a divalent group. Descriptions on the heteroaryl group provided above may be applied thereto except for each being a divalent.

In the present specification, specific examples of the phosphine oxide group may comprise a diphenylphosphine oxide group, a dinaphthylphosphine oxide group and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

One embodiment of the present application provides a compound represented by Chemical Formula 1.

In one embodiment of the present application, X of Chemical Formula 1 may be O or S.

In one embodiment of the present application, X of Chemical Formula 1 may be O.

In one embodiment of the present application, X of Chemical Formula 1 may be S.

In one embodiment of the present application, $X_1$ to $X_3$ of Chemical Formula 1 are the same as or different from each other, and may be each independently N; $CR_3$; or P.

In another embodiment, $X_1$ to $X_3$ of Chemical Formula 1 are the same as or different from each other, and may be each independently N; or $CR_3$.

In one embodiment of the present application, $X_1$ to $X_3$ of Chemical Formula 1 may be N.

In one embodiment of the present application, one of $X_1$ to $X_3$ of Chemical Formula 1 is N, and the rest may be $CR_3$.

In one embodiment of the present application, two of $X_1$ to $X_3$ of Chemical Formula 1 are N, and the rest may be $CR_3$.

In one embodiment of the present application, $X_1$ to $X_3$ of Chemical Formula 1 may be $CR_3$.

In one embodiment of the present application, $R_3$ may be hydrogen; a halogen group; a substituted or unsubstituted alkyl group; a substituted or unsubstituted aryl group; a substituted or unsubstituted heteroaryl group; or P(=O)RR'.

In another embodiment, $R_3$ may be hydrogen; a substituted or unsubstituted C6 to C60 aryl group; a substituted or unsubstituted C2 to C60 heteroaryl group; or P(=O)RR'.

In another embodiment, $R_3$ may be hydrogen; a C6 to C60 aryl group; a C2 to C60 heteroaryl group; or P(=O)RR'.

In another embodiment, $R_3$ may be hydrogen; or P(=O)RR'.

In one embodiment of the present application, $R_a$ and $R_b$ of Chemical Formula 1 are the same as or different from each other, and may be each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other may bond to each other to form a substituted or unsubstituted aliphatic or aromatic hydrocarbon ring.

In another embodiment, $R_a$ and $R_b$ of Chemical Formula 1 are the same as or different from each other, and may be each independently selected from the group consisting of hydrogen; a substituted or unsubstituted alkyl group; a substituted or unsubstituted aryl group; and a substituted or unsubstituted heteroaryl group, or two or more groups adjacent to each other may bond to each other to form a substituted or unsubstituted aromatic hydrocarbon ring.

In another embodiment, $R_a$ and $R_b$ of Chemical Formula 1 are the same as or different from each other, and may be each independently selected from the group consisting of hydrogen; a substituted or unsubstituted C6 to C60 aryl group; and a substituted or unsubstituted C2 to C60 heteroaryl group, or two or more groups adjacent to each other may bond to each other to form a substituted or unsubstituted C6 to C60 aromatic hydrocarbon ring.

In another embodiment, $R_a$ and $R_b$ of Chemical Formula 1 are the same as or different from each other, and may be each independently selected from the group consisting of hydrogen; a C6 to C40 aryl group; and a C2 to C60 heteroaryl group, or two or more groups adjacent to each other may bond to each other to form a C3 to C60 aromatic hydrocarbon ring.

In another embodiment, $R_a$ of Chemical Formula 1 may be hydrogen.

In one embodiment of the present application, $R_1$ and $R_2$ of Chemical Formula 1 are the same as or different from each other, and may be each independently hydrogen; deuterium; a substituted or unsubstituted alkyl group; a substituted or unsubstituted aryl group; a substituted or unsubstituted heteroaryl group; or P(=O)RR'.

In another embodiment, $R_1$ and $R_2$ of Chemical Formula 1 are the same as or different from each other, and may be each independently hydrogen; a substituted or unsubstituted C6 to C60 aryl group; a substituted or unsubstituted C2 to C60 heteroaryl group; or P(=O)RR'.

In another embodiment, $R_1$ and $R_2$ of Chemical Formula 1 are the same as or different from each other, and may be each independently hydrogen; a substituted or unsubstituted C6 to C40 aryl group; a substituted or unsubstituted C2 to C40 heteroaryl group; or P(=O)RR'.

In another embodiment, $R_1$ and $R_2$ of Chemical Formula 1 are the same as or different from each other, and may be each independently hydrogen; a C6 to C40 aryl group unsubstituted or substituted with one or more substituents selected from the group consisting of a C1 to C40 alkyl group and a C2 to C40 heteroaryl group; a C2 to C40 N-containing heteroaryl group; or P(=O)RR'.

In another embodiment, $R_1$ and $R_2$ of Chemical Formula 1 are the same as or different from each other, and may be each independently hydrogen; a phenyl group unsubstituted or substituted with a carbazole group, a dibenzofuran group or a dibenzothiophene group; a biphenyl group; a fluorene group unsubstituted or substituted with a methyl group; a carbazole group; —P(=O)RR' or a pyridine group.

In one embodiment of the present application, $L_1$ and $L_2$ of Chemical Formula 1 may be a substituted or unsubstituted arylene group; or a substituted or unsubstituted heteroarylene group.

In another embodiment, $L_1$ and $L_2$ of Chemical Formula 1 may be a substituted or unsubstituted C6 to C60 arylene group; or a substituted or unsubstituted C2 to C60 heteroarylene group.

In another embodiment, $L_1$ and $L_2$ of Chemical Formula 1 may be a substituted or unsubstituted C6 to C40 arylene group; or a substituted or unsubstituted C2 to C40 heteroarylene group.

In another embodiment, $L_1$ and $L_2$ of Chemical Formula 1 may be a C6 to C40 arylene group; or a C2 to C40 heteroarylene group.

In another embodiment, $L_1$ and $L_2$ of Chemical Formula 1 may be a C6 to C30 arylene group; or a C2 to C30 heteroarylene group.

In another embodiment, $L_1$ and $L_2$ of Chemical Formula 1 may be a phenylene group; a biphenylene group; a naphthalene group; a phenanthrene group; a triphenylenylene group; a divalent dibenzofuran group; a divalent phenanthroline group or a divalent dibenzothiophene group.

In one embodiment of the present application, $L_1$ of Chemical Formula 1 may be a substituted or unsubstituted arylene group.

In another embodiment, $L_1$ of Chemical Formula 1 may be a substituted or unsubstituted C6 to C60 arylene group.

In another embodiment, $L_1$ of Chemical Formula 1 may be a substituted or unsubstituted C6 to C40 arylene group.

In another embodiment, $L_1$ of Chemical Formula 1 may be a C6 to C40 arylene group.

In another embodiment, $L_1$ of Chemical Formula 1 ma be a phenylene group; or a biphenylene group.

In one embodiment of the present application, $L_2$ of Chemical Formula 1 may be a substituted or unsubstituted arylene group; or a substituted or unsubstituted heteroarylene group.

In another embodiment, $L_2$ of Chemical Formula 1 may be a substituted or unsubstituted C6 to C60 arylene group; or a substituted or unsubstituted C2 to C60 heteroarylene group.

In another embodiment, $L_2$ of Chemical Formula 1 may be a substituted or unsubstituted C6 to C40 arylene group; or a substituted or unsubstituted C2 to C40 heteroarylene group.

In another embodiment, $L_2$ of Chemical Formula 1 may be a C6 to C40 arylene group; or a C2 to C40 heteroarylene group.

In another embodiment, $L_2$ of Chemical Formula 1 may be a phenylene group; a naphthylene group; a phenanthrene group; a triphenylenylene group; a divalent dibenzofuran group; or a divalent dibenzothiophene group.

In one embodiment of the present application, $Z_2$ of Chemical Formula 1 may be hydrogen; a substituted or unsubstituted alkyl group; a substituted or unsubstituted aryl group; a substituted or unsubstituted heteroaryl group; —SiRR'R"; or —P(=O)RR'.

In another embodiment, $Z_2$ of Chemical Formula 1 may be hydrogen; a substituted or unsubstituted C6 to C60 aryl group; or a substituted or unsubstituted C2 to C60 heteroaryl group.

In another embodiment, $Z_2$ of Chemical Formula 1 may be hydrogen; a substituted or unsubstituted C6 to C40 aryl group; or a substituted or unsubstituted C2 to C40 heteroaryl group.

In another embodiment, $Z_2$ of Chemical Formula 1 may be hydrogen; a C6 to C40 aryl group; or a C2 to C40 heteroaryl group.

In another embodiment, $Z_2$ of Chemical Formula 1 may be hydrogen; a phenyl group; a naphthyl group; a phenanthrene group; a dibenzofuran group; or a dibenzothiophene group.

In one embodiment of the present application, p of Chemical Formula 1 may be 0.

In one embodiment of the present application, p of Chemical Formula 1 may be 1.

In one embodiment of the present application, q of Chemical Formula 1 may be 0.

In one embodiment of the present application, q of Chemical Formula 1 may be 1.

In one embodiment of the present application, q of Chemical Formula 1 may be 2.

In one embodiment of the present application, s of Chemical Formula 1 may be 1.

In one embodiment of the present application, s of Chemical Formula 1 may be 2.

In one embodiment of the present application, s of Chemical Formula 1 may be 3.

In one embodiment of the present application, s of Chemical Formula 1 may be 4.

In one embodiment of the present application, when q is an integer of 0 and $Z_2$ is hydrogen in Chemical Formula 1, n is an integer of 2 or 3, and $R_b$ may be a substituted or unsubstituted aryl group; or a substituted or unsubstituted heteroaryl group, or two or more groups adjacent to each other may bond to each other to form a substituted or unsubstituted aliphatic or aromatic hydrocarbon ring.

In another embodiment, when q is an integer of 0 and $Z_2$ is hydrogen, n is an integer of 2, and adjacent two $R_b$s may bond to each other to form a substituted or unsubstituted aliphatic or aromatic hydrocarbon ring.

In another embodiment, when q is an integer of 0 and $Z_2$ is hydrogen, n is an integer of 2, and adjacent two $R_b$s may bond to each other to form a substituted or unsubstituted aromatic hydrocarbon ring.

In another embodiment, when q is an integer of 0 and $Z_2$ is hydrogen, n is an integer of 2, and adjacent two $R_b$s may bond to each other to form a substituted or unsubstituted C3 to C60 aromatic hydrocarbon ring.

In another embodiment, when q is an integer of 0 and $Z_2$ is hydrogen, n is an integer of 2, and adjacent two $R_b$s may bond to each other to form a substituted or unsubstituted C3 to C30 aromatic hydrocarbon ring.

In another embodiment, when q is an integer of 0 and $Z_2$ is hydrogen, n is an integer of 2, and adjacent two $R_b$s may bond to each other to form a C3 to C30 aromatic hydrocarbon ring.

In another embodiment, when q is an integer of 0 and $Z_2$ is hydrogen, n is an integer of 2, and adjacent two $R_b$s may bond to each other to form a benzene ring.

In one embodiment of the present application, R, R' and R" are the same as or different from each other, and may be each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group.

In another embodiment, R, R' and R" are the same as or different from each other, and may be each independently hydrogen; a substituted or unsubstituted aryl group; or a substituted or unsubstituted heteroaryl group.

In another embodiment, R, R' and R" are the same as or different from each other, and may be each independently hydrogen; a substituted or unsubstituted C6 to C60 aryl group; or a substituted or unsubstituted C2 to C60 heteroaryl group.

In another embodiment, R, R' and R" are the same as or different from each other, and may be each independently a substituted or unsubstituted C6 to C60 aryl group.

In another embodiment, R, R' and R" are the same as or different from each other, and may be each independently a C6 to C60 aryl group.

In another embodiment, R, R' and R" are the same as or different from each other, and may be each independently a C6 to C40 aryl group.

In another embodiment, R, R' and R" are the same as or different from each other, and may be each independently a phenyl group.

The compound of Chemical Formula 1 is a bipolar-type compound having both P-type and N-type substituents in the core structure, and, when used as an organic material layer of an organic light emitting device afterword, is capable of blocking hole leakage and effectively trapping excitons in a light emitting layer. In addition, hole properties are strengthened in a specific device structure changing electron mobility relatively slowly, which balances electrons and holes in the light emitting layer properly forming a recombination region of the excitons, and as a result, efficiency and lifetime increase.

In addition, when single substituted with a substituent having a small molecular weight, the molecular weight is small, and, when used as an organic material layer of an organic light emitting device afterword, thermal stability decreases structurally. When double substituted as in Chemical Formula 1 of the present application, thermal stability is superior than single substituted compounds.

In the heterocyclic compound provided in one embodiment of the present application, Chemical Formula 1 is represented by any one of the following Chemical Formulae 2 to 5.

[Chemical Formula 2]

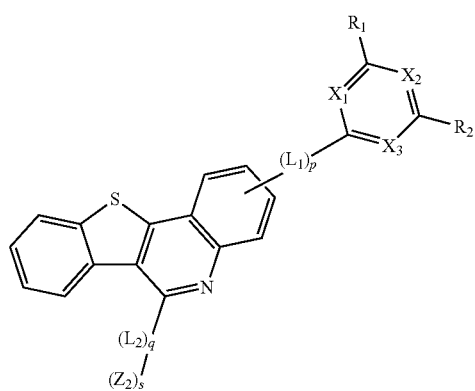

[Chemical Formula 3]

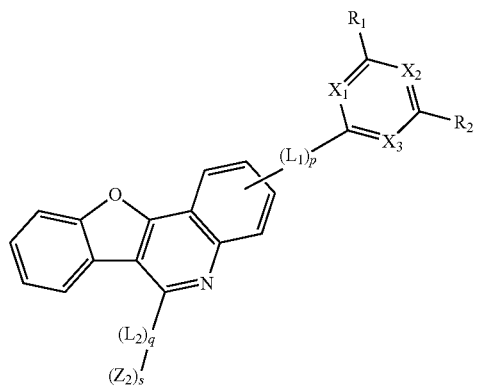

[Chemical Formula 4]

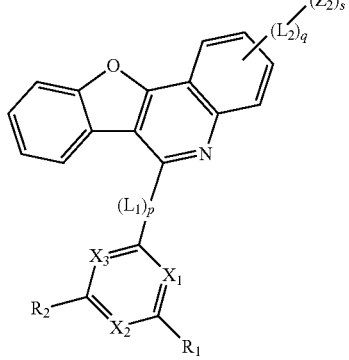

[Chemical Formula 5]

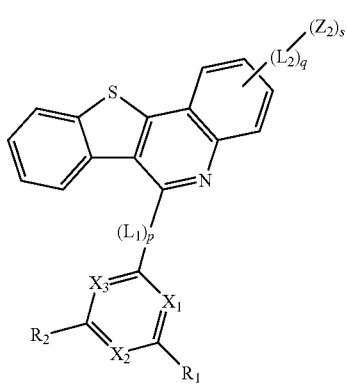

In Chemical Formulae 2 to 5, $X_1$ to $X_3$, $R_1$, $R_2$, $L_1$, $L_2$, $Z_2$ and p have the same definitions as in Chemical Formula 1, and q and s are each an integer of 1 to 3.

In the heterocyclic compound provided in one embodiment of the present application, Chemical Formula 1 is represented by any one of the following Chemical Formulae 6 to 11.

[Chemical Formula 6]

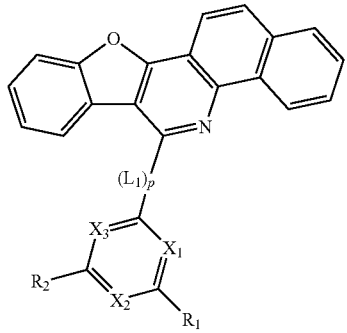

[Chemical Formula 7]

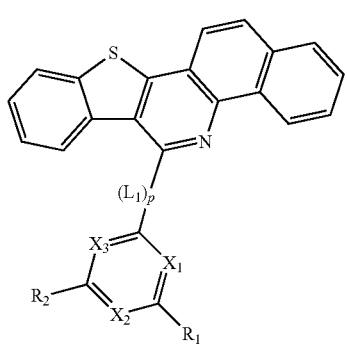

[Chemical Formula 8]

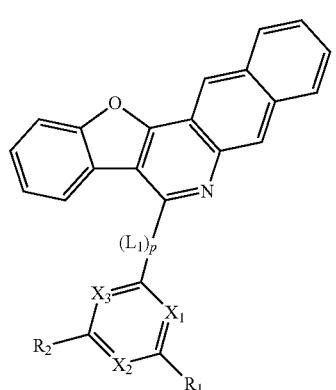

[Chemical Formula 9]

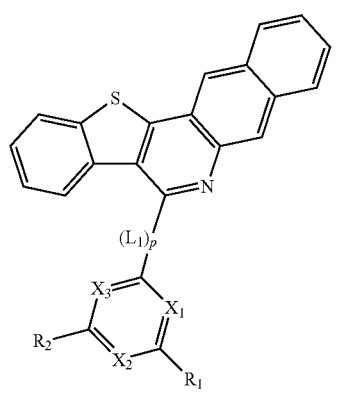

[Chemical Formula 10]

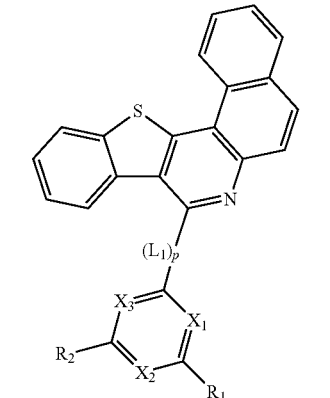

[Chemical Formula 11]

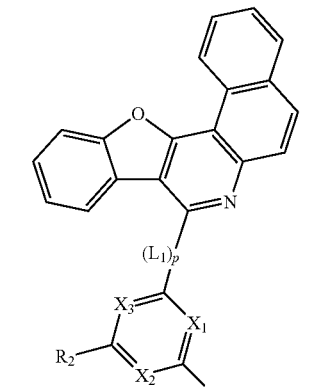

In Chemical Formulae 6 to 11, $X_1$ to $X_3$, $R_1$, $R_2$, $L_1$ and p have the same definitions as in Chemical Formula 1.

In the heterocyclic compound provided in one embodiment of the present application, Chemical Formula 1 is represented by any one of the following compounds.
1
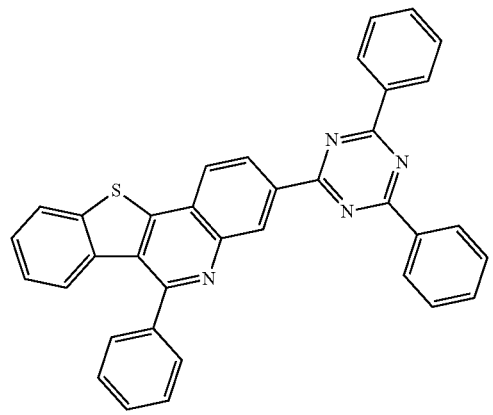
2
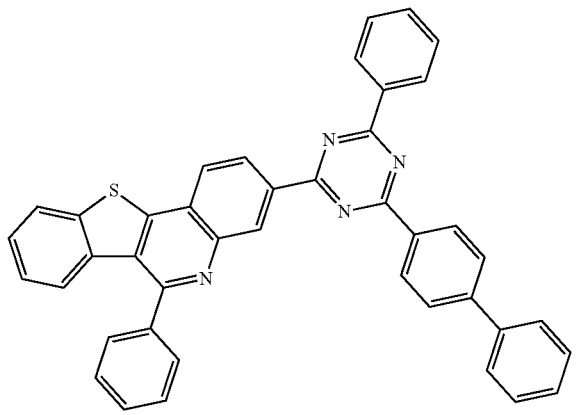
3
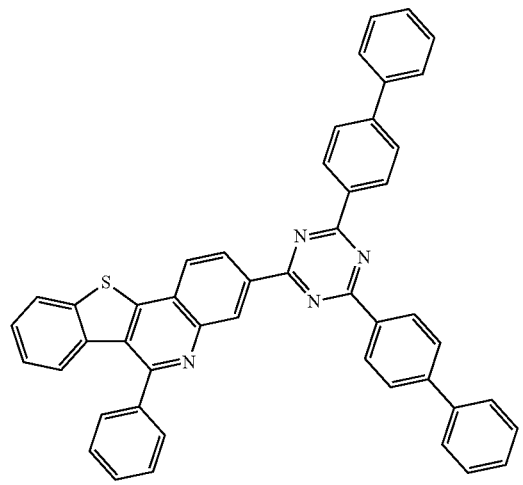
4
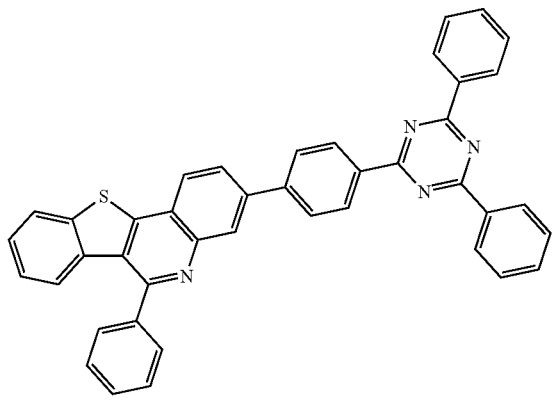 [SMILES: c1ccc(-c2nc(-c3ccccc3)nc(-c3ccc(-c4ccc5c(c4)nc(-c4ccccc4)c4c6ccccc6sc54)cc3)n2)cc1]
5
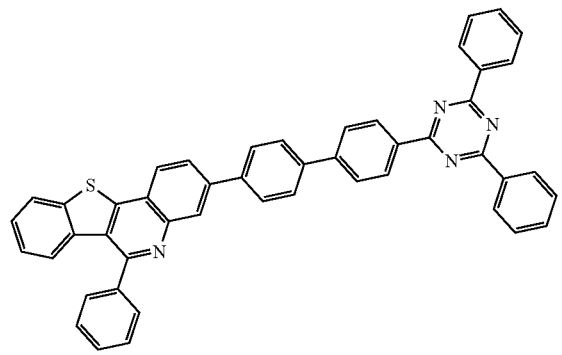 [SMILES: c1ccc(-c2nc(-c3ccccc3)nc(-c3ccc(-c4ccc(-c5ccc6c(c5)nc(-c5ccccc5)c5c7ccccc7sc65)cc4)cc3)n2)cc1]
6
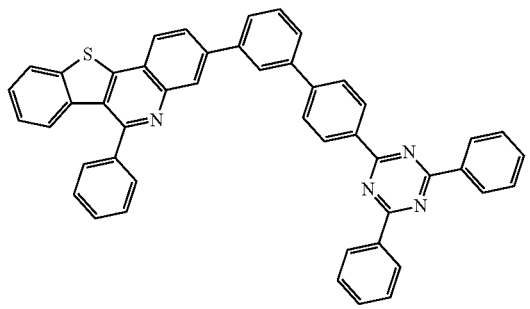

7
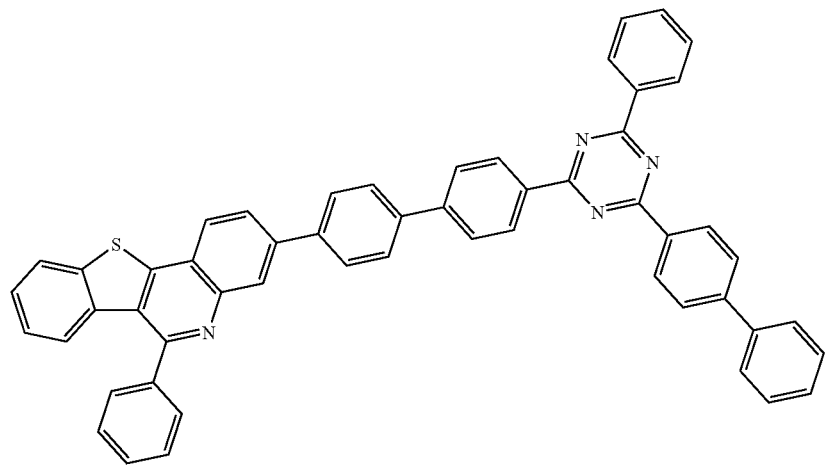
8
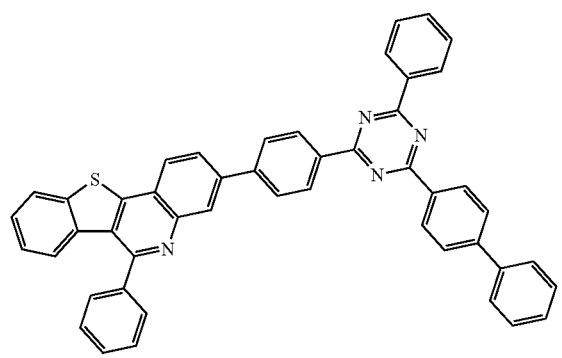
9
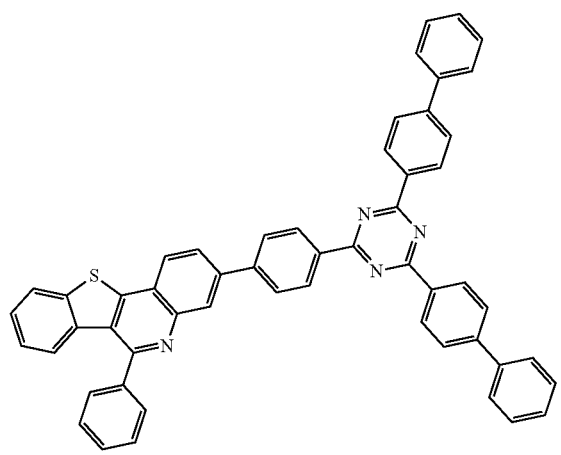 [SMILES: c1ccc(-c2ccc(-c3nc(-c4ccc(-c5ccccc5)cc4)nc(-c4ccc(-c5ccc6c(c5)nc(-c5ccccc5)c5c7ccccc7sc65)cc4)n3)cc2)cc1]
10
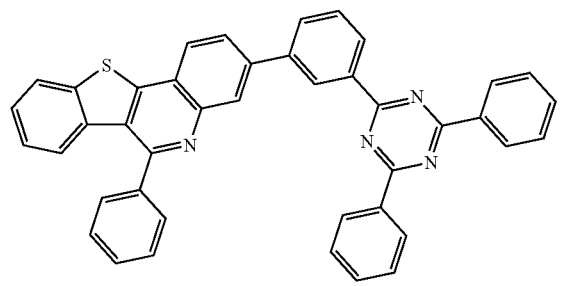
11
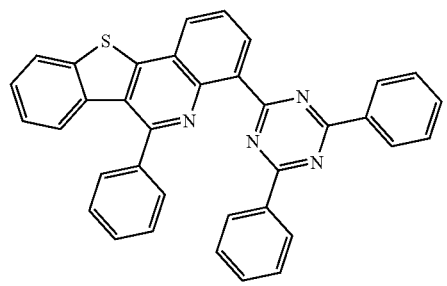
12
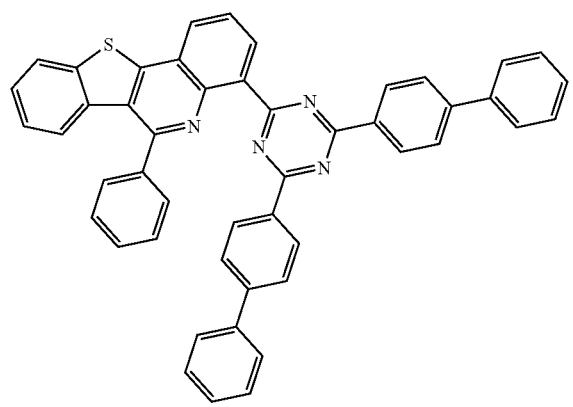
13
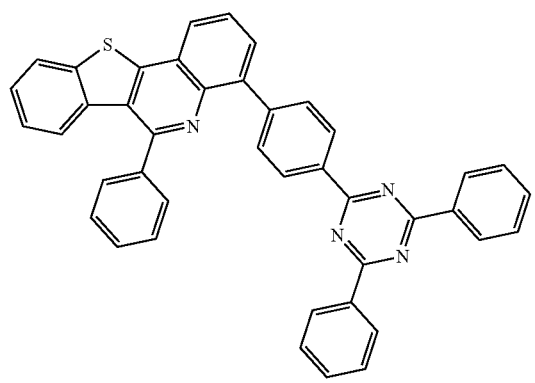

-continued
14
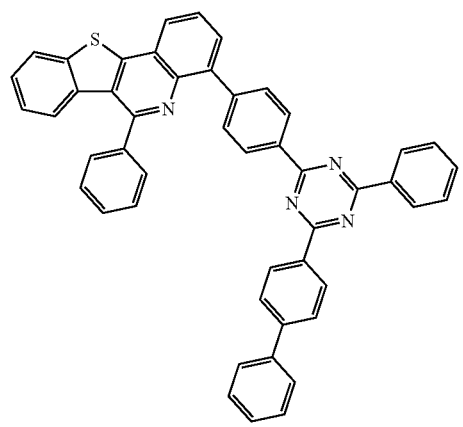
15
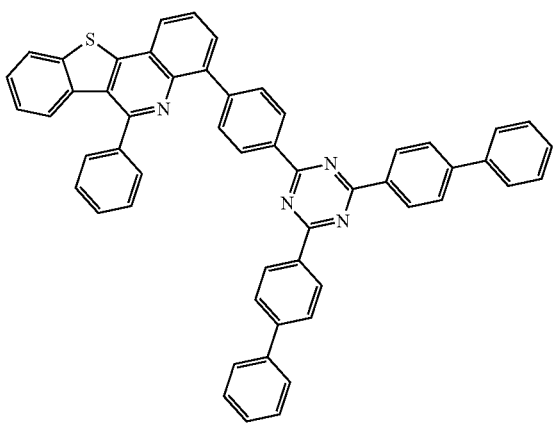
16
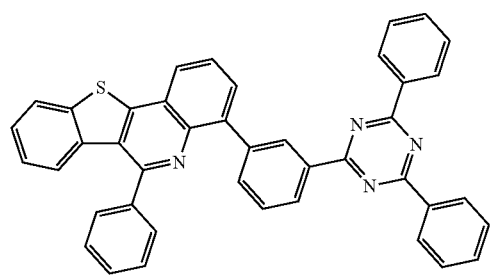
17
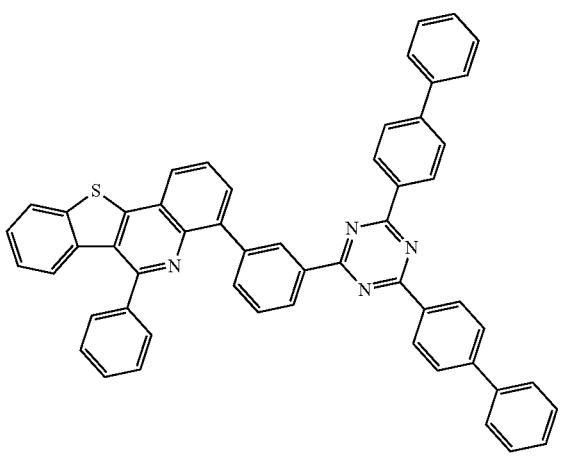
18
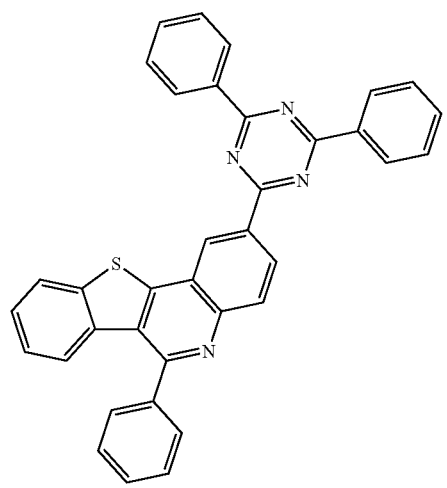
19
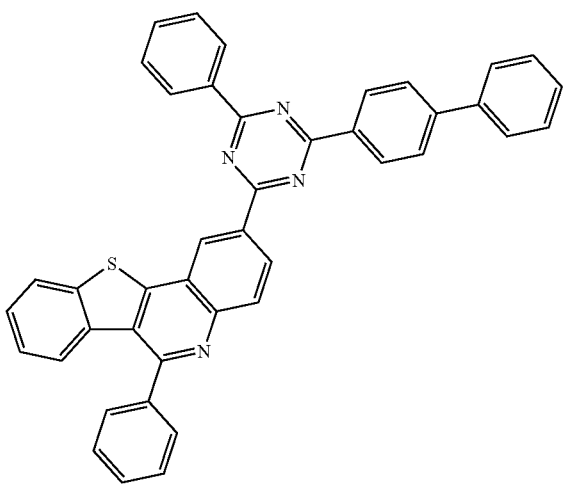

20
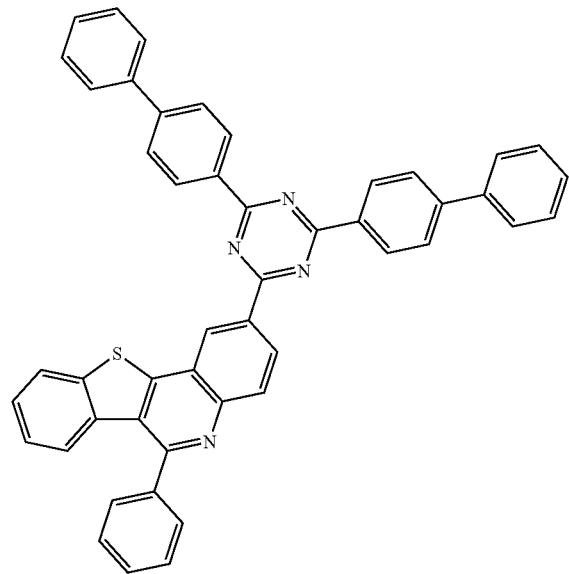
21
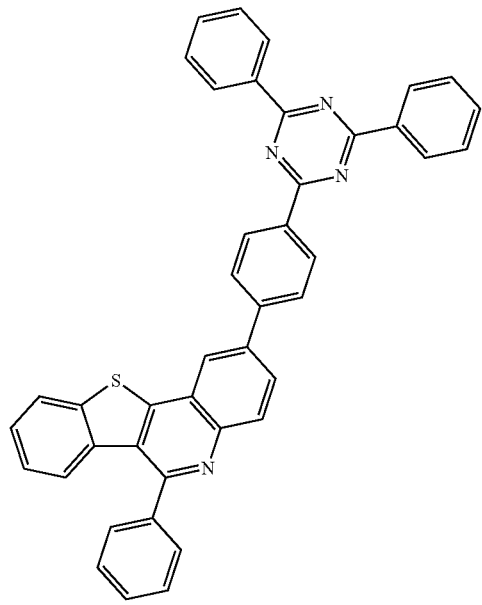
22
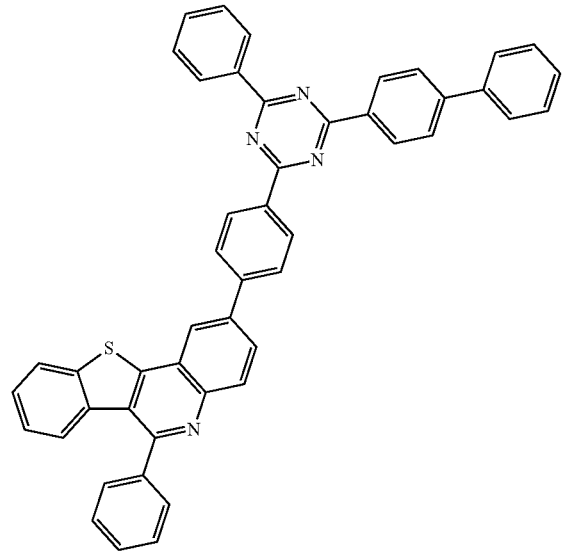
23
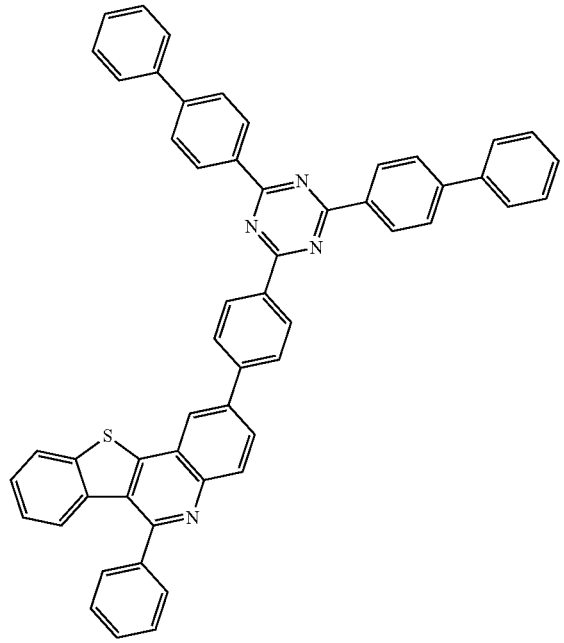

23
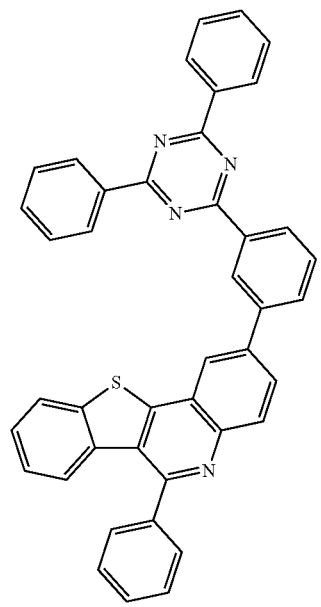
24
-continued
24
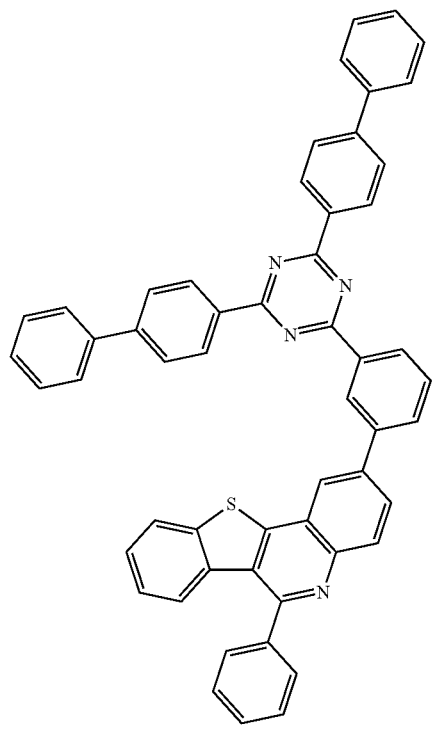
25
26
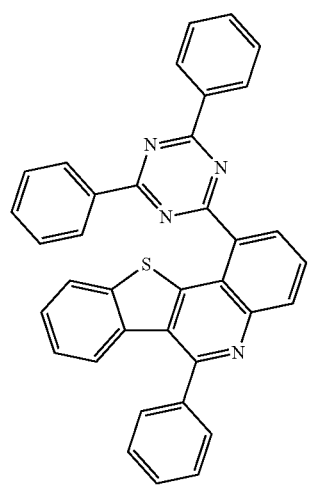
27
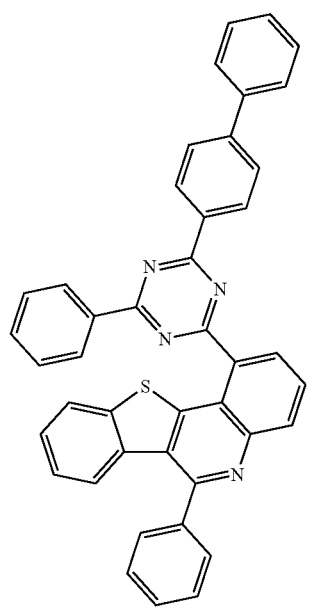

-continued
28
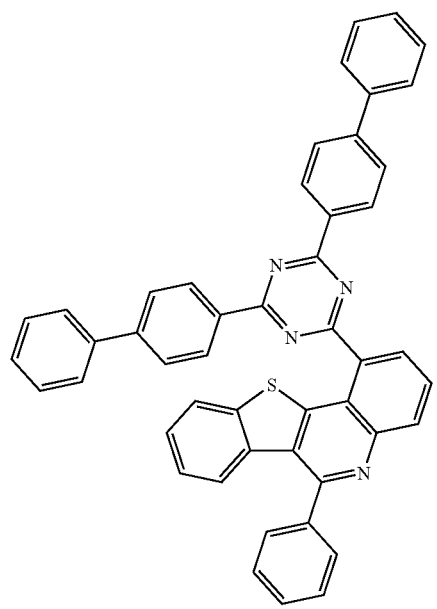
29
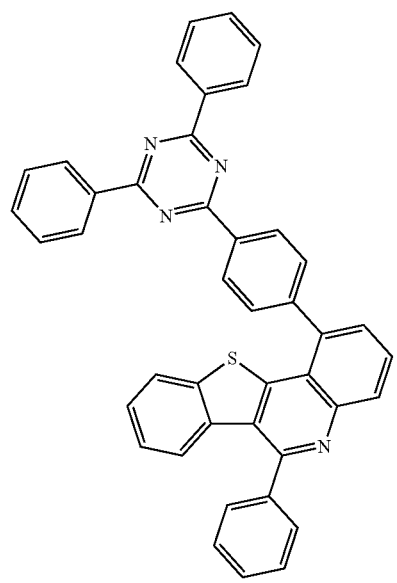
30
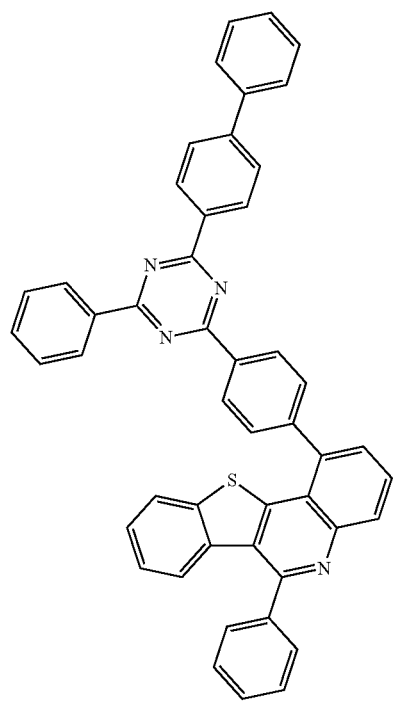
31
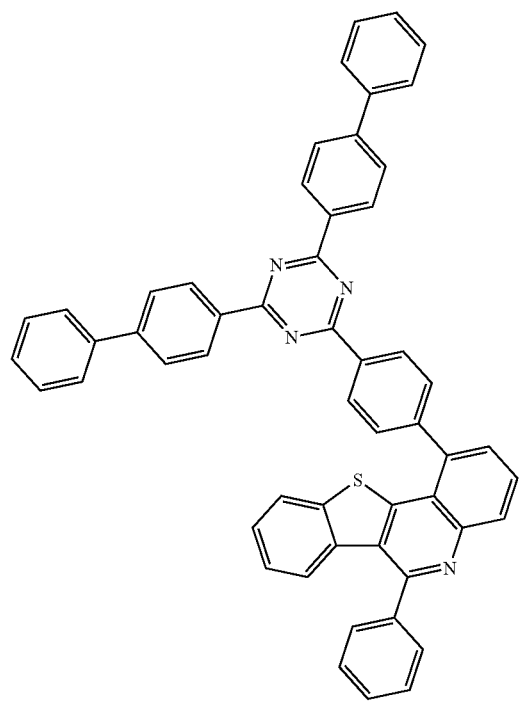

-continued
27
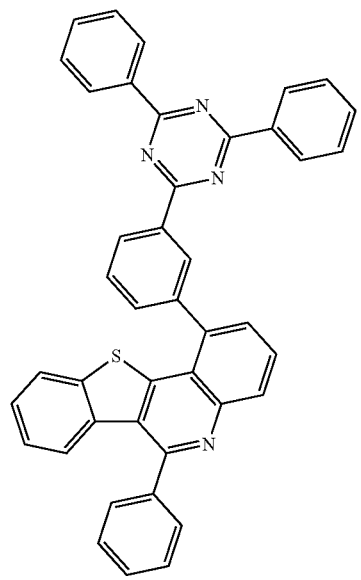
32
28
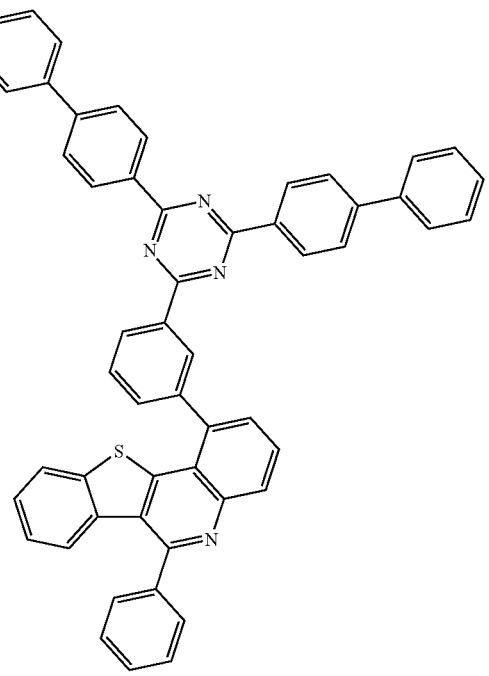
33
34
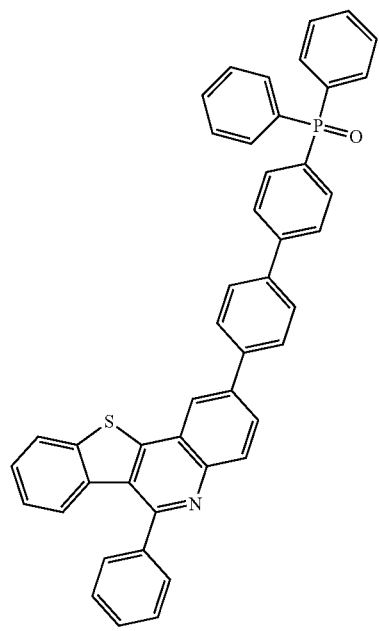
35
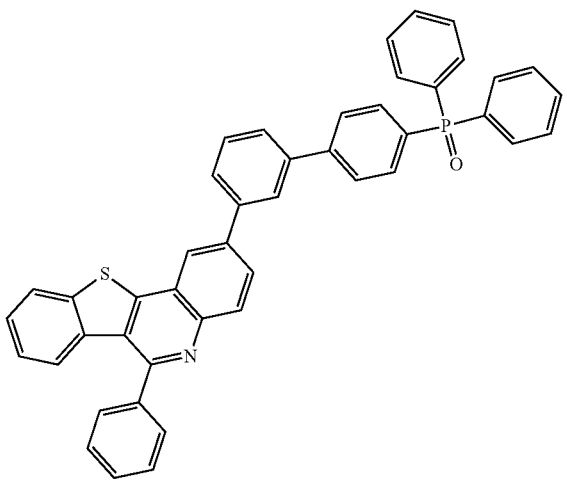

-continued
36
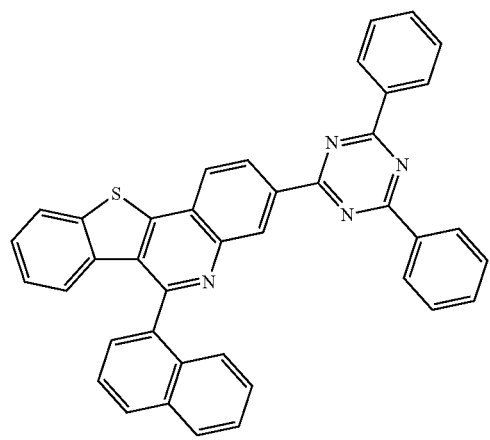
37
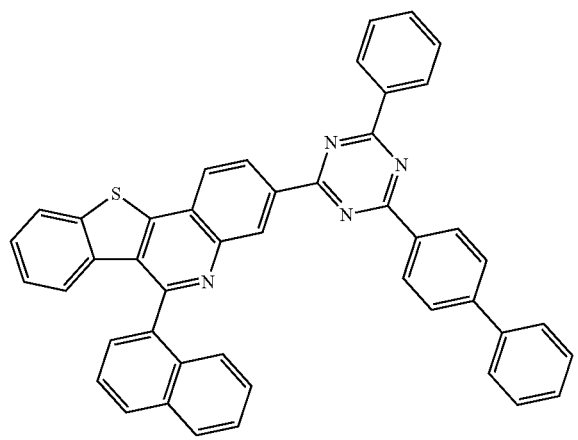
38
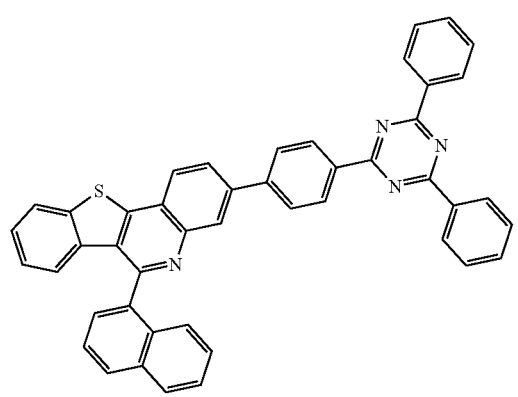
39
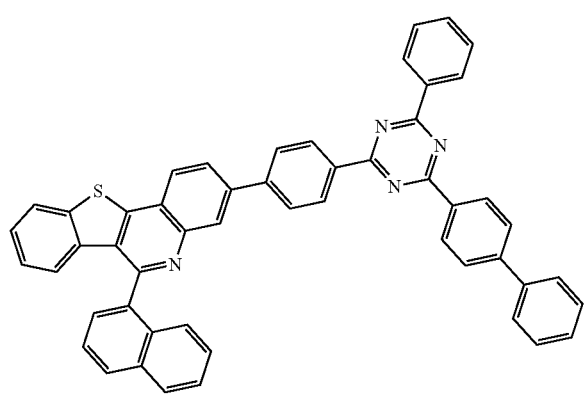
40
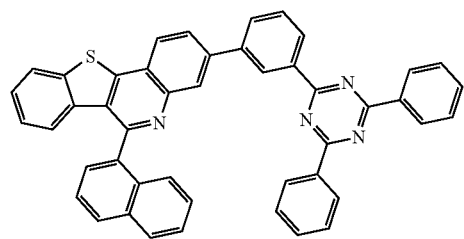
41
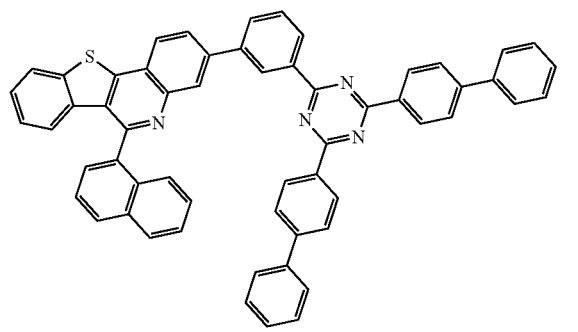
42
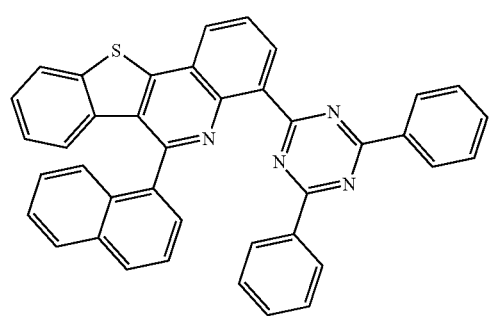
43
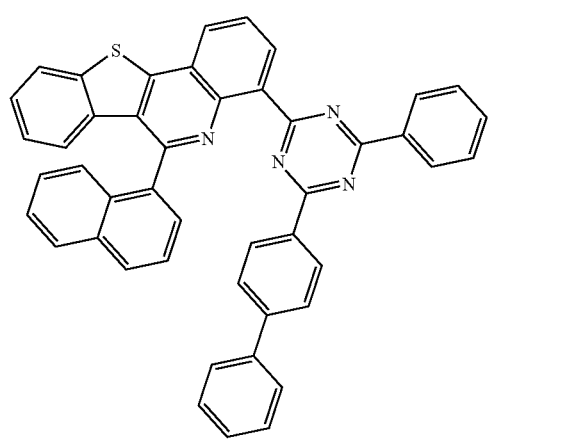

-continued
44
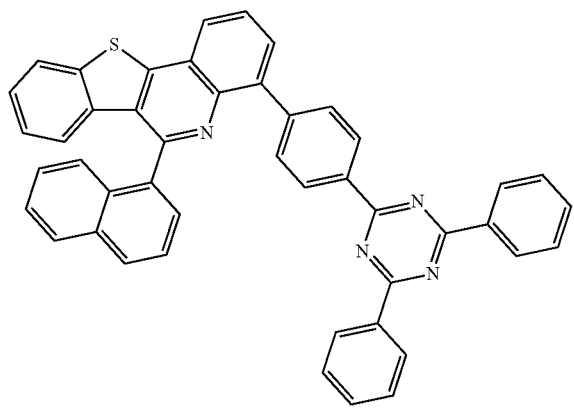
45
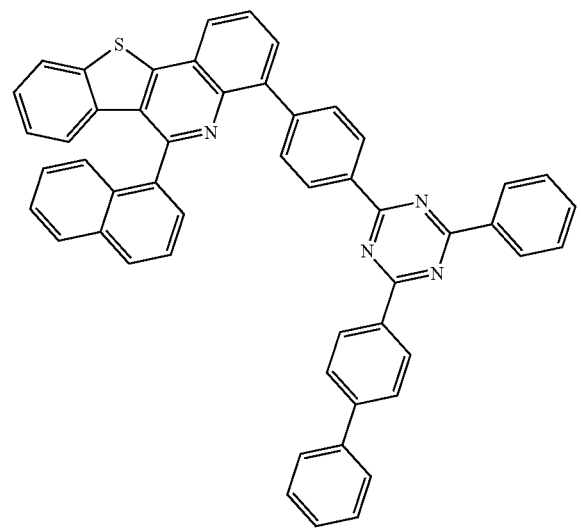
46
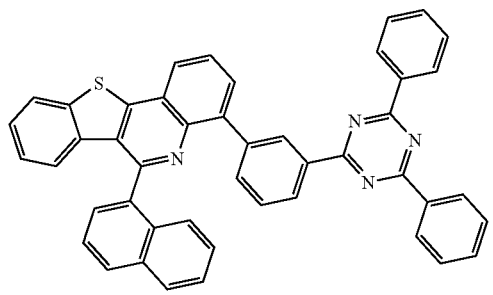
47
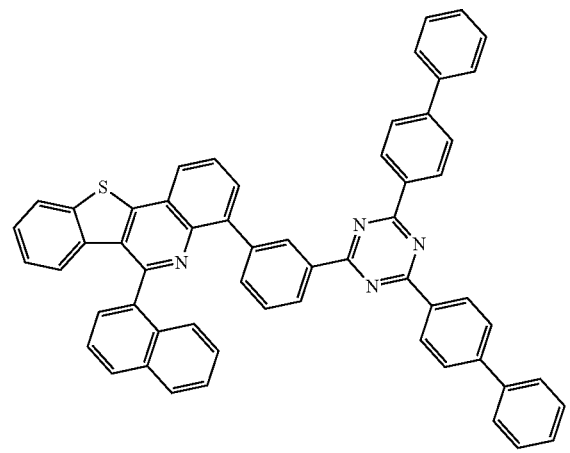
48
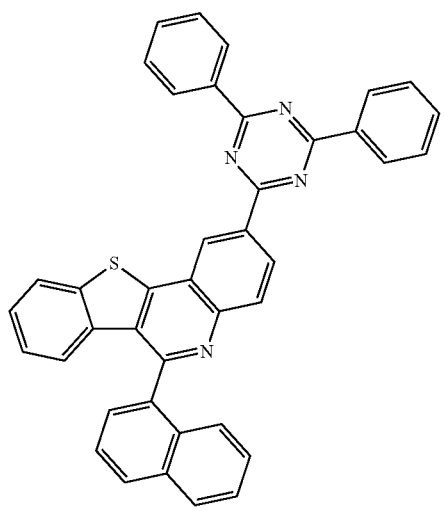
49
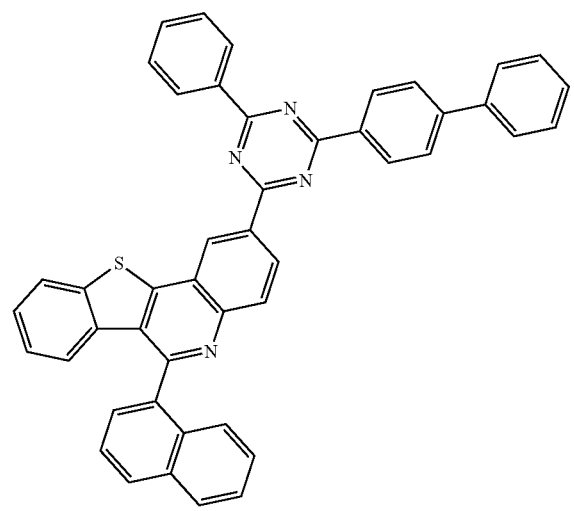

50
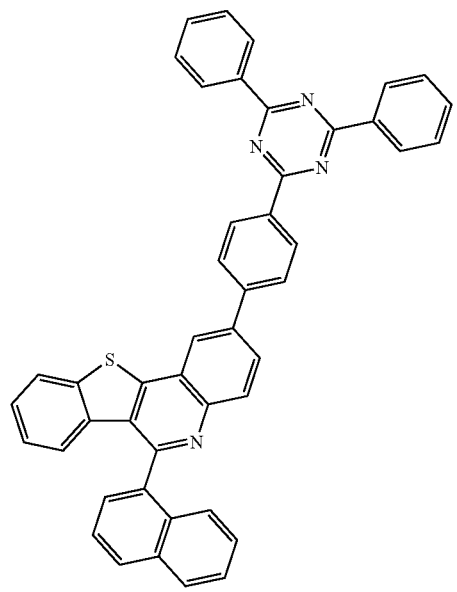
51
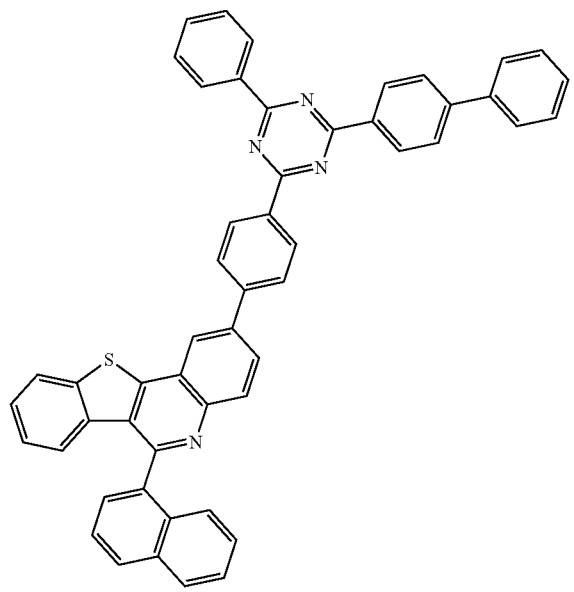
52
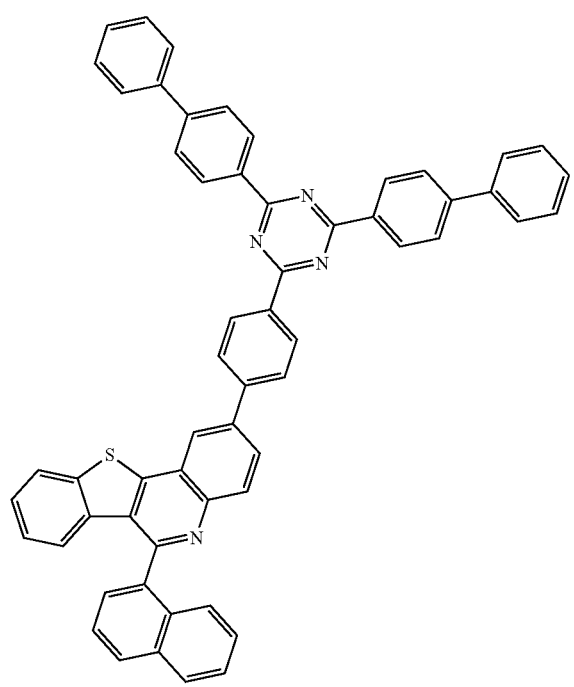
53
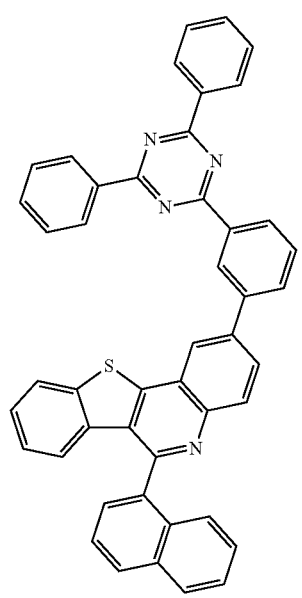

-continued
54
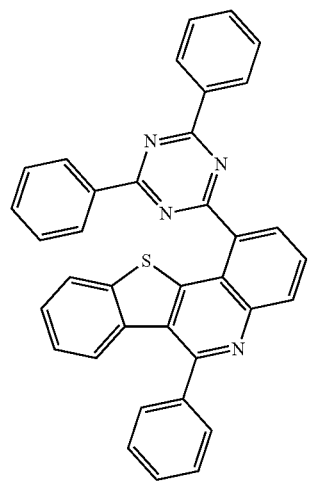
55
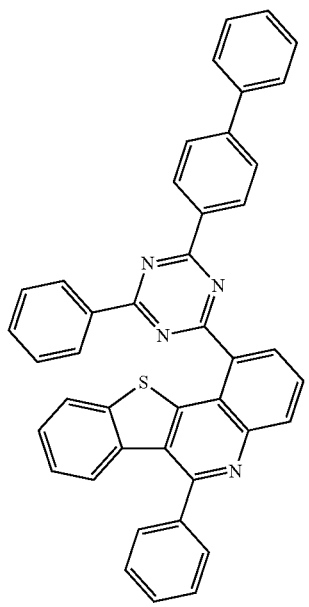
56
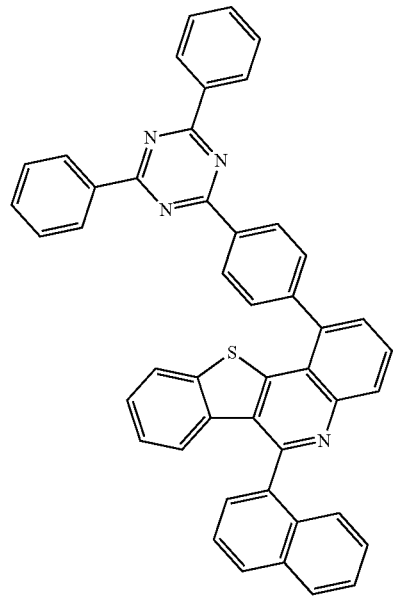
57
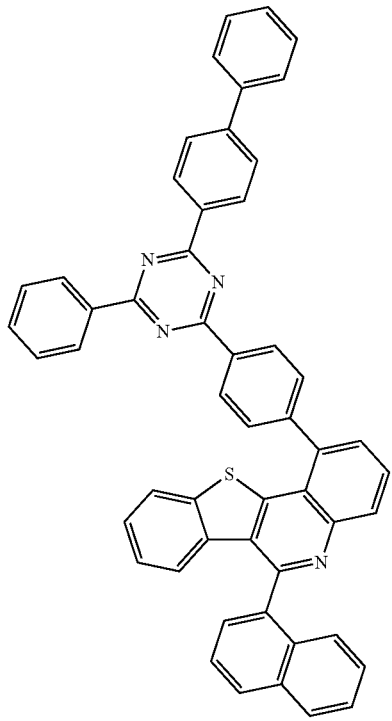

-continued
58
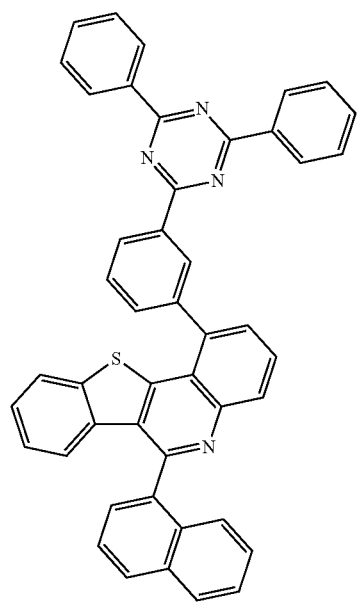
59
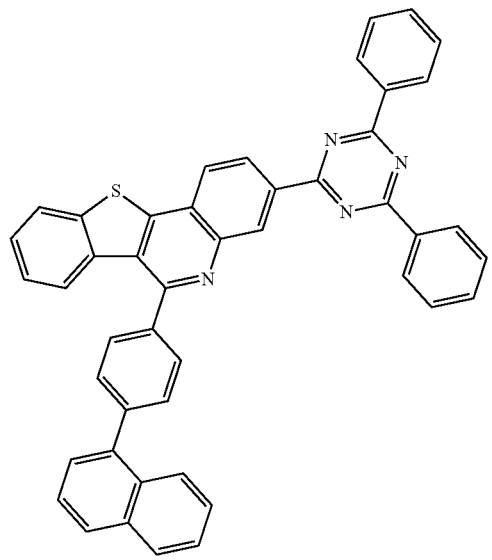
60 61
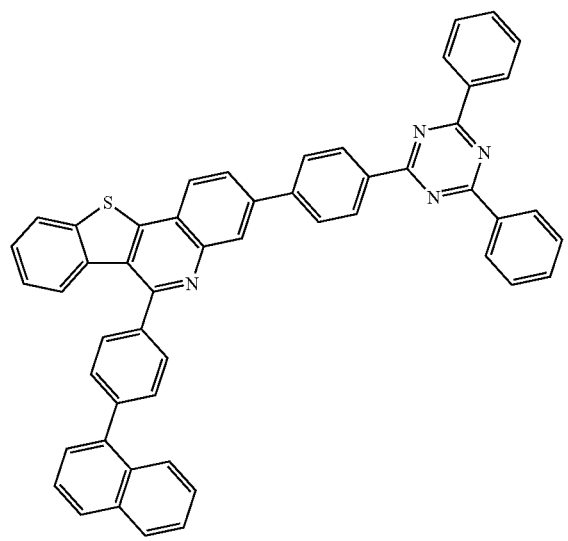
62 63
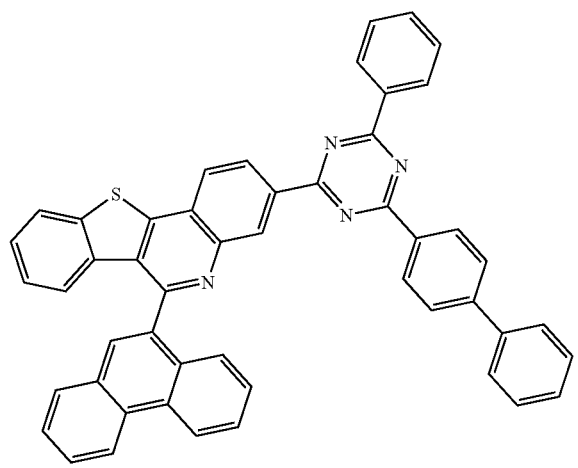

-continued
64
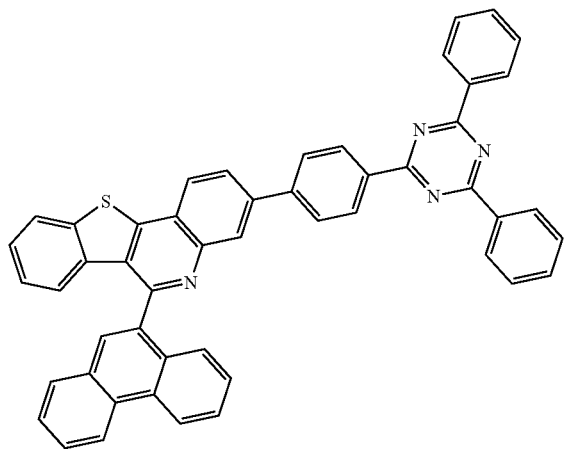
65
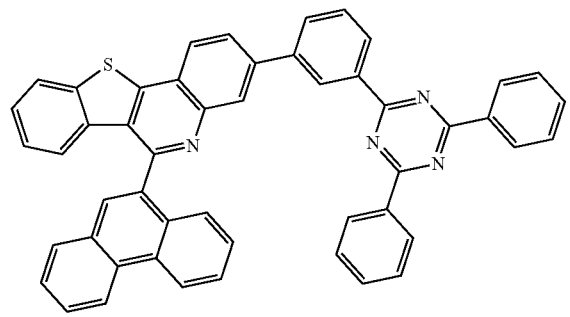
66
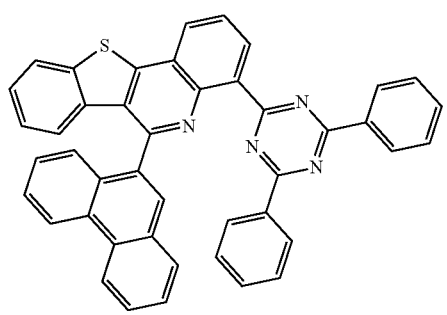
67
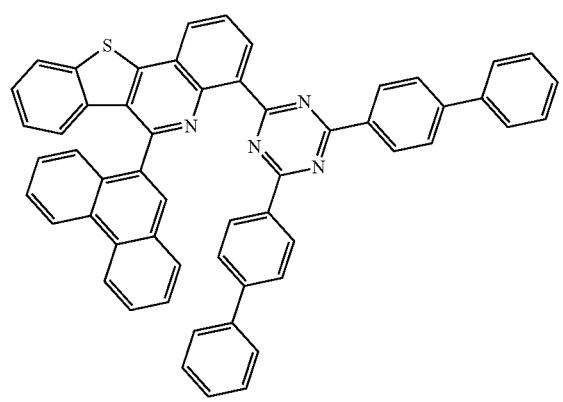
68
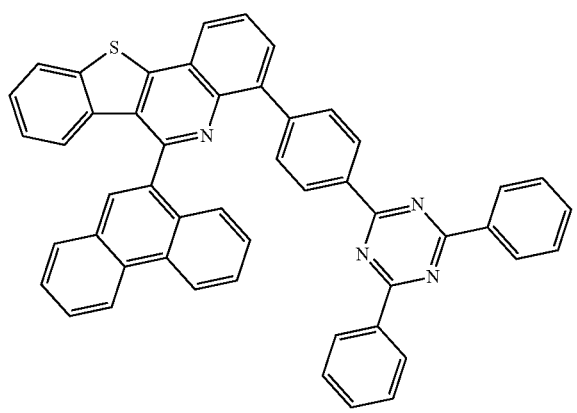
69
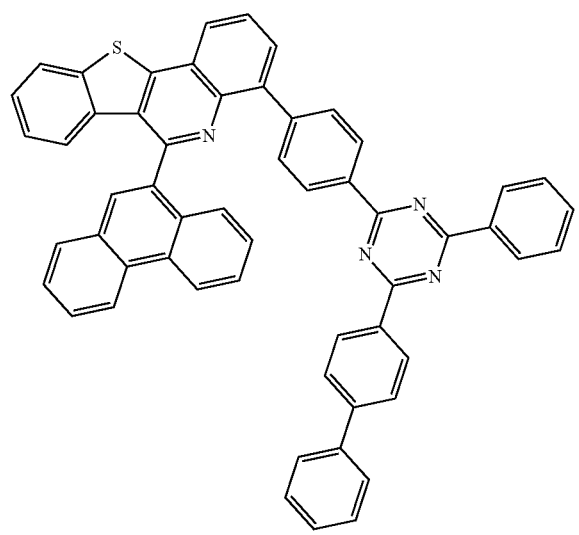

70
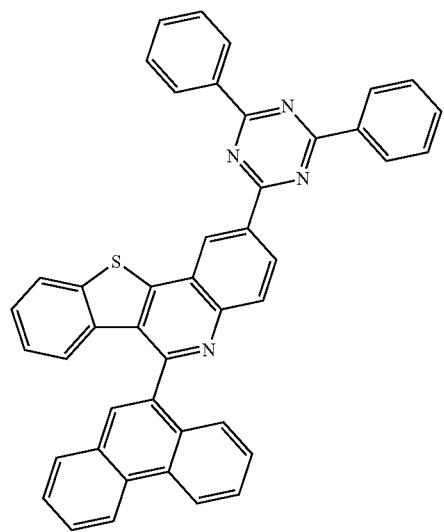
71
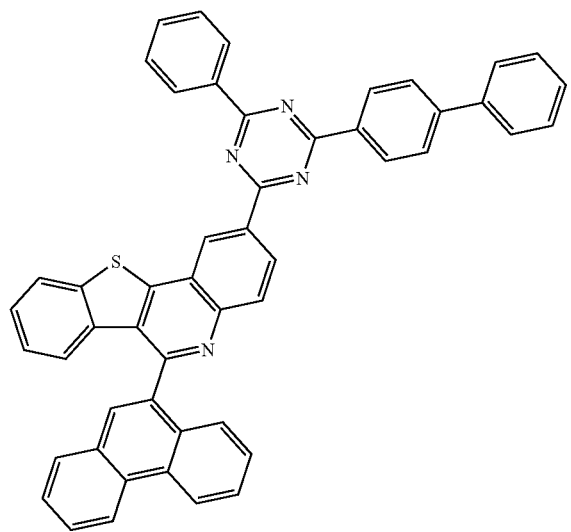
72
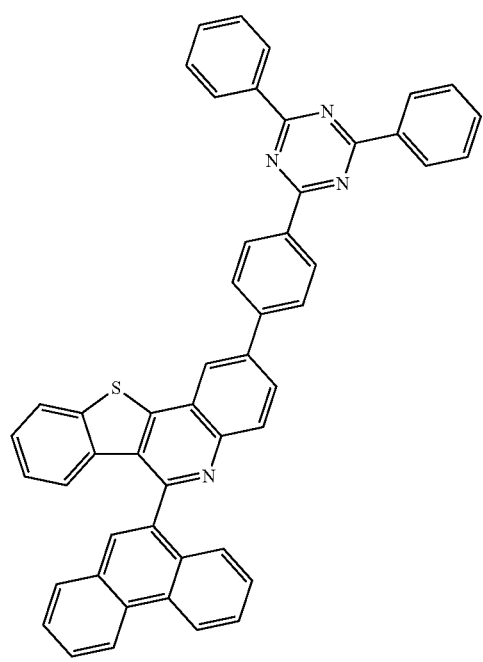
73
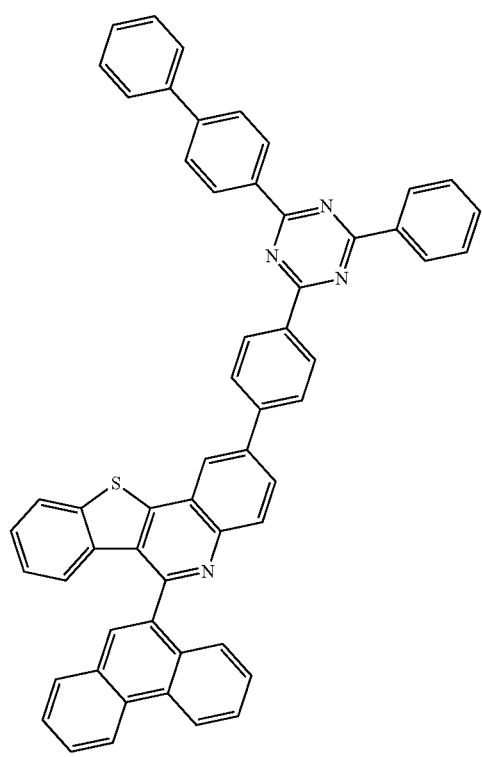

74
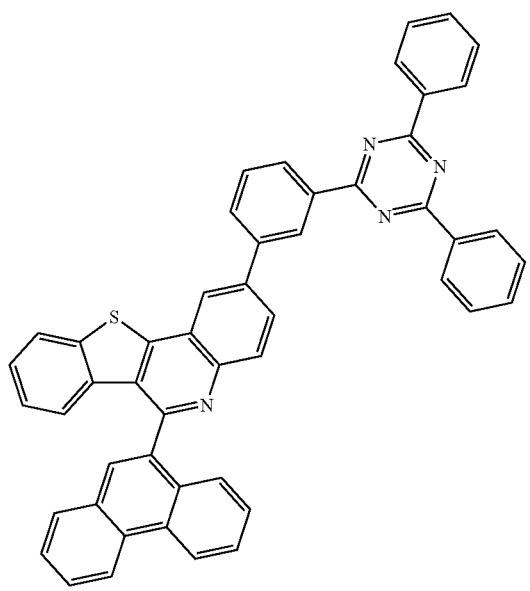
75
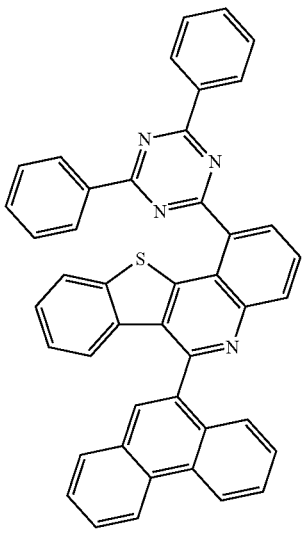
76
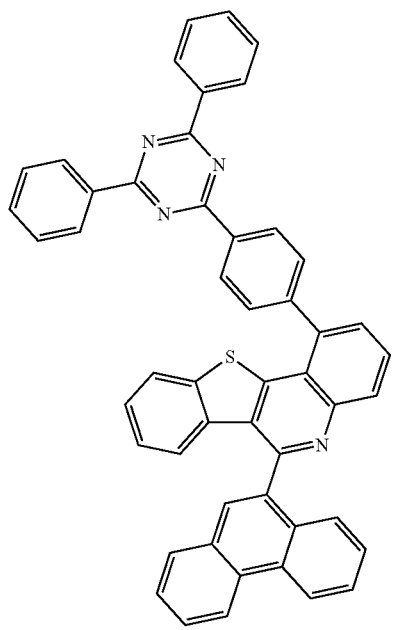
77
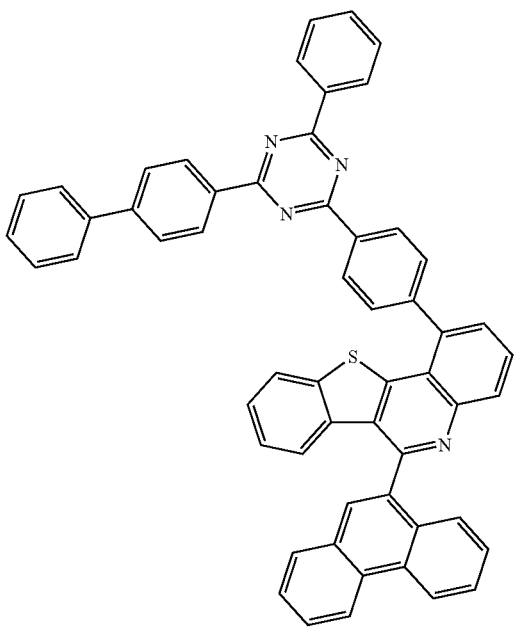

78
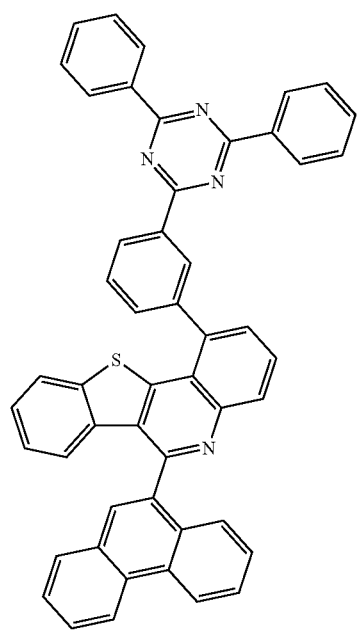
79
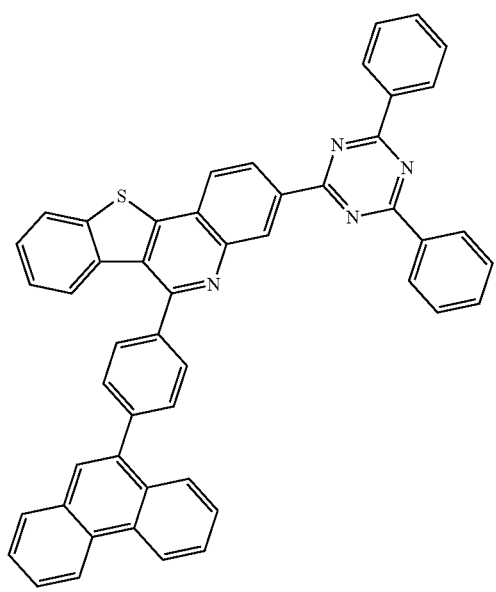
80
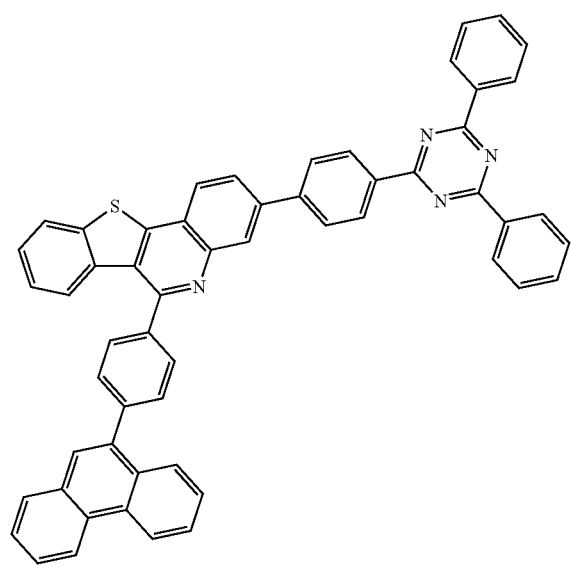
81
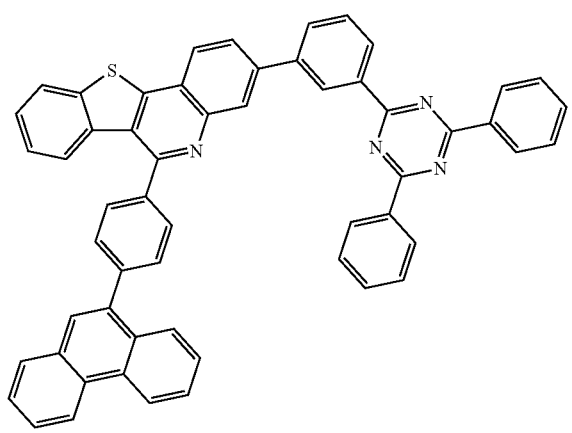

82
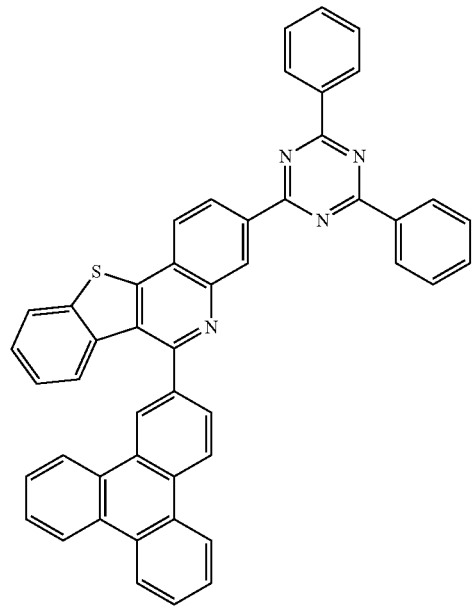
83
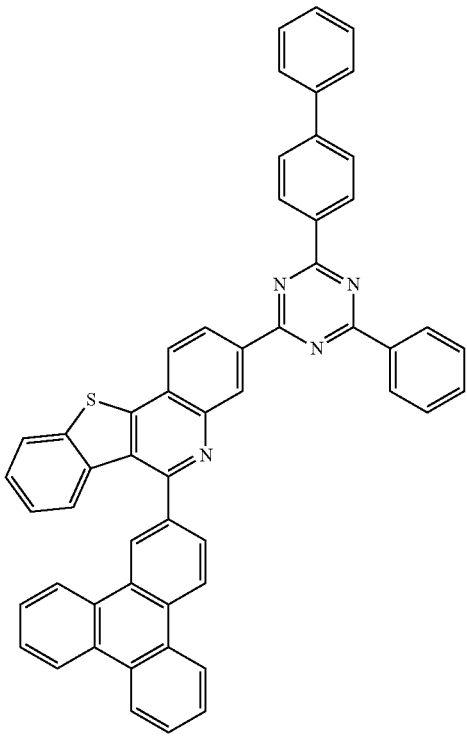
84
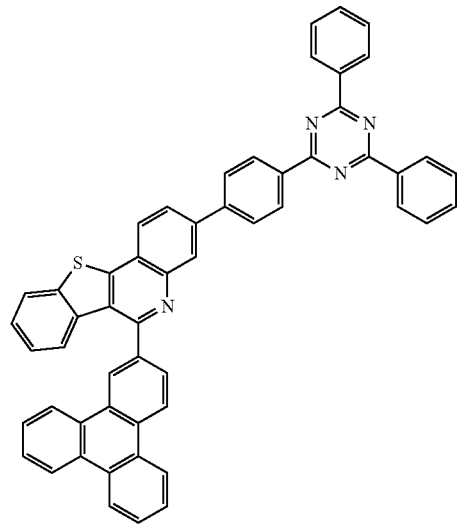
85
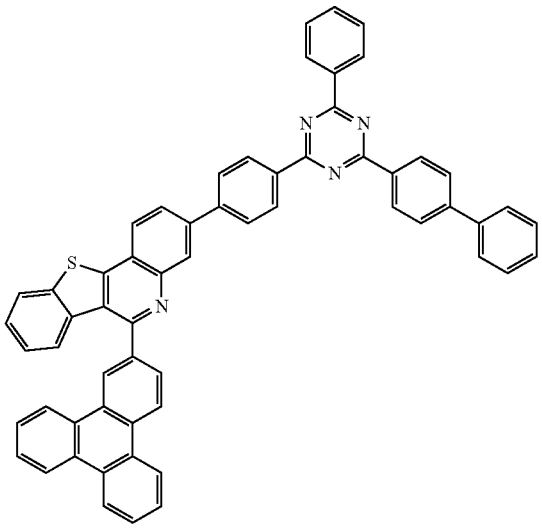

86
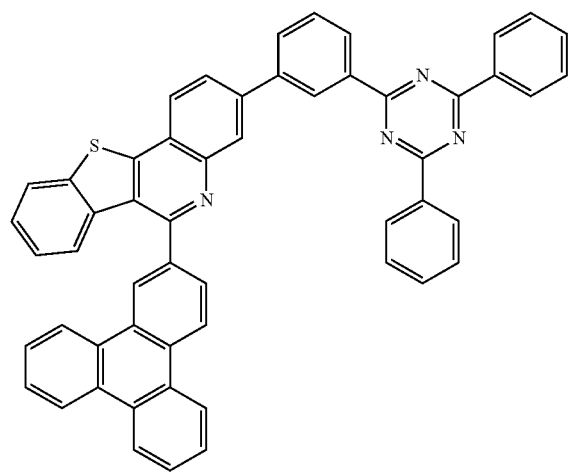
87
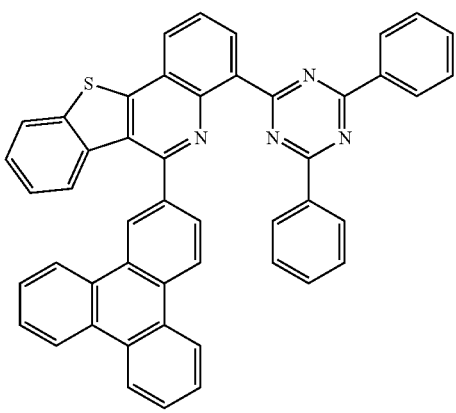
88
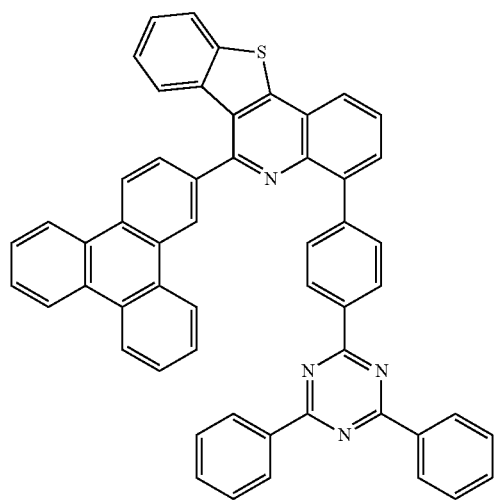
89
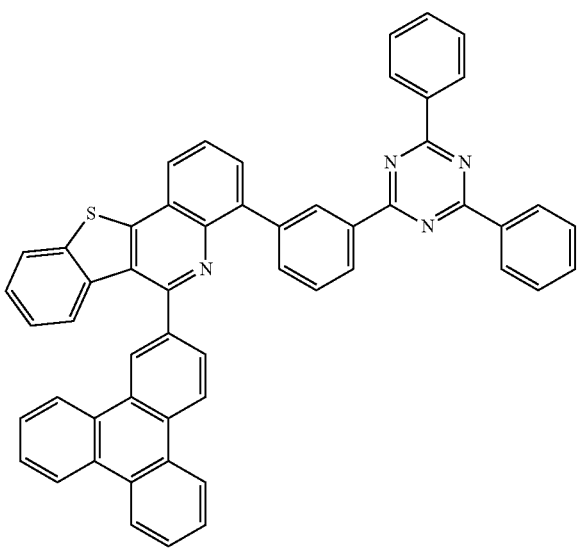

-continued
90
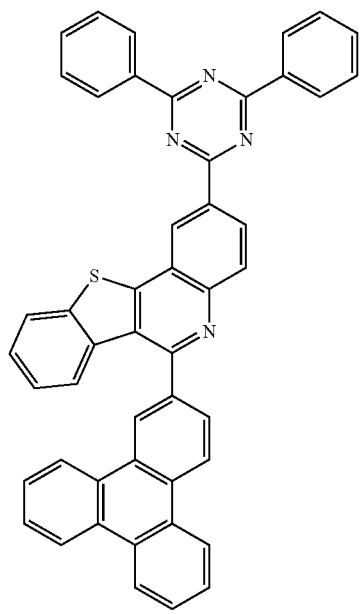
91
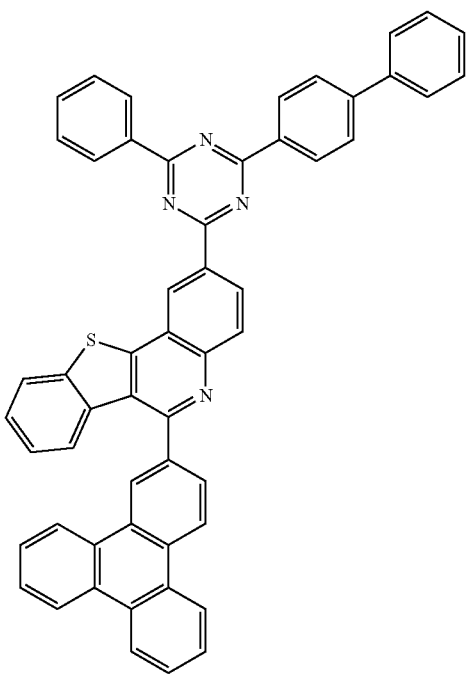
92
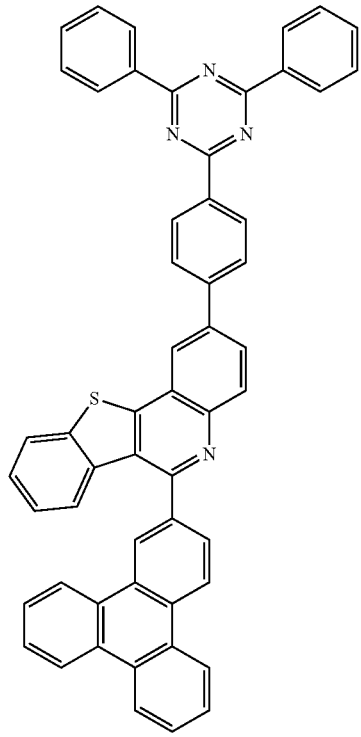
93
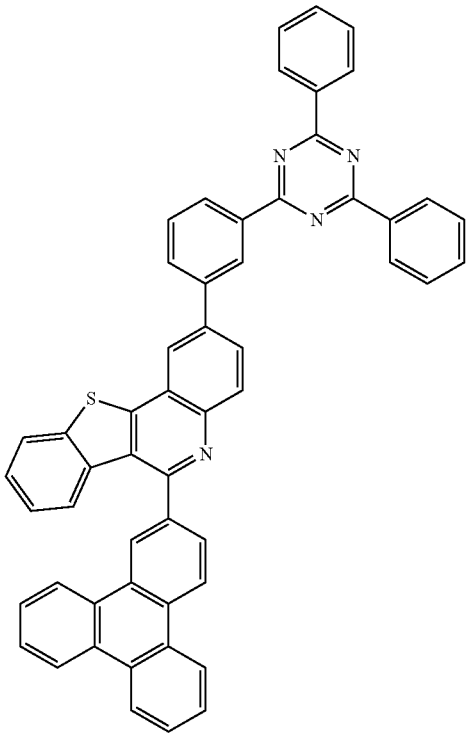

94
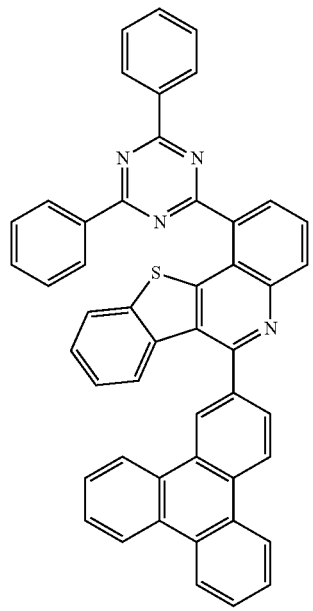
95
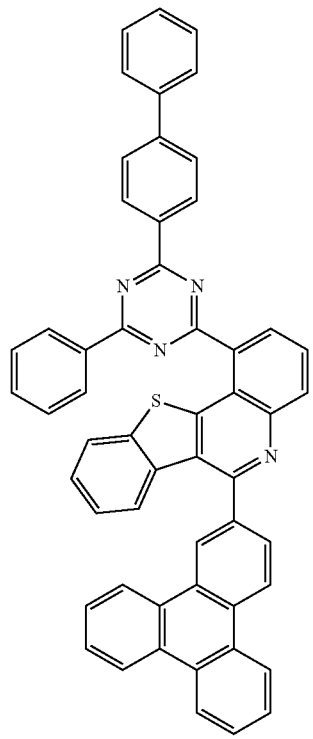
96
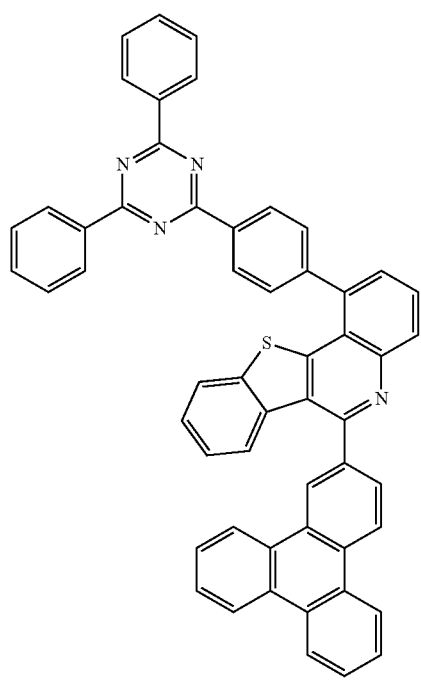
97
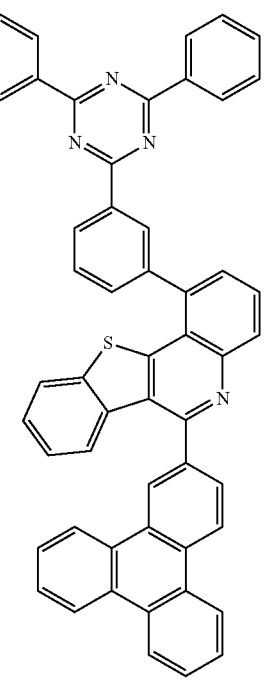

-continued
98
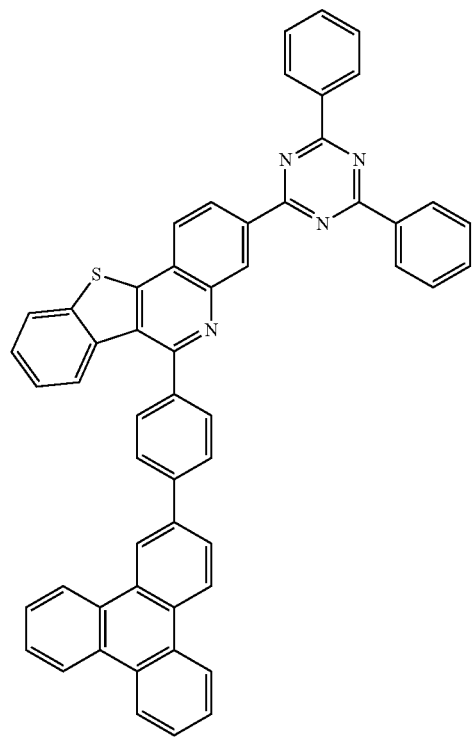
99
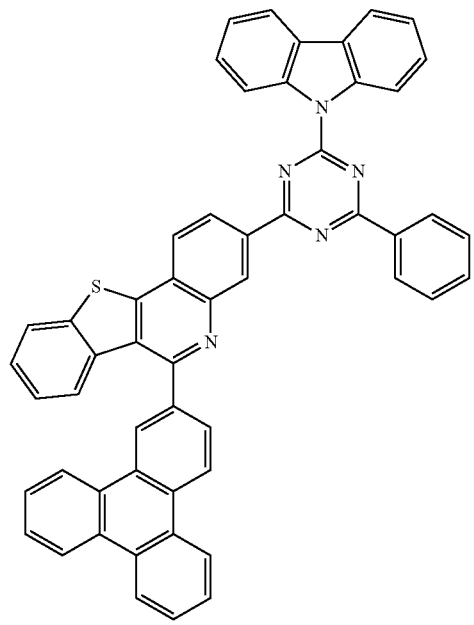
100
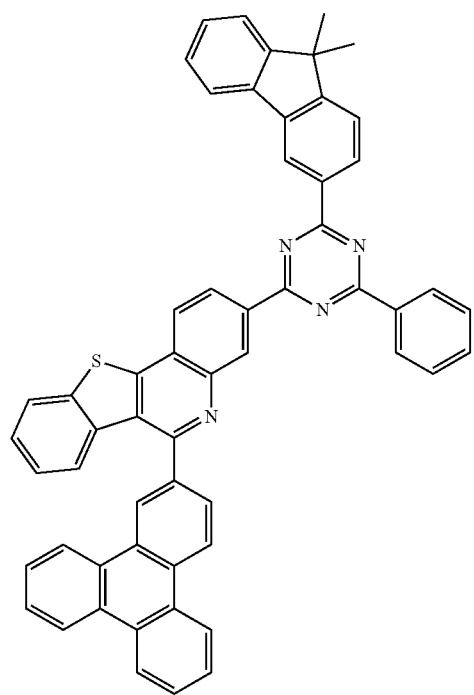
101
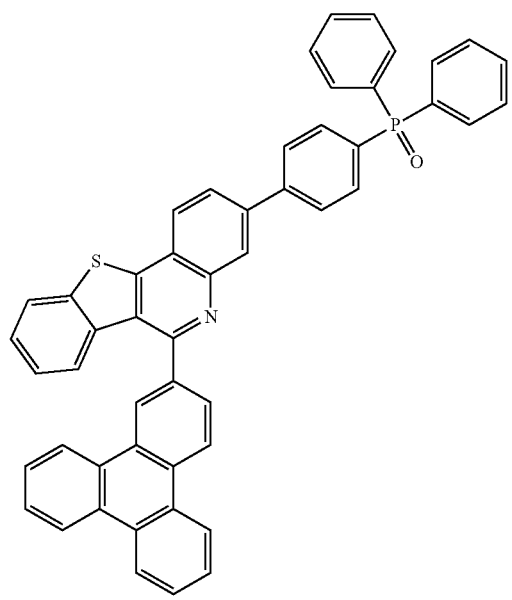

-continued
102
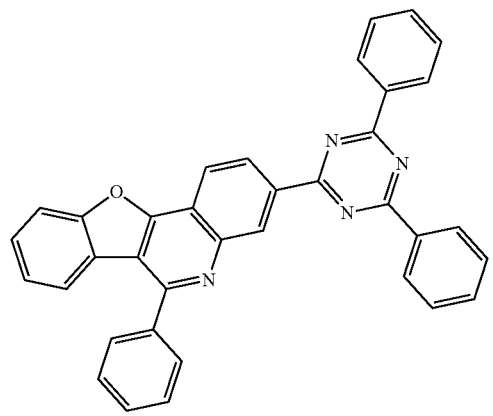 [SMILES: c1ccc(-c2cc(-c3ccc4c(c3)nc(-c3ccccc3)c3c5ccccc5sc43)nc(-c3ccccc3)n2)cc1]
103
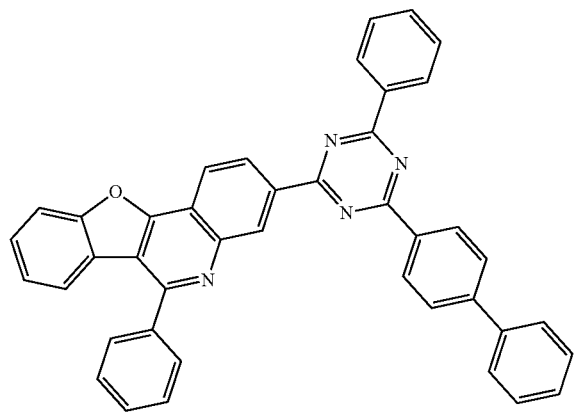
104
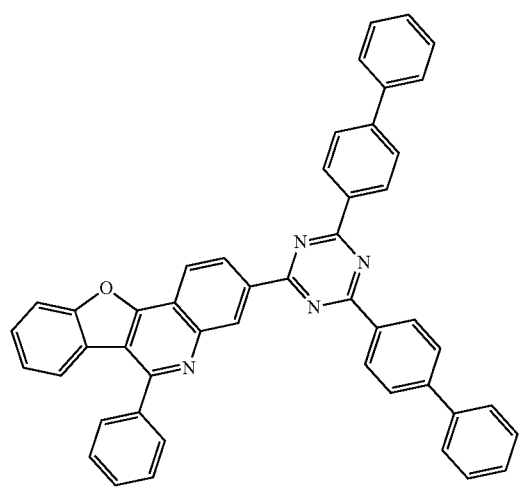
105
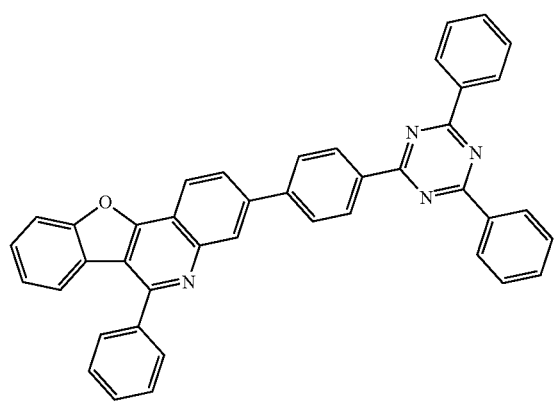
106
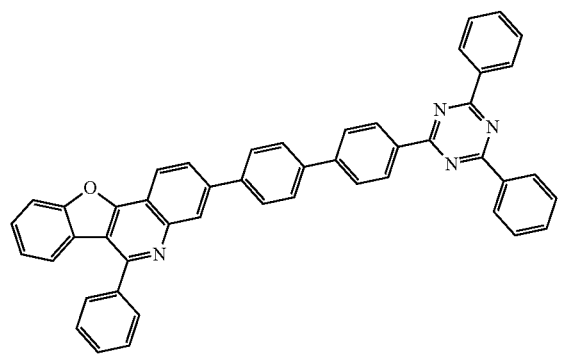 [SMILES: c1ccc(-c2cc(-c3ccccc3)nc(-c3ccc(-c4ccc(-c5ccc6c(c5)nc(-c5ccccc5)c5c7ccccc7sc65)cc4)cc3)n2)cc1]
107
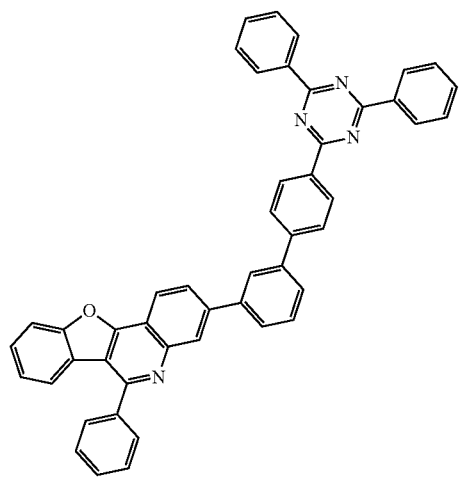

-continued
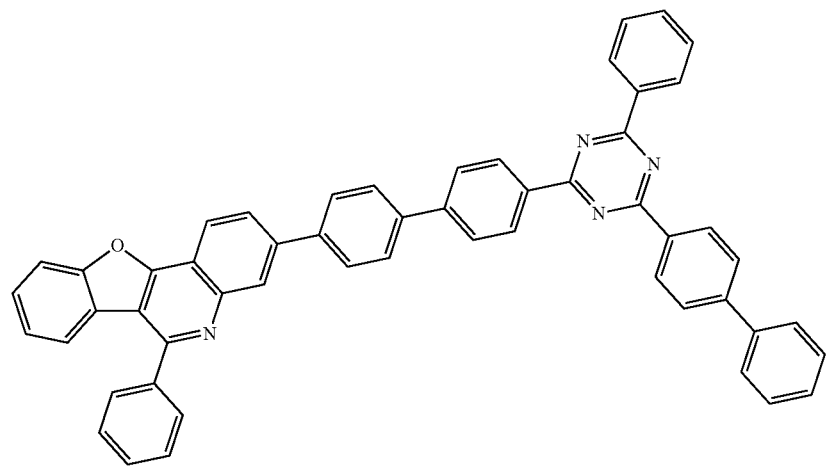
108
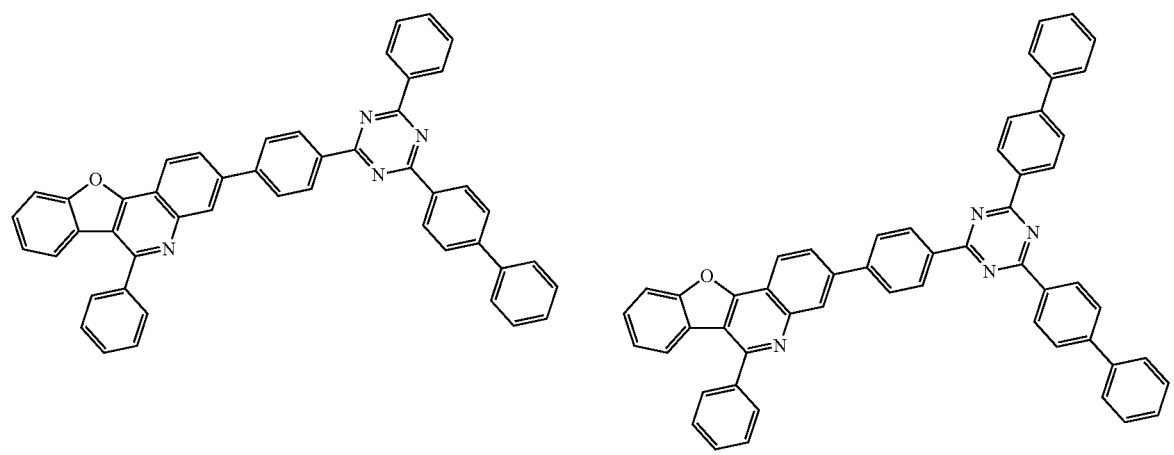
109
110
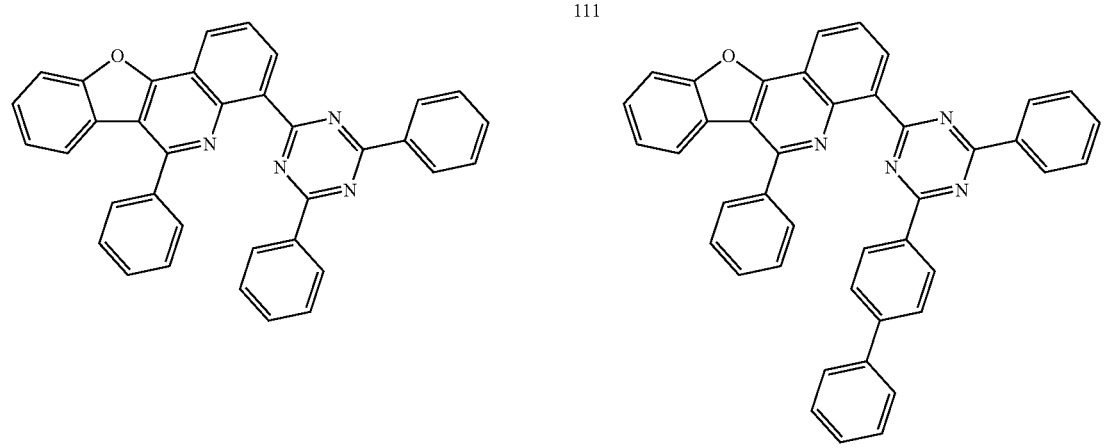
111
112

-continued
113
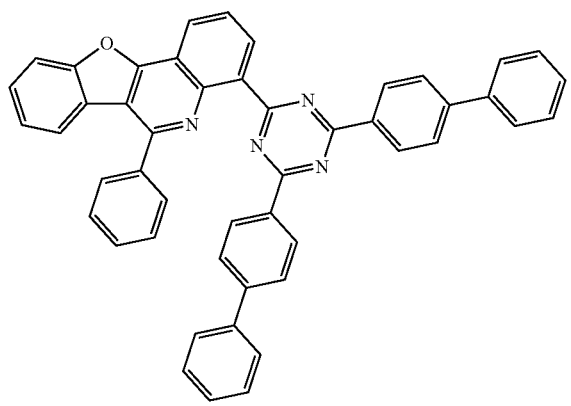
114
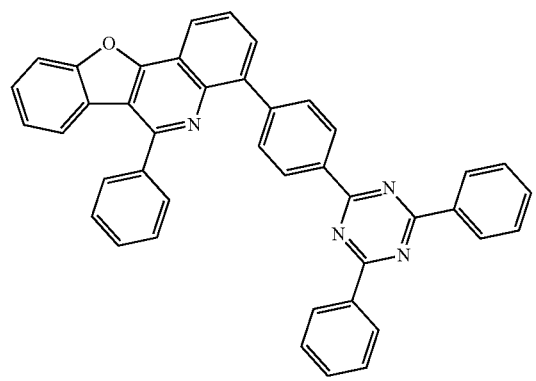 [SMILES: c1ccc(-c2nc(-c3ccccc3)nc(-c3ccc(-c4cccc5c4nc(-c4ccccc4)c4c6ccccc6sc54)cc3)n2)cc1]
115
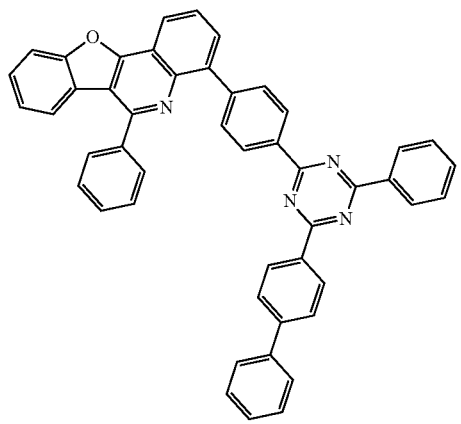
116
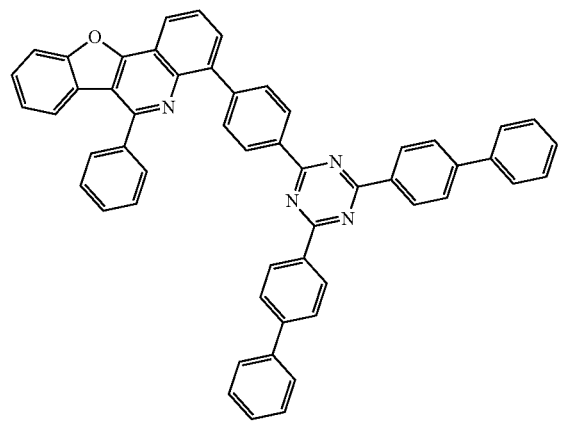
117
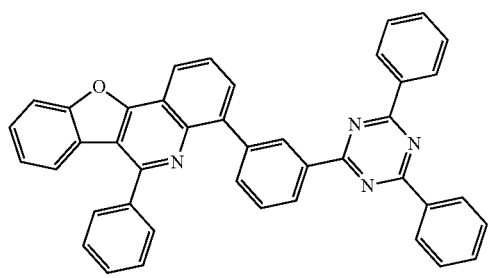
118
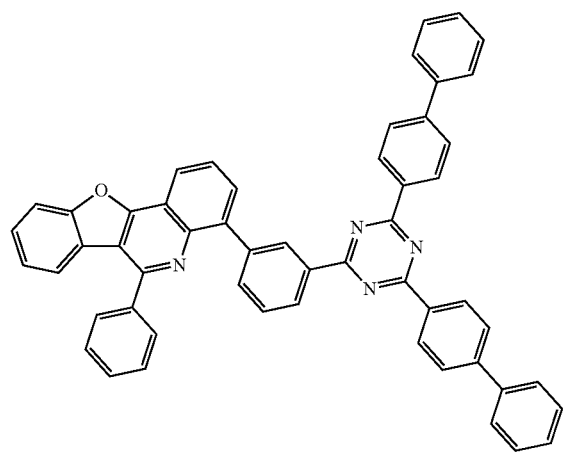

-continued
119
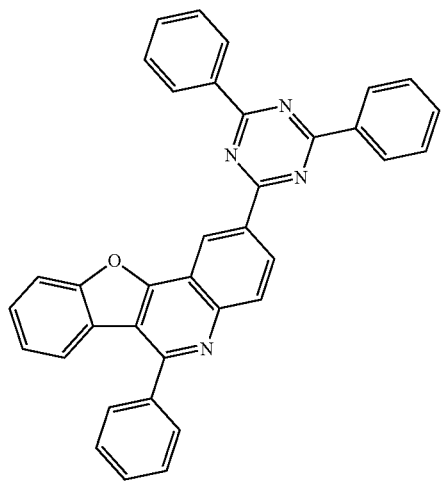
120
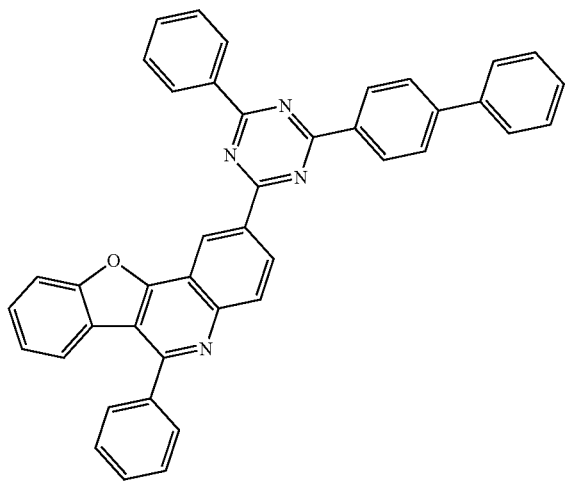
121
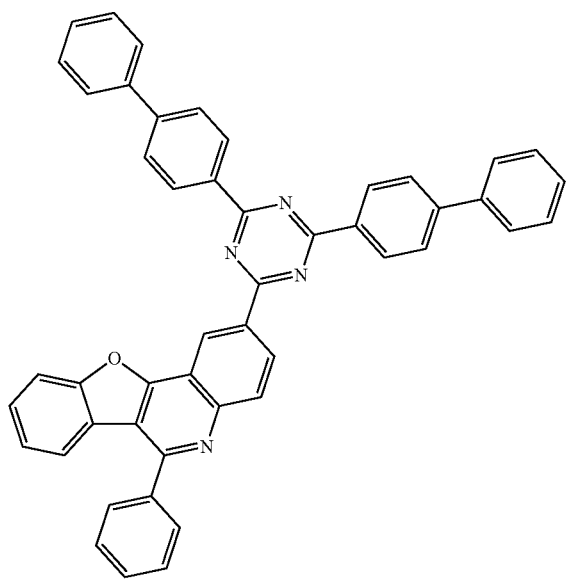
122
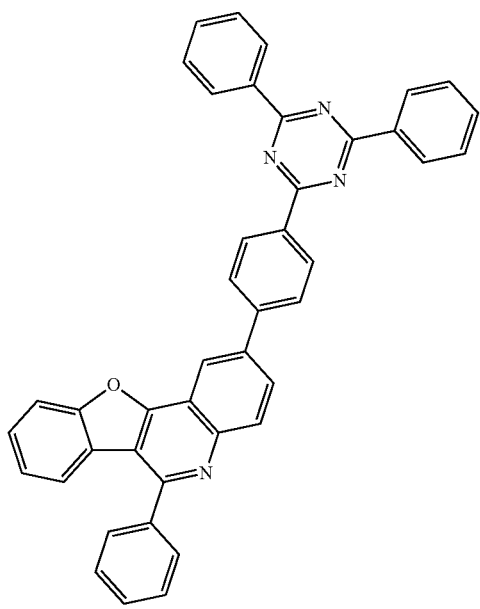

-continued
123
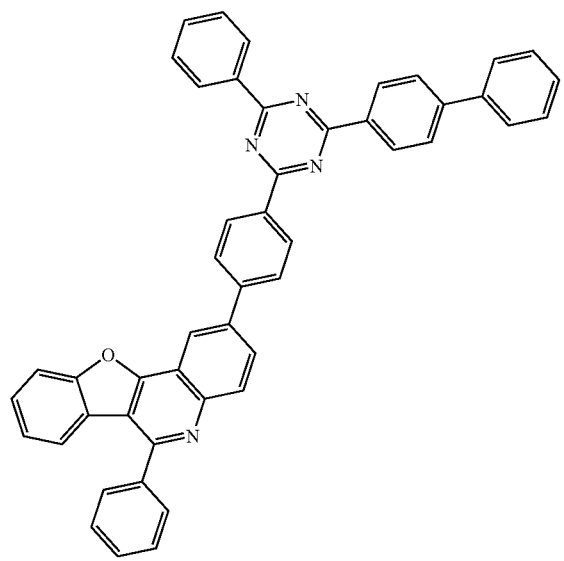
124
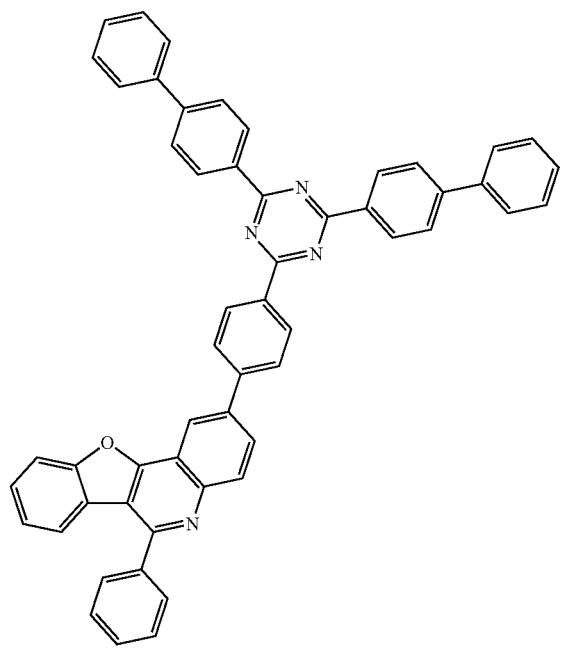
125
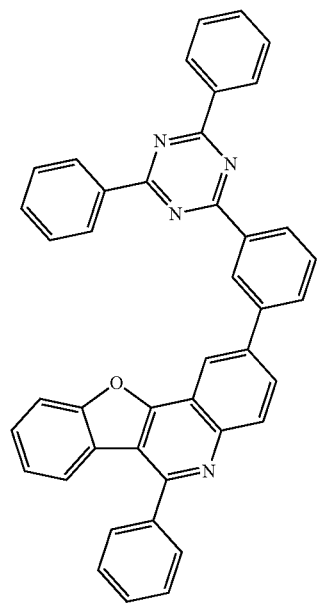 [SMILES: c1ccc(-c2nc(-c3ccccc3)nc(-c3cccc(-c4ccc5nc(-c6ccccc6)c6c7ccccc7sc6c5c4)c3)n2)cc1]
126
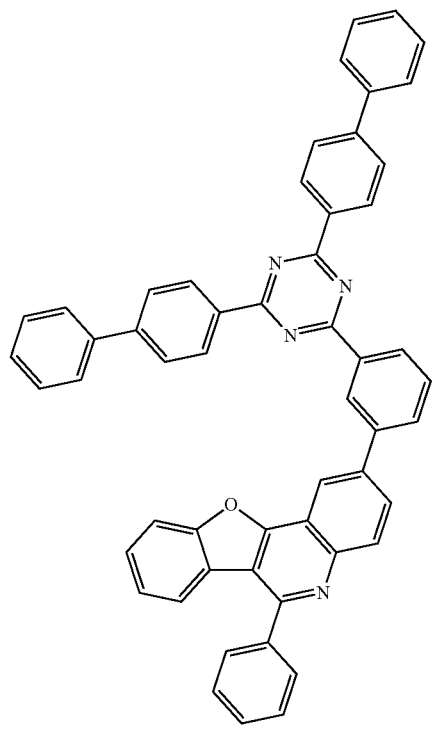

-continued
127 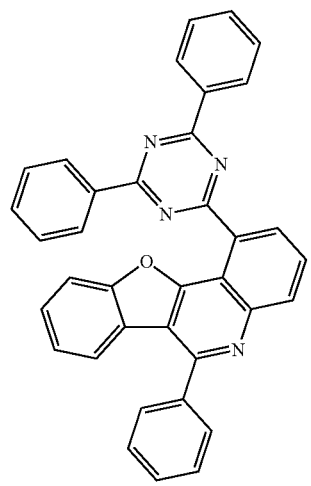
128 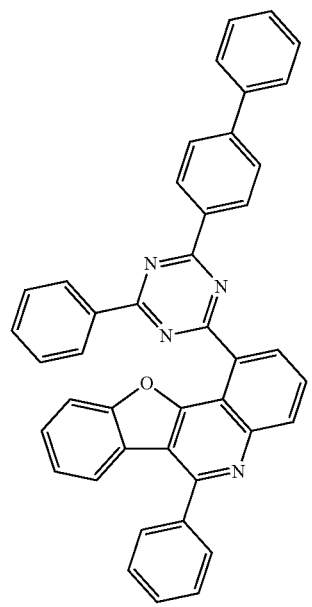
129 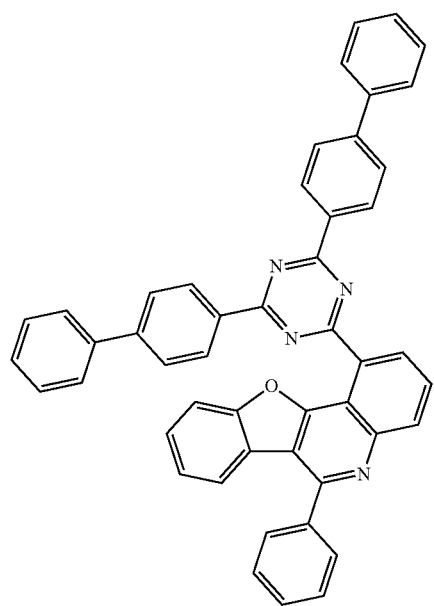
130 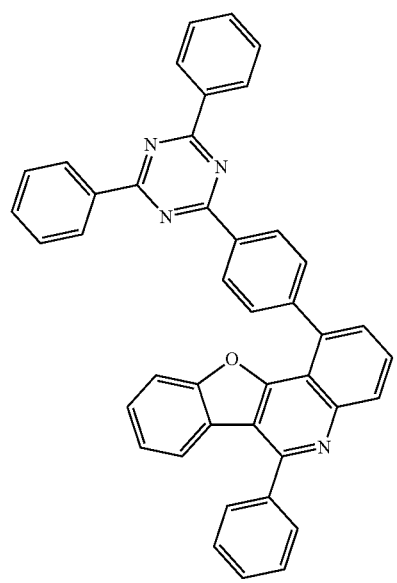

131
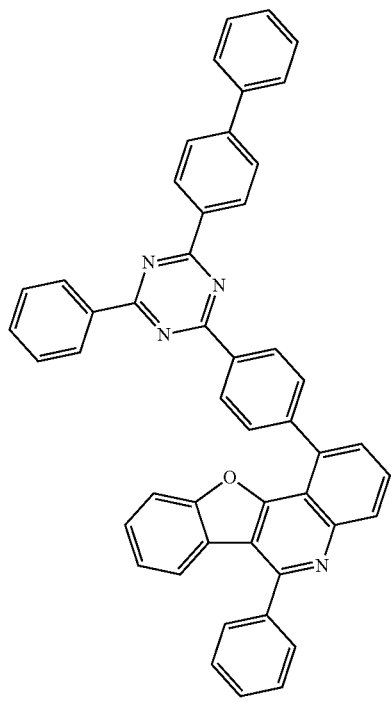
132
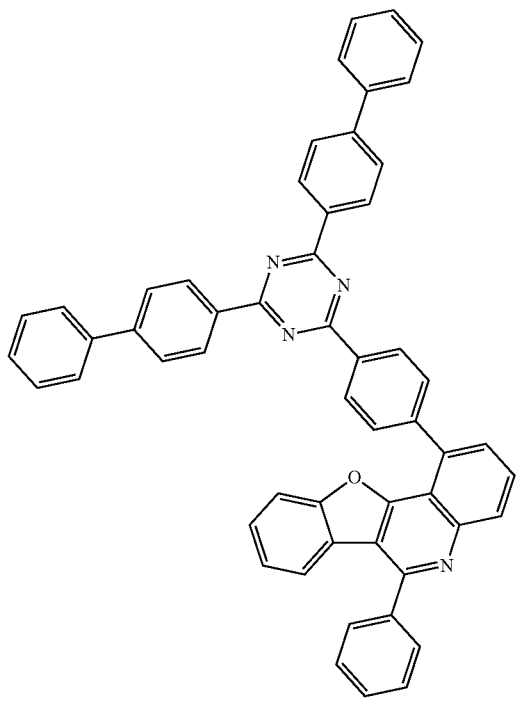
133
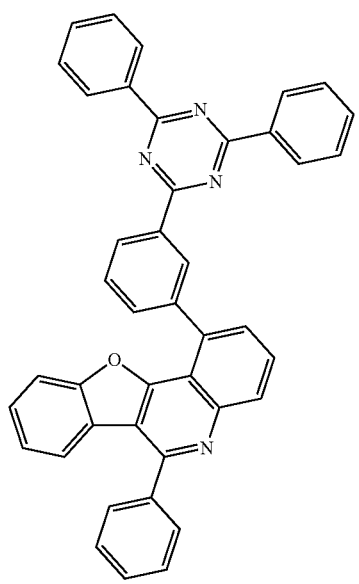
134
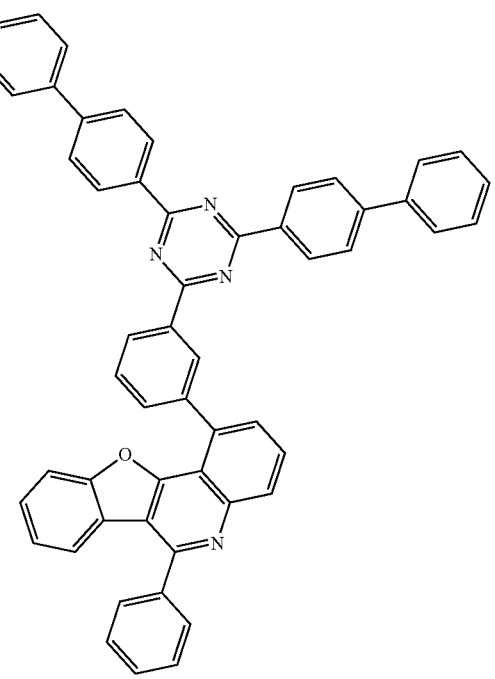

-continued
135
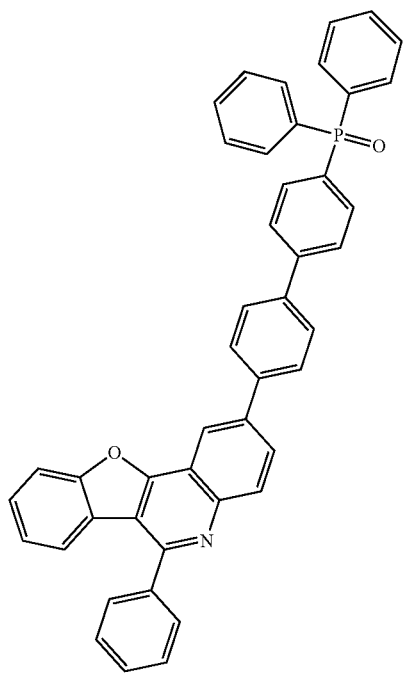 [SMILES: O=P(c1ccccc1)(c1ccccc1)c1ccc(-c2ccc(-c3ccc4nc(-c5ccccc5)c5c6ccccc6sc5c4c3)cc2)cc1]
136
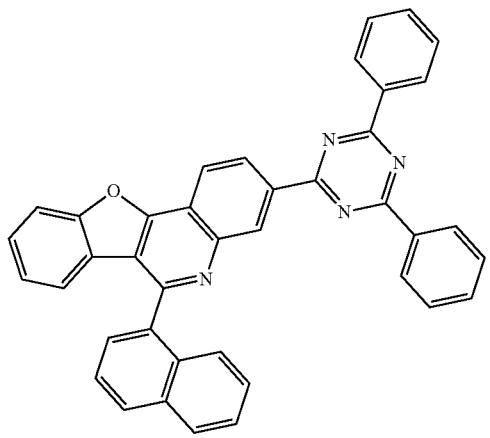
137
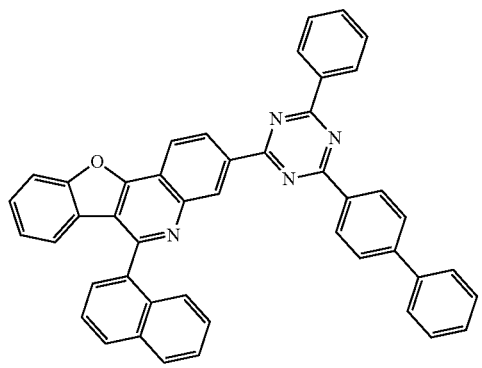
138
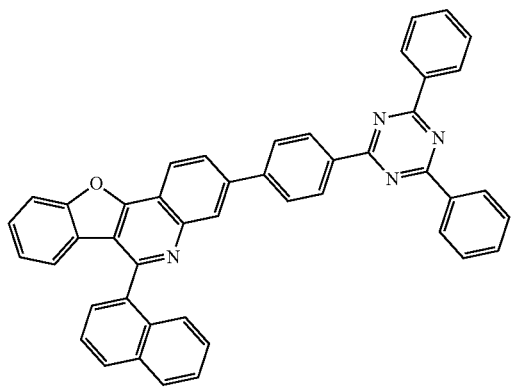
139
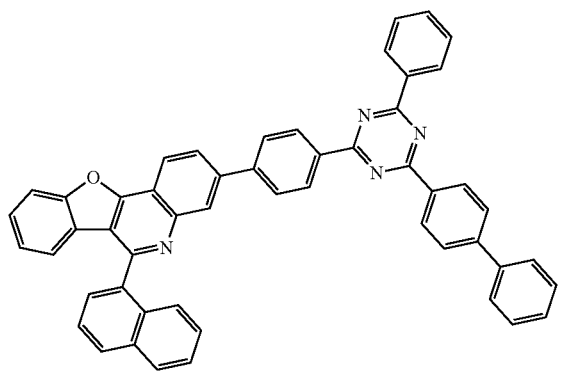
140
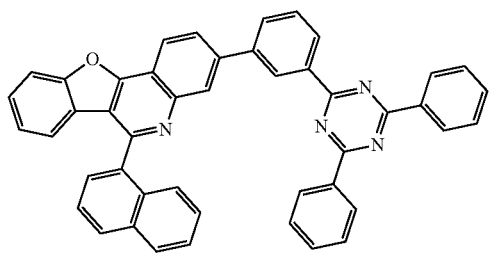

141
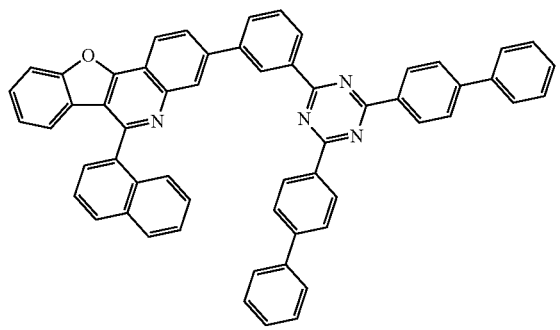
142
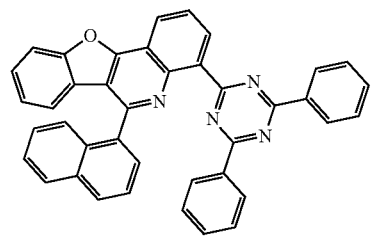
143
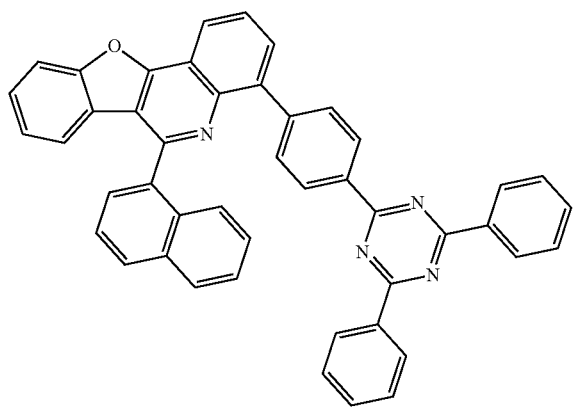
144
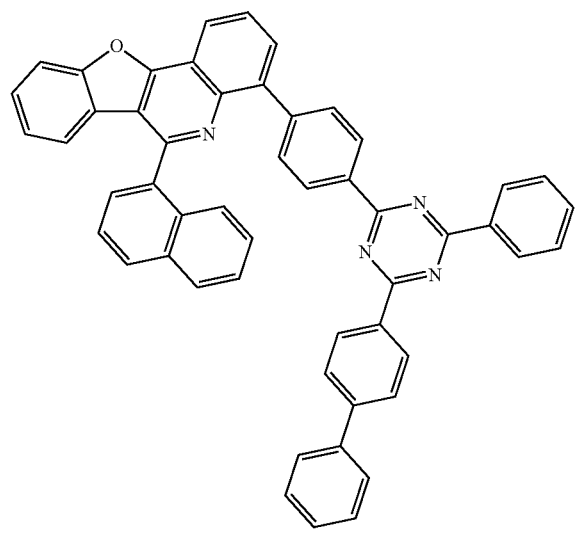
145
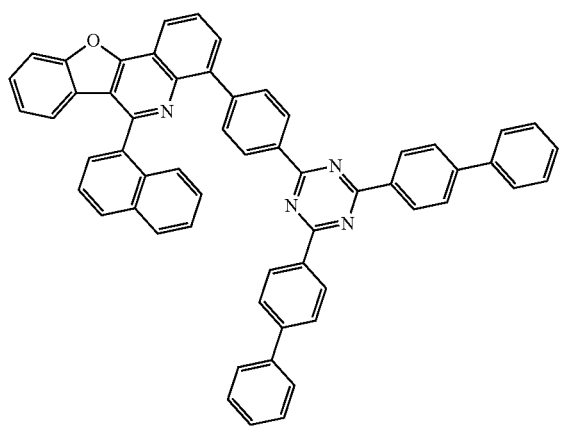
146
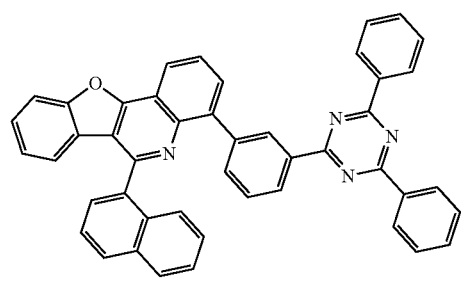

-continued
147
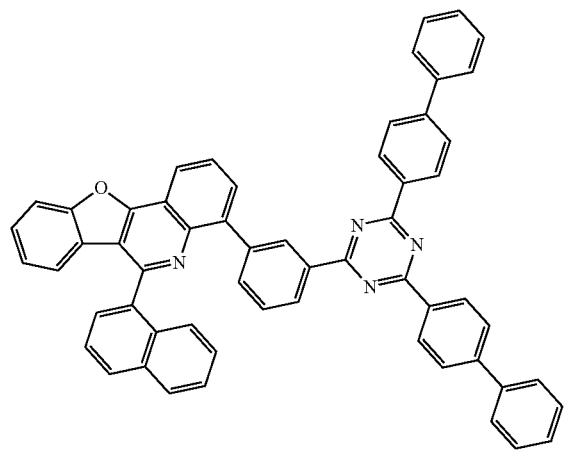
148
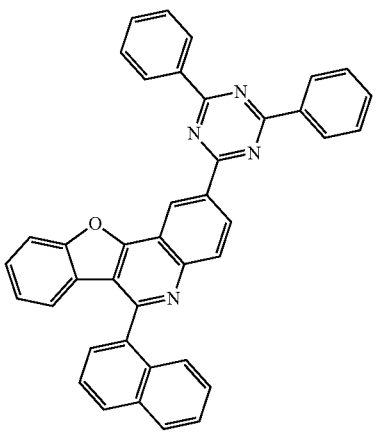
149
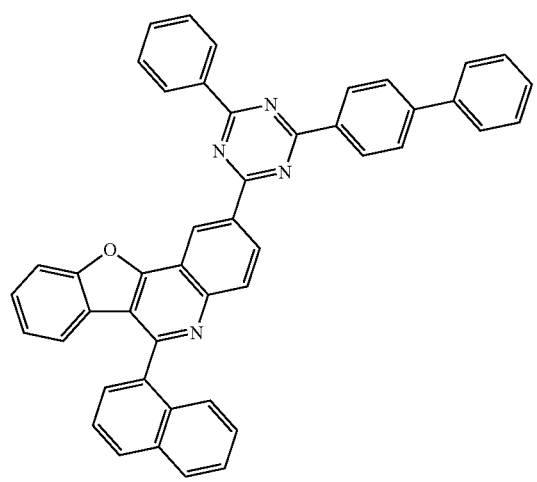
150
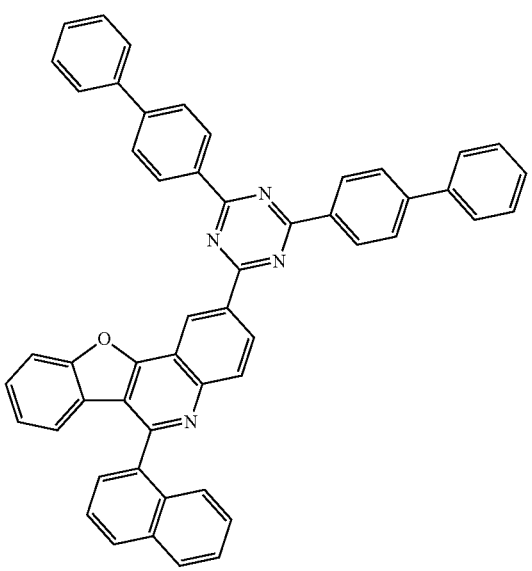
151
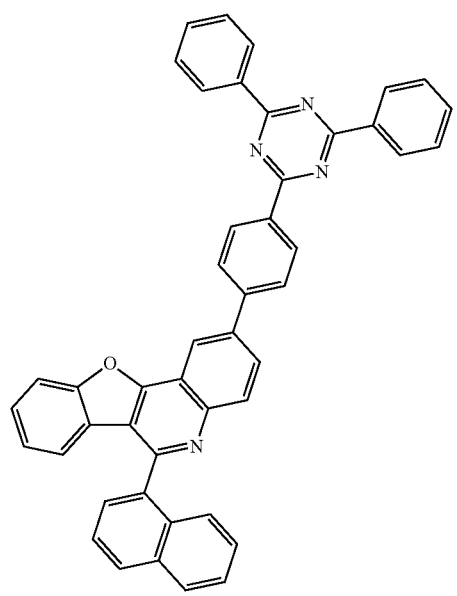
152
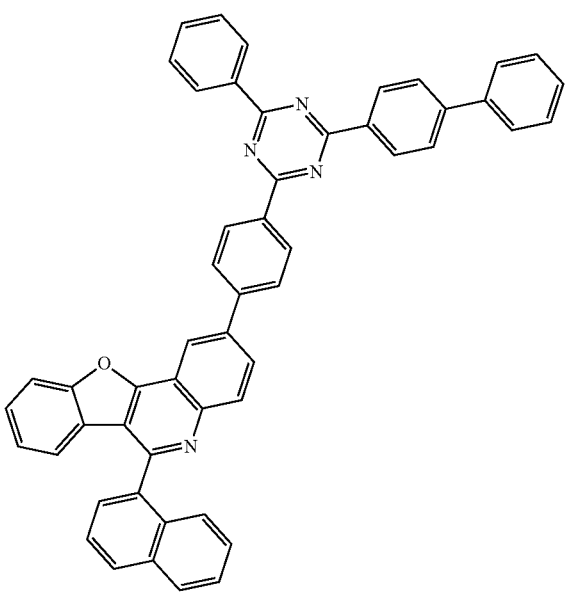

153
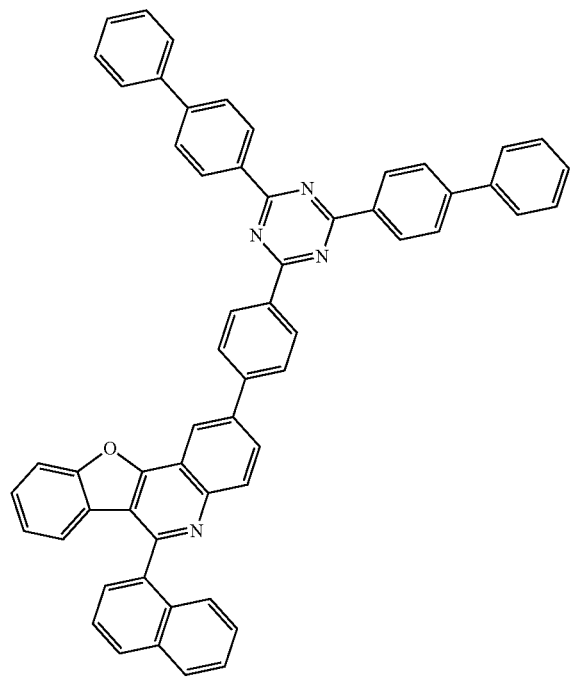
154
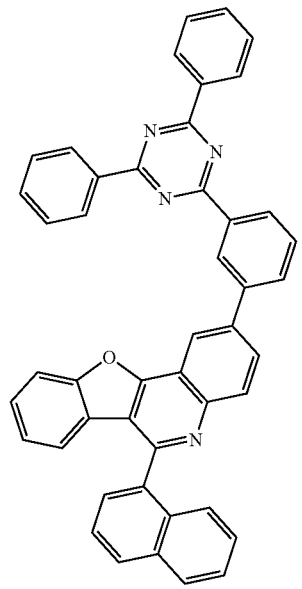
155
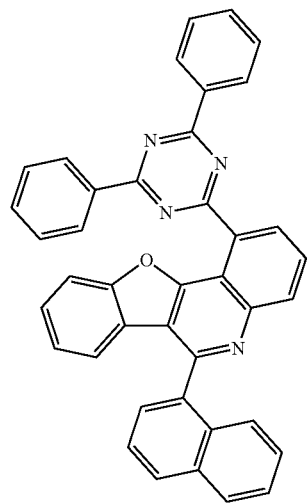
156
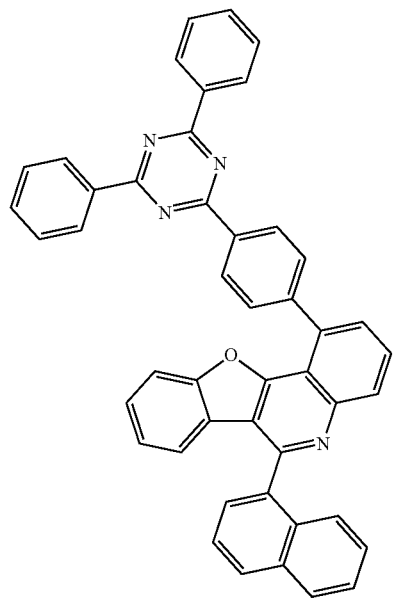

157
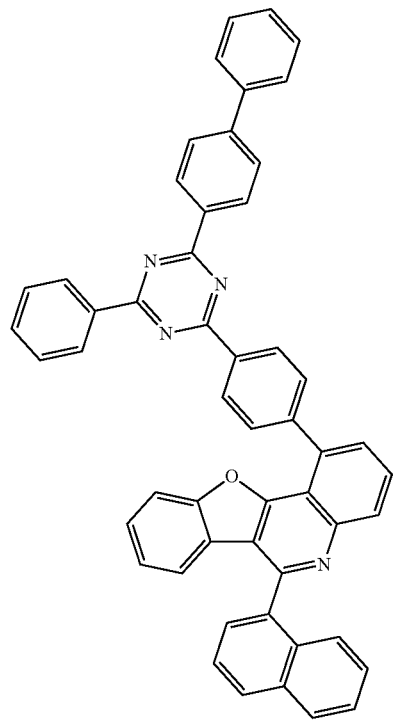
158
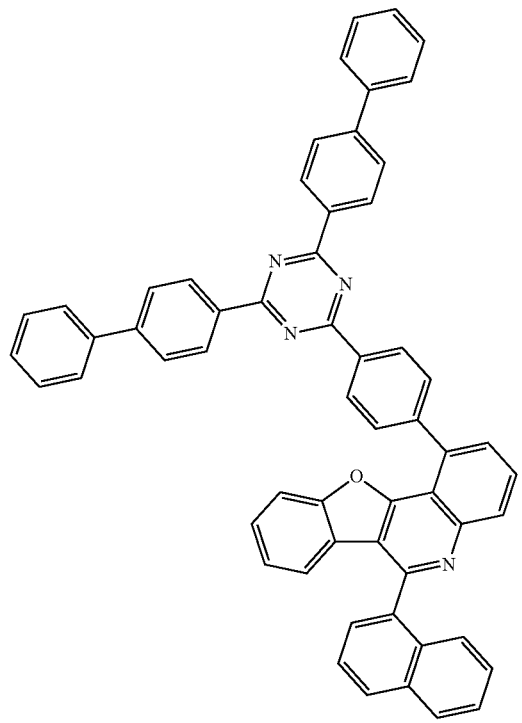
159
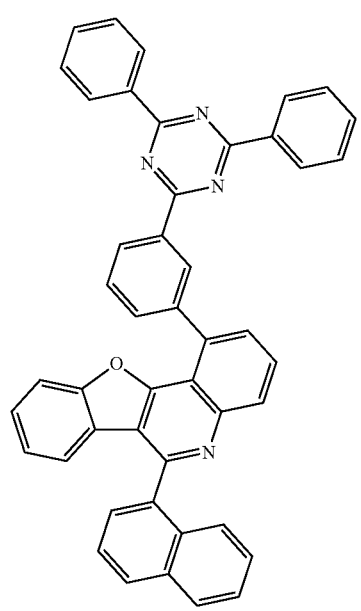
160
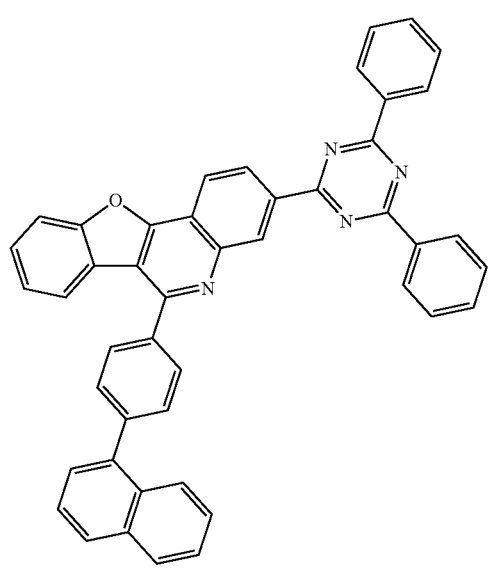

161
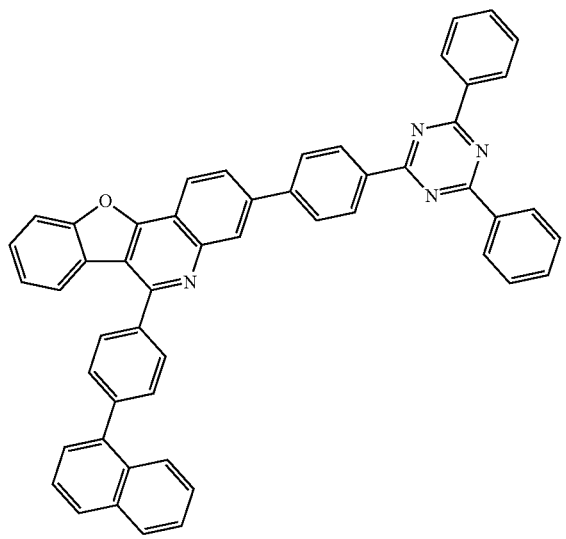
162
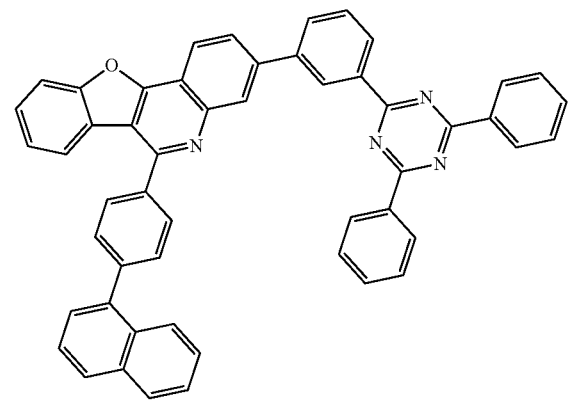
163
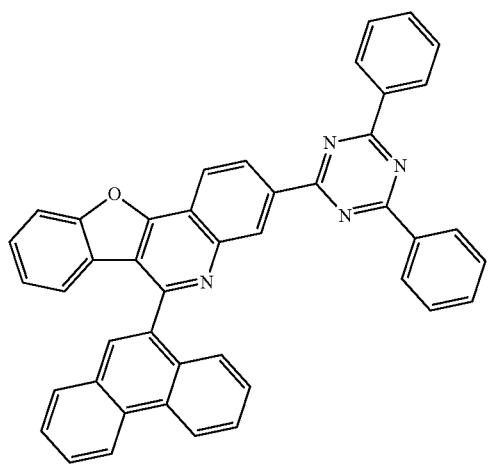
164
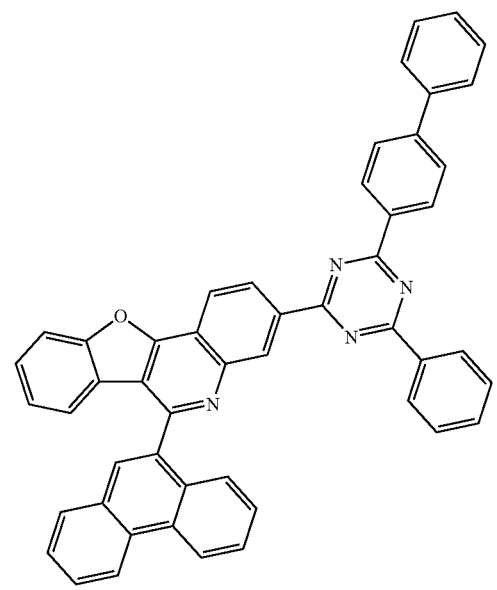
165
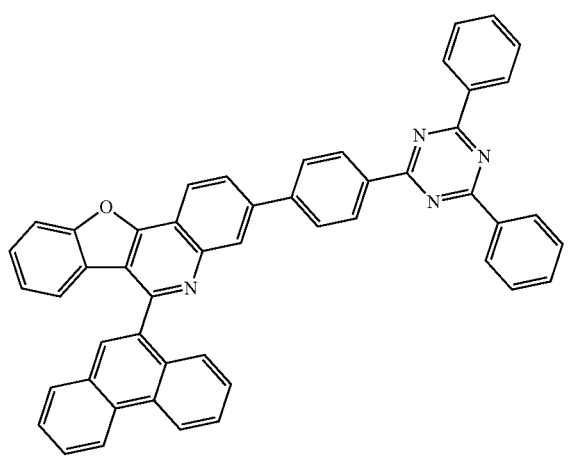
166
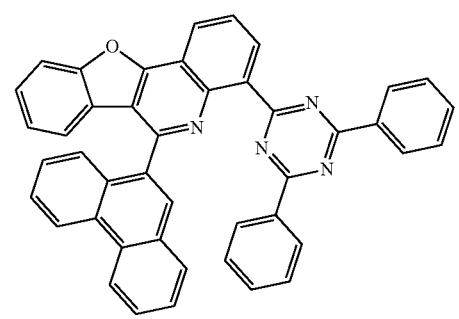

-continued
167
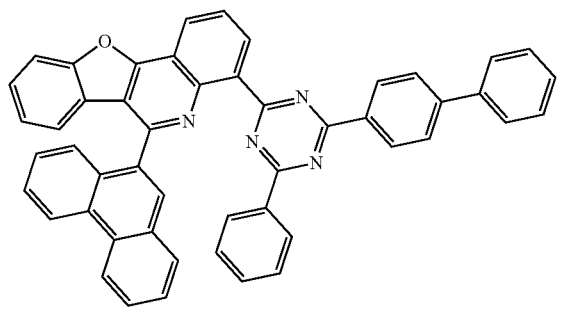
168
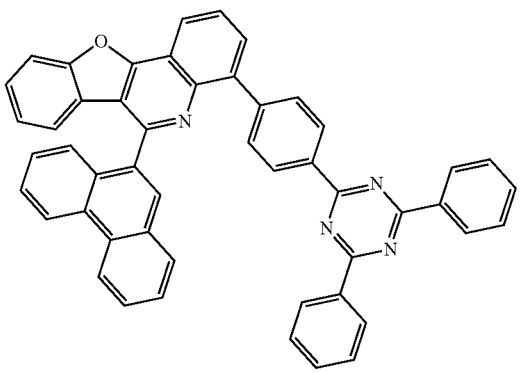
169
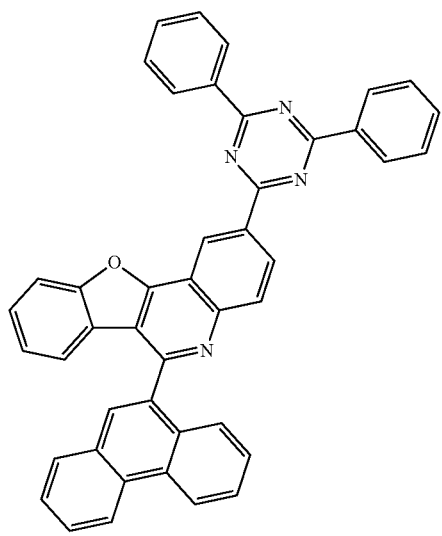
170
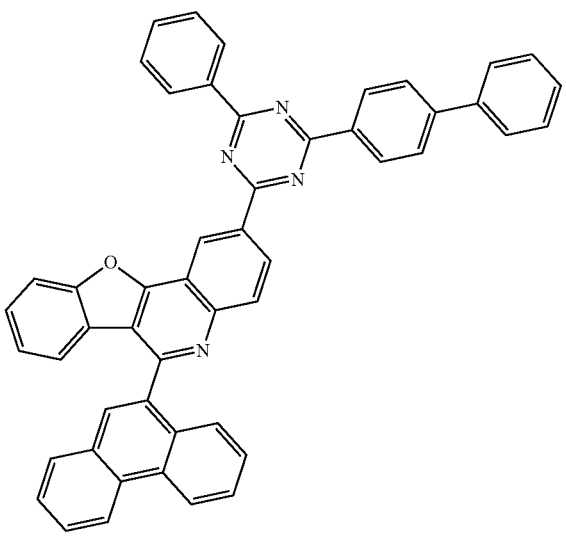
171
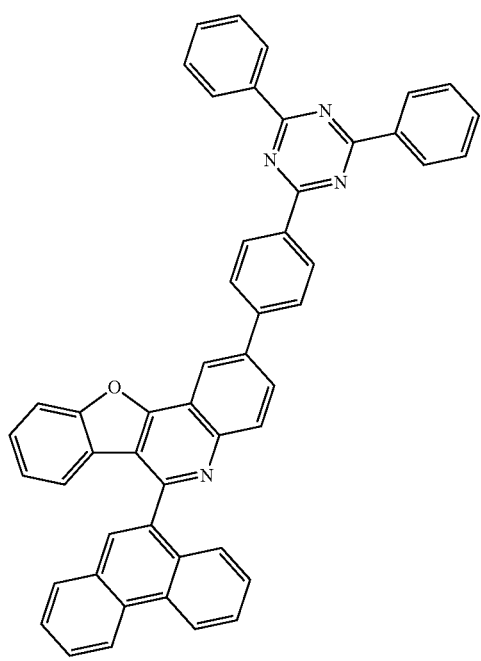
172
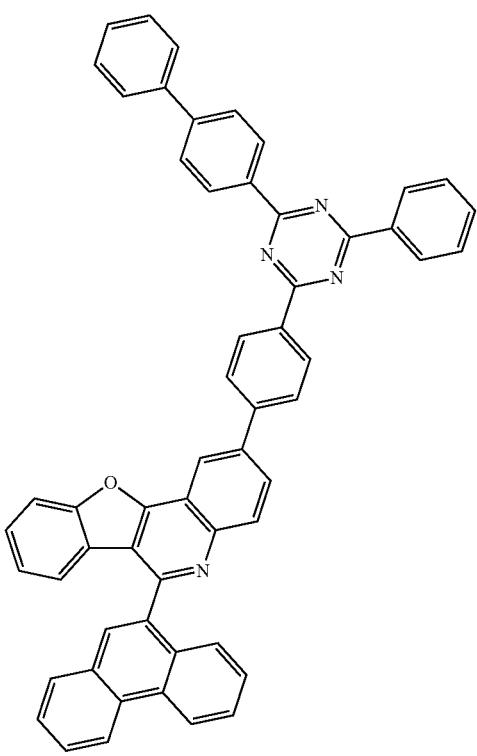

173
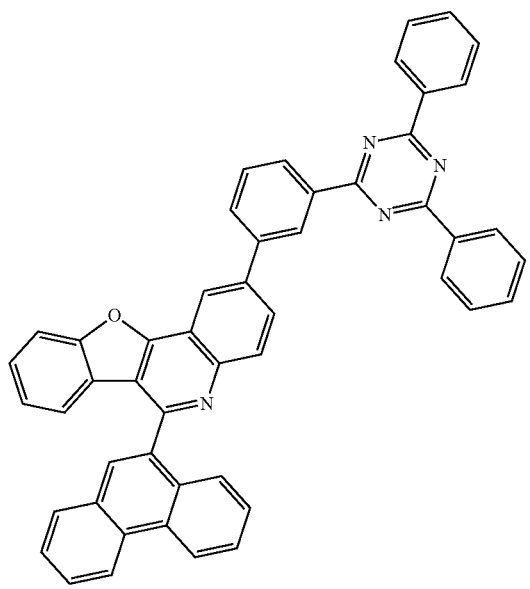
174
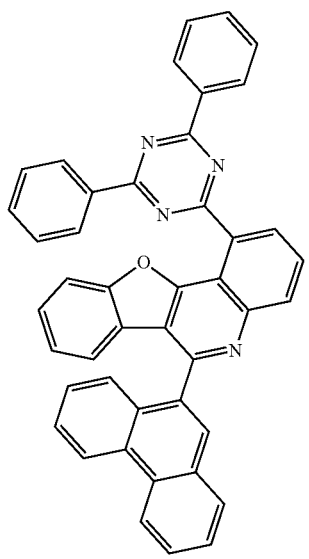
175
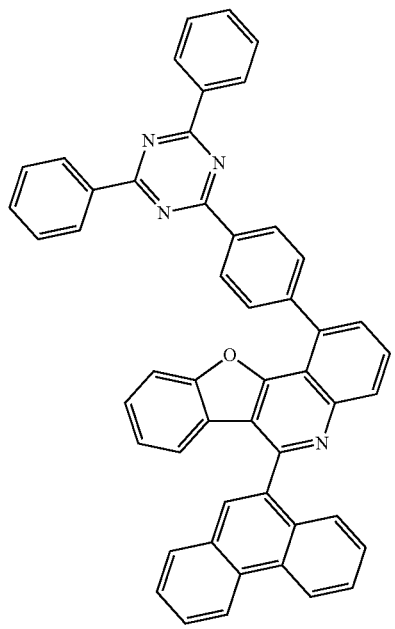
176
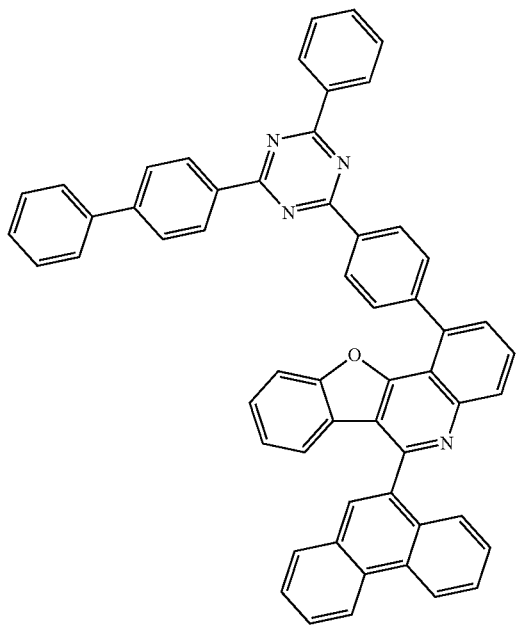

177
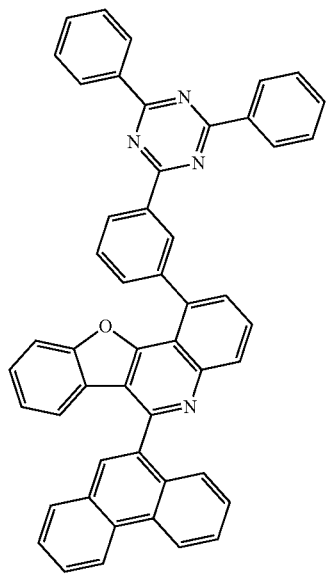
178
179
180
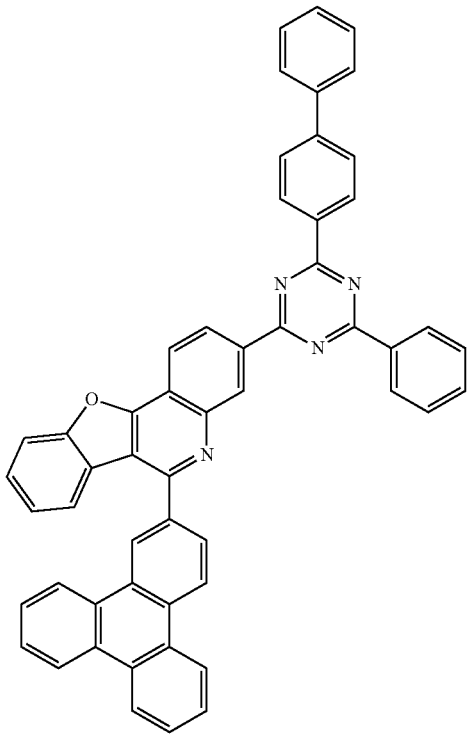

181
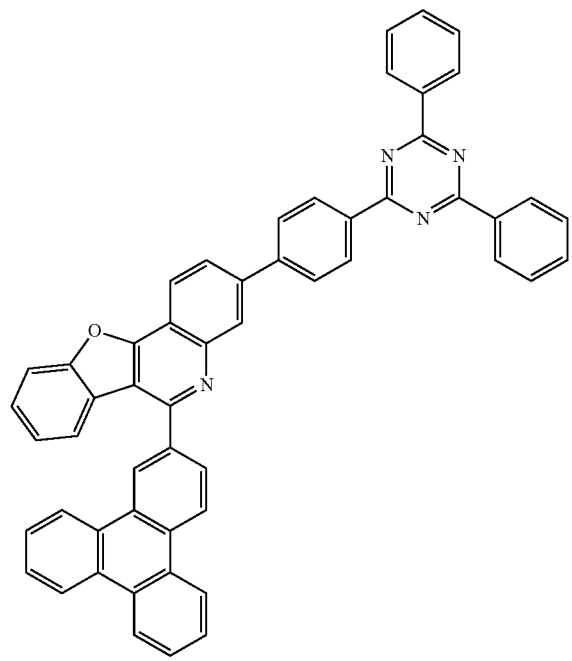
182
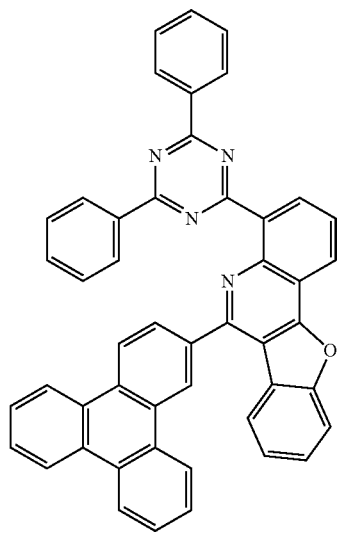
183
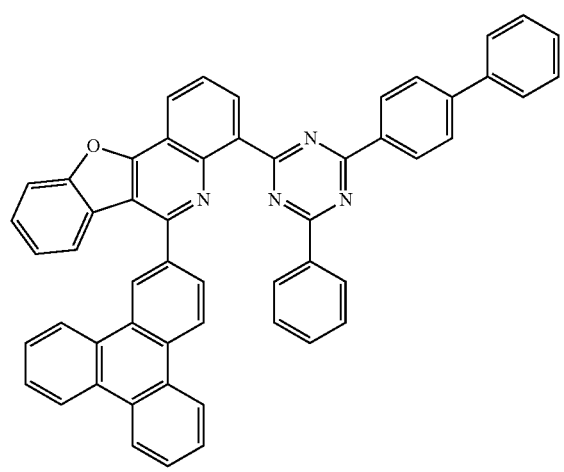
184
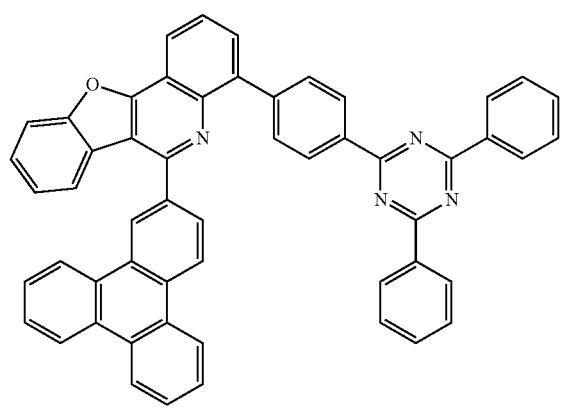

-continued
185
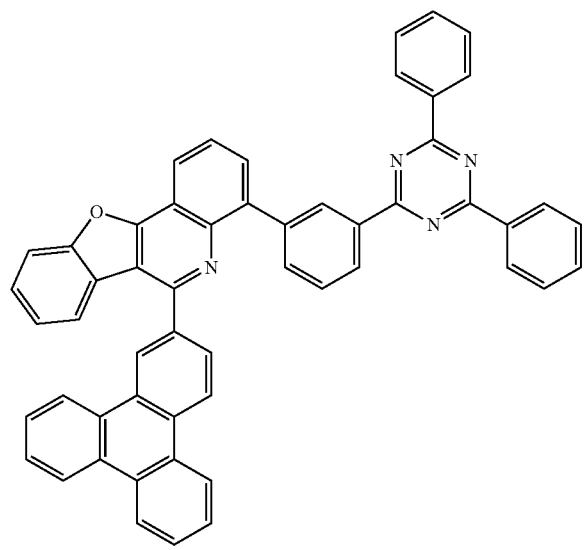
186
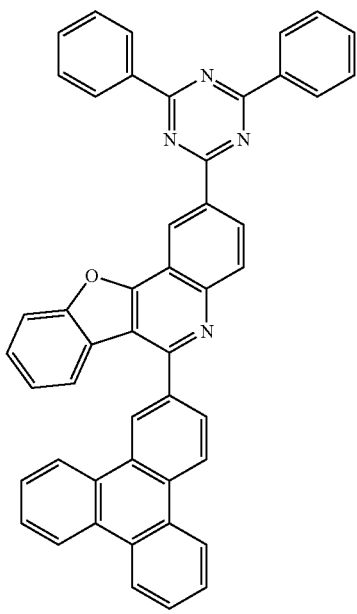
187
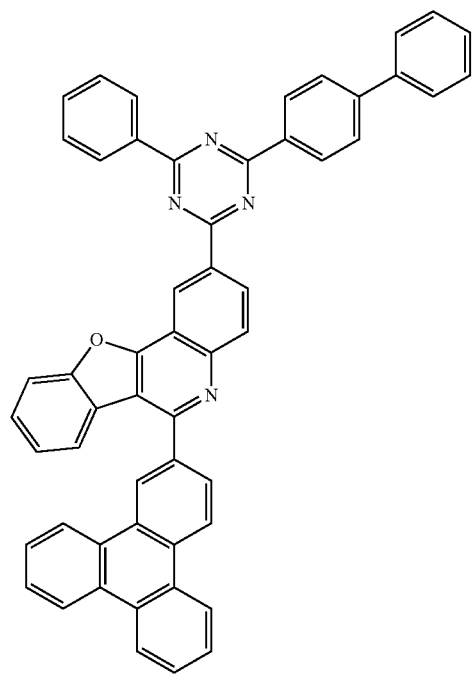
188
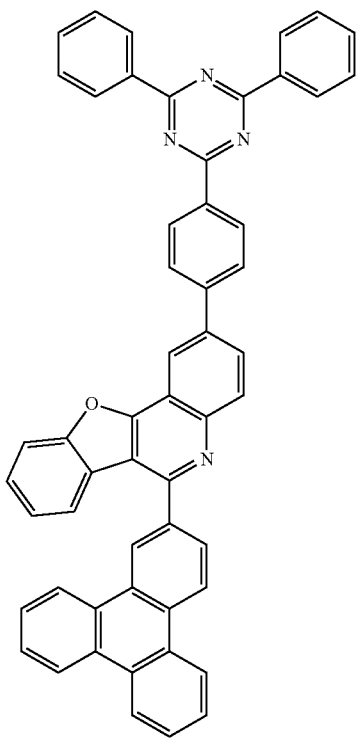

189
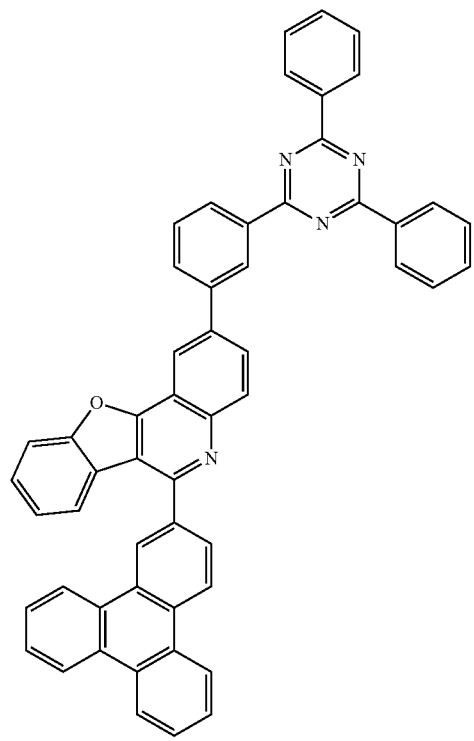
190
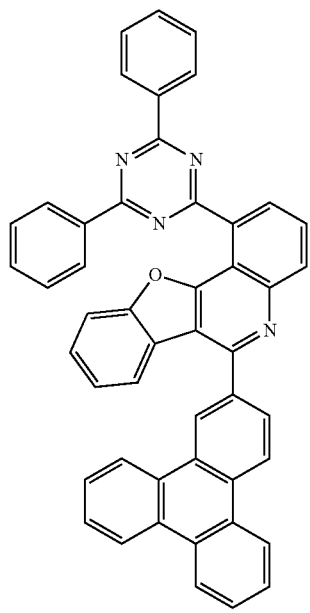
191
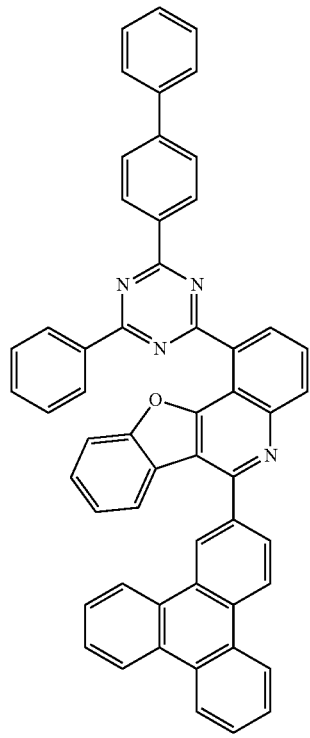
192
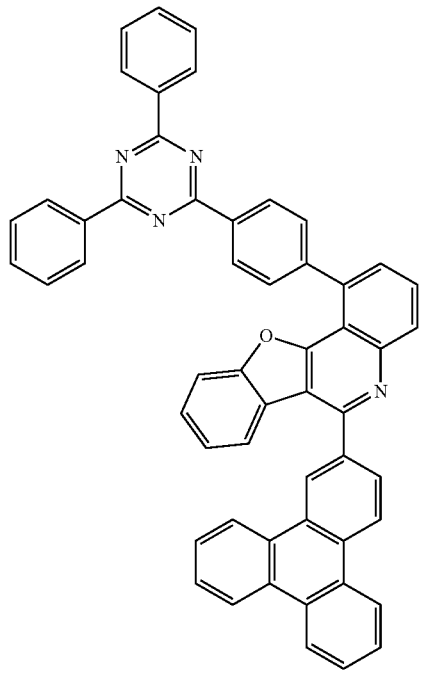

-continued
193
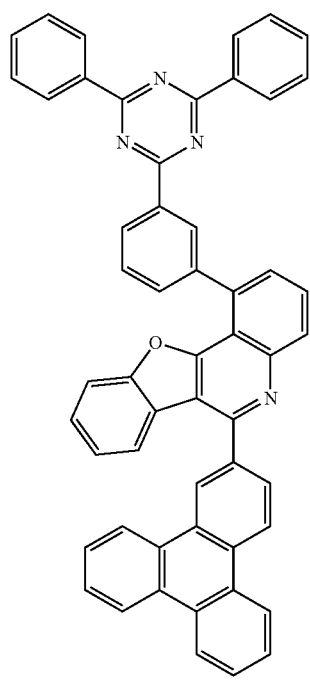
194
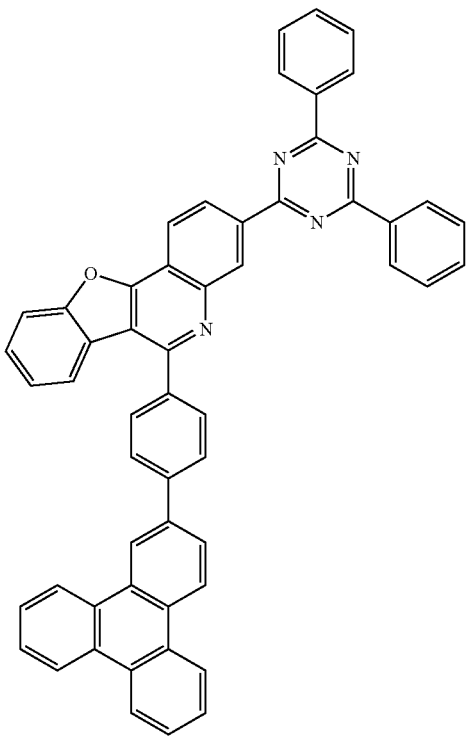
195
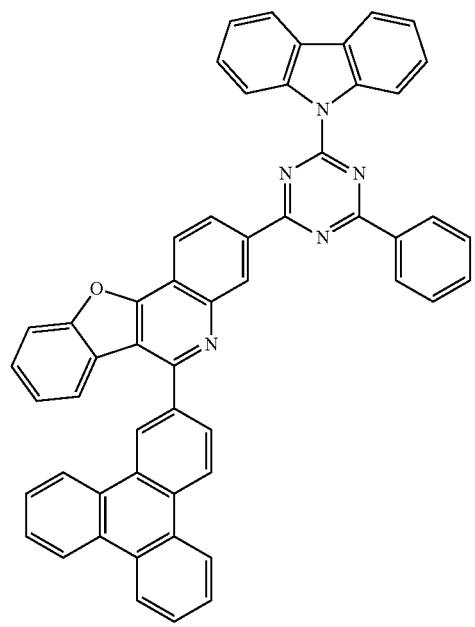
196
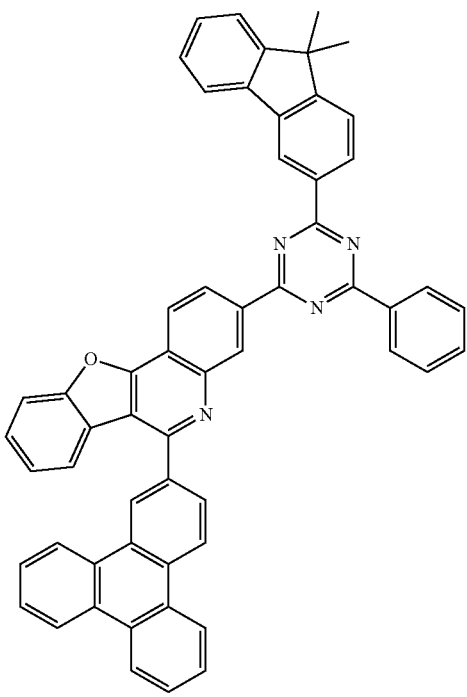

-continued
197
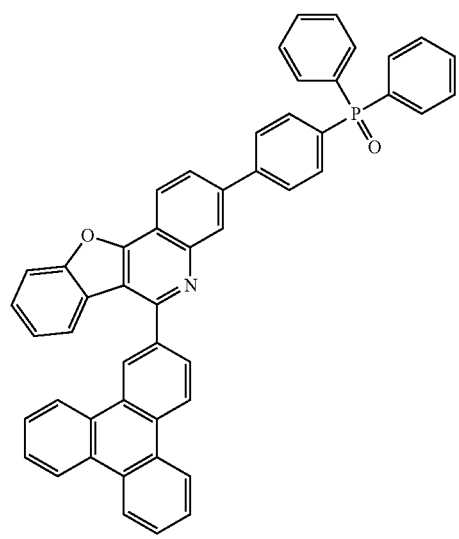
198
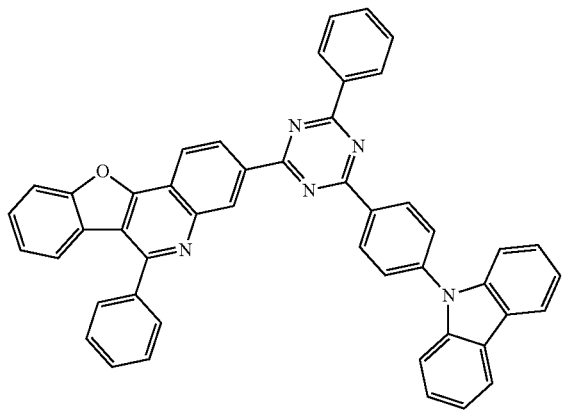
199
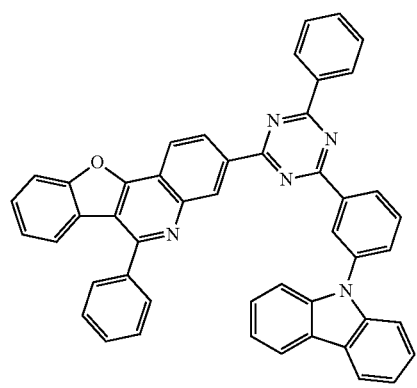
200
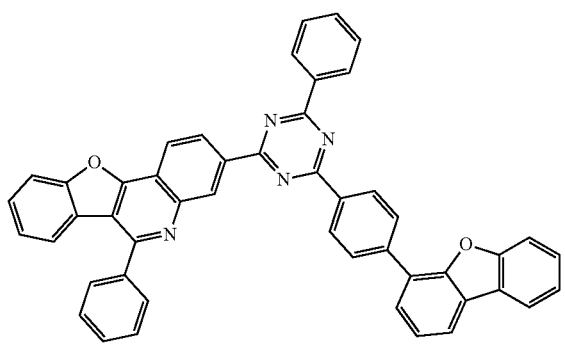
201
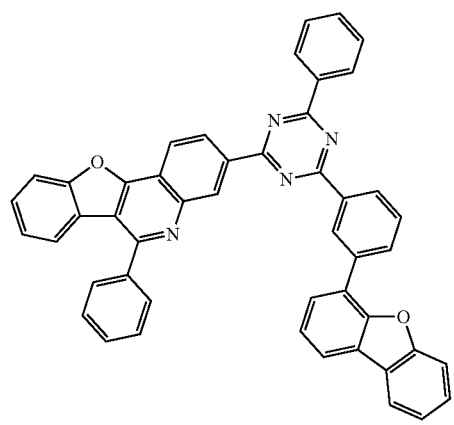
202
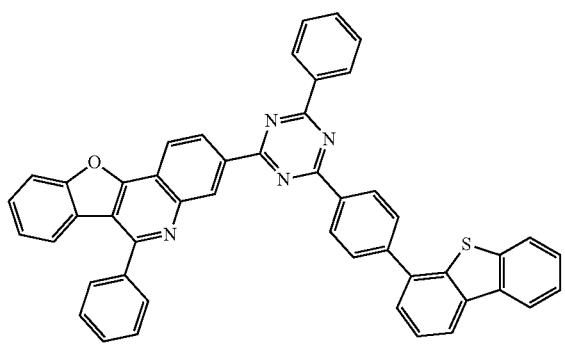

-continued
203
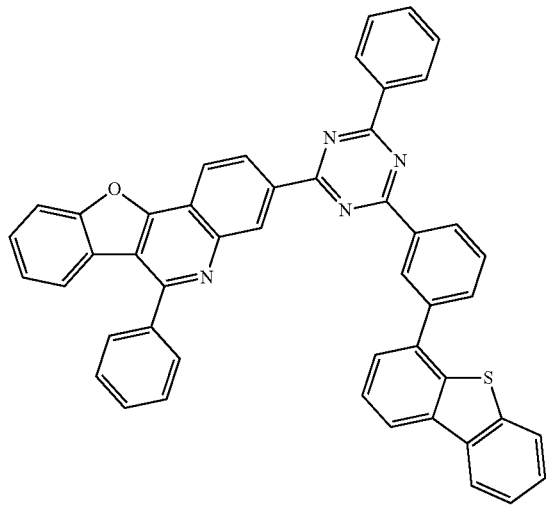
204
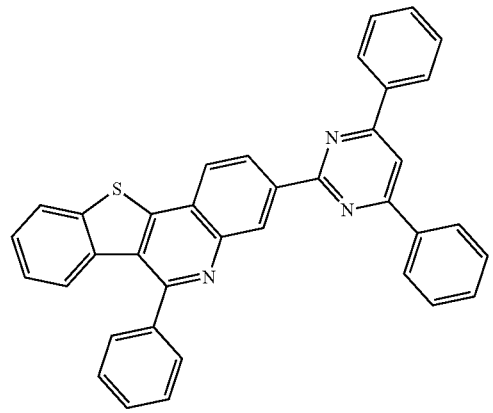
205
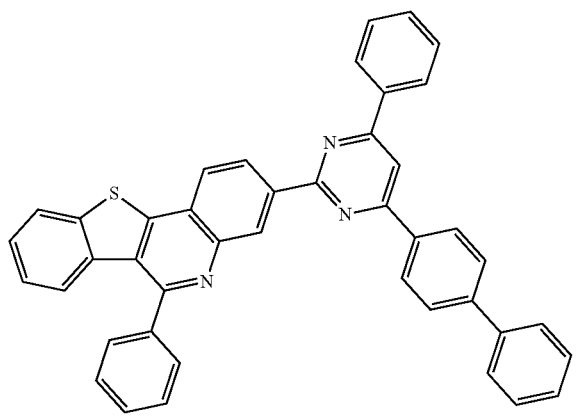
206
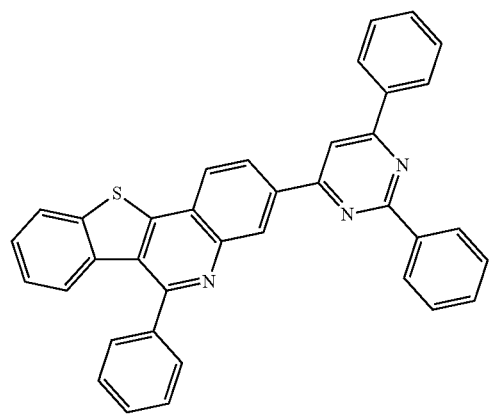
207
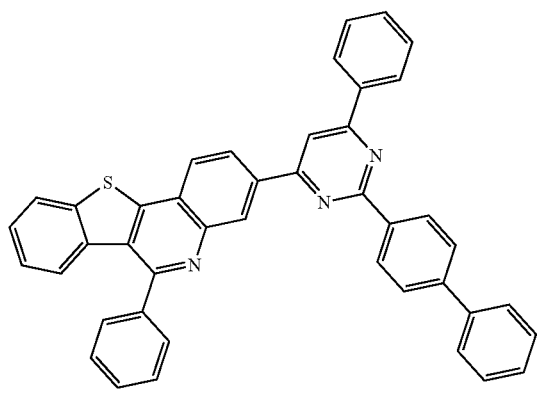
208
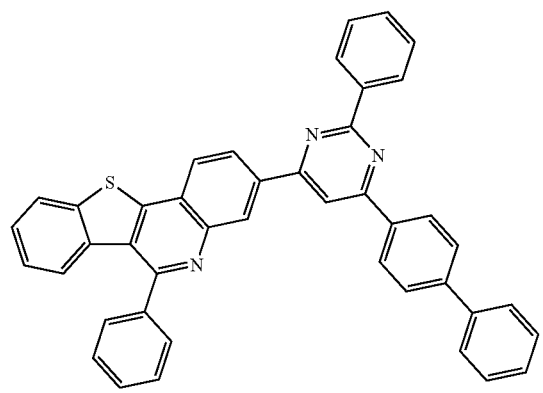

209
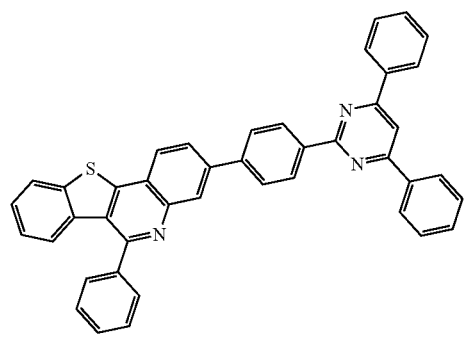
210
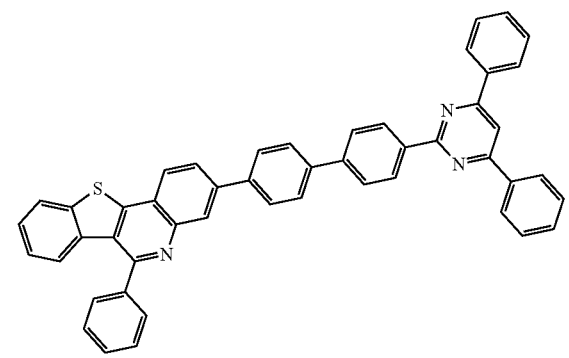
211
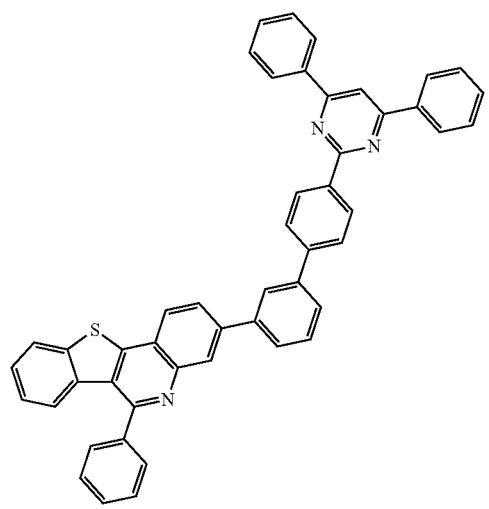
212
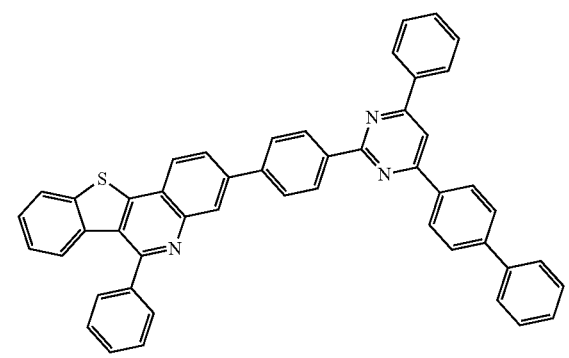
213
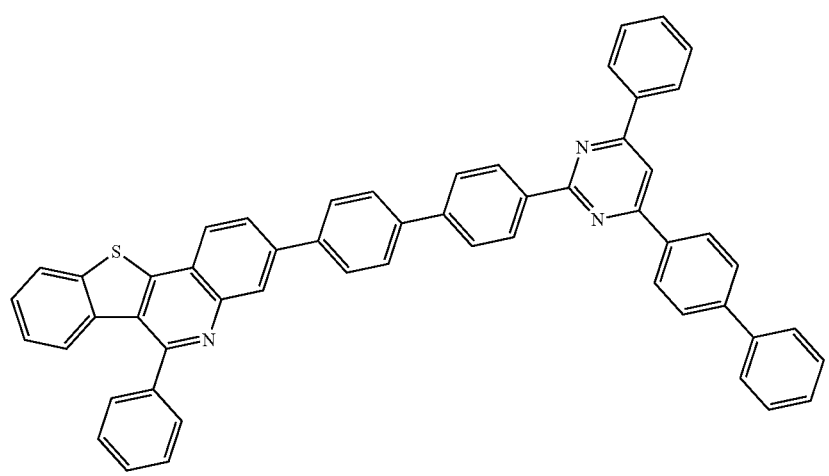

-continued
214
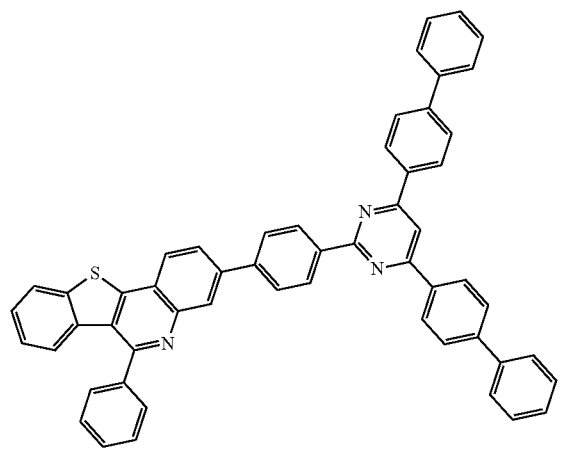
215
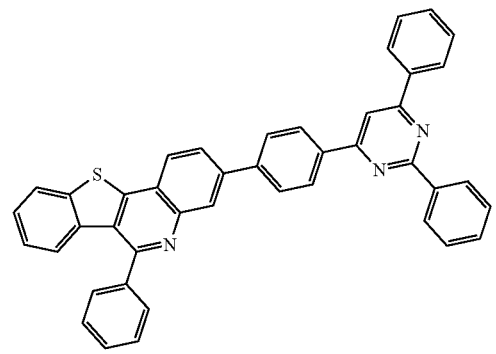
216
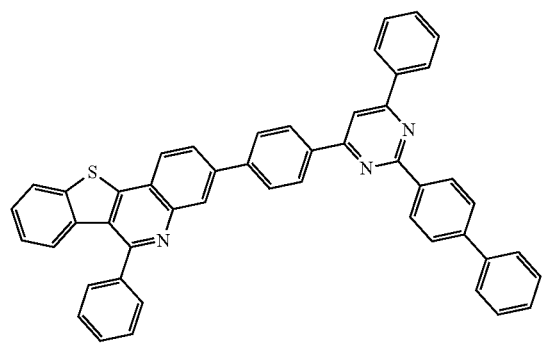
217
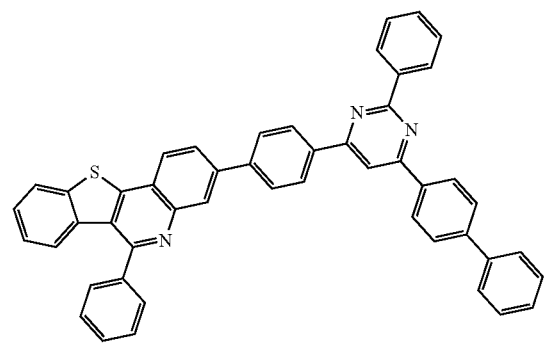
218
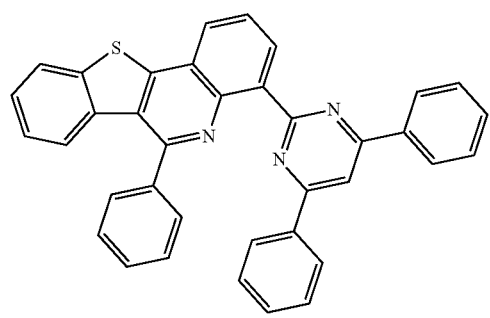
219
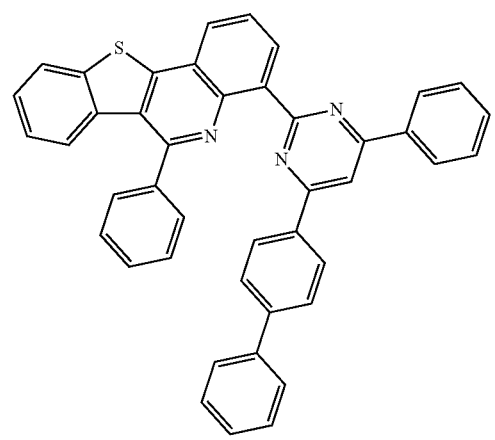

-continued
220
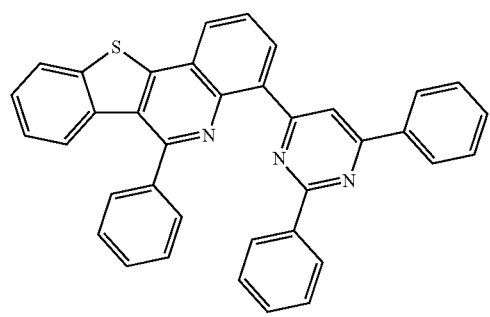
221
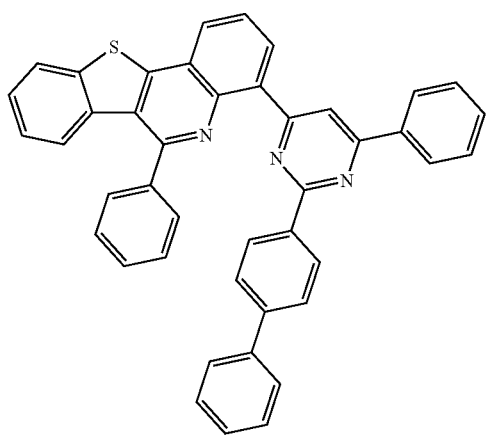
222
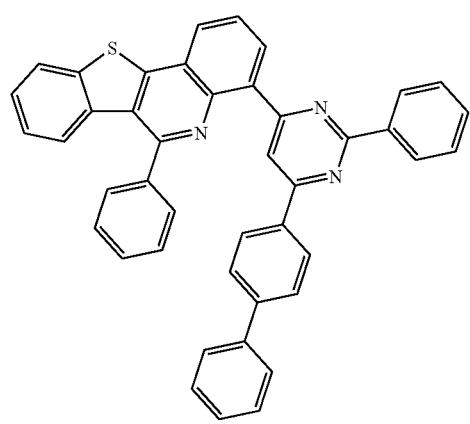
223
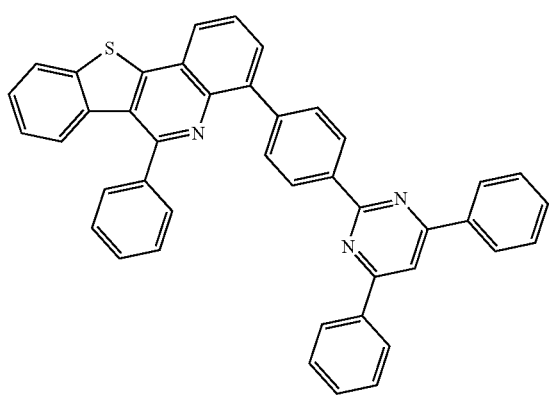
224
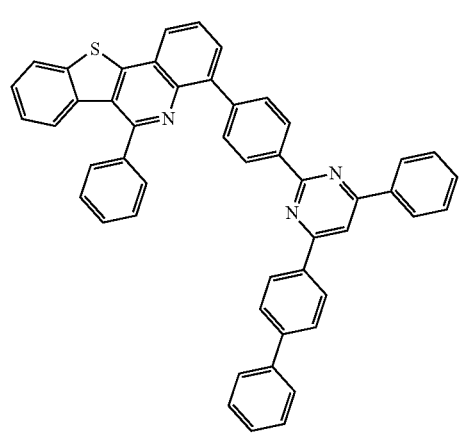
225
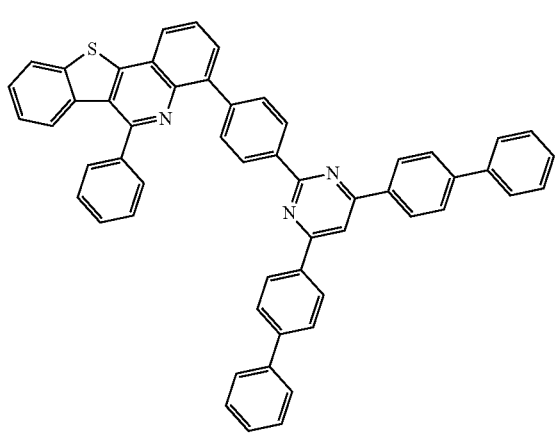

226
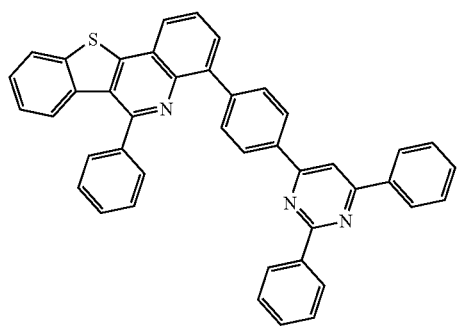
227
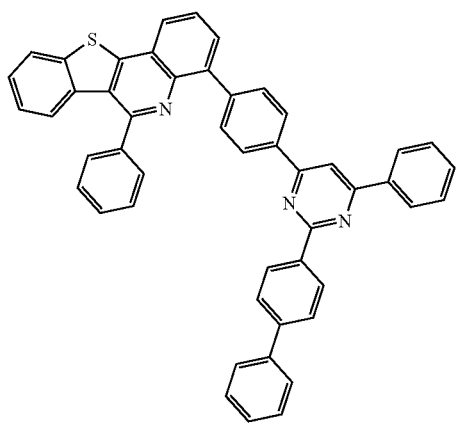
228
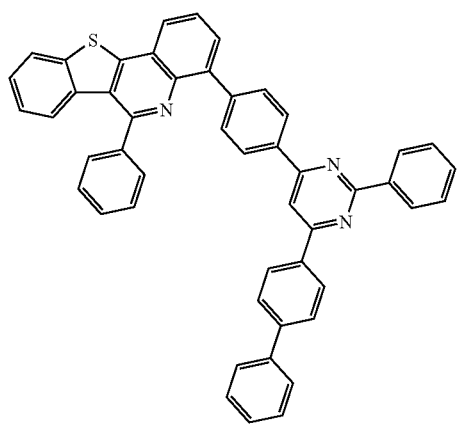
229
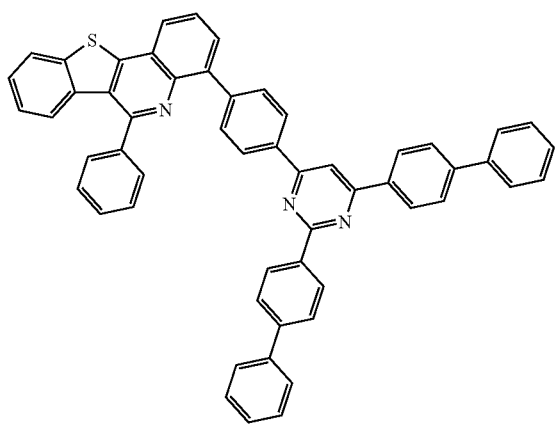
230
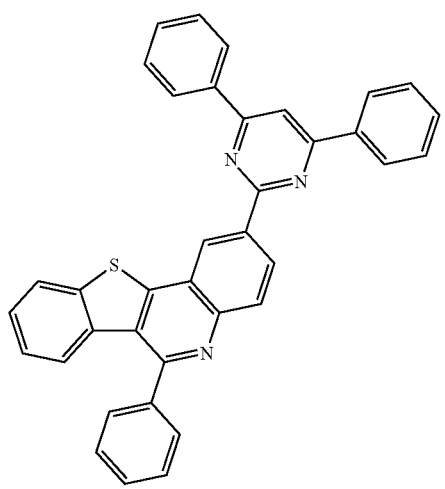
231
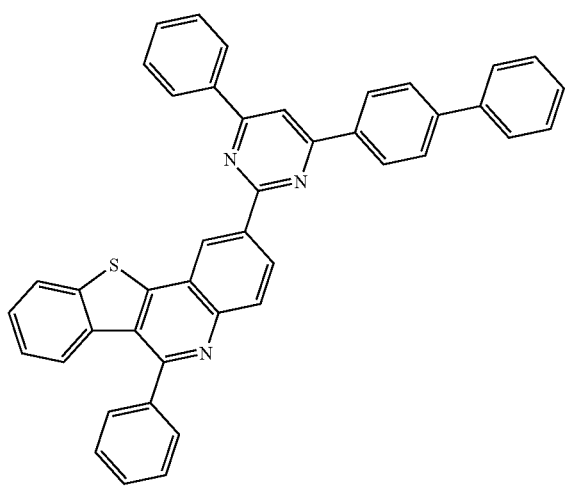

232
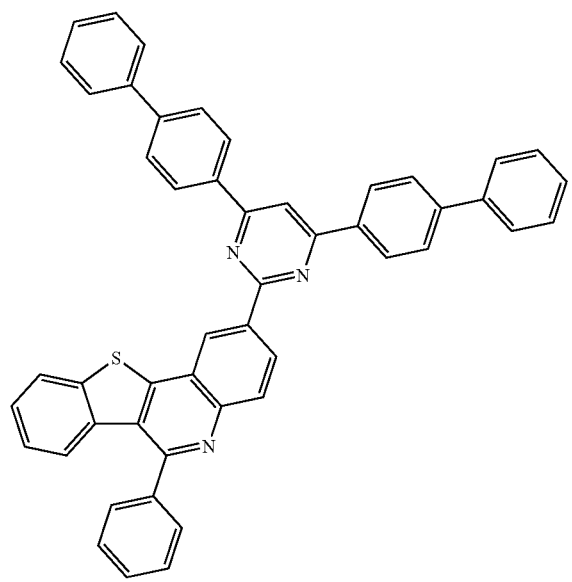
233
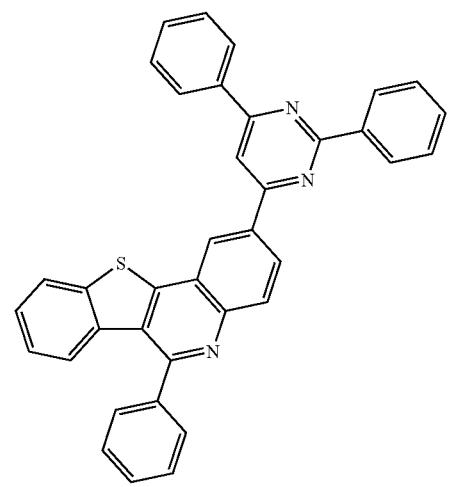
234
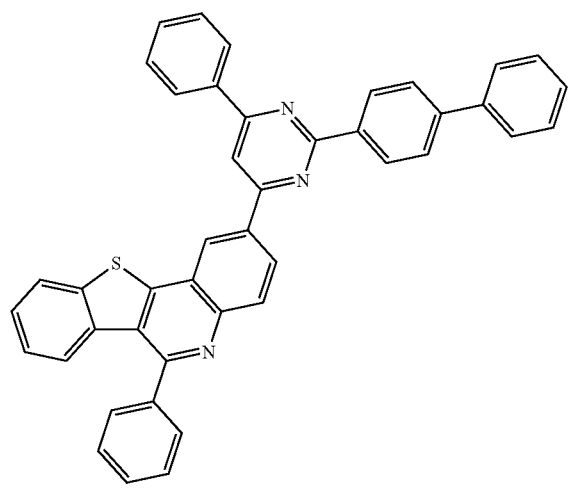
235
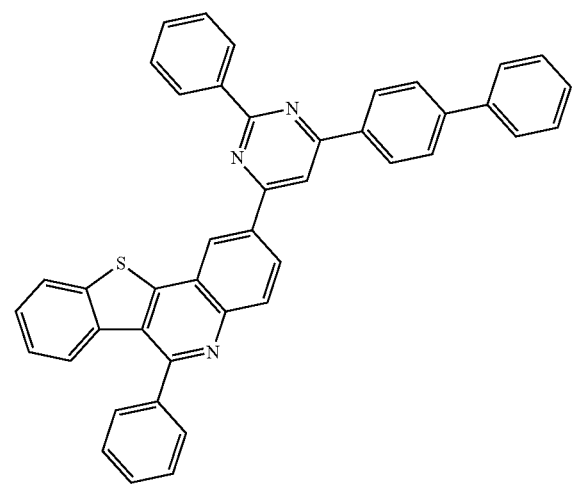 [SMILES: c1ccc(-c2ccc(-c3cc(-c4ccc5nc(-c6ccccc6)c6c7ccccc7sc6c5c4)nc(-c4ccccc4)n3)cc2)cc1]

-continued
236
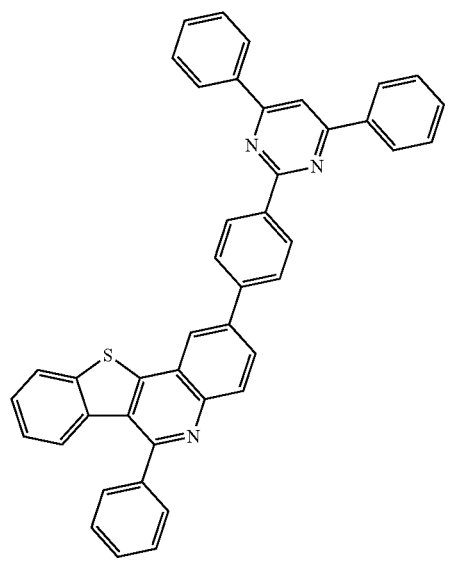
237
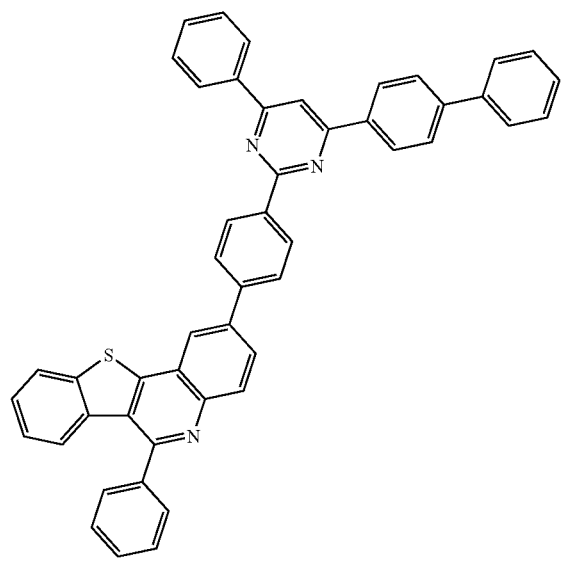
238
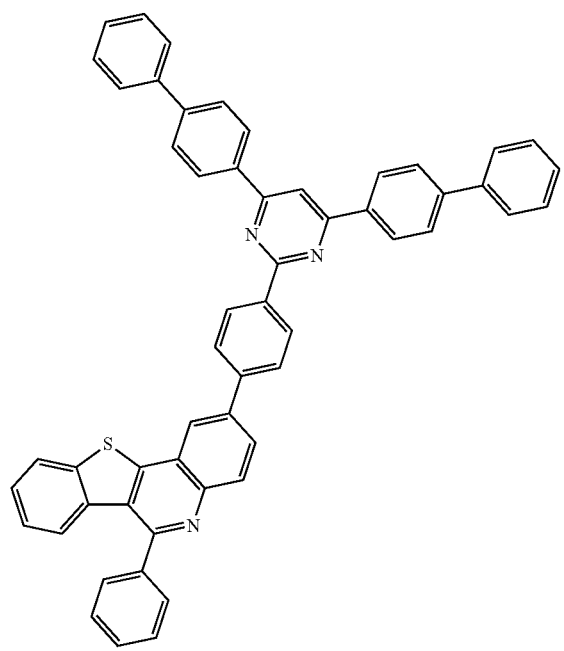 [SMILES: c1ccc(-c2ccc(-c3cc(-c4ccc(-c5ccccc5)cc4)nc(-c4ccc(-c5ccc6nc(-c7ccccc7)c7c8ccccc8sc7c6c5)cc4)n3)cc2)cc1]
239
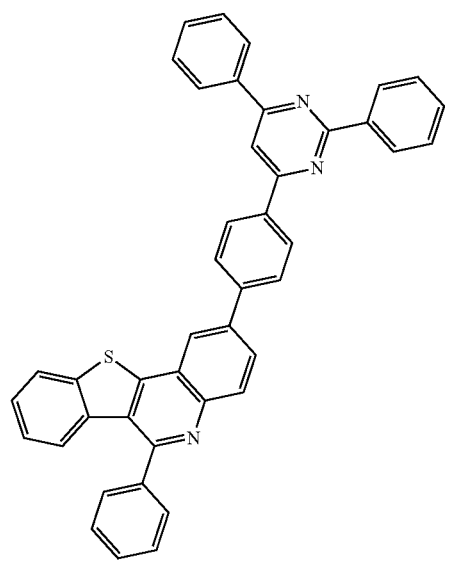

240
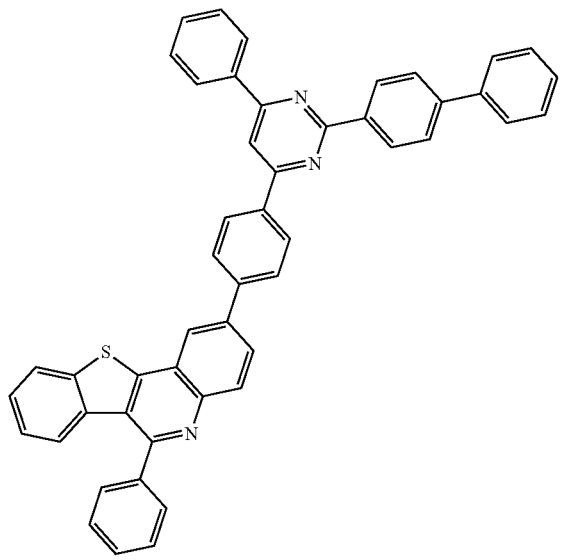
241
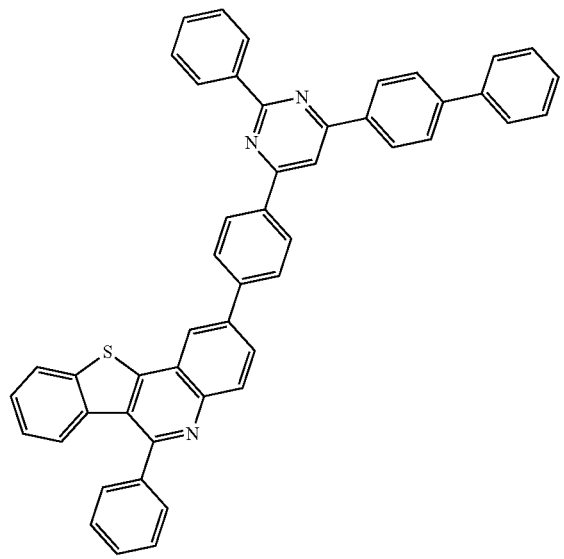
242
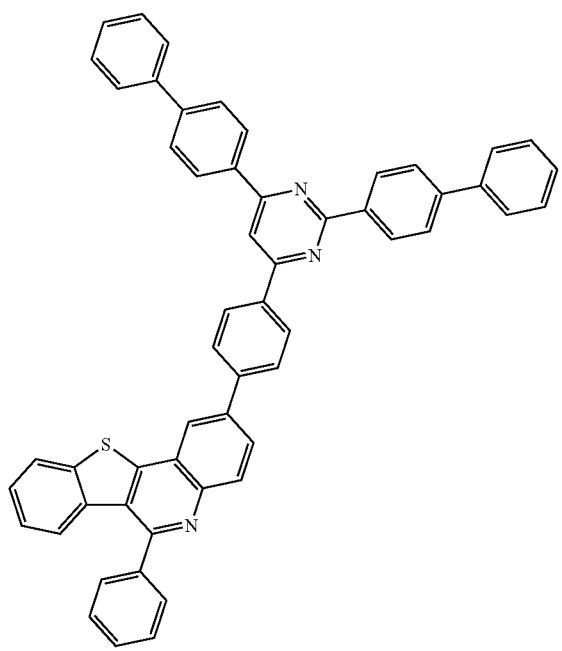
243
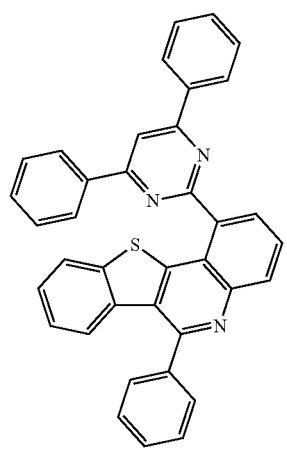

244
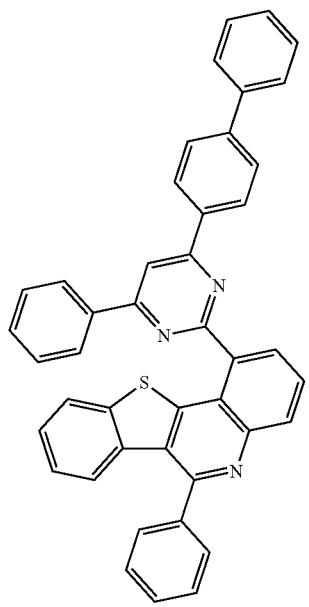
245
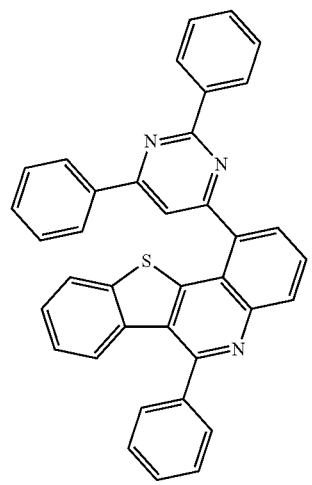
246
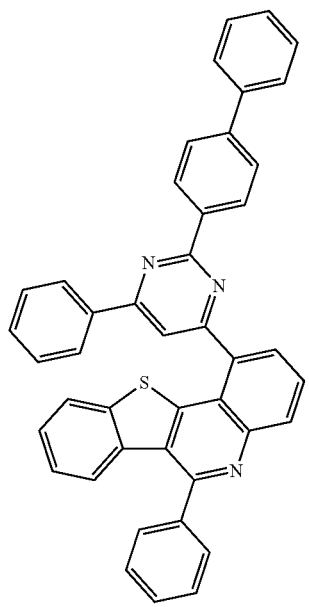
247
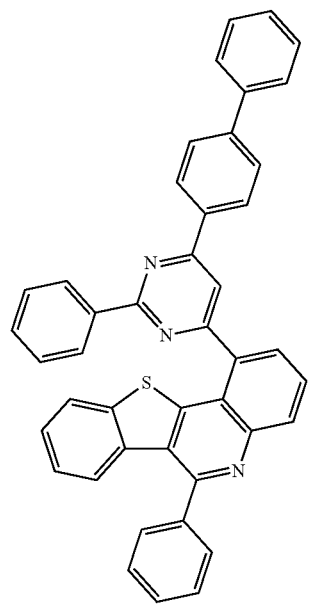

-continued
248
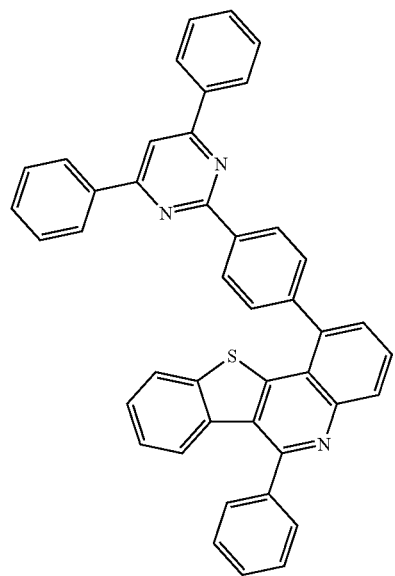
249
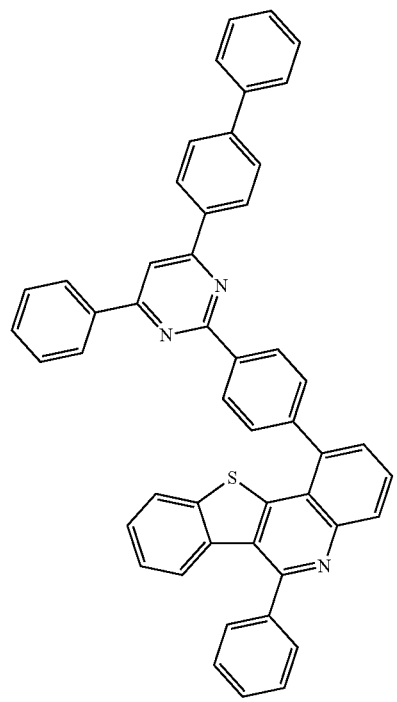
250
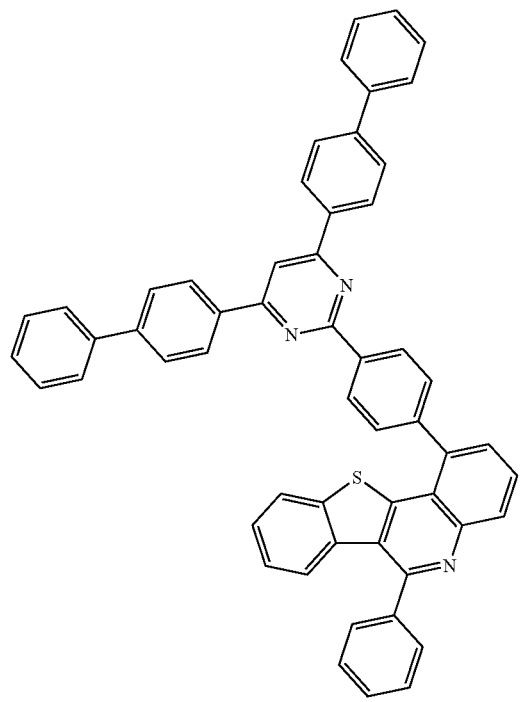
251
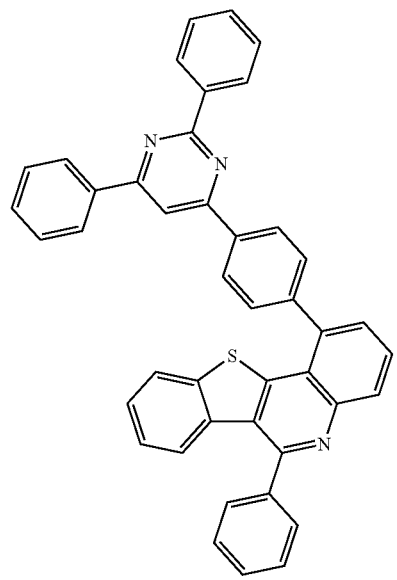 [SMILES: c1ccc(-c2cc(-c3ccccc3)nc(-c3ccc(-c4cccc5nc(-c6ccccc6)c6c7ccccc7sc6c45)cc3)n2)cc1]

-continued
252
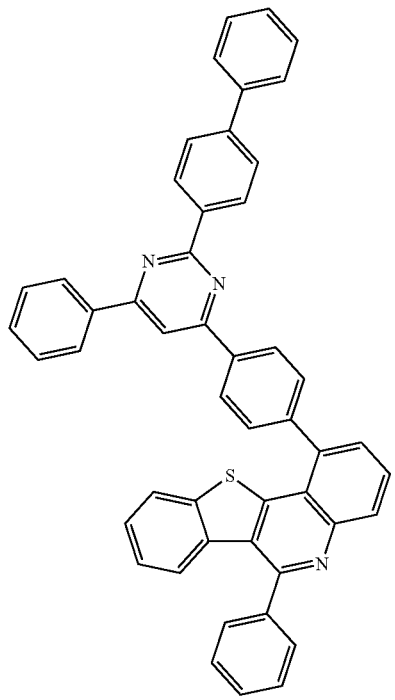
253
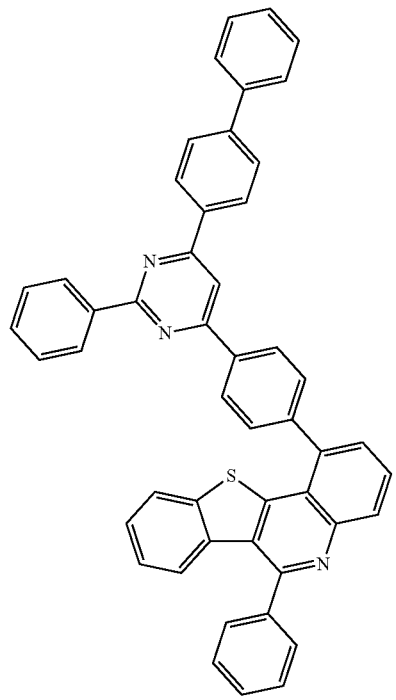
254
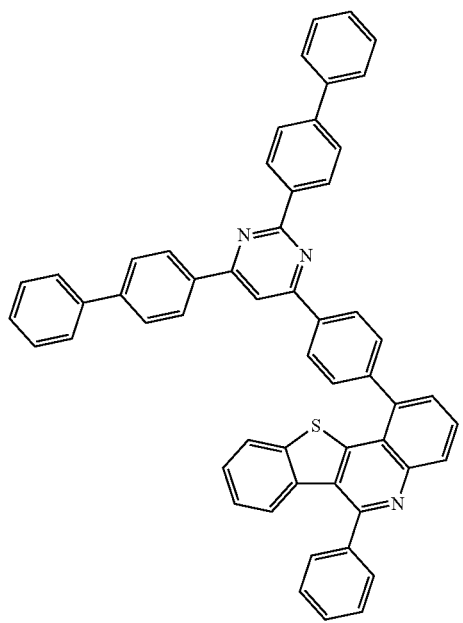
255
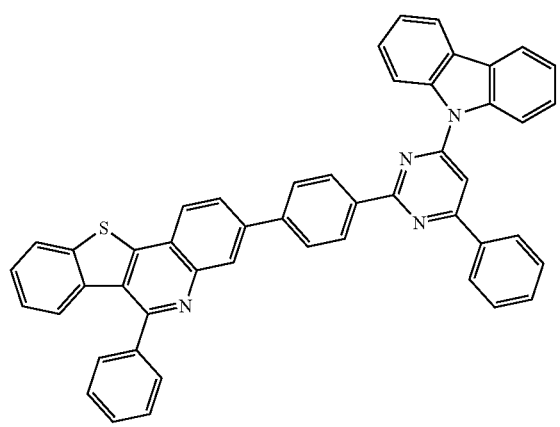

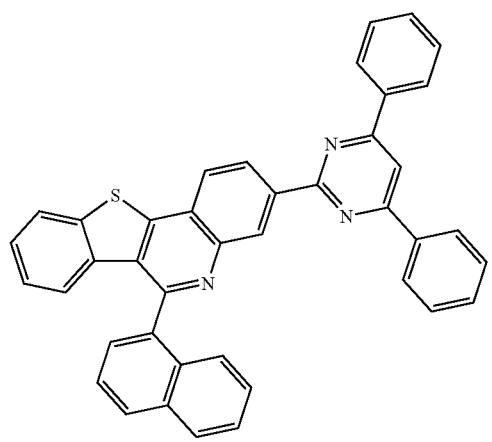
256
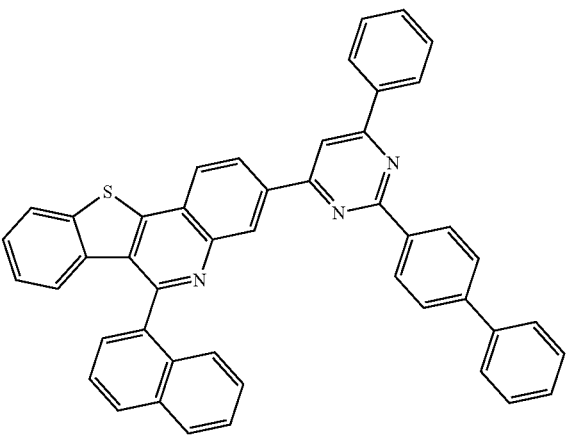
259
257
260
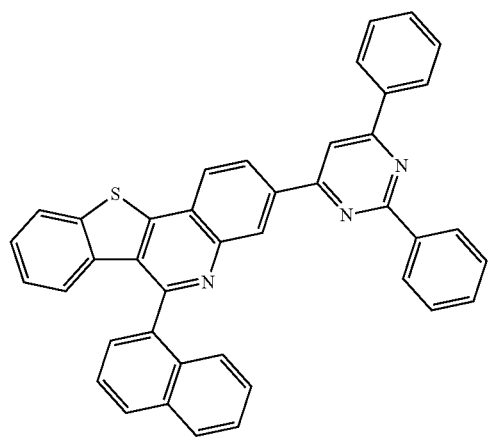
258
261

262
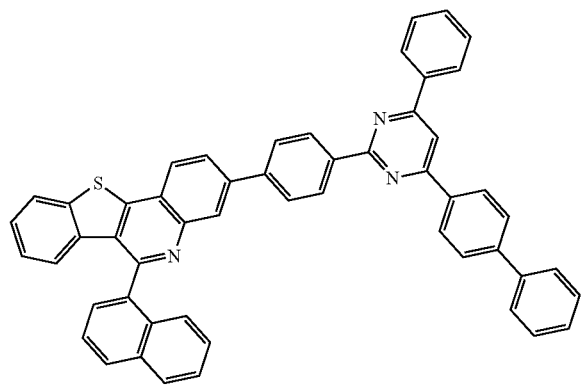
263
265
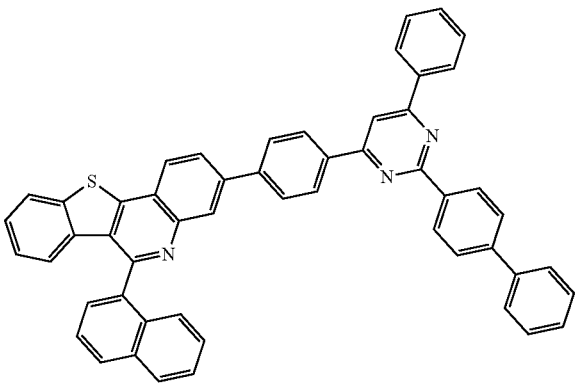
266
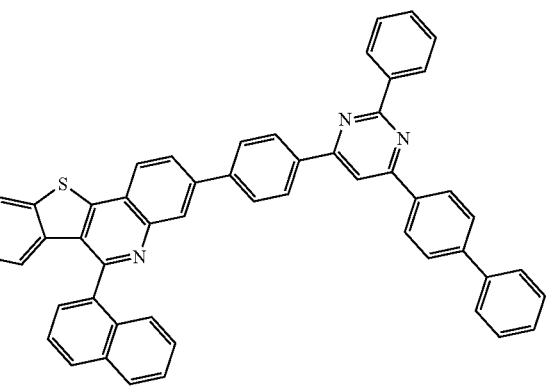
267
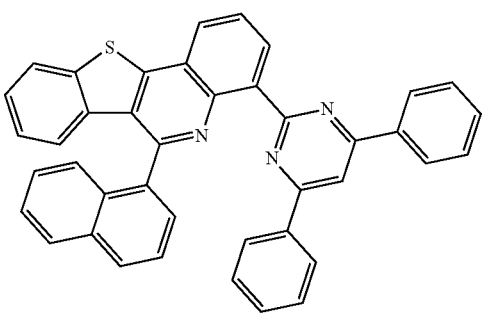
264
268
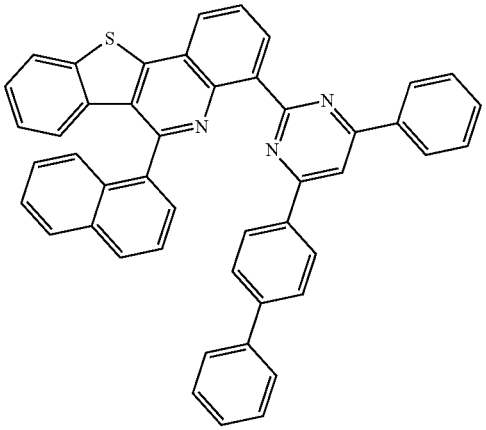

269
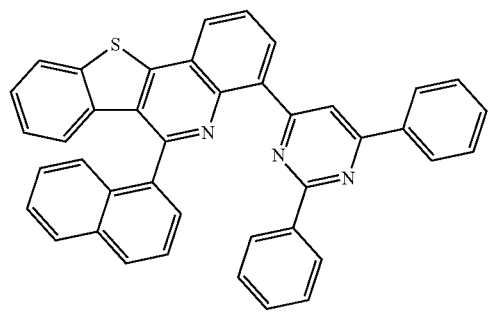
270
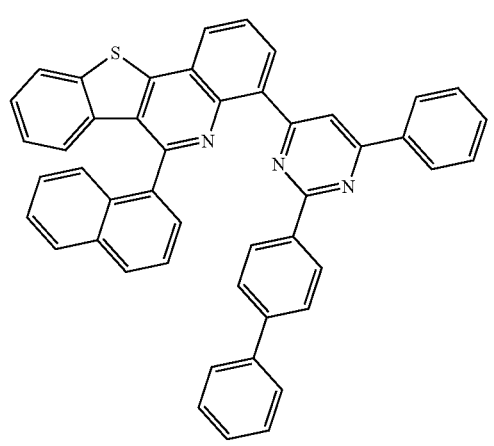
271
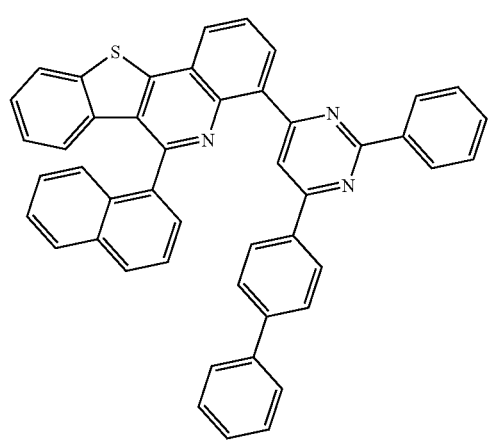
272
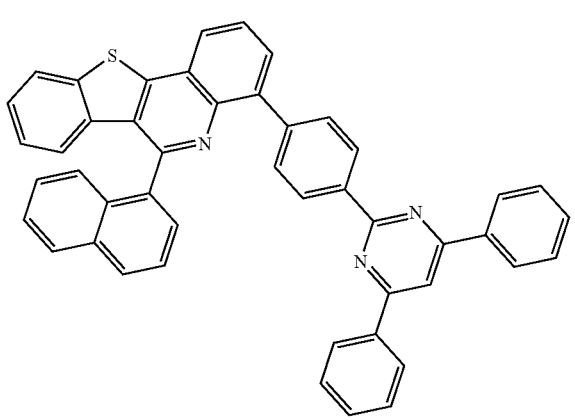
273
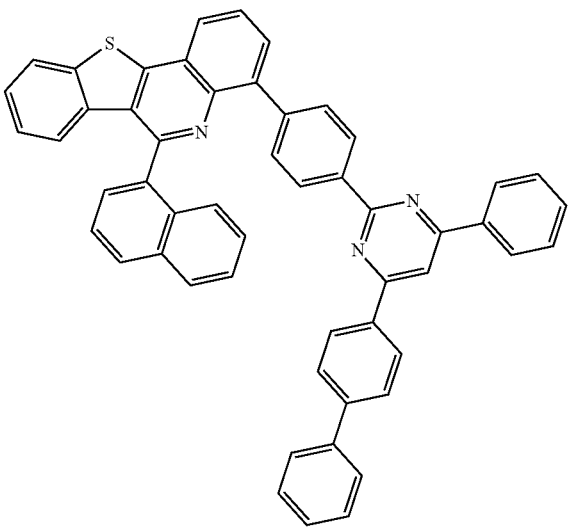
274
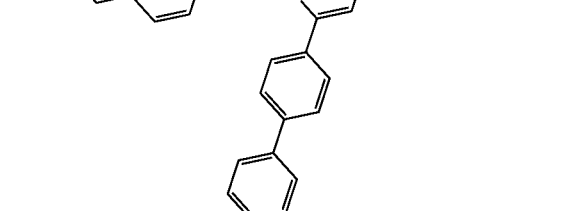
275
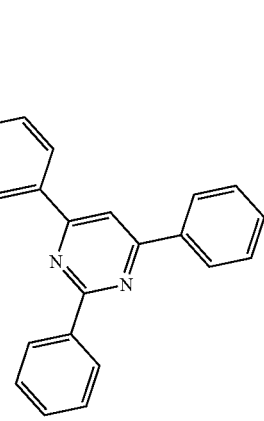

127
-continued
276
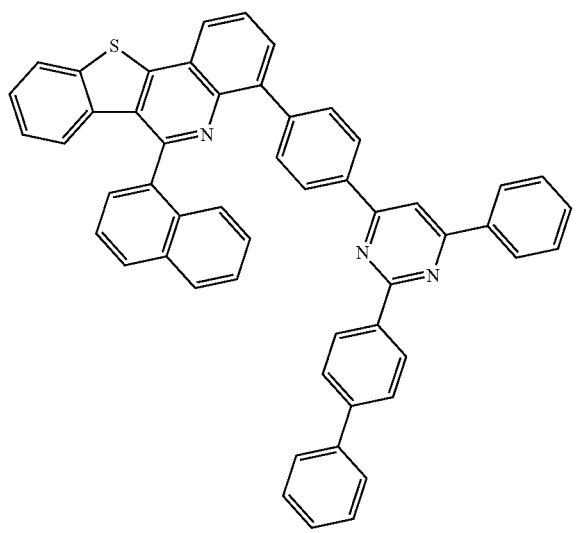
277
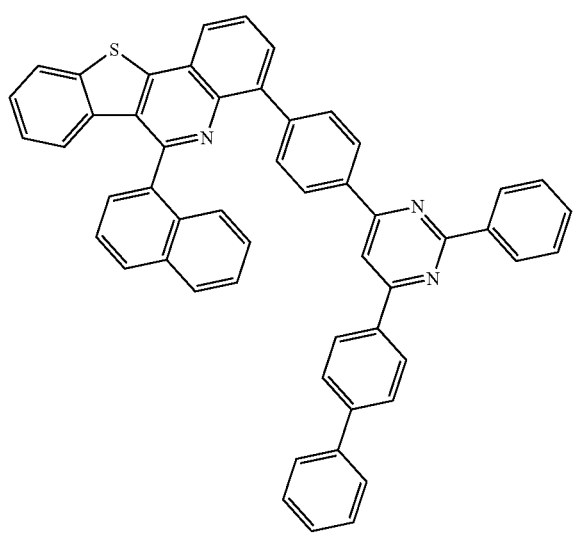
278
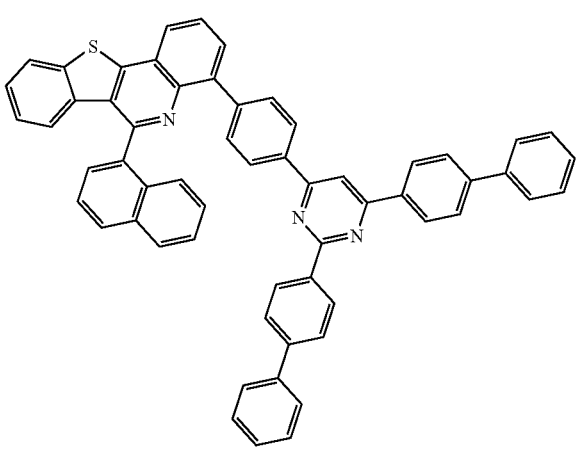
128
-continued
279
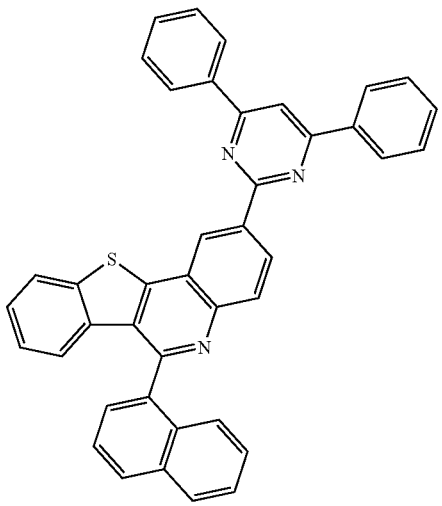
280
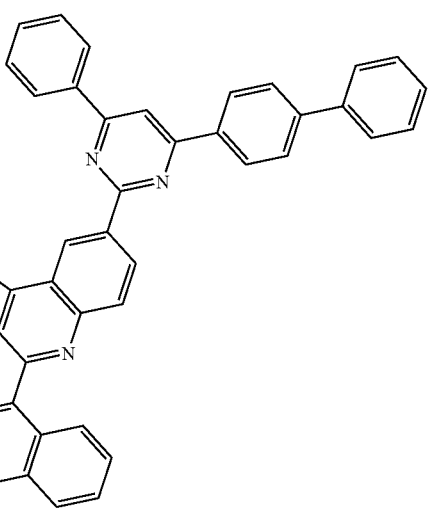
281

282
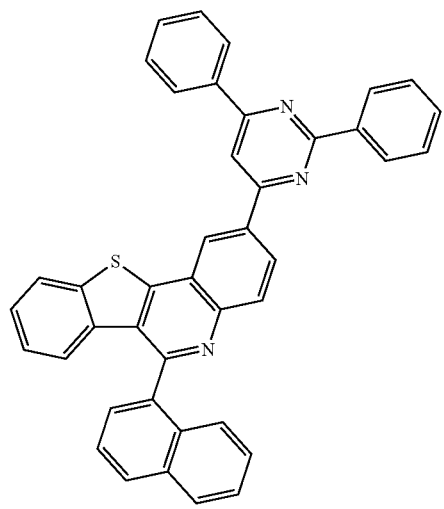
283
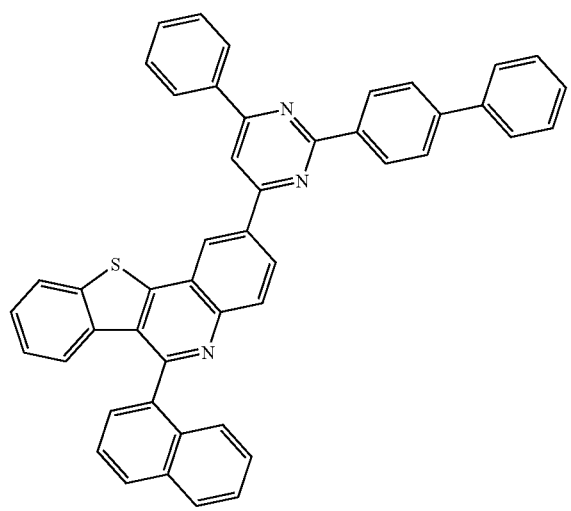
284
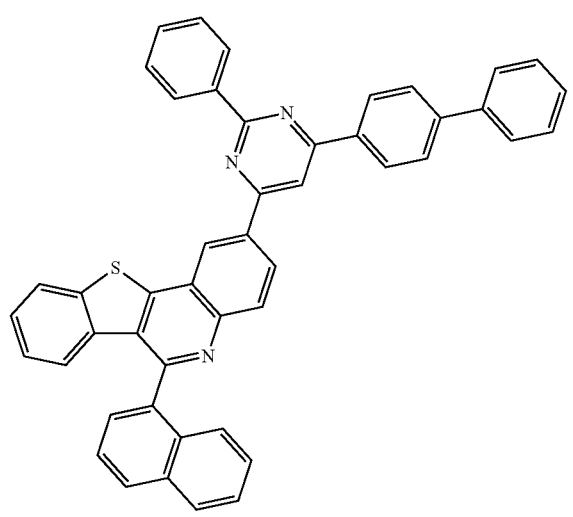
285
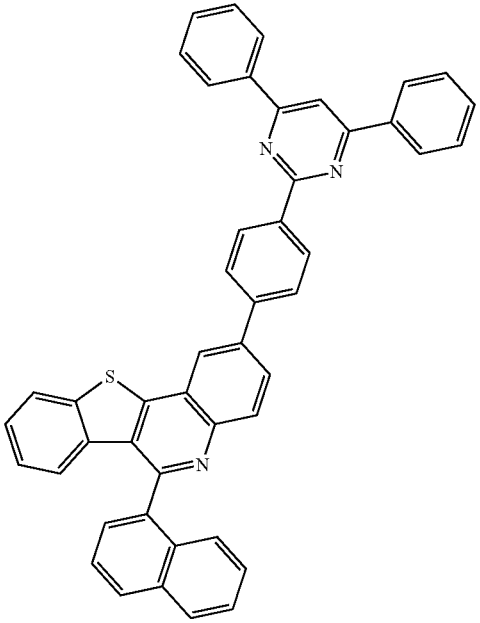
286
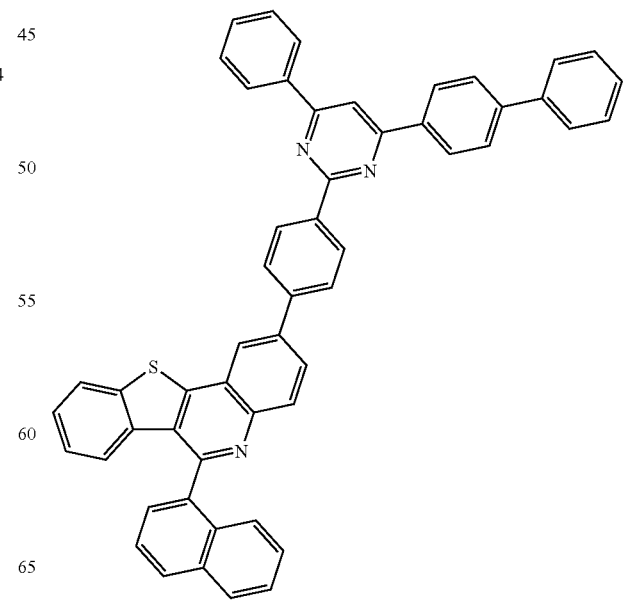

287
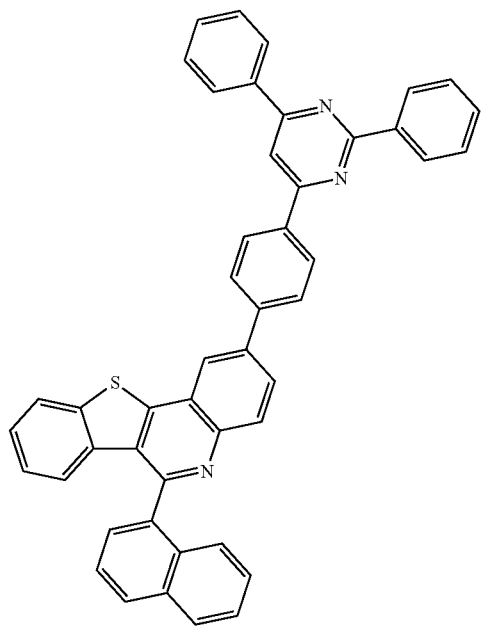
288
289
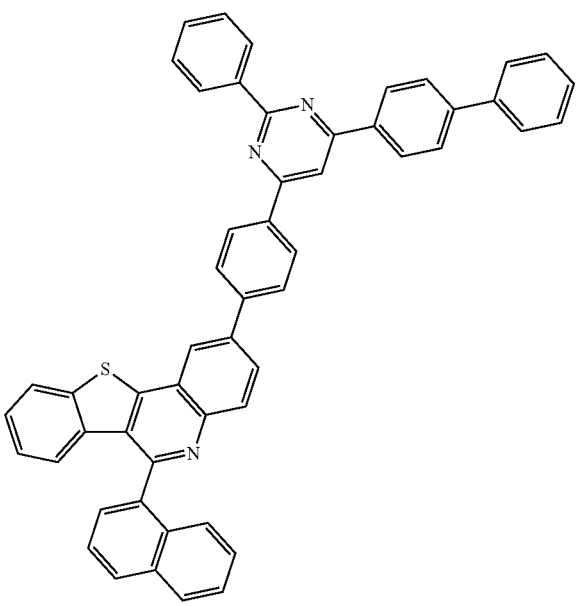
290
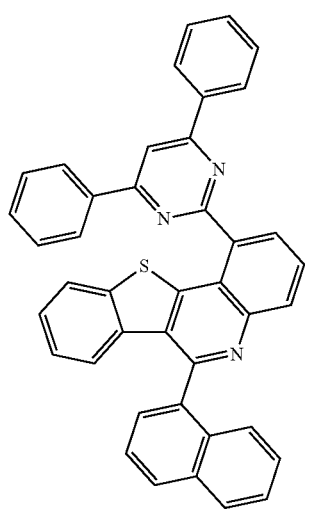

291
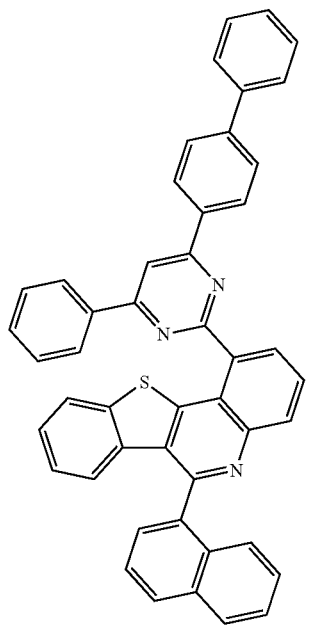
292
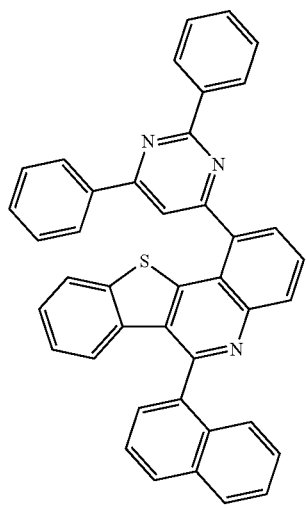
293
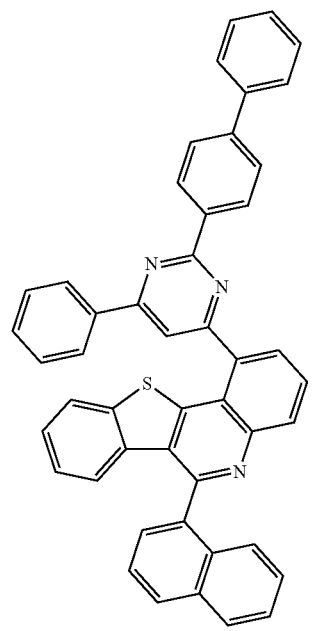
294
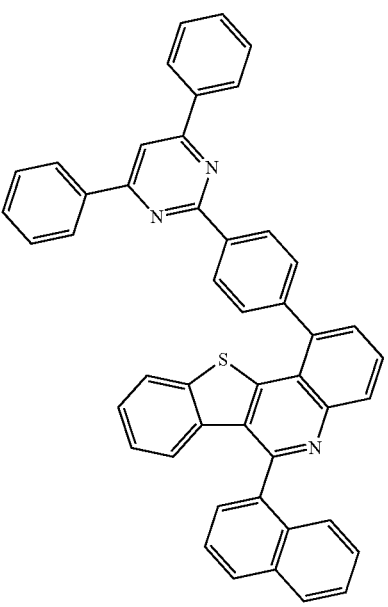

295
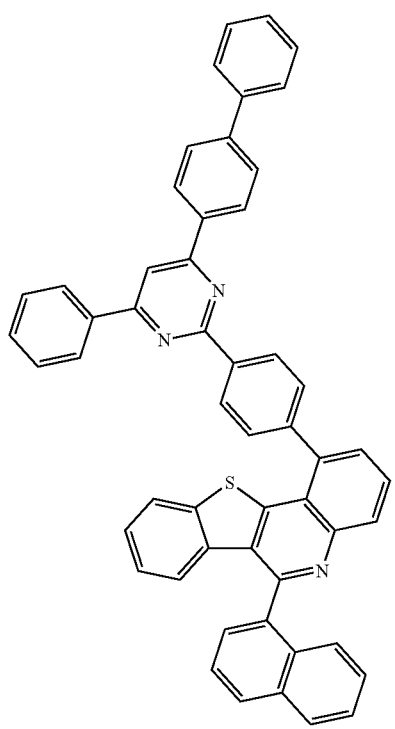
296
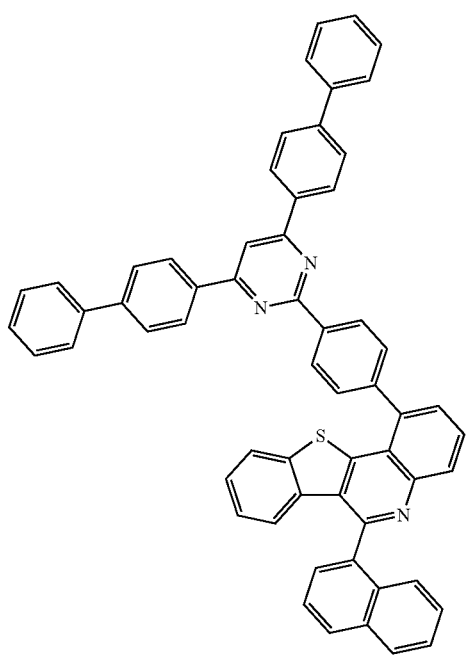
297
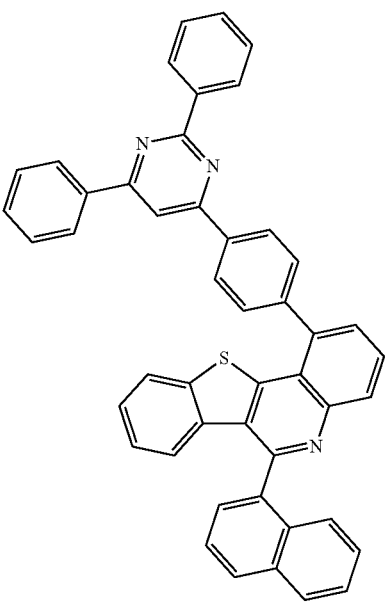
298
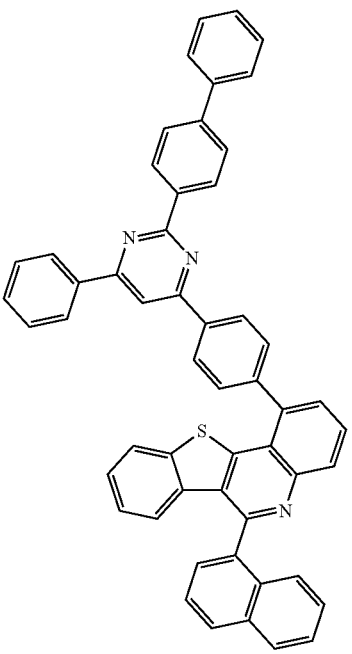

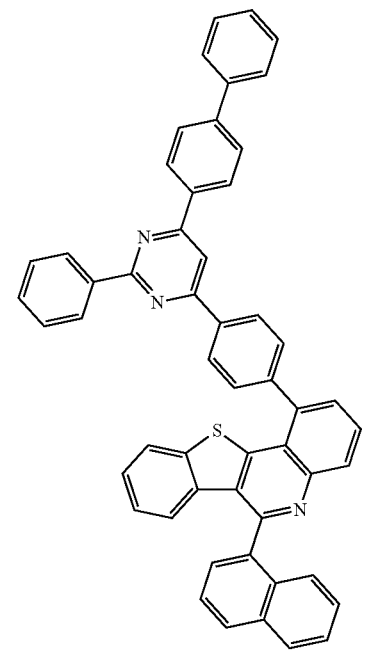
299
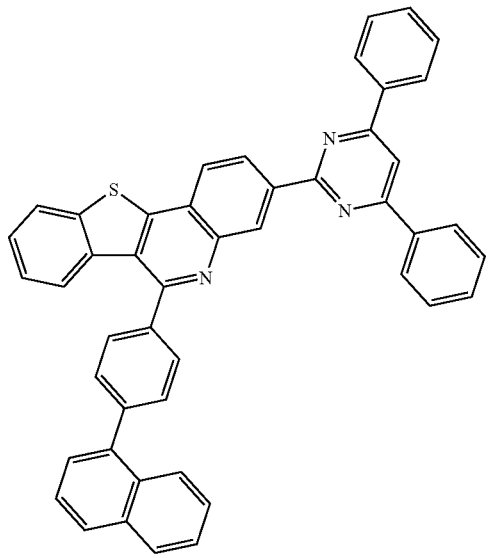
301
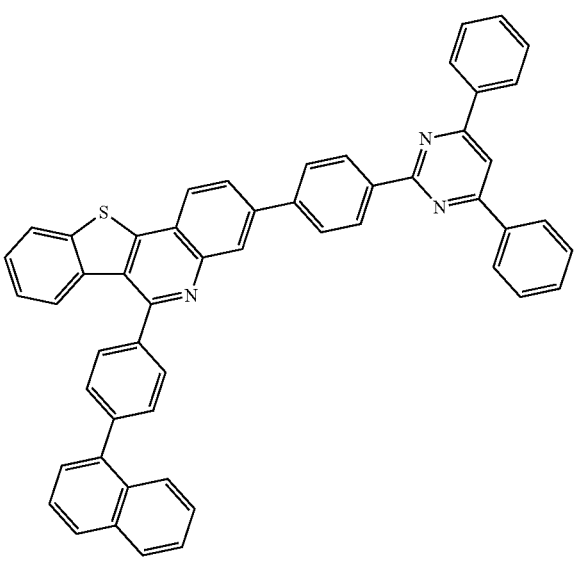
302
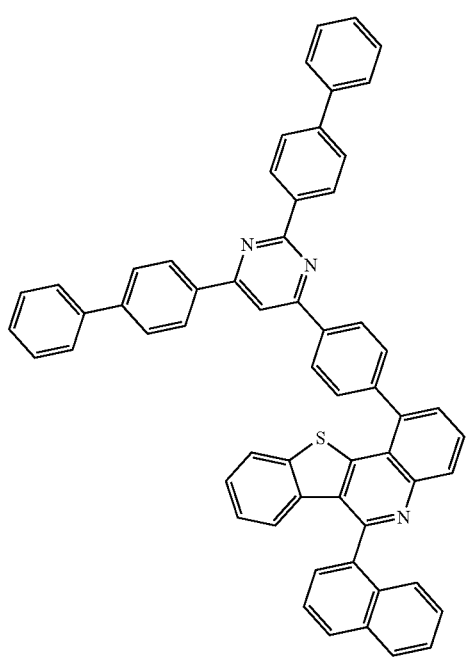
300
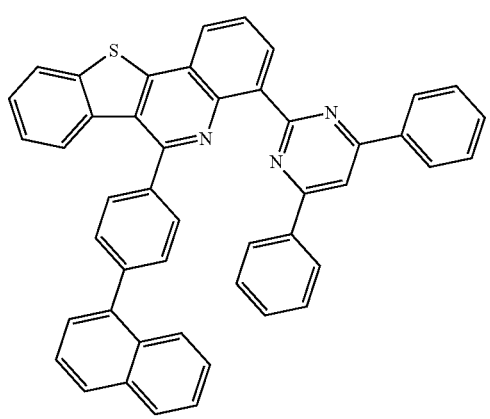
303

304
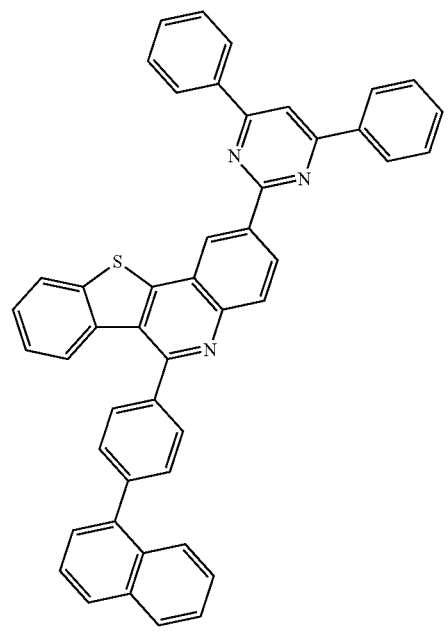
305
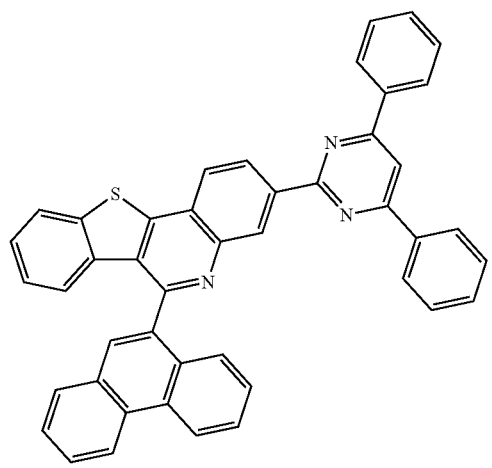
306
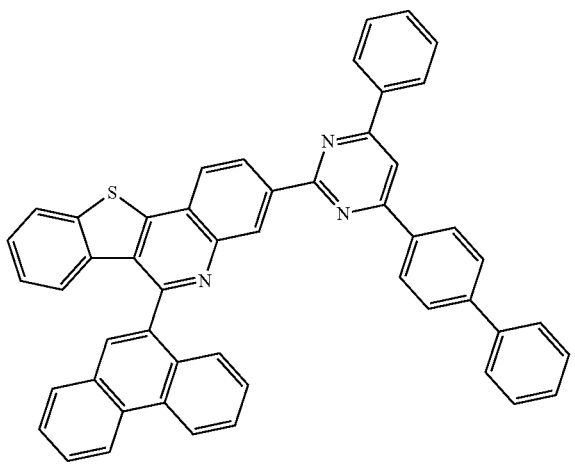
307
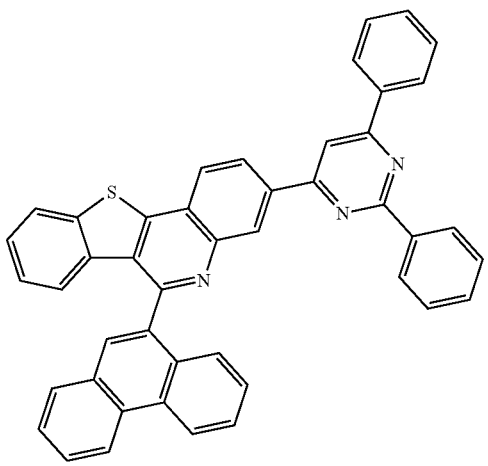
308
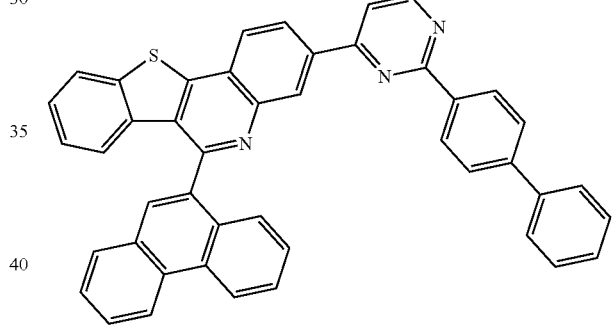
309
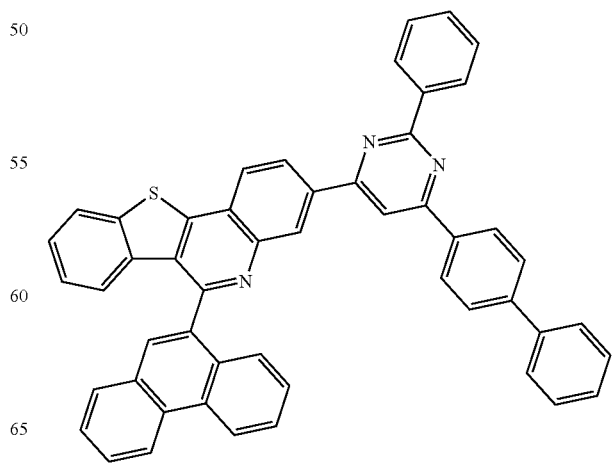

310
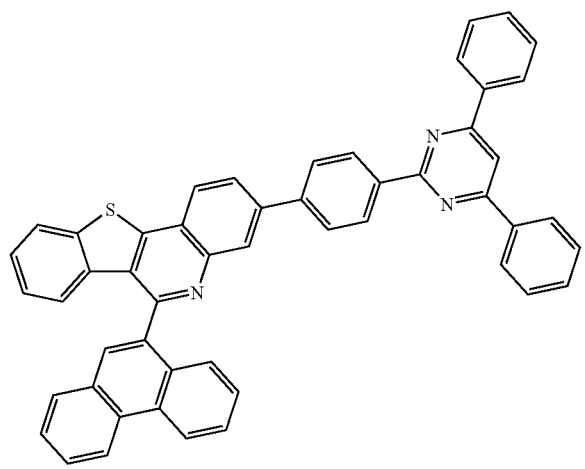
311
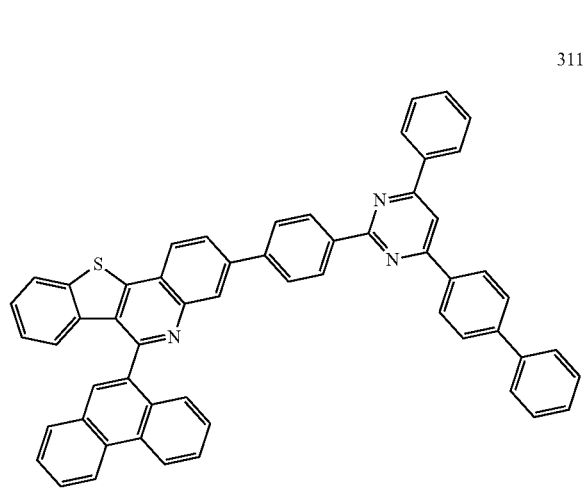
312
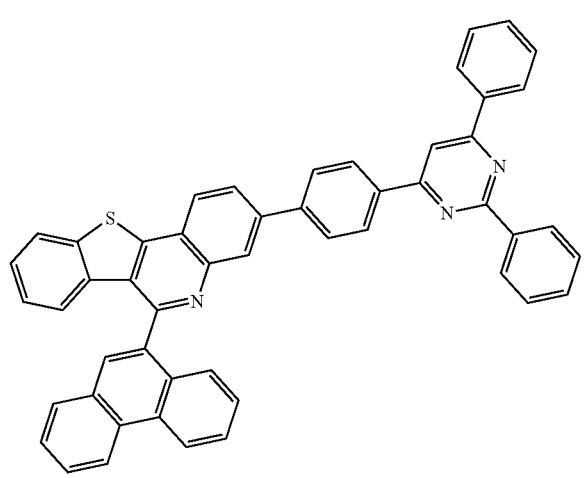
313
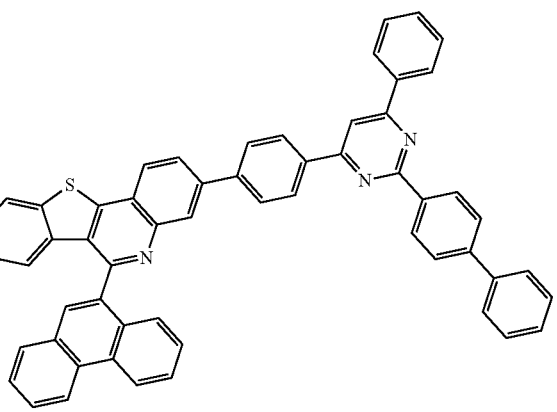
314
315
316
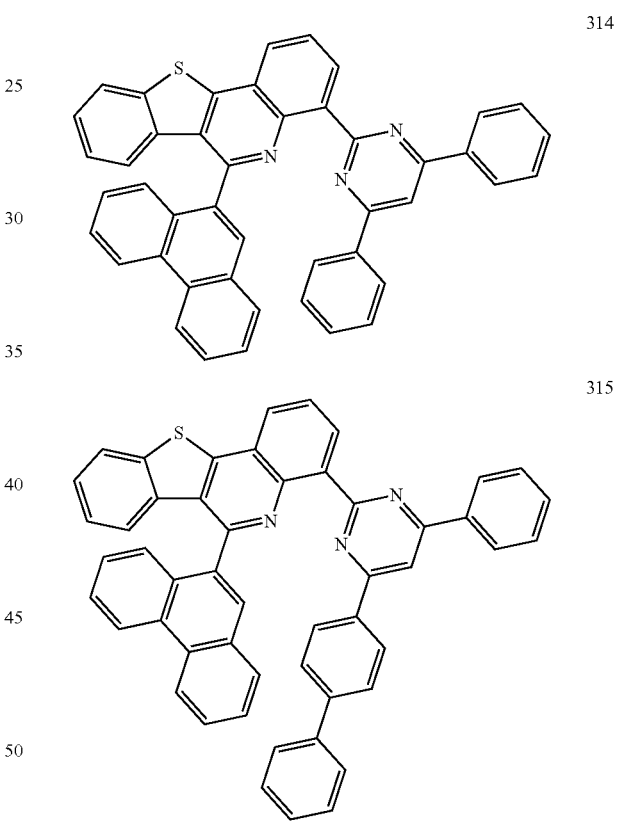

317
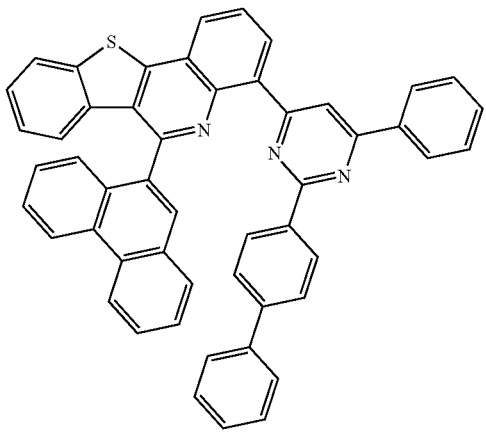
318
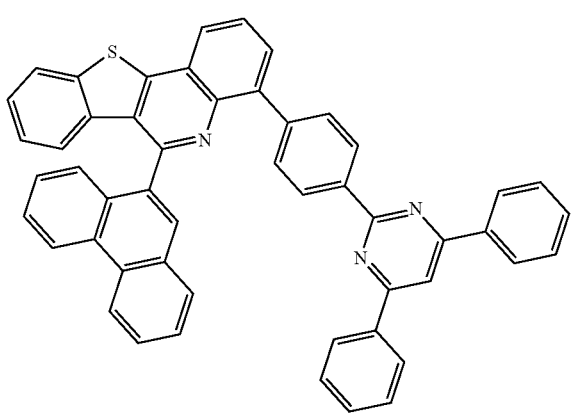
319
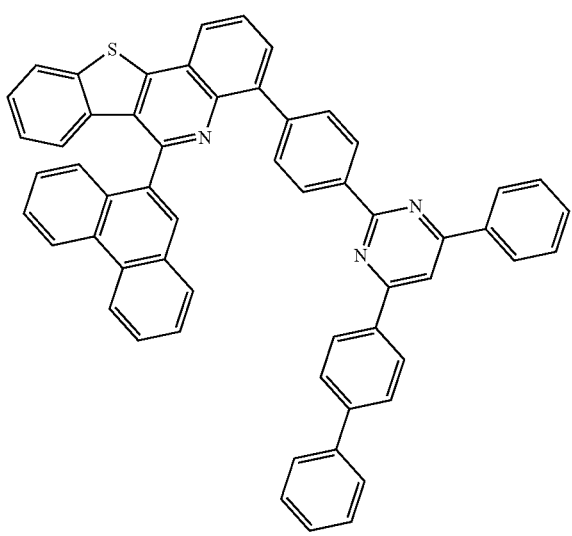
320
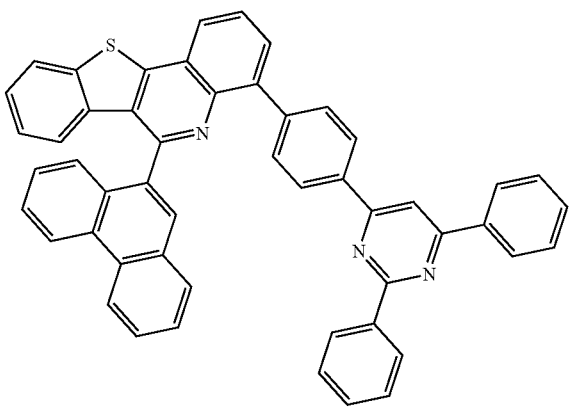
321
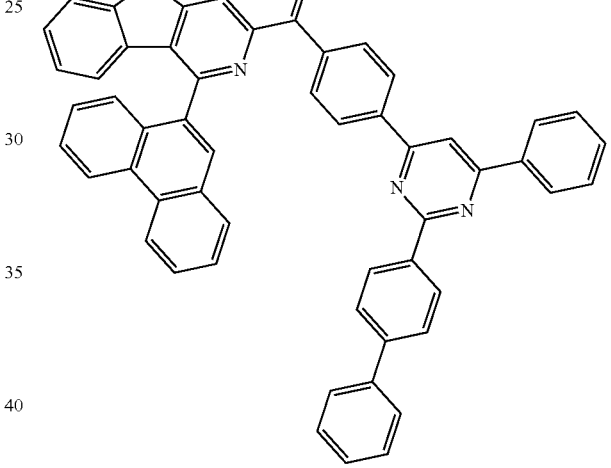
322
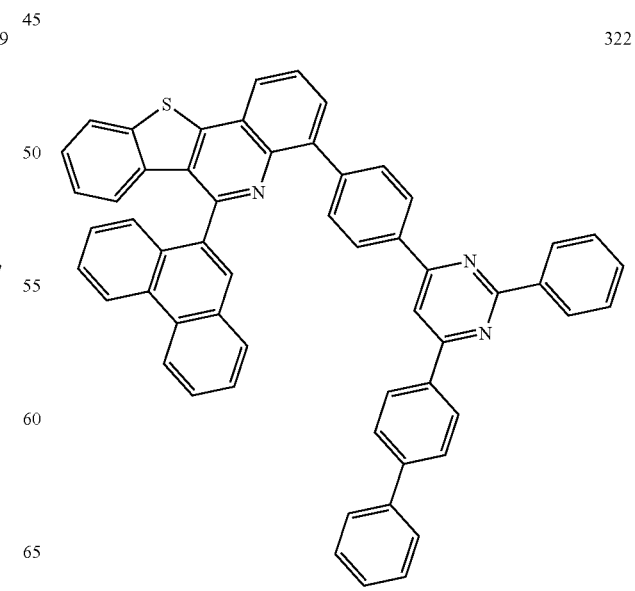

145
-continued
323
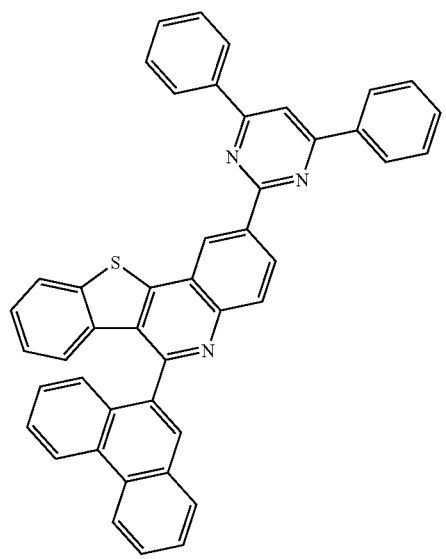
324
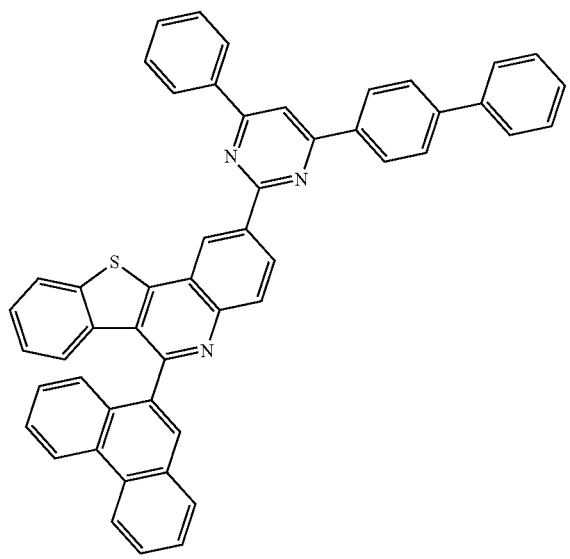
146
-continued
325
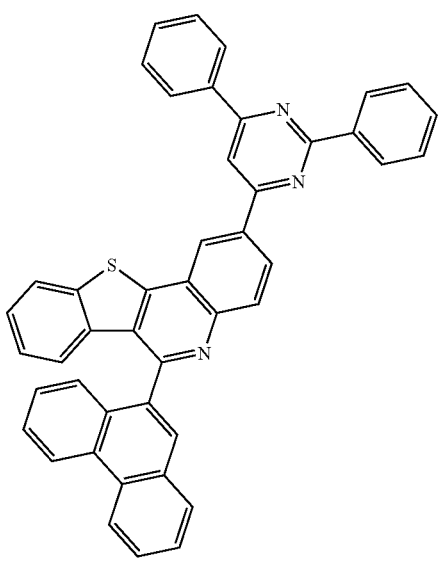
326
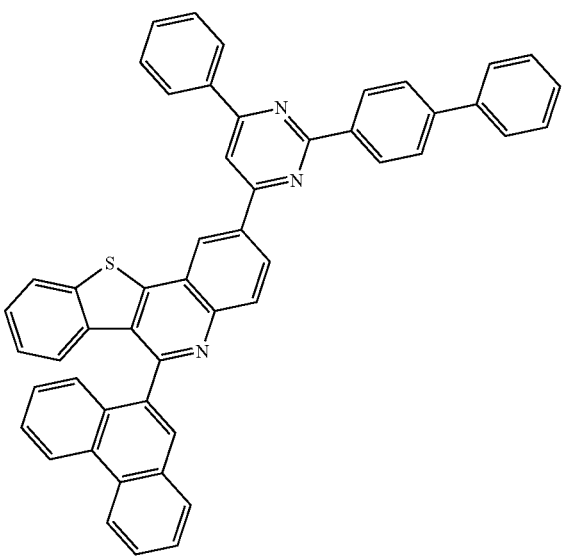

327
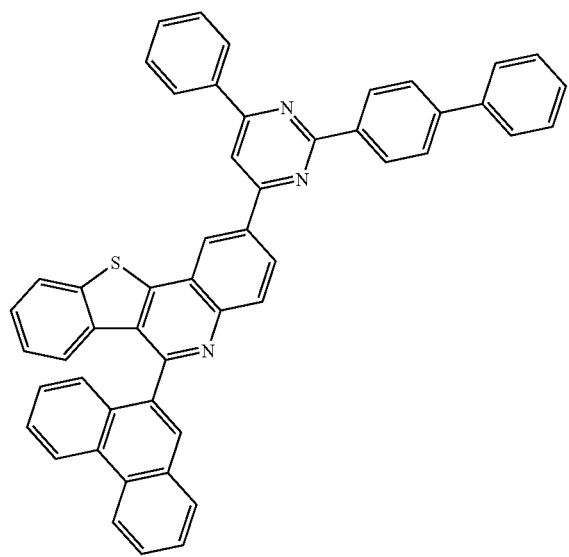
328
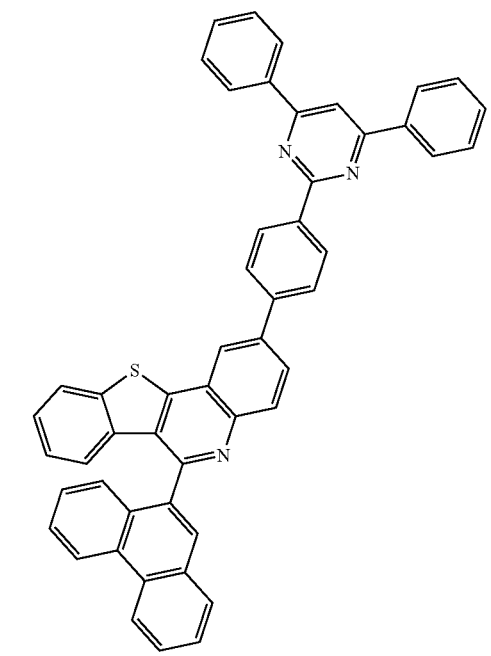
329
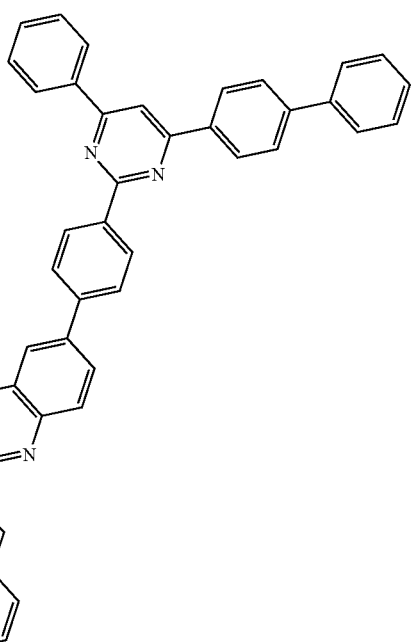
330
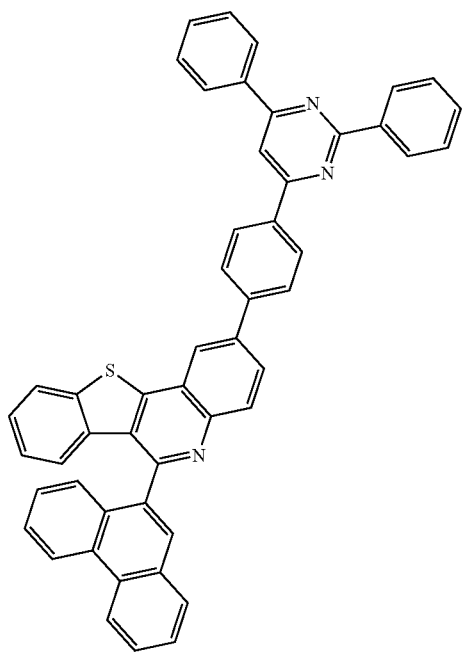

331
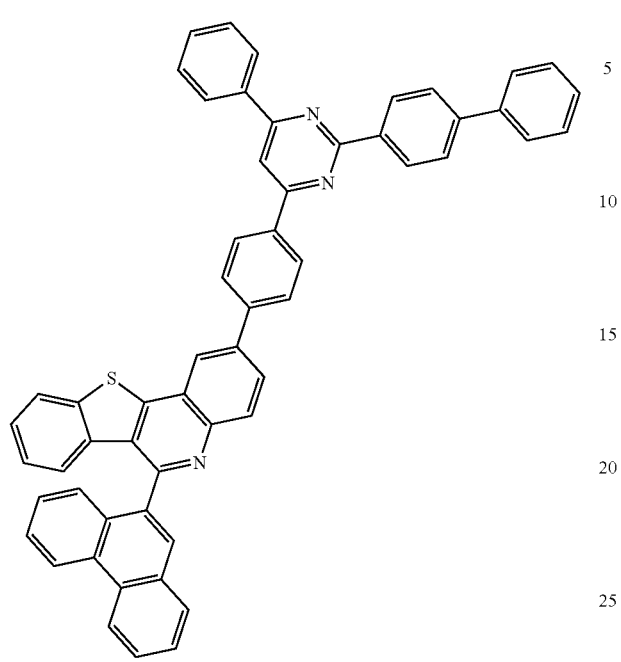
333
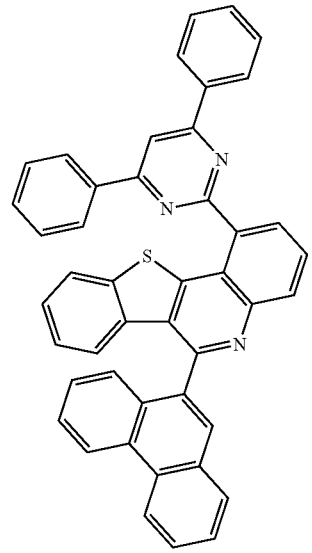
332
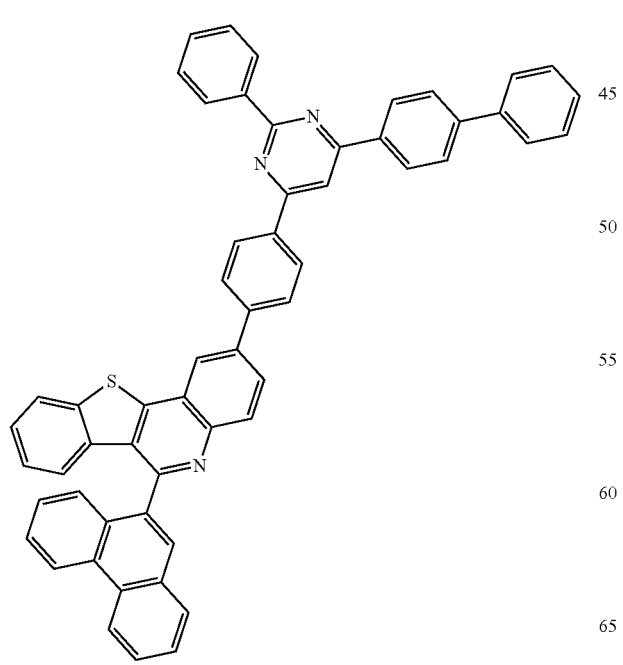
334
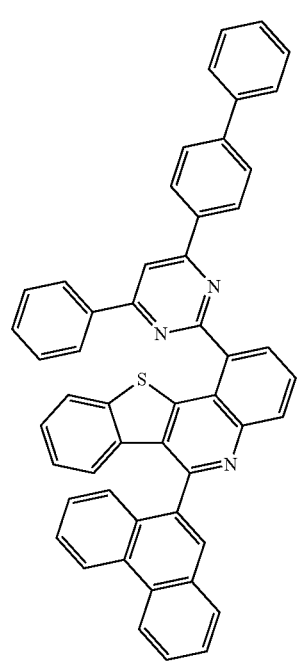

-continued
335
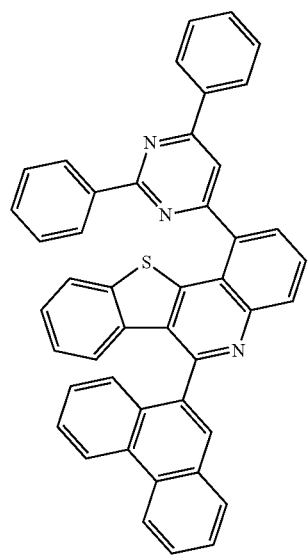
336
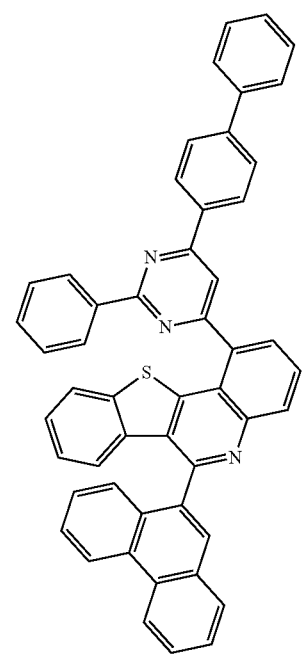
-continued
337
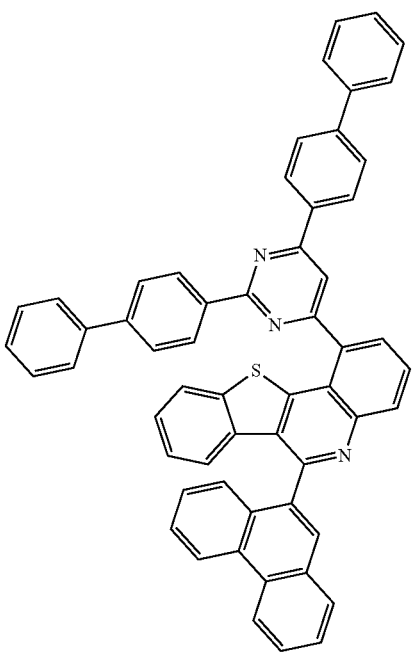
338
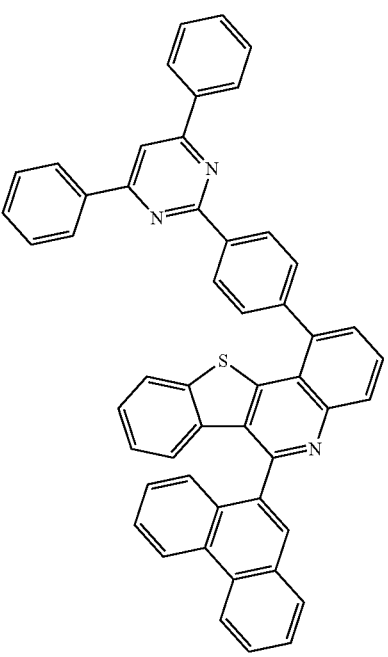

339
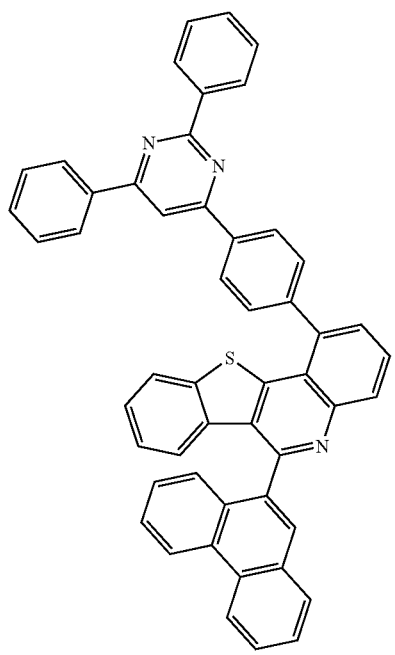
340
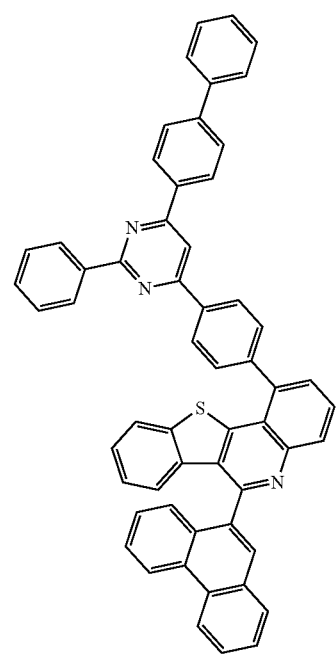
341
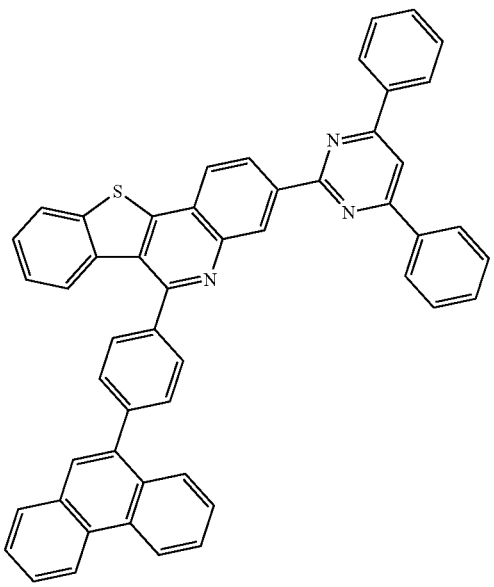
342
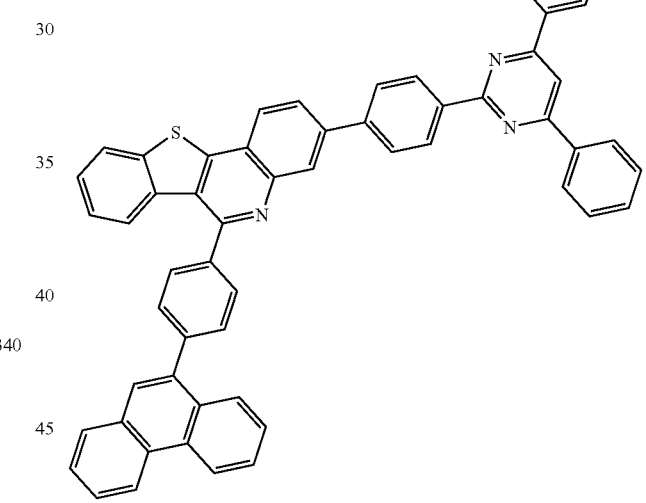
343
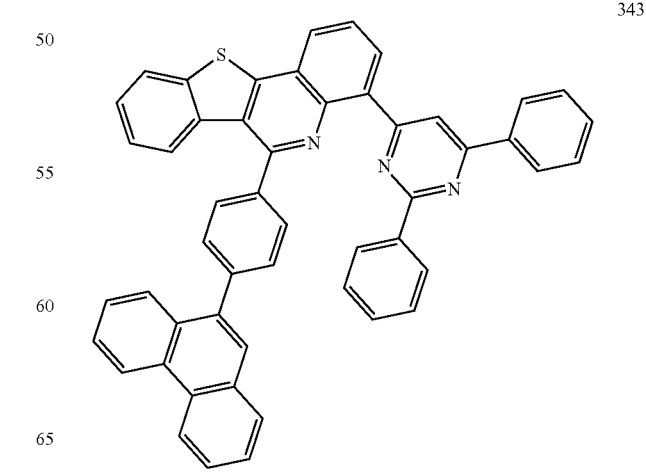

344
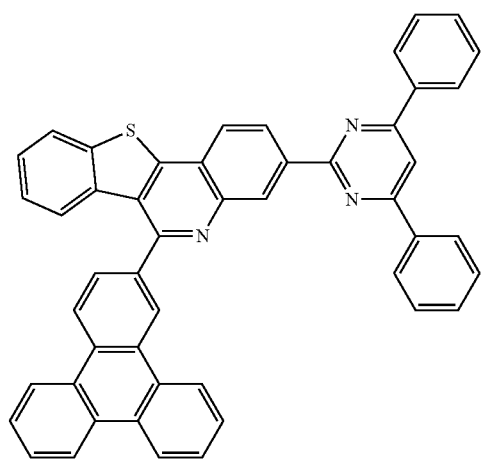
347
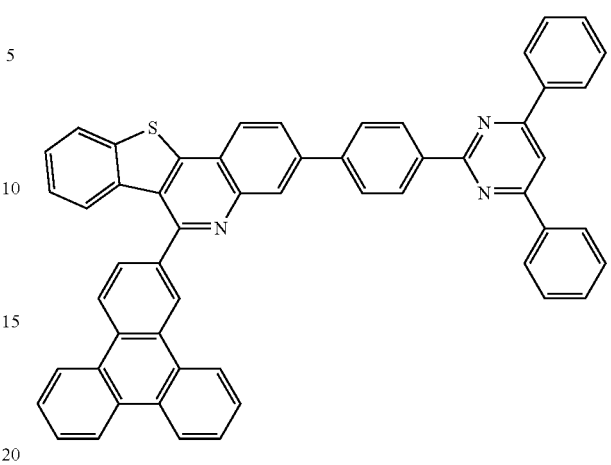
345
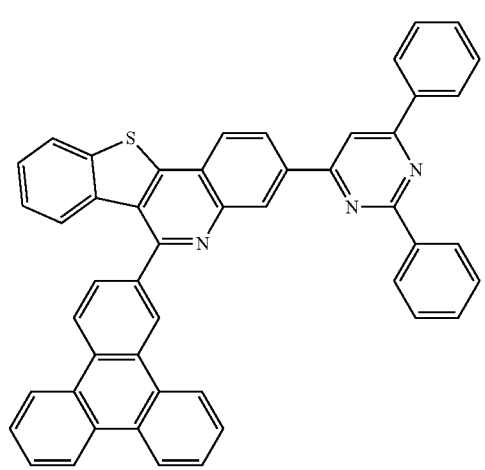
348
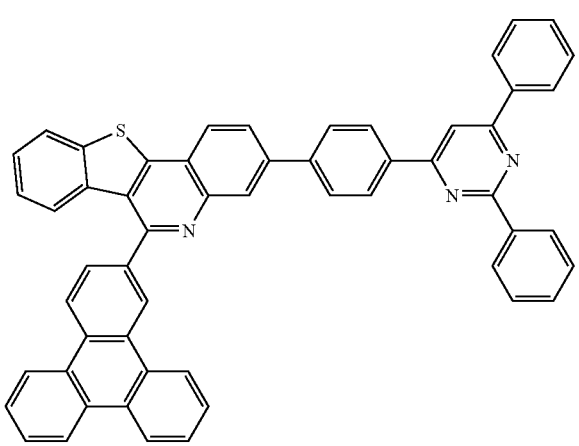
346
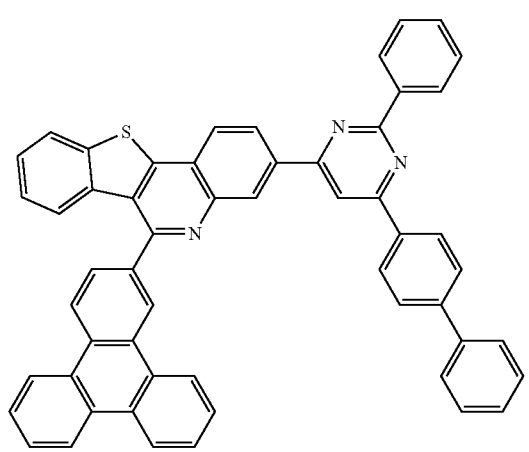
349

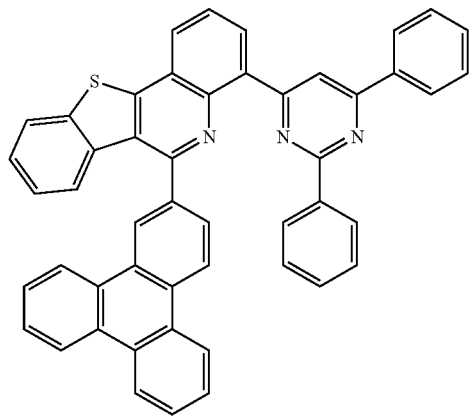
350
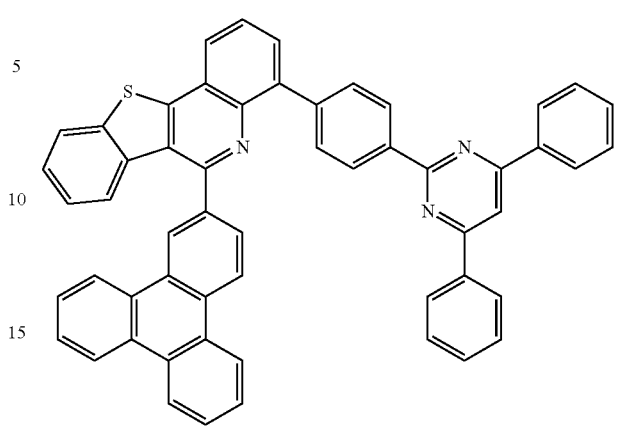
353
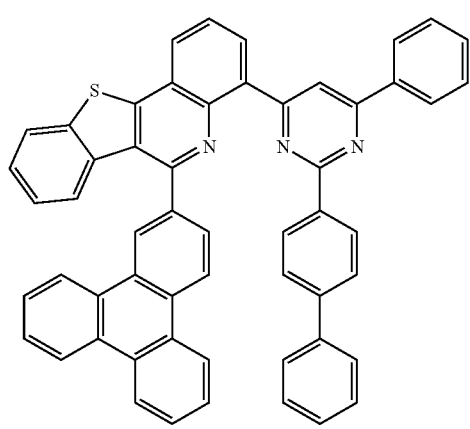
351
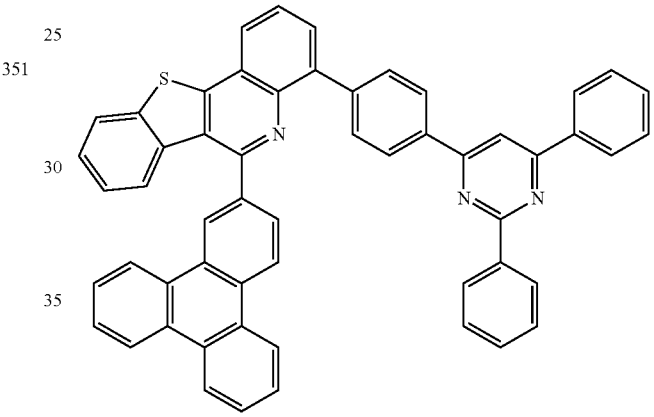
354
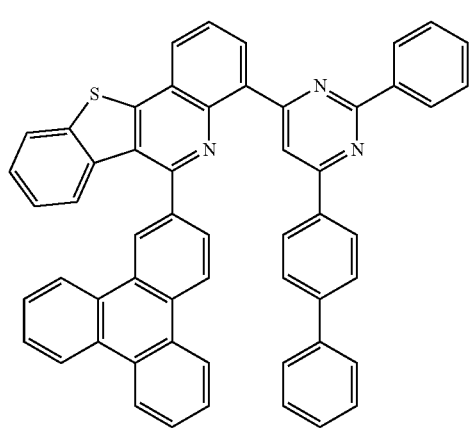
352
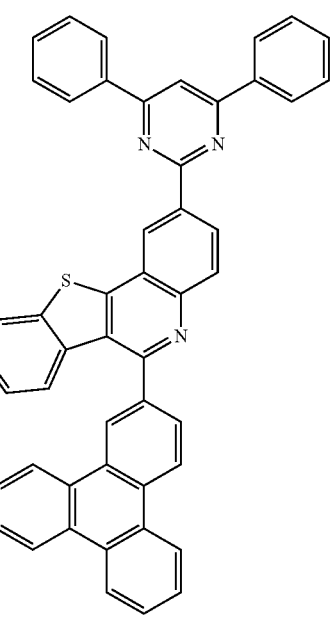
355

356
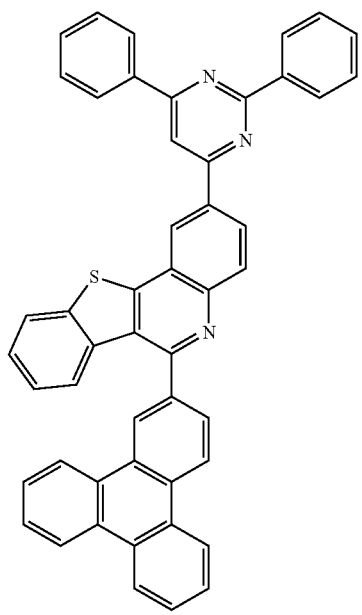
357
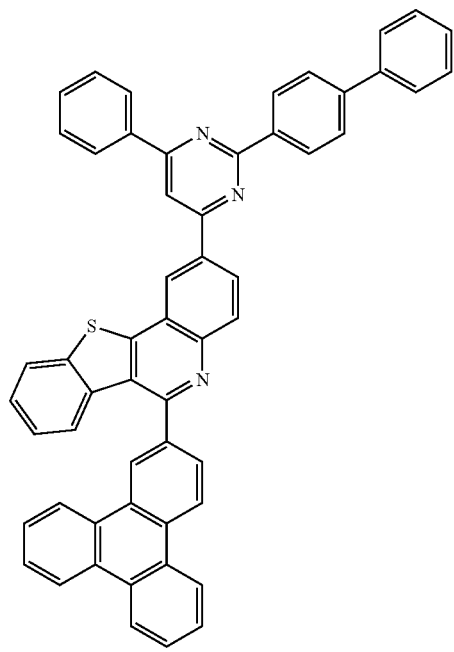
358
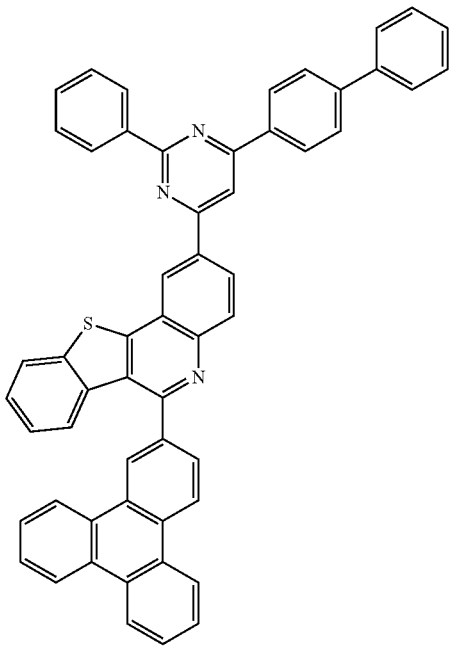
359
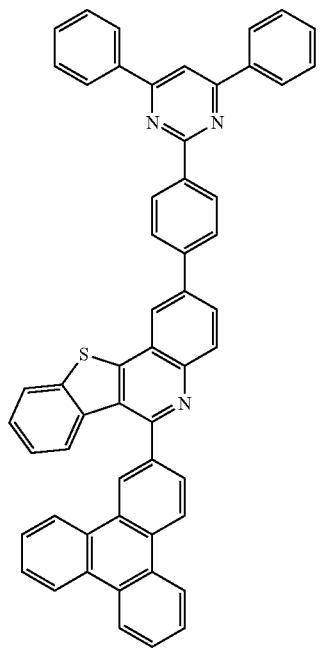

161
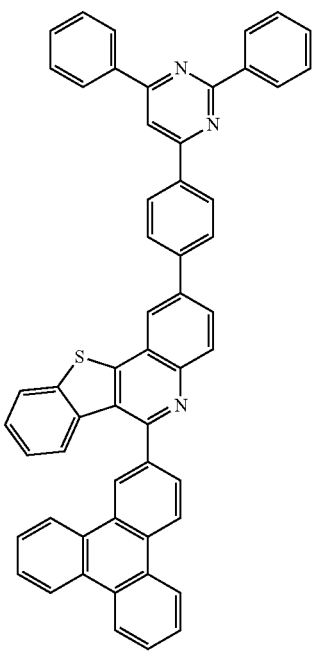
360
162
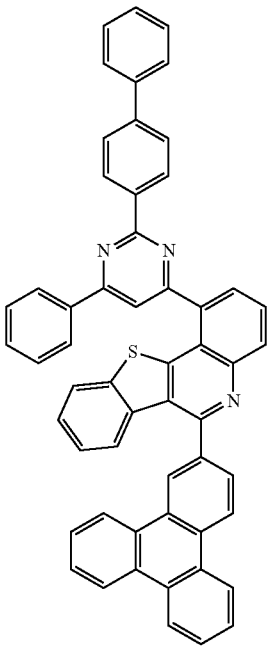
362
361
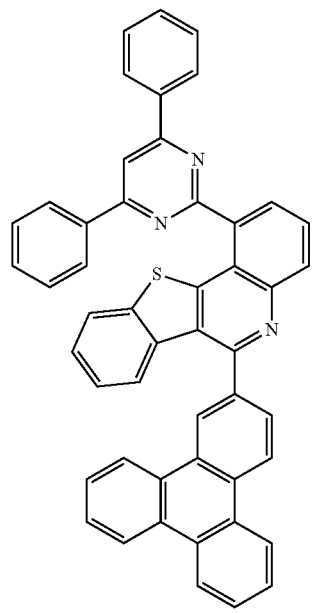
363

163
-continued
364
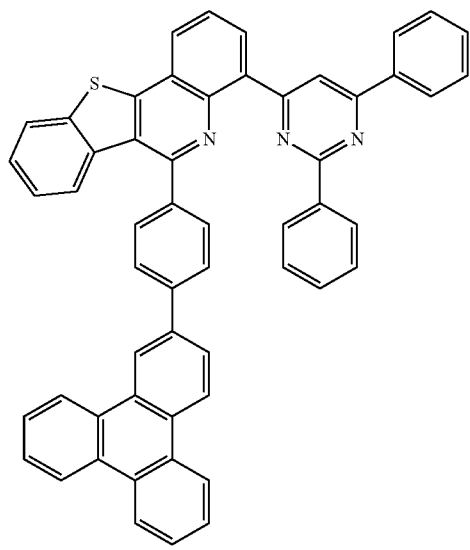
366
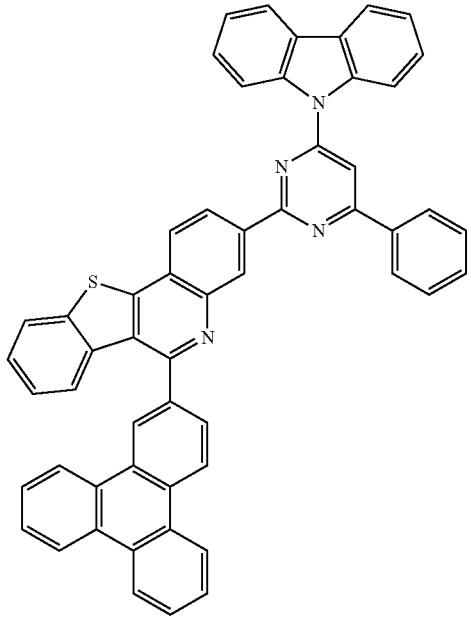
164
-continued
365
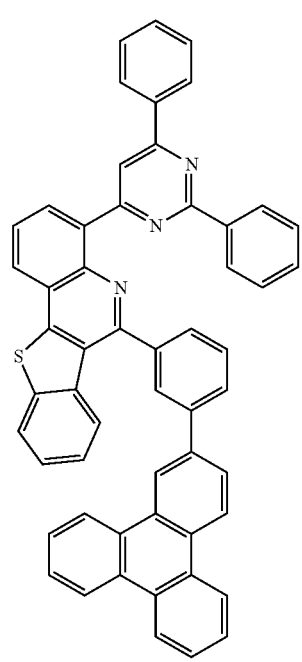
367
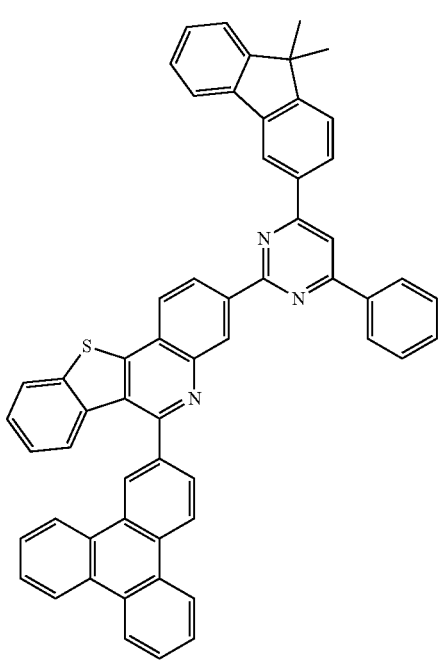

-continued
368
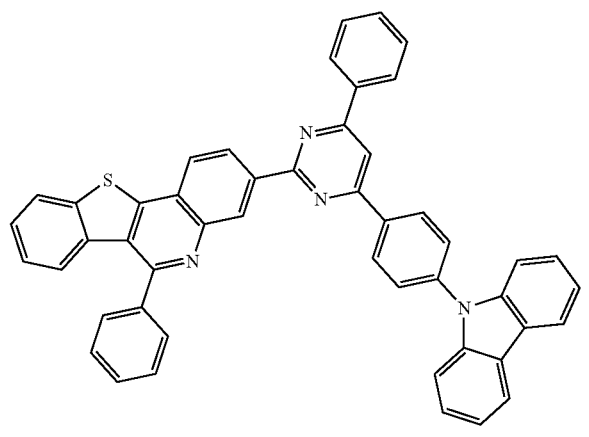
369
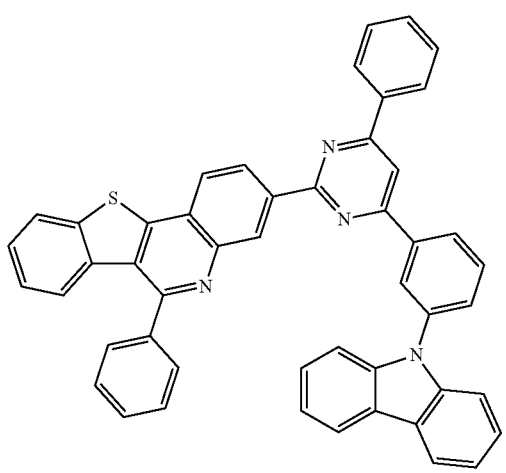
370
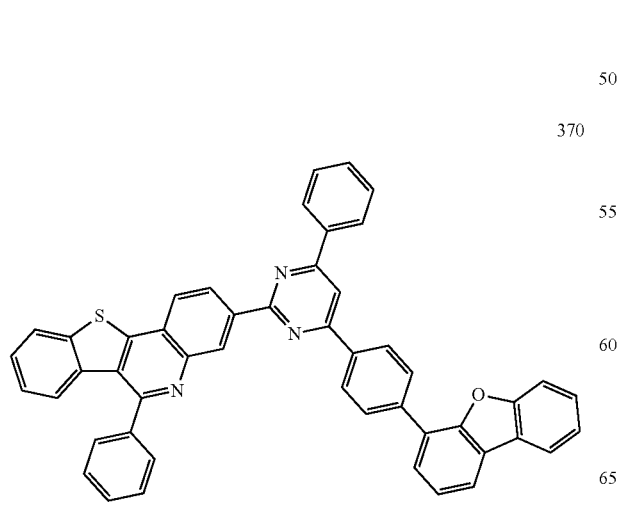
-continued
371
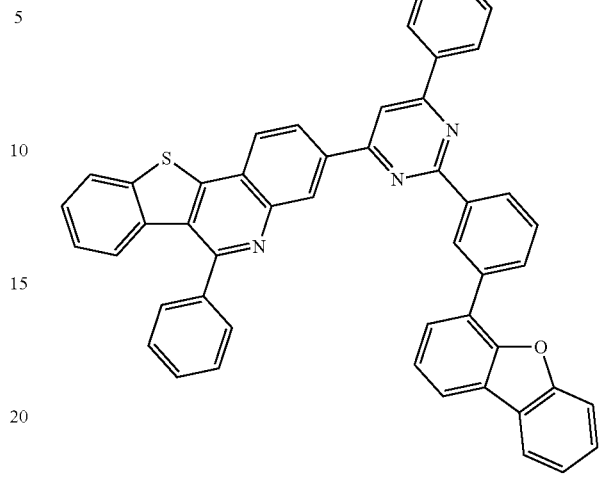
372
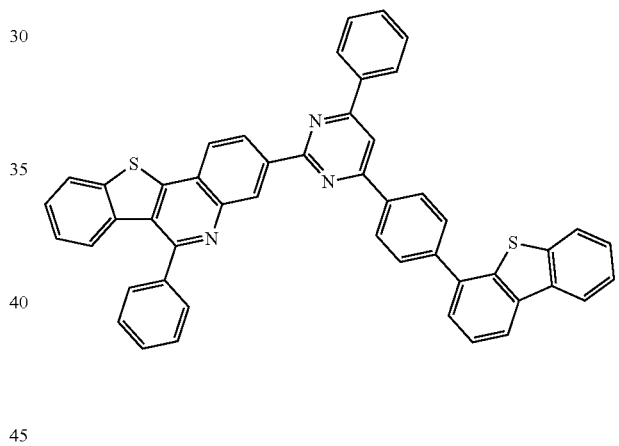
373
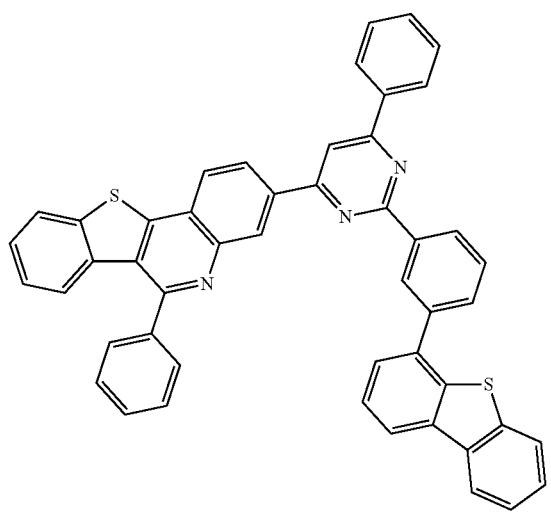

374
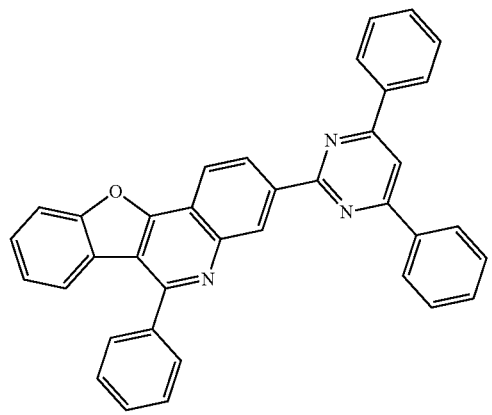
375
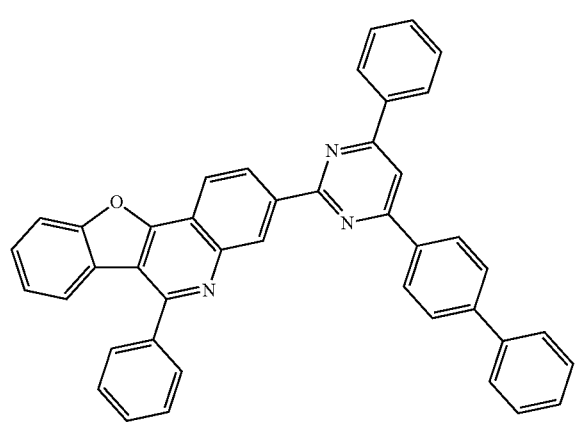
376
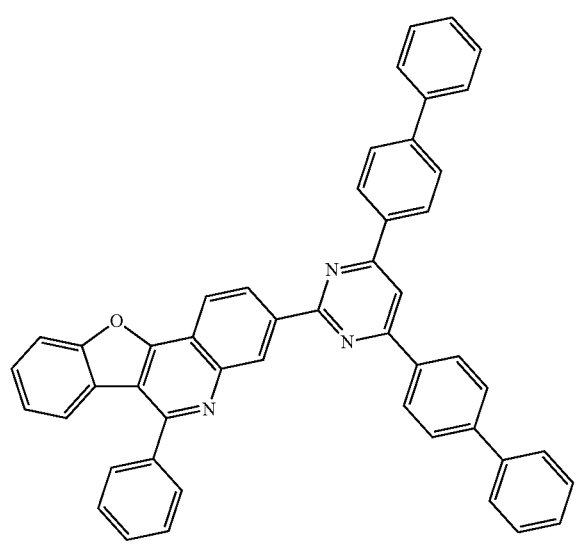
377
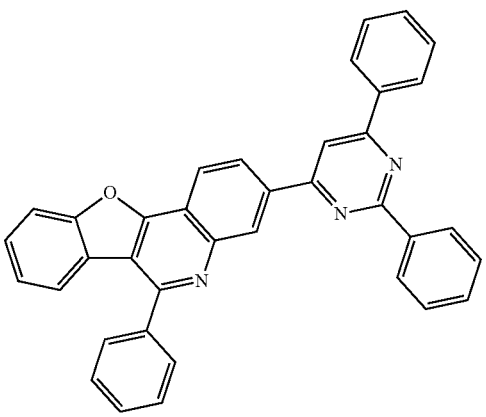
378
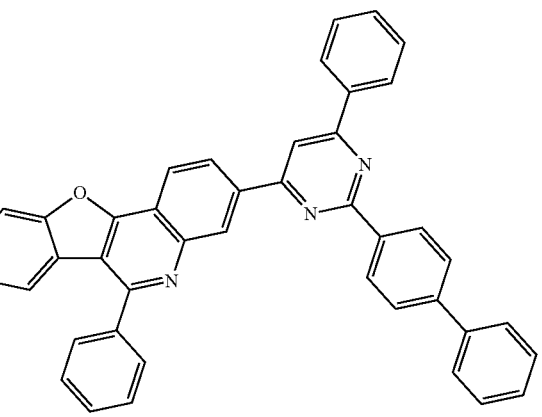
379
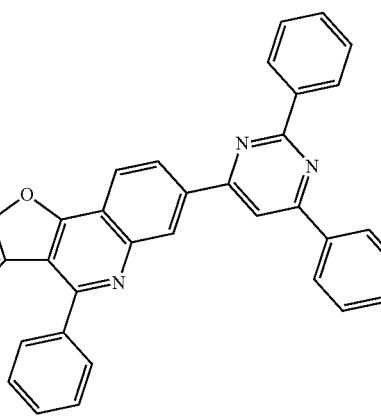

380
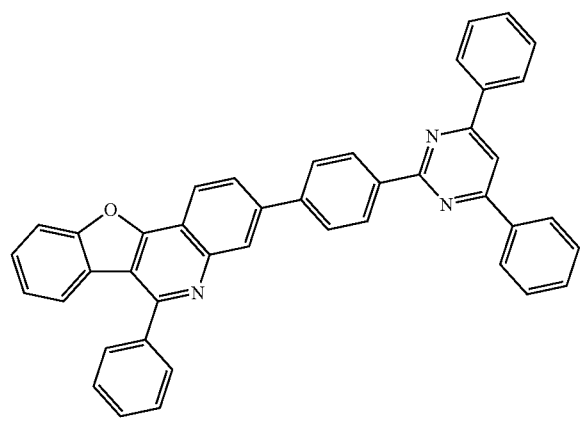
381
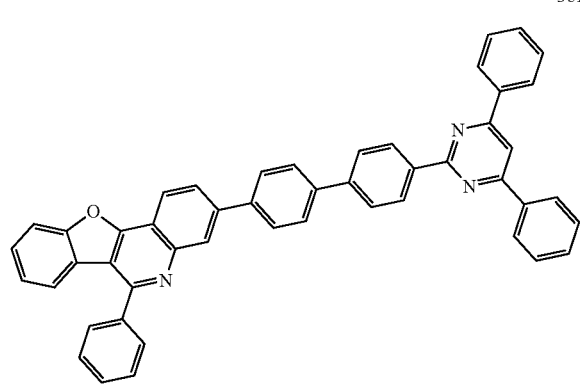
382
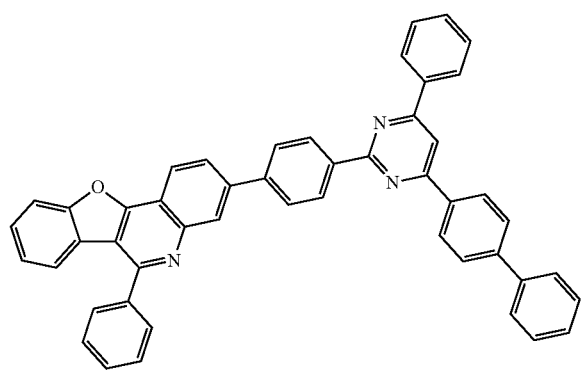
383
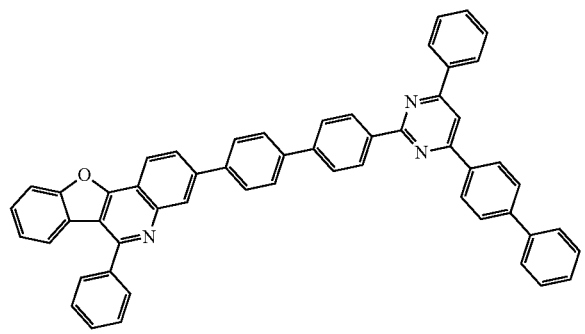
384
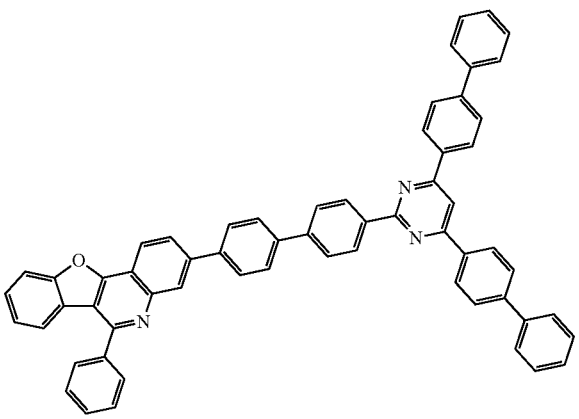
385
386
387
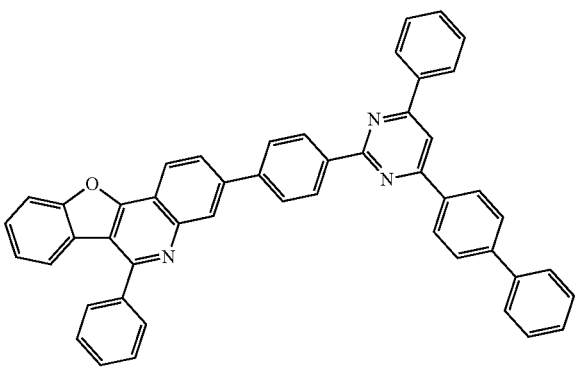

388
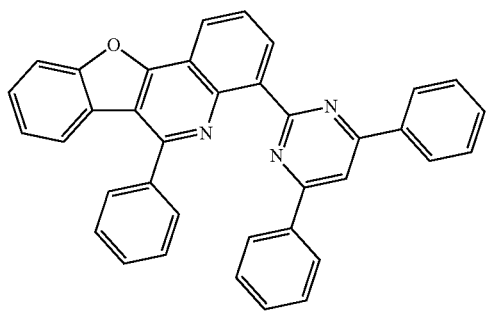
389
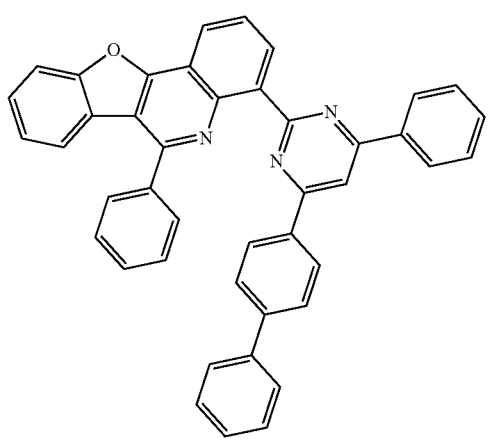
390
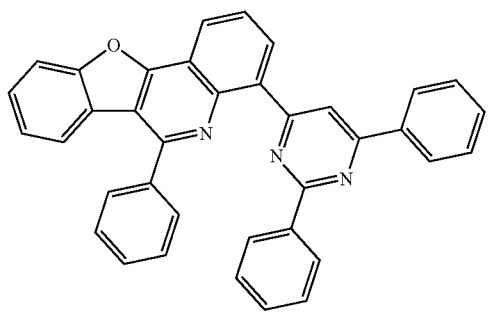
391
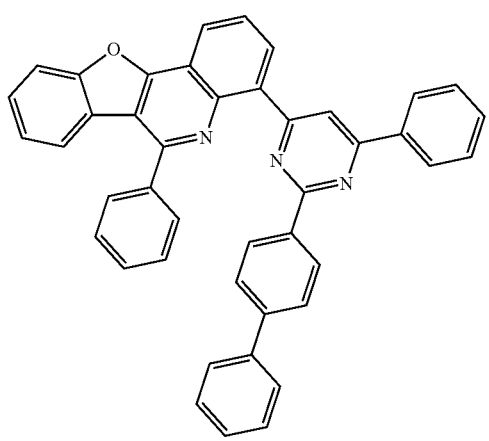
392
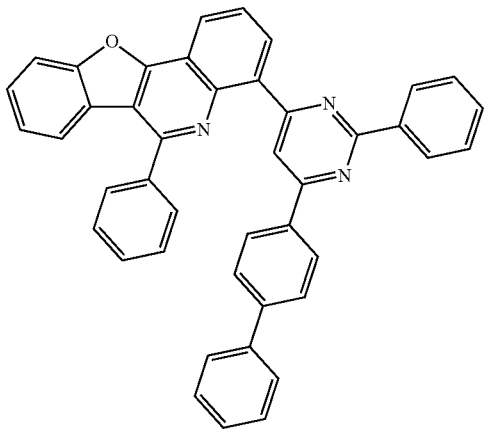
393
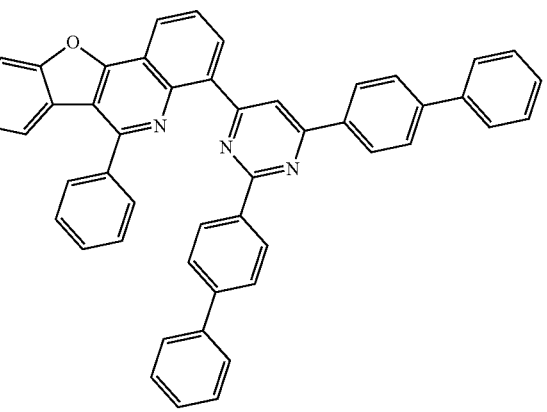
394
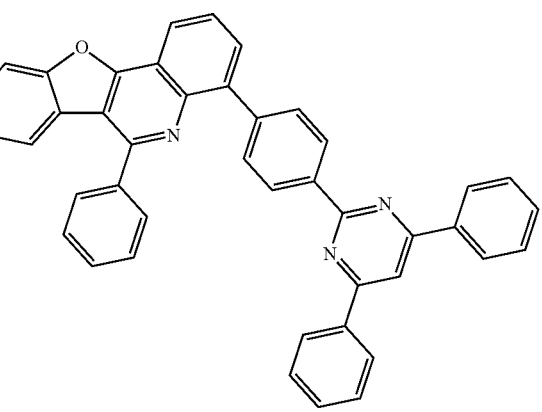

395
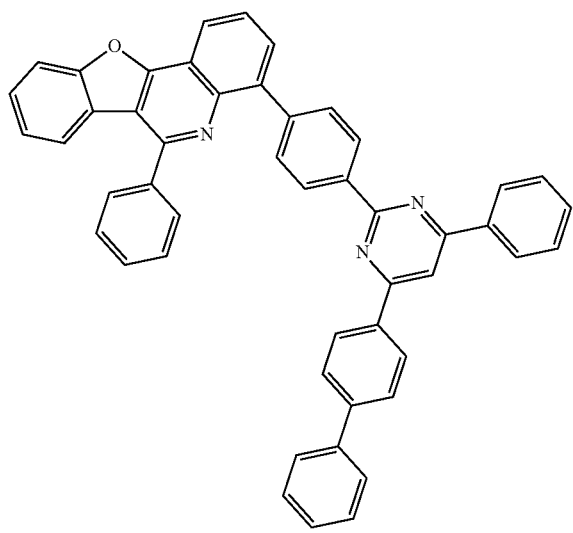
396
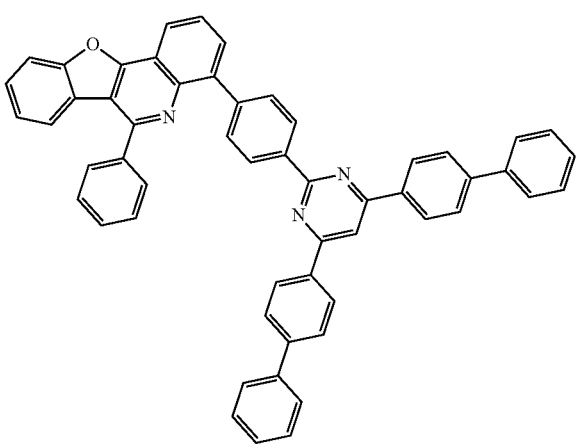
397
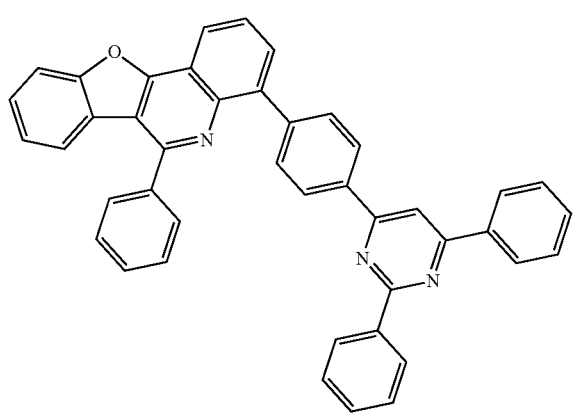
398
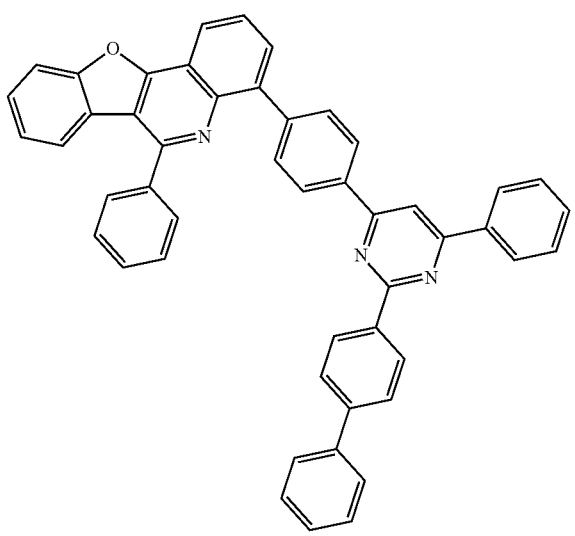
399
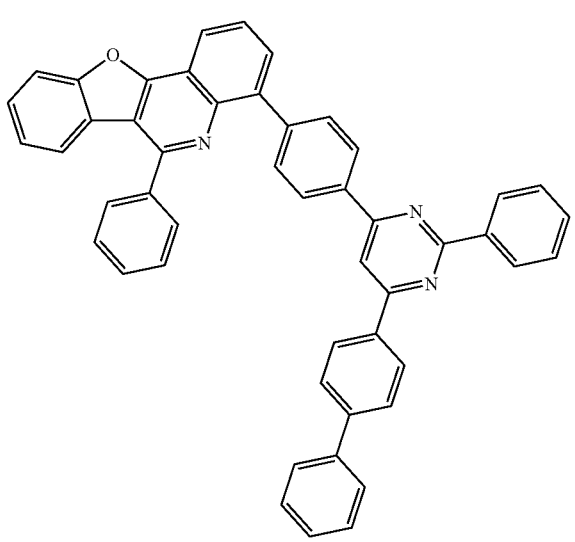
400
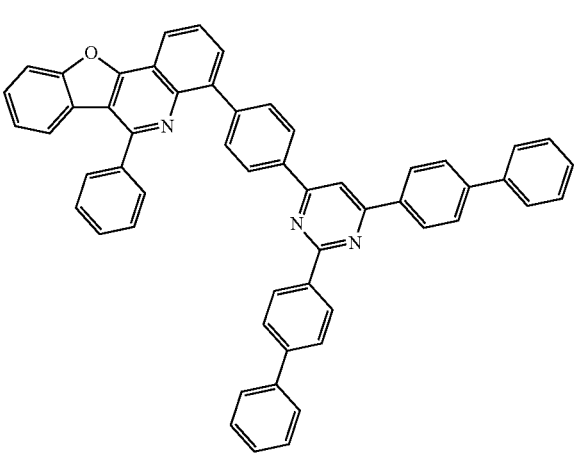

401
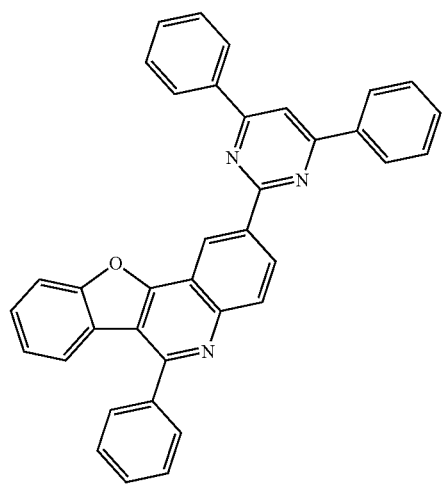
402
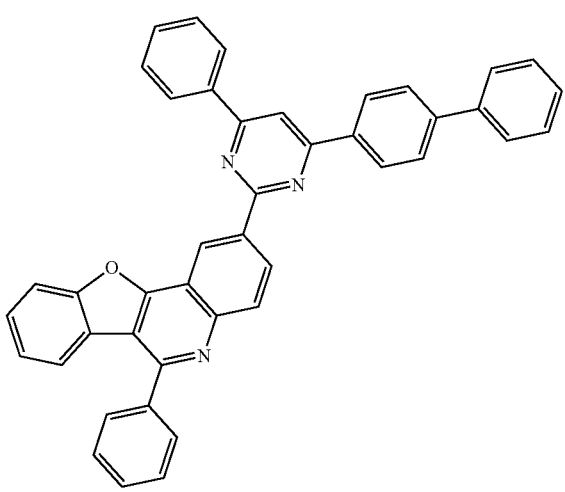
403
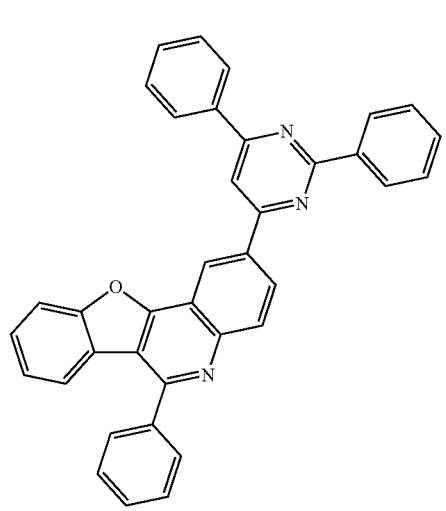
404
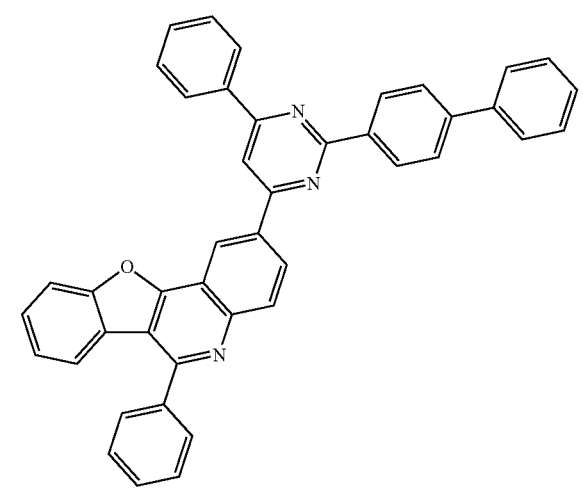
405
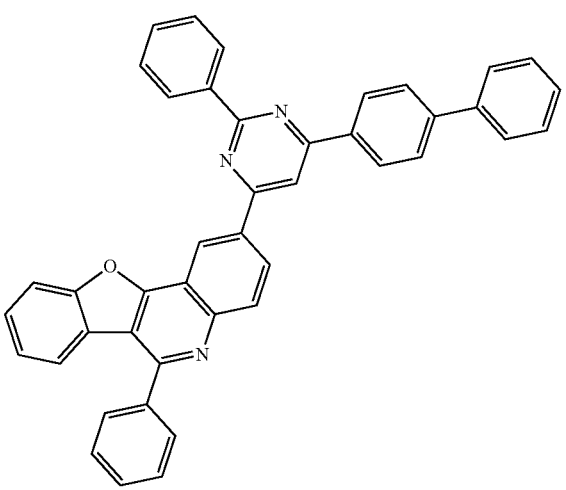
406
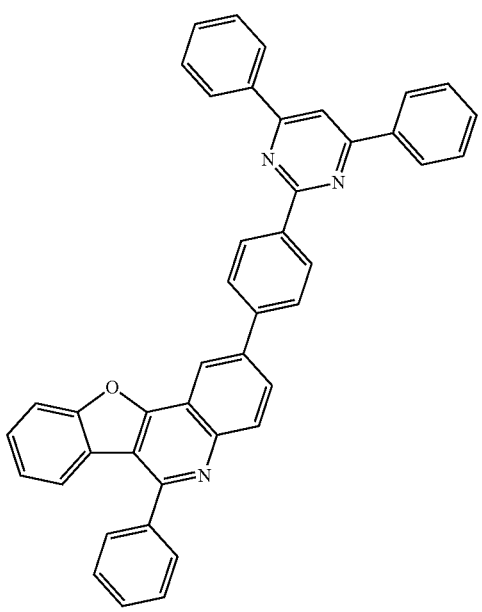

407
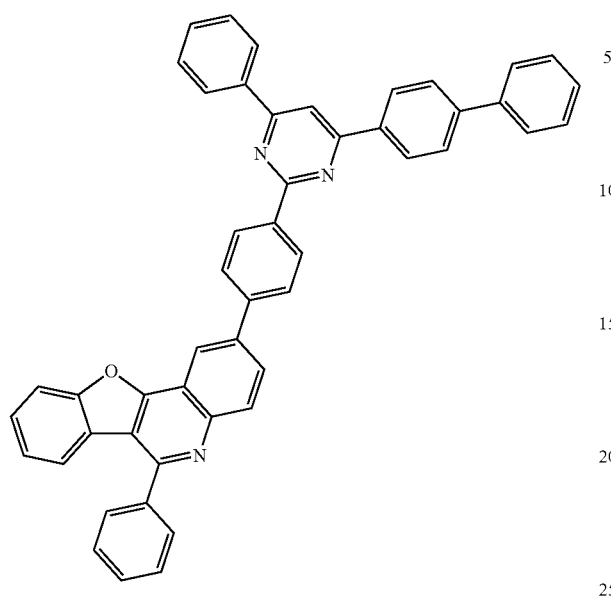
408
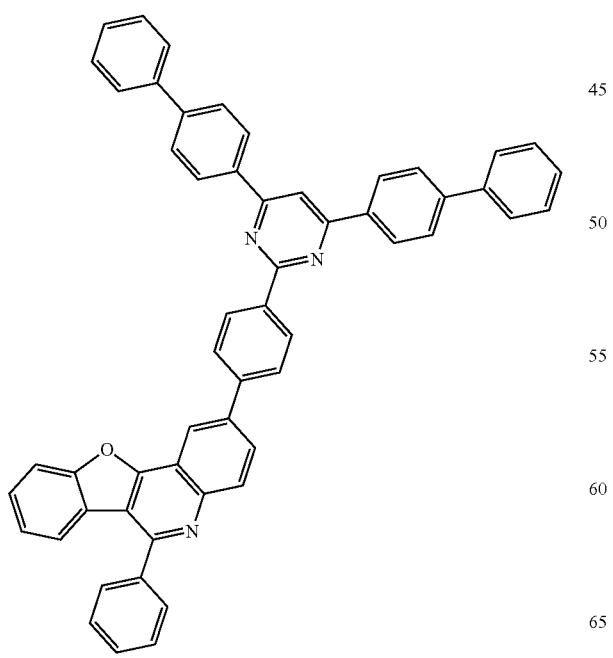
409
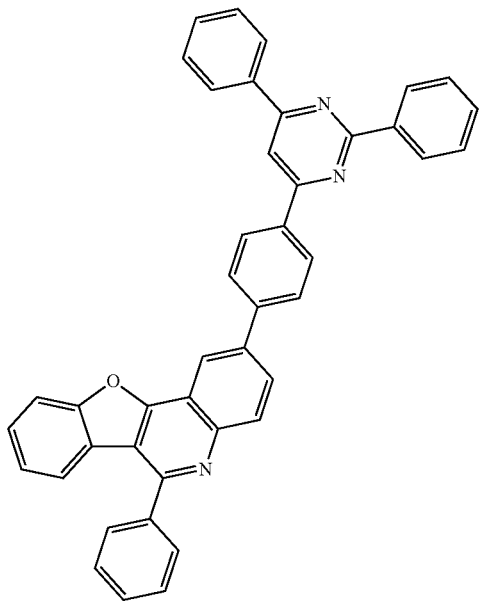
410
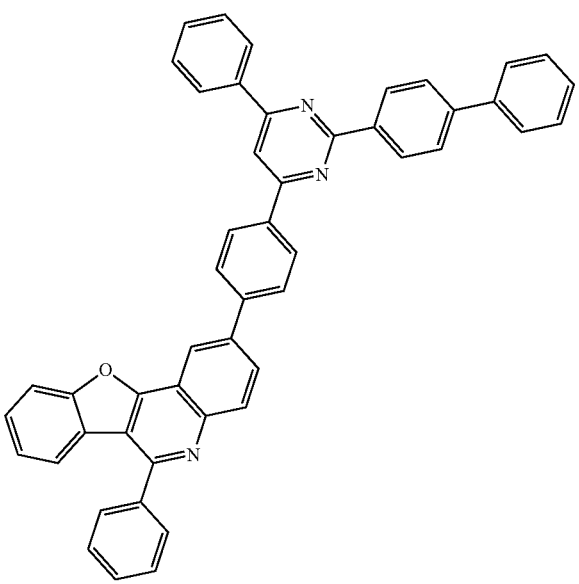

411
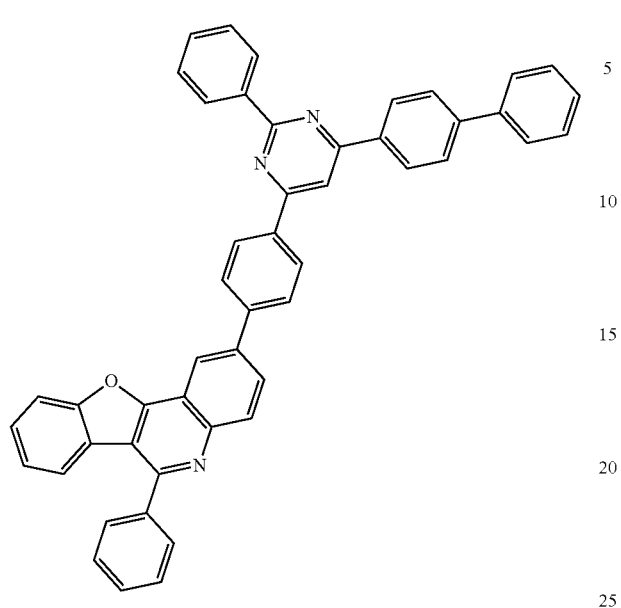
412
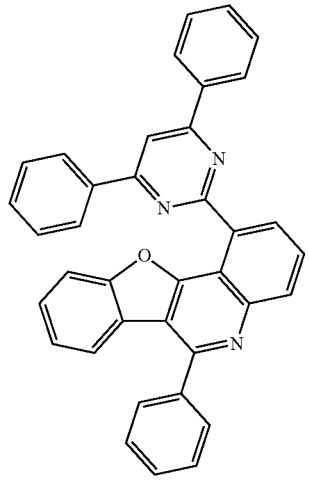
413
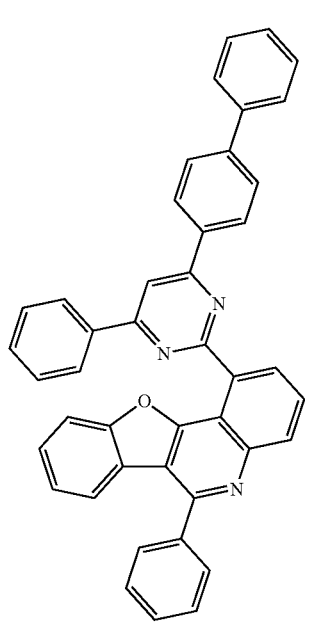
414
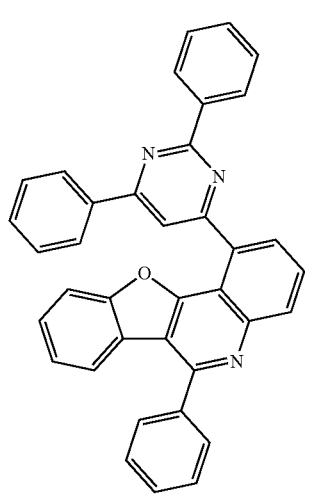
415

416
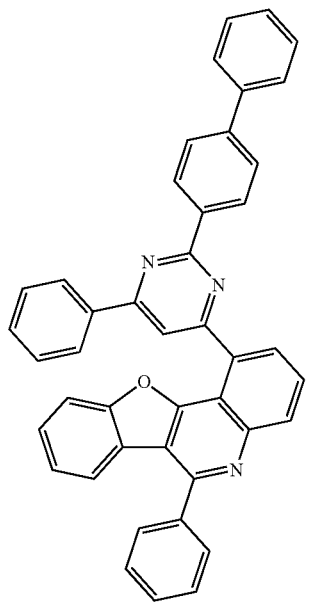
417
418
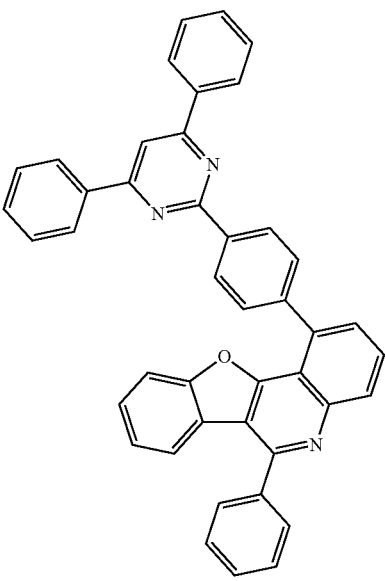
419
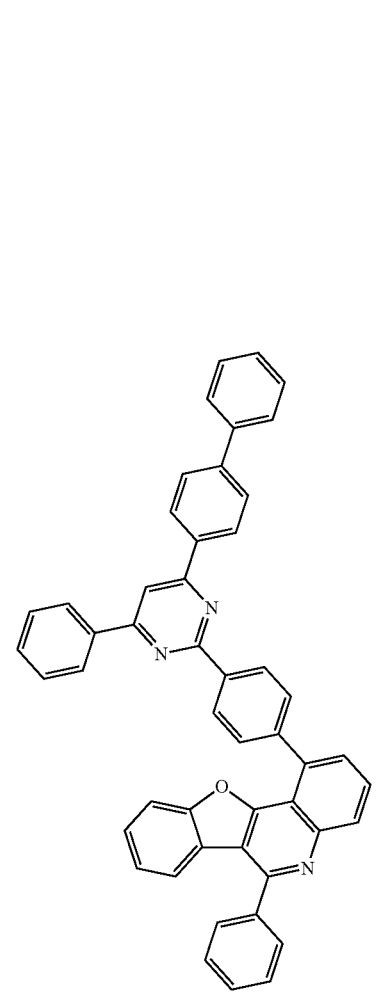

420
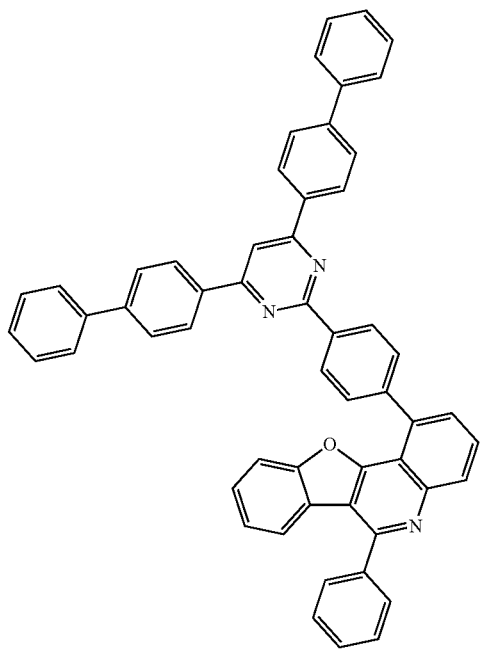
422
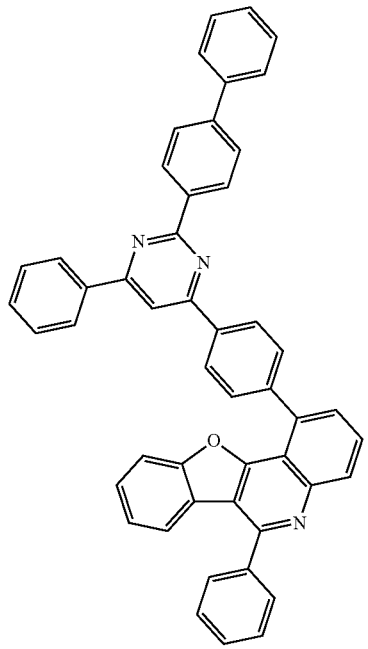
421
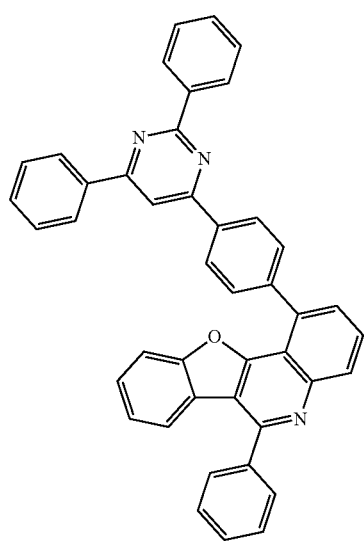
423
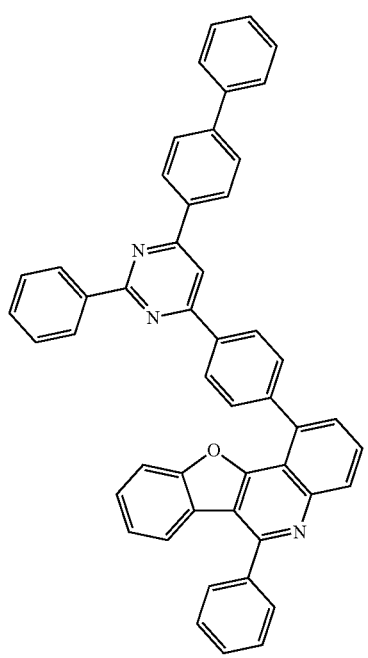

424
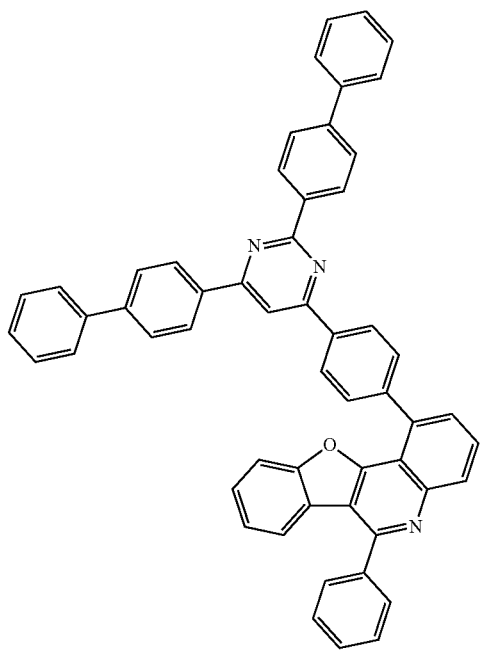
425
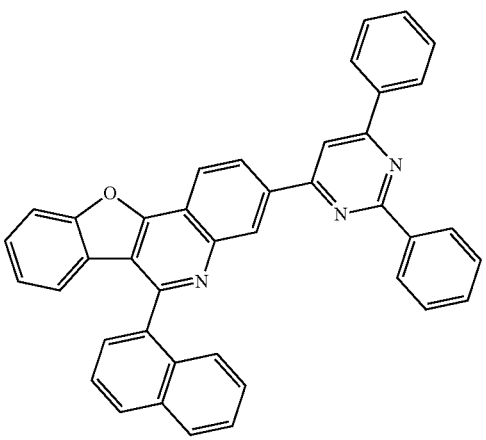
427
428
426
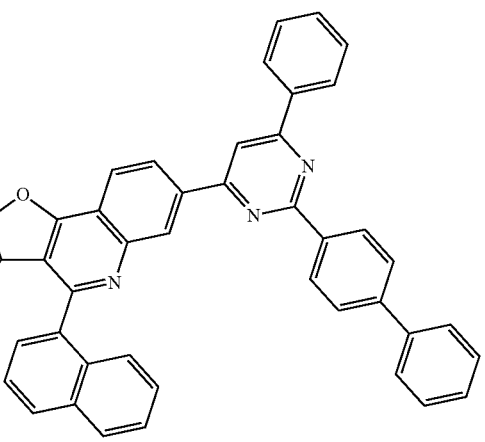
429
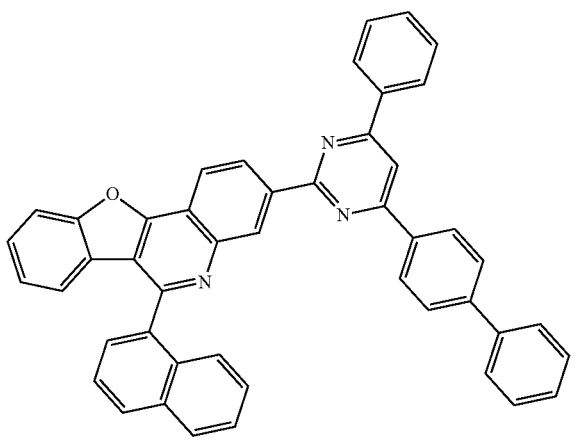
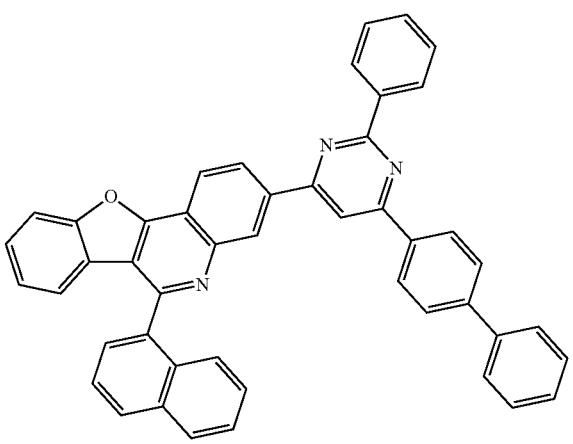 [SMILES: c1ccc(-c2ccc(-c3cc(-c4ccc5c(c4)nc(-c4cccc6ccccc46)c4c6ccccc6sc54)nc(-c4ccccc4)n3)cc2)cc1]

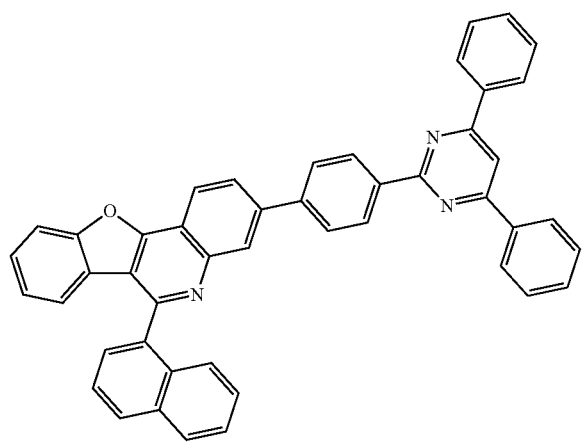 [SMILES: c1ccc(-c2cc(-c3ccc(-c4ccc5c(c4)nc(-c4cccc6ccccc46)c4c6ccccc6sc54)cc3)nc(-c3ccccc3)n2)cc1]
430
431
432
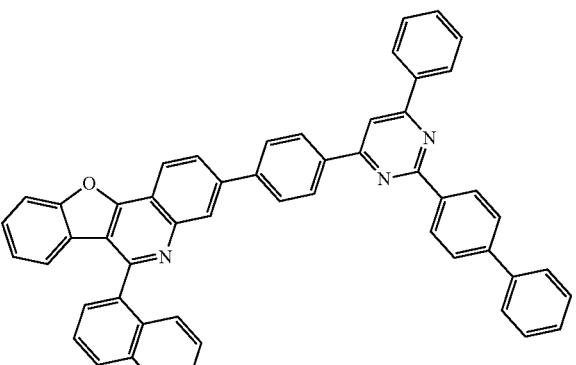
433
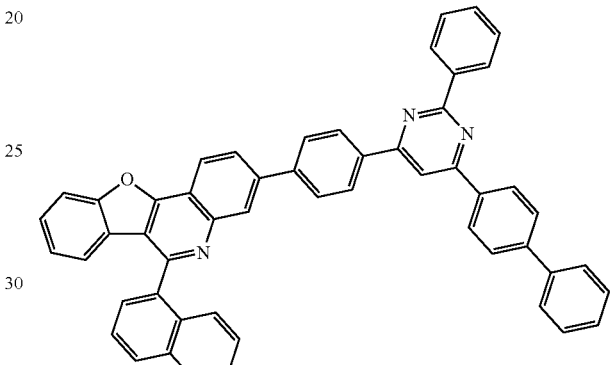
434
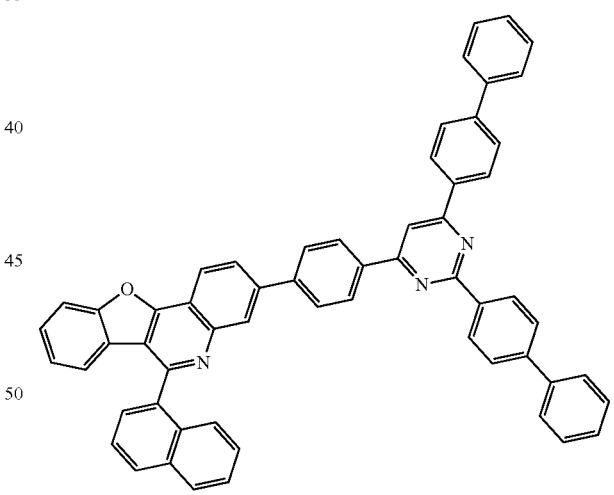
435
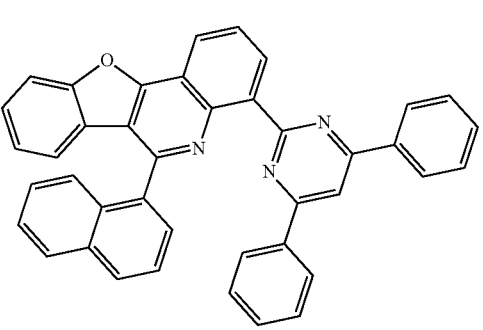
436

437
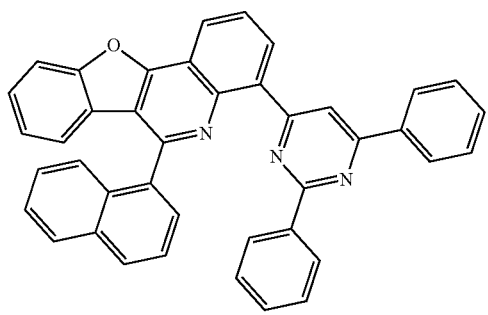
438
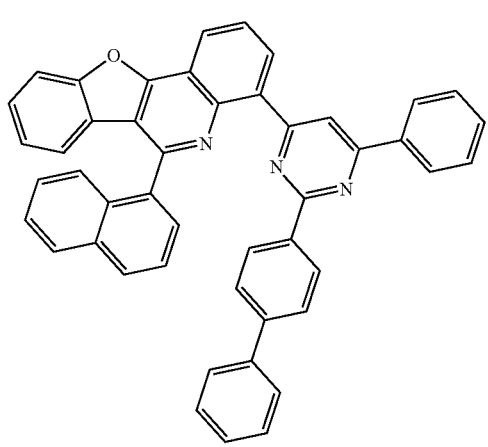
439
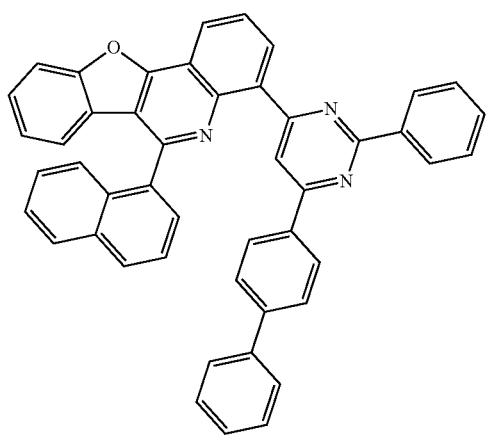
440
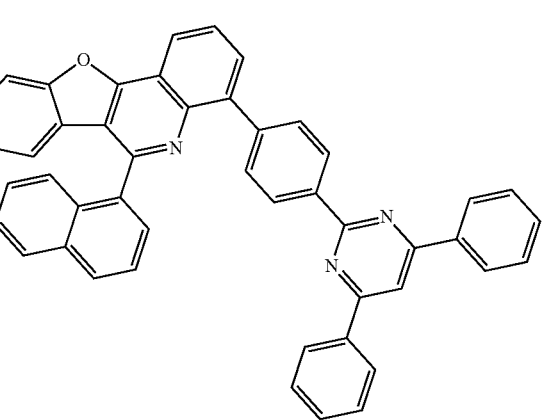
441
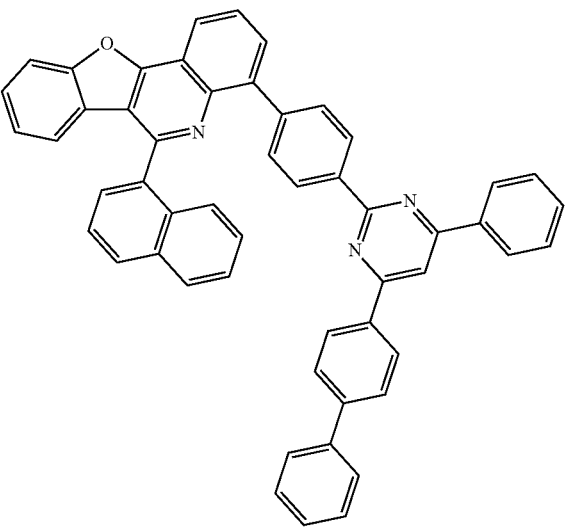
442
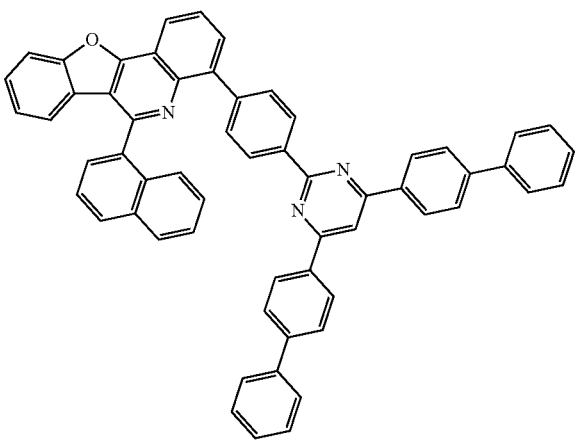
443
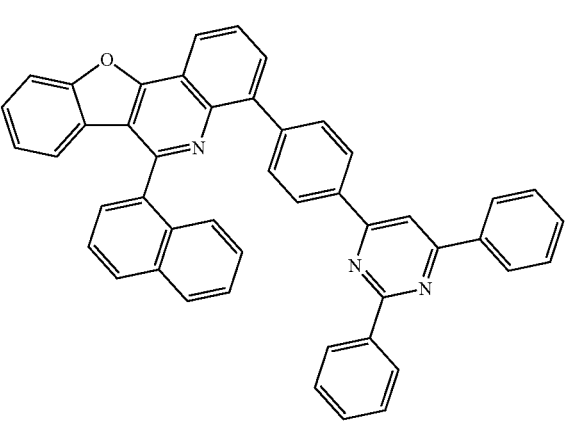 [SMILES: c1ccc(-c2cc(-c3ccc(-c4cccc5c4nc(-c4cccc6ccccc46)c4c6ccccc6sc54)cc3)nc(-c3ccccc3)n2)cc1]

444
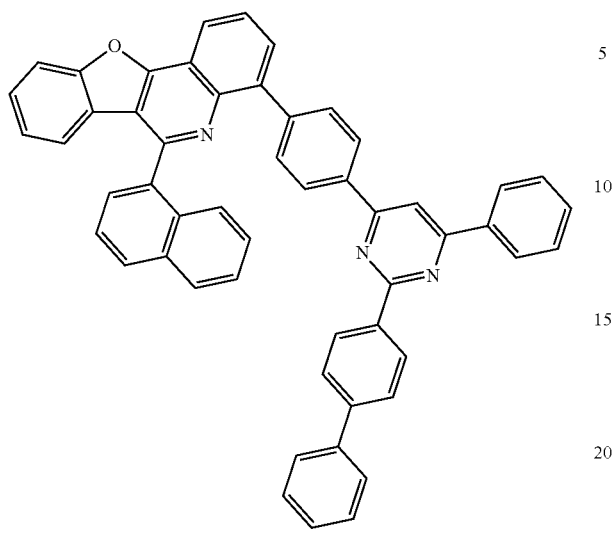
445
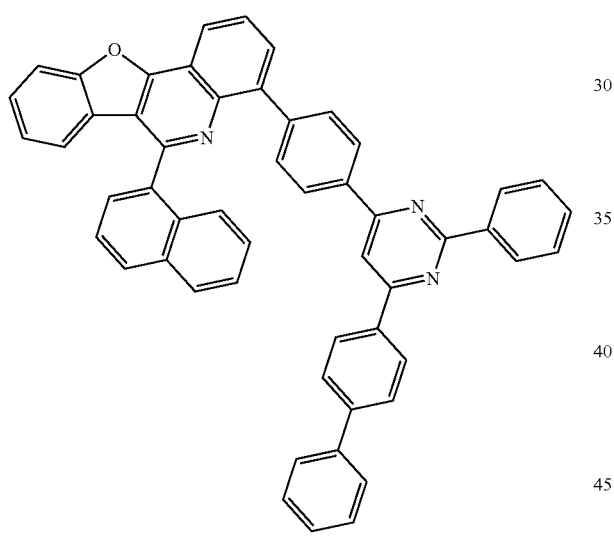
446
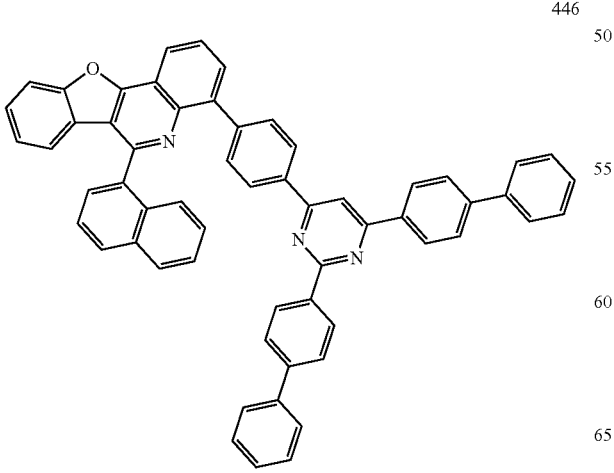
447
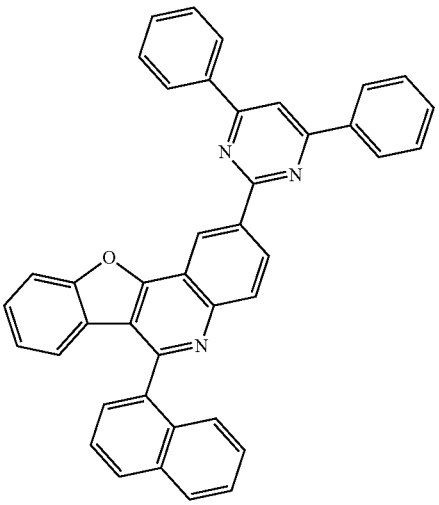
448
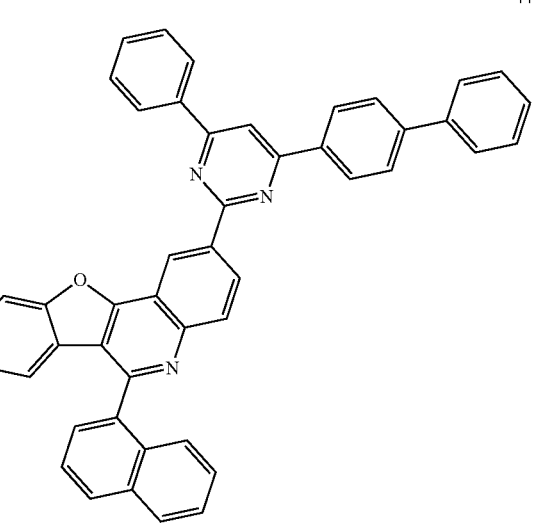
449
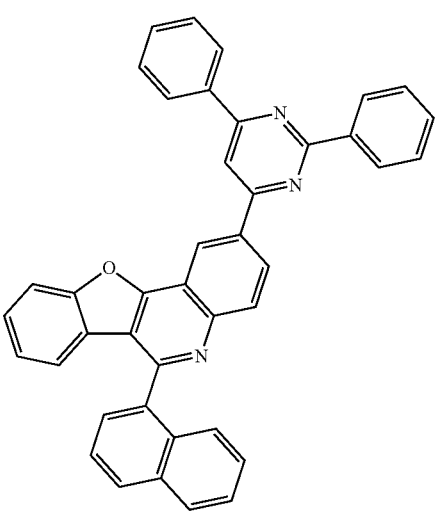

450
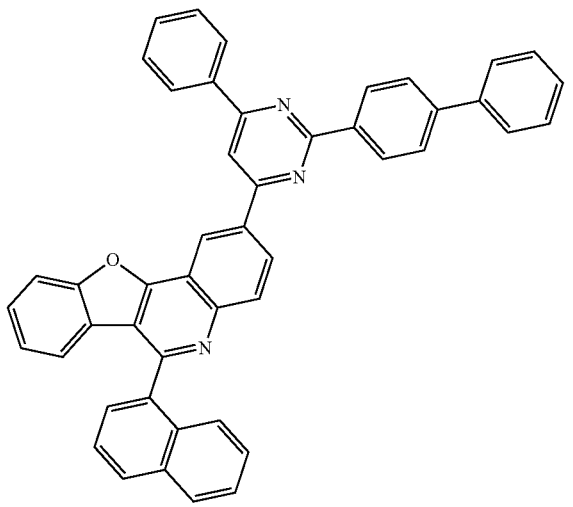
451
453
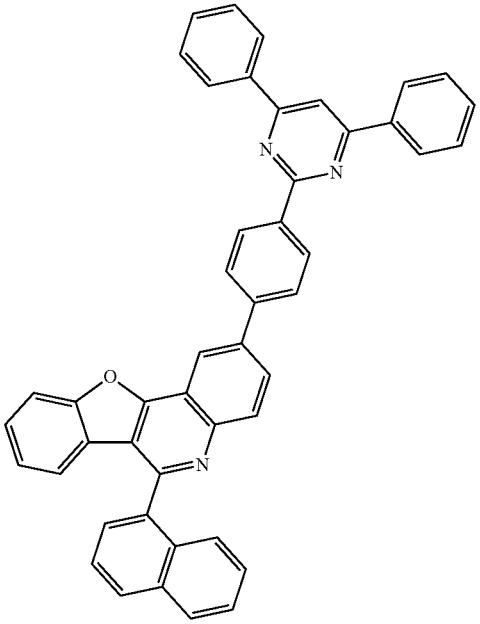
452
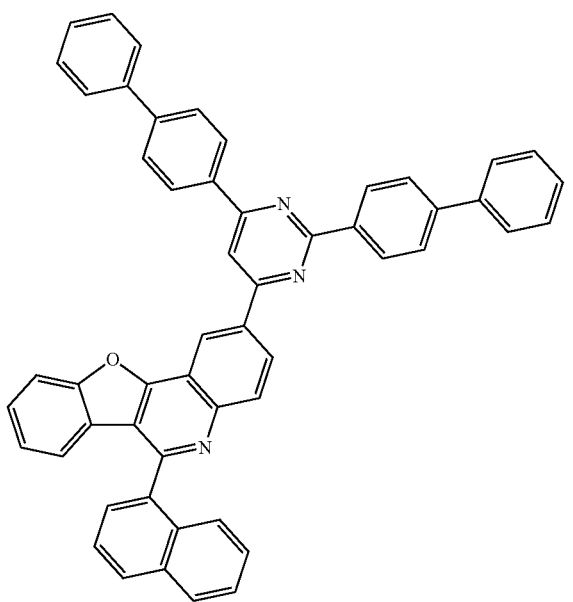
454
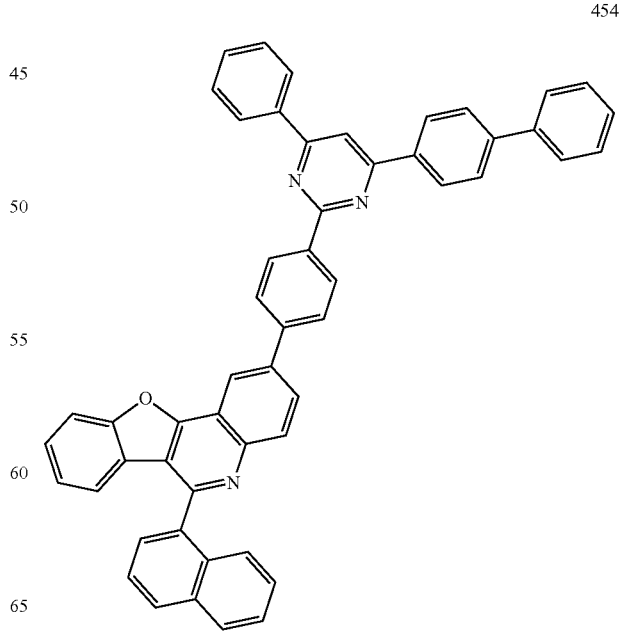

-continued
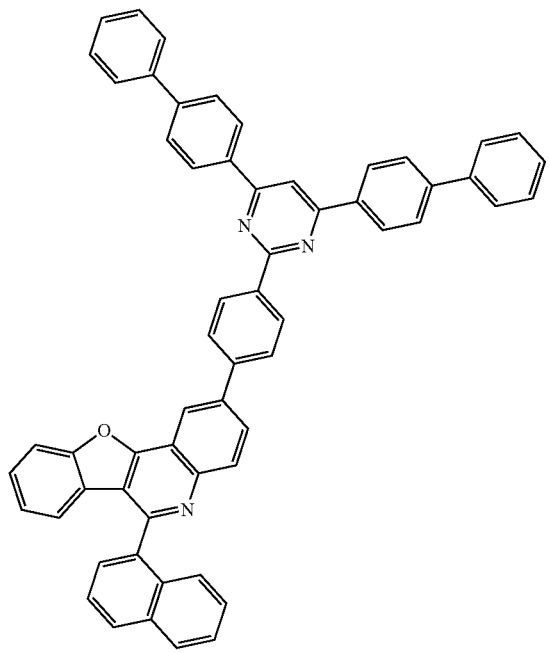
455
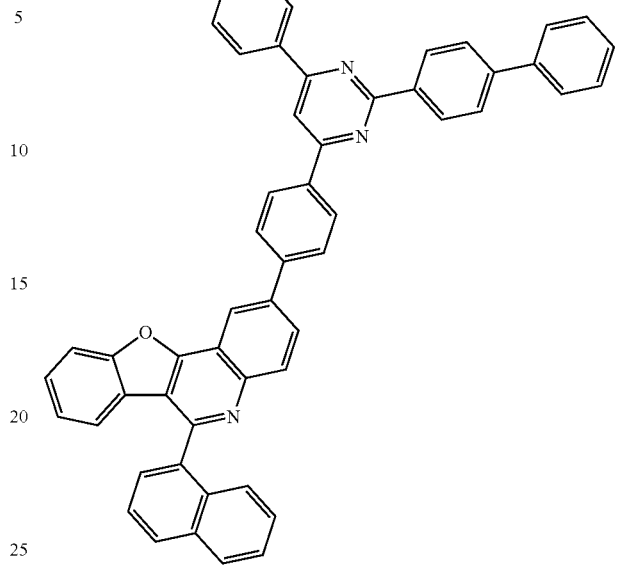
457
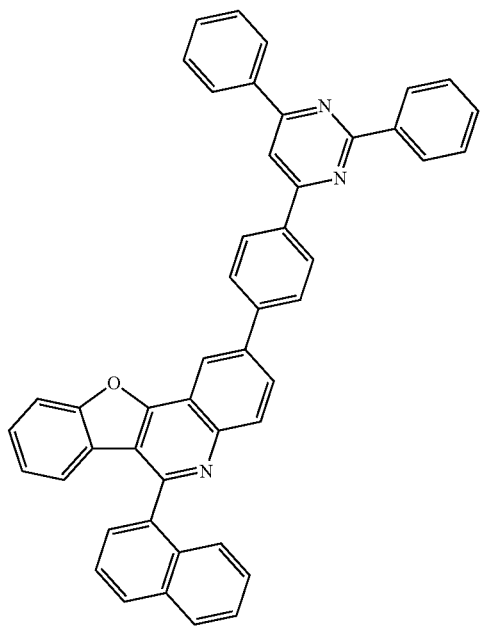
456
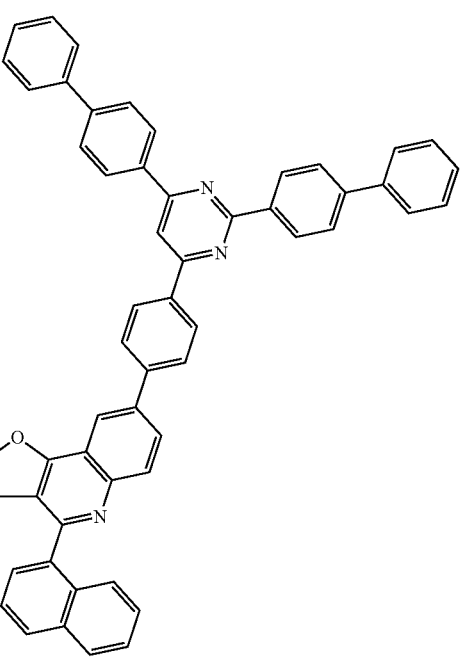
458

459
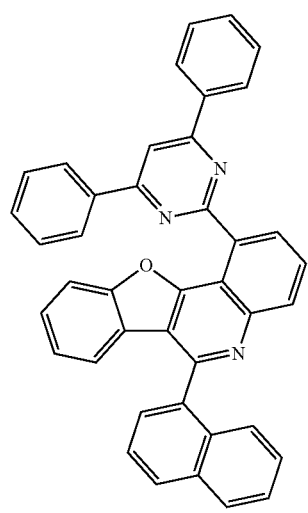
460
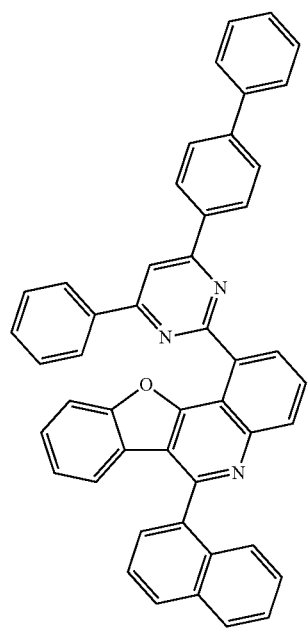
461
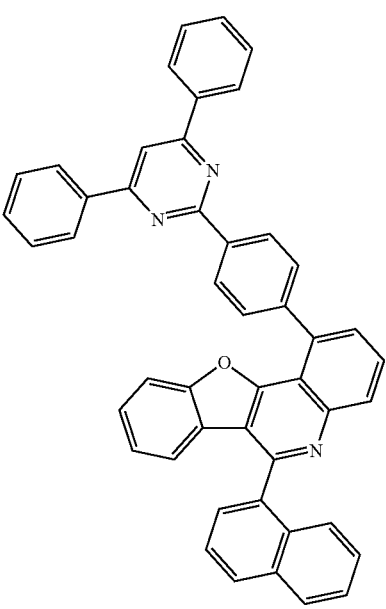
462
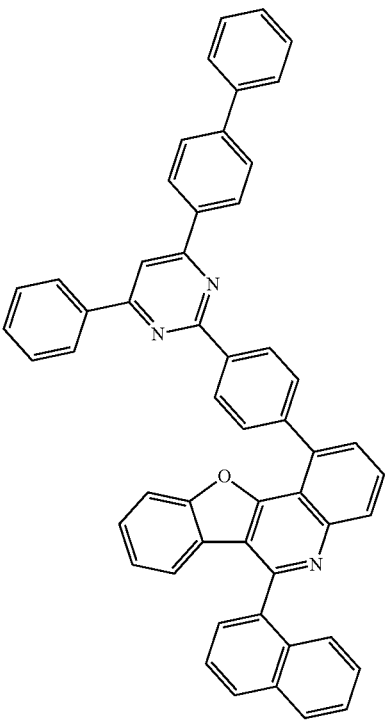

463
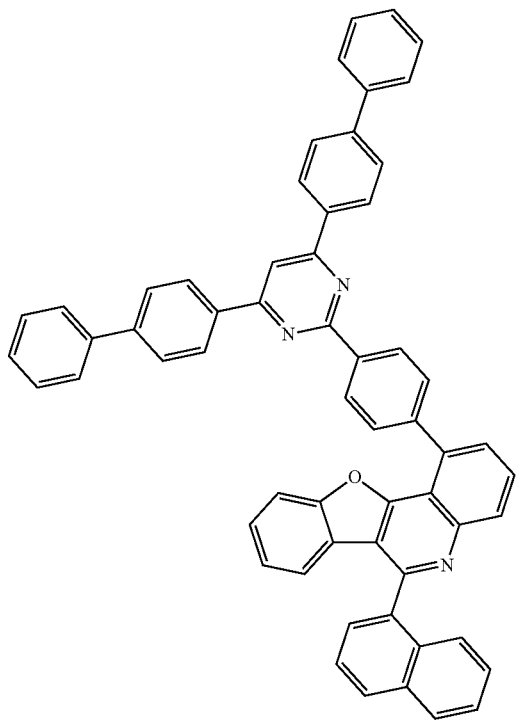
464
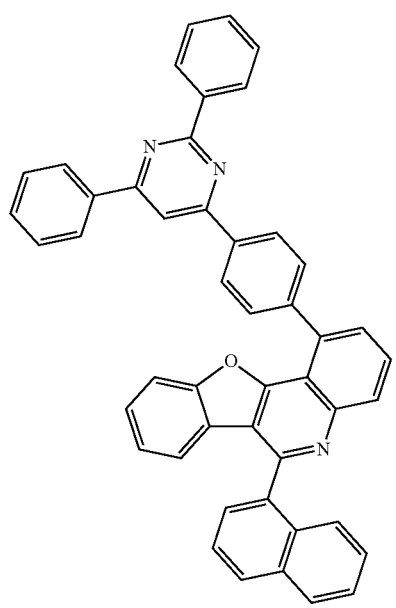
465
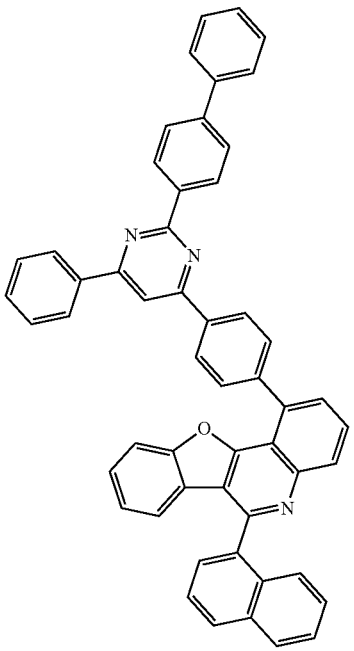
466
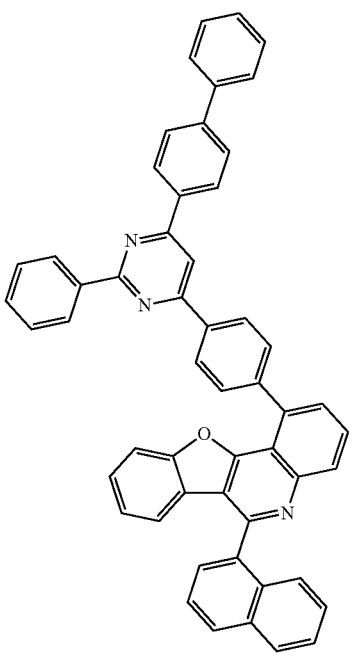

201
-continued
467
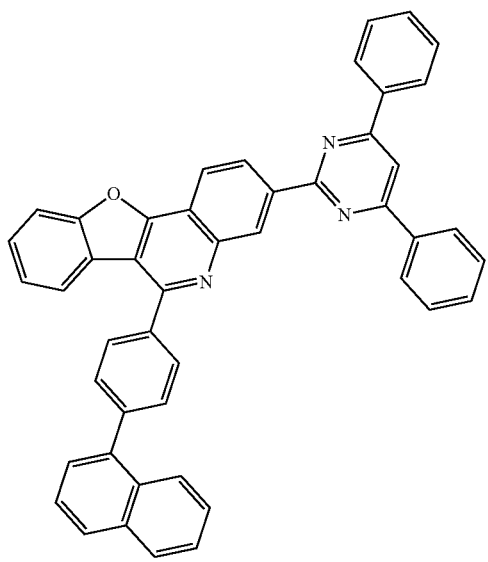
468
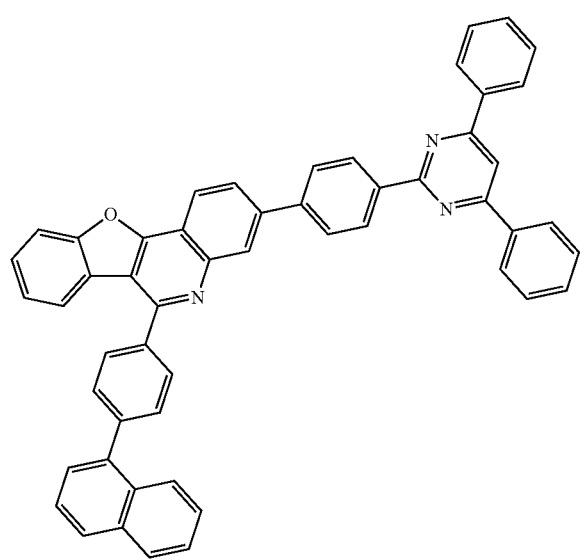
469
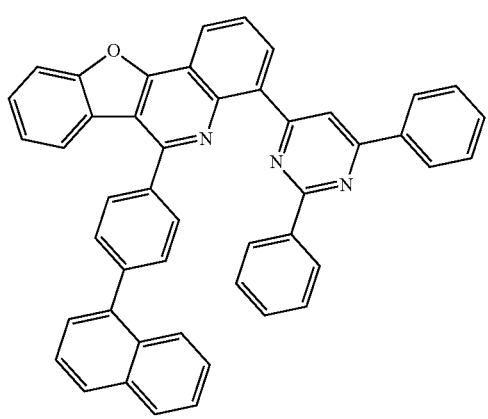
202
-continued
470
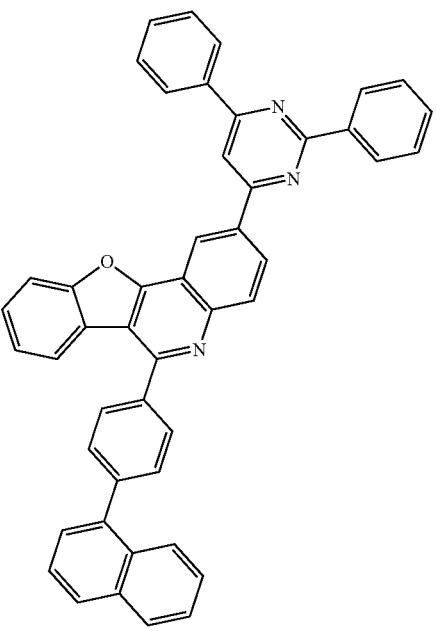
471
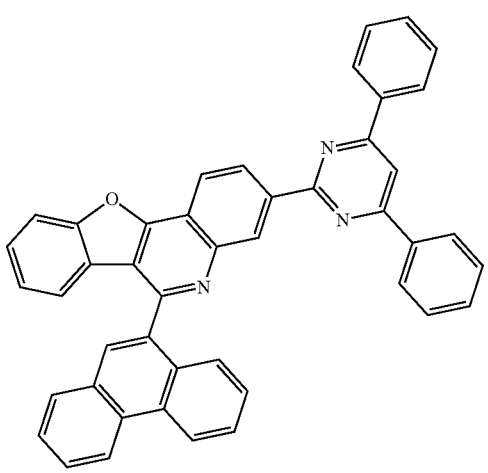
472
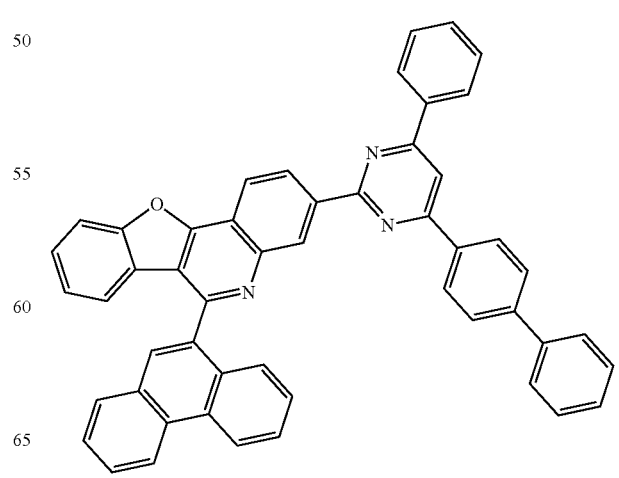

203
-continued
473
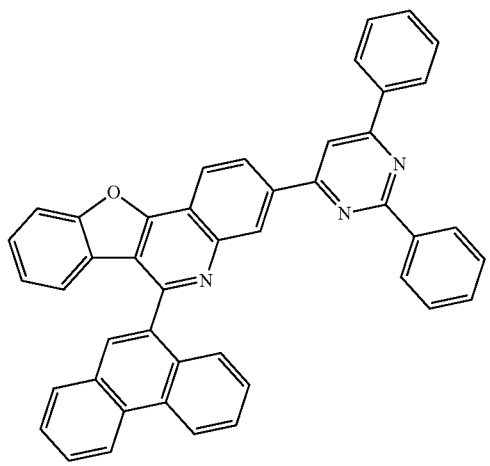
474
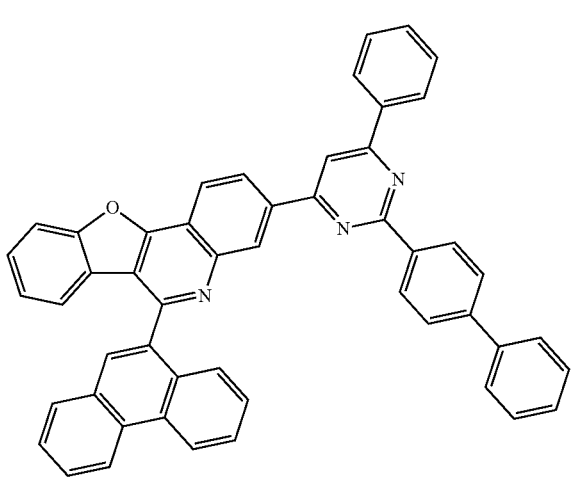
475
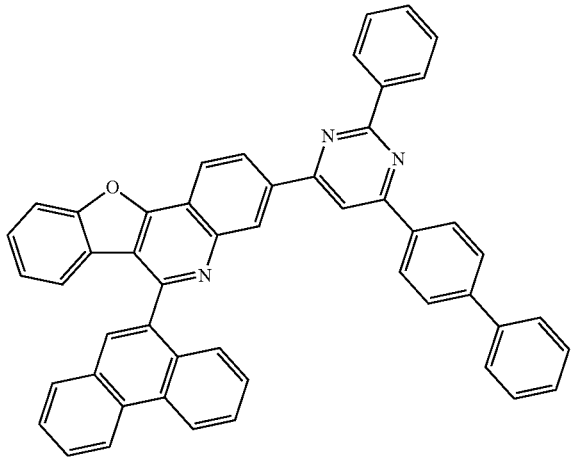
204
-continued
476
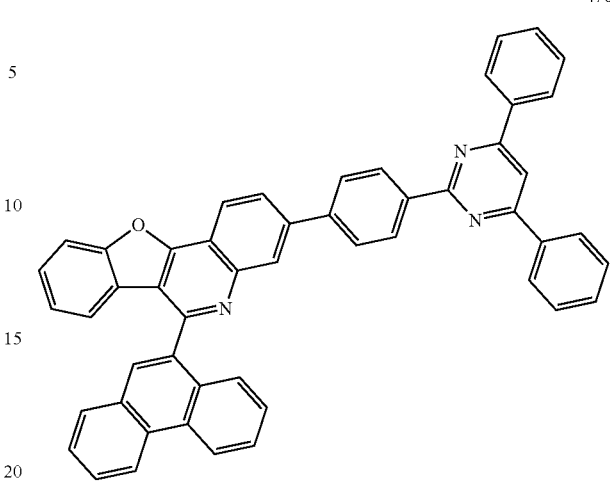
478
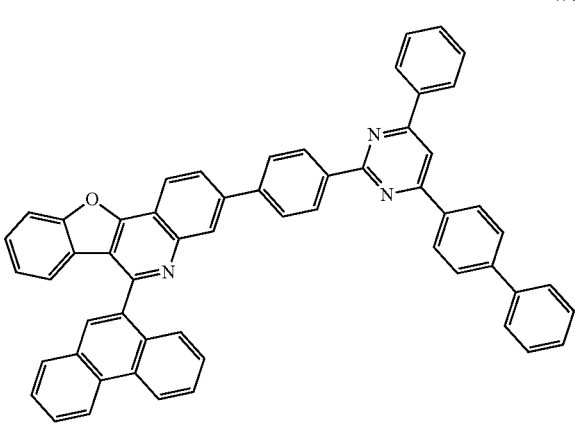
479
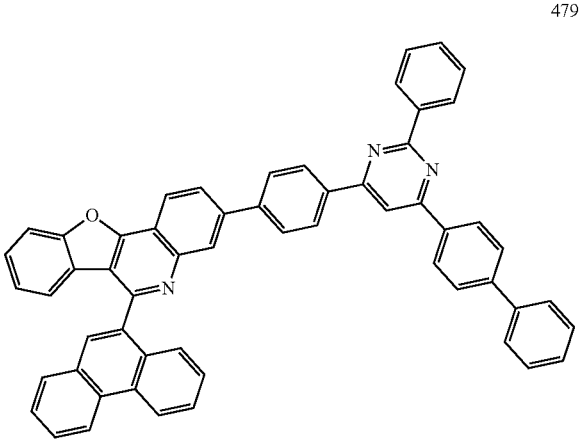

480
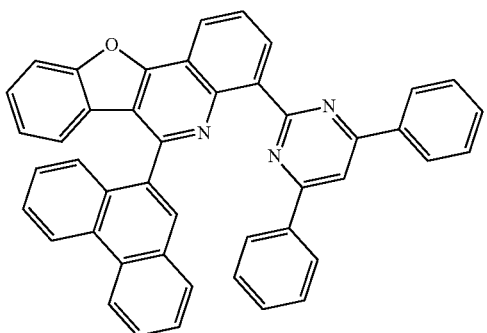
481
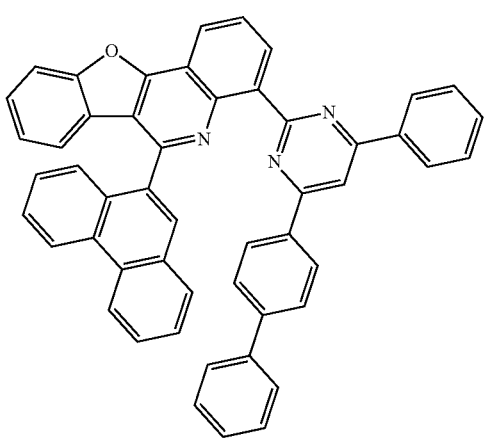
482
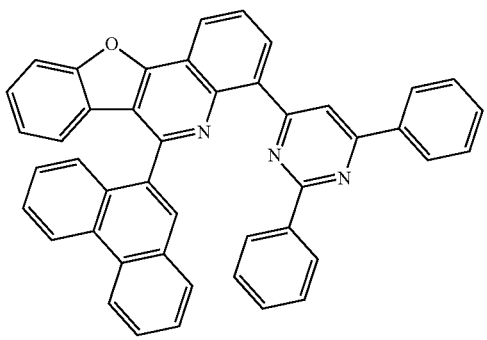
483
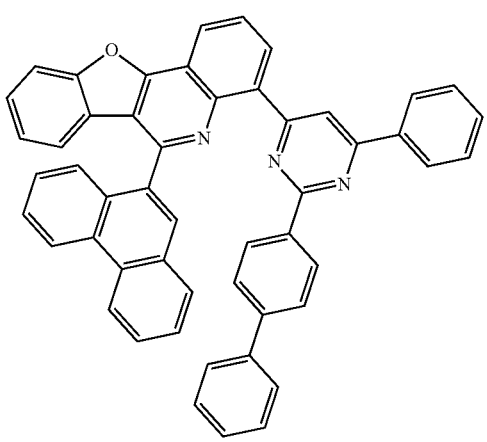
484
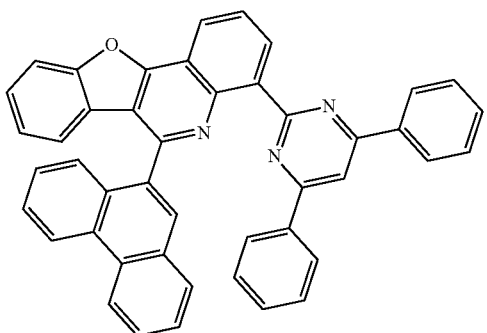
485
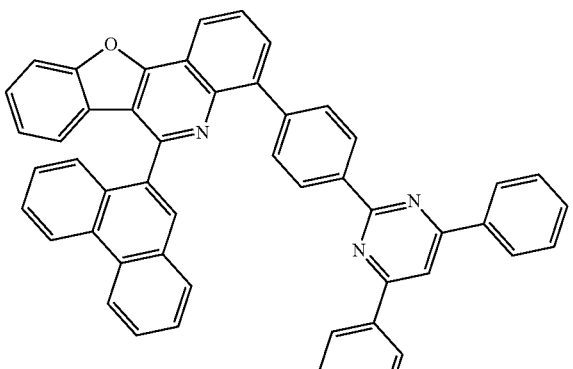
486
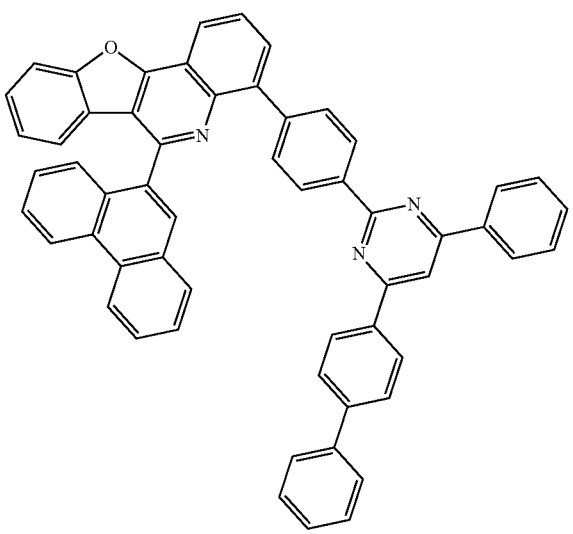

-continued
487
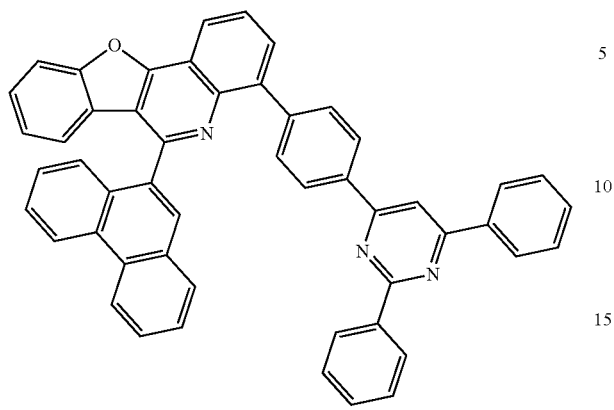
488
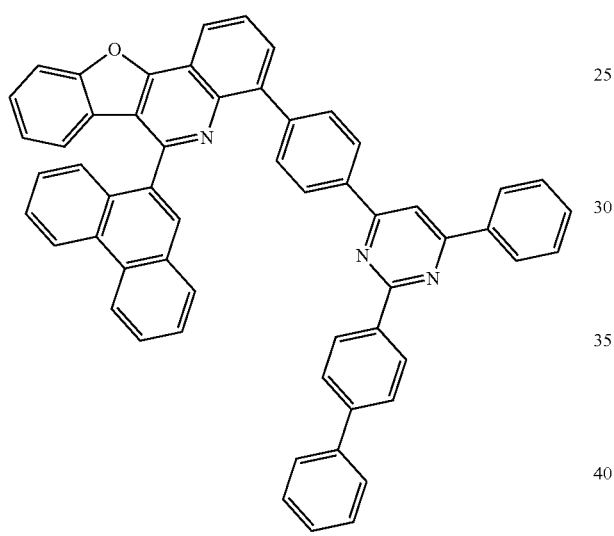
489
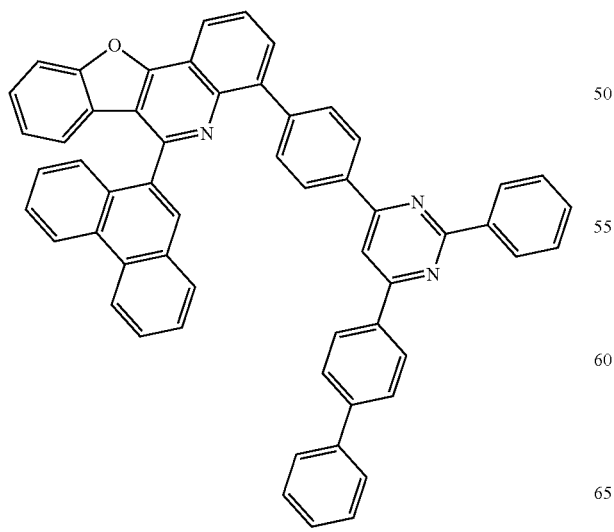
-continued
490
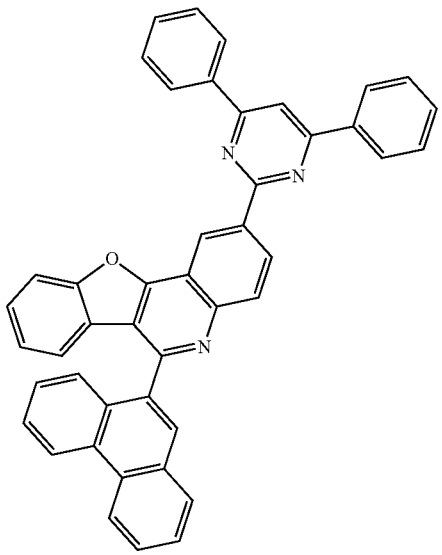
491
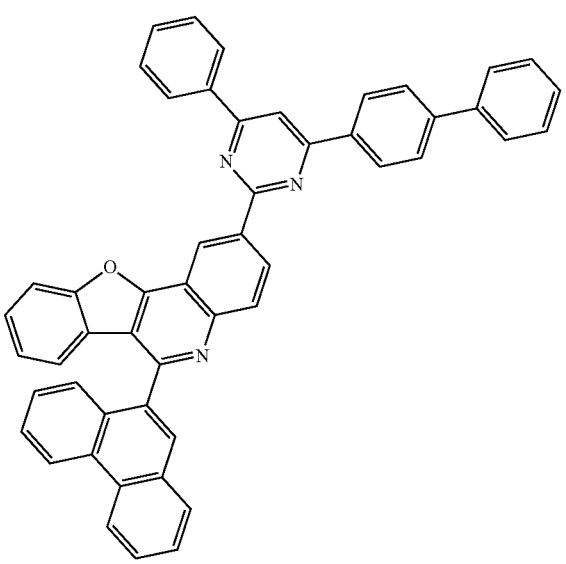

492
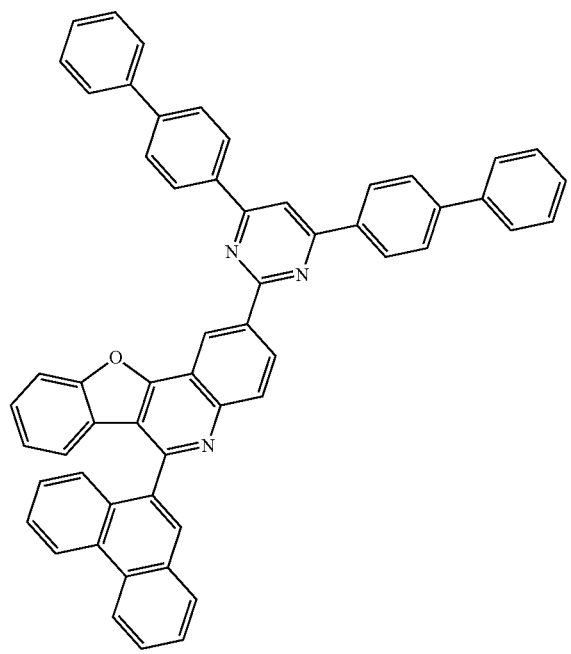
494
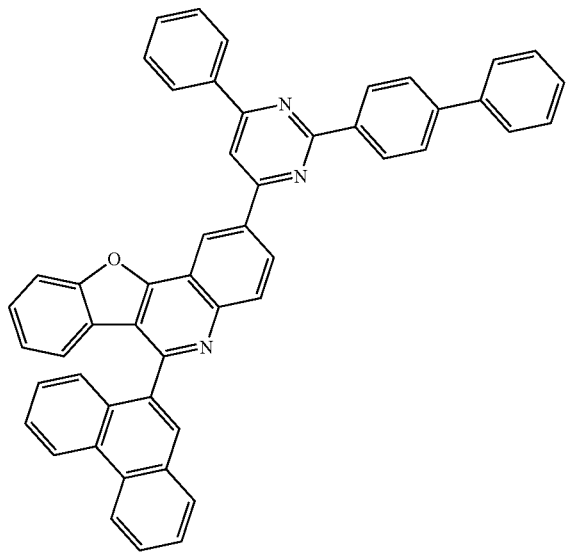
493
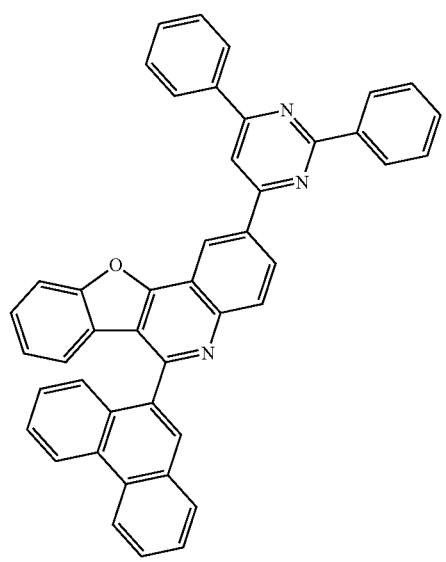
495
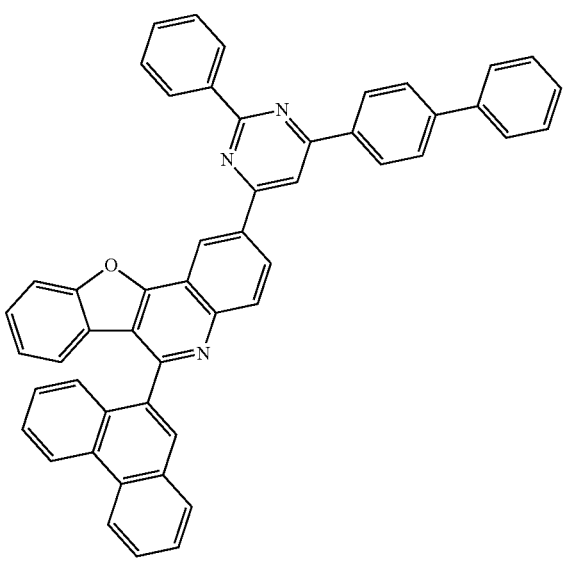

-continued
496
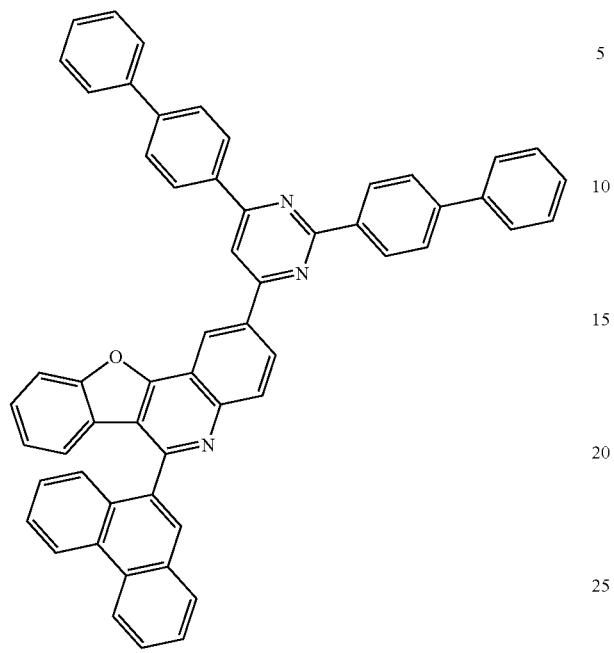
497
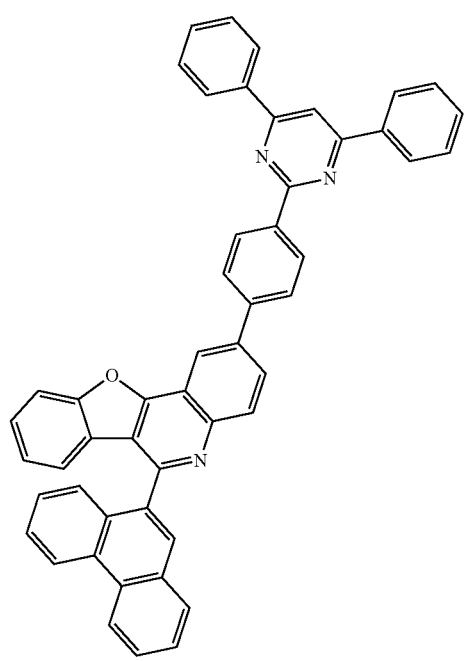
-continued
498
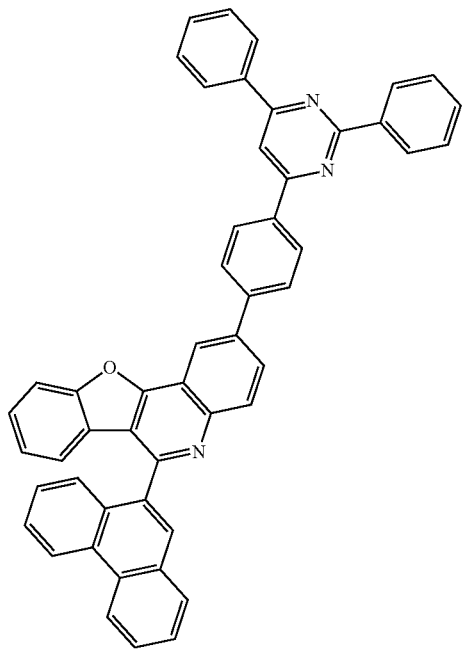
499
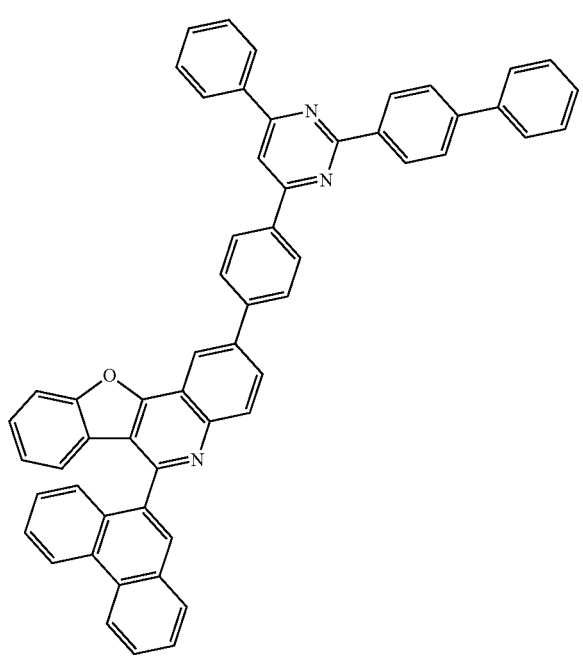

213
-continued
500
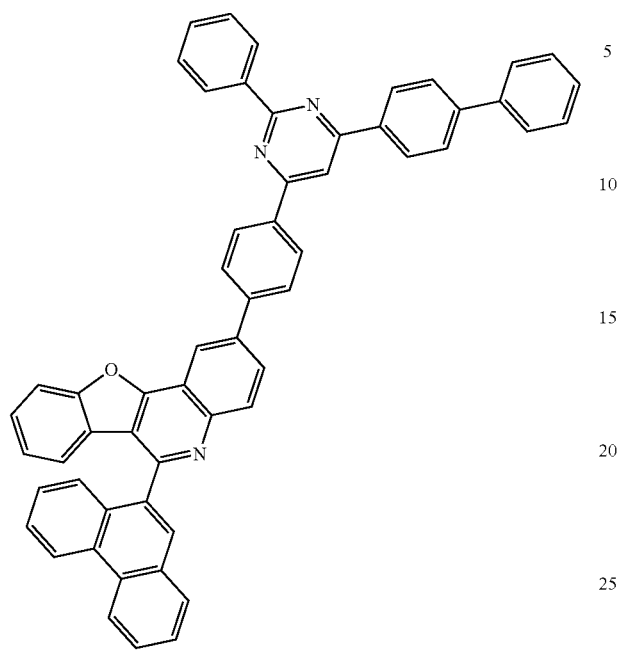
501
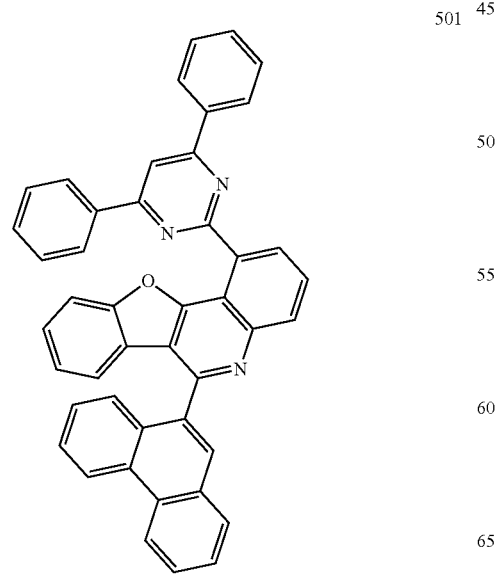
214
-continued
502
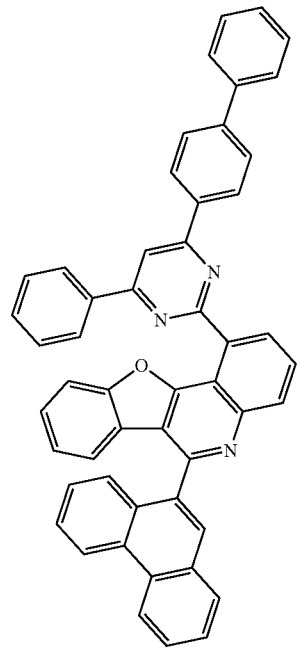
503
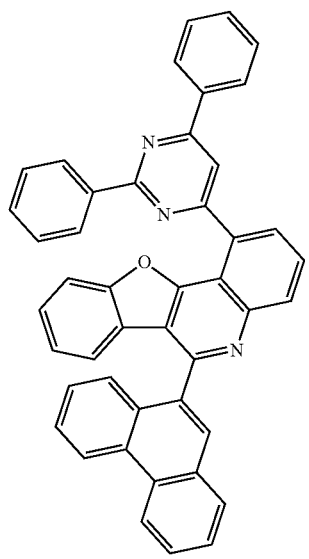

-continued
504
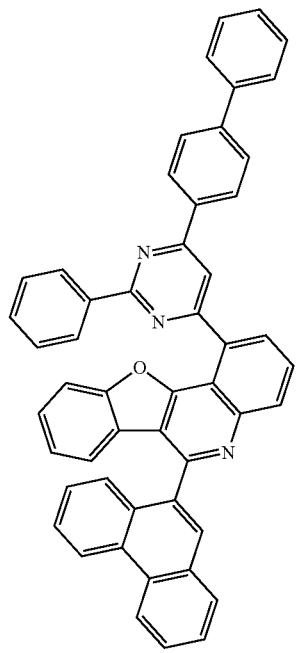
506
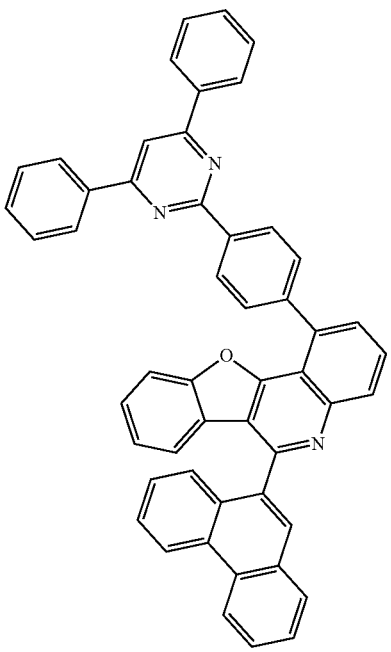
505
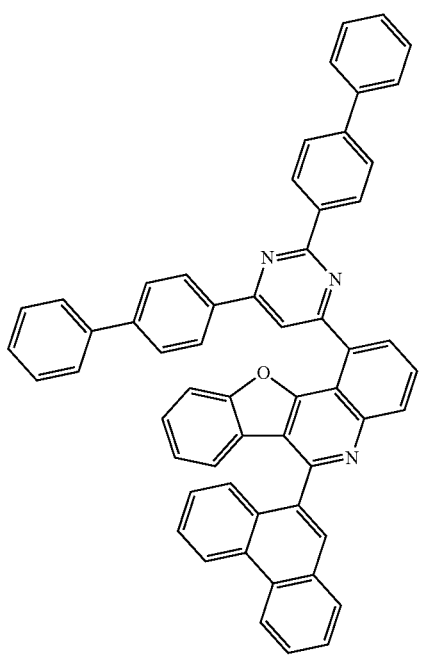
507
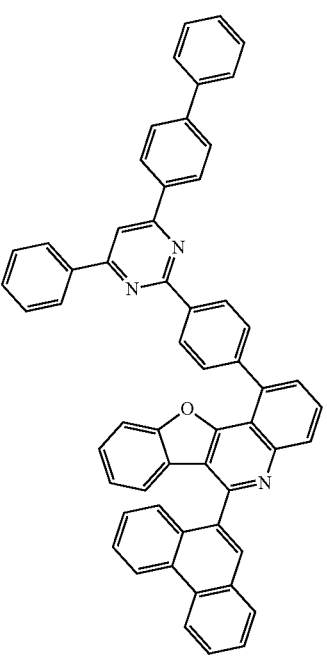

-continued
508
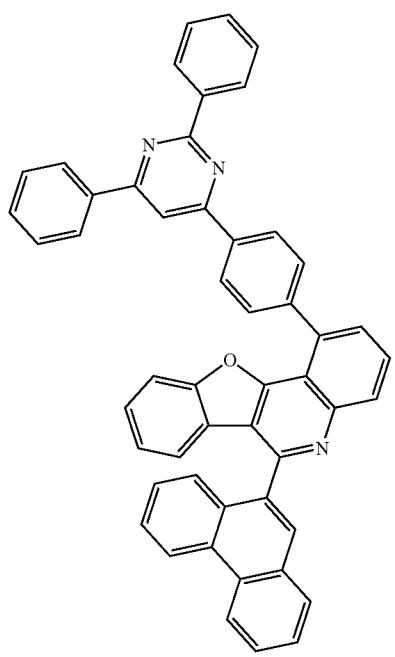
509
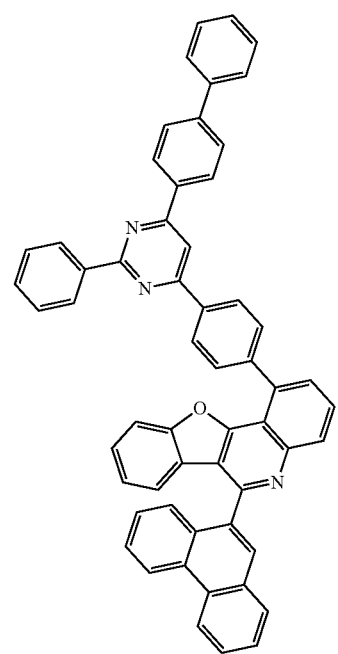
-continued
510
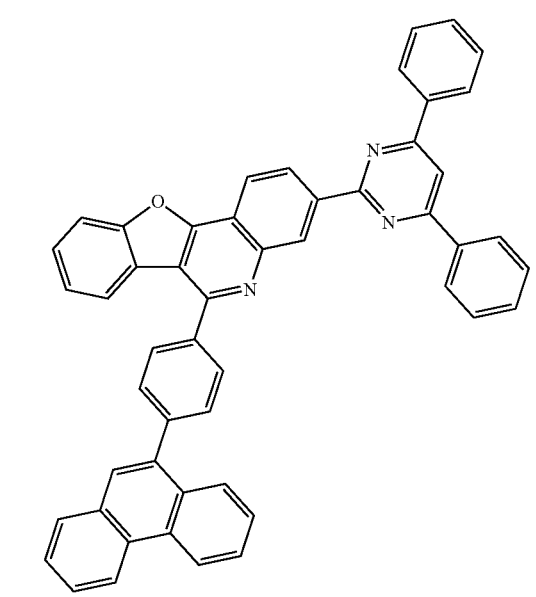
511
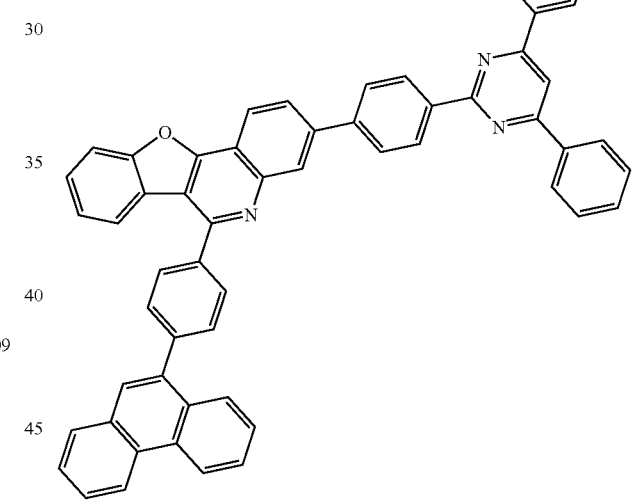
512
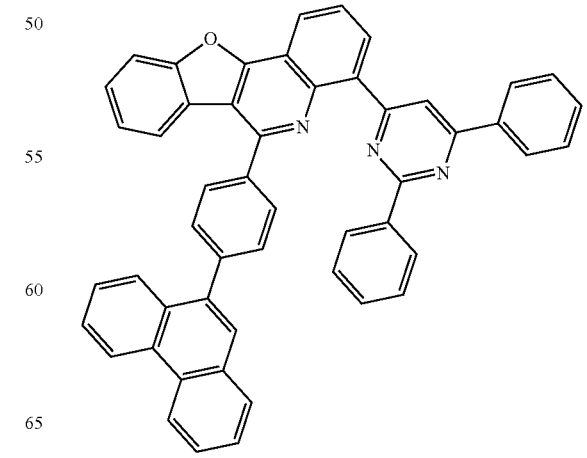

513
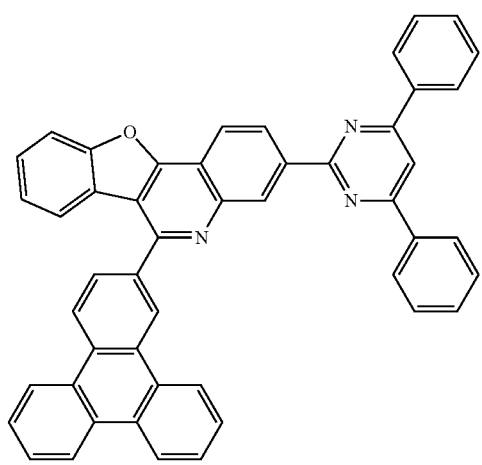
514
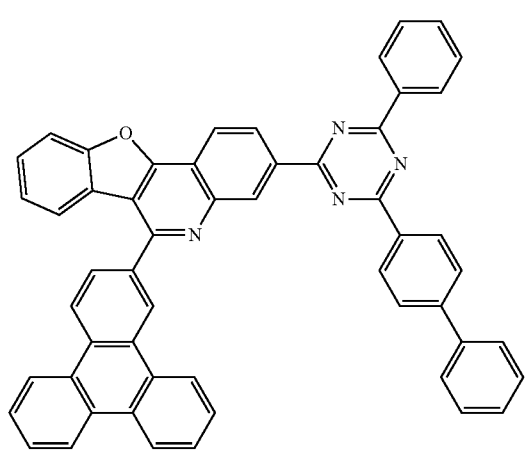
515
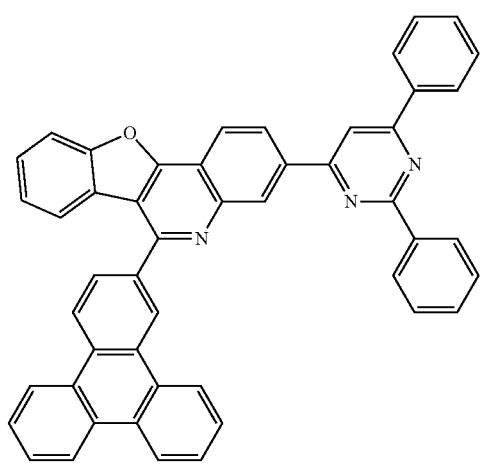
516
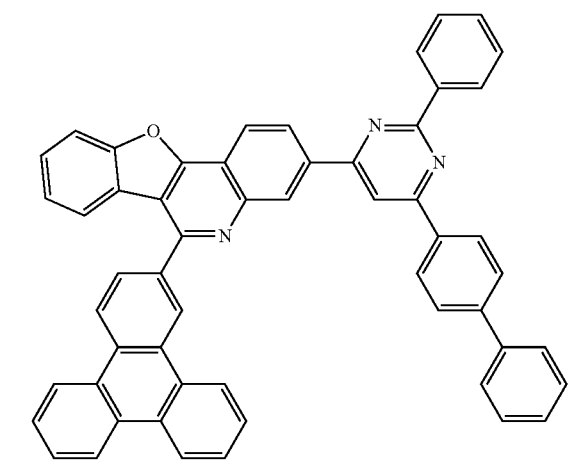
517
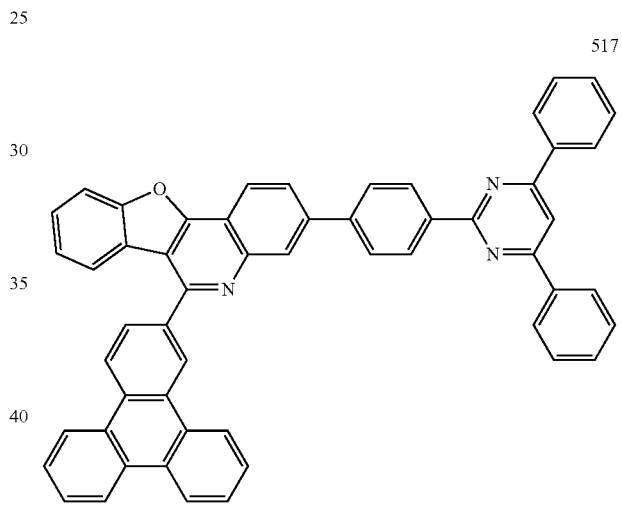
518
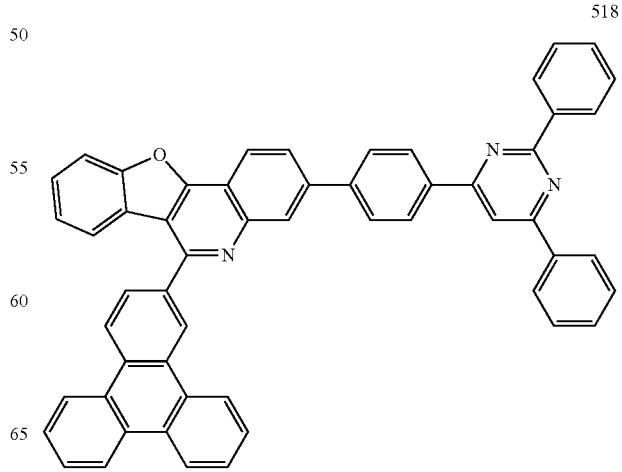

-continued
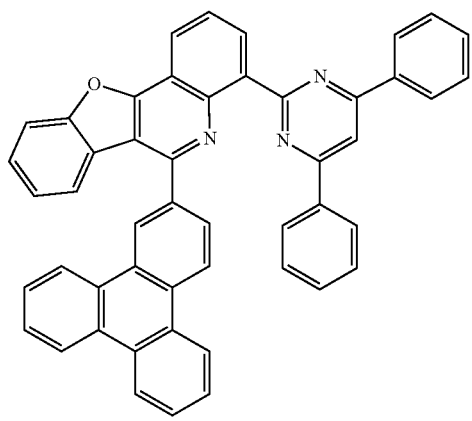
519
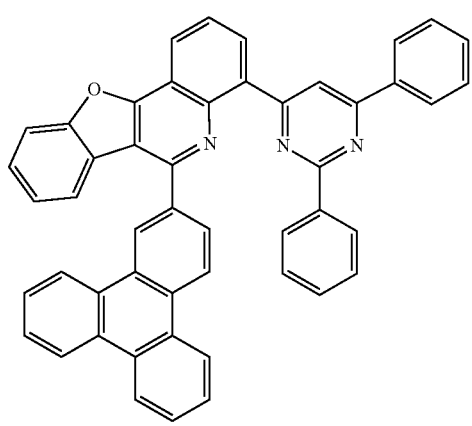
520
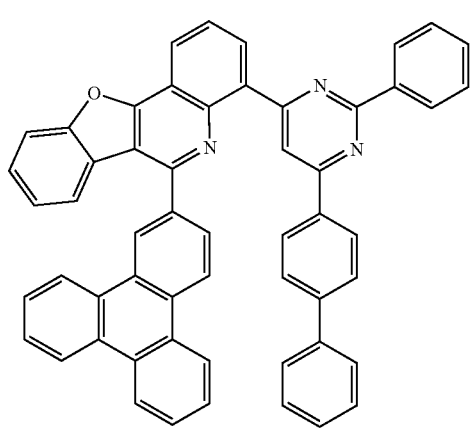
521
-continued
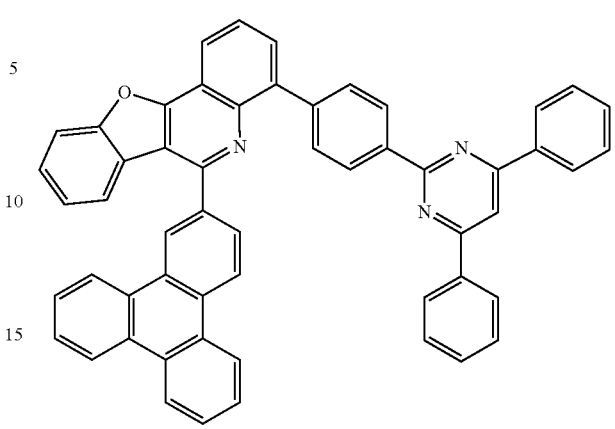
522
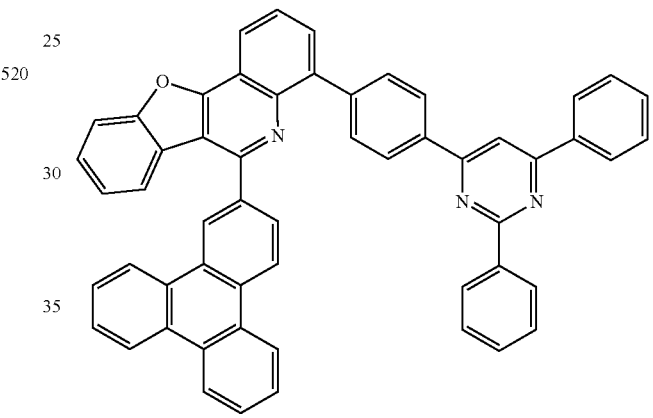
523
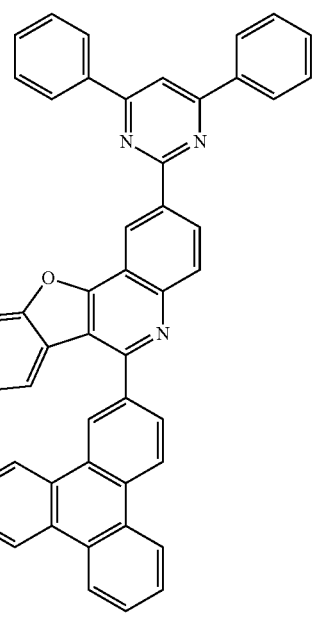
524

223
-continued
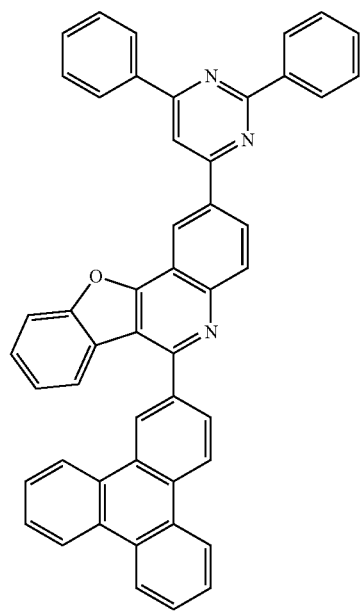
525
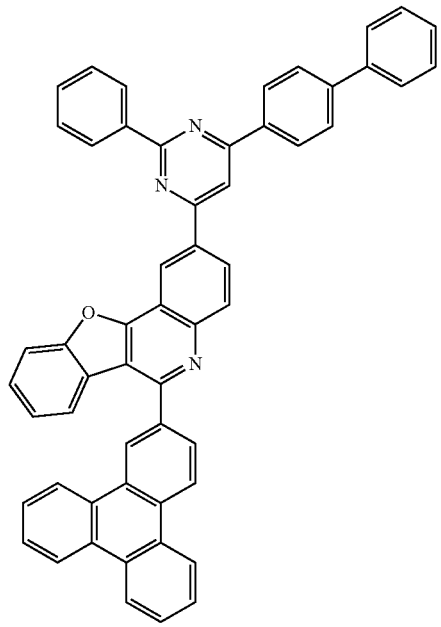
526
224
-continued
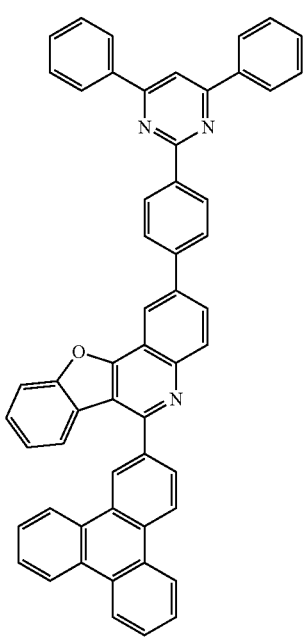
527
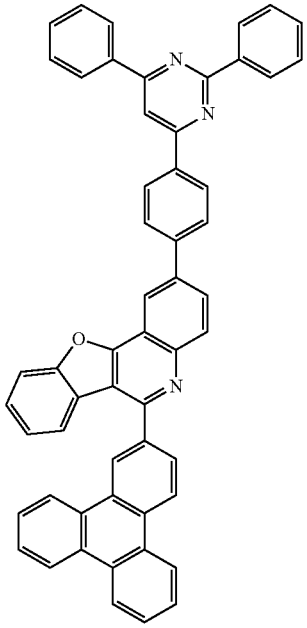
528

225
-continued
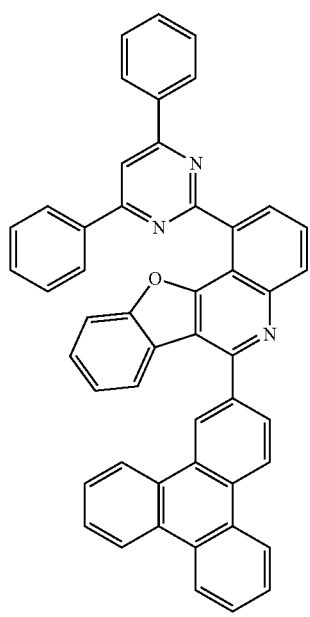
529
226
-continued
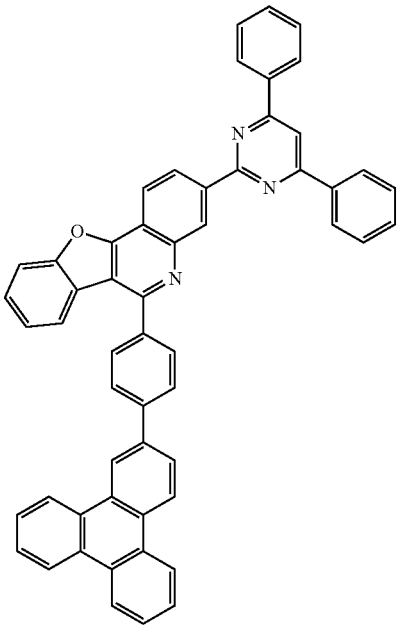
531
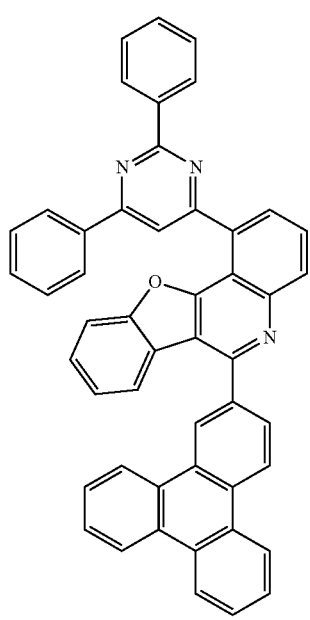
530
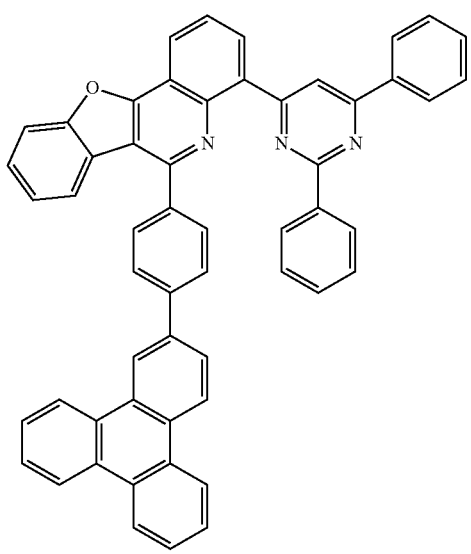
532

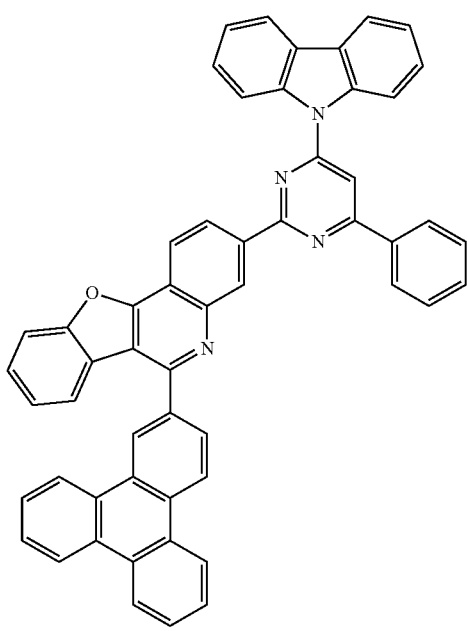
533
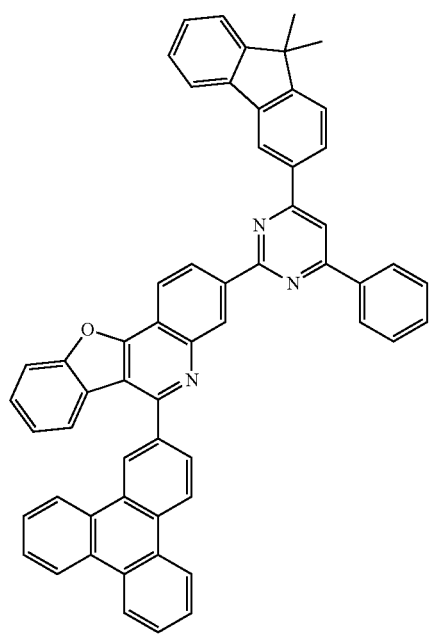
534
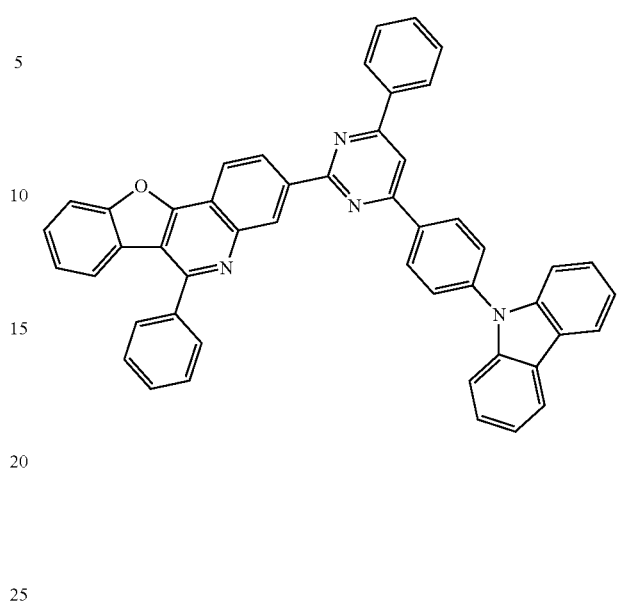
535
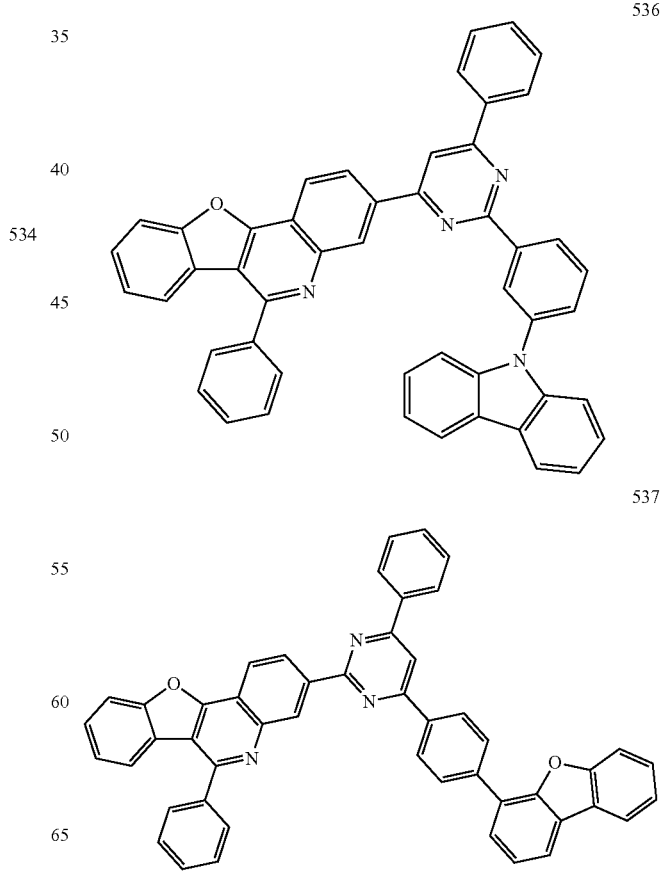
536
537

229
-continued
538
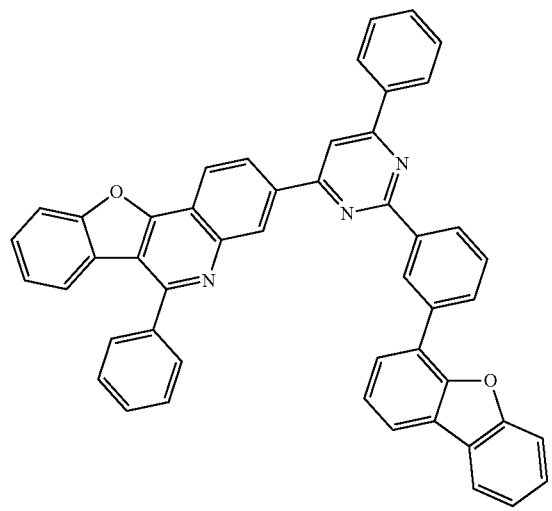
539
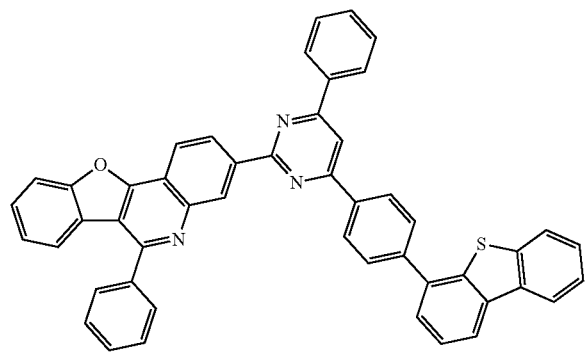
540
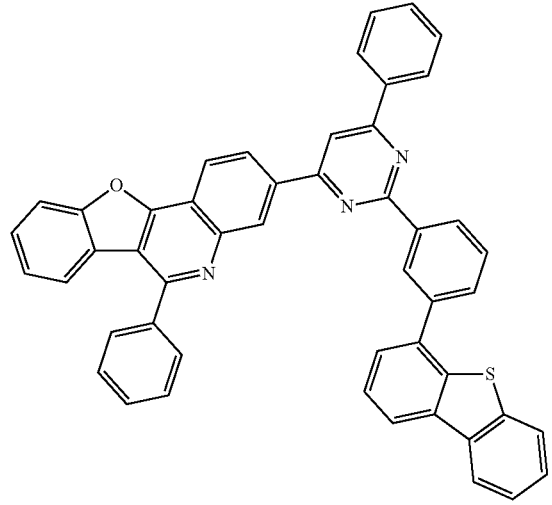
230
-continued
541
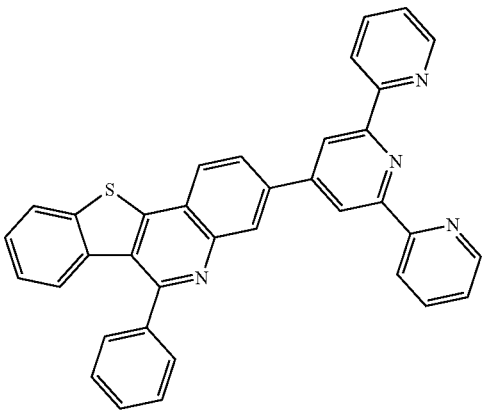
542
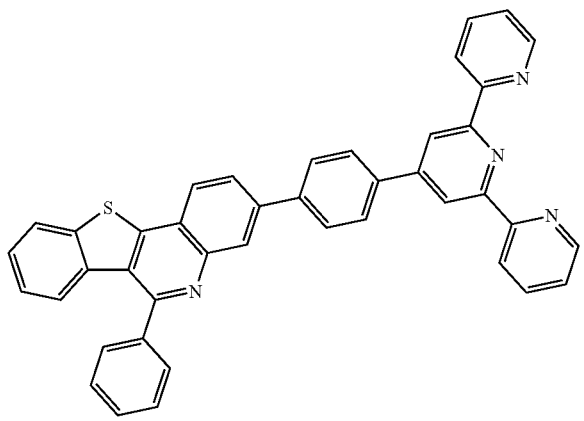
543
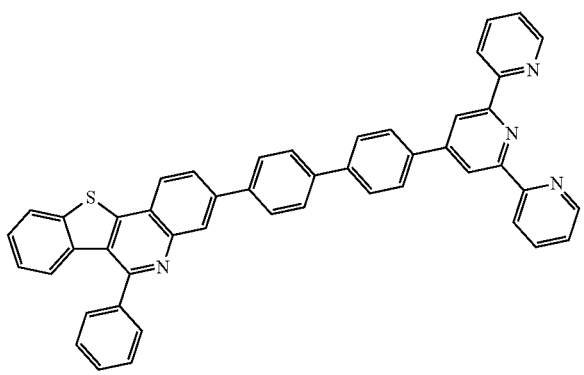
544
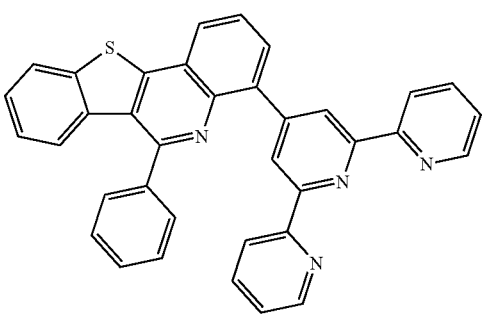

-continued
545
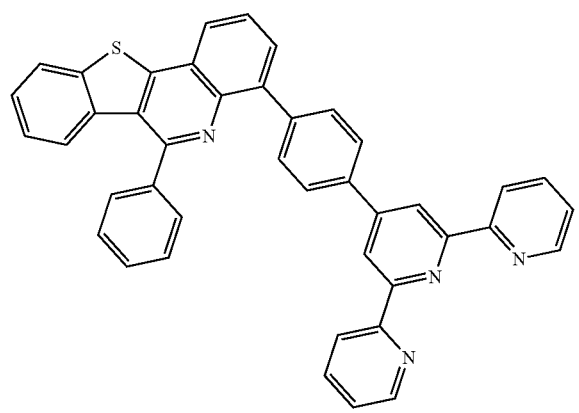
546
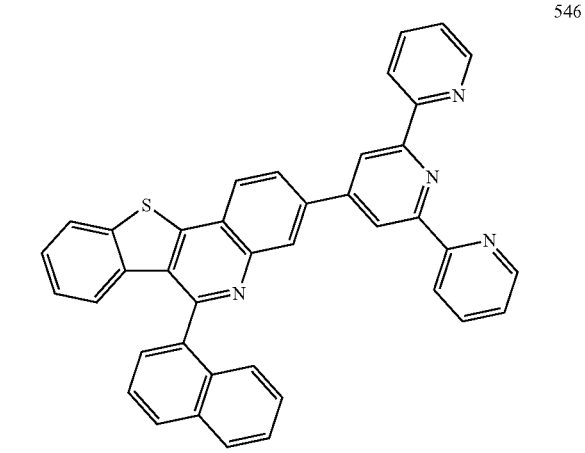
547
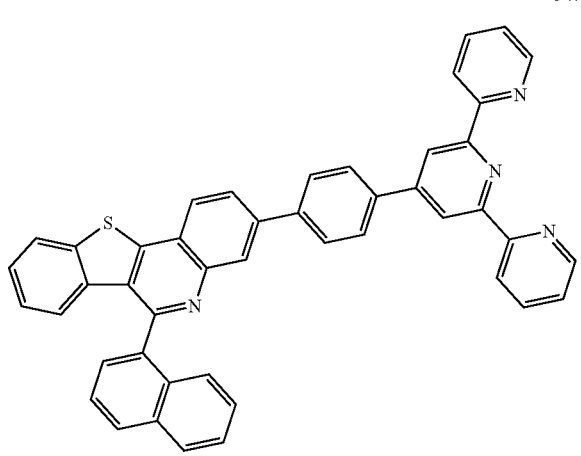
548
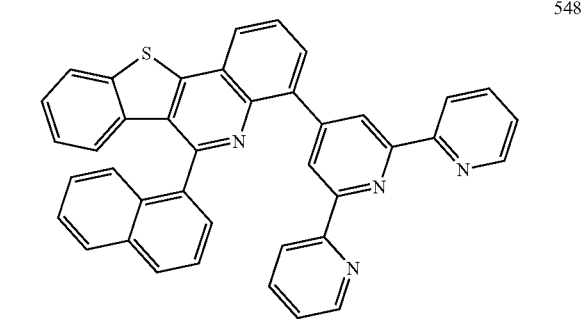
-continued
549
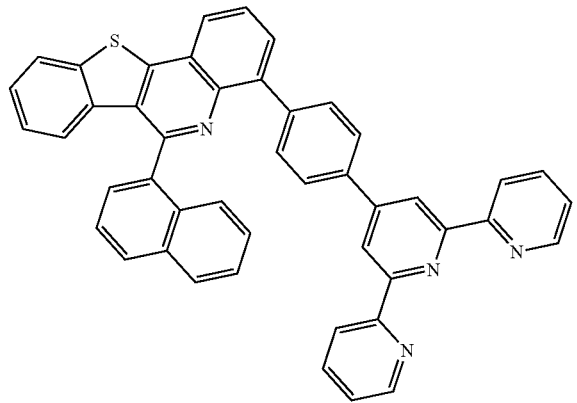
550
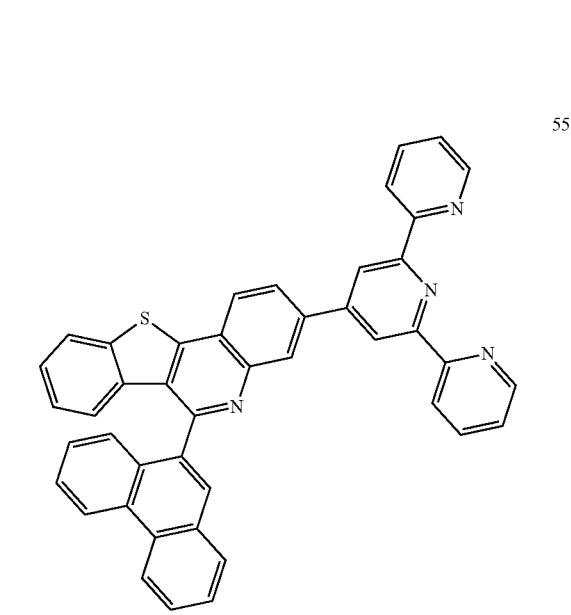
551
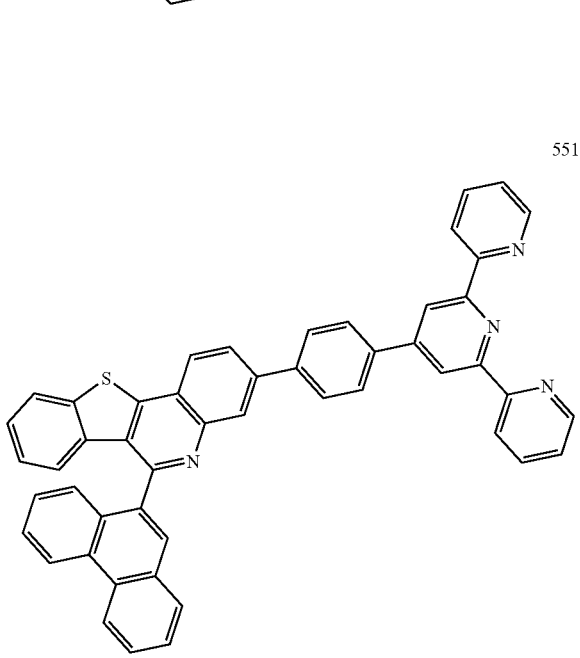

-continued
552
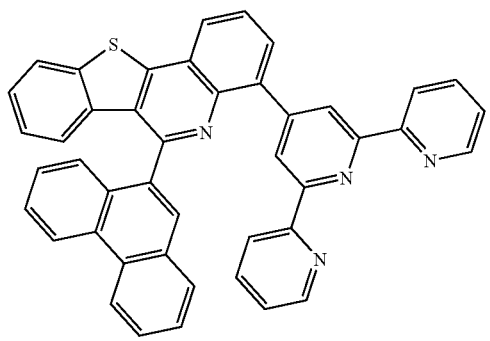
553
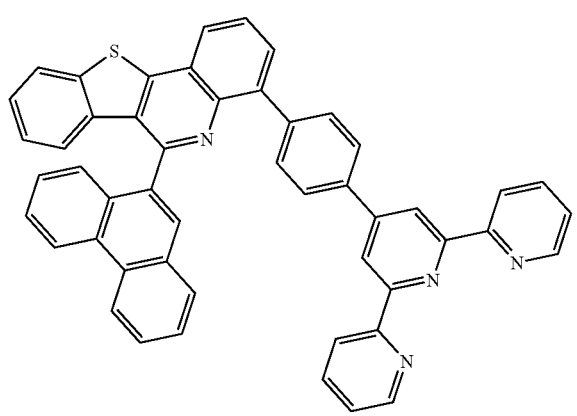
554
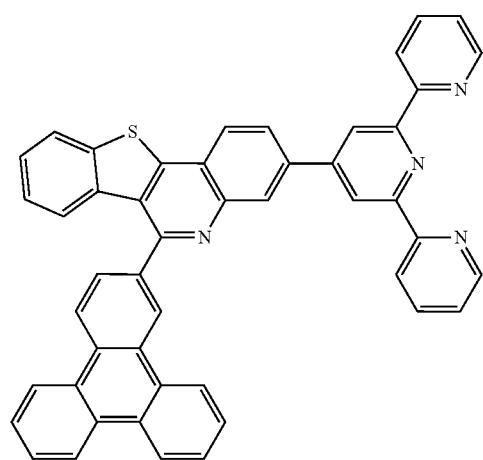
-continued
555
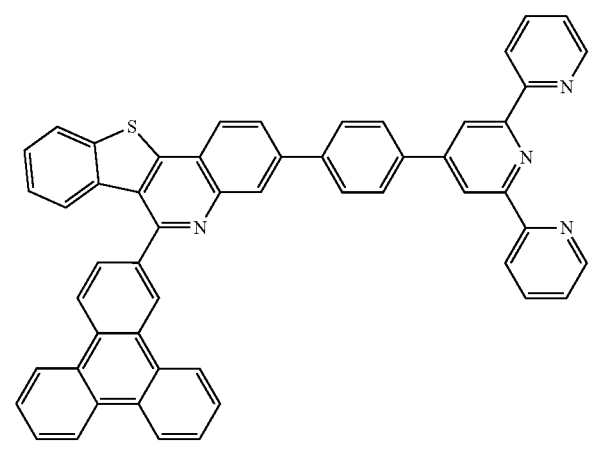
556
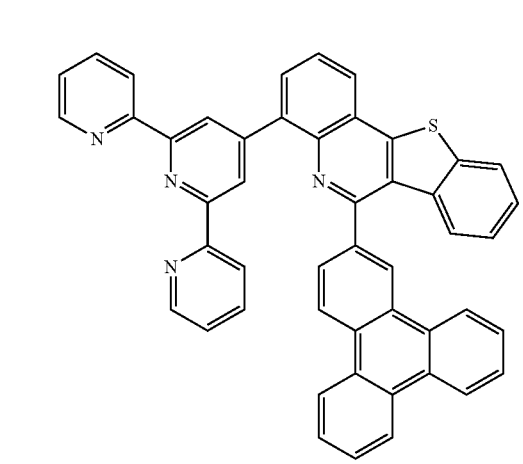
557
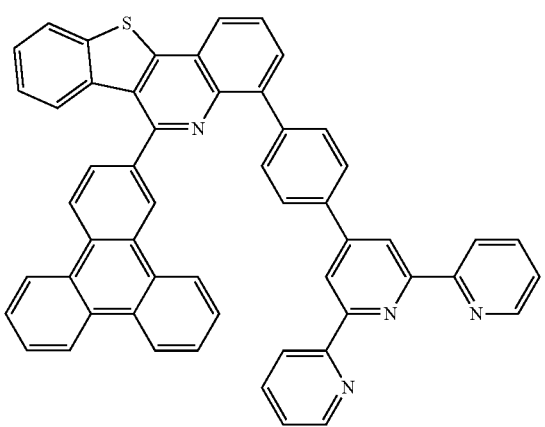

558
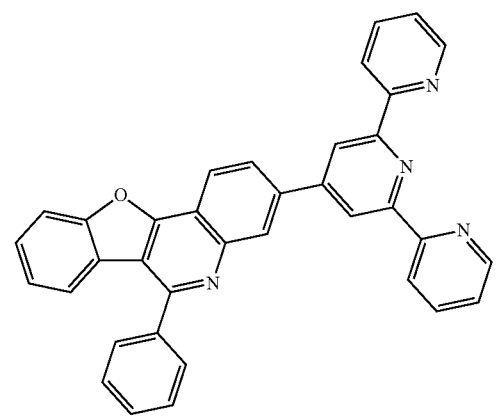
559
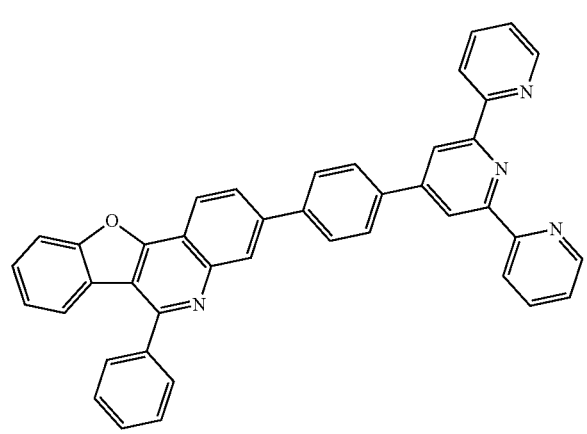
560
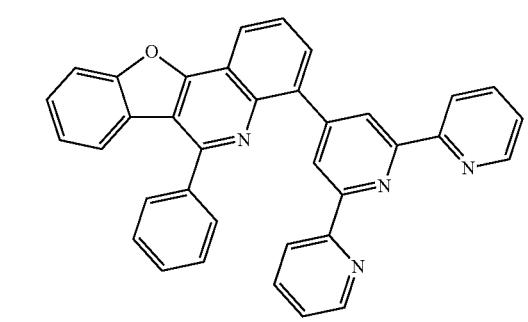
561
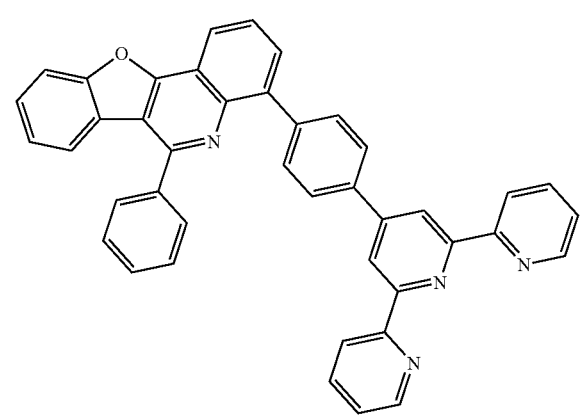
562
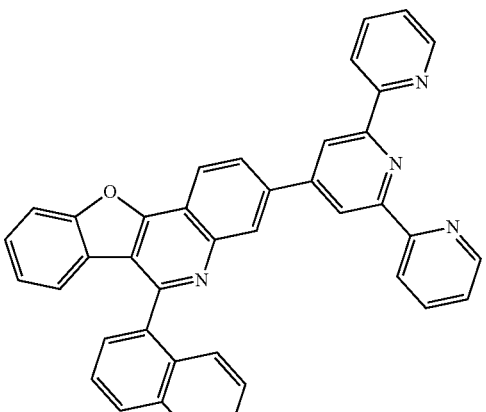
563
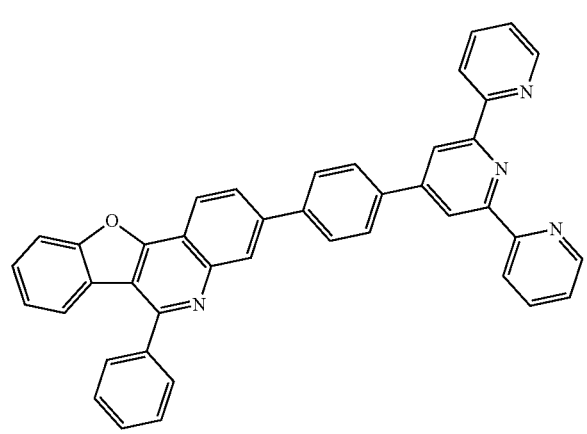
564
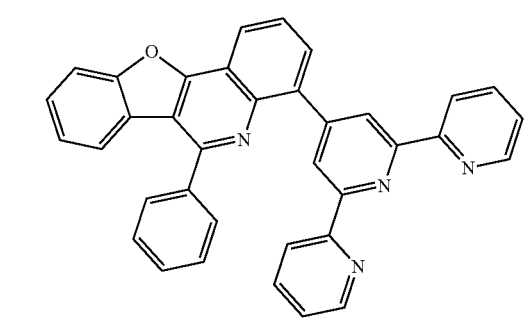
565
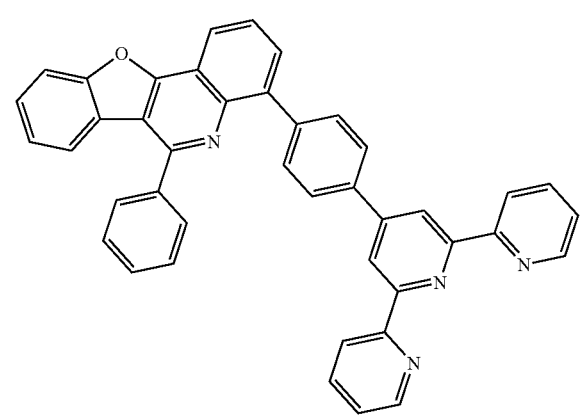

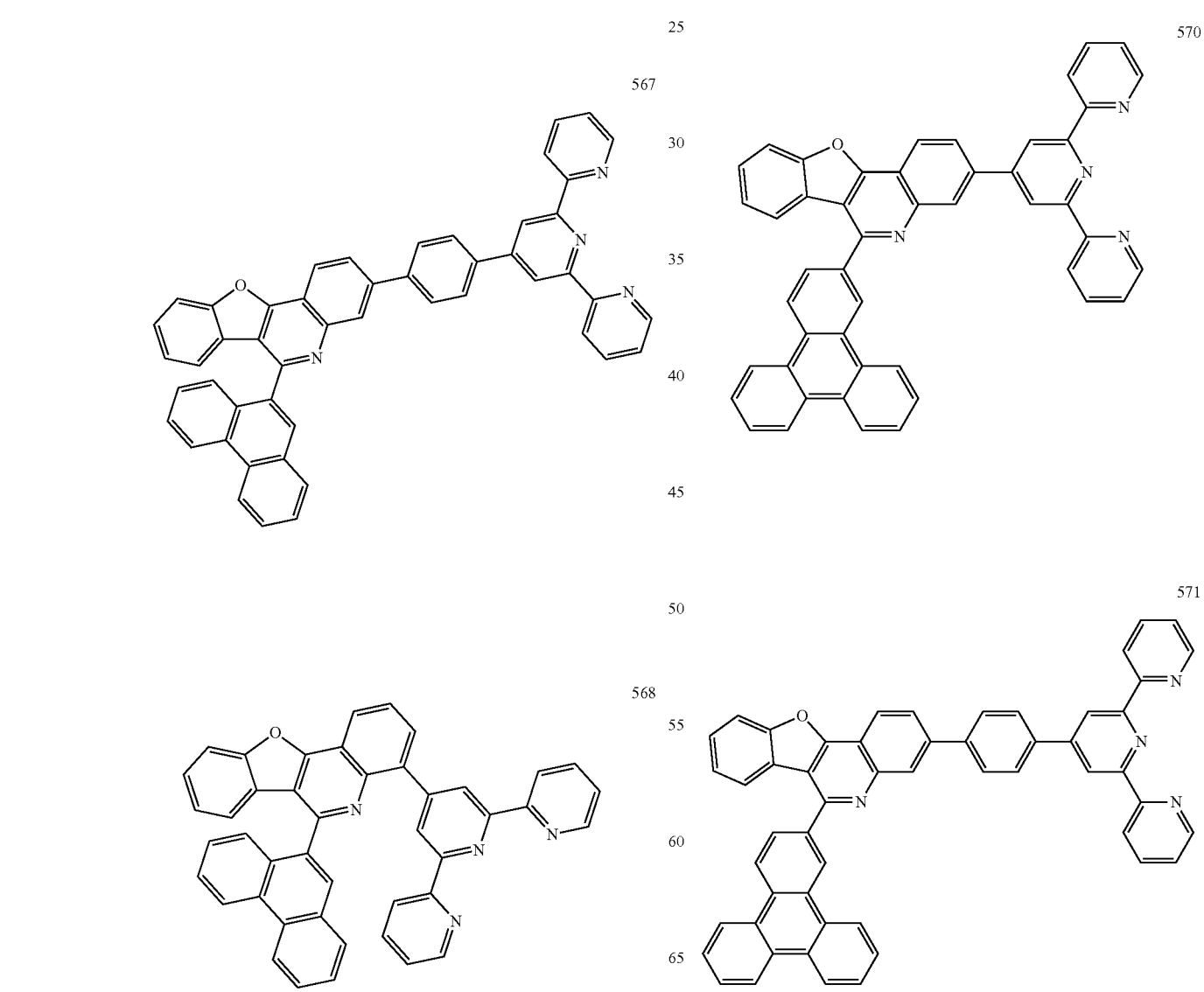

239
-continued
572
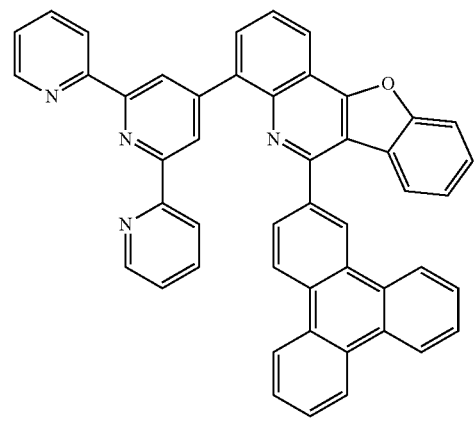
573
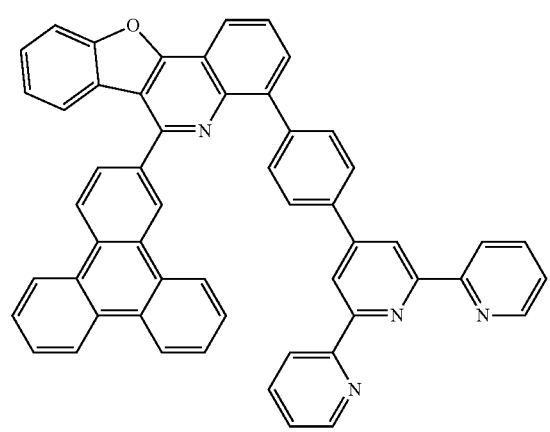
240
-continued
575
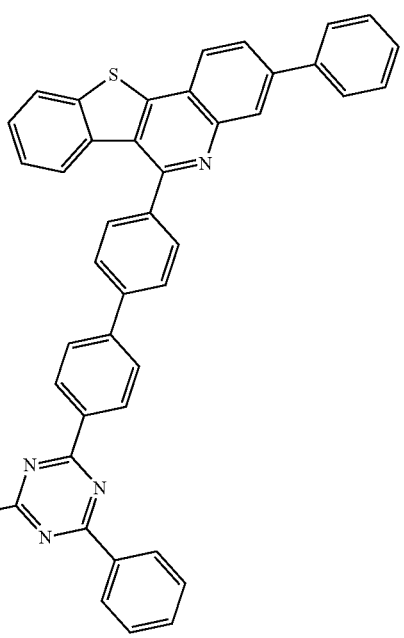
574
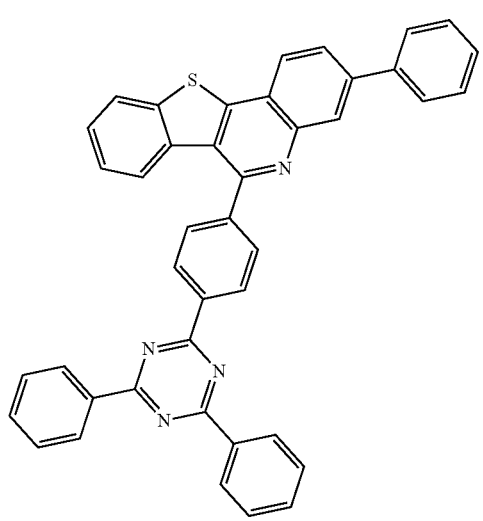
576
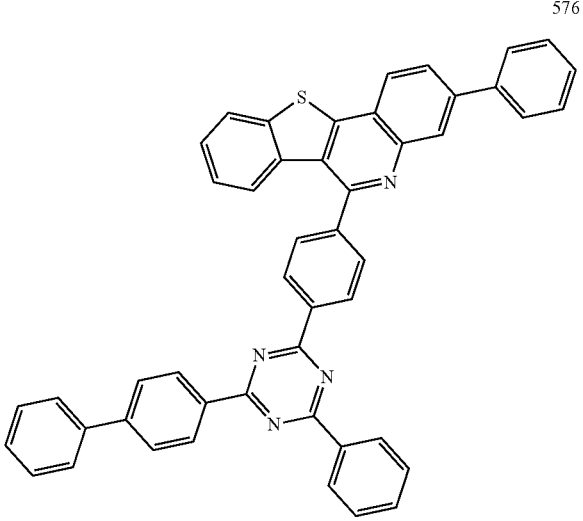

577
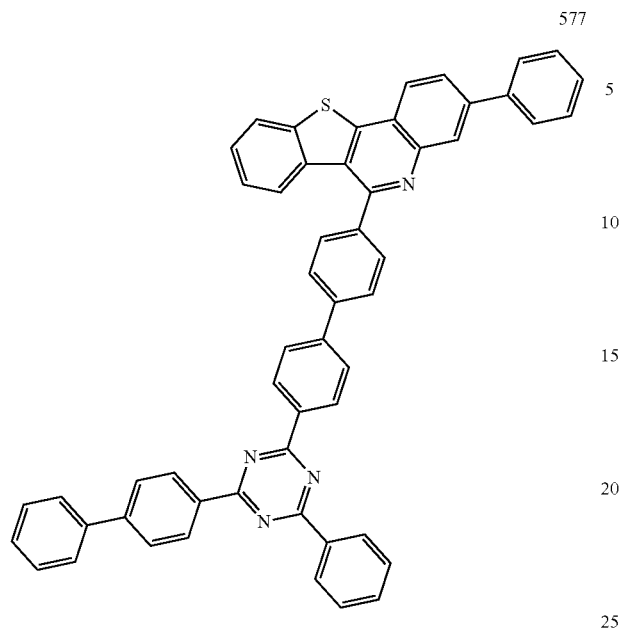
578
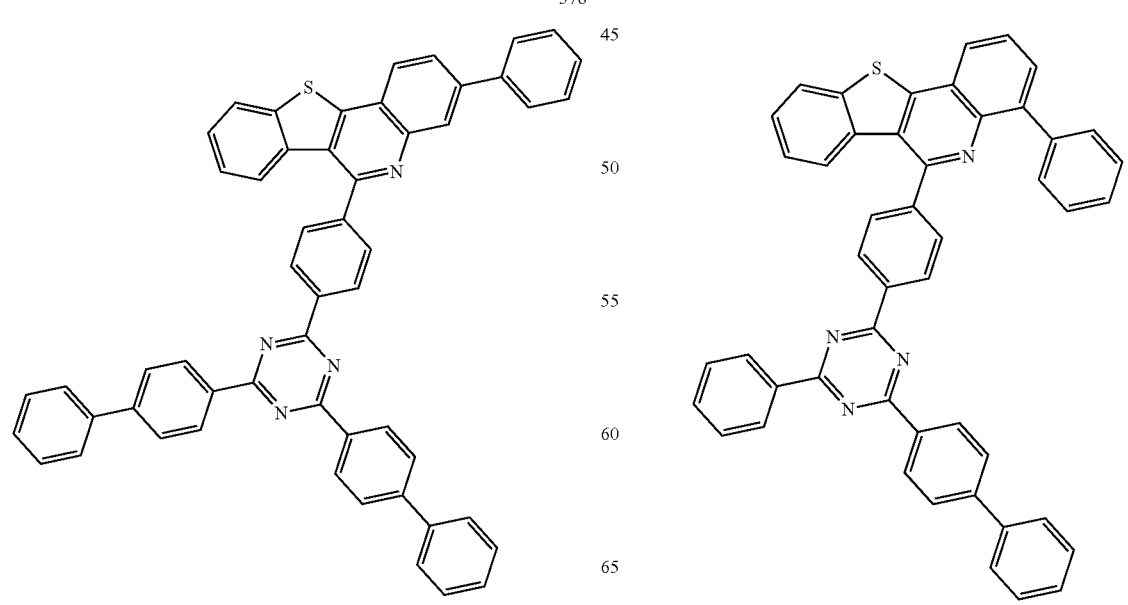
579
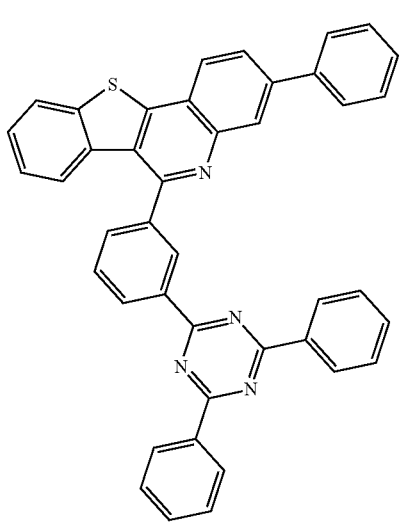
580
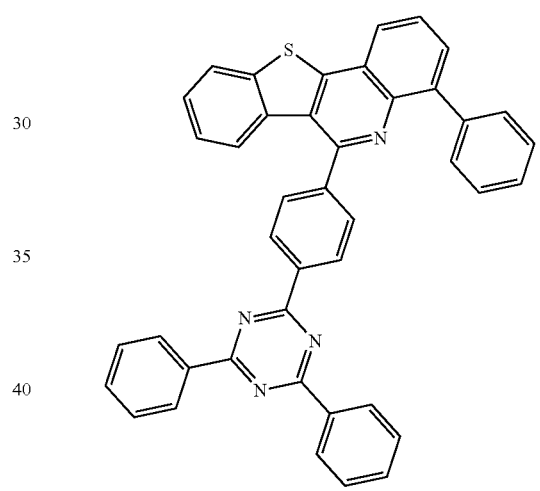
581

582
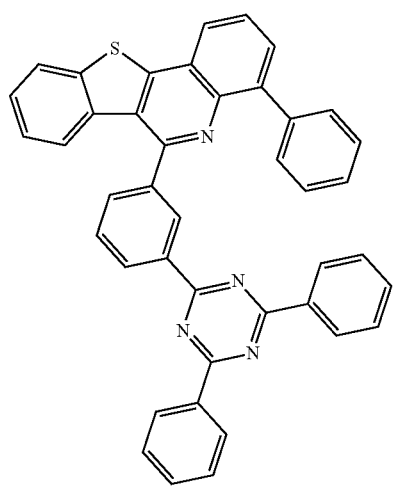
583
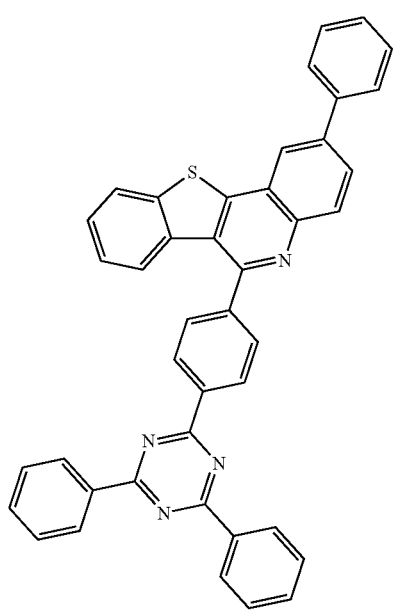
584
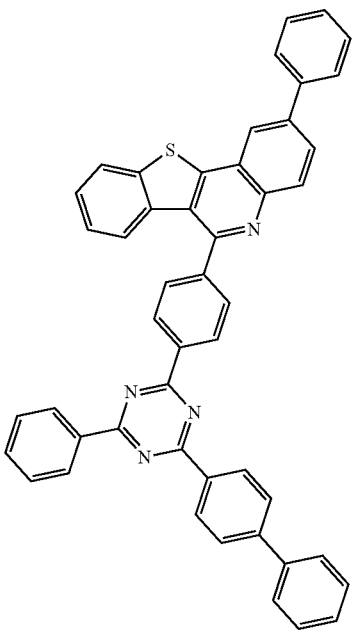
585
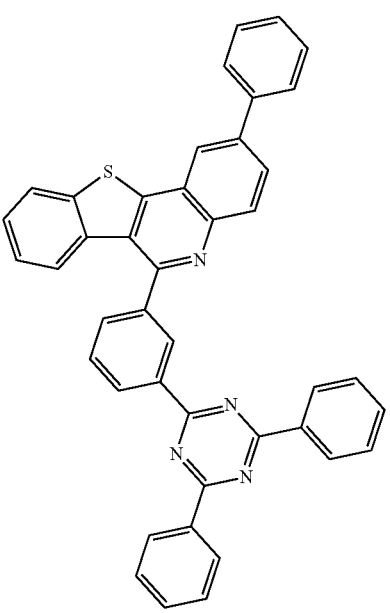

586
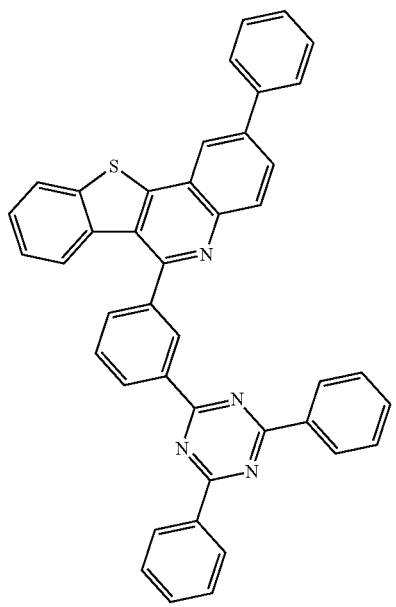
588
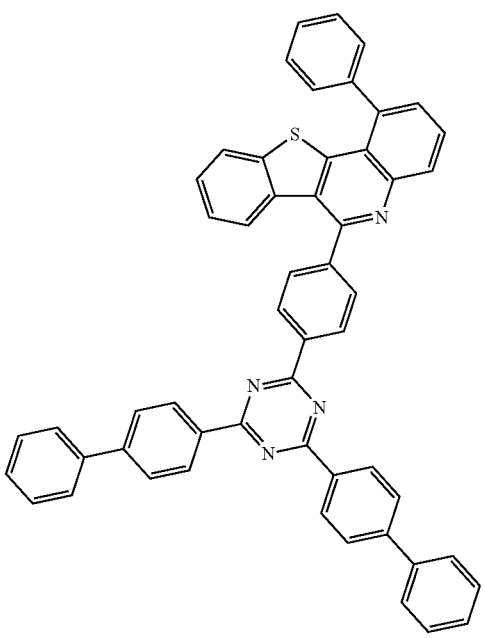
587
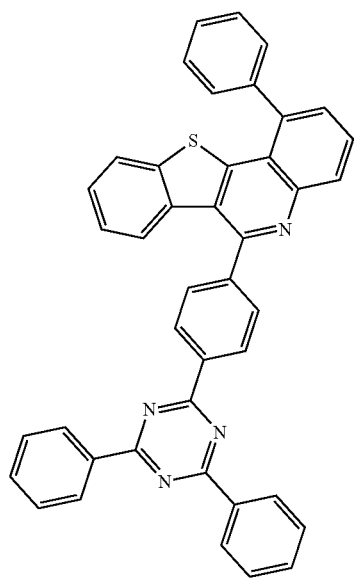
589
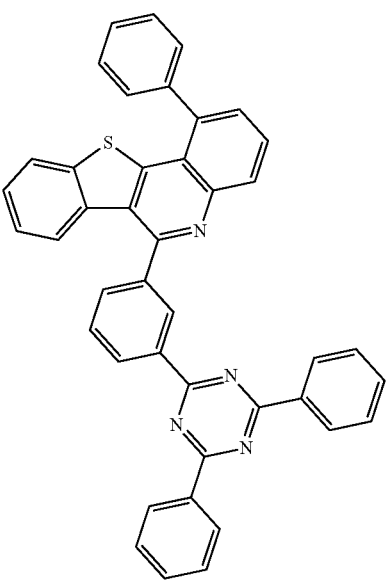

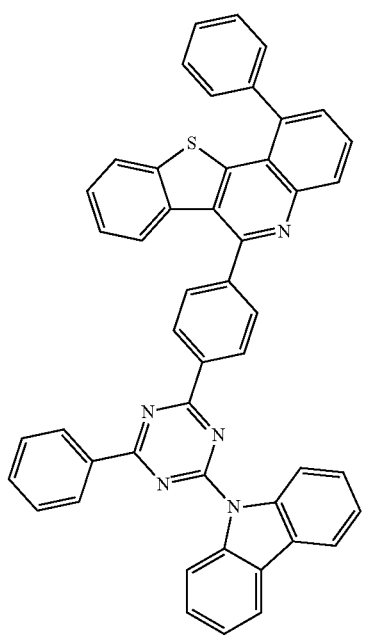
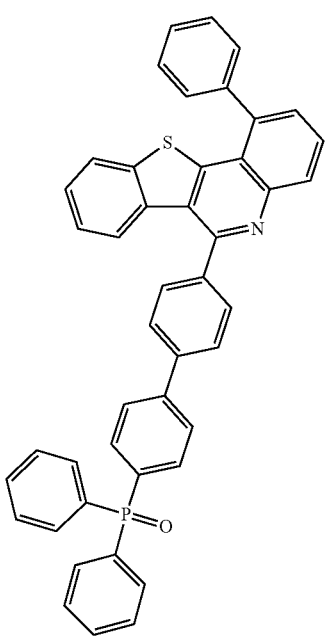

249
-continued
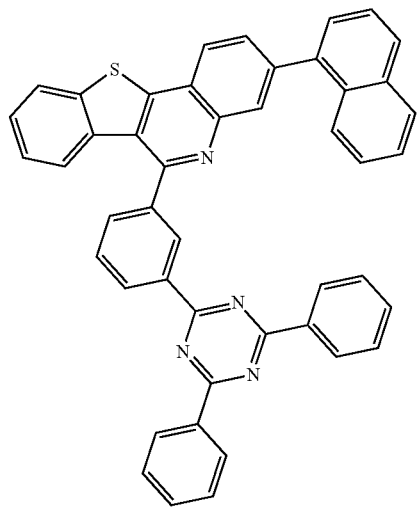
595
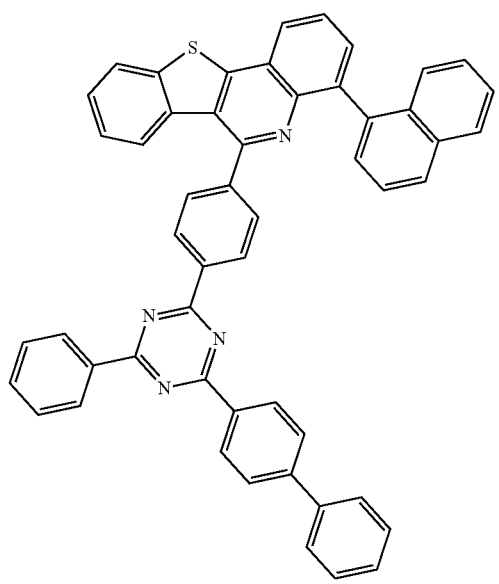
596
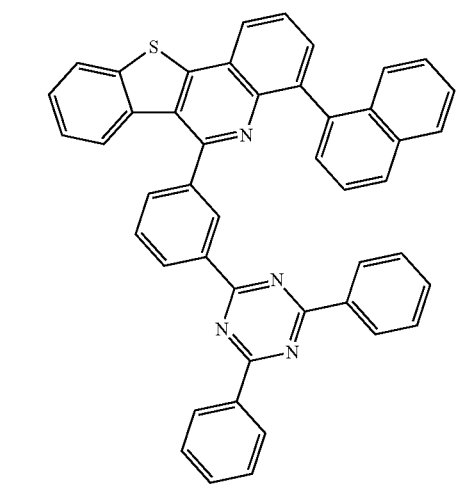
597
250
-continued
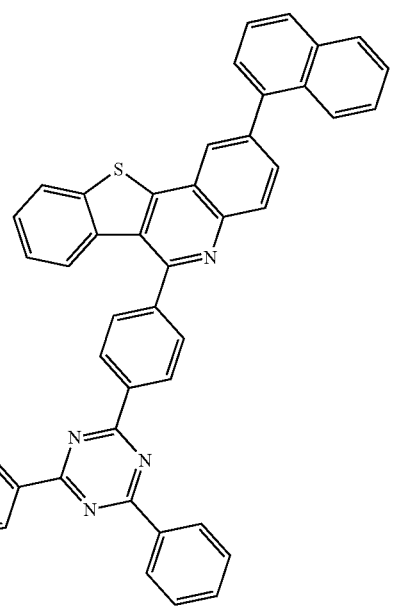
598
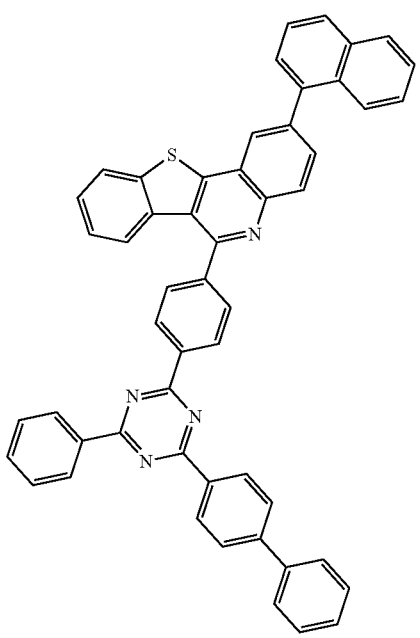
599

-continued
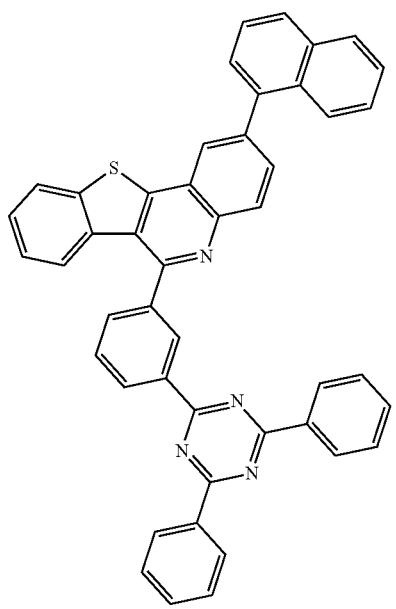
600
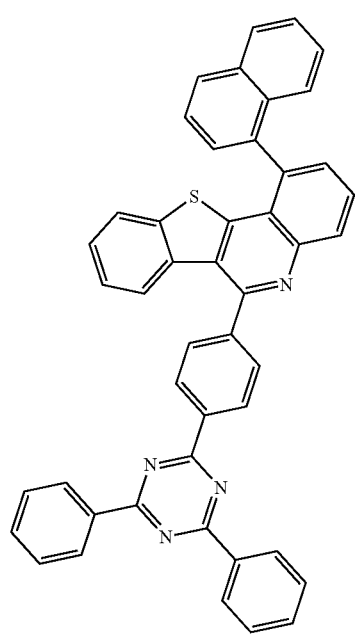
601
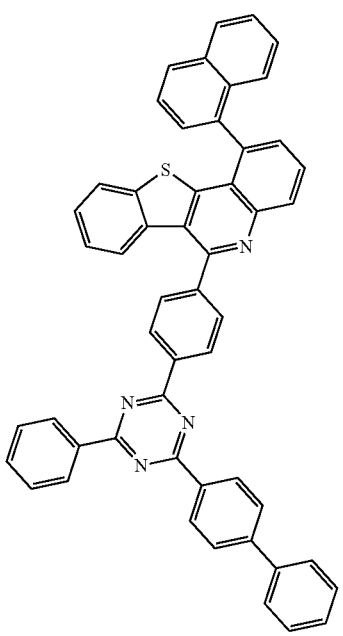
602
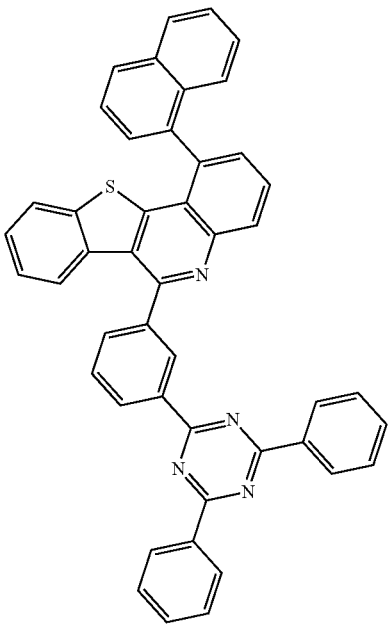
603

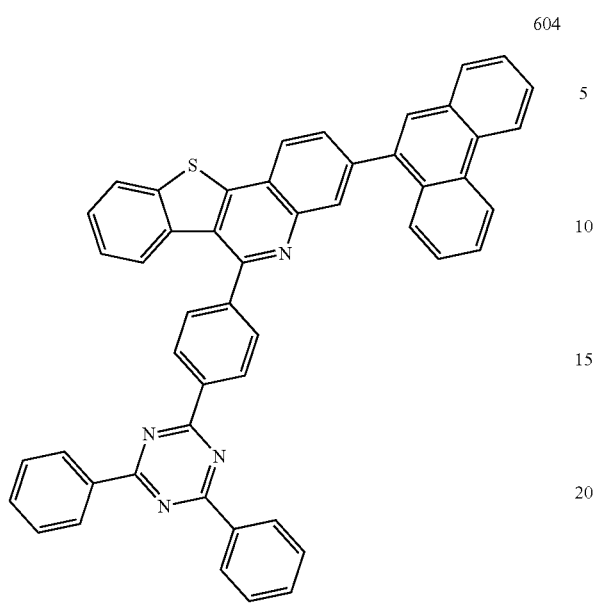
604
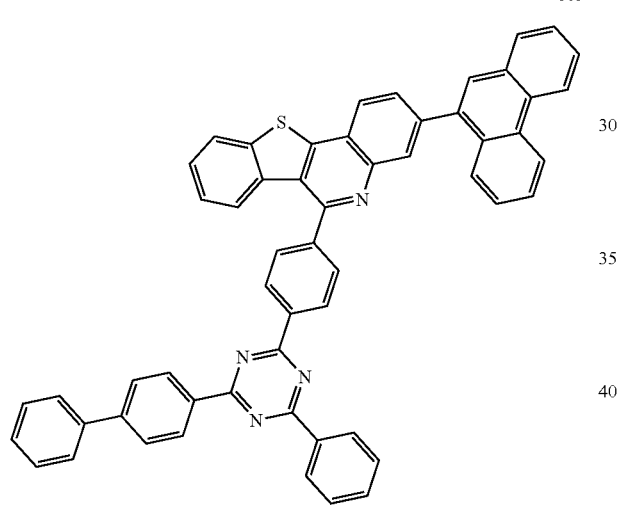
605
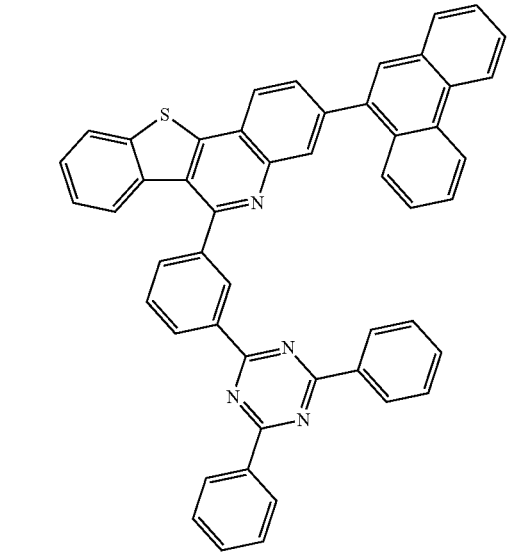
606
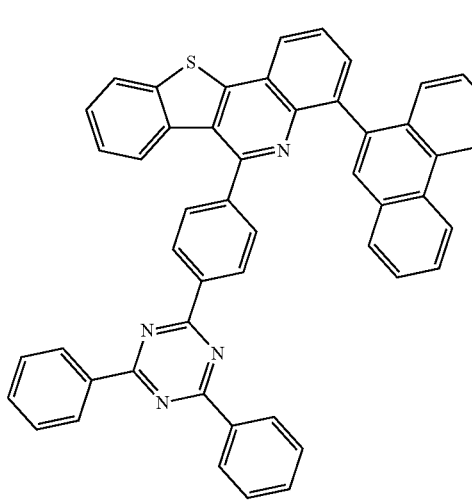
607
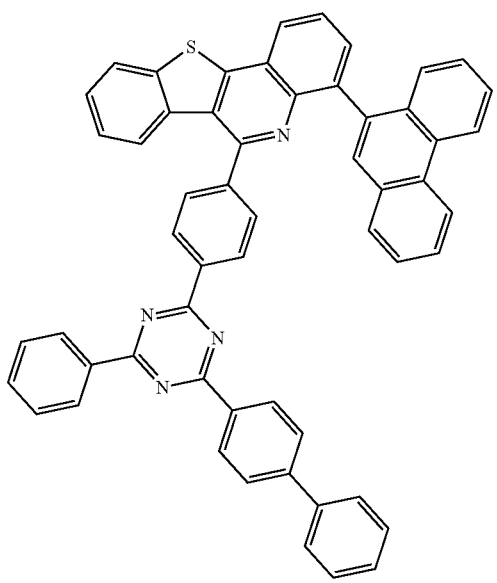
608
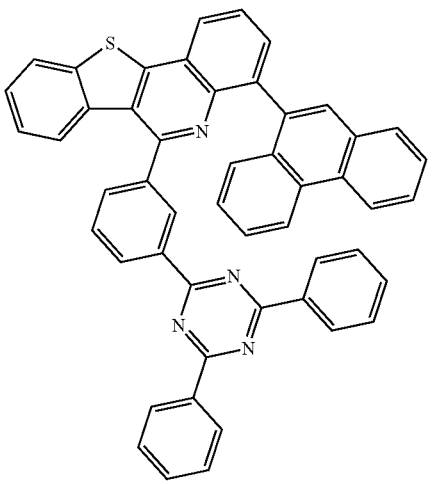
609

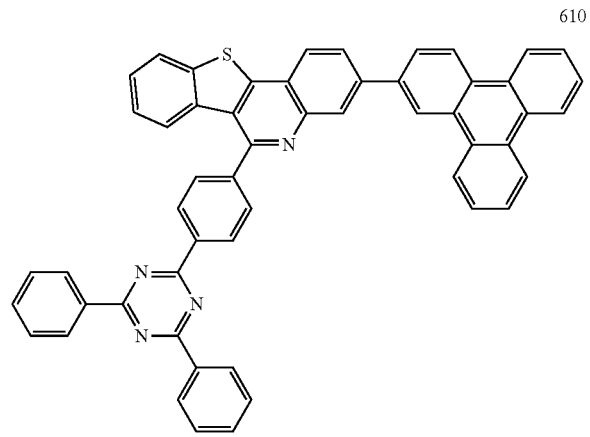
610
611
612
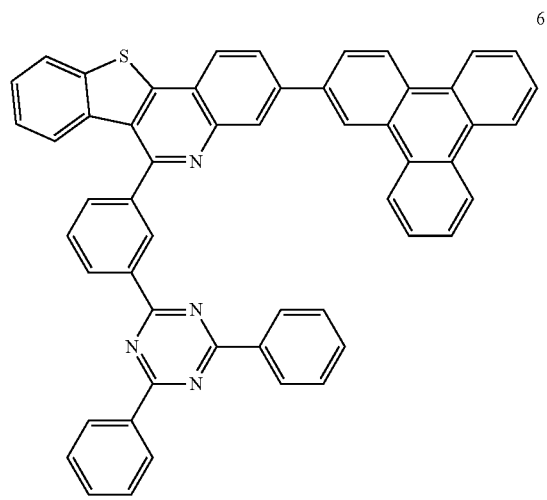
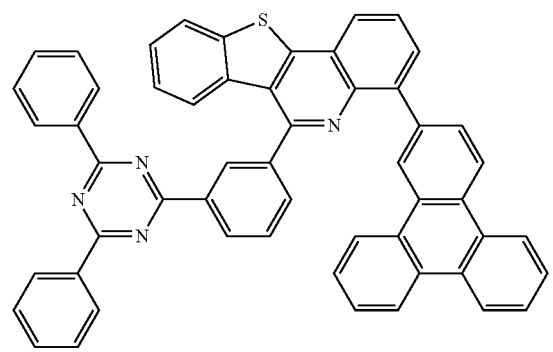
613
614
615
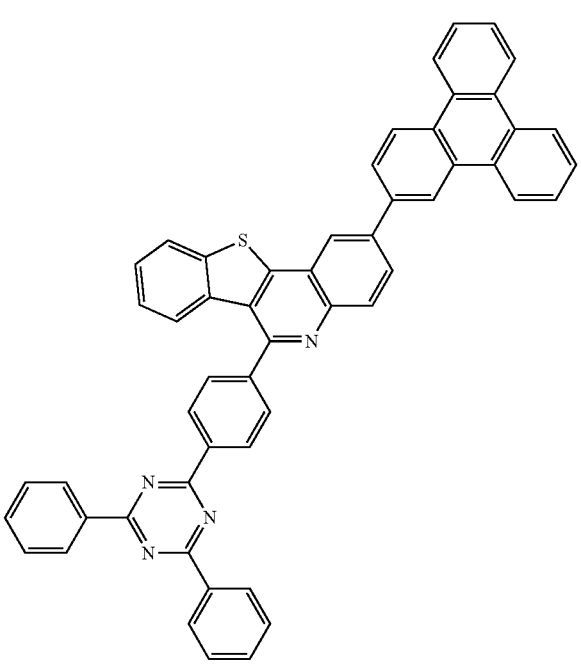

257
-continued
616
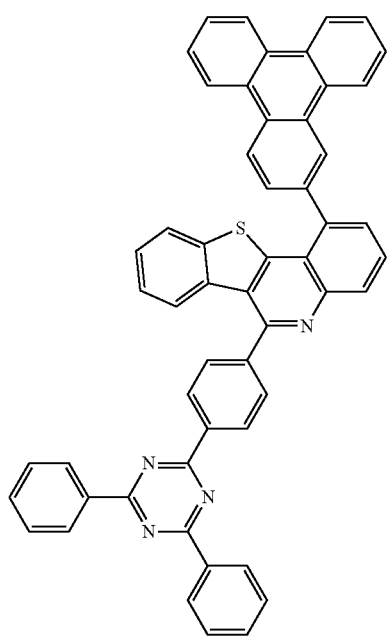
617
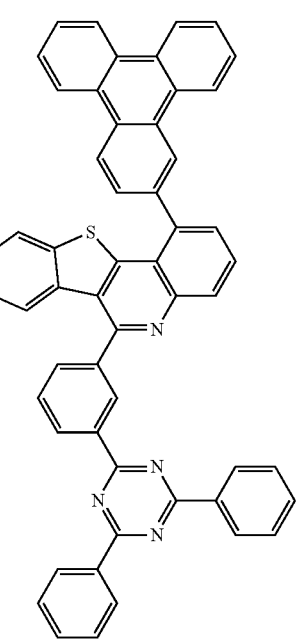
258
-continued
618
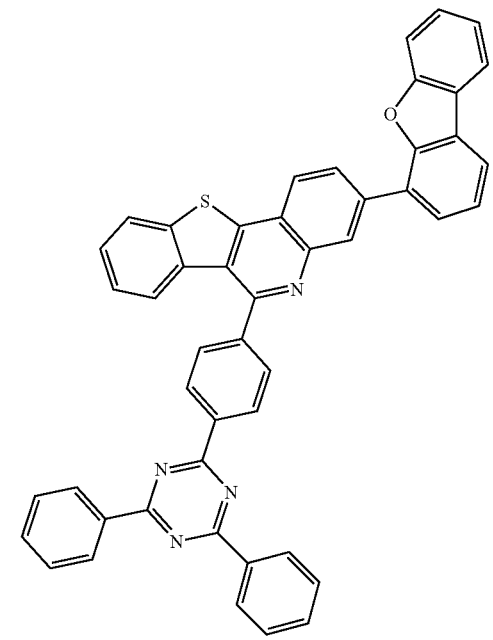
619
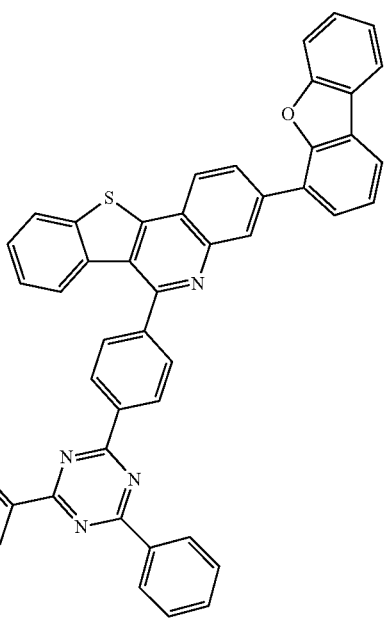

620

621

622

623

624
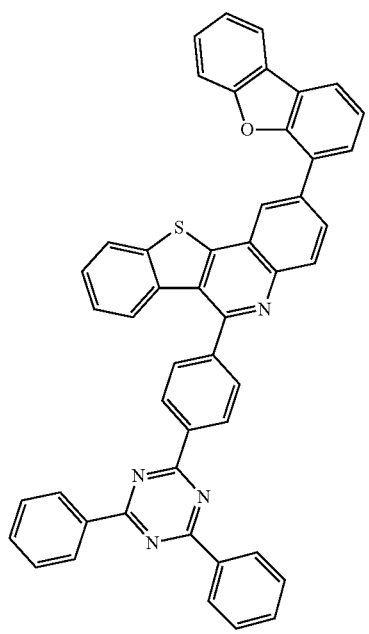
625
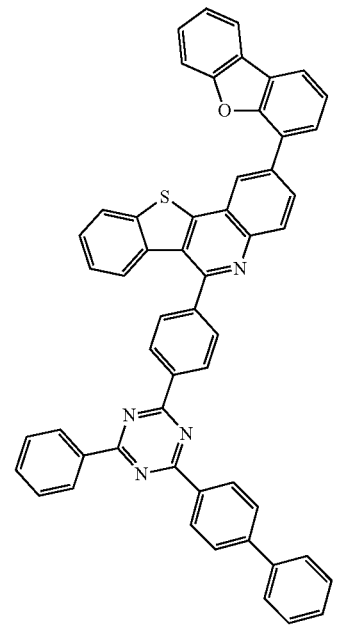
626
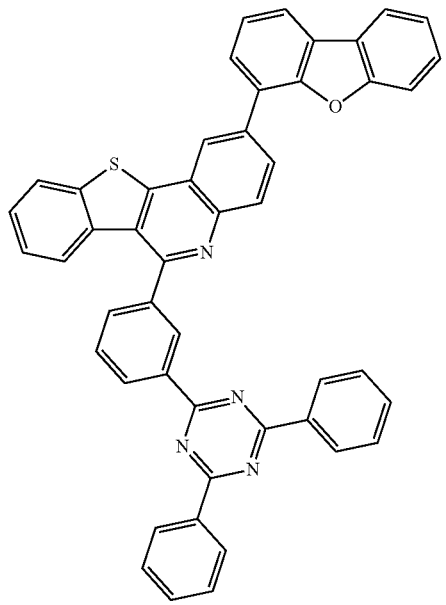
627
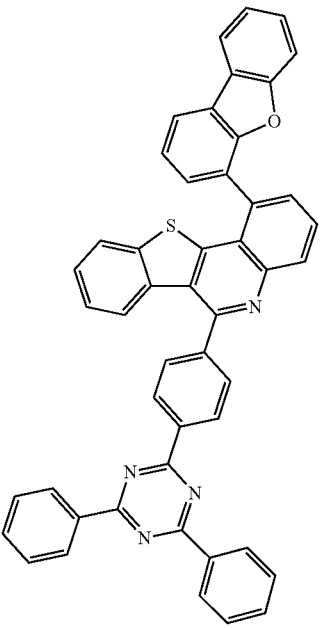

263
-continued
628
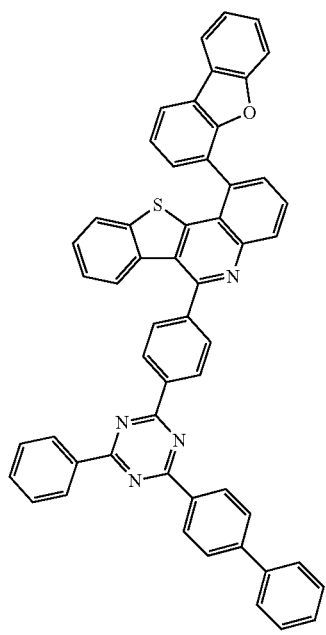
629
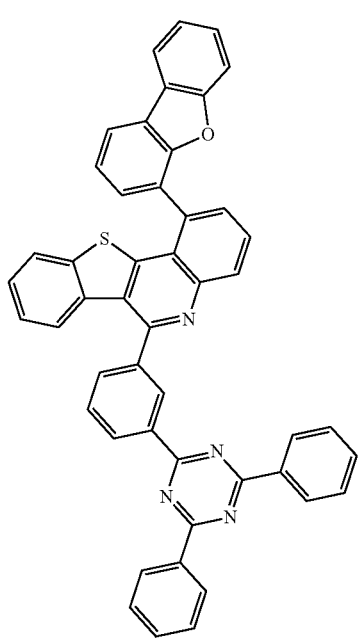
264
-continued
630
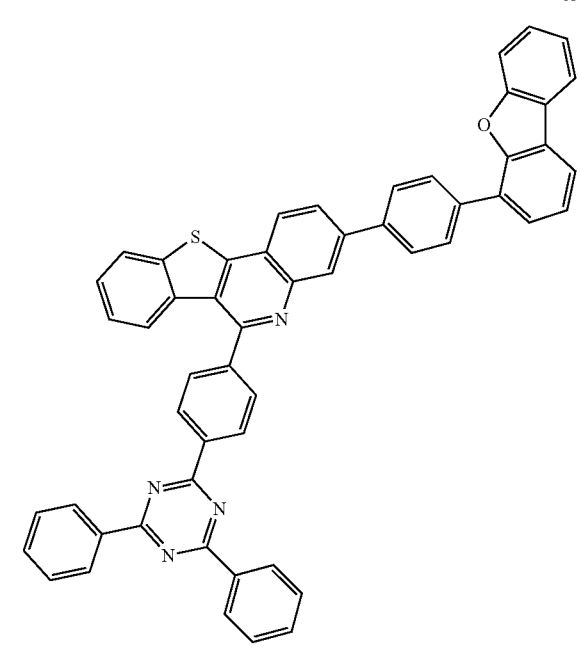
631
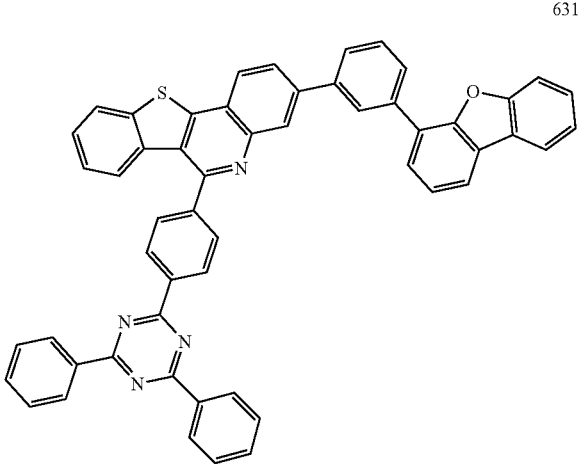

265
-continued
632
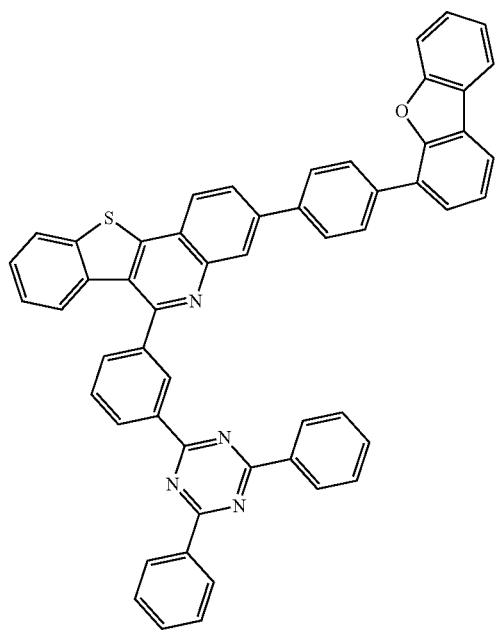
633
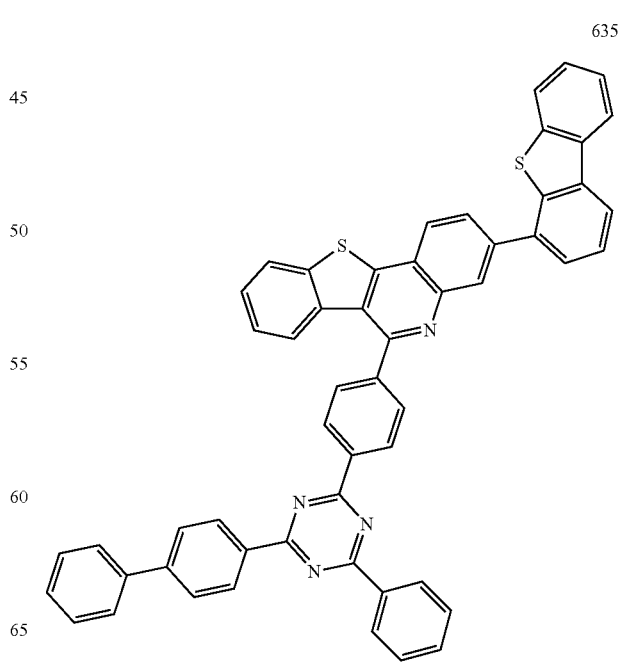
266
-continued
634
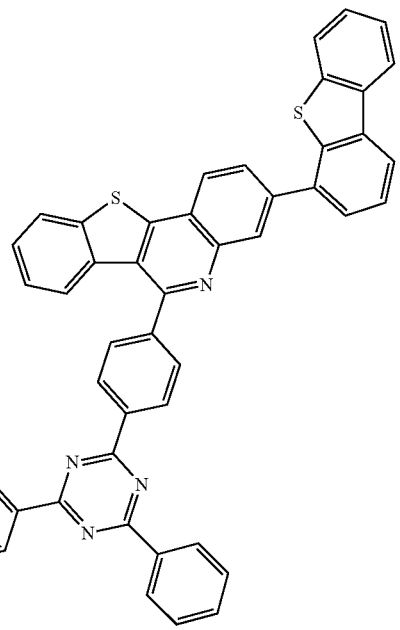
635

636
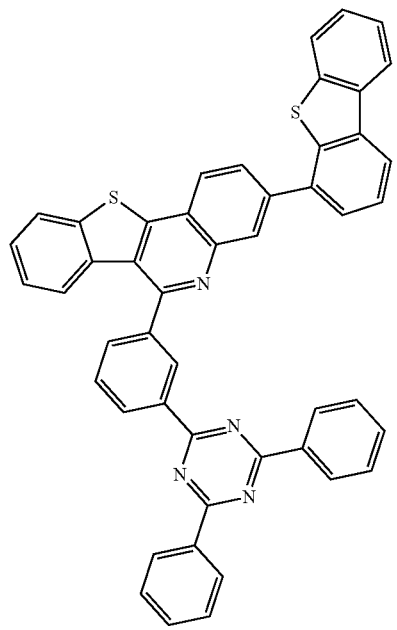
637
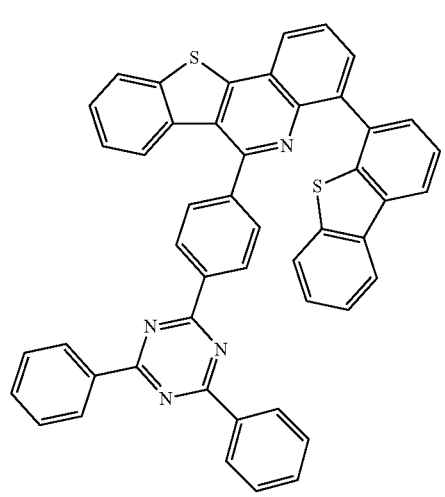
638
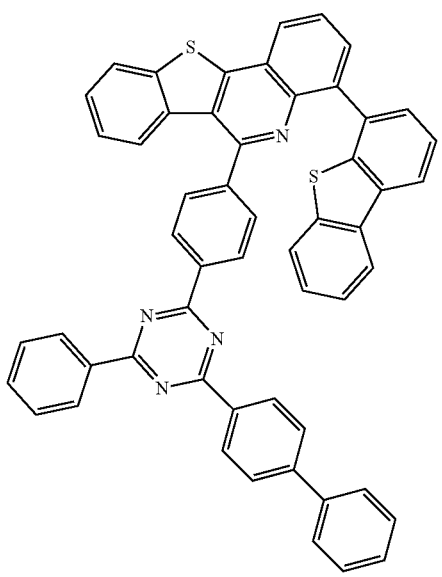
639
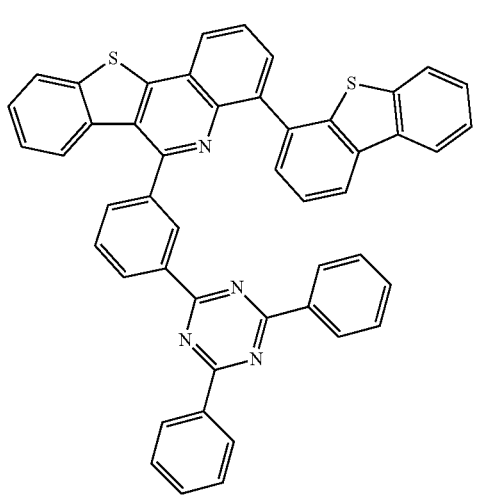

269
-continued
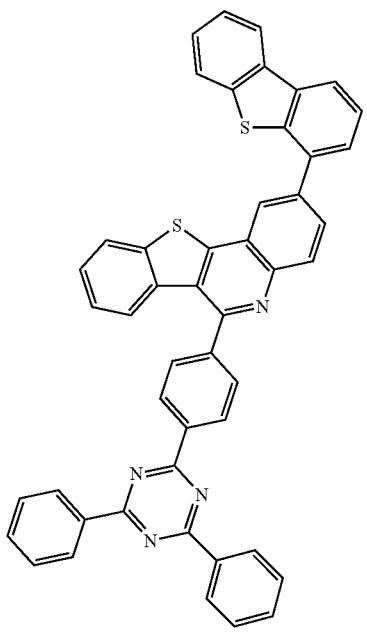
640
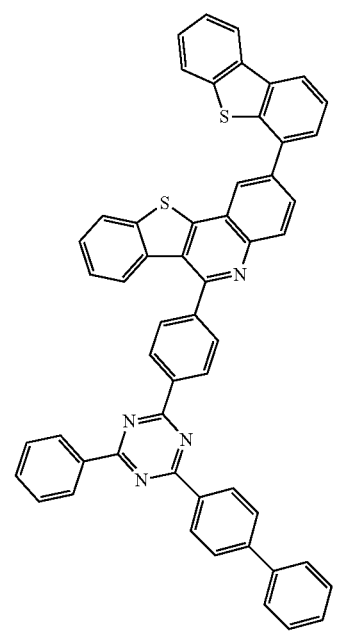
641
270
-continued
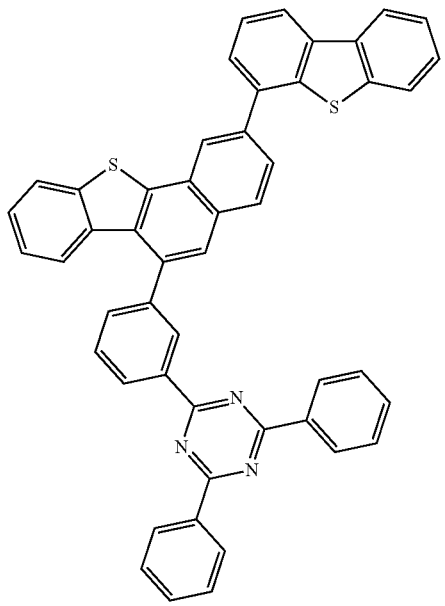
642
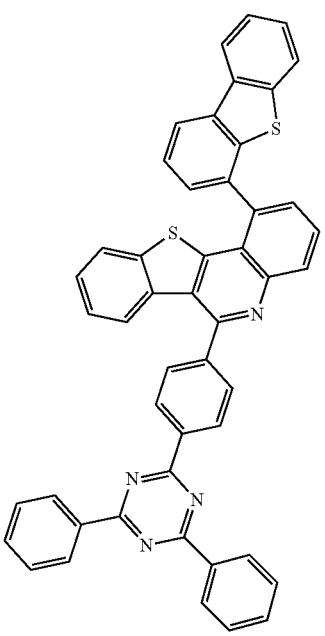
643

271
-continued
644
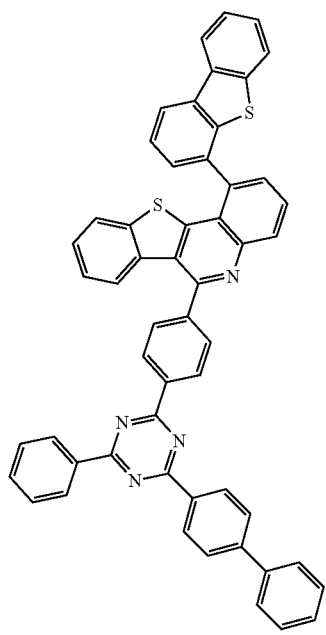
272
-continued
646
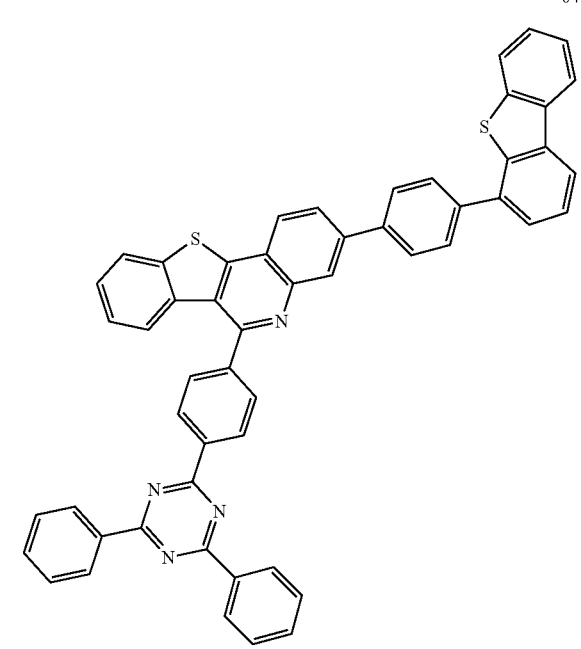
645
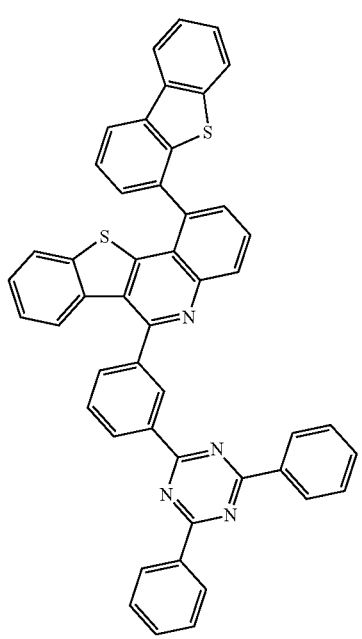
647

648
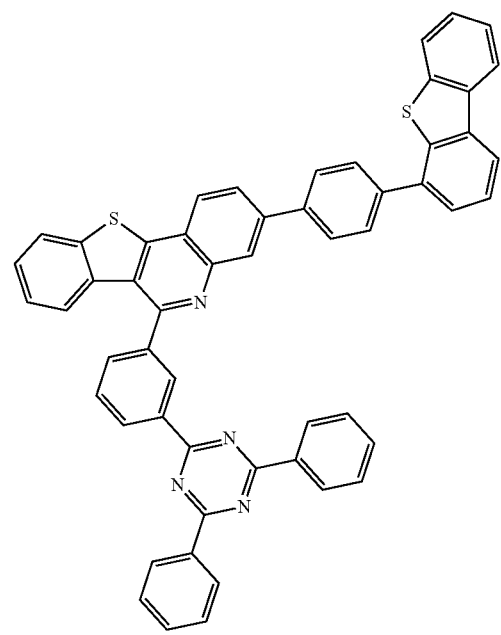
649
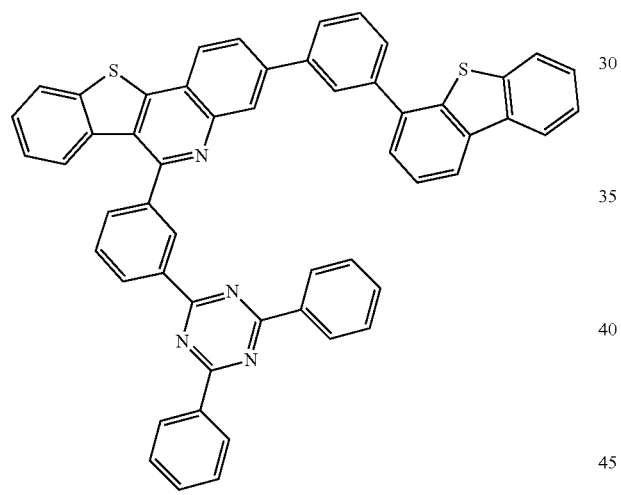
650
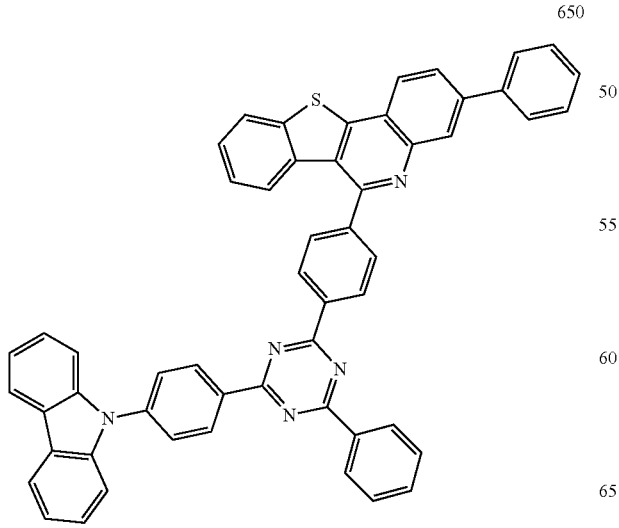
651
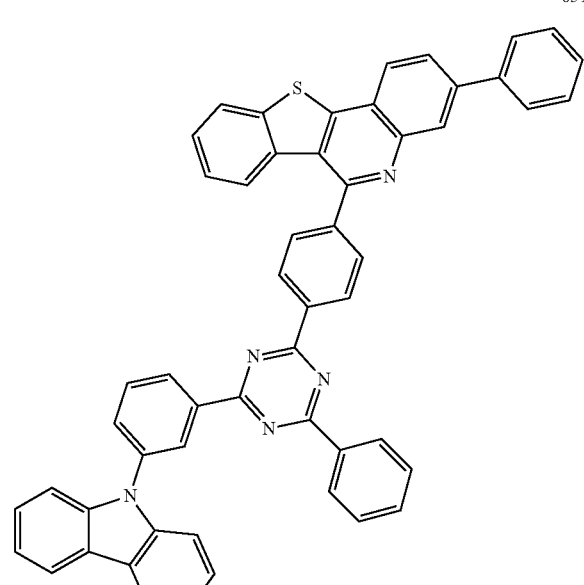
652
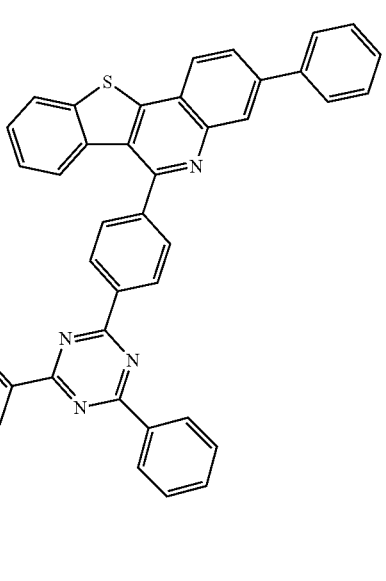

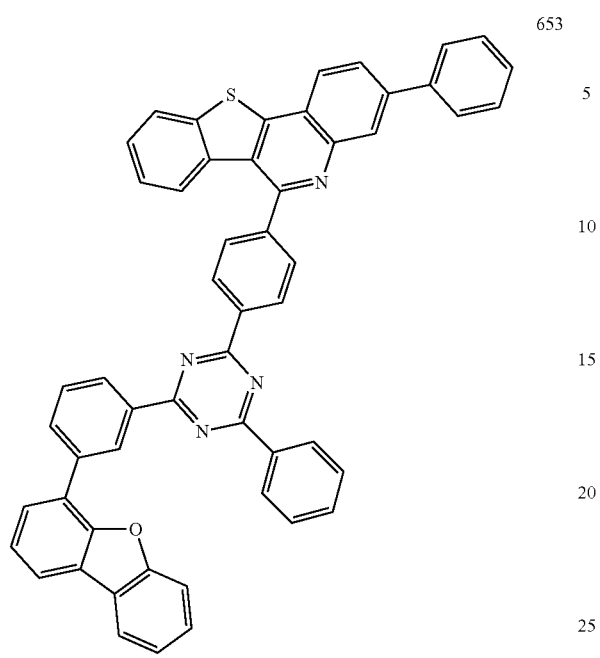
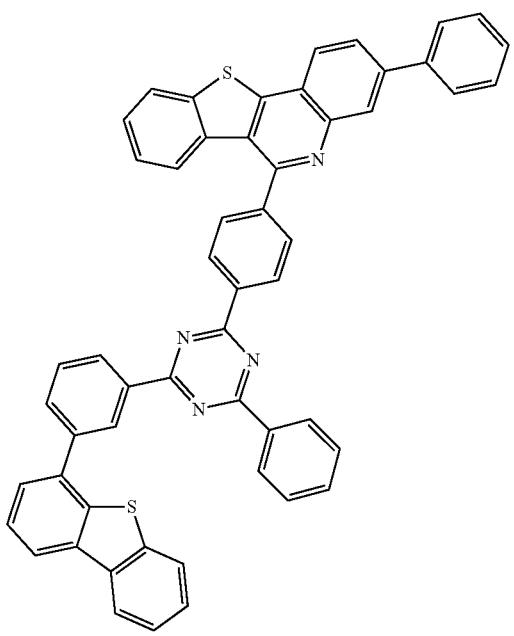

-continued
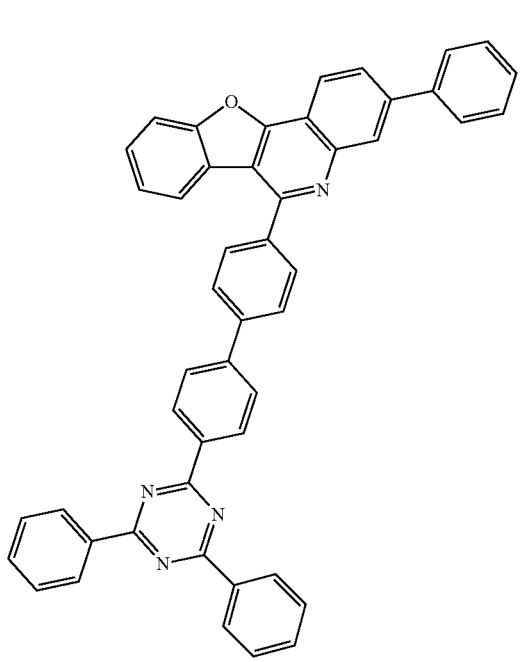
657
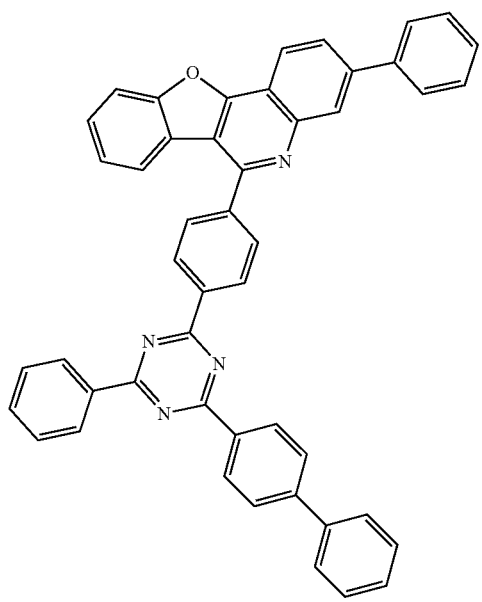
658
-continued
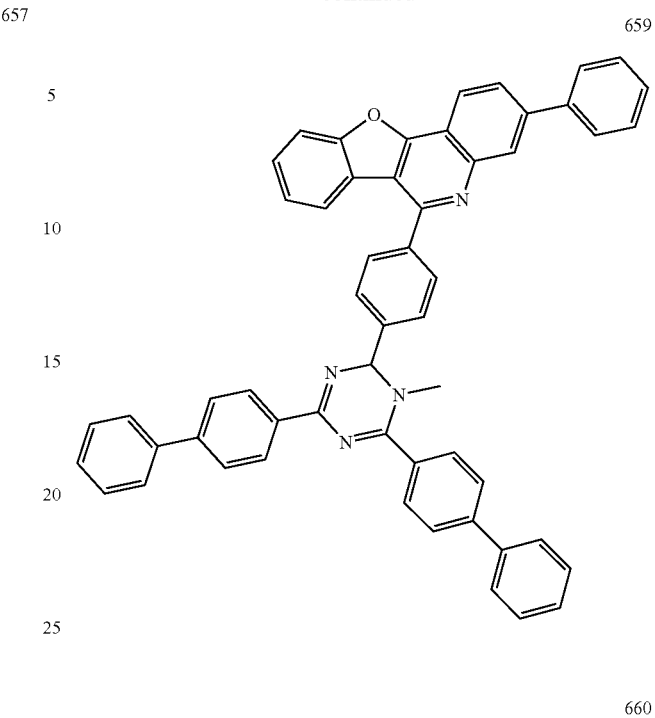
659
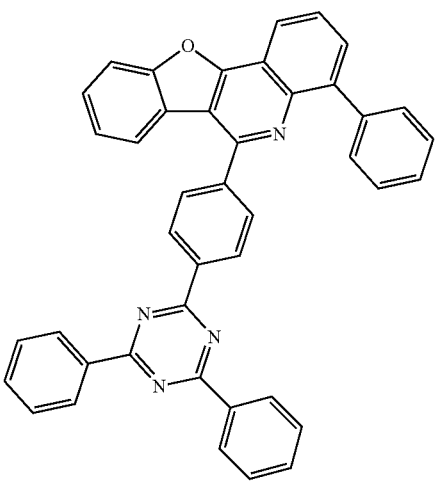
660
661

279
-continued
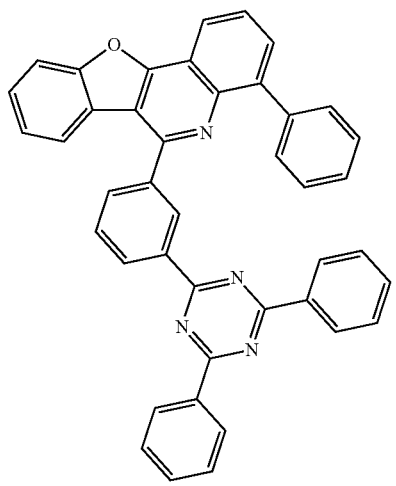
662
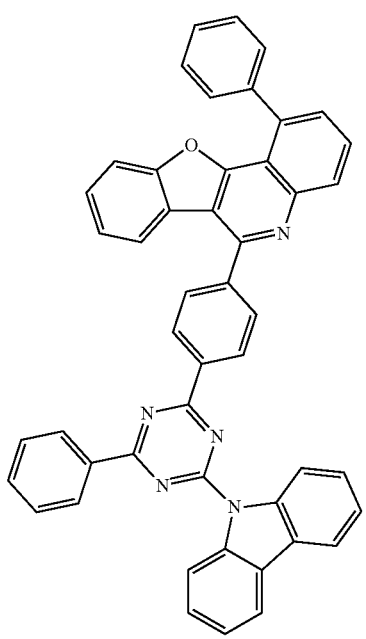
663
280
-continued
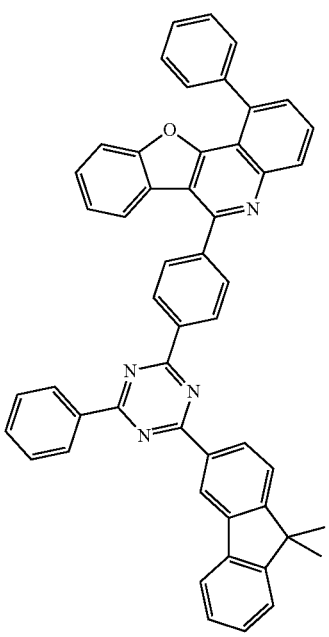
664
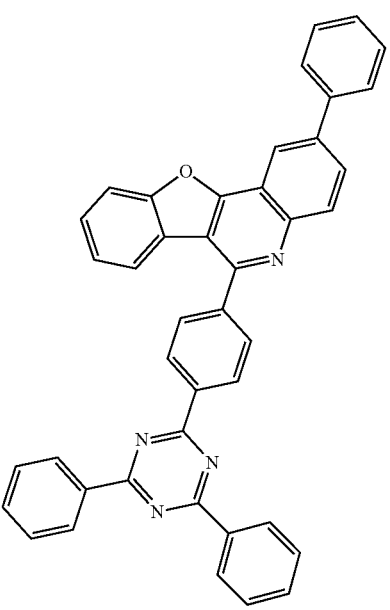
665

666
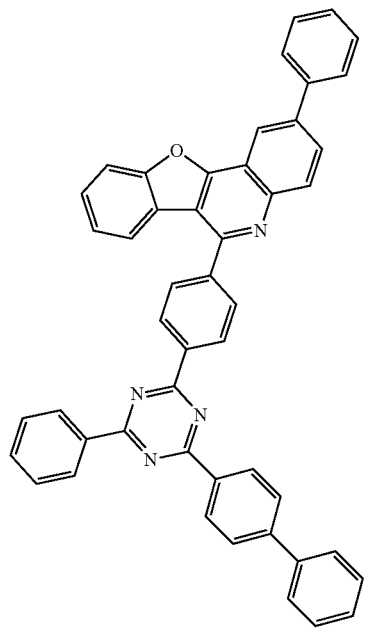
667
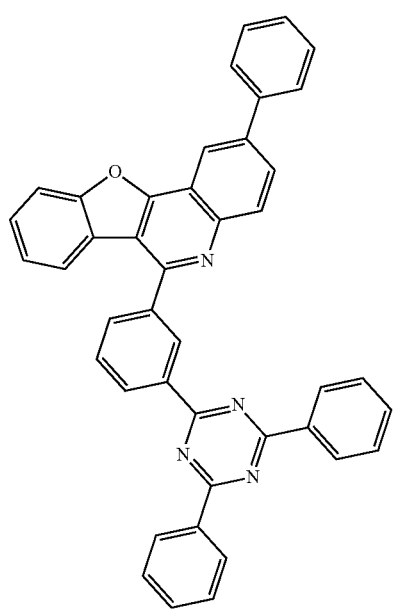
668
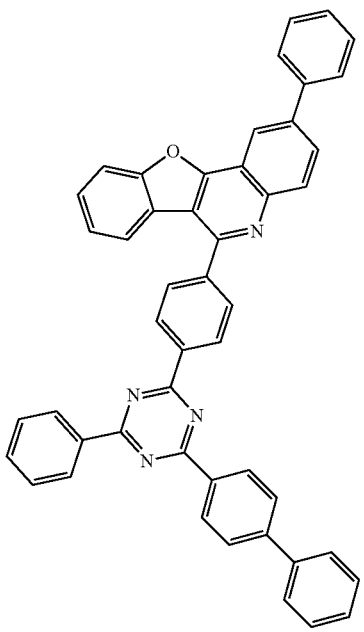
669
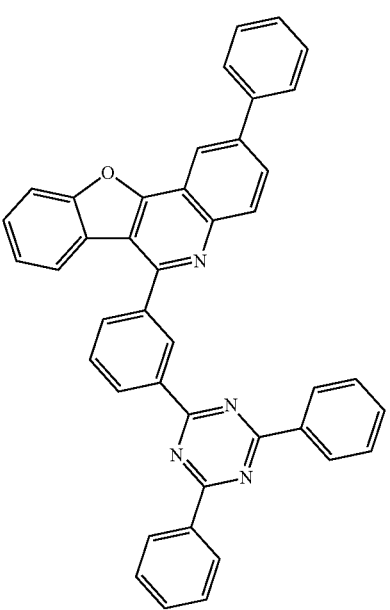

670
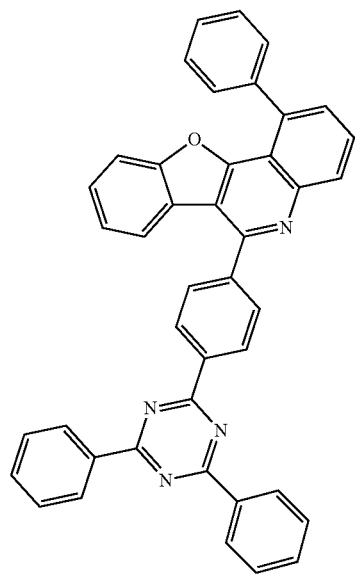
671
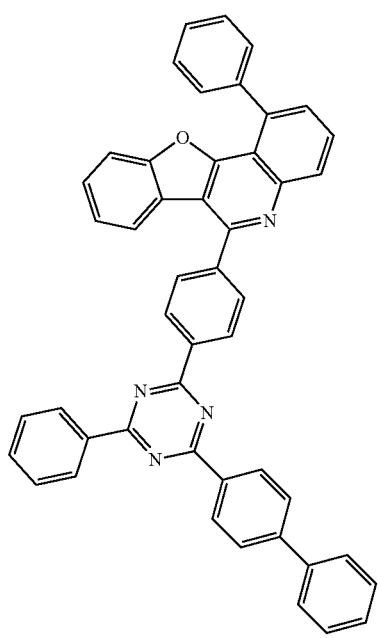
672
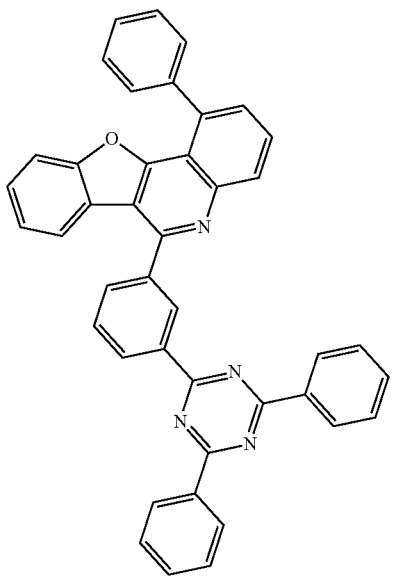
673
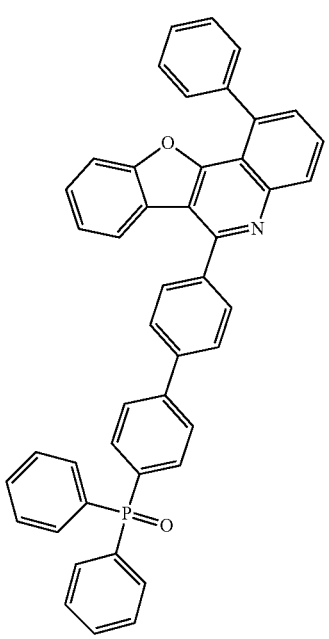

285
-continued
674
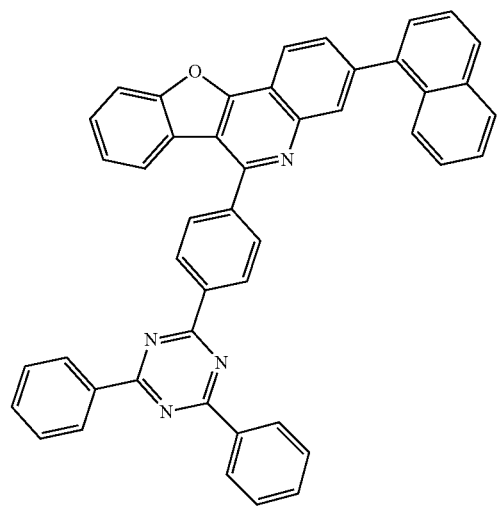
675
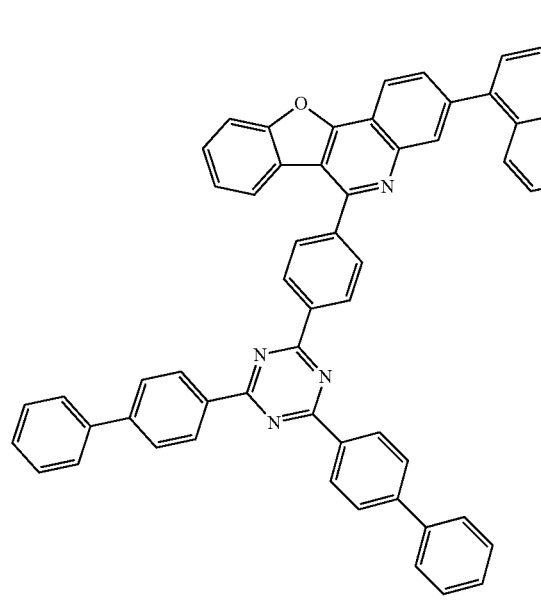
676
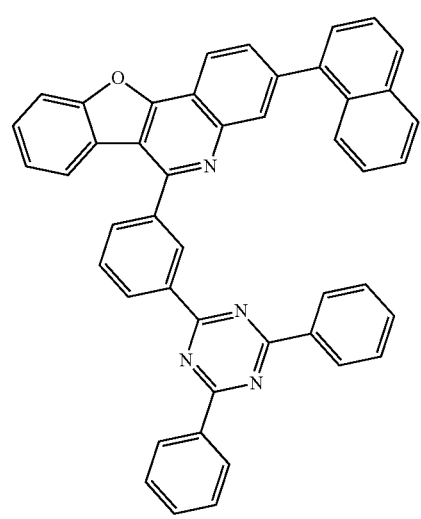
286
-continued
677
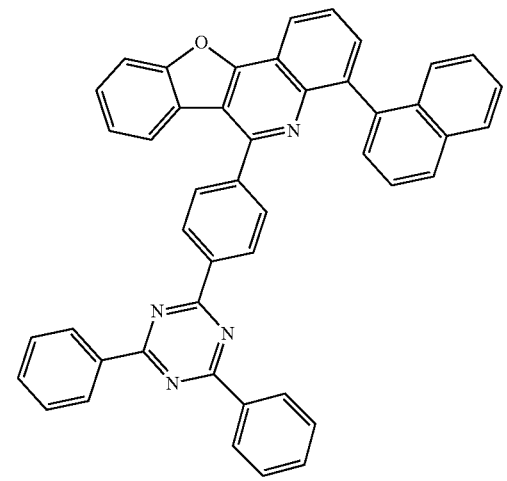
678
679
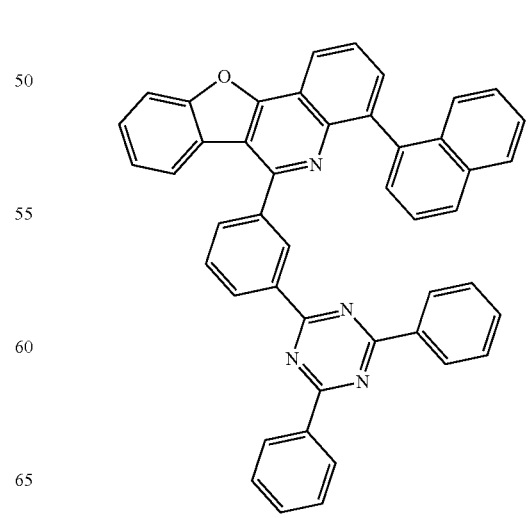

287
-continued
680
681
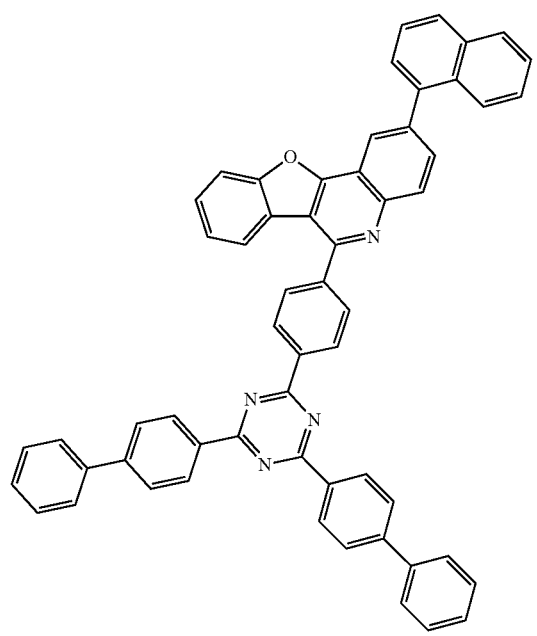
288
-continued
682
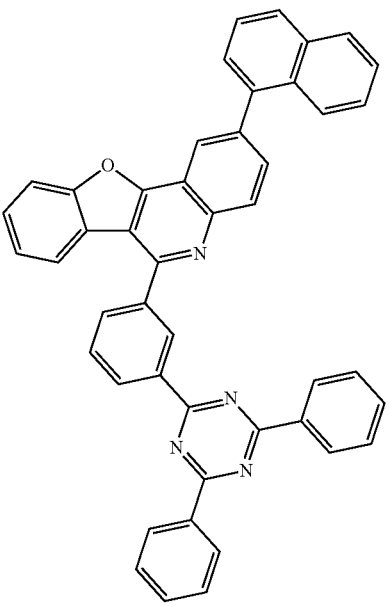
683
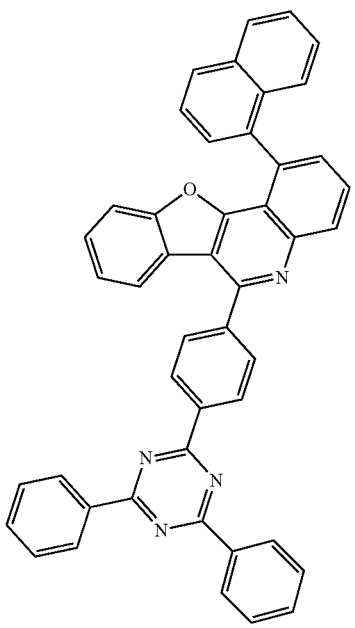

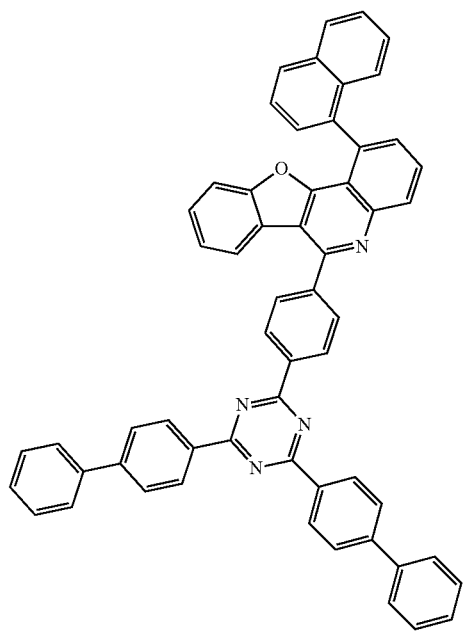
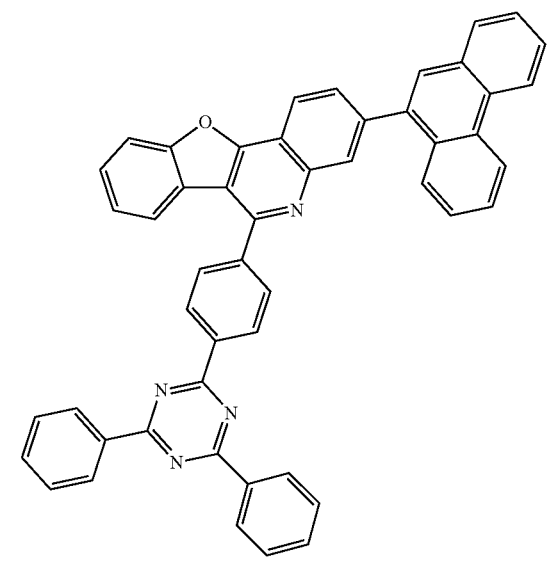
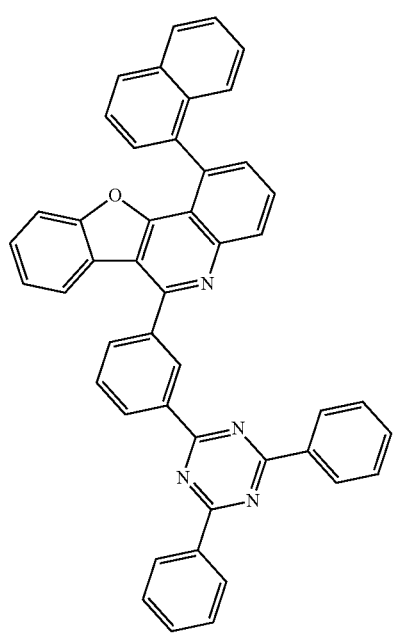
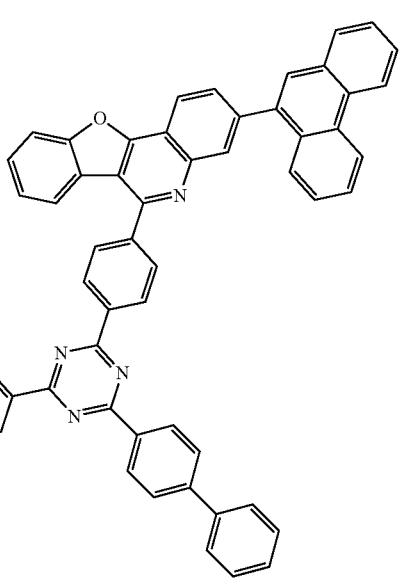

-continued
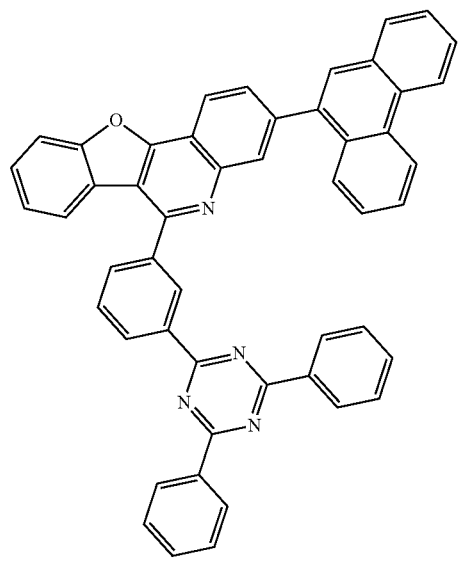
688
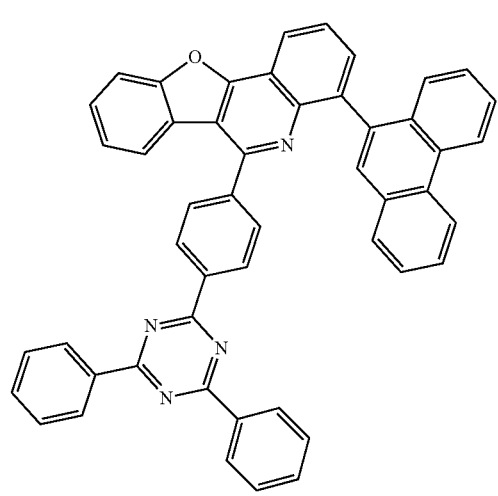
689
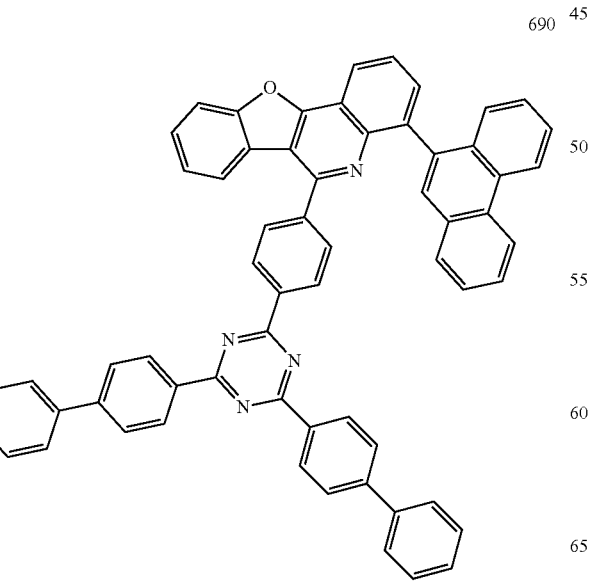
690
-continued
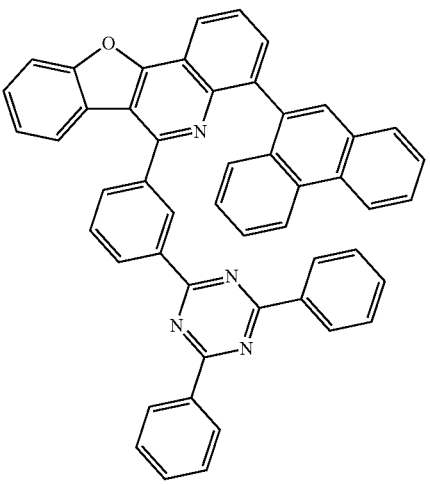
691
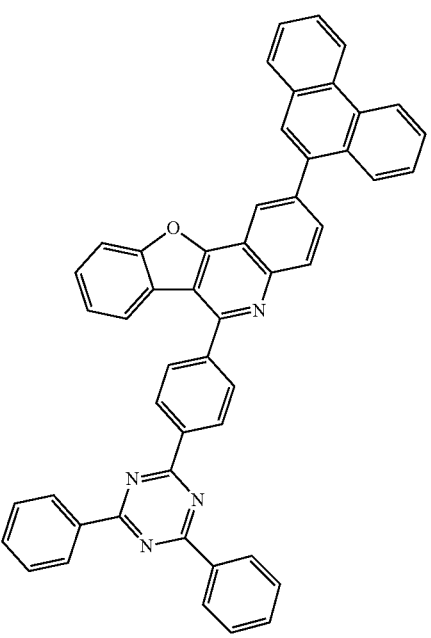
692

-continued
693
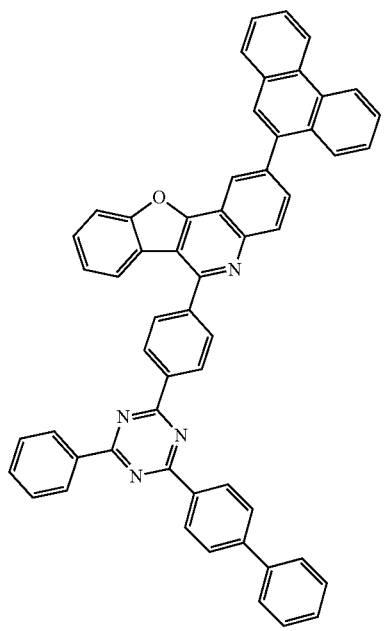
694
695
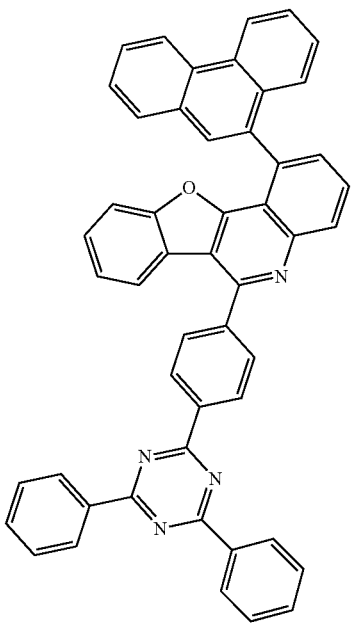
696
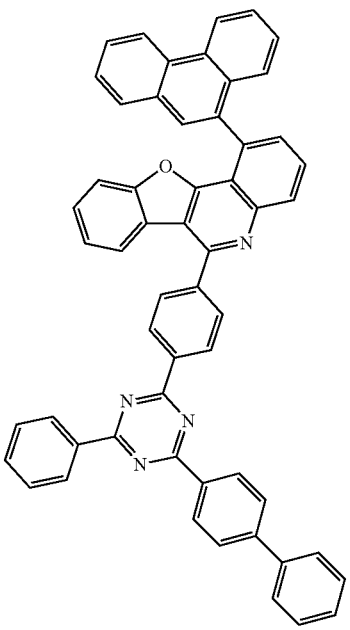

295
-continued
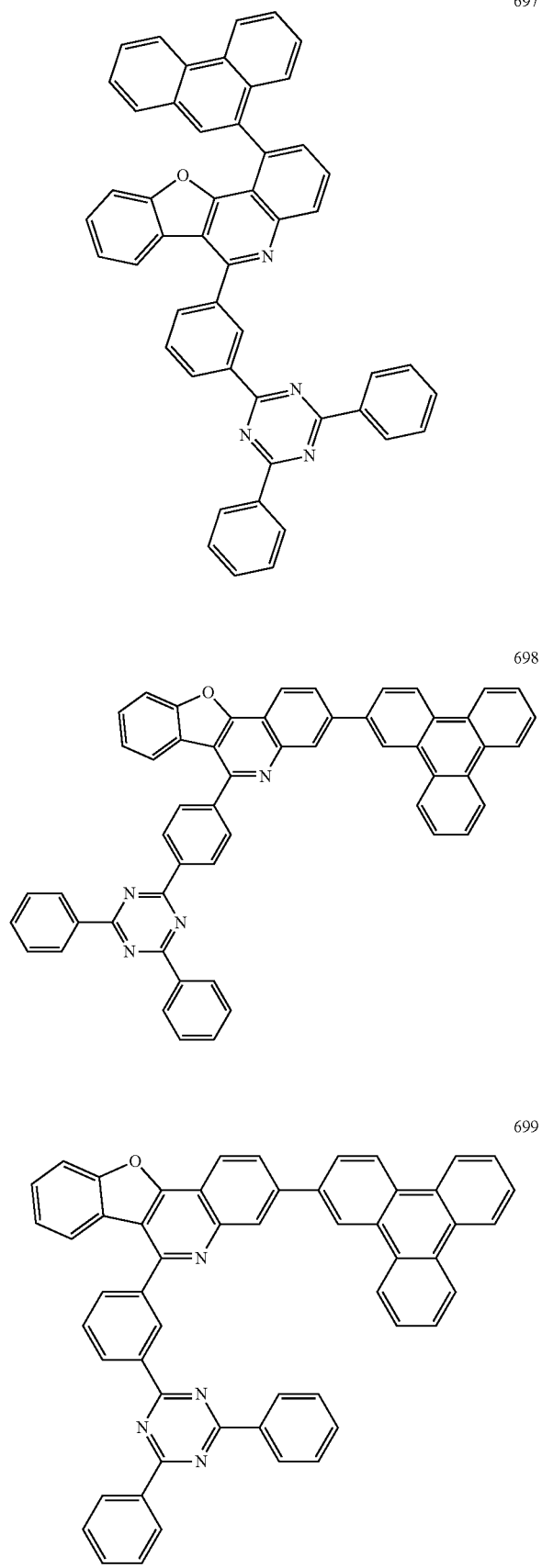
296
-continued
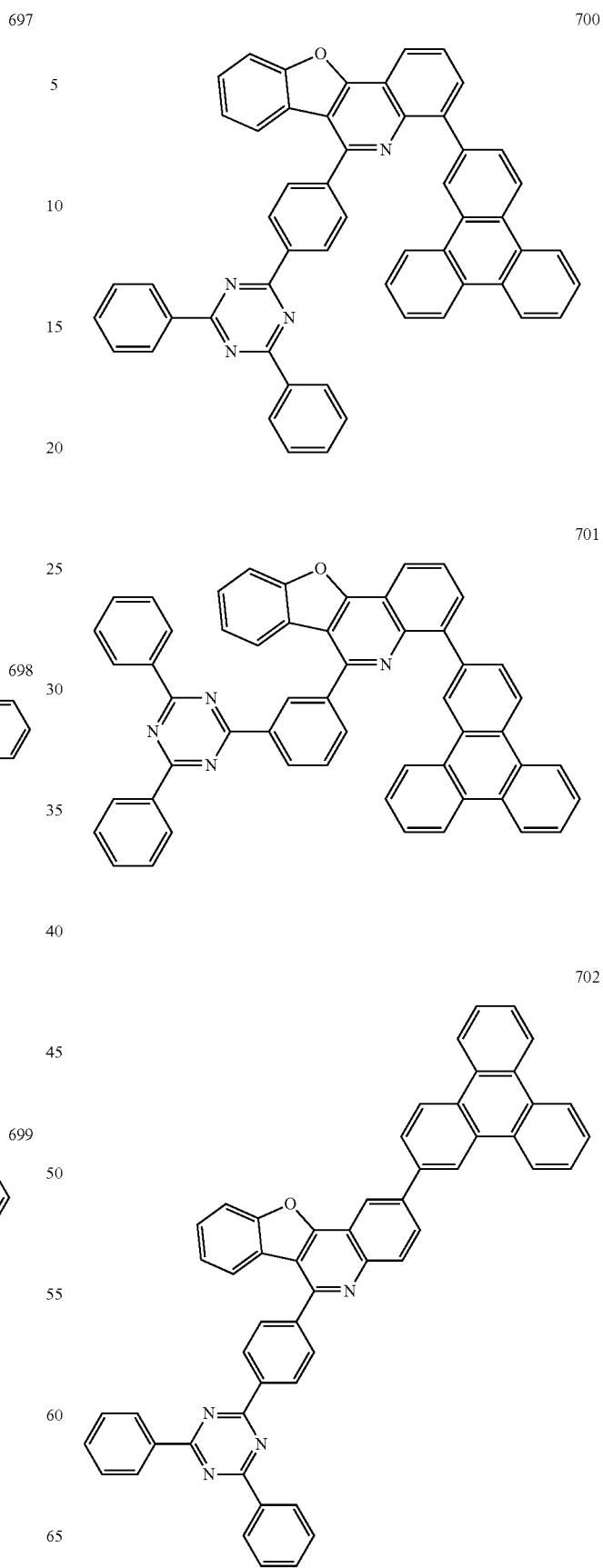

297
-continued
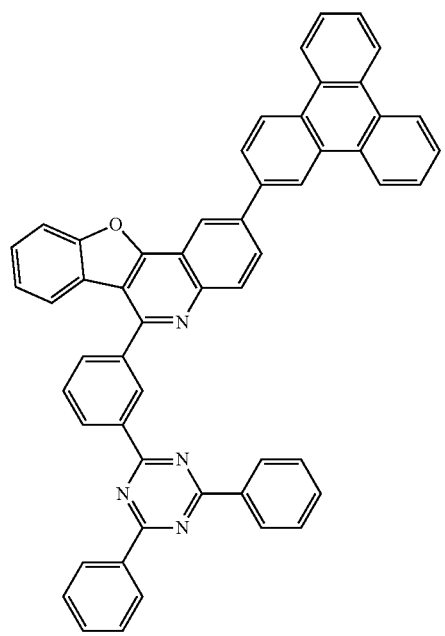
703
298
-continued
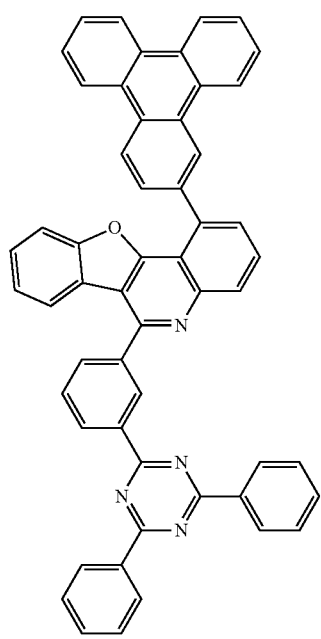
705
704
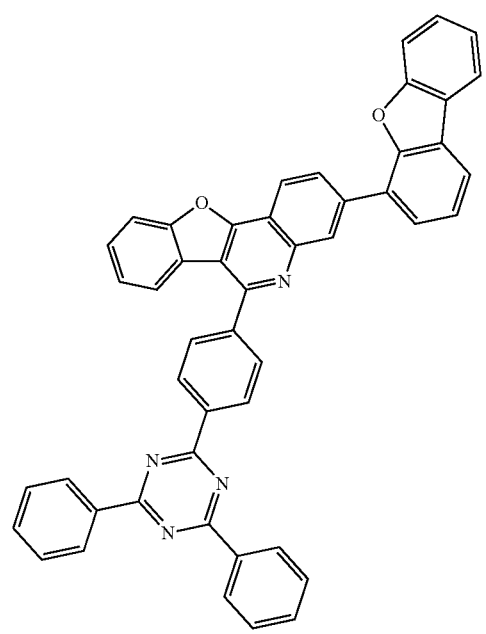
706

707
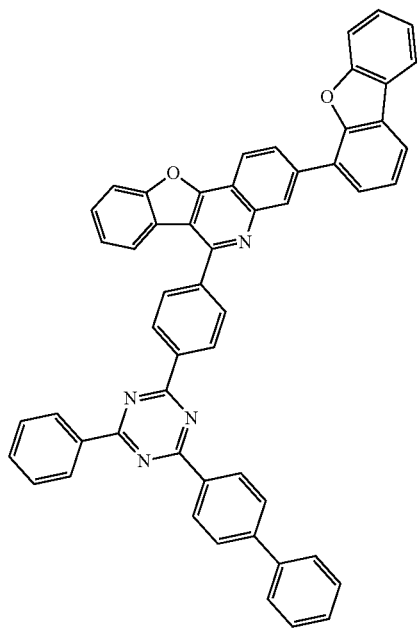
708
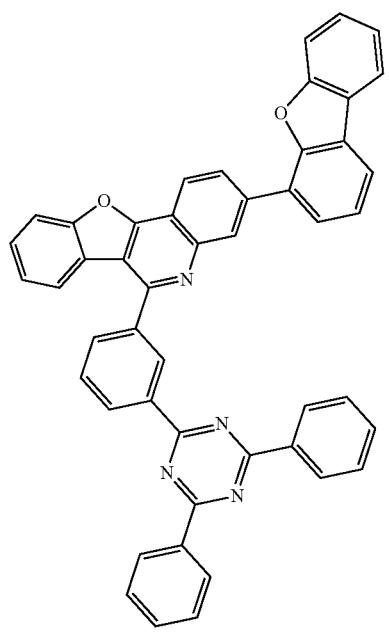
709
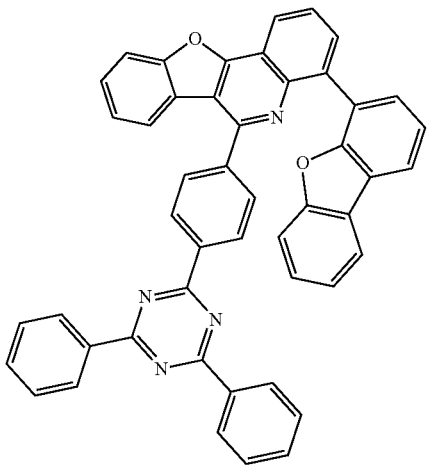
710
711
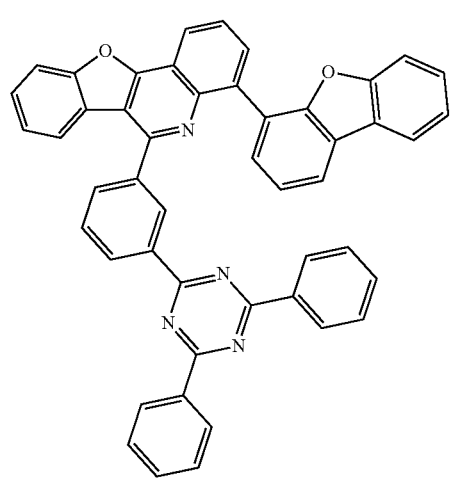

301
-continued
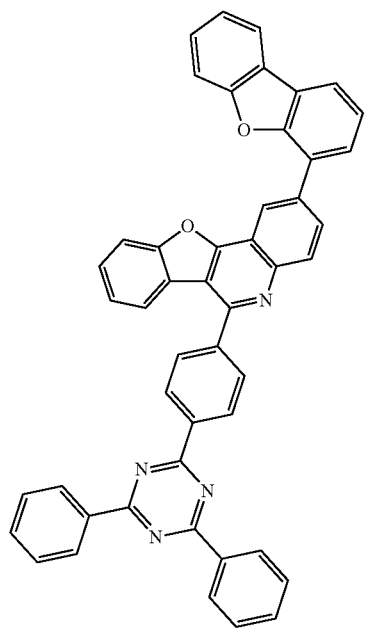
712
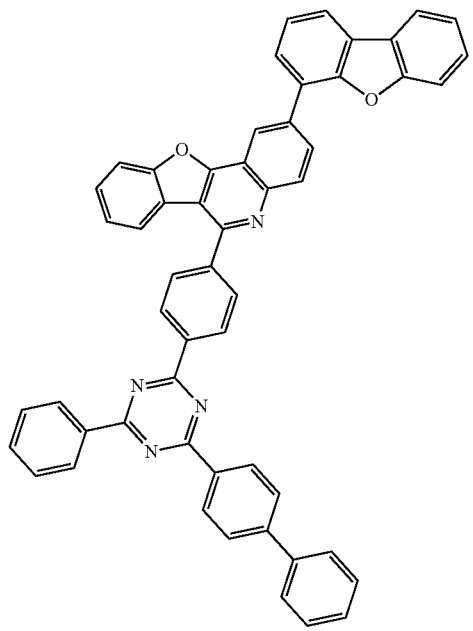
713
302
-continued
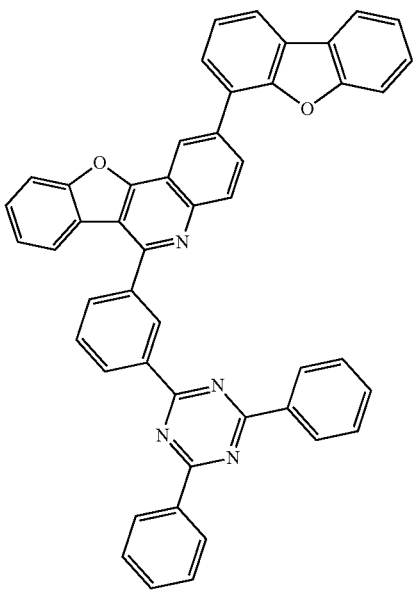
714
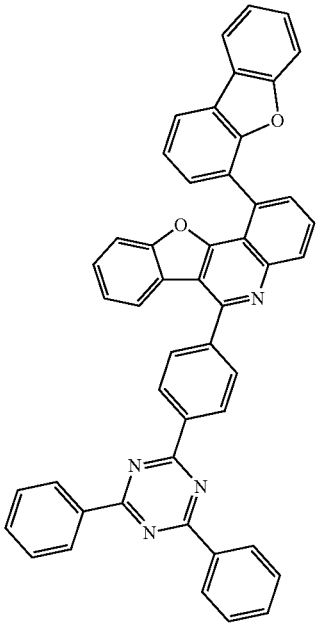
715

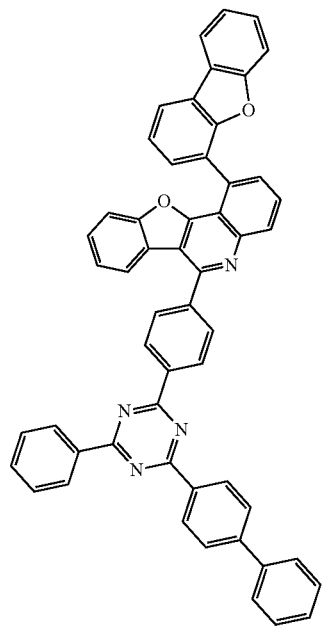
716
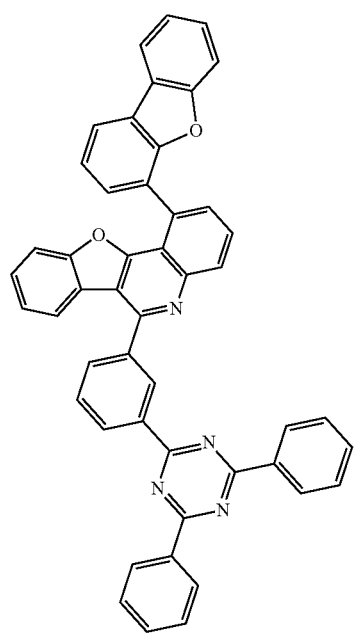
717
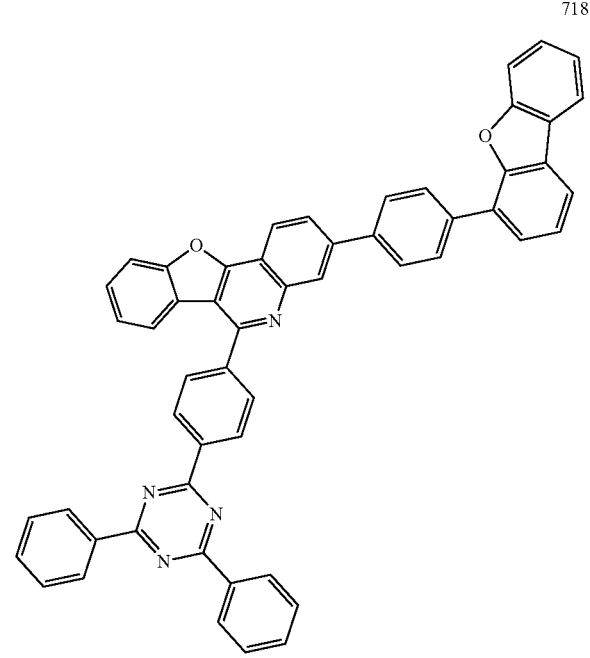
718
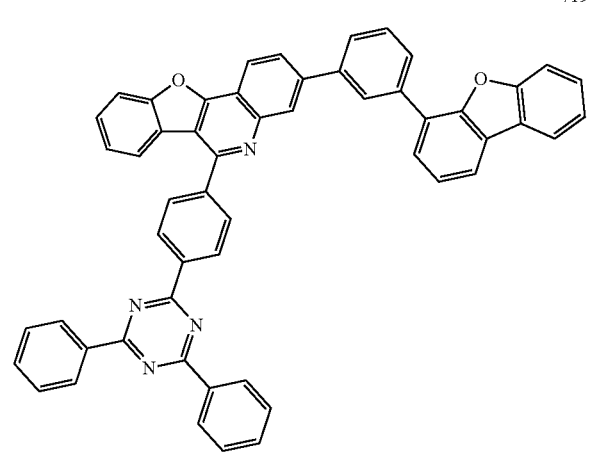
719

305
-continued
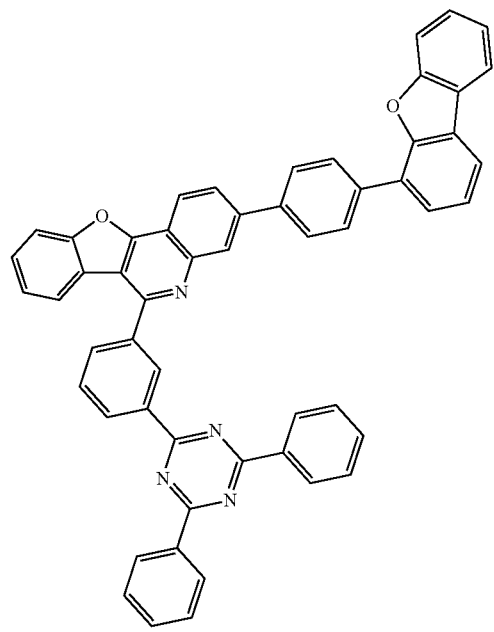
720
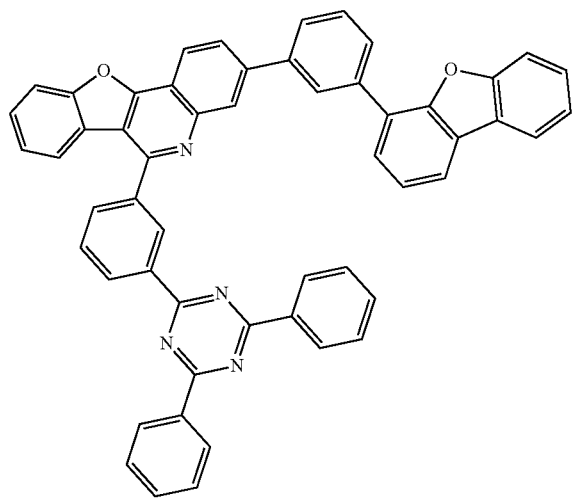
721
306
-continued
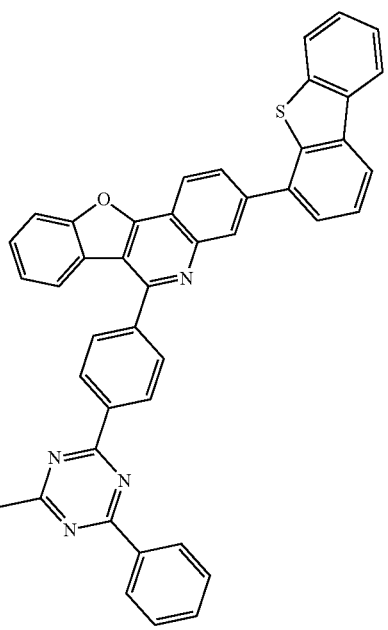
722
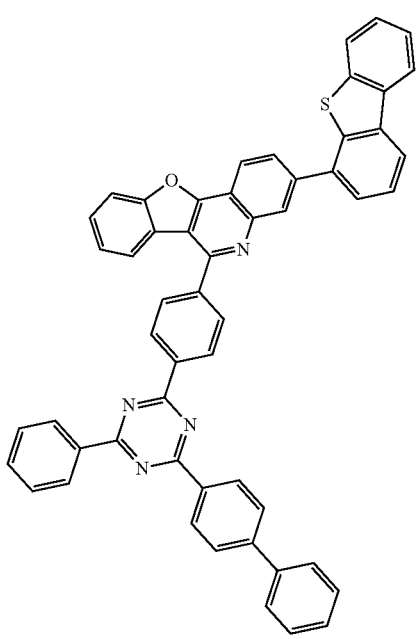
723

307
-continued
724
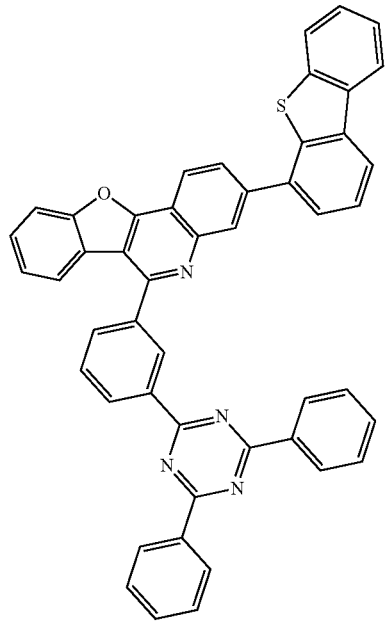
725
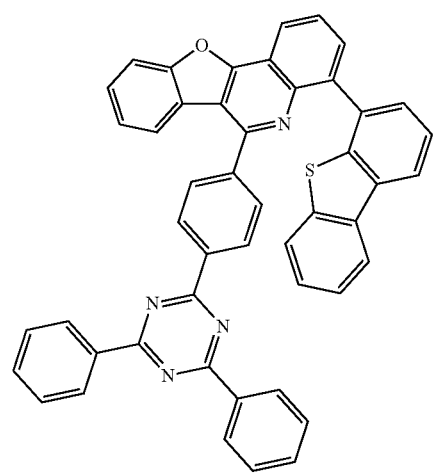
726
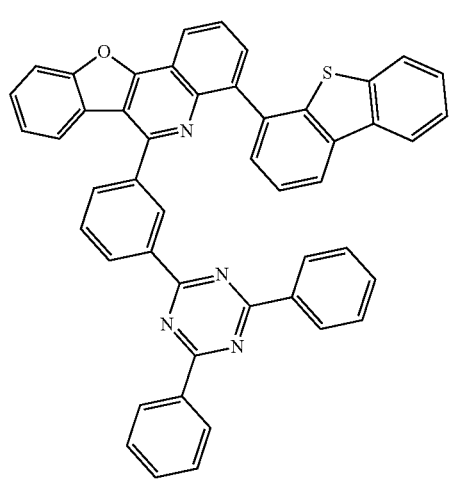
308
-continued
727
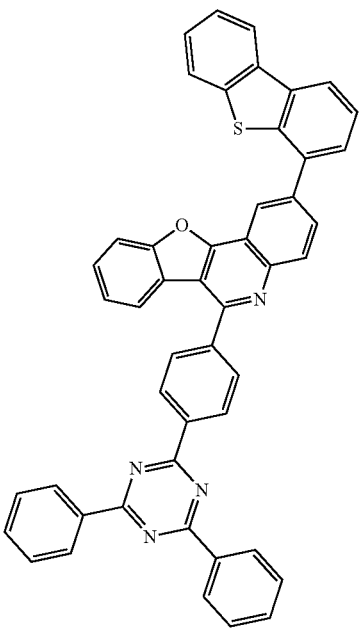
728
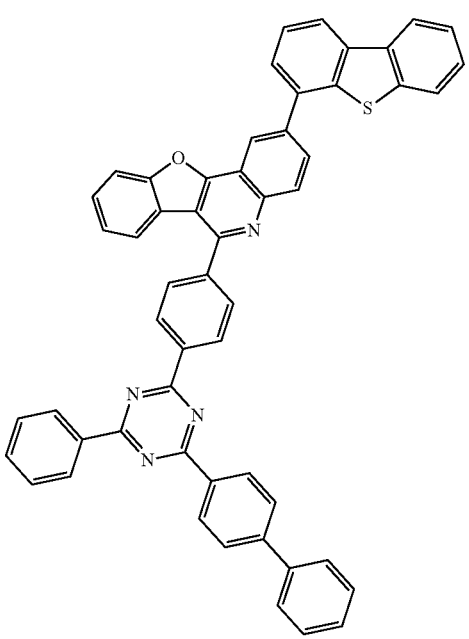

309
-continued
729
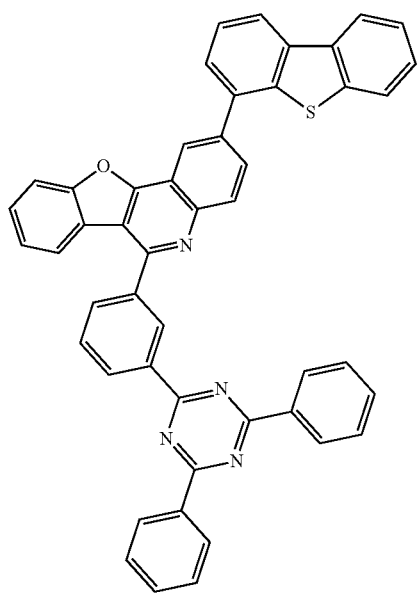
730
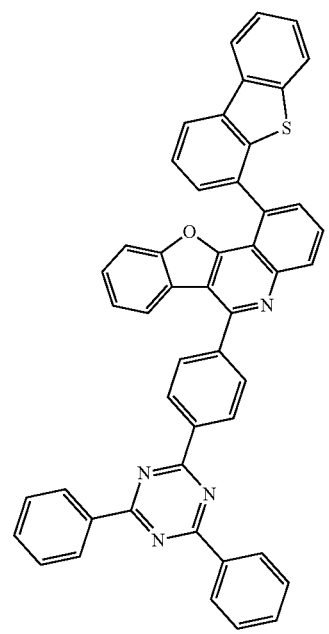
310
-continued
731
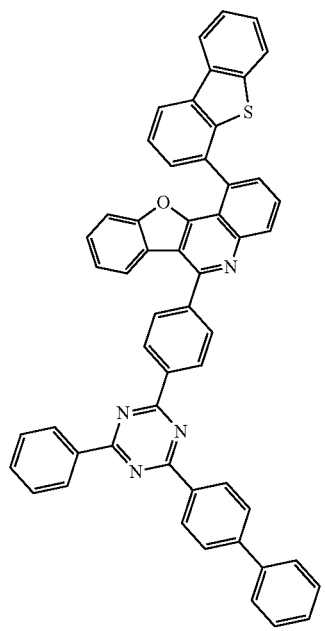
732
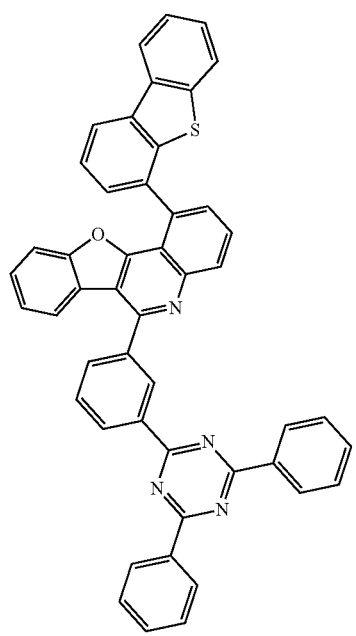

311
-continued
312
-continued
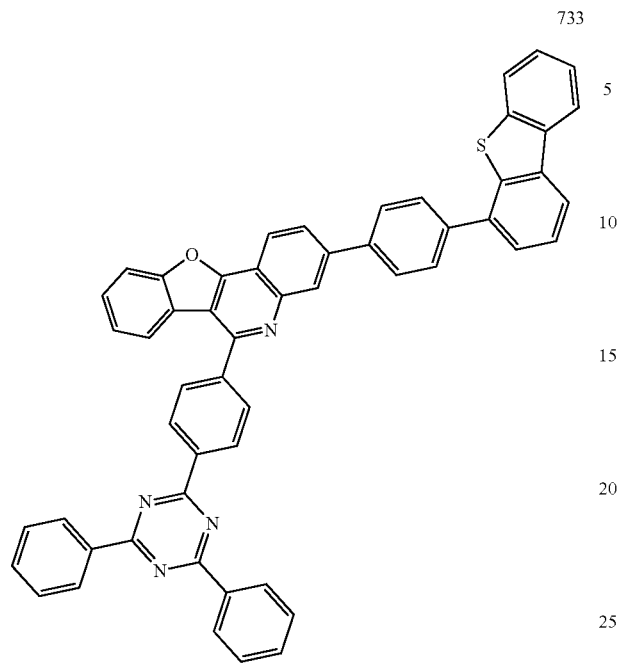
733
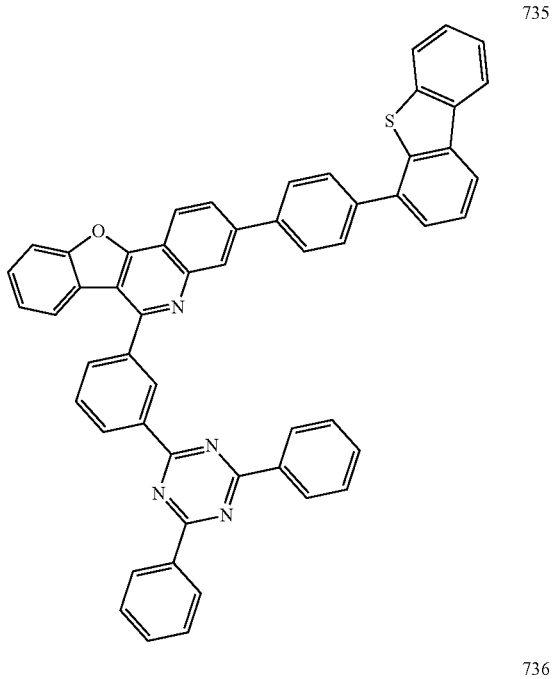
735
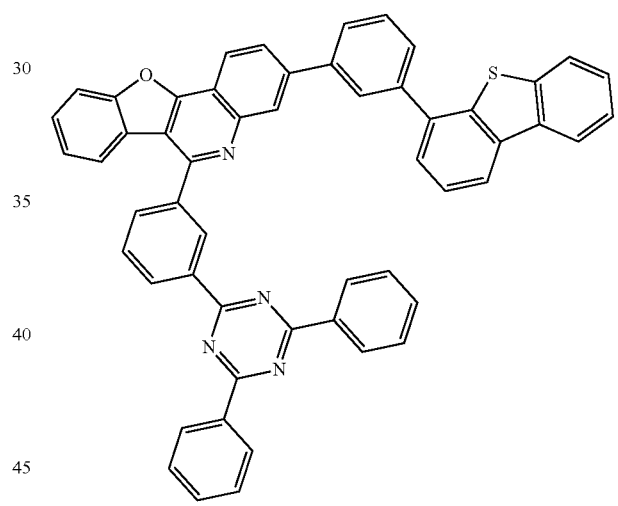
736
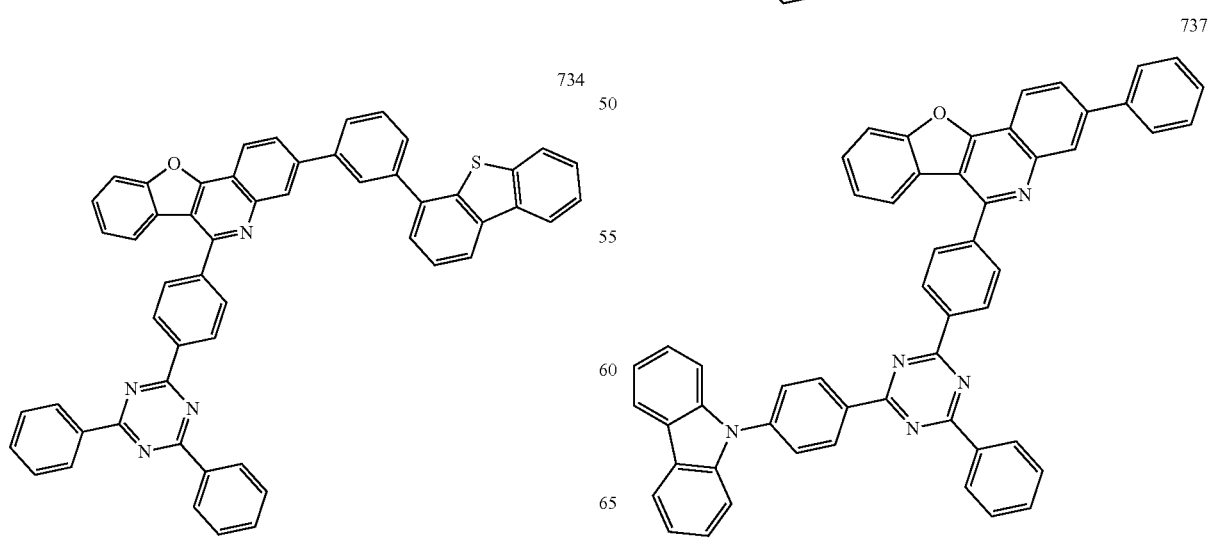
734 737

313
-continued
738
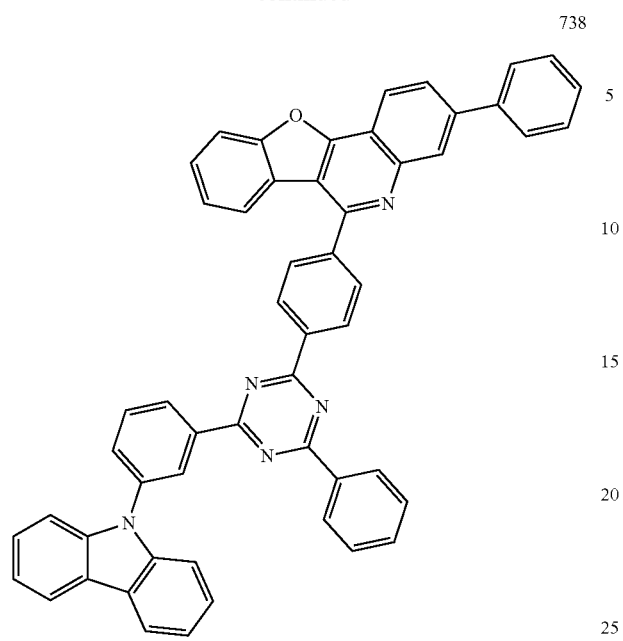
739
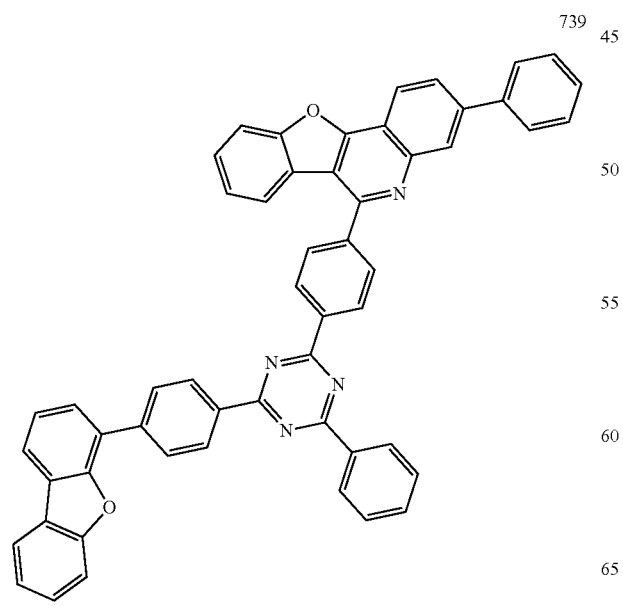
314
-continued
740
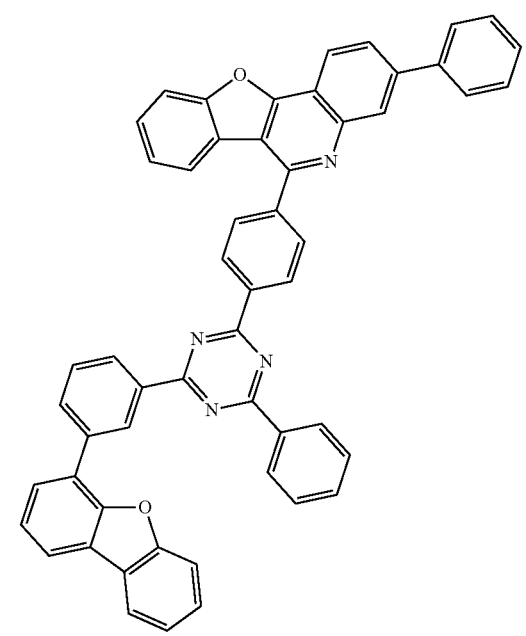
741
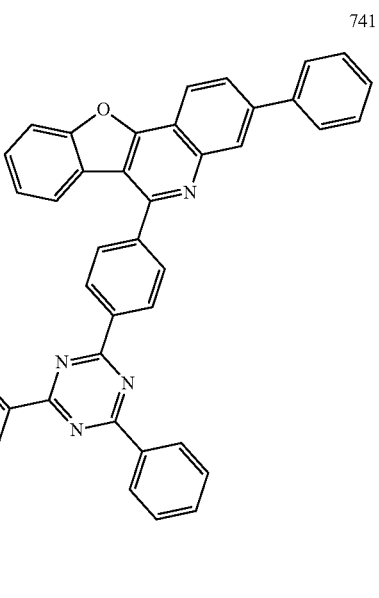

315
-continued
742
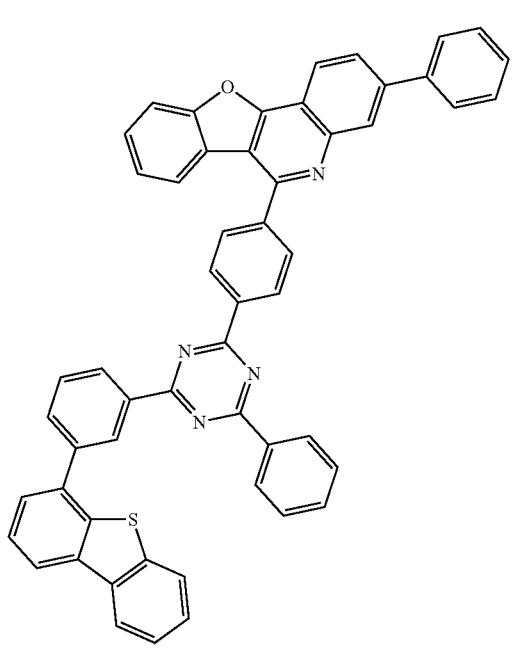
743
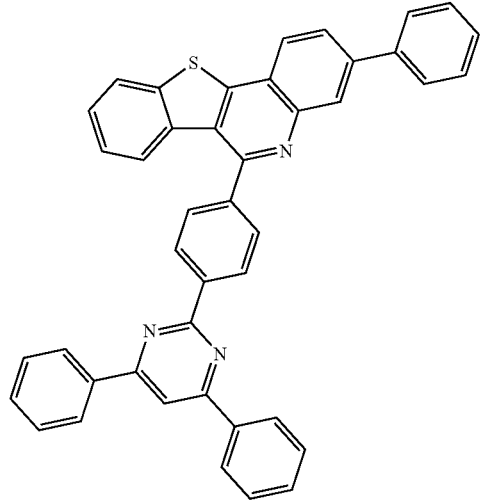
316
-continued
744
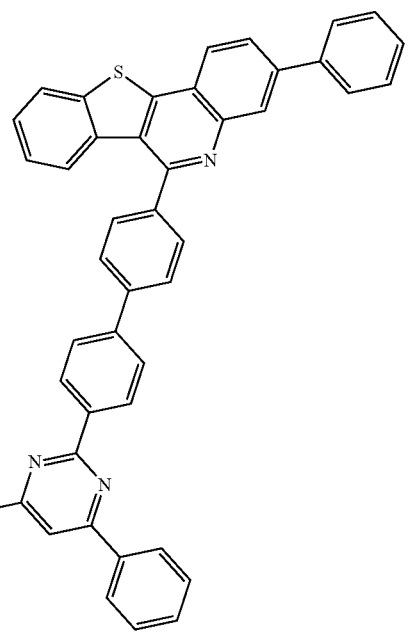
745
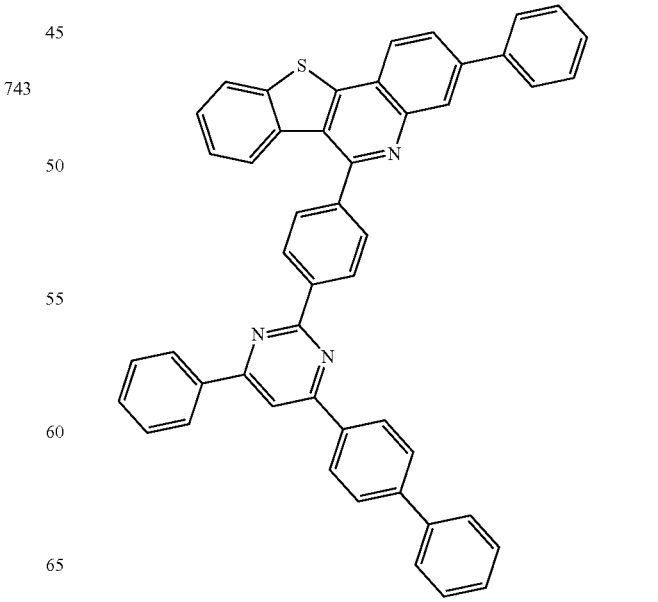

317
-continued
318
-continued
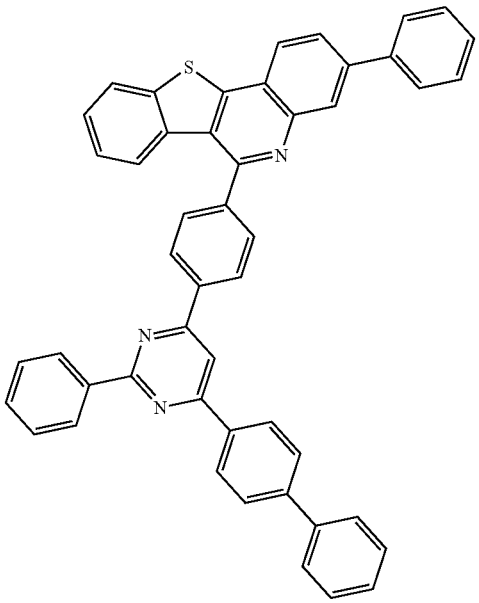
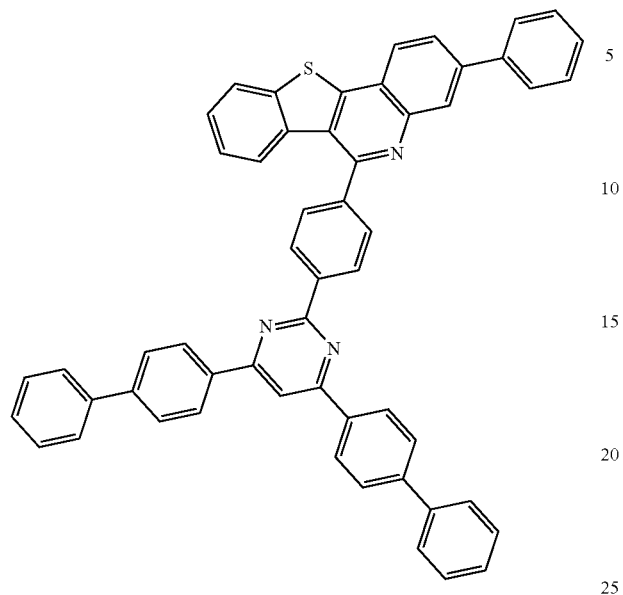
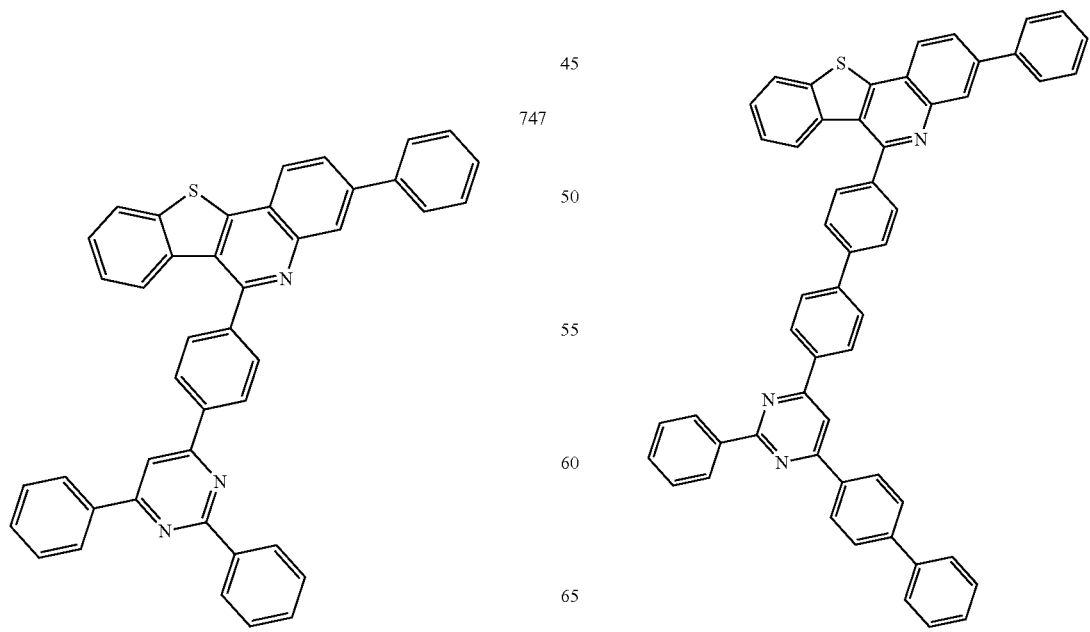

750
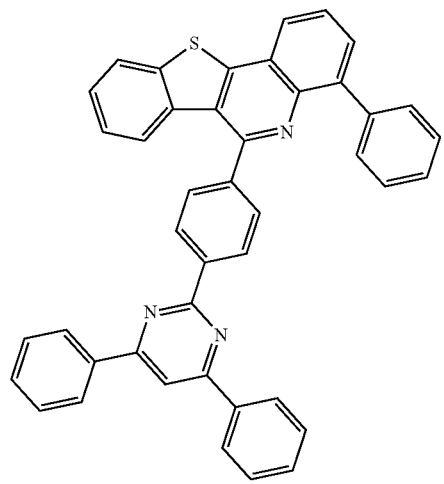
751
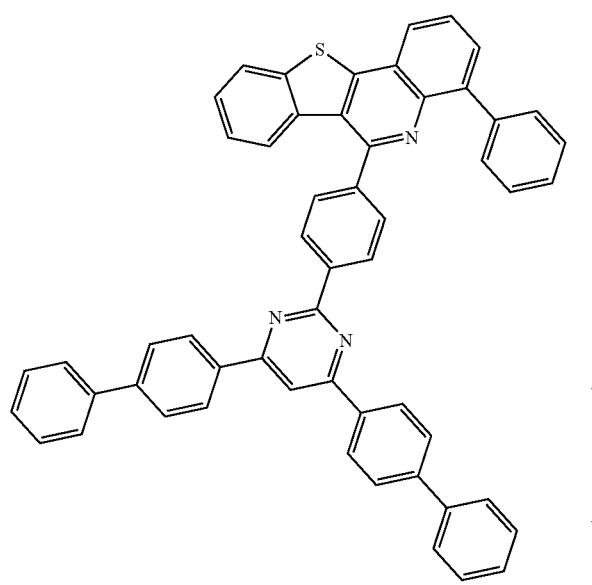
752
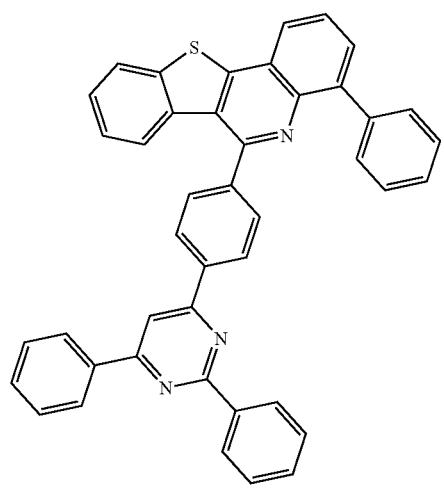
753
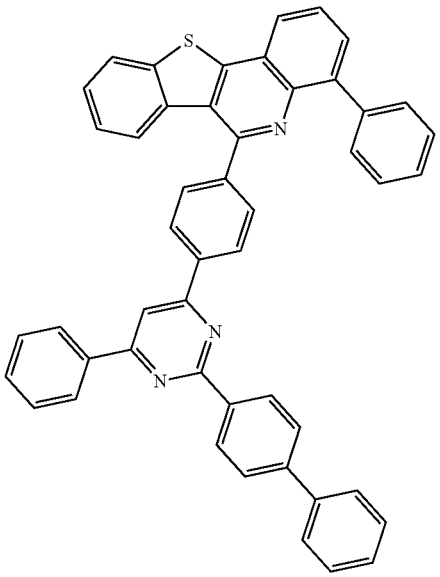
754
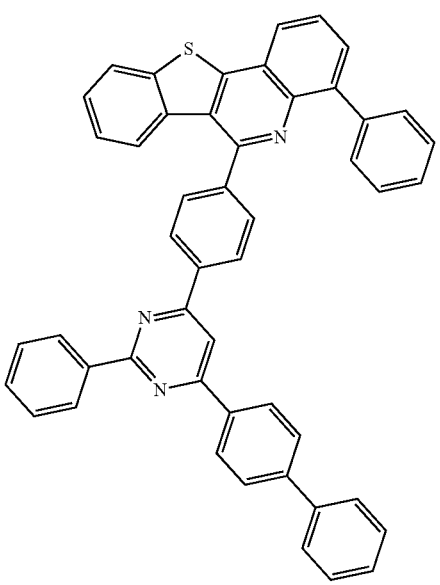
755
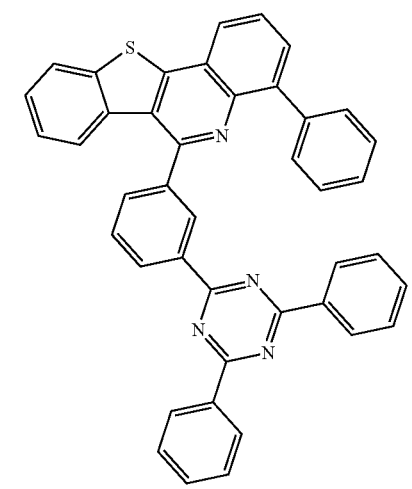

321
-continued
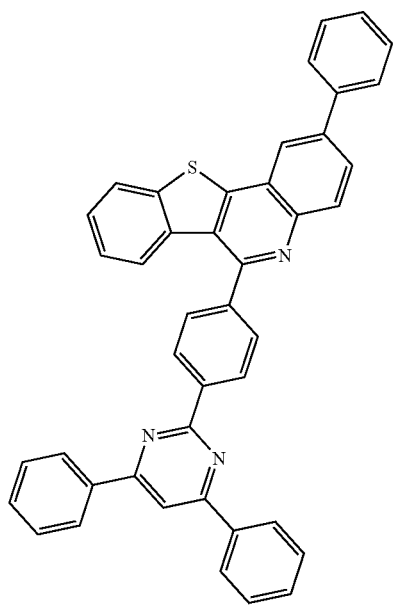
756
322
-continued
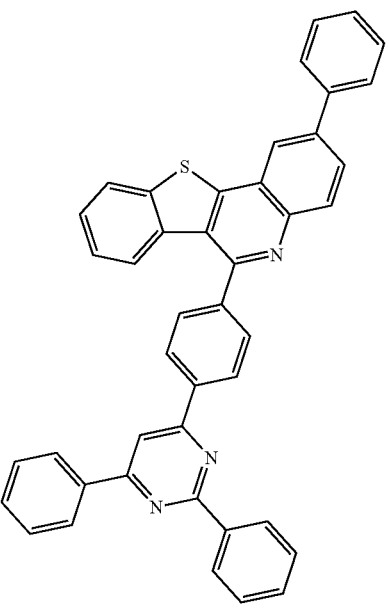
758
757
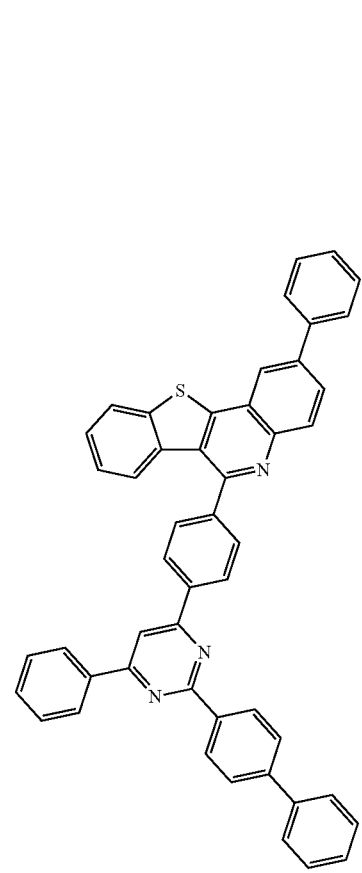
759

323
-continued
760
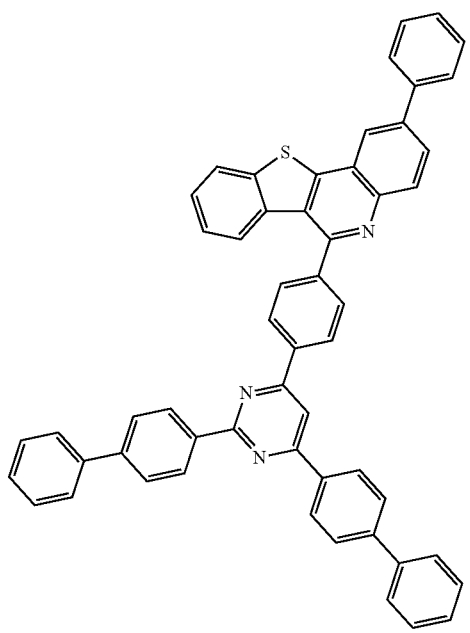
761
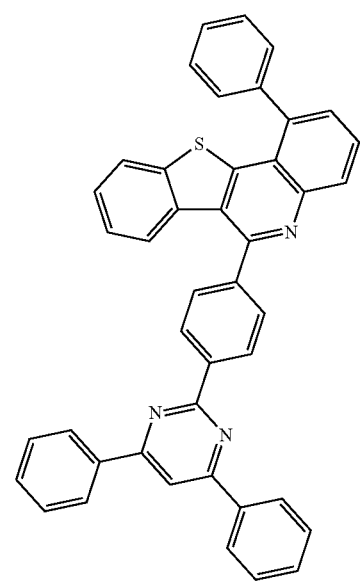
324
-continued
762
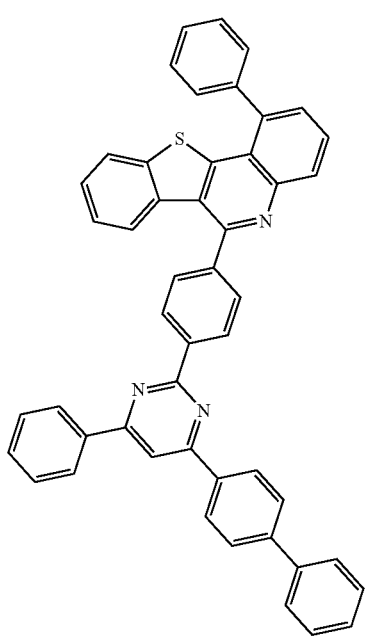
763
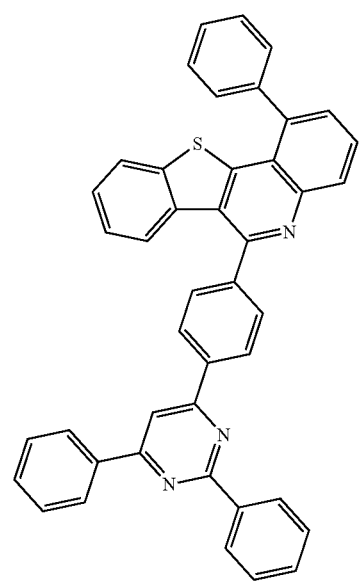

325
-continued
764
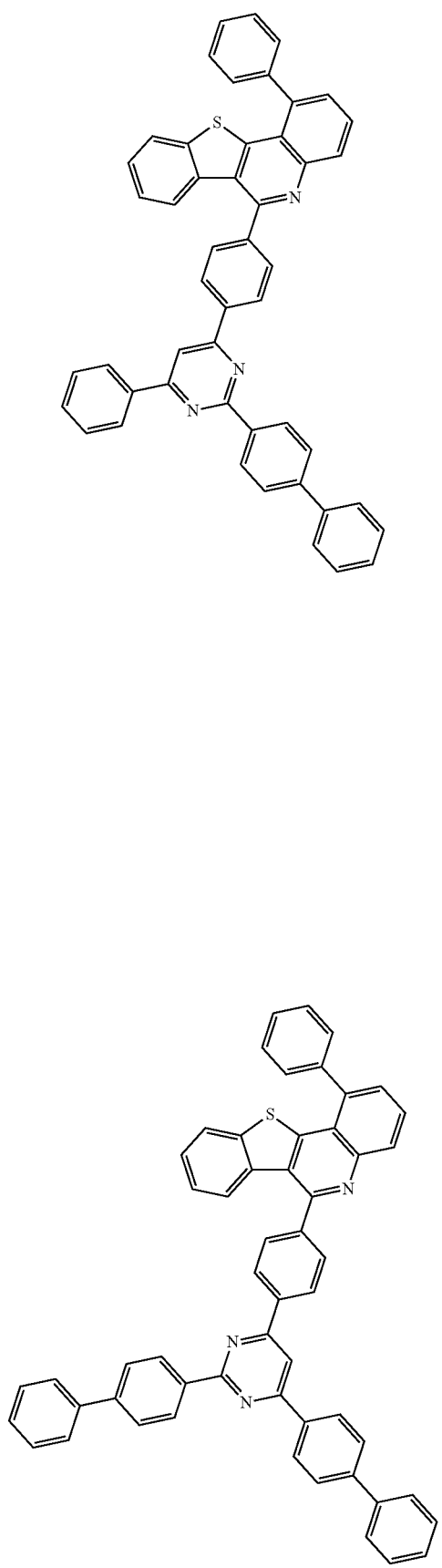
765
326
-continued
766
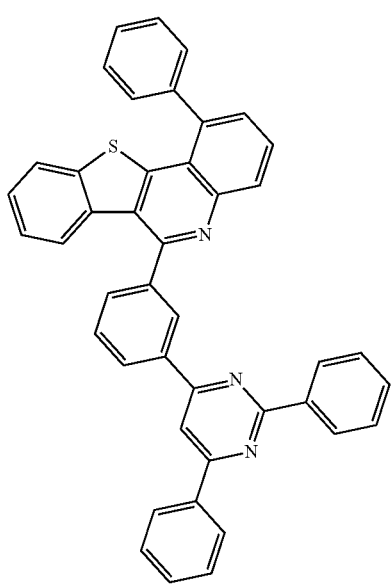
767
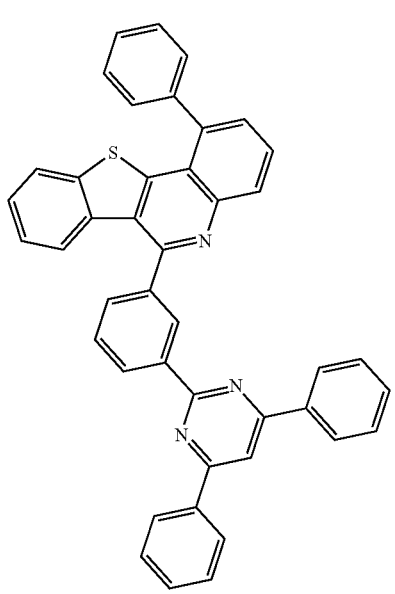
768
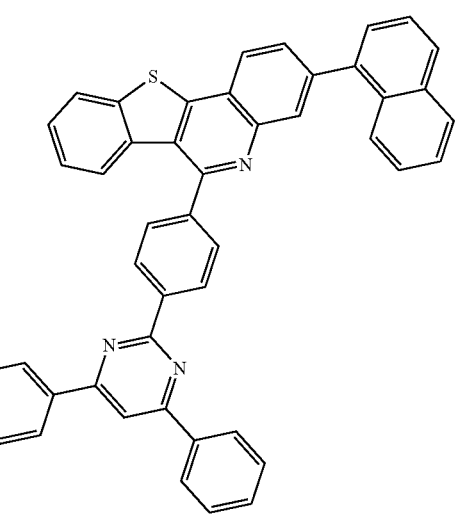

327
-continued
769
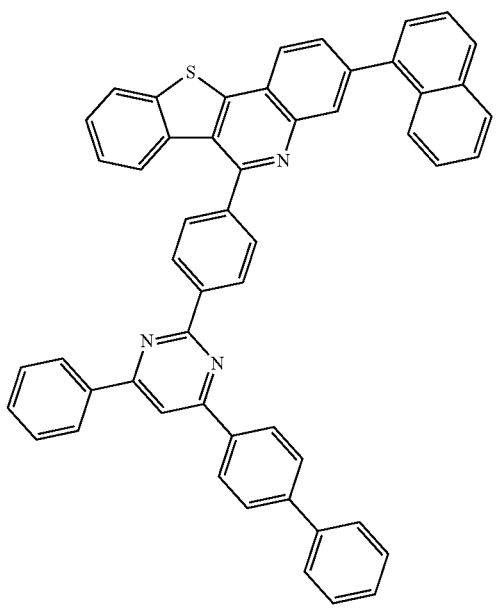
770
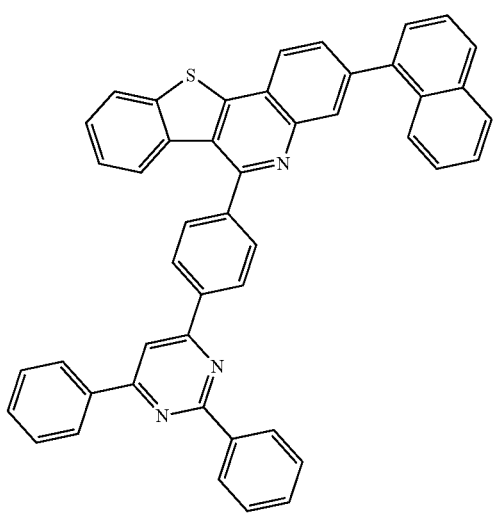
328
-continued
771
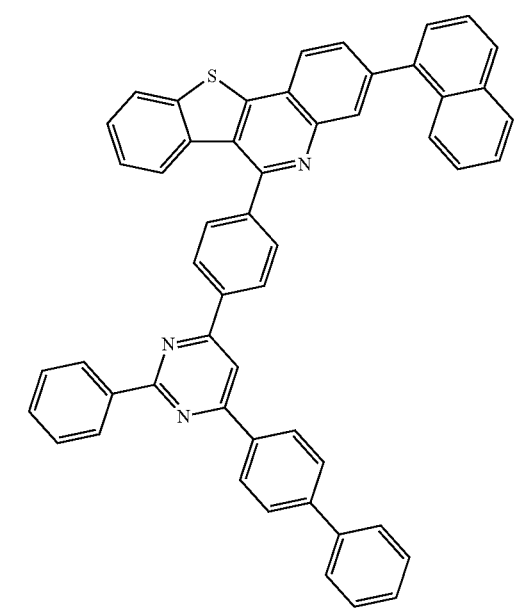
772
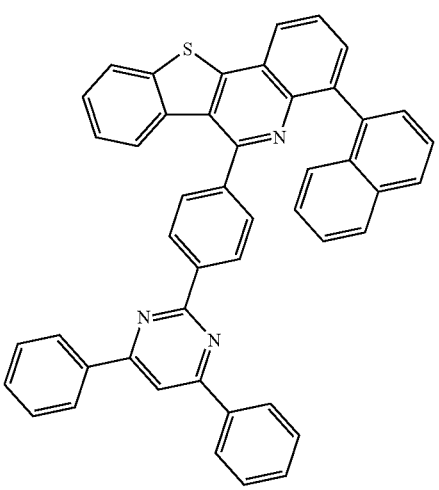
773
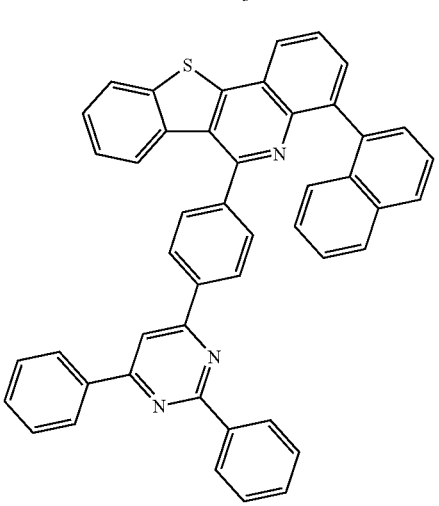

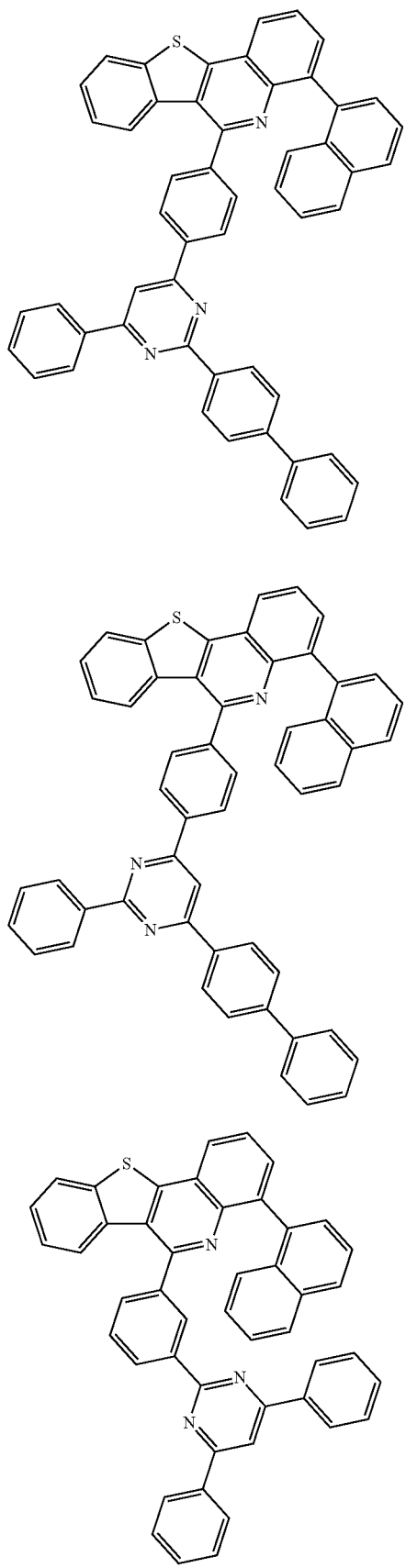
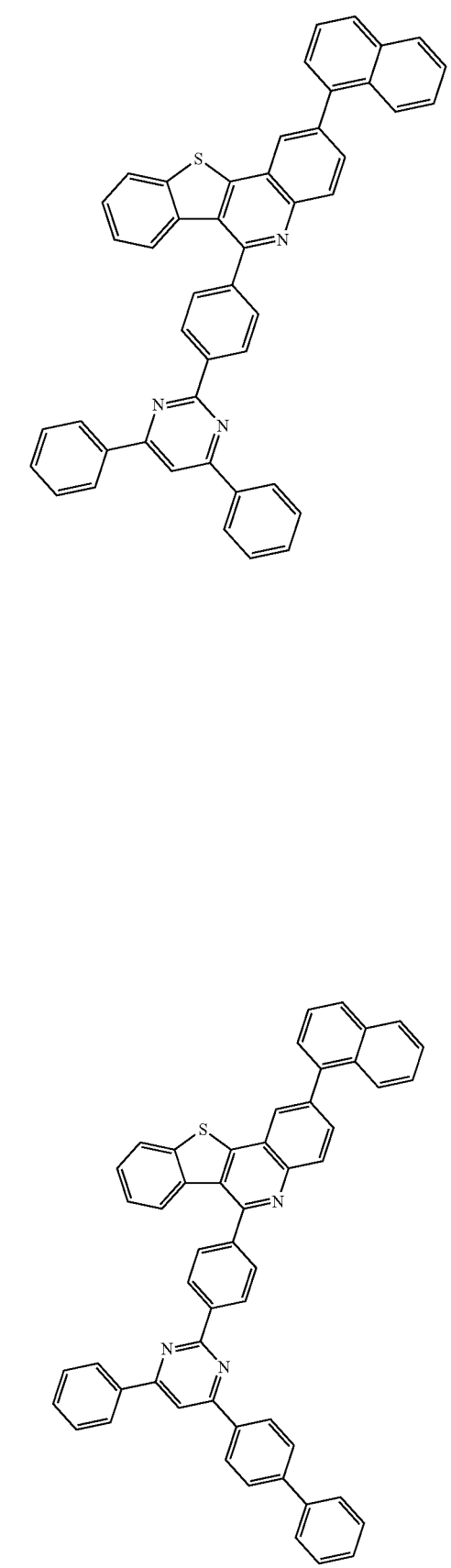

331
-continued
779
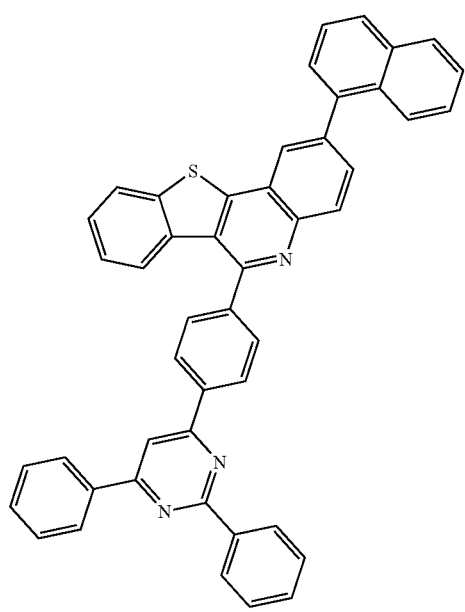
780
781
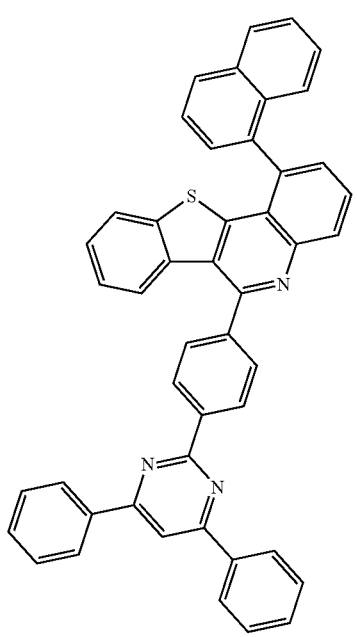
332
-continued
782
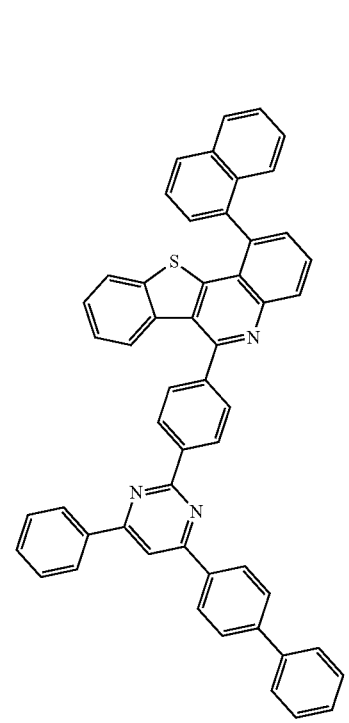

-continued
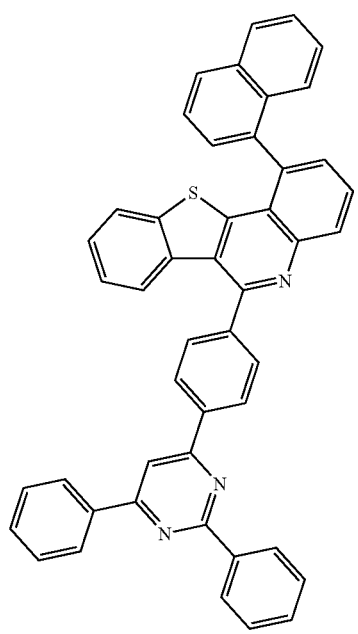
783
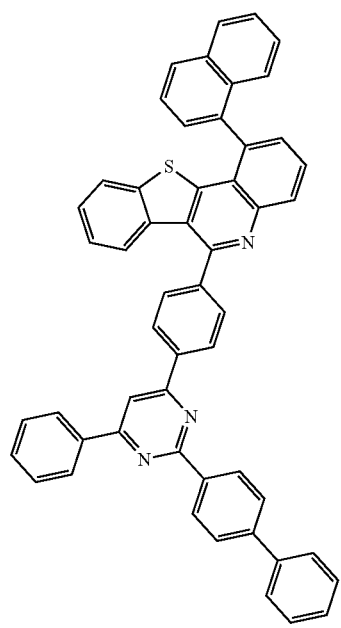
784
-continued
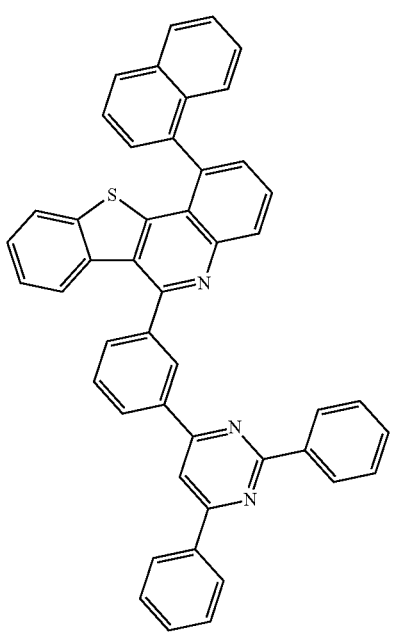
785
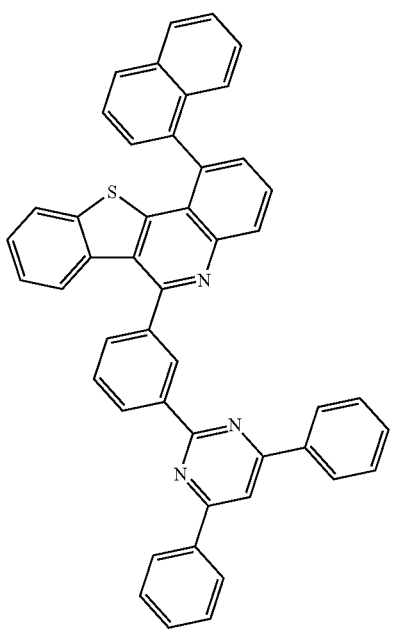
786

335
-continued
787
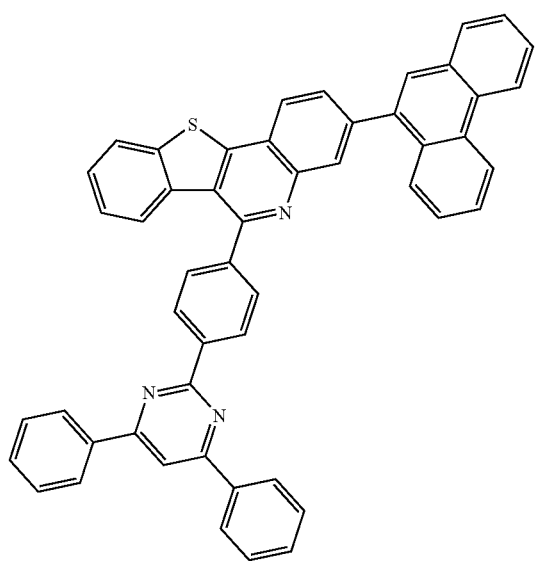
788
789
-continued
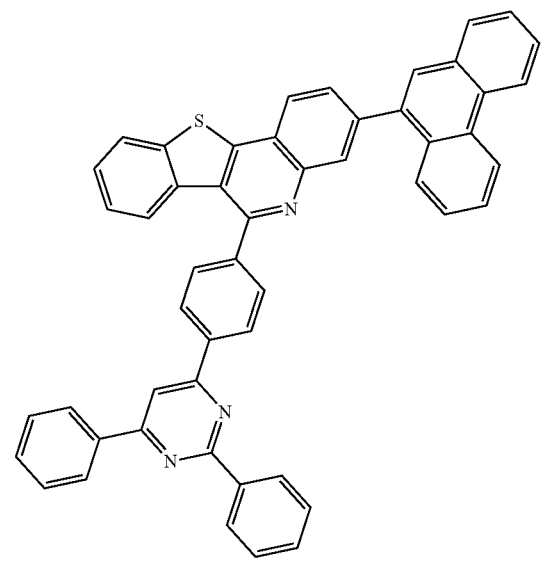
336
790
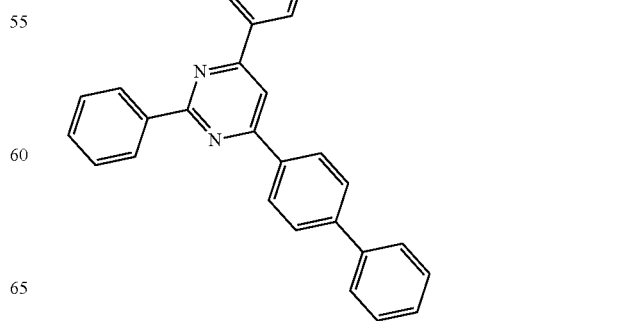

337
-continued
791
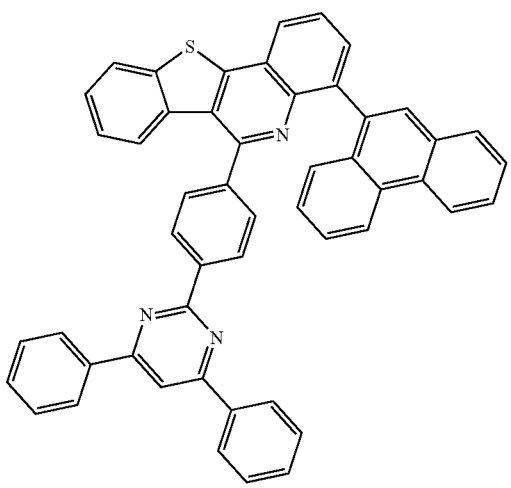
792
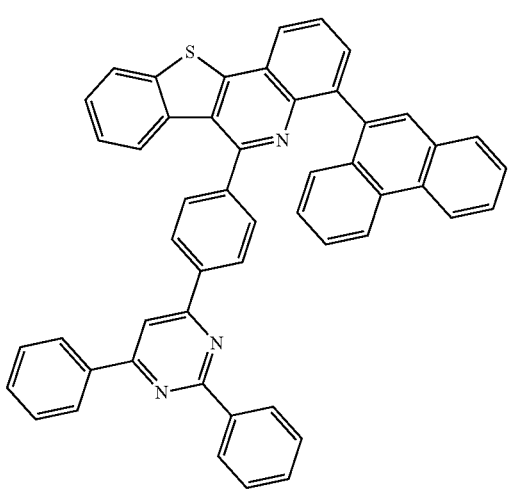
793
338
-continued
794
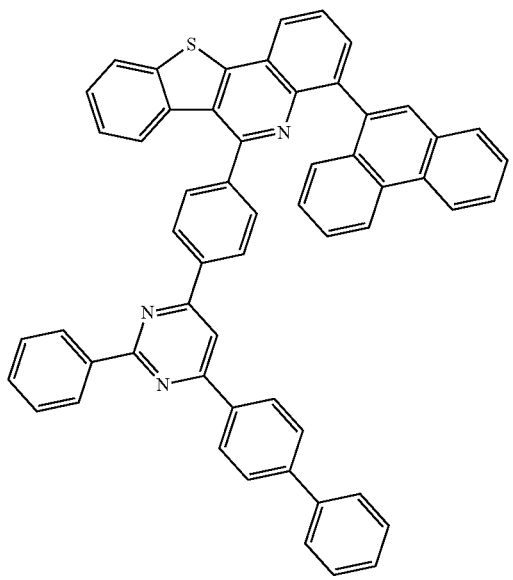
795
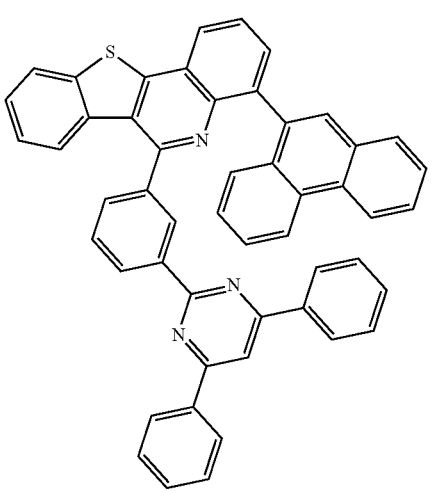

339
-continued
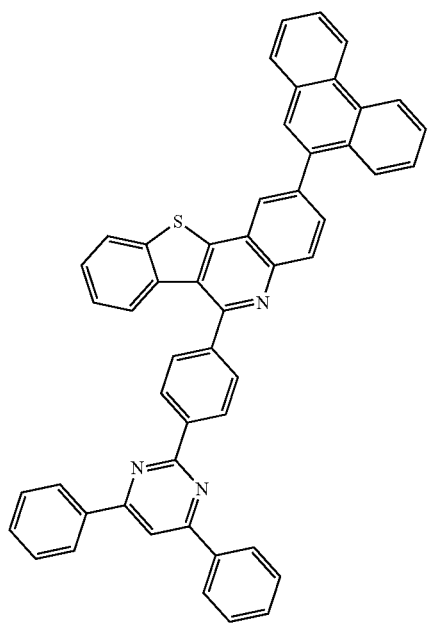
796
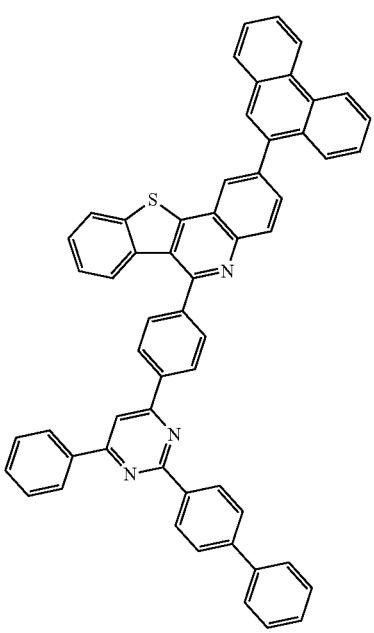
797
340
-continued
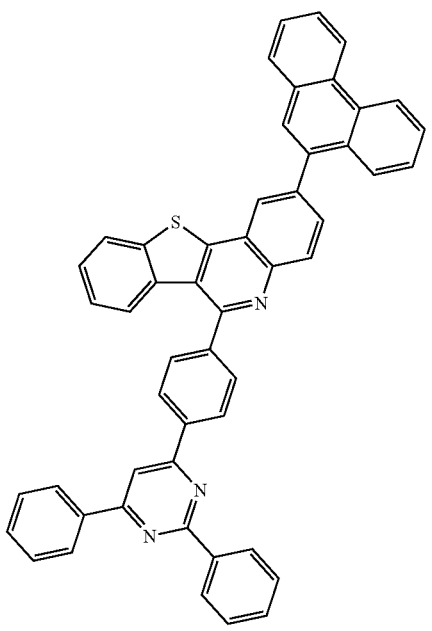
798
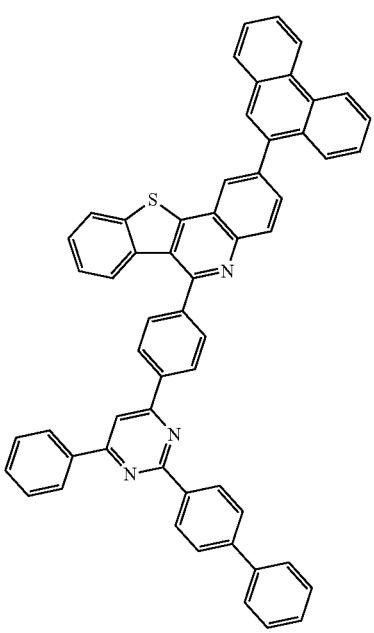
799

341
-continued
342
-continued
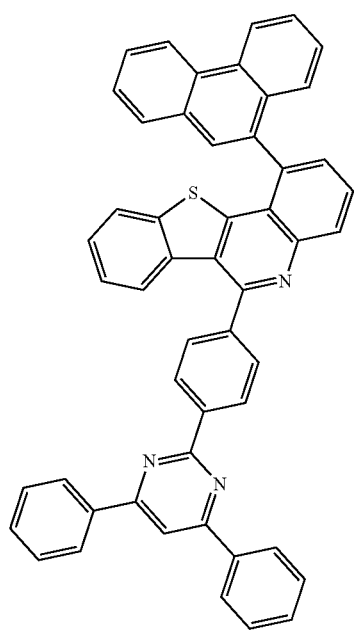
800
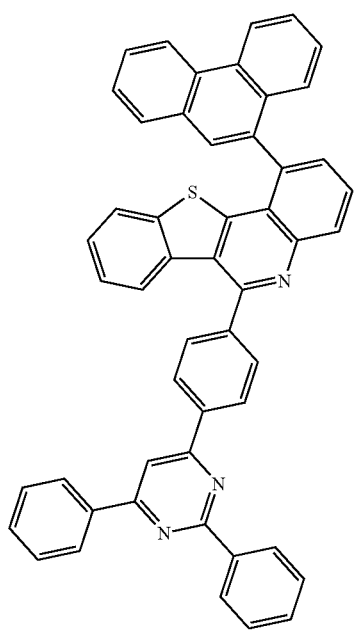
802
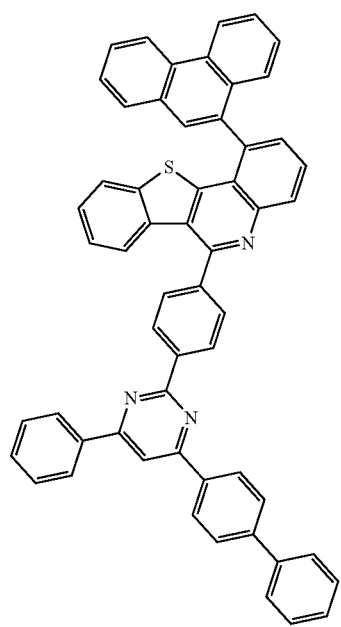
801
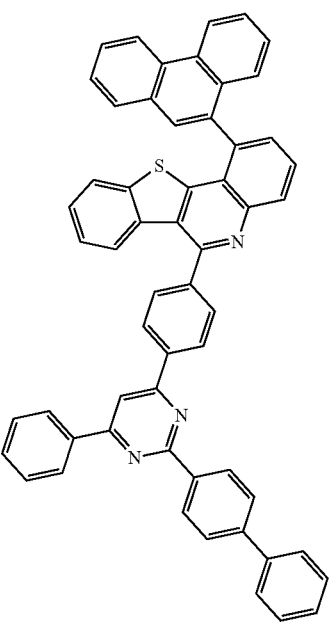
803

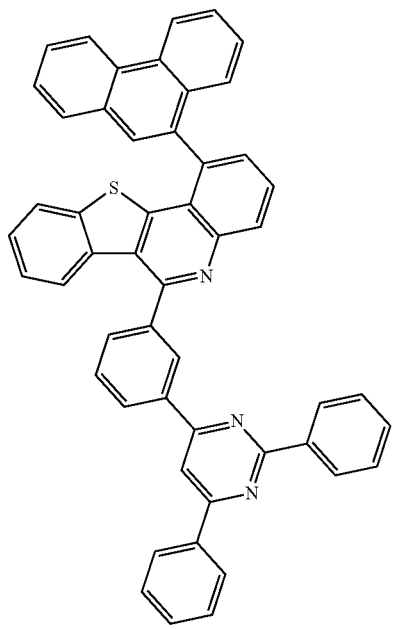
804
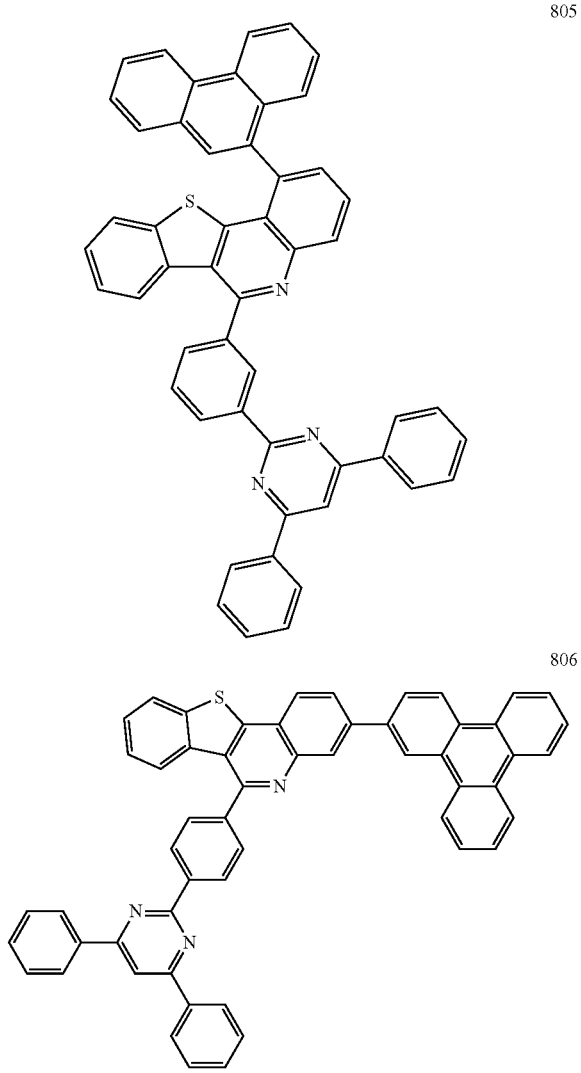
805
806
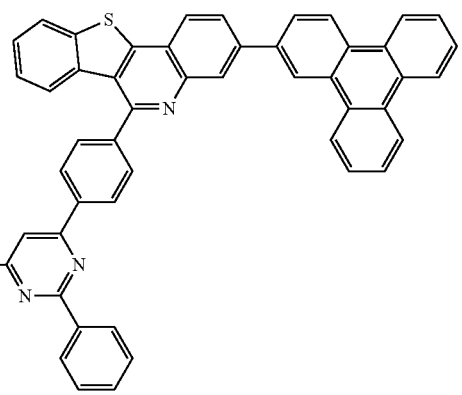
807
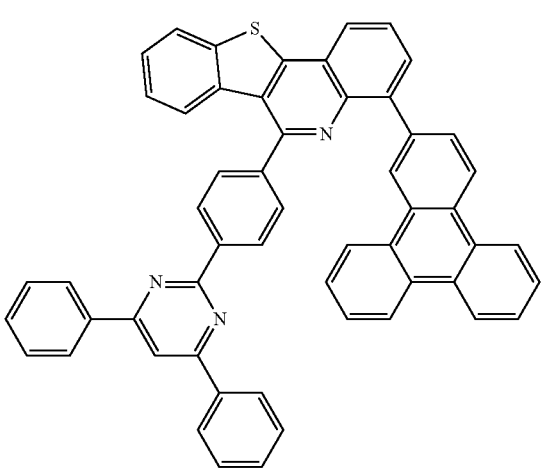
808
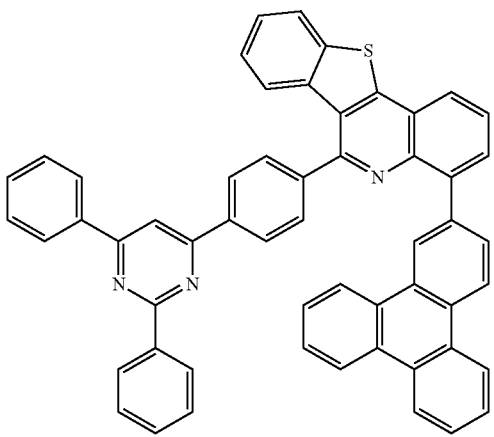
809

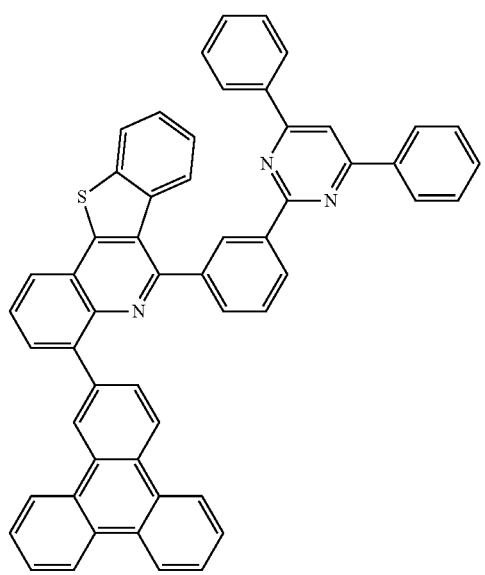
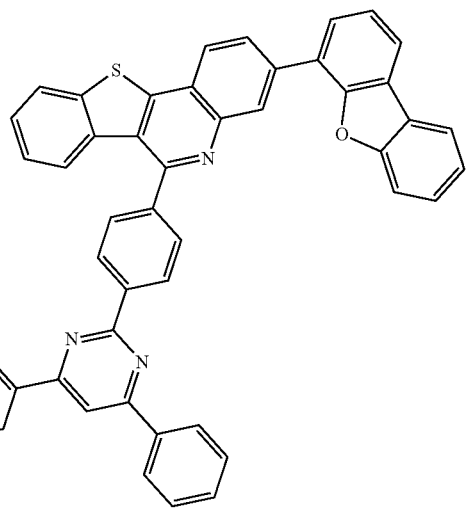
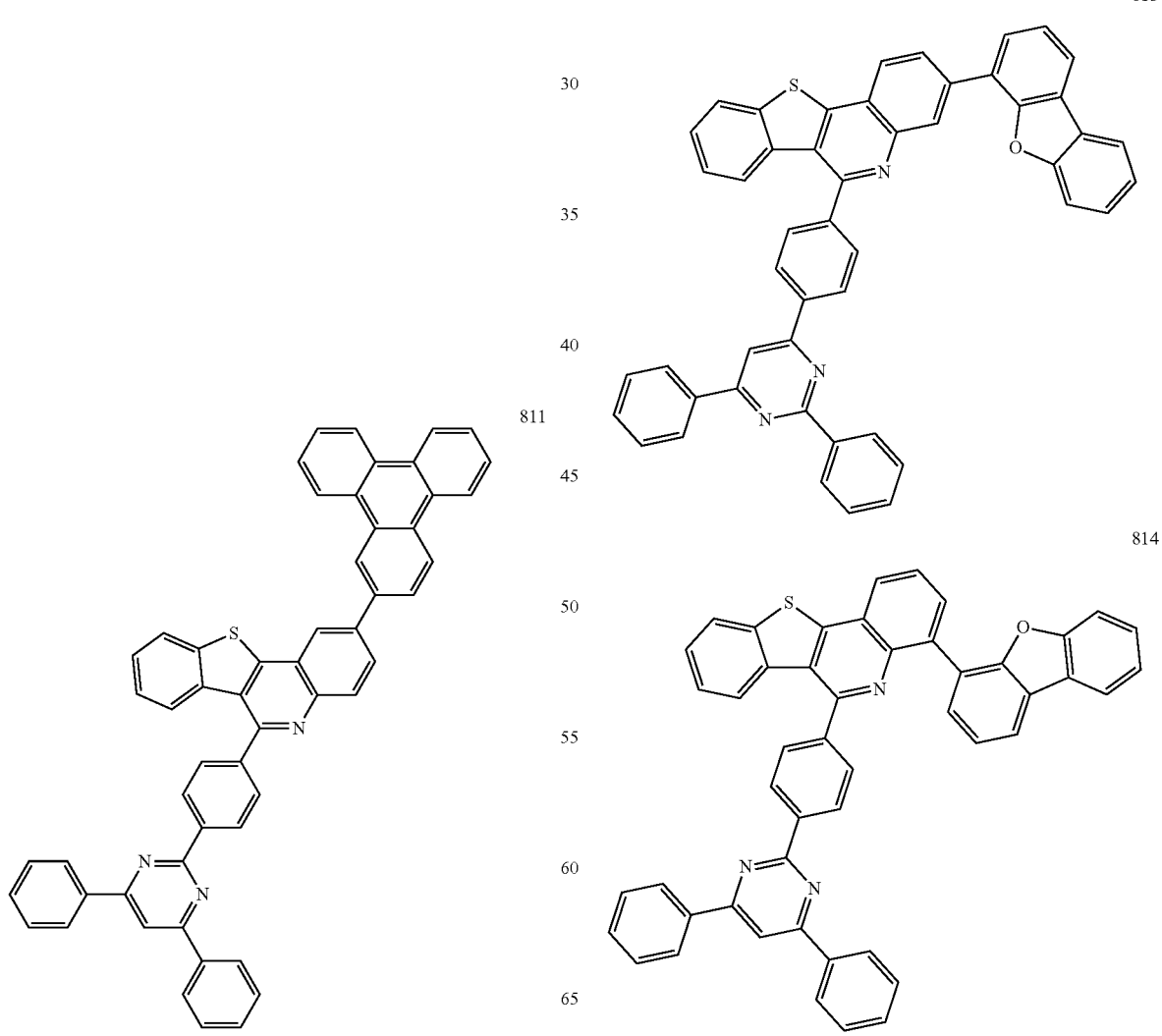

815
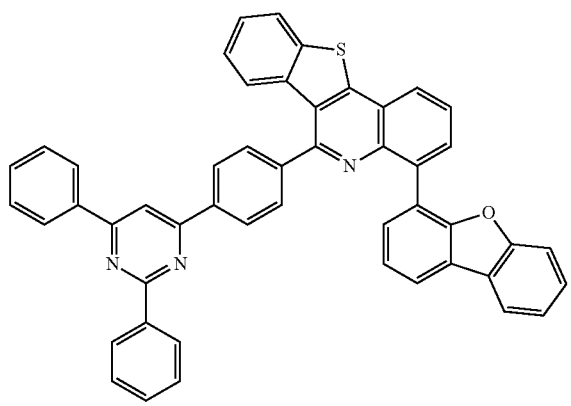
816
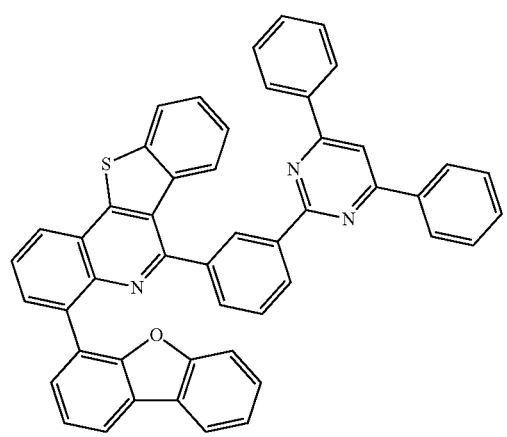
817
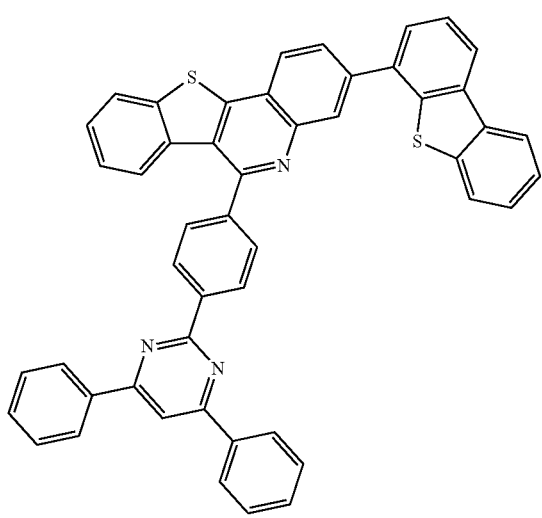
818
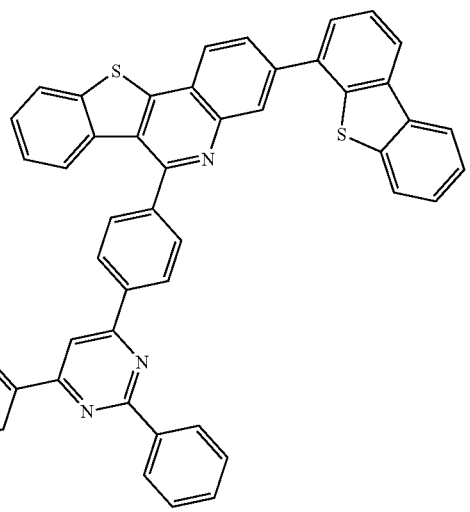
819
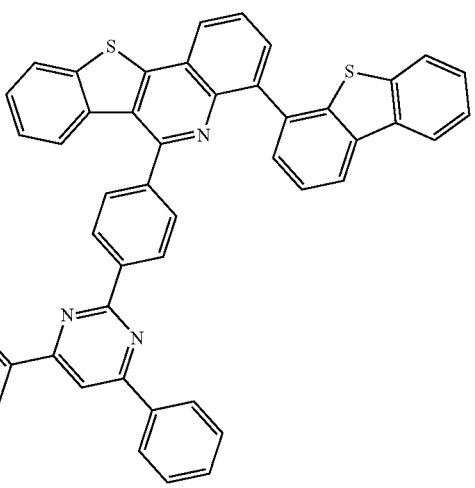
820
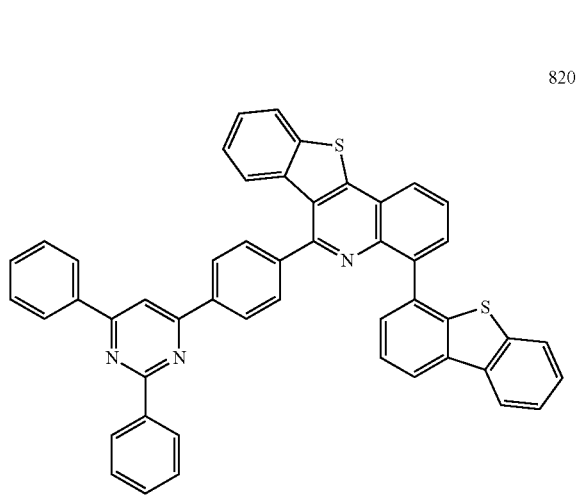

-continued
821
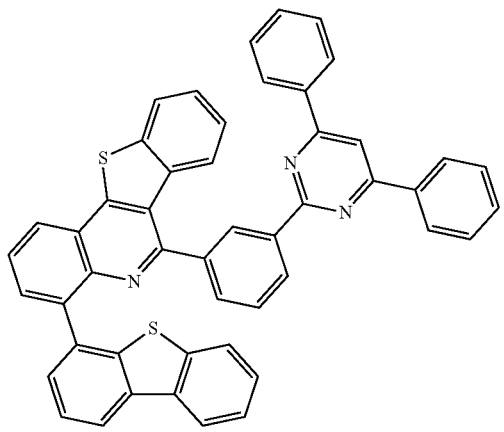
822
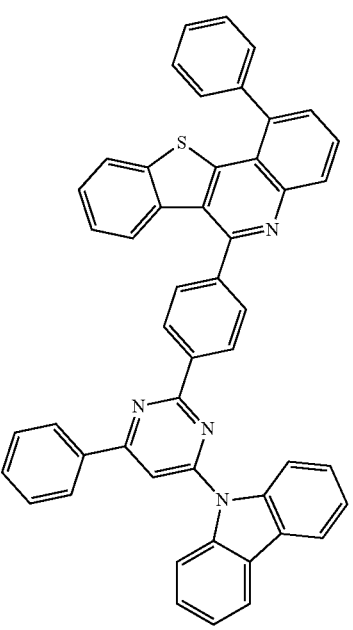
823
-continued
824
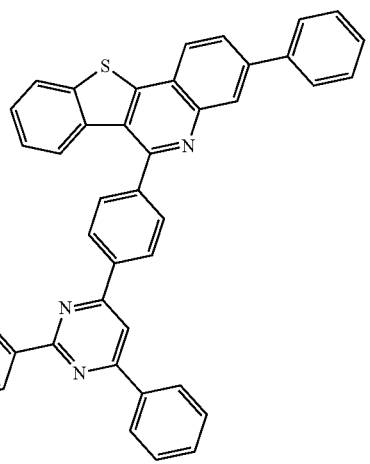
825
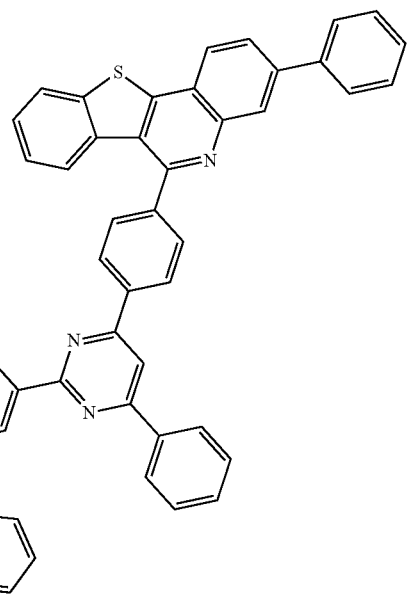

826
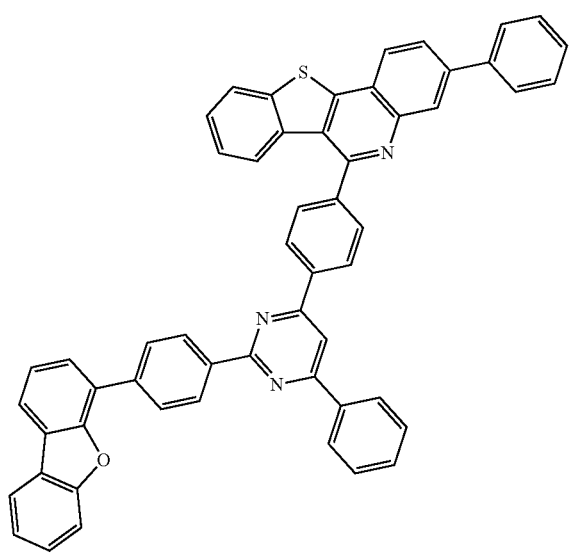
827
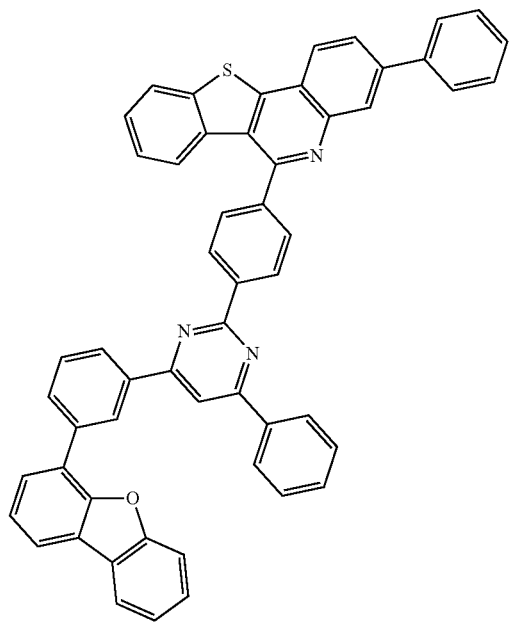
828
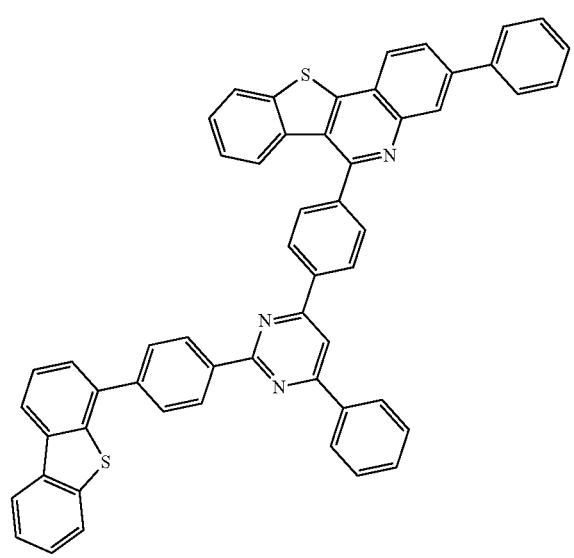
829
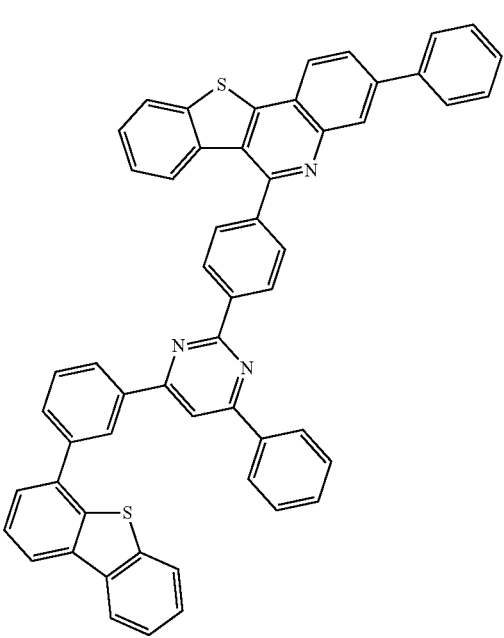

-continued
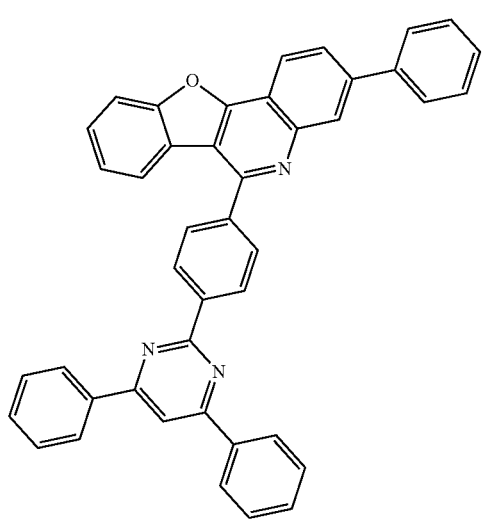
830
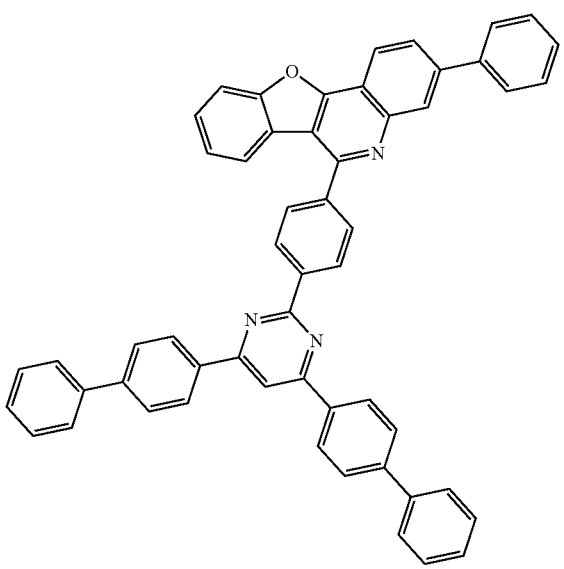
832
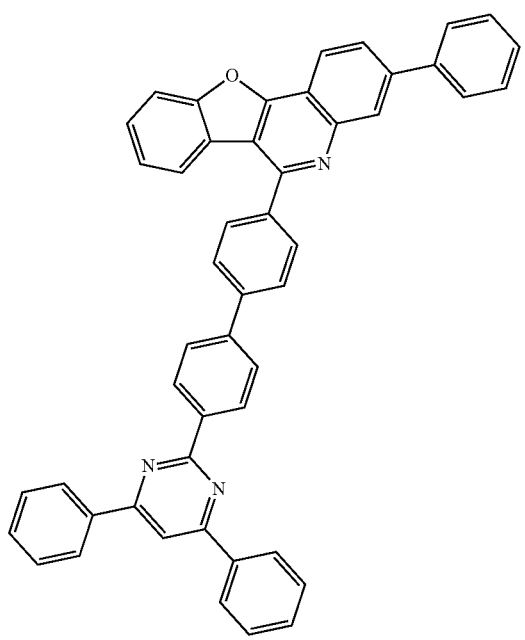
831
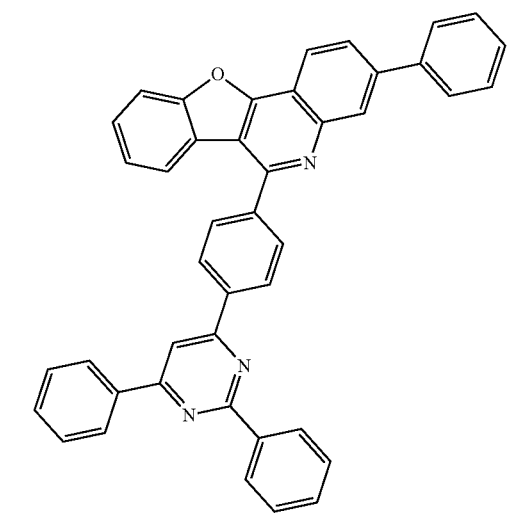
833

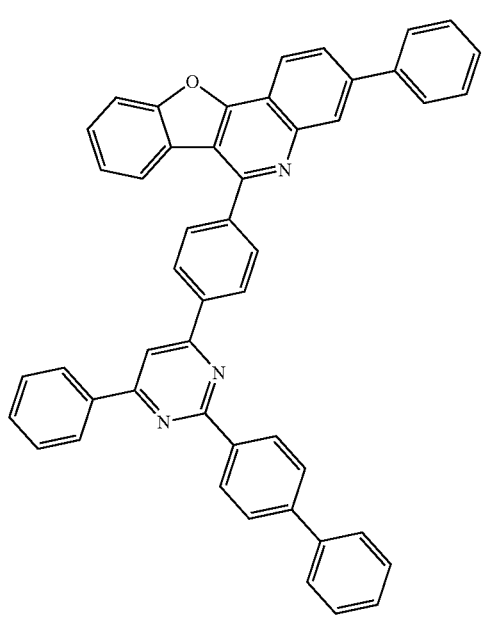
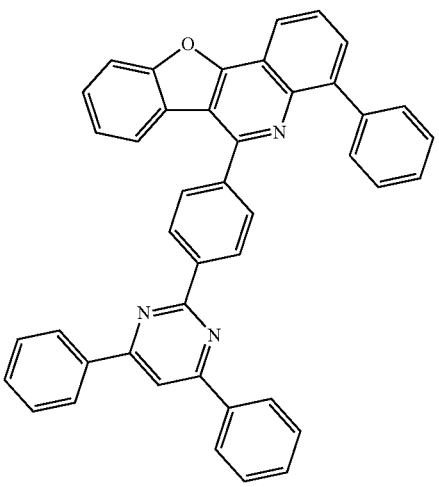
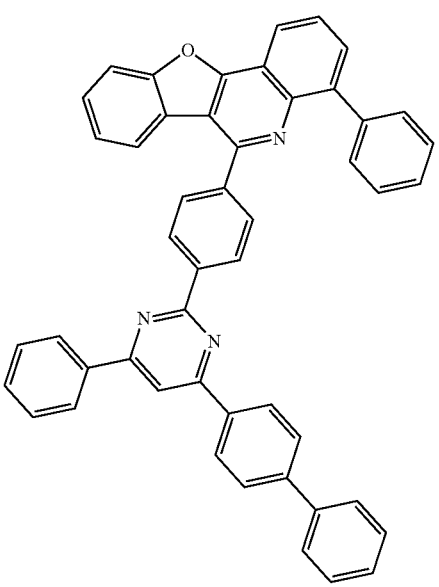
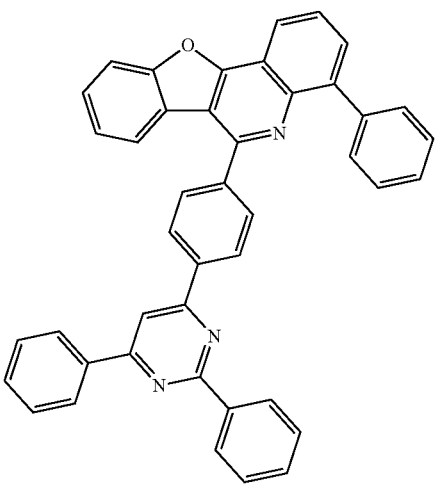

-continued
839
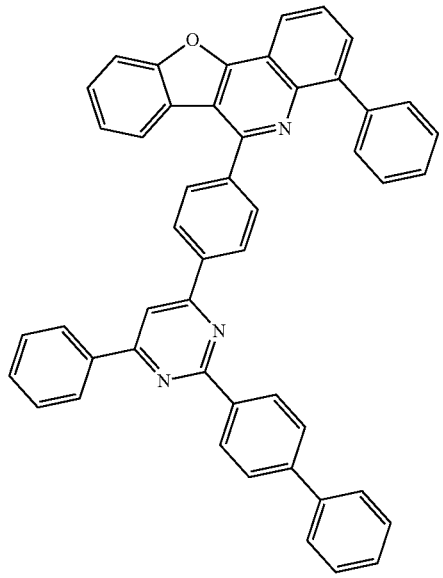
840
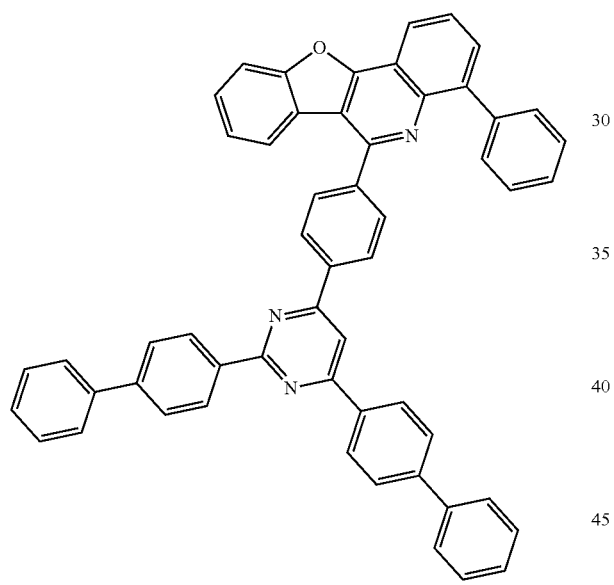
841
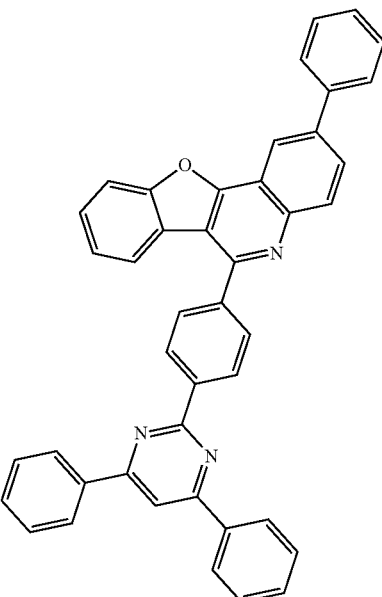
-continued
842
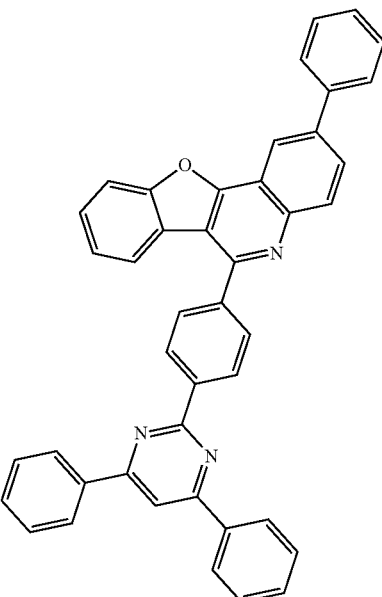
843
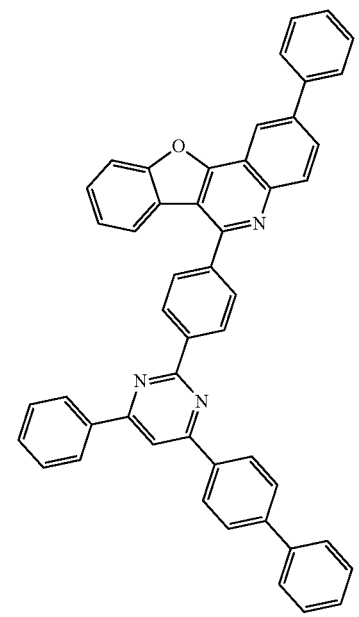

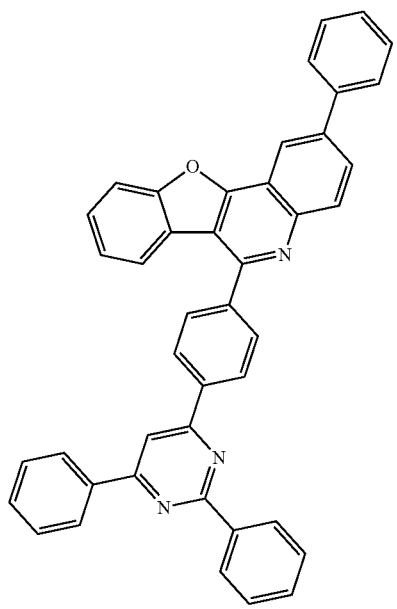
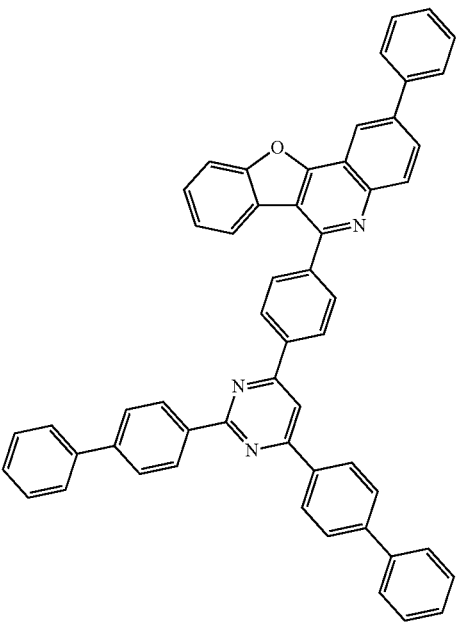
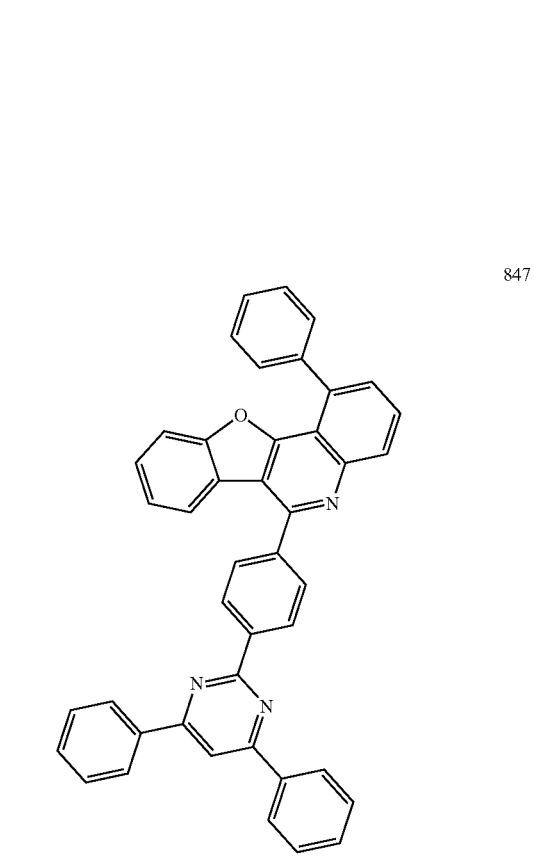

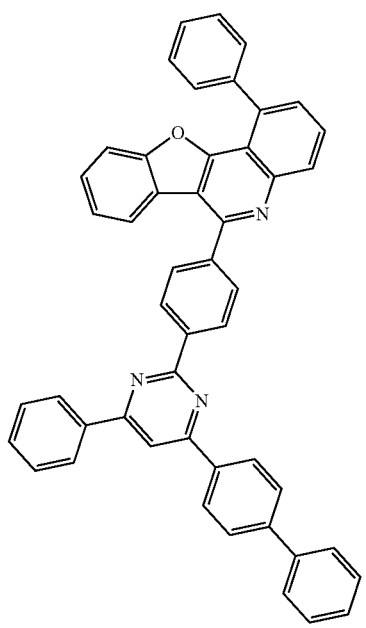
848
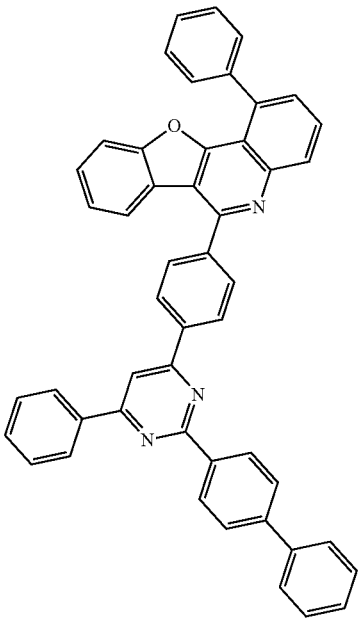
850
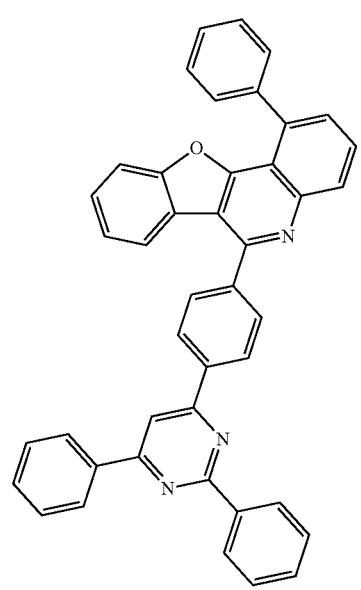
849
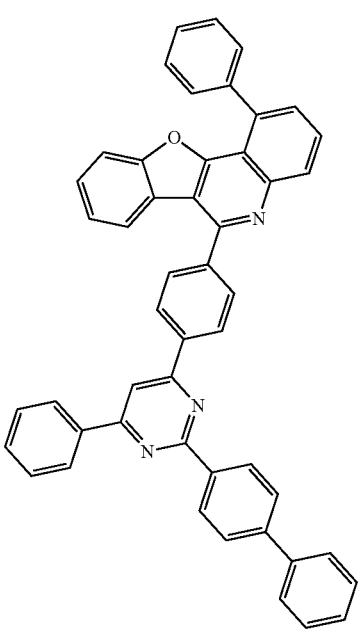
851

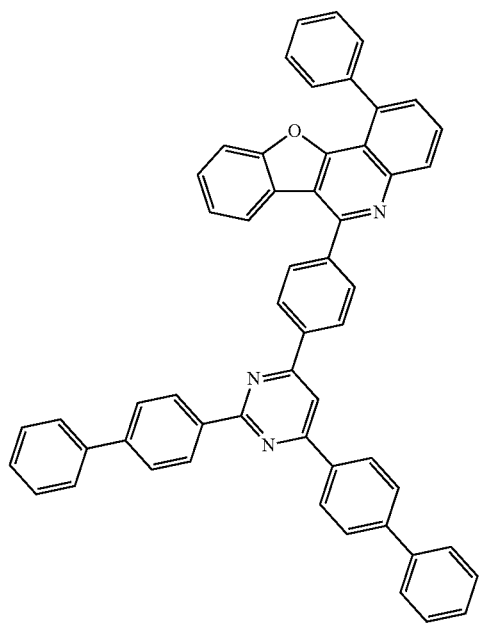
852
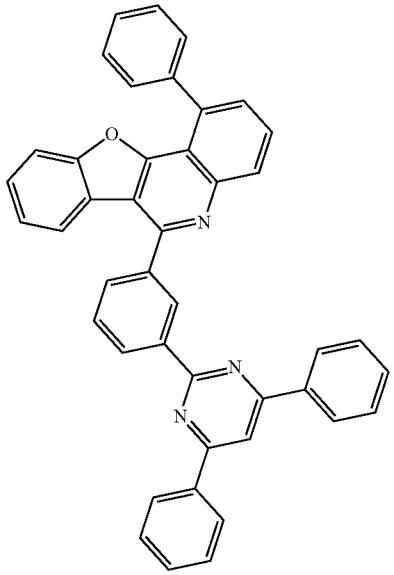
854
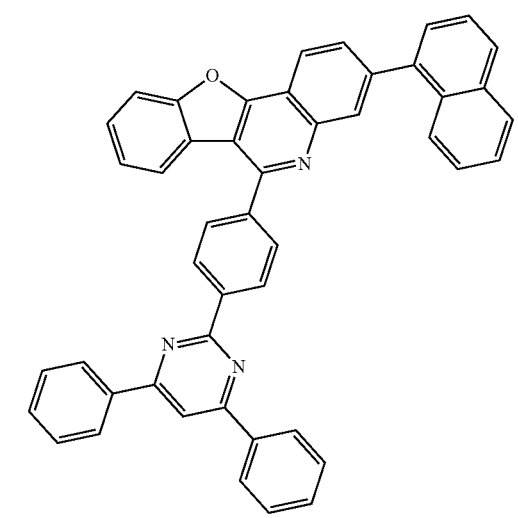
855
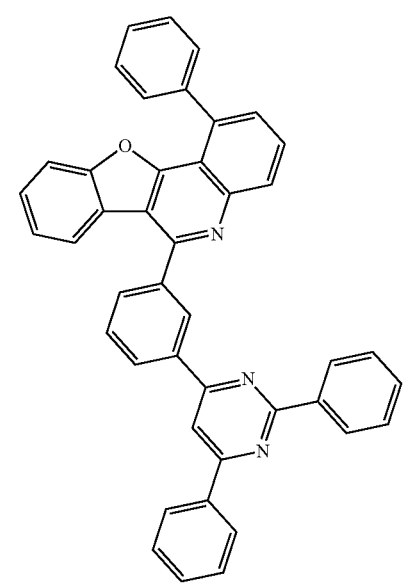
853
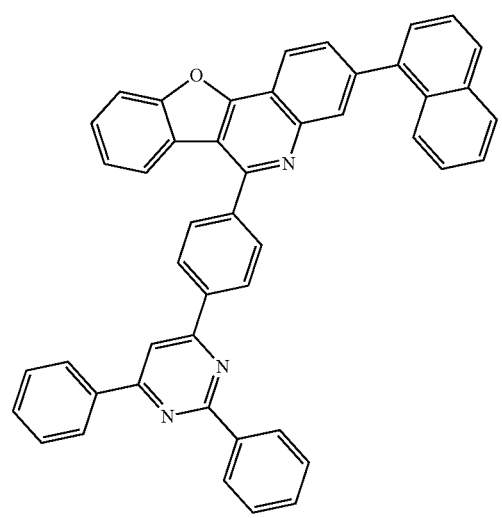
856

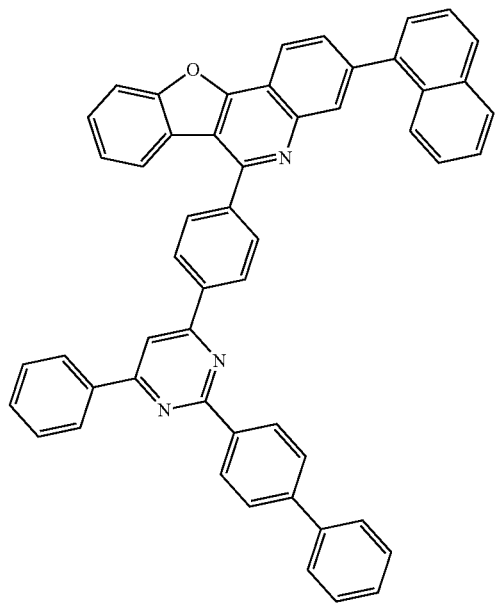
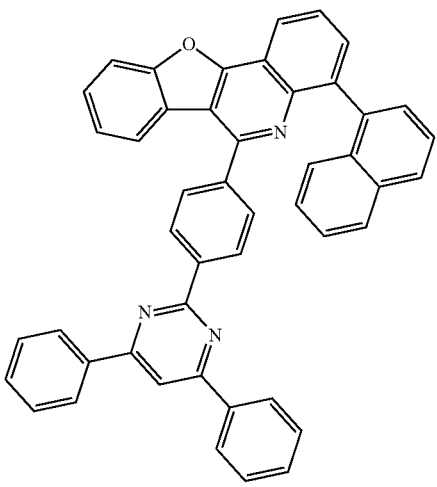
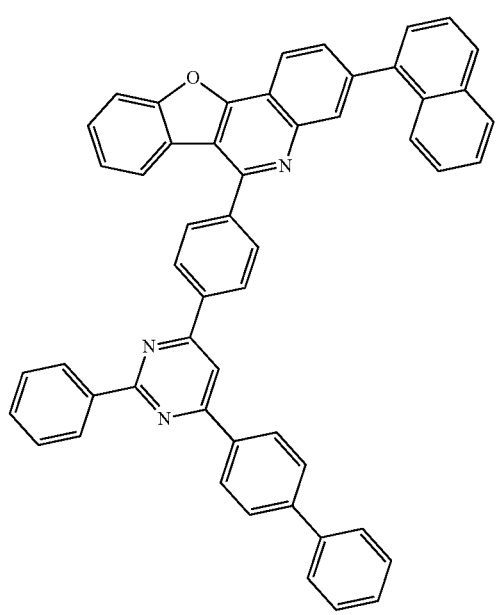

367
-continued
862
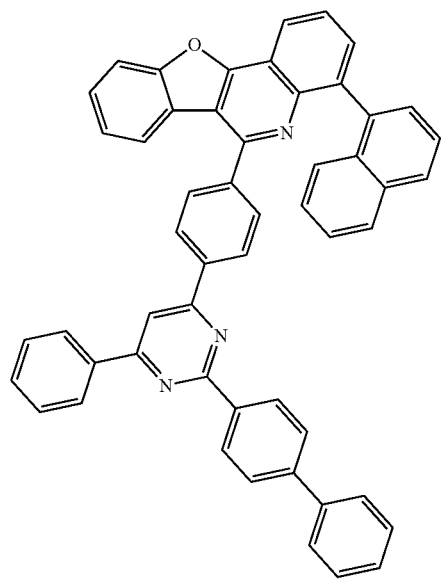
863
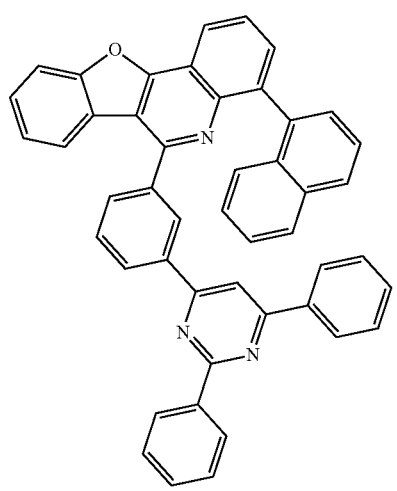
864
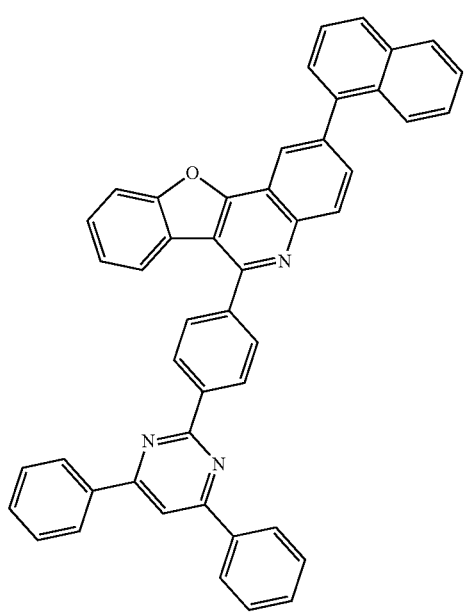
368
-continued
865
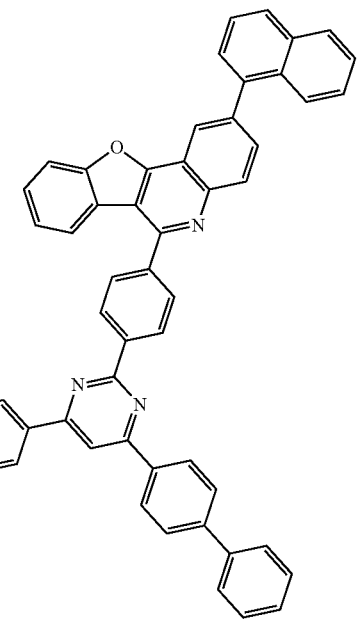
866
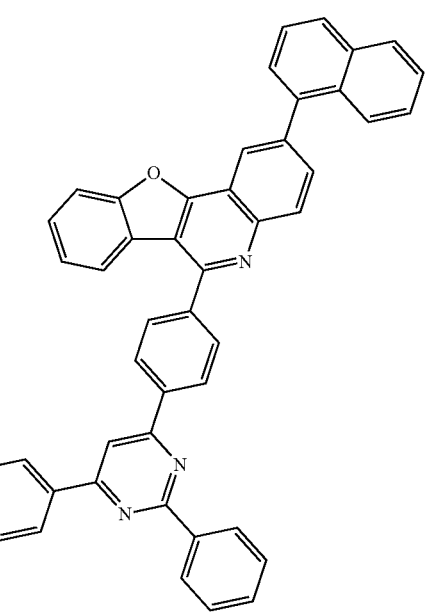

369
-continued
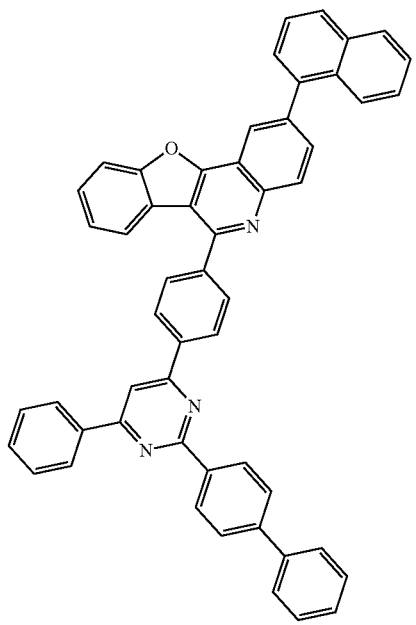
370
-continued
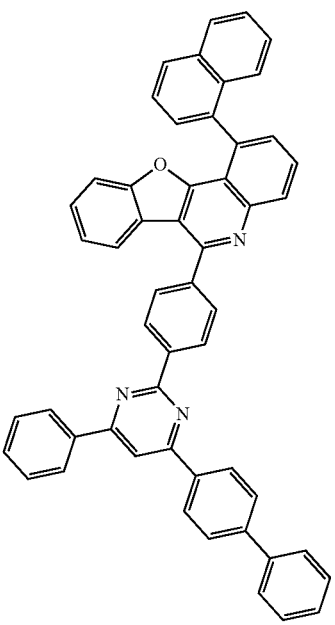
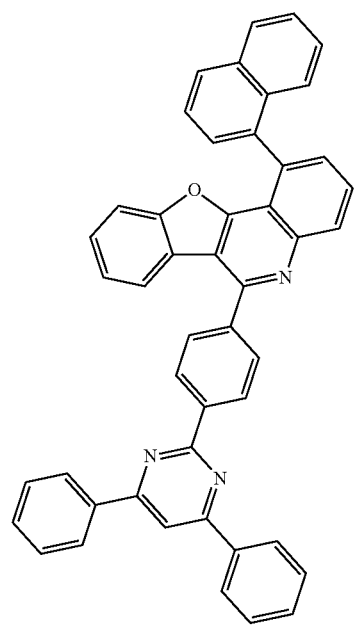
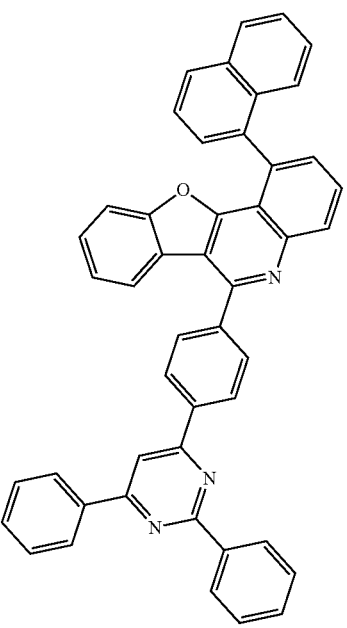

371
-continued
872
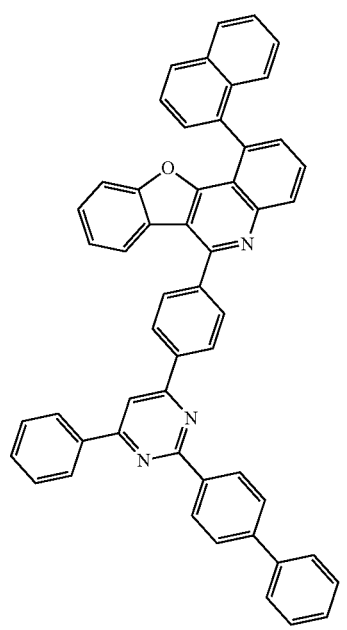
871
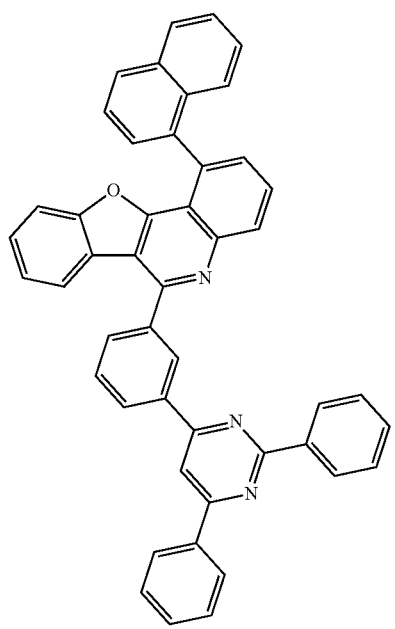
372
-continued
873
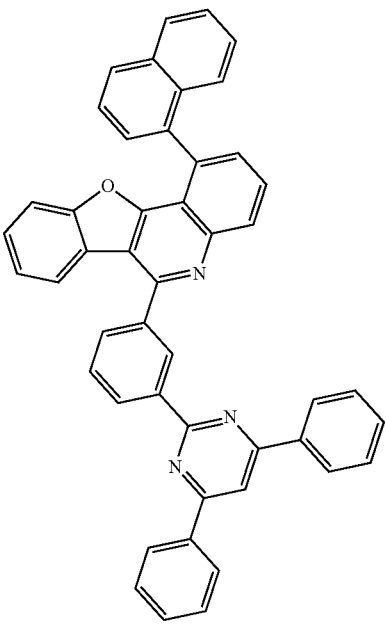
874
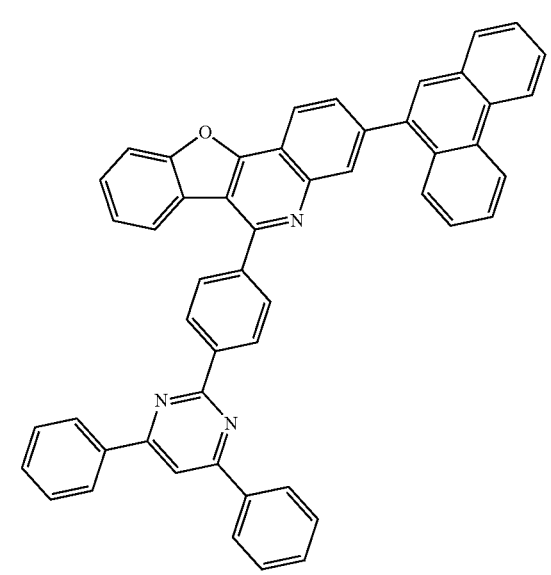

373
-continued
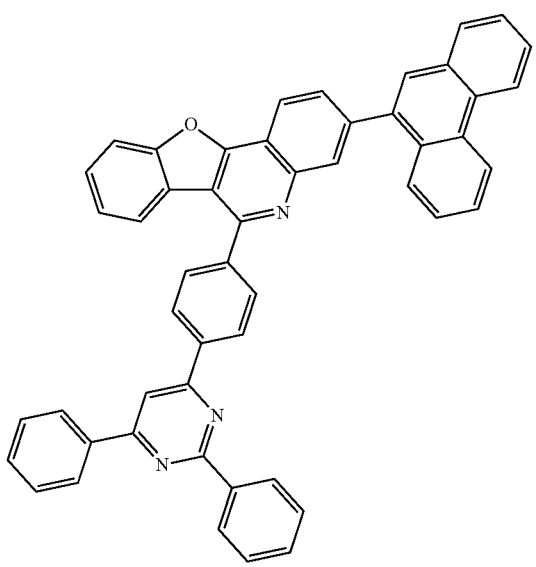
875
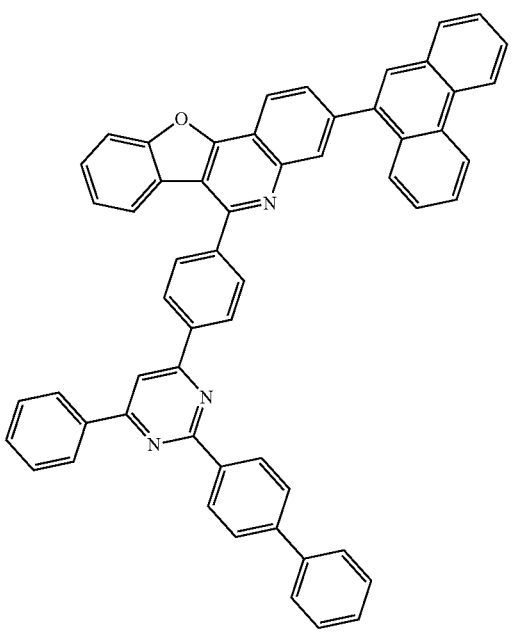
876
374
-continued
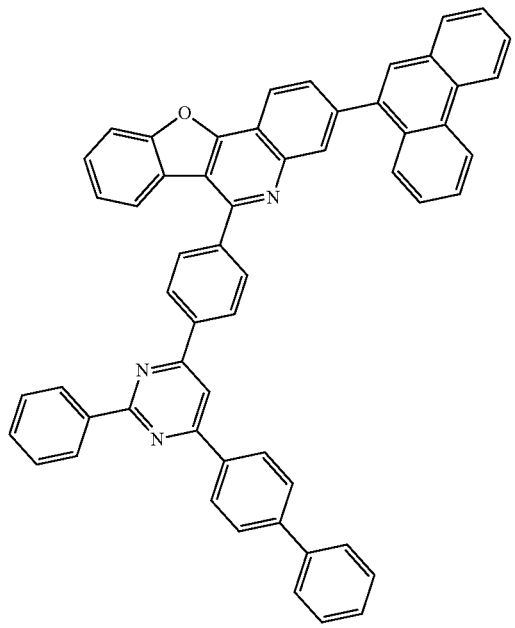
877
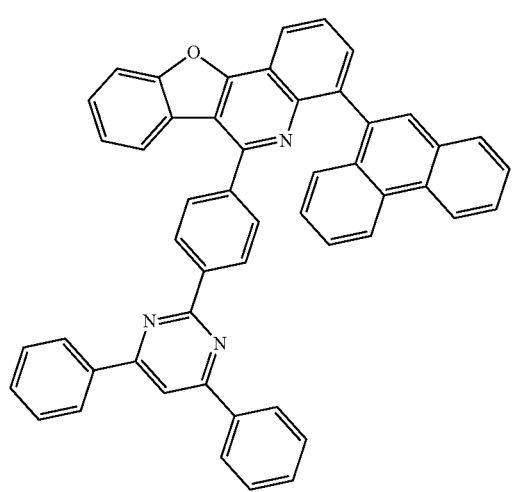
878

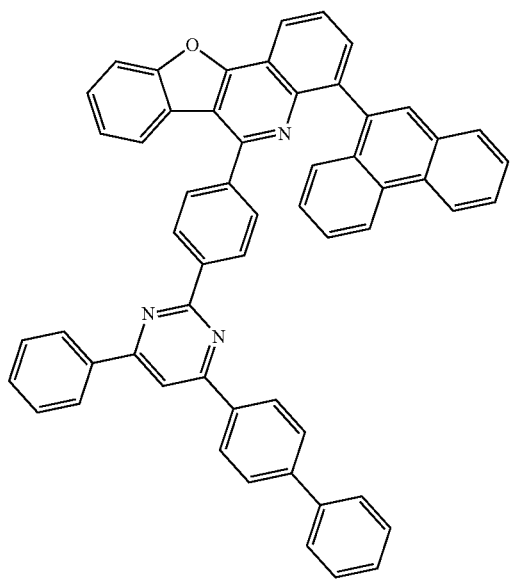
879
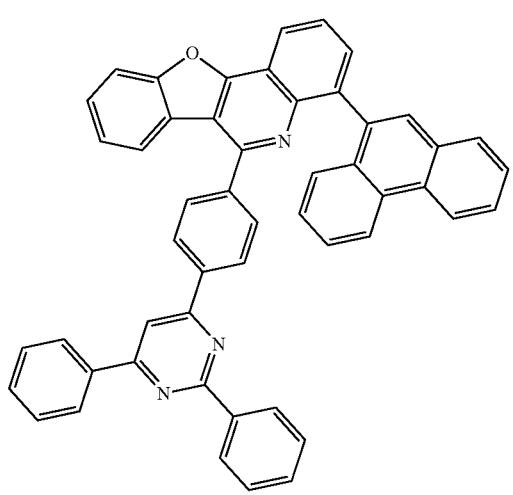
880
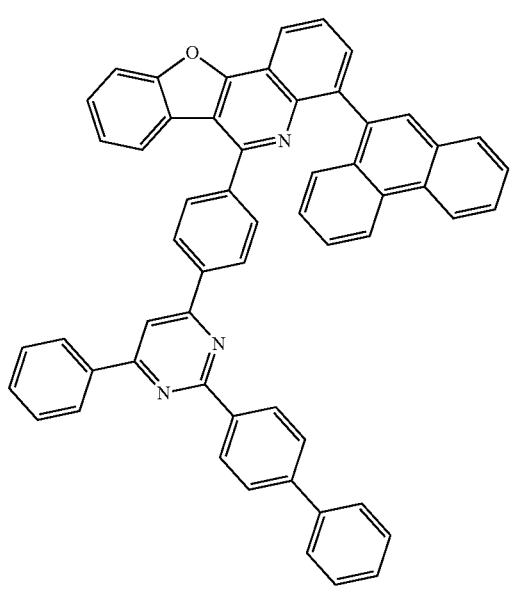
881
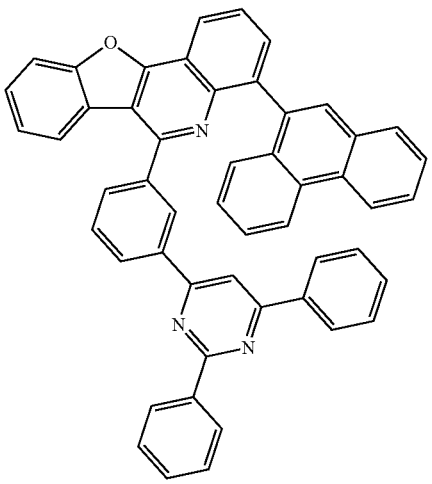
882
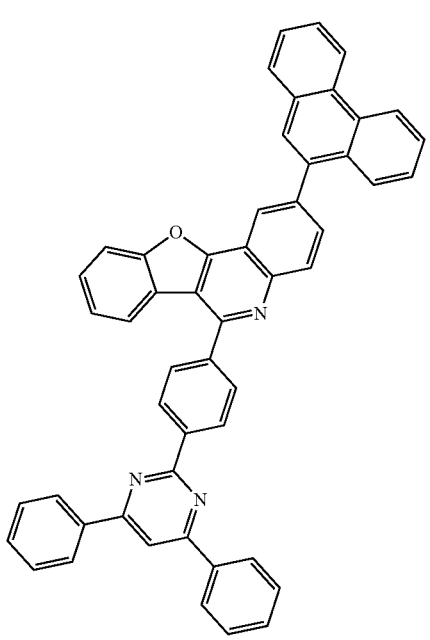
883

884
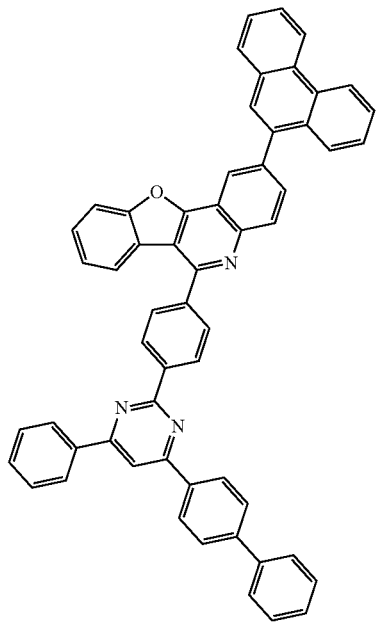
885
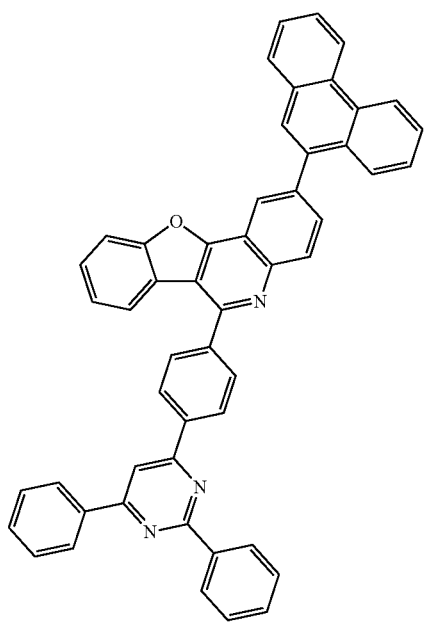
886
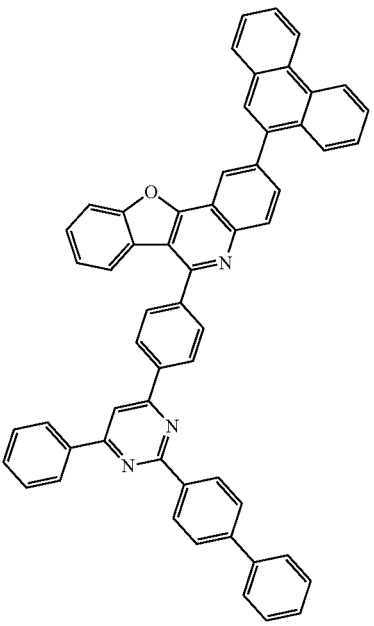
887
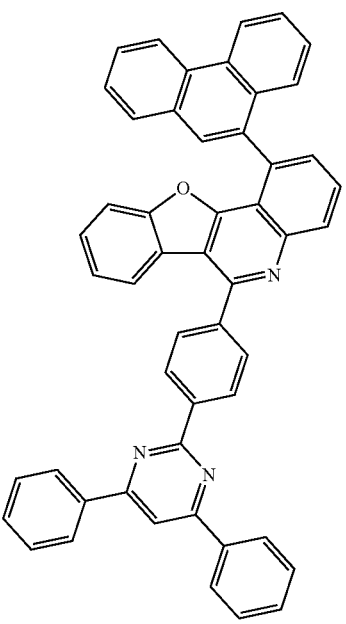

888
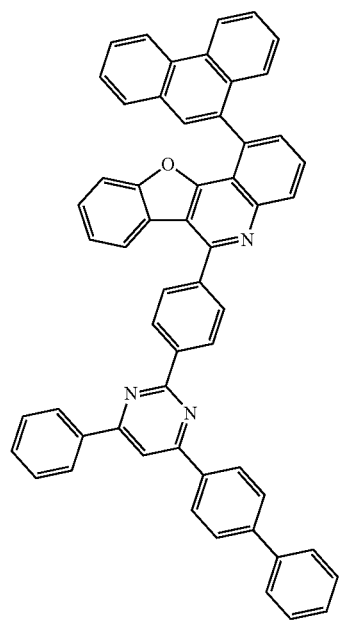
889
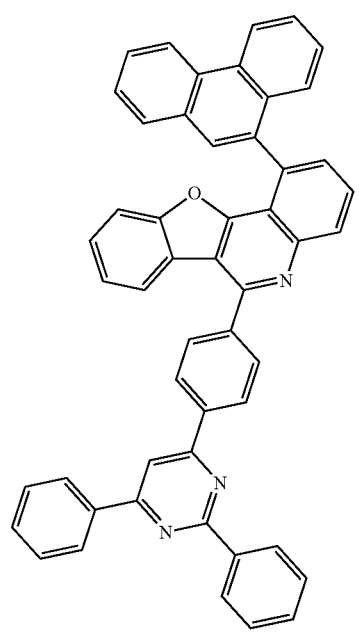
890
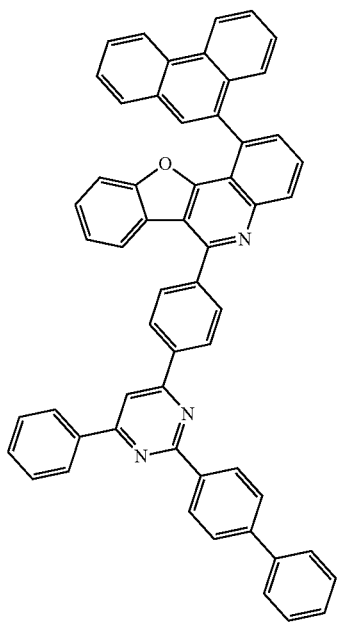
891
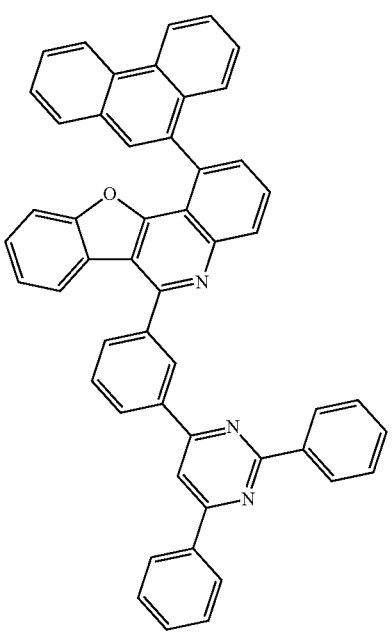

892
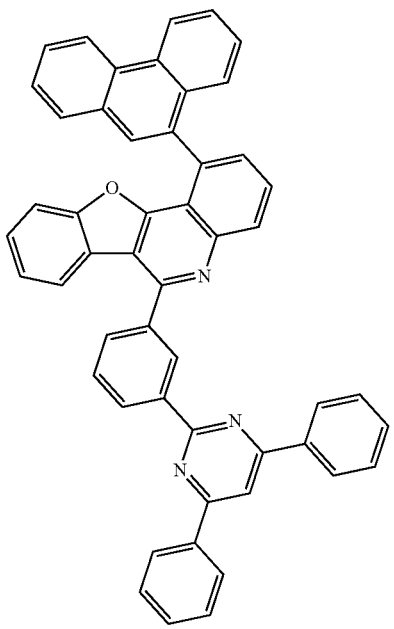
893
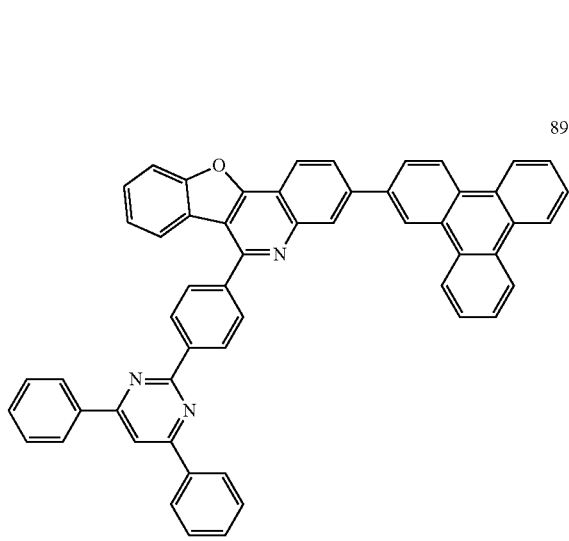
894
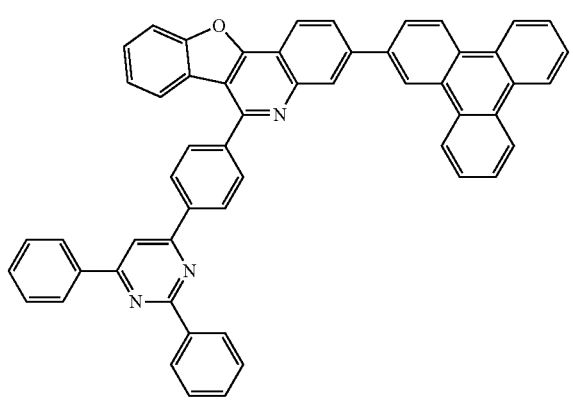
895
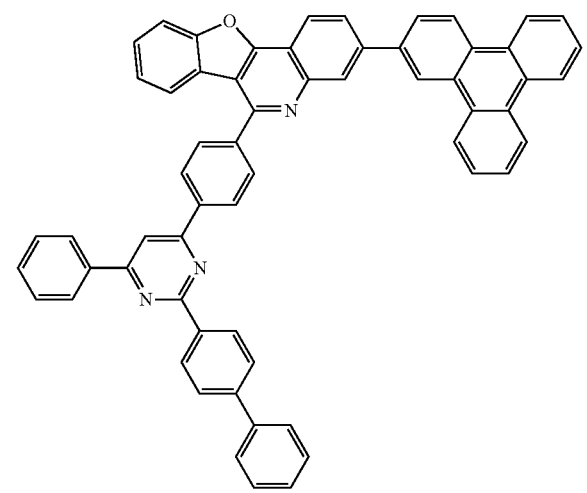
896
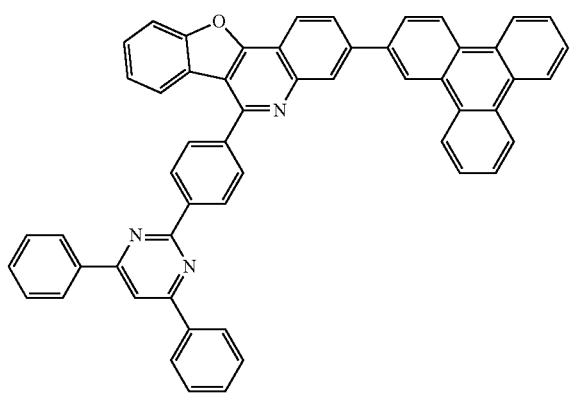
897
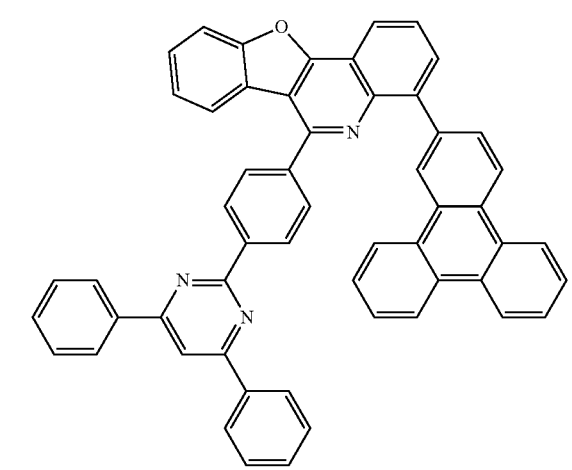

-continued
898
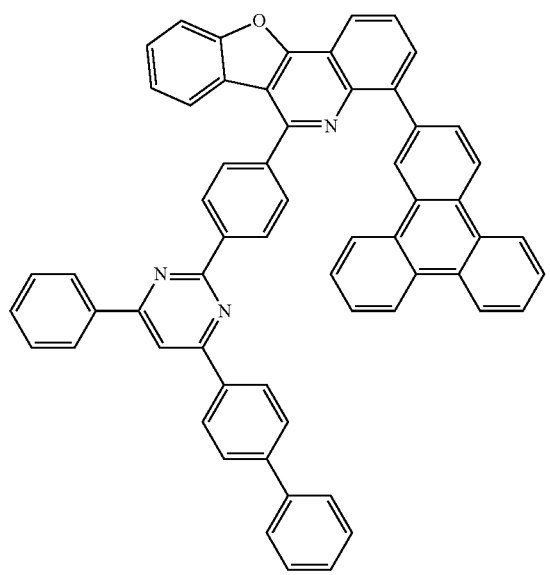
899
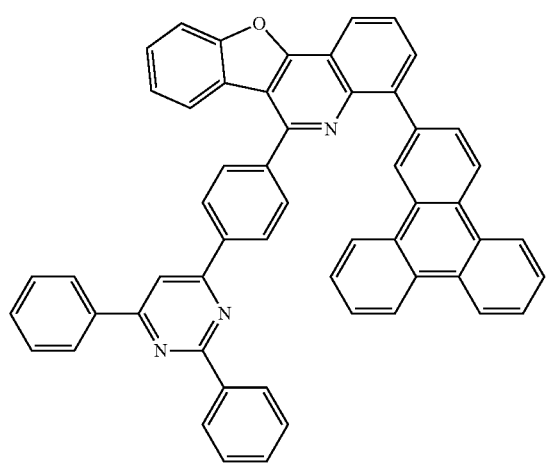
900
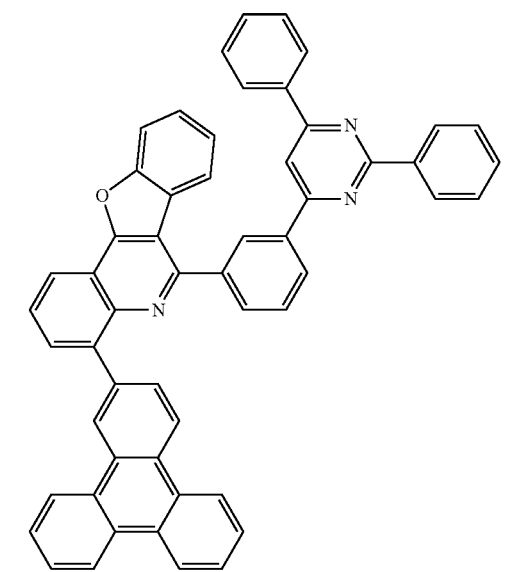
-continued
901
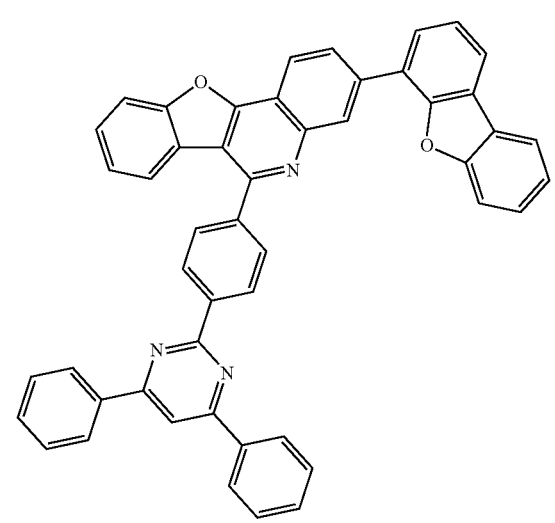
902
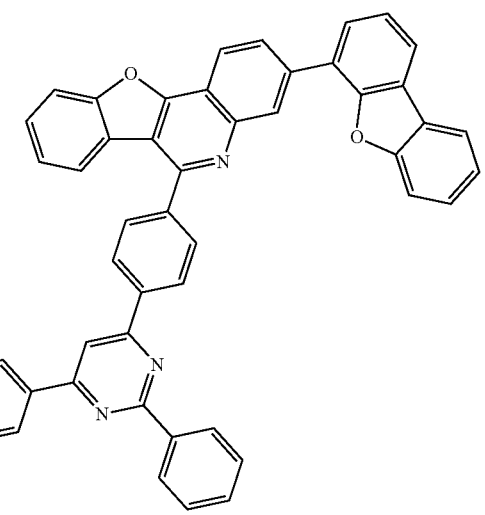

-continued
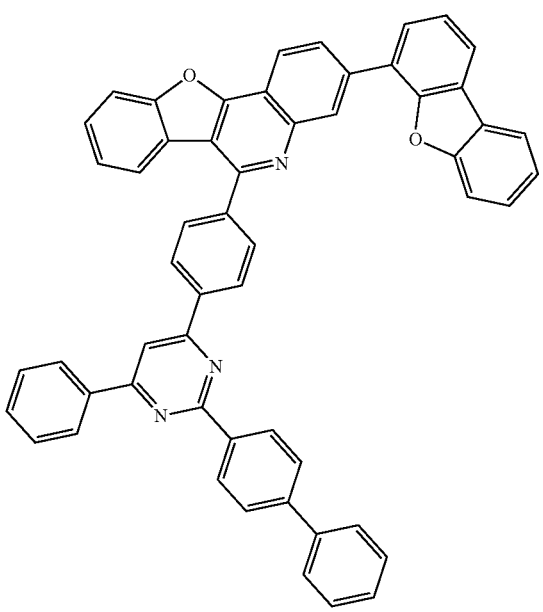
903
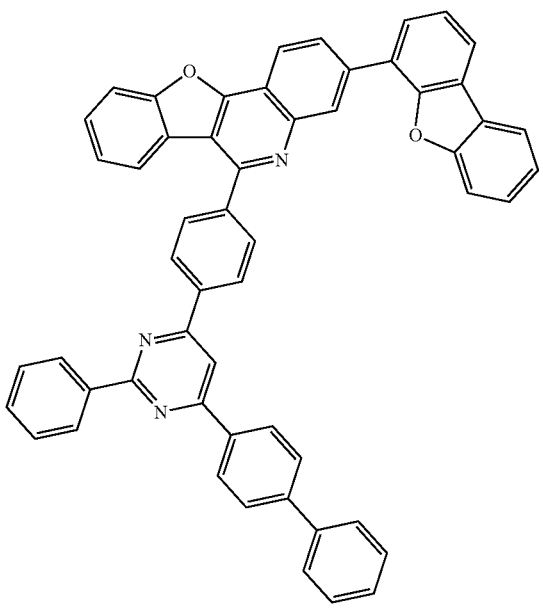
904
-continued
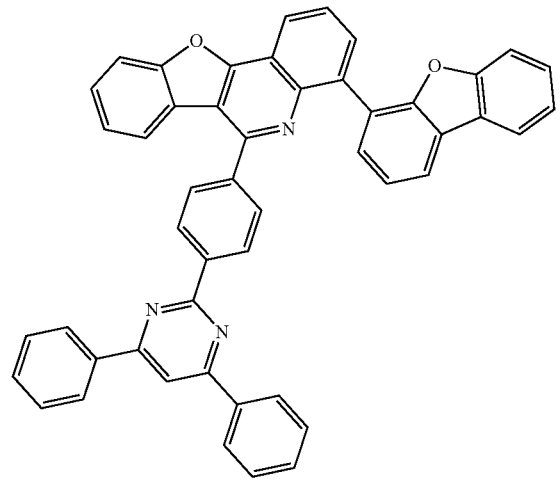
905
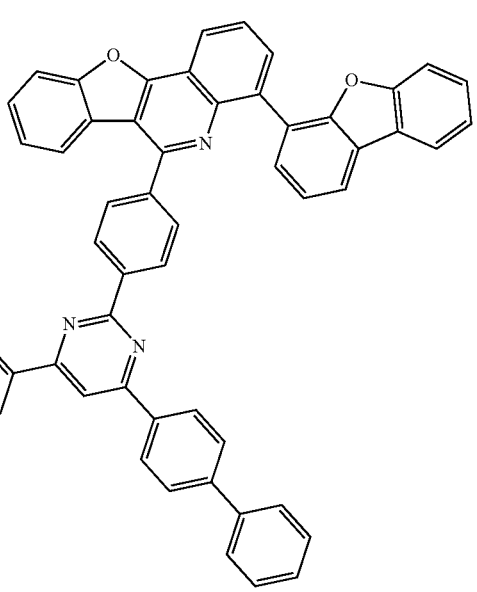
906
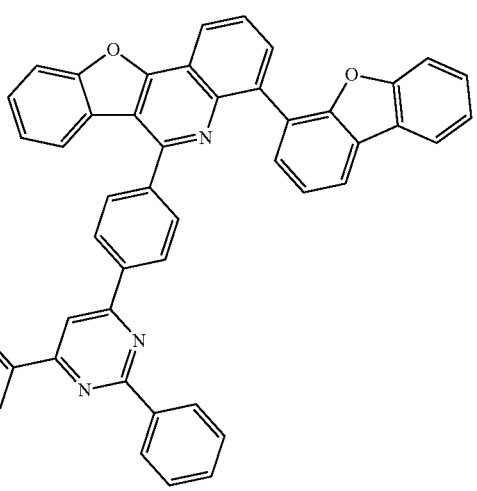
907

908
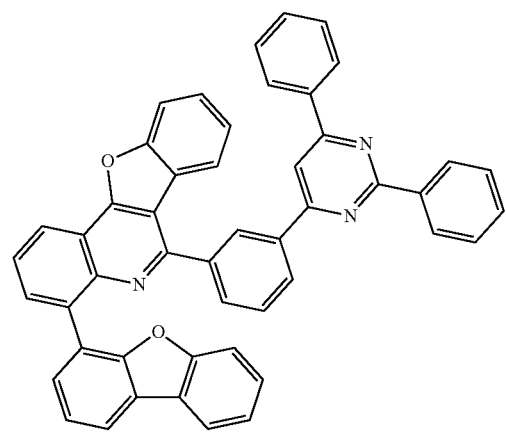
909
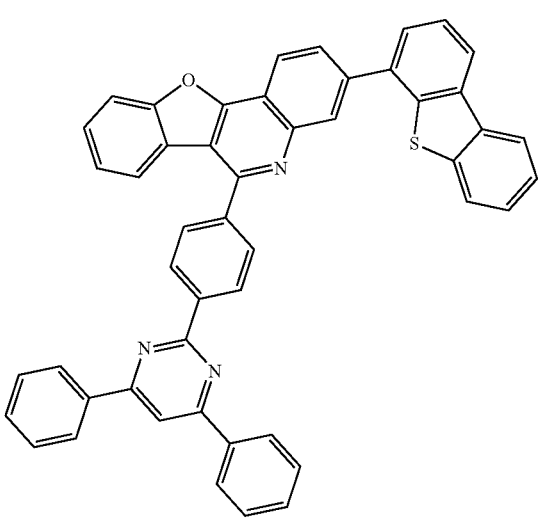
910
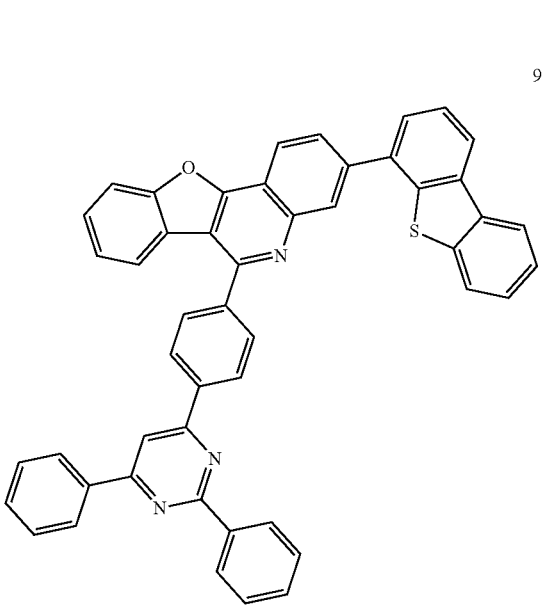
911
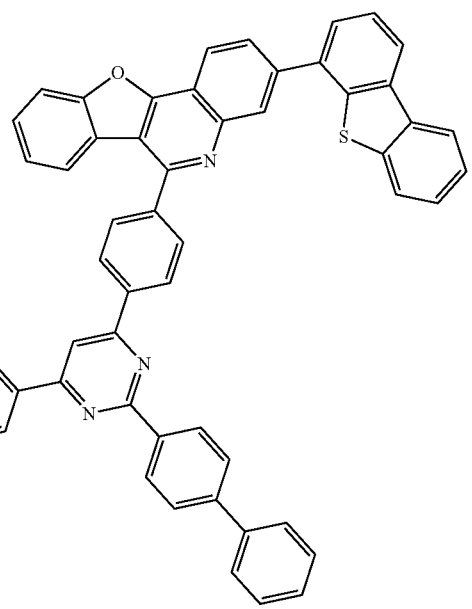
912
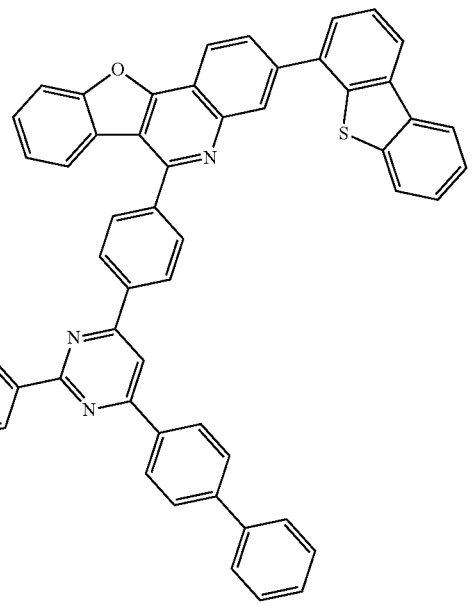

913
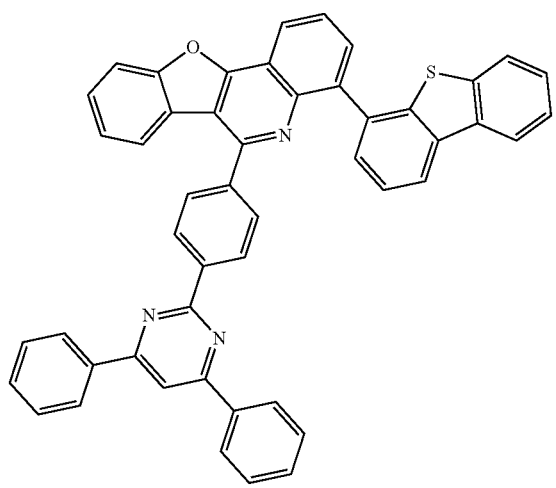
914
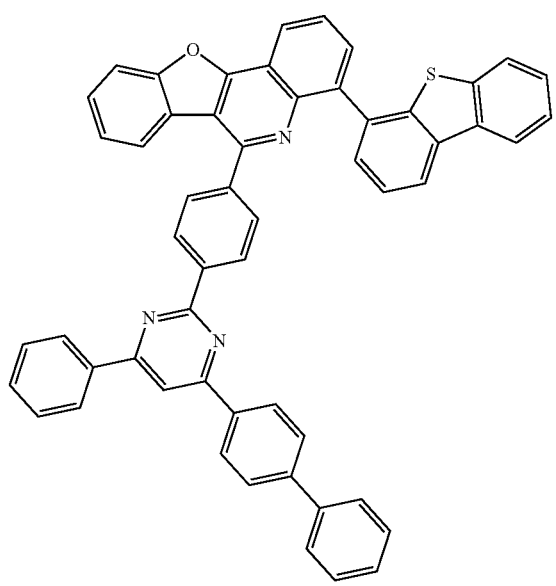
915
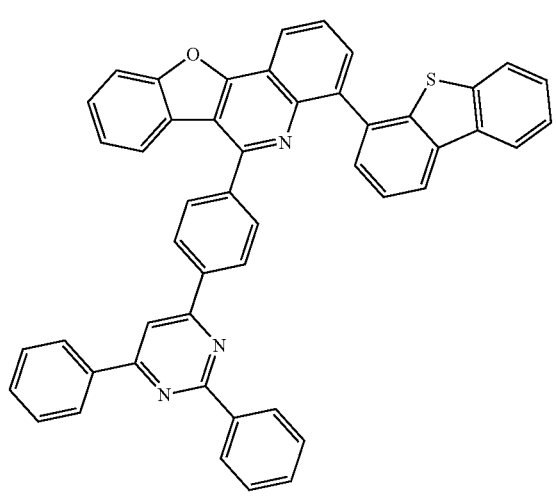
916
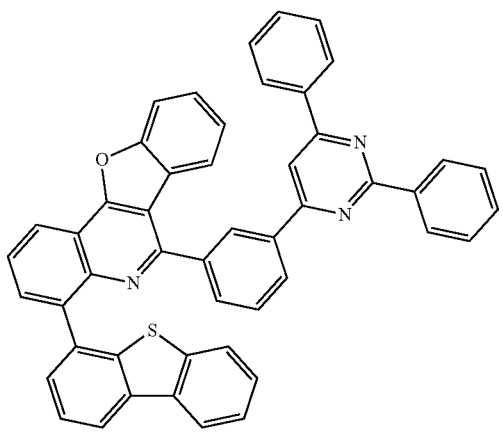
917
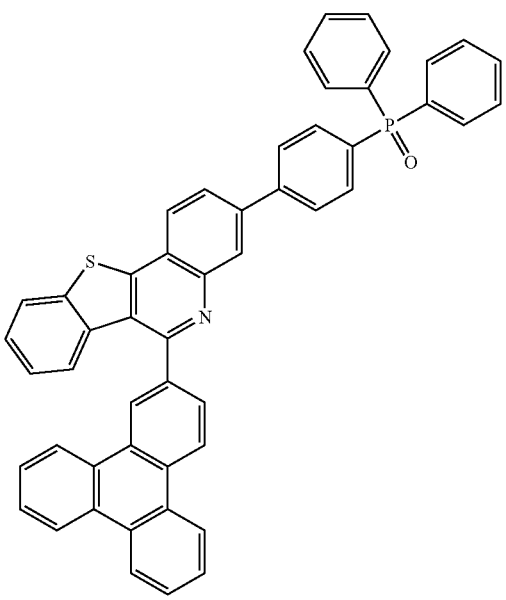
918
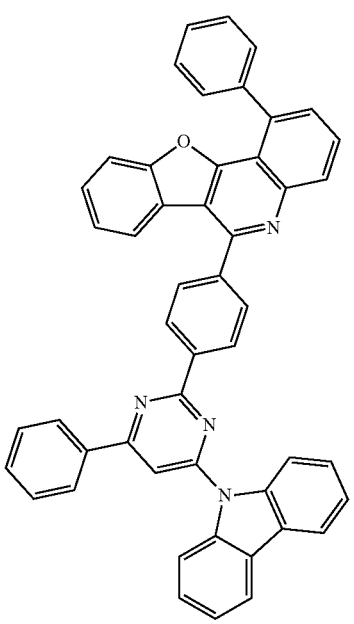

391
-continued
392
-continued
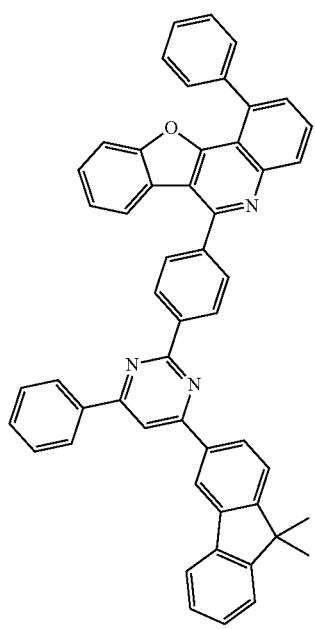
919
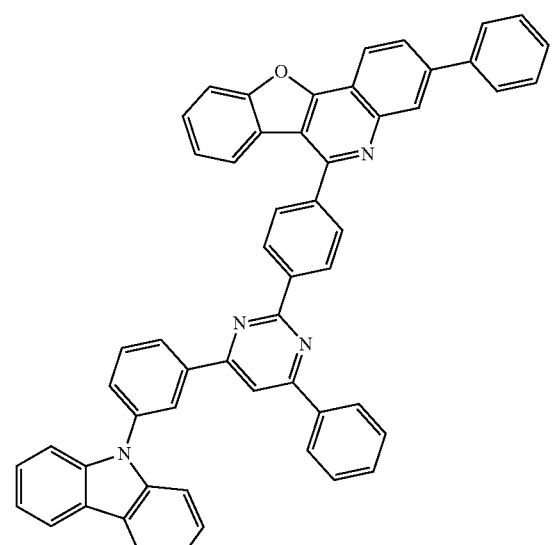
921
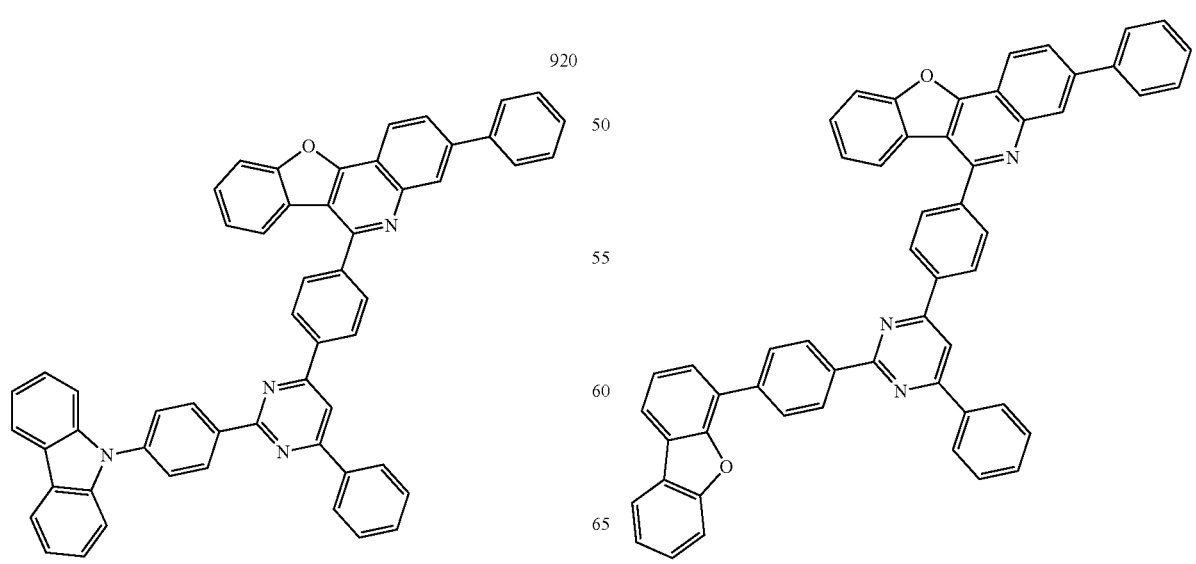

393
-continued
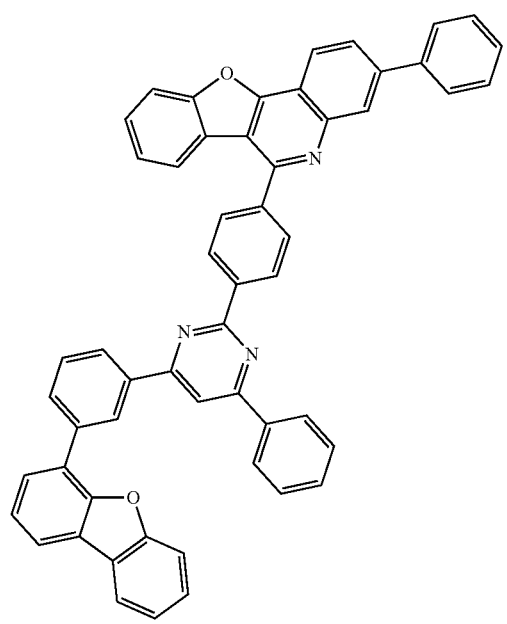
923
924
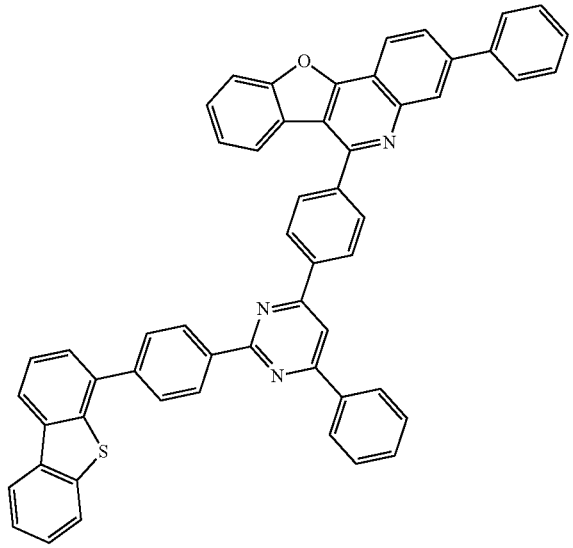
394
-continued
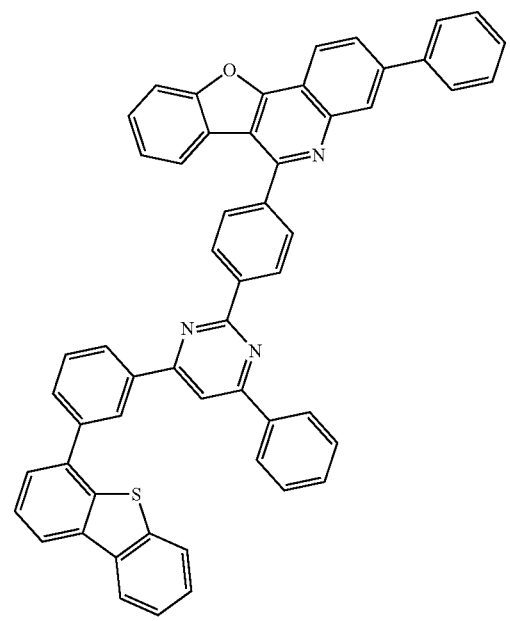
925
926
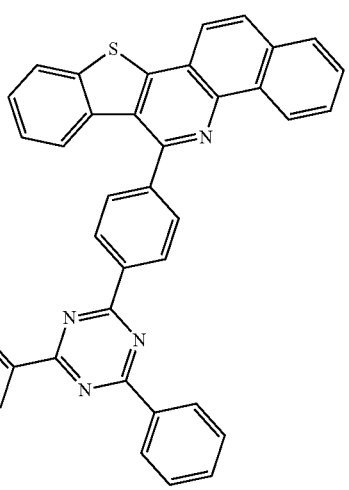
927
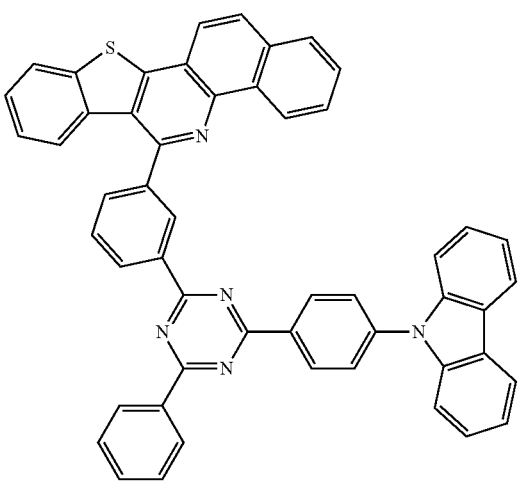

928
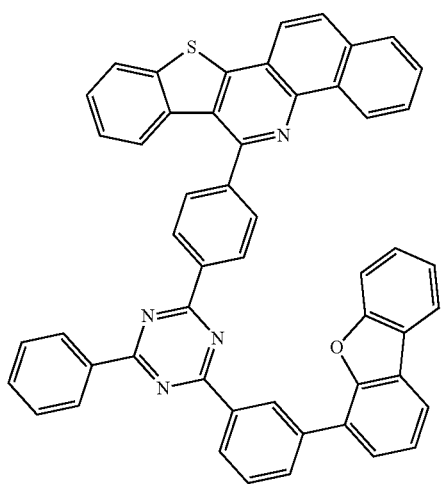
929
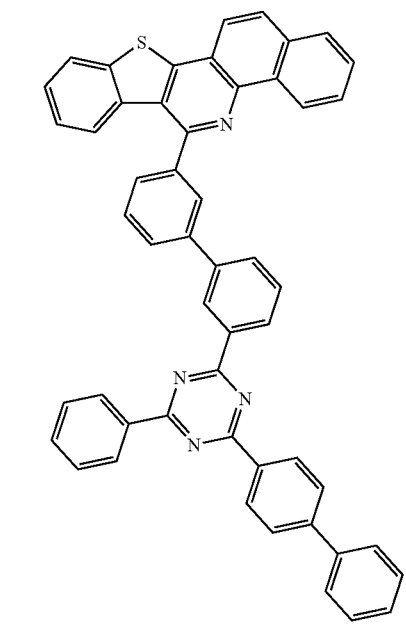
930
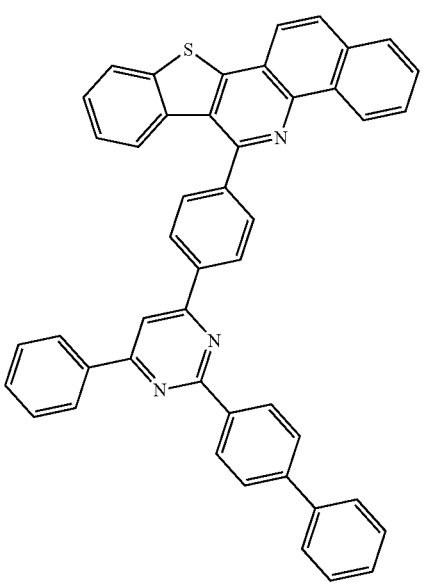
931
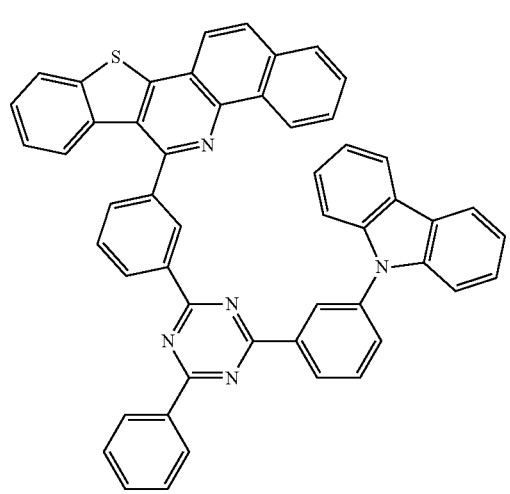
932
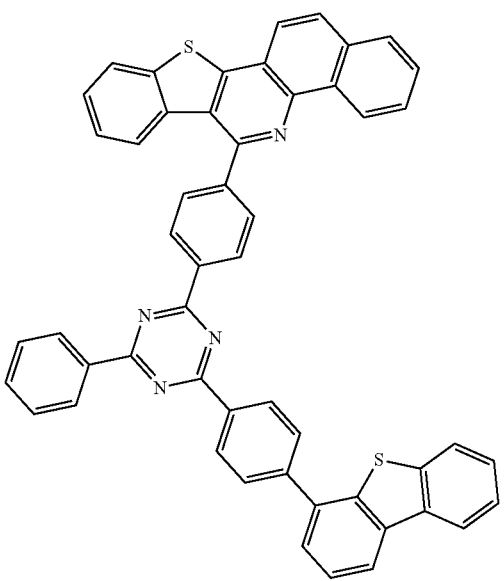

933
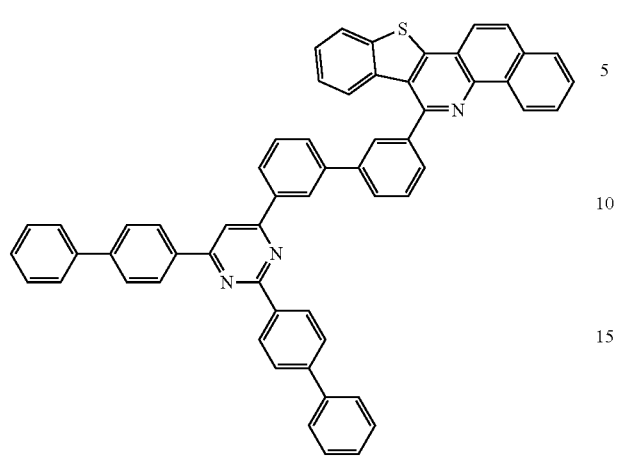
934
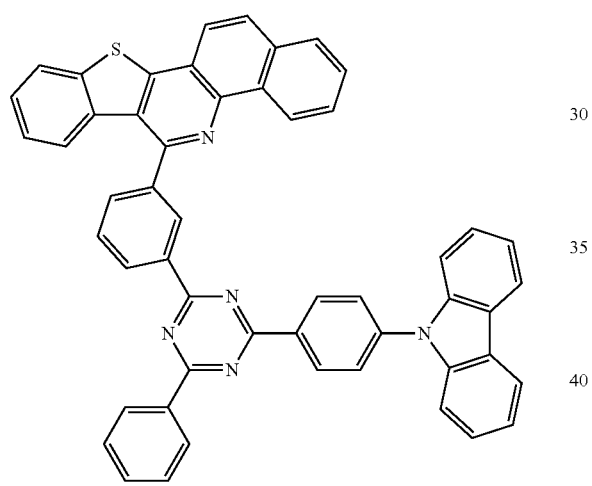
935
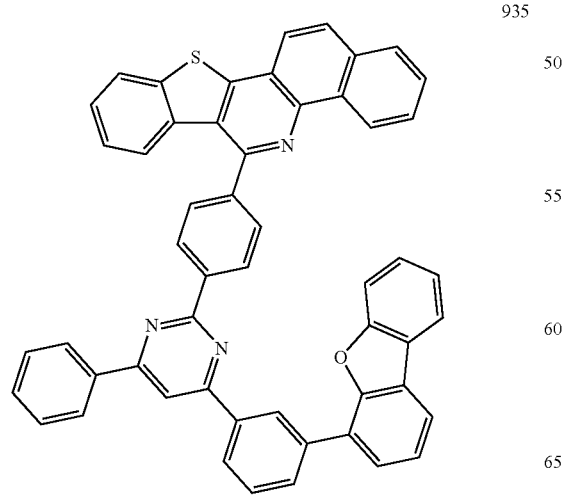
936
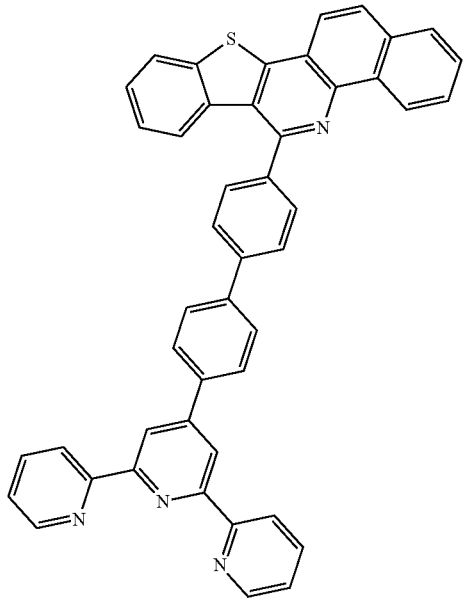
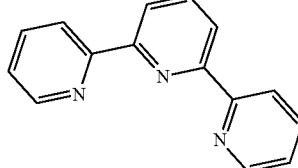
937
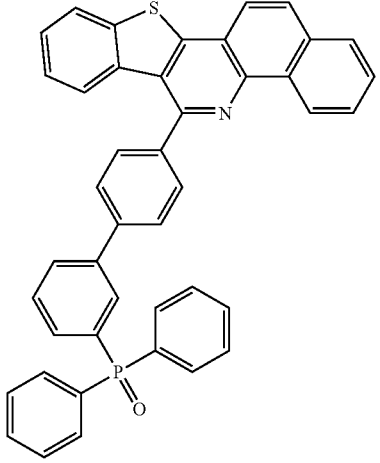
938
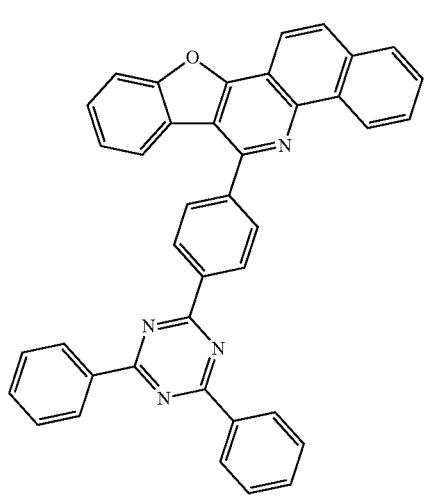

399
-continued
400
-continued
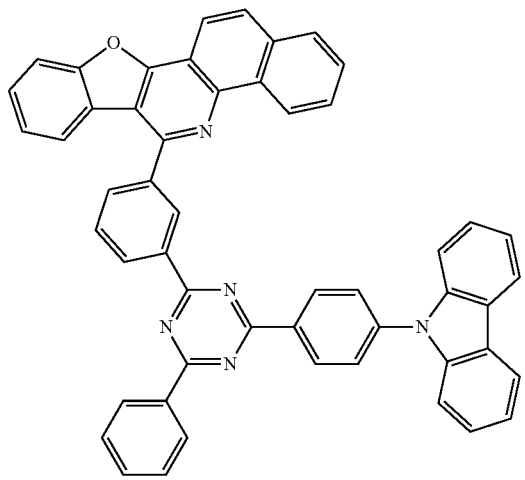
939
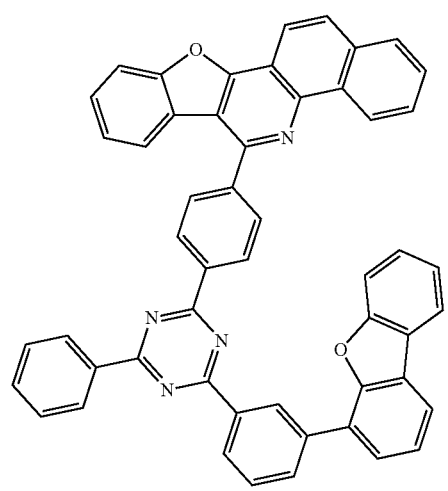
940
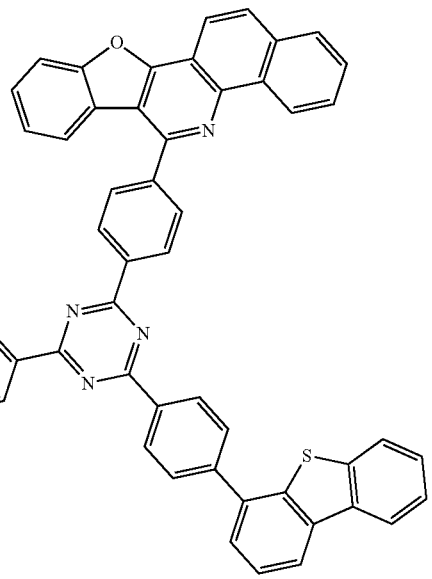
941
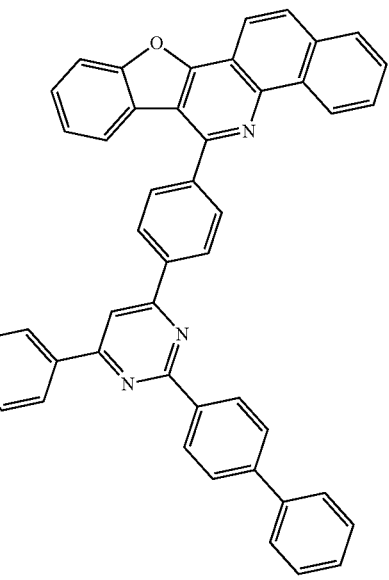
942
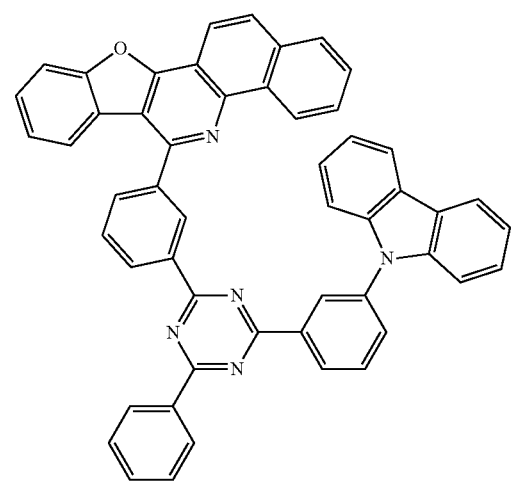
943
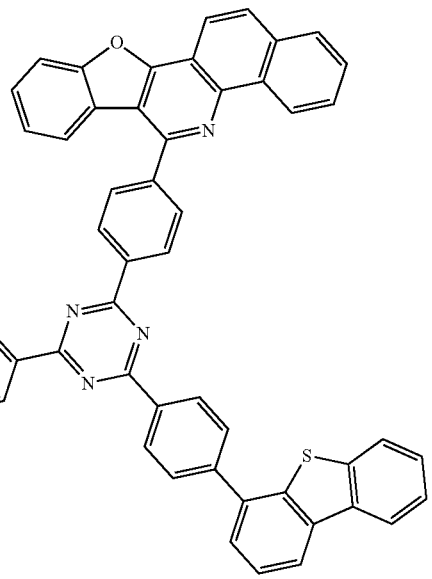
944

401
-continued
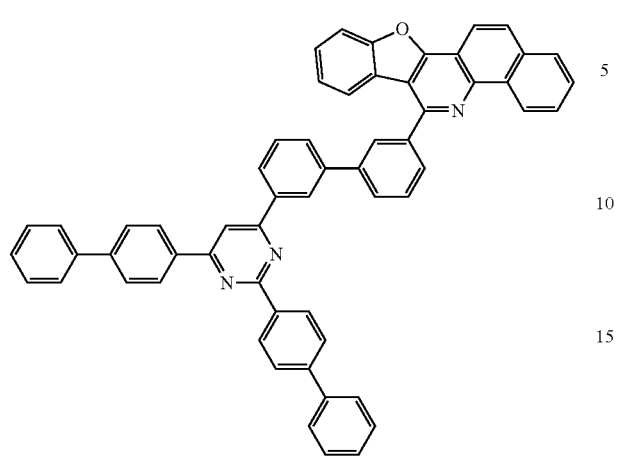
945
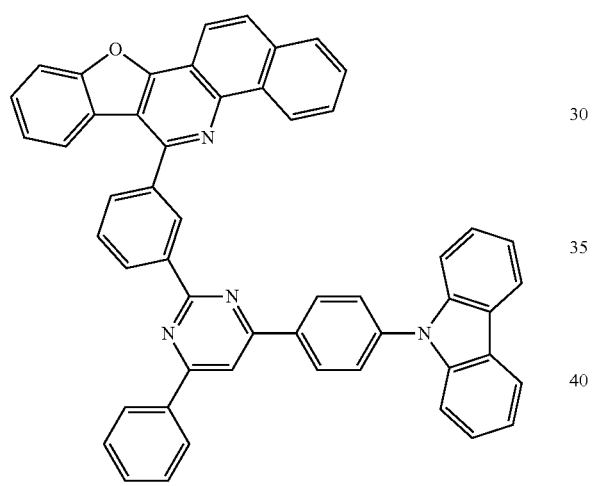
946
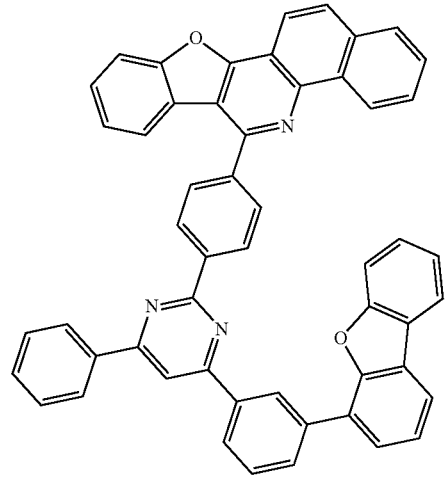
947
402
-continued
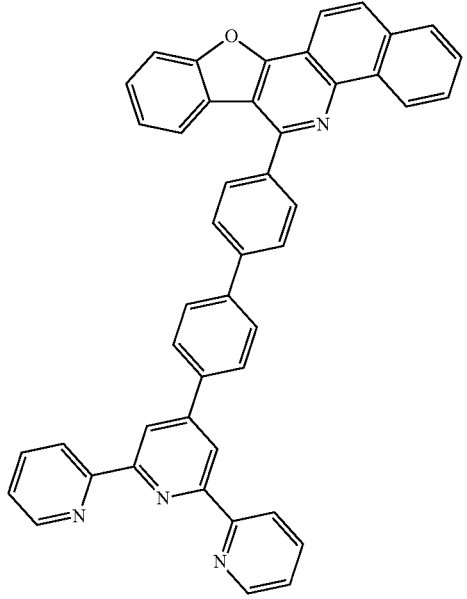
948
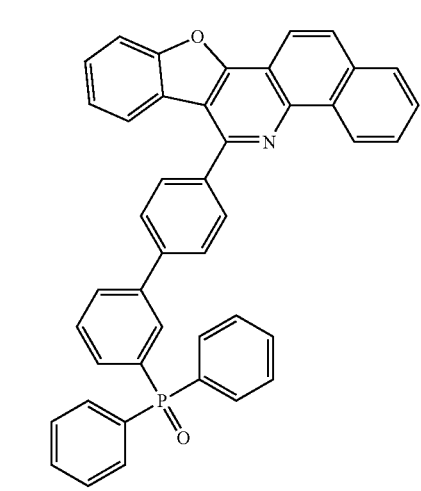
949
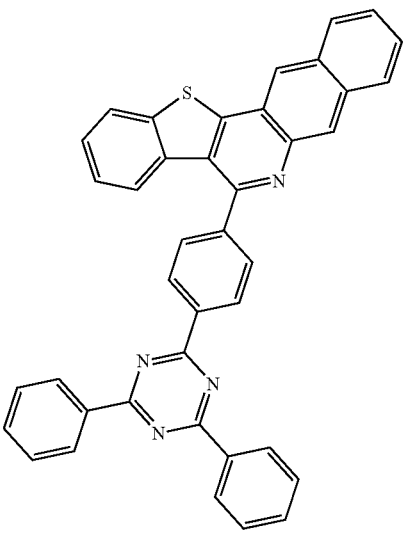
950

951
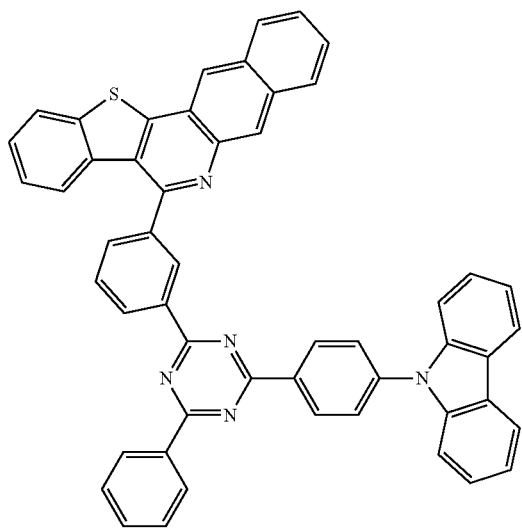
953
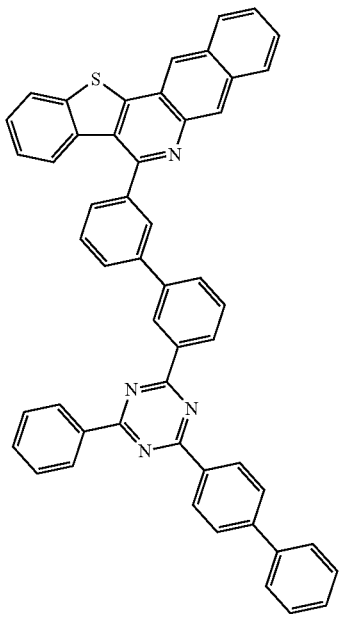
952
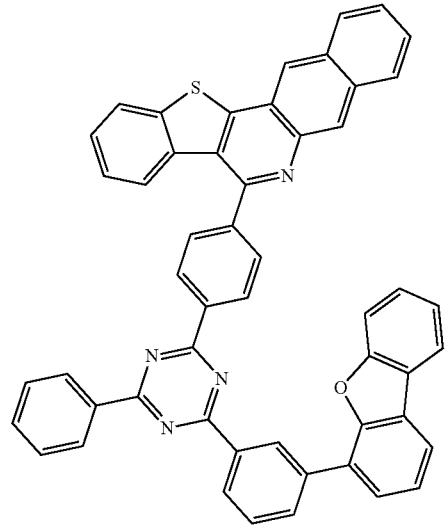
954
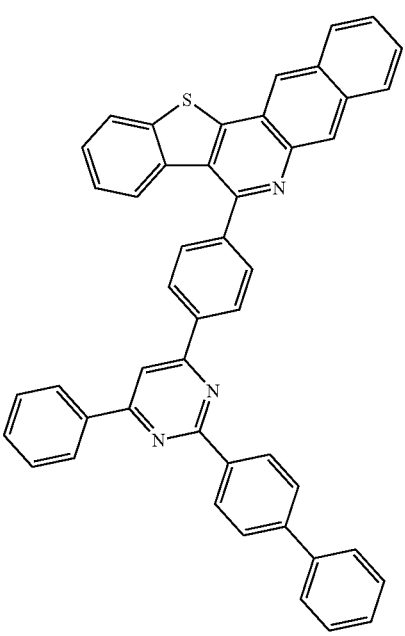

405
-continued
955
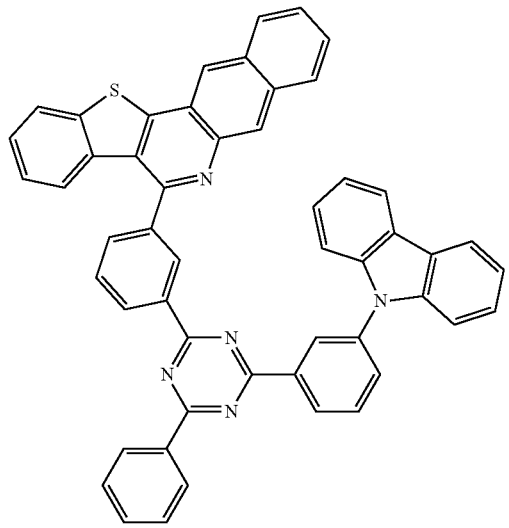
956
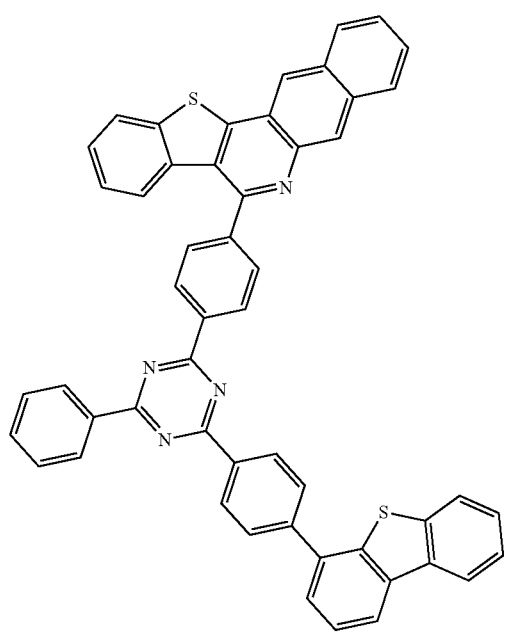
957
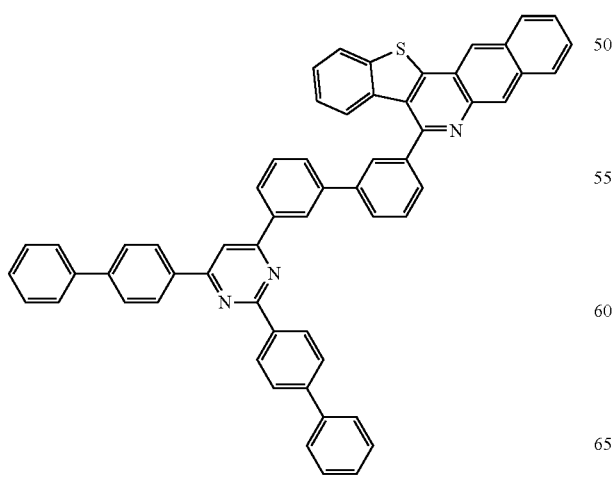
406
-continued
958
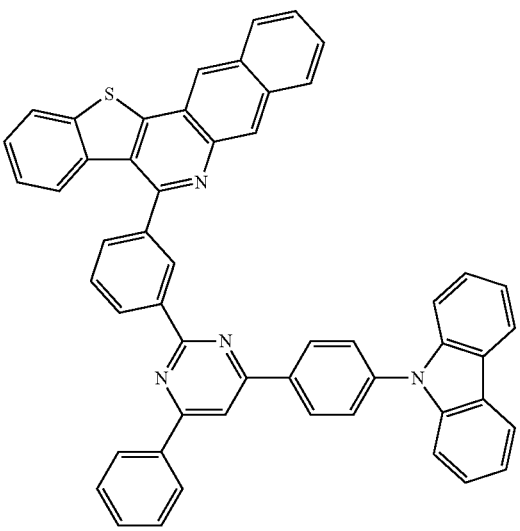
959
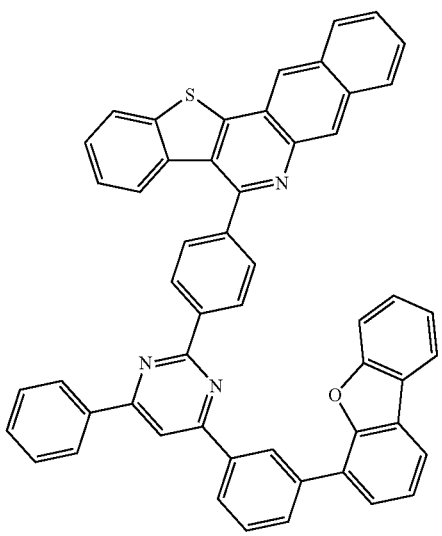

407
-continued
408
-continued
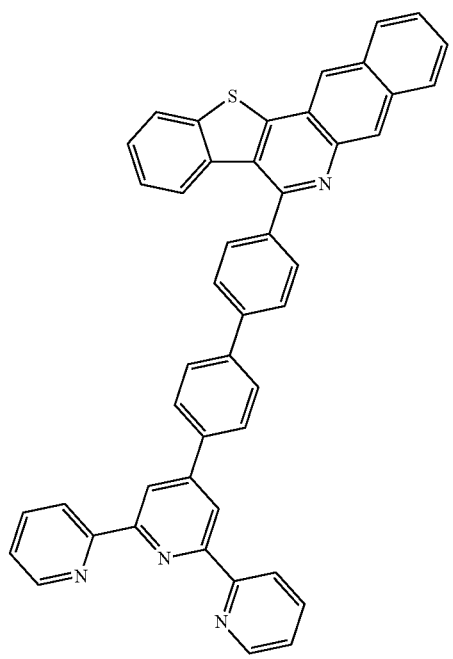
960
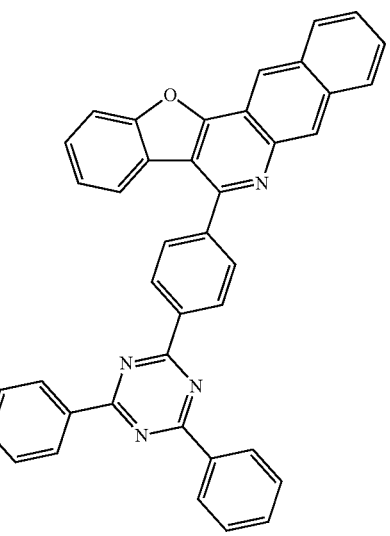
962
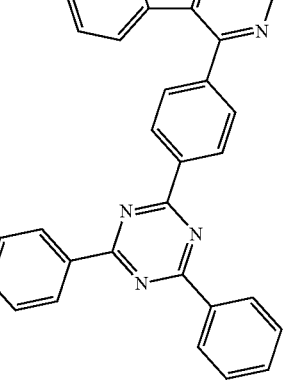
963
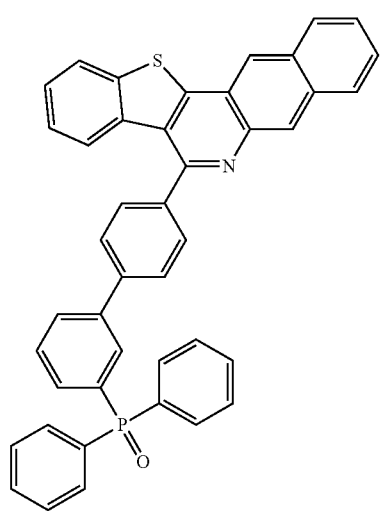
961
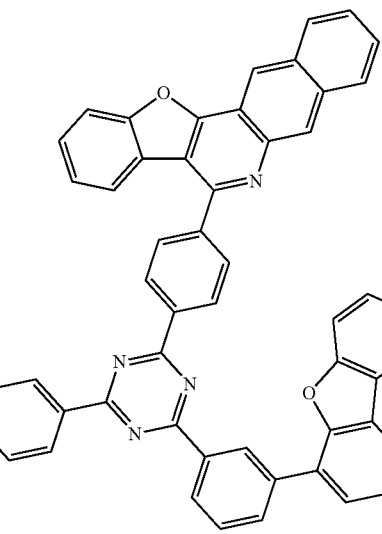
964

409
-continued
410
-continued
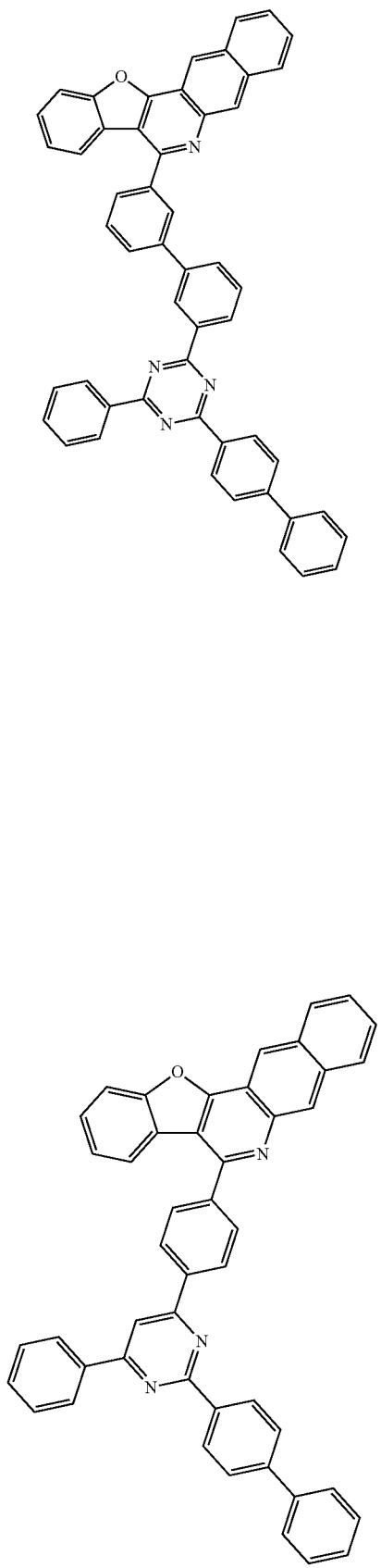
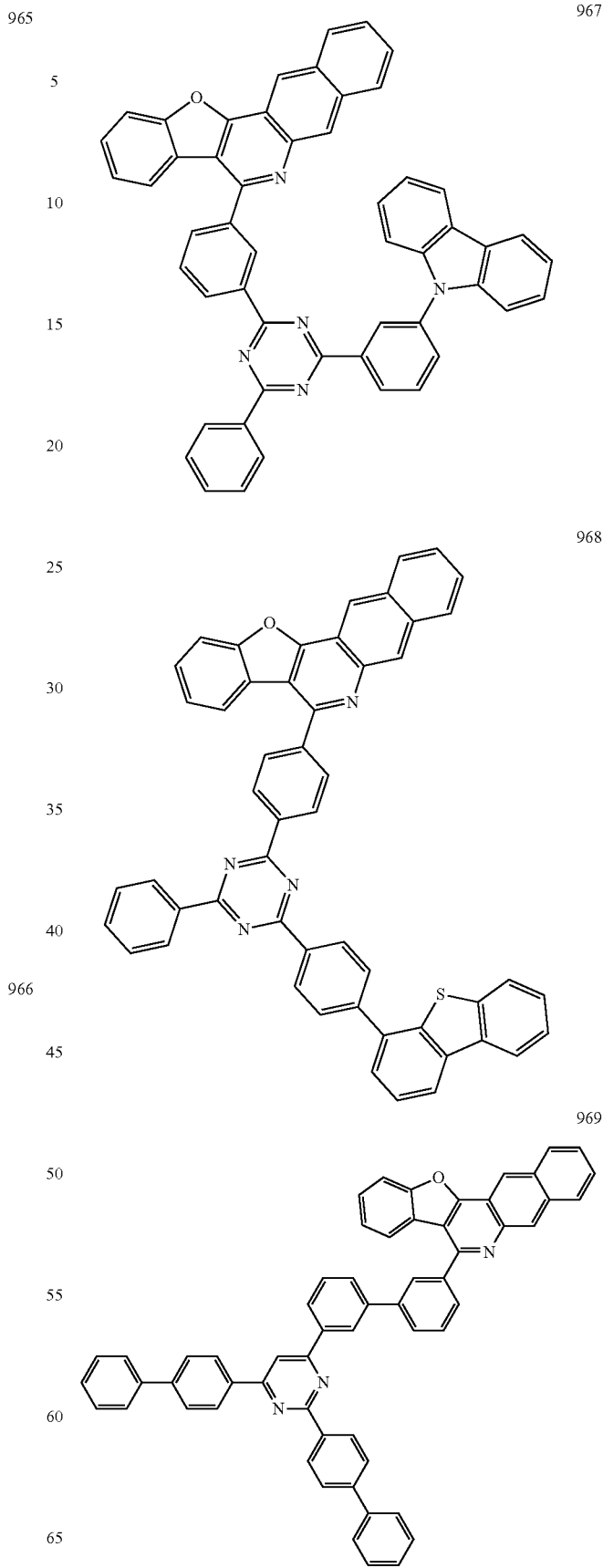

411
-continued
970
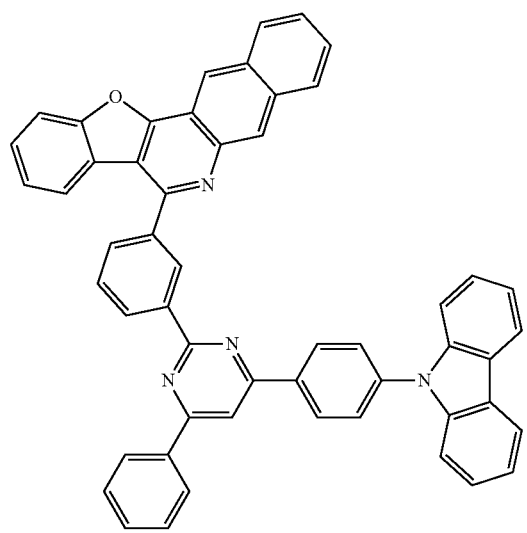
971
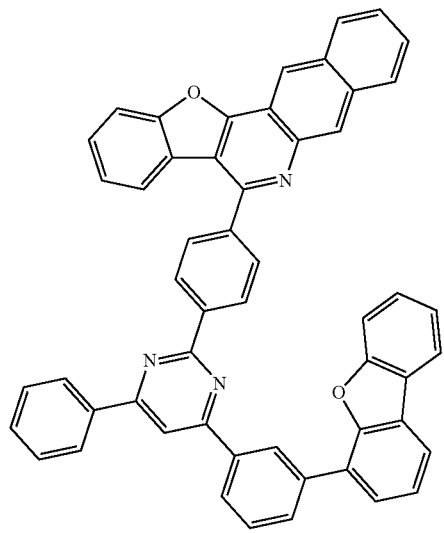
412
-continued
972
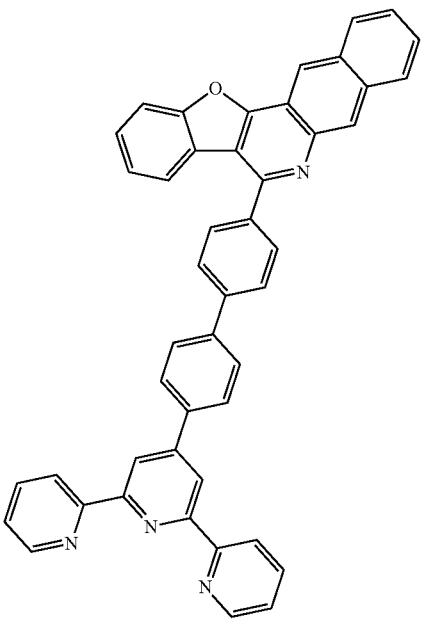
973
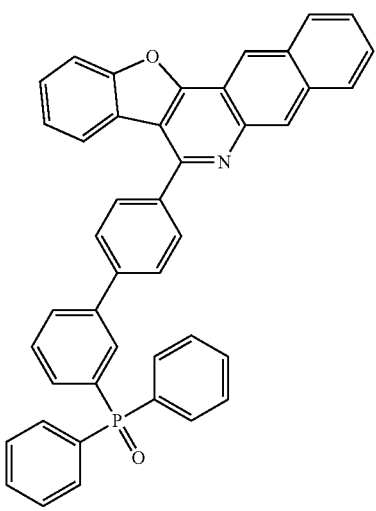

413
-continued
974
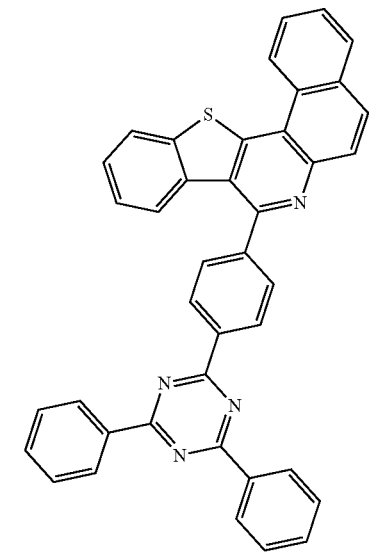
975
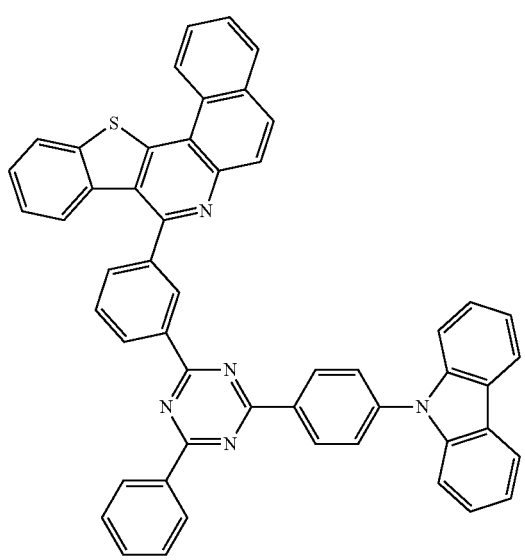
976
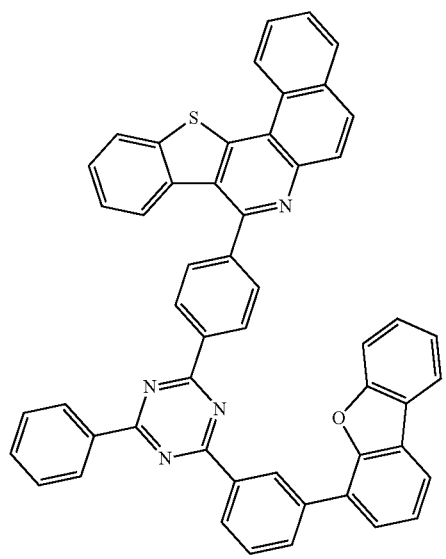
414
-continued
977
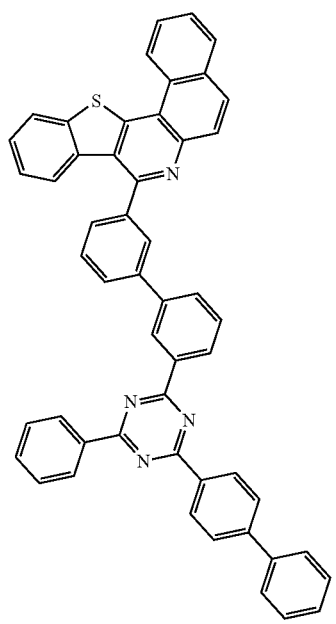
978
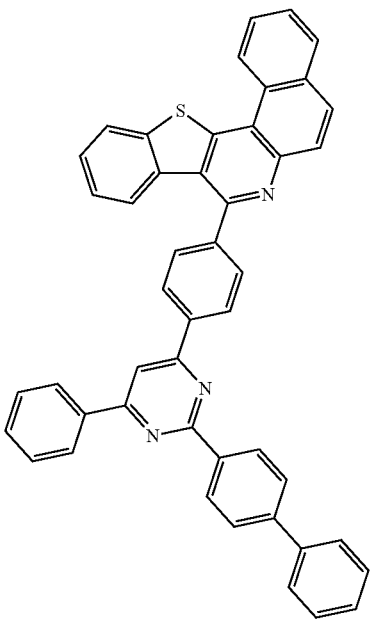

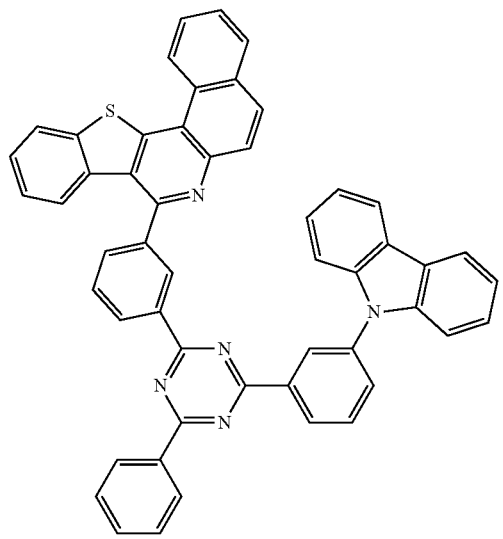
979
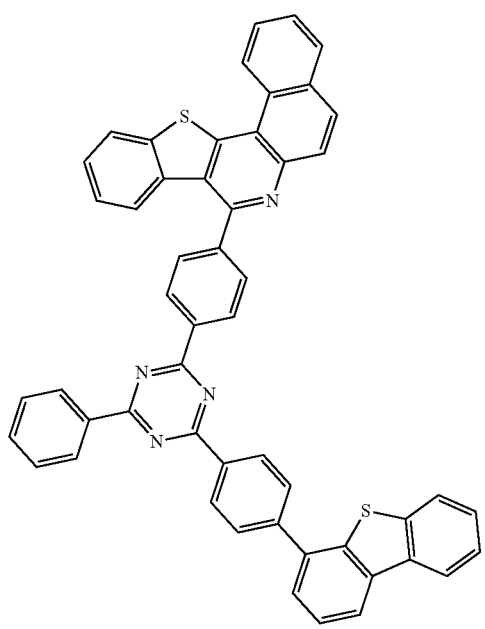
980
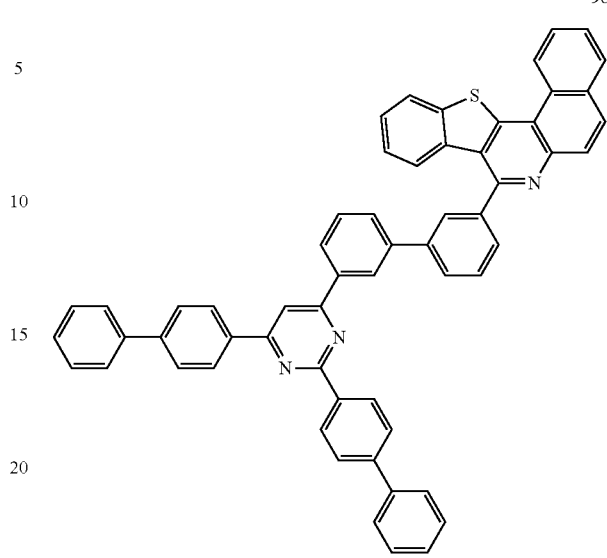
981
982
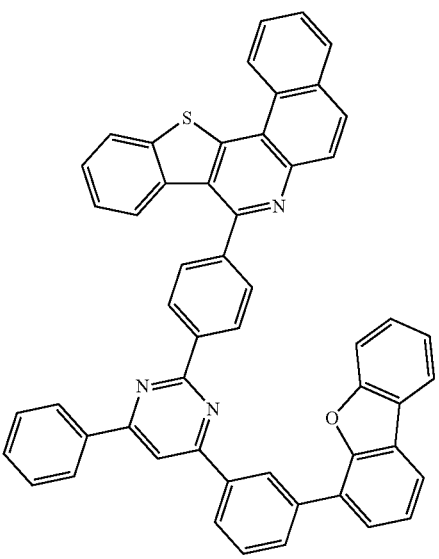
983

417
-continued
984
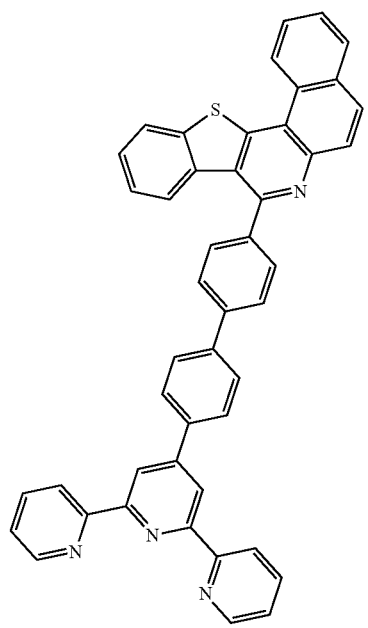
985
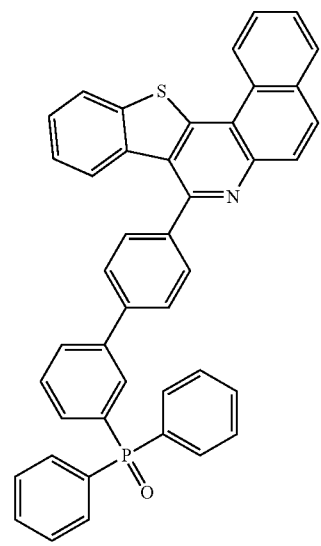
418
-continued
986
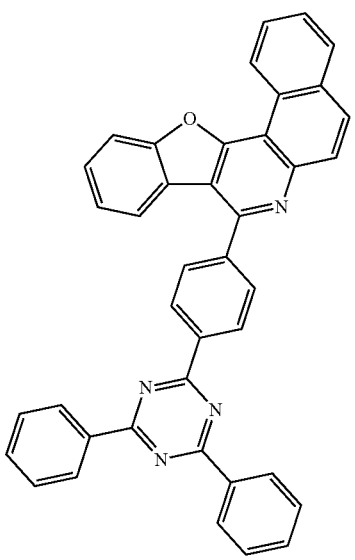
987
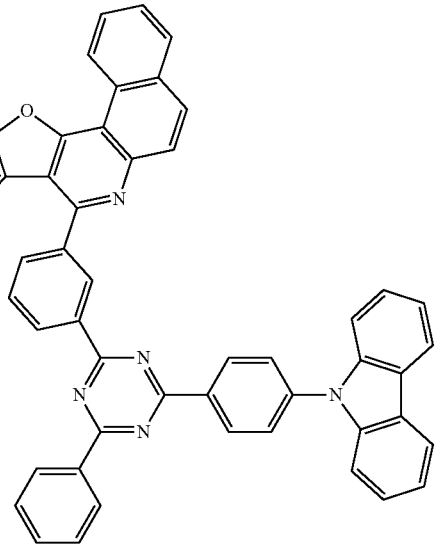

419
-continued
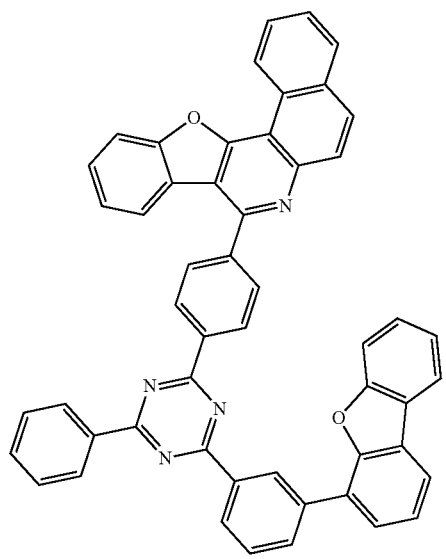
988
989
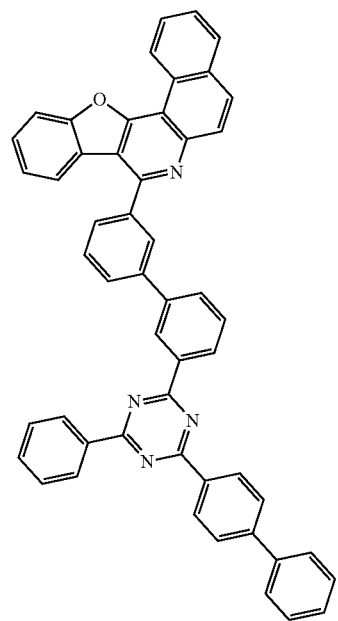
420
-continued
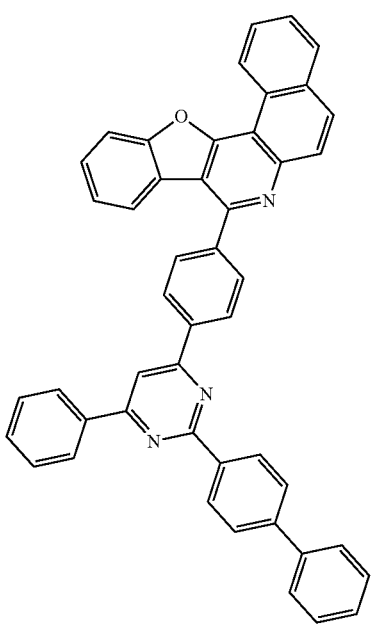
990
991
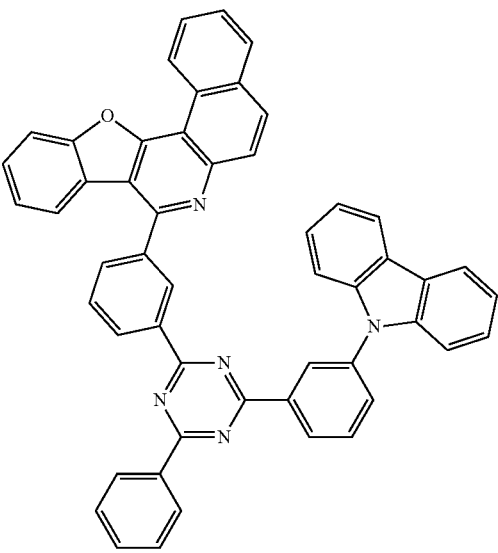

421
-continued
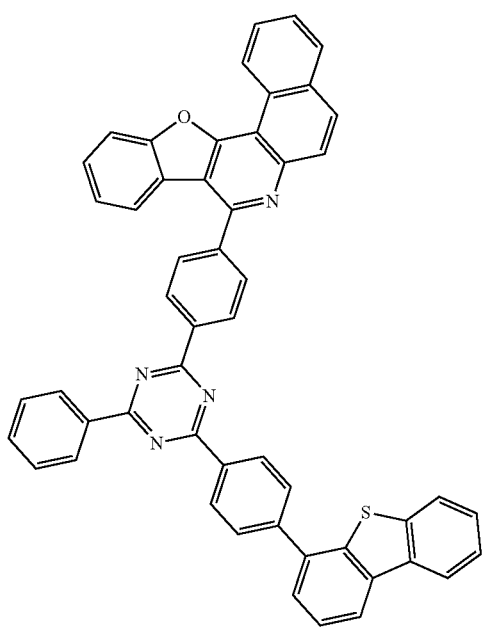
992
422
-continued
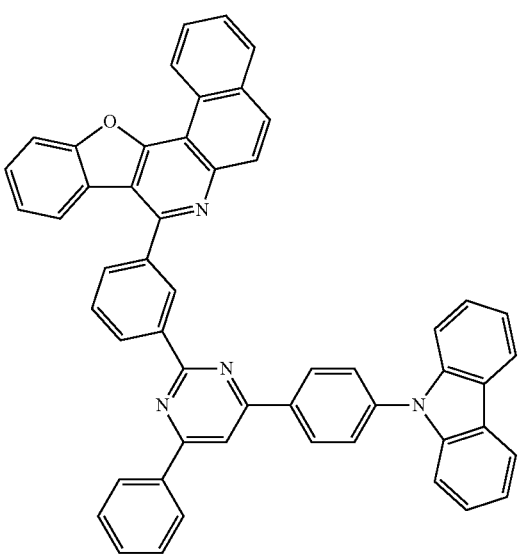
994
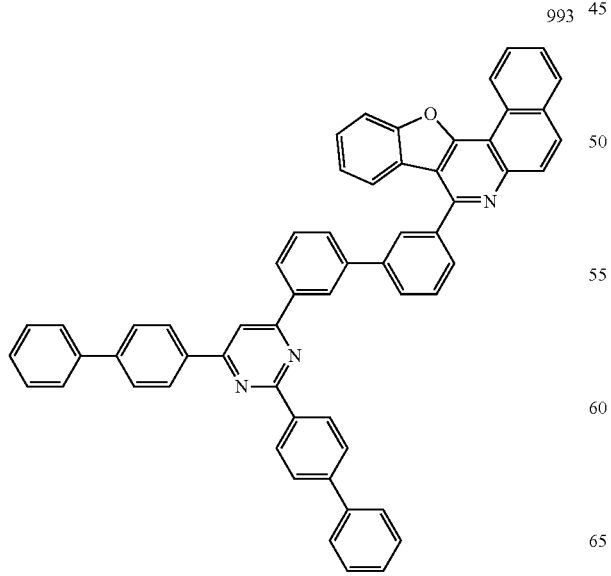
993
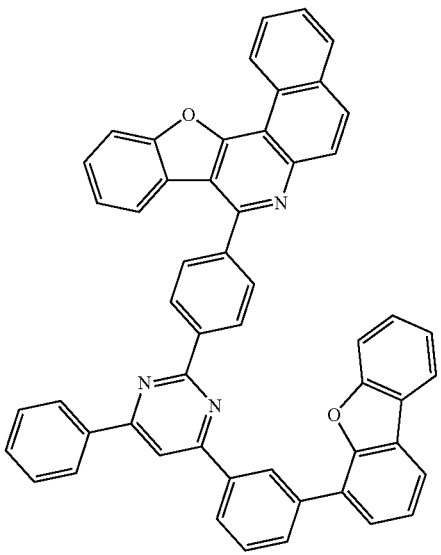
995

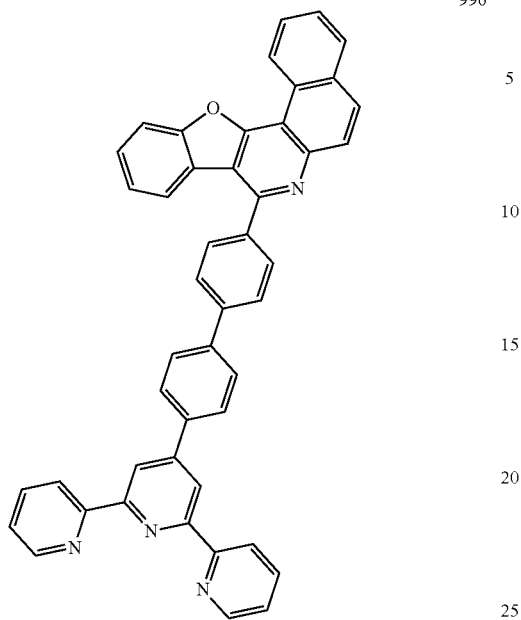
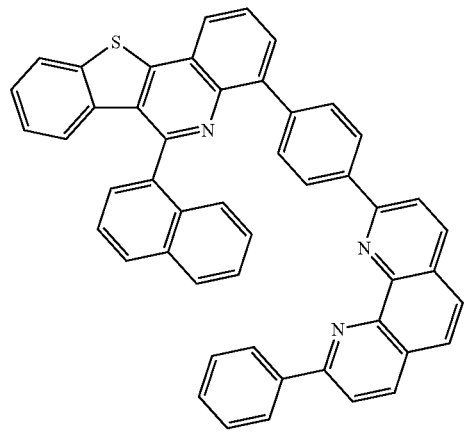
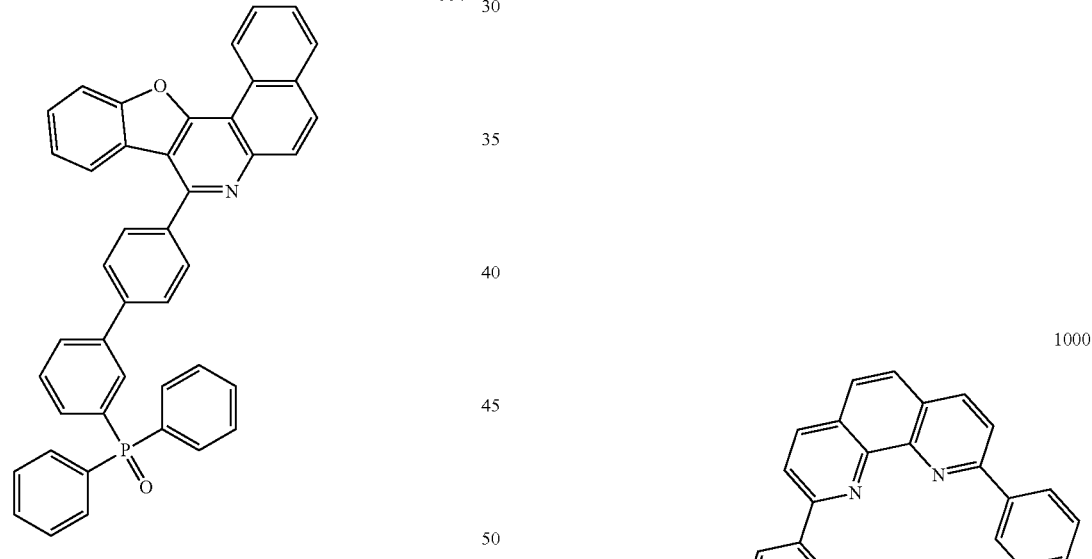
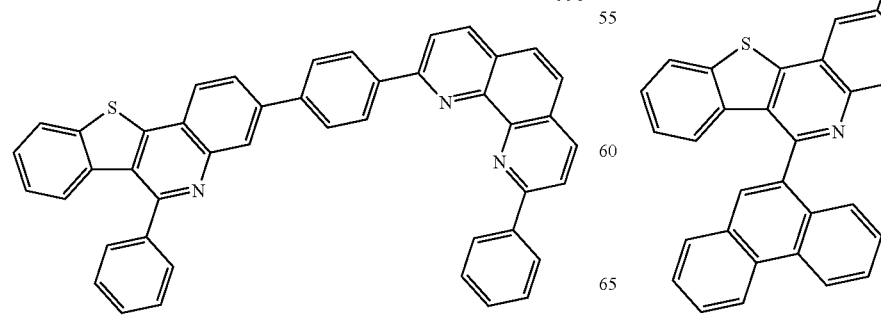

-continued
1001
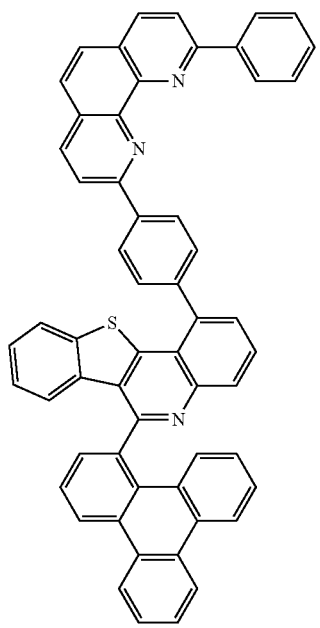
1002
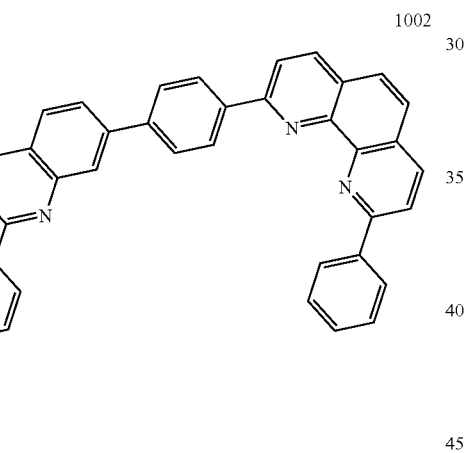
1003
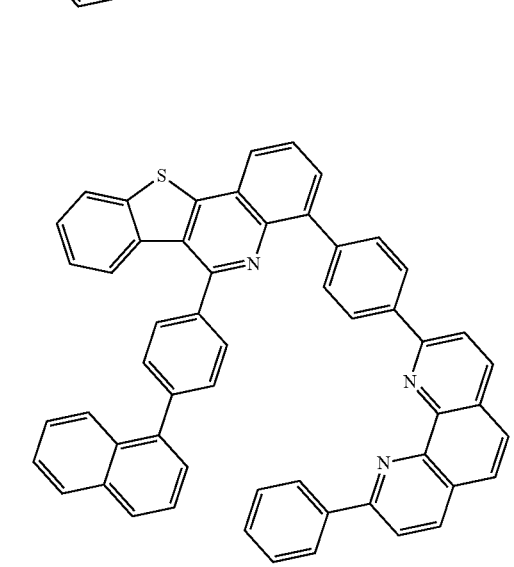
-continued
1004
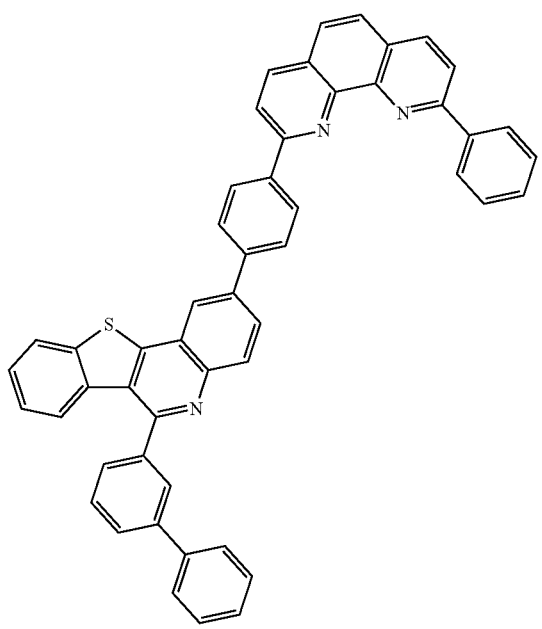
1005
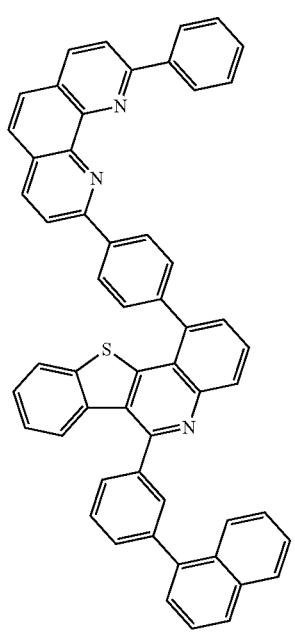
1006
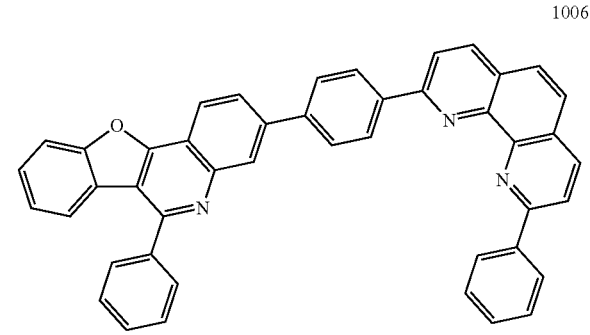

427
-continued
1007
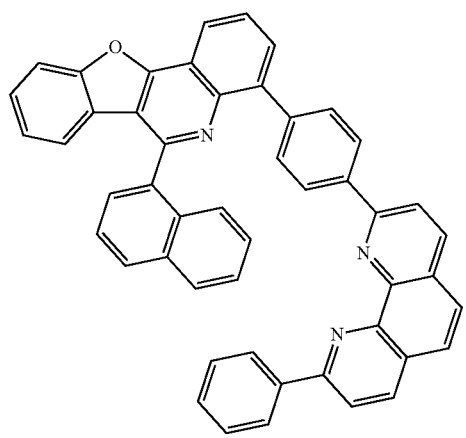 [SMILES: c1ccc(-c2ccc3ccc4ccc(-c5ccc(-c6cccc7c6nc(-c6cccc8ccccc68)c6c8ccccc8sc76)cc5)nc4c3n2)cc1]
428
-continued
1009
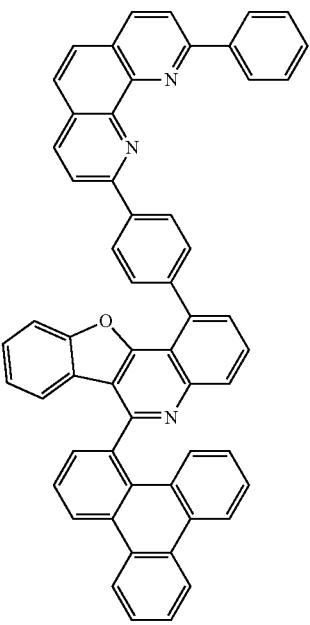
1010
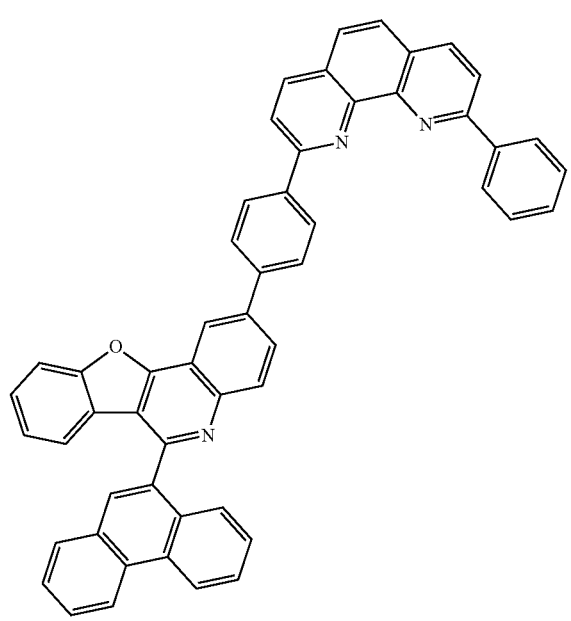
1008
1011
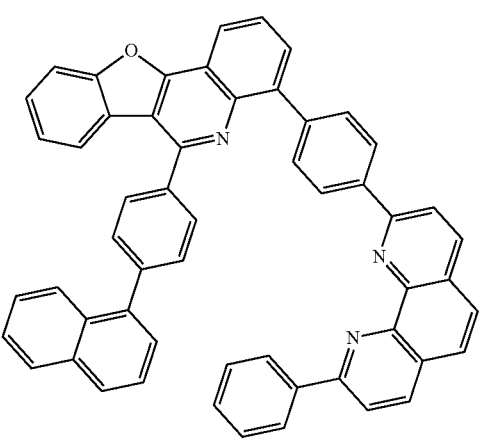

1012
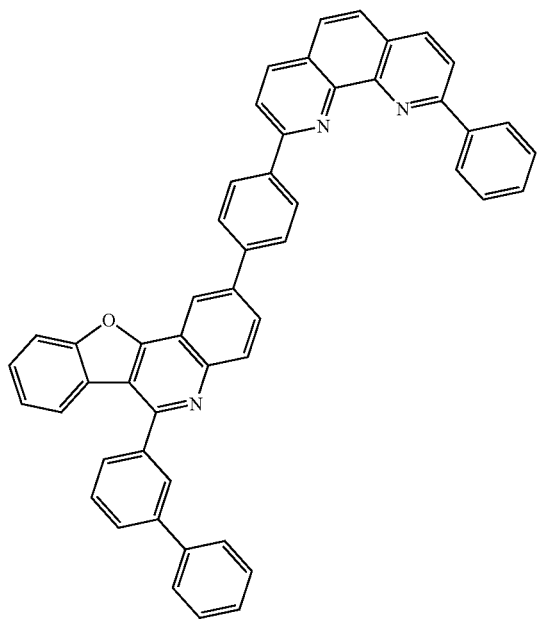
1013
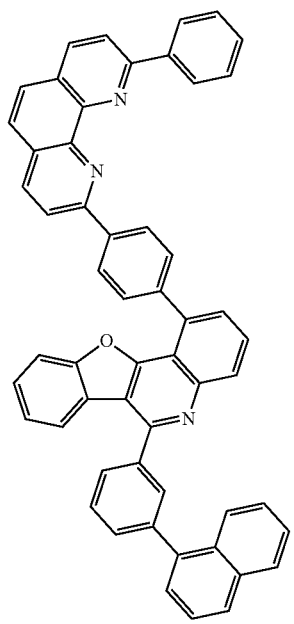
1014
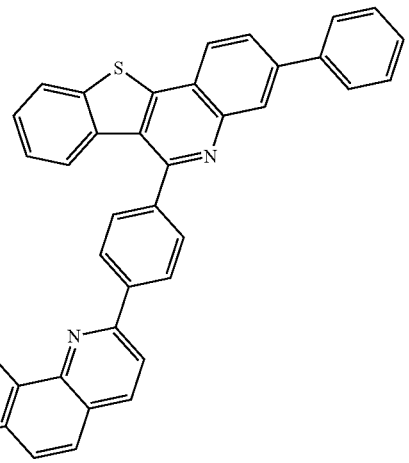
1015
1016
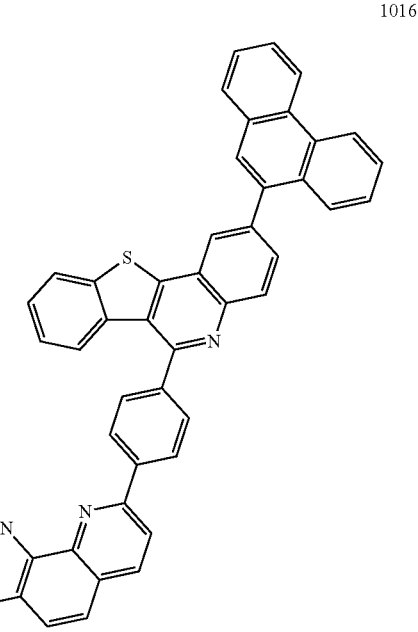

431
-continued
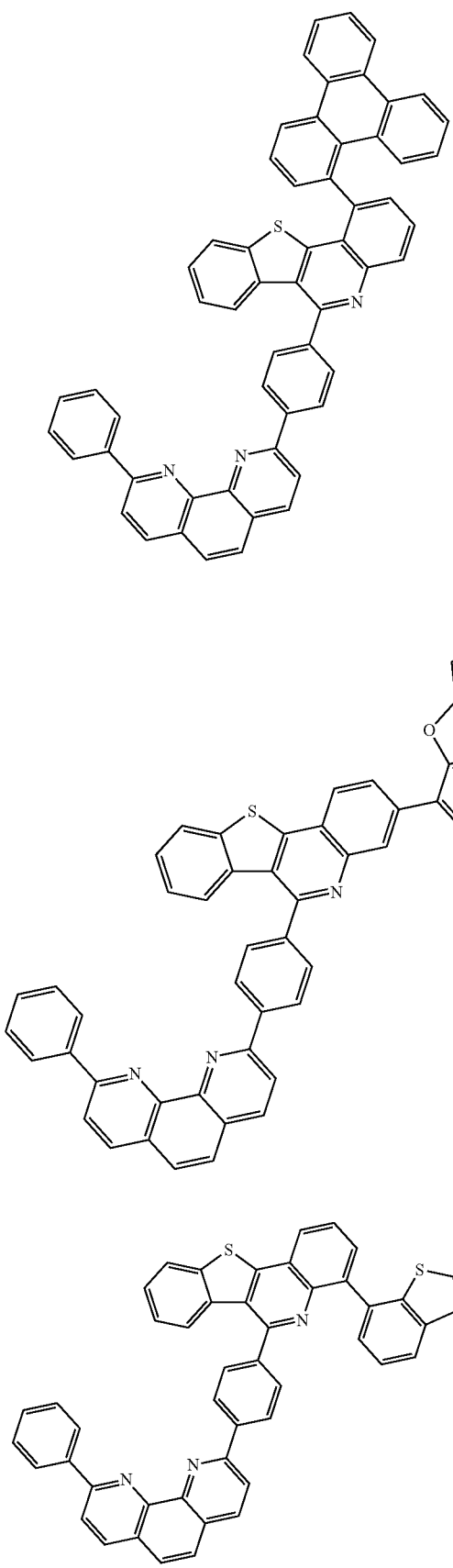
432
-continued
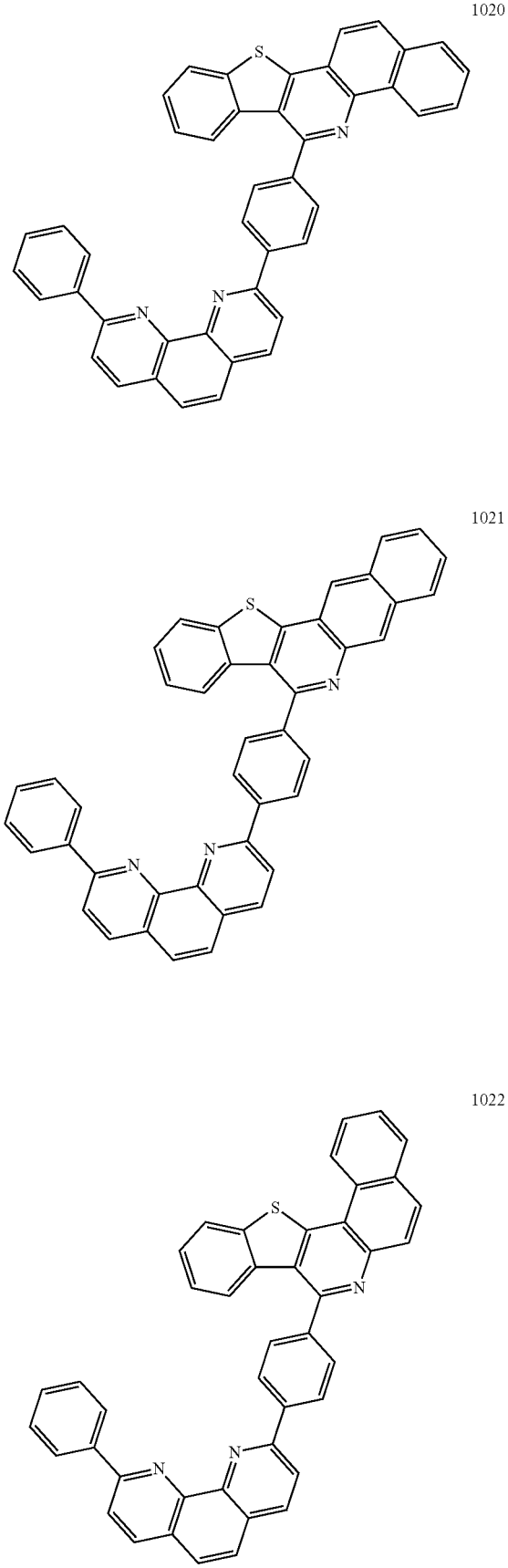

433
-continued
1023
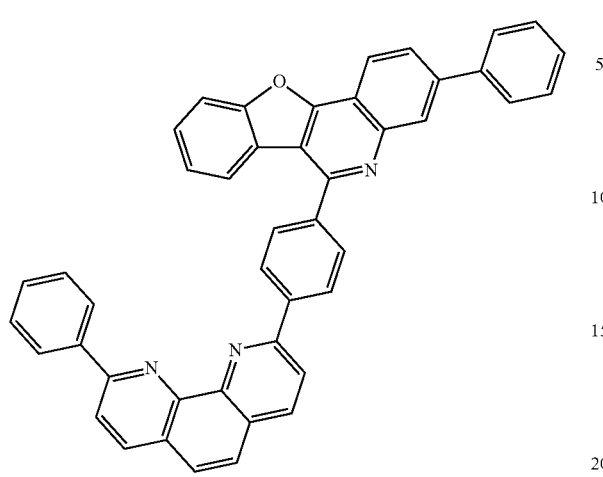
1024
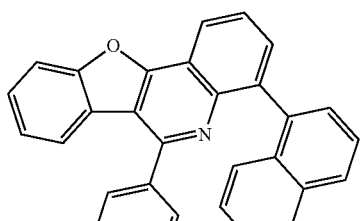
1025
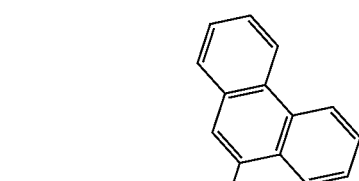
434
-continued
1026
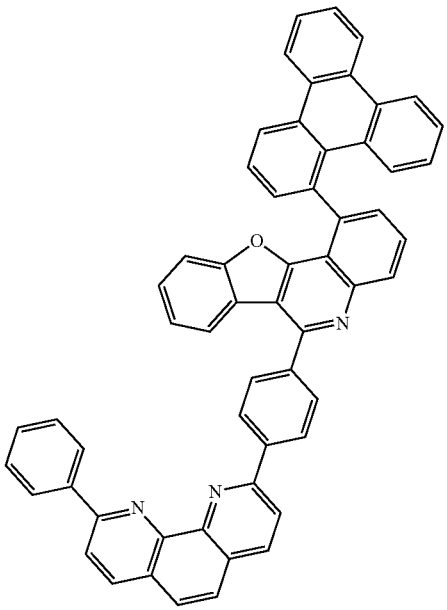
1027
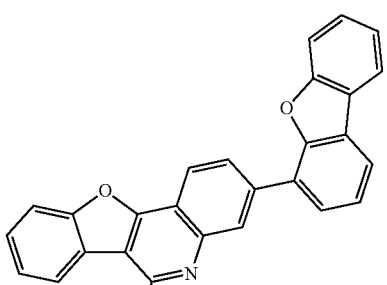
1028
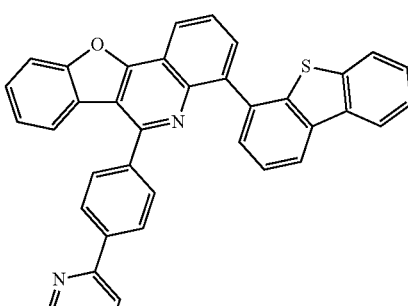
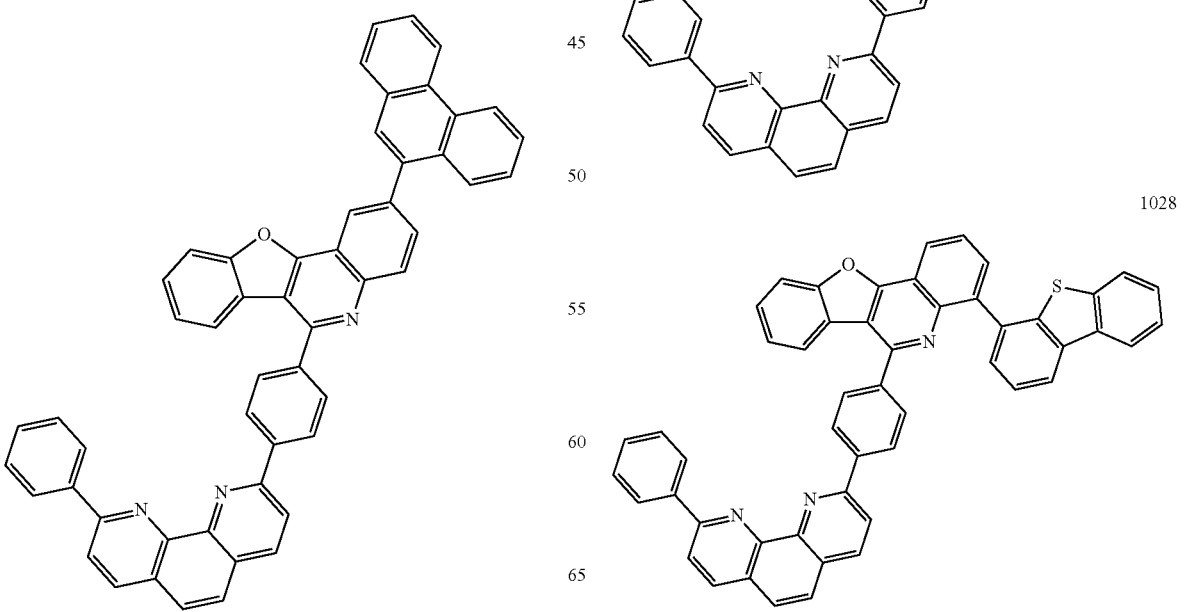

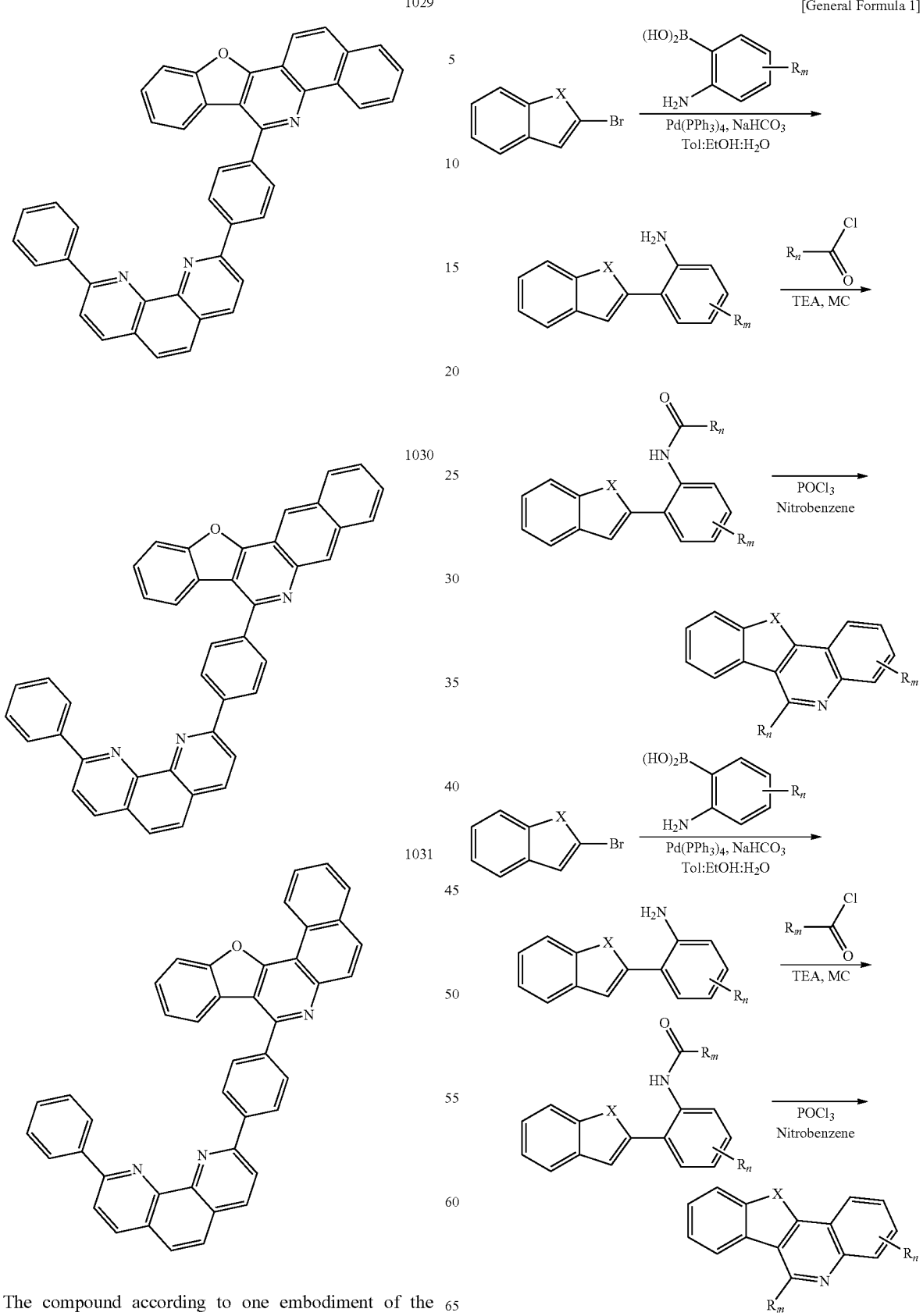
The compound according to one embodiment of the present application may be prepared according to the following General Formula 1.

In General Formula 1, Rm or Rn is

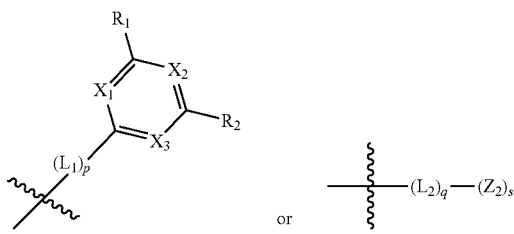

of Chemical Formula 1.

In addition, by introducing various substituents to the structures of Chemical Formulae 1 to 11, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structures of Chemical Formulae 1 to 11, the energy band gap may be finely controlled, and meanwhile, properties at interfaces between organic materials are enhanced, and material applications may become diverse.

Meanwhile, the compound has a high glass transition temperature (Tg), and has excellent thermal stability. Such an increase in the thermal stability becomes an important factor providing driving stability to a device.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device.

In one embodiment of the present application, the organic light emitting device may be a green organic light emitting device, and the heterocyclic compound according to Chemical Formula 1 may be used as a material of the green organic light emitting device.

In one embodiment of the present application, the organic light emitting device may be a red organic light emitting device, and the heterocyclic compound according to Chemical Formula 1 may be used as a material of the red organic light emitting device.

Specific descriptions on the heterocyclic compound represented by Chemical Formula 1 are the same as the descriptions provided above.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a hole blocking layer, a light emitting layer, an electron transfer layer, an electron injection layer and the like as the organic material layer. However, the structure of the organic light emitting device is not limited thereto, and may comprise less numbers of organic material layers.

In the organic light emitting device of the present disclosure, the organic material layer may comprise a light emitting layer, and the light emitting layer may comprise the heterocyclic compound represented by Chemical Formula 1.

In another organic light emitting device, the organic material layer comprises a light emitting layer, the light emitting layer comprises a host material, and the host material may comprise the heterocyclic compound represented by Chemical Formula 1.

In another embodiment, the organic material layer comprising the heterocyclic compound comprises the heterocyclic compound represented by Chemical Formula 1 as a host, and may be used together with a phosphorescent dopant.

In another embodiment, the organic material layer comprising the heterocyclic compound comprises the heterocyclic compound represented by Chemical Formula 1 as a host, and may be used together with an iridium-based dopant.

As a material of the phosphorescent dopant, those known in the art may be used.

For example, phosphorescent dopant materials represented by LL'MX, LL'L"M, LMXX', L2MX and L3M may be used, however, the scope of the present disclosure is not limited to these examples.

Herein, L, L', L", X and X' are bidentate ligands different from each other, and M is a metal forming an octahedral complex.

M may comprise iridium, platinum, osmium or the like.

L is an anionic bidentate ligand coordinated to M as the iridium-based dopant by sp2 carbon and heteroatom, and X may perform a function of trapping electrons or holes. Nonlimiting examples of L may comprise 2-(1naphthyl) benzoxazole, (2-phenylbenzoxazole), (2-phenylbenzothiazole), (2-phenylbenzothiazole), (7,8-benzoquinoline), (thiophene group pyridine), phenylpyridine, benzothiophene group pyridine, 3-methoxy-2-phenylpyridine, tolylpyridine and the like. Nonlimiting examples of X may comprise acetylacetonate (acac), hexafluoroacetylacetonate, salicylidene, picolinate, 8-hydroxyquinolate and the like.

More specific examples thereof are presented below, however, the phosphorescent dopant is not limited to these examples.

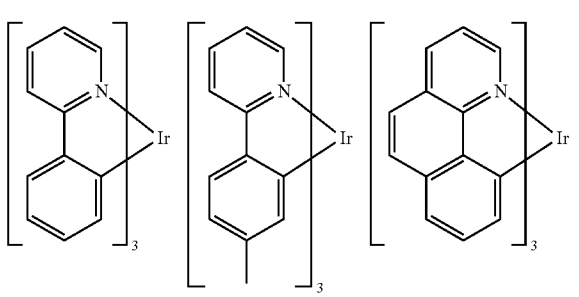
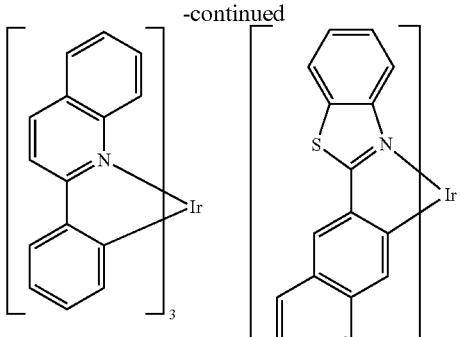
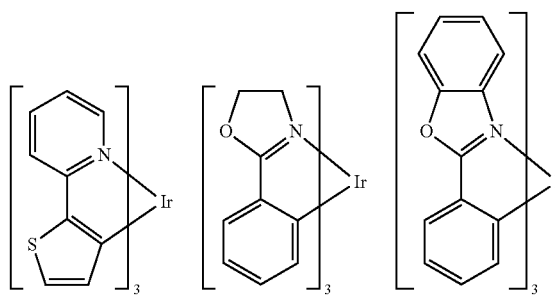
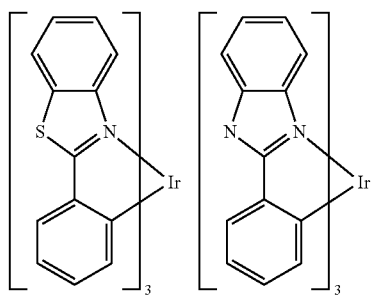
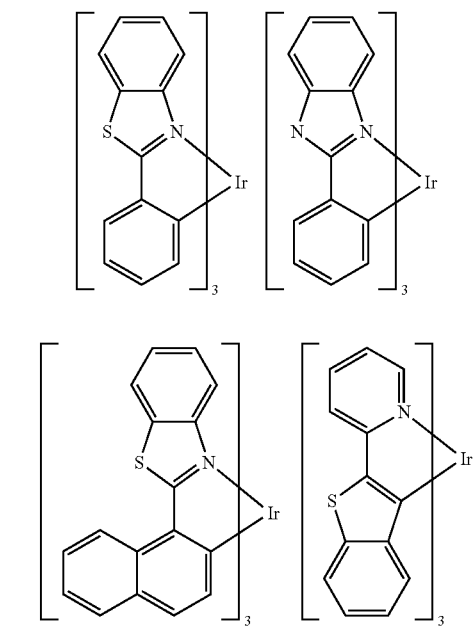
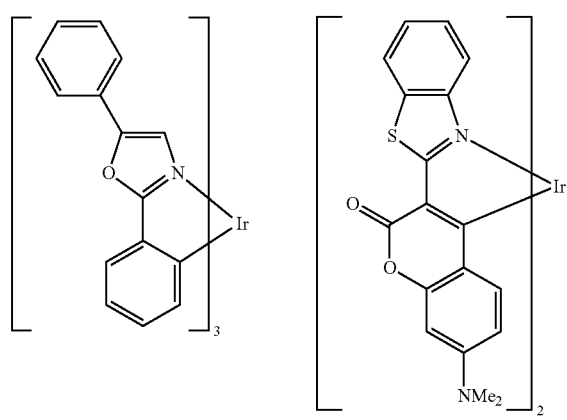

In one embodiment of the present application, as the iridium-based dopant, Ir(ppy)₃ may be used as a green phosphorescent dopant.

In one embodiment of the present application, the dopant content may be from 1% to 15%, preferably from 3% to 10% and more preferably from 5% to 10% based on the whole light emitting layer.

In the organic light emitting device of the present disclosure, the organic material layer comprises an electron injection layer or an electron transfer layer, and the electron injection layer or the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In another organic light emitting device, the organic material layer comprises an electron transfer layer or a hole blocking layer, and the electron transfer layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

In addition, the organic light emitting device according to one embodiment of the present application comprises a first electrode, a second electrode, and two or more stacks provided between the first electrode and the second electrode, wherein the two or more stacks each independently comprise a light emitting layer, a charge generation layer is included between the two or more stacks, and the charge generation layer comprises the heterocyclic compound represented by Chemical Formula 1.

In addition, the organic light emitting device according to one embodiment of the present application may comprise a first electrode, a first stack provided on the first electrode and comprising a first light emitting layer, a charge generation layer provided on the first stack, a second stack provided on the charge generation layer and comprising a second light emitting layer, and a second electrode provided on the second stack. Herein, the charge generation layer may comprise the heterocyclic compound represented by Chemical Formula 1. In addition, the first stack and the second stack may each independently further comprise one or more types of the hole injection layer, the hole transfer layer, the hole blocking layer, the electron transfer layer, the electron injection layer described above and the like.

The charge generation layer may be an N-type charge generation layer, and the charge generation layer may further comprise a dopant known in the art in addition to the heterocyclic compound represented by Chemical Formula 1.

As the organic light emitting device according to one embodiment of the present application, an organic light emitting device having a 2-stack tandem structure is schematically illustrated in FIG. 4.

The organic material layer comprising Chemical Formula 1 may further comprise other materials as necessary.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO$_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyl-diamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involved in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

Preparation Example

<Preparation Example 1> Preparation of Compound 1

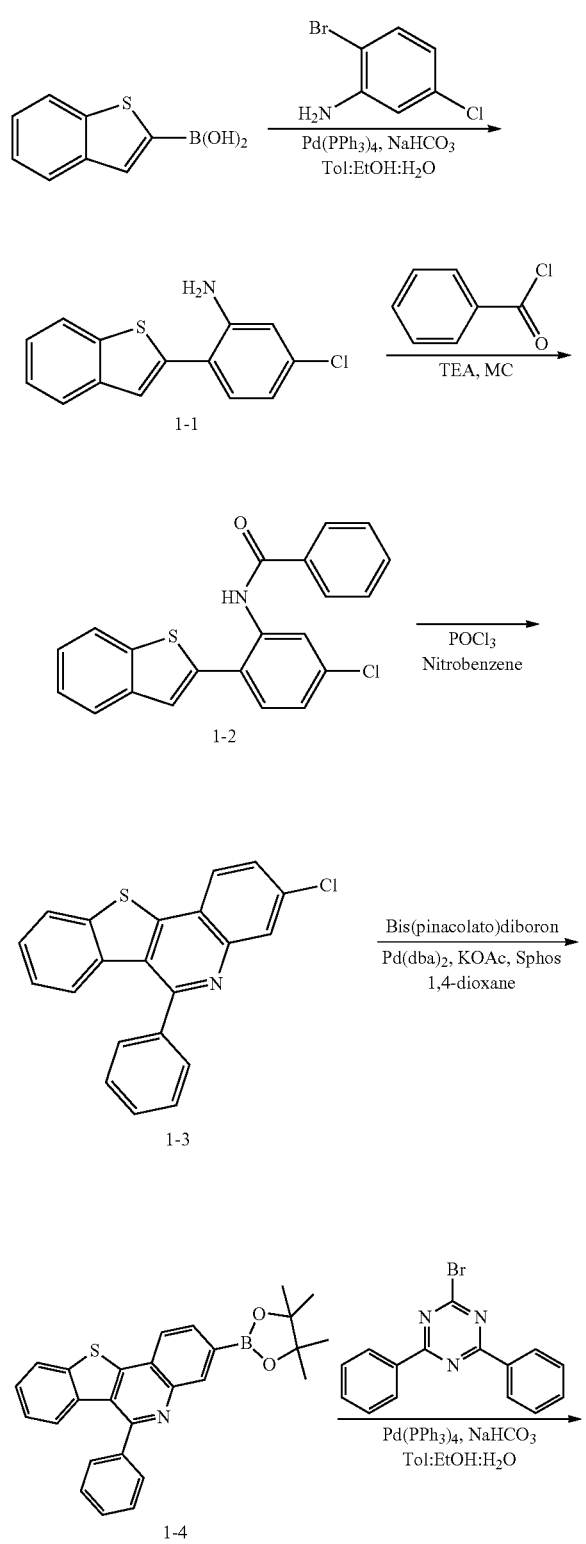

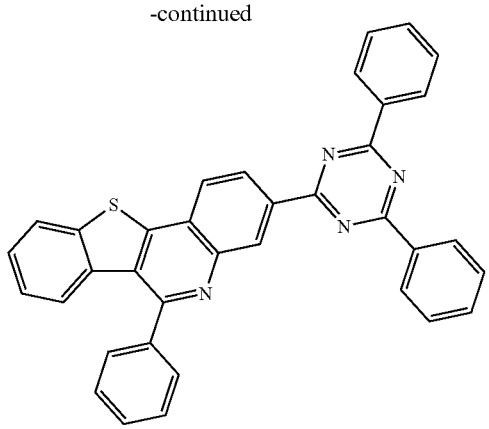

1) Preparation of Compound 1-1

After dissolving (1H-indol-2-yl)boronic acid (100 g, 0.621 mol) and 2-bromo-5-chloroaniline (115 g, 0.558 mol) in toluene, EtOH and H$_2$O (1000 mL:200 mL:200 mL), Pd(PPh$_3$)$_4$ (35.8 g, 0.031 mol) and NaHCO$_3$ (156.5 g, 1.863 mol) were introduced thereto, and the result was stirred for 3 hours at 100° C. After the reaction was completed, MC and distilled water were introduced to the reaction solution for extraction. After that, the result was dried with anhydrous MgSO$_4$, and then the solvent was removed using a rotary evaporator to obtain Compound 1-1 (110 g, 74%) in a liquid form.

2) Preparation of Compound 1-2

Compound 1-1 (110 g, 0.428 mol) and triethylamine (89 mL, 0.642 mol) were introduced to methylene chloride (MC) (1200 mL) and dissolved therein. Benzoyl chloride (90.24 g, 0.642 mol) dissolved in MC (300 mL) was slowly added dropwise to the mixture at 0° C. After the reaction was completed, MC and distilled water were introduced to the reaction solution for extraction. After that, the result was dried with anhydrous MgSO$_4$, and then the solvent was removed using a rotary evaporator to obtain Compound 1-2 (129 g, 83%) in a liquid form.

3) Preparation of Compound 1-3

After dissolving Compound 1-2 (129 g, 0.355 mol) in nitrobenzene (1500 mL), POCl$_3$ (50 mL, 0.533 mol) was slowly added dropwise thereto. The result was reacted for 15 hours at 140° C. After the reaction was completed, a solution dissolving NaHCO$_3$ in distilled water was slowly introduced to the reaction solution, and the result was stirred. Produced solids were filtered and collected. The collected solids were recrystallized with MC and MeOH to obtain Compound 1-3 (65 g, 53%) in a solid form.

4) Preparation of Compound 1-4

After dissolving Compound 1-3 (10 g, 0.029 mol), bis(pinacolato)diboron (8.8 g, 0.035 mol), KOAc (8.5 g, 0.087 mol), Sphos (2.4 g, 0.0058 mol) and Pd(dba)$_2$ (1.7 g, 0.0029 mol) in 1,4-dioxane (200 mL), the result was reacted for 5 hours at 90° C. After the reaction was completed, MC and distilled water were introduced to the reaction solution for extraction. After that, the result was dried with anhydrous MgSO$_4$, and then the solvent was removed using a rotary evaporator to obtain Compound 1-4 (11.4 g, 90%).

5) Preparation of Compound 1

After dissolving Compound 1-4 (11.4 g, 0.026 mol) and 2-bromo-4,6-diphenyl-1,3,5-triazine (7.5 g, 0.024 mol) in toluene, EtOH and H$_2$O (100 mL:20 mL:20 mL), Pd(PPh$_3$)$_4$ (1.4 g, 0.0012 mol) and K$_2$CO$_3$ (9.2 g, 0.072 mol) were introduced thereto, and the result was stirred for 5 hours at 100° C. After the reaction was completed, MC and distilled water were introduced to the reaction solution for extraction. After that, the result was dried with anhydrous MgSO$_4$, and then the solvent was removed using a rotary evaporator to obtain Compound 1 (9.4 g, 72%).

A target compound was synthesized in the same manner as in Preparation Example 1 except that Intermediate A of the following Table 1 was used instead of 2-bromo-4,6-diphenyl-1,3,5-triazine.

TABLE 1

| Compound Number | Intermediate A | Target Compound | Yield |
| --- | --- | --- | --- |
| 1 | | | 72% |
| 4 | | | 67% |
| 5 | | | 66% |

TABLE 1-continued

| Compound Number | Intermediate A | Target Compound | Yield |
|---|---|---|---|
| 9 | | | 75% |
| 206 | | | 72% |
| 210 | | | 77% |

TABLE 1-continued

| Compound Number | Intermediate A | Target Compound | Yield |
|---|---|---|---|
| 217 | | | 67% |
| 255 | | | 66% |
| 368 | | | 75% |
| 370 | | | 74% |

TABLE 1-continued

| Compound Number | Intermediate A | Target Compound | Yield |
|---|---|---|---|
| 372 | | | 69% |
| 542 | | | 70% |
| 543 | | | 79% |
| 998 | | | 69% |

A target compound was synthesized in the same manner as in Preparation Example 1 except that 2-bromo-6-chloroaniline was used instead of 2-bromo-5-chloroaniline, and Intermediate B of the following Table 2 was used instead of 2-bromo-4,6-diphenyl-1,3,5-triazine.

TABLE 2

| Compound Number | Intermediate B | Target Compound | Yield |
|---|---|---|---|
| 13 | 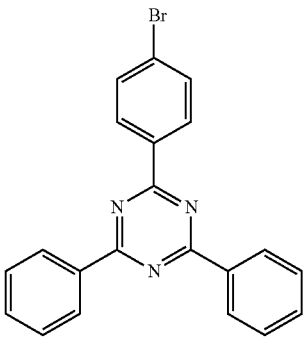 | 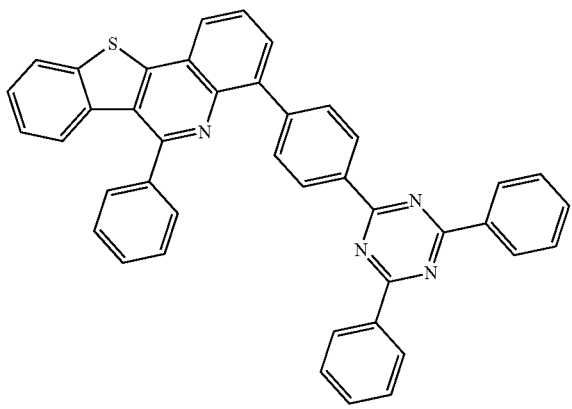 | 72% |

A target compound was synthesized in the same manner as in Preparation Example 1 except that 2-bromo-4-chloroaniline was used instead of 2-bromo-5-chloroaniline, and Intermediate C of the following Table 3 was used instead of 2-bromo-4,6-diphenyl-1,3,5-triazine.

TABLE 3

| Compound Number | Intermediate C | Target Compound | Yield |
|---|---|---|---|
| 24 | 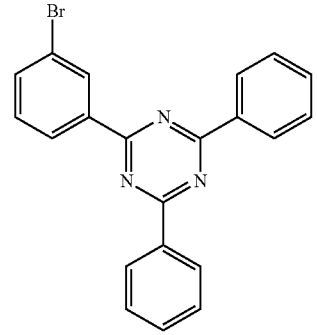 | 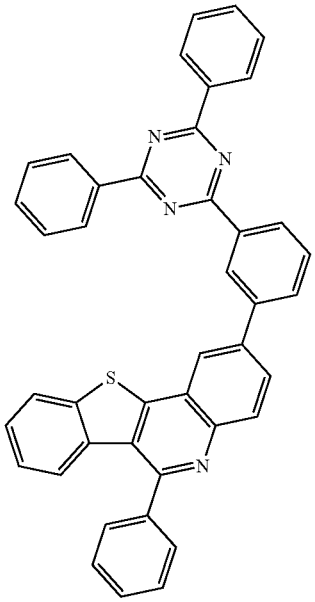 | 68% |

TABLE 3-continued

| Compound Number | Intermediate C | Target Compound | Yield |
|---|---|---|---|
| 34 | (structure) | (structure) | 66% |
| 235 | (structure) | (structure) | 66% |

TABLE 3-continued

| Compound Number | Intermediate C | Target Compound | Yield |
|---|---|---|---|
| 238 | [structure with Br-phenyl-pyrimidine-biphenyl groups] | [target structure] | 67% |

A target compound was synthesized in the same manner as in Preparation Example 1 except that 2-bromo-3-chloroaniline was used instead of 2-bromo-5-chloroaniline, and Intermediate D of the following Table 4 was used instead of 2-bromo-4,6-diphenyl-1,3,5-triazine.

TABLE 4

| Compound Number | Intermediate D | Target Compound | Yield |
|---|---|---|---|
| 248 | [structure with Br-phenyl-diphenylpyrimidine] | [target structure] | 75% |

459

A target compound was synthesized in the same manner as in Preparation Example 1 except that 1-naphthoyl chloride was used instead of benzoyl chloride, and Intermediate E of the following Table 5 was used instead of 2-bromo-4,6-diphenyl-1,3,5-triazine.

460

A target compound was synthesized in the same manner as in Preparation Example 1 except that 1-naphthoyl chloride was used instead of benzoyl chloride, 2-bromo-6-chloroaniline was used instead of 2-bromo-5-chloroaniline, and Intermediate F of the following Table 6 was used instead of 2-bromo-4,6-diphenyl-1,3,5-triazine.

TABLE 5

| Compound Number | Intermediate E | Target Compound | Yield |
|---|---|---|---|
| 260 | | | 69% |
| 264 | | | 68% |
| 547 | | | 70% |

TABLE 6

| Compound Number | Intermediate F | Target Compound | Yield |
|---|---|---|---|
| 44 | | | 76% |
| 272 | | | 77% |
| 275 | | | 67% |

TABLE 6-continued

| Compound Number | Intermediate F | Target Compound | Yield |
|---|---|---|---|
| 277 | | | 64% |
| 999 | | | 62% |

A target compound was synthesized in the same manner as in Preparation Example 1 except that 1-naphthoyl chloride was used instead of benzoyl chloride, 2-bromo-4-chloroaniline was used instead of 2-bromo-5-chloroaniline, and Intermediate G of the following Table 7 was used instead of 2-bromo-4,6-diphenyl-1,3,5-triazine.

TABLE 7
| Compound Number | Intermediate G | Target Compound | Yield |
|---|---|---|---|
| 283 | 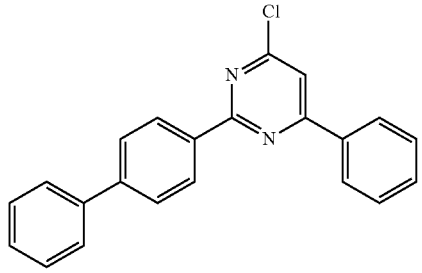 [SMILES: Clc1cc(-c2ccccc2)nc(-c2ccc(-c3ccccc3)cc2)n1] | 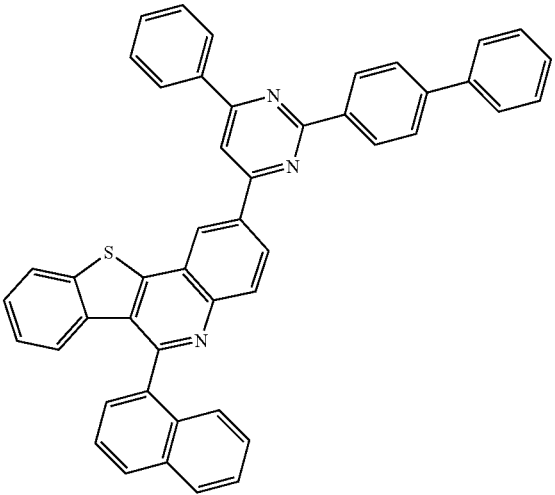 [SMILES: c1ccc(-c2ccc(-c3nc(-c4ccccc4)cc(-c4ccc5nc(-c6cccc7ccccc67)c6c7ccccc7sc6c5c4)n3)cc2)cc1] | 70% |
| 285 | 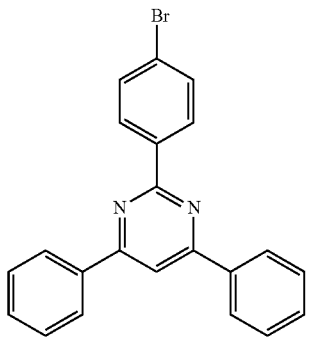 [SMILES: Brc1ccc(-c2nc(-c3ccccc3)cc(-c3ccccc3)n2)cc1] | 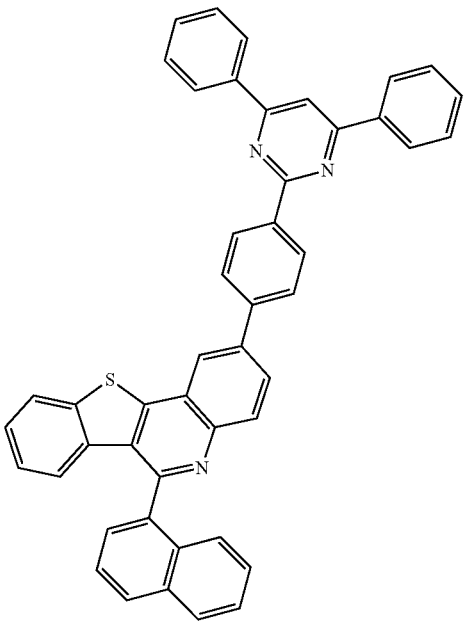 [SMILES: c1ccc(-c2cc(-c3ccccc3)nc(-c3ccc(-c4ccc5nc(-c6cccc7ccccc67)c6c7ccccc7sc6c5c4)cc3)n2)cc1] | 76% |

TABLE 7-continued

| Compound Number | Intermediate G | Target Compound | Yield |
|---|---|---|---|
| 287 | (structure) | (structure) | 80% |

A target compound was synthesized in the same manner as in Preparation Example 1 except that 1-naphthoyl chloride was used instead of benzoyl chloride, 2-bromo-3-chloroaniline was used instead of 2-bromo-5-chloroaniline, and Intermediate H of the following Table 8 was used instead of 2-bromo-4,6-diphenyl-1,3,5-triazine.

TABLE 8

| Compound Number | Intermediate H | Target Compound | Yield |
|---|---|---|---|
| 57 | (structure) | (structure) | 79% |

A target compound was synthesized in the same manner as in Preparation Example 1 except that 9-chlorophenanthrene was used instead of benzoyl chloride, and Intermediate I of the following Table 9 was used instead of 2-bromo-4,6-diphenyl-1,3,5-triazine.

TABLE 9

| Compound Number | Intermediate I | Target Compound | Yield |
|---|---|---|---|
| 64 | | | 74% |
| 65 | | | 66% |
| 312 | | | 68% |

TABLE 9-continued

| Compound Number | Intermediate I | Target Compound | Yield |
|---|---|---|---|
| 551 | 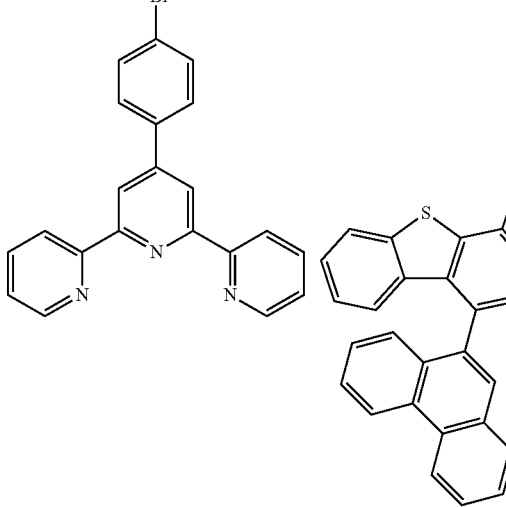 | 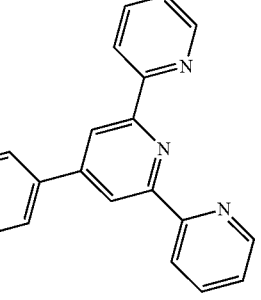 | 71% |

A target compound was synthesized in the same manner as in Preparation Example 1 except that 9-chlorophenanthrene was used instead of benzoyl chloride, 2-bromo-6-chloroaniline was used instead of 2-bromo-5-chloroaniline, and Intermediate J of the following Table 10 was used instead of 2-bromo-4,6-diphenyl-1,3,5-triazine.

TABLE 10

| Compound Number | Intermediate J | Target Compound | Yield |
|---|---|---|---|
| 318 | 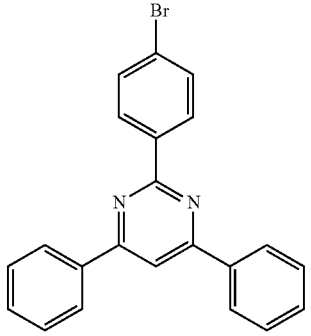 [SMILES: Brc1ccc(-c2nc(-c3ccccc3)cc(-c3ccccc3)n2)cc1] | 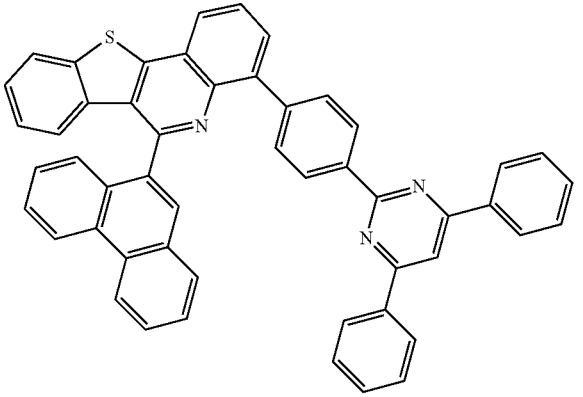 [SMILES: c1ccc(-c2cc(-c3ccccc3)nc(-c3ccc(-c4cccc5c4nc(-c4cc6ccccc6c6ccccc46)c4c6ccccc6sc54)cc3)n2)cc1] | 62% |

A target compound was synthesized in the same manner as in Preparation Example 1 except that 2-bromo-6-chloroaniline was used instead of 2-bromo-5-chloroaniline, 4-(naphthalen-1-yl)benzoyl chloride was used instead of benzoyl chloride, and Intermediate K of the following Table 11 was used instead of 2-bromo-4,6-diphenyl-1,3,5-triazine.

TABLE 11

| Compound Number | Intermediate K | Target Compound | Yield |
|---|---|---|---|
| 1003 | [structure: 2-phenyl-1,10-phenanthroline with 4-bromophenyl substituent] | [structure: target compound] | 71% |

A target compound was synthesized in the same manner as in Preparation Example 1 except that 9-chlorophenanthrene was used instead of benzoyl chloride, 2-bromo-4-chloroaniline was used instead of 2-bromo-5-chloroaniline, and Intermediate L of the following Table 12 was used instead of 2-bromo-4,6-diphenyl-1,3,5-triazine.

TABLE 12

| Compound Number | Intermediate L | Target Compound | Yield |
|---|---|---|---|
| 328 | [structure: 2-(4-bromophenyl)-4,6-diphenylpyrimidine] | [structure: target compound] | 67% |

TABLE 12-continued

| Compound Number | Intermediate L | Target Compound | Yield |
|---|---|---|---|
| 332 | (structure) | (structure) | 70% |

A target compound was synthesized in the same manner as in Preparation Example 1 except that 9-chlorophenanthrene was used instead of benzoyl chloride, 2-bromo-3-chloroaniline was used instead of 2-bromo-5-chloroaniline, and Intermediate M of the following Table 13 was used instead of 2-bromo-4,6-diphenyl-1,3,5-triazine.

TABLE 13

| Compound Number | Intermediate M | Target Compound | Yield |
|---|---|---|---|
| 78 | (structure) | (structure) | 71% |

A target compound was synthesized in the same manner as in Preparation Example 1 except that 2-chlorotriphenylene was used instead of benzoyl chloride, and Intermediate N of the following Table 14 was used instead of 2-bromo-4,6-diphenyl-1,3,5-triazine.
TABLE 14
| Compound Number | Intermediate N | Target Compound | Yield |
|---|---|---|---|
| 84 | 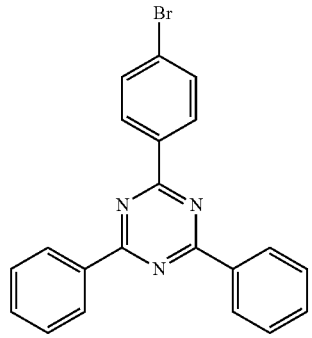 [SMILES: Brc1ccc(-c2nc(-c3ccccc3)nc(-c3ccccc3)n2)cc1] | 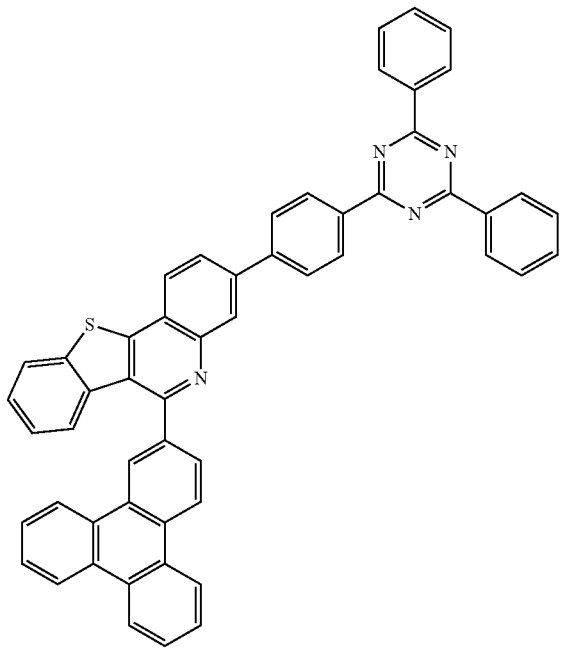 [SMILES: c1ccc(-c2nc(-c3ccccc3)nc(-c3ccc(-c4ccc5c(c4)nc(-c4ccc6c7ccccc7c7ccccc7c6c4)c4c6ccccc6sc54)cc3)n2)cc1] | 68% |
| 100 | 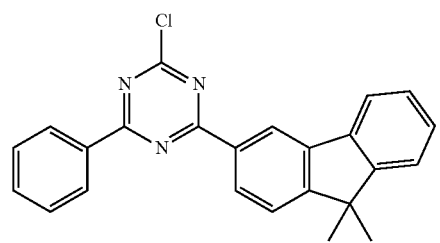 [SMILES: CC1(C)c2ccccc2-c2cc(-c3nc(Cl)nc(-c4ccccc4)n3)ccc21] | 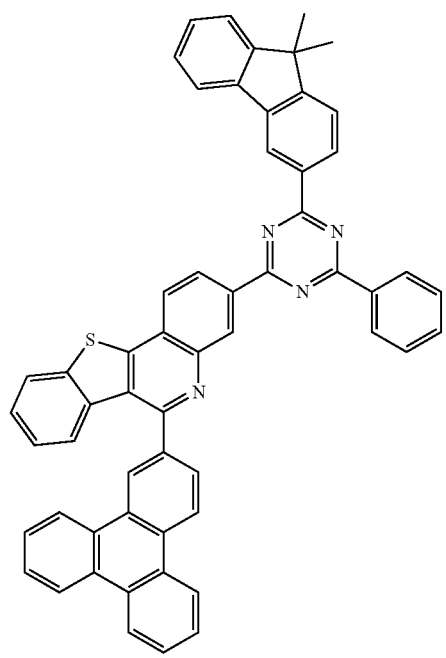 [SMILES: CC1(C)c2ccccc2-c2cc(-c3nc(-c4ccccc4)nc(-c4ccc5c(c4)nc(-c4ccc6c7ccccc7c7ccccc7c6c4)c4c6ccccc6sc54)n3)ccc21] | 70% |

TABLE 14-continued

| Compound Number | Intermediate N | Target Compound | Yield |
|---|---|---|---|
| 101 | | | 64% |
| 346 | | | 78% |
| 348 | | | 76% |

TABLE 14-continued

| Compound Number | Intermediate N | Target Compound | Yield |
|---|---|---|---|
| 555 | | | 77% |

A target compound was synthesized in the same manner as in Preparation Example 1 except that [1,1'-biphenyl]-4-carbonyl chloride was used instead of benzoyl chloride, and Intermediate O of the following Table 15 was used instead of 2-bromo-4,6-diphenyl-1,3,5-triazine.

TABLE 15

| Compound Number | Intermediate O | Target Compound | Yield |
|---|---|---|---|
| 1002 | | | 68% |

A target compound was synthesized in the same manner as in Preparation Example 1 except that 2-chlorotriphenylene was used instead of benzoyl chloride, 2-bromo-4-chloroaniline was used instead of 2-bromo-5-chloroaniline, and Intermediate P of the following Table 16 was used instead of 2-bromo-4,6-diphenyl-1,3,5-triazine.

TABLE 16

| Compound Number | Intermediate P | Target Compound | Yield |
|---|---|---|---|
| 92 | | | 72% |
| 355 | | | 68% |

TABLE 16-continued

| Compound Number | Intermediate P | Target Compound | Yield |
|---|---|---|---|
| 358 | | | 70% |
| 359 | | | 73% |

A target compound was synthesized in the same manner as in Preparation Example 1 except that 4-(naphthalen-1-yl)benzoyl chloride was used instead of benzoyl chloride, and Intermediate Q of the following Table 17 was used instead of 2-bromo-4,6-diphenyl-1,3,5-triazine.

TABLE 17

| Compound Number | Intermediate Q | Target Compound | Yield |
|---|---|---|---|
| 302 | (structure with Br) | (structure) | 69% |

A target compound was synthesized in the same manner as in Preparation Example 1 except that 4-(naphthalen-9-yl)benzoyl chloride was used instead of benzoyl chloride, and Intermediate R of the following Table 18 was used instead of 2-bromo-4,6-diphenyl-1,3,5-triazine.

A target compound was synthesized in the same manner as in Preparation Example 1 except that benzofuran-2-ylboronic acid was used instead of (1H-indol-2-yl)boronic acid, and Intermediate S of the following Table 19 was used instead of 2-bromo-4,6-diphenyl-1,3,5-triazine.

TABLE 18

| Compound Number | Intermediate R | Target Compound | Yield |
|---|---|---|---|
| 342 | (structure with Br) | (structure) | 70% |

TABLE 19

| Compound Number | Intermediate S |
| --- | --- |
| 102 | |
| 105 | |
| 106 | |
| 198 | |

TABLE 19-continued
| 202 | 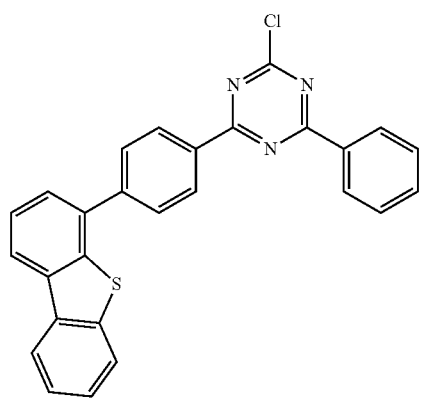 [SMILES: Clc1nc(-c2ccccc2)nc(-c2ccc(-c3cccc4c3sc3ccccc34)cc2)n1] |
| --- | --- |
| 387 | 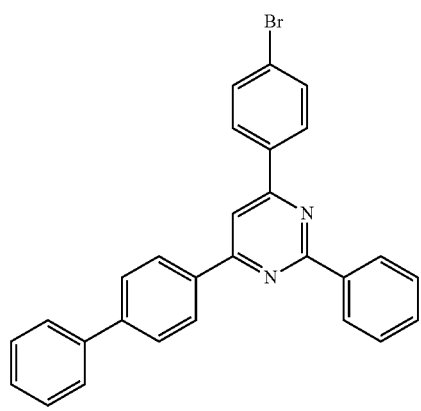 [SMILES: Brc1ccc(-c2cc(-c3ccc(-c4ccccc4)cc3)nc(-c3ccccc3)n2)cc1] |
| 536 | 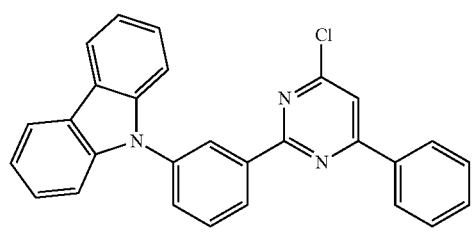 [SMILES: Clc1cc(-c2ccccc2)nc(-c2cccc(-n3c4ccccc4c4ccccc43)c2)n1] |
| 537 | 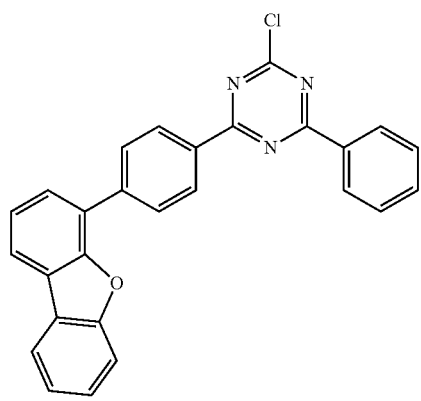 [SMILES: Clc1nc(-c2ccccc2)nc(-c2ccc(-c3cccc4c3oc3ccccc34)cc2)n1] |

TABLE 19-continued
| 539 | 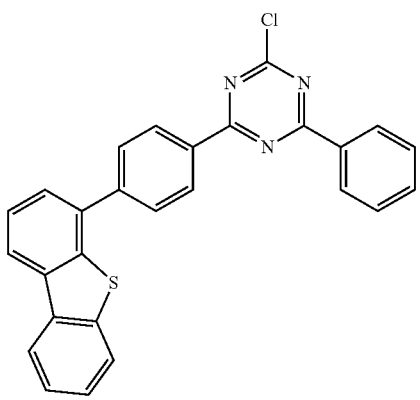 |
| Compound Number | Target Compound | Yield |
|---|---|---|
| 102 | 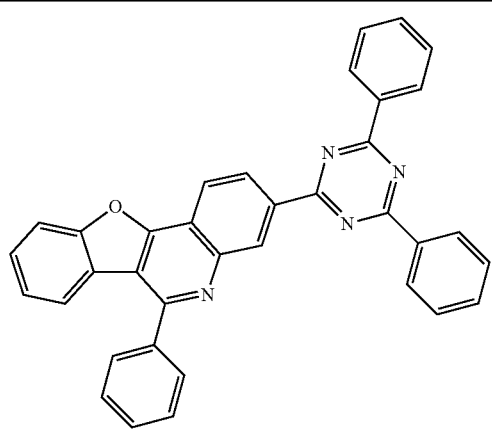 | 79% |
| 105 | 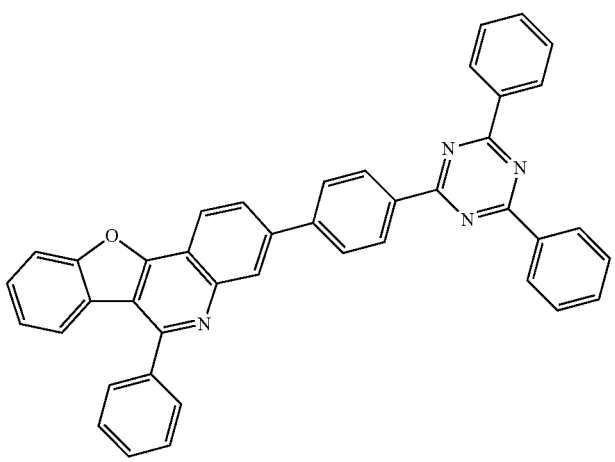 [SMILES: c1ccc(-c2nc(-c3ccccc3)nc(-c3ccc(-c4ccc5c(c4)nc(-c4ccccc4)c4c6ccccc6oc54)cc3)n2)cc1] | 71% |

TABLE 19-continued
| 106 | 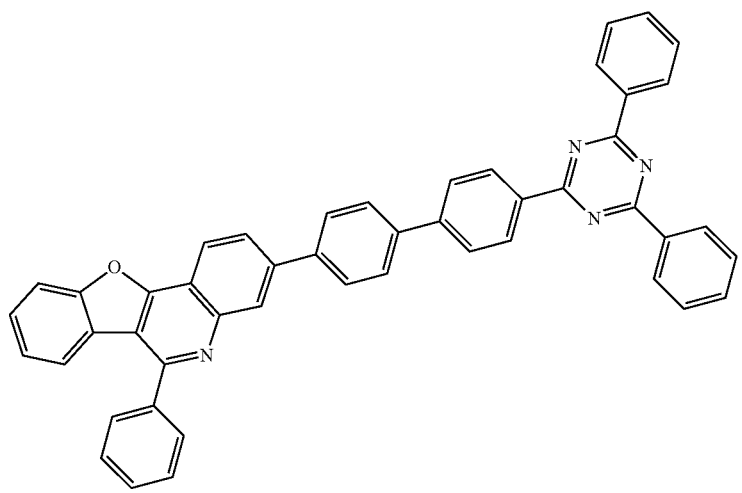 [SMILES: c1ccc(-c2nc(-c3ccccc3)nc(-c3ccc(-c4ccc(-c5ccc6c(c5)nc(-c5ccccc5)c5c7ccccc7oc65)cc4)cc3)n2)cc1] | 74% |
| 198 | | 68% |
| 202 | | 69% |

TABLE 19-continued
387 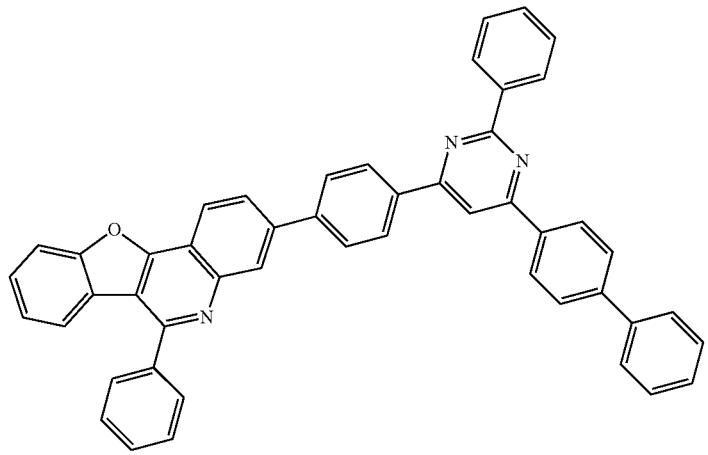 [SMILES: c1ccc(-c2ccc(-c3cc(-c4ccc(-c5ccc6c(c5)nc(-c5ccccc5)c5c7ccccc7oc65)cc4)nc(-c4ccccc4)n3)cc2)cc1] 74%
536 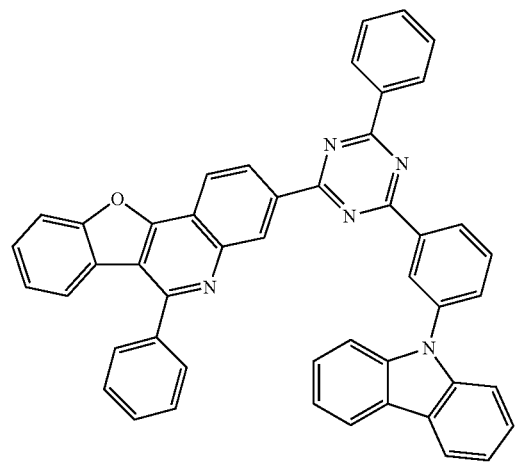 [SMILES: c1ccc(-c2nc(-c3cccc(-n4c5ccccc5c5ccccc54)c3)nc(-c3ccc4c(c3)nc(-c3ccccc3)c3c5ccccc5oc43)n2)cc1] 70%
537 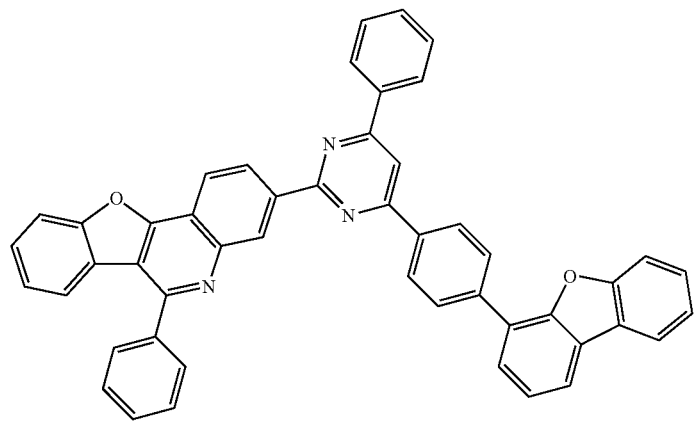 [SMILES: c1ccc(-c2cc(-c3ccc(-c4cccc5c4oc4ccccc45)cc3)nc(-c3ccc4c(c3)nc(-c3ccccc3)c3c5ccccc5oc43)n2)cc1] 77%

TABLE 19-continued

| | | |
|---|---|---|
| 539 | 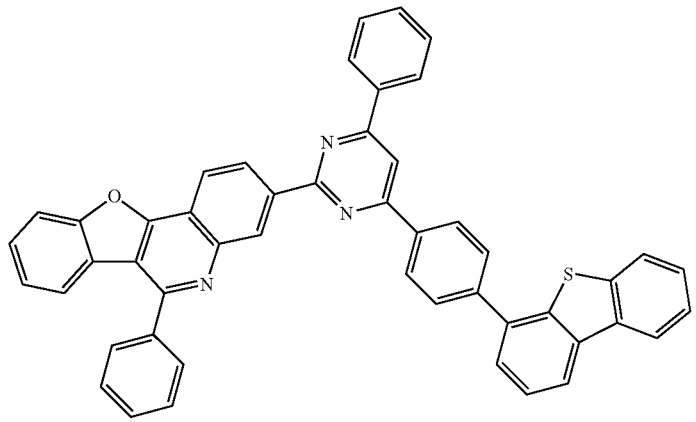 | 74% |

A target compound was synthesized in the same manner as in Preparation Example 1 except that benzofuran-2-ylboronic acid was used instead of (1H-indol-2-yl)boronic acid, 2-bromo-6-chloroaniline was used instead of 2-bromo-5-chloroaniline, and Intermediate T of the following Table 20 was used instead of 2-bromo-4,6-diphenyl-1,3,5-triazine.

A target compound was synthesized in the same manner as in Preparation Example 1 except that benzofuran-2-ylboronic acid was used instead of (1H-indol-2-yl)boronic acid, 2-bromo-4-chloroaniline was used instead of 2-bromo-5-chloroaniline, and Intermediate U of the following Table 21 was used instead of 2-bromo-4,6-diphenyl-1,3,5-triazine.

TABLE 20

| Compound Number | Intermediate T | Target Compound | Yield |
|---|---|---|---|
| 394 | | | 67% |
| 561 | | | 66% |

TABLE 21

| Compound Number | Intermediate U | Target Compound | Yield |
|---|---|---|---|
| 119 | (2-chloro-4,6-diphenyl-1,3,5-triazine) | | 70% |
| 122 | (2-(4-bromophenyl)-4,6-diphenyl-1,3,5-triazine) | | 71% |

TABLE 21-continued
| Compound Number | Intermediate U | Target Compound | Yield |
|---|---|---|---|
| 124 | 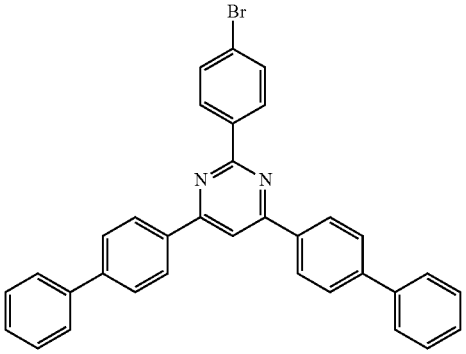 [SMILES: Brc1ccc(-c2nc(-c3ccc(-c4ccccc4)cc3)cc(-c3ccc(-c4ccccc4)cc3)n2)cc1] | 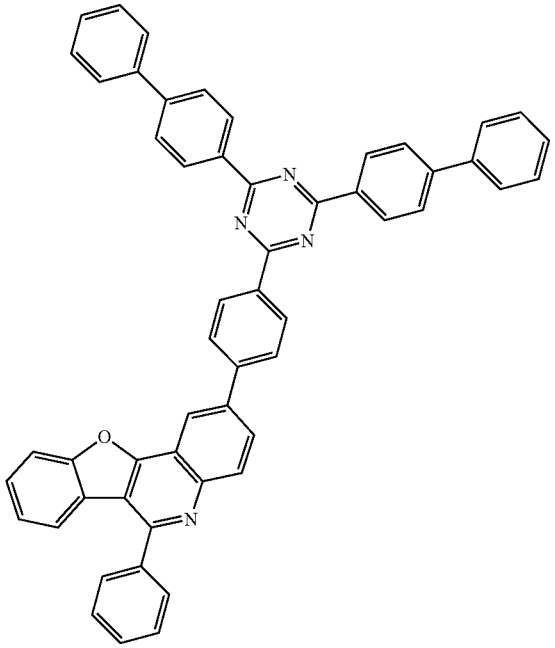 [SMILES: c1ccc(-c2ccc(-c3nc(-c4ccc(-c5ccccc5)cc4)nc(-c4ccc(-c5ccc6nc(-c7ccccc7)c7c8ccccc8oc7c6c5)cc4)n3)cc2)cc1] | 74% |
| 135 | 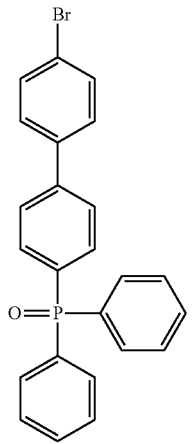 [SMILES: O=P(c1ccccc1)(c1ccccc1)c1ccc(-c2ccc(Br)cc2)cc1] | 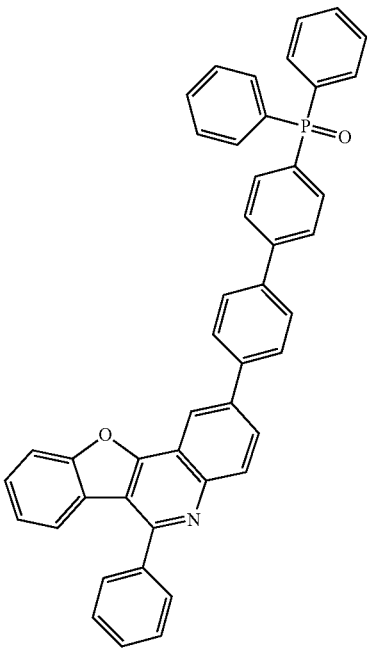 [SMILES: O=P(c1ccccc1)(c1ccccc1)c1ccc(-c2ccc(-c3ccc4nc(-c5ccccc5)c5c6ccccc6oc5c4c3)cc2)cc1] | 80% |

TABLE 21-continued

| Compound Number | Intermediate U | Target Compound | Yield |
|---|---|---|---|
| 403 | (4-chloro-2,6-diphenylpyrimidine) | (target compound structure) | 79% |
| 406 | (2-(4-bromophenyl)-4,6-diphenylpyrimidine) | (target compound structure) | 69% |

A target compound was synthesized in the same manner as in Preparation Example 1 except that benzofuran-2-ylboronic acid was used instead of (1H-indol-2-yl)boronic acid, 2-bromo-4-chloroaniline was used instead of 2-bromo-5-chloroaniline, 9-chlorophenanthrene was used instead of benzoyl chloride, and Intermediate V of the following Table 22 was used instead of 2-bromo-4,6-diphenyl-1,3,5-triazine.

TABLE 22

| Compound Number | Intermediate V | Target Compound | Yield |
|---|---|---|---|
| 1008 | [structure with Cl] | [structure] | 70% |

A target compound was synthesized in the same manner as in Preparation Example 1 except that benzofuran-2-ylboronic acid was used instead of (1H-indol-2-yl)boronic acid, 2-bromo-4-chloroaniline was used instead of 2-bromo-5-chloroaniline, [1,1'-biphenyl]-3-carbonyl chloride was used instead of benzoyl chloride, and Intermediate W of the following Table 23 was used instead of 2-bromo-4,6-diphenyl-1,3,5-triazine.

TABLE 23

| Compound Number | Intermediate W | Target Compound | Yield |
|---|---|---|---|
| 1012 | [structure with Cl] | [structure] | 70% |

A target compound was synthesized in the same manner as in Preparation Example 1 except that benzofuran-2-ylboronic acid was used instead of (1H-indol-2-yl)boronic acid, 2-bromo-3-chloroaniline was used instead of 2-bromo-5-chloroaniline, and Intermediate X of the following Table 24 was used instead of 2-bromo-4,6-diphenyl-1,3,5-triazine.

TABLE 24

| Compound Number | Intermediate X | Target Compound | Yield |
|---|---|---|---|
| 415 | 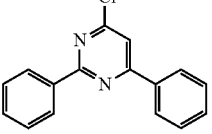 | 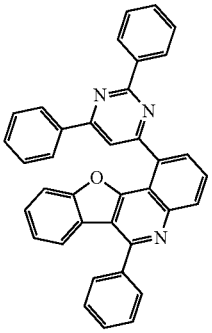 [SMILES: c1ccc(-c2cc(-c3cccc4nc(-c5ccccc5)c5c6ccccc6oc5c34)nc(-c3ccccc3)n2)cc1] | 67% |
| 561 | 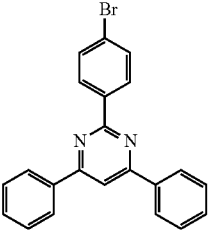 [SMILES: Brc1ccc(-c2nc(-c3ccccc3)cc(-c3ccccc3)n2)cc1] | 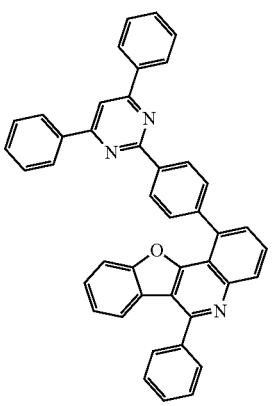 [SMILES: c1ccc(-c2cc(-c3ccccc3)nc(-c3ccc(-c4cccc5nc(-c6ccccc6)c6c7ccccc7oc6c45)cc3)n2)cc1] | 73% |

A target compound was synthesized in the same manner as in Preparation Example 1 except that benzofuran-2-ylboronic acid was used instead of (1H-indol-2-yl)boronic acid, 2-bromo-3-chloroaniline was used instead of 2-bromo-5-chloroaniline, 4-(naphthalen-1-yl)benzoyl chloride was used instead of benzoyl chloride, and Intermediate Y of the following Table 25 was used instead of 2-bromo-4,6-diphenyl-1,3,5-triazine.

TABLE 25

| Compound Number | Intermediate Y | Target Compound | Yield |
|---|---|---|---|
| 1013 | 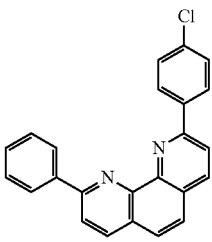 [SMILES: Clc1ccc(-c2ccc3ccc4ccc(-c5ccccc5)nc4c3n2)cc1] | 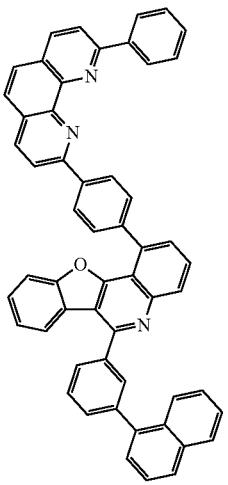 [SMILES: c1ccc(-c2ccc3ccc4ccc(-c5ccc(-c6cccc7nc(-c8cccc(-c9cccc%10ccccc9%10)c8)c8c9ccccc9oc8c67)cc5)nc4c3n2)cc1] | 68% |

511

A target compound was synthesized in the same manner as in Preparation Example 1 except that benzofuran-2-ylboronic acid was used instead of (1H-indol-2-yl)boronic acid, 1-naphthoyl chloride was used instead of benzoyl chloride, and Intermediate Z of the following Table 26 was used instead of 2-bromo-4,6-diphenyl-1,3,5-triazine.

512

A target compound was synthesized in the same manner as in Preparation Example 1 except that benzofuran-2-ylboronic acid was used instead of (1H-indol-2-yl)boronic acid, 1-naphthoyl chloride was used instead of benzoyl chloride, 2-bromo-4-chloroaniline was used instead of 2-bromo-5-chloroaniline, and Intermediate A-1 of the following Table 27 was used instead of 2-bromo-4,6-diphenyl-1,3,5-triazine.

TABLE 26

| Compound Number | Intermediate Z | Target Compound | Yield |
|---|---|---|---|
| 138 | | | 74% |
| 427 | | | 67% |
| 432 | | | 69% |

TABLE 27

| Compound Number | Intermediate A-1 | Target Compound | Yield |
|---|---|---|---|
| 152 | | | 70% |
| 447 | | | 71% |
| 453 | | | 77% |

TABLE 27-continued

| Compound Number | Intermediate A-1 | Target Compound | Yield |
|---|---|---|---|
| 458 | [structure with Br] | [structure] | 72% |

A target compound was synthesized in the same manner as in Preparation Example 1 except that benzofuran-2-ylboronic acid was used instead of (1H-indol-2-yl)boronic acid, 1-naphthoyl chloride was used instead of benzoyl chloride, 2-bromo-3-chloroaniline was used instead of 2-bromo-5-chloroaniline, and Intermediate B-1 of the following Table 28 was used instead of 2-bromo-4,6-diphenyl-1,3,5-triazine.

TABLE 28

| Compound Number | Intermediate B-1 | Target Compound | Yield |
|---|---|---|---|
| 159 | [structure with Br] | [structure] | 80% |

TABLE 28-continued

| Compound Number | Intermediate B-1 | Target Compound | Yield |
|---|---|---|---|
| 464 | 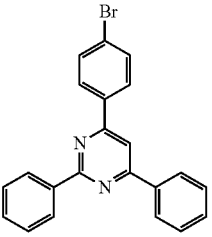 [SMILES: Brc1ccc(-c2cc(-c3ccccc3)nc(-c3ccccc3)n2)cc1] | 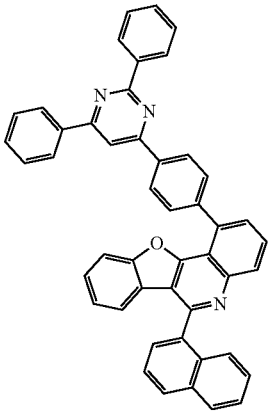 [SMILES: c1ccc(-c2cc(-c3ccc(-c4cccc5nc(-c6cccc7ccccc67)c6c7ccccc7oc6c45)cc3)nc(-c3ccccc3)n2)cc1] | 81% |

A target compound was synthesized in the same manner as in Preparation Example 1 except that benzofuran-2-ylboronic acid was used instead of (1H-indol-2-yl)boronic acid, 9-chlorophenanthrene was used instead of benzoyl chloride, and Intermediate C-1 of the following Table 29 was used instead of 2-bromo-4,6-diphenyl-1,3,5-triazine.

TABLE 29

| Compound Number | Intermediate C-1 | Target Compound | Yield |
|---|---|---|---|
| 473 | 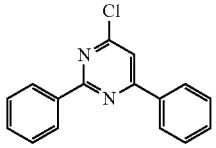 [SMILES: Clc1cc(-c2ccccc2)nc(-c2ccccc2)n1] | 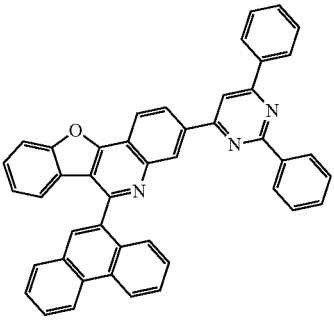 [SMILES: c1ccc(-c2cc(-c3ccc4c(c3)nc(-c3cc5ccccc5c5ccccc35)c3c5ccccc5oc43)nc(-c3ccccc3)n2)cc1] | 76% |
| 476 | 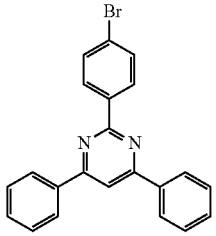 | 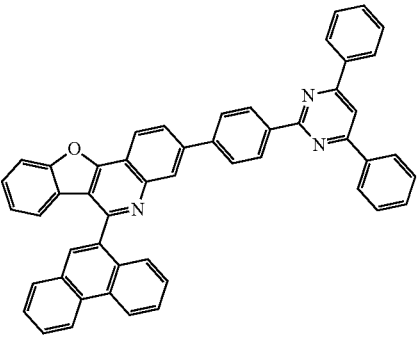 [SMILES: c1ccc(-c2cc(-c3ccccc3)nc(-c3ccc(-c4ccc5c(c4)nc(-c4cc6ccccc6c6ccccc46)c4c6ccccc6oc54)cc3)n2)cc1] | 73% |

TABLE 29-continued

| Compound Number | Intermediate C-1 | Target Compound | Yield |
|---|---|---|---|
| 567 | 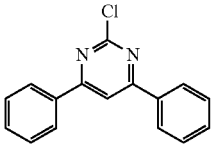 | 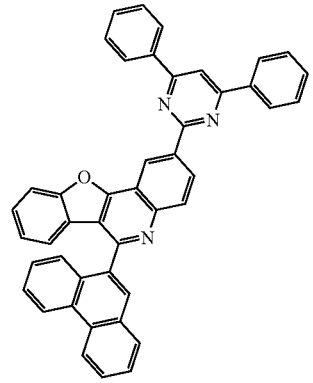 [SMILES: c1ccc(-c2cc(-c3ccccc3)nc(-c3ccc4nc(-c5cc6ccccc6c6ccccc56)c5c6ccccc6oc5c4c3)n2)cc1] | 77% |

A target compound was synthesized in the same manner as in Preparation Example 1 except that benzofuran-2-ylboronic acid was used instead of (1H-indol-2-yl)boronic acid, 9-chlorophenanthrene was used instead of benzoyl chloride, 2-bromo-4-chloroaniline was used instead of 2-bromo-5-chloroaniline, and Intermediate D-1 of the following Table 30 was used instead of 2-bromo-4,6-diphenyl-1,3,5-triazine.

TABLE 30

| Compound Number | Intermediate D-1 | Target Compound | Yield |
|---|---|---|---|
| 490 | 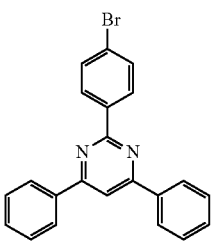 | (see structure) | 76% |
| 497 | 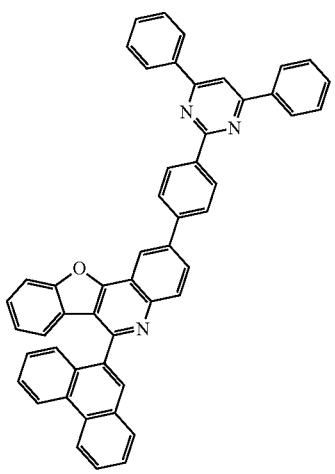 [SMILES: c1ccc(-c2cc(-c3ccccc3)nc(-c3ccc(-c4ccc5nc(-c6cc7ccccc7c7ccccc67)c6c7ccccc7oc6c5c4)cc3)n2)cc1] | (see structure) | 69% |

TABLE 30-continued

| Compound Number | Intermediate D-1 | Target Compound | Yield |
|---|---|---|---|
| 1008 | (4-bromophenyl-substituted phenanthroline structure) | (complex fused heterocyclic structure with phenanthroline and benzofuran-quinoline and phenanthrene groups) | 68% |

A target compound was synthesized in the same manner as in Preparation Example 1 except that benzofuran-2-ylboronic acid was used instead of (1H-indol-2-yl)boronic acid, 9-chlorophenanthrene was used instead of benzoyl chloride, 2-bromo-3-chloroaniline was used instead of 2-bromo-5-chloroaniline, and Intermediate E-1 of the following Table 31 was used instead of 2-bromo-4,6-diphenyl-1,3,5-triazine.

TABLE 31

| Compound Number | Intermediate E-1 | Target Compound | Yield |
|---|---|---|---|
| 175 | 2-(4-bromophenyl)-4,6-diphenyl-1,3,5-triazine | (triazine-phenyl-benzofuranoquinoline-phenanthrene compound) | 68% |
| 505 | 4-chloro-2,6-bis(biphenyl)pyrimidine | (pyrimidine-bis(biphenyl)-benzofuranoquinoline-phenanthrene compound) | 70% |

TABLE 31-continued

| Compound Number | Intermediate E-1 | Target Compound | Yield |
|---|---|---|---|
| 509 | (structure) | (structure) | 73% |

A target compound was synthesized in the same manner as in Preparation Example 1 except that benzofuran-2-ylboronic acid was used instead of (1H-indol-2-yl)boronic acid, 2-chlorotriphenylene was used instead of benzoyl chloride, and Intermediate F-1 of the following Table 32 was used instead of 2-bromo-4,6-diphenyl-1,3,5-triazine.

TABLE 32

| Compound Number | Intermediate F-1 | Target Compound | Yield |
|---|---|---|---|
| 181 | (structure) | (structure) | 71% |

TABLE 32-continued

| Compound Number | Intermediate F-1 | Target Compound | Yield |
|---|---|---|---|
| 195 | | | 70% |
| 196 | | | 66% |
| 197 | | | 69% |

TABLE 32-continued

| Compound Number | Intermediate F-1 | Target Compound | Yield |
|---|---|---|---|
| 517 | | | 74% |
| 534 | | | 68% |
| 571 | | | 70% |

A target compound was synthesized in the same manner as in Preparation Example 1 except that benzofuran-2-ylboronic acid was used instead of (1H-indol-2-yl)boronic acid, 2-chlorotriphenylene was used instead of benzoyl chloride, 2-bromo-4-chloroaniline was used instead of 2-bromo-5-chloroaniline, and Intermediate G-1 of the following Table 33 was used instead of 2-bromo-4,6-diphenyl-1,3,5-triazine.

TABLE 33

| Compound Number | Intermediate G-1 | Target Compound | Yield |
|---|---|---|---|
| 527 | 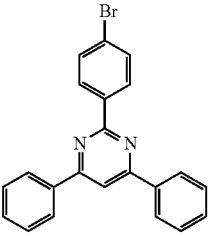 [SMILES: Brc1ccc(-c2nc(-c3ccccc3)cc(-c3ccccc3)n2)cc1] | 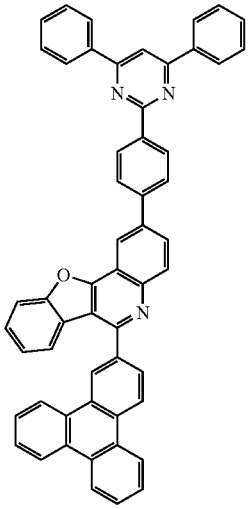 | 69% |

A target compound was synthesized in the same manner as in Preparation Example 1 except that benzofuran-2-ylboronic acid was used instead of (1H-indol-2-yl)boronic acid, 2-chlorotriphenylene was used instead of benzoyl chloride, 2-bromo-3-chloroaniline was used instead of 2-bromo-5-chloroaniline, and Intermediate H-1 of the following Table 34 was used instead of 2-bromo-4,6-diphenyl-1,3,5-triazine.

TABLE 34

| Compound Number | Intermediate H-1 | Target Compound | Yield |
|---|---|---|---|
| 192 | 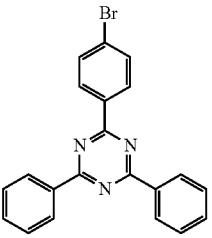 [SMILES: Brc1ccc(-c2nc(-c3ccccc3)nc(-c3ccccc3)n2)cc1] | 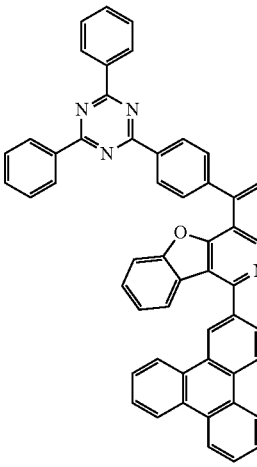 | 73% |

A target compound was synthesized in the same manner as in Preparation Example 1 except that benzofuran-2-ylboronic acid was used instead of (1H-indol-2-yl)boronic acid, 4-(naphthalen-1-yl)benzoyl chloride was used instead of benzoyl chloride, and Intermediate I-1 of the following Table 35 was used instead of 2-bromo-4,6-diphenyl-1,3,5-triazine.

TABLE 35
| Compound Number | Intermediate I-1 | Target Compound | Yield |
|---|---|---|---|
| 161 | 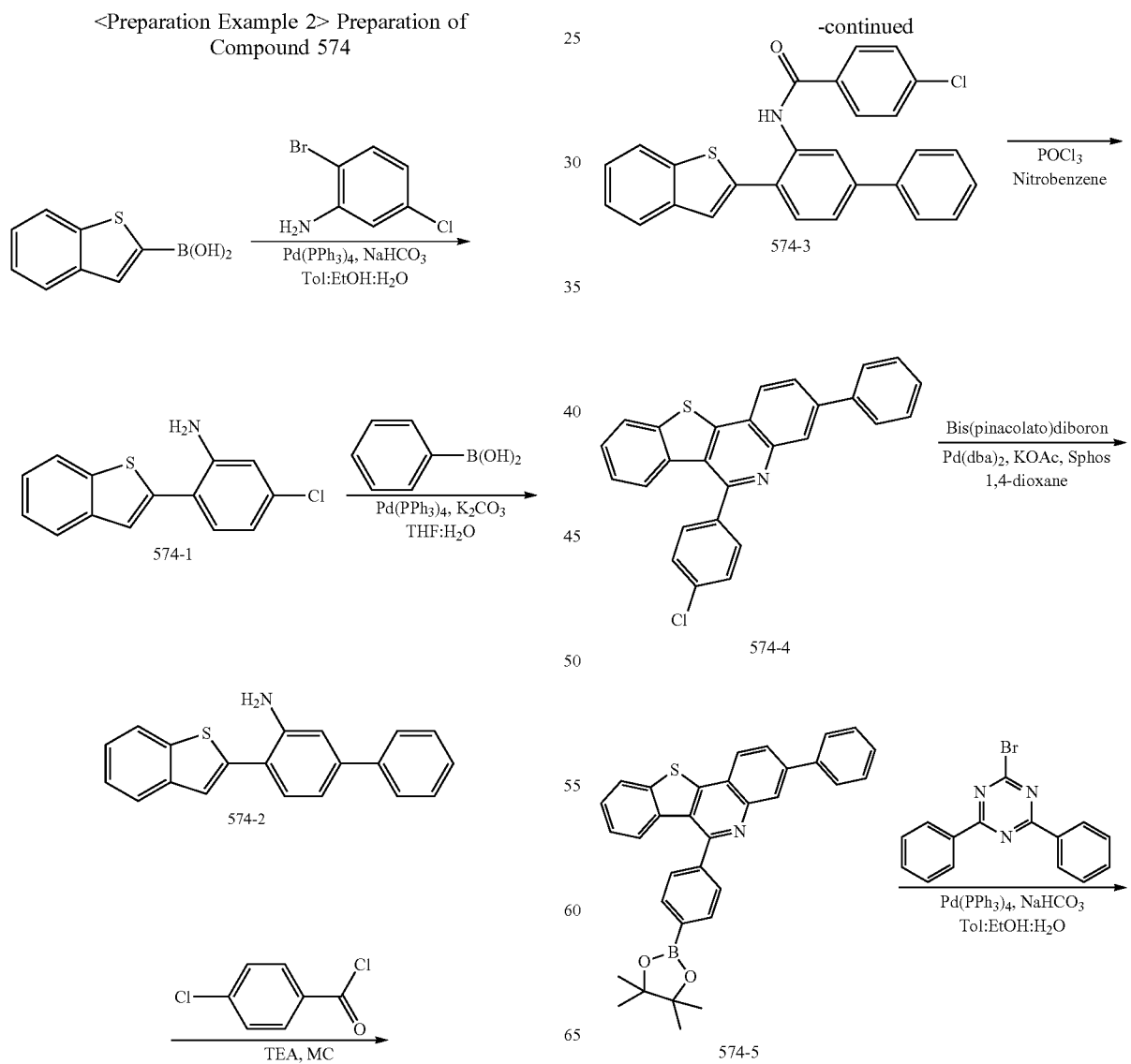 | | 69% |
<Preparation Example 2> Preparation of Compound 574

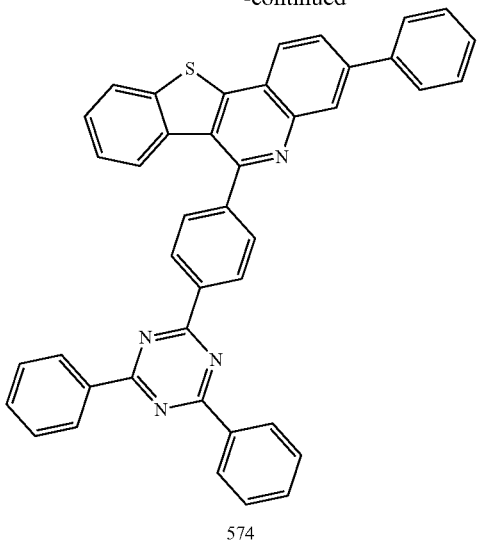

574

1) Preparation of Compound 574-1 After dissolving (1H-indol-2-yl)boronic acid (100 g, 0.621 mol) and 2-bromo-5-chloroaniline (115 g, 0.558 mol) in toluene, EtOH and H$_2$O (1000 mL:200 mL:200 mL), Pd(PPh$_3$)$_4$ (35.8 g, 0.031 mol) and NaHCO$_3$ (156.5 g, 1.863 mol) were introduced thereto, and the result was stirred for 3 hours at 100° C. After the reaction was completed, MC and distilled water were introduced to the reaction solution for extraction. After that, the result was dried with anhydrous MgSO$_4$, and then the solvent was removed using a rotary evaporator to obtain Compound 574-1 (110 g, 74%) in a liquid form.

2) Preparation of Compound 574-2

After dissolving Compound 574-1 (110 g, 0.428 mol) and phenylboronic acid (89 mL, 0.574 mol) in THF and H$_2$O (1000 mL:200 mL), Pd(PPh$_3$)$_4$ (24.7 g, 0.021 mol) and K$_2$CO$_3$ (170 g, 1.284 mol) were introduced thereto, and the result was stirred for 3 hours at 66° C. After the reaction was completed, MC and distilled water were introduced to the reaction solution for extraction. After that, the result was dried with anhydrous MgSO$_4$, and then the solvent was removed using a rotary evaporator to obtain Compound 574-2 (112 g, 87%) in a liquid form.

3) Preparation of Compound 574-3

Compound 574-2 (112 g, 0.372 mol) and triethylamine (78 mL, 0.558 mol) were introduced to MC (1200 mL) and dissolved therein. 4-Chlorobenzoyl chloride (78.12 g, 0.446 mol) dissolved in MC (300 mL) was slowly added dropwise to the mixture at 0° C. After the reaction was completed, MC and distilled water were introduced to the reaction solution for extraction. After that, the result was dried with anhydrous MgSO$_4$, and then the solvent was removed using a rotary evaporator to obtain Compound 574-3 (130 g, 79%) in a liquid form.

4) Preparation of Compound 574-4

After dissolving Compound 574-3 (130 g, 0.295 mol) in nitrobenzene (1500 mL), POCl$_3$ (50 mL, 0.443 mol) was slowly added dropwise thereto. The result was reacted for 15 hours at 140° C. After the reaction was completed, a solution dissolving NaHCO$_3$ in distilled water was slowly introduced to the reaction solution, and the result was stirred. Produced solids were filtered and collected. The collected solids were recrystallized with MC and MeOH to obtain Compound 574-4 (68 g, 53%) in a solid form.

5) Preparation of Compound 574-5

After dissolving Compound 574-4 (10 g, 0.023 mol), bis(pinacolato)diboron (8.8 g, 0.035 mol), KOAc (6.7 g, 0.069 mol), Sphos (1.8 g, 0.0046 mol) and Pd(dba)$_2$ (1.3 g, 0.0023 mol) in 1,4-dioxane (200 mL), the result was reacted for 5 hours at 90° C. After the reaction was completed, MC and distilled water were introduced to the reaction solution for extraction. After that, the result was dried with anhydrous MgSO$_4$, and then the solvent was removed using a rotary evaporator to obtain Compound 574-5 (10.6 g, 90%).

6) Preparation of Compound 574

After dissolving Compound 574-5 (10.6 g, 0.021 mol) and 2-bromo-4,6-diphenyl-1,3,5-triazine (7.5 g, 0.024 mol) in toluene, EtOH and H$_2$O (100 mL:20 mL:20 mL), Pd(PPh$_3$)$_4$ (1.2 g, 0.0010 mol) and K$_2$CO$_3$ (8.1 g, 0.063 mol) were introduced thereto, and the result was stirred for 5 hours at 100° C. After the reaction was completed, MC and distilled water were introduced to the reaction solution for extraction. After that, the result was dried with anhydrous MgSO$_4$, and then the solvent was removed using a rotary evaporator to obtain Compound 574 (9.7 g, 75%).

A target compound was synthesized in the same manner as in Preparation Example 2 except that Intermediate J-1 of the following Table 36 was used instead of phenylboronic acid, and Intermediate K-1 of the following Table 36 was used instead of 2-bromo-4,6-diphenyl-1,3,5-triazine.

TABLE 36

| Compound Number | Intermediate J-1 | Intermediate K-1 | Compound | Yield |
|---|---|---|---|---|
| 574 | PhB(OH)₂ | 2-bromo-4,6-diphenyl-1,3,5-triazine | | 77% |
| 575 | PhB(OH)₂ | 2-(4-bromophenyl)-4,6-diphenyl-1,3,5-triazine | | 79% |
| 594 | 1-naphthyl-B(OH)₂ | 2-bromo-4-(biphenyl-4-yl)-6-phenyl-1,3,5-triazine | | 67% |
| 610 | triphenylen-2-yl-B(OH)₂ | 2-bromo-4,6-diphenyl-1,3,5-triazine | | 77% |

TABLE 36-continued

| Compound Number | Intermediate J-1 | Intermediate K-1 | Compound | Yield |
|---|---|---|---|---|
| 618 | | | | 79% |
| 634 | | | | 80% |
| 650 | | | | 74% |

TABLE 36-continued

| Compound Number | Intermediate J-1 | Intermediate K-1 | Compound | Yield |
|---|---|---|---|---|
| 652 | B(OH)₂-phenyl | | | 79% |
| 744 | B(OH)₂-phenyl | | | 69% |
| 746 | B(OH)₂-phenyl | | | 70% |

TABLE 36-continued

| Compound Number | Intermediate J-1 | Intermediate K-1 | Compound | Yield |
|---|---|---|---|---|
| 768 | naphthalen-1-yl-B(OH)₂ | 2-bromo-4,6-diphenylpyrimidine | | 74% |
| 789 | phenanthren-9-yl-B(OH)₂ | 4-bromo-2,6-diphenylpyrimidine | | 71% |
| 807 | triphenylen-2-yl-B(OH)₂ | 4-bromo-2,6-diphenylpyrimidine | | 71% |
| 813 | dibenzofuran-4-yl-B(OH)₂ | 4-bromo-2,6-diphenylpyrimidine | | 78% |

TABLE 36-continued

| Compound Number | Intermediate J-1 | Intermediate K-1 | Compound | Yield |
|---|---|---|---|---|
| 818 | | | | 69% |
| 824 | | | | 64% |
| 826 | | | | 77% |
| 1014 | | | | 72% |

TABLE 36-continued

| Compound Number | Intermediate J-1 | Intermediate K-1 | Compound | Yield |
|---|---|---|---|---|
| 1018 | B(OH)₂ (dibenzofuran) | 2-bromo-9-phenyl-1,10-phenanthroline | (structure) | |

A target compound was synthesized in the same manner as in Preparation Example 2 except that 2-bromo-6-chloroaniline was used instead of 2-bromo-5-chloroaniline, Intermediate L-1 of the following Table 37 was used instead of phenylboronic acid, and Intermediate M-1 of the following Table 37 was used instead of 2-bromo-4,6-diphenyl-1,3,5-triazine.

TABLE 37

| Compound Number | Intermediate L-1 | Intermediate M-1 | Compound | Yield |
|---|---|---|---|---|
| 607 | B(OH)₂ (phenanthrene) | 2-bromo-4,6-diphenyl-1,3,5-triazine | (structure) | 79% |
| 621 | B(OH)₂ (dibenzofuran) | 2-bromo-4,6-diphenyl-1,3,5-triazine | (structure) | 77% |

A target compound was synthesized in the same manner as in Preparation Example 2 except that 2-bromo-6-chloroaniline was used instead of 2-bromo-5-chloroaniline, Intermediate N-1 of the following Table 38 was used instead of phenylboronic acid, and Intermediate O-1 of the following Table 38 was used instead of 2-bromo-4,6-diphenyl-1,3,5-triazine.

TABLE 38

| Compound Number | Intermediate N-1 | Intermediate O-1 | Compound | Yield |
|---|---|---|---|---|
| 1019 | 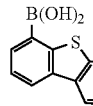 | 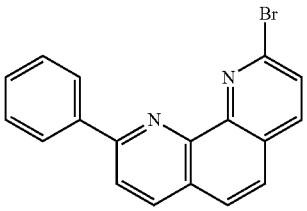 [SMILES: Brc1ccc2ccc3ccc(-c4ccccc4)nc3c2n1] | 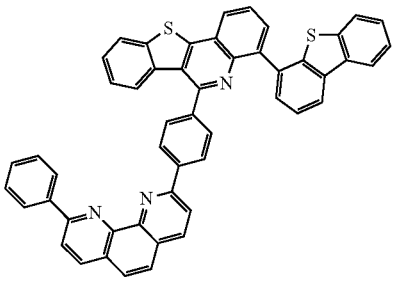 [SMILES: c1ccc(-c2ccc3ccc4ccc(-c5ccc(-c6nc7c(-c8cccc9c8sc8ccccc89)cccc7c7sc8ccccc8c67)cc5)nc4c3n2)cc1] | 71% |

A target compound was synthesized in the same manner as in Preparation Example 2 except that 2-bromo-4-chloroaniline was used instead of 2-bromo-5-chloroaniline, Intermediate P-1 of the following Table 39 was used instead of phenylboronic acid, and Intermediate Q-1 of the following Table 39 was used instead of 2-bromo-4,6-diphenyl-1,3,5-triazine.

TABLE 39

| Compound Number | Intermediate P-1 | Intermediate Q-1 | Compound | Yield |
|---|---|---|---|---|
| 614 | 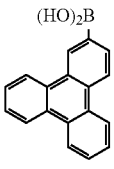 | 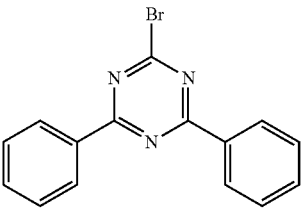 | 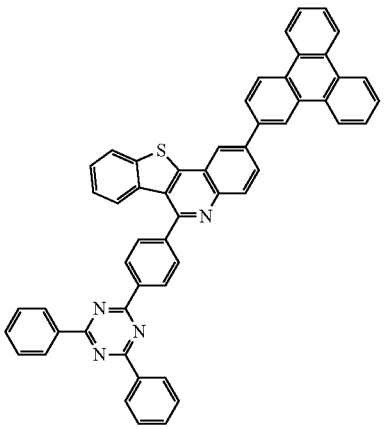 [SMILES: c1ccc(-c2nc(-c3ccccc3)nc(-c3ccc(-c4nc5ccc(-c6ccc7c8ccccc8c8ccccc8c7c6)cc5c5sc6ccccc6c45)cc3)n2)cc1] | 79% |

TABLE 39-continued

| Compound Number | Intermediate P-1 | Intermediate Q-1 | Compound | Yield |
|---|---|---|---|---|
| 758 | B(OH)₂ (phenyl) | 4-bromo-2,6-diphenylpyrimidine | [structure] | 81% |
| 796 | phenanthrenyl-B(OH)₂ | 2-bromo-4,6-diphenylpyrimidine | [structure] | 78% |

A target compound was synthesized in the same manner as in Preparation Example 2 except that 2-bromo-4-chloroaniline was used instead of 2-bromo-5-chloroaniline, Intermediate R-1 of the following Table 40 was used instead of phenylboronic acid, and Intermediate S-1 of the following Table 40 was used instead of 2-bromo-4,6-diphenyl-1,3,5-triazine.

TABLE 40

| Compound Number | Intermediate R-1 | Intermediate S-1 | Compound | Yield |
|---|---|---|---|---|
| 1016 | B(OH)₂ (phenanthrene) | 2-bromo-9-phenyl-1,10-phenanthroline | (structure) | 79% |

A target compound was synthesized in the same manner as in Preparation Example 2 except that 2-bromo-3-chloroaniline was used instead of 2-bromo-5-chloroaniline, Intermediate T-1 of the following Table 41 was used instead of phenylboronic acid, and Intermediate U-1 of the following Table 41 was used instead of 2-bromo-4,6-diphenyl-1,3,5-triazine.

TABLE 41

| Compound Number | Intermediate T-1 | Intermediate U-1 | Compound | Yield |
|---|---|---|---|---|
| 591 | B(OH)₂ (phenyl) | (bromo-triazine-fluorene) | (structure) | 78% |

TABLE 41-continued
| Compound Number | Intermediate T-1 | Intermediate U-1 | Compound | Yield |
|---|---|---|---|---|
| 627 | 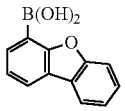 | 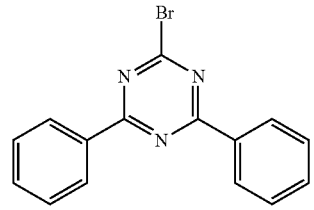 [SMILES: Brc1nc(-c2ccccc2)nc(-c2ccccc2)n1] | 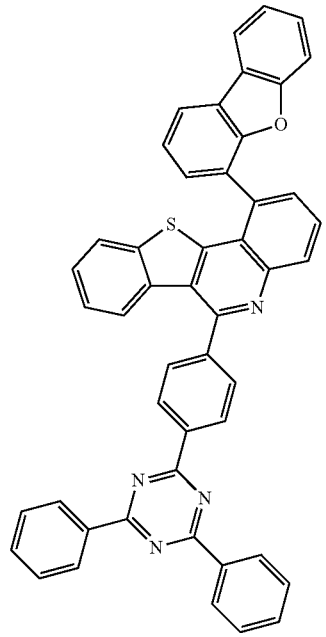 [SMILES: c1ccc(-c2nc(-c3ccccc3)nc(-c3ccc(-c4nc5cccc(-c6cccc7c6oc6ccccc67)c5c5sc6ccccc6c45)cc3)n2)cc1] | 67% |
| 643 | 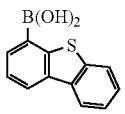 | 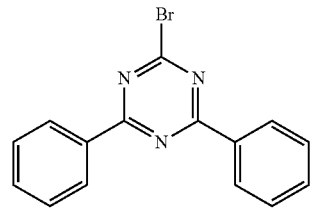 | 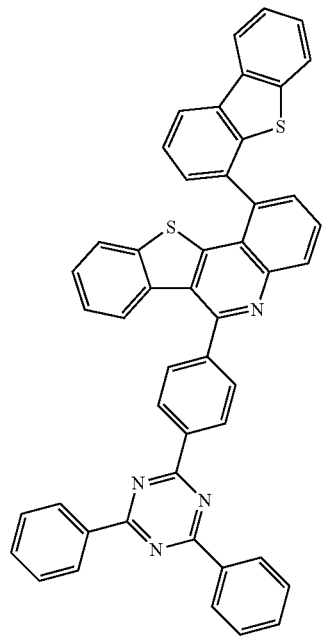 | 66% |

TABLE 41-continued

| Compound Number | Intermediate T-1 | Intermediate U-1 | Compound | Yield |
|---|---|---|---|---|
| 781 | naphthalen-1-yl-B(OH)₂ | 2-bromo-4,6-diphenylpyrimidine | (structure) | 69% |
| 802 | phenanthren-9-yl-B(OH)₂ | 4-bromo-2,6-diphenylpyrimidine | (structure) | 70% |

A target compound was synthesized in the same manner as in Preparation Example 2 except that benzofuran-2-ylboronic acid was used instead of (1H-indol-2-yl)boronic acid, Intermediate V-1 of the following Table 42 was used instead of phenylboronic acid, and Intermediate W-1 of the following Table 42 was used instead of 2-bromo-4,6-diphenyl-1,3,5-triazine.

TABLE 42

| Compound Number | Intermediate V-1 | Intermediate W-1 | Compound | Yield |
|---|---|---|---|---|
| 657 | phenyl-B(OH)₂ | 2-(4-bromophenyl)-4,6-diphenyl-1,3,5-triazine | (structure) | 71% |
| 674 | naphthalen-1-yl-B(OH)₂ | 2-bromo-4,6-diphenyl-1,3,5-triazine | (structure) | 73% |
| 687 | phenanthren-9-yl-B(OH)₂ | 2-bromo-4,6-bis(biphenyl-4-yl)-1,3,5-triazine | (structure) | 76% |

TABLE 42-continued
| Compound Number | Intermediate V-1 | Intermediate W-1 | Compound | Yield |
|---|---|---|---|---|
| 723 | 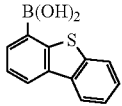 | 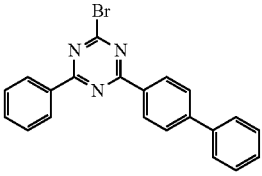 [SMILES: Brc1nc(-c2ccccc2)nc(-c2ccc(-c3ccccc3)cc2)n1] | 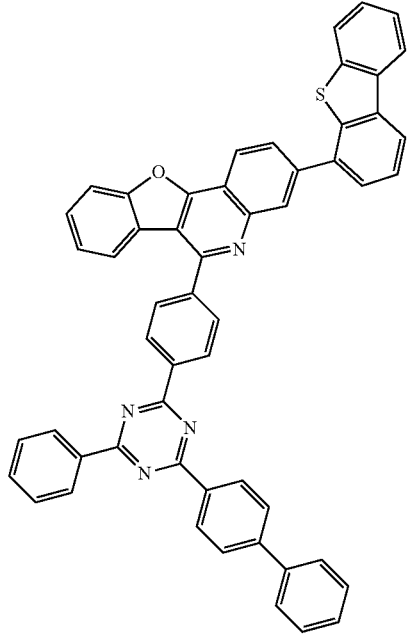 [SMILES: c1ccc(-c2ccc(-c3nc(-c4ccccc4)nc(-c4ccc(-c5nc6cc(-c7cccc8c7sc7ccccc78)ccc6c6oc7ccccc7c56)cc4)n3)cc2)cc1] | 80% |
| 734 | 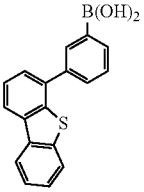 [SMILES: OB(O)c1cccc(-c2cccc3c2sc2ccccc23)c1] | 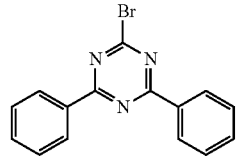 [SMILES: Brc1nc(-c2ccccc2)nc(-c2ccccc2)n1] | 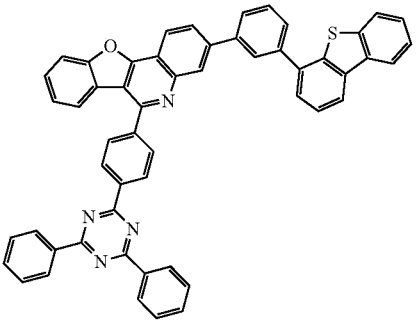 [SMILES: c1ccc(-c2nc(-c3ccccc3)nc(-c3ccc(-c4nc5cc(-c6cccc(-c7cccc8c7sc7ccccc78)c6)ccc5c5oc6ccccc6c45)cc3)n2)cc1] | 79% |
| 737 |  | 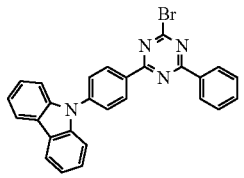 [SMILES: Brc1nc(-c2ccccc2)nc(-c2ccc(-n3c4ccccc4c4ccccc43)cc2)n1] | 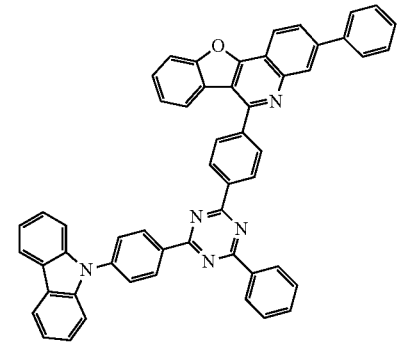 [SMILES: c1ccc(-c2ccc3c(c2)nc(-c2ccc(-c4nc(-c5ccccc5)nc(-c5ccc(-n6c7ccccc7c7ccccc76)cc5)n4)cc2)c2c4ccccc4oc32)cc1] | 80% |

TABLE 42-continued
| Compound Number | Intermediate V-1 | Intermediate W-1 | Compound | Yield |
|---|---|---|---|---|
| 739 |  | 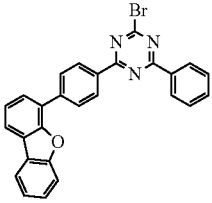 [SMILES: Brc1nc(-c2ccccc2)nc(-c2ccc(-c3cccc4c3oc3ccccc34)cc2)n1] | 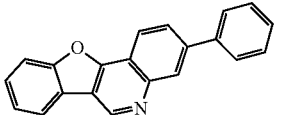 | 71% |
| 741 | 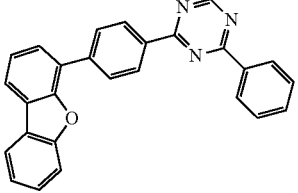 |  | 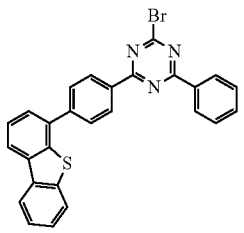 [SMILES: Brc1nc(-c2ccccc2)nc(-c2ccc(-c3cccc4c3sc3ccccc34)cc2)n1] | 74% |
| 830 | 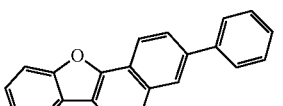 | 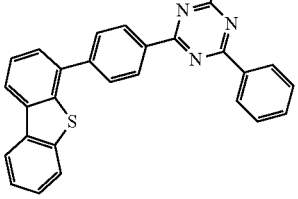 |  | 73% |

TABLE 42-continued
| Compound Number | Intermediate V-1 | Intermediate W-1 | Compound | Yield |
|---|---|---|---|---|
| 831 |  | 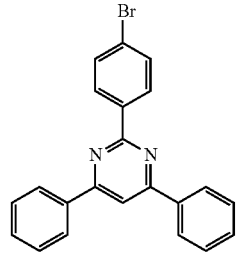 [SMILES: Brc1ccc(-c2nc(-c3ccccc3)cc(-c3ccccc3)n2)cc1] | 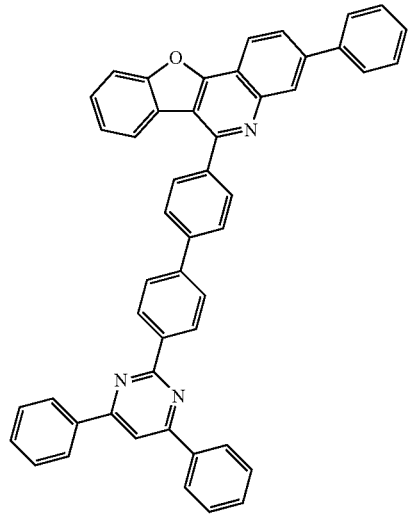 [SMILES: c1ccc(-c2ccc3c(c2)nc(-c2ccc(-c4ccc(-c5nc(-c6ccccc6)cc(-c6ccccc6)n5)cc4)cc2)c2c4ccccc4oc32)cc1] | 71% |
| 855 | 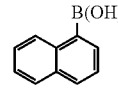 | 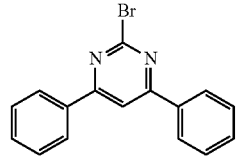 [SMILES: Brc1nc(-c2ccccc2)cc(-c2ccccc2)n1] | 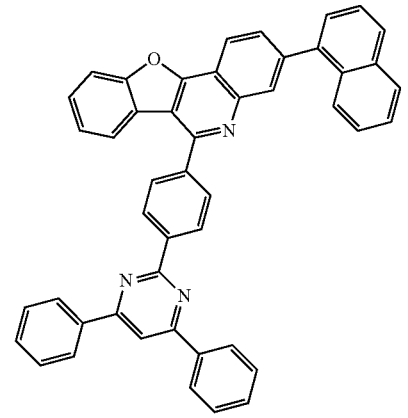 [SMILES: c1ccc(-c2cc(-c3ccccc3)nc(-c3ccc(-c4nc5cc(-c6cccc7ccccc67)ccc5c5oc6ccccc6c45)cc3)n2)cc1] | 66% |
| 877 | 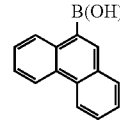 | 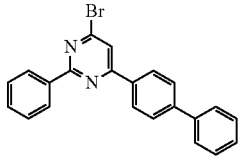 [SMILES: Brc1cc(-c2ccc(-c3ccccc3)cc2)nc(-c2ccccc2)n1] | 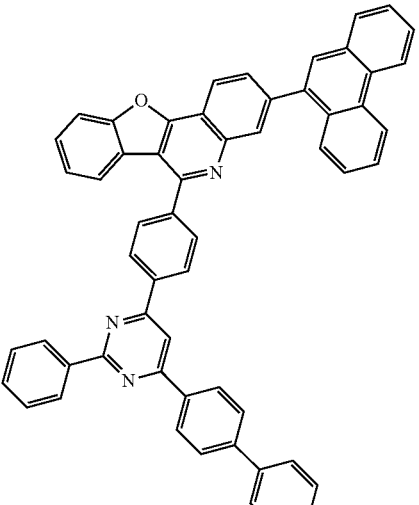 | 67% |

TABLE 42-continued

| Compound Number | Intermediate V-1 | Intermediate W-1 | Compound | Yield |
|---|---|---|---|---|
| 894 | | | | 67% |
| 902 | | | | 70% |
| 910 | | | | 71% |
| 920 | | | | 71% |

TABLE 42-continued

| Compound Number | Intermediate V-1 | Intermediate W-1 | Compound | Yield |
|---|---|---|---|---|
| 923 | B(OH)₂ (phenyl) | (structure) | (structure) | 79% |
| 925 | B(OH)₂ (phenyl) | (structure) | (structure) | 78% |

A target compound was synthesized in the same manner as in Preparation Example 2 except that benzofuran-2-ylboronic acid was used instead of (1H-indol-2-yl)boronic acid, Intermediate X-1 of the following Table 43 was used instead of phenylboronic acid, and Intermediate Y-1 of the following Table 43 was used instead of 2-bromo-4,6-diphenyl-1,3,5-triazine.

TABLE 43

| Compound Number | Intermediate X-1 | Intermediate Y-1 | Compound | Yield |
|---|---|---|---|---|
| 700 | | | | 69% |
| 861 | | | | 69% |
| 907 | | | | 71% |
| 1024 | | | | 68% |

A target compound was synthesized in the same manner as in Preparation Example 2 except that benzofuran-2-ylboronic acid was used instead of (1H-indol-2-yl)boronic acid, Intermediate Z-1 of the following Table 44 was used instead of phenylboronic acid, and Intermediate A-2 of the following Table 44 was used instead of 2-bromo-4,6-diphenyl-1,3,5-triazine.

TABLE 44

| Compound Number | Intermediate Z-1 | Intermediate A-2 | Compound | Yield |
|---|---|---|---|---|
| 692 | | | | 72% |
| 844 | | | | 79% |

TABLE 44-continued

| Compound Number | Intermediate Z-1 | Intermediate A-2 | Compound | Yield |
|---|---|---|---|---|
| 883 | B(OH)₂ (phenanthrene-9-yl) | 2-bromo-4,6-diphenylpyrimidine | (structure) | 71% |

A target compound was synthesized in the same manner as in Preparation Example 2 except that benzofuran-2-ylboronic acid was used instead of (1H-indol-2-yl)boronic acid, 2-bromo-3-chloroaniline was used instead of 2-bromo-5-chloroaniline, Intermediate B-2 of the following Table 45 was used instead of phenylboronic acid, and Intermediate C-2 of the following Table 45 was used instead of 2-bromo-4,6-diphenyl-1,3,5-triazine.

TABLE 45

| Compound Number | Intermediate B-2 | Intermediate C-2 |
|---|---|---|
| 684 | naphthalen-1-ylboronic acid | 2-bromo-4,6-bis(4-biphenyl)-1,3,5-triazine |
| 695 | phenanthren-9-ylboronic acid | 2-bromo-4,6-diphenyl-1,3,5-triazine |

TABLE 45-continued
| 918 | 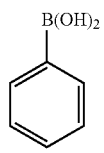 | 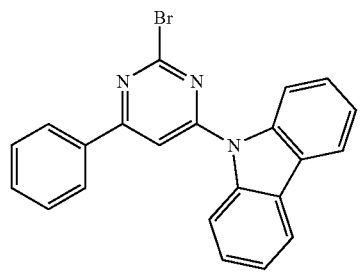 [SMILES: Brc1nc(-c2ccccc2)cc(-n2c3ccccc3c3ccccc32)n1] |
| 919 | 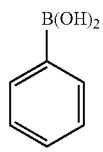 | 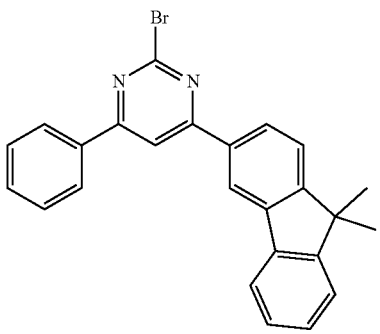 [SMILES: CC1(C)c2ccccc2-c2cc(-c3cc(-c4ccccc4)nc(Br)n3)ccc21] |
| 1026 | 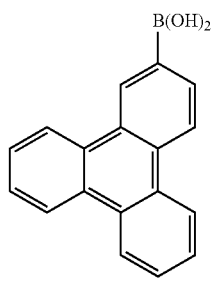 [SMILES: OB(O)c1ccc2c3ccccc3c3ccccc3c2c1] | 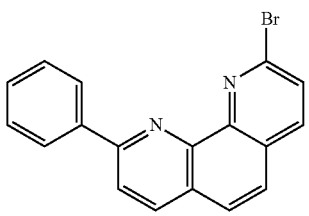 [SMILES: Brc1ccc2ccc3ccc(-c4ccccc4)nc3c2n1] |
| Compound Number | Compound | Yield |
|---|---|---|
| 685 | 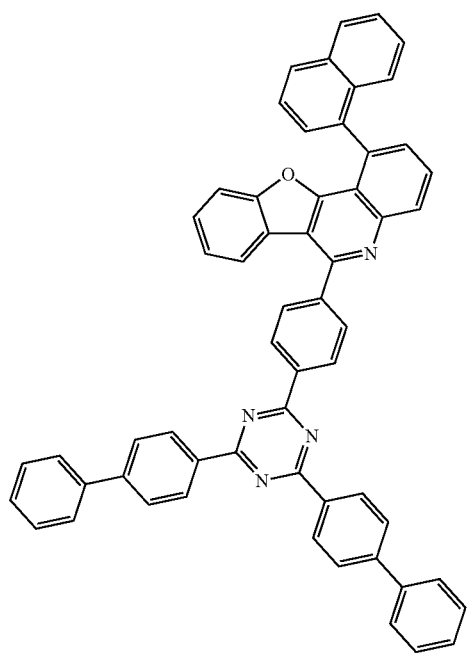 [SMILES: c1ccc(-c2ccc(-c3nc(-c4ccc(-c5ccccc5)cc4)nc(-c4ccc(-c5nc6cccc(-c7cccc8ccccc78)c6c6oc7ccccc7c56)cc4)n3)cc2)cc1] | 66% |

TABLE 45-continued
| 695 | 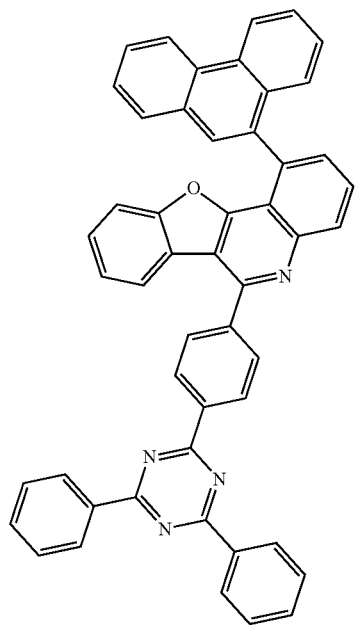 [SMILES: c1ccc(-c2nc(-c3ccccc3)nc(-c3ccc(-c4nc5cccc(-c6cc7ccccc7c7ccccc67)c5c5oc6ccccc6c45)cc3)n2)cc1] | 67% |
| 918 | 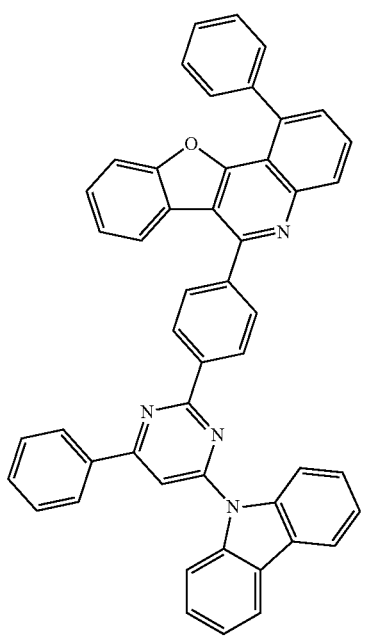 [SMILES: c1ccc(-c2cc(-n3c4ccccc4c4ccccc43)nc(-c3ccc(-c4nc5cccc(-c6ccccc6)c5c5oc6ccccc6c45)cc3)n2)cc1] | 67% |

TABLE 45-continued

| 919 | 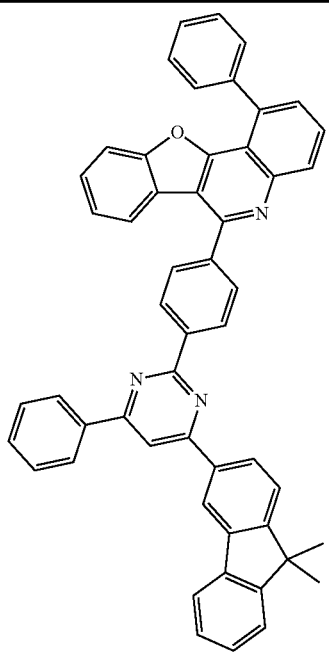 | 70% |

| 1026 | 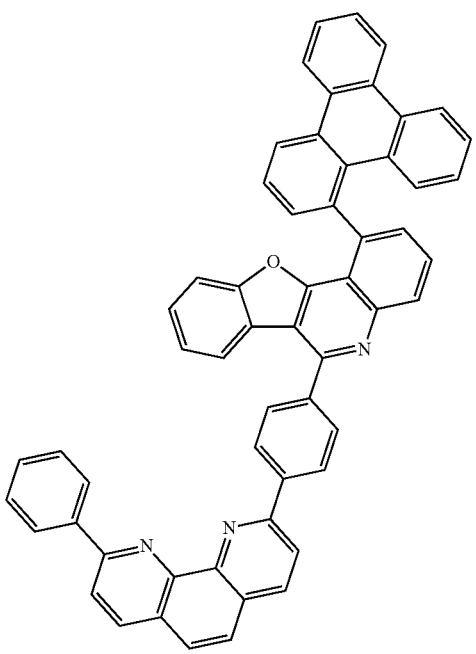 [SMILES: c1ccc(-c2ccc3ccc4ccc(-c5ccc(-c6nc7cccc(-c8cccc9c%10ccccc%10c%10ccccc%10c89)c7c7oc8ccccc8c67)cc5)nc4c3n2)cc1] | 73% |

A target compound was synthesized in the same manner as in Preparation Example 2 except that 2-bromo-4-chloroaniline was used instead of 2-bromo-5-chloroaniline, 3-chlorobenzoyl chloride was used instead of 4-chlorobenzoyl chloride, Intermediate D-2 of the following Table 46 was used instead of phenylboronic acid, and Intermediate E-2 of the following Table 46 was used instead of 2-bromo-4,6-diphenyl-1,3,5-triazine.

TABLE 46

| Compound Number | Intermediate D-2 | Intermediate E-2 | Compound | Yield |
|---|---|---|---|---|
| 585 | B(OH)₂–phenyl | 2-bromo-4,6-diphenyl-1,3,5-triazine | (structure) | 70% |

A target compound was synthesized in the same manner as in Preparation Example 2 except that 2-bromo-3-chloroaniline was used instead of 2-bromo-5-chloroaniline, 3-chlorobenzoyl chloride was used instead of 4-chlorobenzoyl chloride, Intermediate F-2 of the following Table 47 was used instead of phenylboronic acid, and Intermediate G-2 of the following Table 47 was used instead of 2-bromo-4,6-diphenyl-1,3,5-triazine.

TABLE 47

| Compound Number | Intermediate F-2 | Intermediate G-2 | Compound | Yield |
|---|---|---|---|---|
| 804 | phenanthrene-B(OH)₂ | 4-bromo-2,6-diphenylpyrimidine | (structure) | 76% |

A target compound was synthesized in the same manner as in Preparation Example 2 except that benzofuran-2-ylboronic acid was used instead of (1H-indol-2-yl)boronic acid, 3-chlorobenzoyl chloride was used instead of 4-chlorobenzoyl chloride, Intermediate H-2 of the following Table 48 was used instead of phenylboronic acid, and Intermediate I-2 of the following Table 48 was used instead of 2-bromo-4,6-diphenyl-1,3,5-triazine.

TABLE 48

| Compound Number | Intermediate H-2 | Intermediate I-2 | Compound | Yield |
|---|---|---|---|---|
| 708 | 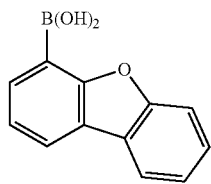 [SMILES: OB(O)c1cccc2c1oc1ccccc12] | 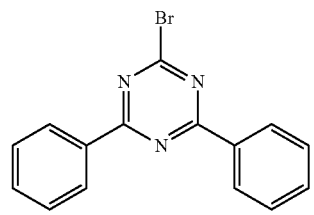 [SMILES: Brc1nc(-c2ccccc2)nc(-c2ccccc2)n1] | 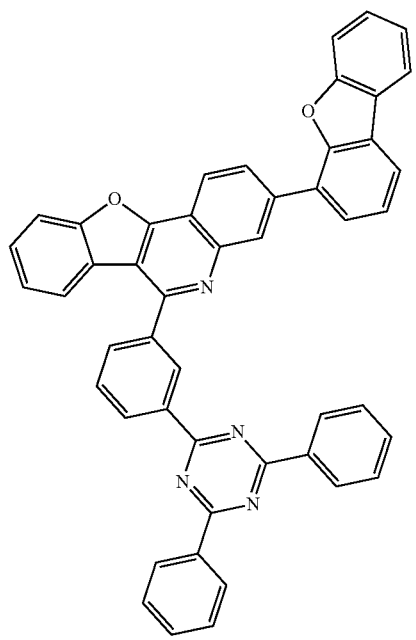 [SMILES: c1ccc(-c2nc(-c3ccccc3)nc(-c3cccc(-c4nc5cc(-c6cccc7c6oc6ccccc67)ccc5c5oc6ccccc6c45)c3)n2)cc1] | 75% |

A target compound was synthesized in the same manner as in Preparation Example 2 except that benzofuran-2-ylboronic acid was used instead of (1H-indol-2-yl)boronic acid, 2-bromo-4-chloroaniline was used instead of 2-bromo-5-chloroaniline, 3-chlorobenzoyl chloride was used instead of 4-chlorobenzoyl chloride, Intermediate J-2 of the following Table 49 was used instead of phenylboronic acid, and Intermediate K-2 of the following Table 49 was used instead of 2-bromo-4,6-diphenyl-1,3,5-triazine.

TABLE 49
| Compound Number | Intermediate J-2 | Intermediate K-2 | Compound | Yield |
|---|---|---|---|---|
| 667 | B(OH)₂–phenyl | 2-bromo-4,6-diphenyl-1,3,5-triazine | | 70% |
| 729 | dibenzothiophene-B(OH)₂ | 2-bromo-4,6-diphenyl-1,3,5-triazine | | 79% |
<Preparation Example 3> Preparation of Compound 926
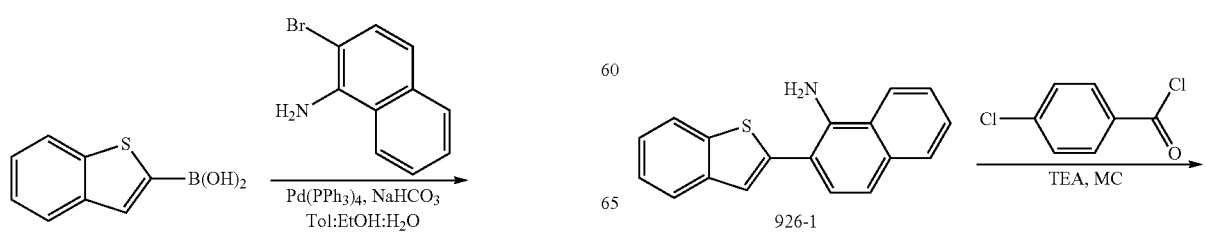
-continued -continued

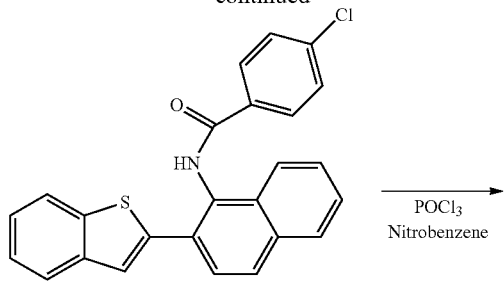

1) Preparation of Compound 926-1

After dissolving benzo[b]thiophen-2-ylboronic acid (100 g, 0.562 mol) and 2-bromonaphthalen-1-amine (125 g, 0.562 mol) in toluene, EtOH and H₂O (1000 mL:200 mL:200 mL), Pd(PPh₃)₄ (32.4 g, 0.028 mol) and NaHCO₃ (141.6 g, 1.686 mol) were introduced thereto, and the result was stirred for 3 hours at 100° C. After the reaction was completed, MC and distilled water were introduced to the reaction solution for extraction. After that, the result was dried with anhydrous MgSO₄, and then the solvent was removed using a rotary evaporator to obtain Compound 926-1 (106 g, 68%) in a liquid form.

2) Preparation of Compound 926-2

Compound 926-1 (106 g, 0.385 mol) and triethylamine (64 mL, 0.462 mol) were introduced to MC (1200 mL) and dissolved therein. 4-Chlorobenzoyl chloride (67.38 g, 0.385 mol) dissolved in MC (300 mL) was slowly added dropwise to the mixture at 0° C. After the reaction was completed, MC and distilled water were introduced to the reaction solution for extraction. After that, the result was dried with anhydrous MgSO₄, and then the solvent was removed using a rotary evaporator to obtain Compound 926-2 (120 g, 75%) in a liquid form.

4) Preparation of Compound 926-3

After dissolving Compound 926-2 (120 g, 0.290 mol) in nitrobenzene (1500 mL), POCl₃ (50 mL, 0.443 mol) was slowly added dropwise thereto. The result was reacted for 15 hours at 140° C. After the reaction was completed, a solution dissolving NaHCO₃ in distilled water was slowly introduced to the reaction solution, and the result was stirred. Produced solids were filtered and collected. The collected solids were recrystallized with MC and MeOH to obtain Compound 926-3 (71 g, 61%) in a solid form.

5) Preparation of Compound 926-4

After dissolving Compound 926-3 (10 g, 0.025 mol), bis(pinacolato)diboron (8.8 g, 0.035 mol), KOAc (6.7 g, 0.069 mol), Sphos (1.8 g, 0.0046 mol) and Pd(dba)₂ (1.3 g, 0.0023 mol) in 1,4-dioxane (200 mL), the result was reacted for 5 hours at 90° C. After the reaction was completed, MC and distilled water were introduced to the reaction solution for extraction. After that, the result was dried with anhydrous MgSO₄, and then the solvent was removed using a rotary evaporator to obtain Compound 926-4 (9.8 g, 80%).

6) Preparation of Compound 926

After dissolving Compound 926-4 (9.8 g, 0.020 mol) and 2-bromo-4,6-diphenyl-1,3,5-triazine (7.5 g, 0.024 mol) in toluene, EtOH and H₂O (100 mL:20 mL:20 mL), Pd(PPh₃)₄ (1.2 g, 0.0010 mol) and K₂CO₃ (8.1 g, 0.063 mol) were introduced thereto, and the result was stirred for 5 hours at 100° C. After the reaction was completed, MC and distilled water were introduced to the reaction solution for extraction. After that, the result was dried with anhydrous MgSO₄, and then the solvent was removed using a rotary evaporator to obtain Compound 926 (9.5 g, 80%).

A target compound was synthesized in the same manner as in Preparation Example 3 except that Intermediate L-2 of the following Table 50 was used instead of 2-bromo-4,6-diphenyl-1,3,5-triazine.

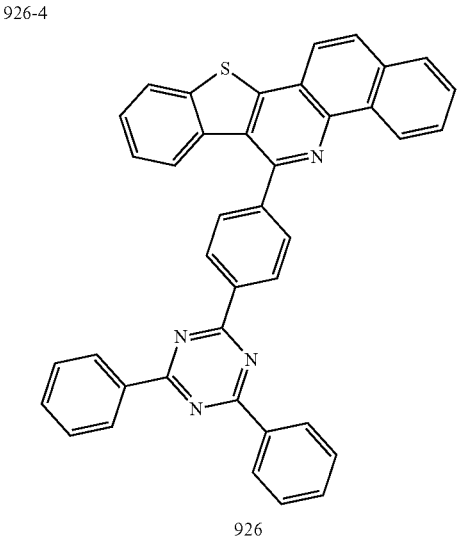

TABLE 50

| Compound Number | Intermediate L-2 | Target Compound | Yield |
| --- | --- | --- | --- |
| 926 | | | 62% |
| 928 | | | 67% |
| 932 | | | 65% |

TABLE 50-continued

| Compound Number | Intermediate L-2 | Target Compound | Yield |
|---|---|---|---|
| 936 | | | 71% |
| 937 | | | 68% |
| 1020 | | | 70% |

A target compound was synthesized in the same manner as in Preparation Example 3 except that 3-chlorobenzoyl chloride was used instead of 4-chlorobenzoyl chloride, and Intermediate M-2 of the following Table 51 was used instead of 2-bromo-4,6-diphenyl-1,3,5-triazine.

TABLE 51

| Compound Number | Intermediate M-2 | Target Compound | Yield |
|---|---|---|---|
| 927 | [structure] | [structure] | 62% |

A target compound was synthesized in the same manner as in Preparation Example 3 except that benzofuran-2-ylboronic acid was used instead of benzo[b]thiophen-2-ylboronic acid, 3-chlorobenzoyl chloride was used instead of 4-chlorobenzoyl chloride, and Intermediate N-2 of the following Table 52 was used instead of 2-bromo-4,6-diphenyl-1,3,5-triazine.

TABLE 52

| Compound Number | Intermediate N-2 | Target Compound | Yield |
|---|---|---|---|
| 943 | [structure] | [structure] | 62% |

TABLE 52-continued

| Compound Number | Intermediate N-2 | Target Compound | Yield |
|---|---|---|---|
| 945 | 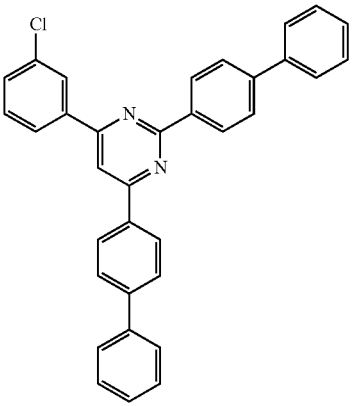 | 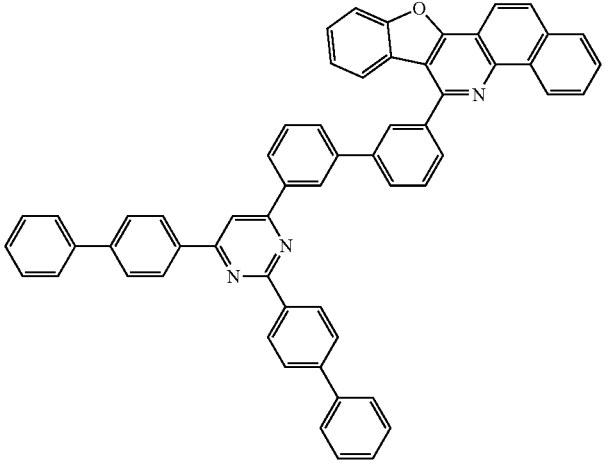 | 74% |

A target compound was synthesized in the same manner as in Preparation Example 3 except that 3-bromonaphthalen-2-amine was used instead of 2-bromonaphthalen-1-amine, and Intermediate O-2 of the following Table 53 was used instead of 2-bromo-4,6-diphenyl-1,3,5-triazine.

TABLE 53

| Compound Number | Intermediate O-2 | Target Compound | Yield |
|---|---|---|---|
| 950 | 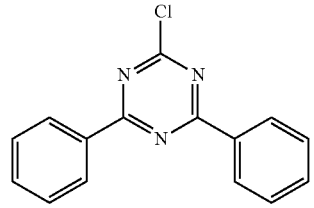 | 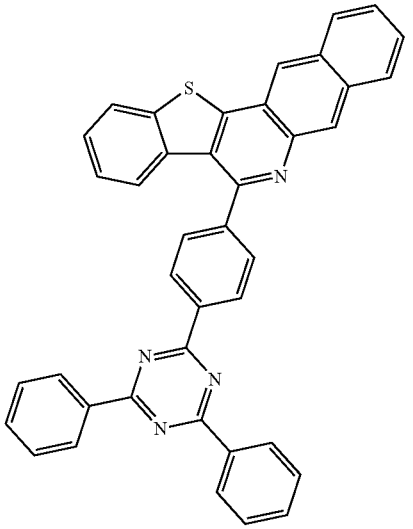 | 63% |

TABLE 53-continued
| Compound Number | Intermediate O-2 | Target Compound | Yield |
|---|---|---|---|
| 952 | 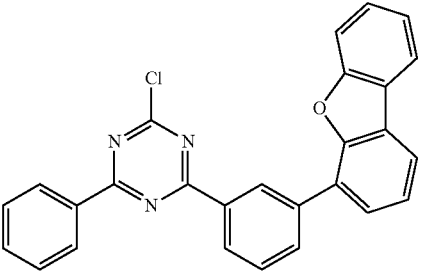 | 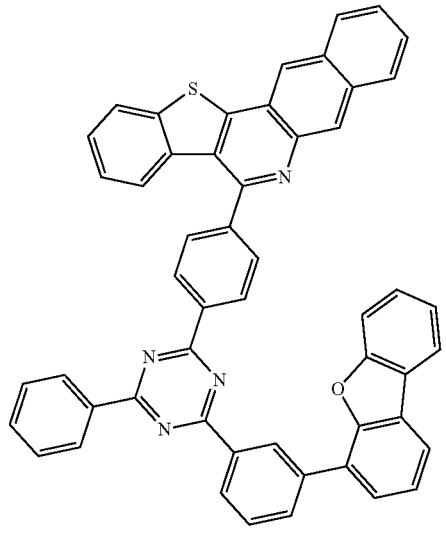 | 66% |
| 954 | 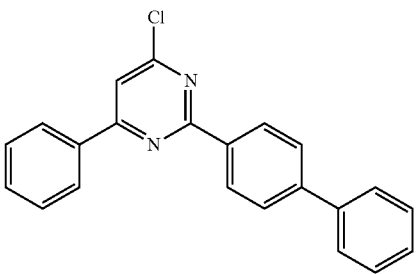 | 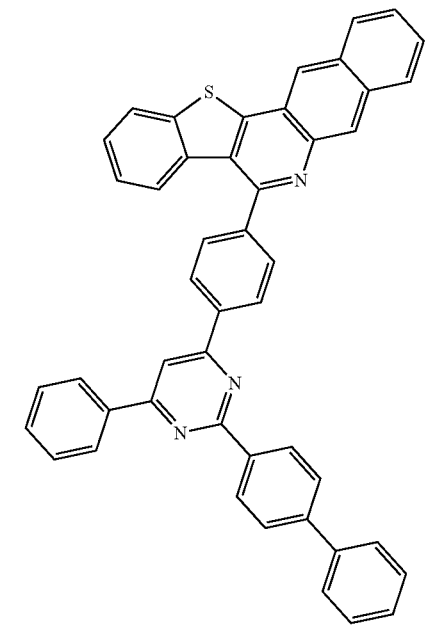 | 67% |

TABLE 53-continued
| Compound Number | Intermediate O-2 | Target Compound | Yield |
|---|---|---|---|
| 956 | 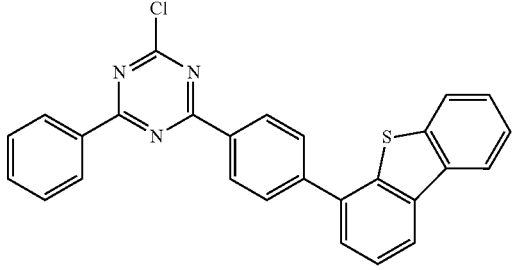 | 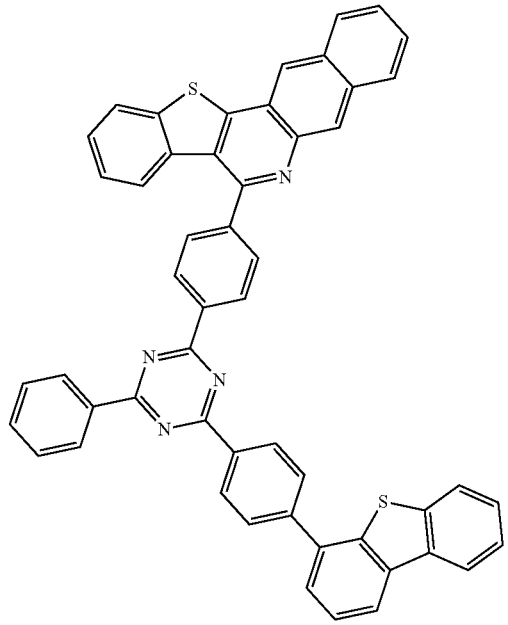 | 70% |
| 959 | 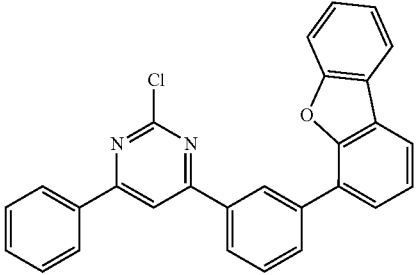 | 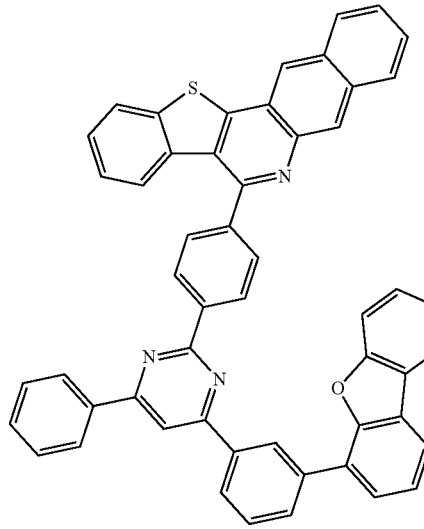 | 69% |

TABLE 53-continued

| Compound Number | Intermediate O-2 | Target Compound | Yield |
|---|---|---|---|
| 961 | (3-bromophenyl)diphenylphosphine oxide | | 65% |

A target compound was synthesized in the same manner as in Preparation Example 3 except that benzofuran-2-ylboronic acid was used instead of benzo[b]thiophen-2-ylboronic acid, 3-bromonaphthalen-2-amine was used instead of 2-bromonaphthalen-1-amine, and Intermediate P-2 of the following Table 54 was used instead of 2-bromo-4,6-diphenyl-1,3,5-triazine.

TABLE 54

| Compound Number | Intermediate P-2 | Target Compound | Yield |
|---|---|---|---|
| 962 | 2-chloro-4,6-diphenyl-1,3,5-triazine | | 69% |

TABLE 54-continued

| Compound Number | Intermediate P-2 | Target Compound | Yield |
|---|---|---|---|
| 969 | (structure) | (structure) | 72% |
| 971 | (structure) | (structure) | 71% |

A target compound was synthesized in the same manner as in Preparation Example 3 except that 1-bromonaphthalen-2-amine was used instead of 2-bromonaphthalen-1-amine, and Intermediate Q-2 of the following Table 55 was used instead of 2-bromo-4,6-diphenyl-1,3,5-triazine.

TABLE 55
| Compound Number | Intermediate Q-2 | Target Compound | Yield |
|---|---|---|---|
| 978 | 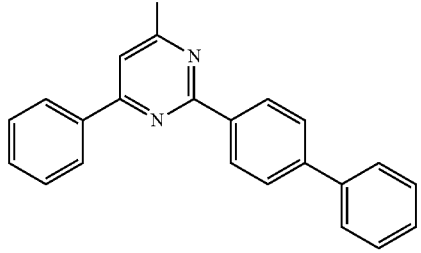 | 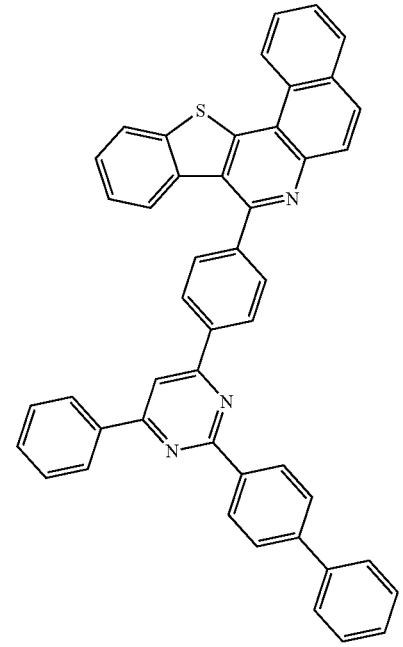 | 76% |
| 980 | 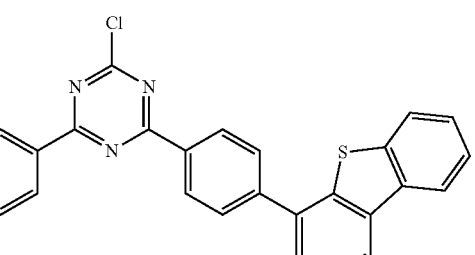 | 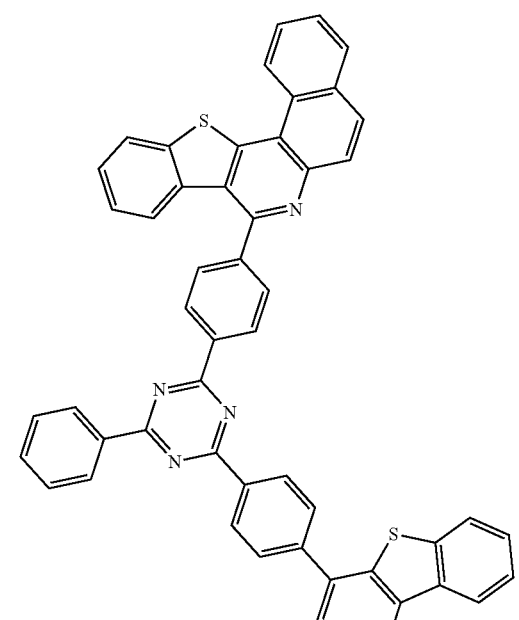 | 76% |

TABLE 55-continued

| Compound Number | Intermediate Q-2 | Target Compound | Yield |
|---|---|---|---|
| 1022 | 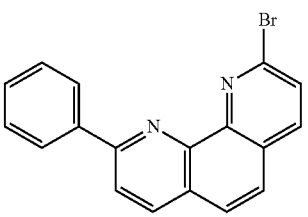 | | 70% |

A target compound was synthesized in the same manner as in Preparation Example 3 except that 1-bromonaphthalen-2-amine was used instead of 2-bromonaphthalen-1-amine, 3-chlorobenzoyl chloride was used instead of 4-chlorobenzoyl chloride, and Intermediate R-2 of the following Table 56 was used instead of 2-bromo-4,6-diphenyl-1,3,5-triazine.

A target compound was synthesized in the same manner as in Preparation Example 3 except that benzofuran-2-ylboronic acid was used instead of benzo[b]thiophen-2-ylboronic acid, 1-bromonaphthalen-2-amine was used instead of 2-bromonaphthalen-1-amine, and Intermediate S-2 of the following Table 57 was used instead of 2-bromo-4,6-diphenyl-1,3,5-triazine.

TABLE 56

| Compound Number | Intermediate R-2 | Target Compound | Yield |
|---|---|---|---|
| 977 | 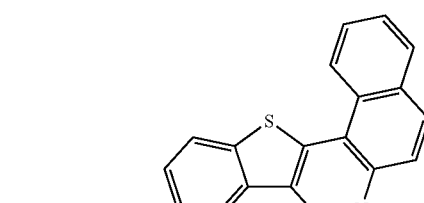 | | 71% |

TABLE 57

| Compound Number | Intermediate S-2 | Target Compound | Yield |
|---|---|---|---|
| 986 | [structure: 2-chloro-4,6-diphenyl-1,3,5-triazine] | [structure] | 74% |
| 990 | [structure: 4-chloro-6-phenyl-2-(4-biphenylyl)pyrimidine] | [structure] | 73% |

TABLE 57-continued

| Compound Number | Intermediate S-2 | Target Compound | Yield |
|---|---|---|---|
| 996 | 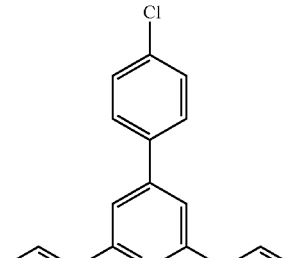 | 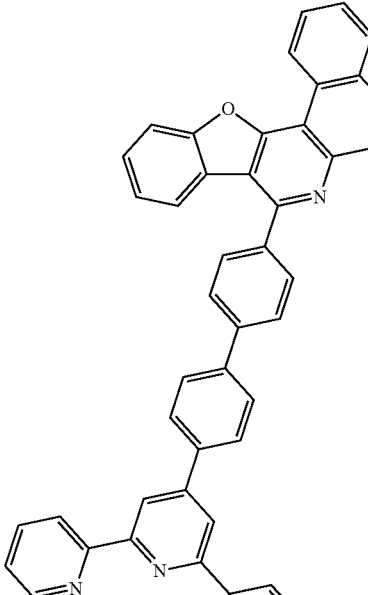 | 78% |

The following Table 58 and Table 59 present 1H NMR data and FD-MS data of the synthesized compounds, and through the following data, syntheses of target compounds may be identified.

TABLE 58

| NO | $^1$H NMR (CDCl$_3$, 300 Mz) |
|---|---|
| 1 | δ = 8.45(1H, m), 8.30~8.27(7H, m), 8.12(1H, d), 8.03~7.98(2H, m), 7.54~7.41(12H, m) |
| 4 | δ = 8.45(1H, t), 8.27~8.30(7H, m), 8.12(1H, d), 7.98~8.03(2H, m), 7.85(2H, d), 7.41~7.54(11H, m), 7.25(2H, d) |
| 5 | δ = 8.45(1H, m), 8.26~8.30(7H, m), 8.12(1H, d), 7.98~8.03(2H, m), 7.85(2H, d), 7.41~7.54(11H, m) |
| 9 | δ = 8.45(2H, d), 8.27~8.30(3H, m), 8.12(1H, d), 7.98~8.03(2H, m), 7.85(6H, d), 7.41~7.54(15H, m), 7.25(6H, d) |
| 13 | δ = 8.45(1H, m), 8.21~8.30(7H, m), 7.98~8.02(2H, m), 7.85(2H, d), 7.66(1H, t), 7.41~7.54(11H, m), 7.25(2H, d) |
| 24 | δ = 8.45(1H, m), 8.21~8.30(8H, m), 8.04(1H, d), 7.98(1H, m), 7.90(1H, s), 7.70 (1H, s), 7.41~7.54(13H, m) |
| 34 | δ = 8.97(2H, d), 8.30(2H, d), 8.21(1H, d), 7.98(1H, d), 8.04(1H, d), 7.90(1H, s), 7.45~7.83(8H, m), 7.45~7.52(11H, m), 7.25(4H, s) |
| 44 | δ = 8.45(1H, m), 8.46~8.55(2H, m), 8.28(4H, d), 8.21(1H, d), 7.98~8.10(4H, m), 7.85(2H, d), 7.41~7.55(12H, m), 7.25 (2H, d) |
| 57 | δ = 8.66(1H, m), 8.46(2H, d), 8.28(2H, d), 7.94~8.10(6H, m), 7.85(4H, d), 7.41~7.64(13H, m), 7.25(4H, d) |
| 64 | δ = 8.93(2H, d), 8.44(2H, d), 8.27~8.28(5H, m), 8.12(3H, d), 7.98~8.03(2H, m), 7.82~7.88(6H, m), 7.41~7.52(8H, m), 7.25(2H, d) |
| 65 | δ = 8.69(2H, d), 8.55(2H, d), 8.24~8.68(6H, m), 8.12(3H, d), 7.98~8.03(2H, m), 7.82~7.88(4H, m), 7.70(1H, s), 7.41~7.57(10H, m) |
| 78 | δ = 8.93(2H, d), 8.44(2H, d), 8.24~8.28(5H, m), 8.12(2H, d), 7.82~7.98(10H, m), 7.70(1H, s), 7.41~7.57(10H, m) |

TABLE 58-continued

| NO | $^1$H NMR (CDCl$_3$, 300 Mz) |
|---|---|
| 84 | δ = 9.66(1H, s), 8.93(2H, d), 8.55(1H, d), 8.45(1H, m), 8.21~8.28(6H, m), 8.12(3H, d), 7.98~8.03(2H, m), 7.82~7.88(6H, m), 7.41~7.51(8H, m), 7.25(2H, d) |
| 92 | δ = 9.66(1H, s), 8.93(2H, d), 8.55(1H, d), 9.66(1H, m), 8.21~8.68(6H, m), 8.12(2H, d), 8.04(1H, d), 7.98(1H, m), 7.82~7.90(7H, m), 7.42~7.51(8H, m), 7.25(2H, d) |
| 100 | δ = 9.66(1H, s), 8.93(2H, d), 8.55(1H, d), 9.66(1H, m), 8.28(2H, d), 8.27(1H, s), 8.21(1H, s), 8.12(3H, d), 7.98~8.06(3H, m), 7.82~7.88(5H, m), 7.38~7.61(9H, m), 7.28(1H, m) |
| 101 | δ = 9.66(1H, s), 8.93(2H, d), 8.55(1H, d), 8.45(1H, m), 8.27(1H, s), 8.21(1H, s), 8.12(3H, d), 7.98~8.03(2H, m), 7.77~7.88(12H, m), 7.45~7.52(8H, m) |
| 102 | δ = 8.27~8.30(7H, m), 8.12(1H, d), 8.03(1H, d), 7.89(1H, d), 7.66(1H, d), 7.41~7.54(11H, m) |
| 105 | δ = 8.27~8.30(7H, m), 8.12(1H, d), 8.03(1H, d), 7.85~7.89(3H, m), 7.66(1H, d), 7.32~7.54(13H, m) |
| 106 | δ = 8.27~8.30(7H, m), 8.12(1H, d), 8.03(1H, d), 7.85~7.89(3H, m), 7.66(1H, d), 7.32~7.54(11H, m), 7.25(6H, t) |
| 119 | δ = 8.28~8.30(6H, m), 8.21(1H, d), 8.04(1H, d), 7.89~7.90(2H, m), 7.66(1H, d), 7.32~7.54(11H, m) |
| 122 | δ = 8.28~8.30(6H, m), 8.21(1H, d), 8.04(1H, d), 7.85~7.90(4H, m), 7.66(1H, d), 7.32~7.54(11H, m), 7.25(2H, d) |
| 124 | δ = 8.30 (2H, d), 8.21(1H, d), 8.04(1H, d), 7.85~7.90(8H, m), 7.66(1H, d), 7.32~7.54(15H, m), 7.25(6H, d) |
| 135 | δ = 8.30(2H, d), 8.21(1H, d), 8.04(1H, d), 7.77~7.89(10H, m), 7.66(1H, d), 7.32~7.54(11H, m), 7.25(4H, s) |
| 138 | δ = 8.55(1H, m), 8.16(1H, d), 8.27~8.28(5H, d), 8.03~8.12(4H, m), 7.85~7.89(3H, m), 7.32~7.66(12H, m), 7.25(2H, d) |
| 152 | δ = 8.55(1H, m), 8.46(1H, d), 8.28(2H, d), 8.21(1H, d), 8.04~8.10(3H, m), 7.85~7.90(6H, m), 7.32~7.66(14H, m), 7.25(4H, d) |
| 159 | δ = 8.55(1H, m), 8.46(1H, d), 8.24~8.28(5H, m), 7.89~8.10(6H, m), 7.32~7.66(15H, m) |

TABLE 58-continued

| NO | ¹H NMR (CDCl₃, 300 Mz) |
|---|---|
| 161 | δ = 8.81(2H, d), 8.55(1H, m), 8.42(1H, d), 8.27~8.28(5H, m), 8.03~8.12(4H, m), 7.85~7.89(3H, m), 7.25~7.66(16H, m) |
| 175 | δ = 8.93(2H, d), 8.44(1H, s), 8.28(4H, d), 8.12(2H, d), 7.82~8.03(10H, m), 7.66(1H, d), 7.32~7.51(10H, m) |
| 181 | δ = 9.66(1H, s), 8.93(1H, d), 8.55(1H, d), 8.21~8.28(6H, m), 8.12(1H, d), 8.03(1H, d), 7.82~7.89(7H, m), 7.66(1H, m), 7.25~7.51(10H, m) |
| 192 | δ = 9.66(1H, s), 8.93(1H, d), 8.55(1H, d), 8.21~8.28(5H, m), 8.12(2H, d), 7.85~8.03(10H, m), 7.66(1H, d), 7.25~7.51(10H, m) |
| 195 | δ = 9.66(1H, s), 8.93(1H, d), 8.55(1H, d), 8.28(2H, d), 8.21(1H, 2), 8.12(4H, d), 8.03(1H, d), 7.82~7.94(6H, m), 7.63~7.66 (2H, m), 7.29~7.51(9H, m) |
| 196 | δ = 9.66(1H, s), 8.93(1H, d), 8.55(1H, d), 8.28(2H, d), 8.27(1H, s), 8.21(1H, d), 8.12(3H, d), 8.03~8.06(2H, m), 7.82~7.89(6H, m), 7.51~7.66(6H, m), 7.28~7.41(5H, m) |
| 197 | δ = 9.66(1H, s), 8.93(1H, d), 8.55(1H, d), 8.27(1H, s), 8.21(1H, d), 8.12(3H, d), 8.03(1H, d), 7.77~7.89(13H, m), 7.66(1H, d), 7.45(6H, m), 7.32~7.38(2H, m) |
| 198 | δ = 8.55(1H, d), 8.27~8.30(5H, m), 8.12(2H, d), 8.03(1H, d), 7.89~7.94(2H, m), 7.79(2H, d), 7.29~7.68(16H, m) |
| 202 | δ = 8.41~8.45(2H, m), 8.20~8.30(6H, m), 8.12(1H, d), 7.98~8.03(2H, m), 7.85~7.89(3H, m), 7.25~7.66(14H, m) |
| 206 | δ = 8.45(1H, m), 8.27~8.30(5H, m), 8.23(1H, s), 8.12(1H, d), 7.98~8.03(2H, m), 7.79(2H, d), 7.41~7.54(11H, m) |
| 210 | δ = 8.46(1H, d), 8.27~8.30(3H, m), 8.23(1H, s), 8.12(1H, d), 7.98~8.03(2H, m), 7.79~7.85(6H, m), 7.41~7.54(11H, m), 7.25(6H, t) |
| 217 | δ = 8.45(1H, d), 8.27~8.30(9H, m), 8.23(1H, s), 8.12(1H, d), 7.98~8.03(2H, m), 7.85(4H, m), 7.41~7.54(13H, m) |
| 235 | δ = 8.45(1H, d), 8.21~8.30(8H, m), 8.04(1H, d), 7.98(1H, m), 7.90(1H, s), 7.85(2H, d), 7.41~7.54(13H, m) |
| 238 | δ = 8.45(1H, d), 8.30(4H, d), 8.23(1H, s), 8.21(1H, d), 8.04(1H, d), 7.98(1H, m), 7.90(1H, s), 7.85(6H, d), 7.41~7.54(15H, m), 7.25(2H, d) |
| 248 | δ = 8.45(1H, m), 8.30(2H, d), 8.23(1H, s), 7.94~8.03(4H, m), 7.79~7.85(6H, m), 7.41~7.54(11H, m), 7.25(2H, d) |
| 255 | δ = 8.45(1H, d), 8.30(2H, d), 8.27(1H, s), 8.23(1H, s), 8.12(1H, d), 7.98~8.06(3H, m), 7.79~7.87(5H, m), 7.41~7.61(12H, m), 7.25(2H, d) |
| 260 | δ = 8.55(1H, m), 8.45~8.46(2H, m), 8.27~8.30(5H, m), 8.23(1H, s), 7.98~8.12(5H, m), 7.85(2H, d), 7.64(1H, t), 7.41~7.55(12H, m) |
| 264 | δ = 8.55(1H, m), 8.46(2H, m), 8.27~8.30(5H, m), 8.23(1H, s), 7.98~8.12(5H, m), 7.85(2H, d), 7.79(2H, d), 7.64(1H, t), 7.41~7.52(10H, m) |
| 272 | δ = 8.55(1H, m), 8.46~8.55(2H, m), 8.23(1H, d), 7.98~8.10(4H, m), 7.85(2H, d), 7.79(4H, d), 7.41~7.66(12H, m), 7.25(2H, d) |
| 275 | δ = 8.55(1H, m), 8.46(2H, m), 8.28~8.30(4H, m), 8.23(1H, s), 8.21(1H, d), 7.98~8.10(4H, m), 7.79(2H, d), 7.41~7.66(12H, m), 7.25(2H, d) |
| 277 | δ = 8.55(1H, m), 8.46(2H, m), 8.21~8.30(8H, m), 7.98~8.10(4H, m), 7.85(2H, d), 7.41~7.66(14H, m) |
| 283 | δ = 8.55(1H, m), 8.45(2H, m), 8.21~8.23(2H, d), 7.98~8.10(4H, m), 7.79~7.90(5H, m), 7.41~7.64(13H, m) |
| 285 | δ = 8.55(1H, m), 8.45(2H, m), 8.21~8.23(2H, d), 7.98~8.10(4H, m), 7.79~7.90(7H, m), 7.41~7.64(11H, m) |
| 287 | δ = 8.55(1H, m), 8.45(2H, m), 8.23~8.30(6H, m), 7.98~8.10(4H, m), 7.79~7.90(5H, m), 7.41~7.64(11H, m) |
| 302 | δ = 8.81(2H, d), 8.55(1H, m), 8.42(2H, m), 8.23~8.27(2H, d), 7.98~8.12(5H, m), 7.79~7.85(6H, m), 7.50~7.61(11H, m) |
| 312 | δ = 8.93(2H, d), 8.44(2H, d), 8.23~8.30(6H, m), 8.12(3H, d), 7.98~8.03(2H, m), 7.79~7.88(8H, m), 7.41~7.52(8H, m) |
| 318 | δ = 8.93(2H, d), 8.44(1H, s), 8.21~8.23(2H, d), 8.12(2H, d), 7.98~8.02(2H, m), 7.79~7.88(10H, m), 7.66(1H, t), 7.41~7.52(8H, m), 7.25(2H, d) |
| 328 | δ = 8.93(2H, d), 8.45(2H, m), 8.21~8.23(2H, d), 8.12(2H, d), 8.04(1H, d), 7.79~7.90(12H, m), 7.41~7.52(8H, m), 7.25(2H, m) |
| 332 | δ = 8.93(2H, d), 8.45(2H, m), 8.21~8.30(8H, m), 8.12(2H, d), 8.04(1H, d), 7.98(1H, m), 7.82~7.90(9H, m), 7.41~7.52(10H, m) |
| 342 | δ = 8.93(2H, d), 8.81(2H, d), 8.81(1H, m), 8.27(1H, s), 8.23(1H, s), 8.12(3H, d), 7.79~8.03(13H, m), 7.41~7.52(8H, m), 7.25~7.28(4H, t) |
| 346 | δ = 9.66(1H, s), 8.93(2H, d), 8.55(1H, d), 8.45(1H, m), 8.21~8.30(7H, m), 8.12(3H, d), 7.98~8.03(2H, m), 7.82~7.88(6H, m), 7.41~7.52(10H, m) |
| 348 | δ = 8.93(2H, d), 8.55(1H, d), 8.45(1H, m), 8.23~8.30(7H, m), 8.12(3H, d), 7.98~8.03(2H, m), 7.79~7.88(8H, m), 7.41~7.52(8H, m) |
| 355 | δ = 9.66(1H, s), 8.93(2H, d), 8.55(1H, d), 8.45(1H, d), 8.23(1H, s), 8.21(2H, d), 8.12(2H, d), 8.04(1H, d), 7.98(1H, m), 7.79~7.90(11H, m), 7.41~7.52(8H, m) |
| 358 | δ = 9.66(1H, s), 8.93(2H, d), 8.55(1H, d), 8.45(1H, d), 8.30(2H, t), 8.28(2H, d), 8.23(1H, s), 8.21(2H, d), 8.12(2H, d), 8.04(1H, d), 7.98(1H, m), 7.82~7.90(7H, m), 7.41~7.52(10H, m) |
| 359 | δ = 9.66(1H, s), 8.93(2H, d), 8.55(1H, d), 8.45(1H, d), 8.21~8.23(2H, d), 8.12(2H, d), 8.04(1H, d), 7.79~7.98(12H, m), 7.41~7.52(8H, m), 7.25(2H, d) |
| 368 | δ = 8.55(1H, d), 8.45(1H, d), 8.23~8.30(4H, m), 8.12(2H, d), 8.03(1H, d), 7.94~7.98(2H, m), 7.79(4H, d), 7.25~7.68(15H, m) |
| 370 | δ = 8.45(1H, d), 8.23~8.30(6H, m), 8.12(1H, d), 7.98~8.03(2H, m), 7.79~7.89(5H, m), 7.66(1H, d), 7.25~7.54(13H, m) |
| 372 | δ = 8.41~8.45(3H, m), 8.20~8.30(7H, m), 8.12(1H, d), 7.98~8.03(2H, m), 7.79~7.89(5H, m), 7.41~7.58(11H, m), 7.25(2H, d) |
| 387 | δ = 8.27~8.30(9H, m), 8.23(1H, s), 8.12(1H, d), 8.03(1H, d), 7.85~7.89(5H, m), 7.66(1H, d), 7.41~7.54(13H, m) |
| 394 | δ = 8.30(2H, d), 8.23(1H, s), 8.21(1H, d), 8.02(1H, d), 7.79~7.89(7H, m), 7.66(2H, m), 7.25~7.54(13H, m) |
| 403 | δ = 8.28~8.30(4H, m), 8.04(1H, d), 7.89~7.90(2H, d), 7.79(2H, d), 7.66(1H, d), 7.32~7.54(11H, m) |
| 406 | δ = 8.30(2H, d), 8.21~8.23(2H, d), 8.04(1H, d), 7.79~7.90(8H, m), 7.66(1H, d), 7.41~7.54 (11H, m), 7.25(2H, d) |
| 415 | δ = 8.28~8.30(4H, m), 8.23(1H, s), 7.89~8.03(4H, m), 7.79(2H, d), 7.66(1H, d), 7.32~7.66(11H, m) |
| 418 | δ = 8.30(2H, d), 8.23(1H, s), 7.79~8.03(10H, m), 7.66(1H, d), 7.41~7.54(11H, m), 7.25(2H, d) |
| 427 | δ = 8.55(1H, t), 8.46(1H, d), 8.28(2H, d), 8.27(1H, s), 8.23(1H, s), 8.03~8.12(4H, m), 7.89(1H, d), 7.79(2H, d), 7.32~7.66(12H, m) |
| 432 | δ = 8.55(1H, t), 8.46(1H, d), 8.27~8.30(5H, m), 8.23(1H, s), 8.03~8.12(4H, m), 7.79~7.85(5H, m), 7.41~7.66(12H, m) |
| 447 | δ = 8.55(1H, t), 8.46(1H, d), 8.21~8.23(2H, d), 8.04~8.10(3H, m), 7.89~7.90(2H, m), 7.79(3H, d), 7.41~7.66(12H, m) |
| 453 | δ = 8.55(1H, t), 8.46(1H, d), 8.21~8.23(2H, d), 8.04~8.10(3H, m), 7.79~7.90(8H, m), 7.41~7.66(12H, m), 7.25(2H, d) |
| 458 | δ = 8.55(1H, t), 8.46(1H, d), 8.30(4H, d), 8.21~8.23(2H, d), 8.04~8.10(3H, m), 7.85~7.90(8H, m), 7.64~7.66(2H, m), 7.32~7.55(14H, m), 7.25(2H, d) |
| 473 | δ = 8.93(2H, d), 8.44(1H, s), 8.23~8.28(4H, m), 8.12(3H, d), 8.03(1H, d), 7.79~7.89(7H, m), 7.66(1H, d), 7.32~7.51(8H, m) |
| 476 | δ = 8.93(2H, d), 8.44(1H, s), 8.27(1H, s), 8.23(1H, s), 8.12(3H, d), 8.03(1H, d), 7.79~7.88(11H, m), 7.66(1H, d), 7.32~7.51(8H, m), 7.25(2H, d) |
| 490 | δ = 8.93(2H, d), 8.44(1H, s), 8.21~8.23(2H, d), 8.12(2H, d), 8.04(1H, d), 7.79~7.90(10H, m), 7.66(1H, d), 7.32~7.51(8H, m) |
| 497 | δ = 8.93(2H, d), 8.44(1H, s), 8.21~8.23(2H, d), 8.12(2H, d), 8.04(1H, d), 7.9~7.60(12H, m), 7.66(1H, d), 7.32~7.51(8H, m), 7.25(2H, d) |
| 505 | δ = 8.93(2H, d), 8.44(1H, s), 8.30(2H, d), 8.23(1H, s), 8.12(2H, d), 7.82~7.95(12H, m), 7.66(1H, d), 7.32~7.52(12H, m), 7.25(2H, d) |
| 509 | δ = 8.93(2H, d), 8.44(1H, s), 8.23~8.30(7H, m), 8.12(2H, d), 7.82~7.95(10H, m), 7.66(1H, d), 7.32~7.52(10H, m), 7.25(2H, d) |
| 512 | δ = 8.93(2H, d), 8.81(2H, d), 8.37(1H, d), 8.28(2H, d), 8.23(1H, s), 8.12(2H, d), 8.02(1H, d), 7.79~7.89(8H, m), 7.66(2H, m), 7.28~7.51(10H, m) |
| 517 | δ = 8.93(2H, d), 8.55(1H, d), 8.27(1H, s), 8.23(1H, s), 8.21(1H, s), 8.12(2H, d), 8.03(1H, d), 7.79~7.89(11H, m), 7.66(1H, d), 7.25~7.51(10H, m) |

TABLE 58-continued

| NO | ¹H NMR (CDCl₃, 300 Mz) |
|---|---|
| 527 | δ = 9.66(1H, s), 8.93(2H, d), 8.55(1H, d), 8.23(1H, s), 8.21(2H, s), 8.12(2H, d), 8.04(1H, d), 7.79~7.89(12H, m), 7.66(1H, d), 7.32~7.51(8H, m), 7.25(2H, d) |
| 534 | δ = 9.66(1H, s), 8.93(2H, d), 8.55(1H, d), 8.27(1H, s), 8.23(1H, s), 8.27(1H, s), 8.12(3H, d), 8.03~8.06(2H, d), 7.79~7.89(8H, m), 7.51~7.61(6H, m), 7.28~7.41(5H, m) |
| 536 | δ = 8.55(1H, d), 8.23~8.30(5H, d), 8.03~8.12(4H, d), 7.89~7.94(2H, m), 7.79(2H, d), 7.29~7.66(16H, m) |
| 537 | δ = 8.30(4H, d) 8.27(1H, s), 8.23(1H, s), 8.12(1H, d), 8.03(1H, d), 7.79~7.89(6H, m), 7.66(2H, d), 7.32~7.54(11H, m), 7.25(2H, d) |
| 539 | δ = 8.41~8.45(2H, m), 8.30(4H, t), 8.27(1H, s), 8.23(1H, s), 8.20(1H, d), 8.12(1H, d), 7.98~8.03(2H, m), 7.89(1H, d), 7.79(2H, d), 7.66(1H, d), 7.32~7.58(11H, m), 7.25(2H, d) |
| 542 | δ = 9.30(2H, d), 9.15(2H, s), 8.53(2H, d), 8.45(1H, d), 8.27~8.30(3H, m), 8.12(1H, d), 7.98~8.03(2H, m), 7.70(2H, m), 7.47~7.54(5H, m), 7.25(4H, s), 7.14(2H, t) |
| 543 | δ = 9.30(2H, d), 9.15(2H, s), 8.53(2H, d), 8.45(1H, d), 8.30(2H, d), 8.27(1H, s), 8.12(1H, d), 7.98~8.03(2H, m), 7.70(2H, m), 7.47~7.54(5H, m), 7.25(8H, s), 7.14(2H, t) |
| 547 | δ = 9.30(2H, d), 9.15(2H, s), 8.53~8.55(3H, m), 8.45(2H, d), 8.27(1H, s), 7.98~8.12(5H, m), 7.50~7.55(4H, m), 7.64~7.70(3H, m), 7.25(4H, s), 7.14(2H, t) |
| 551 | δ = 9.30(2H, d), 9.15(2H, s), 8.93(2H, d), 8.53(2H, d), 8.12(1H, d), 8.27(1H, s), 8.12(3H, d), 7.98~8.03(2H, m), 7.82~7.88(4H, m), 7.70(2H, t), 7.50~7.52(2H, m), 7.25(4H, s), 7.14(2H, t) |
| 555 | δ = 9.66(1H, s), 9.30(2H, d), 9.15(2H, s), 8.93(2H, d), 8.45~8.55(4H, m), 8.271H, s), 8.21(1H, d), 8.12(3H, d), 7.98~8.03(2H, m), 7.82~7.88(4H, m), 7.70(2H, t), 7.50~7.52(2H, m), 7.25(4H, s), 7.14(2H, t) |
| 561 | δ = 9.30(2H, d), 9.15(2H, s), 8.53(2H, d), 8.30(2H, d), 8.21(1H, d), 8.02(1H, d), 7.89(1H, d), 7.66~7.70(4H, m), 7.32~7.54(5H, m), 7.25(4H, s), 7.14(2H, t) |
| 567 | δ = 9.30(2H, d), 9.15(2H, s), 8.93(2H, d), 8.53(2H, d), 8.44(1H, s), 8.27(1H, s), 8.12(3H, d), 8.03(1H, d), 7.82~7.88(5H, m), 7.66~7.70(3H, m), 7.32~7.38(2H, m), 7.25(4H, s), 7.14(2H, t) |
| 571 | δ = 9.66(1H, s), 9.30(2H, d), 9.15(2H, s), 8.93(2H, d), 8.53~8.55(3H, m), 8.27(1H, s), 8.21(1H, d), 8.12(3H, d), 8.03(1H, d), 7.82~7.89(5H, m), 7.66~7.70(3H, m), 7.32~7.38(2H, m), 7.25(4H, s), 7.14(2H, t) |
| 574 | δ = 8.81(2H, m), 8.27~8.28(5H, d), 8.12(1H, d), 7.98~8.03(2H, m), 7.88(2H, d), 7.41~7.52(13H, m) |
| 575 | δ = 8.81(2H, m), 8.45(1H, d), 8.27~8.28(5H, d), 8.12(1H, d), 7.98~8.03(2H, m), 7.85~7.88(4H, t), 7.41~7.52(13H, m), 7.25(2H, d) |
| 585 | δ = 8.45(1H, m), 8.21~8.30(8H, m), 8.04(1H, d), 7.98(1H, m), 7.90(1H, s), 7.60(1H, t), 7.41~7.52(13H, m) |
| 591 | δ = 8.81(2H, d), 8.46(1H, m), 8.28(2H, d), 7.87~8.06(8H, m), 7.79(2H, d), 7.38~7.52(12H, m), 7.28(1H, t), 1.72(6H, s) |
| 594 | δ = 8.81(2H, d), 8.55(1H, t), 8.42~8.45(2H, m), 8.25~8.28(3H, d), 7.98~8.12(5H, m), 7.85~7.88(4H, t), 7.41~7.61(13H, m), 7.25(2H, d) |
| 607 | δ = 8.93(2H, d), 8.81(2H, d), 8.45(1H, m), 8.28(4H, d), 8.21(1H, d), 8.12(2H, d), 7.82~8.02(9H, m), 7.66(1H, t), 7.41~7.52(8H, m) |
| 610 | δ = 9.15(1H, s), 8.93(2H, d), 8.81(2H, d), 8.45(1H, m), 8.27~8.28(5H, d), 8.18(1H, d), 8.12(3H, d), 7.98~8.04(3H, m), 7.82~7.88(6H, m), 7.41~7.52(8H, m) |
| 614 | δ = 9.15(1H, s), 8.93(2H, d), 8.81(2H, d), 8.45(1H, m), 8.28(4H, d), 8.21(1H, d), 8.18(1H, d), 8.12(2H, d), 7.82~8.04(10H, m), 7.41~7.52(8H, m) |
| 618 | δ = 8.81(2H, d), 8.45(1H, m), 8.27~8.28(5H, d), 8.12(1H, d), 7.98~8.03(2H, m), 7.81~7.89(5H, m), 7.66(1H, d), 7.32~7.52(11H, m) |
| 621 | δ = 8.81(2H, d), 8.45(1H, m), 8.21~8.28(5H, d), 7.98~8.02(2H, m), 7.81~7.89(5H, m), 7.66(1H, m), 7.32~7.52(11H, m) |
| 627 | δ = 8.81(2H, d), 8.45(1H, m), 8.28(4H, d), 7.85~7.95(9H, m), 7.66(1H, m), 7.32~7.52(11H, m) |
| 634 | δ = 8.81(2H, d), 8.41~8.45(3H, m), 8.27~8.28(5H, d), 8.20(1H, d), 7.98~8.03(3H, m), 7.88(2H, d), 7.41~7.58(11H, m) |
| 643 | δ = 8.81(2H, d), 8.41~8.45(3H, m), 8.28(4H, d), 8.20(1H, d), 7.88~7.98(7H, m), 7.41~7.58(11H, m) |
| 650 | δ = 8.81(2H, d), 8.55(1H, d), 8.45(1H, m), 8.27~8.28(3H, d), 8.12(2H, d), 7.88~8.03(5H, m), 7.79(2H, d), 7.63~7.68(3H, m), 7.25~7.52(14H, m) |
| 652 | δ = 8.81(2H, d), 8.45(1H, m), 8.27~8.28(3H, d), 8.12(1H, d), 7.98~8.03(2H, m), 7.81~7.88(7H, m), 7.66(1H, d), 7.25~7.52(15H, m) |
| 657 | δ = 8.81(2H, d), 8.27~8.28(5H, d), 8.12(1H, d), 8.03(1H, d), 7.85~7.88(5H, m), 7.66(1H, d), 7.32~7.52(13H, m), 7.25(2H, d) |
| 667 | δ = 8.21~8.30(8H, m), 8.04(1H, d), 7.90(2H, d), 7.32~7.60(15H, m) |
| 674 | δ = 8.81(2H, d), 8.55(1H, d), 8.42(1H, d), 8.25~8.28(5H, d), 8.04~8.12(4H, m), 7.88~7.89(3H, m), 7.32~7.66(12H, m) |
| 684 | δ = 8.81(2H, d), 8.55(1H, d), 8.42(1H, d), 7.85~8.08 (12H, m), 7.32~7.61 (16H, m), 7.25(4H, d) |
| 687 | δ = 8.93(2H, d), 8.81(2H, d), 8.21(1H, s), 8.12(3H, d), 8.03(1H, d), 7.82~7.93(12H, m), 7.66(1H, d), 7.32~7.52 (12H, m), 7.25(4H, d) |
| 692 | δ = 8.93(2H, d), 8.81(2H, d), 8.28(4H, d), 8.21(1H, d), 8.12(2H, d), 8.04(1H, d), 7.82~7.93(9H, m), 7.66(1H, m), 7.32~7.51(8H, m) |
| 695 | δ = 8.93(2H, d), 8.81(2H, d), 8.28(4H, d), 8.12(2H, d), 7.82~8.03(11H, m), 7.66(1H, m), 7.32~7.51(8H, m) |
| 700 | δ = 9.15(1H, s), 8.93(2H, d), 8.81(2H, d), 8.28(4H, d), 8.18(1H, d), 8.12(2H, d), 8.02~8.04(2H, m), 7.82~7.88(7H, m), 7.66(1H, m), 7.32~7.51(8H, m) |
| 708 | δ = 8.27~8.30(8H, m), 8.12(1H, d), 8.03(1H, d), 7.81~7.89(4H, m), 7.32~7.66(14H, m) |
| 723 | δ = 8.81(2H, d), 8.41~8.45(2H, m), 8.27~8.28(3H, d), 8.20(1H, d), 8.12(1H, d), 7.98~8.03(2H, m), 7.85~7.88(5H, m), 7.66(1H, d), 7.32~7.58(15H, m) |
| 729 | δ = 8.41~8.45(2H, m), 8.20~8.28(9H, m), 7.98~8.04(2H, m), 7.89~7.90(2H, m), 7.32~7.66(13H, m) |
| 734 | δ = 8.81(2H, d), 8.41~8.45(2H, m), 8.28(4H, d), 8.27(1H, s), 8.20(1H, d), 7.98~8.03(2H, m), 7.88(3H, d), 7.32~7.70(16H, m) |
| 737 | δ = 8.81(2H, d), 8.55(1H, d), 8.27(3H, d), 8.12(2H, d), 8.03(1H, d), 7.88~7.94(4H, m), 7.79(2H, d), 7.63~7.68(4H, m), 7.29~7.52(14H, m) |
| 739 | δ = 8.81(2H, d), 8.28(3H, d), 8.12(1H, d), 8.03(1H, d), 7.81~7.88(8H, m), 7.66(2H, d), 7.25~7.52(15H, m) |
| 741 | δ = 8.81(2H, d), 8.41~8.45(2H, m), 8.27~8.28(3H, d), 8.20(1H, d), 8.12(1H, d), 7.98~8.03(2H, m), 7.85~7.88(5H, m), 7.25~7.52(16H, m) |
| 744 | δ = 8.81(2H, d), 8.45(1H, m), 8.27(1H, s), 8.23(1H, s), 8.12(1H, d), 7.98~8.03(2H, m), 7.79~7.88(8H, m), 7.41~7.52(13H, m), 7.25(2H, d) |
| 746 | δ = 8.81(2H, d), 8.45(1H, d), 8.30(4H, d), 8.23(1H, s), 8.12(1H, d), 7.98~8.03(2H, m), 7.85(4H, d), 7.88(2H, d), 7.41~7.52(17H, m) |
| 758 | δ = 8.81(2H, d), 8.45(1H, m), 8.21~8.33(6H, m), 7.98(1H, d), 8.04(1H, d), 7.90(1H, s), 7.79(2H, d), 7.41~7.52(13H, m) |
| 768 | δ = 8.81(2H, d), 8.55(1H, m), 8.45(2H, d), 8.23(2H, d), 7.98~8.12(5H, m), 7.88(2H, d), 7.79(4H, d), 7.41~7.61(11H, m) |
| 781 | δ = 8.81(2H, d), 8.55(1H, m), 8.42(2H, d), 8.23(1H, s), 7.94~8.08(6H, m), 7.88(2H, d), 7.79(4H, d), 7.41~7.61(11H, m) |
| 789 | δ = 8.93(2H, d), 8.81(2H, d), 8.45(1H, m), 8.23~8.33(6H, m), 8.12(3H, d), 7.79~8.03(9H, m), 7.41~7.52(8H, m) |
| 796 | δ = 8.93(2H, d), 8.81(2H, d), 8.45(1H, m), 8.21~8.23(2H, d), 8.12(2H, d), 8.04(1H, d), 7.79~7.93(13H, m), 7.41~7.52(8H, m) |
| 802 | δ = 8.93(2H, d), 8.81(2H, d), 8.45(1H, m), 8.23~8.33(5H, m), 8.12(2H, d), 7.79~8.03(11H, m), 7.41~7.52(8H, m) |
| 804 | δ = 8.93(2H, d), 8.46(1H, m), 8.21~8.28(5H, d), 8.12(2H, d), 7.79~7.98(12H, m), 7.41~7.60(9H, m) |
| 807 | δ = 9.15(1H, s), 8.93(2H, d), 8.81(2H, d), 8.45(1H, m), 7.98~8.33(13H, m), 7.79~7.88(6H, m), 7.41~7.52(8H, m) |
| 813 | δ = 8.81(2H, d), 8.46(1H, m), 8.23~8.33(6H, m), 8.12(1H, d), 7.98~8.03(2H, m), 7.79~7.89(5H, m), 7.66(1H, d), 7.32~7.52(11H, m) |
| 818 | δ = 8.81(2H, d), 8.41~8.81(3H, m), 8.20~8.33(7H, m), 8.12(1H, d), 7.98~8.03(3H, m), 7.79(2H, d), 7.41~7.58(11H, m) |

TABLE 58-continued

| NO | $^1$H NMR (CDCl$_3$, 300 Mz) |
|---|---|
| 824 | δ = 8.81(2H, d), 8.55(1H, d), 8.45(1H, m), 8.33(2H, d), 8.27(1H, s), 8.23(1H, s), 8.12(2H, d), 7.94~8.03(3H, m), 7.79(4H, d), 7.63~7.68(3H, m), 7.25~7.52(14H, m) |
| 826 | δ = 8.81(2H, d), 8.45(1H, m), 8.33(2H, d), 8.27(1H, s), 8.23(1H, s), 8.12(1H, d), 7.98~8.03(2H, m), 7.79~7.89(7H, m), 7.66(1H, d), 7.25~7.52(15H, m) |
| 830 | δ = 8.81(2H, d), 8.27(1H, s), 8.23(1H, s), 8.12(1H, d), 8.03(1H, d), 7.88~7.89(3H, m), 7.79(4H, d), 7.66(1H, d), 7.32~7.52(13H, m) |
| 831 | δ = 8.81(2H, d), 8.27(1H, s), 8.23(1H, s), 8.12(1H, d), 8.03(1H, d), 7.79~7.88(9H, m), 7.66(1H, d), 7.32~7.52(13H, m), 7.25(2H, d) |
| 844 | δ = 8.81 (2H, d), 8.21~8.33(6H, m), 8.04(1H, d), 7.89~7.90(2H, d), 7.79(2H, d), 7.66(1H, d), 7.32~7.52(13H, m) |
| 855 | δ = 8.81(2H, d), 8.55(1H, m), 8.42(1H, m), 8.28(1H, s), 8.23(1H, s), 8.03~8.12(4H, m), 7.88(3H, m), 7.79(4H, d), 7.32~7.55(12H, m) |
| 861 | δ = 8.81(2H, d), 8.55(1H, m), 8.42(1H, m), 8.21~8.28(6H, m), 8.02~8.08(3H, m), 7.89(1H, d), 7.79(2H, d), 7.32~7.66(13H, m) |
| 877 | δ = 8.93(2H, d), 8.81(2H, d), 8.28~8.33(8H, m), 8.12(3H, d), 8.03(1H, d), 7.82~7.93(8H, m), 7.66(1H, d), 7.32~7.51(10H, m) |
| 883 | δ = 8.93(2H, d), 8.81(2H, d), 8.21~8.23(2H, m), 8.12(2H, d), 8.04(1H, d), 7.79~7.93(13H, m), 7.66(1H, d), 7.32~7.51(8H, m) |
| 894 | δ = 9.15(1H, s), 8.93(2H, d), 8.81(2H, d), 8.33(2H, m), 8.28(2H, d), 8.27(1H, s), 8.23(1H, s), 8.03~8.12(6H, m), 7.79~7.88(7H, m), 7.66(1H, d), 7.32~7.51(8H, m) |
| 902 | δ = 8.81(2H, d), 8.27~8.33(6H, m), 8.12(1H, m), 8.03(1H, d), 7.79~7.89(6H, m), 7.66(2H, m), 7.32~7.51(11H, m) |
| 907 | δ = 8.81(2H, d), 8.21~8.33(6H, m), 8.02(1H, d), 7.79~7.89(6H, m), 7.66(3H, m), 7.32~7.51(11H, m) |
| 910 | δ = 8.81(2H, d), 8.45(1H, m), 8.20~8.41(8H, m), 8.12(1H, d), 7.98~8.03(2H, m), 7.89(1H, d), 7.79(2H, d), 7.66(1H, d), 7.32~7.58(11H, m) |
| 917 | δ = 9.66(1H, s), 8.93(2H, d), 8.55(1H, d), 8.45(1H, m), 8.27(1H, s), 8.21(1H, s), 8.12(3H, d), 7.98~8.03(2H, m), 7.77~7.88(21H, m), 7.45~7.52(8H, m) |
| 918 | δ = 8.81(2H, d), 8.55(1H, m), 8.12(1H, d), 7.88~8.03(7H, m), 7.79(4H, d), 7.63~7.66(2H, t), 7.29~7.51(13H, m) |
| 919 | δ = 8.81(2H, d), 8.23(1H, s), 8.06(1H, m), 8.23(1H, d), 7.94~7.95(2H, m), 7.79~7.87(6H, d), 7.28~7.66(14H, m), 1.72(6H, s) |
| 920 | δ = 8.81(2H, d), 8.55(1H, d), 8.33(2H, d), 8.27(1H, s), 8.23(1H, s), 8.12(2H, d), 8.03(1H, d), 7.89~7.94(2H, m), 7.79(4H, d), 7.63~7.68(4H, m), 7.25~7.52(14H, m) |
| 923 | δ = 8.81(2H, d), 8.27(1H, s), 8.23(1H, s), 8.12(1H, d), 8.03(1H, d), 7.66~7.89(12H, m), 7.32~7.57(15H, m) |
| 926 | δ = 8.81(2H, d), 8.51(1H, d), 8.45(1H, d), 8.28(4H, d), 8.16(1H, m), 8.06(1H, d), 7.98(1H, d), 7.88(2H, d), 7.81(1H, d), 7.67(2H, t), 7.41~7.52(8H, m) |
| 927 | δ = 8.45~8.55(3H, m), 8.28~8.30(3H, m), 8.12~8.26(4H, m), 8.06(1H, d), 7.94~7.98(2H, m), 7.81~7.79(3H, m), 7.67~7.68(4H, m), 7.60(1H, m), 7.50~7.52(6H, m), 7.25~7.41(3H, m) |
| 928 | δ = 8.81(2H, d), 8.51(1H, t), 8.46(1H, m), 8.24~8.28(3H, m), 8.16(1H, m), 8.06(1H, m), 7.98(1H, m), 7.81~7.89(6H, m), 7.66~7.70(4H, m), 7.32~7.57(10H, m) |
| 932 | δ = 8.81(2H, d), 8.51(1H, d), 8.45(2H, m), 8.41(1H, m), 8.28(2H, d), 8.20(1H, d), 8.16(1H, m), 8.06(1H, d), 7.98(2H, d), 7.81~7.88(5H, m), 7.67(2H, m), 7.41~7.58(8H, m), 7.25(2H, d) |
| 936 | δ = 9.30(2H, d), 9.15(2H, s), 8.81(2H, d), 8.45~8.53(4H, m), 8.16(1H, m), 8.06(1H, d), 7.98(1H, m), 7.88(2H, d), 7.81(1H, m), 7.67~7.70(4H, m), 7.50~7.52(2H, m), 7.25(4H, s), 7.14(1H, t) |
| 937 | δ = 8.81(2H, d), 8.51(1H, m), 8.45(1H, m), 8.15(1H, m), 8.06(1H, d), 7.98(1H, m), 7.88(2H, d), 7.66~7.81(9H, m), 7.45~7.52(10H, m) |
| 943 | δ = 8.51~8.55(2H, m), 8.28~8.30(4H, m), 8.26(1H, s), 8.06~8.21(4H, m), 7.94(1H, d), 7.89(1H, d), 7.81(1H, d), 7.66~7.67(3H, m), 7.25~7.63(12H, m) |
| 945 | δ = 8.51(1H, t), 8.30(2H, d), 8.16~8.26(4H, m), 8.06(1H, d), 7.85~7.89(5H, m), 7.66~7.67(3H, m), 7.54~7.60(3H, m), 7.51~7.52(8H, m), 7.32~7.41(4H, m) |
| 950 | δ = 8.81(2H, d), 8.45(1H, m), 8.28(4H, t), 8.16(2H, m), 8.05(1H, s), 7.98(1H, m), 7.88(2H, m), 7.67~7.68(3H, m), 7.50~7.52(6H, m), 7.41(2H, m) |
| 952 | δ = 8.81(2H, d), 8.45(1H, m), 8.28(2H, m), 8.24(1H, m), 8.16(2H, m), 8.05(1H, s), 7.98(1H, m), 7.81~7.89(5H, m), 7.70(1H, m), 7.66~7.68(4H, m), 7.50~7.52(4H, m), 7.32~7.48(4H, m) |
| 954 | δ = 8.81(2H, d), 8.45(1H, m), 8.33(2H, d), 8.23(1H, d), 8.16(2H, m), 8.05(1H, s), 7.98(1H, m), 7.85(2H, d), 7.79(2H, d), 7.67~7.68(2H, m), 7.50~7.52(8H, m), 7.41(2H, m), 7.25(2H, d) |
| 956 | δ = 8.81(2H, d), 8.41~8.45(3H, m), 8.28(2H, d), 8.16~8.20(3H, m), 8.05(1H, s), 7.98(1H, d), 7.88(2H, d), 7.85(2H, d), 7.68(1H, m), 7.67(2H, m), 7.50~7.53(7H, m), 7.41(1H, m), 7.25(2H, d) |
| 959 | δ = 8.81(2H, d), 8.45(1H, m), 8.23(1H, s), 8.16(2H, m), 8.05(1H, s), 7.79~7.98(6H, m), 7.50~7.75(9H, m), 7.32~7.48(5H, m) |
| 961 | δ = 8.81(2H, d), 8.45(1H, m), 8.16(2H, m), 8.05(1H, s), 7.98(1H, m), 7.88(2H, d), 7.66~7.68(4H, m), 7.73~7.77(4H, m), 7.50~7.52(4H, m), 7.45(5H, m) |
| 962 | δ = 8.81(2H, d), 8.28(4H, m), 8.16(2H, m), 8.05(1H, s), 7.88~7.89(3H, m), 7.67~7.68(3H, m), 7.51(4H, m), 7.41(2H, m), 7.32~7.38(2H, m) |
| 969 | δ = 8.30(2H, d), 8.21~8.26(3H, m), 8.05(1H, s), 7.89(1H, d), 7.85(4H, m), 7.32~7.75(22H, m), 7.25(2H, d) |
| 971 | δ = 8.81(2H, d), 8.23(1H, s), 8.16(2H, m), 8.05(1H, s), 7.81~7.89(8H, m), 7.66~7.79(9H, m), 7.32~7.51(7H, m) |
| 977 | δ = 8.54(1H, m), 8.45(1H, m), 8.16~8.28(6H, m), 7.98~7.99(3H, m), 7.85(2H, d), 7.41~7.67(17H, m), 7.25(2H, d) |
| 978 | δ = 8.81(2H, d), 8.54(1H, m), 8.45(1H, m), 8.33(2H, d), 8.23(1H, s), 8.16(1H, m), 7.98~7.99(2H, m), 7.85(2H, d), 7.79(2H, d), 7.67(2H, m), 7.50~7.52(8H, m), 7.41(2H, m), 7.25(2H, d) |
| 980 | δ = 8.81(2H, d), 8.54(1H, m), 8.41~8.45(3H, m), 8.28(2H, m), 8.16~8.20(2H, m), 7.98~7.99(4H, m), 7.88(2H, m), 7.85(2H, d), 7.67(2H, m), 7.58(1H, s), 7.50~7.52(6H, m), 7.41(1H, m), 7.25(2H, d) |
| 986 | δ = 8.81(2H, d), 8.54(1H, m), 8.28(4H, m), 8.16(1H, m), 7.89~7.99(2H, s), 7.88~7.89(3H, m), 7.66~7.67(3H, m), 7.51(4H, m), 7.41(2H, m), 7.32~7.38(2H, m) |
| 990 | δ = 8.81(2H, d), 8.54(1H, m), 8.33(2H, d), 8.16(1H, m), 7.89~7.99(2H, m), 7.79~7.89(5H, m), 7.66~7.67(3H, m), 7.51~7.52(6H, m), 7.32~7.41(4H, m), 7.25(2H, d) |
| 996 | δ = 9.30(2H, d), 9.15(2H, s), 8.81(2H, d), 8.53~8.54(3H, m), 8.16(1H, m), 7.98~7.99(2H, s), 7.88~7.89(2H, m), 7.66~7.70(5H, m), 7.32~7.38(2H, m), 7.25(4H, s), 7.14(2H, t) |
| 998 | δ = 8.81(2H, d), 8.45(1H, m), 8.27~8.30(5H, m), 7.98~8.12(6H, m), 7.88(2H, m), 7.81(1H, d), 7.47~7.54(8H, m), 7.35(2H, d) |
| 999 | δ = 8.81(2H, d), 8.55(1H, m), 8.45~8.46(2H, m), 8.30(2H, d), 8.21(1H, d), 7.98~8.10(7H, m), 7.81(1H, d), 7.64~7.66(2H, m), 7.47~7.55(7H, m), 7.35(2H, d), 7.28(2H, d) |
| 1002 | δ = 8.81(4H, d), 8.45(1H, m), 8.27~8.30(3H, m), 7.98~8.12(6H, m), 7.88(4H, m), 7.81(1H, d), 7.47~7.54(9H, m), 7.35~7.41(3H, m) |
| 1003 | δ = 8.81(4H, d), 8.55(1H, m), 8.45(2H, m), 8.30(2H, d), 8.21(1H, d), 7.98~8.10(7H, m), 7.81(1H, d), 7.50~7.66(9H, m), 7.35(2H, d), 7.28(4H, d) |
| 1008 | δ = 8.93(2H, d), 8.81(2H, d), 8.44(1H, s), 8.30(2H, d), 8.21(1H, d), 8.04~8.12(6H, m), 7.81~7.90(9H, m), 7.66(1H, d), 7.32~7.54(7H, m) |
| 1012 | δ = 8.81(2H, d), 8.21~8.30(5H, m), 8.04~8.10(4H, m), 7.88~7.90(4H, m), 7.81(1H, d), 7.32~7.66(15H, m) |
| 1013 | δ = 8.81(2H, d), 8.55(1H, m), 8.42(1H, m), 8.24~8.30(4H, m), 7.89~8.10(8H, m), 7.81(1H, d), 7.28~7.66(15H, m) |
| 1014 | δ = 8.84(4H, d), 8.45(1H, m), 8.27~8.30(3H, m), 7.98~8.12(6H, m), 7.81(1H, d), 7.47~7.54(9H, m), 7.35~7.41(3H, m) |
| 1016 | δ = 8.93(2H, d), 8.84(4H, s), 8.45(1H, m), 8.30(2H, d), 8.21(1H, d), 7.81~8.12(14H, m), 7.47~7.54(5H, m), 7.35(2H, d) |
| 1018 | δ = 8.84(4H, s), 8.45(4H, m), 8.27~8.60(3H, m), 7.98~8.12(6H, m), 7.81~7.89(4H, m), 7.66(1H, m), 7.32~7.54(10H, m) |

TABLE 58-continued

| NO | $^1$H NMR (CDCl$_3$, 300 Mz) |
|---|---|
| 1019 | δ = 8.84(4H, s), 8.41~8.45(3H, m), 8.30(2H, d), 8.20(1H, m), 7.98~8.10(6H, m), 7.81(1H, d), 7.47~7.66(9H, m), 7.35(2H, d) |
| 1020 | δ = 8.84(4H, s), 8.45(1H, m), 8.51(1H, m), 8.30(2H, d), 7.98~8.10(6H, m), 7.81(2H, d), 7.67(2H, m), 7.47~7.54(5H, m), 7.35(2H, d) |
| 1022 | δ = 8.84(4H, s), 8.54(1H, m), 8.45(1H, m), 8.30(2H, d), 7.98~8.10(7H, m), 7.81(1H, d), 7.67(2H, m), 7.47~7.54(5H, m), 7.35(2H, d) |
| 1024 | δ = 8.84(4H, s), 8.55(1H, m), 8.42(1H, d), 8.30(2H, d), 8.21(1H, d), 8.02~8.10(6H, m), 7.89(1H, d), 7.81(1H, d), 7.32~7.66(12H, m) |
| 1026 | δ = 8.93(2H, d), 8.84(4H, s), 8.30(2H, d), 7.81~8.12(17H, m), 7.68(1H, d), 7.32~7.54(7H, m) |

TABLE 59

| Compound | FD-MS | Compound | FD-MS |
|---|---|---|---|
| 1 | m/z = 542.65 (C36H22N4S = 542.16) | 2 | m/z = 618.75 (C42H26N4S = 618.19) |
| 3 | m/z = 694.84 (C48H30N4S = 694.22) | 4 | m/z = 618.75 (C42H26N4S = 618.19) |
| 5 | m/z = 694.84 (C48H30N4S = 694.22) | 6 | m/z = 694.84 (C48H30N4S = 694.22) |
| 7 | m/z = 770.94 (C54H34N4S = 770.25) | 8 | m/z = 694.84 (C48H30N4S = 694.22) |
| 9 | m/z = 770.94 (C54H34N4S = 770.25) | 10 | m/z = 618.75 (C42H26N4S = 618.19) |
| 11 | m/z = 542.65 (C36H22N4S = 542.16) | 12 | m/z = 694.84 (C48H30N4S = 694.22) |
| 13 | m/z = 618.75 (C42H26N4S = 618.19) | 14 | m/z = 694.84 (C48H30N4S = 694.22) |
| 15 | m/z = 770.94 (C54H34N4S = 770.25) | 16 | m/z = 618.75 (C42H26N4S = 618.19) |
| 17 | m/z = 770.94 (C54H34N4S = 770.25) | 18 | m/z = 542.65 (C36H22N4S = 542.16) |
| 19 | m/z = 618.75 (C42H26N4S = 618.19) | 20 | m/z = 694.84 (C48H30N4S = 694.22) |
| 21 | m/z = 618.75 (C42H26N4S = 618.19) | 22 | m/z = 694.84 (C48H30N4S = 694.22) |
| 23 | m/z = 770.94 (C54H34N4S = 770.25) | 24 | m/z = 618.75 (C42H26N4S = 618.19) |
| 25 | m/z = 770.94 (C54H34N4S = 770.25) | 26 | m/z = 542.65 (C36H22N4S = 542.16) |
| 27 | m/z = 618.75 (C42H26N4S = 618.19) | 28 | m/z = 694.84 (C48H30N4S = 694.22) |
| 29 | m/z = 618.75 (C42H26N4S = 618.19) | 30 | m/z = 694.84 (C48H30N4S = 694.22) |
| 31 | m/z = 770.94 (C54H34N4S = 770.25) | 32 | m/z = 618.75 (C42H26N4S = 618.19) |
| 33 | m/z = 770.94 (C54H34N4S = 770.25) | 34 | m/z = 663.76 (C45H30NOPS = 663.18) |
| 35 | m/z = 663.76 (C45H30NOPS = 663.18) | 36 | m/z = 592.71 (C40H24N4S = 592.17) |
| 37 | m/z = 668.81 (C46H28N4S = 668.20) | 38 | m/z = 668.81 (C46H28N4S = 668.20) |
| 39 | m/z = 744.90 (C52H32N4S = 744.23) | 40 | m/z = 668.81 (C46H28N4S = 668.20) |
| 41 | m/z = 821.00 (C58H36N4S = 820.27) | 42 | m/z = 592.71 (C40H24N4S = 592.17) |
| 43 | m/z = 668.81 (C46H28N4S = 668.20) | 44 | m/z = 668.81 (C46H28N4S = 668.20) |
| 45 | m/z = 744.90 (C52H32N4S = 744.23) | 46 | m/z = 668.81 (C46H28N4S = 668.20) |
| 47 | m/z = 821.00 (C58H36N4S = 820.27) | 48 | m/z = 592.71 (C40H24N4S = 592.17) |
| 49 | m/z = 668.81 (C46H28N4S = 668.20) | 50 | m/z = 668.81 (C46H28N4S = 668.20) |
| 51 | m/z = 744.90 (C52H32N4S = 744.23) | 52 | m/z = 821.00 (C58H36N4S = 820.27) |
| 53 | m/z = 668.81 (C46H28N4S = 668.20) | 54 | m/z = 542.65 (C36H22N4S = 542.16) |
| 55 | m/z = 618.75 (C42H26N4S = 618.19) | 56 | m/z = 668.81 (C46H28N4S = 668.20) |
| 57 | m/z = 744.90 (C52H32N4S = 744.23) | 58 | m/z = 668.81 (C46H28N4S = 668.20) |
| 59 | m/z = 668.81 (C46H28N4S = 668.20) | 60 | m/z = 744.90 (C52H32N4S = 744.23) |
| 61 | m/z = 744.90 (C52H32N4S = 744.23) | 62 | m/z = 642.77 (C44H26N4S = 642.19) |

TABLE 59-continued

| Compound | FD-MS | Compound | FD-MS |
|---|---|---|---|
| 63 | m/z = 718.87 (C50H30N4S = 718.22) | 64 | m/z = 718.87 (C50H30N4S = 718.22) |
| 65 | m/z = 718.87 (C50H30N4S = 718.22) | 66 | m/z = 642.77 (C44H26N4S = 642.19) |
| 67 | m/z = 794.96 (C56H34N4S = 794.25) | 68 | m/z = 718.87 (C50H30N4S = 718.22) |
| 69 | m/z = 794.96 (C56H34N4S = 794.25) | 70 | m/z = 642.77 (C44H26N4S = 642.19) |
| 71 | m/z = 718.87 (C50H30N4S = 718.22) | 72 | m/z = 718.87 (C50H30N4S = 718.22) |
| 73 | m/z = 794.96 (C56H34N4S = 794.25) | 74 | m/z = 718.87 (C50H30N4S = 718.22) |
| 75 | m/z = 642.77 (C44H26N4S = 642.19) | 76 | m/z = 718.87 (C50H30N4S = 718.22) |
| 77 | m/z = 794.96 (C56H34N4S = 794.25) | 78 | m/z = 718.87 (C50H30N4S = 718.22) |
| 79 | m/z = 718.87 (C50H30N4S = 718.22) | 80 | m/z = 794.96 (C56H34N4S = 794.25) |
| 81 | m/z = 794.96 (C56H34N4S = 794.25) | 82 | m/z = 692.83 (C48H28N4S = 692.20) |
| 83 | m/z = 766.91 (C54H30N4S = 766.22) | 84 | m/z = 768.92 (C54H32N4S = 768.23) |
| 85 | m/z = 845.02 (C60H36N4S = 844.27) | 86 | m/z = 768.92 (C54H32N4S = 768.23) |
| 87 | m/z = 692.83 (C48H28N4S = 692.20) | 88 | m/z = 768.92 (C54H32N4S = 768.23) |
| 89 | m/z = 768.92 (C54H32N4S = 768.23) | 90 | m/z = 692.83 (C48H28N4S = 692.20) |
| 91 | m/z = 768.92 (C54H32N4S = 768.23) | 92 | m/z = 768.92 (C54H32N4S = 768.23) |
| 93 | m/z = 768.92 (C54H32N4S = 768.23) | 94 | m/z = 692.83 (C48H28N4S = 692.20) |
| 95 | m/z = 768.92 (C54H32N4S = 768.23) | 96 | m/z = 768.92 (C54H32N4S = 768.23) |
| 97 | m/z = 768.92 (C54H32N4S = 768.23) | 98 | m/z = 768.92 (C54H32N4S = 768.23) |
| 99 | m/z = 781.92 (C54H31N5S = 781.23) | 100 | m/z = 808.99 (C57H36N4S = 808.27) |
| 101 | m/z = 737.84 (C51H32NOPS = 737.19) | 102 | m/z = 526.59 (C36H22N4O = 526.18) |
| 103 | m/z = 602.68 (C42H26N4O = 602.21) | 104 | m/z = 678.78 (C48H30N4O = 678.24) |
| 105 | m/z = 602.68 (C42H26N4O = 602.21) | 106 | m/z = 678.78 (C48H30N4O = 678.24) |
| 107 | m/z = 678.78 (C48H30N4O = 678.24) | 108 | m/z = 754.87 (C54H34N4O = 754.27) |
| 109 | m/z = 678.78 (C48H30N4O = 678.24) | 110 | m/z = 754.87 (C54H34N4O = 754.27) |
| 111 | m/z = 526.59 (C36H22N4O = 526.18) | 112 | m/z = 602.68 (C42H26N4O = 602.21) |
| 113 | m/z = 678.78 (C48H30N4O = 678.24) | 114 | m/z = 602.68 (C42H26N4O = 602.21) |
| 115 | m/z = 678.78 (C48H30N4O = 678.24) | 116 | m/z = 754.87 (C54H34N4O = 754.27) |
| 117 | m/z = 602.68 (C42H26N4O = 602.21) | 118 | m/z = 754.87 (C54H34N4O = 754.27) |
| 119 | m/z = 526.59 (C36H22N4O = 526.18) | 120 | m/z = 602.68 (C42H26N4O = 602.21) |
| 121 | m/z = 678.78 (C48H30N4O = 678.24) | 122 | m/z = 602.68 (C42H26N4O = 602.21) |
| 123 | m/z = 678.78 (C48H30N4O = 678.24) | 124 | m/z = 754.87 (C54H34N4O = 754.27) |
| 125 | m/z = 602.68 (C42H26N4O = 602.21) | 126 | m/z = 754.87 (C54H34N4O = 754.27) |
| 127 | m/z = 526.59 (C36H22N4O = 526.18) | 128 | m/z = 602.68 (C42H26N4O = 602.21) |
| 129 | m/z = 678.78 (C48H30N4O = 678.24) | 130 | m/z = 602.68 (C42H26N4O = 602.21) |
| 131 | m/z = 678.78 (C48H30N4O = 678.24) | 132 | m/z = 754.87 (C54H34N4O = 754.27) |
| 133 | m/z = 602.68 (C42H26N4O = 602.21) | 134 | m/z = 754.87 (C54H34N4O = 754.27) |
| 135 | m/z = 647.70 (C45H30NO2P = 647.20) | 136 | m/z = 576.64 (C40H24N4O = 576.20) |
| 137 | m/z = 652.74 (C46H28N4O = 652.23) | 138 | m/z = 652.74 (C46H28N4O = 652.23) |
| 139 | m/z = 728.84 (C52H32N4O = 728.26) | 140 | m/z = 652.74 (C46H28N4O = 652.23) |

TABLE 59-continued

| Compound | FD-MS | Compound | FD-MS |
| --- | --- | --- | --- |
| 141 | m/z = 804.93 (C58H36N4O = 804.29) | 142 | m/z = 576.64 (C40H24N4O = 576.20) |
| 143 | m/z = 652.74 (C46H28N4O = 652.23) | 144 | m/z = 728.84 (C52H32N4O = 728.26) |
| 145 | m/z = 804.93 (C58H36N4O = 804.29) | 146 | m/z = 652.74 (C46H28N4O = 652.23) |
| 147 | m/z = 804.93 (C58H36N4O = 804.29) | 148 | m/z = 576.64 (C40H24N4O = 576.20) |
| 149 | m/z = 652.74 (C46H28N4O = 652.23) | 150 | m/z = 728.84 (C52H32N4O = 728.26) |
| 151 | m/z = 652.74 (C46H28N4O = 652.23) | 152 | m/z = 728.84 (C52H32N4O = 728.26) |
| 153 | m/z = 804.93 (C58H36N4O = 804.29) | 154 | m/z = 652.74 (C46H28N4O = 652.23) |
| 155 | m/z = 576.64 (C40H24N4O = 576.20) | 156 | m/z = 652.74 (C46H28N4O = 652.23) |
| 157 | m/z = 728.84 (C52H32N4O = 728.26) | 158 | m/z = 804.93 (C58H36N4O = 804.29) |
| 159 | m/z = 652.74 (C46H28N4O = 652.23) | 160 | m/z = 652.74 (C46H28N4O = 652.23) |
| 161 | m/z = 728.84 (C52H32N4O = 728.26) | 162 | m/z = 728.84 (C52H32N4O = 728.26) |
| 163 | m/z = 626.70 (C44H26N4O = 626.21) | 164 | m/z = 702.80 (C50H30N4O = 702.24) |
| 165 | m/z = 702.80 (C50H30N4O = 702.24) | 166 | m/z = 626.70 (C44H26N4O = 626.21) |
| 167 | m/z = 702.80 (C50H30N4O = 702.24) | 168 | m/z = 702.80 (C50H30N4O = 702.24) |
| 169 | m/z = 626.70 (C44H26N4O = 626.21) | 170 | m/z = 702.80 (C50H30N4O = 702.24) |
| 171 | m/z = 702.80 (C50H30N4O = 702.24) | 172 | m/z = 778.90 (C56H34N4O = 778.27) |
| 173 | m/z = 702.80 (C50H30N4O = 702.24) | 174 | m/z = 626.70 (C44H26N4O = 626.21) |
| 175 | m/z = 702.80 (C50H30N4O = 702.24) | 176 | m/z = 778.90 (C56H34N4O = 778.27) |
| 177 | m/z = 702.80 (C50H30N4O = 702.24) | 178 | m/z = 778.90 (C56H34N4O = 778.27) |
| 179 | m/z = 676.76 (C48H28N4O = 676.23) | 180 | m/z = 752.86 (C54H32N4O = 752.26) |
| 181 | m/z = 752.86 (C54H32N4O = 752.26) | 182 | m/z = 676.76 (C48H28N4O = 676.23) |
| 183 | m/z = 752.86 (C54H32N4O = 752.26) | 184 | m/z = 752.86 (C54H32N4O = 752.26) |
| 185 | m/z = 752.86 (C54H32N4O = 752.26) | 186 | m/z = 676.76 (C48H28N4O = 676.23) |
| 187 | m/z = 752.86 (C54H32N4O = 752.26) | 188 | m/z = 752.86 (C54H32N4O = 752.26) |
| 189 | m/z = 752.86 (C54H32N4O = 752.26) | 190 | m/z = 676.76 (C48H28N4O = 676.23) |
| 191 | m/z = 752.86 (C54H32N4O = 752.26) | 192 | m/z = 752.86 (C54H32N4O = 752.26) |
| 193 | m/z = 752.86 (C54H32N4O = 752.26) | 194 | m/z = 752.86 (C54H32N4O = 752.26) |
| 195 | m/z = 765.86 (C54H31N5O = 765.25) | 196 | m/z = 792.92 (C57H36N4O = 792.29) |
| 197 | m/z = 721.78 (C51H32NO2P = 721.22) | 198 | m/z = 691.78 (C48H29N5O = 691.24) |
| 199 | m/z = 691.78 (C48H29N5O = 691.24) | 200 | m/z = 692.76 (C48H28N4O2 = 692.22) |
| 201 | m/z = 692.76 (C48H28N4O2 = 692.22) | 202 | m/z = 708.83 (C48H28N4OS = 708.20) |
| 203 | m/z = 708.83 (C48H28N4OS = 708.20) | 204 | m/z = 541.66 (C37H23N3S = 541.16) |
| 205 | m/z = 617.76 (C43H27N3S = 617.19) | 206 | m/z = 541.66 (C37H23N3S = 541.16) |
| 207 | m/z = 617.76 (C43H27N3S = 617.19) | 208 | m/z = 617.76 (C43H27N3S = 617.19) |
| 209 | m/z = 617.76 (C43H27N3S = 617.19) | 210 | m/z = 693.86 (C49H31N3S = 693.22) |
| 211 | m/z = 693.86 (C49H31N3S = 693.22) | 212 | m/z = 693.86 (C49H31N3S = 693.22) |
| 213 | m/z = 769.95 (C55H35N3S = 769.26) | 214 | m/z = 769.95 (C55H35N3S = 769.26) |
| 215 | m/z = 617.76 (C43H27N3S = 617.19) | 216 | m/z = 693.86 (C49H31N3S = 693.22) |
| 217 | m/z = 693.86 (C49H31N3S = 693.22) | 218 | m/z = 541.66 (C37H23N3S = 541.16) |

TABLE 59-continued

| Compound | FD-MS | Compound | FD-MS |
|---|---|---|---|
| 219 | m/z = 617.76 (C43H27N3S = 617.19) | 220 | m/z = 541.66 (C37H23N3S = 541.16) |
| 221 | m/z = 617.76 (C43H27N3S = 617.19) | 222 | m/z = 617.76 (C43H27N3S = 617.19) |
| 223 | m/z = 617.76 (C43H27N3S = 617.19) | 224 | m/z = 693.86 (C49H31N3S = 693.22) |
| 225 | m/z = 769.95 (C55H35N3S = 769.26) | 226 | m/z = 617.76 (C43H27N3S = 617.19) |
| 227 | m/z = 693.86 (C49H31N3S = 693.22) | 228 | m/z = 693.86 (C49H31N3S = 693.22) |
| 229 | m/z = 769.95 (C55H35N3S = 769.26) | 230 | m/z = 541.66 (C37H23N3S = 541.16) |
| 231 | m/z = 617.76 (C43H27N3S = 617.19) | 232 | m/z = 693.86 (C49H31N3S = 693.22) |
| 233 | m/z = 541.66 (C37H23N3S = 541.16) | 234 | m/z = 617.76 (C43H27N3S = 617.19) |
| 235 | m/z = 617.76 (C43H27N3S = 617.19) | 236 | m/z = 837.06 (C59H36N2S2 = 836.23) |
| 237 | m/z = 693.86 (C49H31N3S = 693.22) | 238 | m/z = 769.95 (C55H35N3S = 769.26) |
| 239 | m/z = 617.76 (C43H27N3S = 617.19) | 240 | m/z = 693.86 (C49H31N3S = 693.22) |
| 241 | m/z = 693.86 (C49H31N3S = 693.22) | 242 | m/z = 769.95 (C55H35N3S = 769.26) |
| 243 | m/z = 617.76 (C43H27N3S = 617.19) | 244 | m/z = 617.76 (C43H27N3S = 617.19) |
| 245 | m/z = 541.66 (C37H23N3S = 541.16) | 246 | m/z = 617.76 (C43H27N3S = 617.19) |
| 247 | m/z = 617.76 (C43H27N3S = 617.19) | 248 | m/z = 617.76 (C43H27N3S = 617.19) |
| 249 | m/z = 693.86 (C49H31N3S = 693.22) | 250 | m/z = 769.95 (C55H35N3S = 769.26) |
| 251 | m/z = 617.76 (C43H27N3S = 617.19) | 252 | m/z = 693.86 (C49H31N3S = 693.22) |
| 253 | m/z = 693.86 (C49H31N3S = 693.22) | 254 | m/z = 769.95 (C55H35N3S = 769.26) |
| 255 | m/z = 733.92 (C52H35N3S = 733.26) | 256 | m/z = 591.72 (C41H25N3S = 591.18) |
| 257 | m/z = 667.82 (C47H29N3S = 667.21) | 258 | m/z = 591.72 (C41H25N3S = 591.18) |
| 259 | m/z = 667.82 (C47H29N3S = 667.21) | 260 | m/z = 667.82 (C47H29N3S = 667.21) |
| 261 | m/z = 667.82 (C47H29N3S = 667.21) | 262 | m/z = 743.91 (C53H33N3S = 743.24) |
| 263 | m/z = 820.01 (C59H37N3S = 819.27) | 264 | m/z = 667.82 (C47H29N3S = 667.21) |
| 265 | m/z = 743.91 (C53H33N3S = 743.24) | 266 | m/z = 743.91 (C53H33N3S = 743.24) |
| 267 | m/z = 855.03 (C63H42N4 = 854.34) | 268 | m/z = 829.00 (C61H40N4 = 828.33) |
| 269 | m/z = 591.72 (C41H25N3S = 591.18) | 270 | m/z = 667.82 (C47H29N3S = 667.21) |
| 271 | m/z = 667.82 (C47H29N3S = 667.21) | 272 | m/z = 667.82 (C47H29N3S = 667.21) |
| 273 | m/z = 743.91 (C53H33N3S = 743.24) | 274 | m/z = 820.01 (C59H37N3S = 819.27) |
| 275 | m/z = 667.82 (C47H29N3S = 667.21) | 276 | m/z = 743.91 (C53H33N3S = 743.24) |
| 277 | m/z = 743.91 (C53H33N3S = 743.24) | 278 | m/z = 820.01 (C59H37N3S = 819.27) |
| 279 | m/z = 591.72 (C41H25N3S = 591.18) | 280 | m/z = 667.82 (C47H29N3S = 667.21) |
| 281 | m/z = 743.91 (C53H33N3S = 743.24) | 282 | m/z = 591.72 (C41H25N3S = 591.18) |
| 283 | m/z = 667.82 (C47H29N3S = 667.21) | 284 | m/z = 667.82 (C47H29N3S = 667.21) |
| 285 | m/z = 667.82 (C47H29N3S = 667.21) | 286 | m/z = 743.91 (C53H33N3S = 743.24) |
| 287 | m/z = 667.82 (C47H29N3S = 667.21) | 288 | m/z = 743.91 (C53H33N3S = 743.24) |
| 289 | m/z = 743.91 (C53H33N3S = 743.24) | 290 | m/z = 591.72 (C41H25N3S = 591.18) |
| 291 | m/z = 667.82 (C47H29N3S = 667.21) | 292 | m/z = 591.72 (C41H25N3S = 591.18) |
| 293 | m/z = 667.82 (C47H29N3S = 667.21) | 294 | m/z = 667.82 (C47H29N3S = 667.21) |
| 295 | m/z = 743.91 (C53H33N3S = 743.24) | 296 | m/z = 820.01 (C59H37N3S = 819.27) |

TABLE 59-continued

| Compound | FD-MS | Compound | FD-MS |
|---|---|---|---|
| 297 | m/z = 667.82 (C47H29N3S = 667.21) | 298 | m/z = 743.91 (C53H33N3S = 743.24) |
| 299 | m/z = 743.91 (C53H33N3S = 743.24) | 300 | m/z = 820.01 (C59H37N3S = 819.27) |
| 301 | m/z = 667.82 (C47H29N3S = 667.21) | 302 | m/z = 743.91 (C53H33N3S = 743.24) |
| 303 | m/z = 667.82 (C47H29N3S = 667.21) | 304 | m/z = 667.82 (C47H29N3S = 667.21) |
| 305 | m/z = 641.78 (C45H27N3S = 641.19) | 306 | m/z = 717.88 (C51H31N3S = 717.22) |
| 307 | m/z = 641.78 (C45H27N3S = 641.19) | 308 | m/z = 717.88 (C51H31N3S = 717.22) |
| 309 | m/z = 717.88 (C51H31N3S = 717.22) | 310 | m/z = 717.88 (C51H31N3S = 717.22) |
| 311 | m/z = 793.97 (C57H35N3S = 793.26) | 312 | m/z = 717.88 (C51H31N3S = 717.22) |
| 313 | m/z = 793.97 (C57H35N3S = 793.26) | 314 | m/z = 641.78 (C45H27N3S = 641.19) |
| 315 | m/z = 717.88 (C51H31N3S = 717.22) | 316 | m/z = 641.78 (C45H27N3S = 641.19) |
| 317 | m/z = 717.88 (C51H31N3S = 717.22) | 318 | m/z = 717.88 (C51H31N3S = 717.22) |
| 319 | m/z = 793.97 (C57H35N3S = 793.26) | 320 | m/z = 717.88 (C51H31N3S = 717.22) |
| 321 | m/z = 793.97 (C57H35N3S = 793.26) | 322 | m/z = 793.97 (C57H35N3S = 793.26) |
| 323 | m/z = 641.78 (C45H27N3S = 641.19) | 324 | m/z = 717.88 (C51H31N3S = 717.22) |
| 325 | m/z = 641.78 (C45H27N3S = 641.19) | 326 | m/z = 717.88 (C51H31N3S = 717.22) |
| 327 | m/z = 717.88 (C51H31N3S = 717.22) | 328 | m/z = 717.88 (C51H31N3S = 717.22) |
| 329 | m/z = 793.97 (C57H35N3S = 793.26) | 330 | m/z = 717.88 (C51H31N3S = 717.22) |
| 331 | m/z = 793.97 (C57H35N3S = 793.26) | 332 | m/z = 793.97 (C57H35N3S = 793.26) |
| 333 | m/z = 641.78 (C45H27N3S = 641.19) | 334 | m/z = 717.88 (C51H31N3S = 717.22) |
| 335 | m/z = 641.78 (C45H27N3S = 641.19) | 336 | m/z = 717.88 (C51H31N3S = 717.22) |
| 337 | m/z = 793.97 (C57H35N3S = 793.26) | 338 | m/z = 717.88 (C51H31N3S = 717.22) |
| 339 | m/z = 717.88 (C51H31N3S = 717.22) | 340 | m/z = 793.97 (C57H35N3S = 793.26) |
| 341 | m/z = 717.88 (C51H31N3S = 717.22) | 342 | m/z = 793.97 (C57H35N3S = 793.26) |
| 343 | m/z = 717.88 (C51H31N3S = 717.22) | 344 | m/z = 691.84 (C49H29N3S = 691.21) |
| 345 | m/z = 691.84 (C49H29N3S = 691.21) | 346 | m/z = 767.94 (C55H33N3S = 767.24) |
| 347 | m/z = 767.94 (C55H33N3S = 767.24) | 348 | m/z = 767.94 (C55H33N3S = 767.24) |
| 349 | m/z = 691.84 (C49H29N3S = 691.21) | 350 | m/z = 691.84 (C49H29N3S = 691.21) |
| 351 | m/z = 767.94 (C55H33N3S = 767.24) | 352 | m/z = 767.94 (C55H33N3S = 767.24) |
| 353 | m/z = 767.94 (C55H33N3S = 767.24) | 354 | m/z = 767.94 (C55H33N3S = 767.24) |
| 355 | m/z = 691.84 (C49H29N3S = 691.21) | 356 | m/z = 691.84 (C49H29N3S = 691.21) |
| 357 | m/z = 767.94 (C55H33N3S = 767.24) | 358 | m/z = 767.94 (C55H33N3S = 767.24) |
| 359 | m/z = 767.94 (C55H33N3S = 767.24) | 360 | m/z = 767.94 (C55H33N3S = 767.24) |
| 361 | m/z = 691.84 (C49H29N3S = 691.21) | 362 | m/z = 767.94 (C55H33N3S = 767.24) |
| 363 | m/z = 767.94 (C55H33N3S = 767.24) | 364 | m/z = 767.94 (C55H33N3S = 767.24) |
| 365 | m/z = 767.94 (C55H33N3S = 767.24) | 366 | m/z = 780.93 (C55H32N4S = 780.23) |
| 367 | m/z = 808.00 (C58H37N3S = 807.27) | 368 | m/z = 706.85 (C49H30N4S = 706.22) |
| 369 | m/z = 706.85 (C49H30N4S = 706.22) | 370 | m/z = 707.84 (C49H29N3OS = 707.20) |
| 371 | m/z = 707.84 (C49H29N3OS = 707.20) | 372 | m/z = 723.90 (C49H29N3S2 = 723.18) |
| 373 | m/z = 723.90 (C49H29N3S2 = 723.18) | 374 | m/z = 525.60 (C37H23N3O = 525.18) |

TABLE 59-continued

| Compound | FD-MS | Compound | FD-MS |
|---|---|---|---|
| 375 | m/z = 601.69 (C43H27N3O = 601.22) | 376 | m/z = 677.79 (C49H31N3O = 677.25) |
| 377 | m/z = 525.60 (C37H23N3O = 525.18) | 378 | m/z = 601.69 (C43H27N3O = 601.22) |
| 379 | m/z = 601.69 (C43H27N3O = 601.22) | 380 | m/z = 601.69 (C43H27N3O = 601.22) |
| 381 | m/z = 677.79 (C49H31N3O = 677.25) | 382 | m/z = 677.79 (C49H31N3O = 677.25) |
| 383 | m/z = 753.89 (C55H35N3O = 753.28) | 384 | m/z = 753.89 (C55H35N3O = 753.28) |
| 385 | m/z = 601.69 (C43H27N3O = 601.22) | 386 | m/z = 677.79 (C49H31N3O = 677.25) |
| 387 | m/z = 677.79 (C49H31N3O = 677.25) | 388 | m/z = 525.60 (C37H23N3O = 525.18) |
| 389 | m/z = 601.69 (C43H27N3O = 601.22) | 390 | m/z = 525.60 (C37H23N3O = 525.18) |
| 391 | m/z = 601.69 (C43H27N3O = 601.22) | 392 | m/z = 601.69 (C43H27N3O = 601.22) |
| 393 | m/z = 677.79 (C49H31N3O = 677.25) | 394 | m/z = 601.69 (C43H27N3O = 601.22) |
| 395 | m/z = 677.79 (C49H31N3O = 677.25) | 396 | m/z = 753.89 (C55H35N3O = 753.28) |
| 397 | m/z = 601.69 (C43H27N3O = 601.22) | 398 | m/z = 677.79 (C49H31N3O = 677.25) |
| 399 | m/z = 677.79 (C49H31N3O = 677.25) | 400 | m/z = 753.89 (C55H35N3O = 753.28) |
| 401 | m/z = 525.60 (C37H23N3O = 525.18) | 402 | m/z = 601.69 (C43H27N3O = 601.22) |
| 403 | m/z = 525.60 (C37H23N3O = 525.18) | 404 | m/z = 601.69 (C43H27N3O = 601.22) |
| 405 | m/z = 601.69 (C43H27N3O = 601.22) | 406 | m/z = 601.69 (C43H27N3O = 601.22) |
| 407 | m/z = 677.79 (C49H31N3O = 677.25) | 408 | m/z = 753.89 (C55H35N3O = 753.28) |
| 409 | m/z = 601.69 (C43H27N3O = 601.22) | 410 | m/z = 677.79 (C49H31N3O = 677.25) |
| 411 | m/z = 677.79 (C49H31N3O = 677.25) | 412 | m/z = 753.89 (C55H35N3O = 753.28) |
| 413 | m/z = 525.60 (C37H23N3O = 525.18) | 414 | m/z = 601.69 (C43H27N3O = 601.22) |
| 415 | m/z = 525.60 (C37H23N3O = 525.18) | 416 | m/z = 601.69 (C43H27N3O = 601.22) |
| 417 | m/z = 601.69 (C43H27N3O = 601.22) | 418 | m/z = 601.69 (C43H27N3O = 601.22) |
| 419 | m/z = 677.79 (C49H31N3O = 677.25) | 420 | m/z = 753.89 (C55H35N3O = 753.28) |
| 421 | m/z = 601.69 (C43H27N3O = 601.22) | 422 | m/z = 677.79 (C49H31N3O = 677.25) |
| 423 | m/z = 677.79 (C49H31N3O = 677.25) | 424 | m/z = 753.89 (C55H35N3O = 753.28) |
| 425 | m/z = 575.66 (C41H25N3O = 575.20) | 426 | m/z = 651.75 (C47H29N3O = 651.23) |
| 427 | m/z = 575.66 (C41H25N3O = 575.20) | 428 | m/z = 651.75 (C47H29N3O = 651.23) |
| 429 | m/z = 651.75 (C47H29N3O = 651.23) | 430 | m/z = 651.75 (C47H29N3O = 651.23) |
| 431 | m/z = 727.85 (C53H33N3O = 717.22) | 432 | m/z = 651.75 (C47H29N3O = 651.23) |
| 433 | m/z = 727.85 (C53H33N3O = 727.26) | 434 | m/z = 727.85 (C53H33N3O = 727.26) |
| 435 | m/z = 803.94 (C59H37N3O = 803.29) | 436 | m/z = 575.66 (C41H25N3O = 575.20) |
| 437 | m/z = 575.66 (C41H25N3O = 641.19) | 438 | m/z = 651.75 (C47H29N3O = 651.23) |
| 439 | m/z = 651.75 (C47H29N3O = 651.23) | 440 | m/z = 651.75 (C47H29N3O = 651.23) |
| 441 | m/z = 727.85 (C53H33N3O = 727.26) | 442 | m/z = 803.94 (C59H37N3O = 803.29) |
| 443 | m/z = 651.75 (C47H29N3O = 651.23) | 444 | m/z = 727.85 (C53H33N3O = 727.26) |
| 445 | m/z = 727.85 (C53H33N3O = 727.26) | 446 | m/z = 803.94 (C59H37N3O = 803.29) |
| 447 | m/z = 575.66 (C41H25N3O = 575.20) | 448 | m/z = 651.75 (C47H29N3O = 651.23) |
| 449 | m/z = 575.66 (C41H25N3O = 575.20) | 450 | m/z = 651.75 (C47H29N3O = 651.23) |
| 451 | m/z = 651.75 (C47H29N3O = 651.23) | 452 | m/z = 727.85 (C53H33N3O = 727.26) |

TABLE 59-continued

| Compound | FD-MS | Compound | FD-MS |
|---|---|---|---|
| 453 | m/z = 651.75 (C47H29N3O = 651.23) | 454 | m/z = 727.85 (C53H33N3O = 727.26) |
| 455 | m/z = 803.94 (C59H37N3O = 803.29) | 456 | m/z = 651.75 (C47H29N3O = 651.23) |
| 457 | m/z = 727.85 (C53H33N3O = 727.26) | 458 | m/z = 803.94 (C59H37N3O = 803.29) |
| 459 | m/z = 575.66 (C41H25N3O = 575.20) | 460 | m/z = 651.75 (C47H29N3O = 651.23) |
| 461 | m/z = 651.75 (C47H29N3O = 651.23) | 462 | m/z = 727.85 (C53H33N3O = 727.26) |
| 463 | m/z = 803.94 (C59H37N3O = 803.29) | 464 | m/z = 651.75 (C47H29N3O = 651.23) |
| 465 | m/z = 727.85 (C53H33N3O = 727.26) | 466 | m/z = 727.85 (C53H33N3O = 727.26) |
| 467 | m/z = 651.75 (C47H29N3O = 651.23) | 468 | m/z = 727.85 (C53H33N3O = 727.26) |
| 469 | m/z = 651.75 (C47H29N3O = 793.26) | 470 | m/z = 651.75 (C47H29N3O = 651.23) |
| 471 | m/z = 625.72 (C45H27N3O = 625.22) | 472 | m/z = 701.81 (C51H31N3O = 701.25) |
| 473 | m/z = 625.72 (C45H27N3O = 625.22) | 474 | m/z = 701.81 (C51H31N3O = 701.25) |
| 475 | m/z = 701.81 (C51H31N3O = 701.25) | 476 | m/z = 701.81 (C51H31N3O = 701.25) |
| 478 | m/z = 777.91 (C57H35N3O = 777.28) | 479 | m/z = 777.91 (C57H35N3O = 777.28) |
| 480 | m/z = 625.72 (C45H27N3O = 625.22) | 481 | m/z = 701.81 (C51H31N3O = 701.25) |
| 482 | m/z = 625.72 (C45H27N3O = 625.22) | 483 | m/z = 701.81 (C51H31N3O = 701.25) |
| 484 | m/z = 701.81 (C51H31N3O = 701.25) | 485 | m/z = 701.81 (C51H31N3O = 701.25) |
| 486 | m/z = 777.91 (C57H35N3O = 777.28) | 487 | m/z = 701.81 (C51H31N3O = 701.25) |
| 488 | m/z = 777.91 (C57H35N3O = 777.28) | 489 | m/z = 777.91 (C57H35N3O = 777.28) |
| 490 | m/z = 625.72 (C45H27N3O = 625.22) | 491 | m/z = 701.81 (C51H31N3O = 701.25) |
| 492 | m/z = 777.91 (C57H35N3O = 777.28) | 493 | m/z = 625.72 (C45H27N3O = 625.22) |
| 494 | m/z = 701.81 (C51H31N3O = 701.25) | 495 | m/z = 701.81 (C51H31N3O = 701.25) |
| 496 | m/z = 777.91 (C57H35N3O = 777.28) | 497 | m/z = 701.81 (C51H31N3O = 701.25) |
| 498 | m/z = 701.81 (C51H31N3O = 701.25) | 499 | m/z = 777.91 (C57H35N3O = 777.28) |
| 500 | m/z = 777.91 (C57H35N3O = 777.28) | 501 | m/z = 625.72 (C45H27N3O = 625.22) |
| 502 | m/z = 701.81 (C51H31N3O = 701.25) | 503 | m/z = 625.72 (C45H27N3O = 625.22) |
| 504 | m/z = 701.81 (C51H31N3O = 701.25) | 505 | m/z = 777.91 (C57H35N3O = 777.28) |
| 506 | m/z = 701.81 (C51H31N3O = 701.25) | 507 | m/z = 777.91 (C57H35N3O = 777.28) |
| 508 | m/z = 701.81 (C51H31N3O = 701.25) | 509 | m/z = 777.91 (C57H35N3O = 777.28) |
| 510 | m/z = 701.81 (C51H31N3O = 701.25) | 511 | m/z = 777.91 (C57H35N3O = 777.28) |
| 512 | m/z = 701.81 (C51H31N3O = 701.25) | 513 | m/z = 675.77 (C49H29N3O = 675.23) |
| 514 | m/z = 751.87 (C55H33N3O = 751.26) | 515 | m/z = 675.77 (C49H29N3O = 675.23) |
| 516 | m/z = 751.87 (C55H33N3O = 751.26) | 517 | m/z = 751.87 (C55H33N3O = 751.26) |
| 518 | m/z = 751.87 (C55H33N3O = 751.26) | 519 | m/z = 675.77 (C49H29N3O = 675.23) |
| 520 | m/z = 675.77 (C49H29N3O = 675.23) | 521 | m/z = 751.87 (C55H33N3O = 751.26) |
| 522 | m/z = 751.87 (C55H33N3O = 751.26) | 523 | m/z = 751.87 (C55H33N3O = 751.26) |
| 524 | m/z = 675.77 (C49H29N3O = 675.23) | 525 | m/z = 675.77 (C49H29N3O = 675.23) |
| 526 | m/z = 751.87 (C55H33N3O = 751.26) | 527 | m/z = 751.87 (C55H33N3O = 751.26) |
| 528 | m/z = 751.87 (C55H33N3O = 751.26) | 529 | m/z = 675.77 (C49H29N3O = 675.23) |
| 530 | m/z = 675.77 (C49H29N3O = 675.23) | 531 | m/z = 751.87 (C55H33N3O = 751.26) |

TABLE 59-continued

| Compound | FD-MS | Compound | FD-MS |
|---|---|---|---|
| 532 | m/z = 751.87 (C55H33N3O = 751.26) | 533 | m/z = 764.87 (C55H32N4O = 764.26) |
| 534 | m/z = 791.93 (C58H37N3O = 791.29) | 535 | m/z = 690.79 (C49H30N4O = 690.24) |
| 536 | m/z = 690.79 (C49H30N4O = 690.24) | 537 | m/z = 691.77 (C49H29N3O2 = 691.23) |
| 538 | m/z = 691.77 (C49H29N3O2 = 691.23) | 539 | m/z = 707.84 (C49H29N3OS = 707.20) |
| 540 | m/z = 707.84 (C49H29N3OS = 707.20) | 541 | m/z = 542.65 (C36H22N4S = 542.16) |
| 542 | m/z = 618.75 (C42H26N4S = 618.19) | 543 | m/z = 694.84 (C48H30N4S = 694.22) |
| 544 | m/z = 542.65 (C36H22N4S = 542.16) | 545 | m/z = 618.75 (C42H26N4S = 618.19) |
| 546 | m/z = 592.71 (C40H24N4S = 592.17) | 547 | m/z = 668.81 (C46H28N4S = 668.20) |
| 548 | m/z = 592.71 (C40H24N4S = 592.17) | 549 | m/z = 668.81 (C46H28N4S = 668.20) |
| 550 | m/z = 642.77 (C44H26N4S = 642.19) | 551 | m/z = 718.87 (C50H30N4S = 718.22) |
| 552 | m/z = 642.77 (C44H26N4S = 642.19) | 553 | m/z = 718.87 (C50H30N4S = 718.22) |
| 554 | m/z = 692.83 (C48H28N4S = 692.20) | 555 | m/z = 768.92 (C54H32N4S = 768.23) |
| 556 | m/z = 692.83 (C48H28N4S = 692.20) | 557 | m/z = 768.92 (C54H32N4S = 768.23) |
| 558 | m/z = 526.59 (C36H22N4O = 526.18) | 559 | m/z = 602.68 (C42H26N4O = 602.21) |
| 560 | m/z = 526.59 (C36H22N4O = 526.18) | 561 | m/z = 602.68 (C42H26N4O = 602.21) |
| 562 | m/z = 576.64 (C40H24N4O = 576.20) | 563 | m/z = 652.74 (C46H28N4O = 652.23) |
| 564 | m/z = 576.64 (C40H24N4O = 576.20) | 565 | m/z = 652.74 (C46H28N4O = 652.23) |
| 566 | m/z = 626.70 (C44H26N4O = 626.21) | 567 | m/z = 702.80 (C50H30N4O = 702.24) |
| 568 | m/z = 626.70 (C44H26N4O = 626.21) | 569 | m/z = 702.80 (C50H30N4O = 702.24) |
| 570 | m/z = 676.76 (C48H28N4O = 676.23) | 571 | m/z = 752.86 (C54H32N4O = 752.26) |
| 572 | m/z = 676.76 (C48H28N4O = 676.23) | 573 | m/z = 752.86 (C54H32N4O = 752.26) |
| 574 | m/z = 618.75 (C42H26N4S = 618.19) | 575 | m/z = 694.84 (C48H30N4S = 694.22) |
| 576 | m/z = 694.84 (C48H30N4S = 694.22) | 577 | m/z = 770.94 (C54H34N4S = 770.25) |
| 578 | m/z = 770.94 (C54H34N4S = 770.25) | 579 | m/z = 618.75 (C42H26N4S = 618.19) |
| 580 | m/z = 618.75 (C42H26N4S = 618.19) | 581 | m/z = 694.84 (C48H30N4S = 694.22) |
| 582 | m/z = 618.75 (C42H26N4S = 618.19) | 583 | m/z = 618.75 (C42H26N4S = 618.19) |
| 584 | m/z = 694.84 (C48H30N4S = 694.22) | 585 | m/z = 618.75 (C42H26N4S = 618.19) |
| 586 | m/z = 618.75 (C42H26N4S = 618.19) | 587 | m/z = 618.75 (C42H26N4S = 618.19) |
| 588 | m/z = 770.94 (C54H34N4S = 770.25) | 589 | m/z = 618.75 (C42H26N4S = 618.19) |
| 590 | m/z = 707.84 (C48H29N5S = 707.21) | 591 | m/z = 734.91 (C51H34N4S = 734.25) |
| 592 | m/z = 663.76 (C45H30NOPS = 663.18) | 593 | m/z = 668.81 (C46H28N4S = 668.20) |
| 594 | m/z = 744.90 (C52H32N4S = 744.23) | 595 | m/z = 668.81 (C46H28N4S = 668.20) |
| 596 | m/z = 744.90 (C52H32N4S = 744.23) | 597 | m/z = 668.81 (C46H28N4S = 668.20) |
| 598 | m/z = 668.81 (C46H28N4S = 668.20) | 599 | m/z = 744.90 (C52H32N4S = 744.23) |
| 600 | m/z = 668.81 (C46H28N4S = 668.20) | 601 | m/z = 668.81 (C46H28N4S = 668.20) |
| 602 | m/z = 744.90 (C52H32N4S = 744.23) | 603 | m/z = 668.81 (C46H28N4S = 668.20) |
| 604 | m/z = 718.87 (C50H30N4S = 718.22) | 605 | m/z = 794.96 (C56H34N4S = 794.25) |
| 606 | m/z = 718.87 (C50H30N4S = 718.22) | 607 | m/z = 718.87 (C50H30N4S = 718.22) |
| 608 | m/z = 794.96 (C56H34N4S = 794.25) | 609 | m/z = 718.87 (C50H30N4S = 718.22) |

TABLE 59-continued

| Compound | FD-MS | Compound | FD-MS |
| --- | --- | --- | --- |
| 610 | m/z = 768.92 (C54H32N4S = 768.23) | 611 | m/z = 768.92 (C54H32N4S = 768.23) |
| 612 | m/z = 768.92 (C54H32N4S = 768.23) | 613 | m/z = 768.92 (C54H32N4S = 768.23) |
| 614 | m/z = 768.92 (C54H32N4S = 768.23) | 615 | m/z = 768.92 (C54H32N4S = 768.23) |
| 616 | m/z = 768.92 (C54H32N4S = 768.23) | 617 | m/z = 768.92 (C54H32N4S = 768.23) |
| 618 | m/z = 708.83 (C48H28N4OS = 708.20) | 619 | m/z = 784.92 (C54H32N4OS = 784.23) |
| 620 | m/z = 708.83 (C48H28N4OS = 708.20) | 621 | m/z = 708.83 (C48H28N4OS = 708.20) |
| 622 | m/z = 784.92 (C54H32N4OS = 784.23) | 623 | m/z = 708.83 (C48H28N4OS = 708.20) |
| 624 | m/z = 708.83 (C48H28N4OS = 708.20) | 625 | m/z = 784.92 (C54H32N4OS = 784.23) |
| 626 | m/z = 708.83 (C48H28N4OS = 708.20) | 627 | m/z = 708.83 (C48H28N4OS = 708.20) |
| 628 | m/z = 784.92 (C54H32N4OS = 784.23) | 629 | m/z = 708.83 (C48H28N4OS = 708.20) |
| 630 | m/z = 784.92 (C54H32N4OS = 784.23) | 631 | m/z = 784.92 (C54H32N4OS = 784.23) |
| 632 | m/z = 784.92 (C54H32N4OS = 784.23) | 633 | m/z = 784.92 (C54H32N4OS = 784.23) |
| 634 | m/z = 724.89 (C48H28N4S2 = 724.18) | 635 | m/z = 800.99 (C54H32N4S2 = 717.22) |
| 636 | m/z = 724.89 (C48H28N4S2 = 724.18) | 637 | m/z = 724.89 (C48H28N4S2 = 724.18) |
| 638 | m/z = 800.99 (C54H32N4S2 = 800.21) | 639 | m/z = 724.89 (C48H28N4S2 = 717.22) |
| 640 | m/z = 724.89 (C48H28N4S2 = 724.18) | 641 | m/z = 800.99 (C51H31N3S = 717.22) |
| 642 | m/z = 723.90 (C49H29N3S2 = 723.18) | 643 | m/z = 724.89 (C48H28N4S2 = 724.18) |
| 644 | m/z = 800.99 (C54H32N4S2 = 800.21) | 645 | m/z = 724.89 (C48H28N4S2 = 724.18) |
| 646 | m/z = 800.99 (C54H32N4S2 = 800.21) | 647 | m/z = 800.99 (C54H32N4S2 = 800.21) |
| 648 | m/z = 800.99 (C54H32N4S2 = 800.21) | 649 | m/z = 800.99 (C54H32N4S2 = 717.22) |
| 650 | m/z = 783.94 (C54H33N5S = 783.25) | 651 | m/z = 783.94 (C54H33N5S = 783.25) |
| 652 | m/z = 784.92 (C54H32N4OS = 784.23) | 653 | m/z = 784.92 (C54H32N4OS = 784.23) |
| 654 | m/z = 800.99 (C54H32N4S2 = 800.21) | 655 | m/z = 800.99 (C54H32N4S2 = 800.21) |
| 656 | m/z = 602.68 (C42H26N4O = 602.21) | 657 | m/z = 678.78 (C48H30N4O = 678.24) |
| 658 | m/z = 678.78 (C48H30N4O = 678.24) | 659 | m/z = 754.87 (C54H34N4O = 754.27) |
| 660 | m/z = 602.68 (C42H26N4O = 602.21) | 661 | m/z = 602.68 (C42H26N4O = 602.21) |
| 662 | m/z = 602.68 (C42H26N4O = 602.21) | 663 | m/z = 691.78 (C48H29N5O = 691.24) |
| 664 | m/z = 718.84 (C51H34N4S = 718.27) | 665 | m/z = 602.68 (C42H26N4O = 602.21) |
| 666 | m/z = 678.78 (C48H30N4O = 678.24) | 667 | m/z = 602.68 (C42H26N4O = 602.21) |
| 668 | m/z = 678.78 (C48H30N4O = 678.24) | 669 | m/z = 602.68 (C42H26N4O = 602.21) |
| 670 | m/z = 602.68 (C42H26N4O = 602.21) | 671 | m/z = 678.78 (C48H30N4O = 678.24) |
| 672 | m/z = 602.68 (C42H26N4O = 602.21) | 673 | m/z = 647.70 (C45H30NO2P = 647.20) |
| 674 | m/z = 652.74 (C46H28N4O = 652.23) | 675 | m/z = 804.93 (C58H36N4O = 804.29) |
| 676 | m/z = 652.74 (C46H28N4O = 652.23) | 677 | m/z = 652.74 (C46H28N4O = 652.23) |
| 678 | m/z = 804.93 (C58H36N4O = 804.29) | 679 | m/z = 652.74 (C46H28N4O = 641.19) |
| 680 | m/z = 652.74 (C46H28N4O = 652.23) | 681 | m/z = 804.93 (C58H36N4O = 804.29) |
| 682 | m/z = 652.74 (C46H28N4O = 652.23) | 683 | m/z = 652.74 (C46H28N4O = 652.23) |
| 684 | m/z = 804.93 (C58H36N4O = 804.29) | 685 | m/z = 652.74 (C46H28N4O = 652.23) |
| 686 | m/z = 702.80 (C50H30N4O = 702.24) | 687 | m/z = 854.99 (C62H38N4O = 854.30) |

TABLE 59-continued

| Compound | FD-MS | Compound | FD-MS |
|---|---|---|---|
| 688 | m/z = 702.80 (C50H30N4O = 702.24) | 689 | m/z = 702.80 (C50H30N4O = 702.24) |
| 690 | m/z = 854.99 (C62H38N4O = 854.30) | 691 | m/z = 702.80 (C50H30N4O = 702.24) |
| 692 | m/z = 702.80 (C50H30N4O = 702.24) | 693 | m/z = 778.90 (C56H34N4O = 778.27) |
| 694 | m/z = 702.80 (C50H30N4O = 702.24) | 695 | m/z = 702.80 (C50H30N4O = 702.24) |
| 696 | m/z = 778.90 (C56H34N4O = 778.27) | 697 | m/z = 702.80 (C50H30N4O = 702.24) |
| 698 | m/z = 752.86 (C54H32N4O = 752.26) | 699 | m/z = 752.86 (C54H32N4O = 752.26) |
| 700 | m/z = 752.86 (C54H32N4O = 752.26) | 701 | m/z = 752.86 (C54H32N4O = 752.26) |
| 702 | m/z = 752.86 (C54H32N4O = 752.26) | 703 | m/z = 752.86 (C54H32N4O = 752.26) |
| 704 | m/z = 752.86 (C54H32N4O = 752.26) | 705 | m/z = 752.86 (C54H32N4O = 752.26) |
| 706 | m/z = 692.76 (C48H28N4O2 = 692.22) | 707 | m/z = 768.86 (C54H32N4O2 = 768.25) |
| 708 | m/z = 692.76 (C48H28N4O2 = 692.22) | 709 | m/z = 692.76 (C48H28N4O2 = 692.22) |
| 710 | m/z = 768.86 (C54H32N4O2 = 768.25) | 711 | m/z = 692.76 (C48H28N4O2 = 692.22) |
| 712 | m/z = 692.76 (C48H28N4O2 = 692.22) | 713 | m/z = 768.86 (C54H32N4O2 = 768.25) |
| 714 | m/z = 692.76 (C48H28N4O2 = 692.22) | 715 | m/z = 692.76 (C48H28N4O2 = 692.22) |
| 716 | m/z = 768.86 (C54H32N4O2 = 768.25) | 717 | m/z = 692.76 (C48H28N4O2 = 692.22) |
| 718 | m/z = 768.86 (C54H32N4O2 = 768.25) | 719 | m/z = 768.86 (C54H32N4O2 = 768.25) |
| 720 | m/z = 768.86 (C54H32N4O2 = 768.25) | 721 | m/z = 768.86 (C54H32N4O2 = 768.25) |
| 722 | m/z = 708.83 (C48H28N4OS = 708.20) | 723 | m/z = 784.92 (C54H32N4OS = 784.23) |
| 724 | m/z = 708.83 (C48H28N4OS = 708.20) | 725 | m/z = 708.83 (C48H28N4OS = 708.20) |
| 726 | m/z = 708.83 (C48H28N4OS = 708.20) | 727 | m/z = 708.83 (C48H28N4OS = 708.20) |
| 728 | m/z = 784.92 (C54H32N4OS = 784.23) | 729 | m/z = 708.83 (C48H28N4OS = 708.20) |
| 730 | m/z = 708.83 (C48H28N4OS = 708.20) | 731 | m/z = 784.92 (C54H32N4OS = 784.23) |
| 732 | m/z = 708.83 (C48H28N4OS = 708.20) | 733 | m/z = 784.92 (C54H32N4OS = 784.23) |
| 734 | m/z = 784.92 (C54H32N4OS = 784.23) | 735 | m/z = 784.92 (C54H32N4OS = 784.23) |
| 736 | m/z = 784.92 (C54H32N4OS = 784.23) | 737 | m/z = 767.87 (C54H33N5O = 767.27) |
| 738 | m/z = 767.87 (C54H33N5O = 767.27) | 739 | m/z = 768.86 (C54H32N4O2 = 768.25) |
| 740 | m/z = 768.86 (C54H32N4O2 = 768.25) | 741 | m/z = 784.92 (C54H32N4OS = 784.23) |
| 742 | m/z = 784.92 (C54H32N4OS = 784.23) | 743 | m/z = 617.76 (C43H27N3S = 617.19) |
| 744 | m/z = 693.86 (C49H31N3S = 693.22) | 745 | m/z = 693.86 (C49H31N3S = 693.22) |
| 746 | m/z = 769.95 (C55H35N3S = 769.26) | 747 | m/z = 617.76 (C43H27N3S = 617.19) |
| 748 | m/z = 693.86 (C49H31N3S = 693.22) | 749 | m/z = 769.95 (C55H35N3S = 769.26) |
| 750 | m/z = 617.76 (C43H27N3S = 617.19) | 751 | m/z = 769.95 (C55H35N3S = 769.26) |
| 752 | m/z = 617.76 (C43H27N3S = 617.19) | 753 | m/z = 693.86 (C49H31N3S = 693.22) |
| 754 | m/z = 693.86 (C49H31N3S = 693.22) | 755 | m/z = 618.75 (C42H26N4S = 618.19) |
| 756 | m/z = 617.76 (C43H27N3S = 617.19) | 757 | m/z = 693.86 (C49H31N3S = 693.22) |
| 758 | m/z = 617.76 (C43H27N3S = 617.19) | 759 | m/z = 693.86 (C49H31N3S = 693.22) |
| 760 | m/z = 769.95 (C55H35N3S = 769.26) | 761 | m/z = 617.76 (C43H27N3S = 617.19) |
| 762 | m/z = 693.86 (C49H31N3SS = 693.22) | 763 | m/z = 617.76 (C43H27N3S = 617.19) |
| 764 | m/z = 693.86 (C49H31N3S = 693.22) | 765 | m/z = 769.95 (C55H35N3S = 769.26) |

TABLE 59-continued

| Compound | FD-MS | Compound | FD-MS |
| --- | --- | --- | --- |
| 766 | m/z = 617.76 (C43H27N3S = 617.19) | 767 | m/z = 617.76 (C43H27N3S = 617.19) |
| 768 | m/z = 667.82 (C47H29N3S = 667.21) | 769 | m/z = 743.91 (C53H33N3S = 743.24) |
| 770 | m/z = 667.82 (C47H29N3S = 667.21) | 771 | m/z = 743.91 (C53H33N3S = 743.24) |
| 772 | m/z = 667.82 (C47H29N3S = 667.21) | 773 | m/z = 667.82 (C47H29N3S = 667.21) |
| 774 | m/z = 743.91 (C53H33N3S = 743.24) | 775 | m/z = 743.91 (C53H33N3S = 743.24) |
| 776 | m/z = 667.82 (C47H29N3S = 667.21) | 777 | m/z = 667.82 (C47H29N3S = 667.21) |
| 778 | m/z = 743.24 (C53H33N3S = 743.24) | 779 | m/z = 667.82 (C47H29N3S = 667.21) |
| 780 | m/z = 743.91 (C53H33N3S = 743.24) | 781 | m/z = 667.21 (C47H29N3S = 667.21) |
| 782 | m/z = 743.91 (C53H33N3S = 743.24) | 783 | m/z = 667.82 (C47H29N3S = 667.21) |
| 784 | m/z = 743.91 (C53H33N3S = 743.24) | 785 | m/z = 667.82 (C47H29N3S = 667.21) |
| 786 | m/z = 667.82 (C47H29N3S = 667.21) | 787 | m/z = 717.88 (C51H31N3S = 717.22) |
| 788 | m/z = 793.97 (C57H35N3S = 793.26) | 789 | m/z = 717.88 (C51H31N3S = 717.22) |
| 790 | m/z = 793.97 (C57H35N3S = 793.26) | 791 | m/z = 717.88 (C51H31N3S = 717.22) |
| 792 | m/z = 717.88 (C51H31N3S = 717.22) | 793 | m/z = 793.97 (C57H35N3S = 793.26) |
| 794 | m/z = 793.97 (C57H35N3S = 793.26) | 795 | m/z = 717.88 (C51H31N3S = 717.22) |
| 796 | m/z = 717.88 (C51H31N3S = 717.22) | 797 | m/z = 793.97 (C57H35N3S = 793.26) |
| 798 | m/z = 717.88 (C51H31N3S = 717.22) | 799 | m/z = 793.97 (C57H35N3S = 793.26) |
| 800 | m/z = 717.88 (C51H31N3S = 717.22) | 801 | m/z = 793.97 (C57H35N3S = 793.26) |
| 802 | m/z = 717.88 (C51H31N3S = 717.22) | 803 | m/z = 793.97 (C57H35N3S = 793.26) |
| 804 | m/z = 717.88 (C51H31N3S = 717.22) | 805 | m/z = 717.88 (C51H31N3S = 717.22) |
| 806 | m/z = 767.94 (C55H33N3S = 767.24) | 807 | m/z = 767.94 (C55H33N3S = 767.24) |
| 808 | m/z = 767.94 (C55H33N3S = 767.24) | 809 | m/z = 767.94 (C55H33N3S = 767.24) |
| 810 | m/z = 767.94 (C55H33N3S = 767.24) | 811 | m/z = 767.94 (C55H33N3S = 767.24) |
| 812 | m/z = 707.84 (C49H29N3OS = 707.20) | 813 | m/z = 707.84 (C49H29N3OS = 707.20) |
| 814 | m/z = 707.84 (C49H29N3OS = 707.20) | 815 | m/z = 707.84 (C49H29N3OS = 707.20) |
| 816 | m/z = 707.84 (C49H29N3OS = 707.20) | 817 | m/z = 723.90 (C49H29N3S2 = 723.18) |
| 818 | m/z = 723.90 (C49H29N3S2 = 723.18) | 819 | m/z = 723.90 (C49H29N3S2 = 723.18) |
| 820 | m/z = 723.90 (C49H29N3S2 = 723.18) | 821 | m/z = 723.90 (C49H29N3S2 = 723.18) |
| 822 | m/z = 706.85 (C49H30N4S = 706.22) | 823 | m/z = 733.92 (C52H35N3S = 733.26) |
| 824 | m/z = 782.95 (C55H34N4S = 782.25) | 825 | m/z = 782.95 (C55H34N4S = 782.25) |
| 826 | m/z = 783.94 (C55H33N3OS = 783.23) | 827 | m/z = 783.94 (C55H33N3OS = 783.23) |
| 828 | m/z = 800.00 (C55H33N3S2 = 799.21) | 829 | m/z = 800.00 (C55H33N3S2 = 799.21) |
| 830 | m/z = 601.69 (C43H27N3O = 601.22) | 831 | m/z = 677.79 (C49H31N3O = 677.25) |
| 832 | m/z = 753.89 (C55H35N3O = 753.28) | 833 | m/z = 601.69 (C43H27N3O = 601.22) |
| 834 | m/z = 677.79 (C49H31N3O = 677.25) | 835 | m/z = 677.79 (C49H31N3O = 677.25) |
| 836 | m/z = 601.69 (C43H27N3O = 601.22) | 837 | m/z = 677.79 (C49H31N3O = 677.25) |
| 838 | m/z = 601.69 (C43H27N3O = 601.22) | 839 | m/z = 677.79 (C49H31N3O = 677.25) |
| 840 | m/z = 753.89 (C55H35N3O = 753.28) | 841 | m/z = 602.68 (C42H26N4O = 602.21) |
| 842 | m/z = 601.69 (C43H27N3O = 601.22) | 843 | m/z = 677.79 (C49H31N3O = 677.25) |

TABLE 59-continued

| Compound | FD-MS | Compound | FD-MS |
|---|---|---|---|
| 844 | m/z = 601.69 (C43H27N3O = 601.22) | 845 | m/z = 677.79 (C49H31N3O = 677.25) |
| 846 | m/z = 753.89 (C55H35N3O = 753.28) | 847 | m/z = 601.69 (C43H27N3O = 601.22) |
| 848 | m/z = 677.79 (C49H31N3O = 677.25) | 849 | m/z = 601.69 (C43H27N3O = 601.22) |
| 850 | m/z = 677.79 (C49H31N3O = 677.25) | 851 | m/z = 677.79 (C49H31N3O = 677.25) |
| 852 | m/z = 753.89 (C55H35N3O = 753.28) | 853 | m/z = 601.69 (C43H27N3O = 601.22) |
| 854 | m/z = 601.69 (C43H27N3O = 601.22) | 855 | m/z = 651.75 (C47H29N3O = 651.23) |
| 856 | m/z = 651.75 (C47H29N3O = 651.23) | 857 | m/z = 727.85 (C53H33N3O = 727.26) |
| 858 | m/z = 727.85 (C53H33N3O = 727.26) | 859 | m/z = 651.75 (C47H29N3O = 651.23) |
| 860 | m/z = 727.85 (C53H33N3O = 727.26) | 861 | m/z = 651.75 (C47H29N3O = 651.23) |
| 862 | m/z = 727.85 (C53H33N3O = 727.26) | 863 | m/z = 651.75 (C47H29N3O = 651.23) |
| 864 | m/z = 651.75 (C47H29N3O = 651.23) | 865 | m/z = 727.85 (C53H33N3O = 727.26) |
| 866 | m/z = 651.75 (C47H29N3O = 651.23) | 867 | m/z = 727.85 (C53H33N3O = 727.26) |
| 868 | m/z = 651.75 (C47H29N3O = 651.23) | 869 | m/z = 727.85 (C53H33N3O = 727.26) |
| 870 | m/z = 651.75 (C47H29N3O = 651.23) | 871 | m/z = 727.85 (C53H33N3O = 727.26) |
| 872 | m/z = 651.75 (C47H29N3O = 651.23) | 873 | m/z = 651.75 (C47H29N3O = 651.23) |
| 874 | m/z = 701.81 (C51H31N3O = 701.25) | 875 | m/z = 701.81 (C51H31N3O = 701.25) |
| 876 | m/z = 777.91 (C57H35N3O = 777.28) | 877 | m/z = 777.91 (C57H35N3O = 777.28) |
| 878 | m/z = 701.81 (C51H31N3O = 701.25) | 879 | m/z = 777.91 (C57H35N3O = 777.28) |
| 880 | m/z = 701.81 (C51H31N3O = 701.25) | 881 | m/z = 777.91 (C57H35N3O = 777.28) |
| 882 | m/z = 701.81 (C51H31N3O = 701.25) | 883 | m/z = 701.81 (C51H31N3O = 701.25) |
| 884 | m/z = 777.91 (C57H35N3O = 777.28) | 885 | m/z = 701.81 (C51H31N3O = 701.25) |
| 886 | m/z = 777.91 (C57H35N3O = 777.28) | 887 | m/z = 701.81 (C51H31N3O = 701.25) |
| 888 | m/z = 777.91 (C57H35N3O = 777.28) | 889 | m/z = 701.81 (C51H31N3O = 701.25) |
| 890 | m/z = 777.91 (C57H35N3O = 777.28) | 891 | m/z = 701.81 (C51H31N3O = 701.25) |
| 892 | m/z = 701.81 (C51H31N3O = 701.25) | 893 | m/z = 751.87 (C55H33N3O = 751.26) |
| 894 | m/z = 751.87 (C55H33N3O = 751.26) | 895 | m/z = 827.97 (C61H37N3O = 827.29) |
| 896 | m/z = 827.97 (C61H37N3O = 827.29) | 897 | m/z = 751.87 (C55H33N3O = 751.26) |
| 898 | m/z = 827.97 (C61H37N3O = 827.29) | 899 | m/z = 751.87 (C55H33N3O = 751.26) |
| 900 | m/z = 751.87 (C55H33N3O = 751.26) | 901 | m/z = 691.77 (C49H29N3O2 = 691.23) |
| 902 | m/z = 691.77 (C49H29N3O2 = 691.23) | 903 | m/z = 767.87 (C55H33N3O2 = 767.26) |
| 904 | m/z = 767.87 (C55H33N3O2 = 767.26) | 905 | m/z = 691.77 (C49H29N3O2 = 691.23) |
| 906 | m/z = 767.87 (C55H33N3O2 = 767.26) | 907 | m/z = 691.77 (C49H29N3O2 = 691.23) |
| 908 | m/z = 691.77 (C49H29N3O2 = 691.23) | 909 | m/z = 707.84 (C49H29N3OS = 707.20) |
| 910 | m/z = 707.84 (C49H29N3OS = 707.20) | 911 | m/z = 783.94 (C55H33N3OS = 783.23) |
| 912 | m/z = 783.94 (C55H33N3OS = 783.23) | 913 | m/z = 707.84 (C49H29N3OS = 707.20) |
| 914 | m/z = 783.94 (C55H33N3OS = 783.23) | 915 | m/z = 707.84 (C49H29N3OS = 707.20) |
| 916 | m/z = 707.84 (C49H29N3OS = 707.20) | 917 | m/z = 737.84 (C51H32NOPS = 737.19) |
| 918 | m/z = 690.79 (C49H30N4O = 690.24) | 919 | m/z = 717.85 (C52H35N3O = 717.28) |
| 920 | m/z = 766.88 (C55H34N4O = 766.27) | 921 | m/z = 766.88 (C55H34N4O = 766.27) |

TABLE 59-continued

| Compound | FD-MS | Compound | FD-MS |
|---|---|---|---|
| 922 | m/z = 767.87 (C55H33N3O2 = 767.26) | 923 | m/z = 767.87 (C55H33N3O2 = 767.26) |
| 924 | m/z = 783.94 (C55H33N3OS = 783.23) | 925 | m/z = 783.94 (C55H33N3OS = 783.23) |
| 926 | m/z = 592.71 (C40H24N4S = 592.17) | 927 | m/z = 757.90 (C52H31N5S = 757.23) |
| 928 | m/z = 758.89 (C52H30N4OS = 758.21) | 929 | m/z = 744.90 (C52H32N4S = 744.23) |
| 930 | m/z = 667.82 (C47H29N3S = 667.21) | 931 | m/z = 757.90 (C52H31N5S = 757.23) |
| 932 | m/z = 774.95 (C52H30N4S2 = 774.19) | 933 | m/z = 820.01 (C59H37N3S = 819.27) |
| 934 | m/z = 756.91 (C53H32N4S = 756.23) | 935 | m/z = 757.90 (C53H31N3OS = 757.22) |
| 936 | m/z = 668.81 (C46H28N4S = 668.20) | 937 | m/z = 637.73 (C43H28NOPS = 637.16) |
| 938 | m/z = 576.64 (C40H24N4O = 576.20) | 939 | m/z = 741.84 (C52H31N5O = 741.25) |
| 940 | m/z = 742.82 (C52H30N4O2 = 742.24) | 941 | m/z = 728.84 (C52H32N4O = 728.26) |
| 942 | m/z = 651.75 (C47H29N3O = 651.23) | 943 | m/z = 741.84 (C52H31N5O = 741.25) |
| 944 | m/z = 758.89 (C52H30N4OS = 758.21) | 945 | m/z = 803.94 (C59H37N3O = 803.29) |
| 946 | m/z = 740.85 (C53H32N4O = 740.26) | 947 | m/z = 741.83 (C53H31N3O2 = 741.24) |
| 948 | m/z = 652.74 (C46H28N4O = 652.23) | 949 | m/z = 621.66 (C43H28NO2P = 621.19) |
| 950 | m/z = 592.71 (C40H24N4S = 592.17) | 951 | m/z = 757.90 (C52H31N5S = 757.23) |
| 952 | m/z = 758.89 (C52H30N4OS = 758.21) | 953 | m/z = 744.90 (C52H32N4S = 744.23) |
| 954 | m/z = 667.82 (C47H29N3S = 667.21) | 955 | m/z = 757.90 (C52H31N5S = 757.23) |
| 956 | m/z = 774.95 (C52H30N4S2 = 774.19) | 957 | m/z = 820.01 (C59H37N3S = 819.27) |
| 958 | m/z = 756.91 (C53H32N4S = 756.23) | 959 | m/z = 757.90 (C53H31N3OS = 757.22) |
| 960 | m/z = 668.81 (C46H28N4S = 668.20) | 961 | m/z = 637.73 (C43H28NOPS = 637.16) |
| 962 | m/z = 576.64 (C40H24N4O = 576.20) | 963 | m/z = 741.84 (C52H31N5O = 741.25) |
| 964 | m/z = 742.82 (C52H30N4O2 = 742.24) | 965 | m/z = 728.84 (C52H32N4O = 728.26) |
| 966 | m/z = 651.75 (C47H29N3O = 651.23) | 967 | m/z = 741.84 (C52H31N5O = 741.25) |
| 968 | m/z = 758.89 (C52H30N4OS = 758.21) | 969 | m/z = 803.94 (C59H37N3O = 803.29) |
| 970 | m/z = 740.85 (C53H32N4O = 740.26) | 971 | m/z = 741.83 (C53H31N3O2 = 741.24) |
| 972 | m/z = 652.74 (C46H28N4O = 652.23) | 973 | m/z = 621.66 (C43H28NO2P = 621.19) |
| 974 | m/z = 592.71 (C40H24N4S = 592.17) | 975 | m/z = 757.90 (C52H31N5S = 757.23) |
| 976 | m/z = 758.89 (C52H30N4OS = 758.21) | 977 | m/z = 744.90 (C52H32N4S = 744.23) |
| 978 | m/z = 667.82 (C47H29N3S = 667.21) | 979 | m/z = 757.90 (C52H31N5S = 757.23) |
| 980 | m/z = 774.95 (C52H30N4S2 = 774.19) | 981 | m/z = 820.01 (C59H37N3S = 819.27) |
| 982 | m/z = 756.91 (C53H32N4S = 756.23) | 983 | m/z = 757.90 (C53H31N3OS = 757.22) |
| 984 | m/z = 668.81 (C46H28N4S = 668.20) | 985 | m/z = 637.73 (C43H28NOPS = 637.16) |
| 986 | m/z = 576.64 (C40H24N4O = 576.20) | 987 | m/z = 741.84 (C52H31N5O = 741.25) |
| 988 | m/z = 742.82 (C52H30N4O2 = 742.24) | 989 | m/z = 728.84 (C52H32N4O = 728.26) |
| 990 | m/z = 651.75 (C47H29N3O = 651.23) | 991 | m/z = 741.84 (C52H31N5O = 741.25) |
| 992 | m/z = 758.89 (C52H30N4OS = 758.21) | 993 | m/z = 803.94 (C59H37N3O = 803.29) |
| 994 | m/z = 740.85 (C53H32N4O = 740.26) | 995 | m/z = 741.83 (C53H31N3O2 = 741.24) |
| 996 | m/z = 652.74 (C46H28N4O = 652.23) | 997 | m/z = 621.66 (C43H28NO2P = 621.19) |
| 998 | m/z = 641.78 (C45H27N3S = 641.19) | 999 | m/z = 691.84 (C49H29N3S = 691.21) |

TABLE 59-continued

| Compound | FD-MS | Compound | FD-MS |
|---|---|---|---|
| 1000 | m/z = 741.90 ($C_{53}H_{31}N_3S$ = 741.22) | 1001 | m/z = 791.96 ($C_{57}H_{33}N_3S$ = 791.24) |
| 1002 | m/z = 717.88 ($C_{51}H_{31}N_3S$ = 717.22) | 1003 | m/z = 767.94 ($C_{55}H_{33}N_3S$ = 767.24) |
| 1004 | m/z = 717.88 ($C_{51}H_{31}N_3S$ = 717.22) | 1005 | m/z = 767.94 ($C_{55}H_{33}N_3S$ = 767.24) |
| 1006 | m/z = 625.72 ($C_{45}H_{27}N_3O$ = 625.22) | 1007 | m/z = 675.77 ($C_{49}H_{29}N_3O$ = 675.23) |
| 1008 | m/z = 725.83 ($C_{53}H_{31}N_3O$ = 725.25) | 1009 | m/z = 775.89 ($C_{57}H_{33}N_3O$ = 775.26) |
| 1010 | m/z = 701.81 ($C_{51}H_{31}N_3O$ = 701.25) | 1011 | m/z = 751.87 ($C_{55}H_{33}N_3O$ = 751.26) |
| 1012 | m/z = 701.81 ($C_{51}H_{31}N_3O$ = 701.25) | 1013 | m/z = 751.87 ($C_{55}H_{33}N_3O$ = 751.26) |
| 1014 | m/z = 641.78 ($C_{45}H_{27}N_3S$ = 641.19) | 1015 | m/z = 691.84 ($C_{49}H_{29}N_3S$ = 691.21) |
| 1016 | m/z = 741.90 ($C_{53}H_{31}N_3S$ = 741.22) | 1017 | m/z = 791.96 ($C_{57}H_{33}N_3S$ = 791.24) |
| 1018 | m/z = 731.86 ($C_{51}H_{29}N_3OS$ = 731.20) | 1019 | m/z = 747.93 ($C_{51}H_{29}N_3S_2$ = 747.18) |
| 1020 | m/z = 615.74 ($C_{43}H_{25}N_3S$ = 615.18) | 1021 | m/z = 615.74 ($C_{43}H_{25}N_3S$ = 615.18) |
| 1022 | m/z = 783.94 ($C_{43}H_{25}N_3S$ = 615.18) | 1023 | m/z = 625.72 ($C_{45}H_{27}N_3O$ = 625.22) |
| 1024 | m/z = 675.77 ($C_{49}H_{29}N_3O$ = 675.23) | 1025 | m/z = 725.83 ($C_{53}H_{31}N_3O$ = 725.25) |
| 1026 | m/z = 775.89 ($C_{57}H_{33}N_3O$ = 775.26) | 1027 | m/z = 715.79 ($C_{51}H_{29}N_3O_2$ = 715.23) |
| 1028 | m/z = 731.86 ($C_{51}H_{29}N_3OS$ = 731.20) | 1029 | m/z = 599.68 ($C_{43}H_{25}N_3O$ = 599.20) |
| 1030 | m/z = 599.68 ($C_{43}H_{25}N_3O$ = 599.20) | 1031 | m/z = 599.68 ($C_{43}H_{25}N_3O$ = 599.20) |

<Experimental Example 1>—Manufacture of Organic Light Emitting Device

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum depositor, and the following 4,4',4"-tris(N,N-(2-naphthyl)-phenylamino)triphenylamine (2-TNATA) was introduced to a cell in the vacuum depositor.

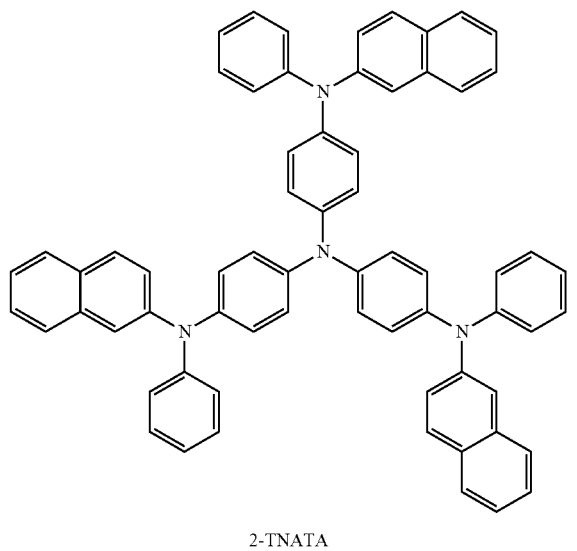

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum depositor, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

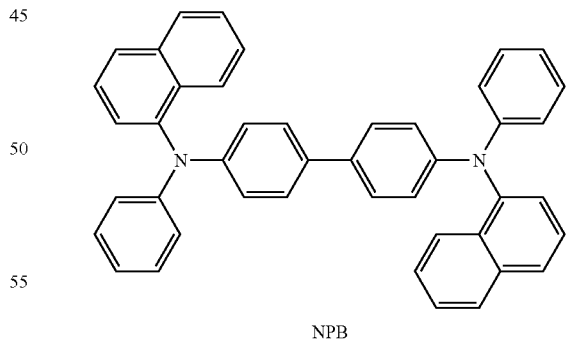

NPB

After forming the hole injection layer and the hole transfer layer as above, a blue light emitting material having a structure as below was deposited thereon as a light emitting layer. Specifically, in one side cell in the vacuum depositor, H1, a blue light emitting host material, was vacuum deposited to a thickness of 200 Å, and D1, a blue light emitting dopant material, was vacuum deposited thereon by 5% with respect to the host material.

H1

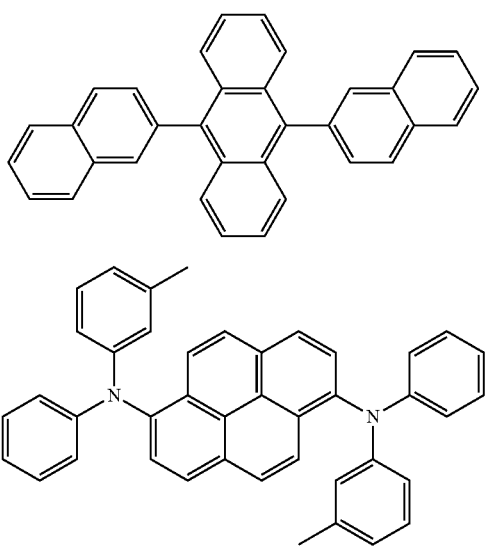

D1

Subsequently, one of compounds described in the following Table 60 was deposited to a thickness of 300 Å as an electron transfer layer.

As an electron injection layer, lithium fluoride (LiF) was deposited to a thickness of 10 Å, and an Al cathode was employed to have a thickness of 1,000 Å to manufacture an OLED.

Meanwhile, all the organic compounds required to manufacture the OLED were vacuum sublimation purified under $10^{-6}$ torr to $10^{-8}$ torr by each material to be used in the OLED manufacture.

Results of measuring a driving voltage, light emission efficiency, a color coordinate (CIE) and a lifetime of the blue organic light emitting device manufactured according to the present disclosure are as shown in the following Table 60.

TABLE 60

| | Compound | Driving Voltage (V) | Light Emission Efficiency (cd/A) | CIE (x, y) | Lifetime (T95) |
|---|---|---|---|---|---|
| Comparative Example 1 | E1 | 5.70 | 6.00 | (0.134, 0.102) | 20 |
| Comparative Example 2 | E2 | 5.71 | 5.98 | (0.134, 0.100) | 22 |
| Comparative Example 3 | E3 | 5.70 | 6.03 | (0.134, 0.101) | 22 |
| Comparative Example 4 | E4 | 5.73 | 6.00 | (0.134, 0.102) | 20 |
| Example 1 | 1 | 5.44 | 6.11 | (0.134, 0.101) | 34 |
| Example 2 | 4 | 5.46 | 6.21 | (0.134, 0.102) | 36 |
| Example 3 | 5 | 5.63 | 5.93 | (0.134, 0.103) | 40 |
| Example 4 | 9 | 4.98 | 6.45 | (0.134, 0.100) | 39 |
| Example 5 | 13 | 5.61 | 6.39 | (0.134, 0.101) | 35 |
| Example 6 | 24 | 4.77 | 6.21 | (0.134, 0.102) | 37 |
| Example 7 | 16 | 5.48 | 6.40 | (0.134, 0.103) | 37 |
| Example 8 | 34 | 5.46 | 6.32 | (0.134, 0.102) | 36 |
| Example 9 | 44 | 5.65 | 6.25 | (0.134, 0.102) | 40 |
| Example 10 | 57 | 5.42 | 6.20 | (0.134, 0.103) | 45 |
| Example 11 | 64 | 5.61 | 6.25 | (0.134, 0.102) | 42 |
| Example 12 | 65 | 5.44 | 6.21 | (0.134, 0.102) | 38 |
| Example 13 | 78 | 4.97 | 6.33 | (0.134, 0.100) | 41 |
| Example 14 | 84 | 5.63 | 6.24 | (0.134, 0.100) | 39 |
| Example 15 | 92 | 4.71 | 6.13 | (0.134, 0.100) | 44 |
| Example 16 | 100 | 4.89 | 6.20 | (0.134, 0.101) | 40 |

TABLE 60-continued

| | Compound | Driving Voltage (V) | Light Emission Efficiency (cd/A) | CIE (x, y) | Lifetime (T95) |
|---|---|---|---|---|---|
| Example 17 | 101 | 4.99 | 6.21 | (0.134, 0.100) | 38 |
| Example 18 | 102 | 5.63 | 5.94 | (0.134, 0.100) | 35 |
| Example 19 | 105 | 5.40 | 6.11 | (0.134, 0.102) | 22 |
| Example 20 | 106 | 5.37 | 6.40 | (0.134, 0.101) | 40 |
| Example 21 | 119 | 5.36 | 6.22 | (0.134, 0.102) | 39 |
| Example 22 | 122 | 5.38 | 6.20 | (0.134, 0.101) | 42 |
| Example 23 | 124 | 4.95 | 6.22 | (0.134, 0.101) | 39 |
| Example 24 | 135 | 4.91 | 6.25 | (0.134, 0.101) | 37 |
| Example 25 | 138 | 4.91 | 6.13 | (0.134, 0.101) | 43 |
| Example 26 | 152 | 4.97 | 6.50 | (0.134, 0.101) | 38 |
| Example 27 | 159 | 5.63 | 6.22 | (0.134, 0.100) | 42 |
| Example 28 | 161 | 5.40 | 5.94 | (0.134, 0.100) | 35 |
| Example 29 | 175 | 5.37 | 5.83 | (0.134, 0.101) | 37 |
| Example 30 | 181 | 5.39 | 6.35 | (0.134, 0.101) | 41 |
| Example 31 | 192 | 5.38 | 6.20 | (0.134, 0.103) | 40 |
| Example 32 | 195 | 5.39 | 6.42 | (0.134, 0.102) | 43 |
| Example 33 | 196 | 4.97 | 6.20 | (0.134, 0.101) | 38 |
| Example 34 | 197 | 4.94 | 6.23 | (0.134, 0.102) | 34 |
| Example 35 | 198 | 4.90 | 6.11 | (0.134, 0.101) | 38 |
| Example 36 | 202 | 5.38 | 6.38 | (0.134, 0.101) | 39 |
| Example 37 | 206 | 5.37 | 6.22 | (0.134, 0.103) | 40 |
| Example 38 | 210 | 5.38 | 6.61 | (0.134, 0.102) | 41 |
| Example 39 | 217 | 4.96 | 6.21 | (0.134, 0.101) | 37 |
| Example 40 | 235 | 4.91 | 6.22 | (0.134, 0.102) | 33 |
| Example 41 | 238 | 4.90 | 6.14 | (0.134, 0.101) | 40 |
| Example 42 | 248 | 4.98 | 6.51 | (0.134, 0.101) | 39 |
| Example 43 | 255 | 5.61 | 6.21 | (0.134, 0.100) | 41 |
| Example 44 | 260 | 5.39 | 5.95 | (0.134, 0.101) | 35 |
| Example 45 | 264 | 5.10 | 6.88 | (0.134, 0.100) | 41 |
| Example 46 | 272 | 5.38 | 6.39 | (0.134, 0.101) | 39 |
| Example 47 | 275 | 5.37 | 6.21 | (0.134, 0.103) | 40 |
| Example 48 | 277 | 5.10 | 6.62 | (0.134, 0.102) | 43 |
| Example 49 | 283 | 4.96 | 6.22 | (0.134, 0.100) | 41 |
| Example 50 | 285 | 4.98 | 6.92 | (0.134, 0.100) | 43 |
| Example 51 | 287 | 5.62 | 5.97 | (0.134, 0.100) | 39 |
| Example 52 | 302 | 4.74 | 6.53 | (0.134, 0.102) | 41 |
| Example 53 | 312 | 4.72 | 6.33 | (0.134, 0.102) | 42 |
| Example 54 | 318 | 4.91 | 6.92 | (0.134, 0.100) | 45 |
| Example 55 | 328 | 4.91 | 6.95 | (0.134, 0.100) | 40 |
| Example 56 | 332 | 4.96 | 6.21 | (0.134, 0.100) | 40 |
| Example 57 | 342 | 5.62 | 5.99 | (0.134, 0.100) | 36 |
| Example 58 | 346 | 5.31 | 6.53 | (0.134, 0.102) | 34 |
| Example 59 | 348 | 4.79 | 6.55 | (0.134, 0.102) | 47 |
| Example 60 | 355 | 5.40 | 6.12 | (0.134, 0.101) | 39 |
| Example 61 | 358 | 5.44 | 6.10 | (0.134, 0.100) | 41 |
| Example 62 | 359 | 5.38 | 6.01 | (0.134, 0.101) | 34 |
| Example 63 | 368 | 4.95 | 6.86 | (0.134, 0.100) | 45 |
| Example 64 | 370 | 4.95 | 6.95 | (0.134, 0.100) | 39 |
| Example 65 | 372 | 4.98 | 6.20 | (0.134, 0.100) | 40 |
| Example 66 | 387 | 5.61 | 5.98 | (0.134, 0.100) | 33 |
| Example 67 | 394 | 4.75 | 6.43 | (0.134, 0.102) | 43 |
| Example 68 | 403 | 5.40 | 6.12 | (0.134, 0.101) | 39 |
| Example 69 | 406 | 5.43 | 6.21 | (0.134, 0.100) | 40 |
| Example 70 | 415 | 5.39 | 6.26 | (0.134, 0.101) | 36 |
| Example 71 | 418 | 5.39 | 6.87 | (0.134, 0.100) | 45 |
| Example 72 | 427 | 5.21 | 6.93 | (0.134, 0.100) | 44 |
| Example 73 | 432 | 5.13 | 6.95 | (0.134, 0.100) | 40 |
| Example 74 | 447 | 5.03 | 6.22 | (0.134, 0.100) | 40 |
| Example 75 | 453 | 4.91 | 5.88 | (0.134, 0.100) | 33 |
| Example 76 | 458 | 4.72 | 6.43 | (0.134, 0.102) | 48 |
| Example 77 | 464 | 5.47 | 6.15 | (0.134, 0.101) | 39 |
| Example 78 | 473 | 5.44 | 6.53 | (0.134, 0.102) | 49 |
| Example 79 | 476 | 5.33 | 6.53 | (0.134, 0.102) | 42 |
| Example 80 | 490 | 4.91 | 6.98 | (0.134, 0.100) | 43 |
| Example 81 | 497 | 4.91 | 6.11 | (0.134, 0.100) | 35 |
| Example 82 | 505 | 4.92 | 6.22 | (0.134, 0.100) | 40 |
| Example 83 | 509 | 5.63 | 5.99 | (0.134, 0.100) | 38 |
| Example 84 | 517 | 4.72 | 6.54 | (0.134, 0.102) | 48 |
| Example 85 | 527 | 4.72 | 6.33 | (0.134, 0.102) | 40 |
| Example 86 | 534 | 4.63 | 6.53 | (0.134, 0.102) | 43 |
| Example 87 | 536 | 4.91 | 6.82 | (0.134, 0.100) | 41 |
| Example 88 | 537 | 4.99 | 6.95 | (0.134, 0.100) | 39 |
| Example 89 | 539 | 4.94 | 6.25 | (0.134, 0.102) | 40 |
| Example 90 | 542 | 5.61 | 5.98 | (0.134, 0.100) | 33 |
| Example 91 | 543 | 5.44 | 6.53 | (0.134, 0.102) | 41 |

TABLE 60-continued

| Compound | Driving Voltage (V) | Light Emission Efficiency (cd/A) | CIE (x, y) | Lifetime (T95) |
|---|---|---|---|---|
| Example 92 | 547 | 4.88 | 6.88 | (0.134, 0.102) | 42 |
| Example 93 | 551 | 5.41 | 6.12 | (0.134, 0.101) | 40 |
| Example 94 | 555 | 5.41 | 5.89 | (0.134, 0.100) | 39 |
| Example 95 | 561 | 5.39 | 6.01 | (0.134, 0.101) | 31 |
| Example 96 | 567 | 4.63 | 6.54 | (0.134, 0.102) | 48 |
| Example 97 | 571 | 4.90 | 6.82 | (0.134, 0.100) | 43 |
| Example 98 | 574 | 4.72 | 6.52 | (0.134, 0.102) | 38 |
| Example 99 | 575 | 4.91 | 6.78 | (0.134, 0.100) | 42 |
| Example 100 | 585 | 4.90 | 6.94 | (0.134, 0.100) | 40 |
| Example 101 | 591 | 4.99 | 6.22 | (0.134, 0.100) | 40 |
| Example 102 | 594 | 5.64 | 5.97 | (0.134, 0.100) | 33 |
| Example 103 | 607 | 5.22 | 6.01 | (0.134, 0.101) | 33 |
| Example 104 | 610 | 5.39 | 6.01 | (0.134, 0.101) | 36 |
| Example 105 | 614 | 5.35 | 6.04 | (0.134, 0.101) | 33 |
| Example 106 | 618 | 4.91 | 6.94 | (0.134, 0.100) | 43 |
| Example 107 | 621 | 4.77 | 6.96 | (0.134, 0.100) | 41 |
| Example 108 | 627 | 4.99 | 6.22 | (0.134, 0.100) | 40 |
| Example 109 | 634 | 5.03 | 5.98 | (0.134, 0.100) | 42 |
| Example 110 | 643 | 4.71 | 6.50 | (0.134, 0.102) | 41 |
| Example 111 | 650 | 4.77 | 6.53 | (0.134, 0.102) | 48 |
| Example 112 | 652 | 4.73 | 6.59 | (0.134, 0.102) | 45 |
| Example 113 | 657 | 5.42 | 6.12 | (0.134, 0.101) | 39 |
| Example 114 | 667 | 4.72 | 6.53 | (0.134, 0.102) | 37 |
| Example 115 | 674 | 4.91 | 6.78 | (0.134, 0.100) | 42 |
| Example 116 | 684 | 5.45 | 5.89 | (0.134, 0.100) | 41 |
| Example 117 | 687 | 5.36 | 6.03 | (0.134, 0.101) | 32 |
| Example 118 | 692 | 4.96 | 6.83 | (0.134, 0.100) | 45 |
| Example 119 | 695 | 4.94 | 6.93 | (0.134, 0.100) | 43 |
| Example 120 | 700 | 4.94 | 6.95 | (0.134, 0.100) | 41 |
| Example 121 | 708 | 5.34 | 6.13 | (0.134, 0.101) | 38 |
| Example 122 | 723 | 4.86 | 6.77 | (0.134, 0.100) | 45 |
| Example 123 | 729 | 4.95 | 6.73 | (0.134, 0.102) | 42 |
| Example 124 | 734 | 4.91 | 6.55 | (0.134, 0.100) | 42 |
| Example 125 | 737 | 5.31 | 6.29 | (0.134, 0.100) | 44 |
| Example 126 | 739 | 5.26 | 6.10 | (0.134, 0.100) | 34 |
| Example 127 | 741 | 5.34 | 6.25 | (0.134, 0.102) | 41 |
| Example 128 | 744 | 5.31 | 6.57 | (0.134, 0.102) | 44 |
| Example 129 | 746 | 4.72 | 6.53 | (0.134, 0.102) | 38 |
| Example 130 | 758 | 4.79 | 6.54 | (0.134, 0.102) | 48 |
| Example 131 | 768 | 5.41 | 6.13 | (0.134, 0.101) | 39 |
| Example 132 | 781 | 5.13 | 5.89 | (0.134, 0.100) | 41 |
| Example 133 | 789 | 5.31 | 6.03 | (0.134, 0.101) | 34 |
| Example 134 | 796 | 5.19 | 6.88 | (0.134, 0.100) | 47 |
| Example 135 | 802 | 5.26 | 6.71 | (0.134, 0.100) | 39 |
| Example 136 | 804 | 5.21 | 6.66 | (0.134, 0.100) | 45 |
| Example 137 | 807 | 4.94 | 6.83 | (0.134, 0.100) | 38 |
| Example 138 | 813 | 5.34 | 6.53 | (0.134, 0.100) | 46 |
| Example 139 | 818 | 5.33 | 6.04 | (0.134, 0.100) | 41 |
| Example 140 | 824 | 5.11 | 6.88 | (0.134, 0.100) | 45 |
| Example 141 | 826 | 5.11 | 6.88 | (0.134, 0.100) | 45 |
| Example 142 | 830 | 5.61 | 5.92 | (0.134, 0.100) | 33 |
| Example 143 | 831 | 5.44 | 6.53 | (0.134, 0.102) | 40 |
| Example 144 | 844 | 4.88 | 6.88 | (0.134, 0.102) | 42 |
| Example 145 | 855 | 5.40 | 6.12 | (0.134, 0.101) | 41 |
| Example 146 | 861 | 5.44 | 5.88 | (0.134, 0.100) | 39 |
| Example 147 | 877 | 5.39 | 6.02 | (0.134, 0.101) | 31 |
| Example 148 | 883 | 4.66 | 6.54 | (0.134, 0.102) | 48 |
| Example 149 | 894 | 4.90 | 6.82 | (0.134, 0.100) | 40 |
| Example 150 | 902 | 4.72 | 6.52 | (0.134, 0.102) | 38 |
| Example 151 | 907 | 4.91 | 6.77 | (0.134, 0.100) | 42 |
| Example 152 | 910 | 4.93 | 6.94 | (0.134, 0.100) | 40 |
| Example 153 | 917 | 4.99 | 6.22 | (0.134, 0.100) | 40 |
| Example 154 | 918 | 5.44 | 5.89 | (0.134, 0.100) | 41 |
| Example 155 | 919 | 5.36 | 6.03 | (0.134, 0.101) | 38 |
| Example 156 | 920 | 4.97 | 6.83 | (0.134, 0.100) | 45 |
| Example 157 | 923 | 4.94 | 6.96 | (0.134, 0.100) | 44 |
| Example 158 | 925 | 4.92 | 6.95 | (0.134, 0.100) | 39 |
| Example 159 | 926 | 5.19 | 6.88 | (0.134, 0.100) | 47 |
| Example 160 | 927 | 5.49 | 6.16 | (0.134, 0.101) | 39 |
| Example 161 | 928 | 5.44 | 6.53 | (0.134, 0.100) | 48 |
| Example 162 | 932 | 5.37 | 6.53 | (0.134, 0.102) | 42 |
| Example 163 | 936 | 4.91 | 6.96 | (0.134, 0.100) | 44 |
| Example 164 | 937 | 4.90 | 6.11 | (0.134, 0.100) | 35 |
| Example 165 | 943 | 4.92 | 6.22 | (0.134, 0.100) | 42 |
| Example 166 | 945 | 5.64 | 5.99 | (0.134, 0.100) | 38 |
| Example 167 | 950 | 4.72 | 6.55 | (0.134, 0.102) | 48 |
| Example 168 | 952 | 4.72 | 6.33 | (0.134, 0.102) | 41 |
| Example 169 | 954 | 4.64 | 6.53 | (0.134, 0.102) | 43 |
| Example 170 | 956 | 4.91 | 6.82 | (0.134, 0.100) | 43 |
| Example 171 | 959 | 4.97 | 6.95 | (0.134, 0.100) | 39 |
| Example 172 | 961 | 4.94 | 6.24 | (0.134, 0.100) | 40 |
| Example 173 | 962 | 5.61 | 5.98 | (0.134, 0.100) | 34 |
| Example 174 | 969 | 5.42 | 6.53 | (0.134, 0.102) | 41 |
| Example 175 | 971 | 4.88 | 6.88 | (0.134, 0.102) | 45 |
| Example 176 | 977 | 5.40 | 6.12 | (0.134, 0.101) | 40 |
| Example 177 | 978 | 5.41 | 5.89 | (0.134, 0.100) | 39 |
| Example 178 | 980 | 5.38 | 6.01 | (0.134, 0.101) | 31 |
| Example 179 | 986 | 4.63 | 6.54 | (0.134, 0.102) | 46 |
| Example 180 | 990 | 4.90 | 6.81 | (0.134, 0.100) | 43 |
| Example 181 | 996 | 5.48 | 6.15 | (0.134, 0.101) | 40 |
| Example 182 | 998 | 5.44 | 6.55 | (0.134, 0.102) | 49 |
| Example 183 | 999 | 5.33 | 6.53 | (0.134, 0.102) | 41 |
| Example 184 | 1002 | 4.90 | 6.98 | (0.134, 0.100) | 43 |
| Example 185 | 1003 | 4.91 | 6.13 | (0.134, 0.100) | 35 |
| Example 186 | 1008 | 4.92 | 6.22 | (0.134, 0.100) | 42 |
| Example 187 | 1012 | 5.66 | 5.99 | (0.134, 0.100) | 38 |
| Example 188 | 1013 | 4.72 | 6.54 | (0.134, 0.102) | 47 |
| Example 189 | 1014 | 4.71 | 6.33 | (0.134, 0.102) | 40 |
| Example 190 | 1016 | 4.63 | 6.56 | (0.134, 0.102) | 43 |
| Example 191 | 1018 | 4.91 | 6.82 | (0.134, 0.100) | 40 |
| Example 192 | 1019 | 4.98 | 6.95 | (0.134, 0.100) | 39 |
| Example 193 | 1020 | 4.94 | 6.25 | (0.134, 0.100) | 42 |
| Example 194 | 1022 | 5.64 | 5.98 | (0.134, 0.100) | 33 |
| Example 195 | 1024 | 5.44 | 6.53 | (0.134, 0.102) | 40 |
| Example 196 | 1026 | 4.87 | 6.88 | (0.134, 0.102) | 42 |

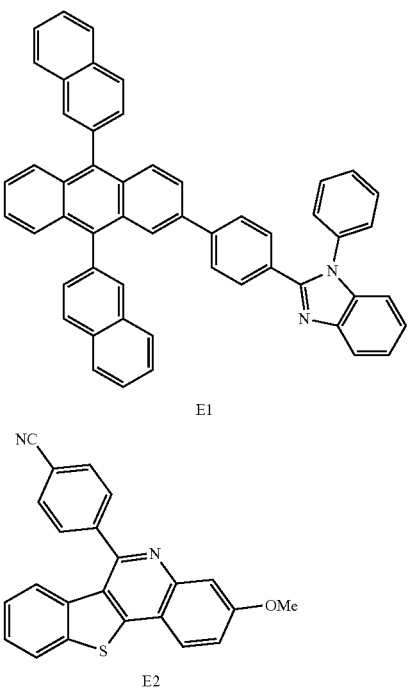

E1

E2

TABLE 60-continued

| Compound | Driving Voltage (V) | Light Emission Efficiency (cd/A) | CIE (x, y) | Lifetime (T95) |
|---|---|---|---|---|

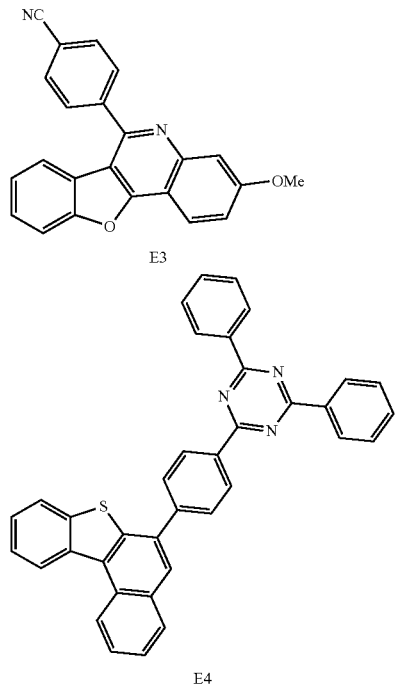

As seen from the results of Table 60, the organic light emitting device using the electron transfer layer material of the blue organic light emitting device of the present disclosure had a lower driving voltage, and significantly improved light emission efficiency and lifetime compared to Comparative Examples 1, 2, 3 and 4. Such a result is considered to be due to the fact that, when using the disclosed compound having proper length and strength as an electron transfer layer, a compound in an excited state is made by receiving electrons under a specific condition, and particularly when a hetero-skeleton site of the compound is formed in an excited state, excited energy moves to a stable state before the excited hetero-skeleton site goes through other reactions, and a relatively stabilized compound is capable of efficiently transfer electrons without being decomposed or destroyed. Those that are stable when excited as above are aryl or acene compounds, or polycyclic hetero-compounds. Accordingly, it is considered that excellent results in all aspects of driving voltage, efficiency and lifetime are obtained by the compound of the present disclosure with enhanced electron-transfer properties or improved stability.

<Experimental Example 2>—Manufacture of Organic Light Emitting Device

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum depositor, and the following 4,4',4"-tris(N,N-(2-naphthyl)-phenylamino)triphenylamine (2-TNATA) was introduced to a cell in the vacuum depositor.

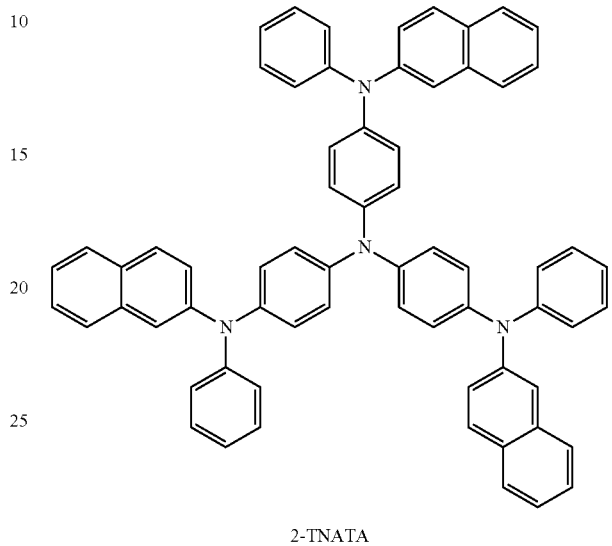

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum depositor, the following N,N'-bis(a-naphthyl)-N,N'-diphenyl-4,4'-diamine (NPB) was introduced, and evaporated by applying a current to the cell to deposit a hole transfer layer having a thickness of 300 Å on the hole injection layer.

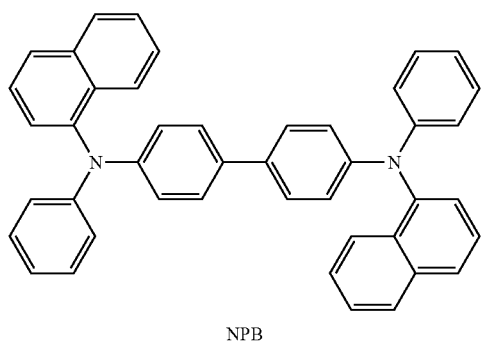

NPB

After forming the hole injection layer and the hole transfer layer as above, a blue light emitting material having a structure as below was deposited thereon as a light emitting layer. Specifically, in one side cell in the vacuum depositor, H1, a blue light emitting host material, was vacuum deposited to a thickness of 200 Å, and D1, a blue light emitting dopant material, was vacuum deposited thereon by 5% with respect to the host material.

H1

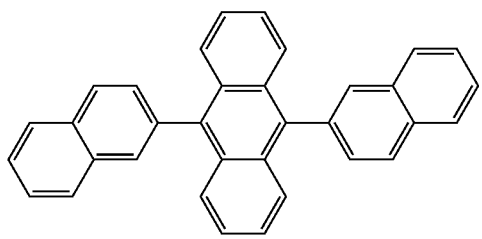

D1

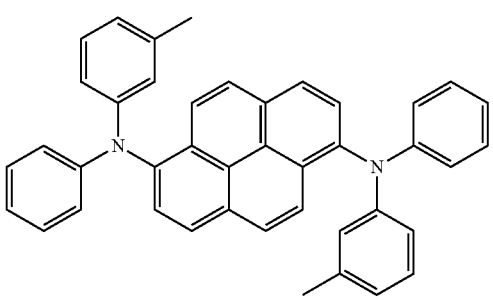

Subsequently, a compound of the following structural formula E1 was deposited to a thickness of 300 Å as an electron transfer layer.

E1

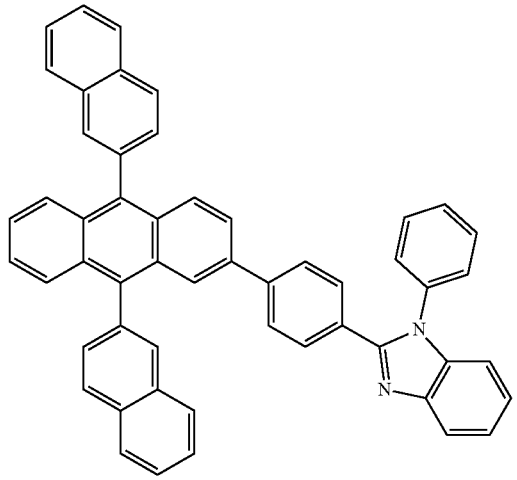

As an electron injection layer, lithium fluoride (LiF) was deposited to a thickness of 10 Å, and an Al cathode was employed to have a thickness of 1,000 Å to manufacture an OLED.

Meanwhile, all the organic compounds required to manufacture the OLED were vacuum sublimation purified under $10^{-6}$ torr to $10^{-8}$ torr by each material to be used in the OLED manufacture.

An organic light emitting device was manufactured in the same manner as in Experimental Example 2 except that, after forming the electron transfer layer E1 to a thickness of 250 Å, a hole blocking layer was formed on the electron transfer layer to a thickness of 50 Å using a compound presented in the following Table 61.

Results of measuring a driving voltage, light emission efficiency, a color coordinate (CIE) and a lifetime of the blue organic light emitting device manufactured according to the present disclosure are as shown in Table 61.

TABLE 61

| | Compound | Driving Voltage (V) | Light Emission Efficiency (cd/A) | CIE (x, y) | Lifetime (T95) |
|---|---|---|---|---|---|
| Comparative Example 5 | E1 | 5.70 | 6.00 | (0.134, 0.102) | 20 |
| Comparative Example 6 | E2 | 5.71 | 5.98 | (0.134, 0.100) | 22 |
| Comparative Example 7 | E3 | 5.70 | 6.03 | (0.134, 0.101) | 22 |
| Comparative Example 8 | E4 | 5.73 | 6.00 | (0.134, 0.102) | 20 |
| Example 197 | 9 | 5.45 | 6.10 | (0.134, 0.101) | 33 |
| Example 198 | 16 | 5.46 | 6.22 | (0.134, 0.102) | 36 |
| Example 199 | 57 | 5.62 | 5.93 | (0.134, 0.103) | 41 |
| Example 200 | 65 | 4.98 | 6.46 | (0.134, 0.100) | 39 |
| Example 201 | 78 | 5.61 | 6.38 | (0.134, 0.101) | 35 |
| Example 202 | 100 | 4.77 | 6.21 | (0.134, 0.102) | 39 |
| Example 203 | 102 | 5.47 | 6.40 | (0.134, 0.103) | 37 |
| Example 204 | 119 | 5.48 | 6.32 | (0.134, 0.102) | 39 |
| Example 205 | 152 | 5.65 | 6.26 | (0.134, 0.102) | 41 |
| Example 206 | 159 | 5.41 | 6.20 | (0.134, 0.103) | 45 |
| Example 207 | 181 | 5.61 | 6.28 | (0.134, 0.102) | 41 |
| Example 208 | 197 | 5.44 | 6.21 | (0.134, 0.101) | 38 |
| Example 209 | 206 | 4.97 | 6.35 | (0.134, 0.100) | 41 |
| Example 210 | 210 | 5.63 | 6.24 | (0.134, 0.100) | 38 |
| Example 211 | 235 | 4.70 | 6.13 | (0.134, 0.100) | 44 |
| Example 212 | 255 | 4.89 | 6.20 | (0.134, 0.101) | 41 |
| Example 213 | 277 | 4.98 | 6.21 | (0.134, 0.100) | 38 |
| Example 214 | 283 | 5.63 | 5.94 | (0.134, 0.100) | 37 |
| Example 215 | 302 | 5.41 | 6.11 | (0.134, 0.102) | 22 |
| Example 216 | 332 | 5.37 | 6.43 | (0.134, 0.101) | 40 |
| Example 217 | 358 | 5.36 | 6.22 | (0.134, 0.102) | 38 |
| Example 218 | 372 | 5.37 | 6.20 | (0.134, 0.101) | 42 |
| Example 219 | 394 | 4.96 | 6.22 | (0.134, 0.101) | 39 |
| Example 220 | 406 | 4.91 | 6.25 | (0.134, 0.101) | 39 |
| Example 221 | 415 | 4.90 | 6.14 | (0.134, 0.101) | 43 |
| Example 222 | 447 | 4.98 | 6.50 | (0.134, 0.101) | 38 |
| Example 223 | 464 | 5.63 | 6.22 | (0.134, 0.100) | 45 |
| Example 224 | 527 | 5.41 | 5.94 | (0.134, 0.100) | 35 |
| Example 225 | 536 | 5.37 | 5.84 | (0.134, 0.101) | 37 |
| Example 226 | 567 | 5.39 | 6.35 | (0.134, 0.101) | 40 |
| Example 227 | 591 | 5.37 | 6.20 | (0.134, 0.103) | 40 |
| Example 228 | 607 | 5.39 | 6.43 | (0.134, 0.102) | 43 |
| Example 229 | 621 | 4.97 | 6.20 | (0.134, 0.101) | 39 |

TABLE 61-continued

| | Compound | Driving Voltage (V) | Light Emission Efficiency (cd/A) | CIE (x, y) | Lifetime (T95) |
|---|---|---|---|---|---|
| Example 230 | 643 | 4.93 | 6.23 | (0.134, 0.102) | 34 |
| Example 231 | 700 | 4.90 | 6.13 | (0.134, 0.101) | 39 |
| Example 232 | 708 | 5.38 | 6.38 | (0.134, 0.101) | 39 |
| Example 233 | 734 | 5.37 | 6.23 | (0.134, 0.103) | 40 |
| Example 234 | 746 | 5.37 | 6.61 | (0.134, 0.101) | 41 |
| Example 235 | 781 | 4.96 | 6.21 | (0.134, 0.101) | 39 |
| Example 236 | 826 | 4.91 | 6.22 | (0.134, 0.102) | 33 |
| Example 237 | 830 | 4.90 | 6.14 | (0.134, 0.101) | 40 |
| Example 238 | 861 | 4.98 | 6.53 | (0.134, 0.101) | 39 |
| Example 239 | 883 | 5.61 | 6.21 | (0.134, 0.100) | 43 |
| Example 240 | 910 | 5.38 | 5.95 | (0.134, 0.101) | 35 |
| Example 241 | 927 | 5.10 | 6.89 | (0.134, 0.100) | 41 |
| Example 242 | 936 | 5.38 | 6.39 | (0.134, 0.101) | 38 |
| Example 243 | 950 | 5.38 | 6.21 | (0.134, 0.103) | 40 |
| Example 244 | 952 | 5.10 | 6.63 | (0.134, 0.102) | 43 |
| Example 245 | 959 | 4.96 | 6.22 | (0.134, 0.100) | 40 |
| Example 246 | 969 | 4.99 | 6.92 | (0.134, 0.100) | 43 |
| Example 247 | 980 | 5.62 | 5.97 | (0.134, 0.100) | 38 |
| Example 248 | 990 | 4.75 | 6.53 | (0.134, 0.102) | 41 |
| Example 249 | 1002 | 4.72 | 6.34 | (0.134, 0.102) | 42 |
| Example 250 | 1008 | 4.91 | 6.92 | (0.134, 0.100) | 44 |
| Example 251 | 1014 | 4.90 | 6.95 | (0.134, 0.100) | 40 |
| Example 252 | 1019 | 5.37 | 6.20 | (0.134, 0.103) | 40 |
| Example 253 | 1020 | 5.36 | 6.22 | (0.134, 0.102) | 38 |
| Example 254 | 1026 | 5.37 | 5.84 | (0.134, 0.101) | 37 |

As seen from the results of Table 61, the organic light emitting device using the hole blocking layer material of the blue organic light emitting device of the present disclosure had a lower driving voltage, and significantly improved light emission efficiency and lifetime compared to Comparative Examples 5, 6, 7 and 8. Such a reason is due to the fact that the compound of Chemical Formula 1 of the present application is a bipolar type having both p-type and n-type substituents, and is capable of blocking hole leakage and effectively trapping excitons in the light emitting layer.

<Experimental Example 3>—Manufacture of Organic Light Emitting Device

1) Manufacture of Organic Light Emitting Device

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treatment was carried out for 5 minutes in a UV cleaner using UV. After that, the substrate was transferred to a plasma cleaner (PT), and plasma treatment was carried out under vacuum for ITO work function and remaining film removal, and the substrate was transferred to a thermal deposition apparatus for organic deposition.

On the transparent ITO electrode (anode), an organic material was formed in a 2 stack white organic light emitting device (WOLED) structure. As for the first stack, TAPC was thermal vacuum deposited to a thickness of 300 Å first to form a hole transfer layer. After forming the hole transfer layer, a light emitting layer was thermal vacuum deposited thereon as follows. The light emitting layer was deposited to 300 Å by doping Flrpic to TCz1, a host, by 8% as a blue phosphorescent dopant. After forming an electron transfer layer to 400 Å using TmPyPB, a charge generation layer was formed to 100 Å by doping $Cs_2CO_3$ to the compound described in the following Table 62 by 20%.

As for the second stack, $MoO_3$ was thermal vacuum deposited to a thickness of 50 Å first to form a hole injection layer. A hole transfer layer, a common layer, was formed by doping $MoO_3$ to TAPC by 20% to 100 Å and depositing TAPC to 300 Å. A light emitting layer was deposited thereon to 300 Å by doping $Ir(ppy)_3$, a green phosphorescent dopant, to TCz1, a host, by 8%, and an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å to manufacture an organic electroluminescent device.

Meanwhile, all the organic compounds required to manufacture the OLED were vacuum sublimation purified under $10^{-6}$ torr to $10^{-8}$ torr by each material to be used in the OLED manufacture.

TAPC

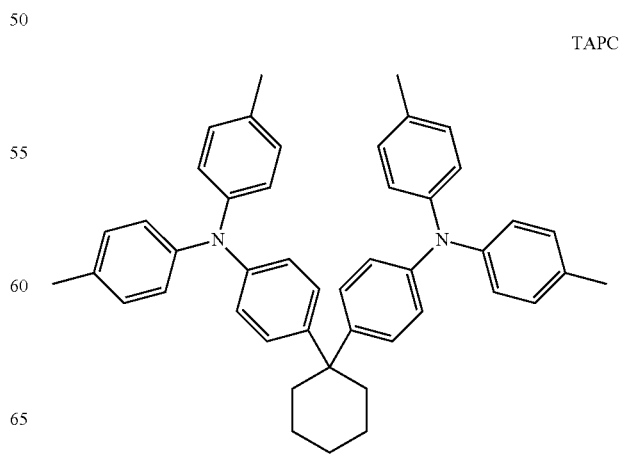

TCz1
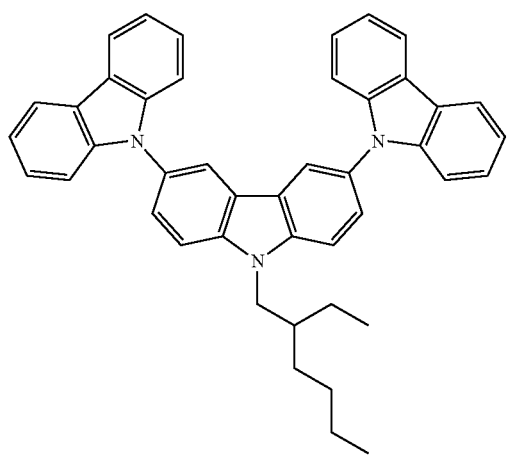
E1
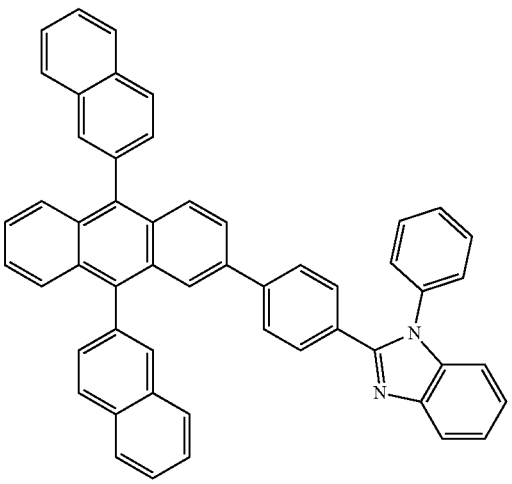
Firpic
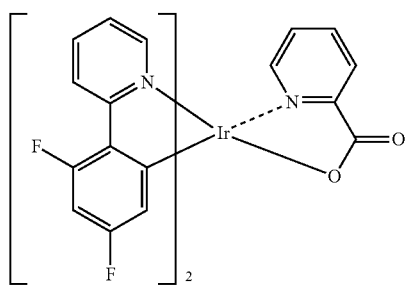
E2
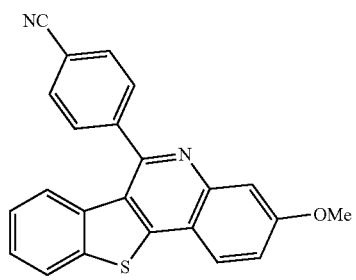
TmPyPB
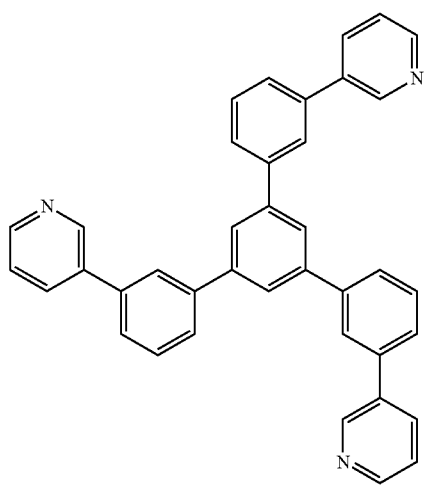
E3
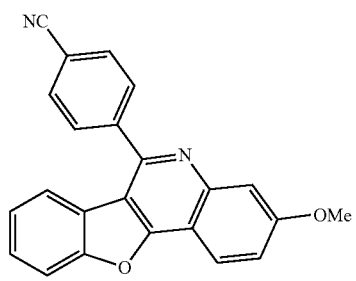
E4
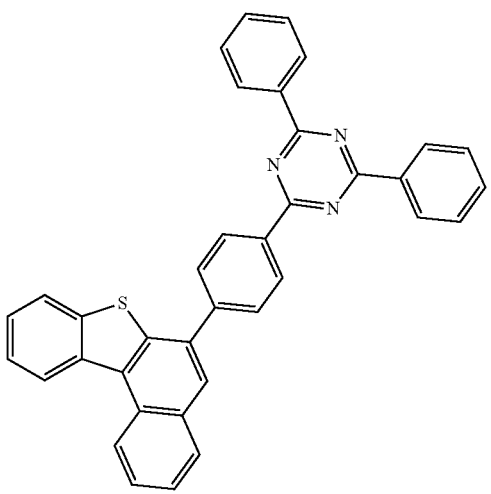
Ir(ppy)3
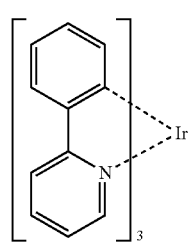

TABLE 62

| Compound | | Driving Voltage (V) | Light Emission Efficiency (cd/A) | CIE (x, y) | Lifetime (T95) |
|---|---|---|---|---|---|
| Comparative Example 9 | E1 | 5.70 | 6.00 | (0.134, 0.102) | 20 |
| Comparative Example 10 | E2 | 5.71 | 5.98 | (0.134, 0.100) | 22 |
| Comparative Example 11 | E3 | 5.70 | 6.03 | (0.134, 0.101) | 22 |
| Comparative Example 12 | E4 | 5.73 | 6.00 | (0.134, 0.102) | 20 |
| Example 255 | 1014 | 5.45 | 6.10 | (0.134, 0.101) | 33 |
| Example 256 | 1016 | 5.46 | 6.22 | (0.134, 0.102) | 36 |
| Example 257 | 1018 | 5.62 | 5.93 | (0.134, 0.103) | 41 |
| Example 258 | 1019 | 4.98 | 6.46 | (0.134, 0.100) | 39 |
| Example 259 | 1020 | 5.61 | 6.38 | (0.134, 0.101) | 35 |
| Example 260 | 1022 | 4.77 | 6.21 | (0.134, 0.102) | 39 |
| Example 261 | 1024 | 5.47 | 6.40 | (0.134, 0.103) | 37 |
| Example 262 | 1026 | 5.48 | 6.32 | (0.134, 0.102) | 39 |

As seen from the results of Table 62, the organic electroluminescent device using the charge generation layer material of the 2-stack white organic electroluminescent device of the present disclosure had a lower driving voltage and improved light emission efficiency compared to Comparative Examples 9, 10, 11 and 12.

Such a result is considered to be due to the fact that the compound of the present disclosure used as the N-type charge generation layer formed with the disclosed skeleton having proper length, strength and flat properties and a proper hetero-compound capable of binding with a metal forms a gap state in the N-type charge generation layer by doping an alkali metal or an alkaline earth metal, and electrons produced from the P-type charge generation layer are readily injected to the electron transfer layer through the gap state produced in the N-type charge generation layer. Accordingly, it is considered that the P-type charge generation layer favorably injects and transfers electrons to the N-type charge generation layer, and as a result, a driving voltage was lowered, and efficiency and lifetime were improved in the organic light emitting device.

The invention claimed is:

1. A heterocyclic compound represented by the following Chemical Formula 1:

[Chemical Formula 1]

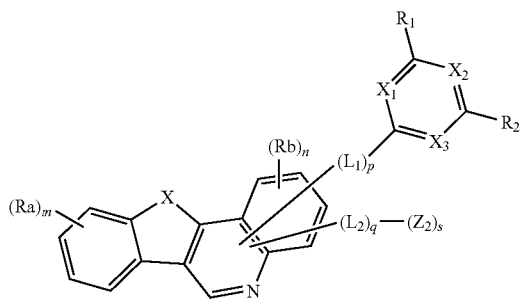

wherein, in Chemical Formula 1,

X is O or S;

$L_1$ and $L_2$ are a substituted or unsubstituted arylene group; or a substituted or unsubstituted heteroarylene group;

$Z_2$ is hydrogen; a substituted or unsubstituted alkyl group; a substituted or unsubstituted aryl group; a substituted or unsubstituted heteroaryl group; —SiRR'R''; or —P(=O)RR';

$X_1$ and $X_3$ are the same as or different from each other, and each independently N; $CR_3$; or P;

$R_1$ and $R_2$ are the same as or different from each other, and each independently hydrogen; deuterium; a substituted or unsubstituted alkyl group; a substituted or unsubstituted aryl group; a substituted or unsubstituted heteroaryl group; or P(=O)RR';

$R_3$ is hydrogen; a halogen group; a substituted or unsubstituted alkyl group; a substituted or unsubstituted aryl group; a substituted or unsubstituted heteroaryl group; or P(=O)RR';

$R_a$ and $R_b$ are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R''; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aliphatic or aromatic hydrocarbon ring;

R, R' and R'' are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group;

m is an integer of 0 to 4;

p and n are an integer of 0 to 3;

q is an integer of 0 to 3;

s is an integer of 1 to 4; and when q is an integer of 0 and $Z_2$ is hydrogen, n is an integer of 2 or 3, and $R_b$ is a substituted or unsubstituted aryl group; or a substituted or unsubstituted heteroaryl group, or two or more groups adjacent to each other bond to each other to form a substituted or unsubstituted aliphatic or aromatic hydrocarbon ring.

2. The heterocyclic compound of claim 1, wherein the "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R''; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted; and R, R' and R" have the same definitions as in Chemical Formula 1.

3. The heterocyclic compound of claim 1, wherein $R_a$ and $R_b$ are hydrogen.

4. The heterocyclic compound of claim 1, wherein $R_1$ and $R_2$ are hydrogen; a C6 to C40 aryl group unsubstituted or substituted with one or more substituents selected from the group consisting of a C1 to C40 alkyl group and a C2 to C40 heteroaryl group; P(=O)RR' or a C2 to C40 N-containing heteroaryl group.

5. The heterocyclic compound of claim 1, wherein $L_1$ and $L_2$ are a C6 to C30 arylene group; or a C2 to C30 heteroarylene group; and $Z_2$ is hydrogen; a C6 to C40 aryl group; or a C2 to C40 heteroaryl group.

6. The heterocyclic compound of claim 1, wherein Chemical Formula 1 is represented by any one of the following Chemical Formulae 2 to 5:

[Chemical Formula 2]

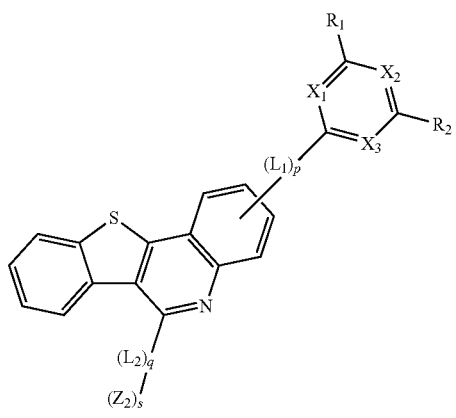

[Chemical Formula 3]

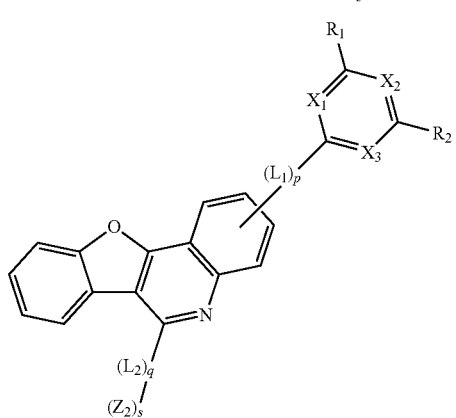

[Chemical Formula 4]

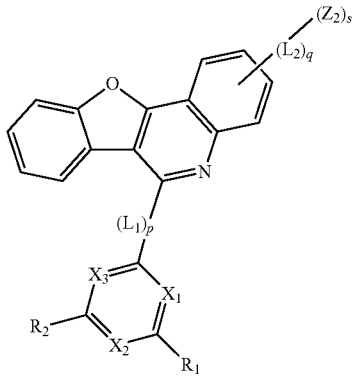

[Chemical Formula 5]

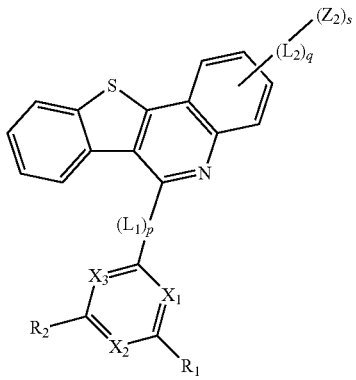

in Chemical Formulae 2 to 5, $X_1$ to $X_3$, $R_1$, $R_2$, $L_1$, $L_2$, $Z_2$ and p have the same definitions as in Chemical Formula 1; and q and s are each an integer of 1 to 3.

7. The heterocyclic compound of claim 1, wherein Chemical Formula 1 is represented by any one of the following Chemical Formulae 6 to 11:

[Chemical Formula 6]

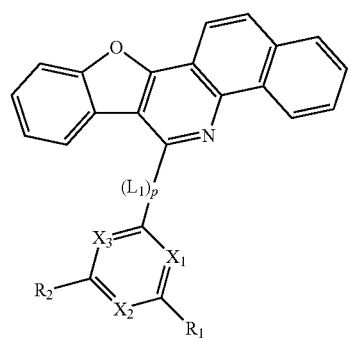

[Chemical Formula 7]
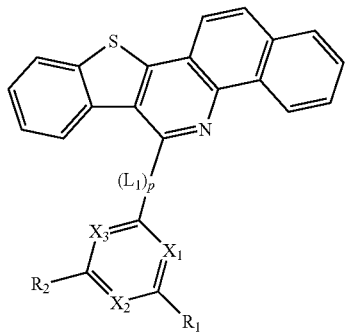
[Chemical Formula 8]
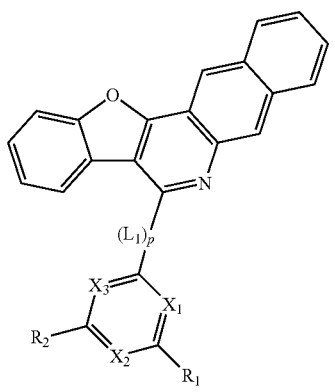
[Chemical Formula 9]
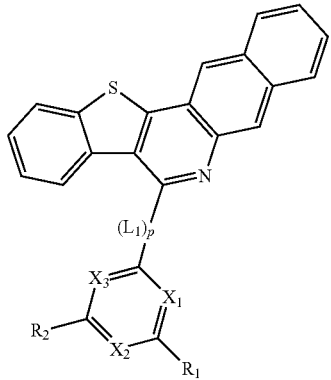
[Chemical Formula 10]
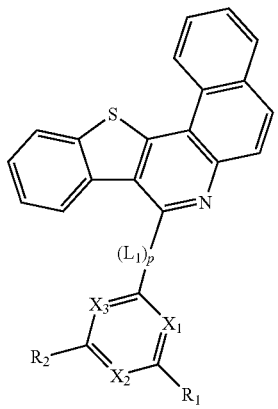
[Chemical Formula 11]
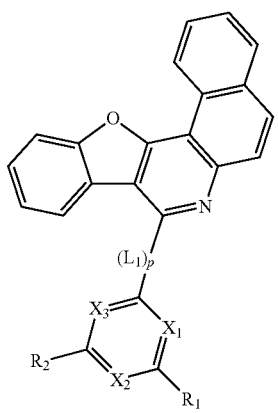
in Chemical Formulae 6 to 11,
$X_1$ to $X_3$, $R_1$, $R_2$, $L_1$ and p have the same definitions as in Chemical Formula 1.
8. The heterocyclic compound of claim 1, wherein Chemical Formula 1 is represented by any one of the following compounds:
1
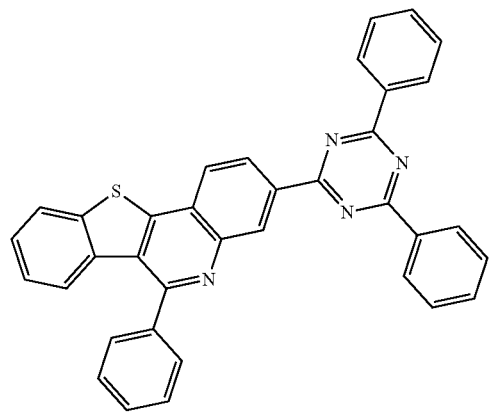
2
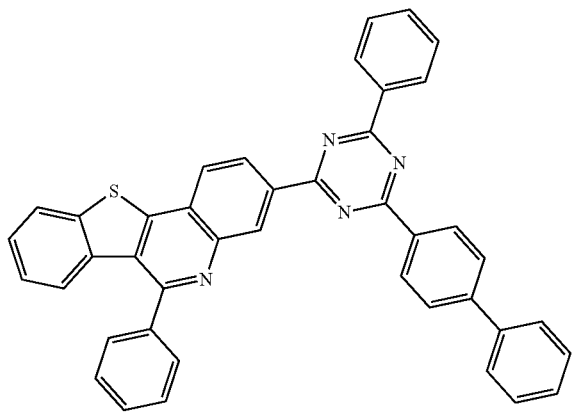

-continued
3
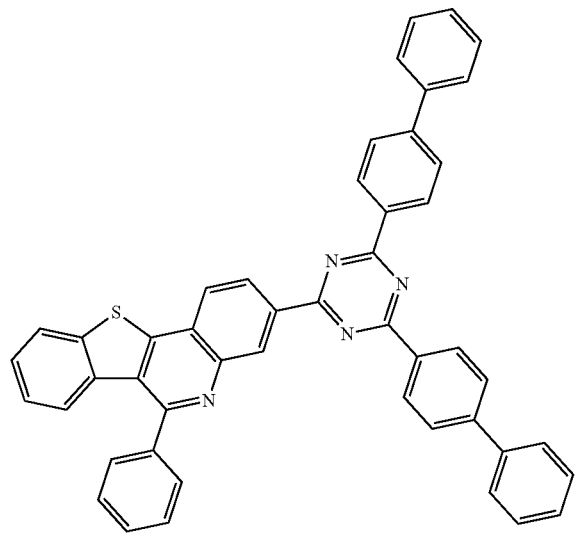
4
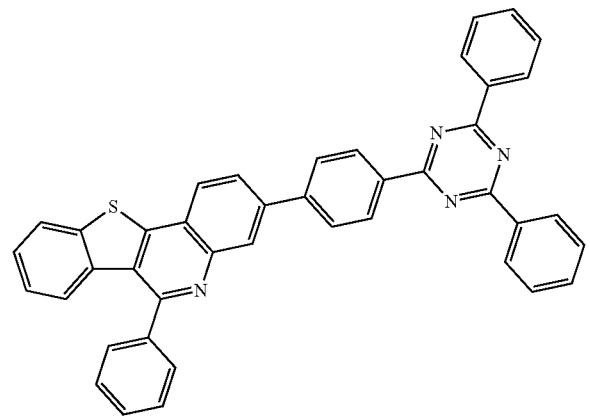
5
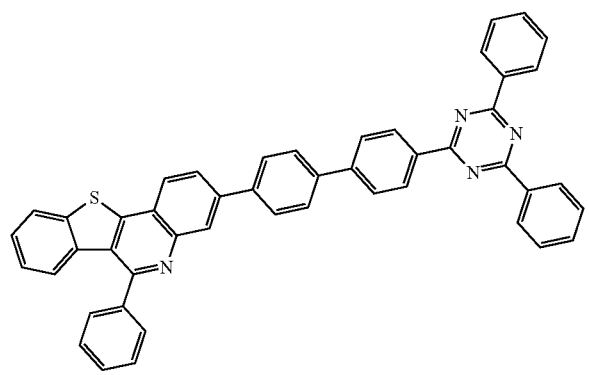
6
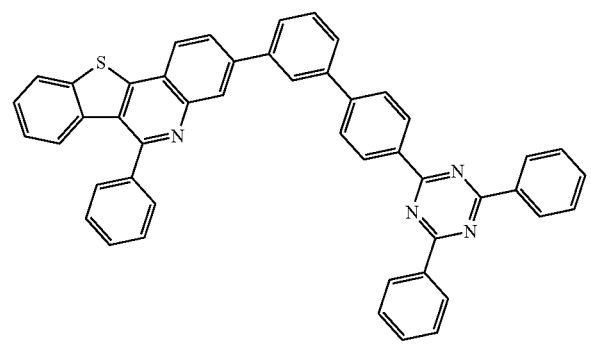
7
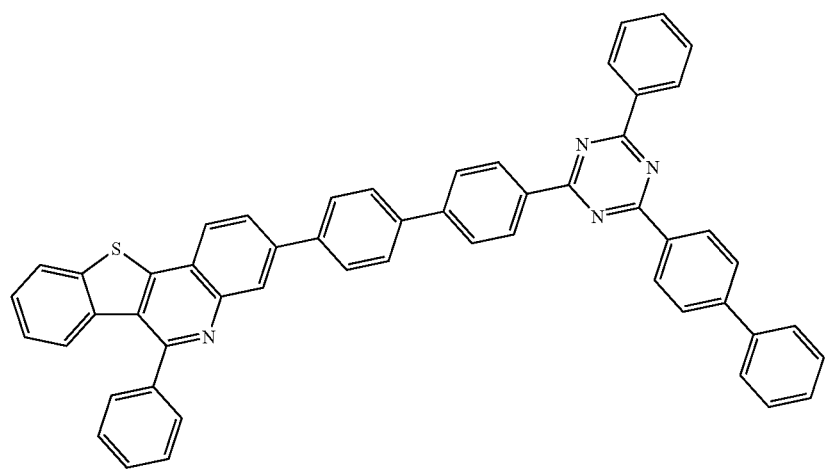

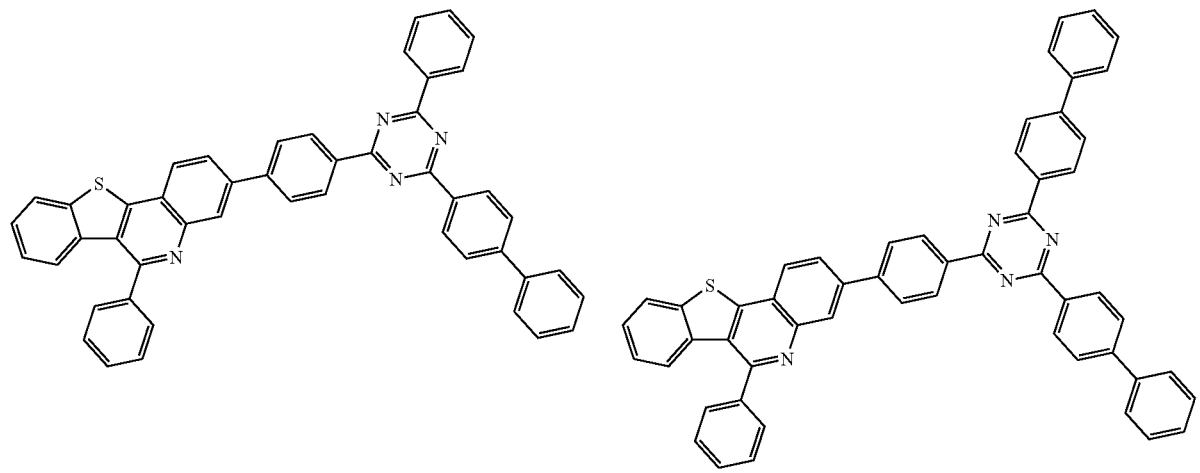
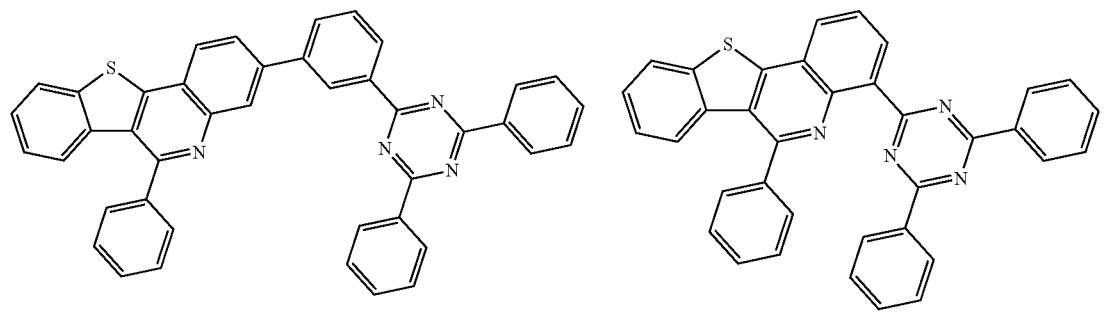
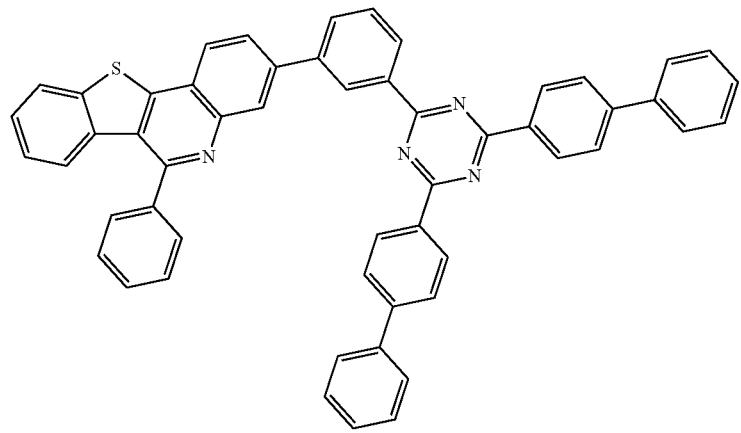

13
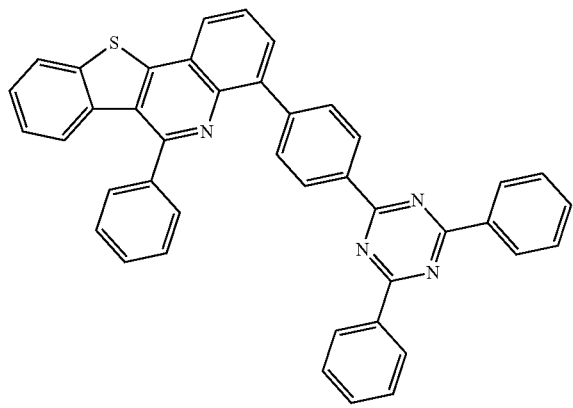
14
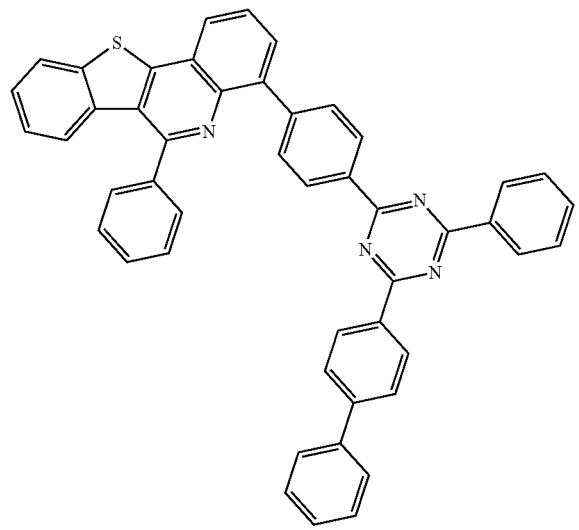
15
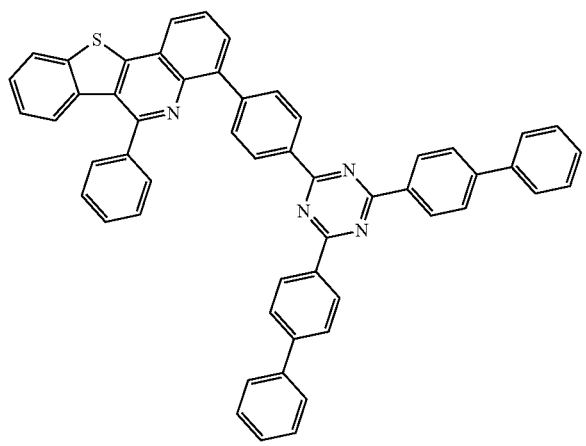
16
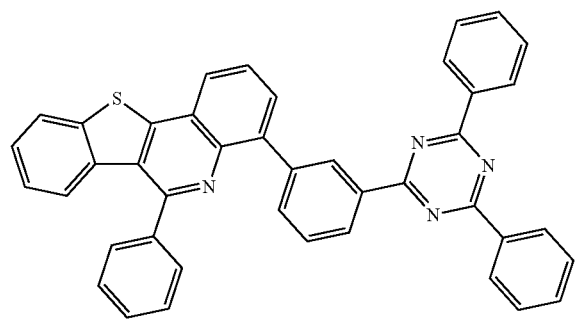
17
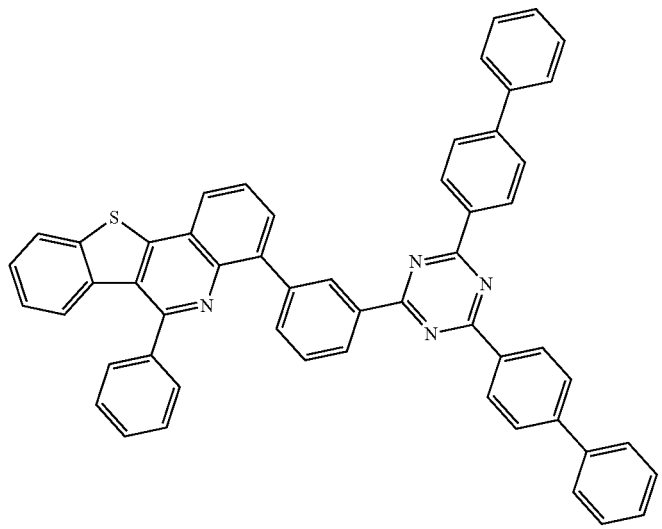

-continued
18
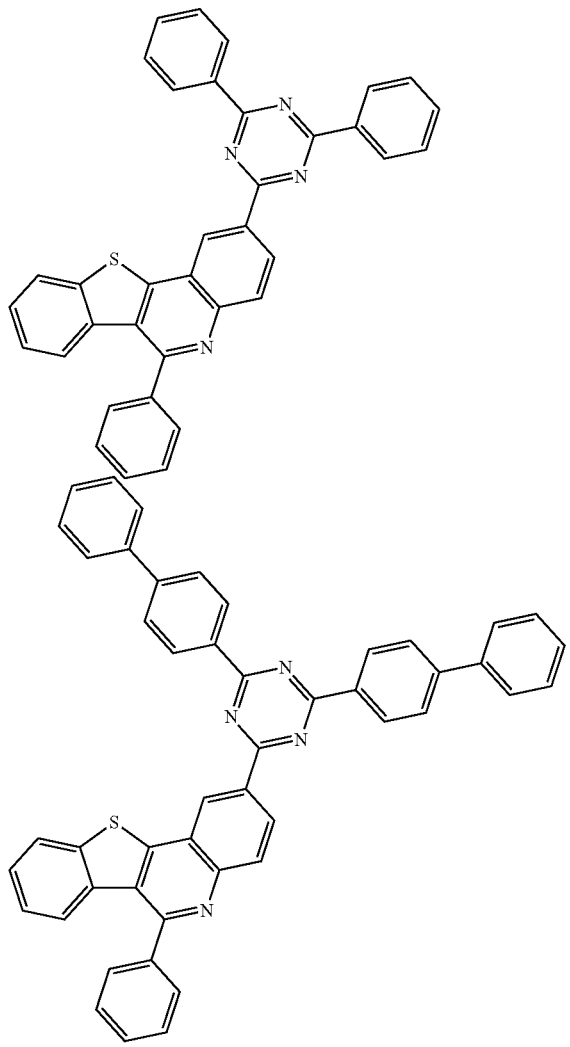
19
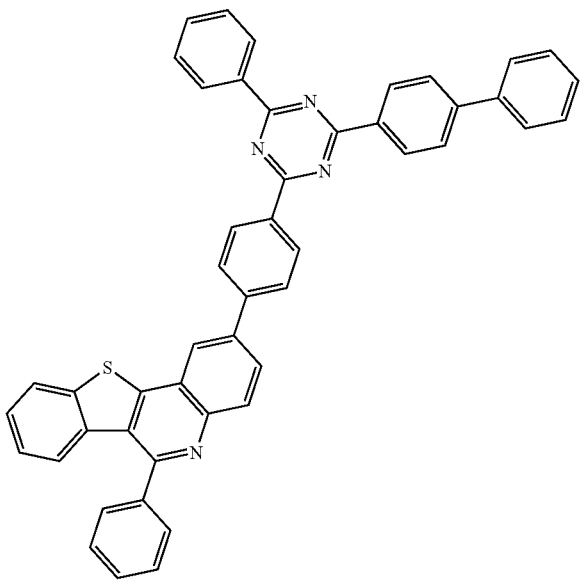
20
21
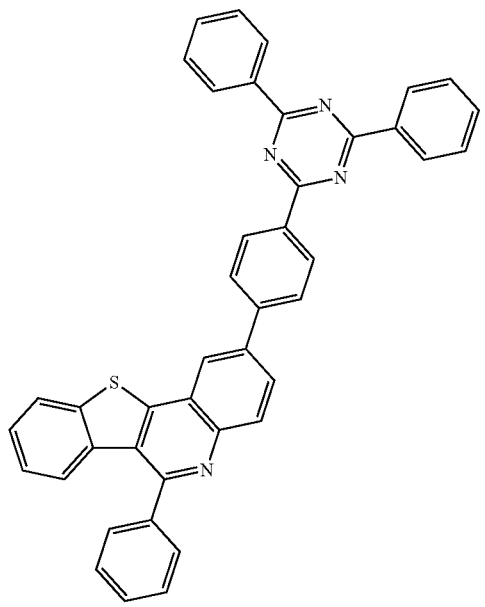
22

23
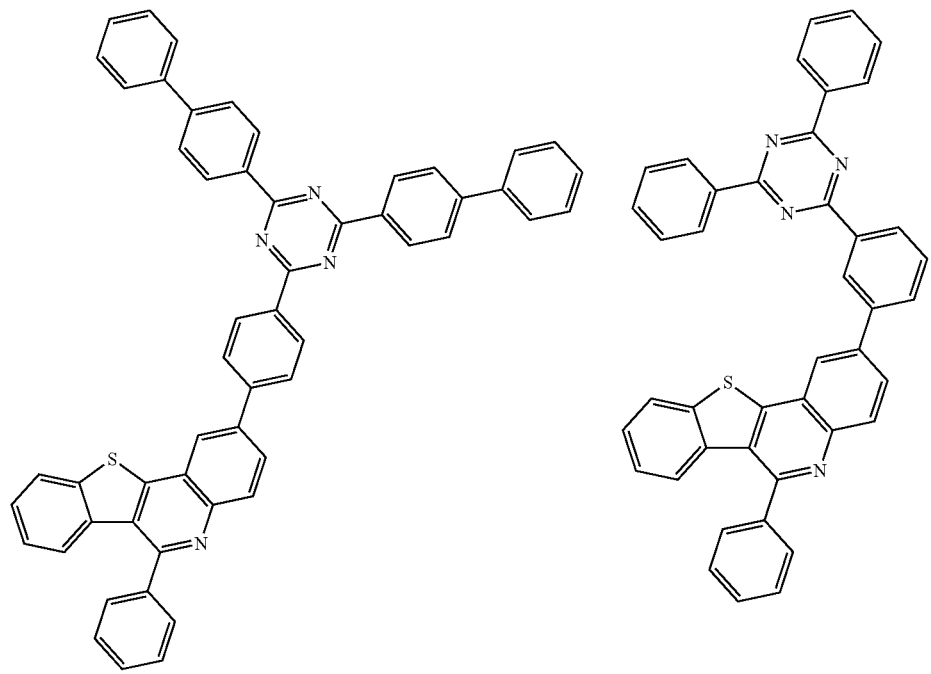
24
25
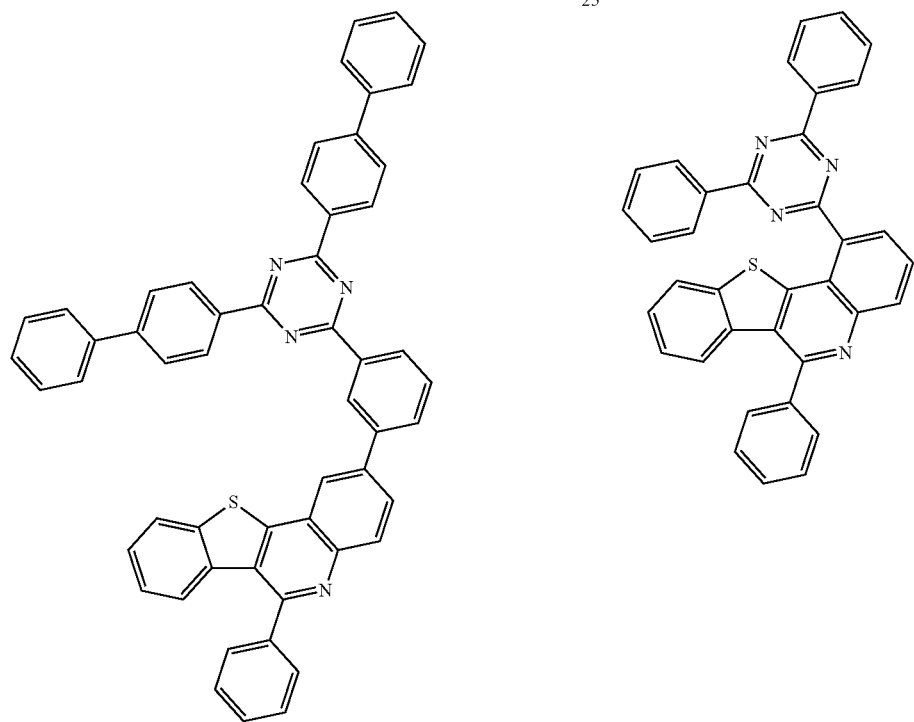
26

-continued
27
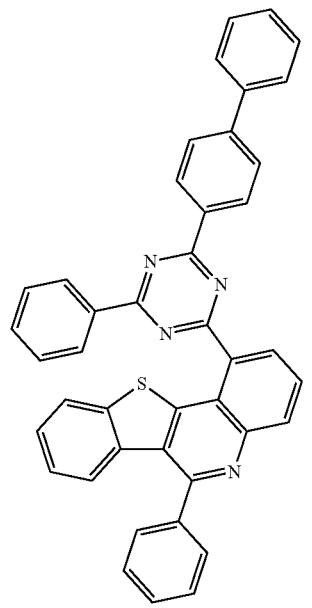
28
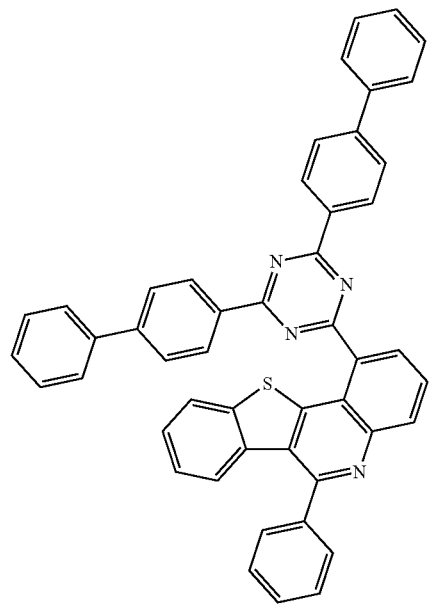
29
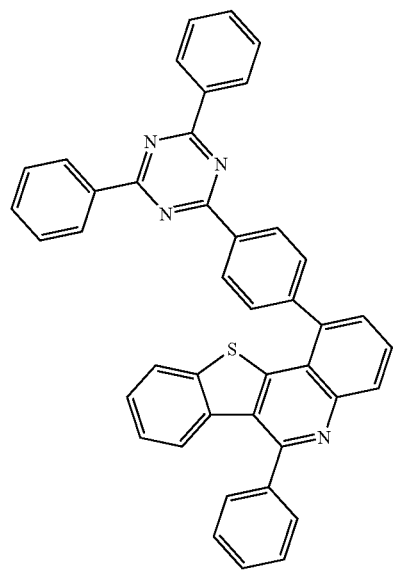
30
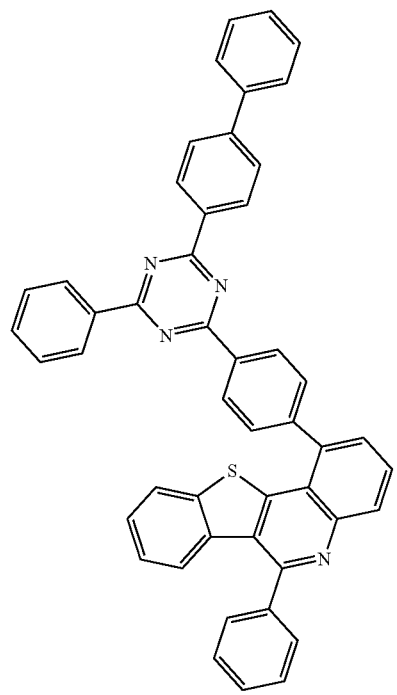

-continued
31
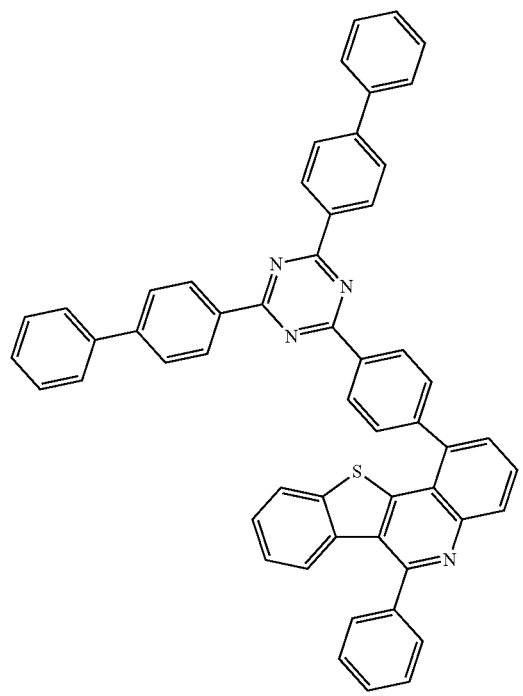
32
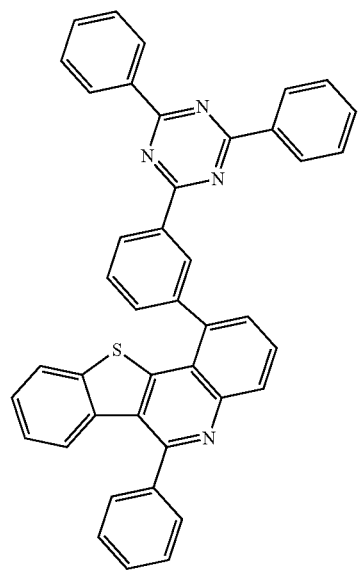
33
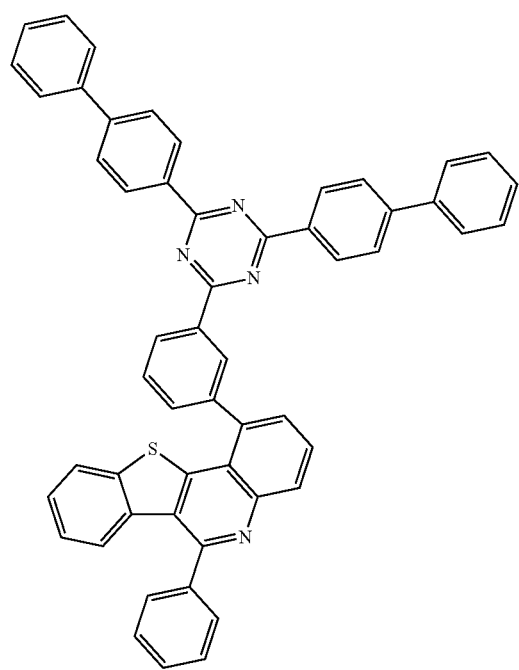
34
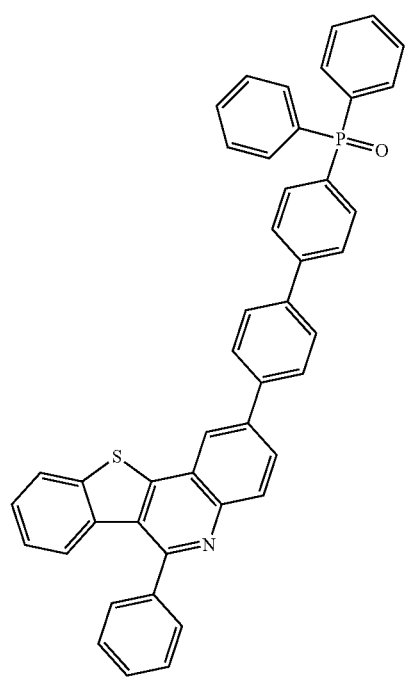

-continued
35
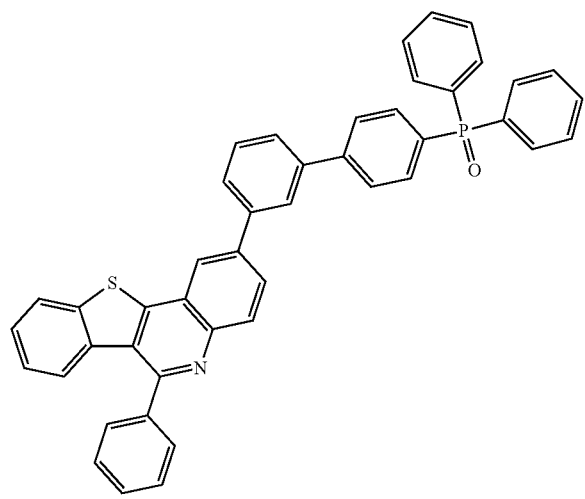
36
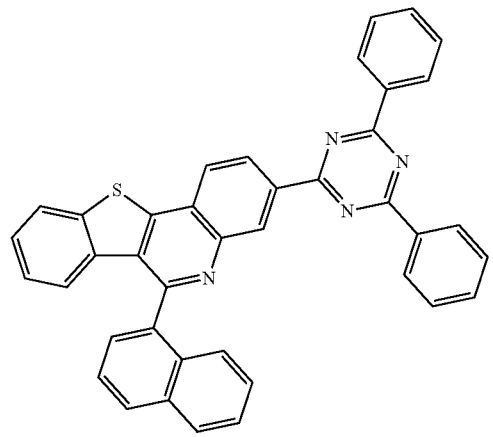
37
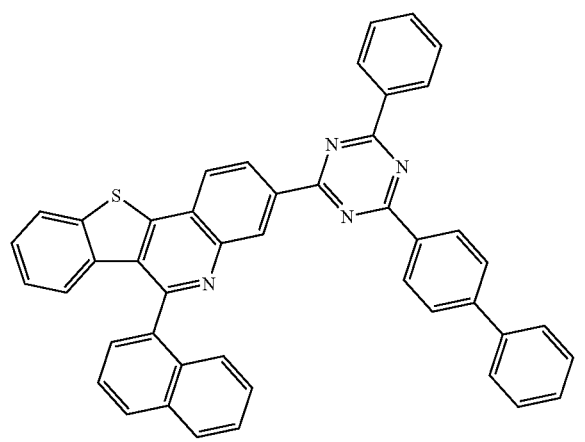
38
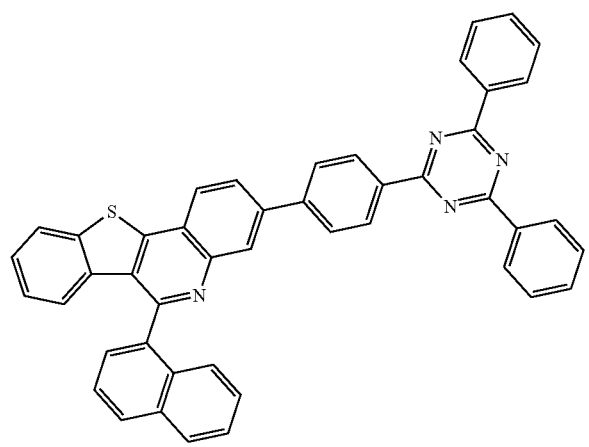
39
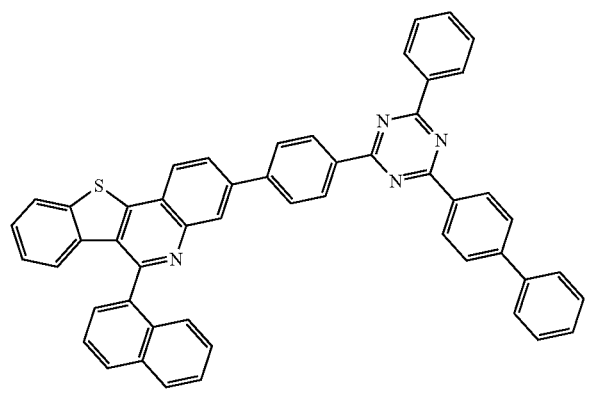
40
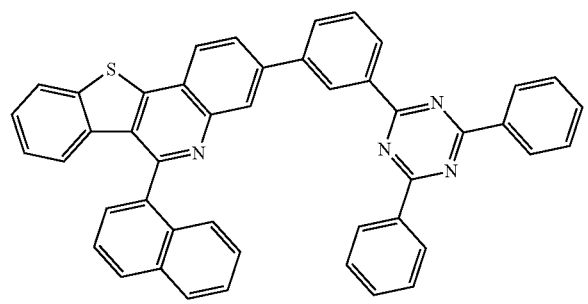

681
-continued
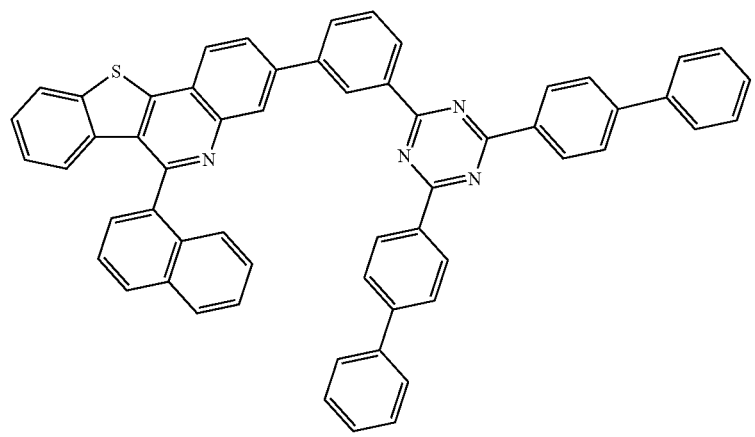
41
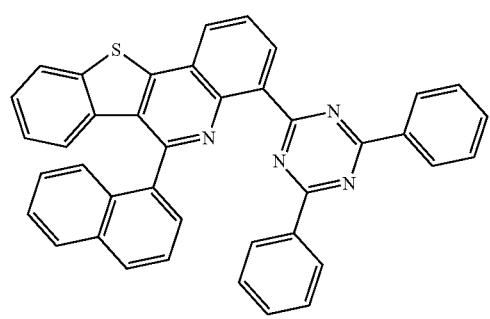
42
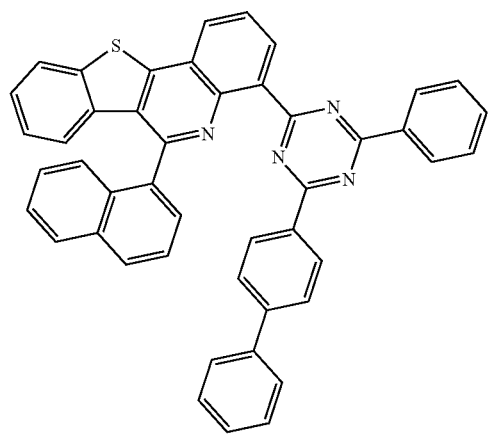
43
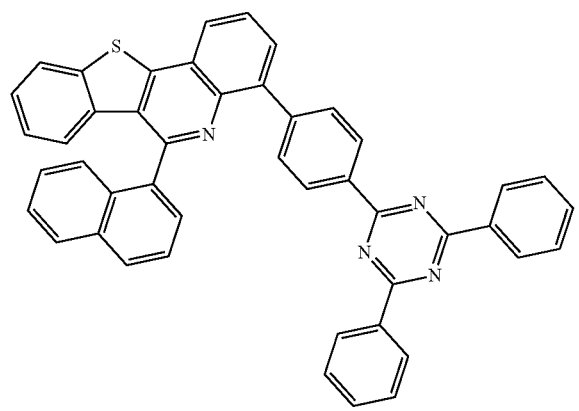
44
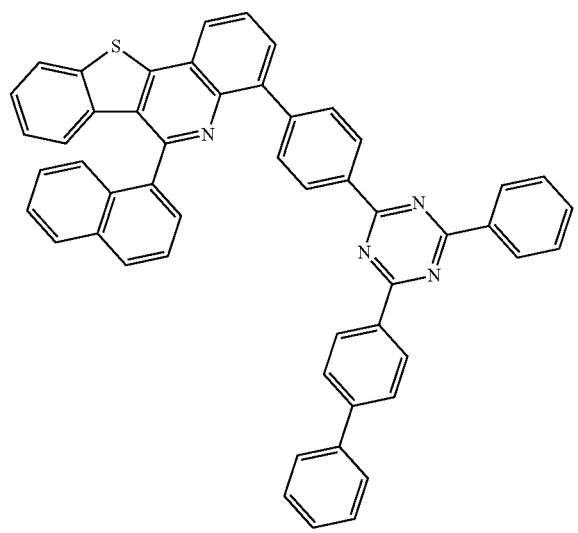
45

-continued
46
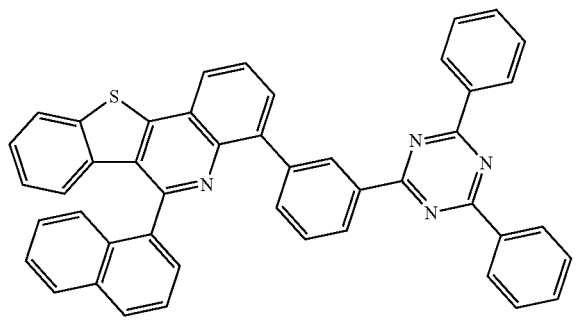
47
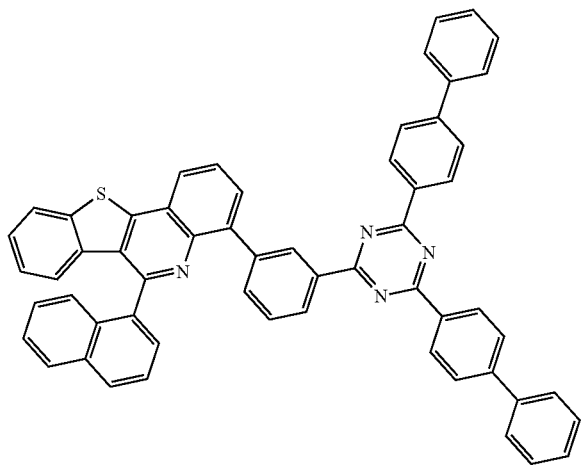
48
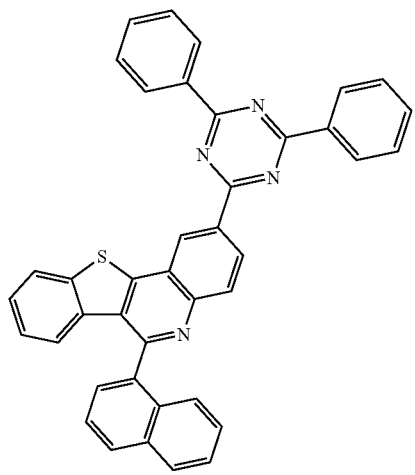
49
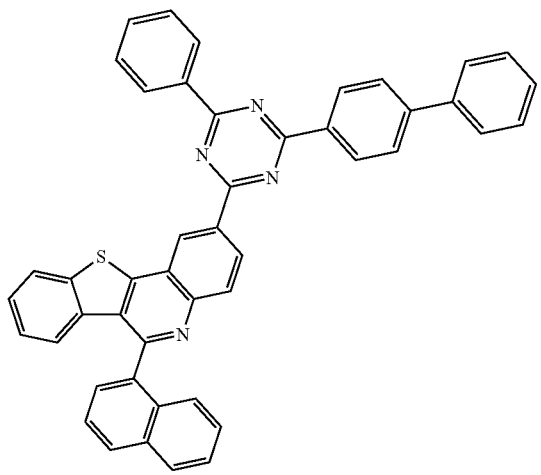
50
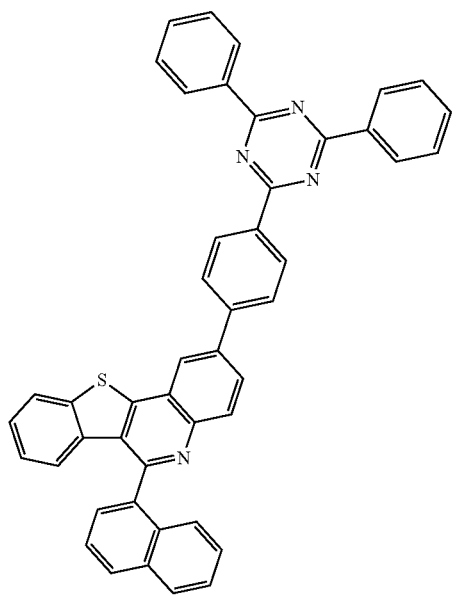
51
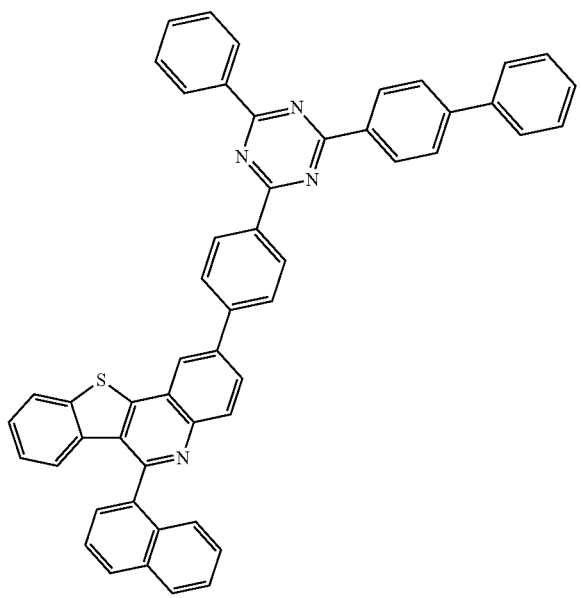

52 53
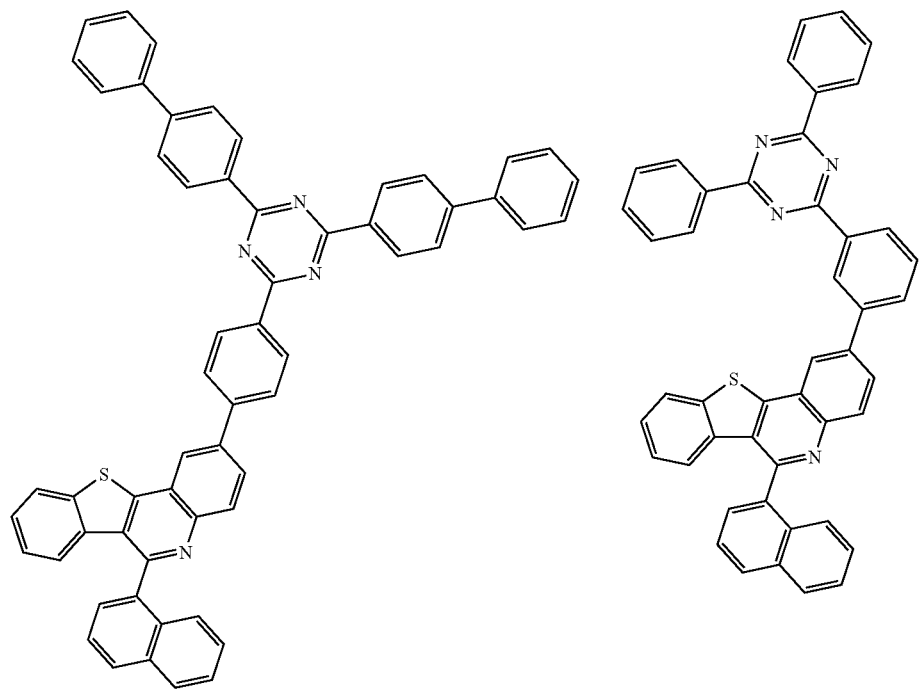
54 55
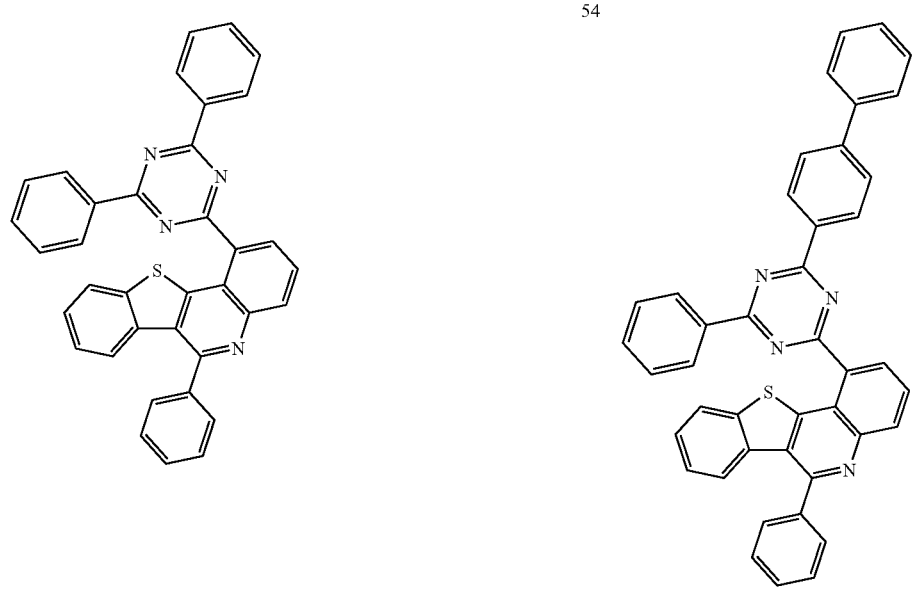

56
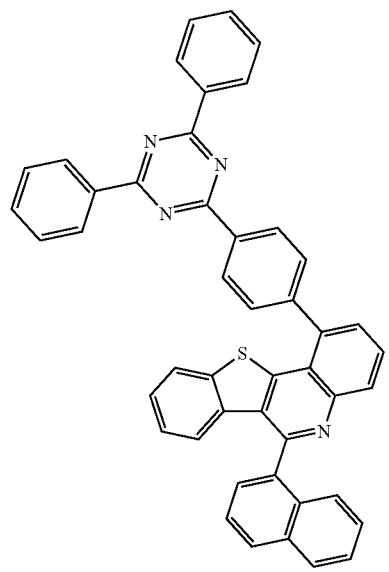
57
58
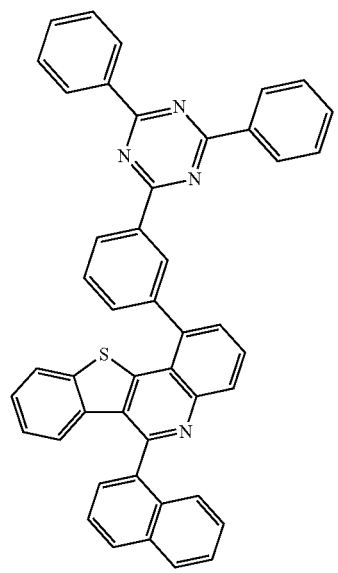
59
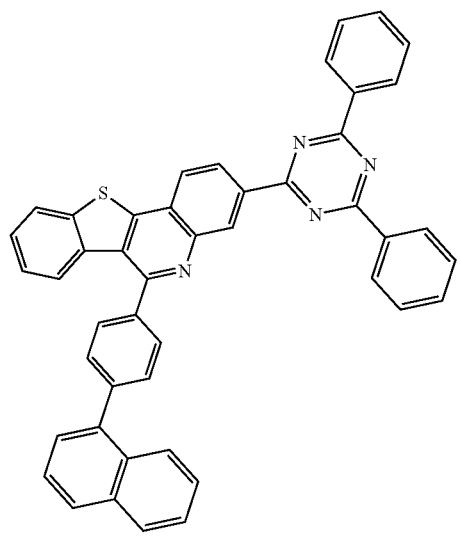

-continued
60
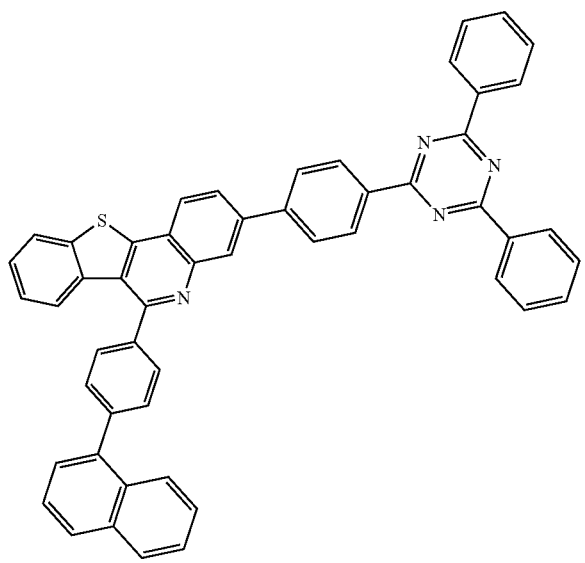
61
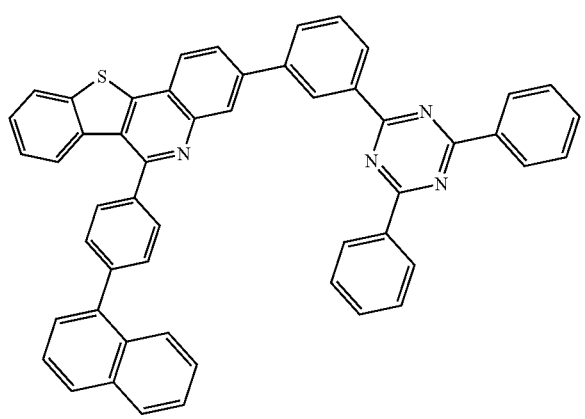
62
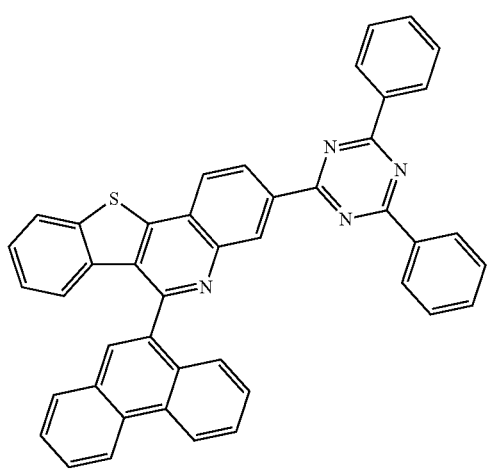
63
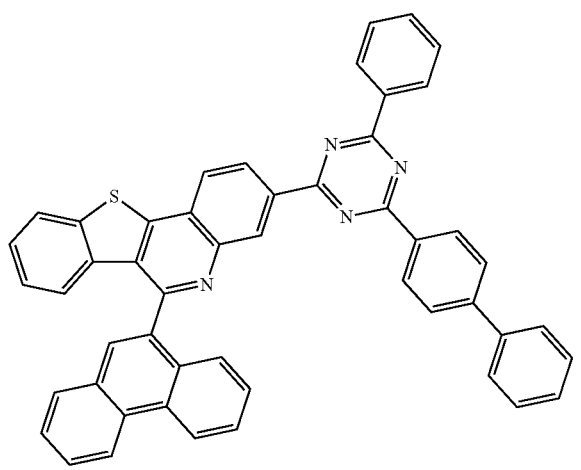
64
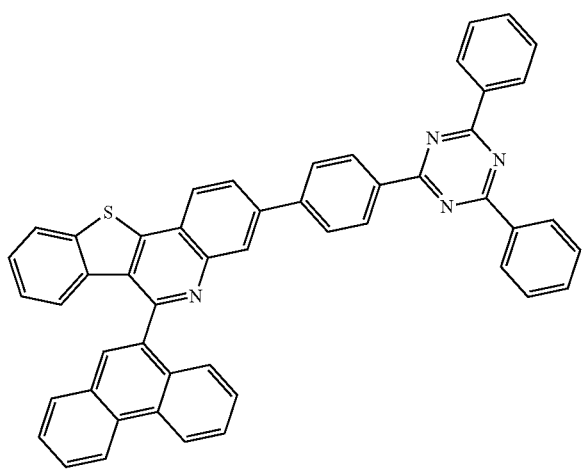

691
692
-continued
65
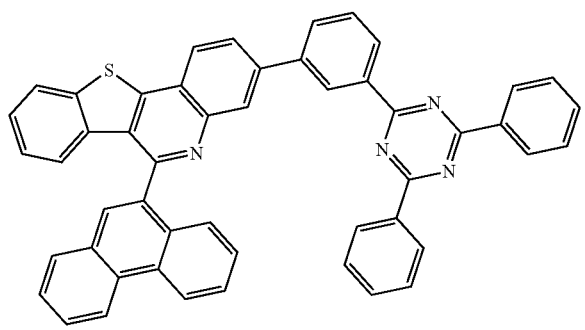
66
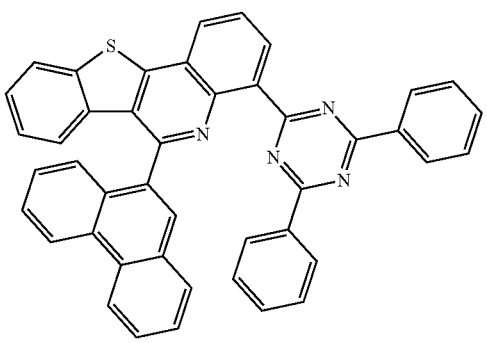
67
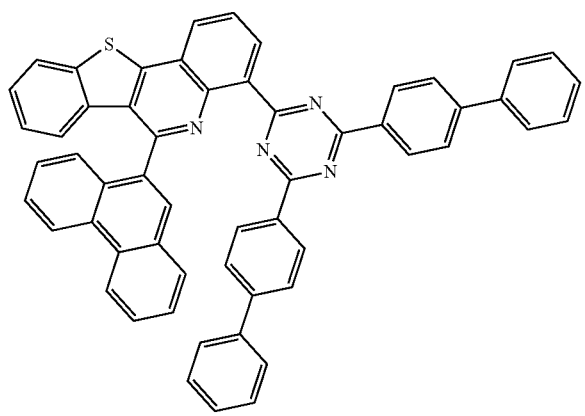
68
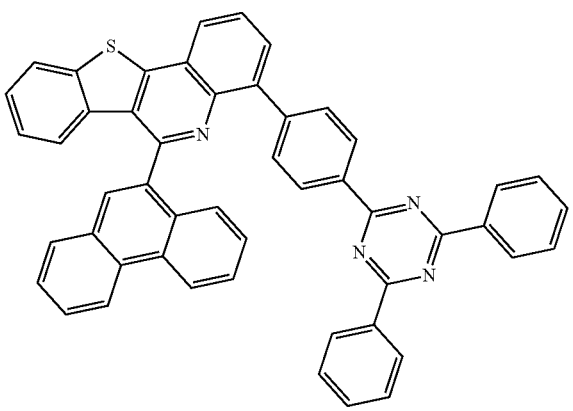
69
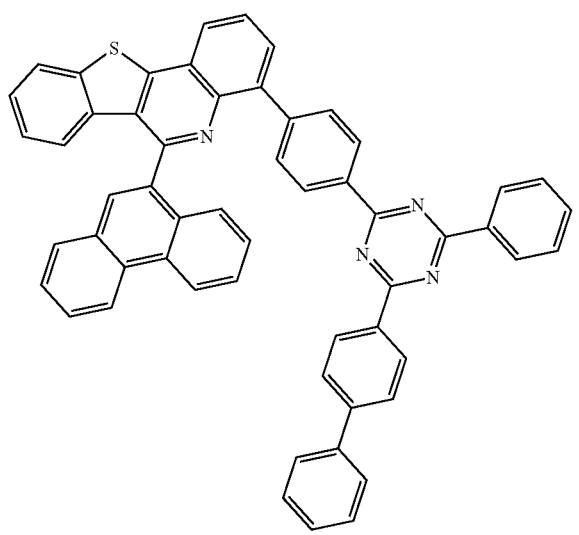
70
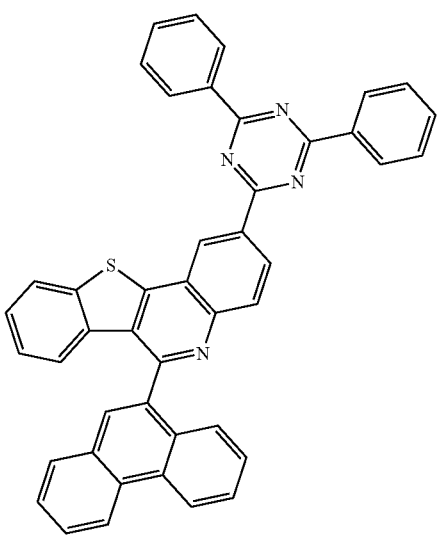

693 694
| | |
|---|---|
| 71 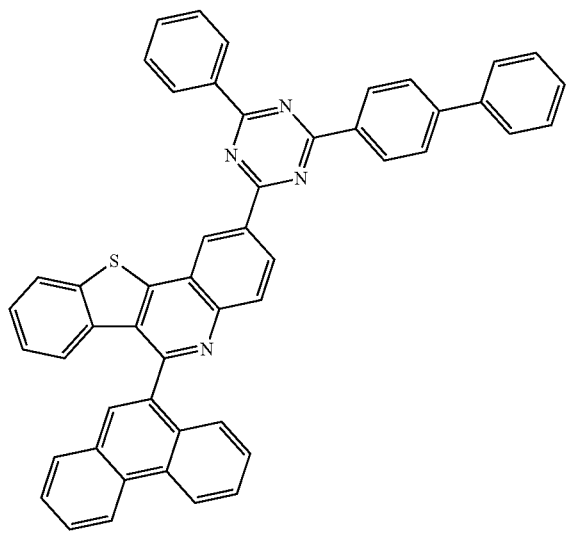 | 72 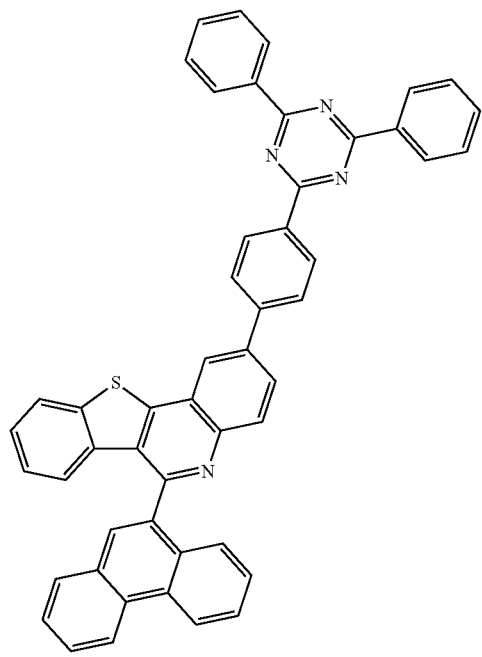 |
| 73 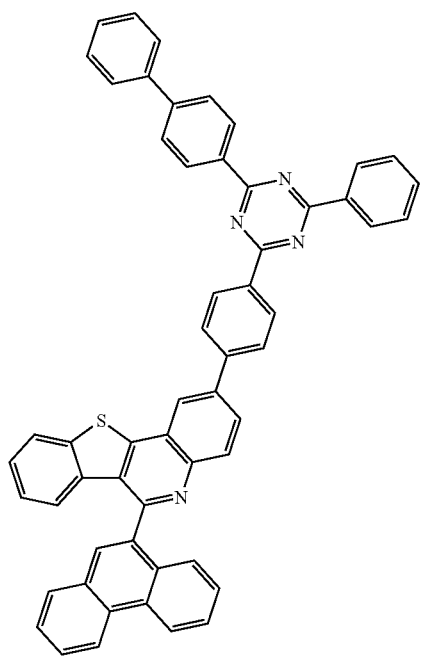 | 74 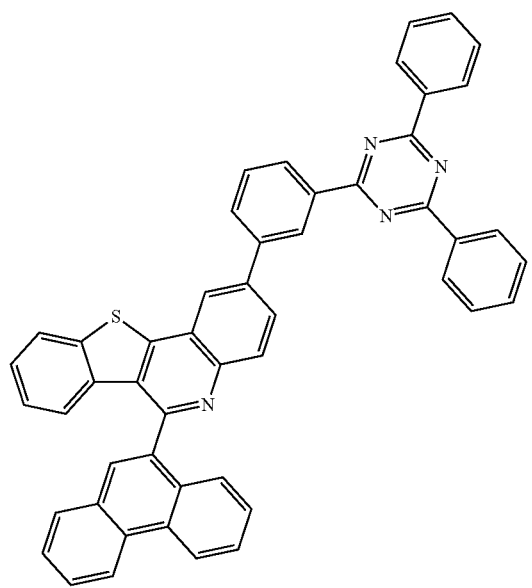 |

-continued
75
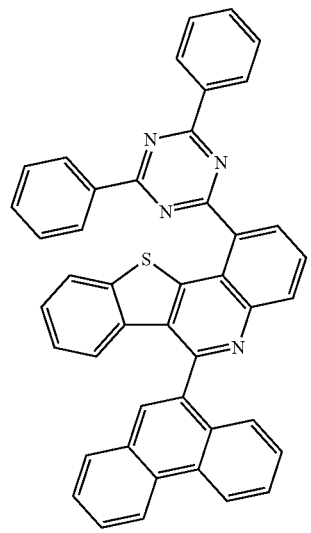
76
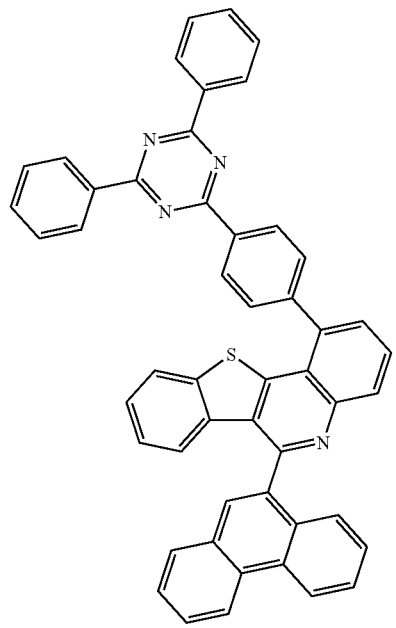
77
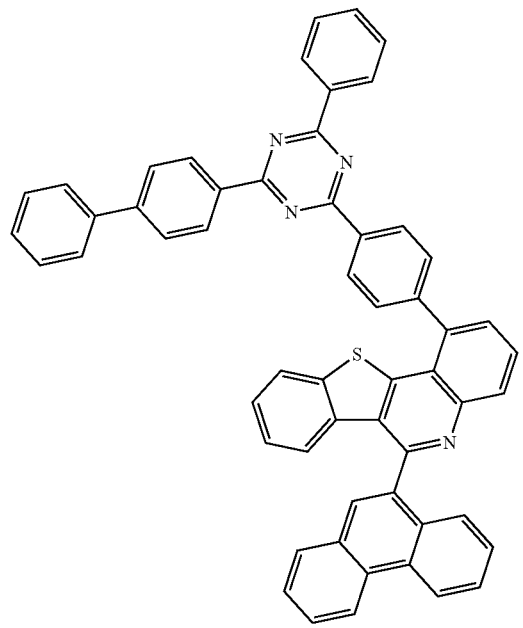
78
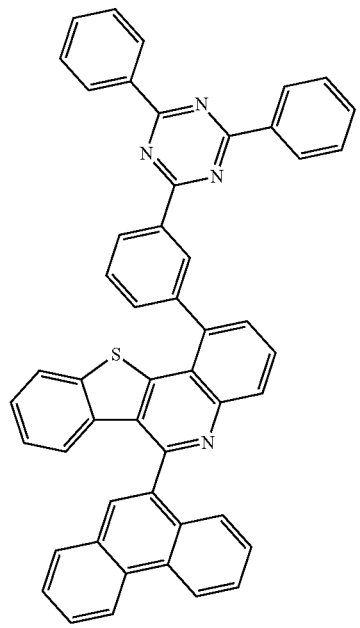

79
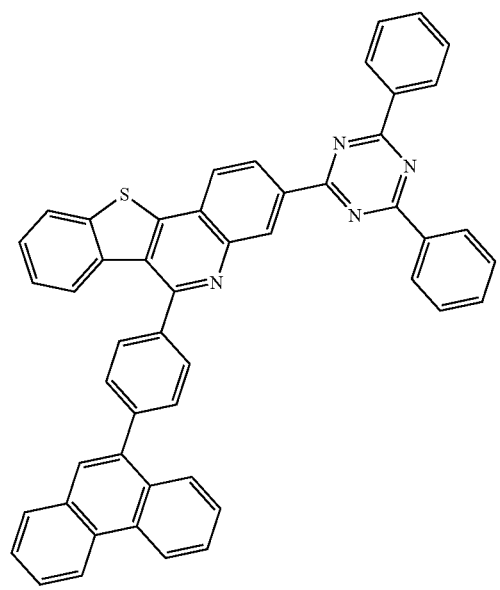
80
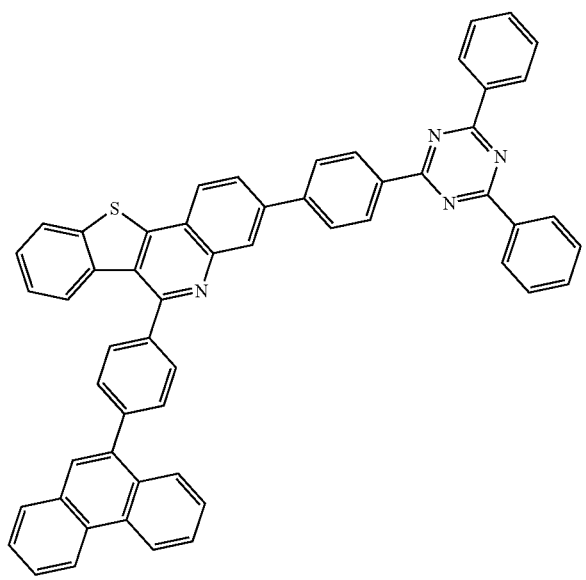
81
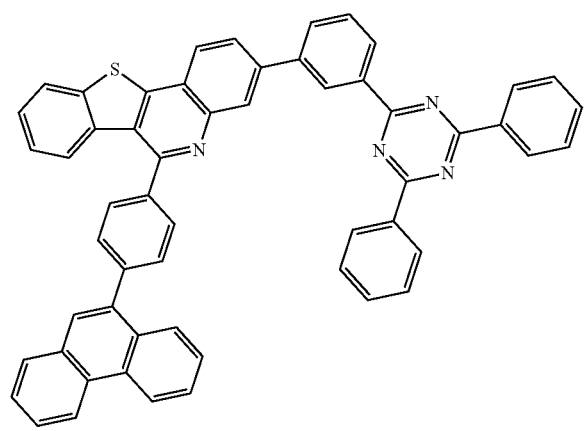
82
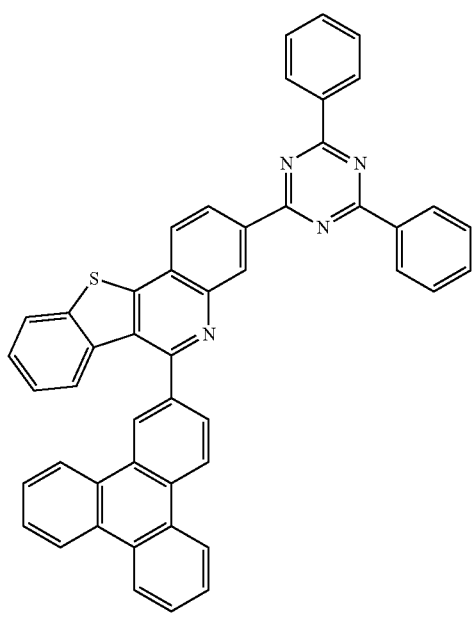

-continued
83
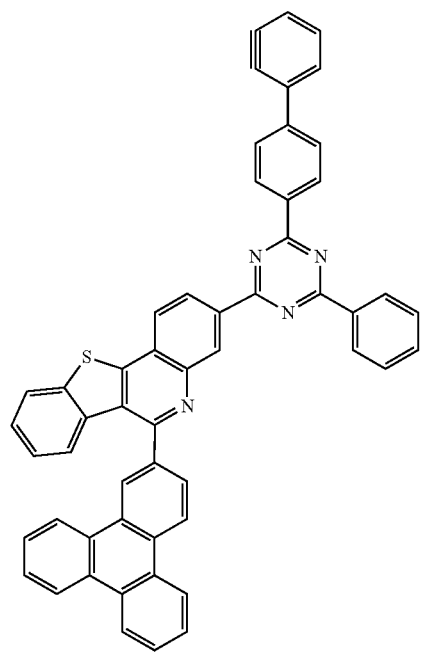
84
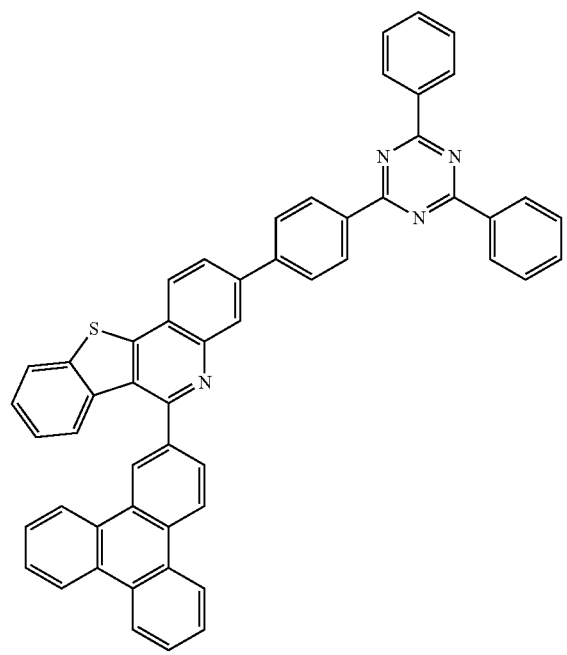
85
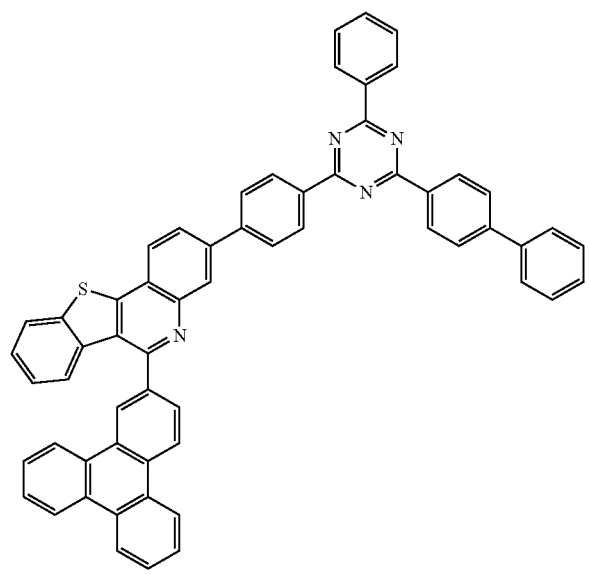
86
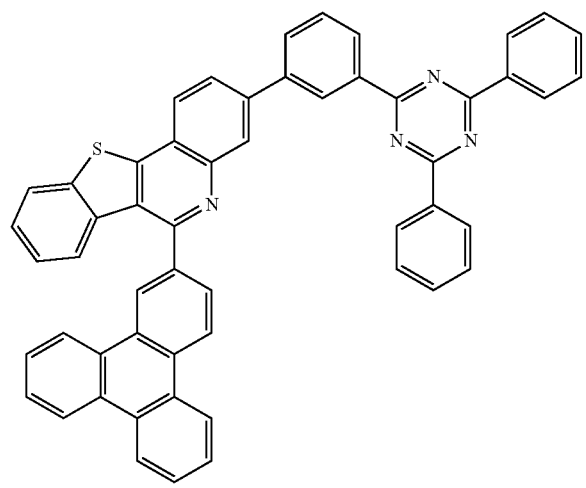

-continued
87
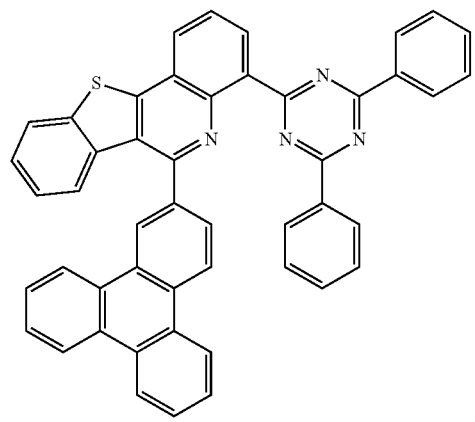
701
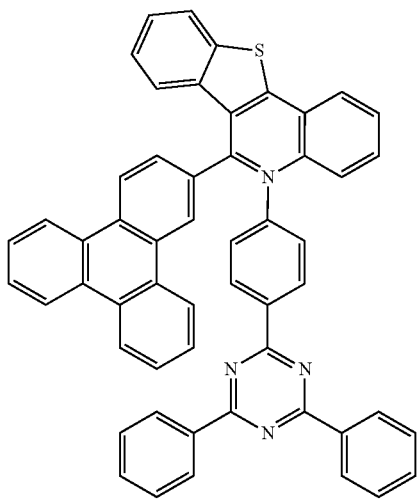
702
88
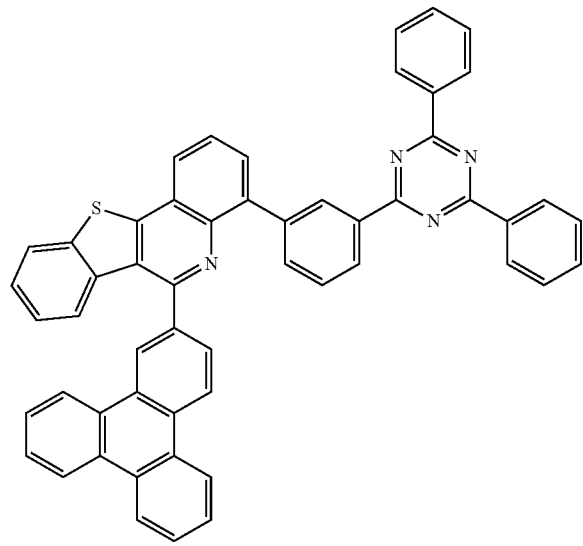
89
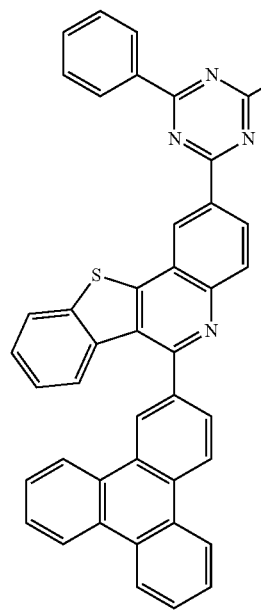
90
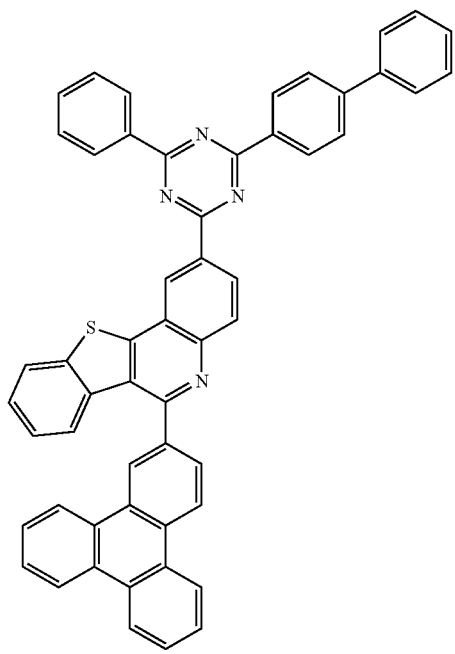
91

-continued
703
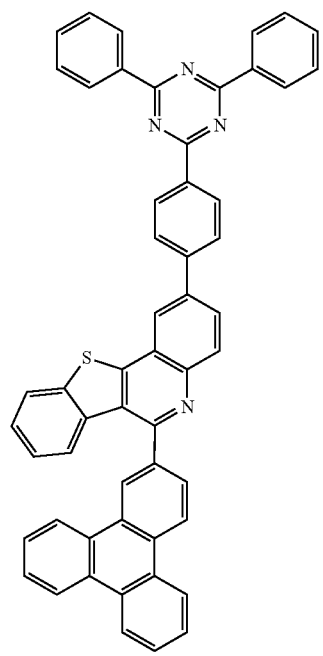
92
704
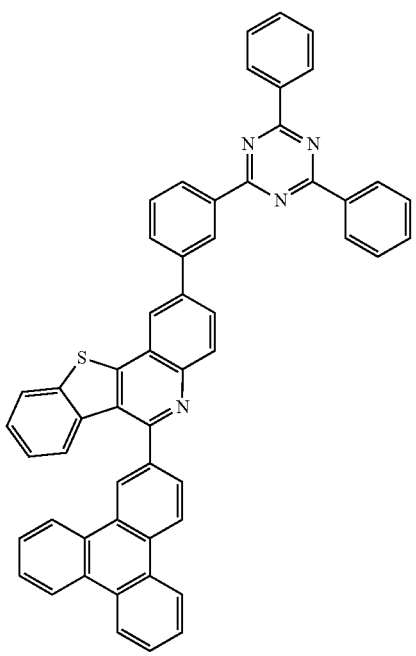
93
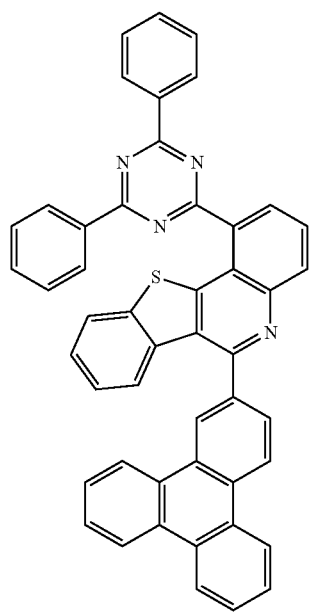
94
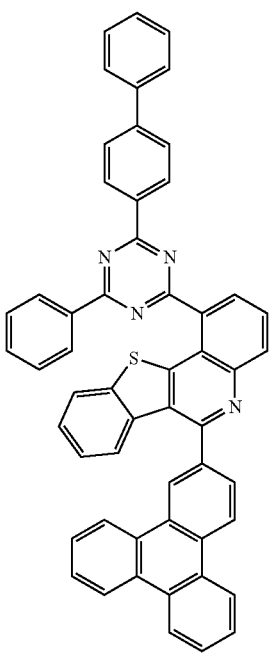
95

705
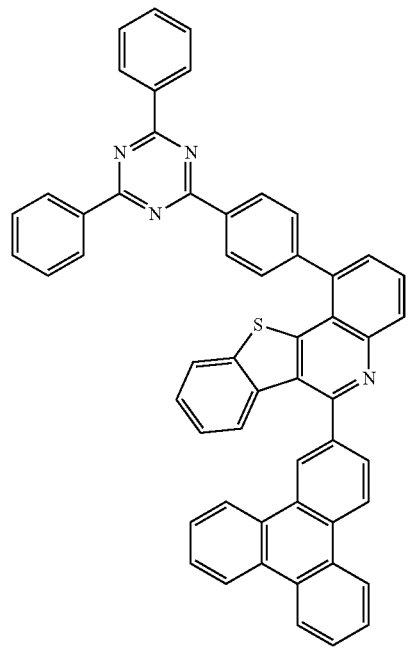
706
-continued
96
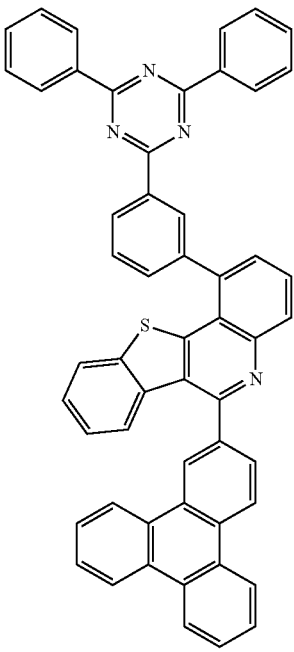
97
98
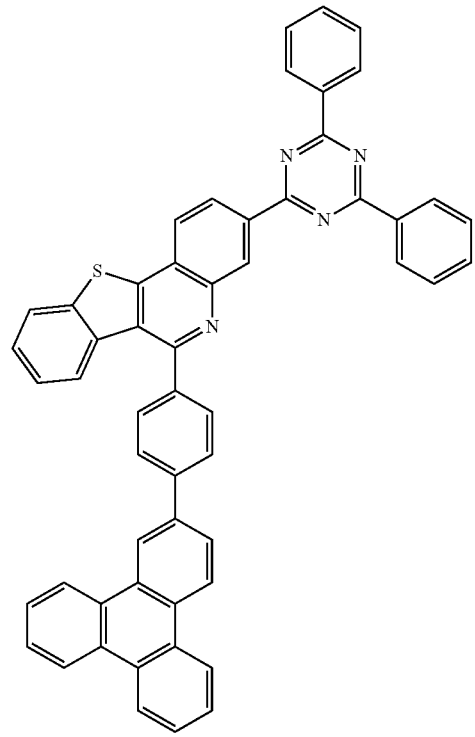
99
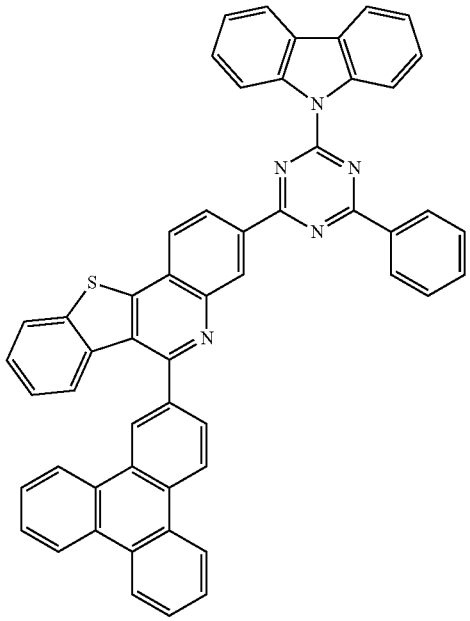

-continued
707
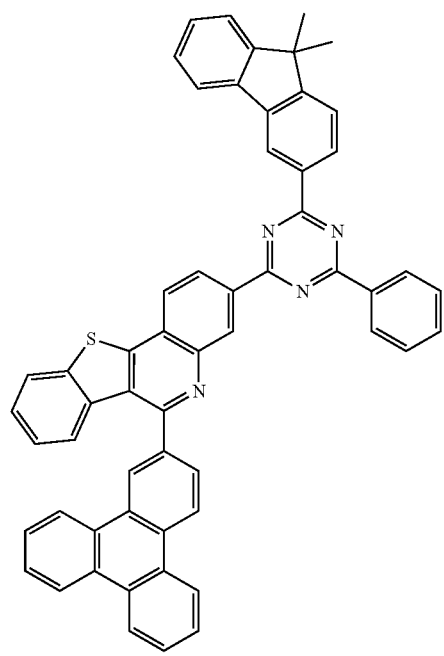
100
708
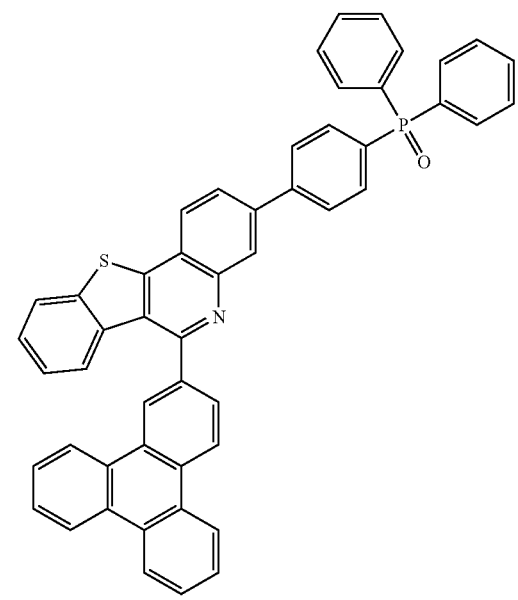
101
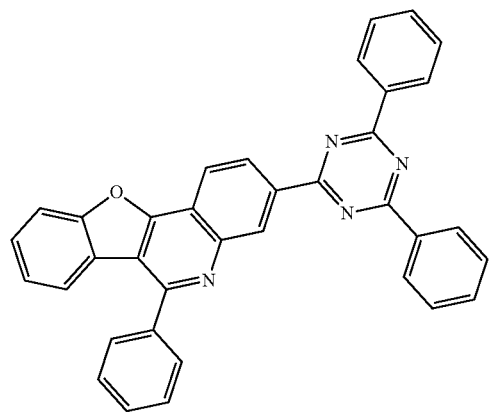
102
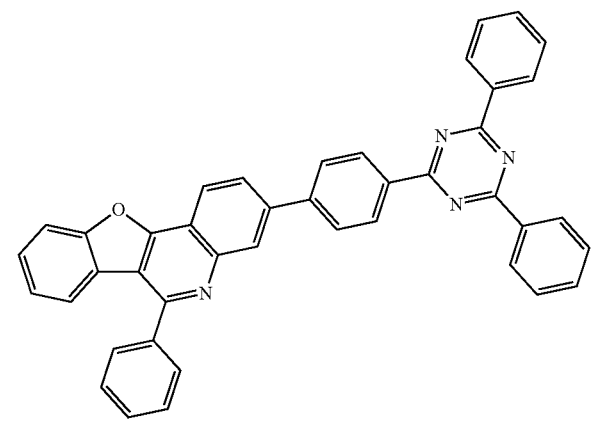
103
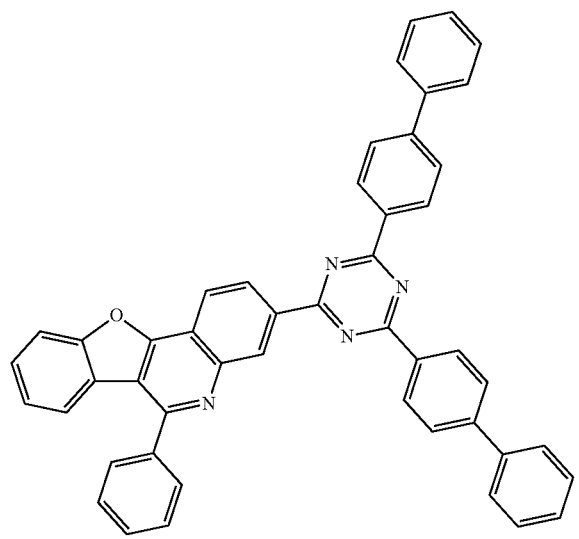
104
105

-continued
106
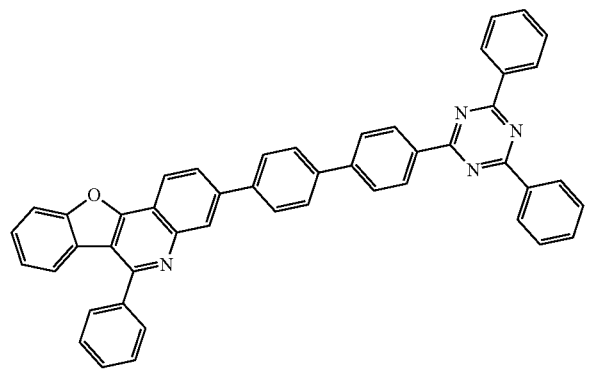
107
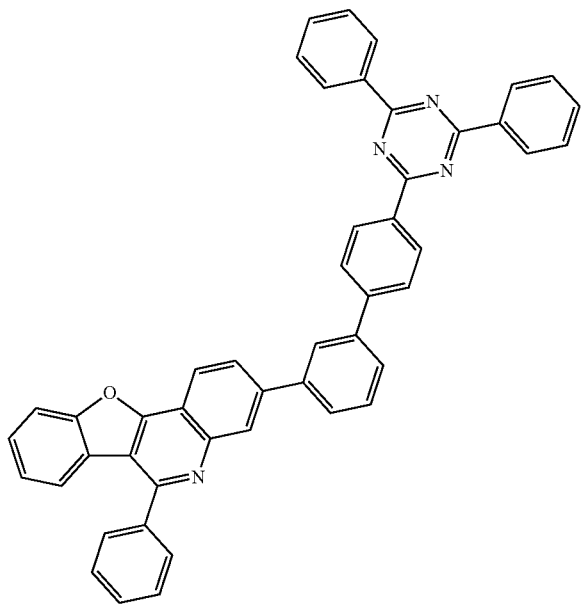
108
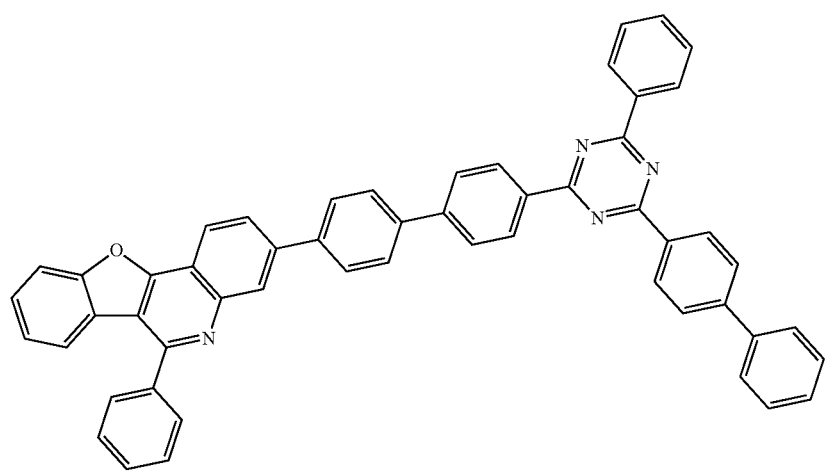
109
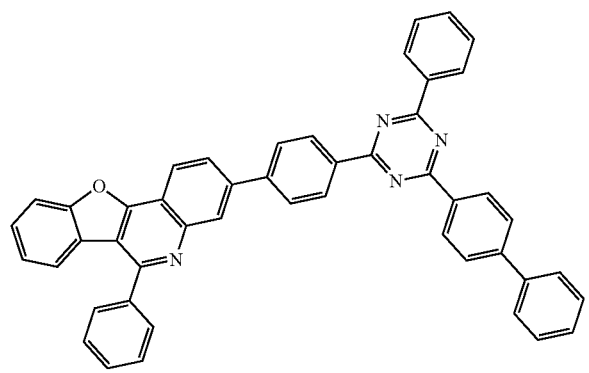
110
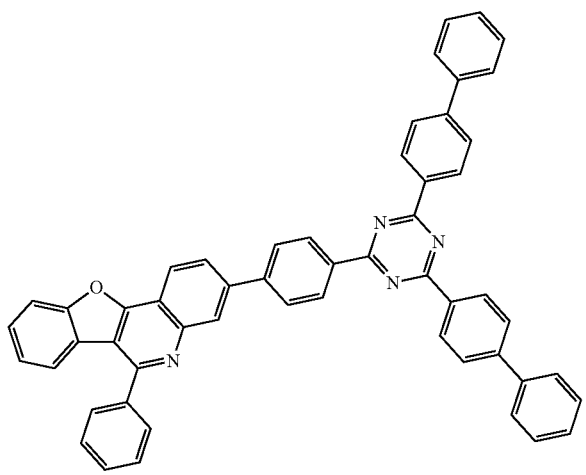

111
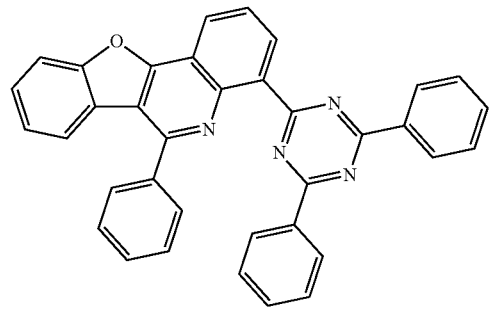
112
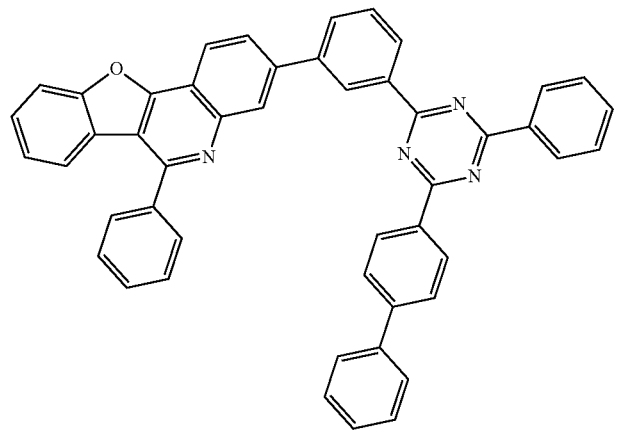
113
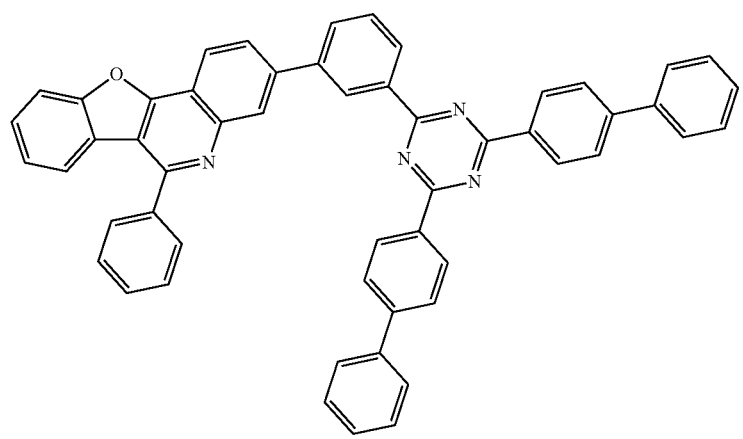

-continued
114
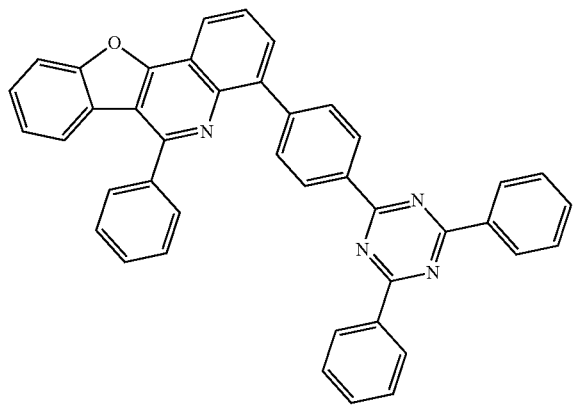
115
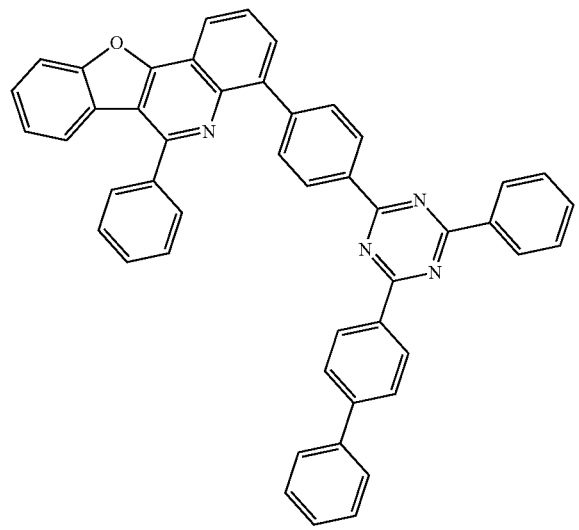
116
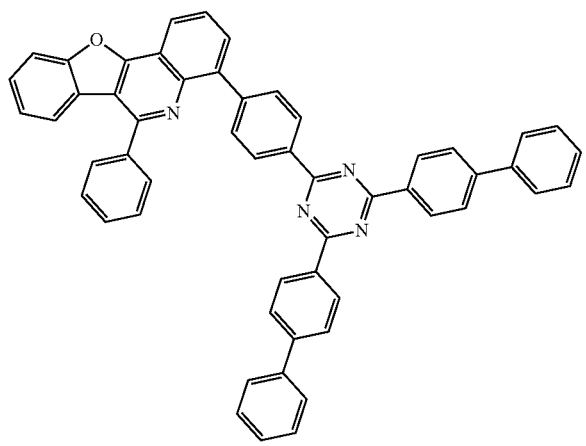
117
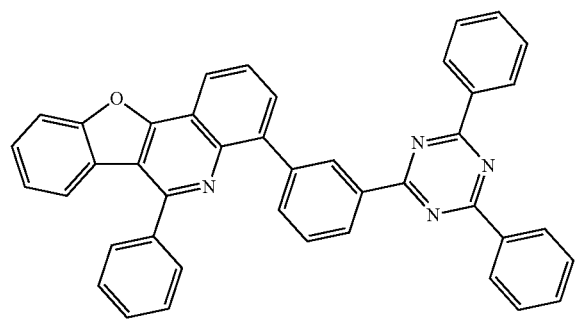
118
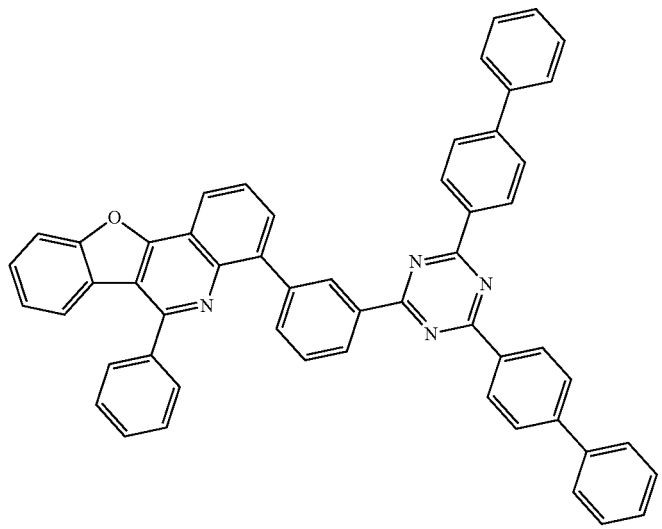

119 120
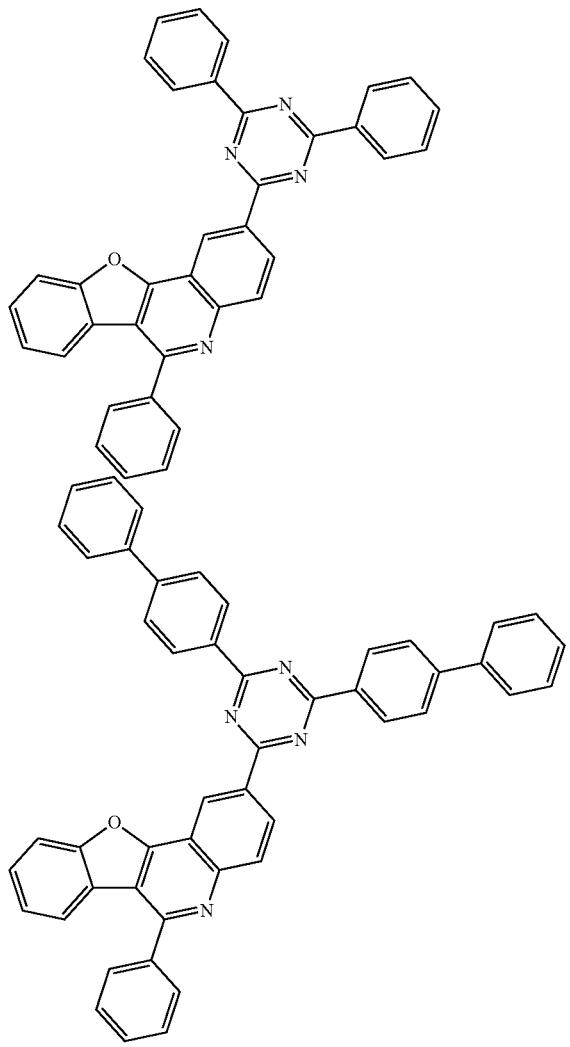 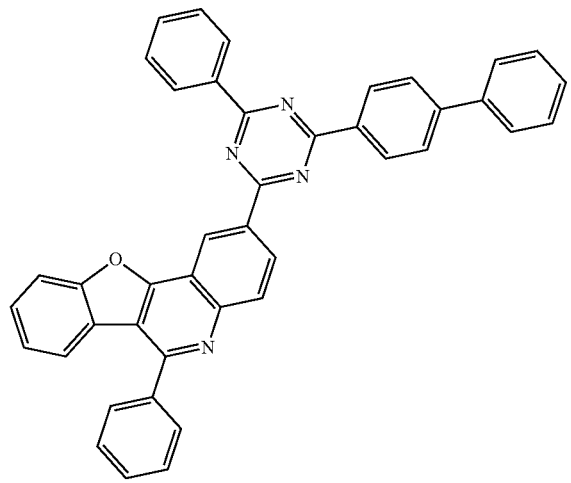
121
122 123
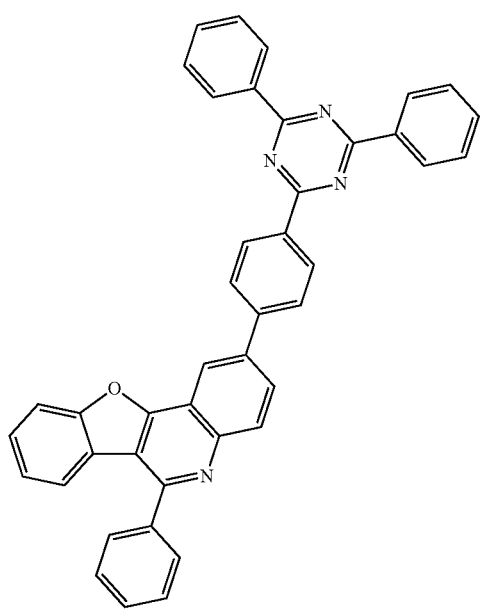 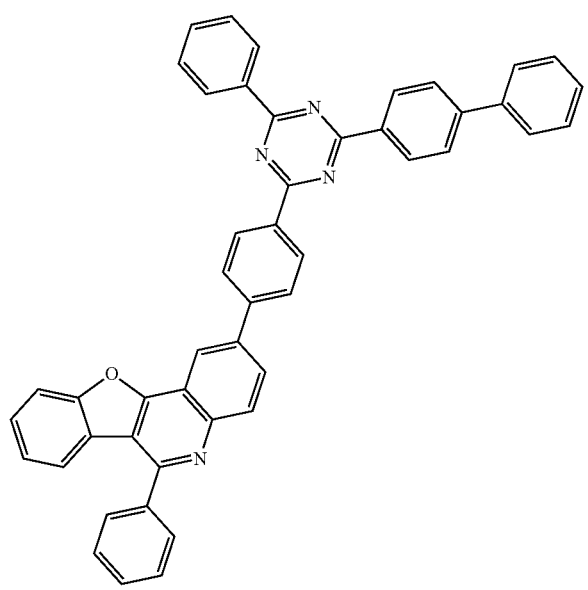

124
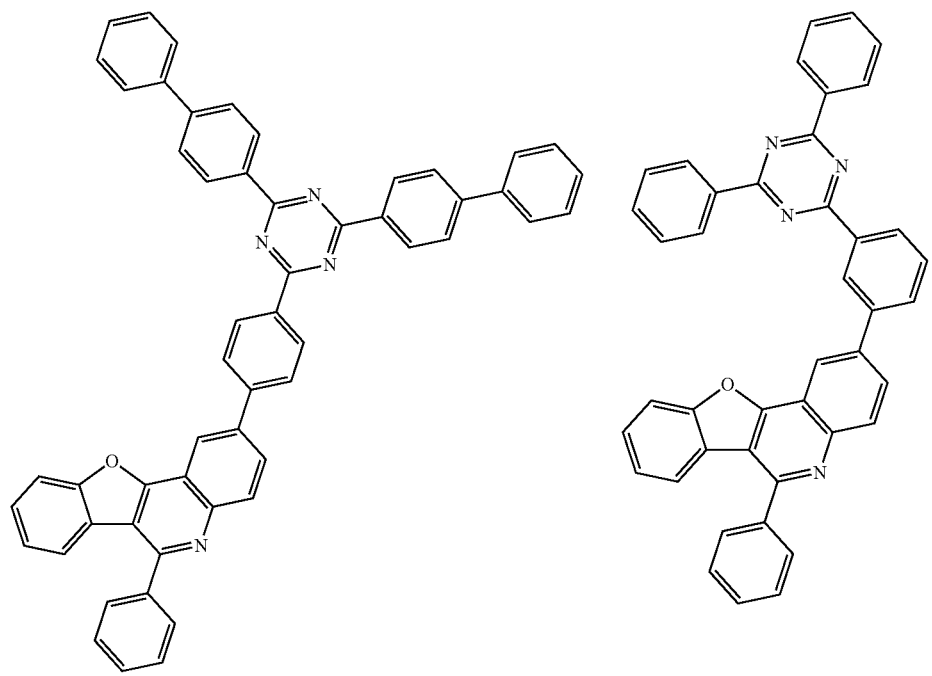
125
126
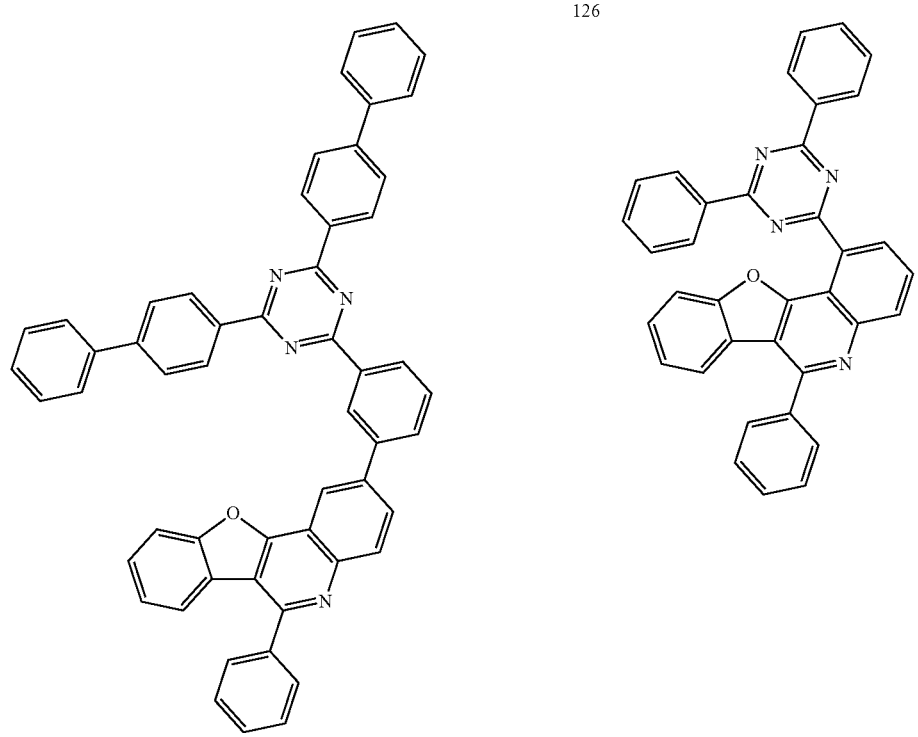
127

-continued
719
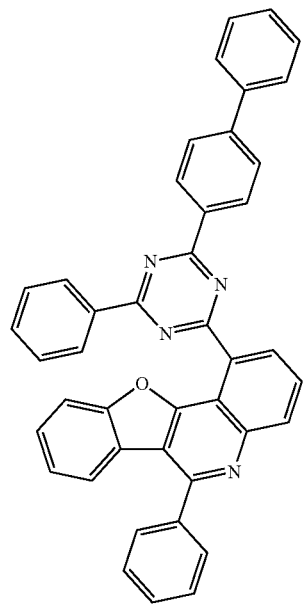
128
720
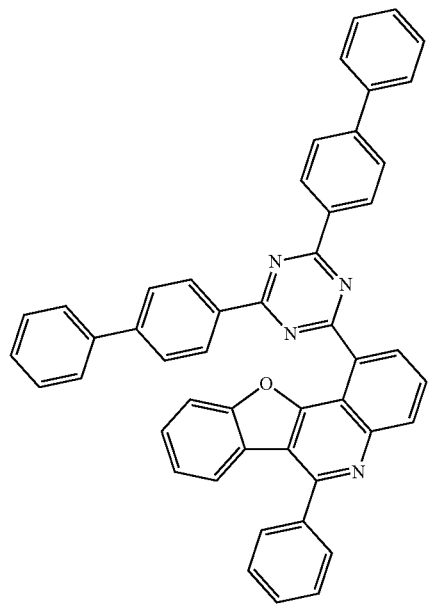
129
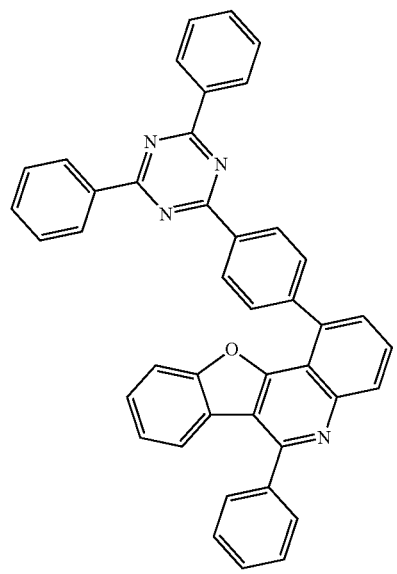
130
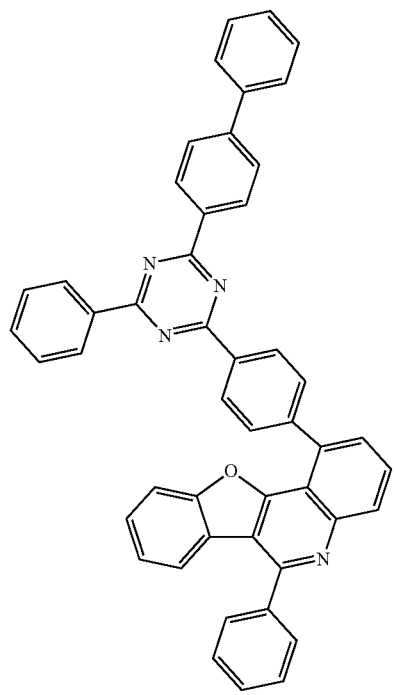
131

132
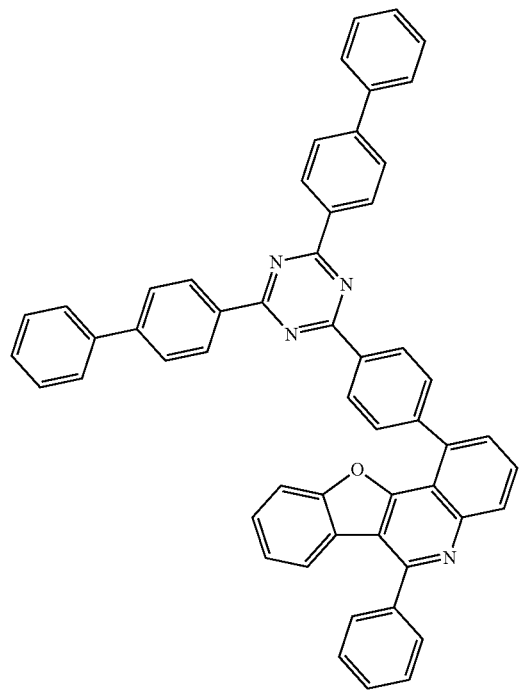
133
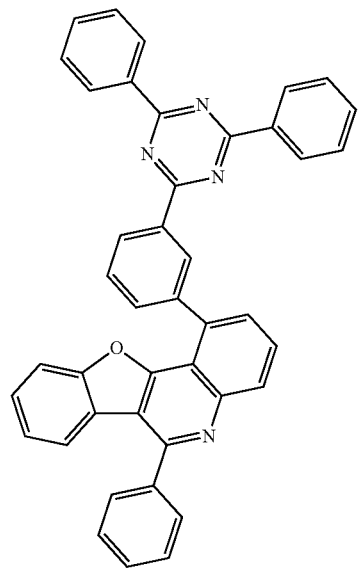
134
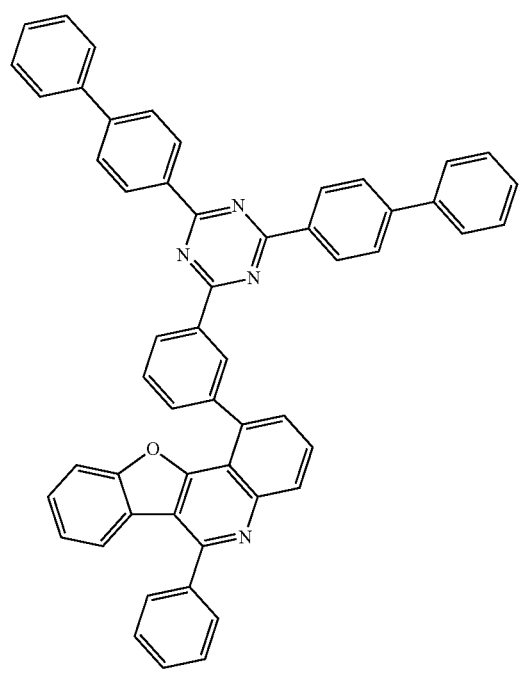
135
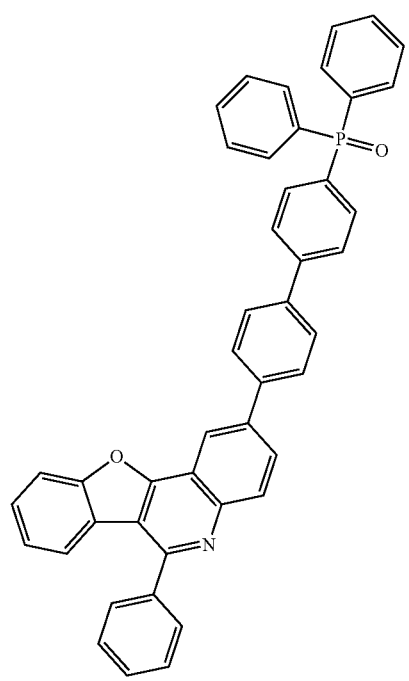

-continued
136
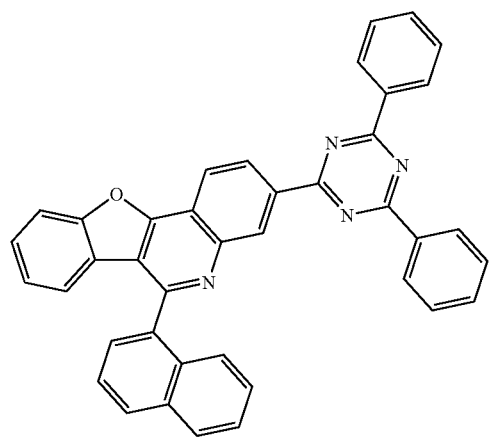
137
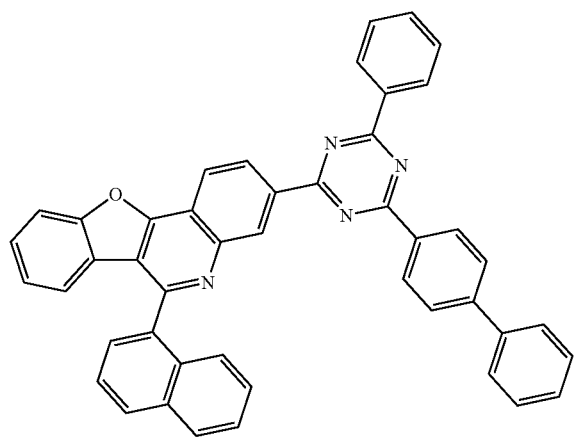
138
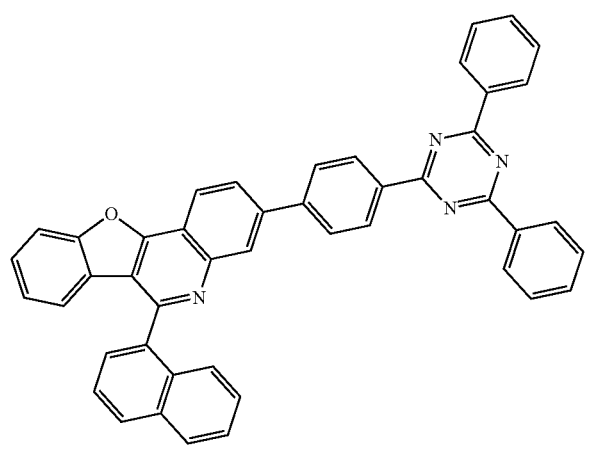
139
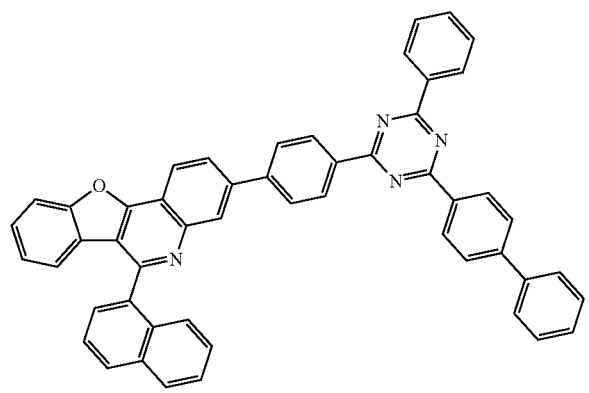
140
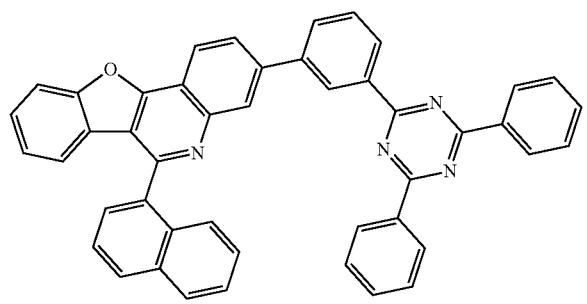

141
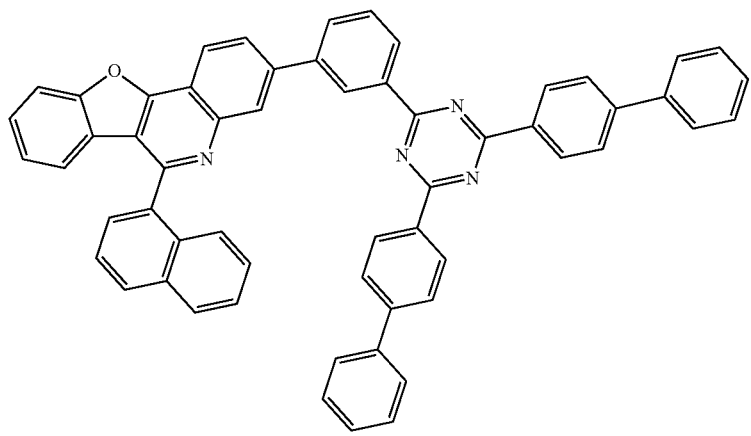
142
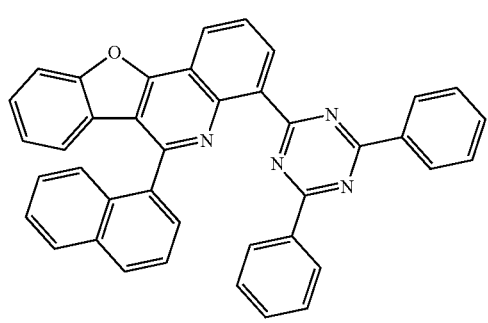
143
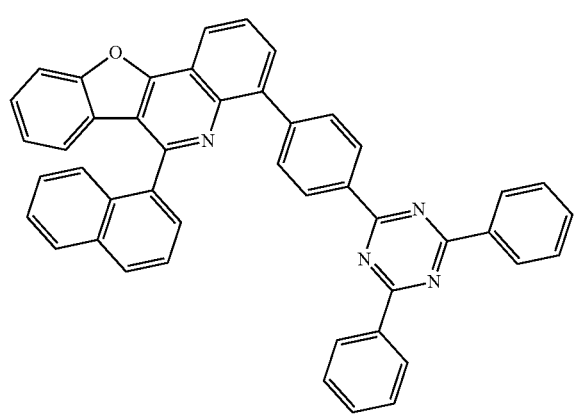
144
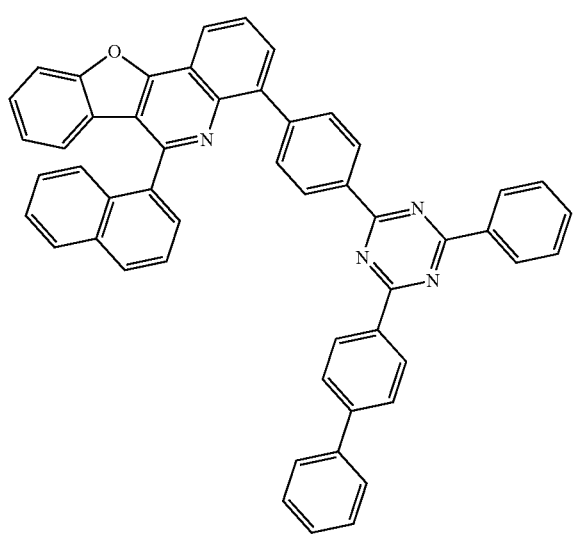
145
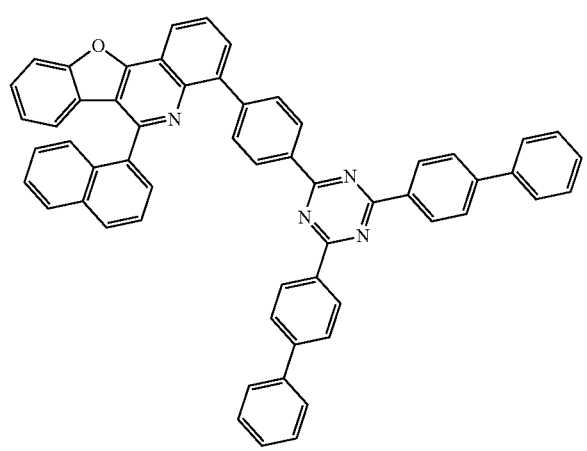

-continued
146
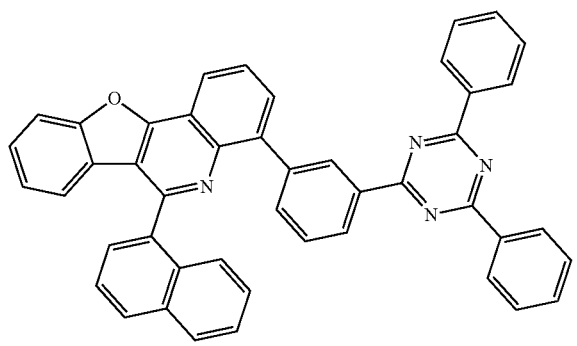
147
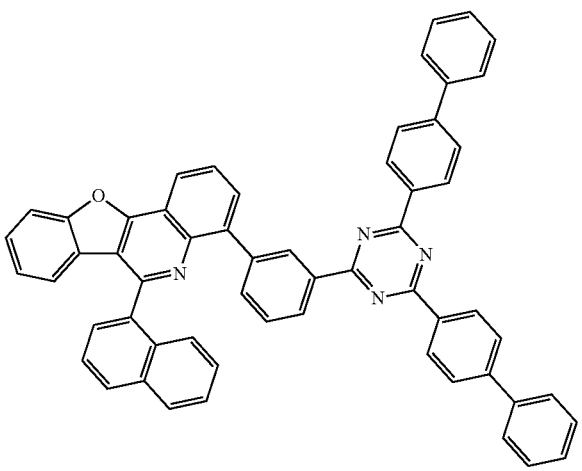
148
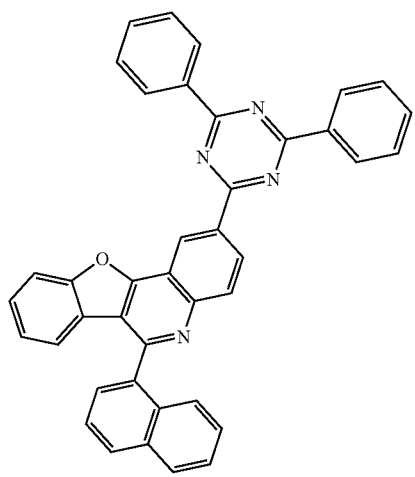
149
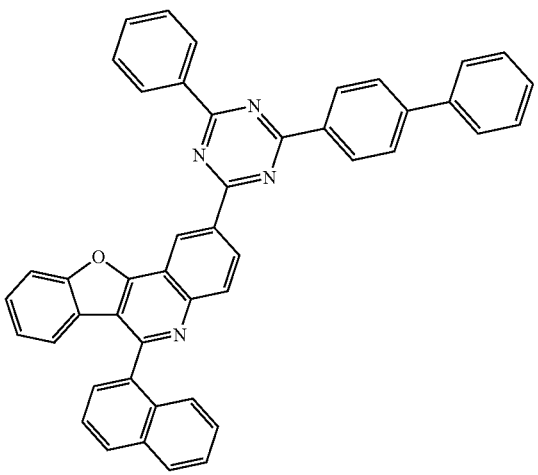
150
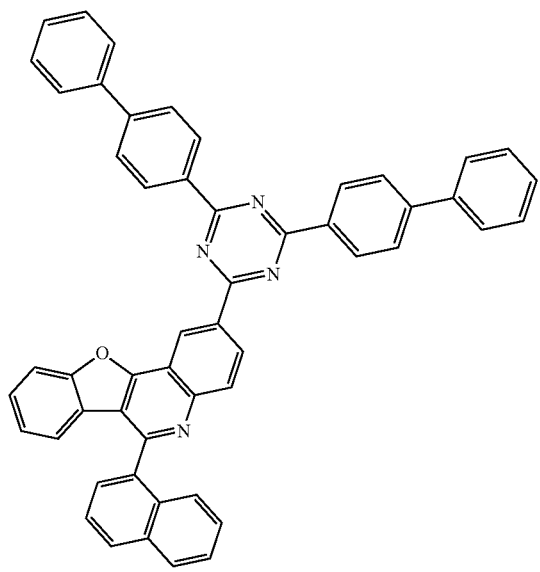

-continued
151
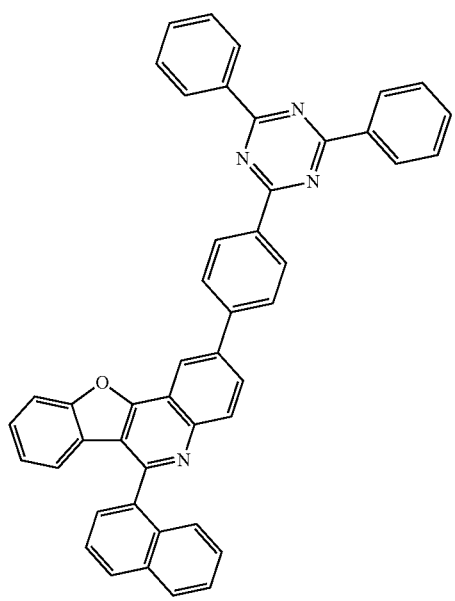
152
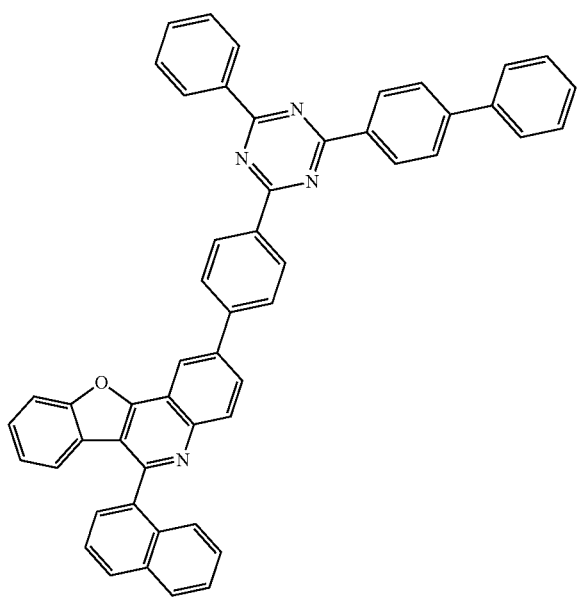
153
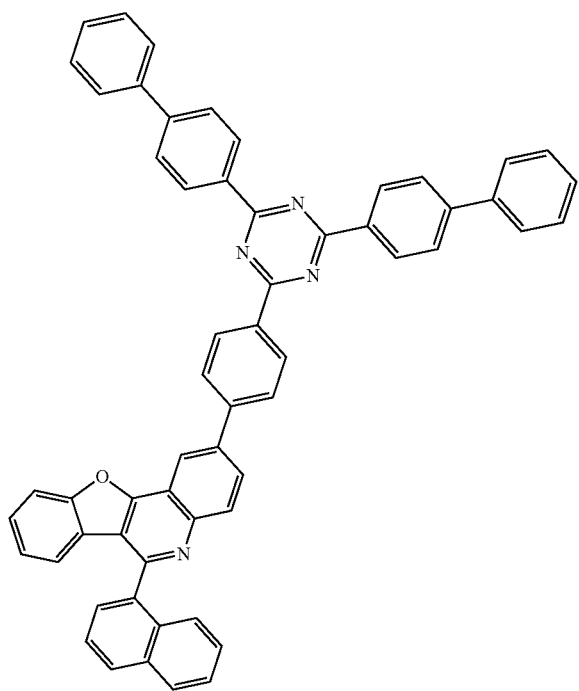
154
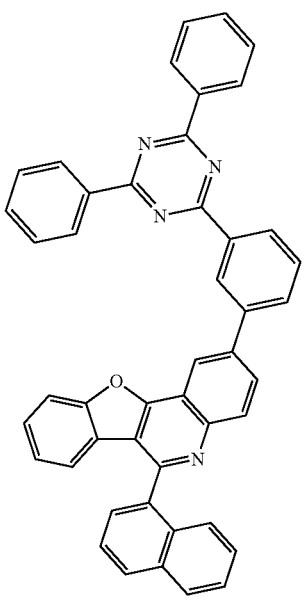

731
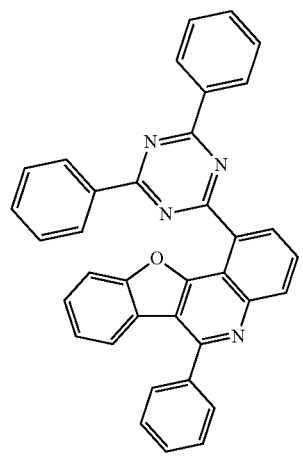
732
-continued
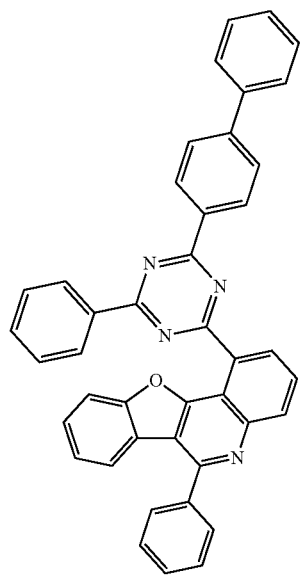
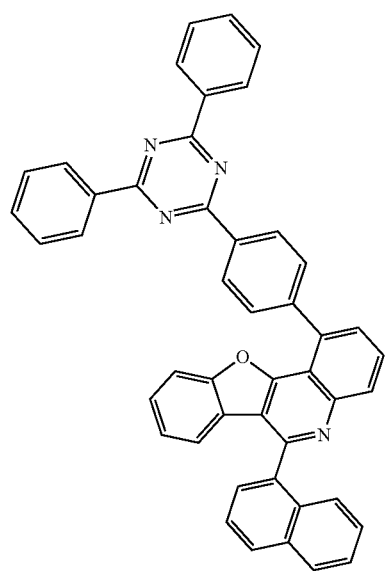
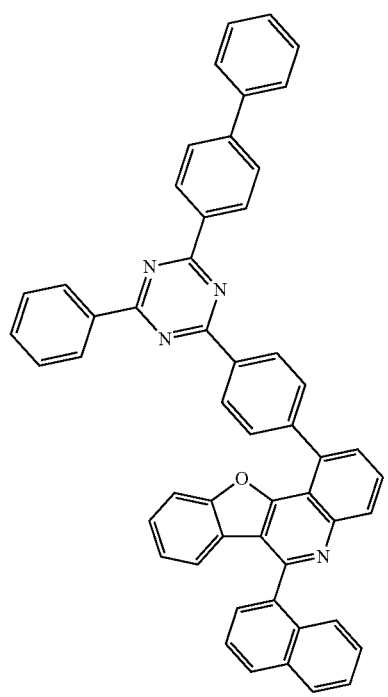

158
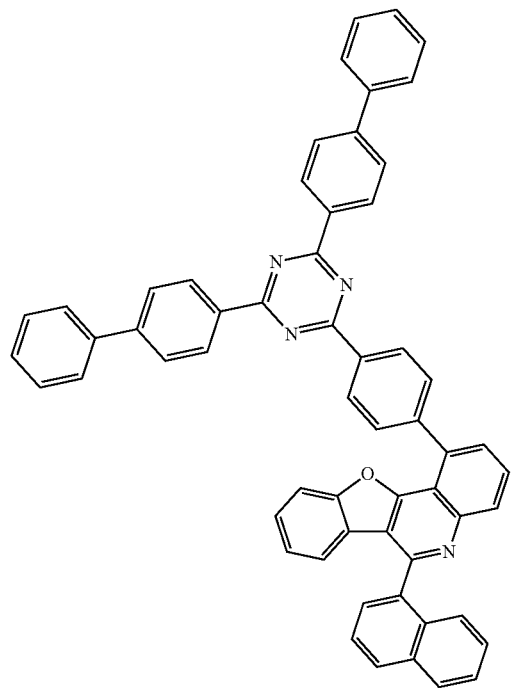
159
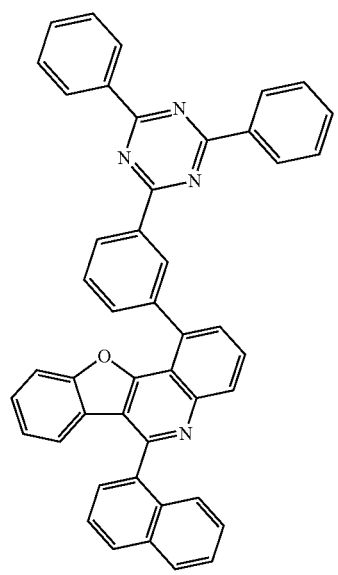
160
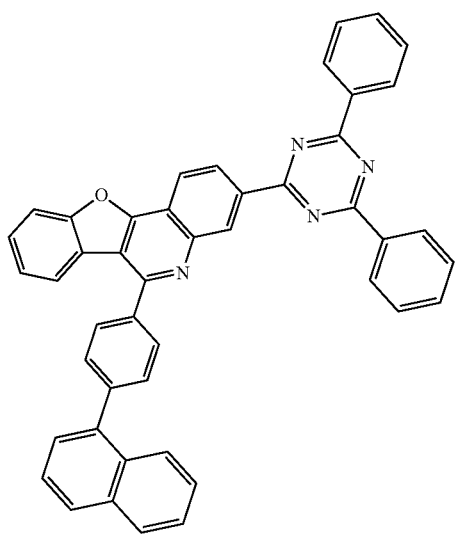

-continued
161
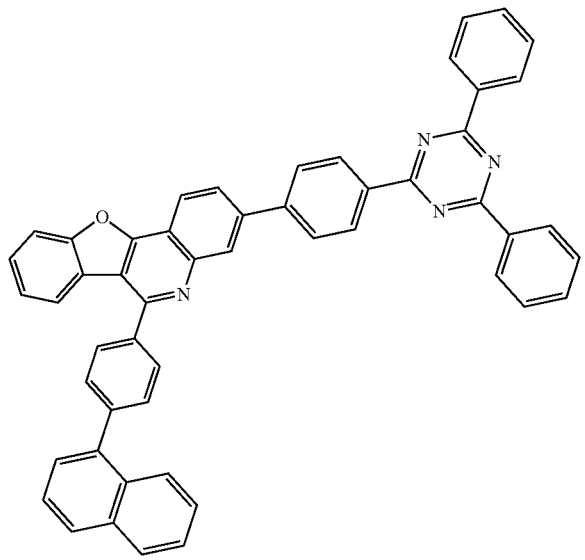
162
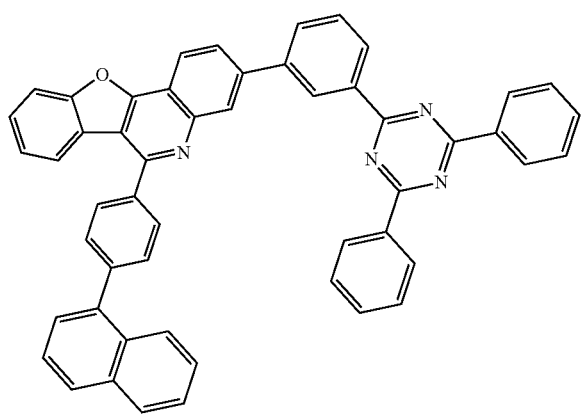
163
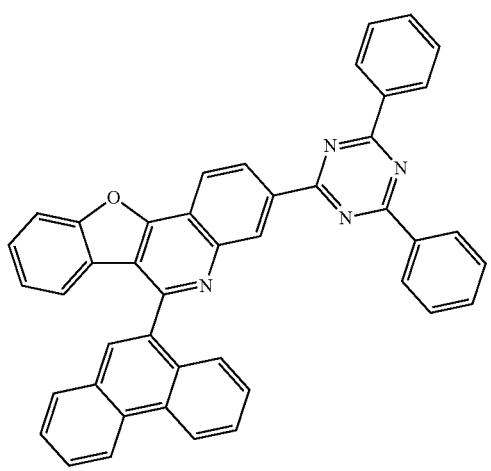
164
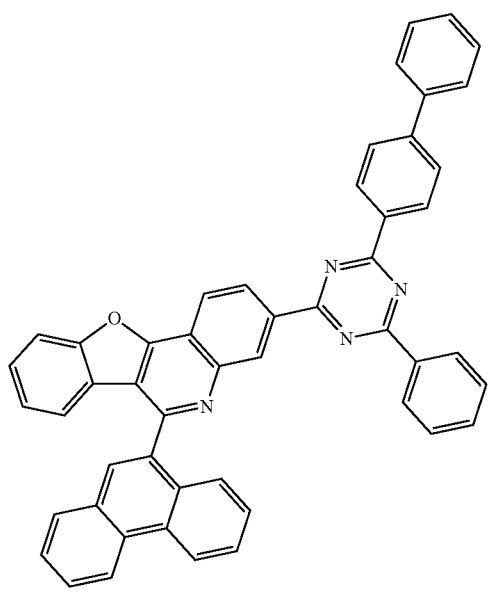
165
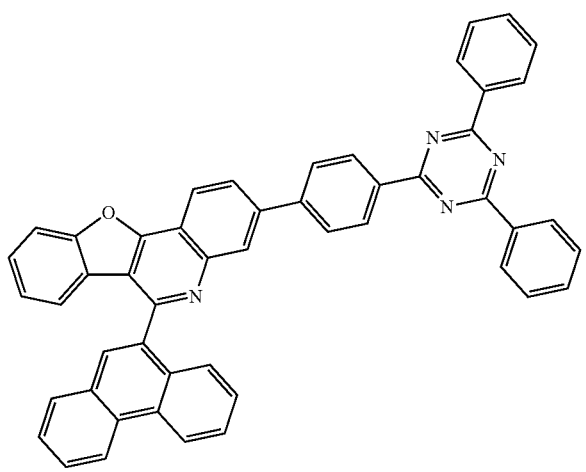

166
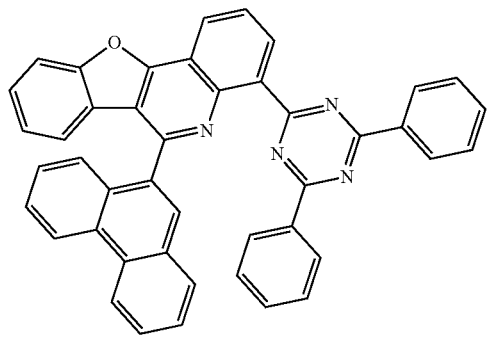
167
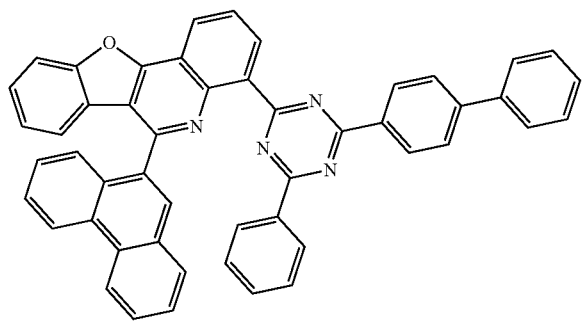
168
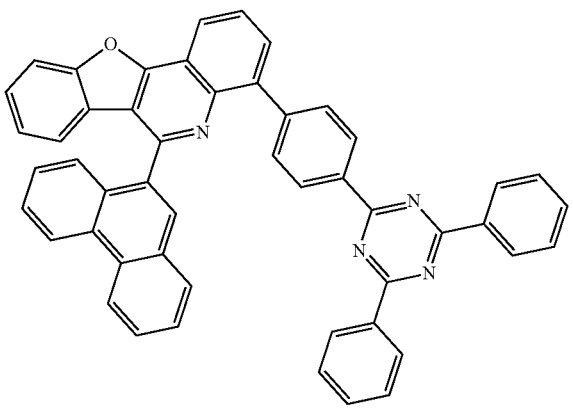
169
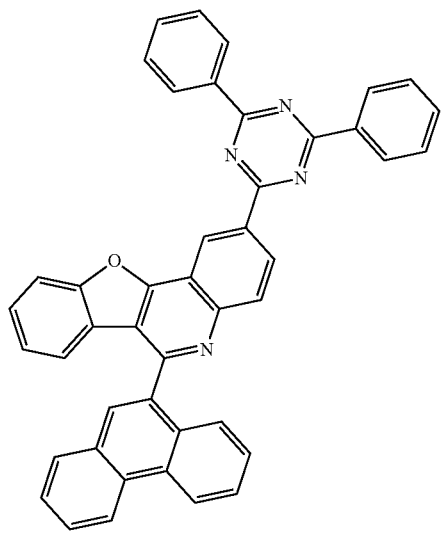

170
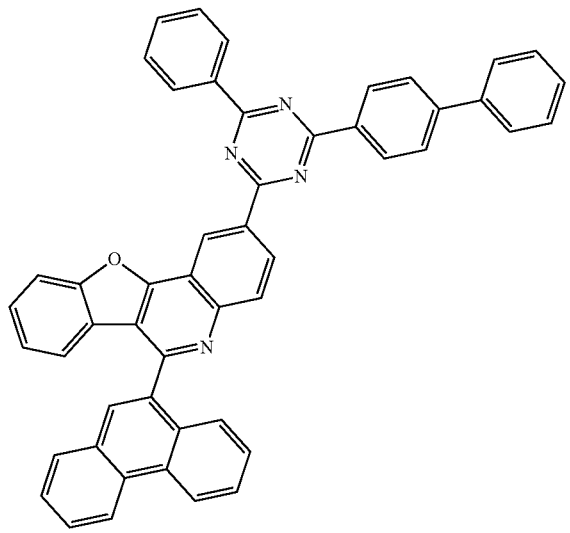
171
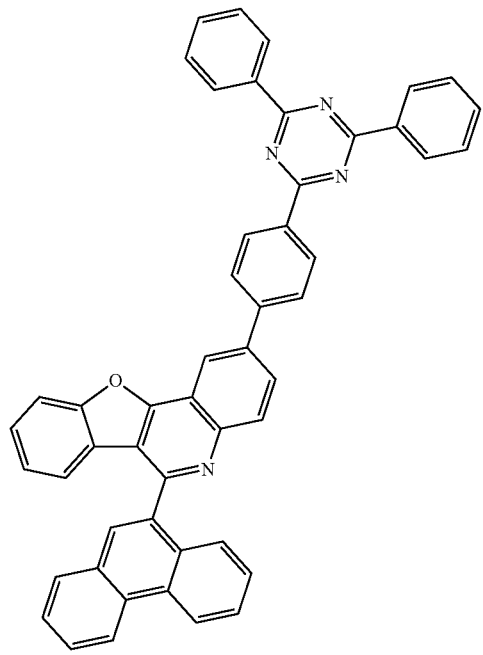
172
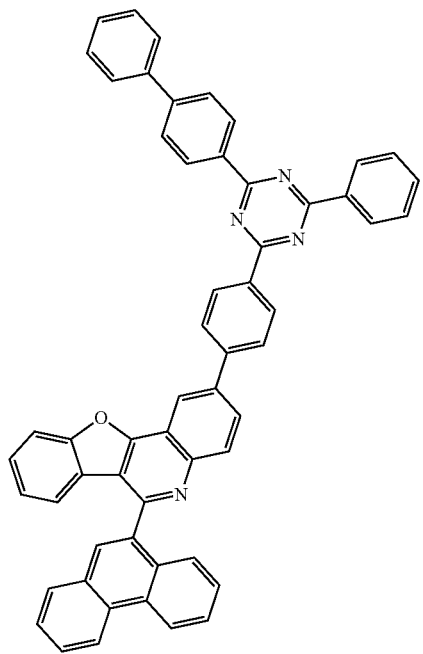
173
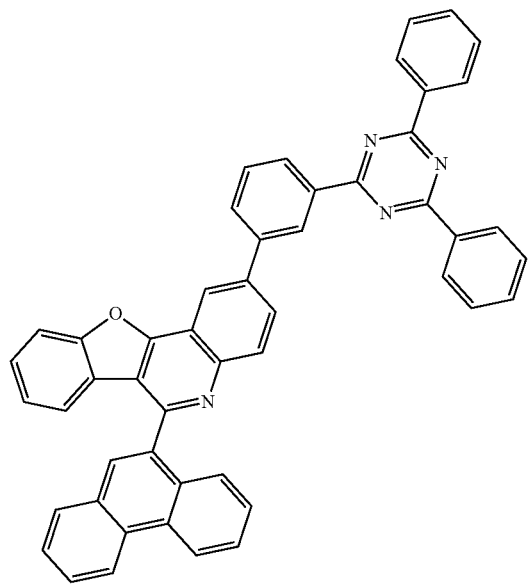

-continued
741
174
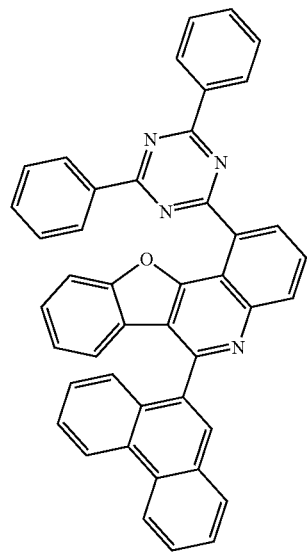
742
175
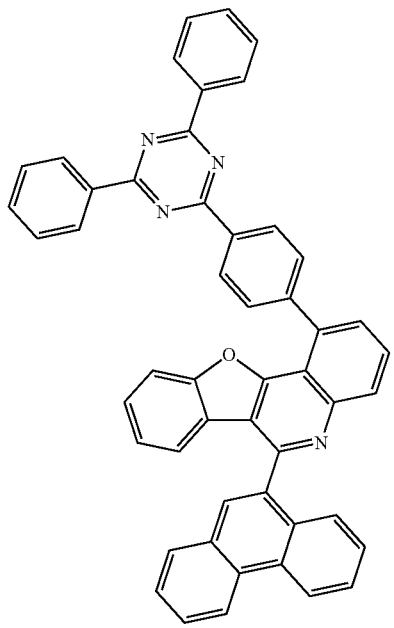
176
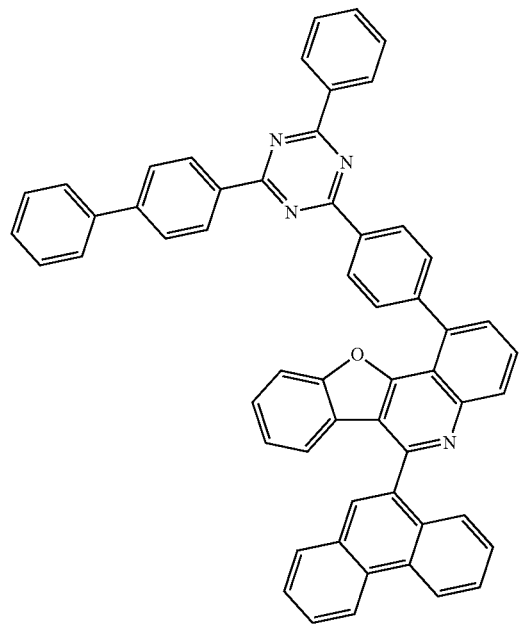
177
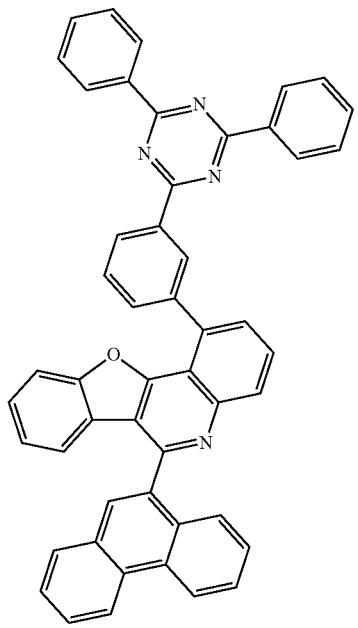

743
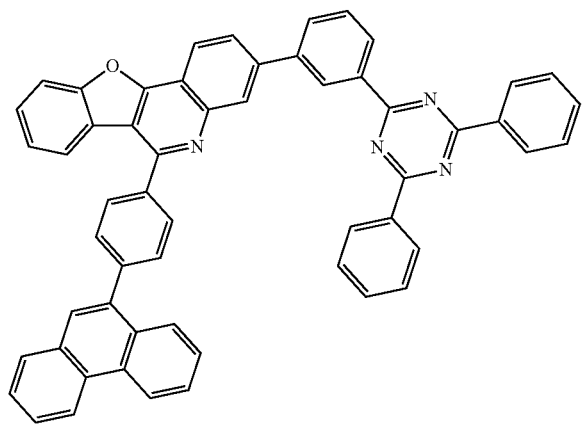
744
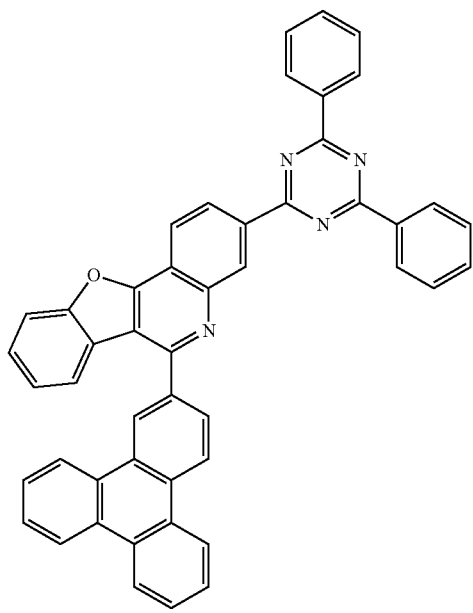
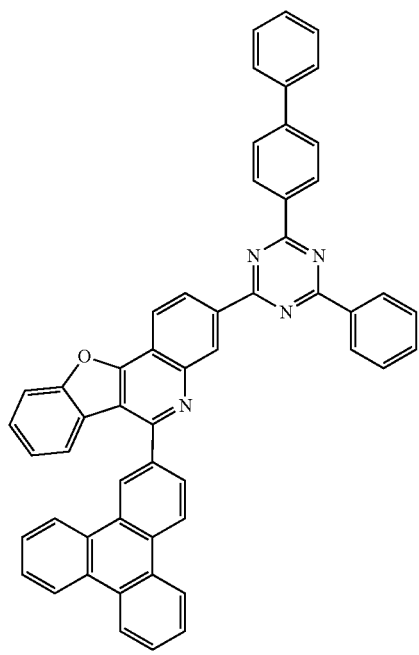
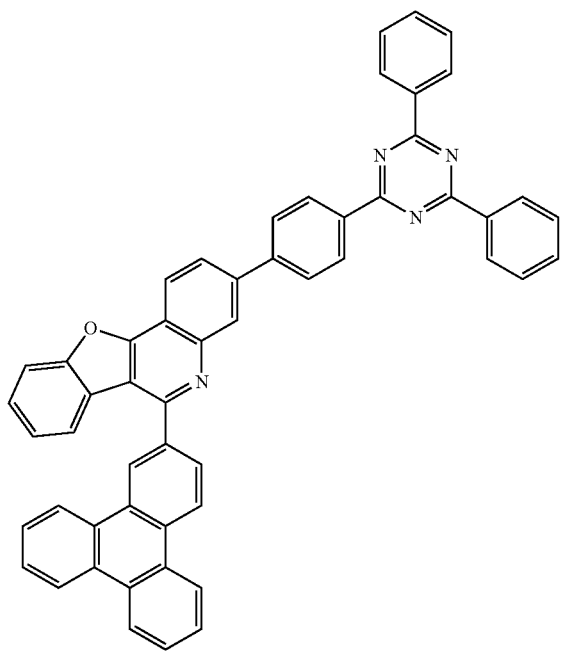

-continued
745
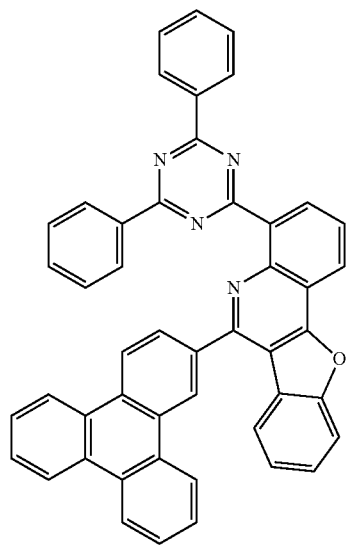
746
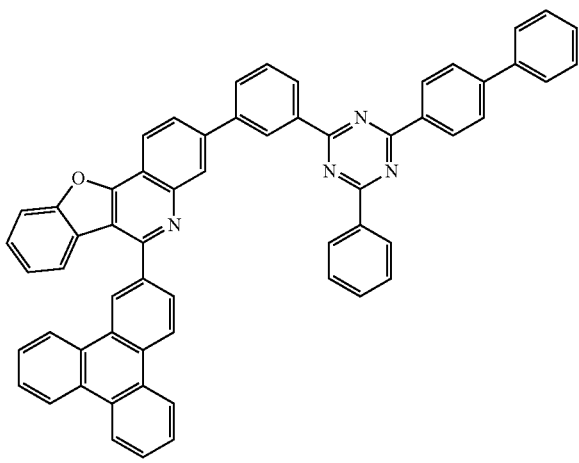
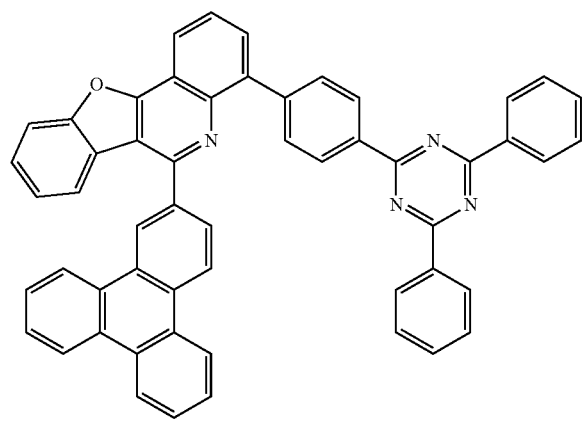
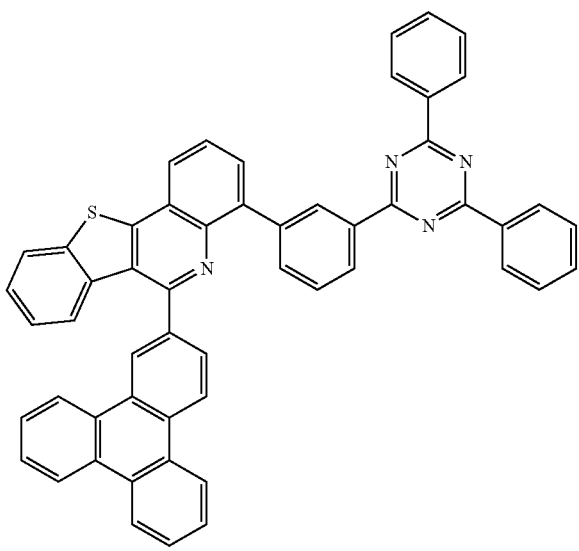

747
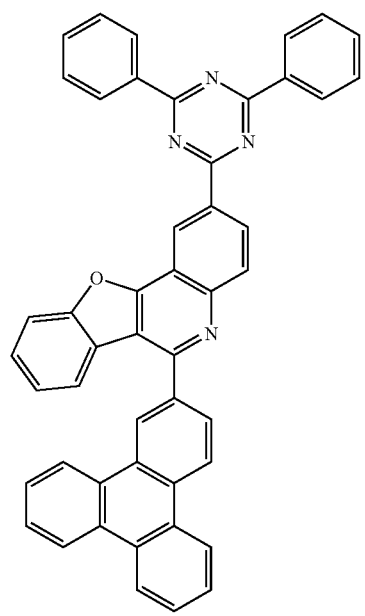
748
-continued
186
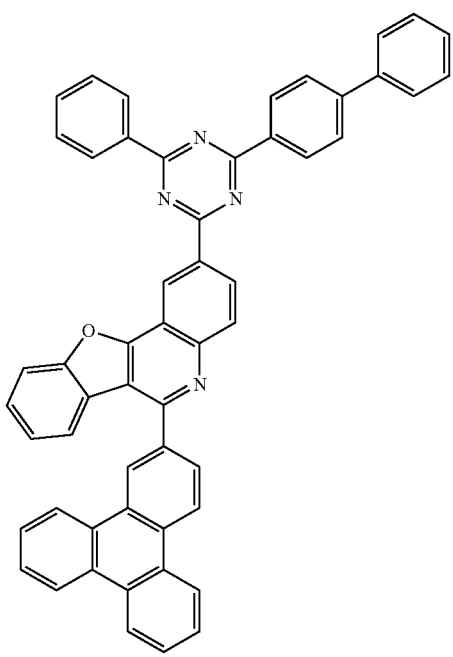
187
188
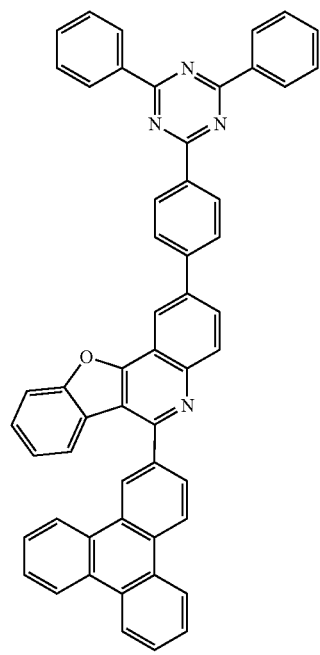
189
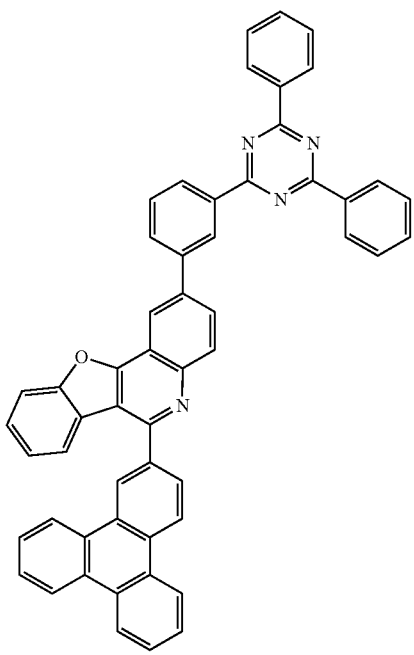

-continued
189
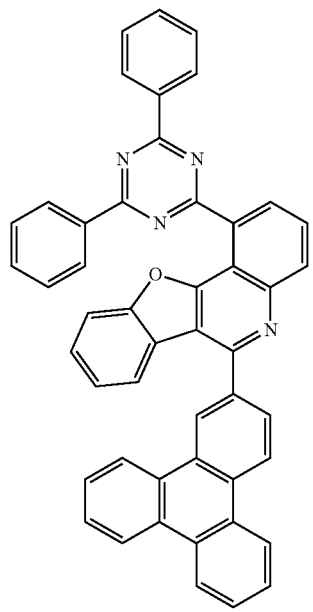
190
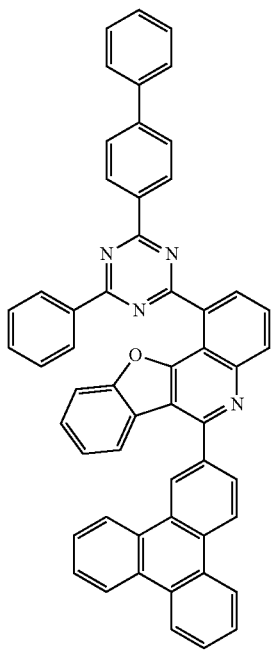
191
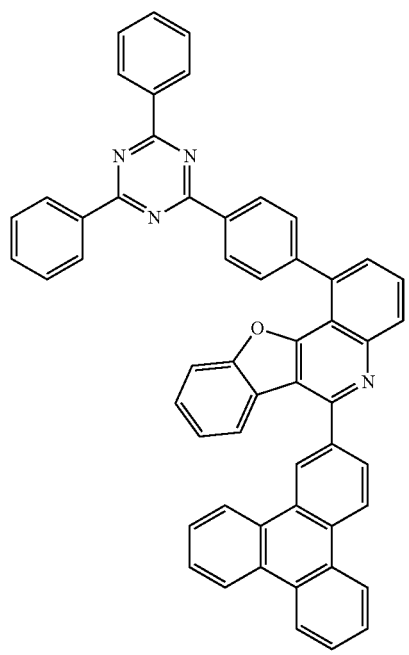
192
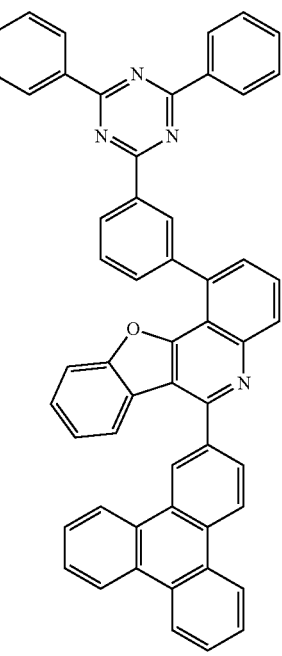

-continued
751
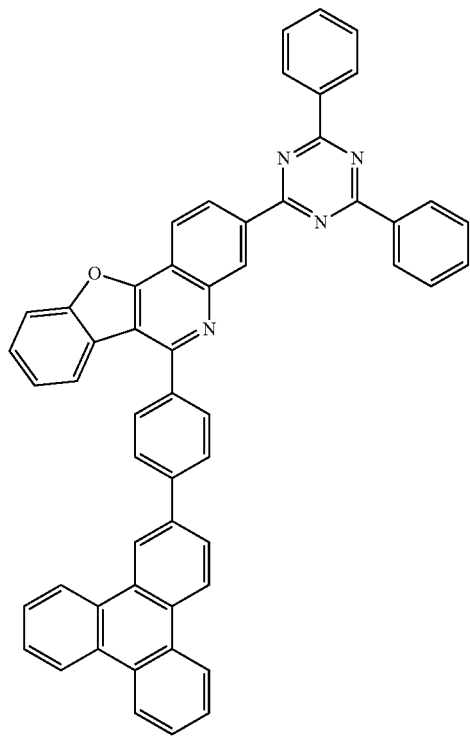
194
752
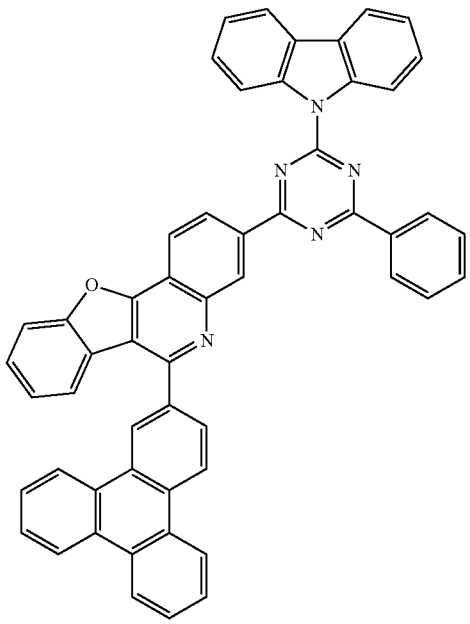
195
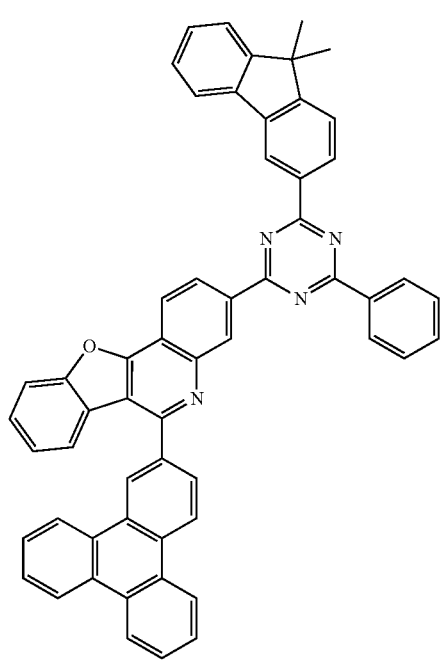
196
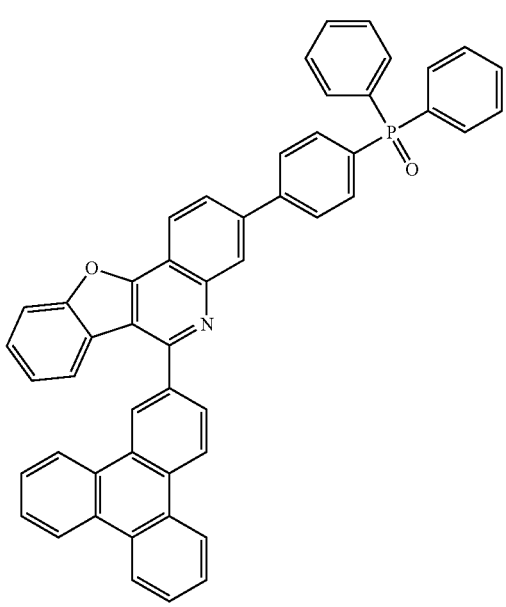
197

198
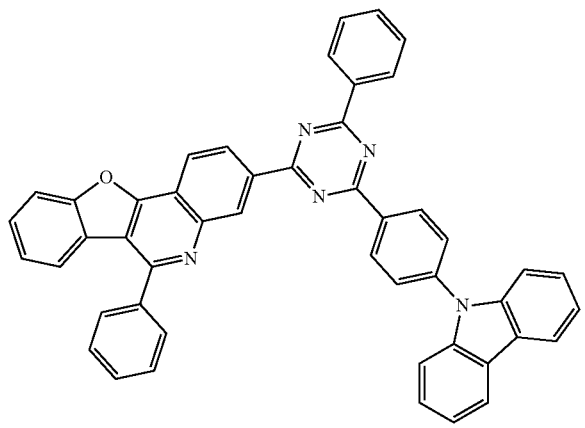
199
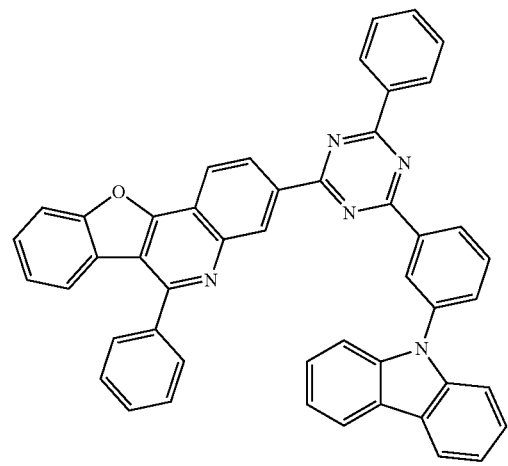
200
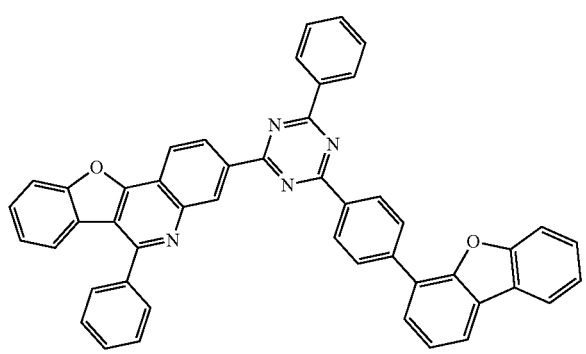
201
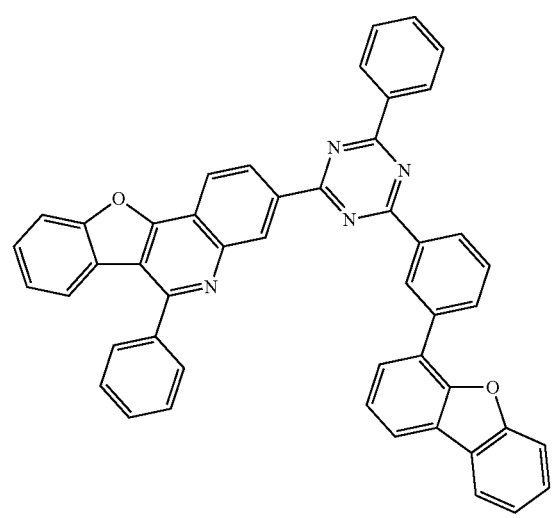
202
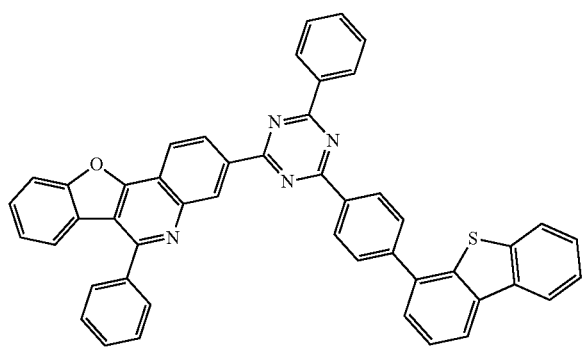
203
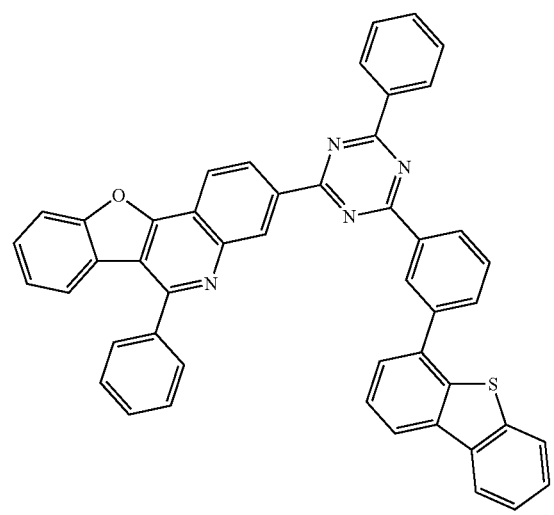

204
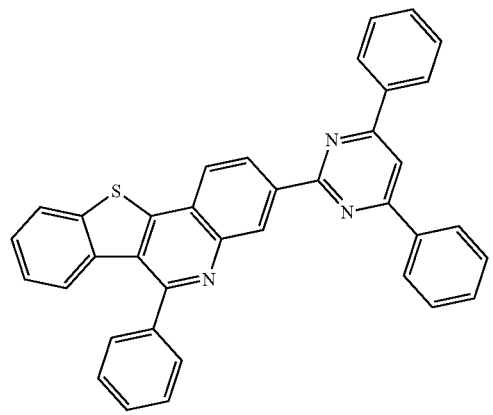
205
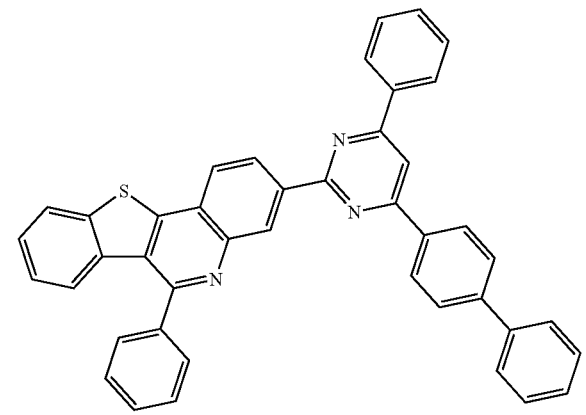
206
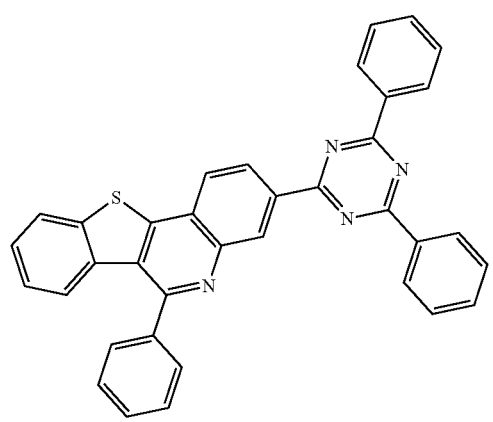
207
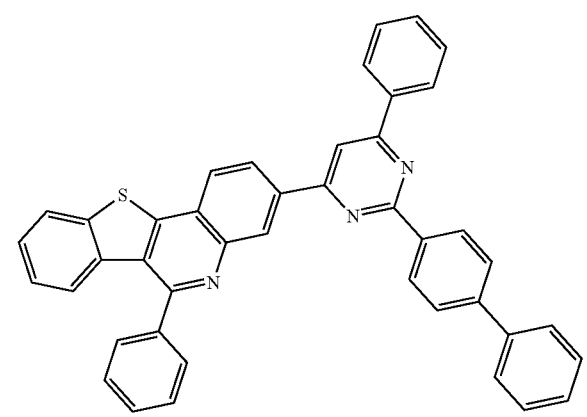
208
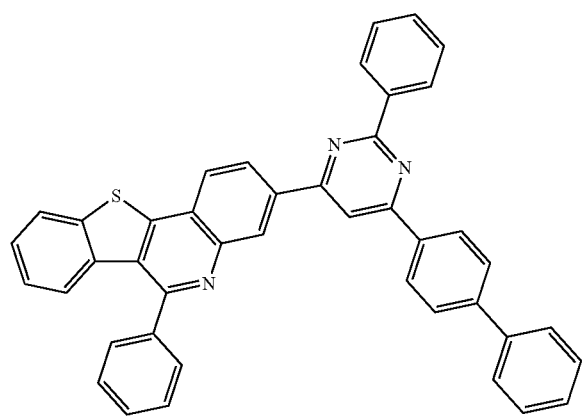

-continued
209
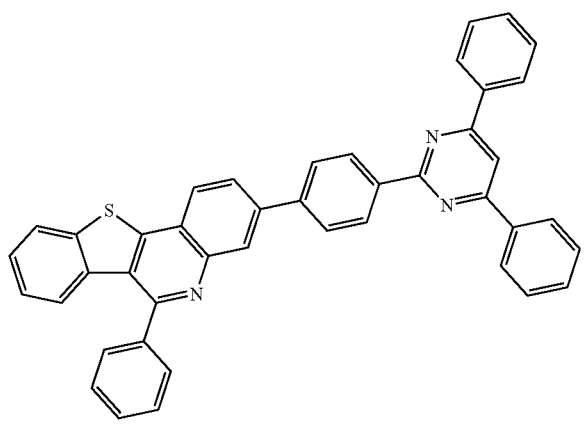
210
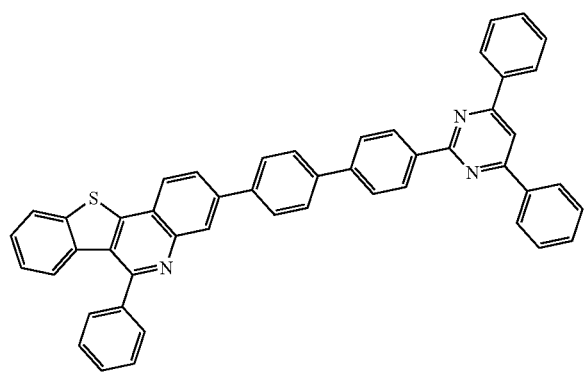
211
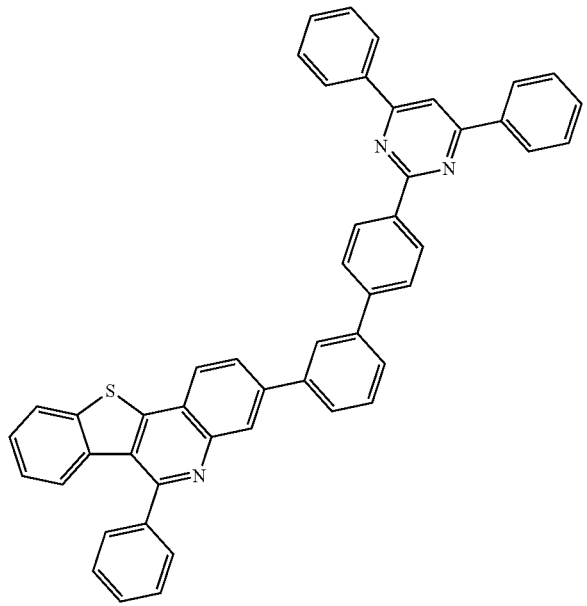
212
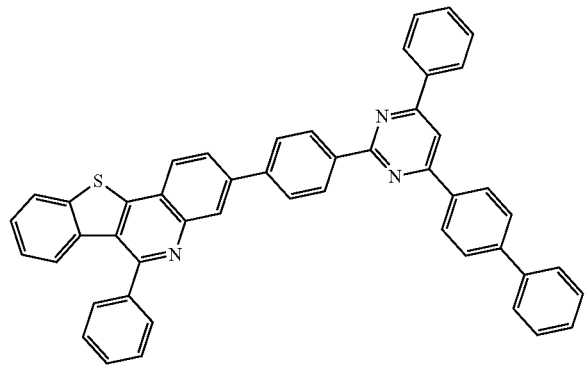
213
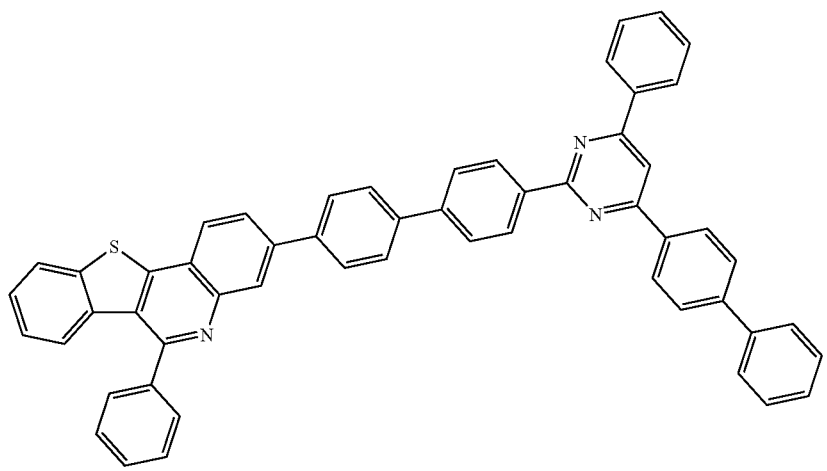

-continued
214
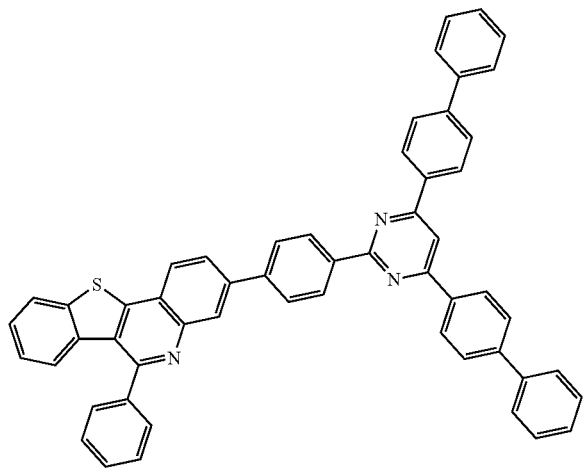
215
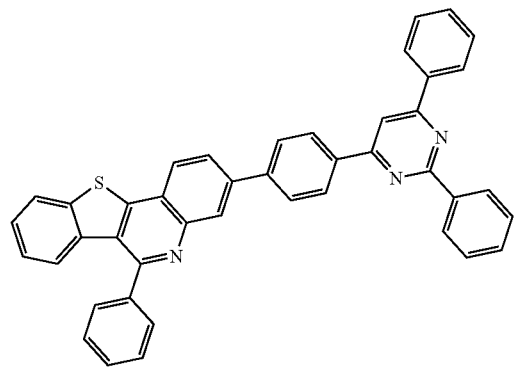
216
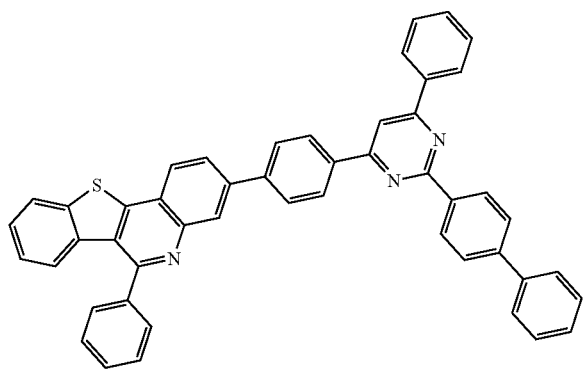
217
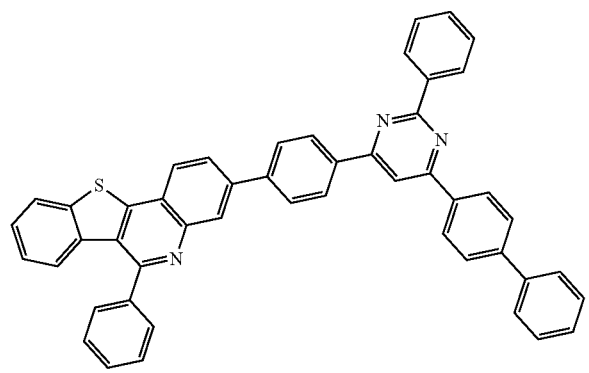
218
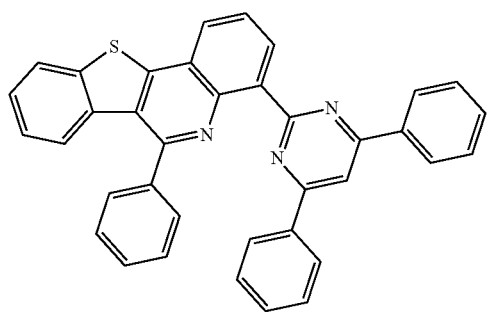
219
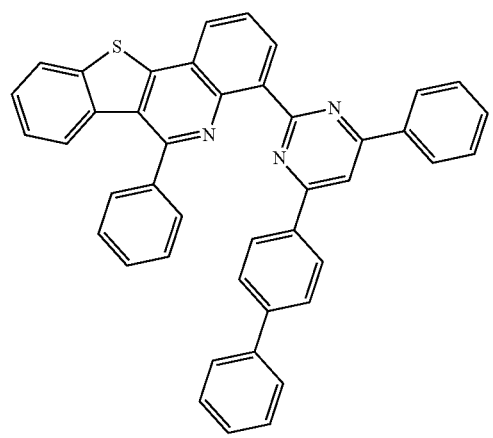

-continued
220
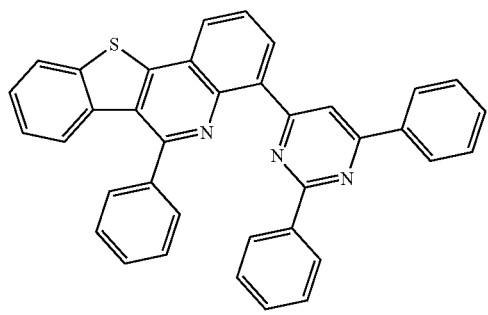
221
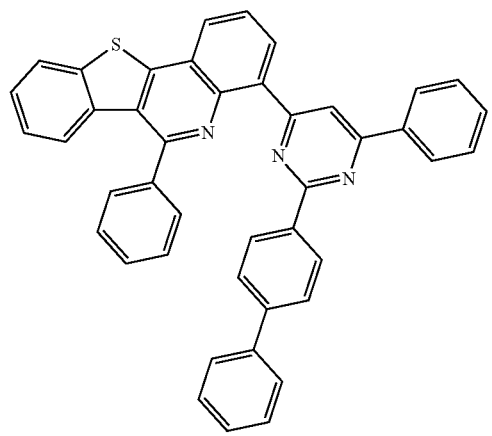
222
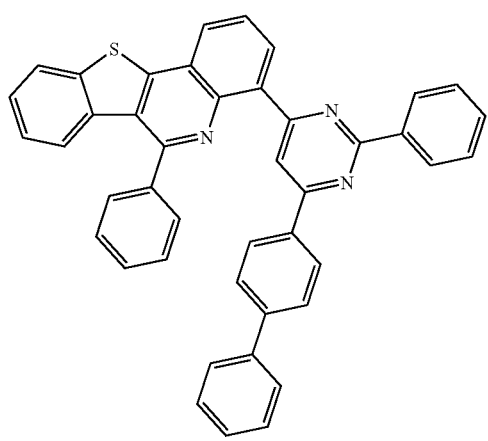
223
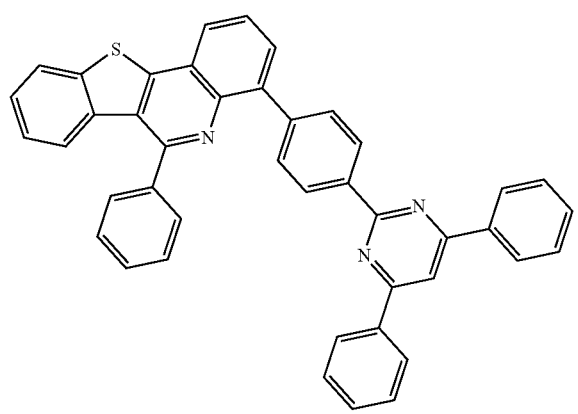
224
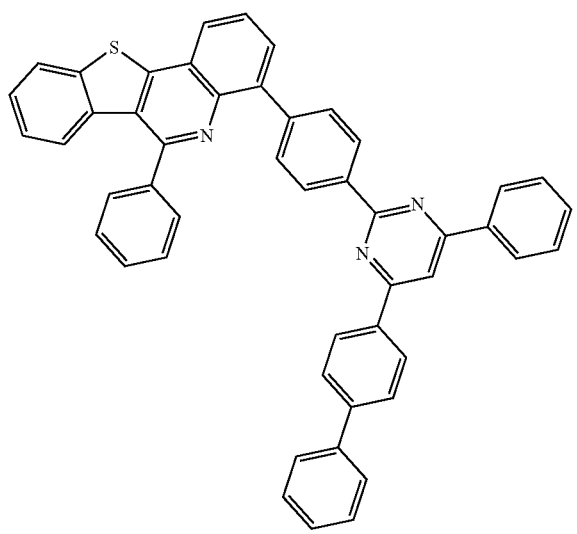
225
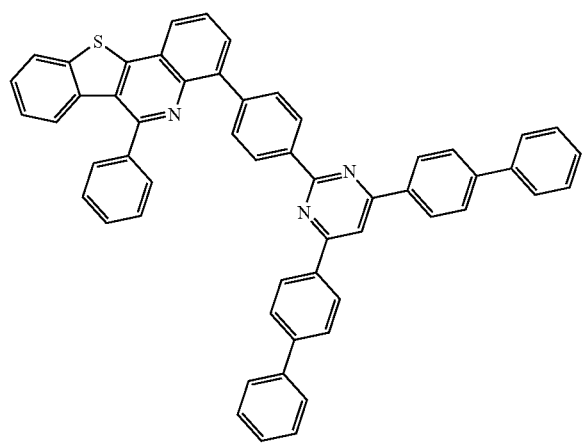

-continued
226
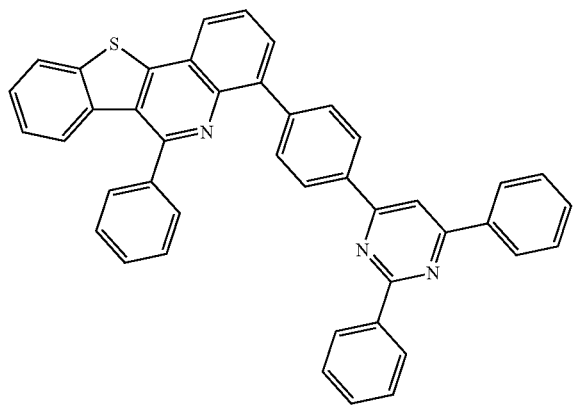
227
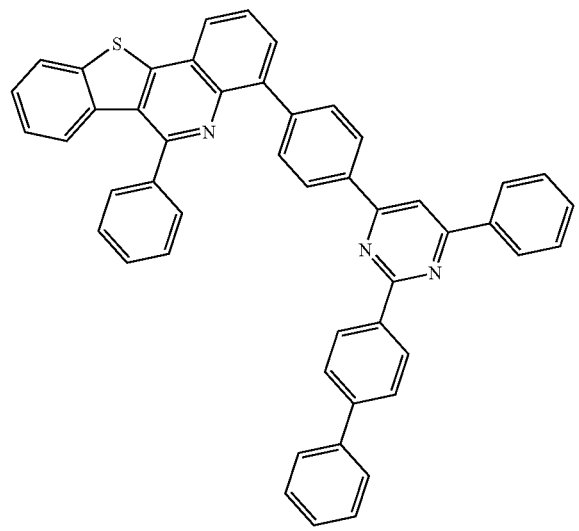
228
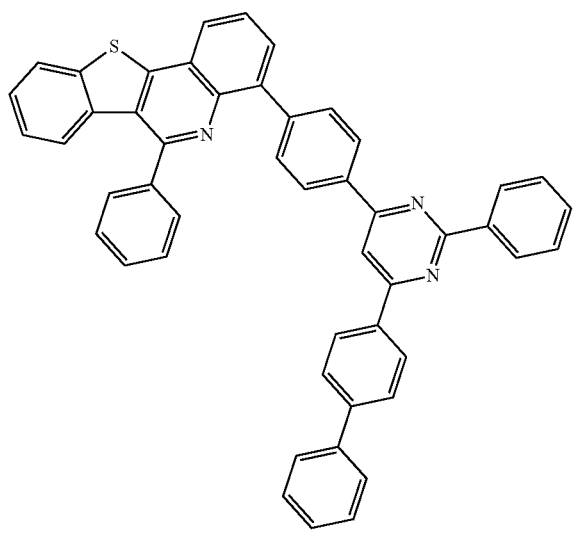
229
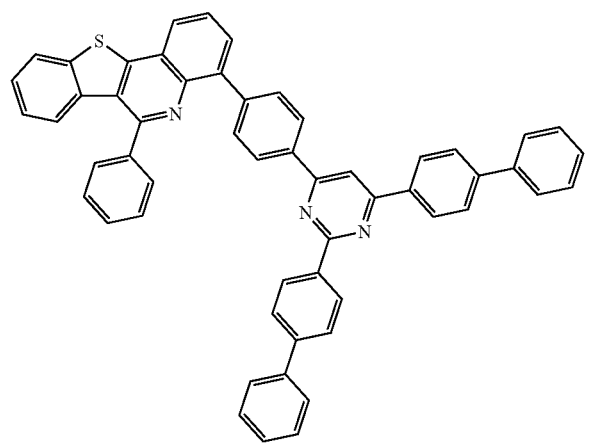
230
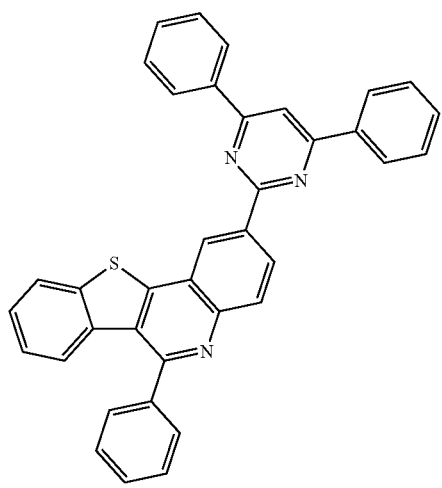
231
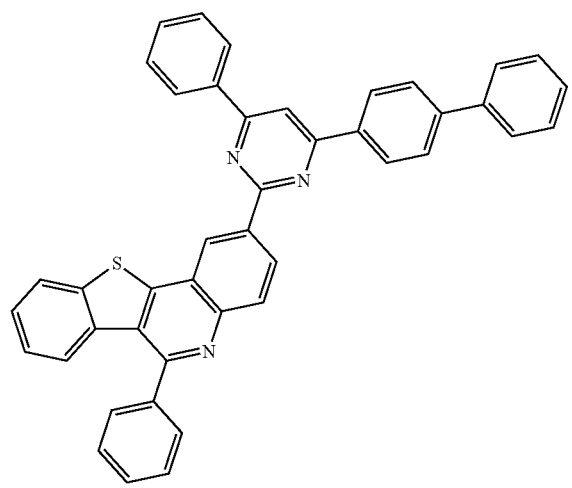

-continued
232
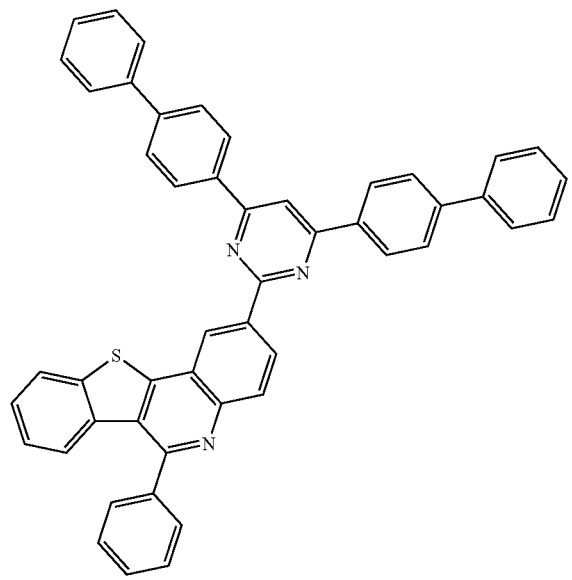
233
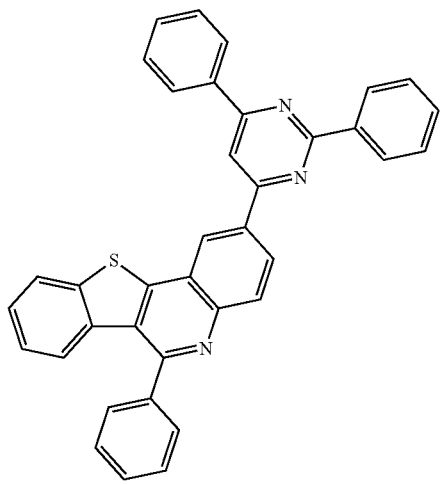
234
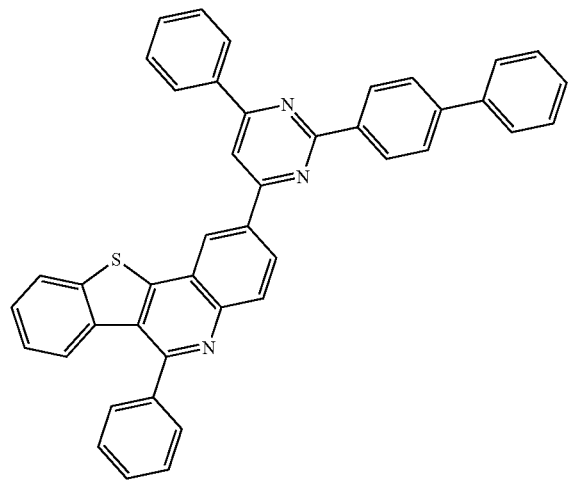
235
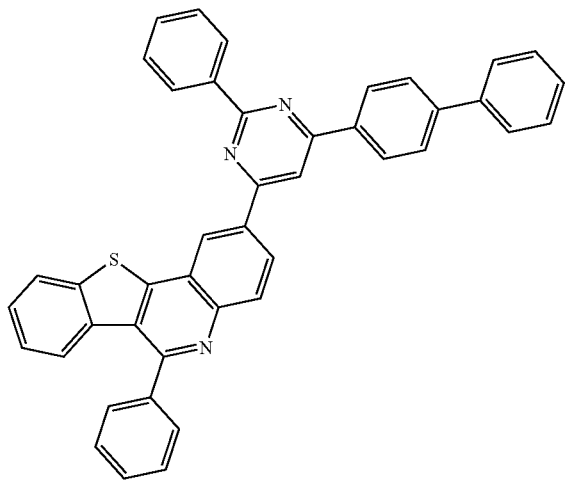
236
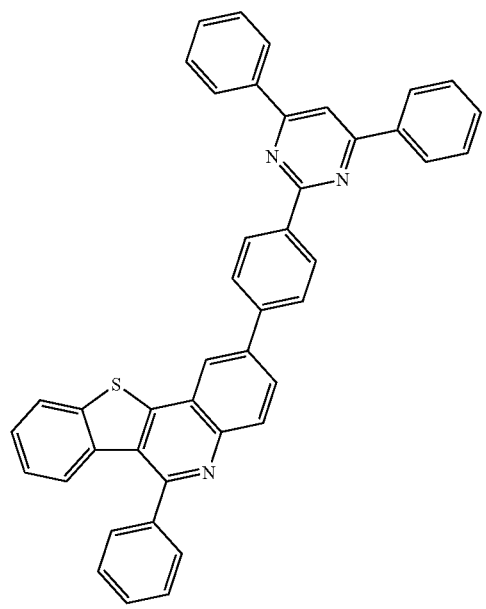
237
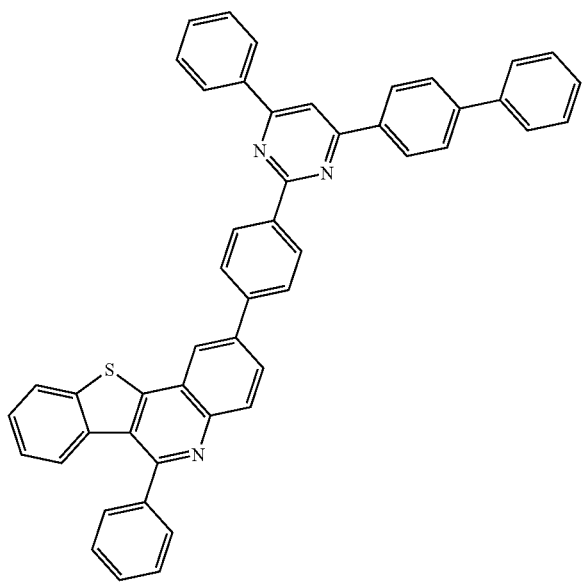

-continued
238
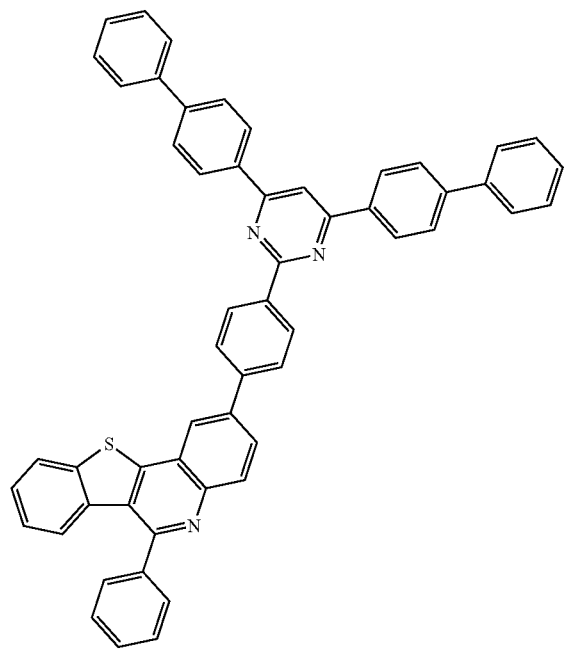
239
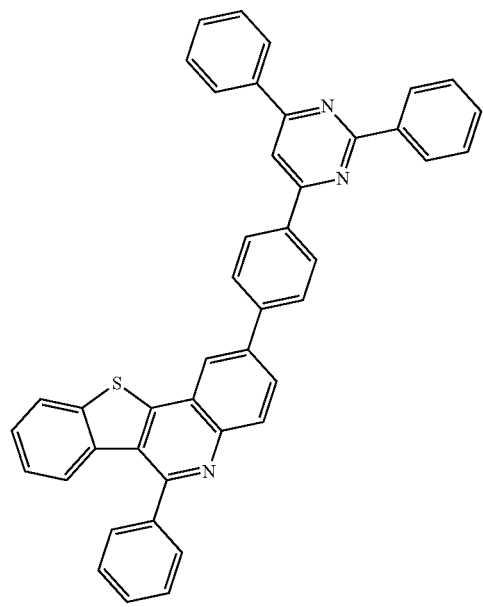
240
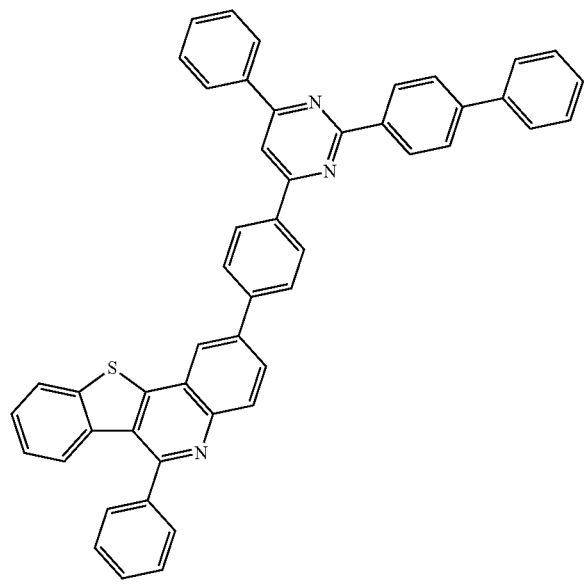
241
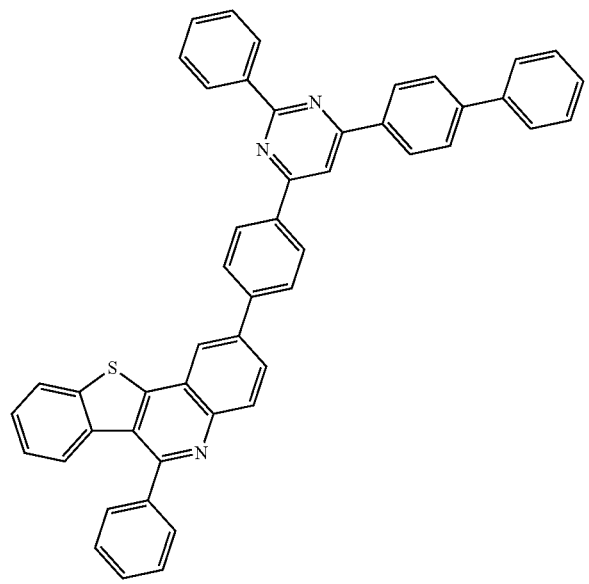

242
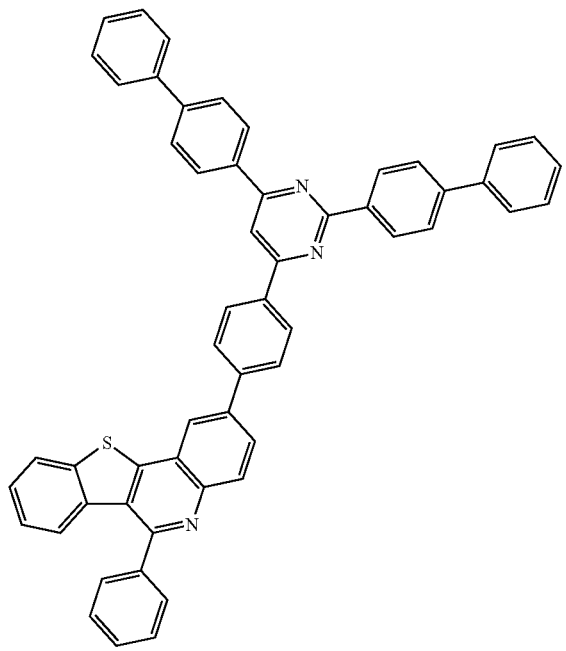
243
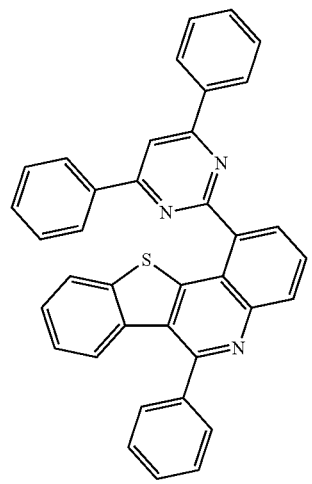
244
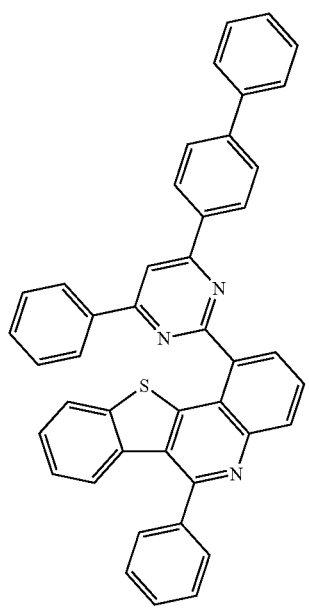
245
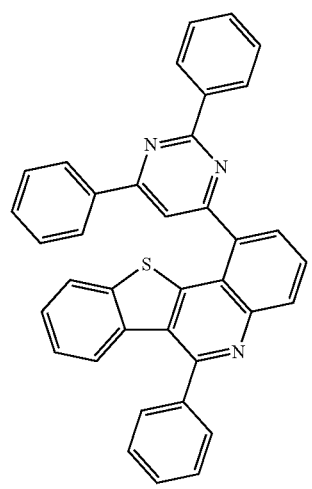

246
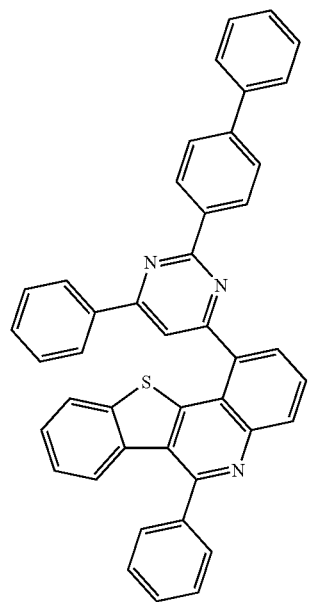
247
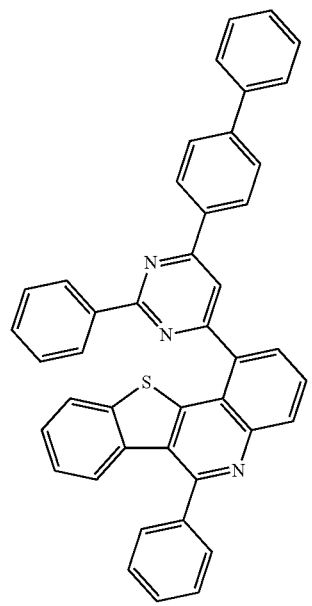
248
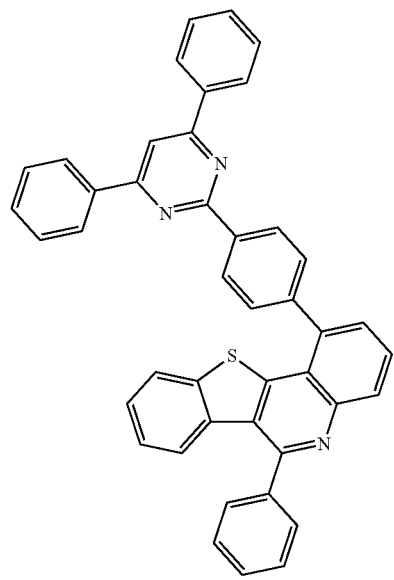
249
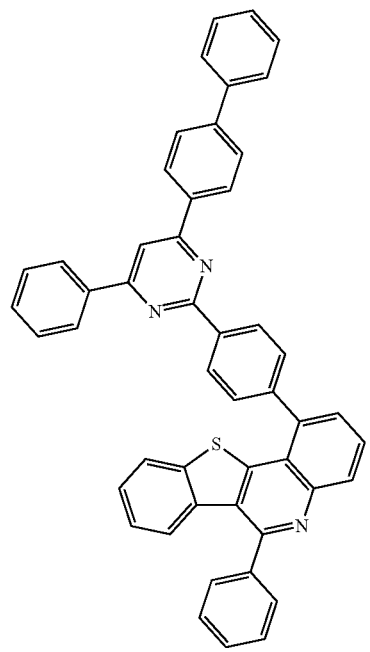

-continued
250
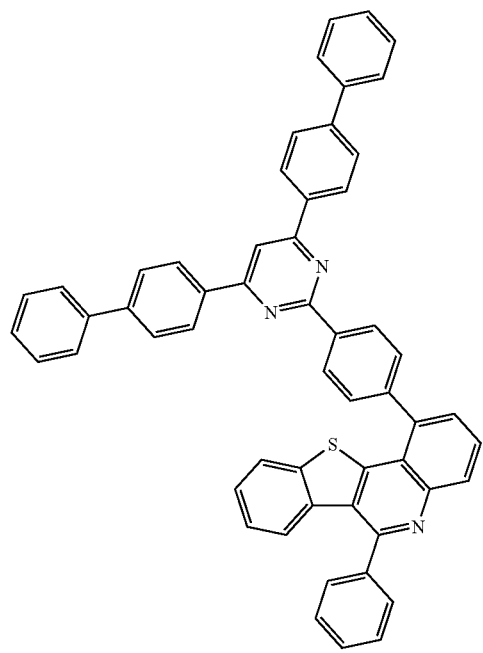
251
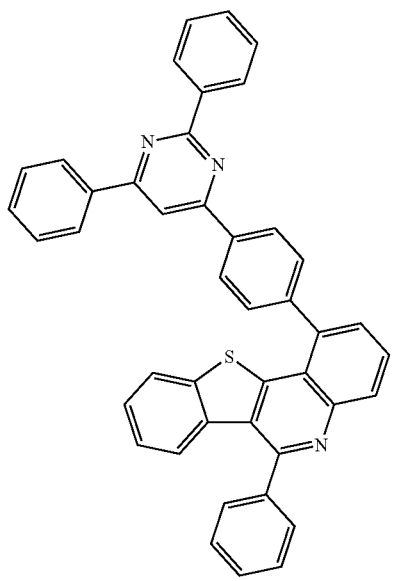
252
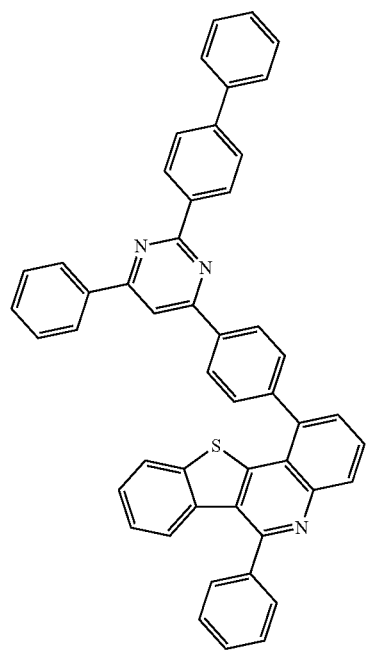
253
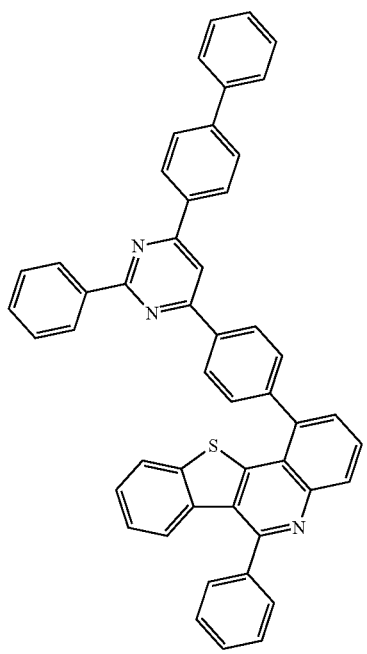

-continued
254
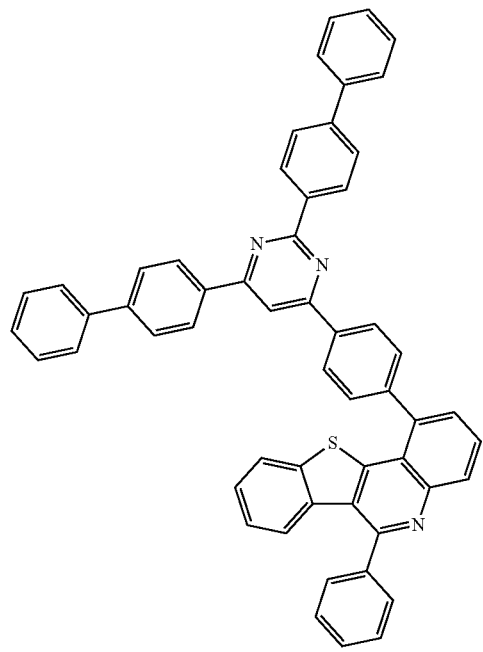
255
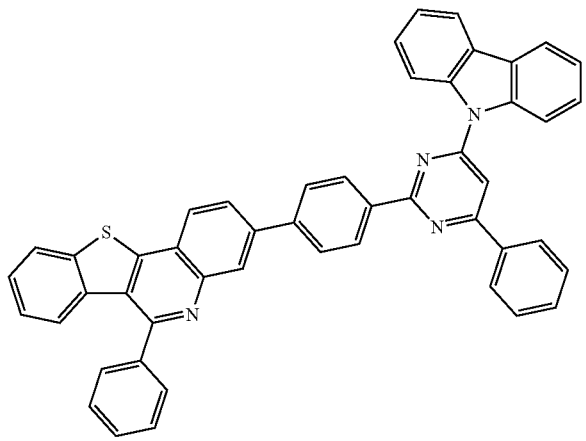
256
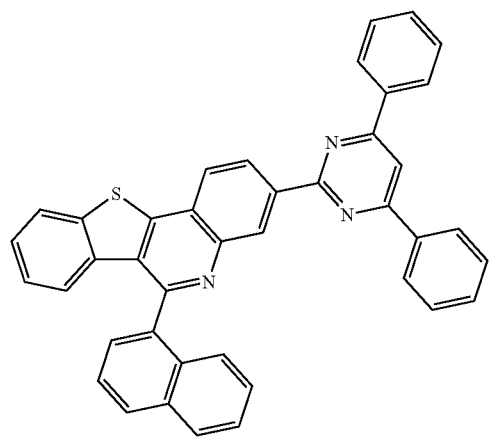
257
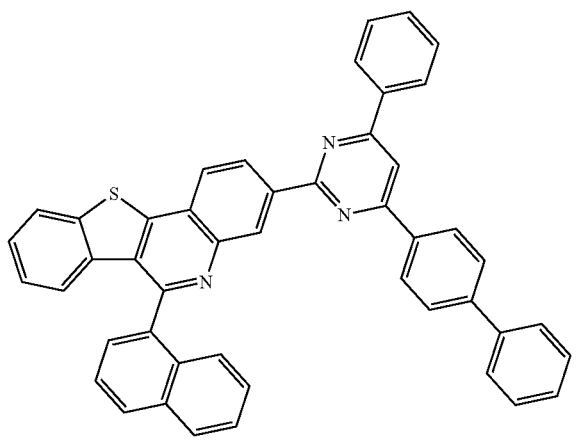
258
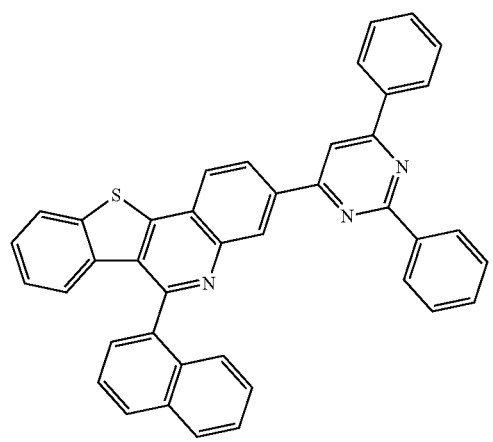
259
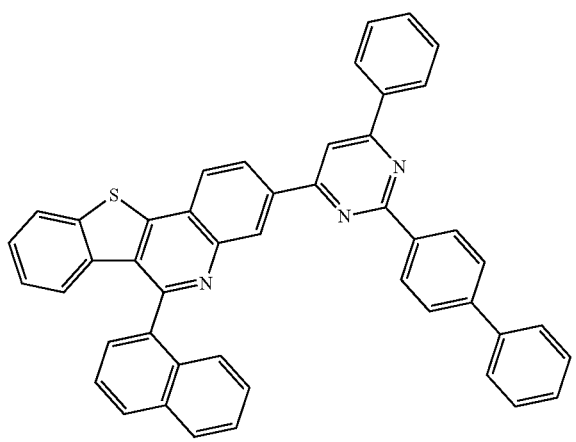

-continued
260
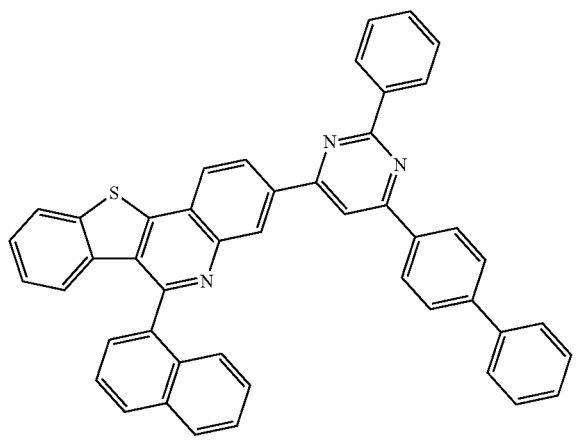
261
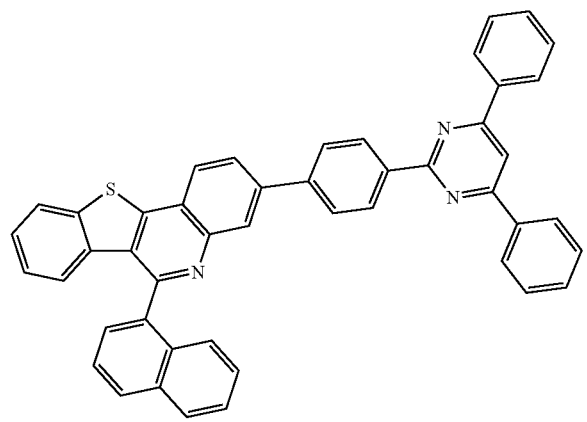
262
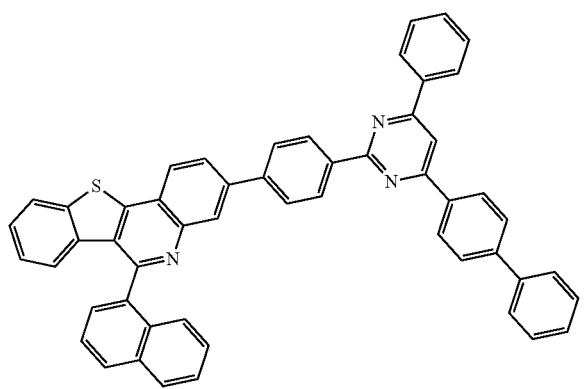
263
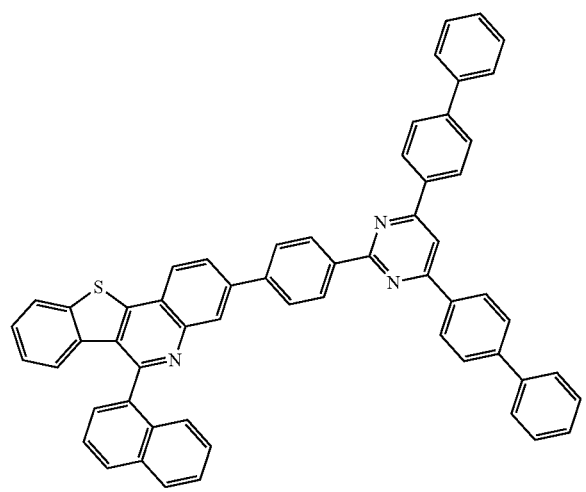
264
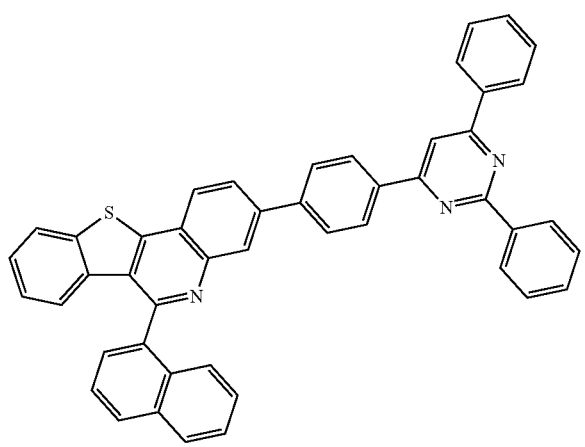
265
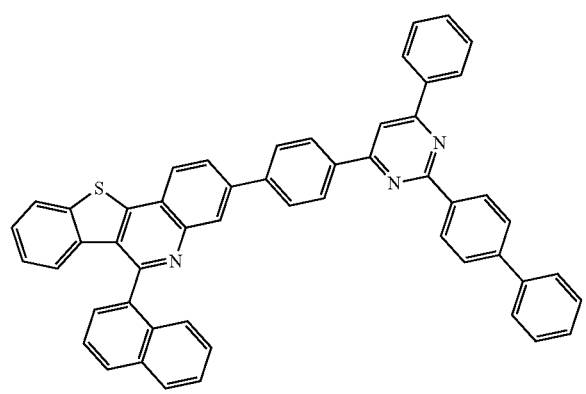

-continued
266
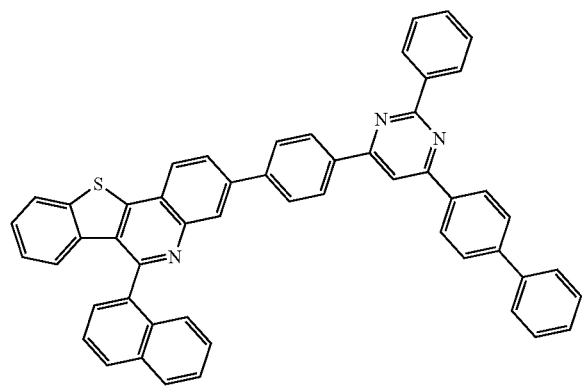
267
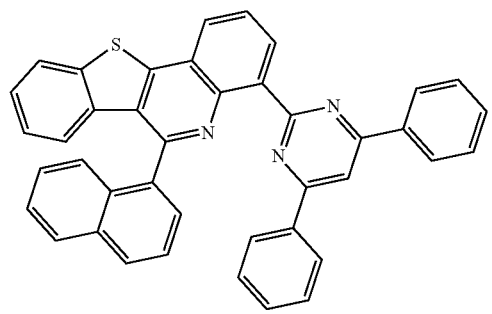
268
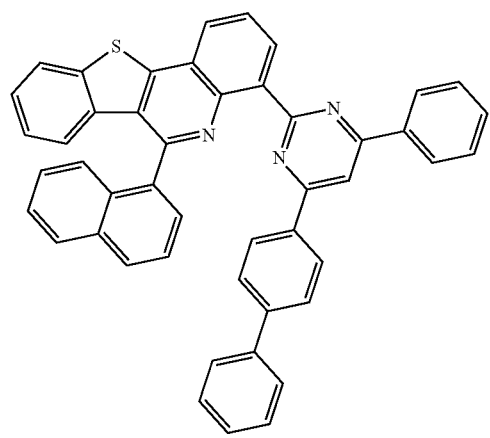
269
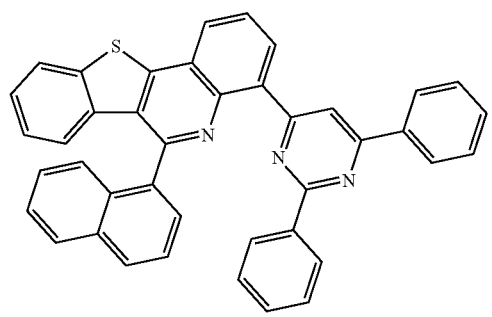
270
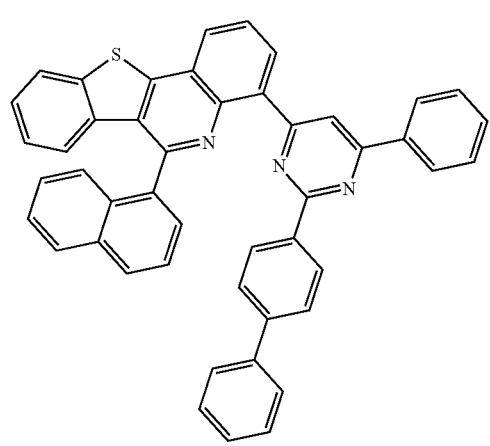
271
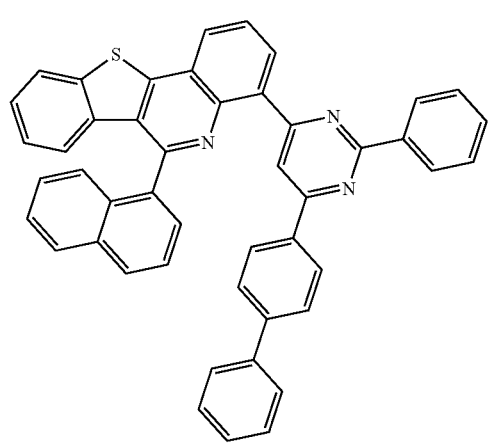

-continued
272
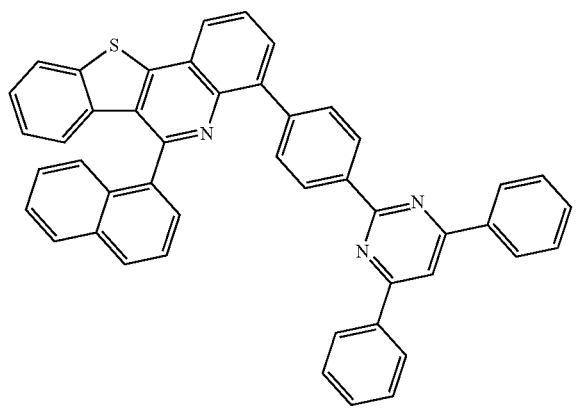
273
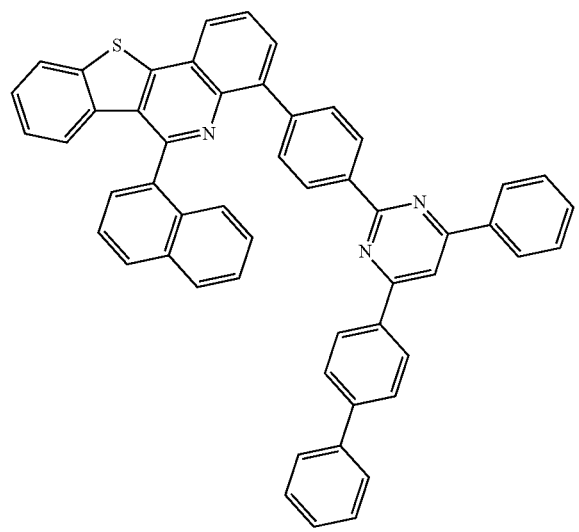
274
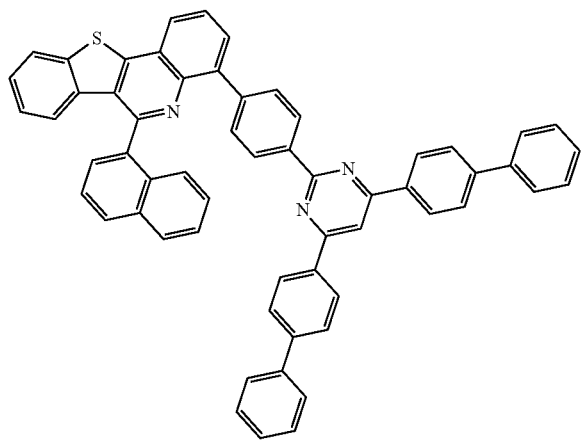
275
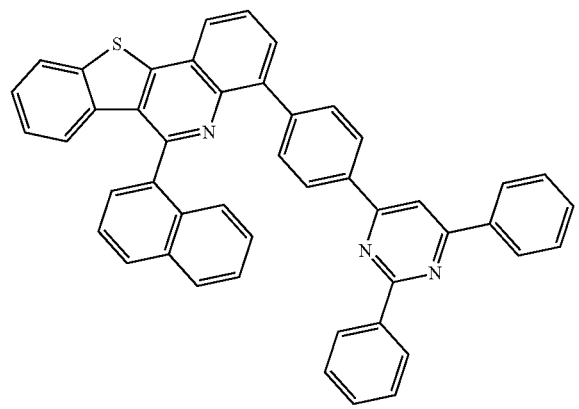
276
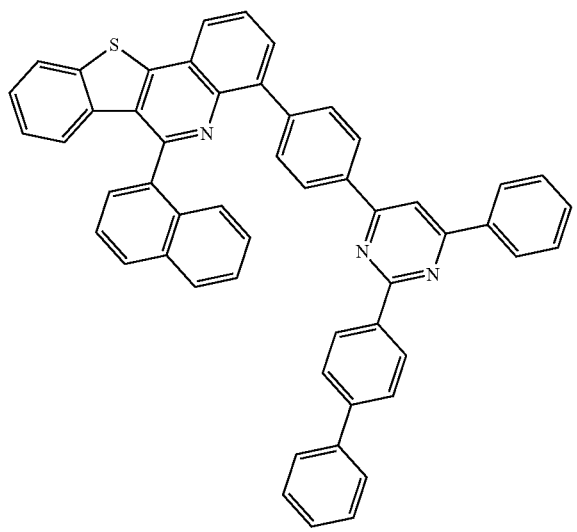
277
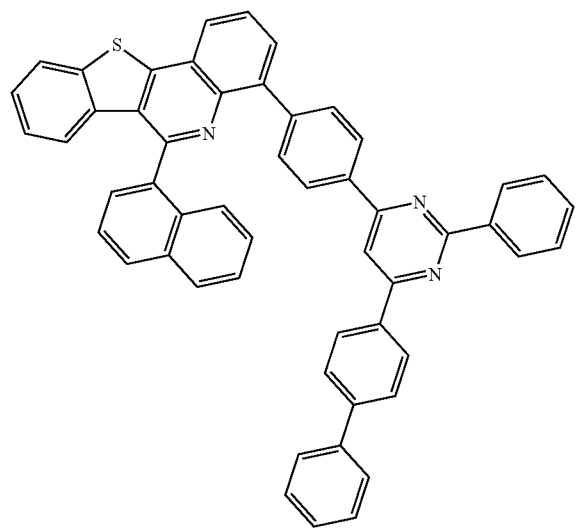

-continued
278
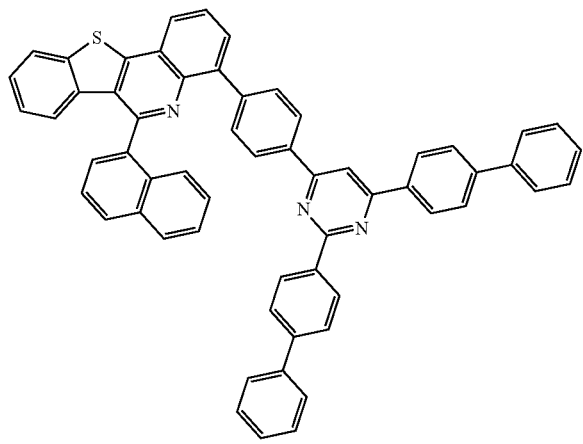
279
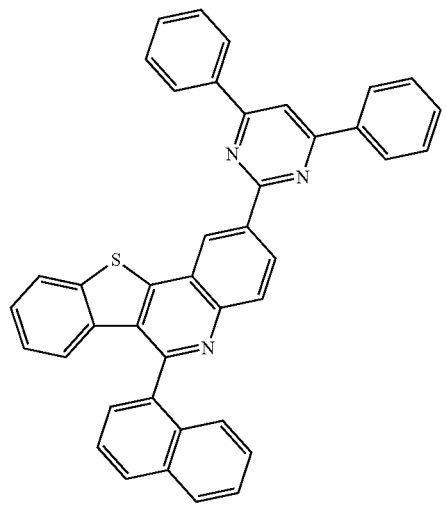
280
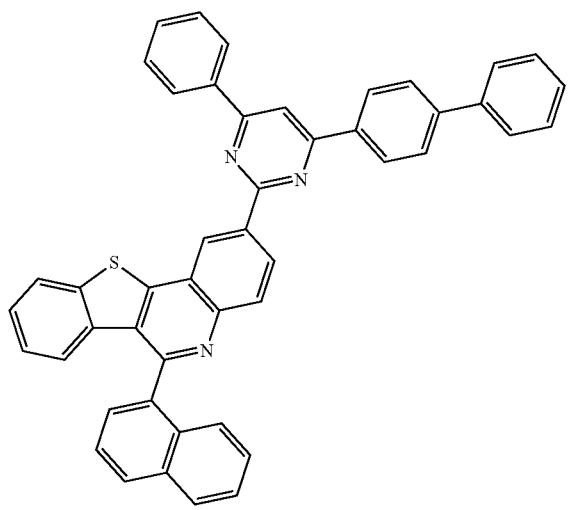
281
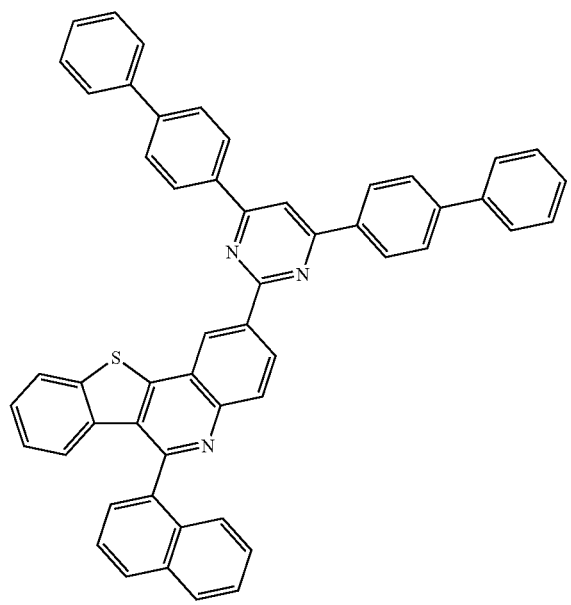
282
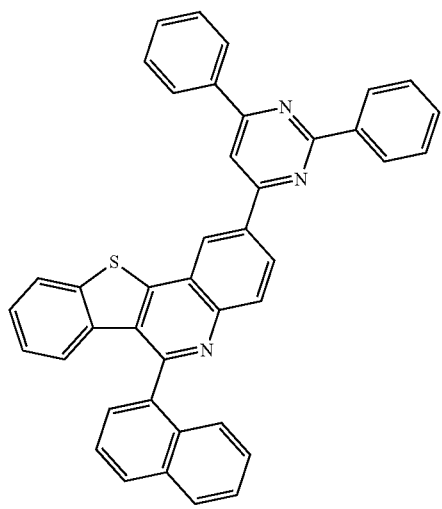
283
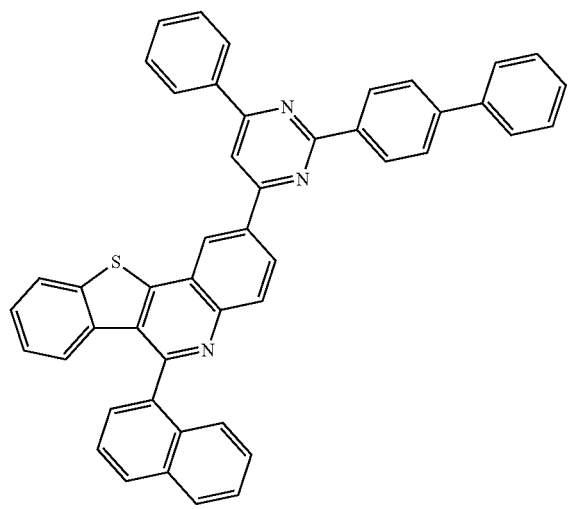

284
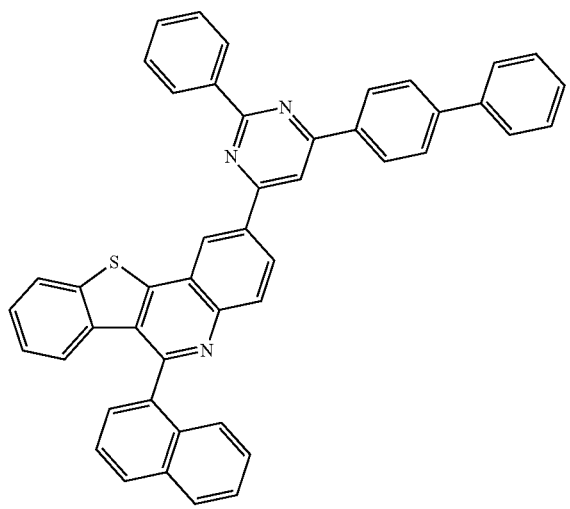
285
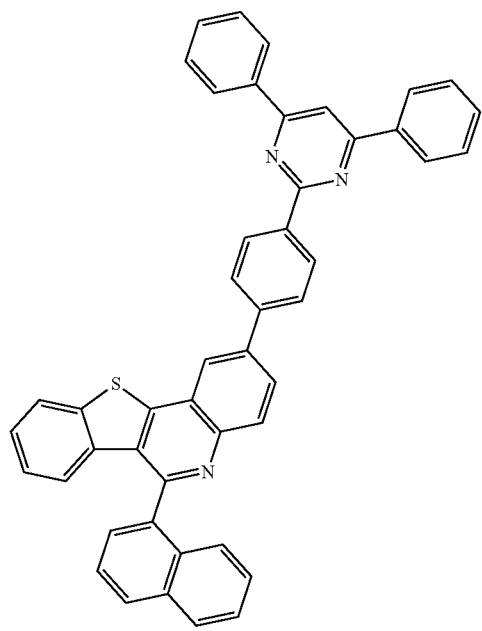
286
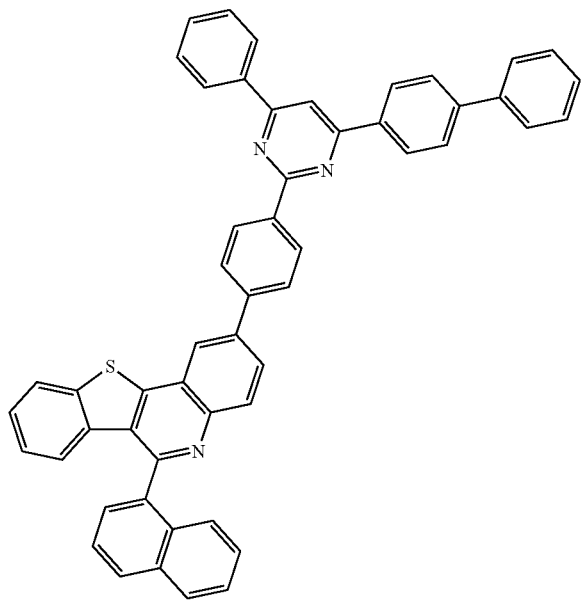
287
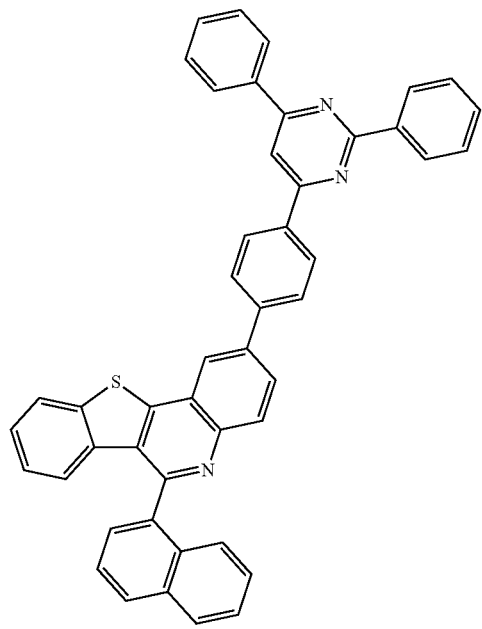

-continued
288 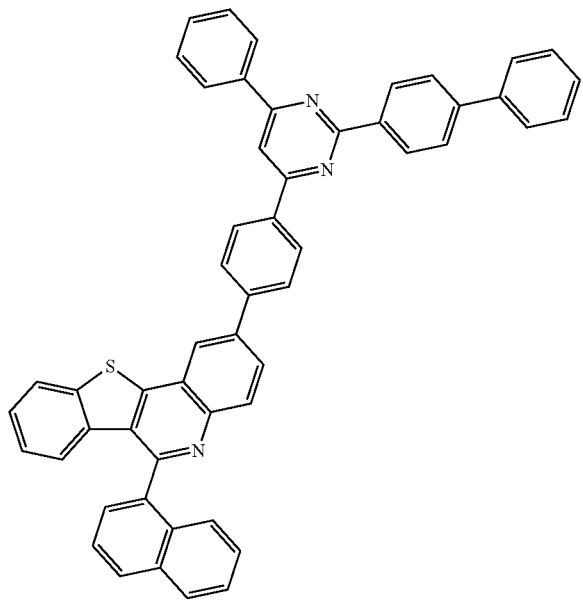
289 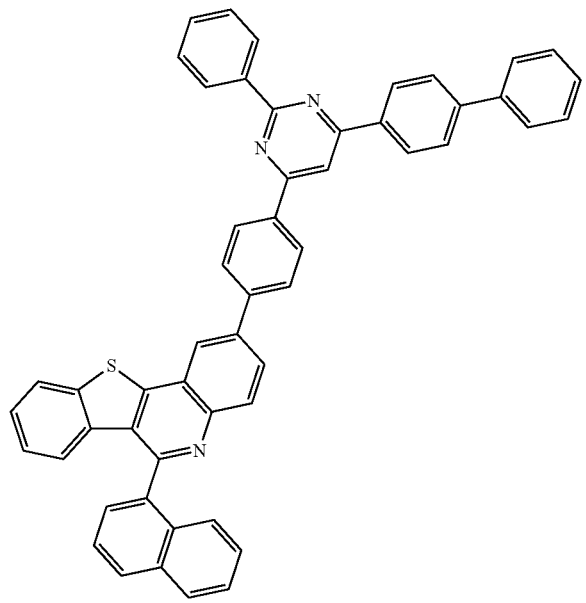
290 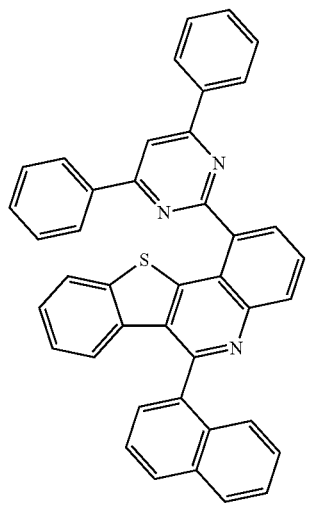
291 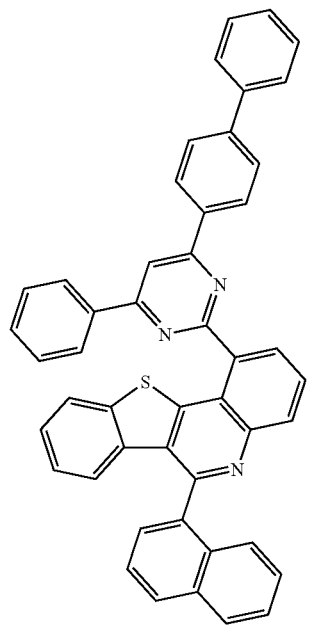

-continued
292 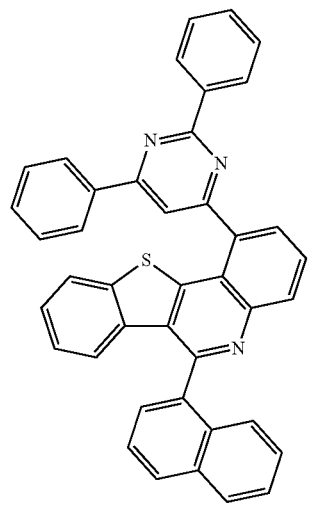
293 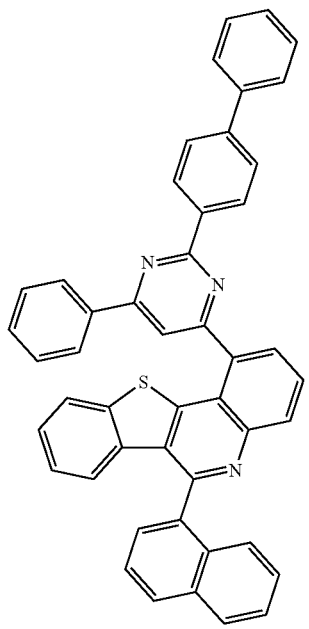
294 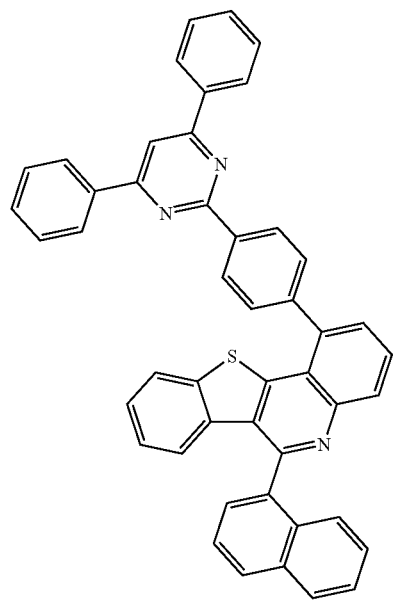
295 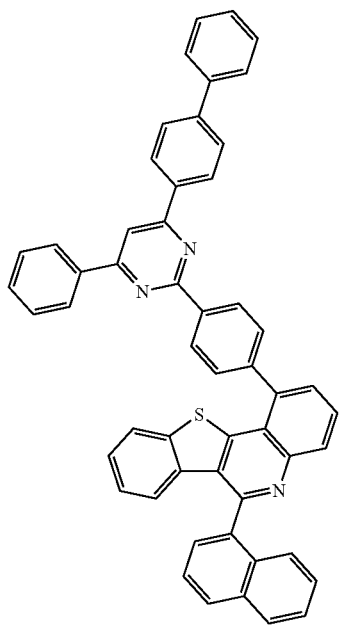

296
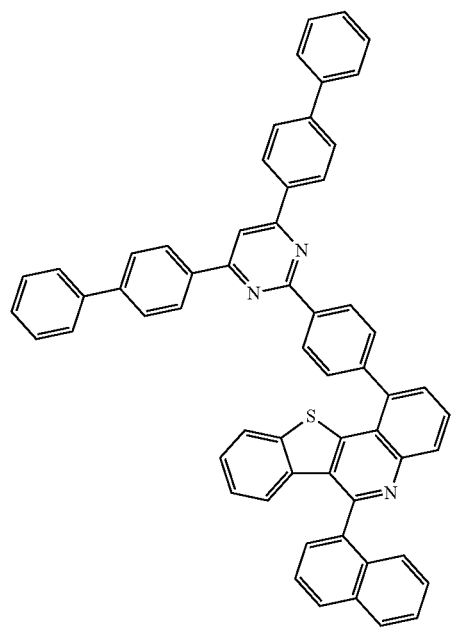
297
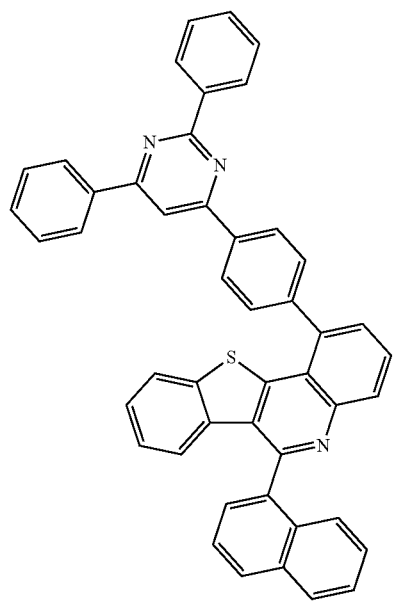
298
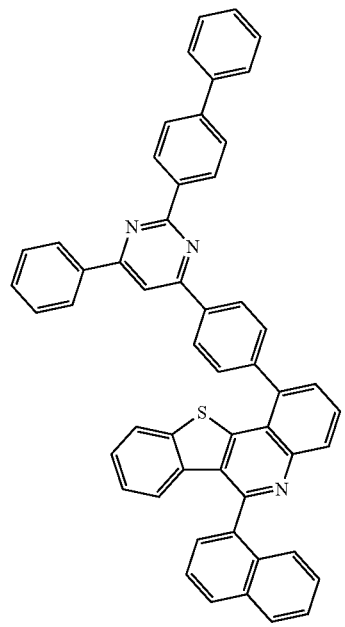
299
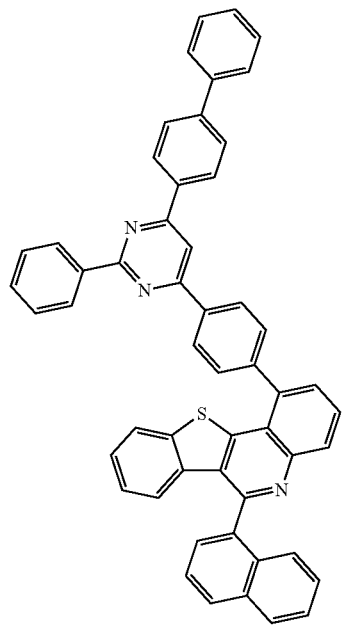

-continued
793 | 794
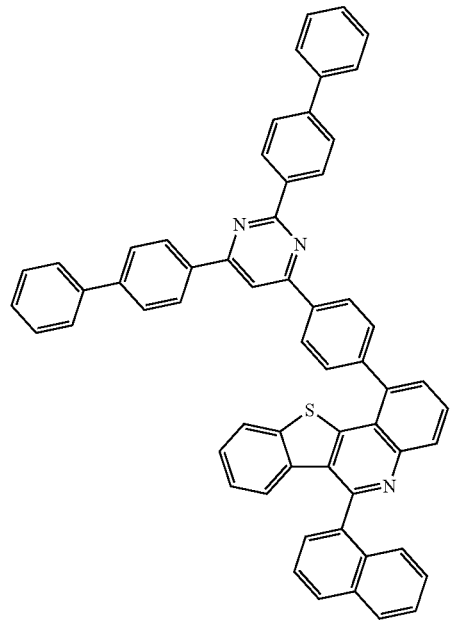
300
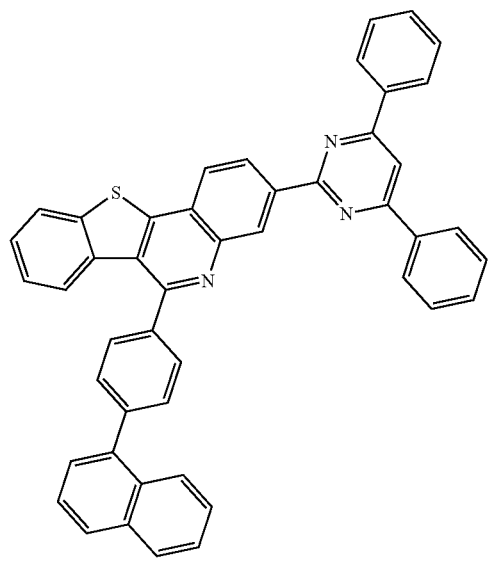
301
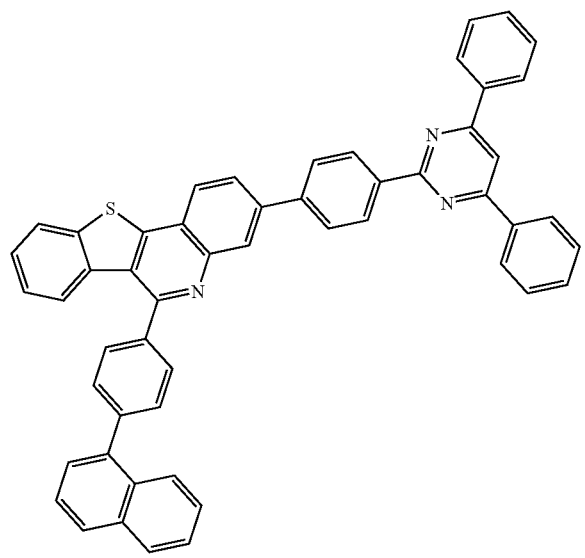
302
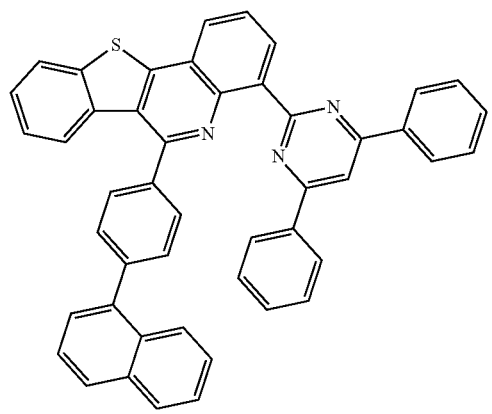
303

-continued
304
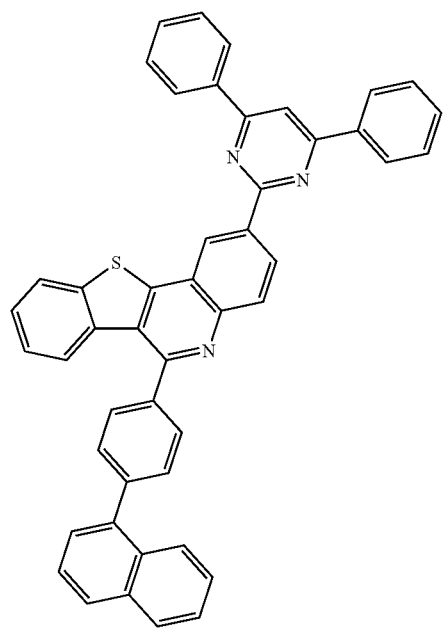
305
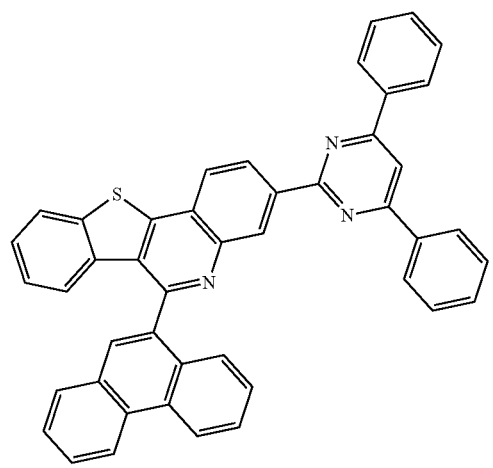
306
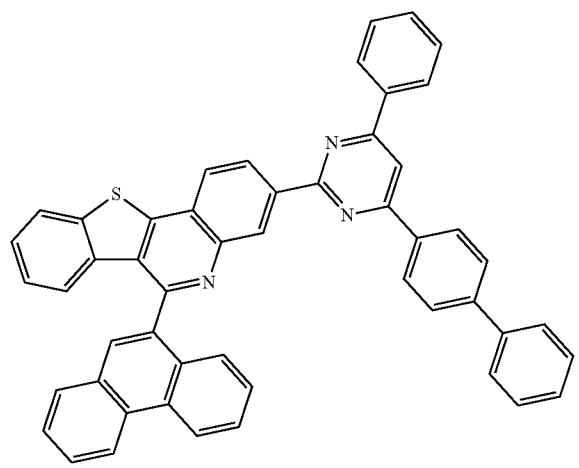
307
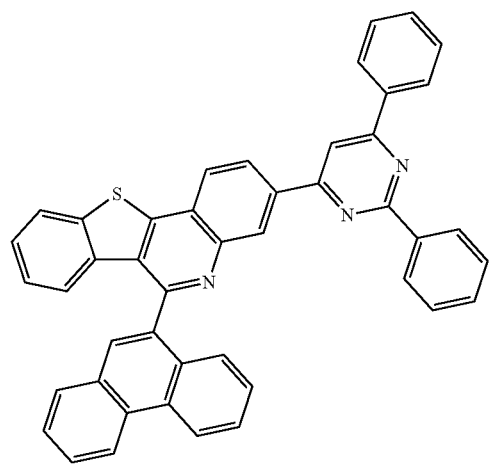
308
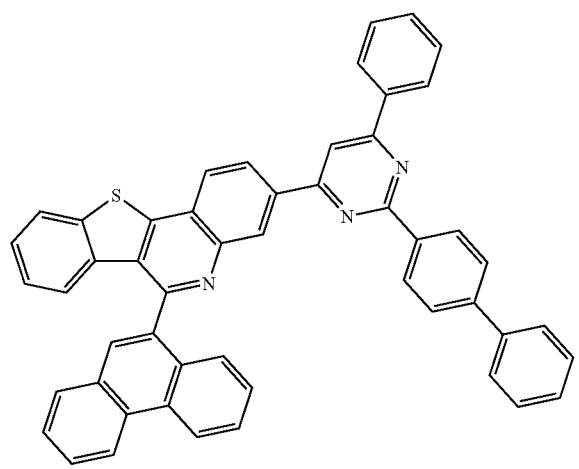
309
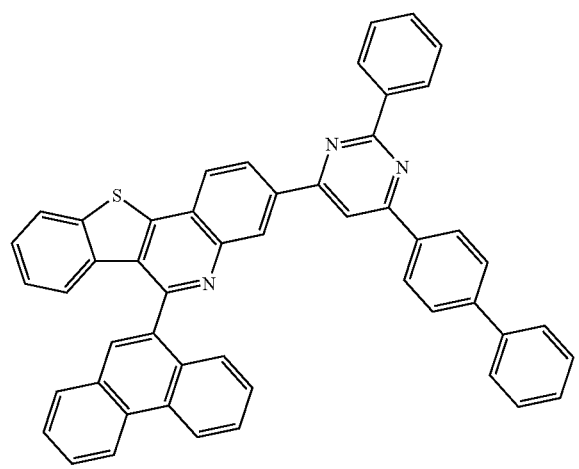

-continued
310
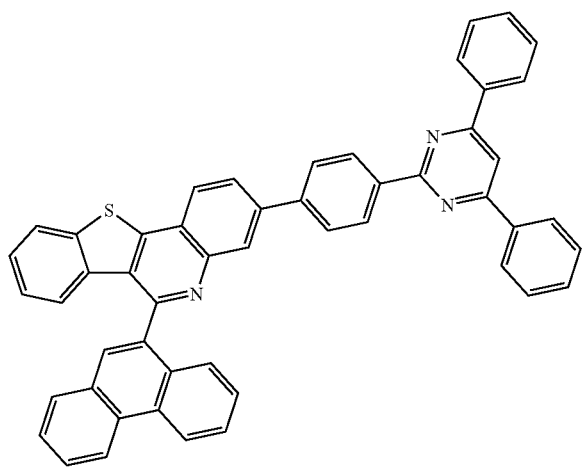
311
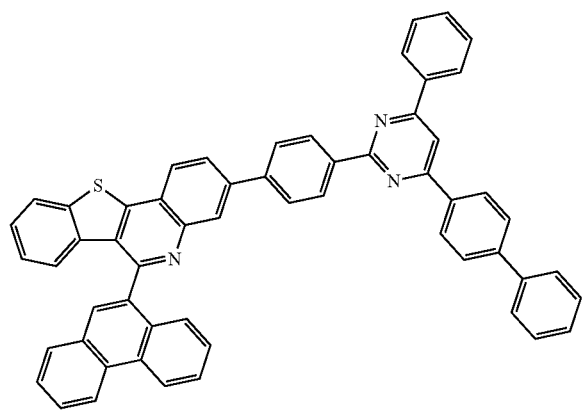
312
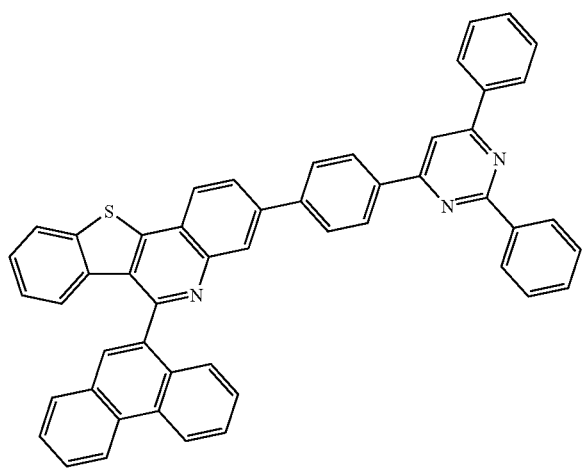
313
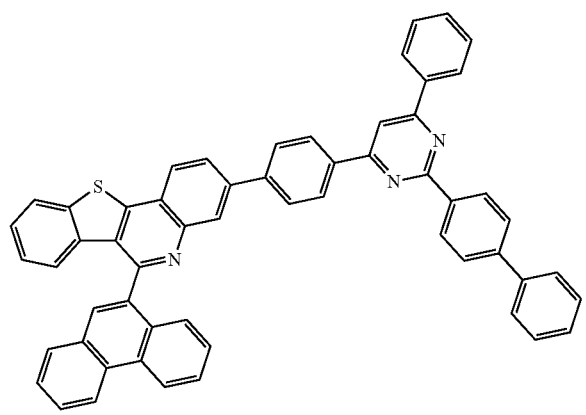
314
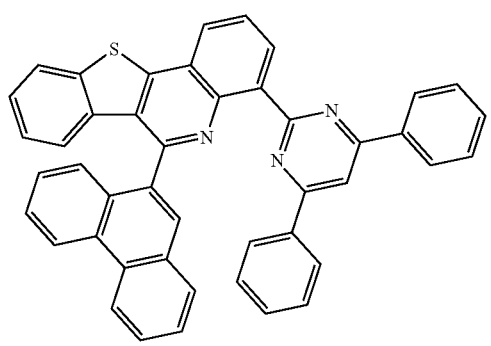
315
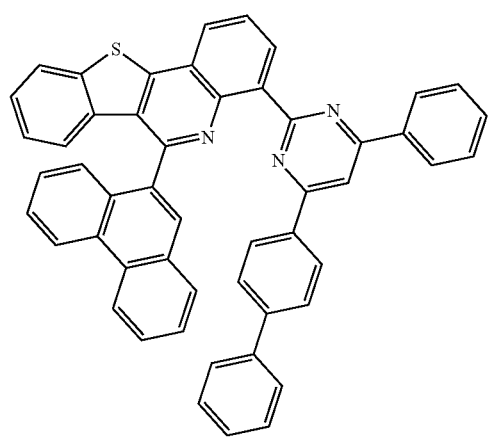

-continued
316
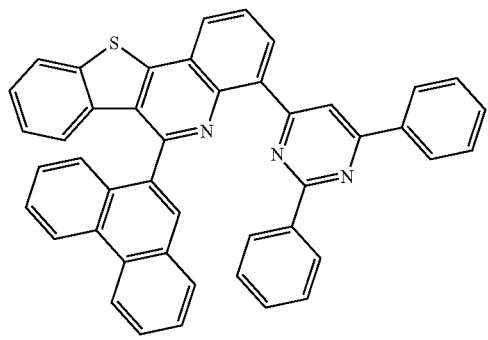
317
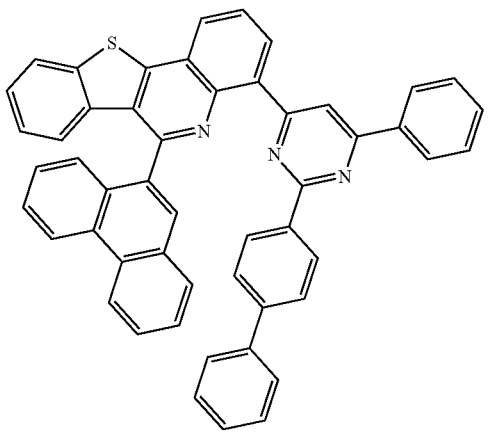
318
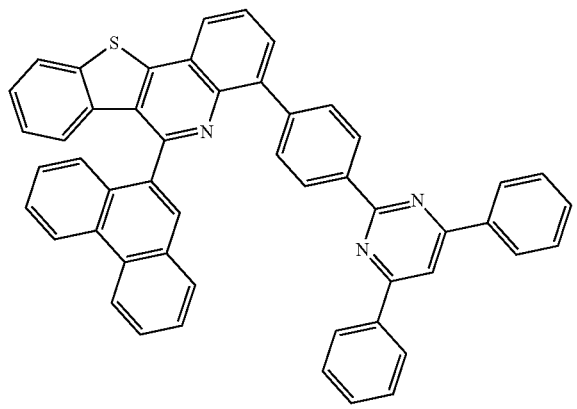
319
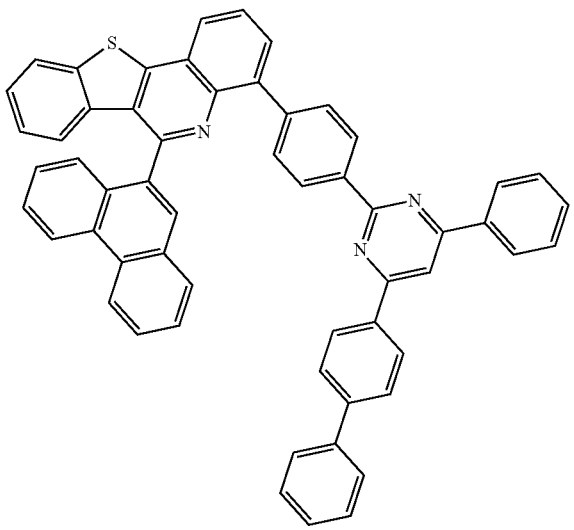
320
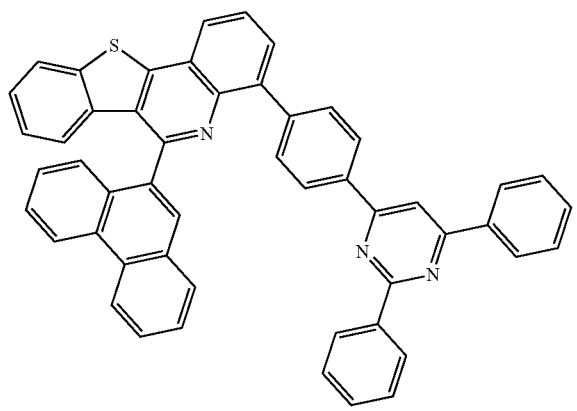
321
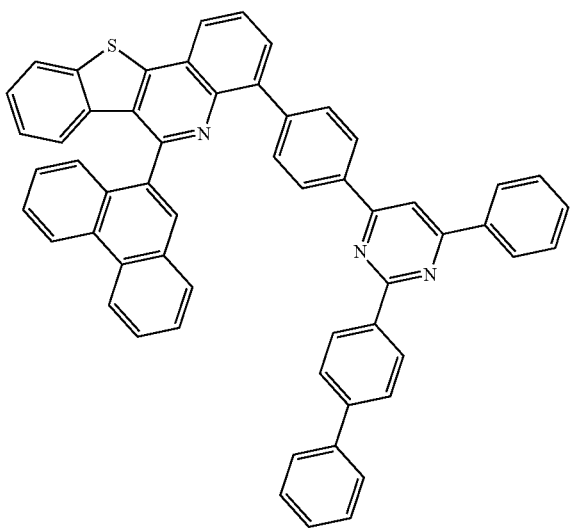

-continued
322
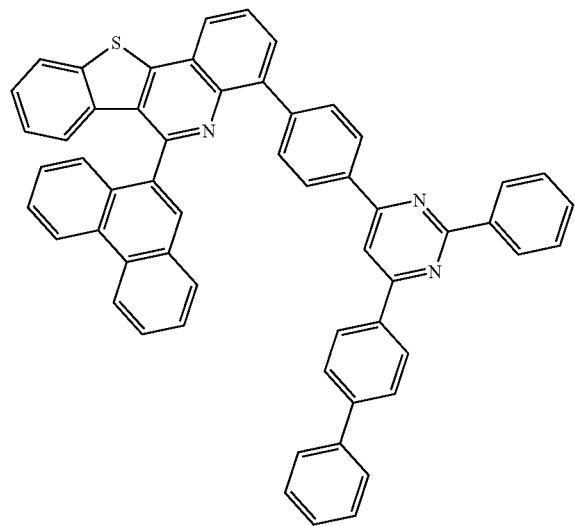
323
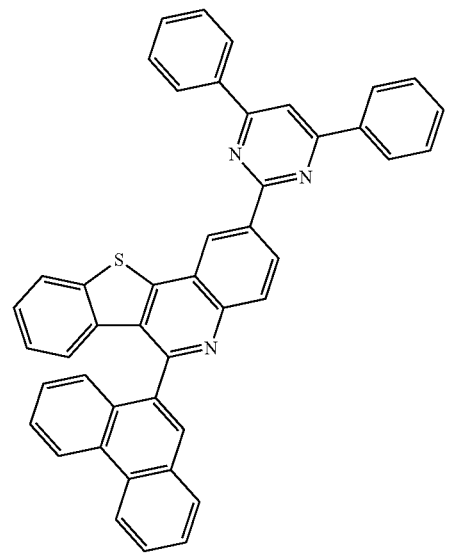
324
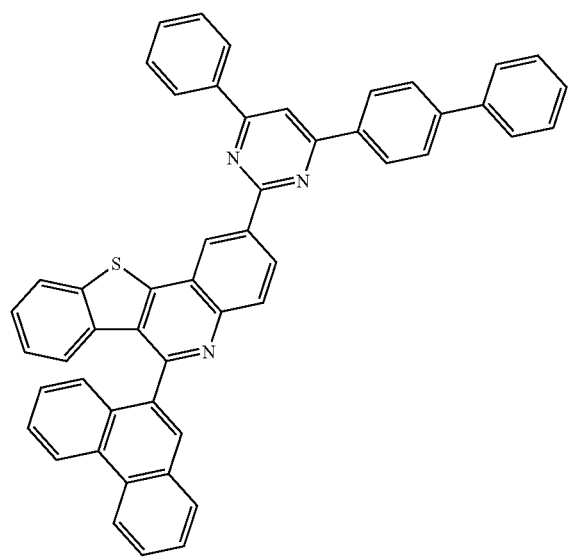
325
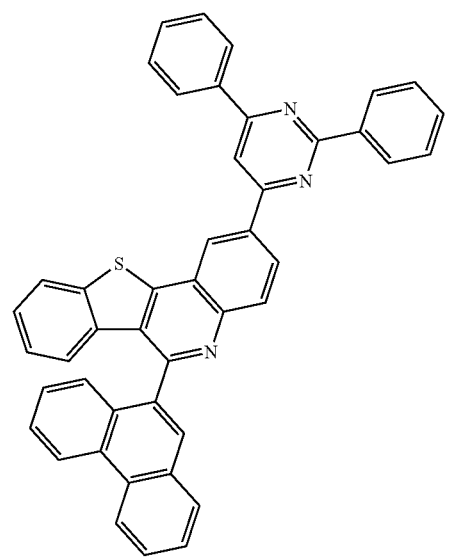

-continued
326
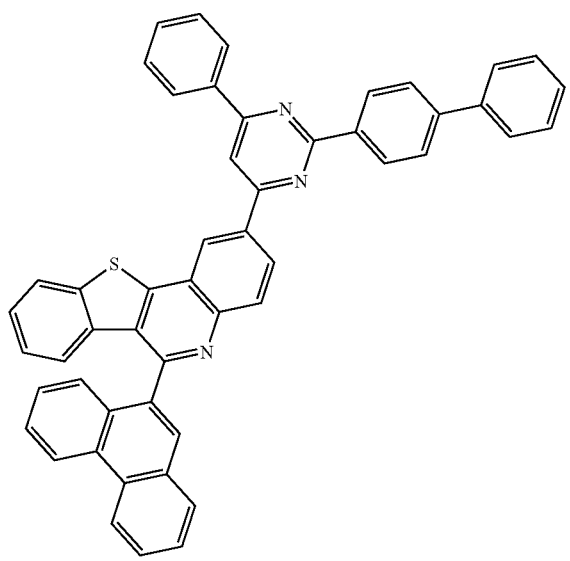
327
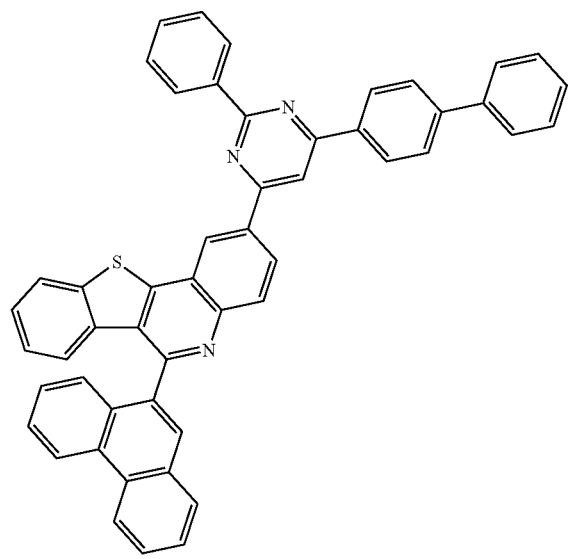
328
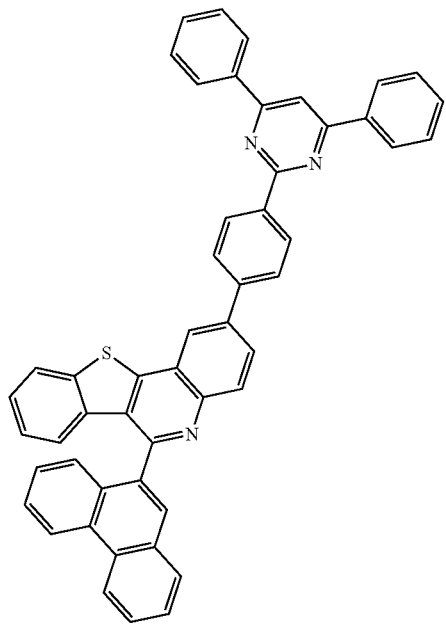
329
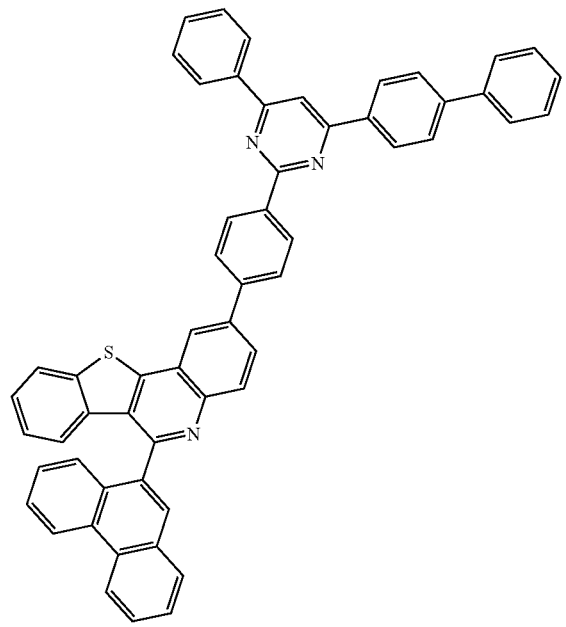

-continued
805 330 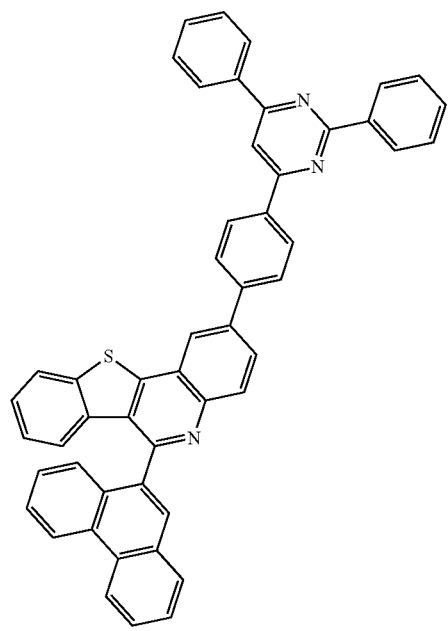
806 331 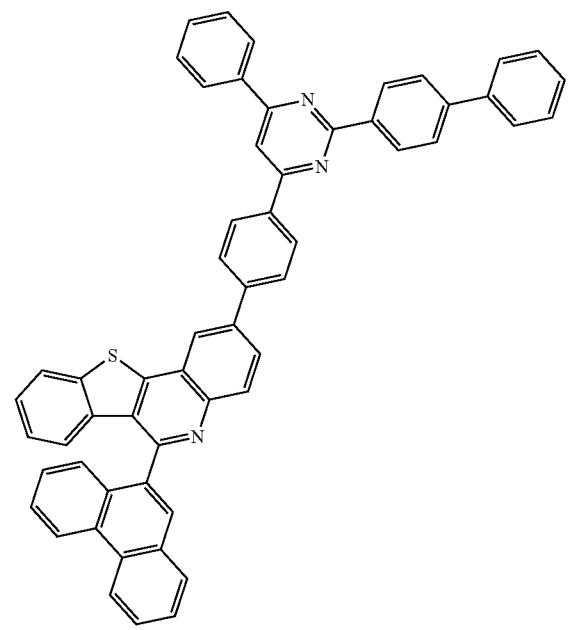
332 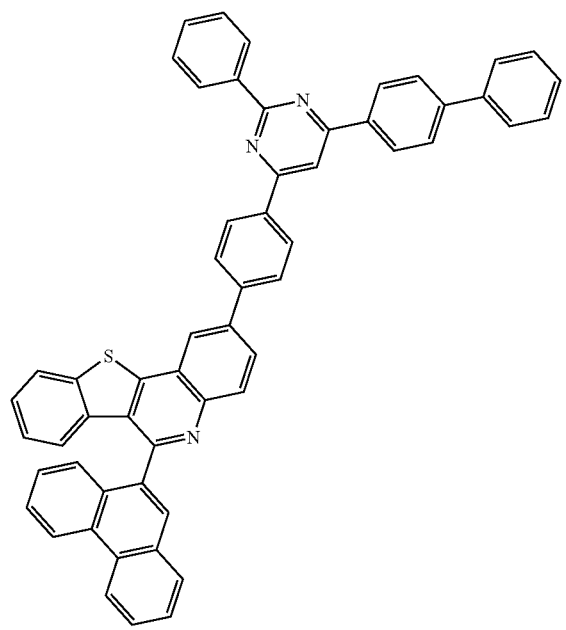
333 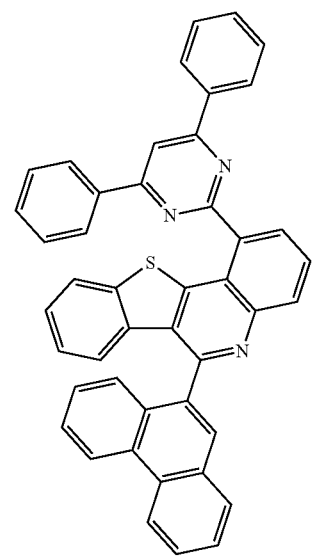

-continued
334
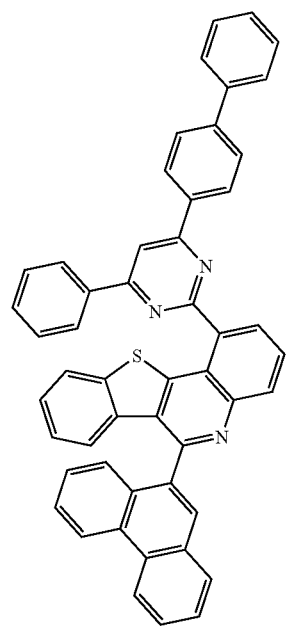
335
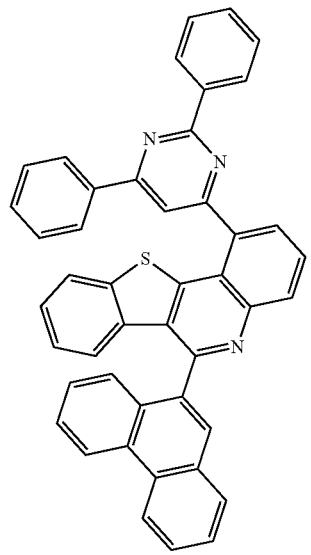
336
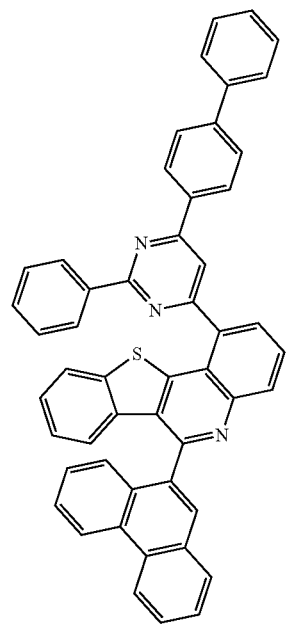
337
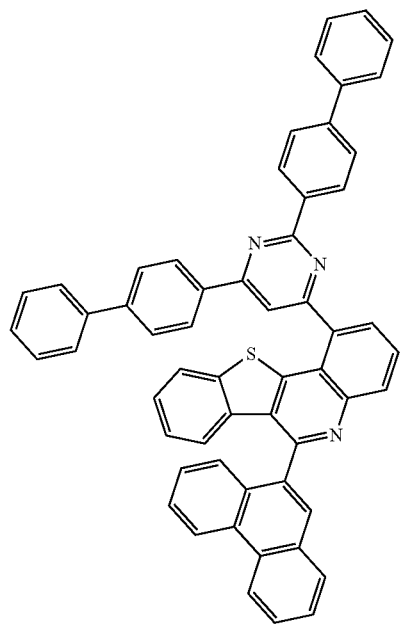

-continued
338
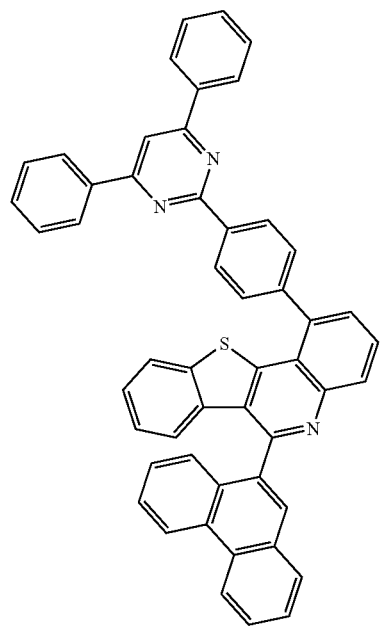
339
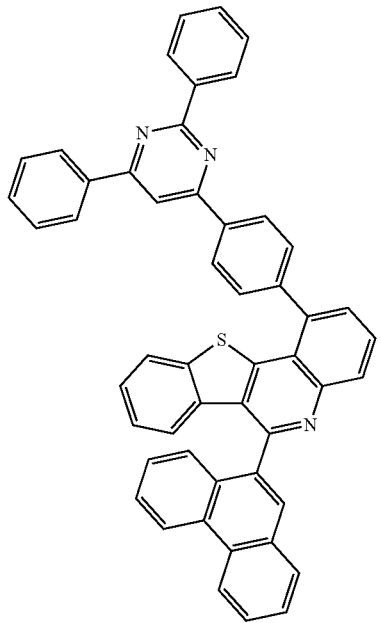
340
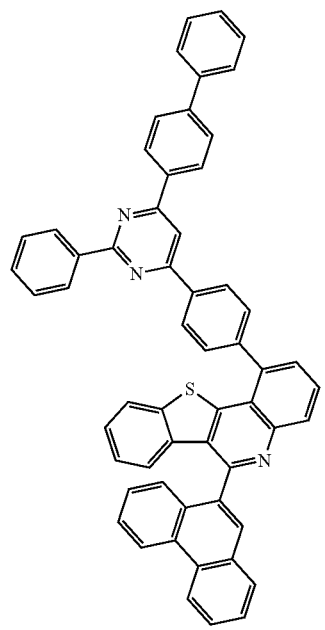
341
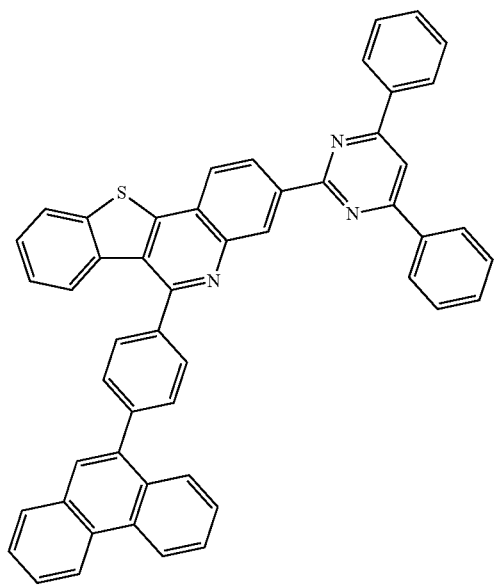

-continued
| 811 | 812 |
|---|---|
| 342 | 343 |
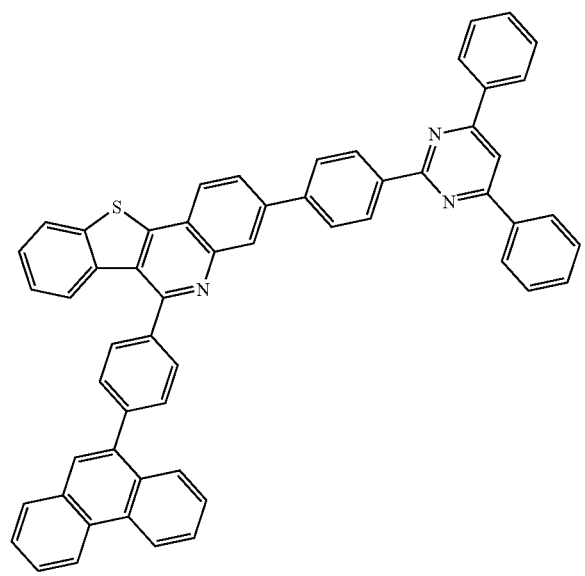
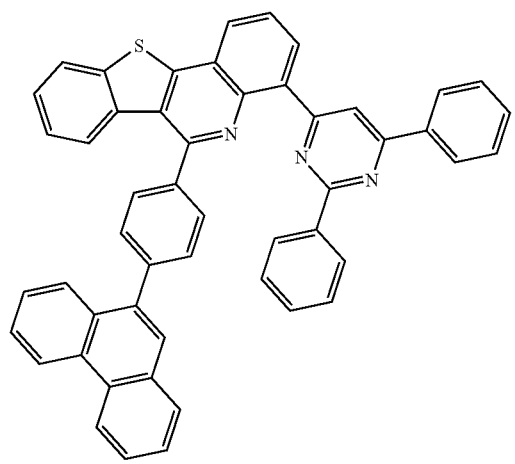
| 344 | 345 |
|---|---|
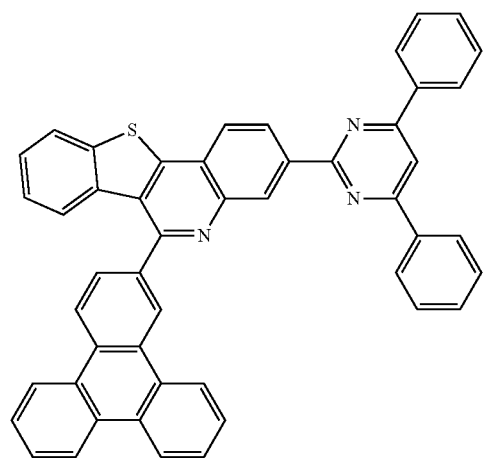
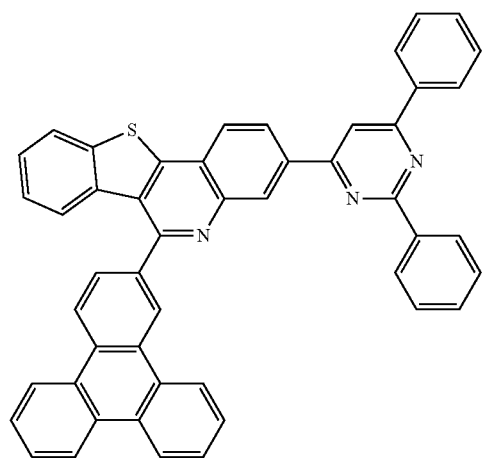
| 346 | 347 |
|---|---|
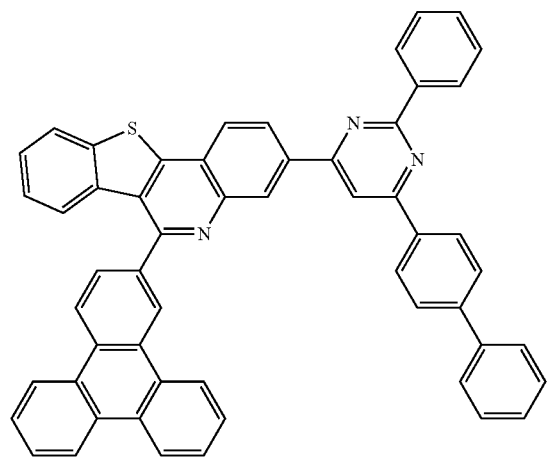
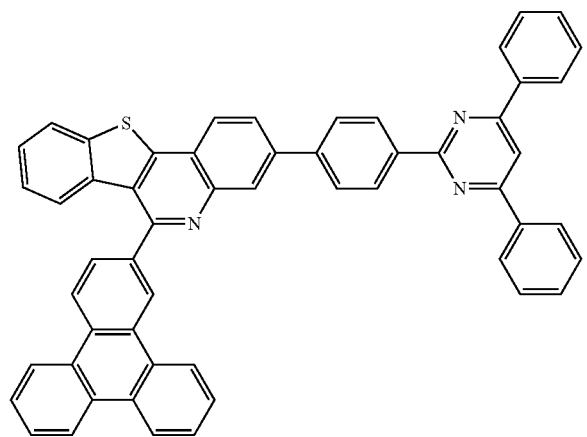

-continued
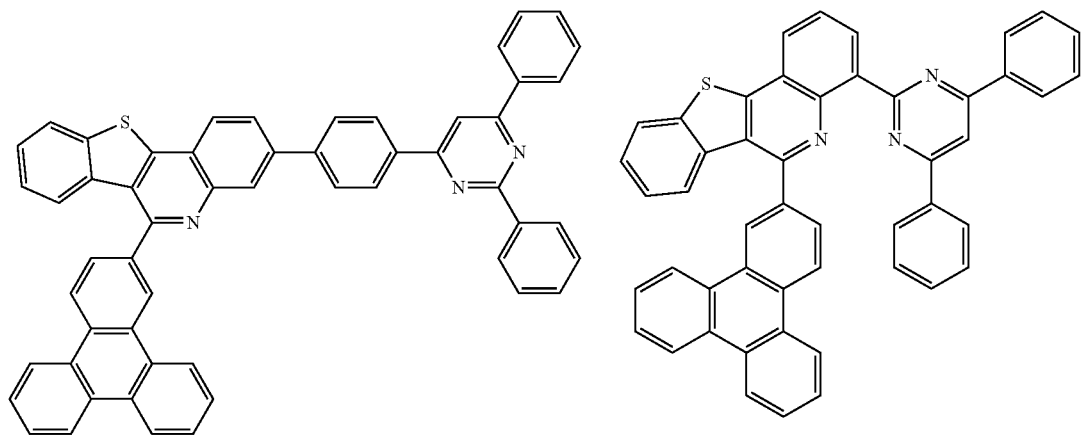
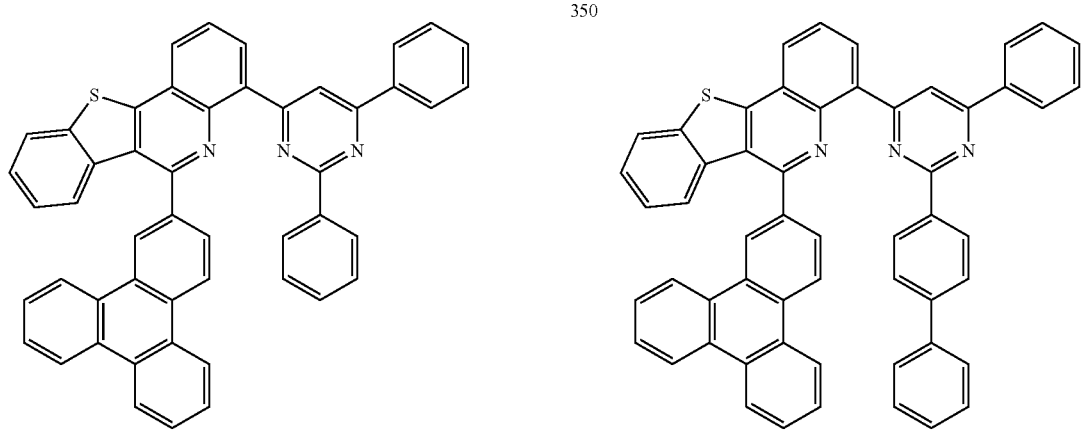
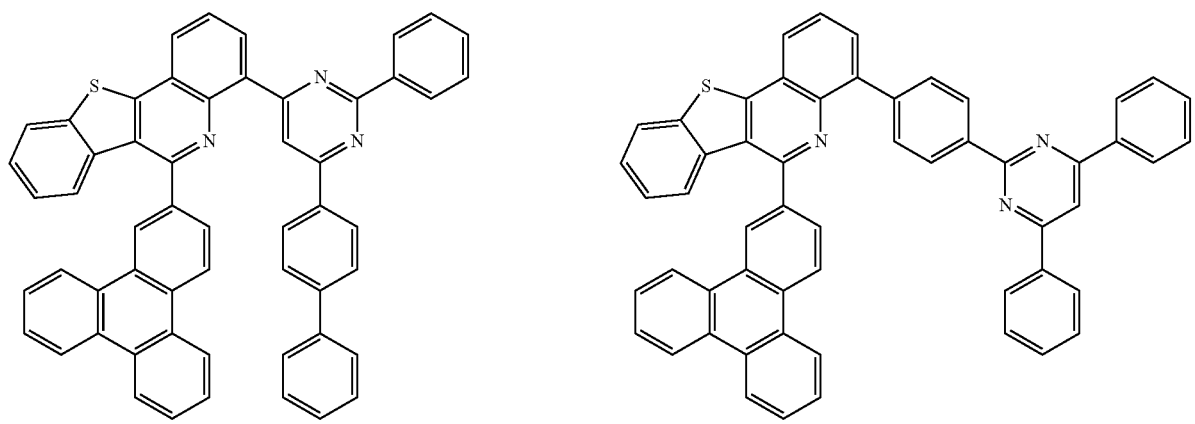

815 816
354
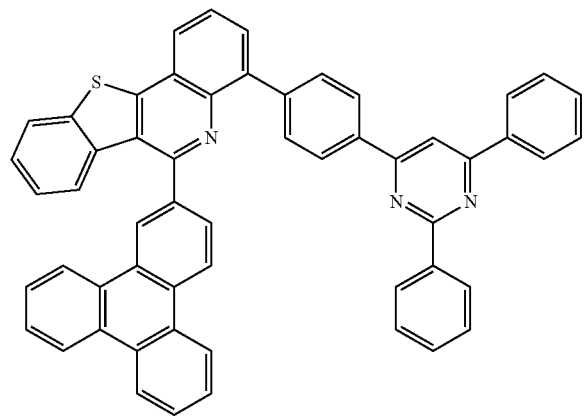
355
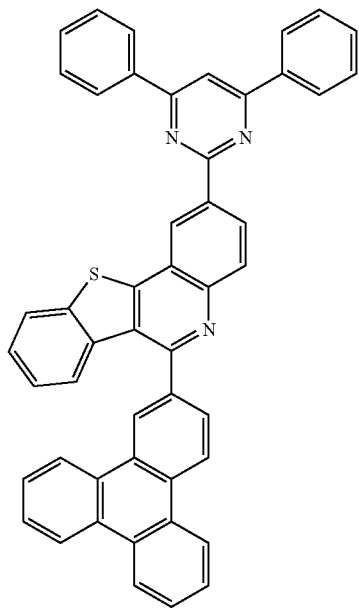
356
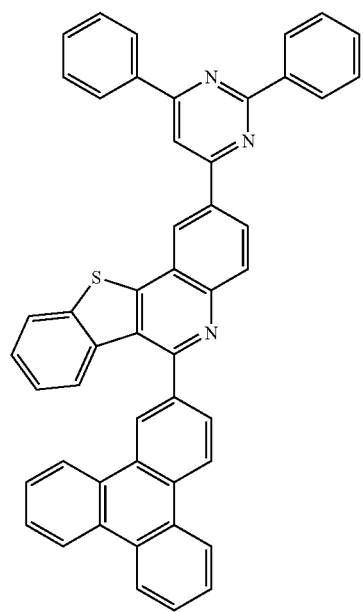
357
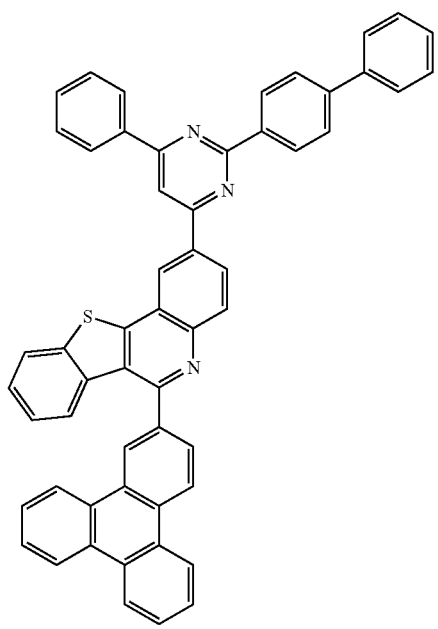

-continued
817
358
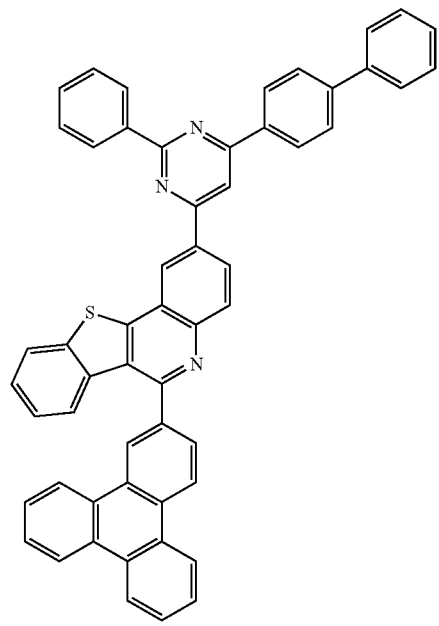
818
359
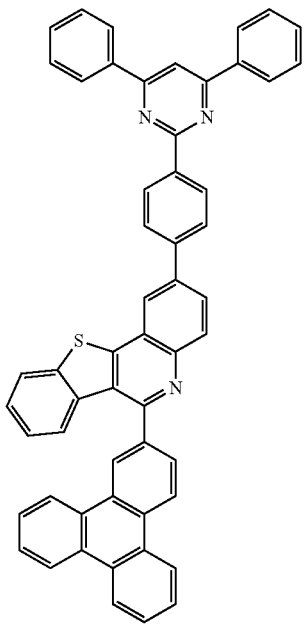
360
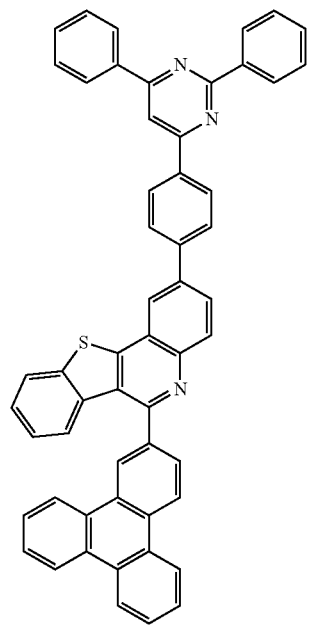
361
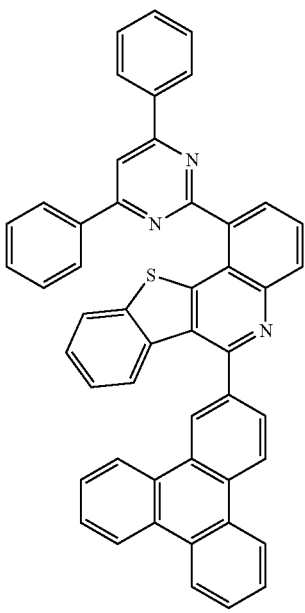

-continued
362
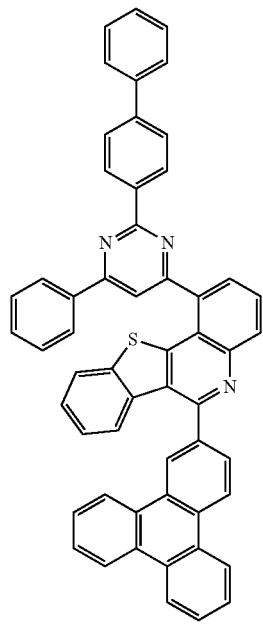
363
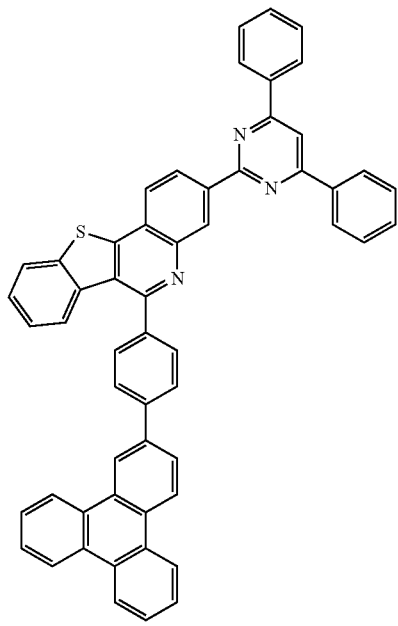
364
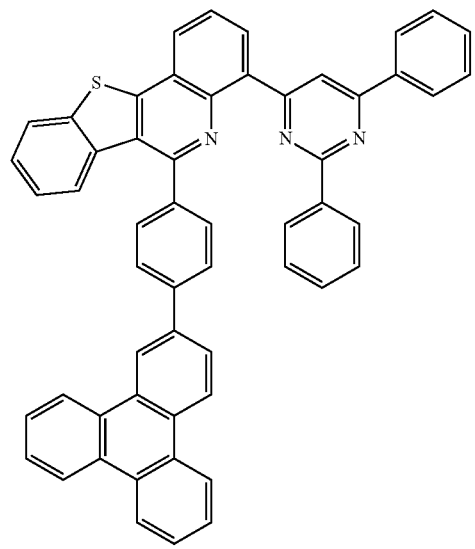
365
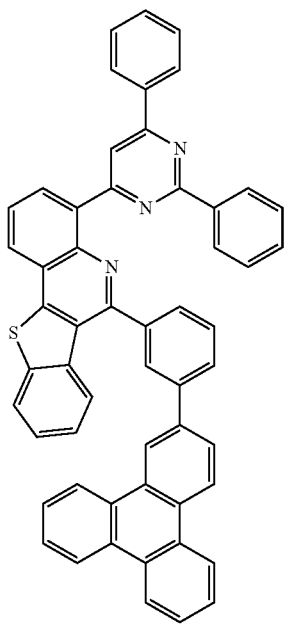

821 822
366 367
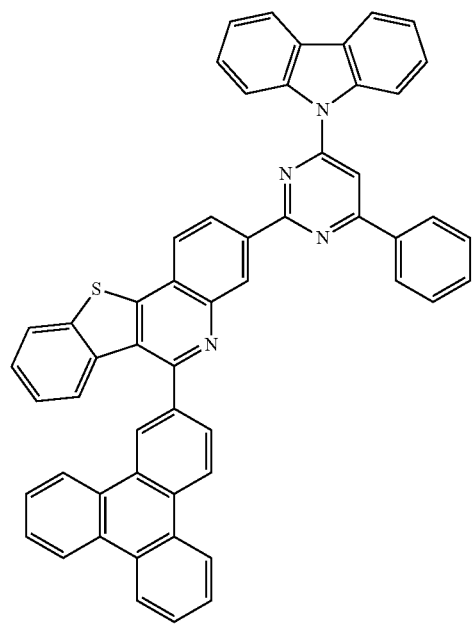 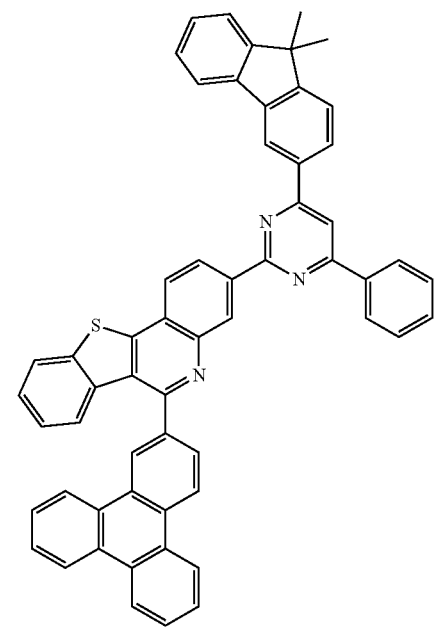
368 369
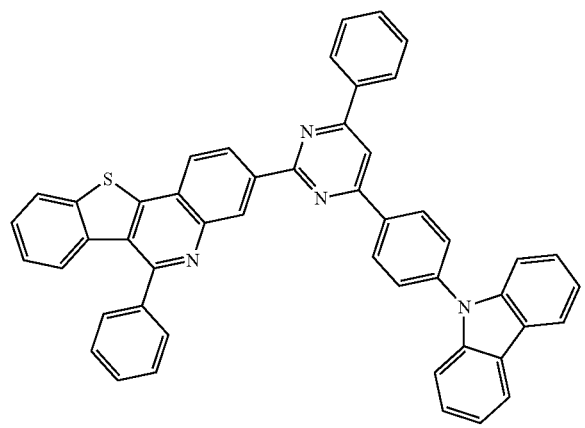
370 371
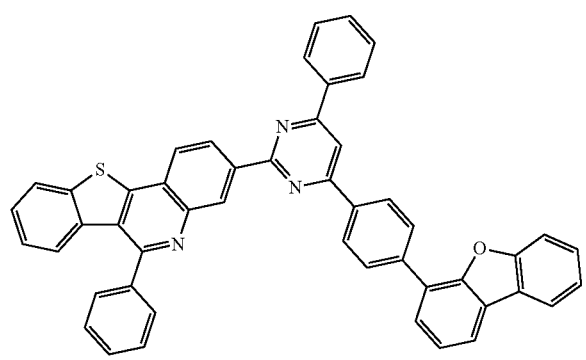 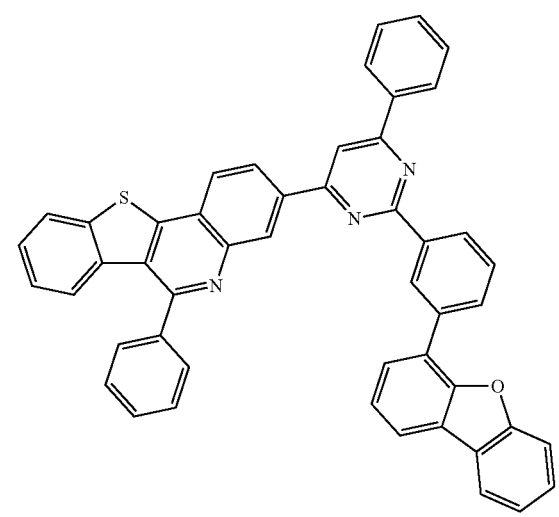

823 824
-continued
372
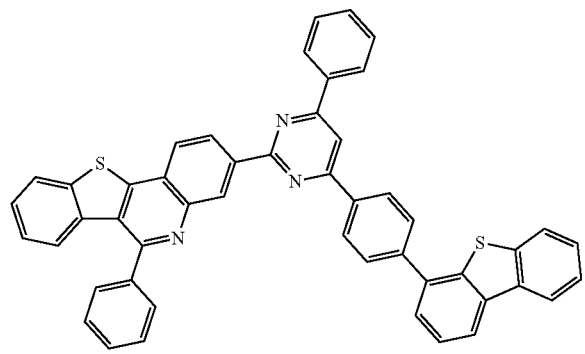
373
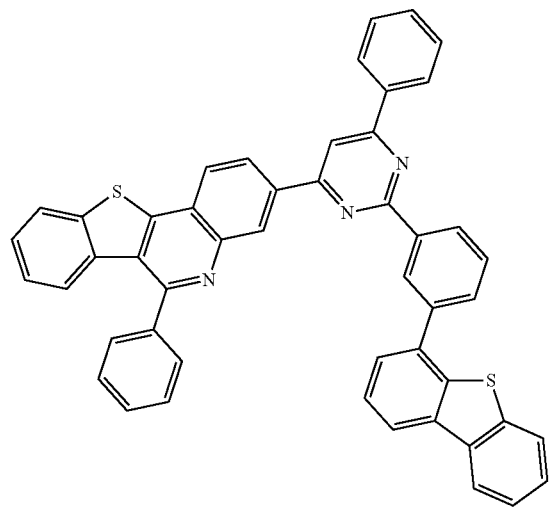
374
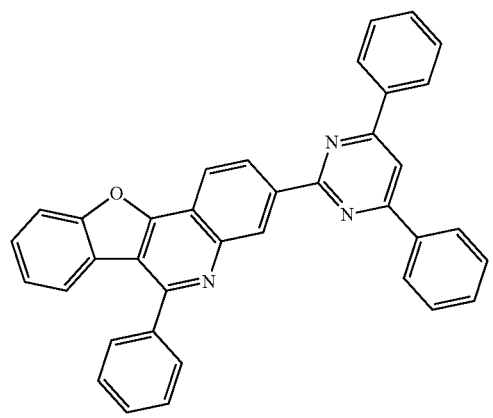
375
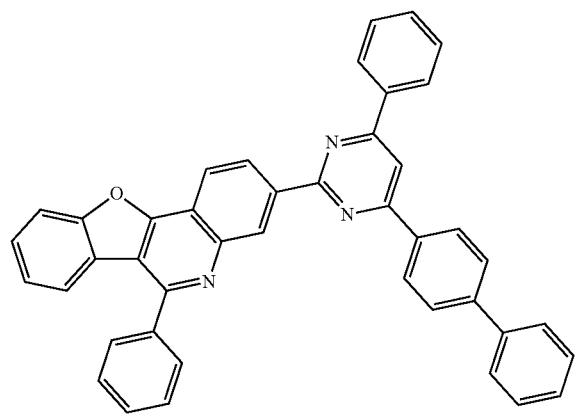
376
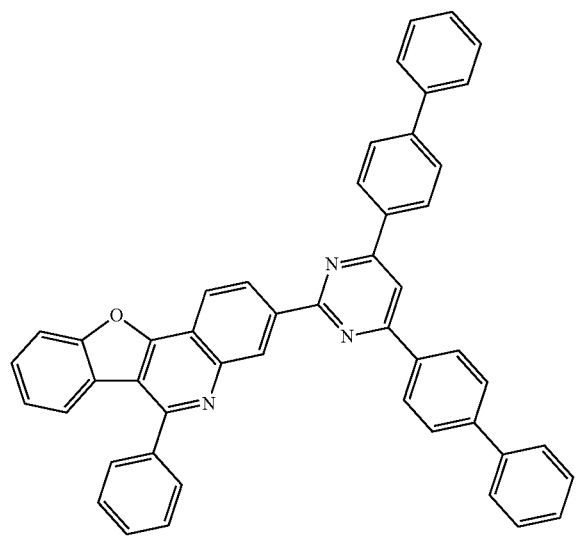
377
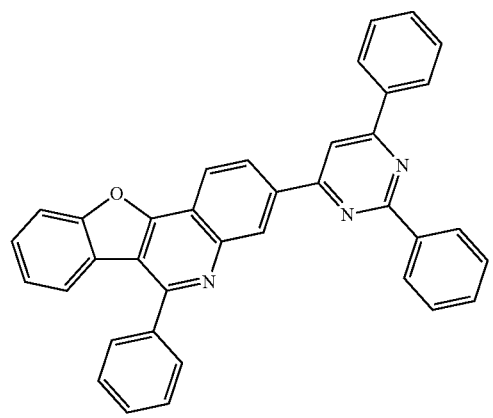

378
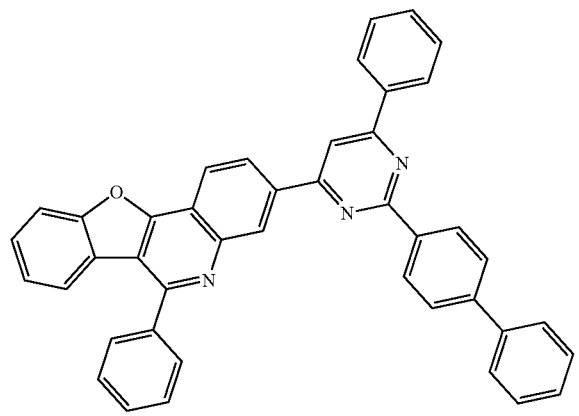
379
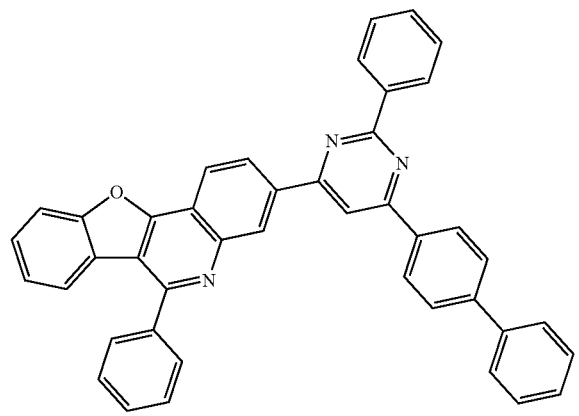
380
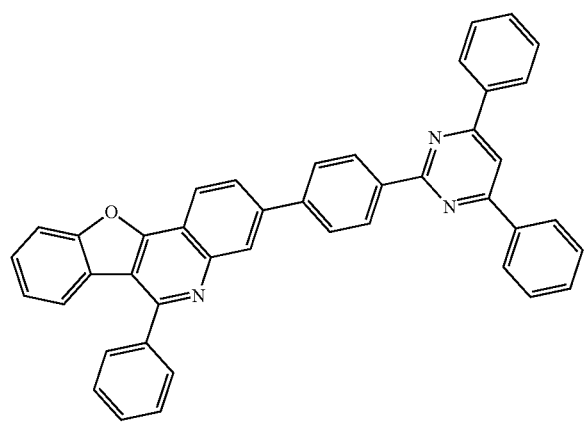
381
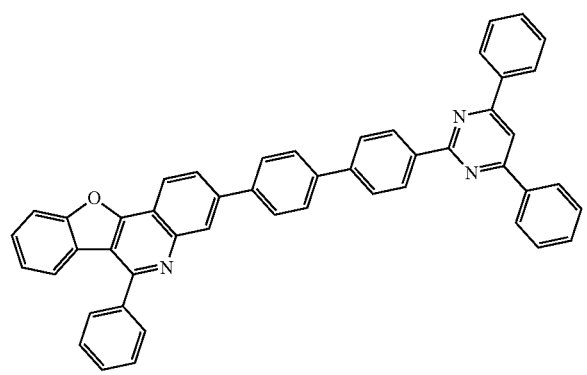
382
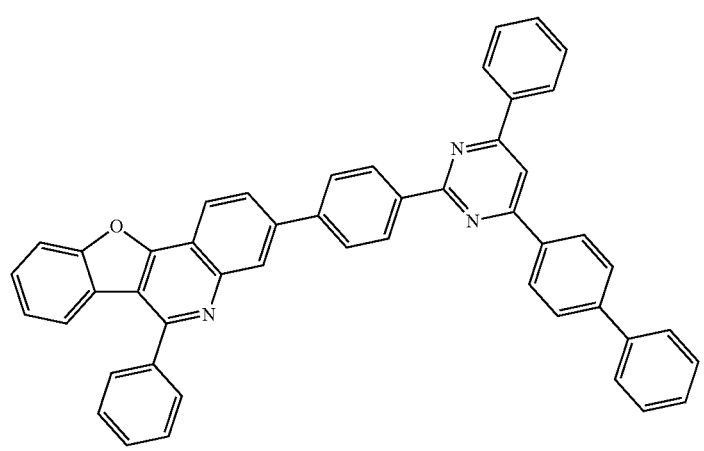

-continued
383
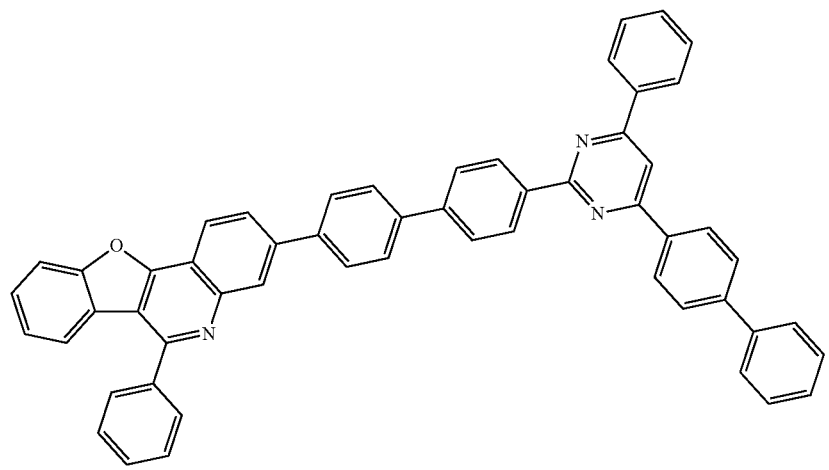
384
385
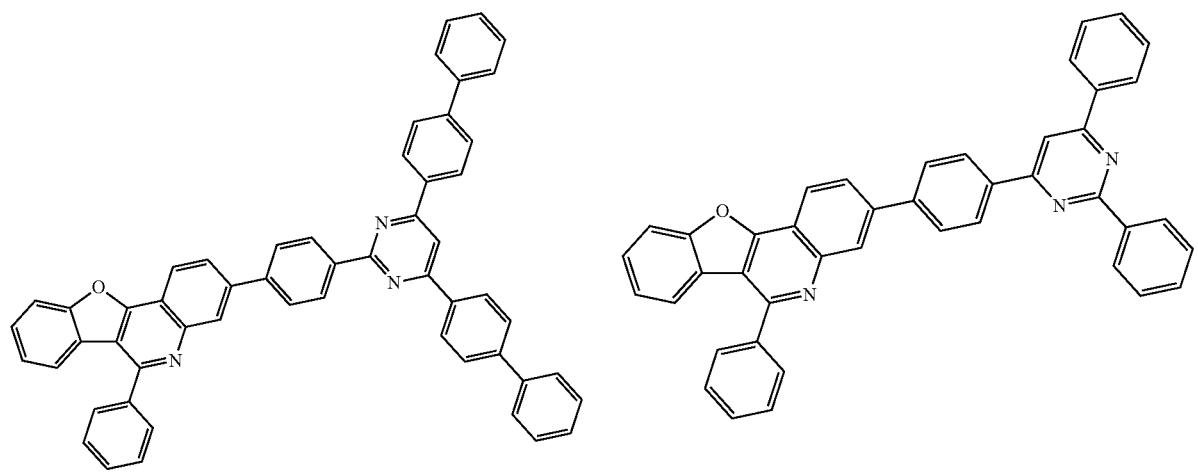
386
387
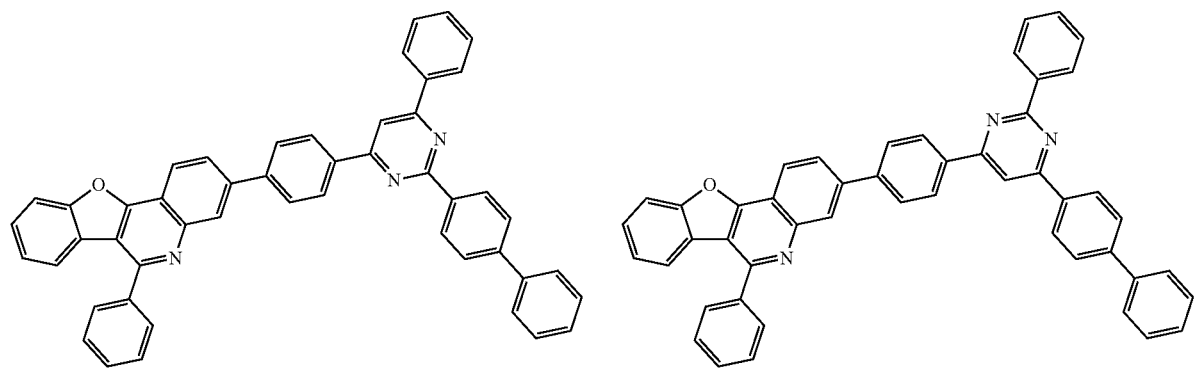

-continued
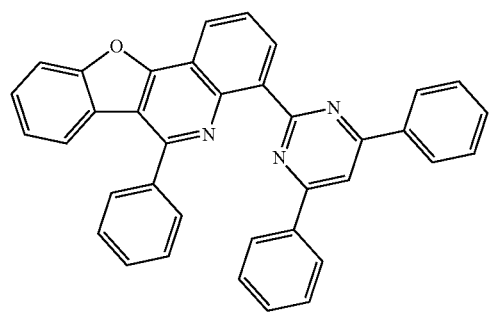
388
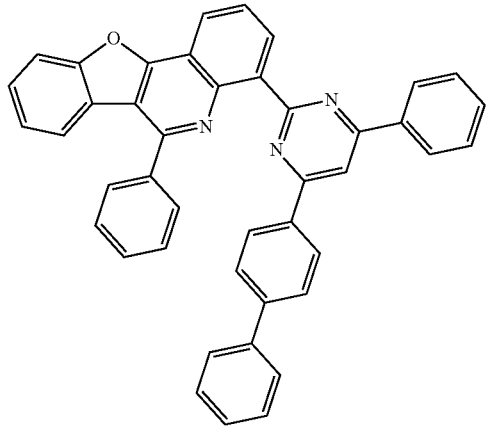
389
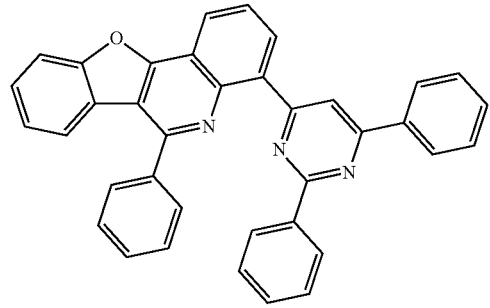
390
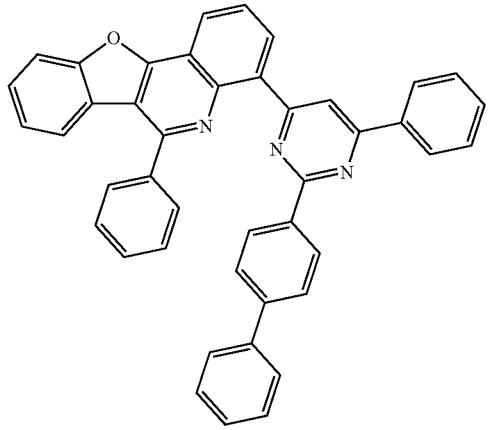
391
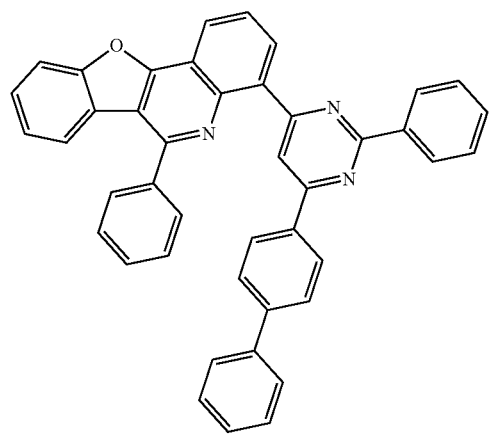
392
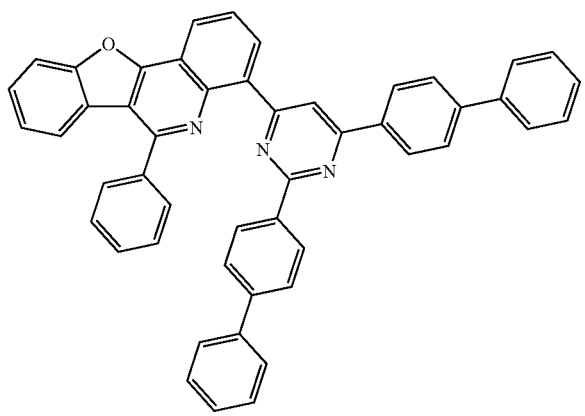
393

394
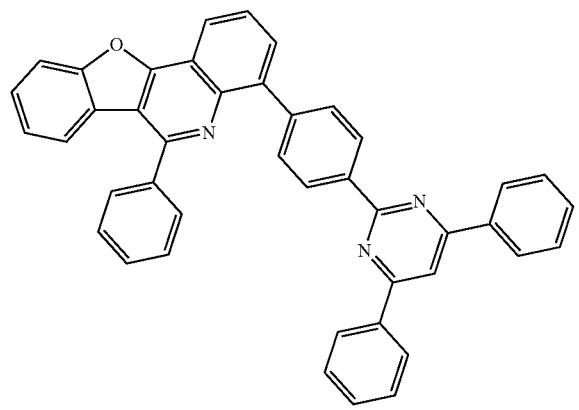
395
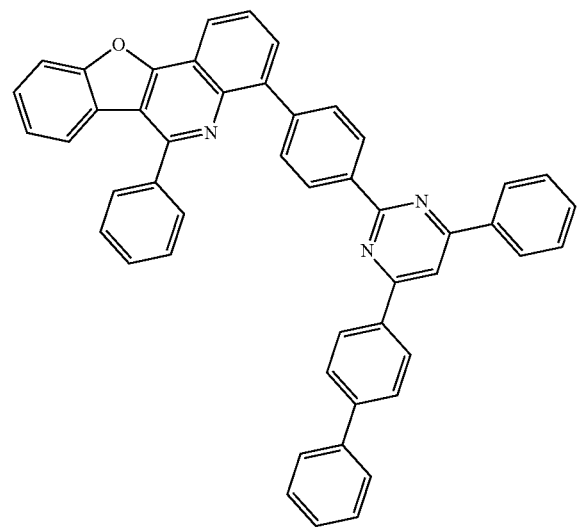
396
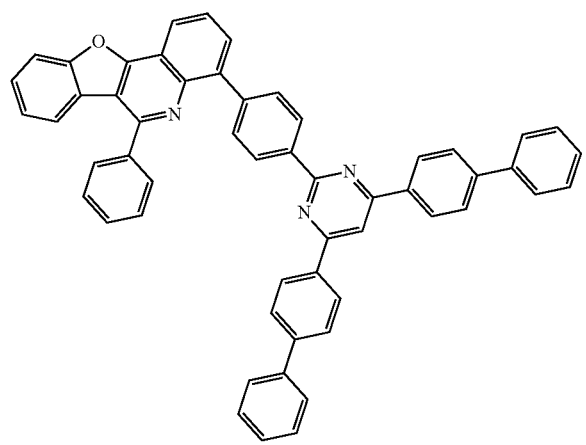
397
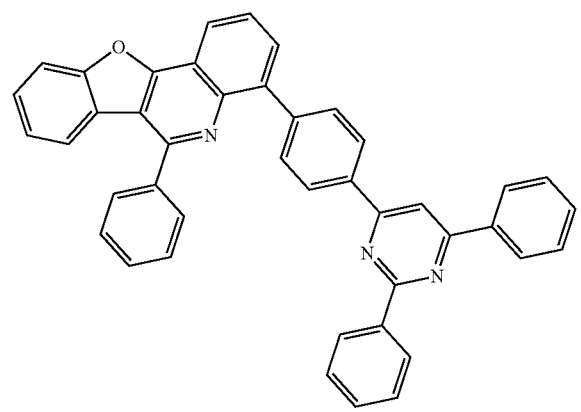
398
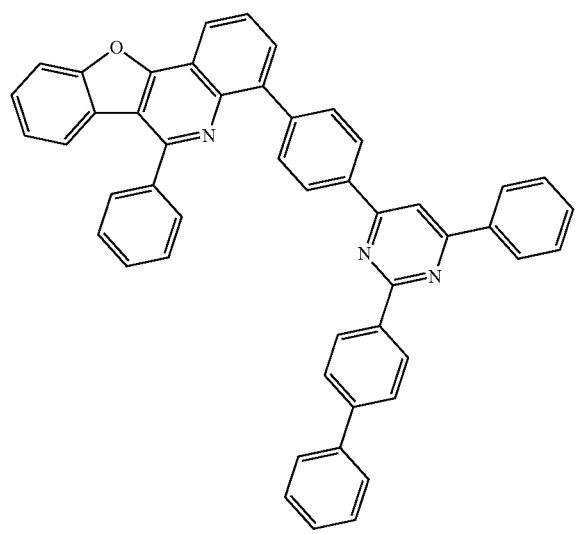
399
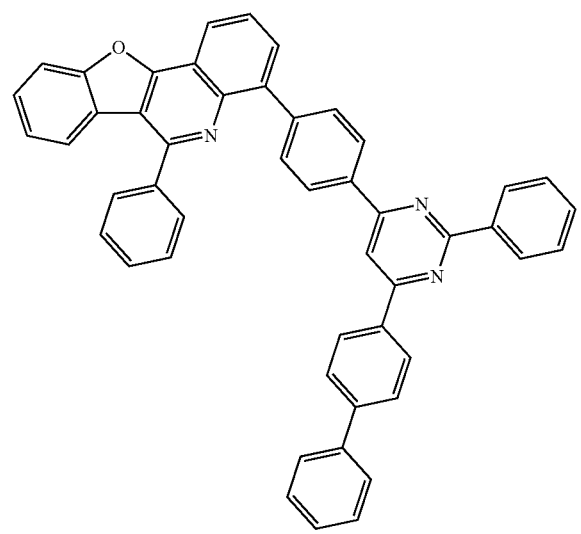

-continued
400
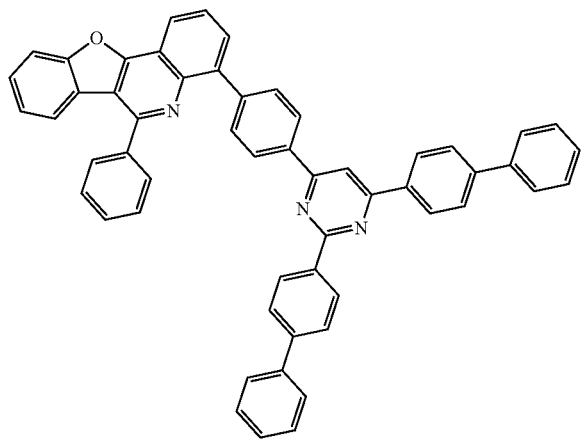
401
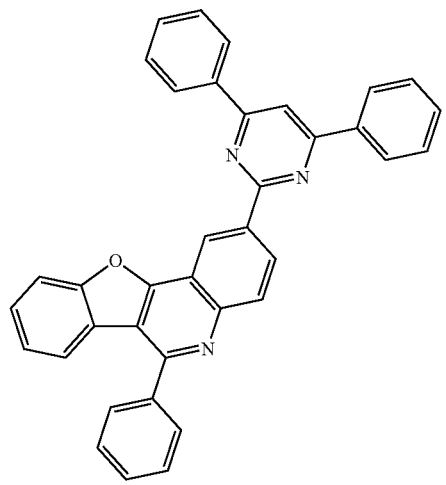
402
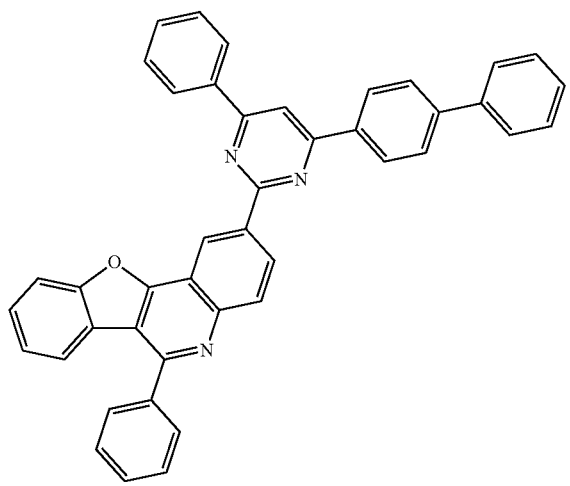
403
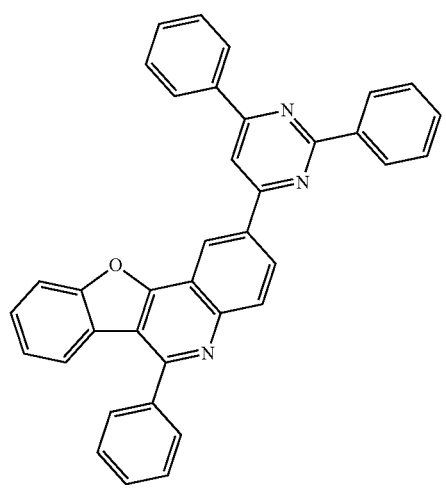
404
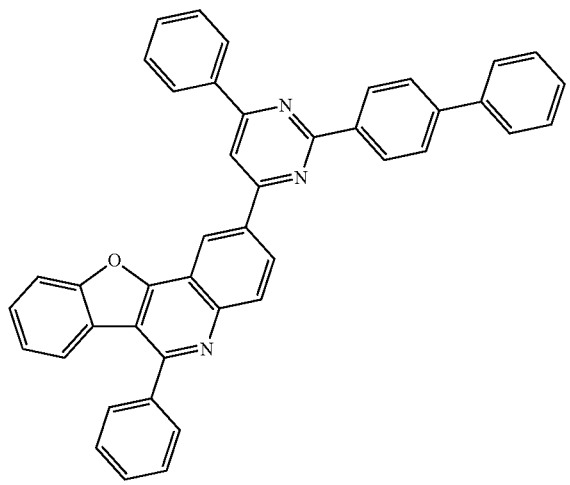
405
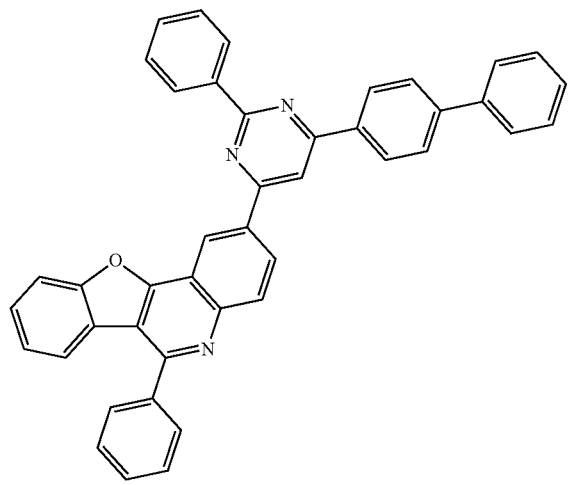

-continued
835
406
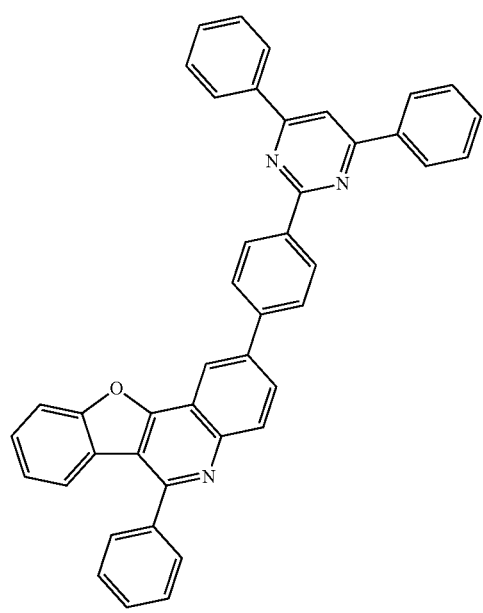
836
407
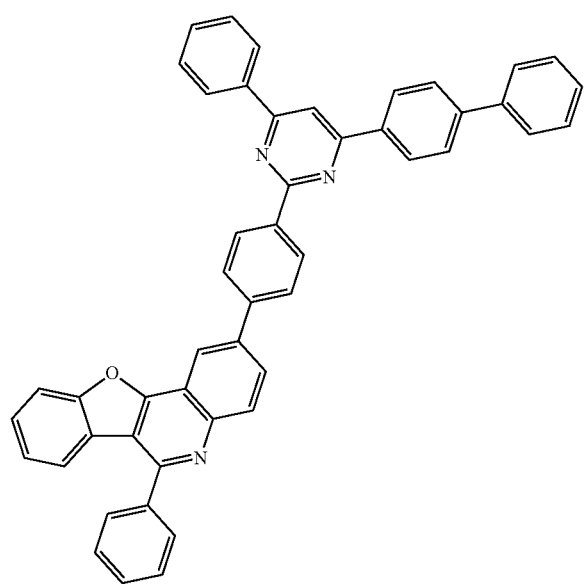
408
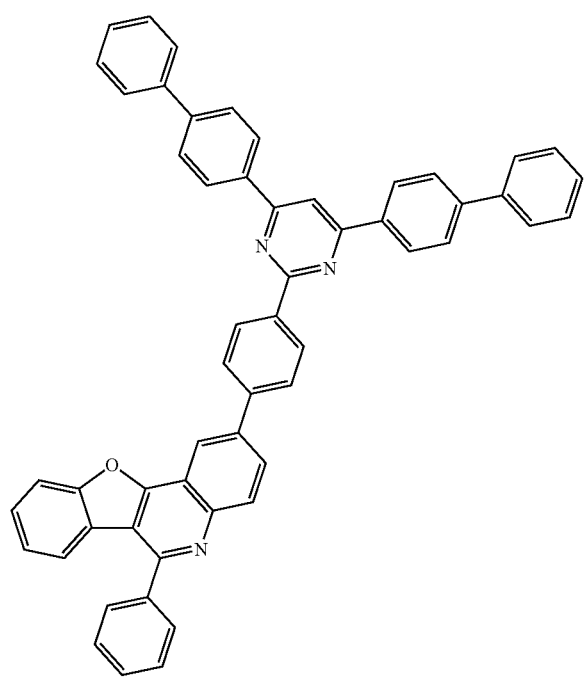
409
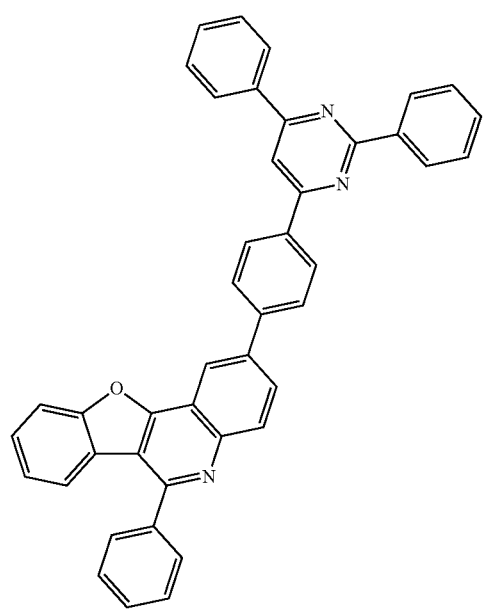

837 838
410 411
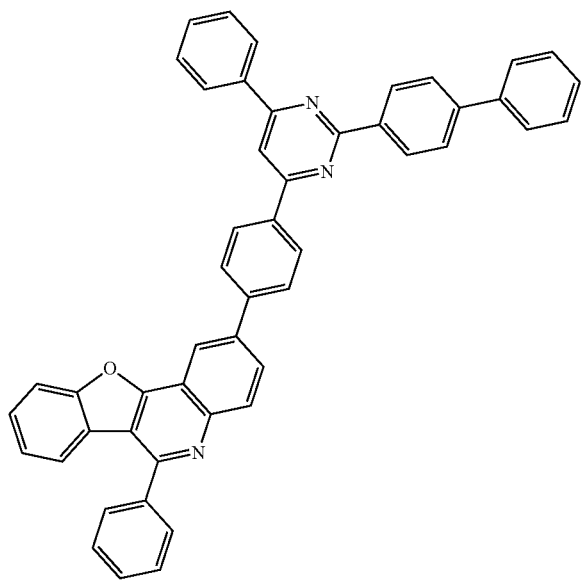
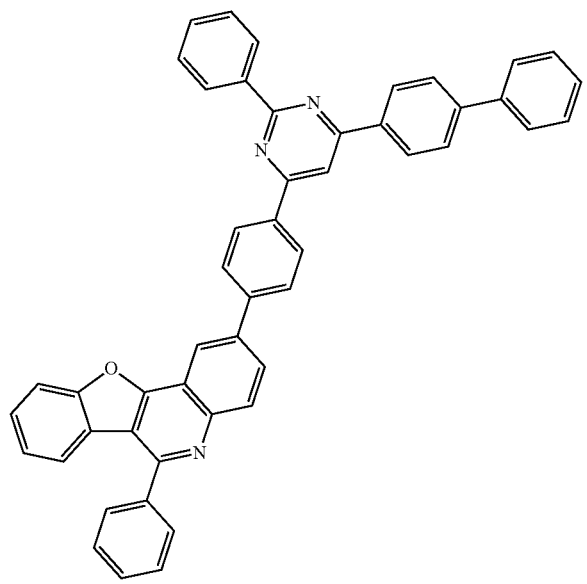
412 413
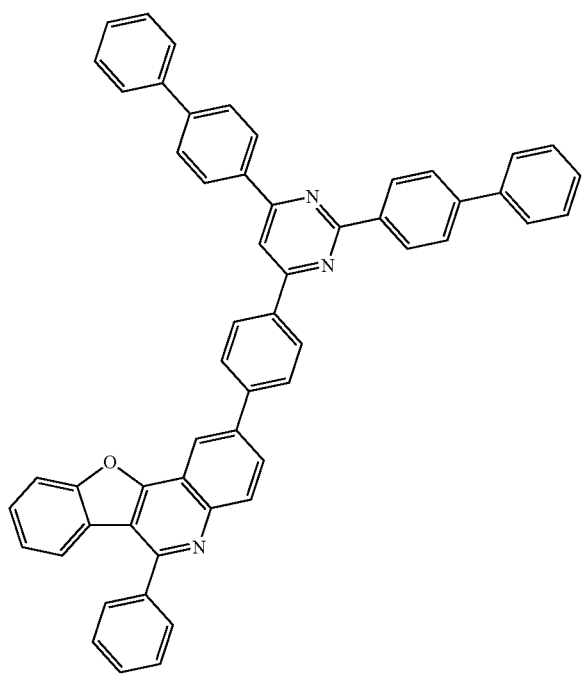
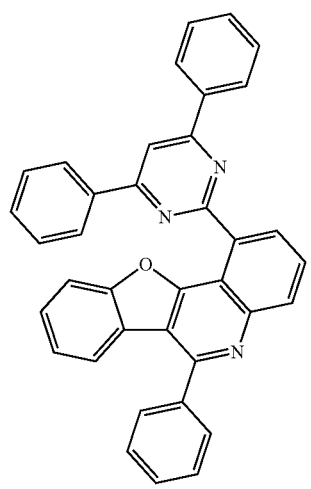

-continued
414
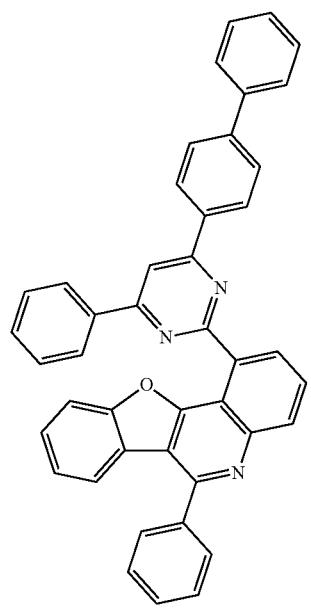
415
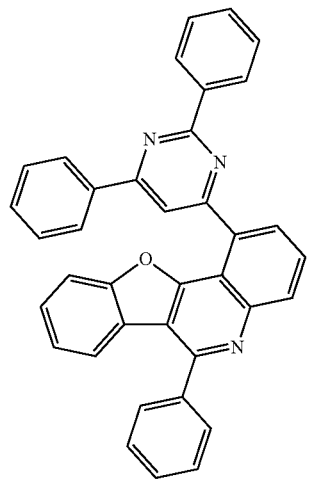
416
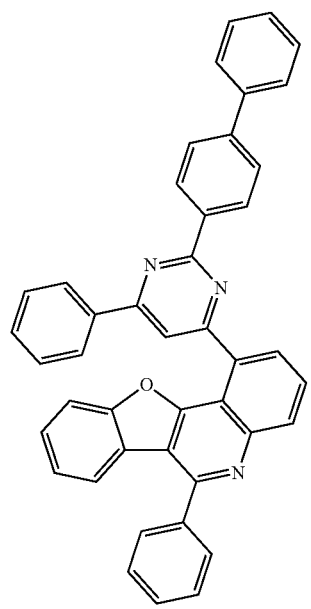
417
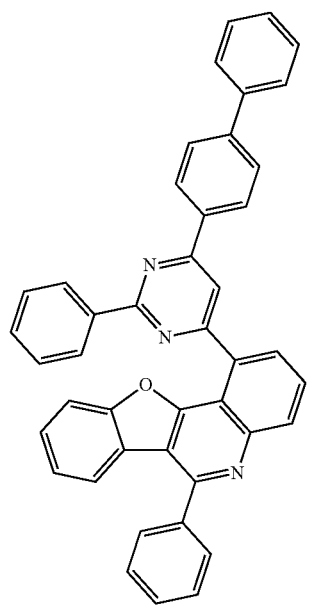

-continued
418
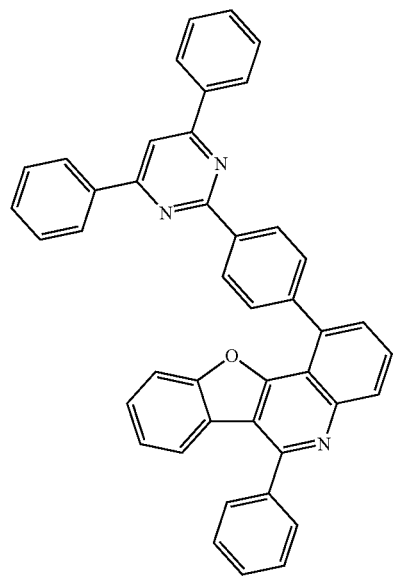
419
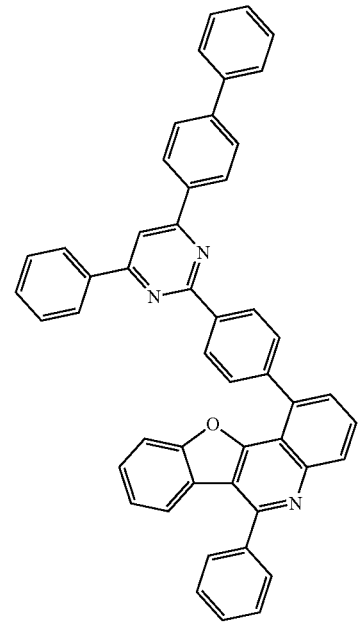
420
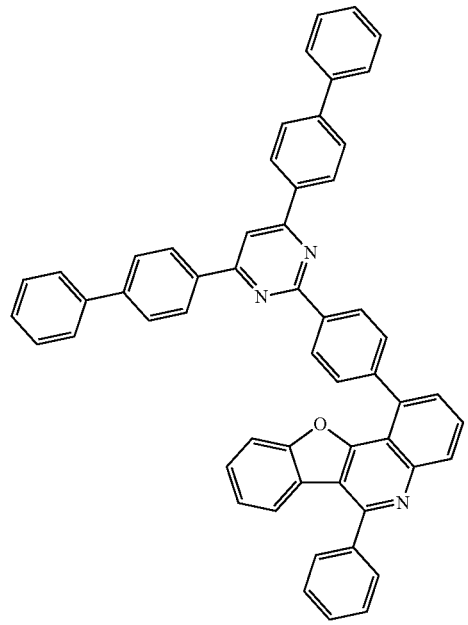
421
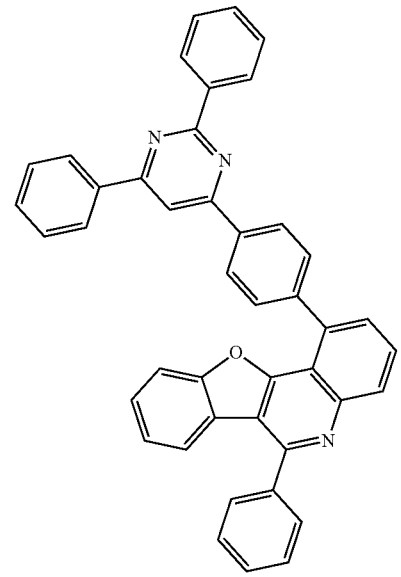

-continued
422
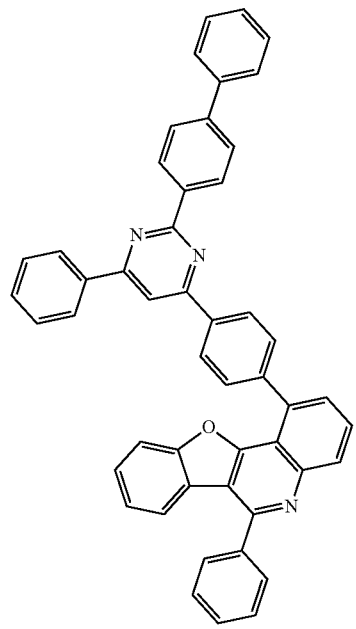
423
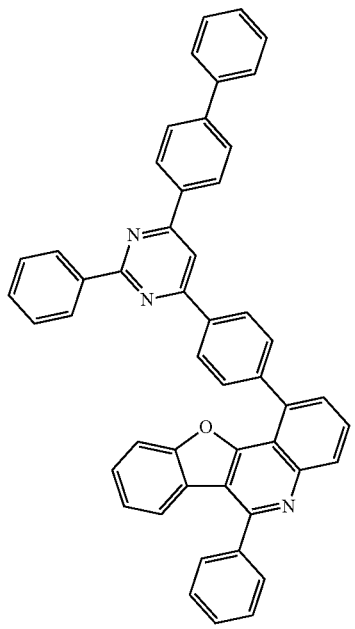
424
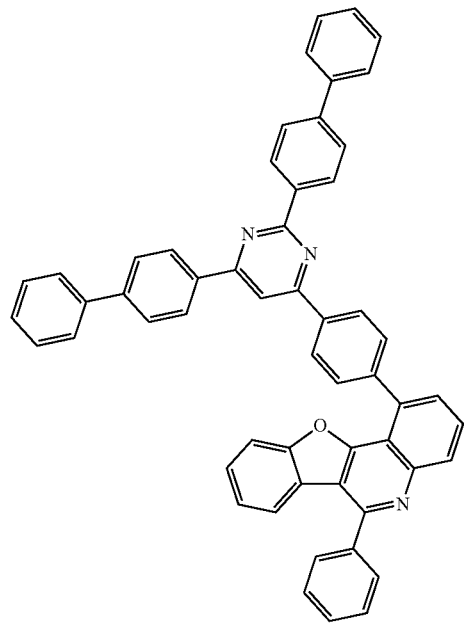
425
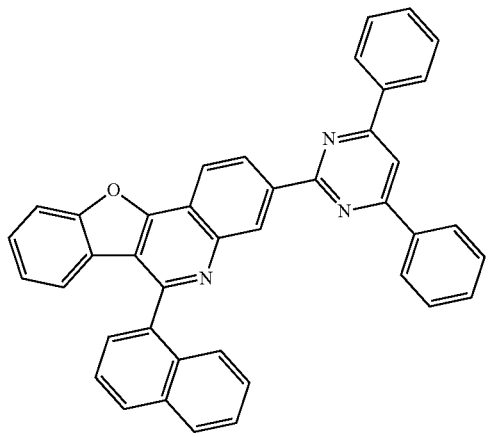

-continued
426
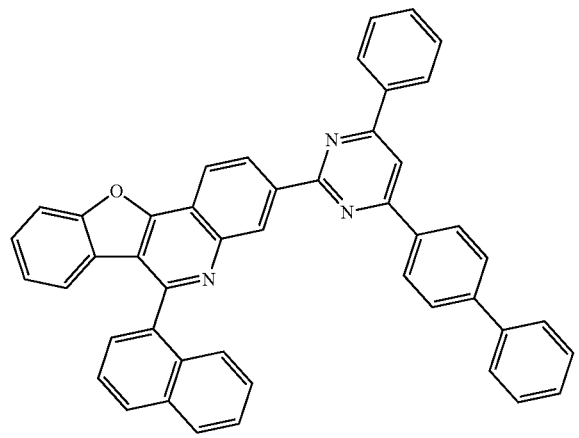
427
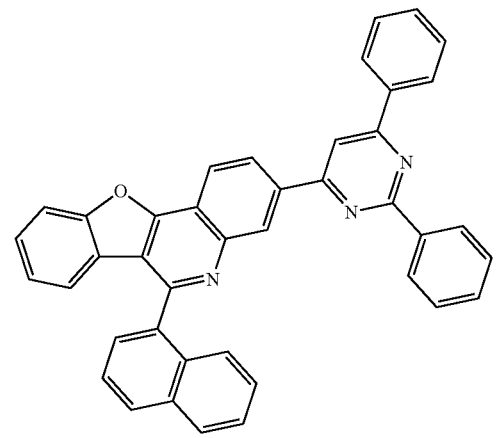
428
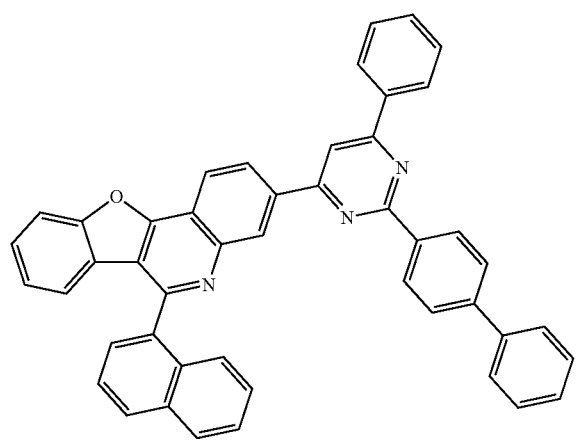
429
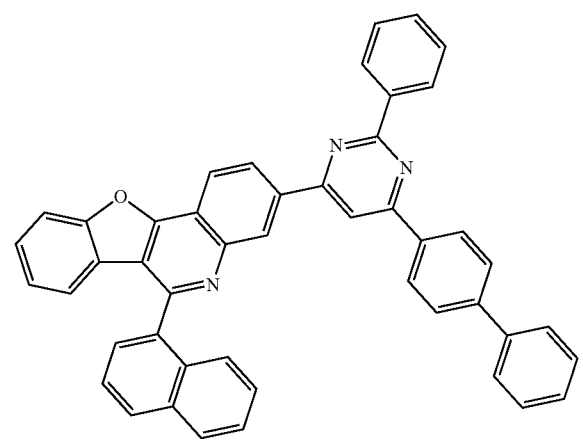
430
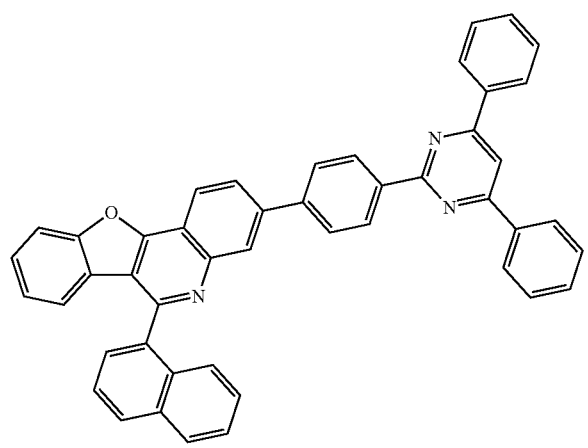
431
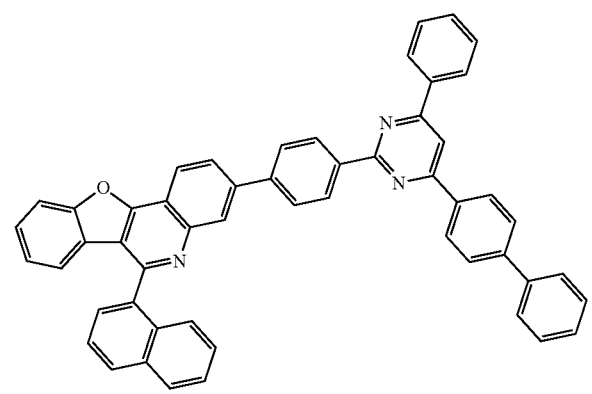

-continued
432
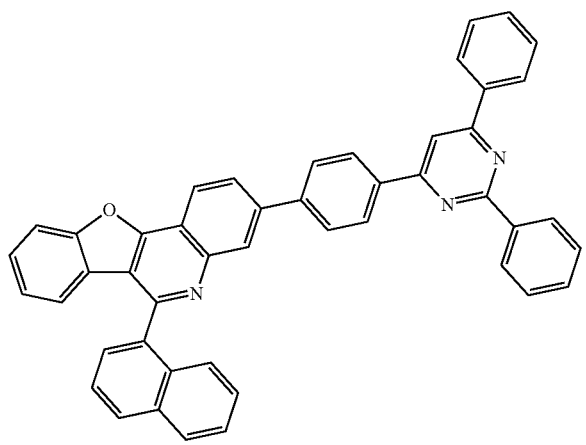
433
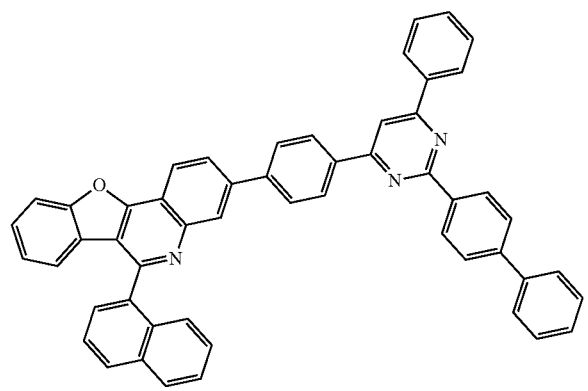
434
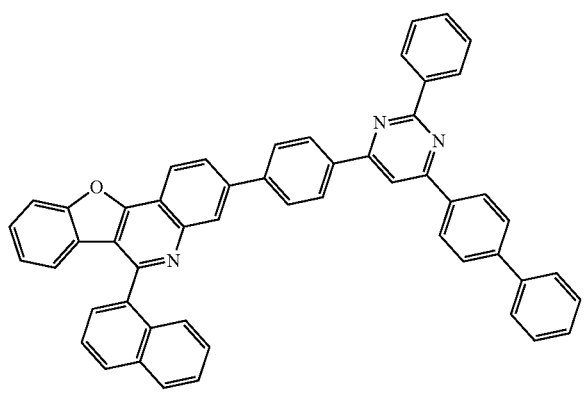
435
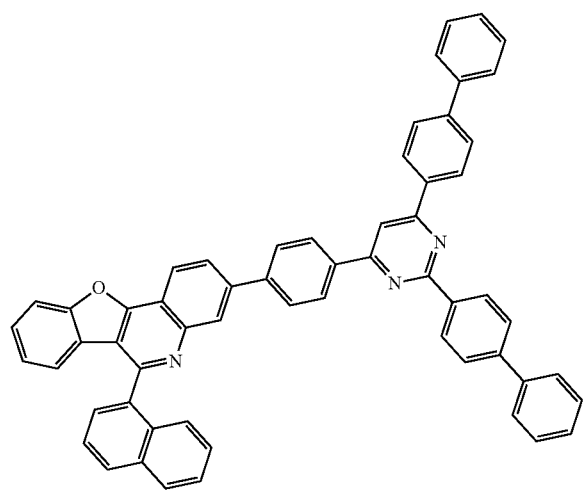
436
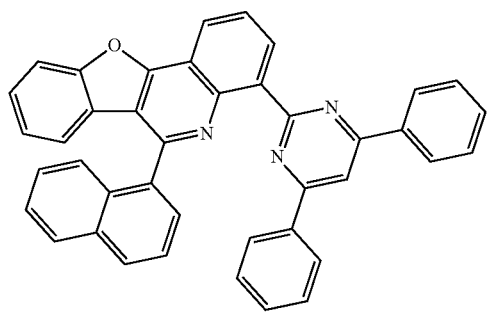
437
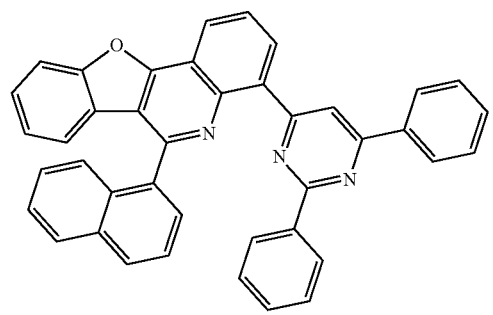

-continued
849
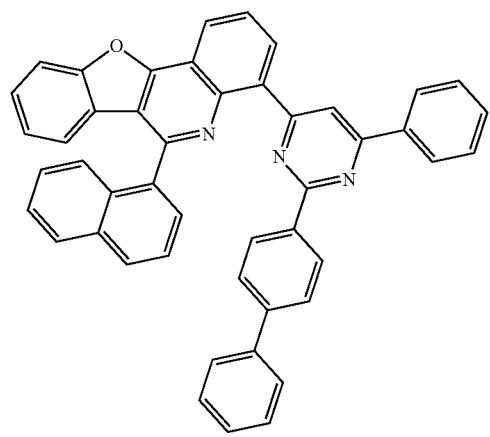
438
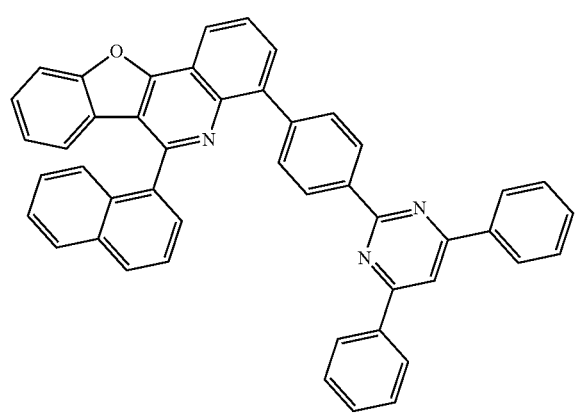
440
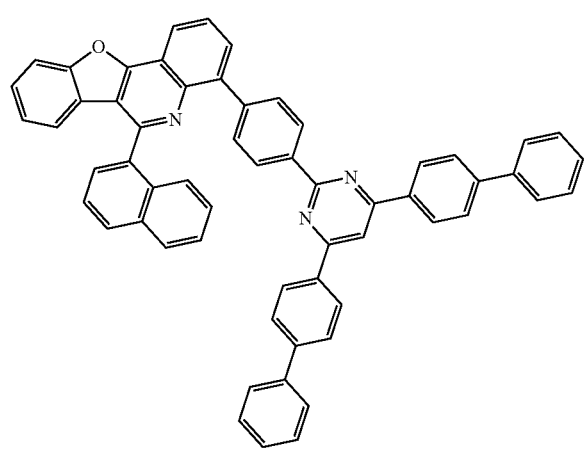
442
850
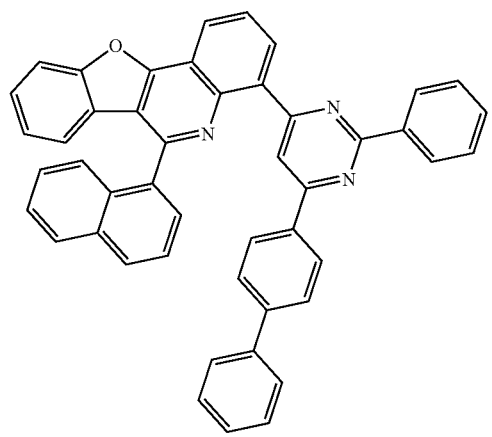
439
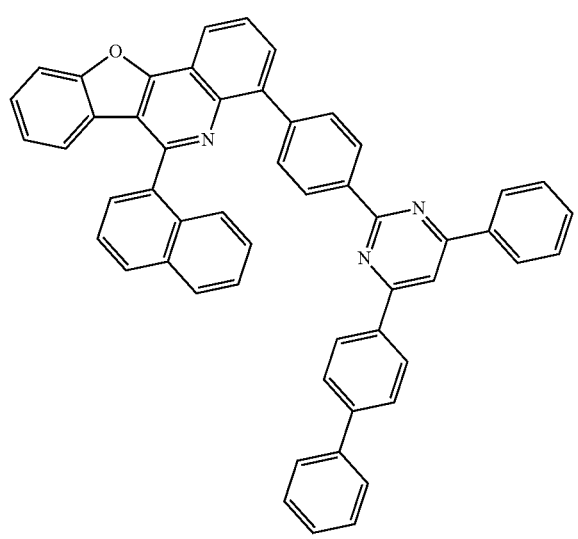
441
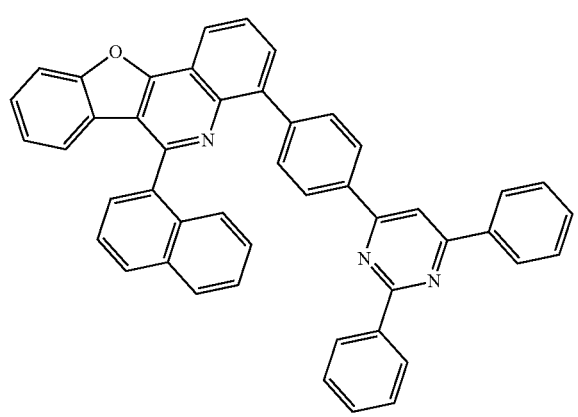
443

-continued
444
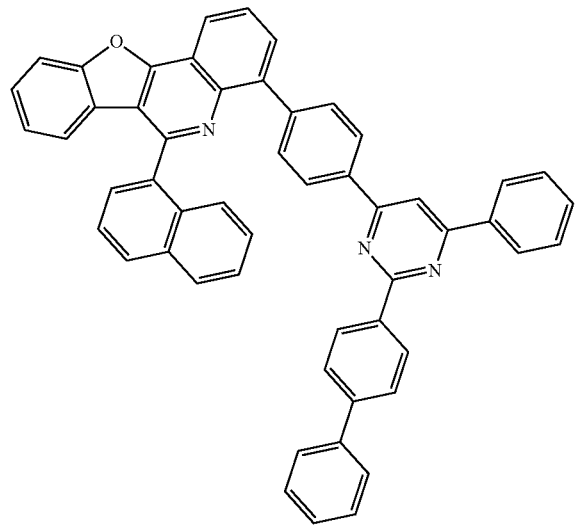
445
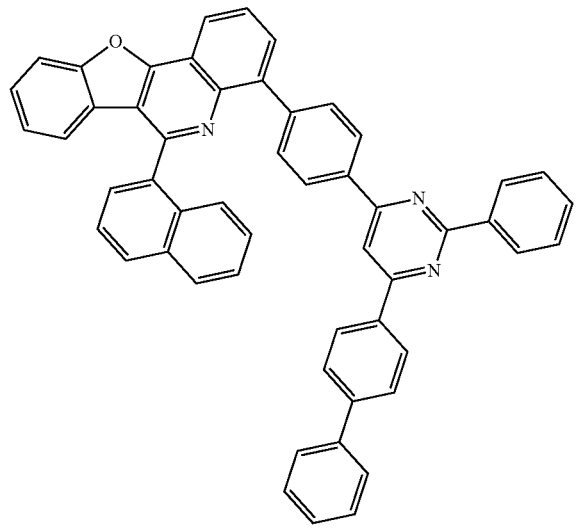
446
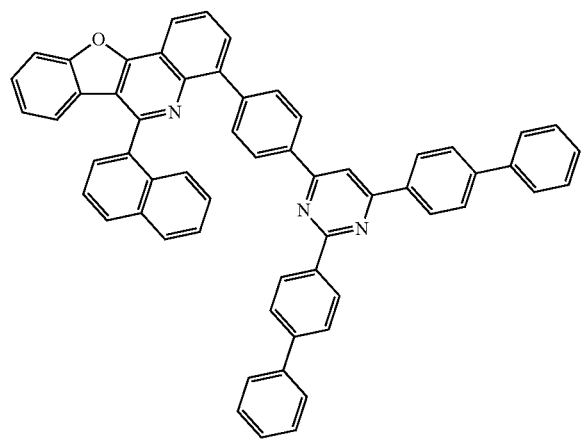
447
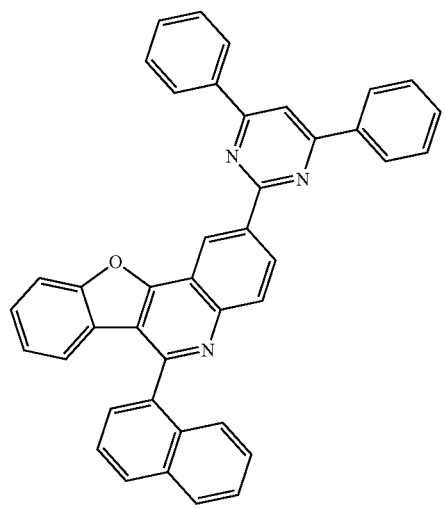
448
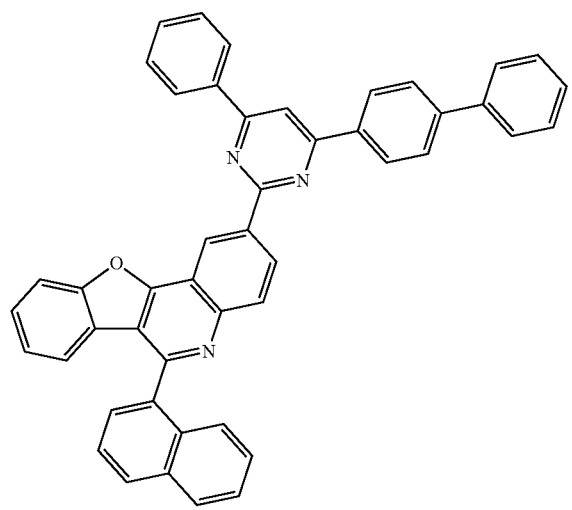
449
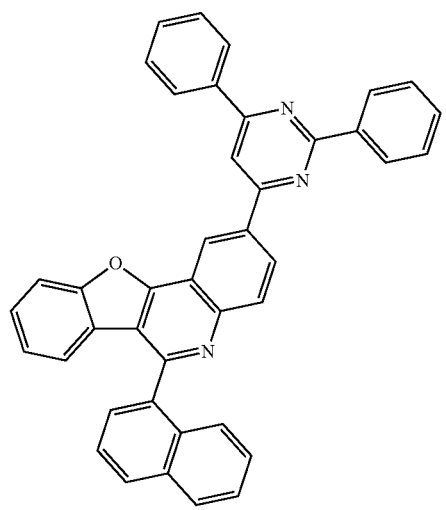

-continued
| 450 | 451 |
|---|---|
| 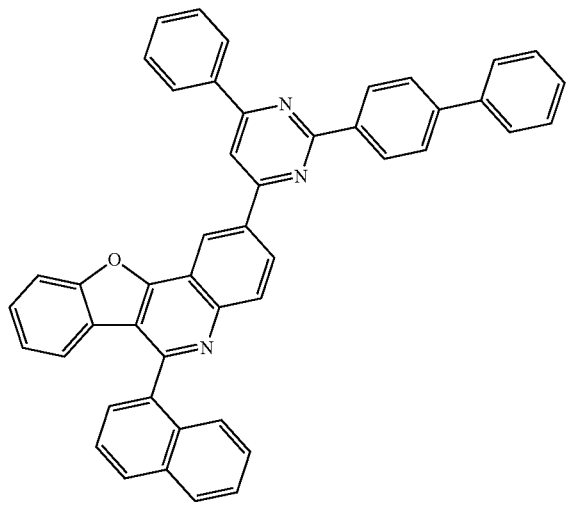 | 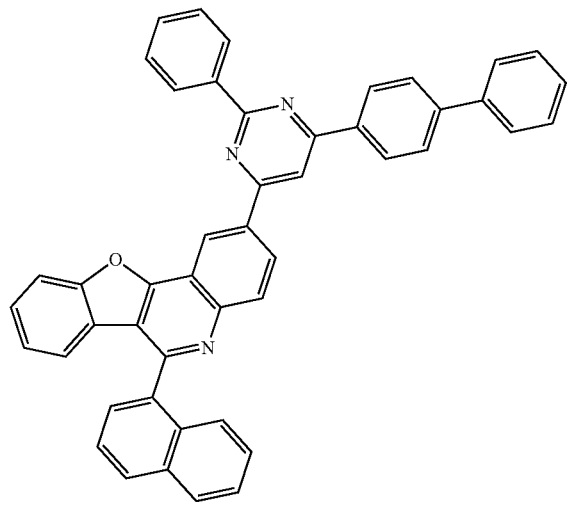 |
| 452 | 453 |
| 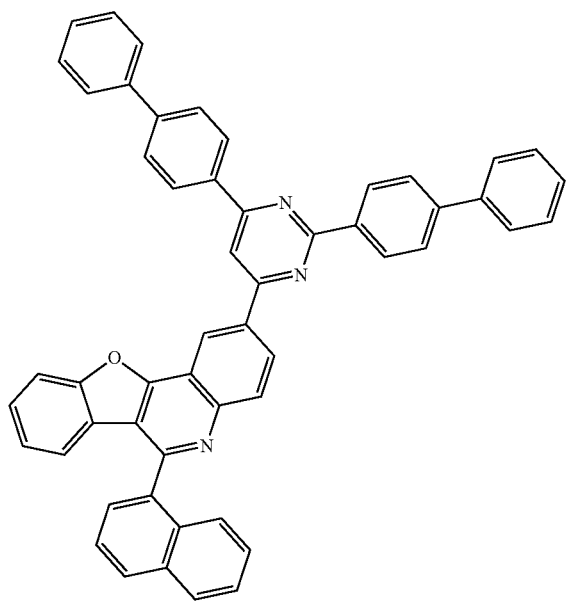 | 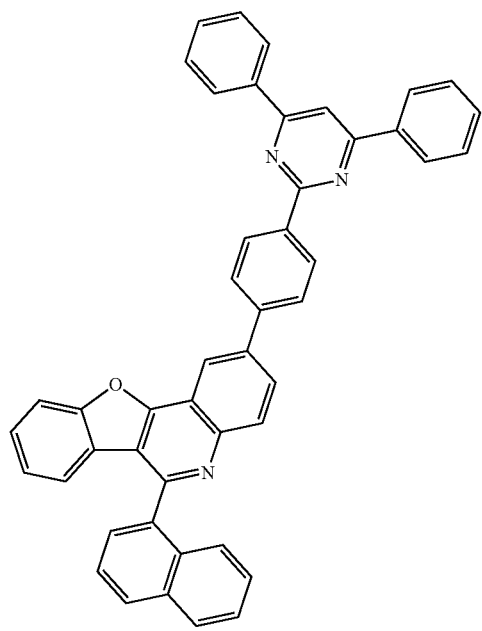 |

855 856
-continued
454 455
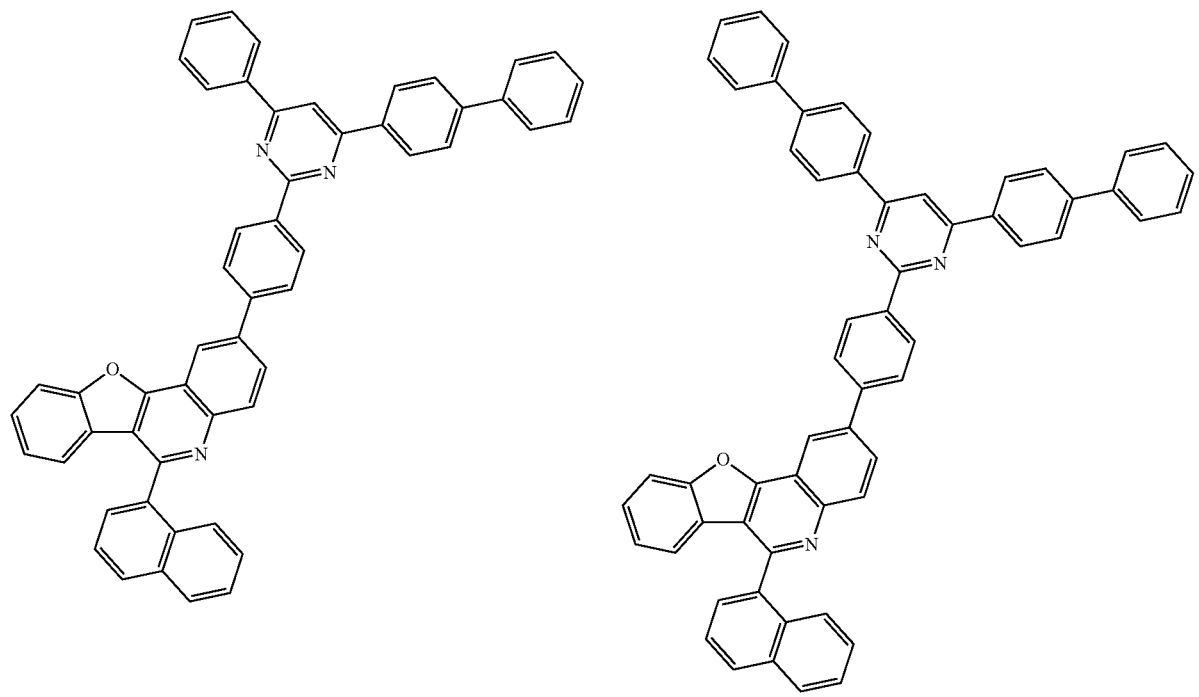
456 457
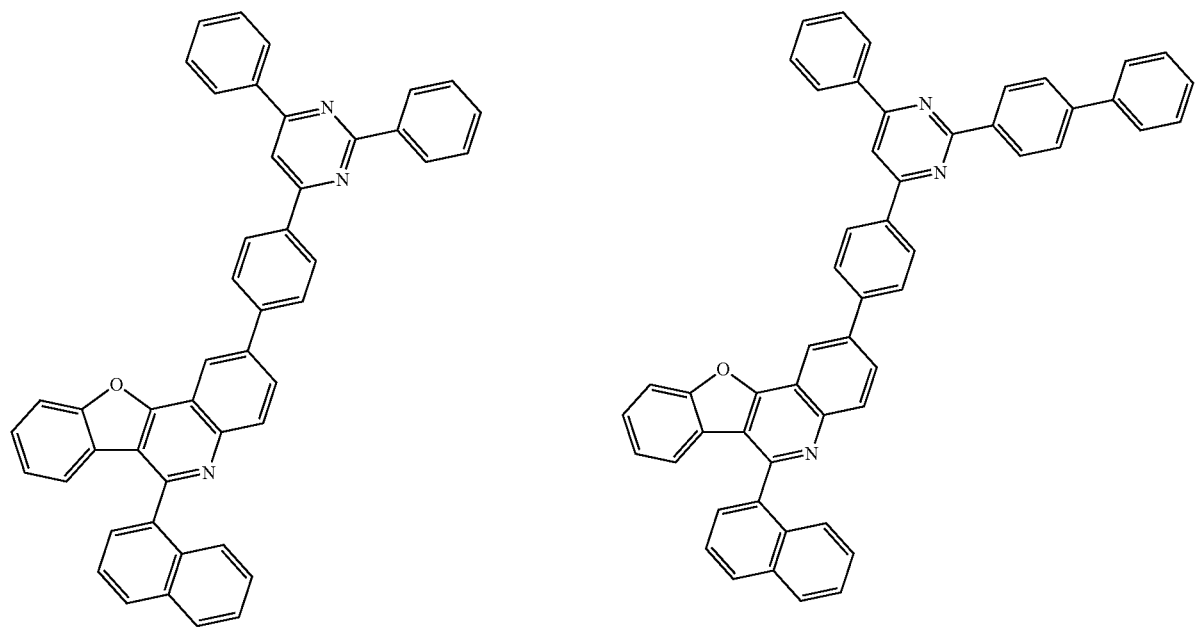

857 858
-continued
458 459
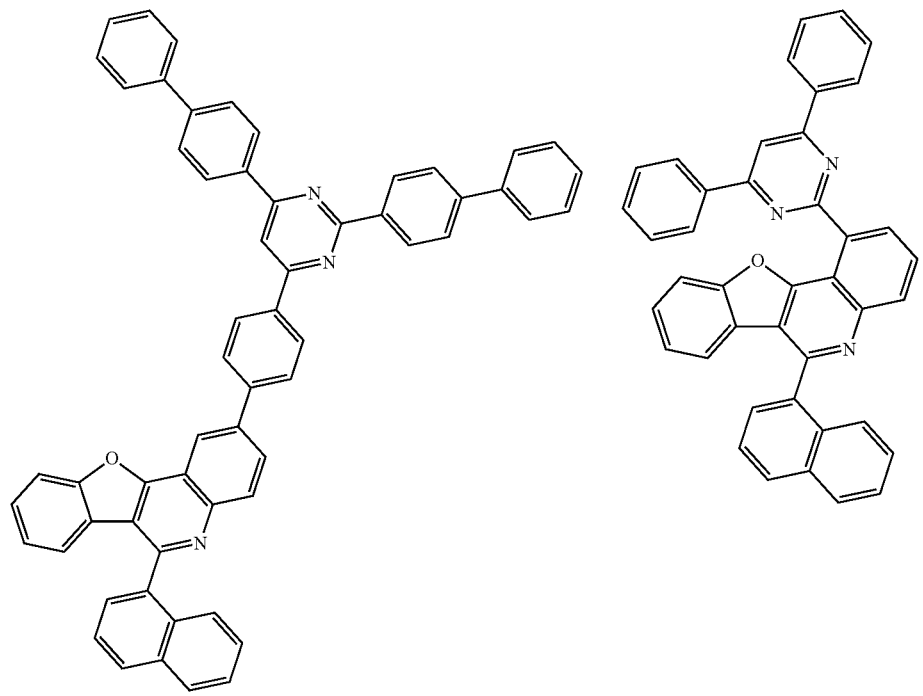
460 461
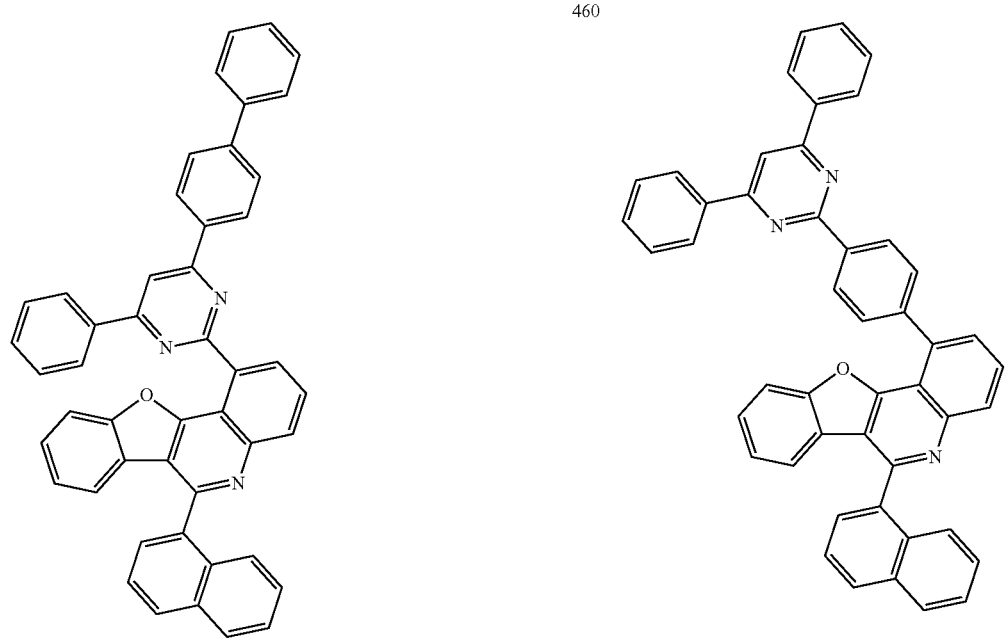

462 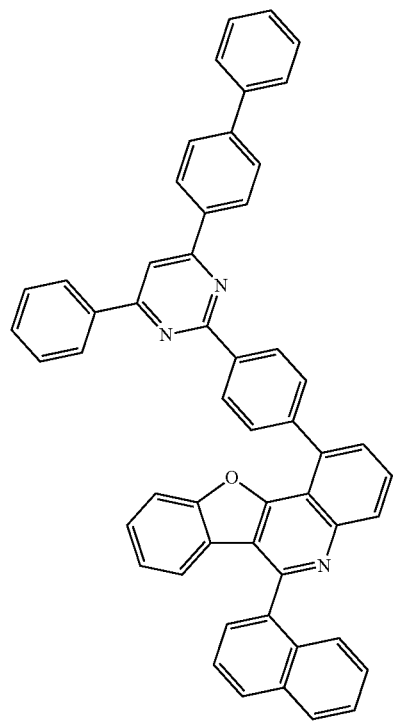
463 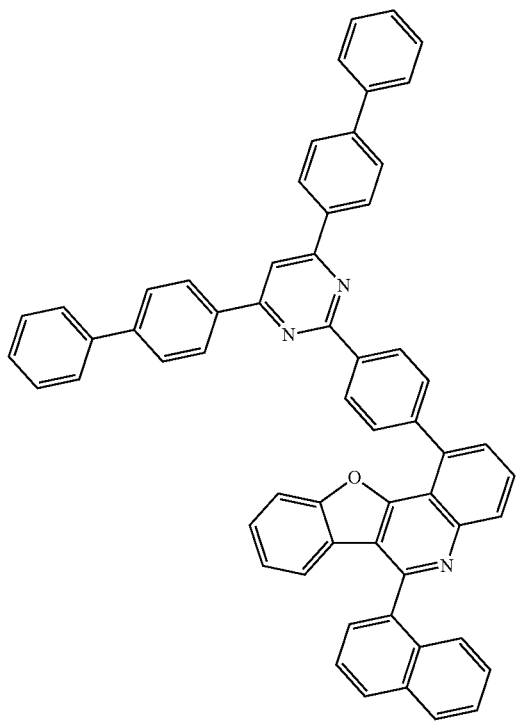
464 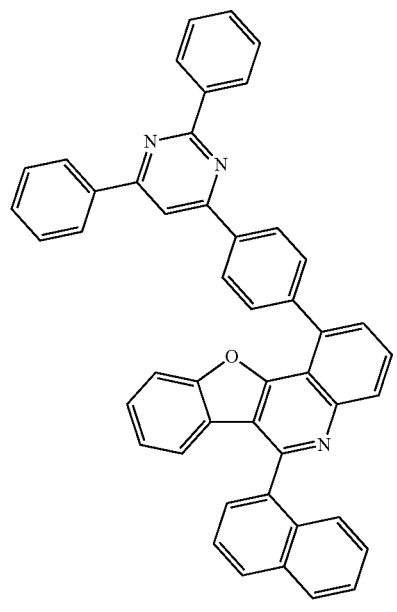
465 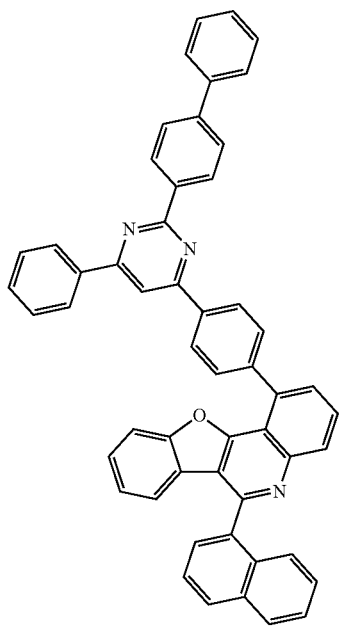

861
466
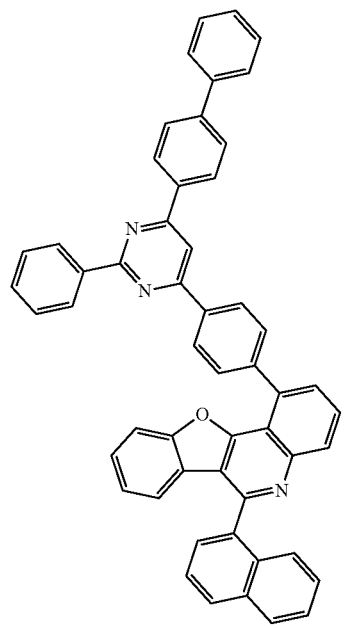
862
467
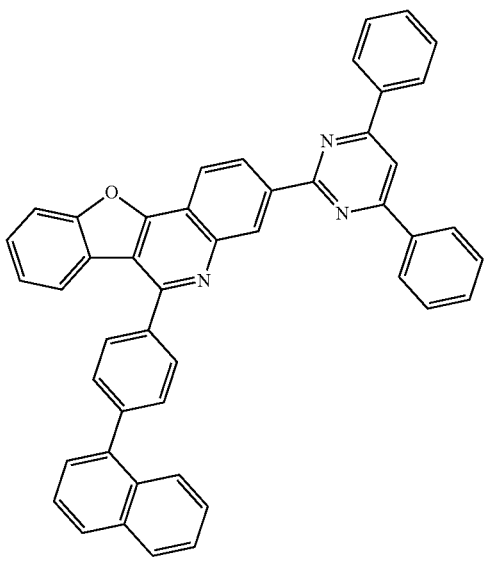
468
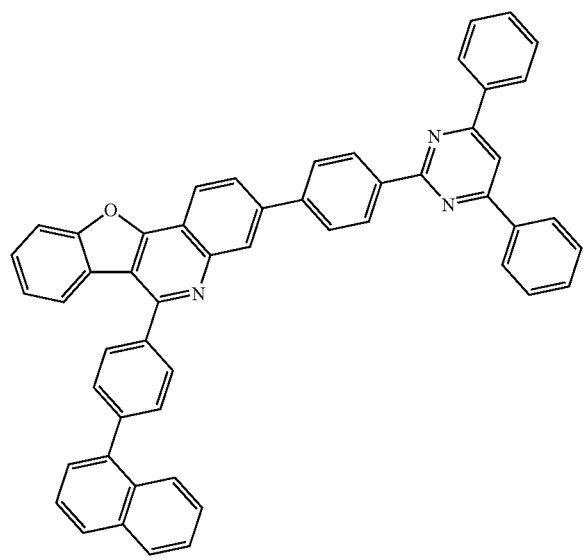
469
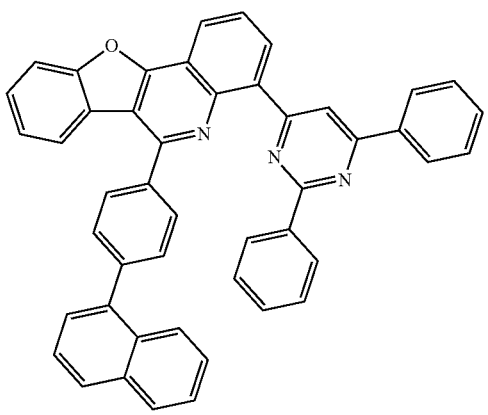

863 864
-continued
470
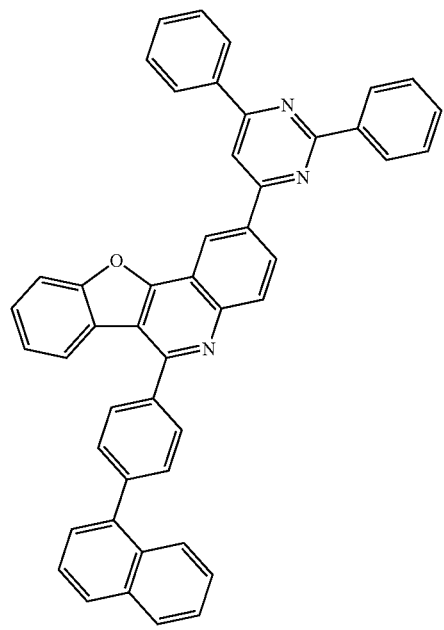
471
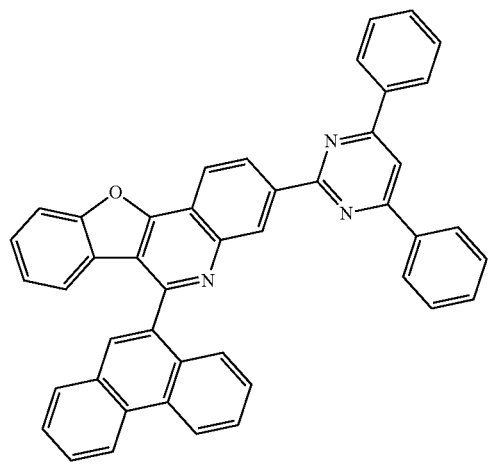
472
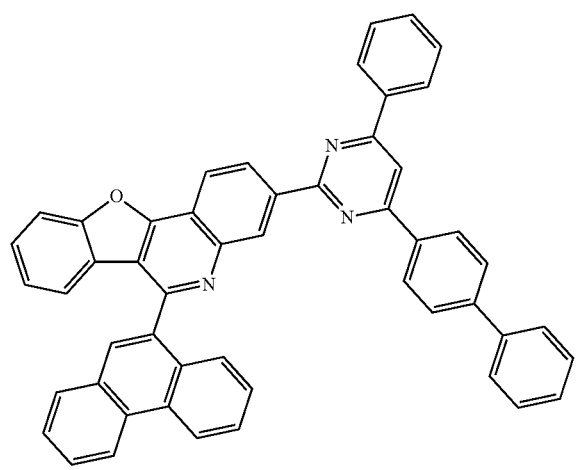
473
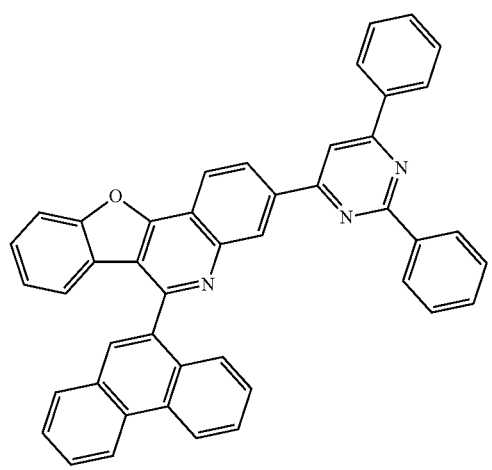
474
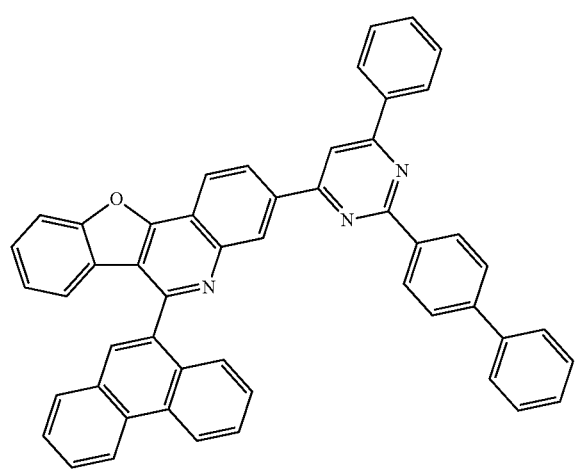
475
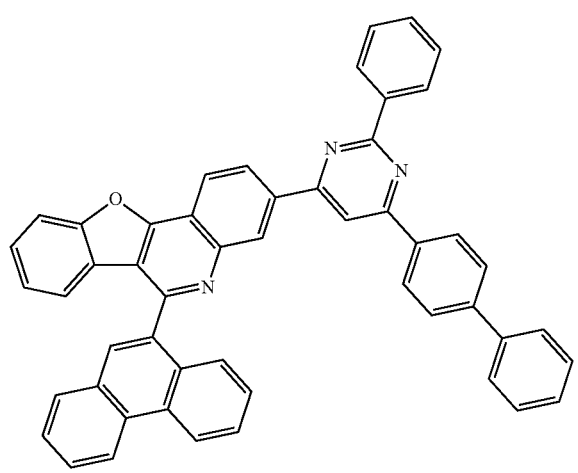

476
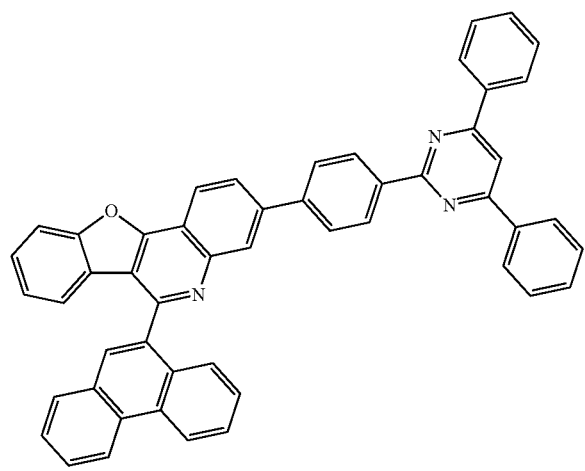
478
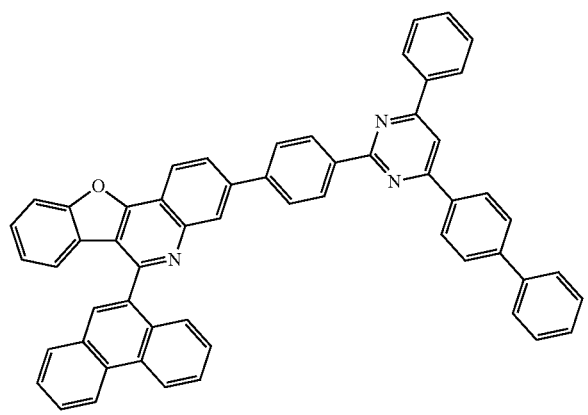
479
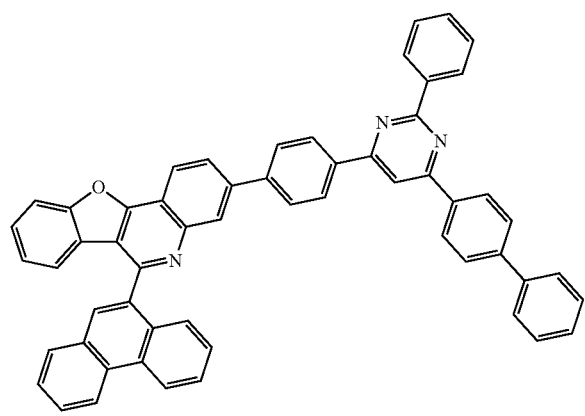
480
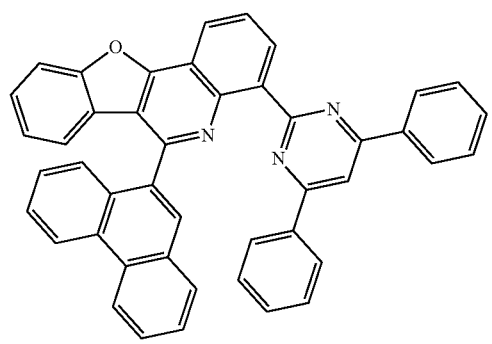
481
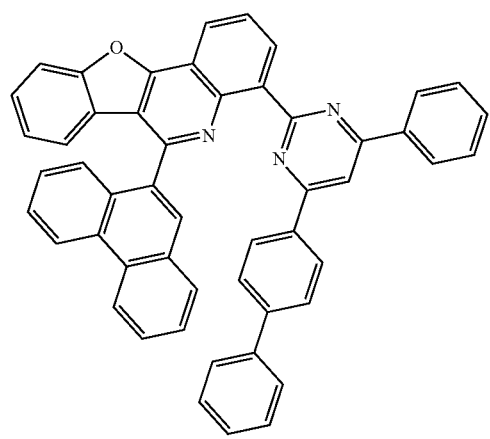
482
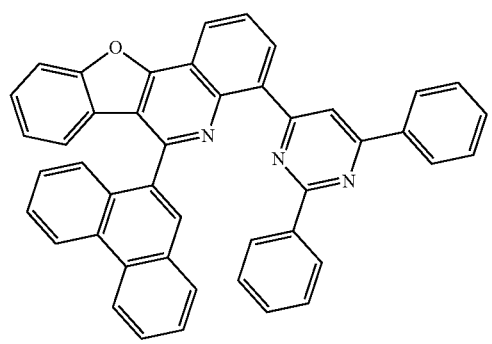

483
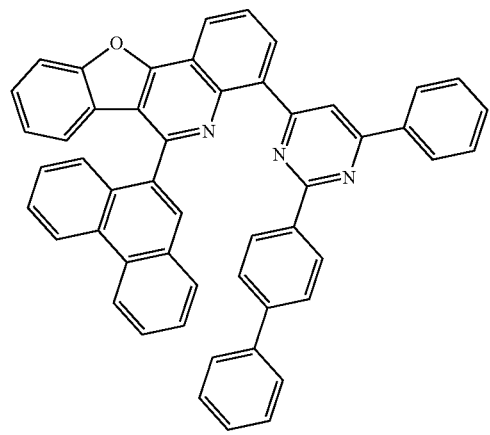
484
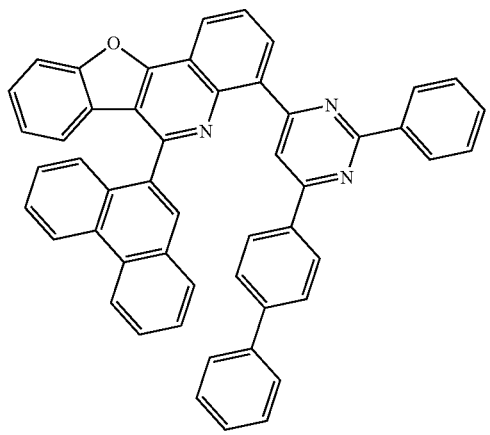
485
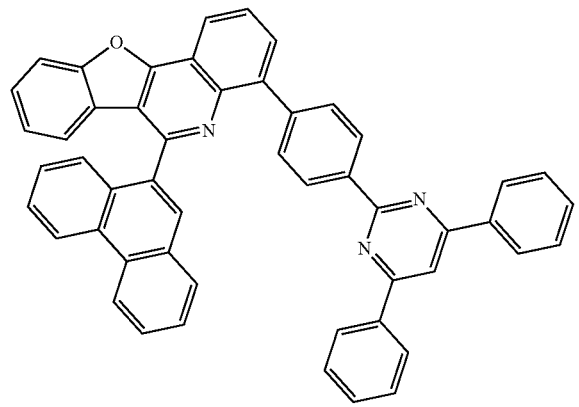
486
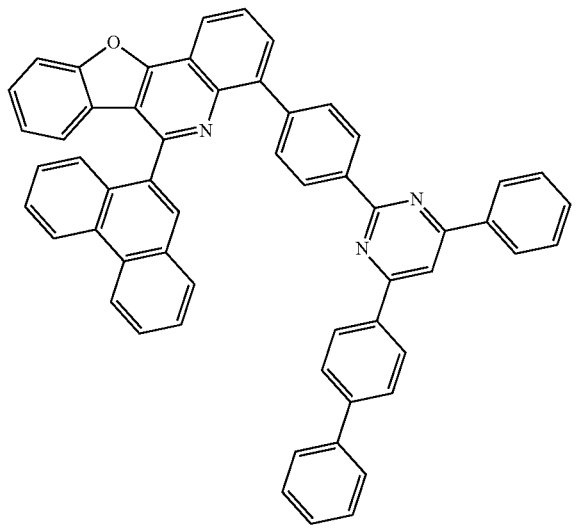
487
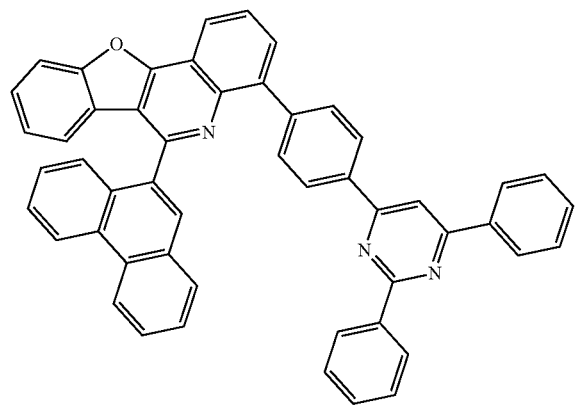
488
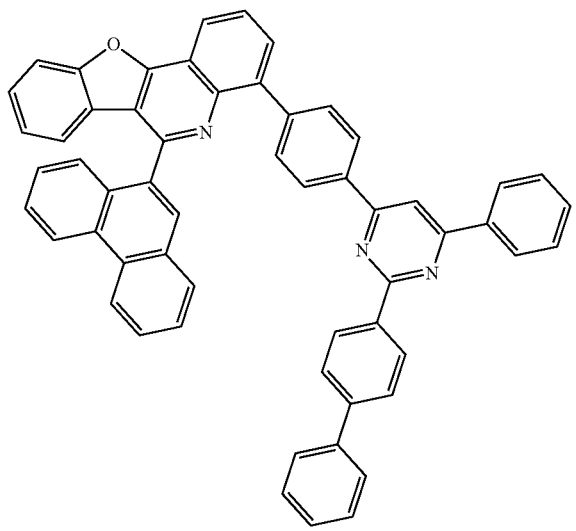

489
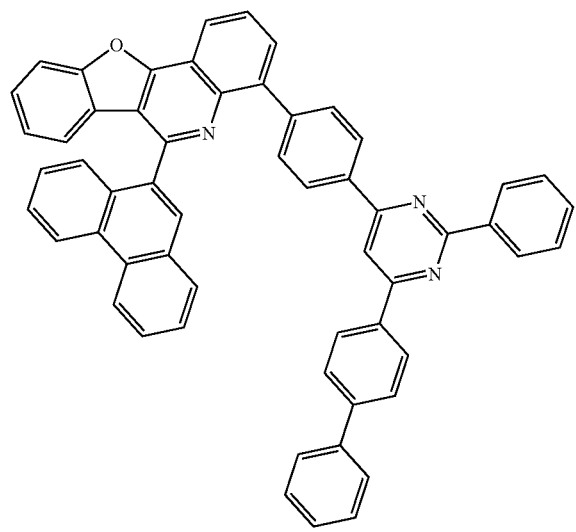
490
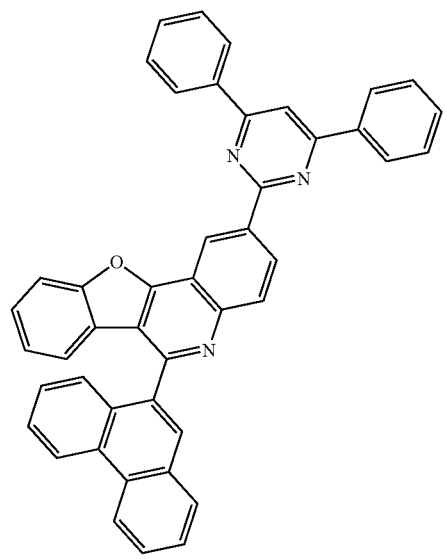
491
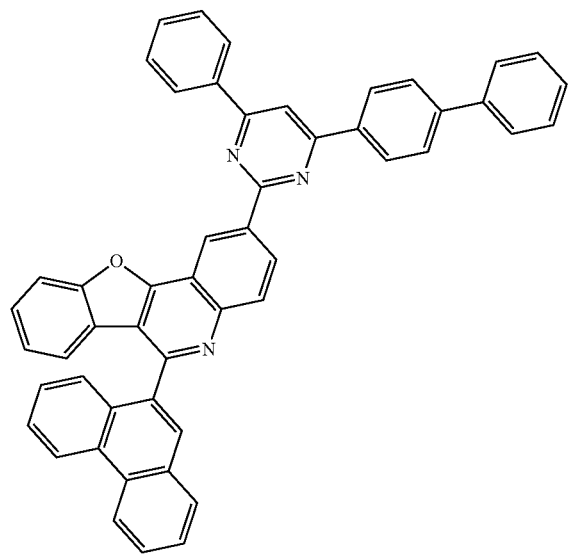
492
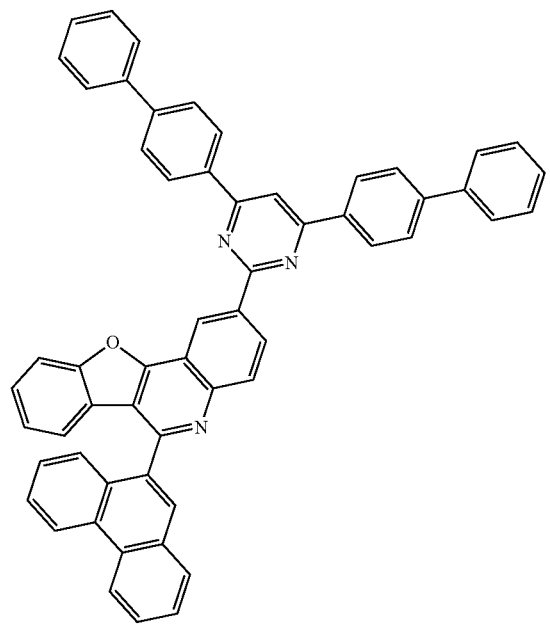

493
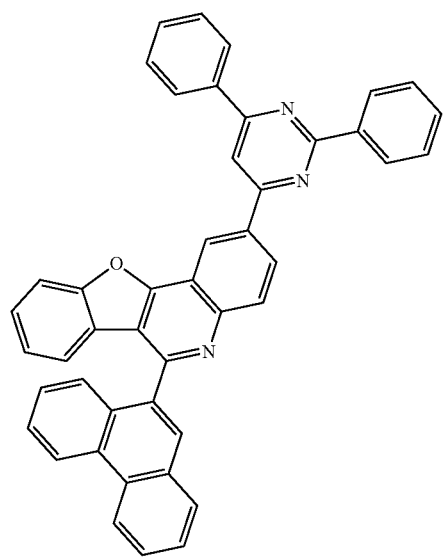
494
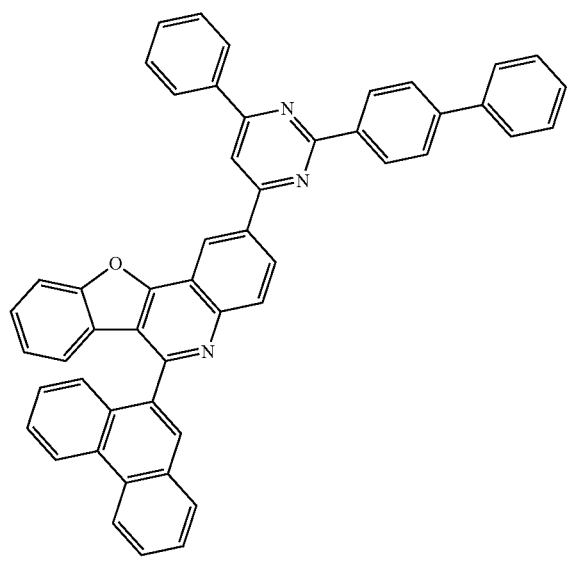
495
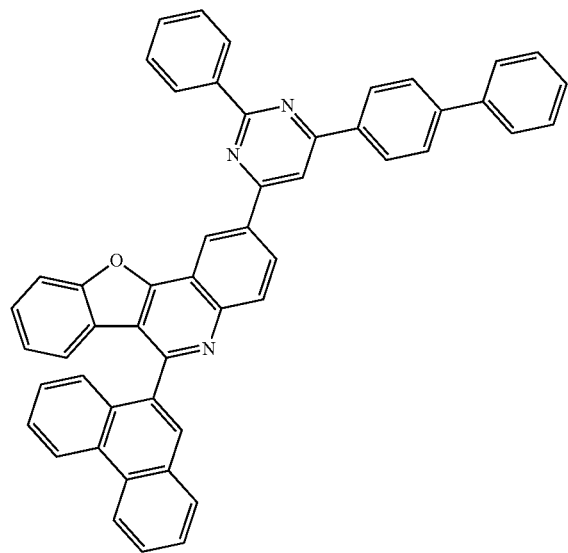
496
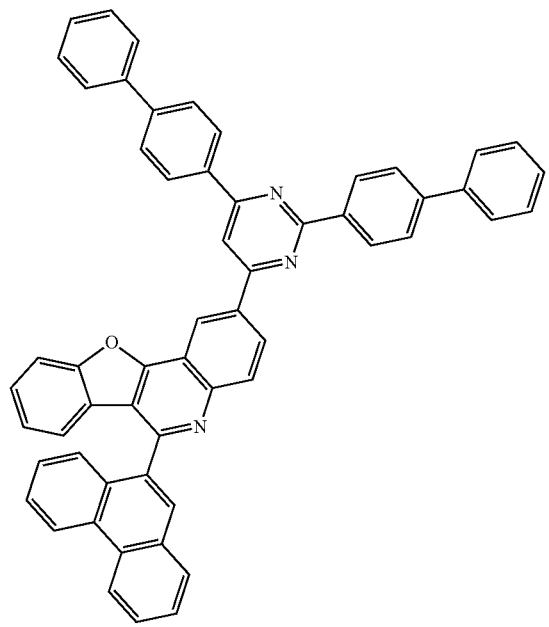

-continued
873 497
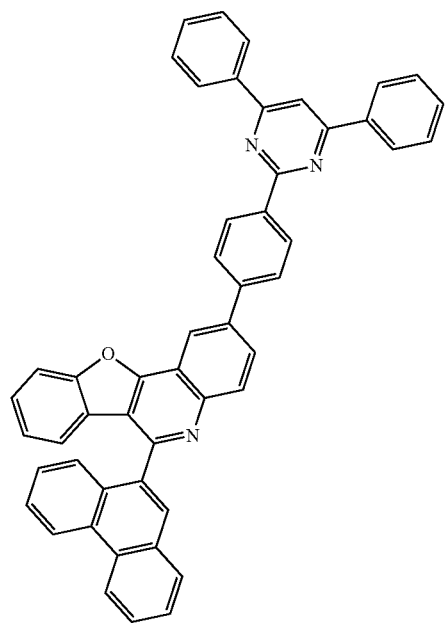
874 498
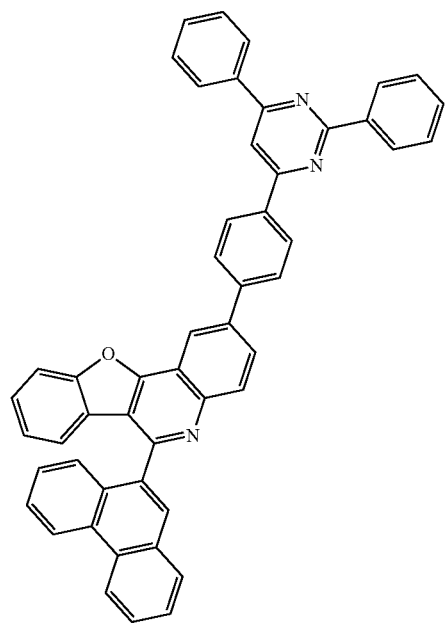
499
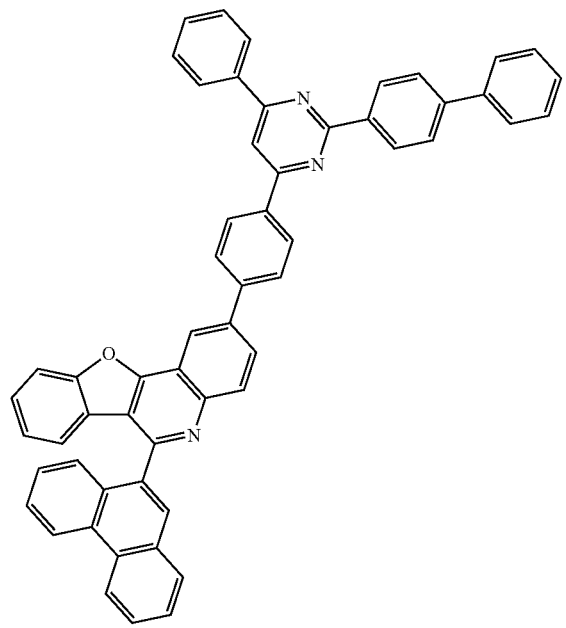
500
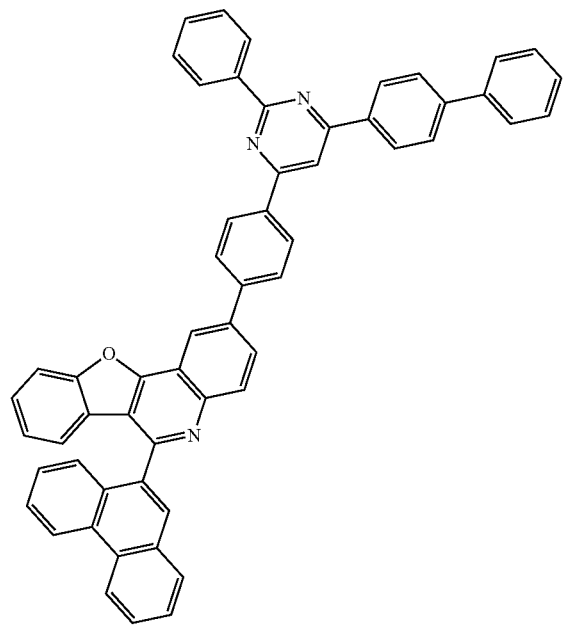

-continued
501
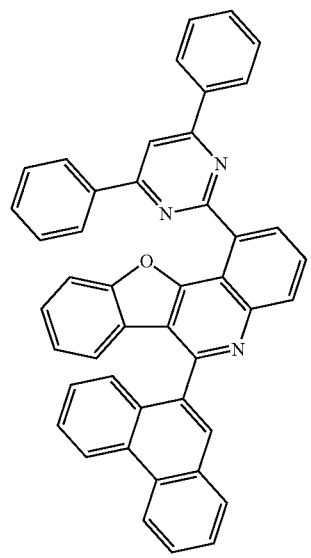
502
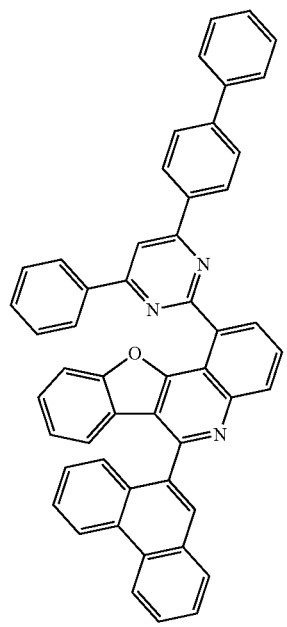
503
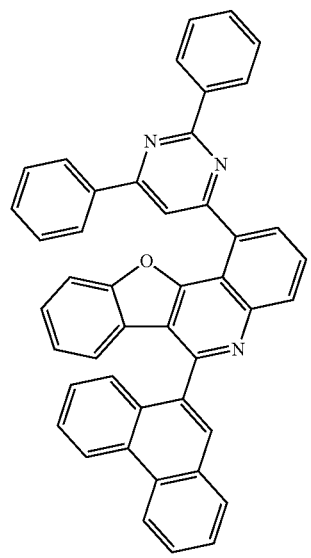
504
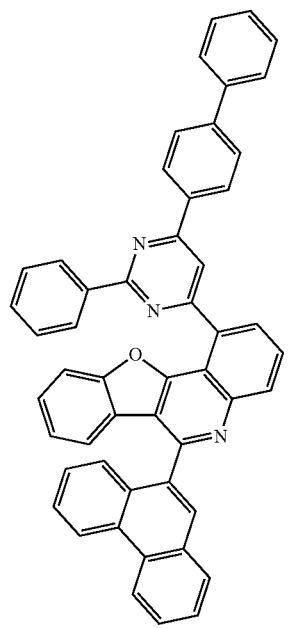

-continued
505
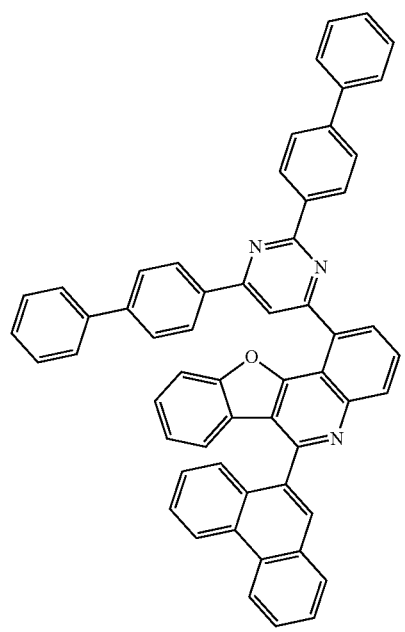
506
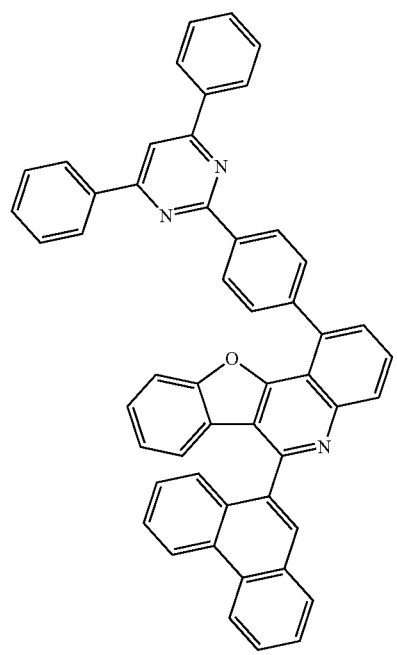
507
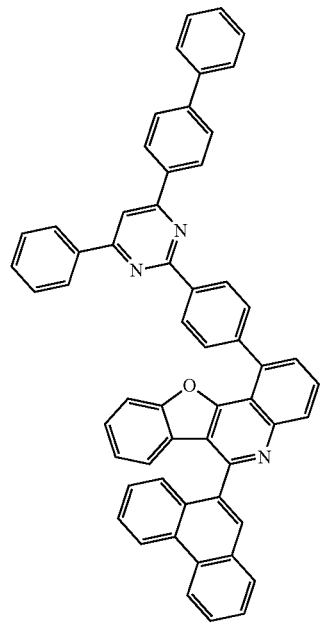
508
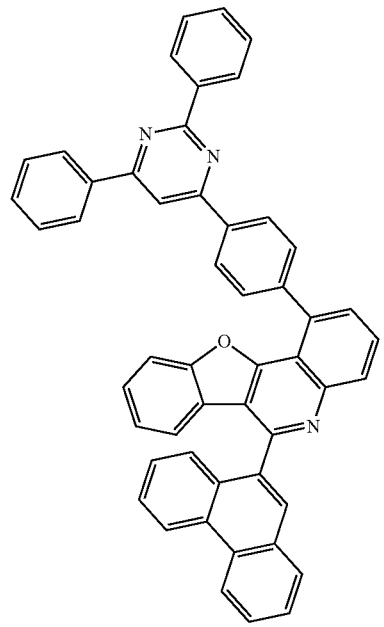

-continued
509
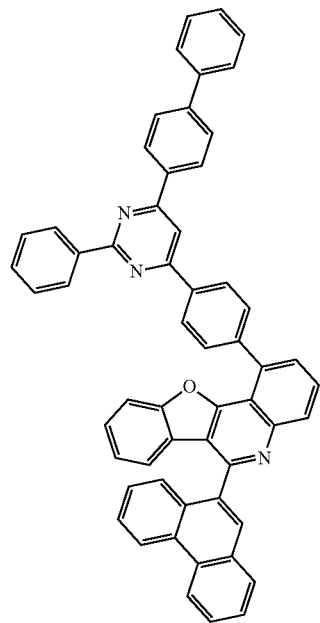
510
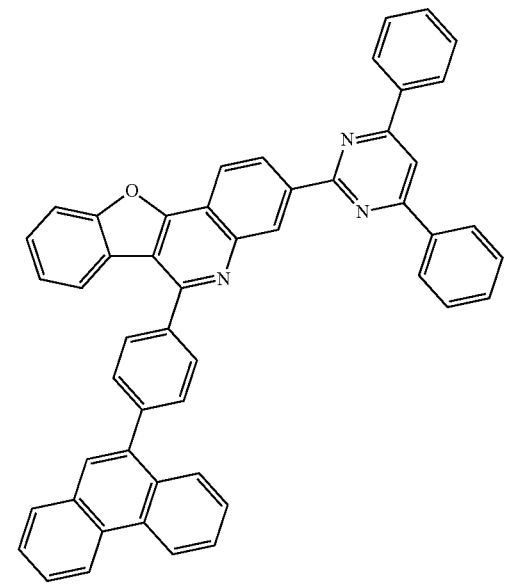
511
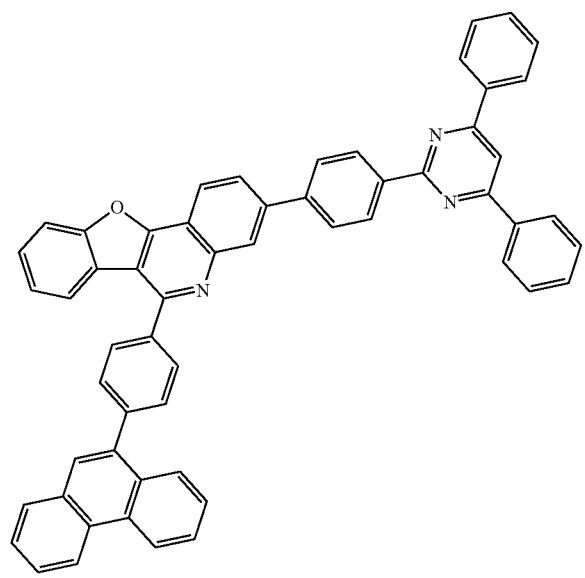
512
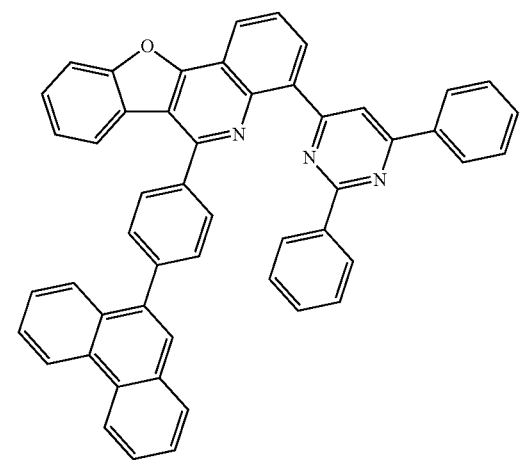
513
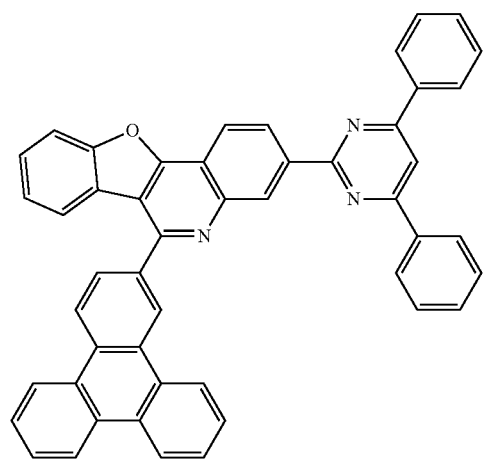
514
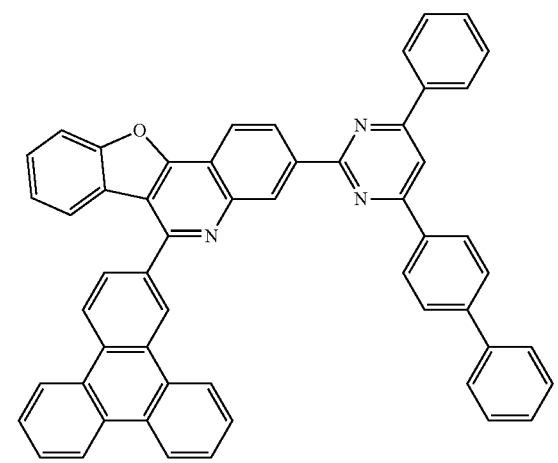

-continued
| 881 | 882 |
|---|---|
| 515 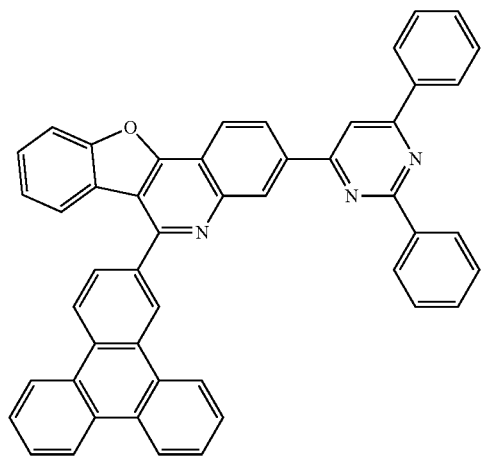 | 516 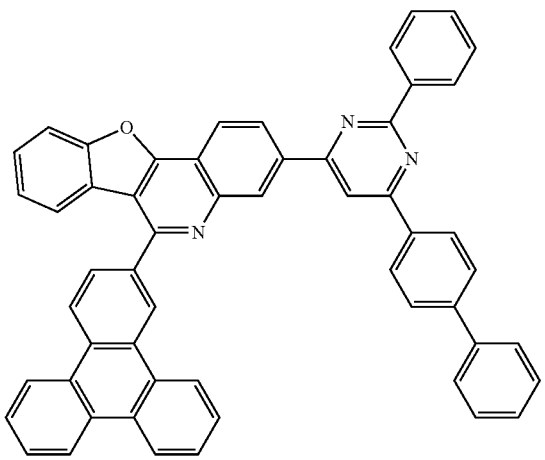 |
| 517 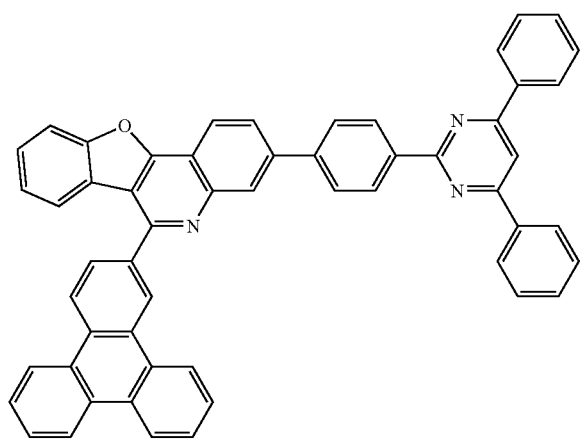 | 518 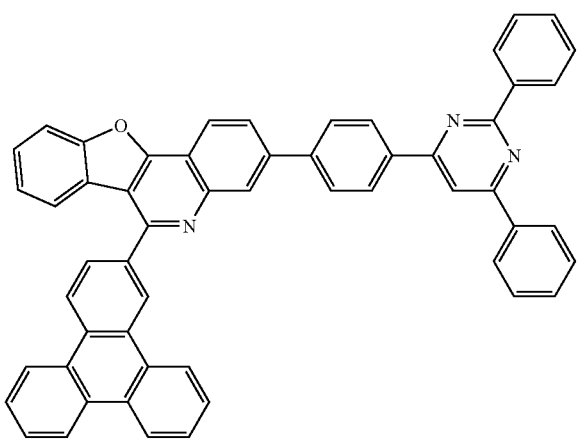 |
| 519 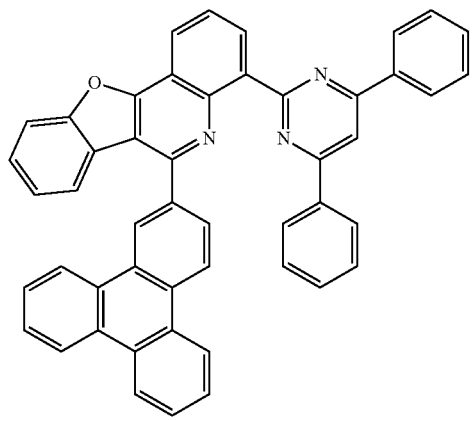 | 520 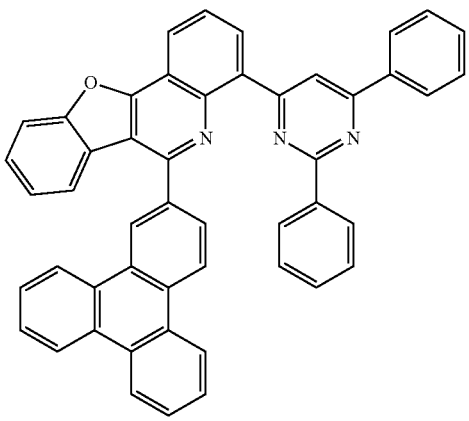 |

-continued
521
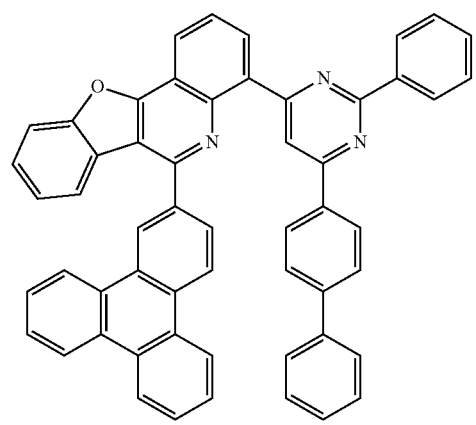
522
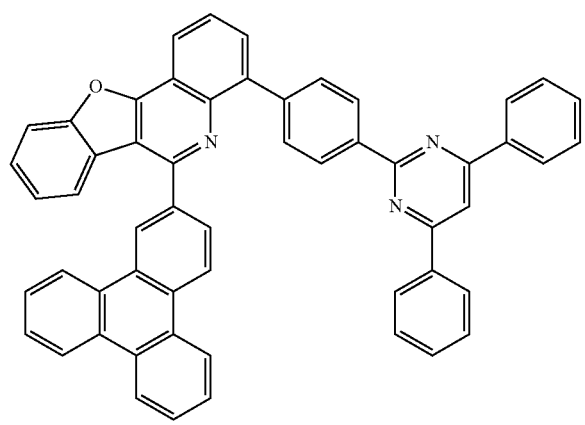
523
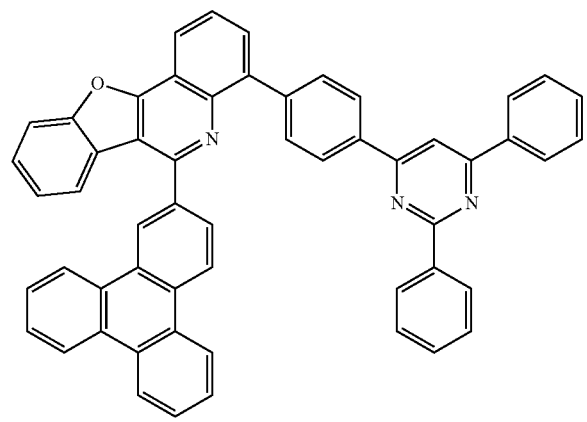
524
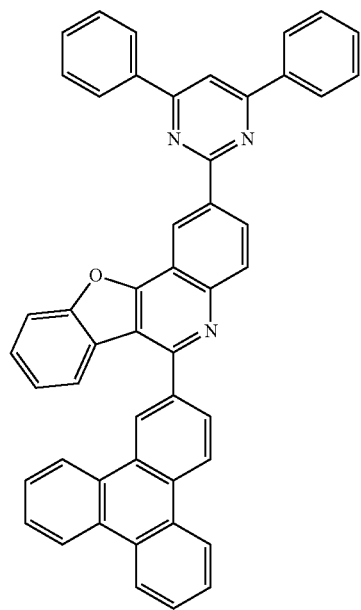

885
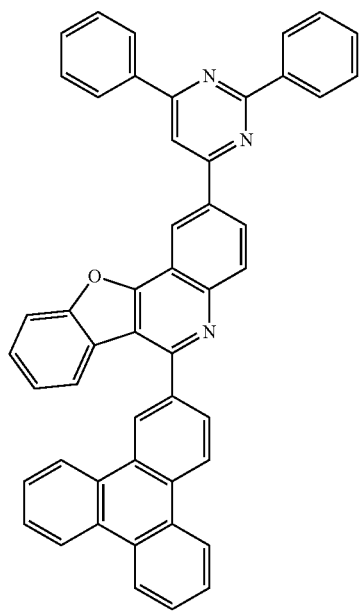
886
-continued
525
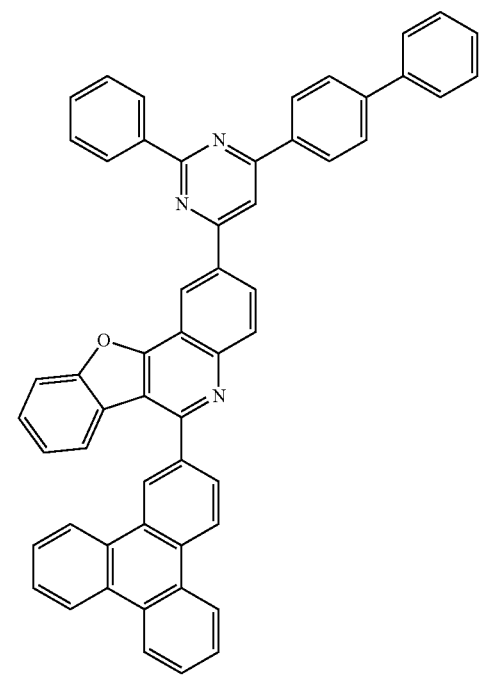
527
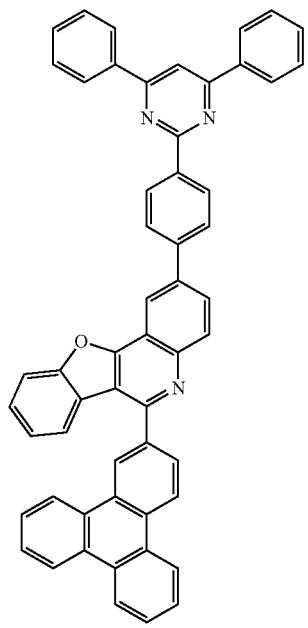
526
528
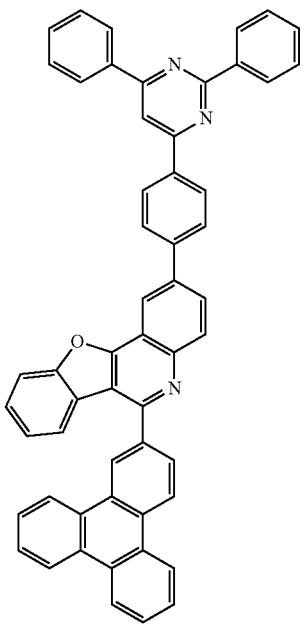

-continued
887
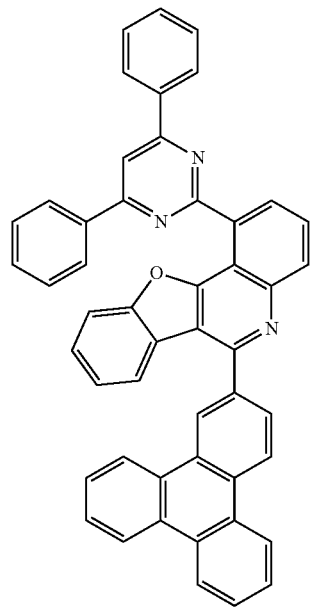
529
888
530
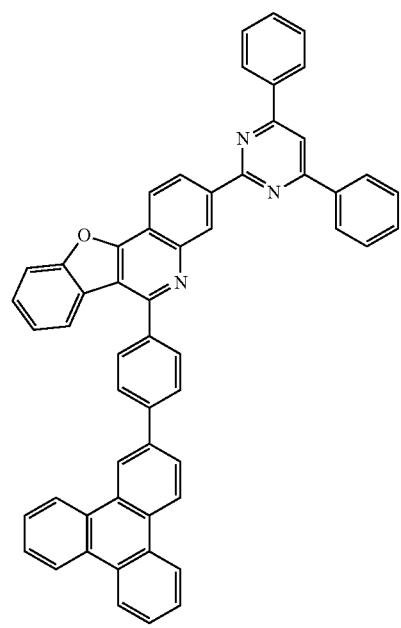
531
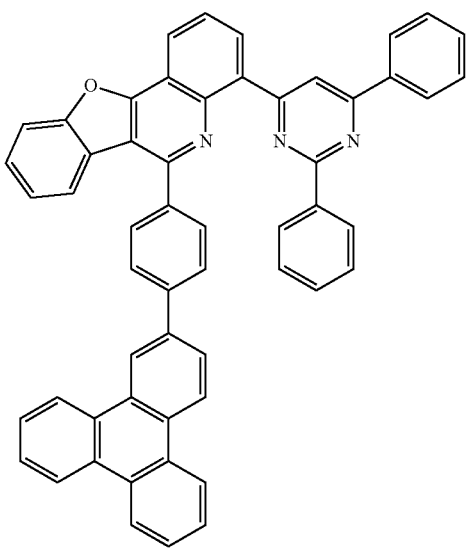
532

-continued
533
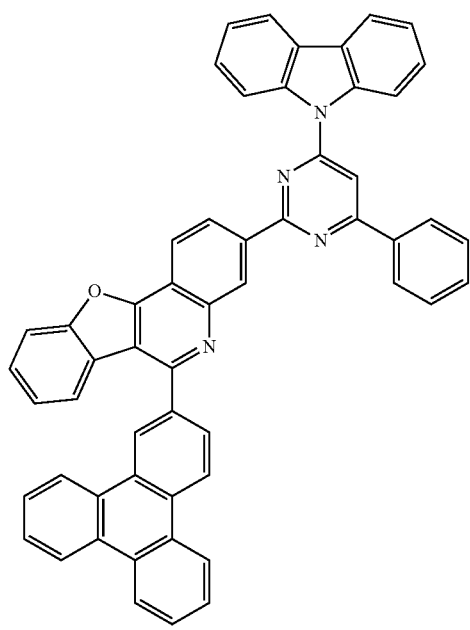
889
534
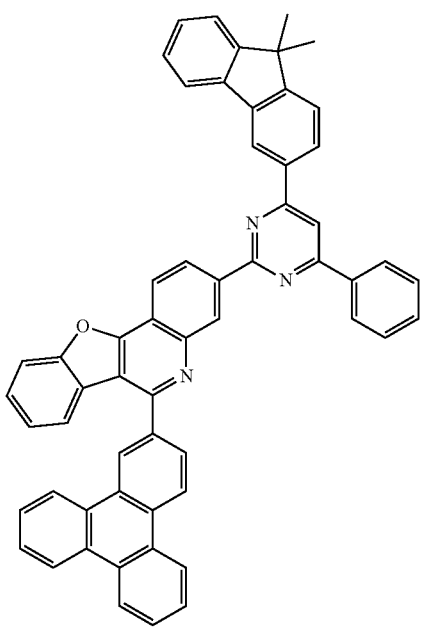
890
-continued
535
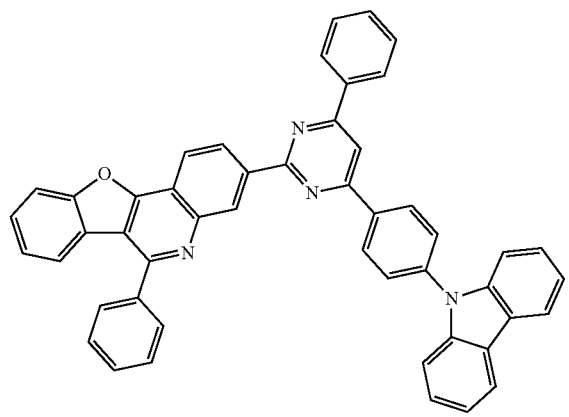
537
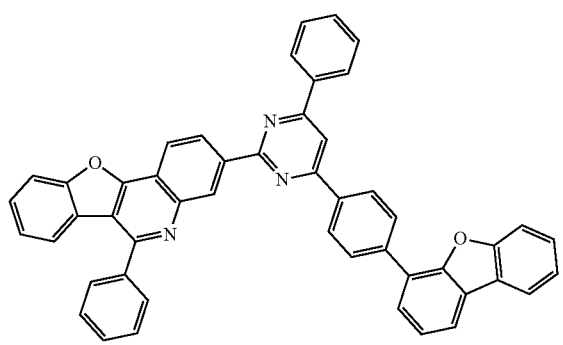
536
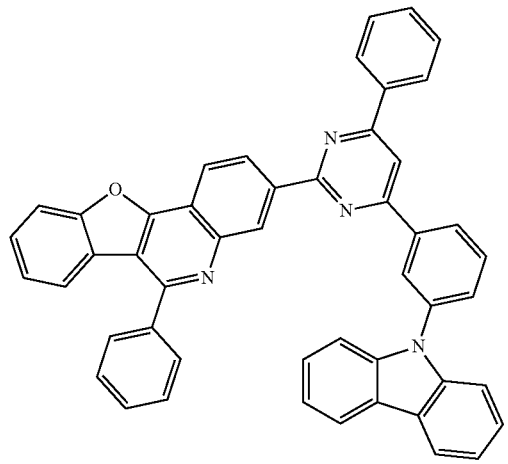
538
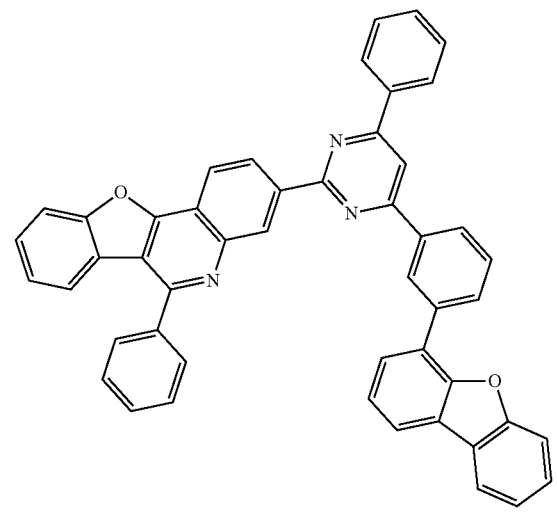

539
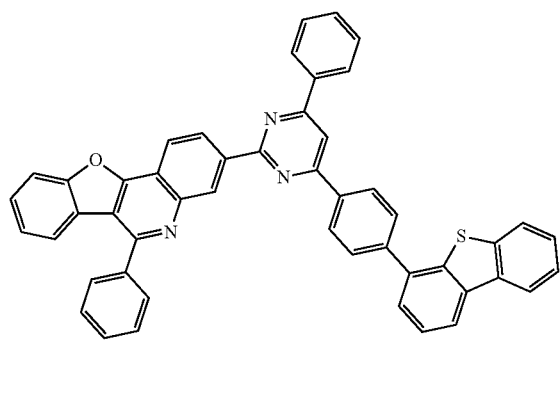
540
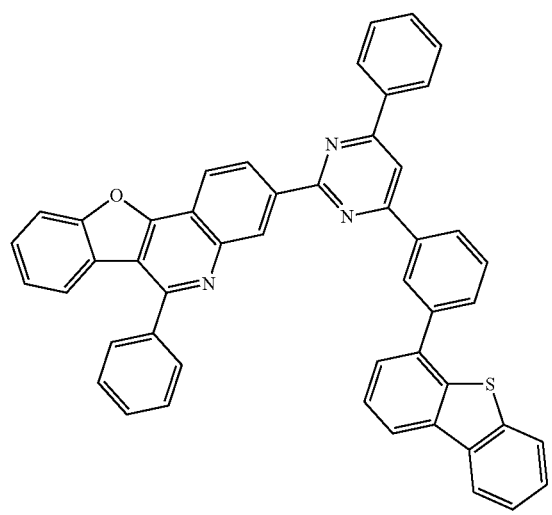
541
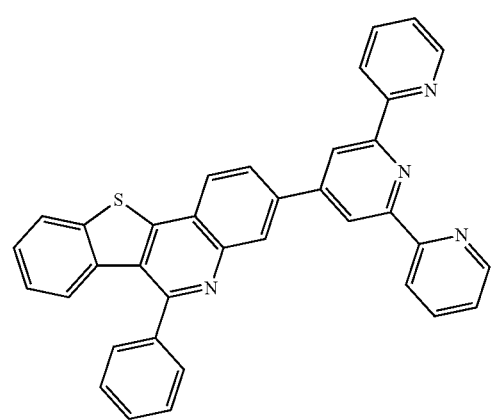
542
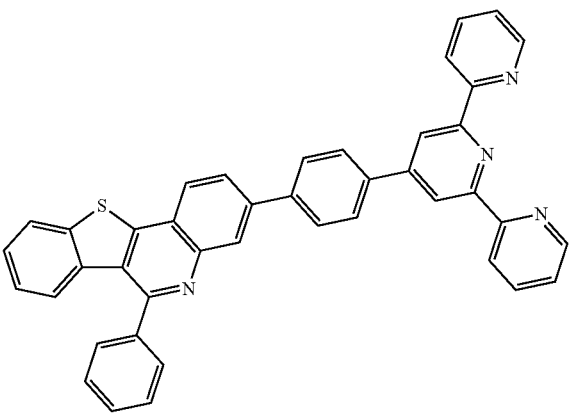
543
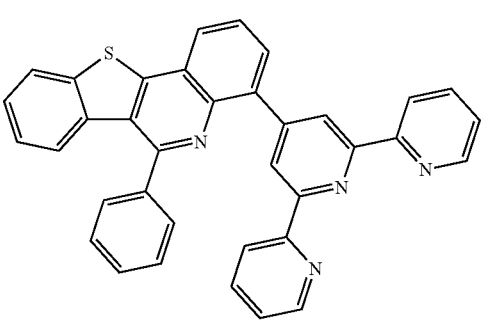
544
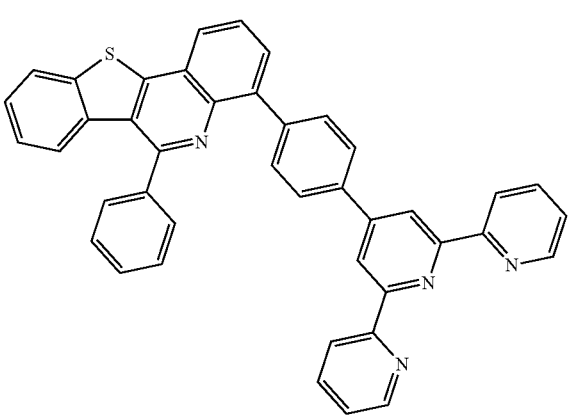
545

-continued
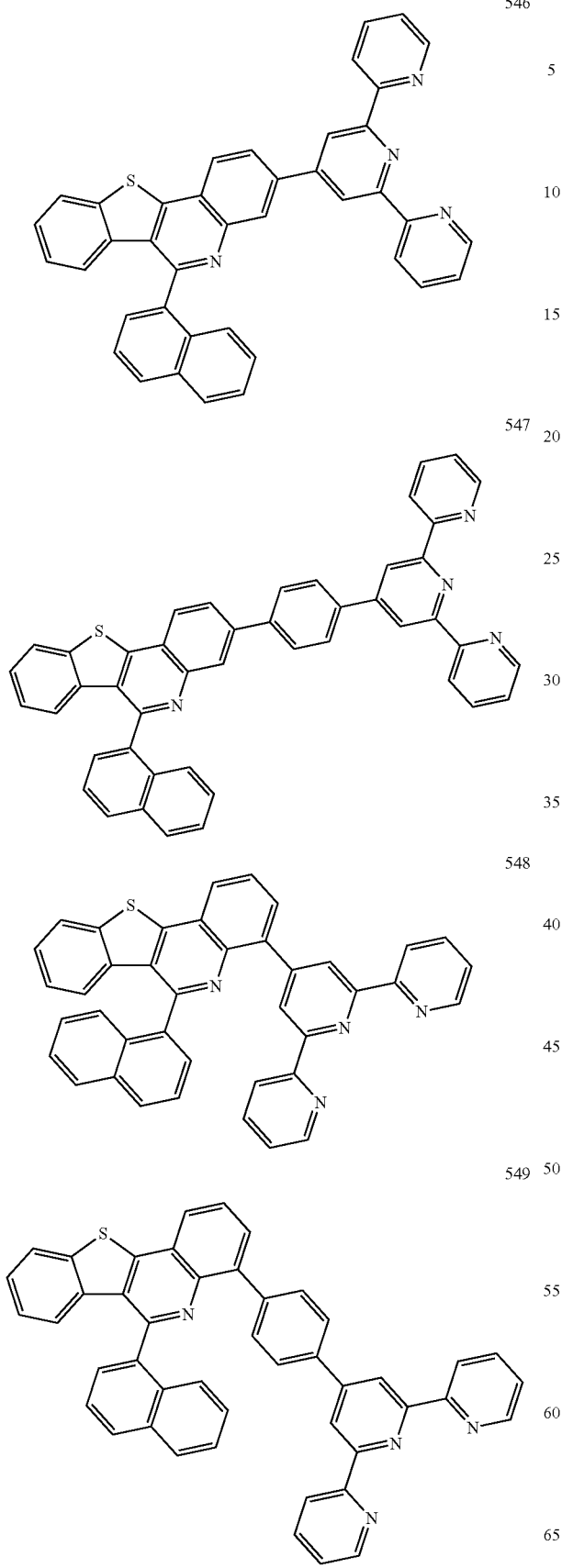
-continued
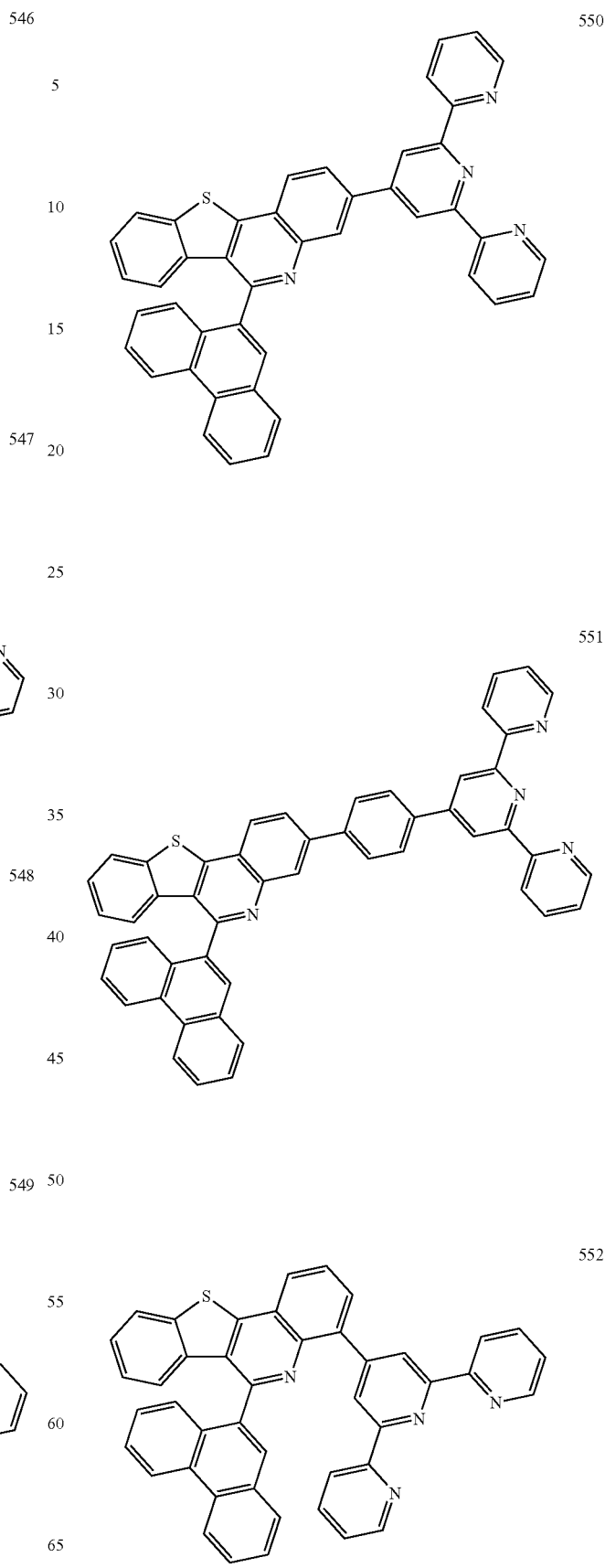

553
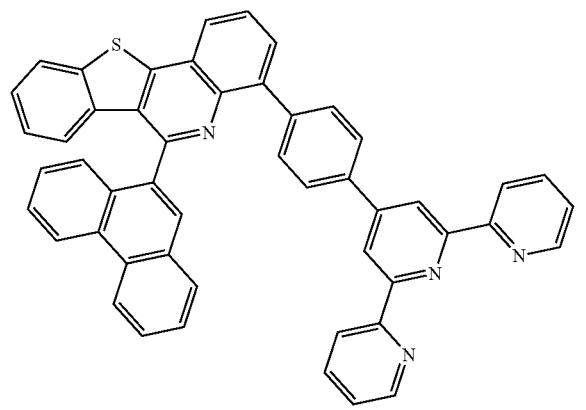
556
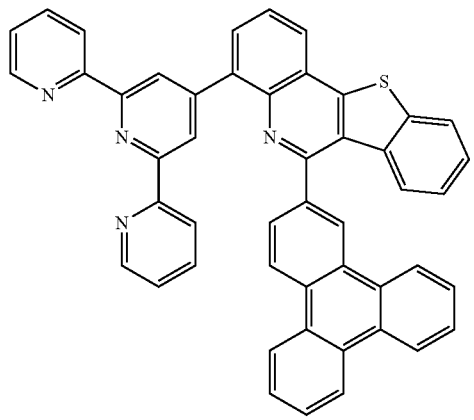
554
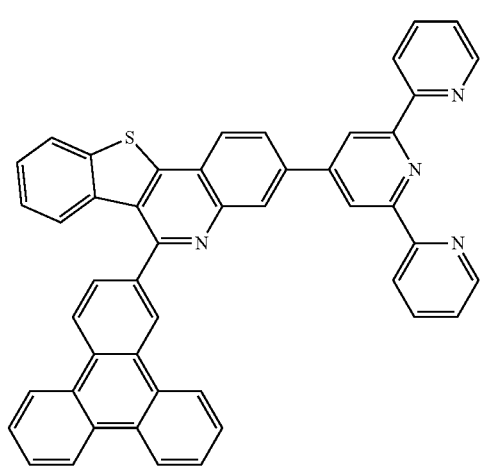
557
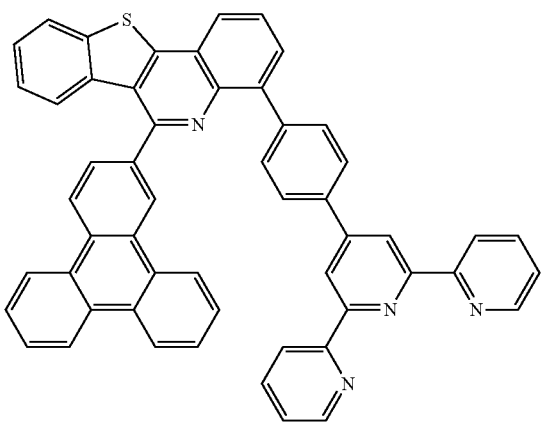
555
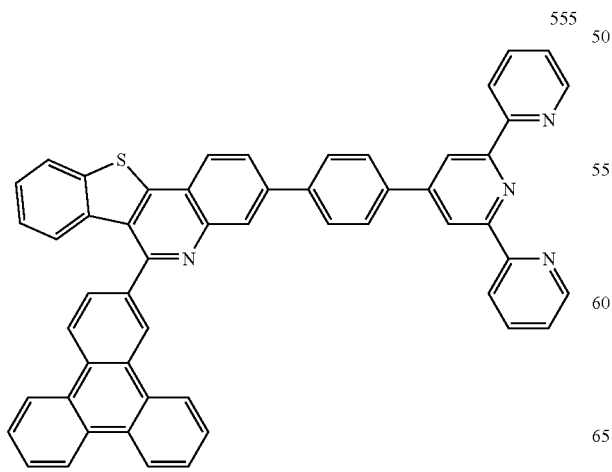
558
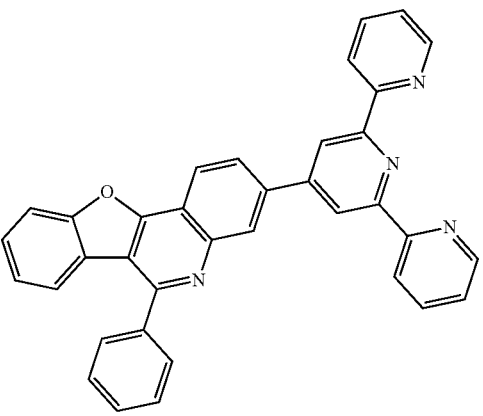

559
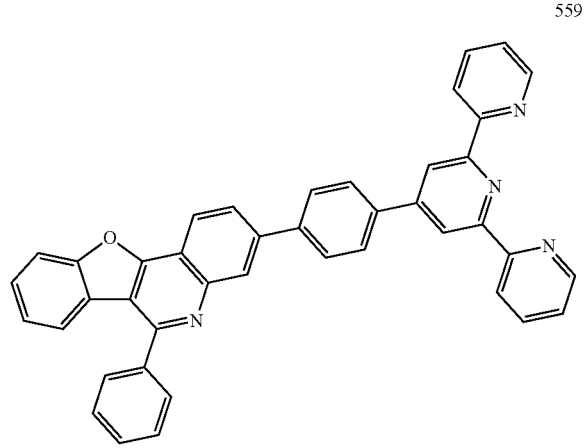
560
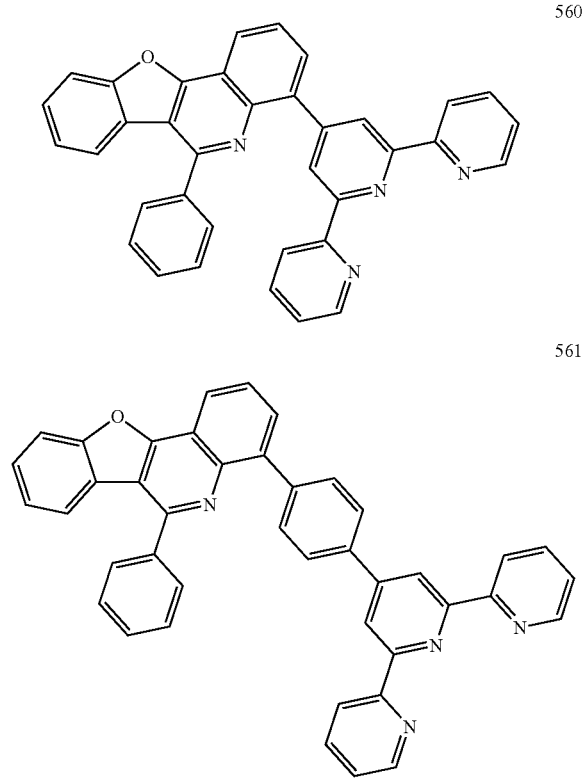
561
562
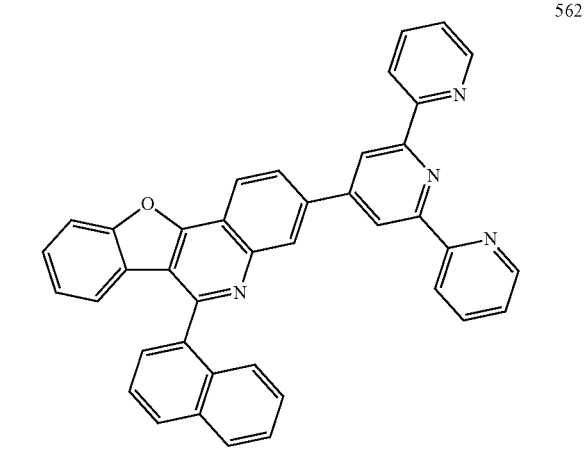
563
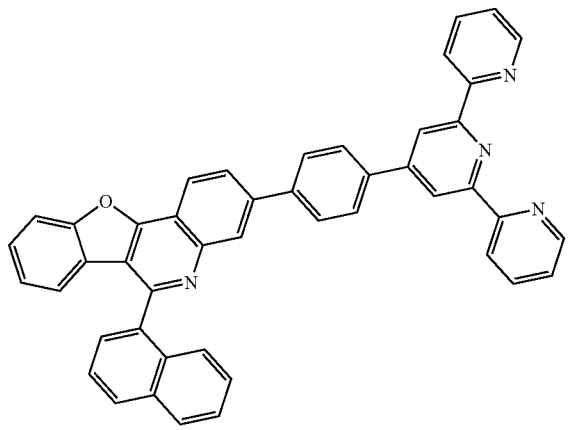
564
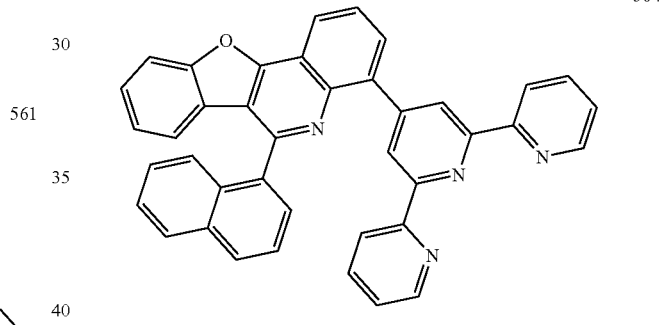
565
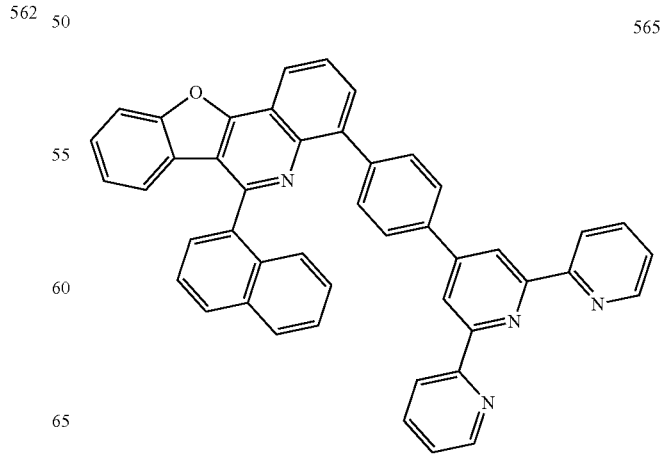

899
-continued
566
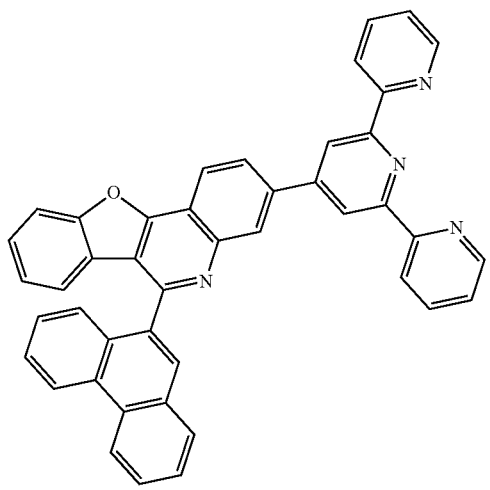
567
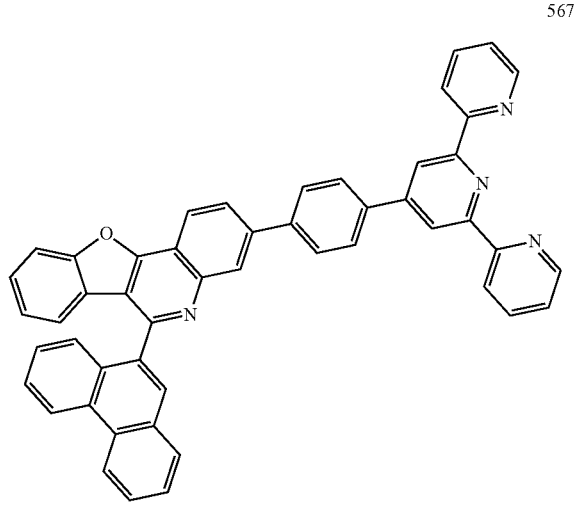
568
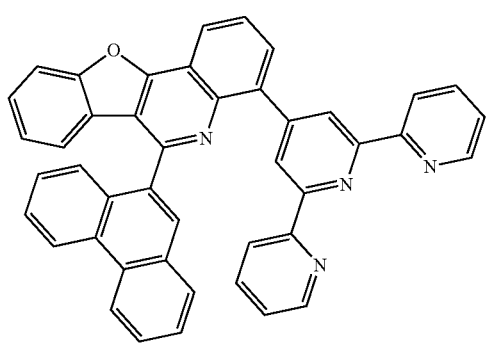
900
-continued
569
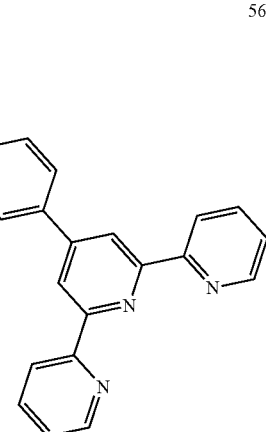
570
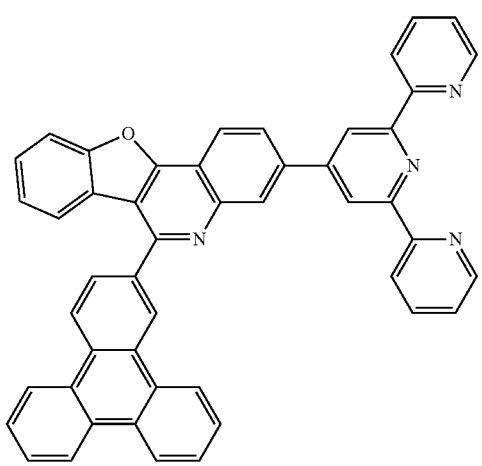
571
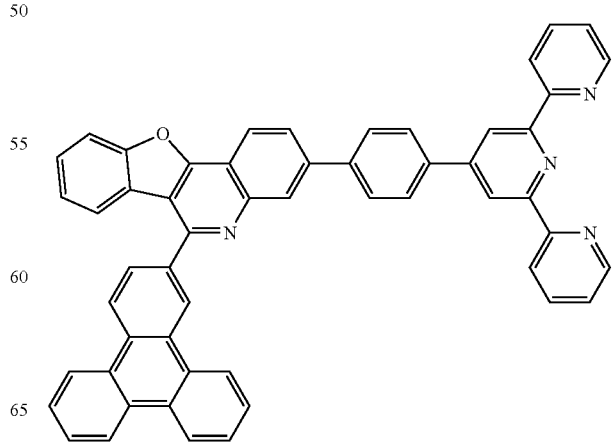

901
-continued
572
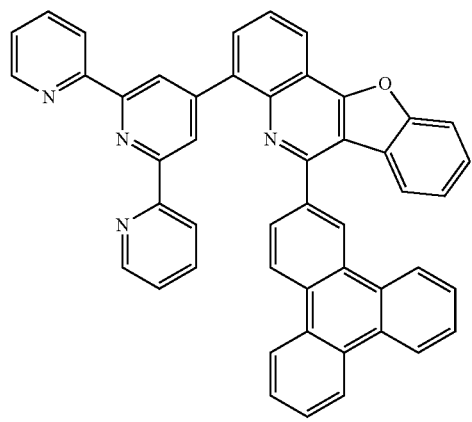
573
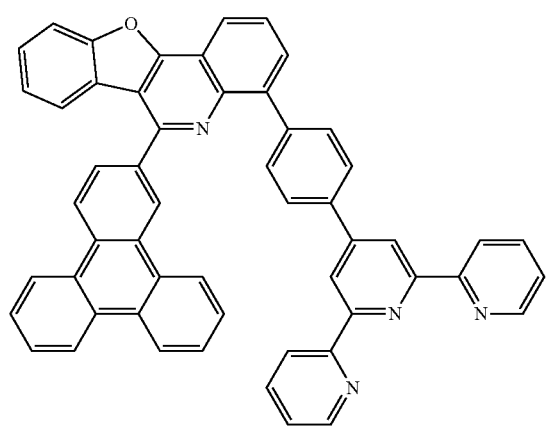
574
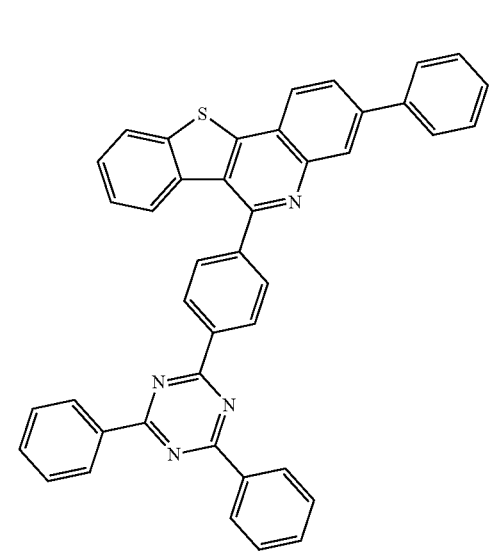
902
-continued
575
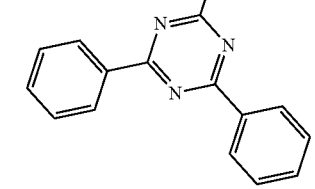
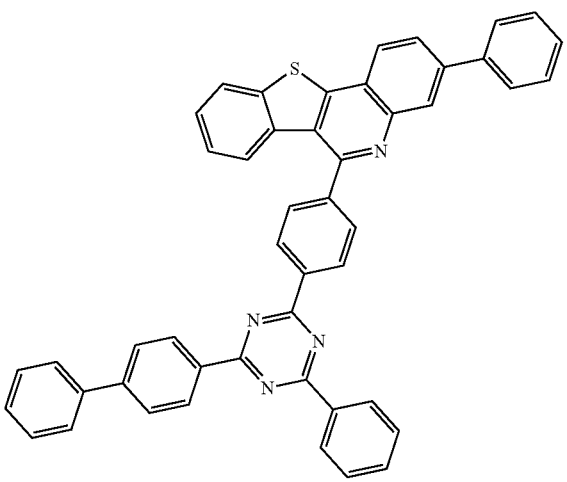
576
577
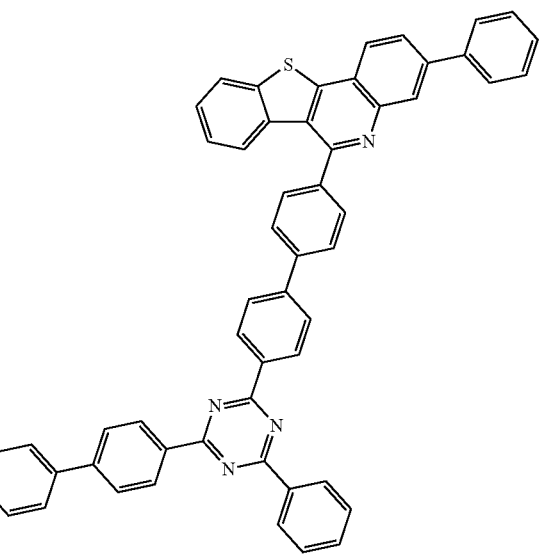

903
-continued
578
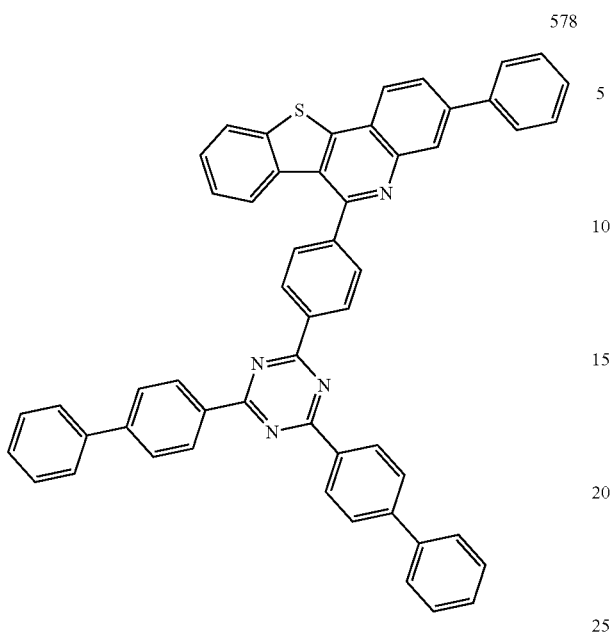
579
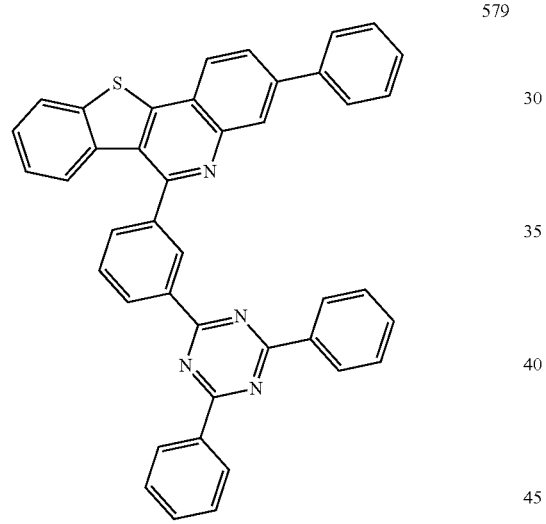
580
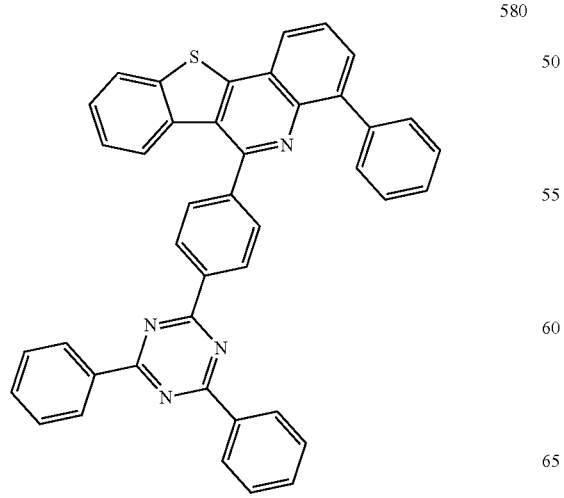
904
-continued
581
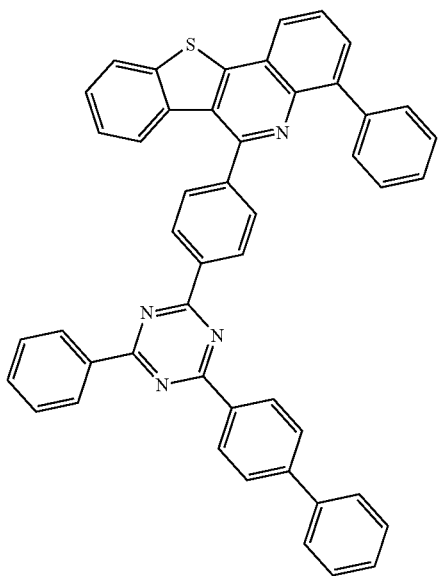
582
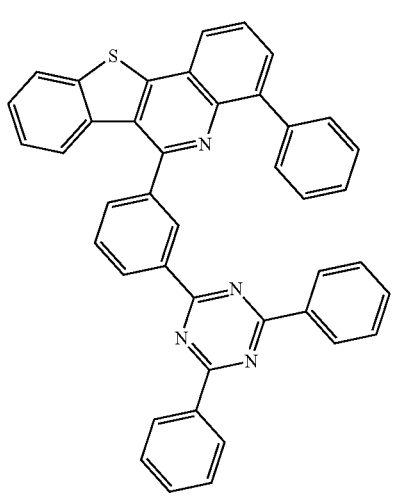
583
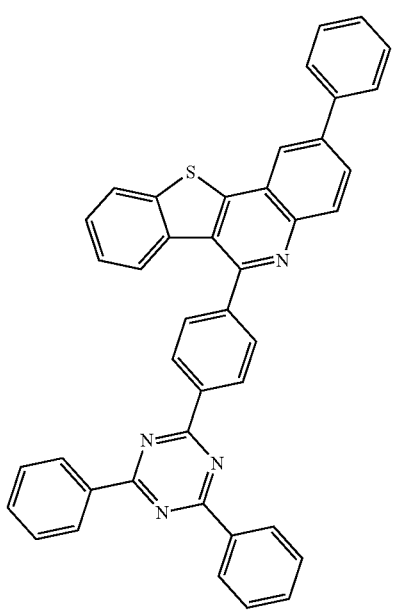

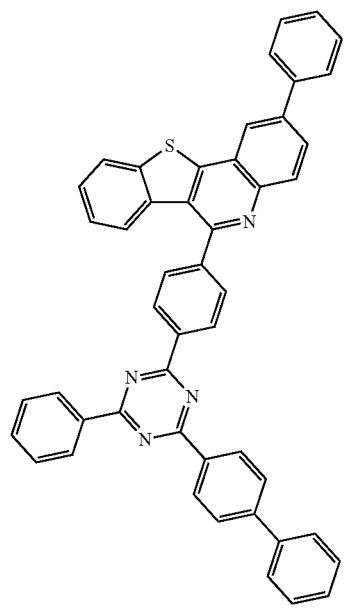
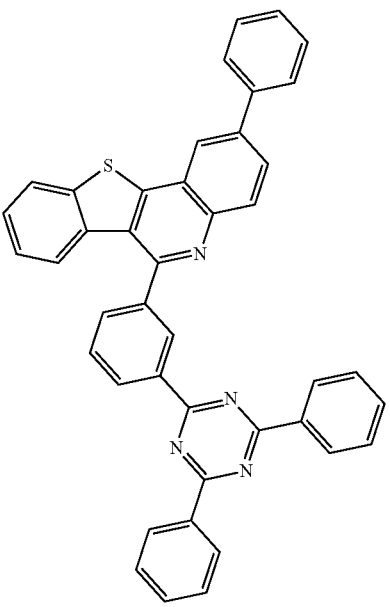
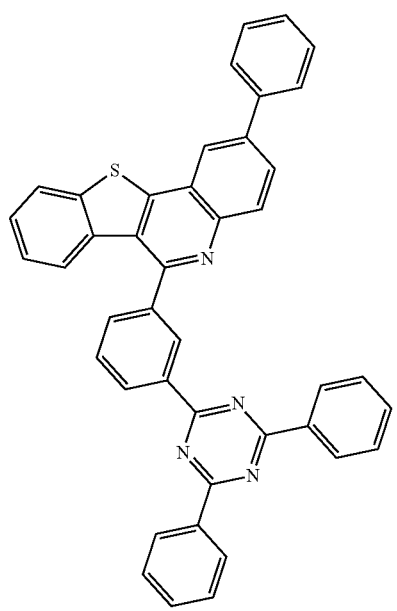 [SMILES: c1ccc(-c2ccc3nc(-c4cccc(-c5nc(-c6ccccc6)nc(-c6ccccc6)n5)c4)c4c5ccccc5oc4c3c2)cc1]
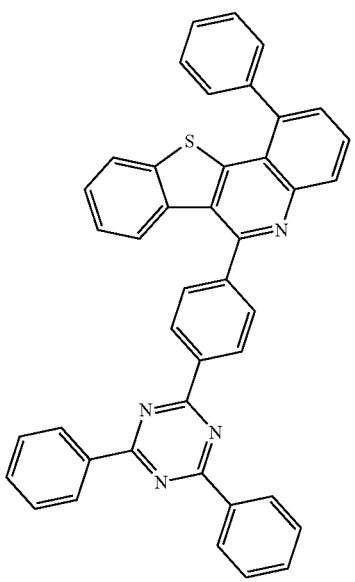

907
-continued
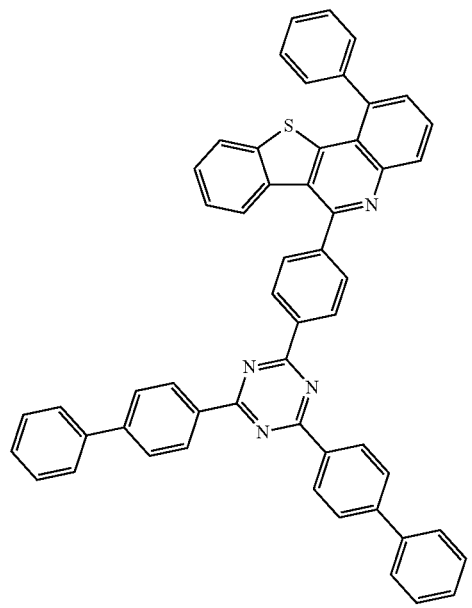
588
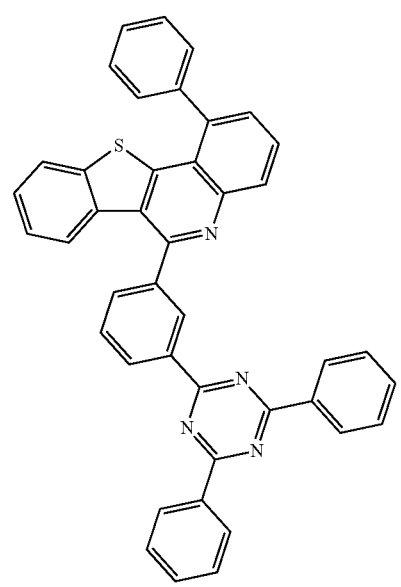
589
908
-continued
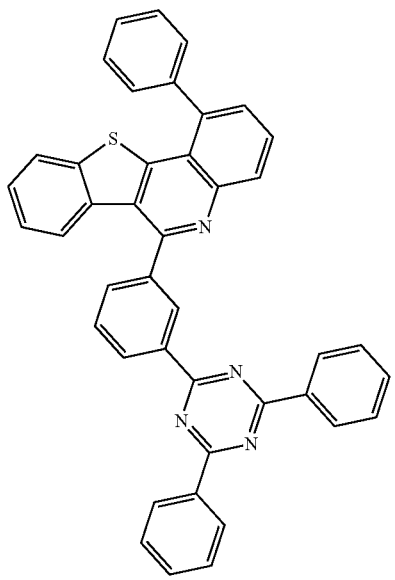
590
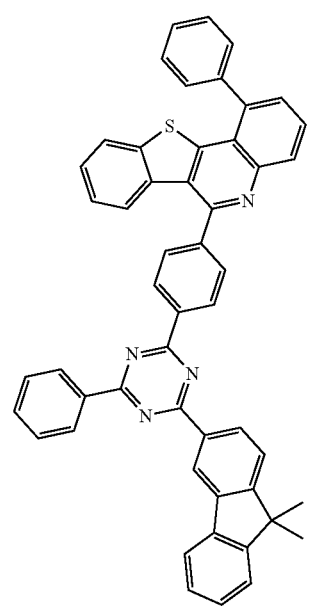
591

909 -continued
592
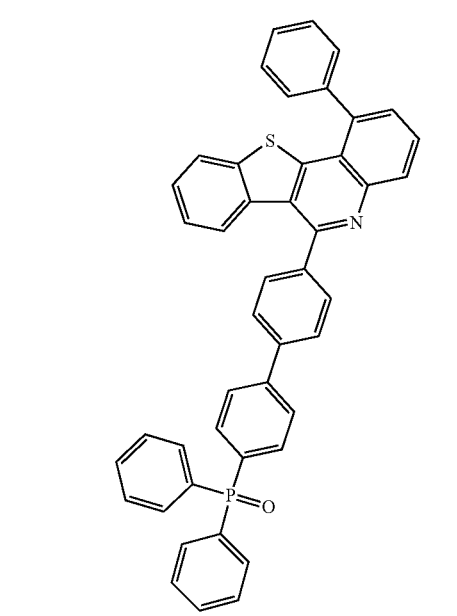
593
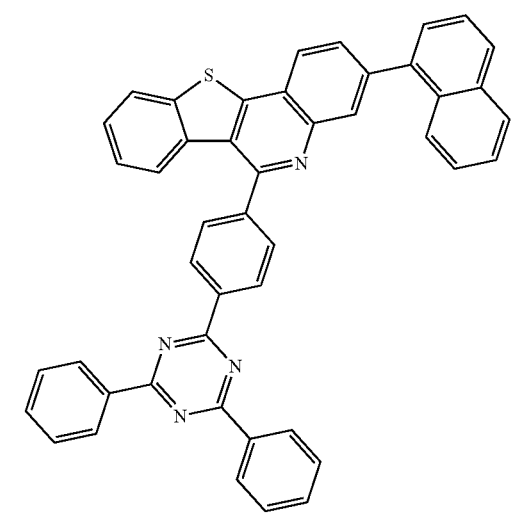
594
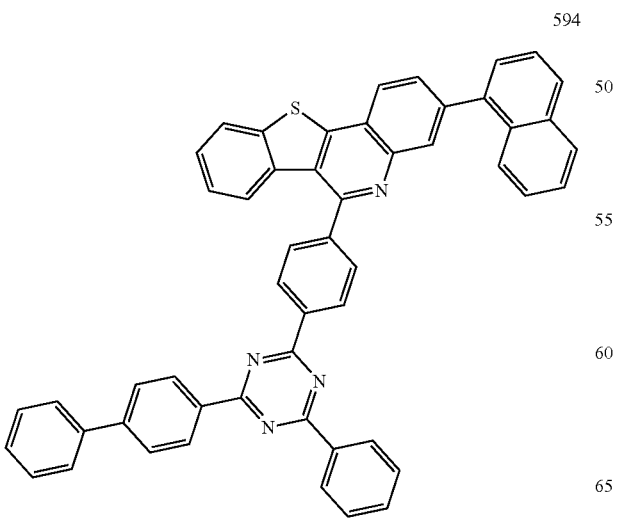
910 -continued
595
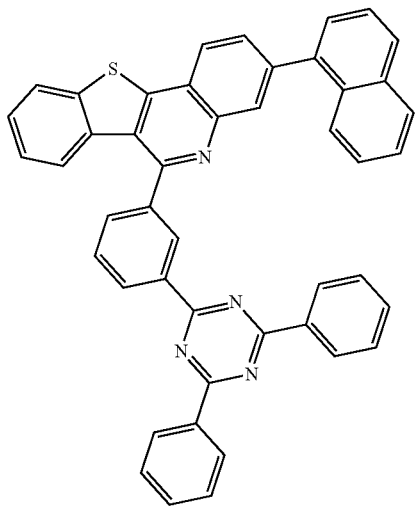
596
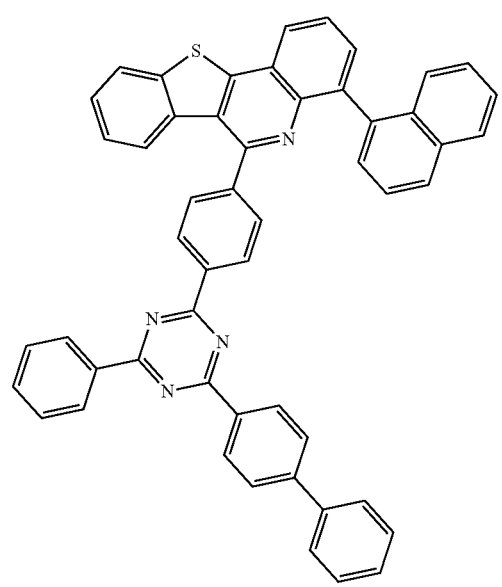
597
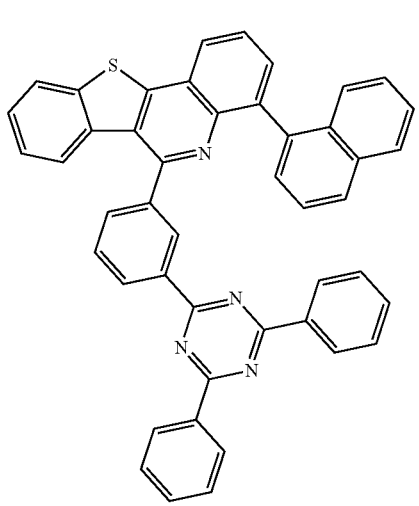

911
-continued
912
-continued
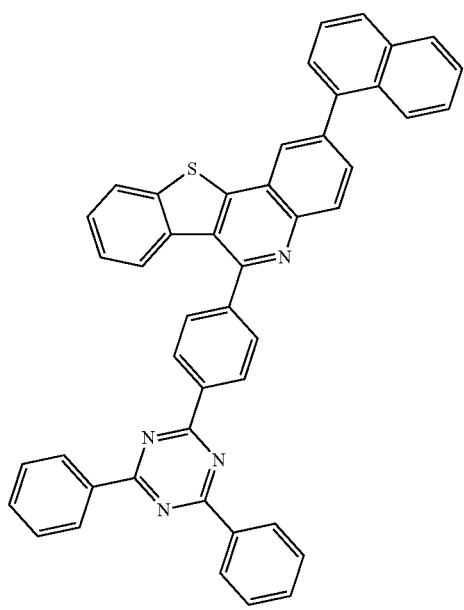
598
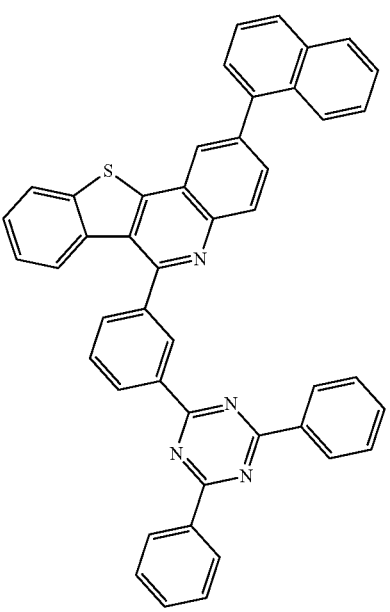
600
599
601

913
-continued
914
-continued
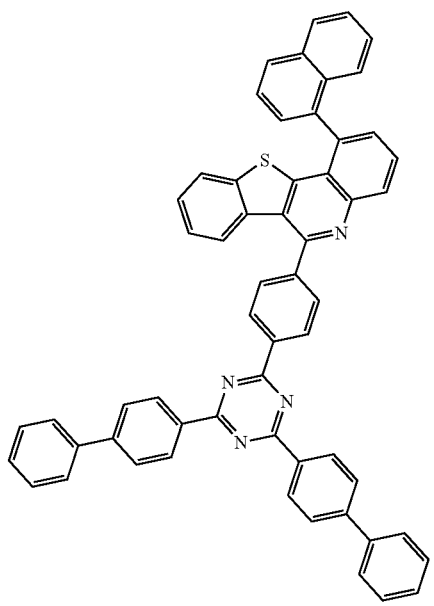
602
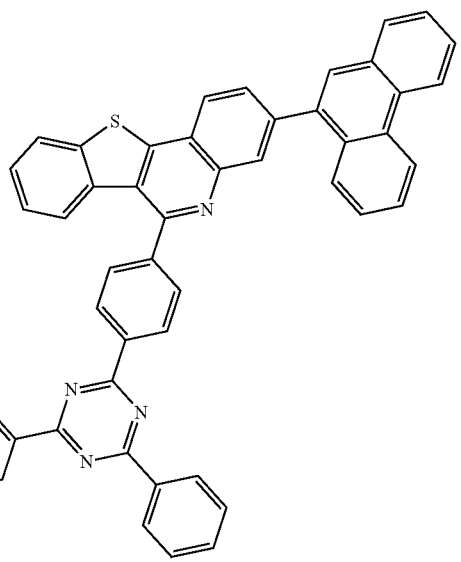
604
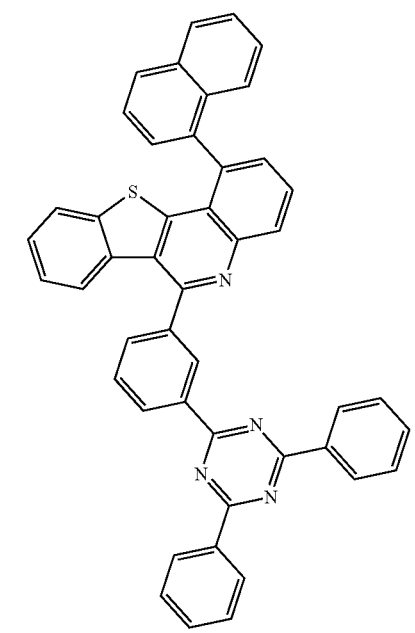
603
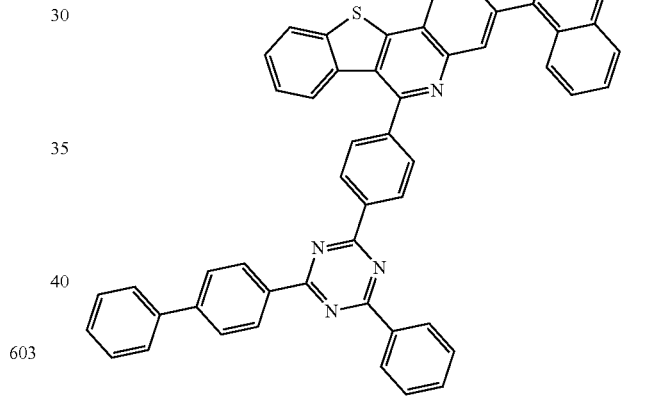
605
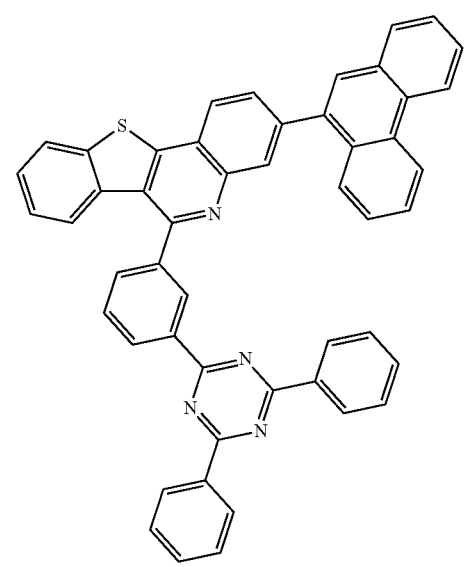
606

-continued
915
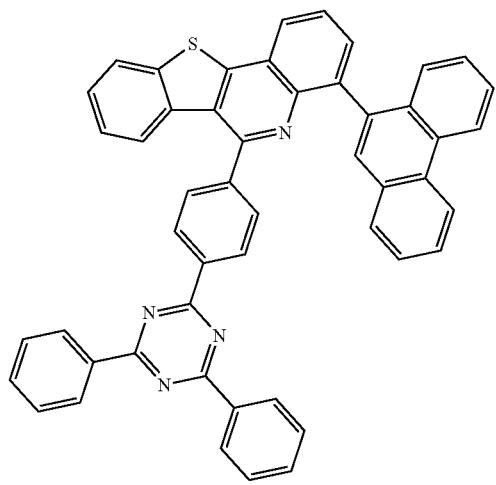
607
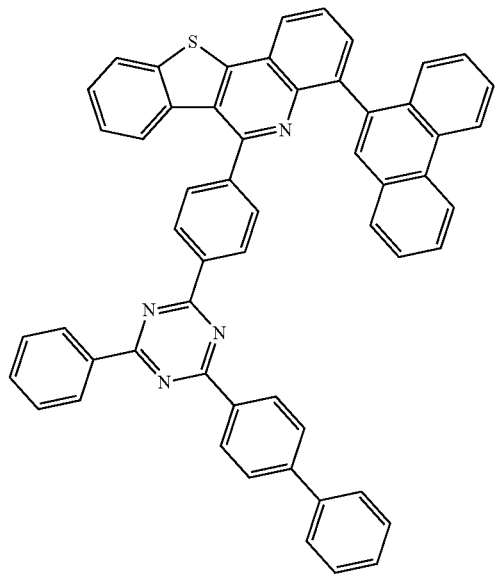
608
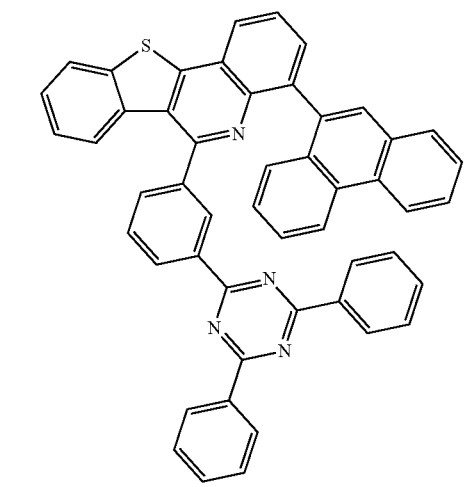
609
-continued
916
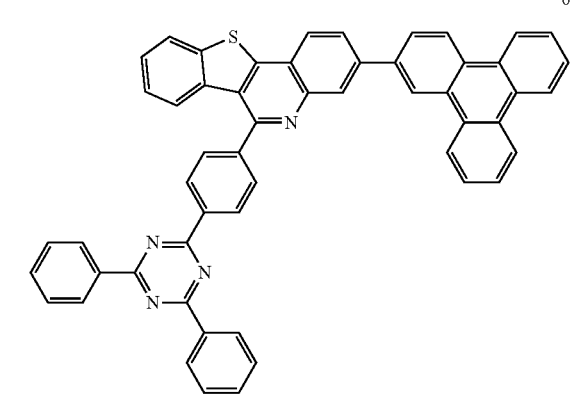
610
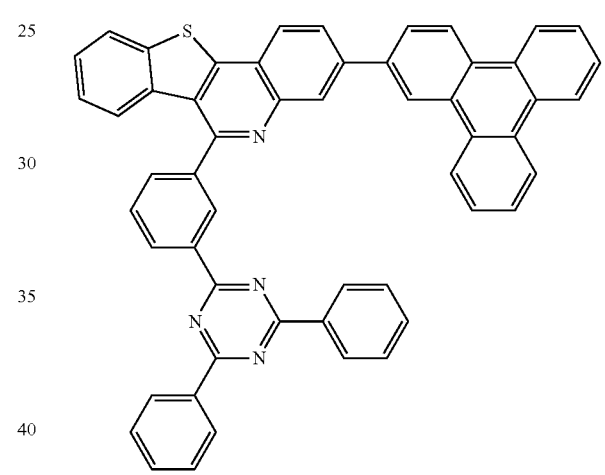
611
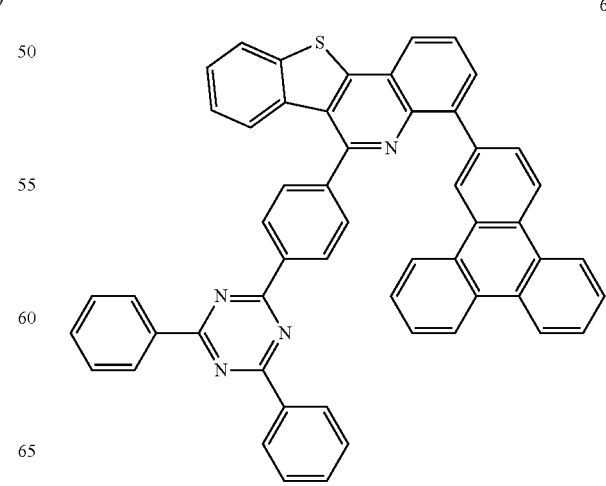
612

917
-continued
613
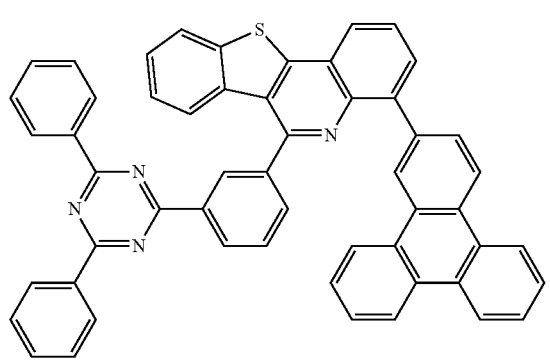
614
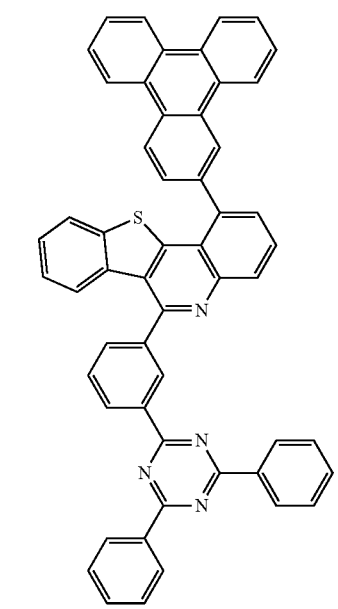
918
-continued
616
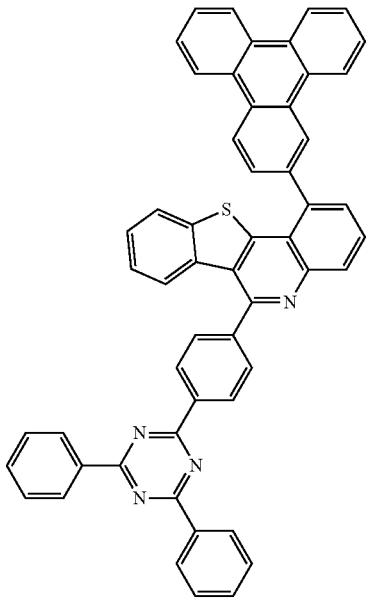
615
617

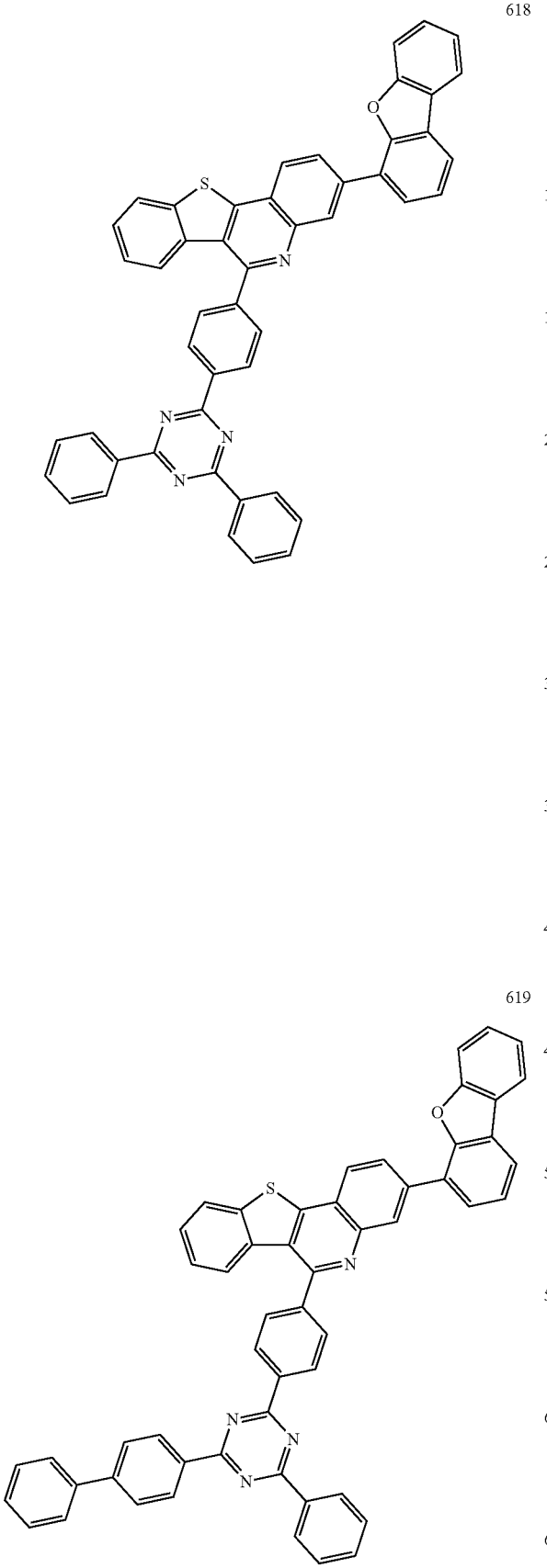
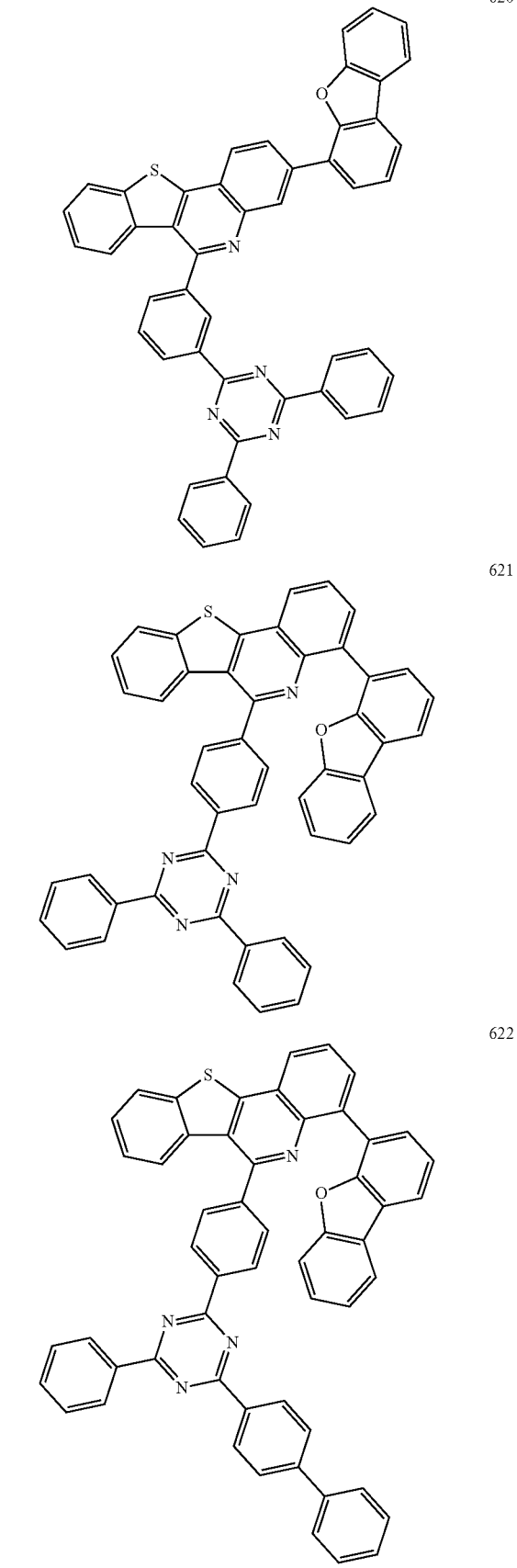

921
-continued
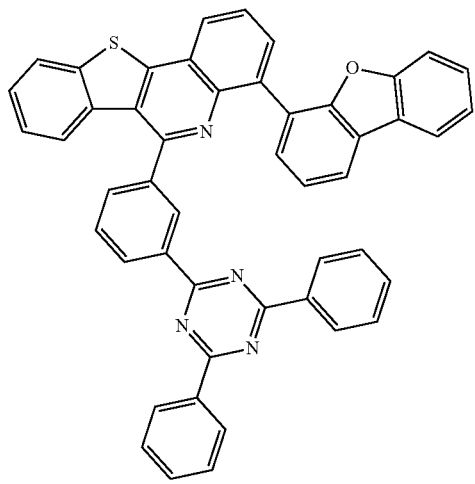
623
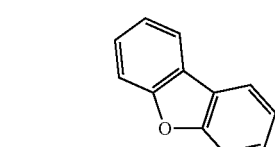
624
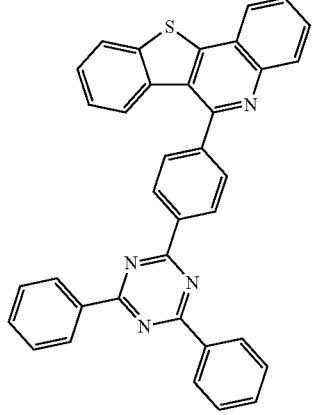
625
922
-continued
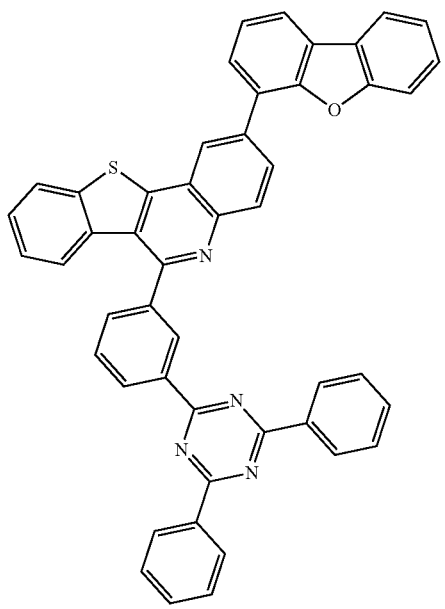
626
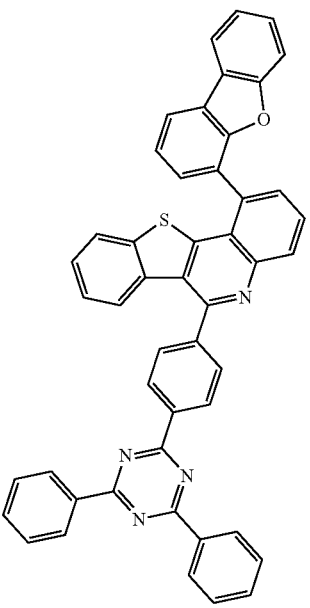
627

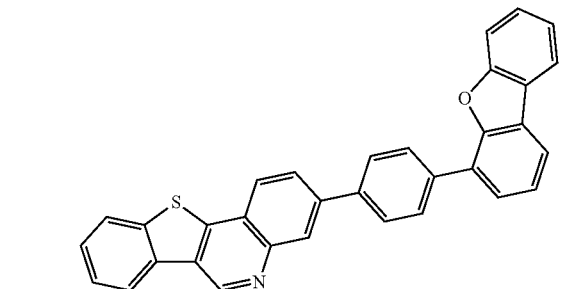
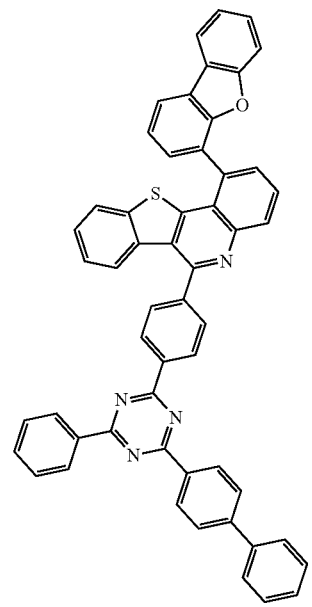
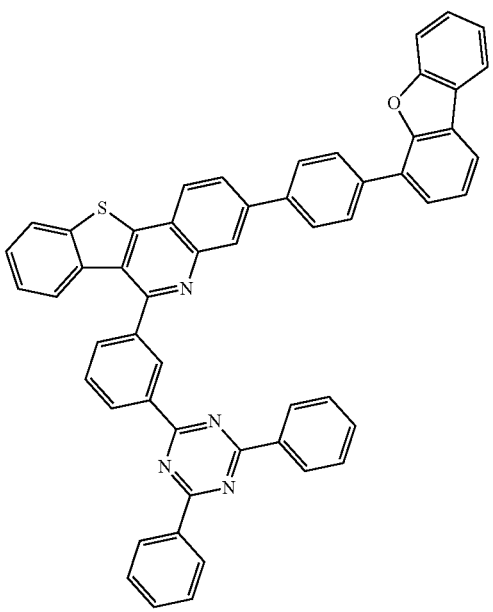
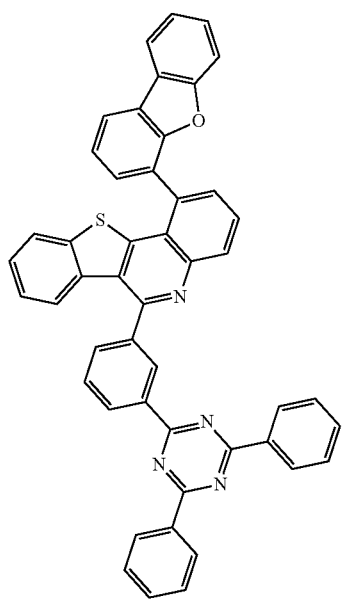

925
-continued
633
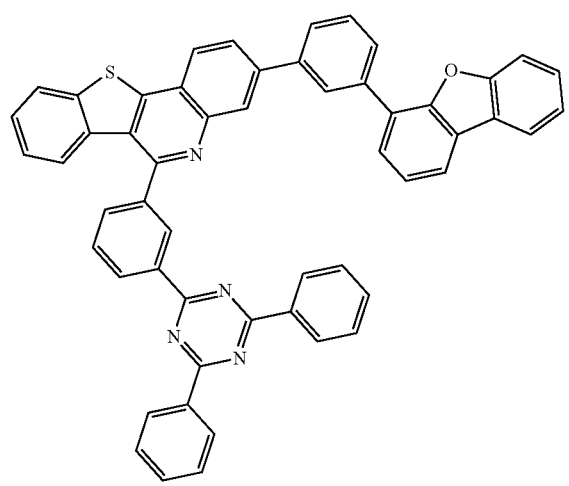
634
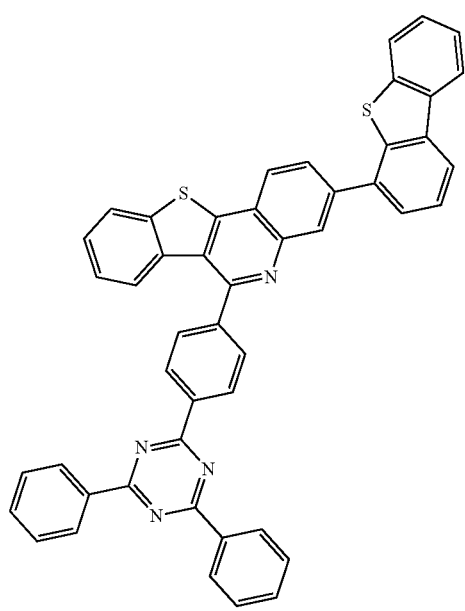
926
-continued
635
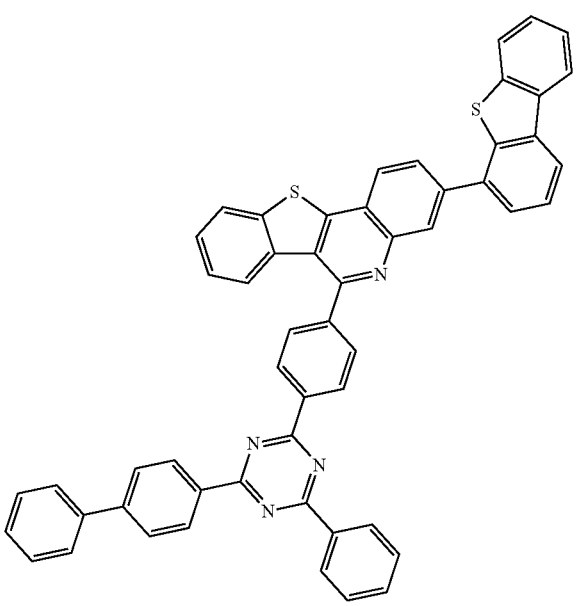
636
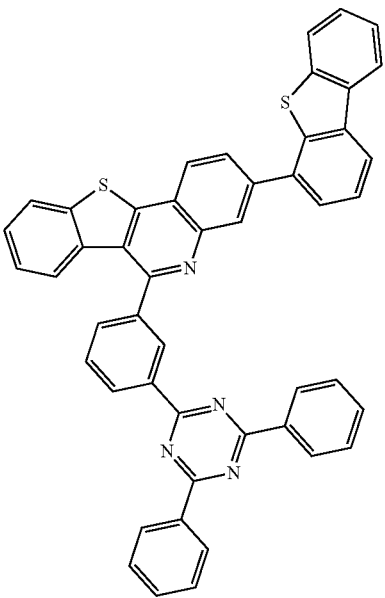

927
-continued
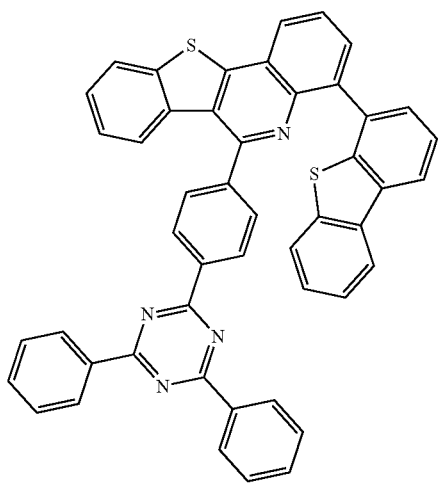
928
-continued
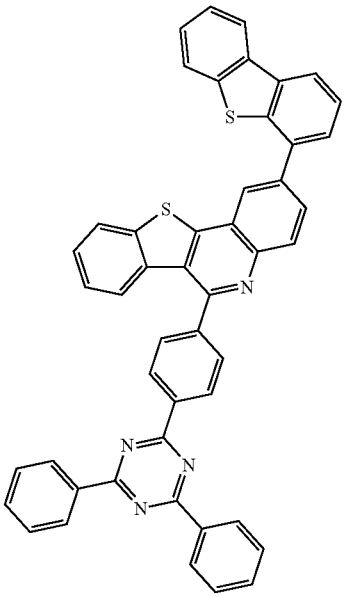
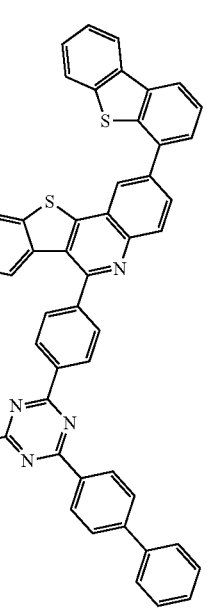

929
-continued
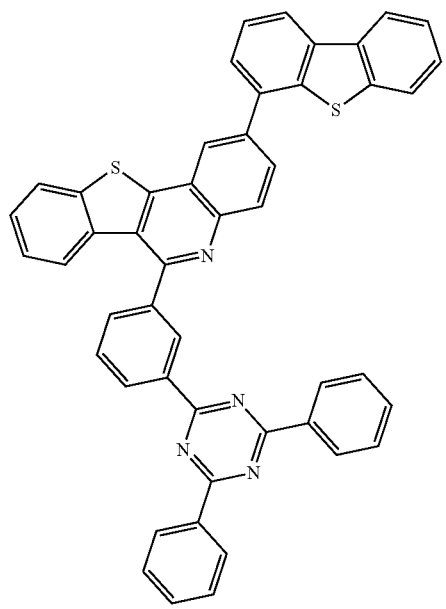 [SMILES: c1ccc(-c2nc(-c3ccccc3)nc(-c3cccc(-c4nc5ccc(-c6cccc7c6sc6ccccc67)cc5c5oc6ccccc6c45)c3)n2)cc1]
642
930
-continued
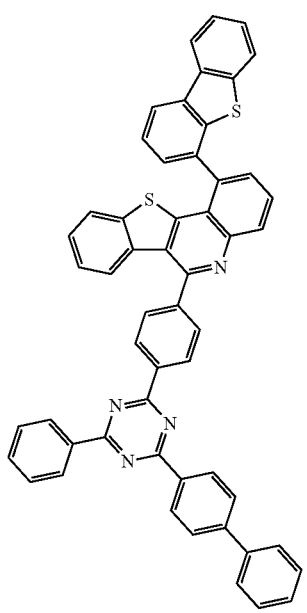
644
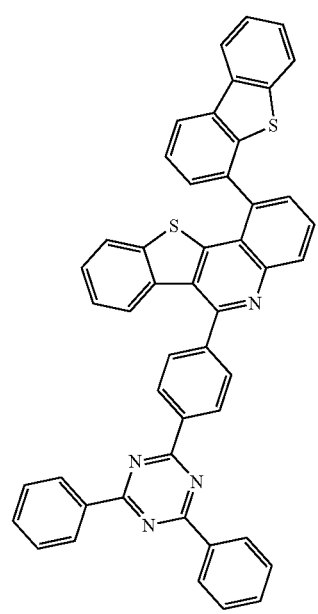
643
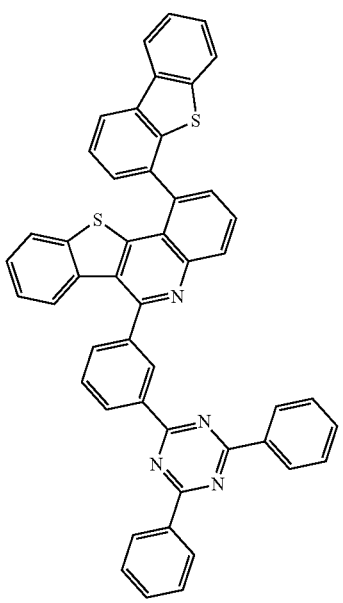
645

931
-continued
646
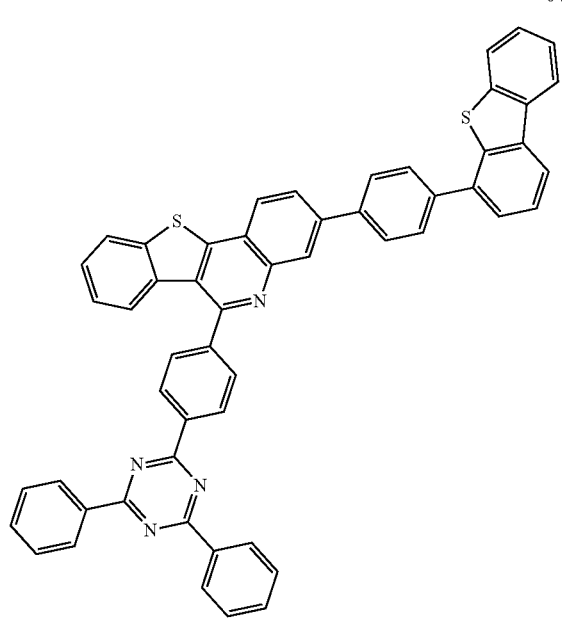
647
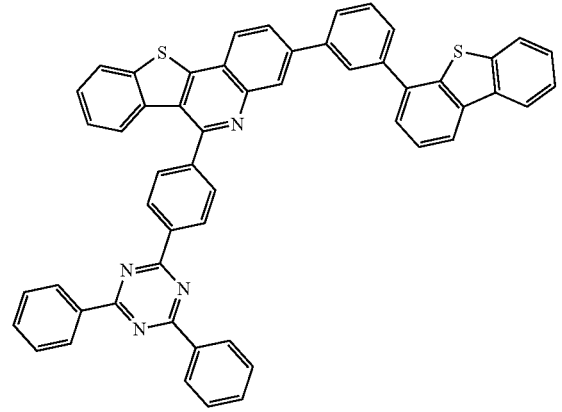
648
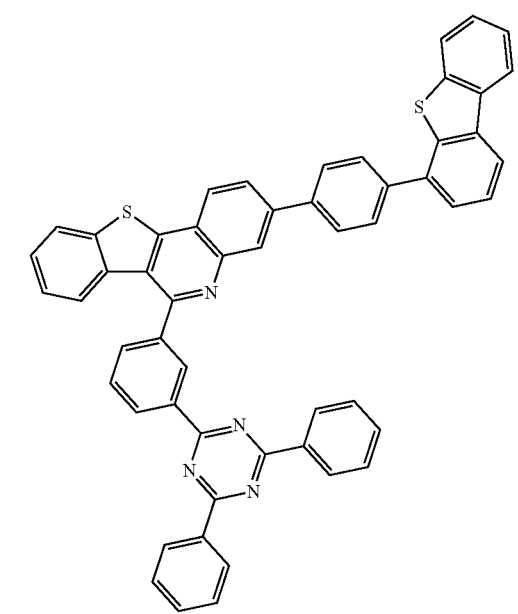
932
-continued
649
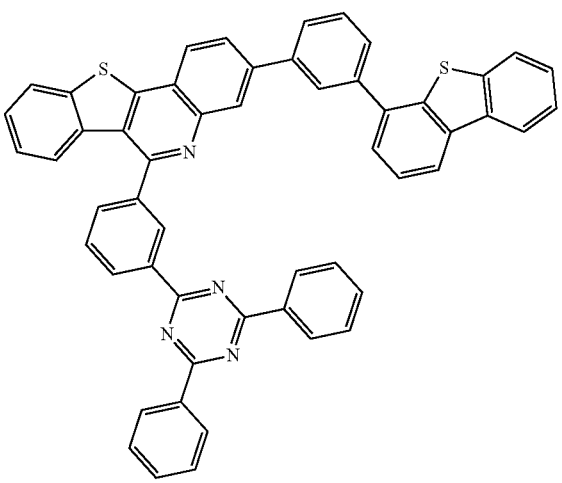
650
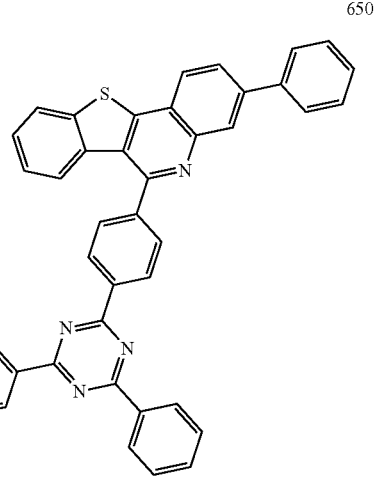
651
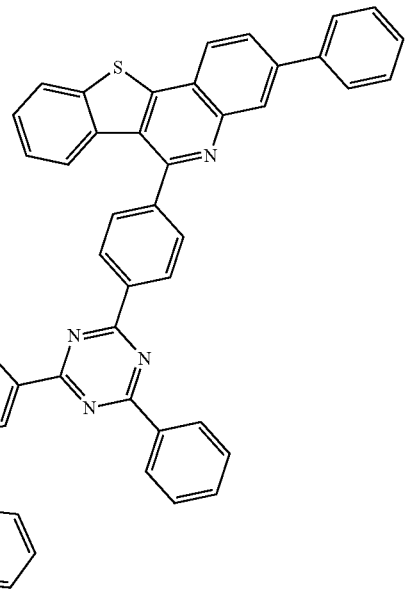

933
-continued
652
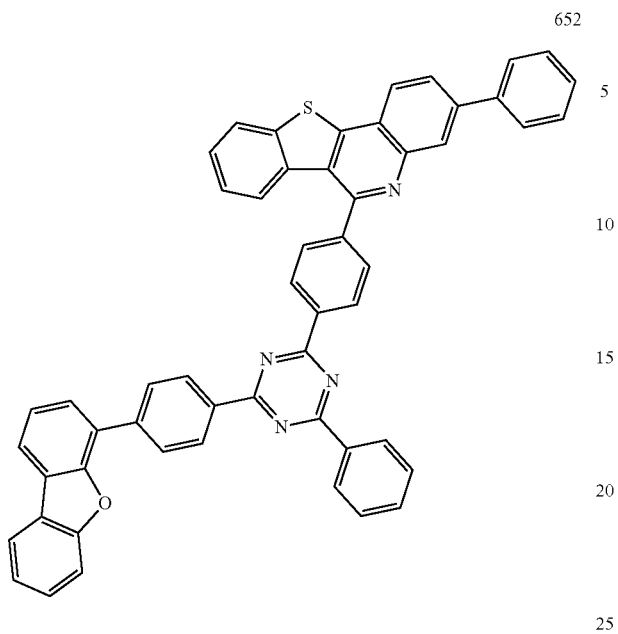
934
-continued
654
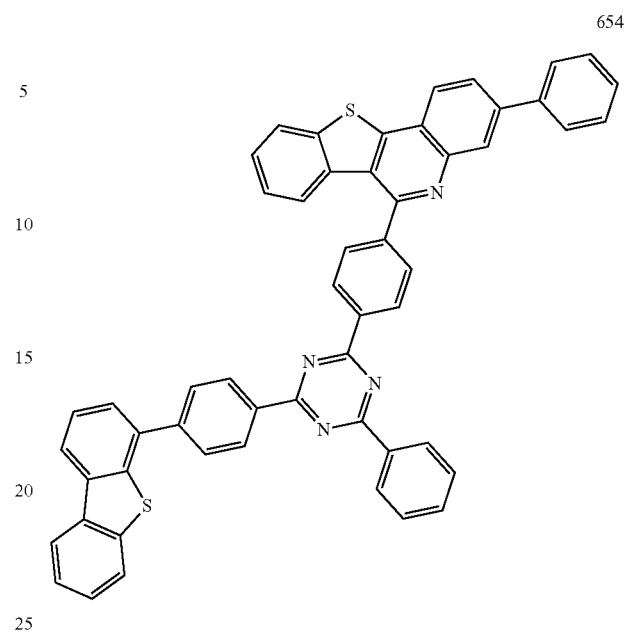
653
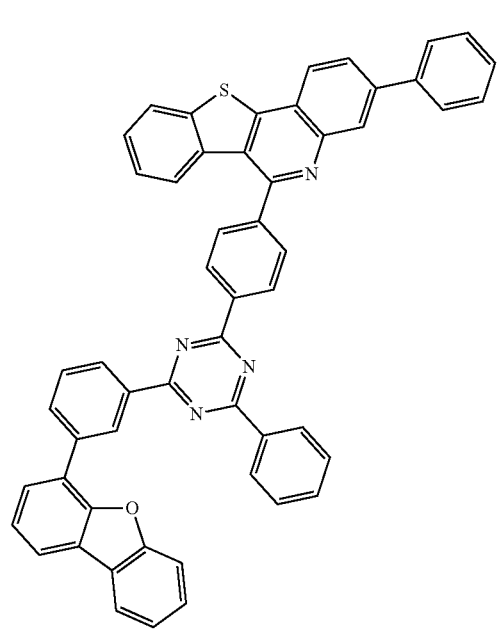
655
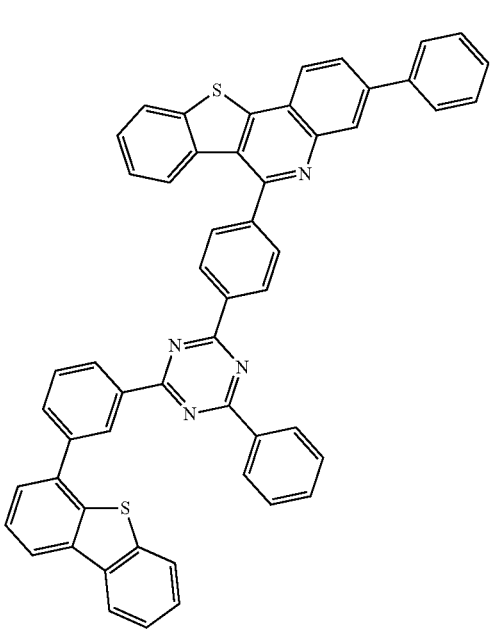

935
-continued
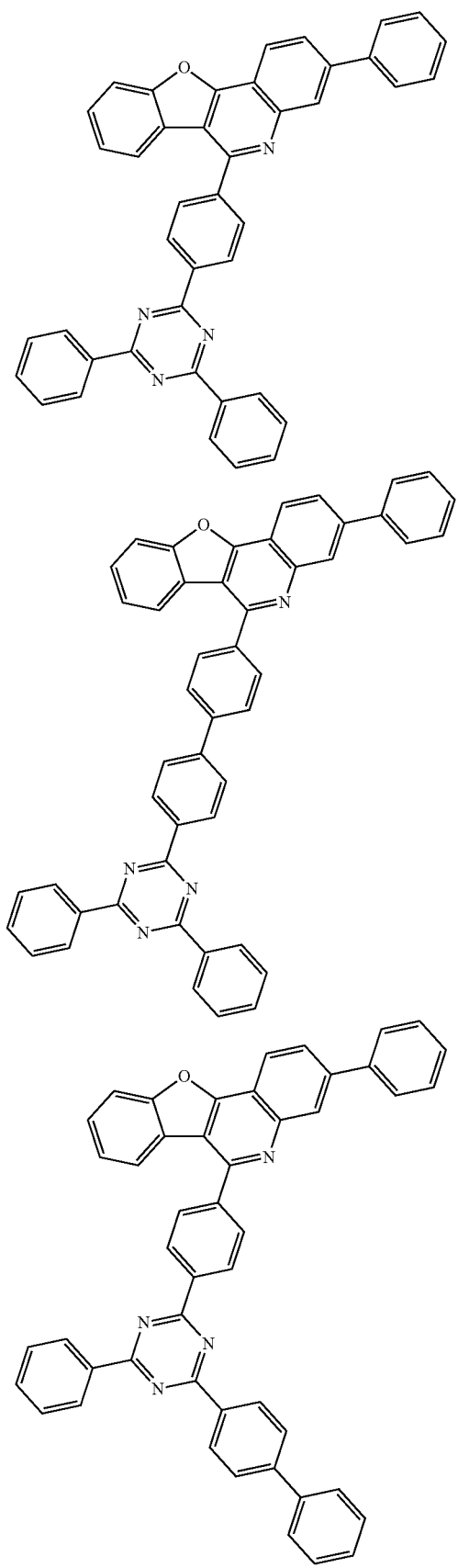
936
-continued
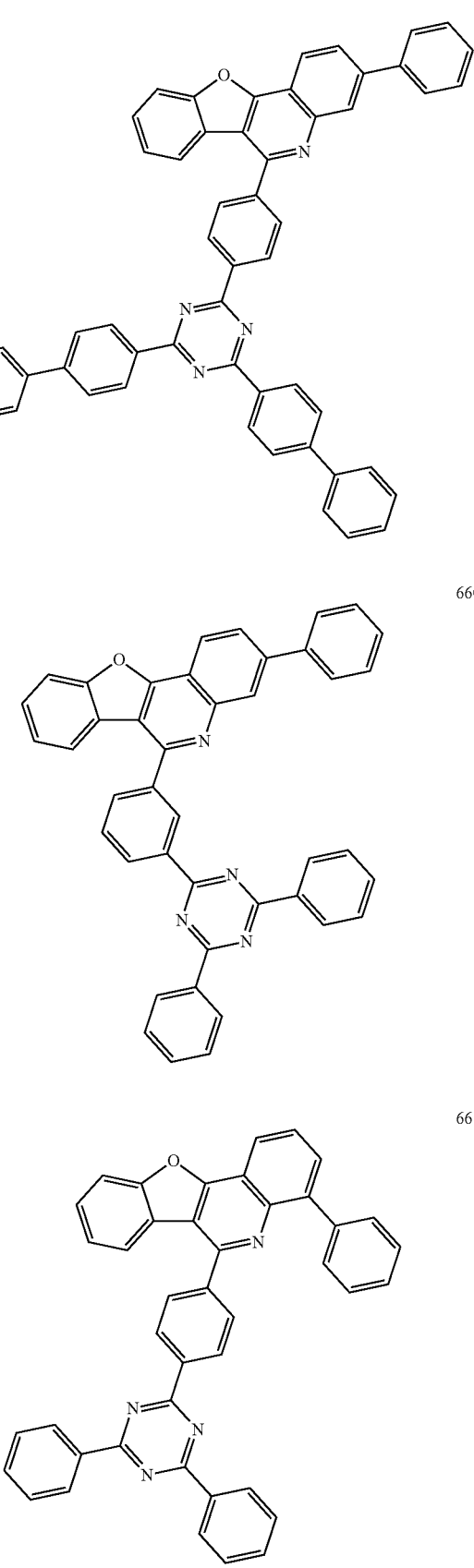

937
-continued
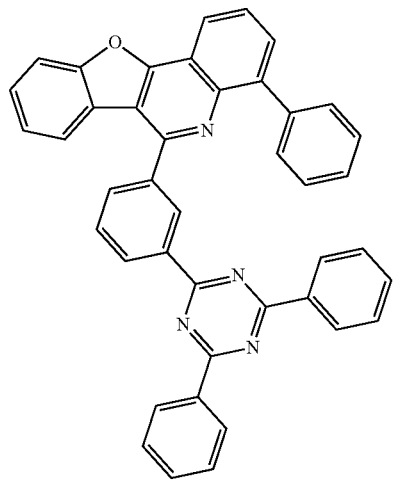
662
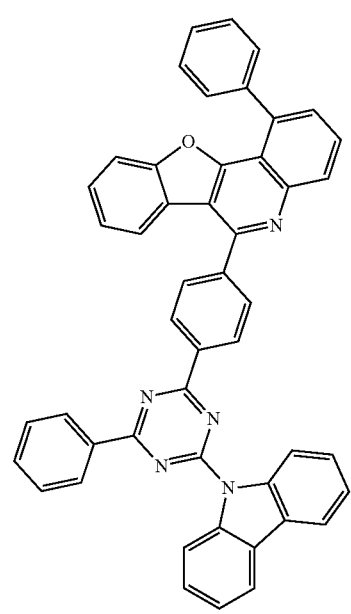
663
938
-continued
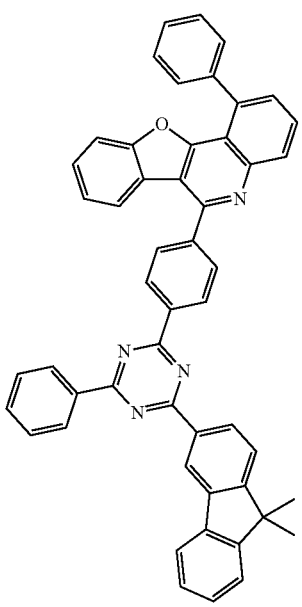
664
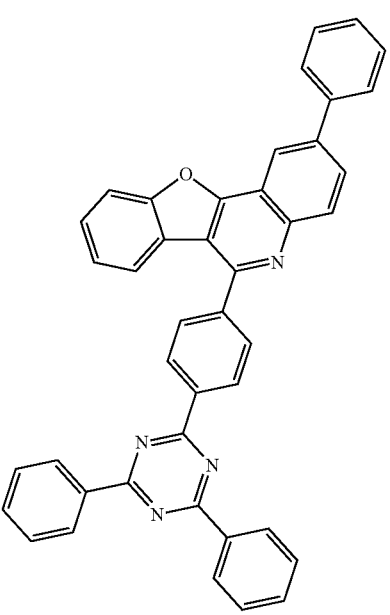
665

939
-continued
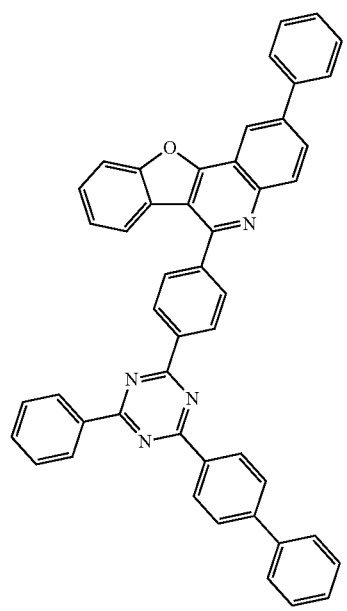
940
-continued
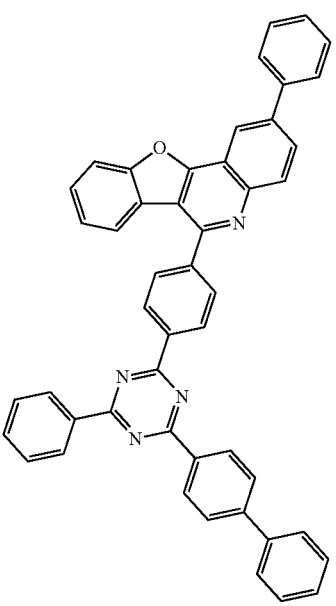
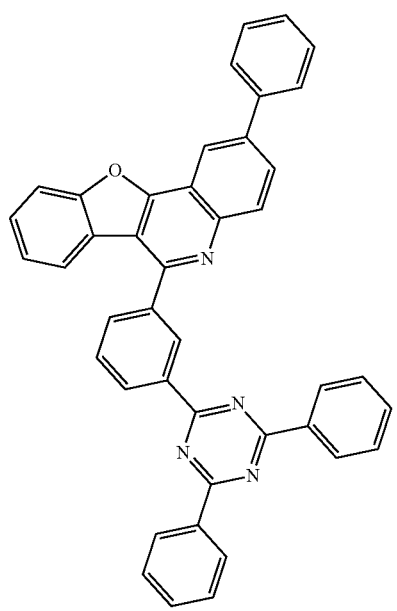
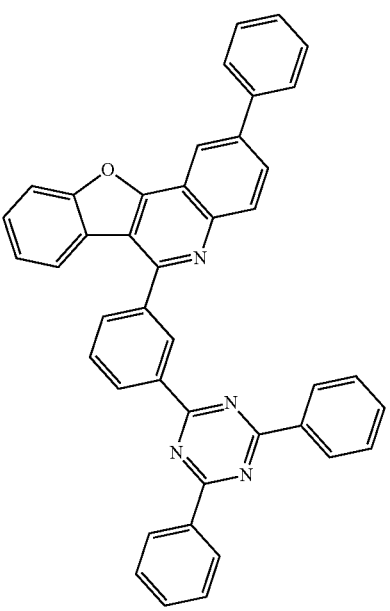

941
-continued
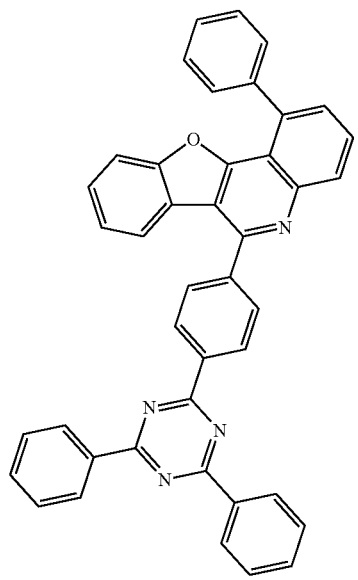
670
942
-continued
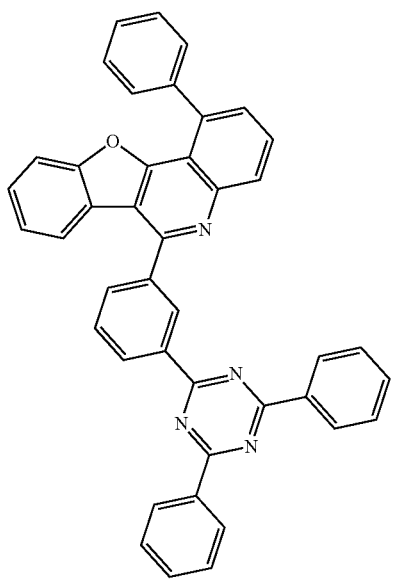
672
671
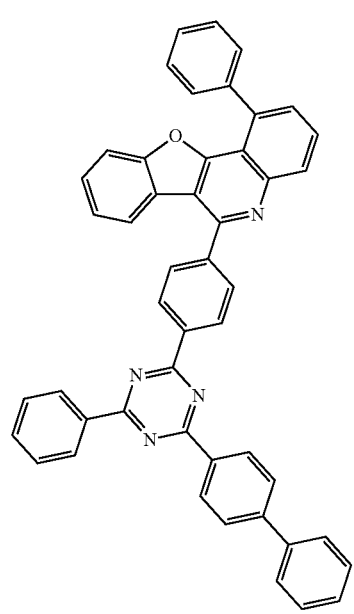
673
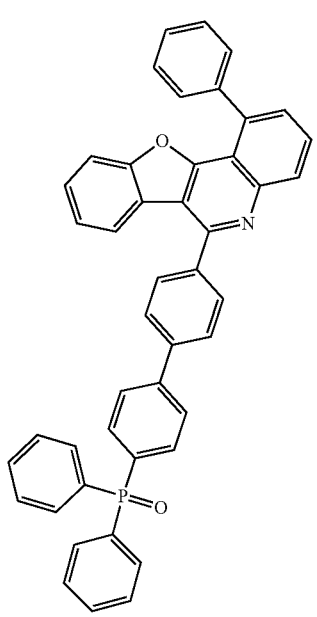

-continued
674
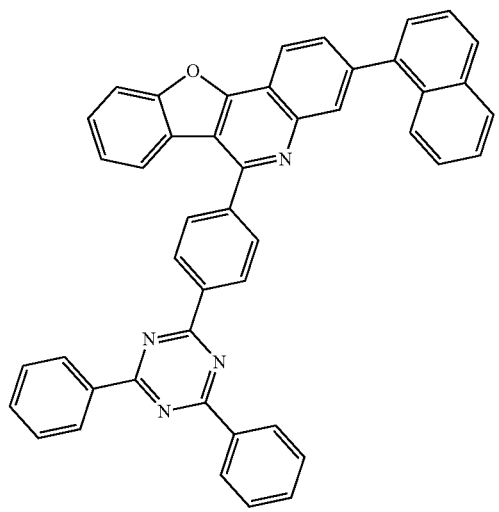
675
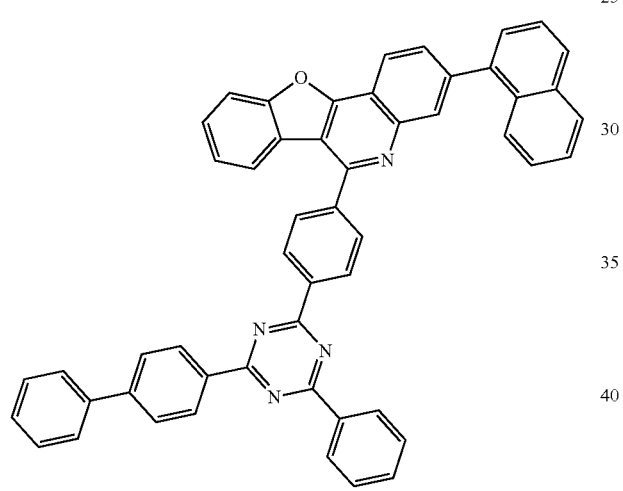
676
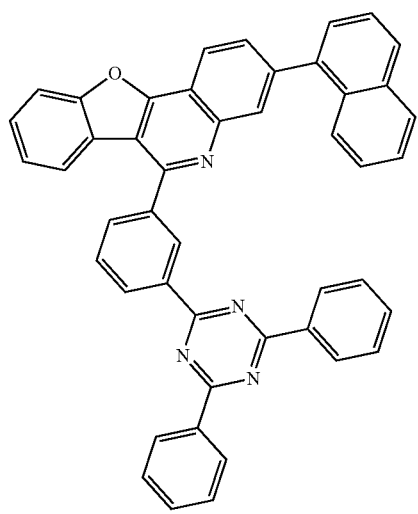
-continued
677
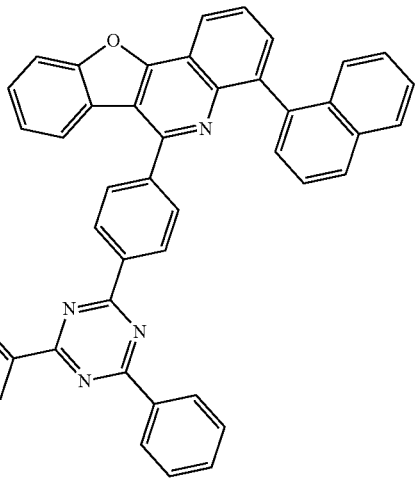
678
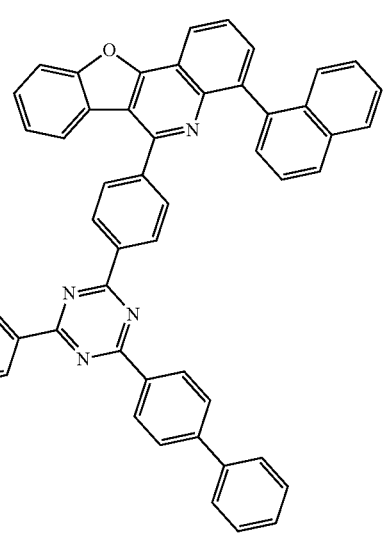
679
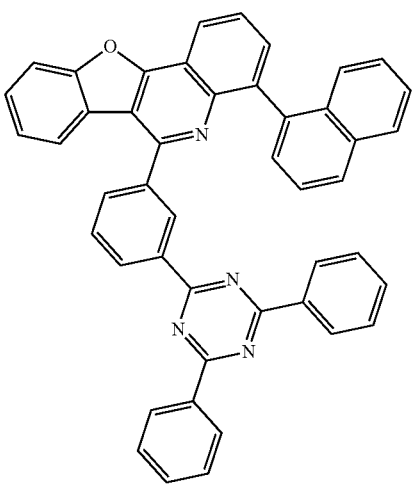

945
-continued
680
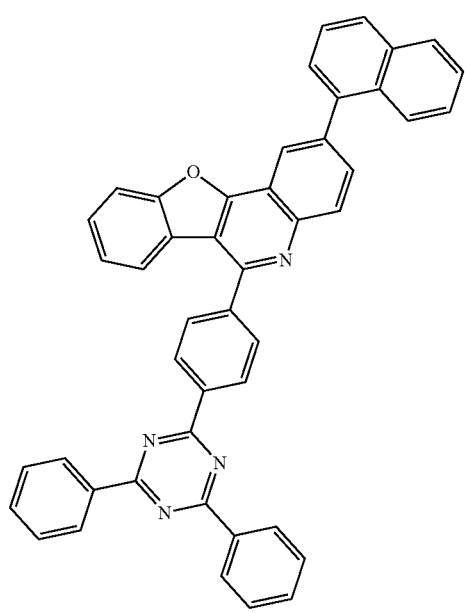
681
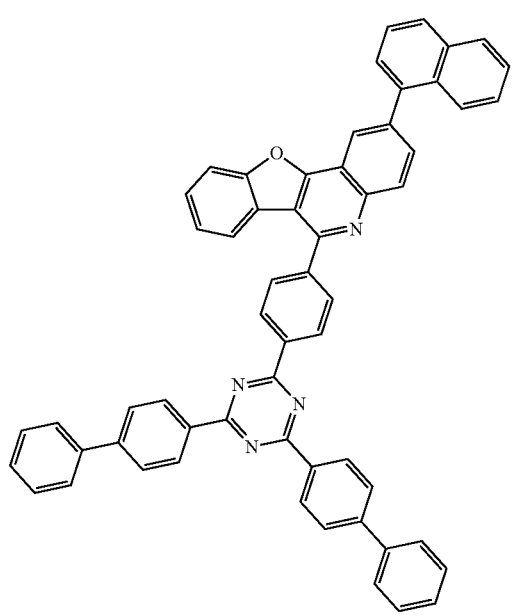
946
-continued
682
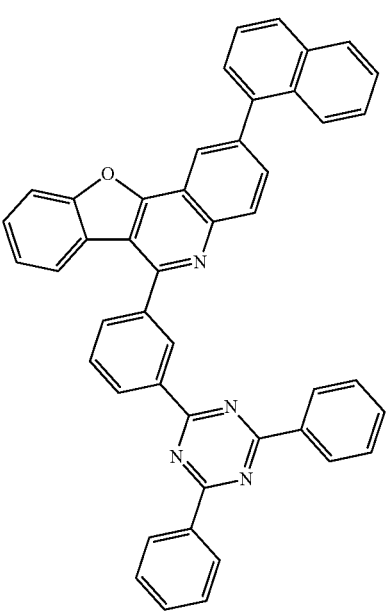
683
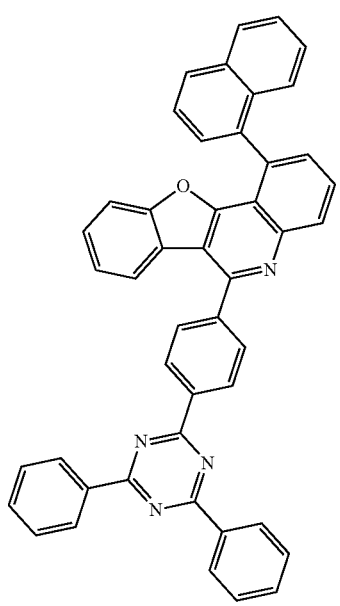

947
-continued
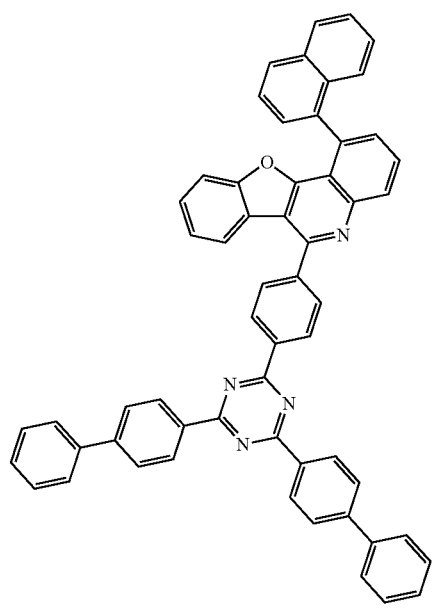
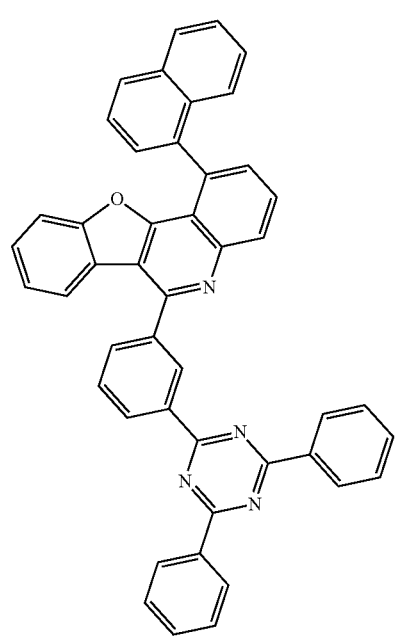
948
-continued
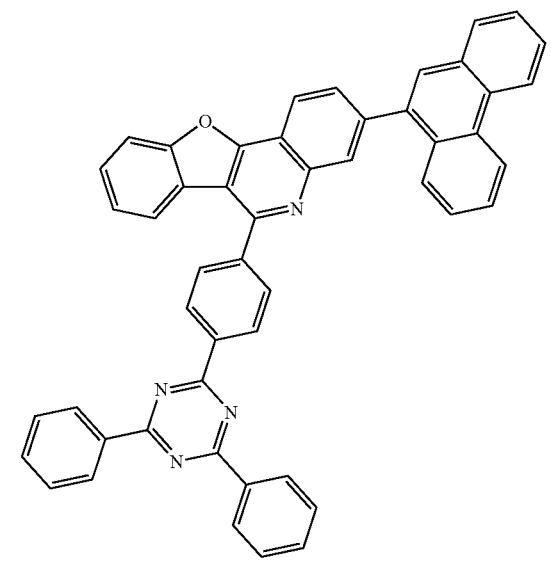
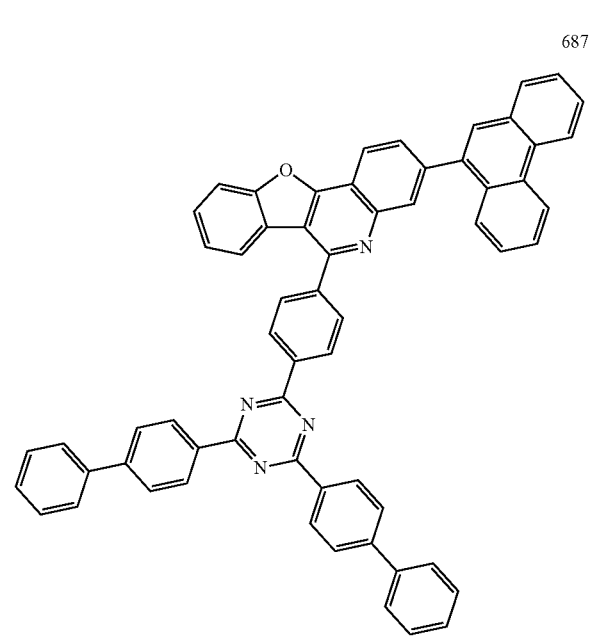

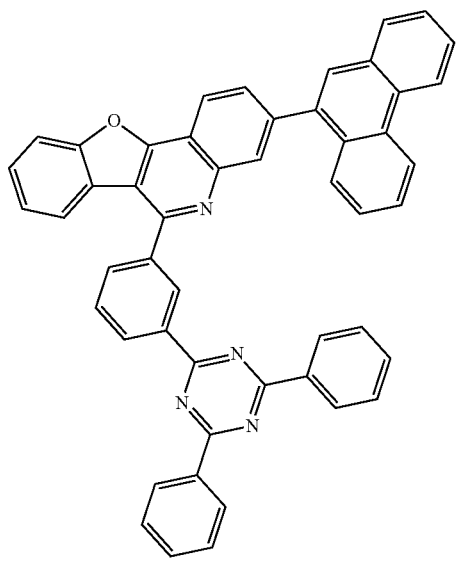
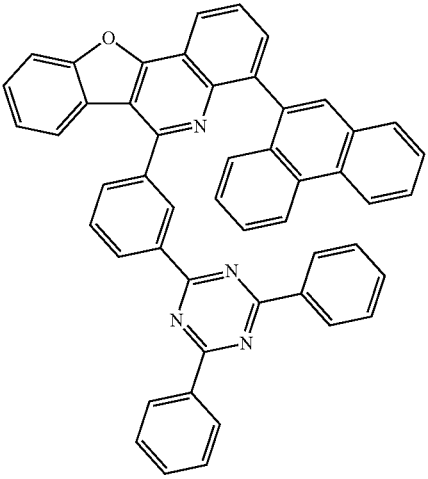
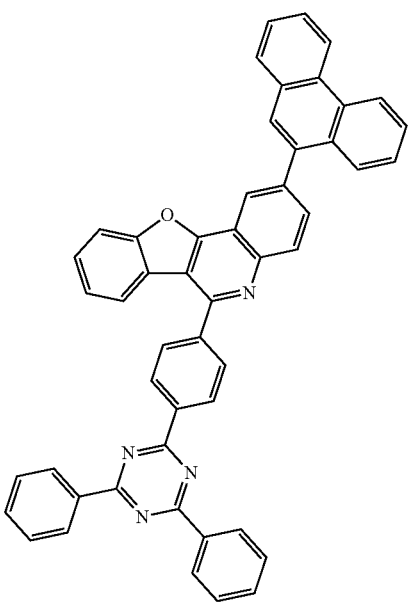

951
-continued
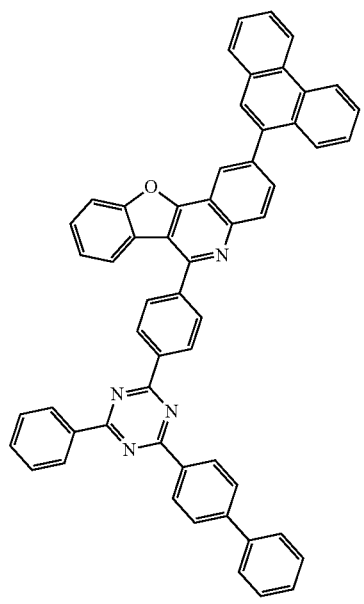
693
952
-continued
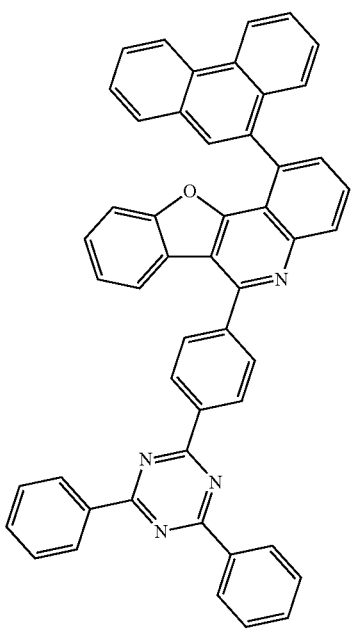
695
694
952
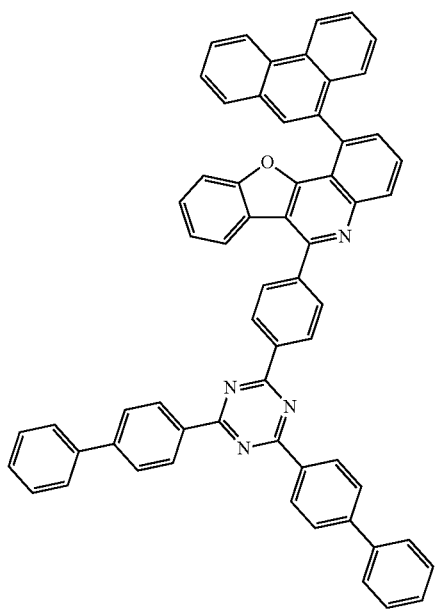
696

953
-continued
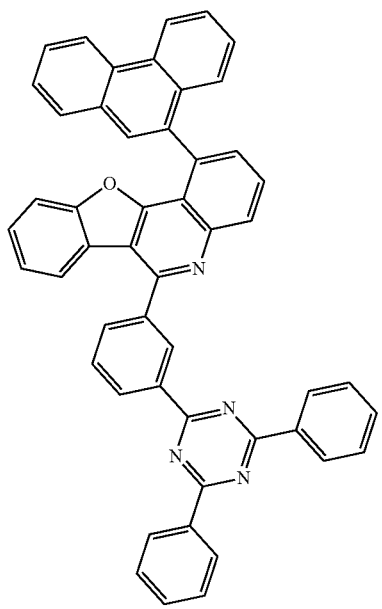
697
954
-continued
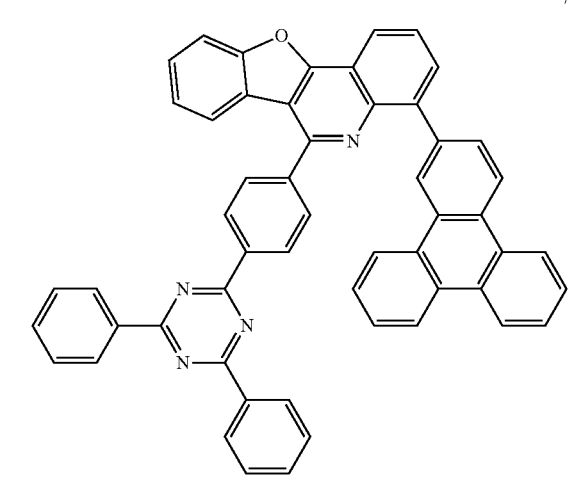
700
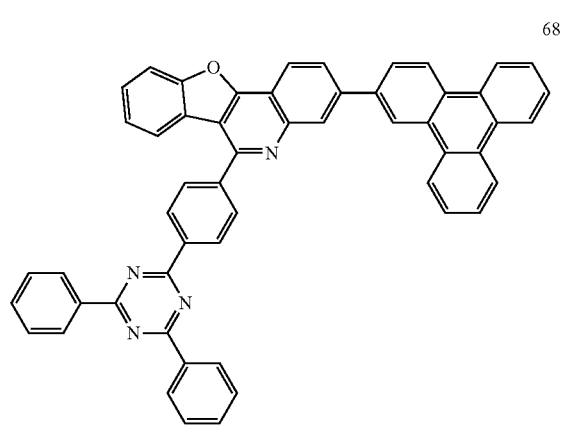
689
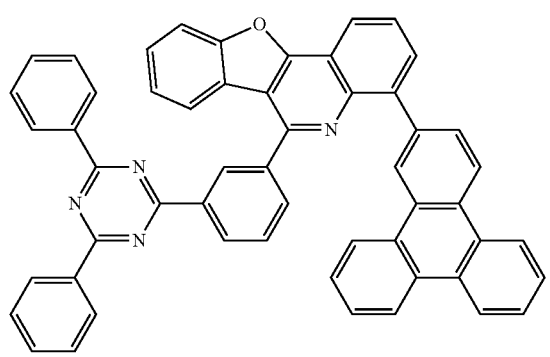
701
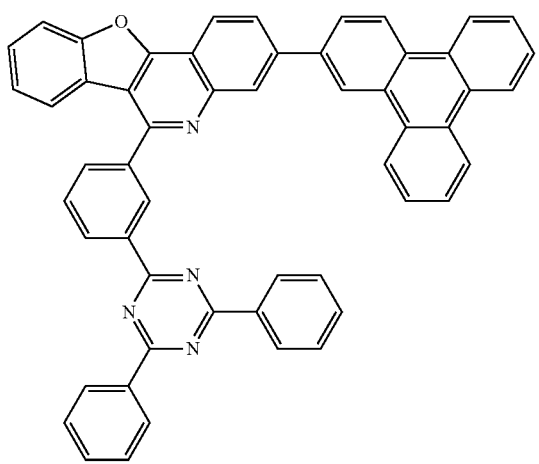
699
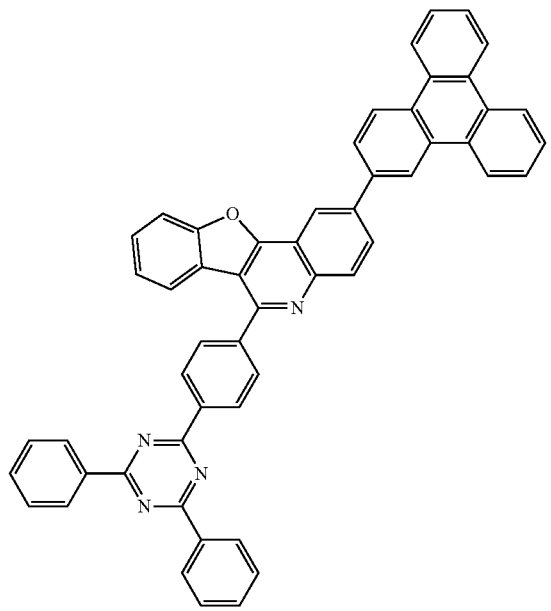
702

955
-continued
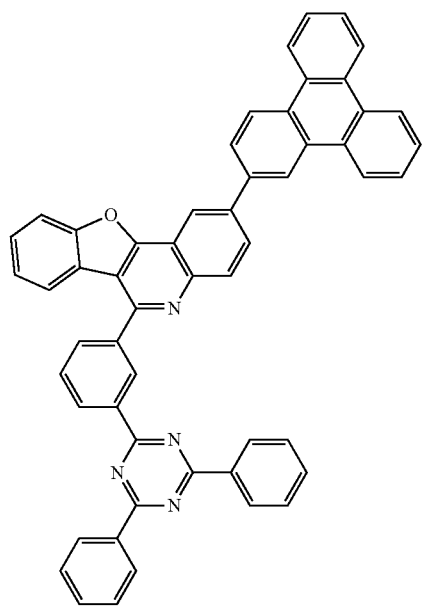
956
-continued
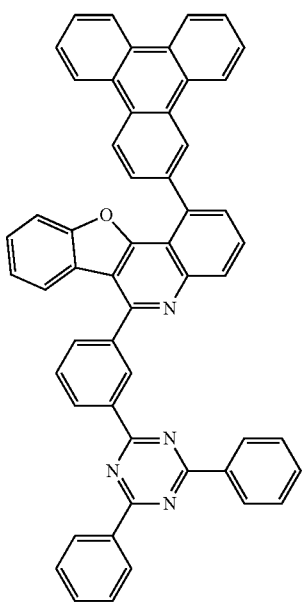
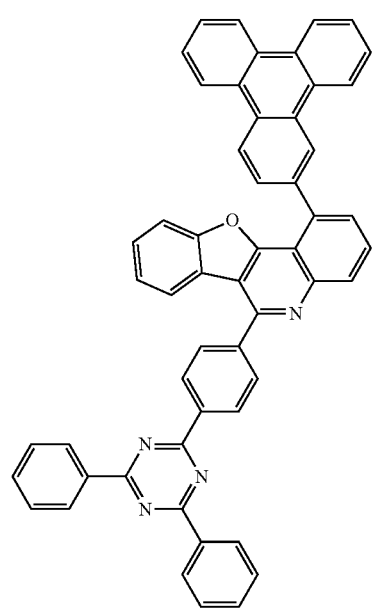
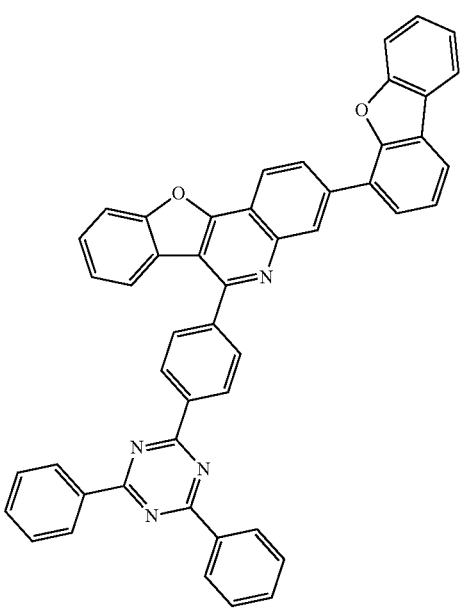

957
-continued
707
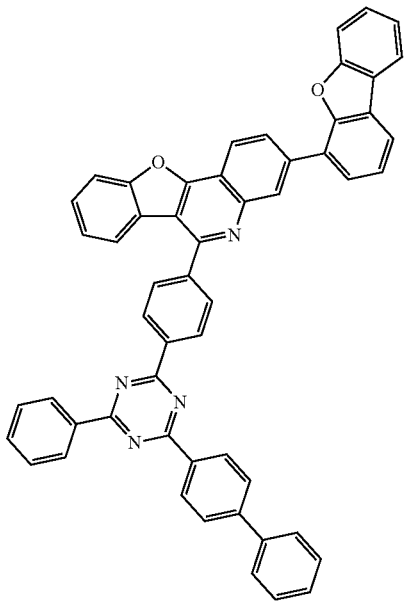
708
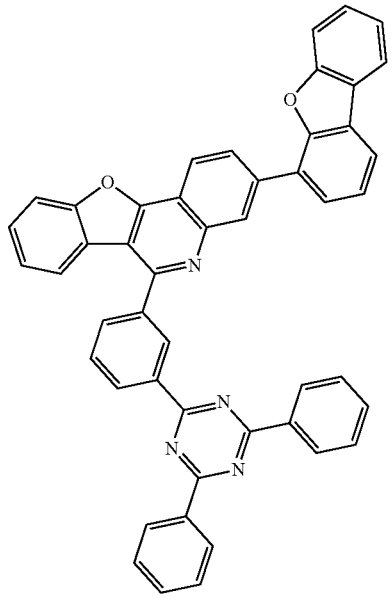
958
-continued
709
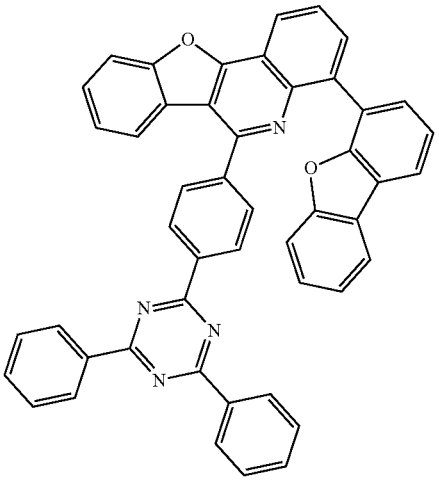
710
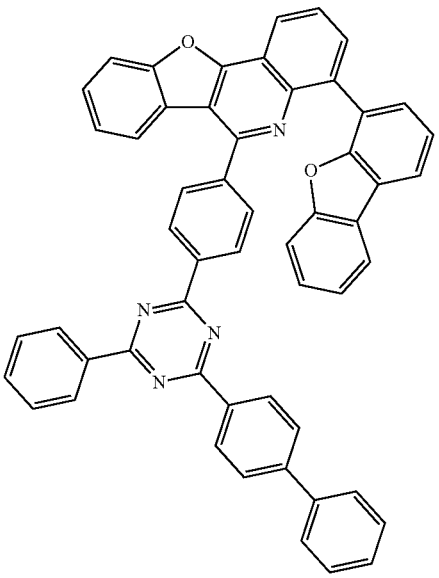
711
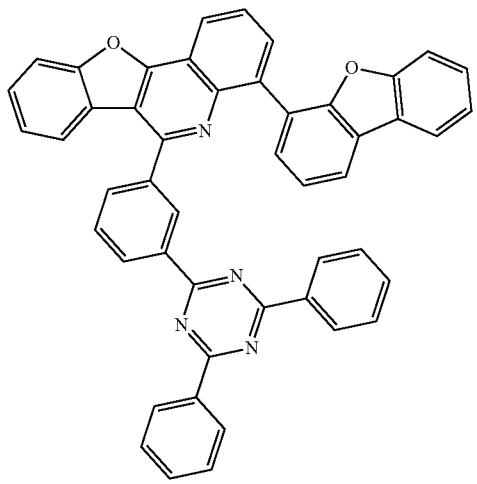

959
-continued
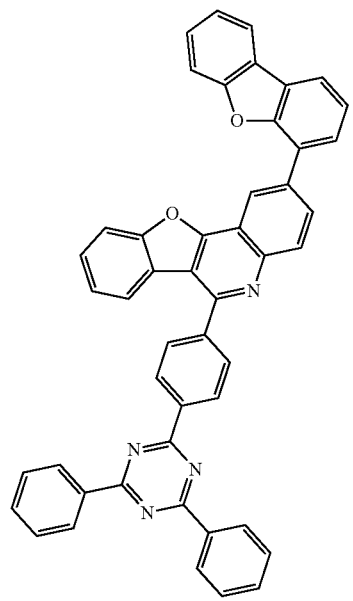
712
960
-continued
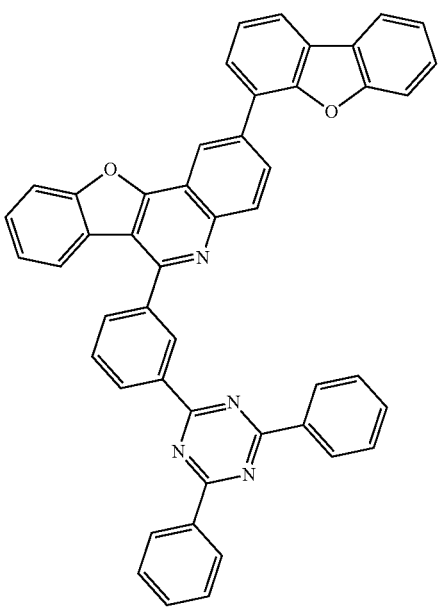
714
713
715
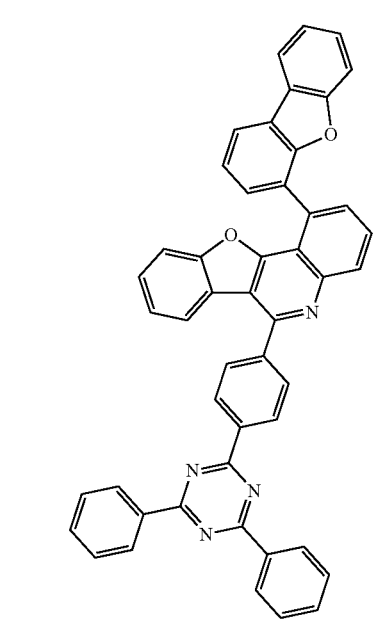

961
-continued
716
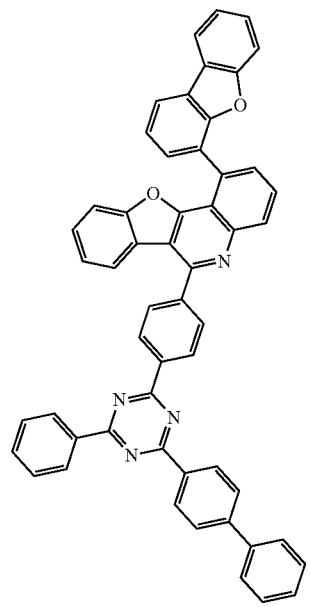
717
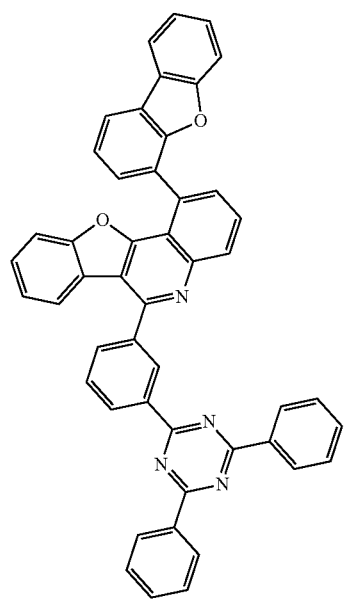
962
-continued
718
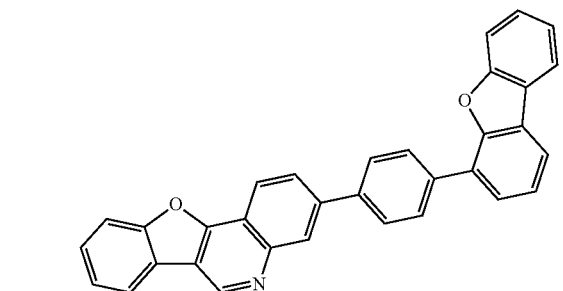
719
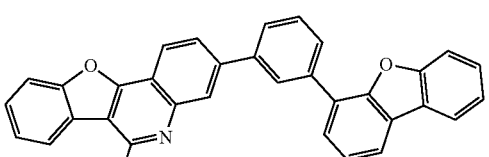
720
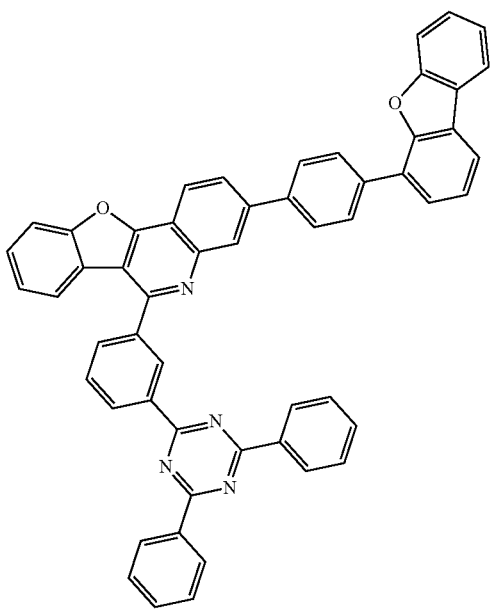

-continued
721
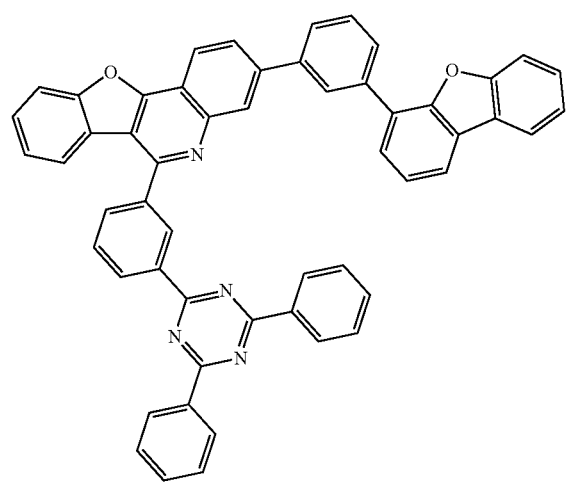
-continued
723
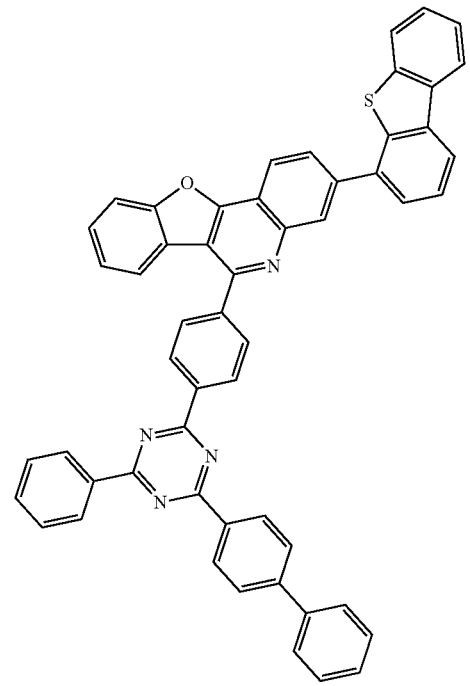
722
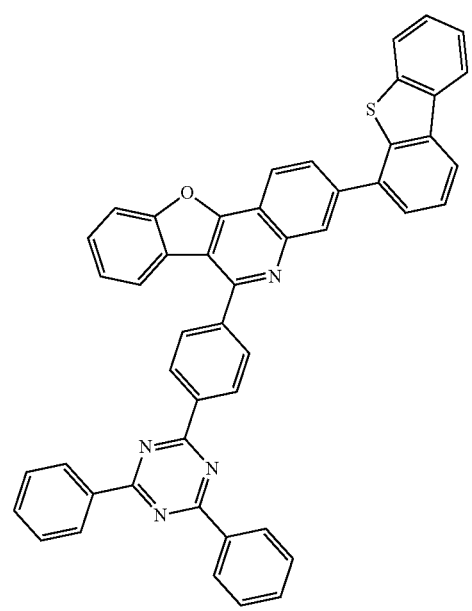
724
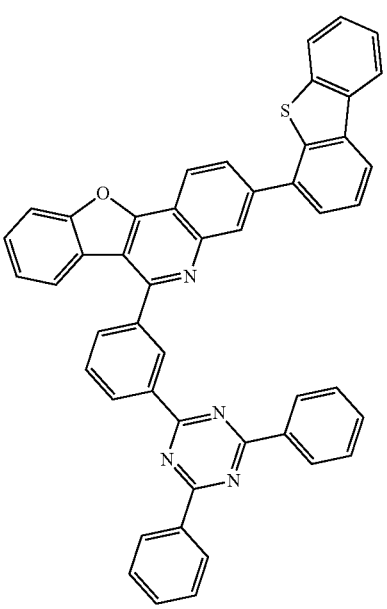

965
-continued
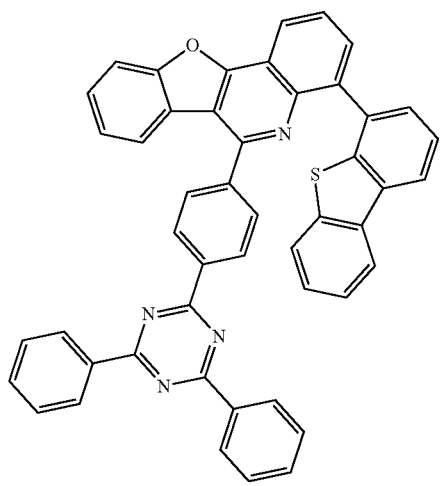
725
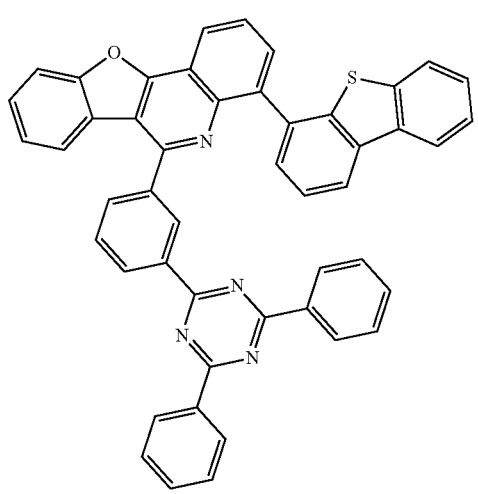
726
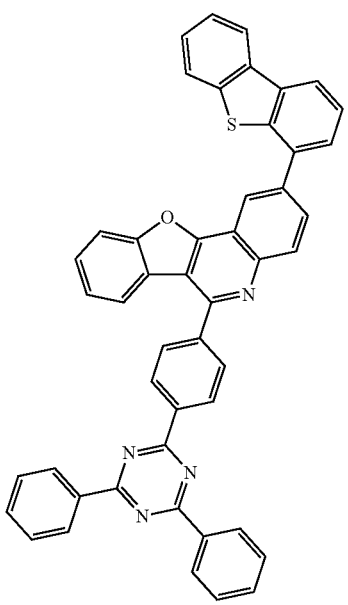
727
966
-continued
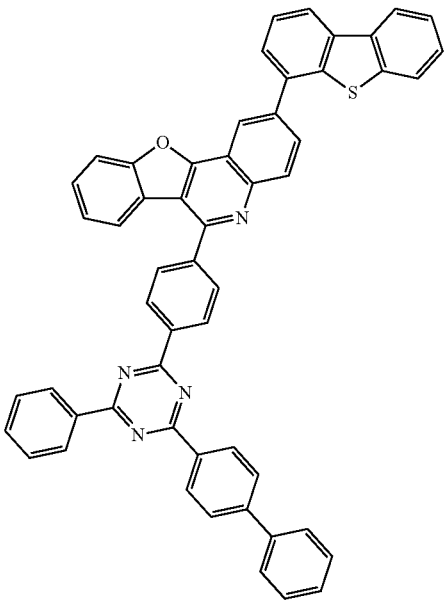
728
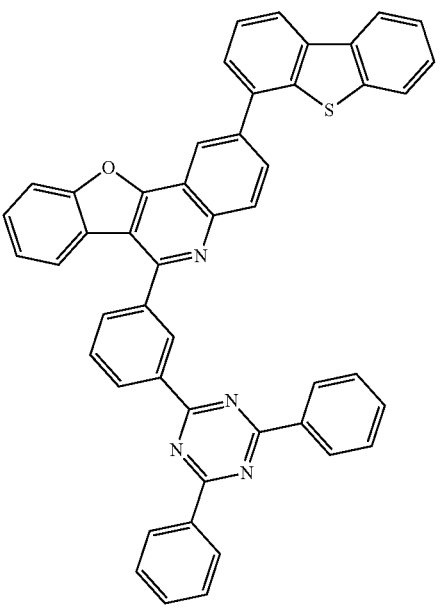
729

967
-continued
968
-continued
730
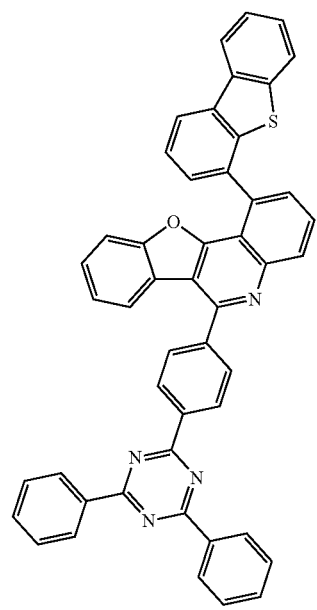
732
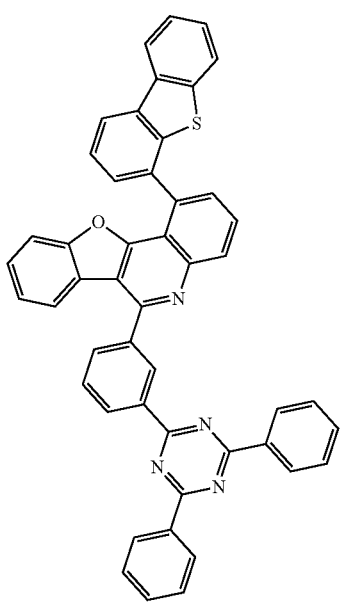
733
731
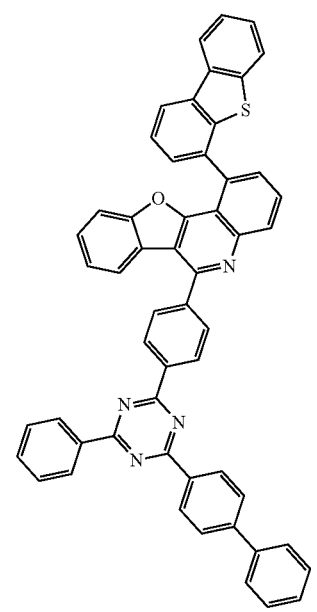
734
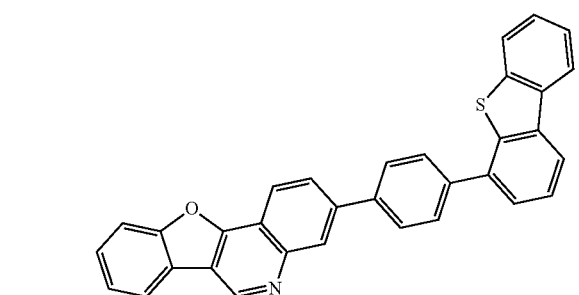

969
-continued
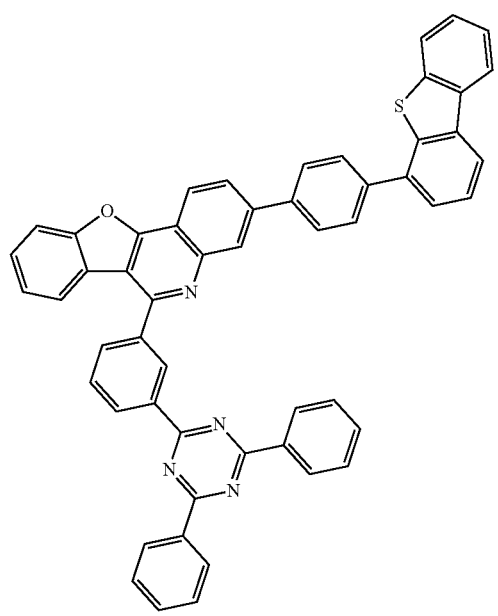
735
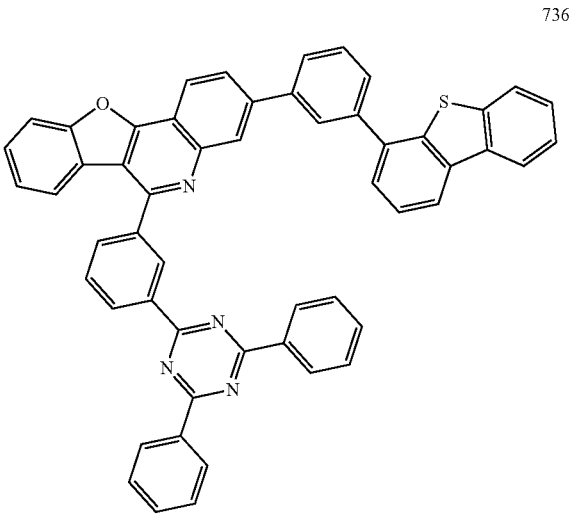
736
737
970
-continued
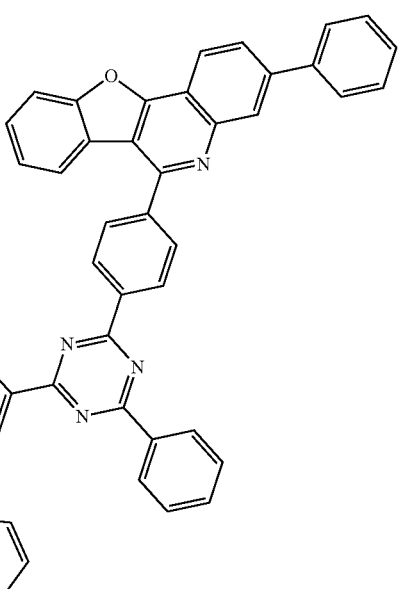
738
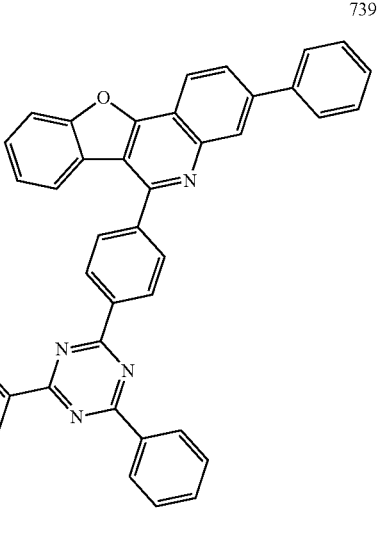
739

-continued
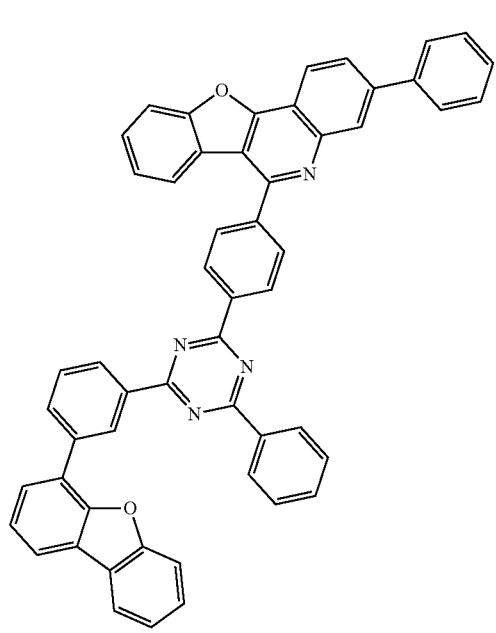
740
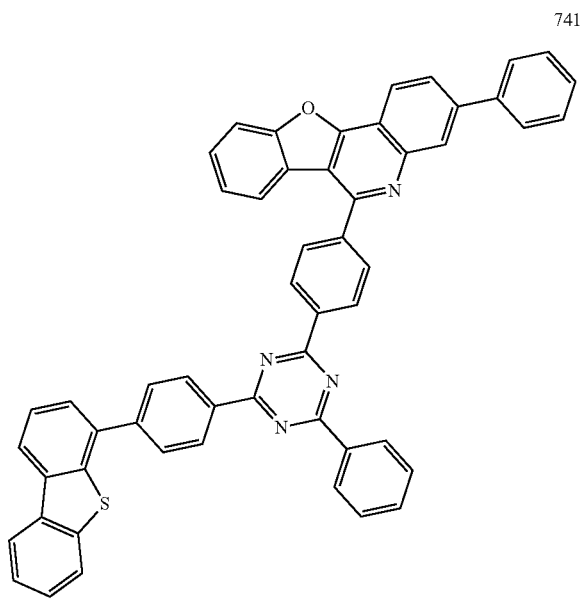
741
-continued
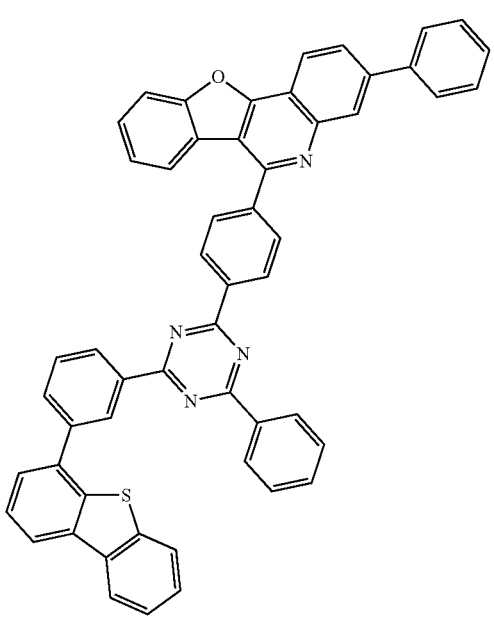
742
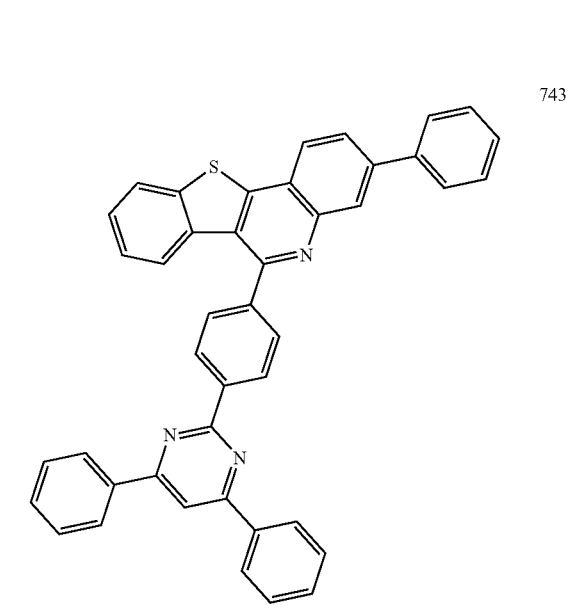
743

973
-continued
744
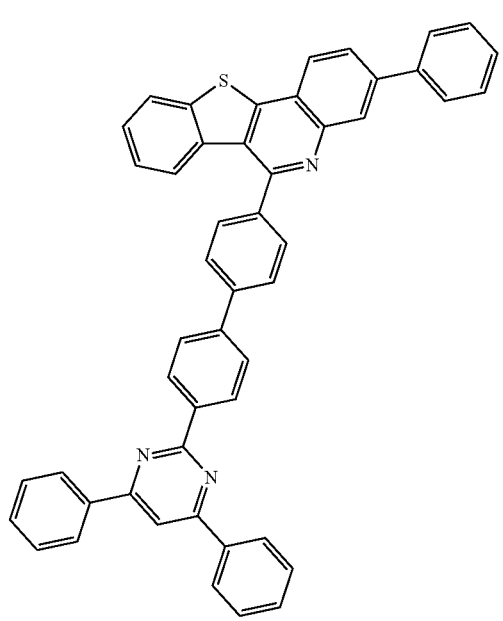
745
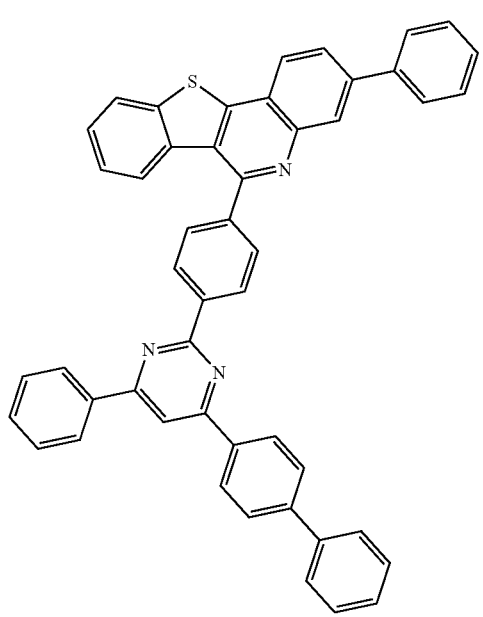
974
-continued
746
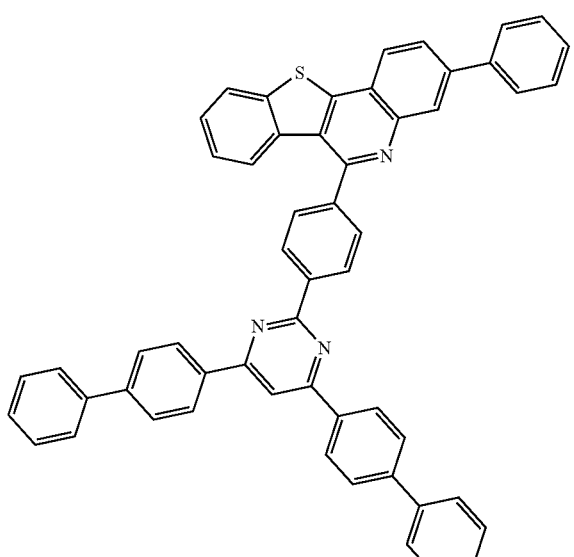
747
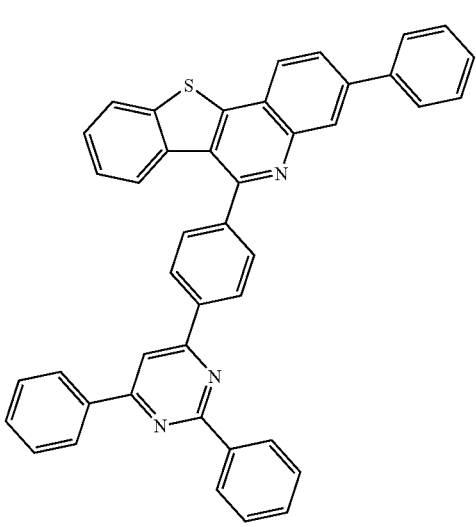

975
-continued
976
-continued
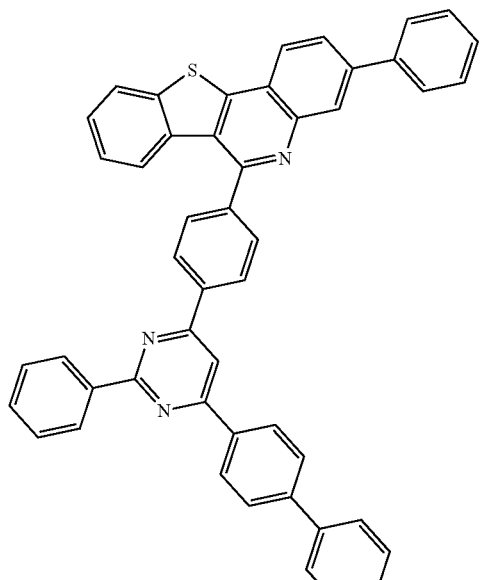
748
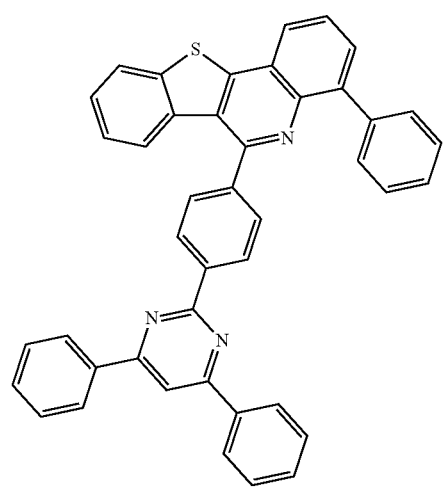
750
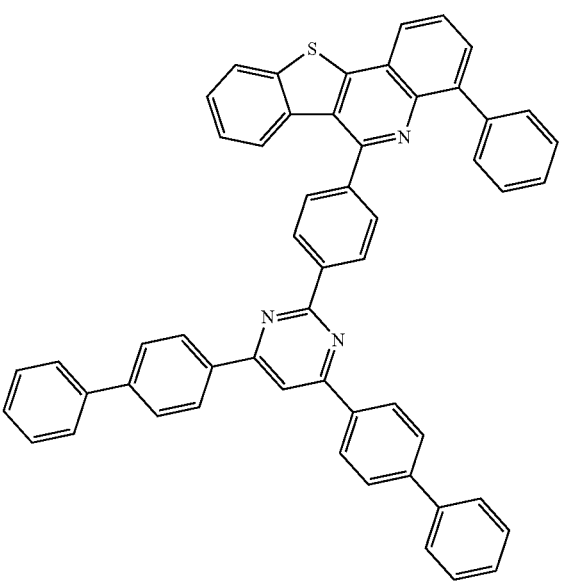
751
749
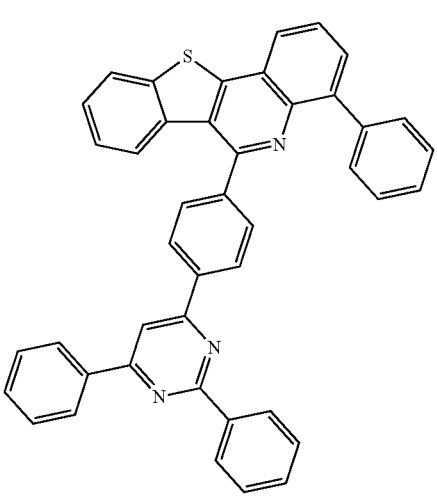
752

977
-continued
753
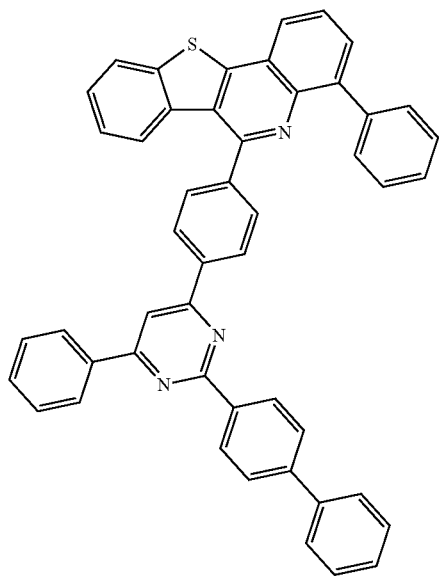
754
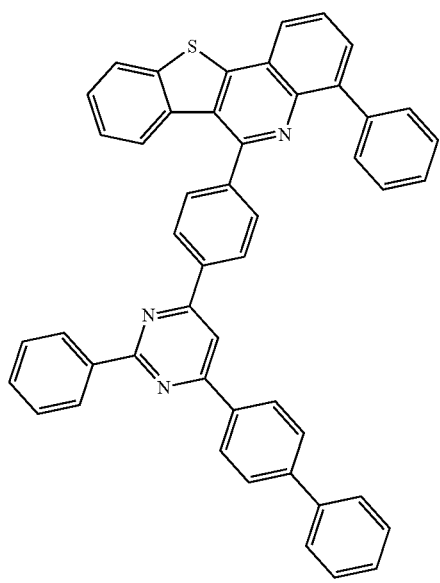
755
978
-continued
756
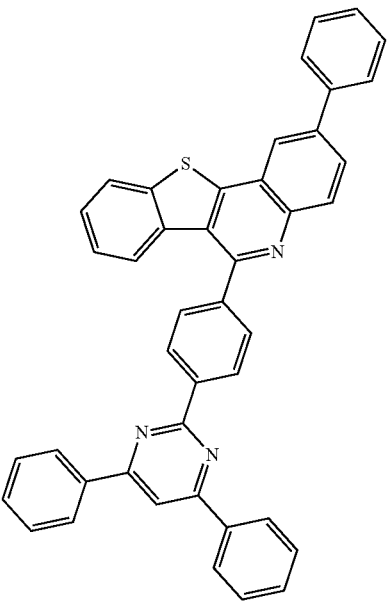
757
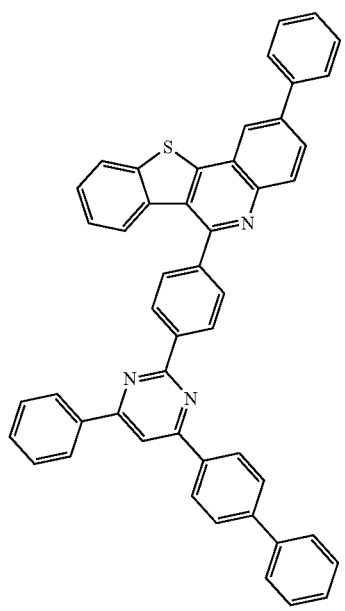

979
-continued
758
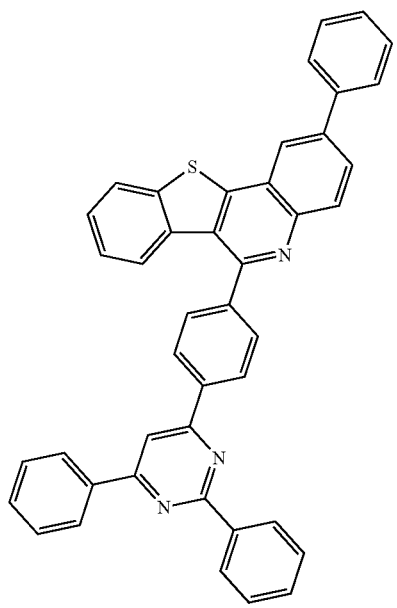
759
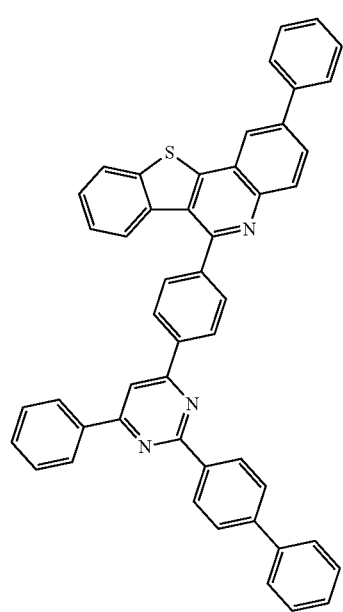
980
-continued
760
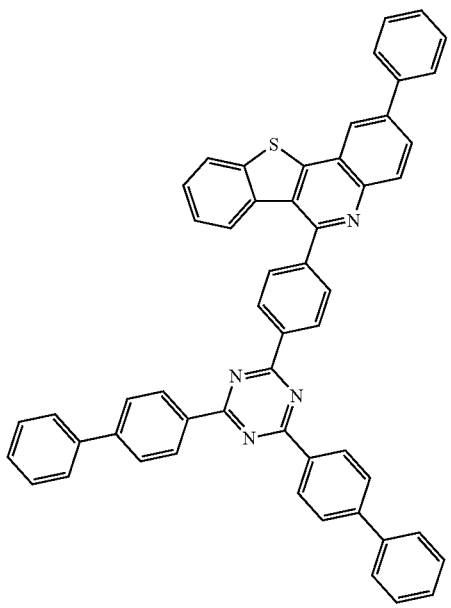
761
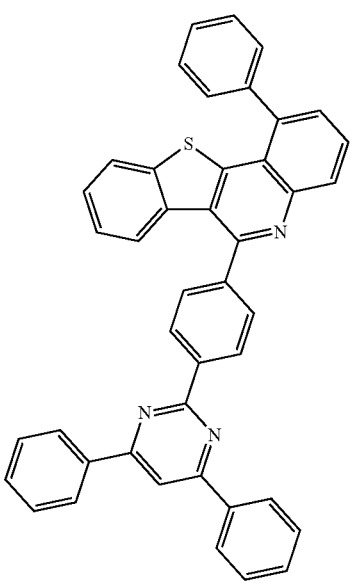

981
-continued
982
-continued
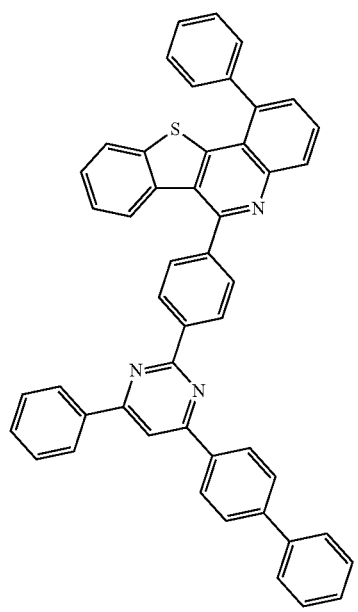
762
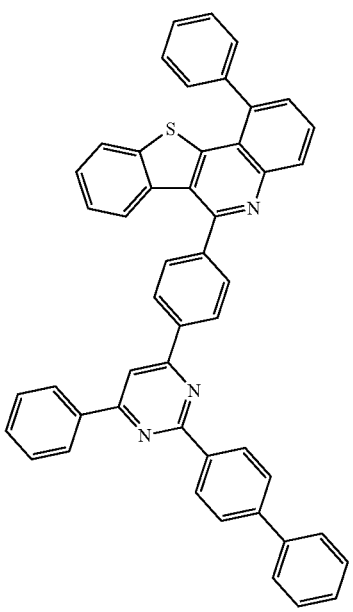
764
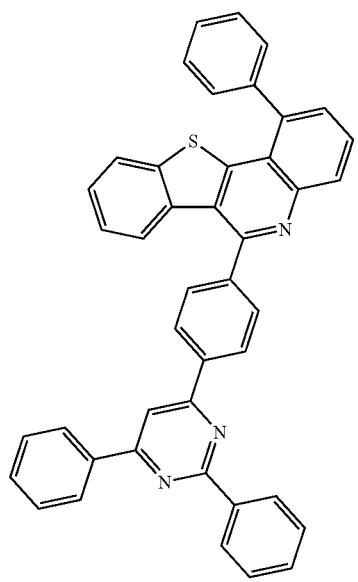
763
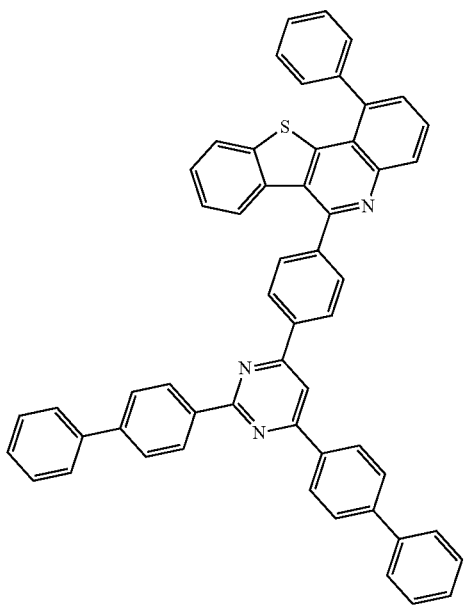
765

983
-continued
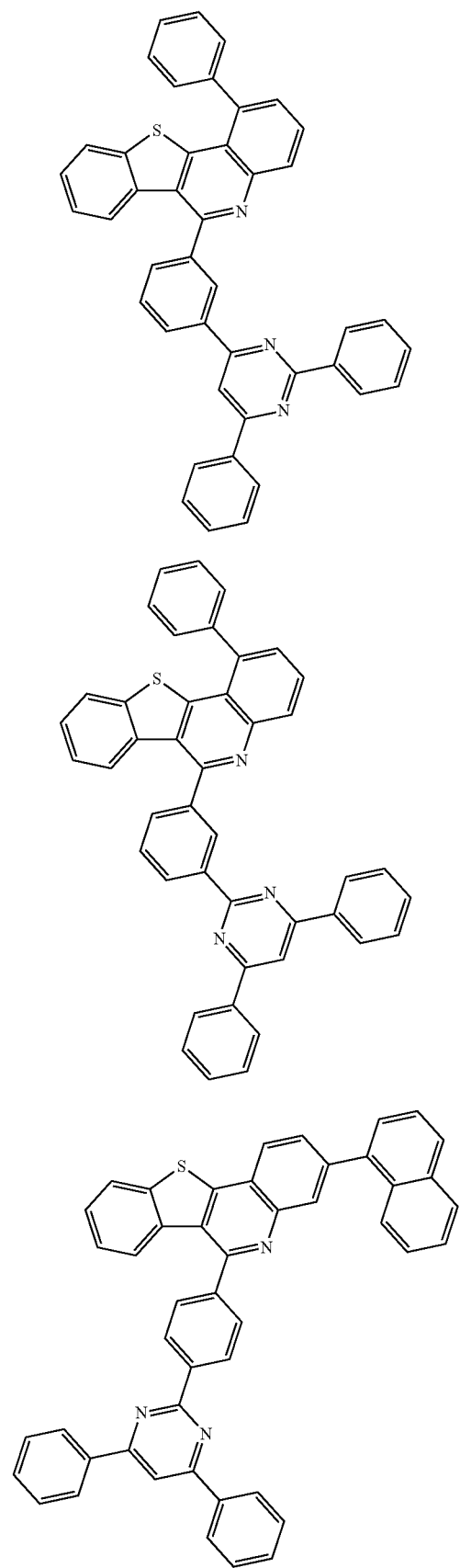
984
-continued
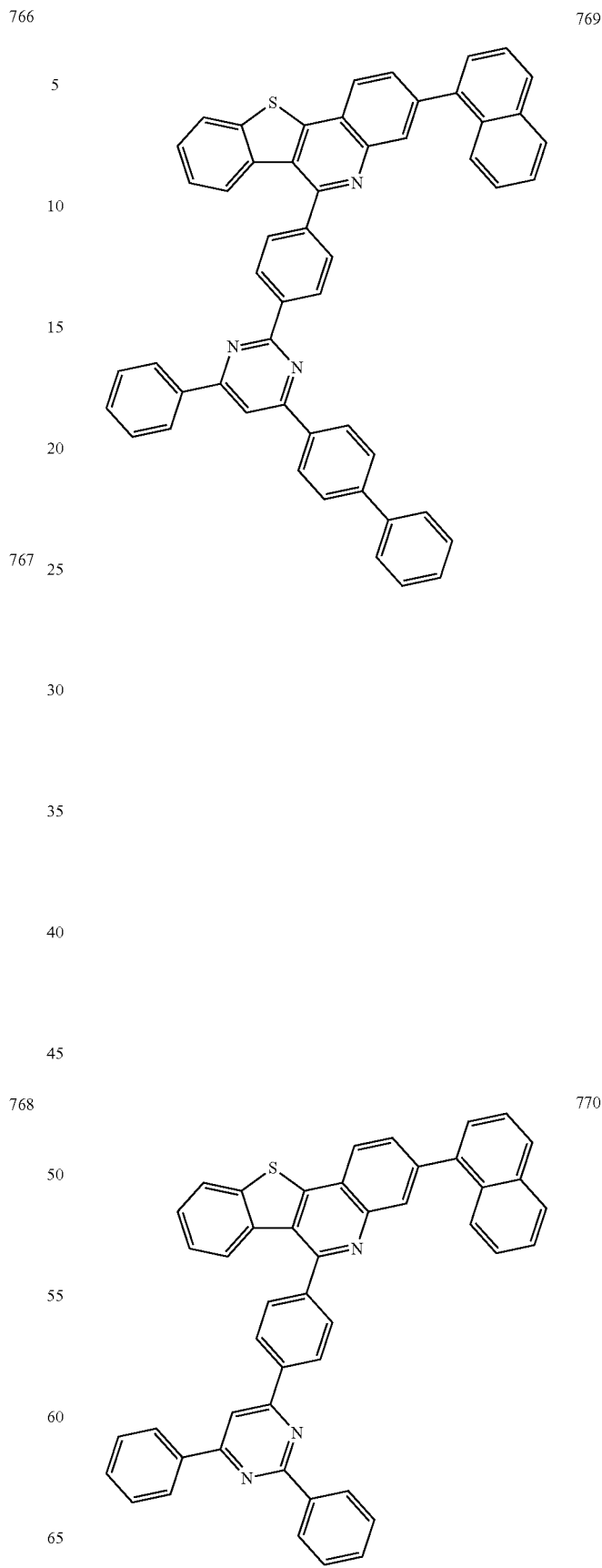

985
-continued
986
-continued
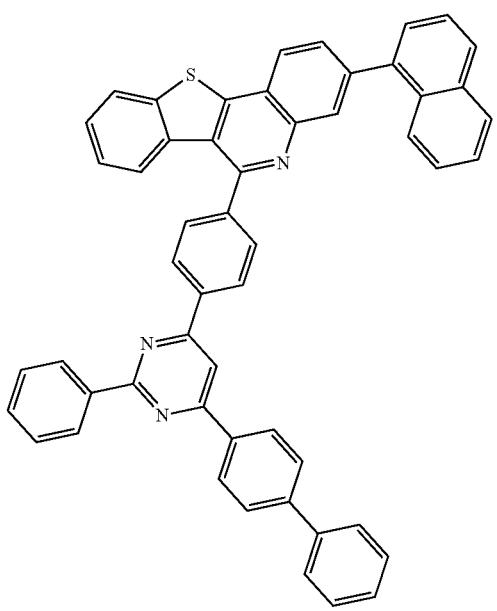
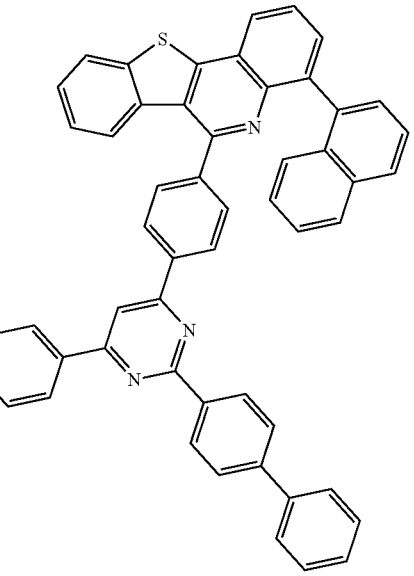
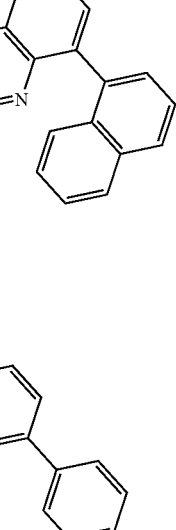
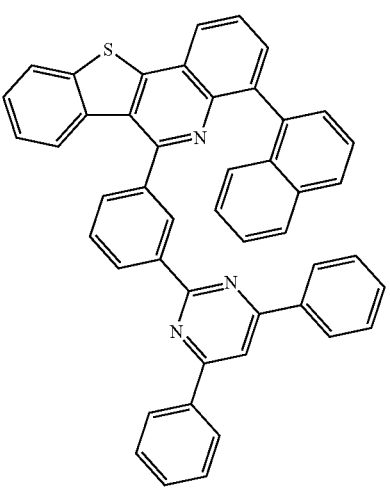

987
-continued
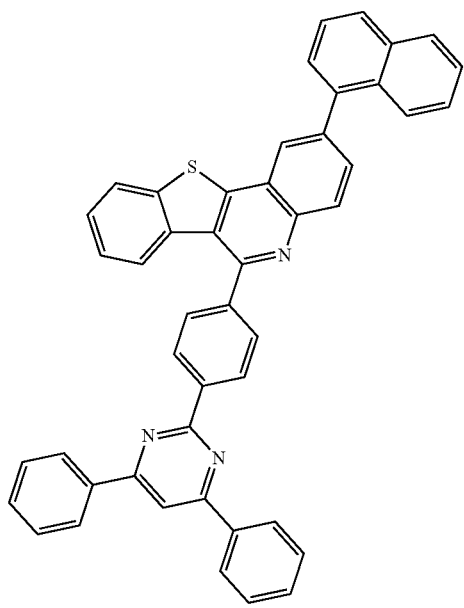
777
988
-continued
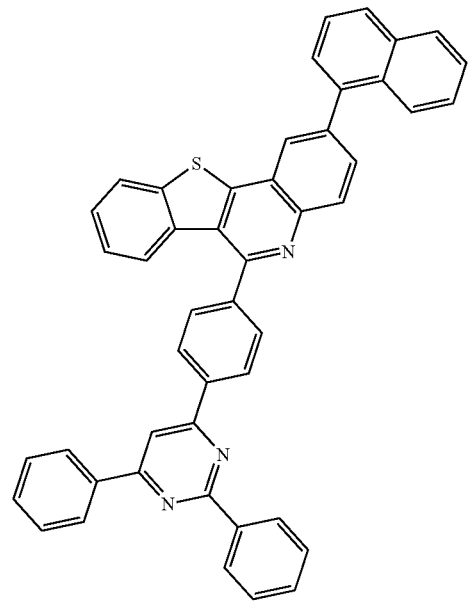
779
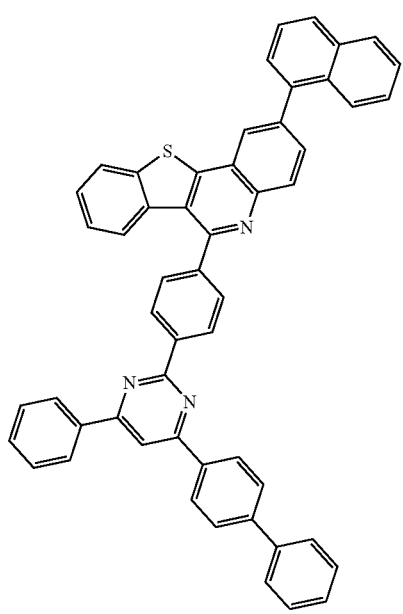
778
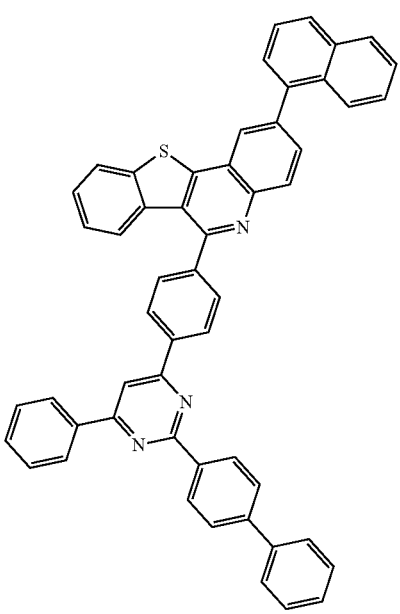
780

989
-continued
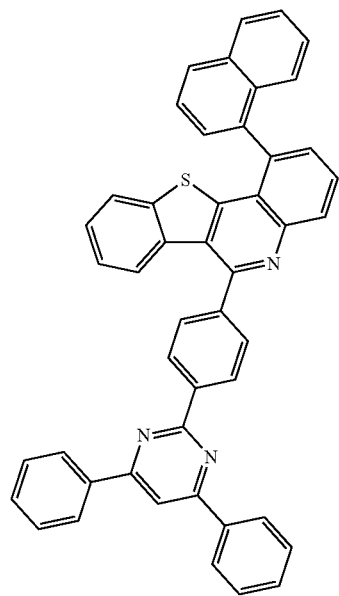
781
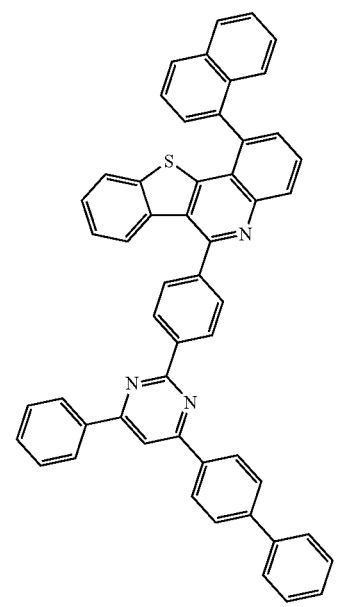
782
990
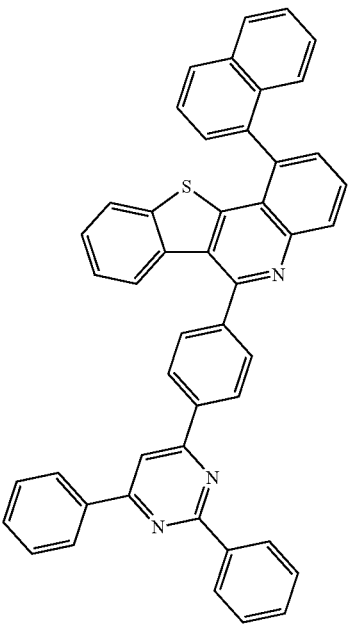
783
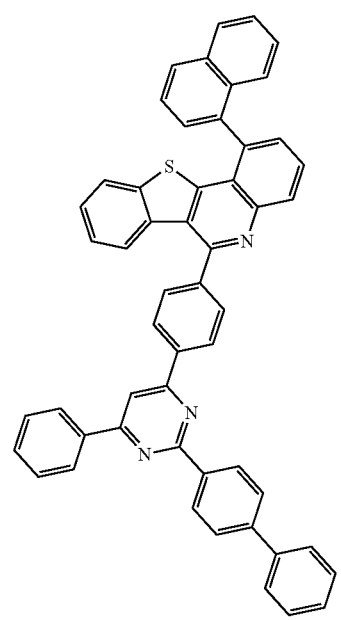
784

991
-continued
992
-continued
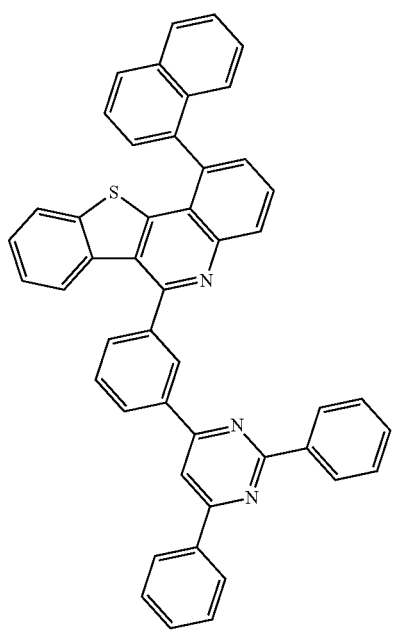
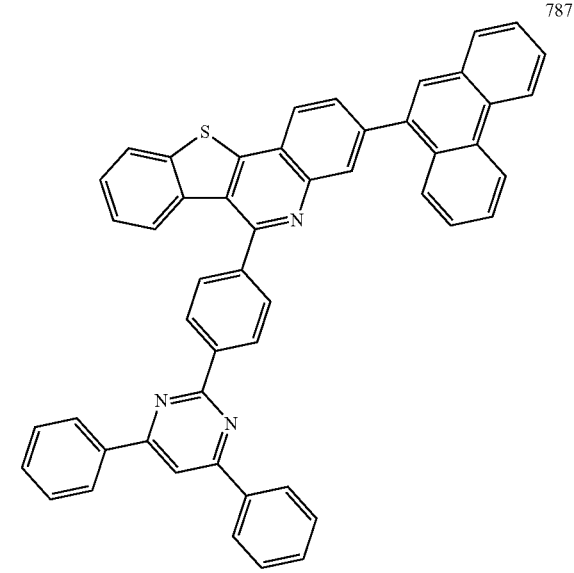

993
-continued
789
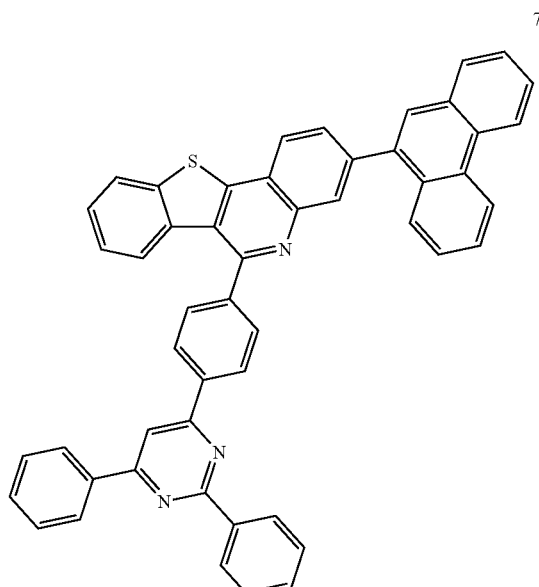
790
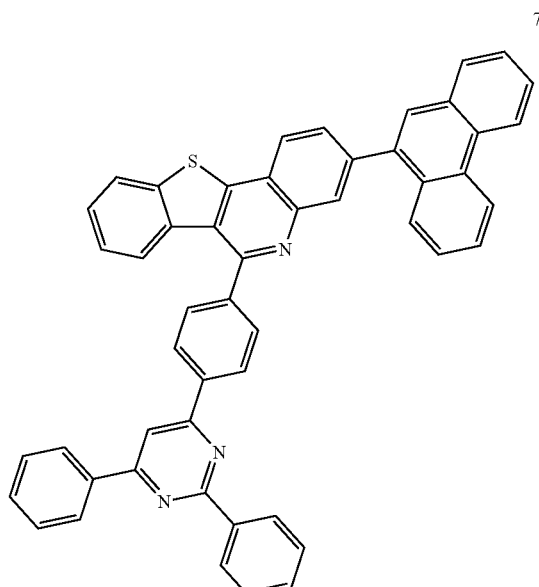
994
-continued
791
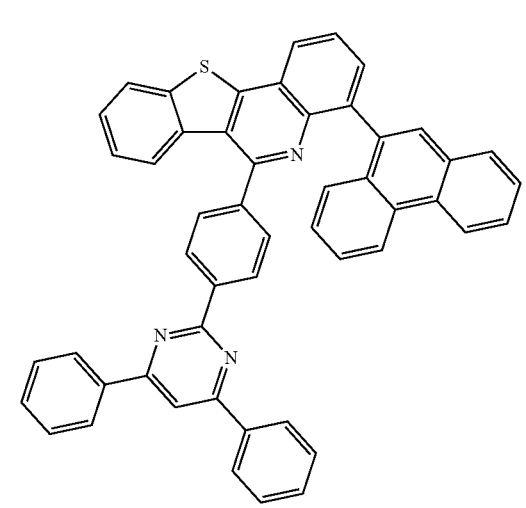
792
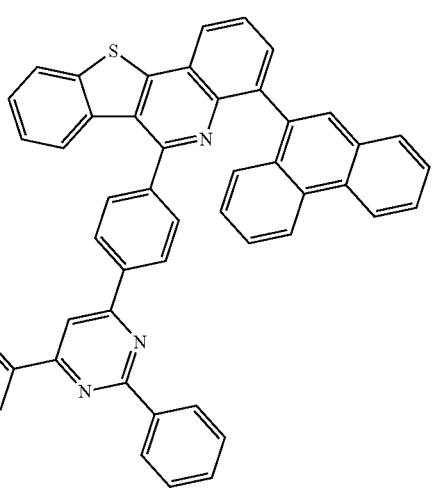
793
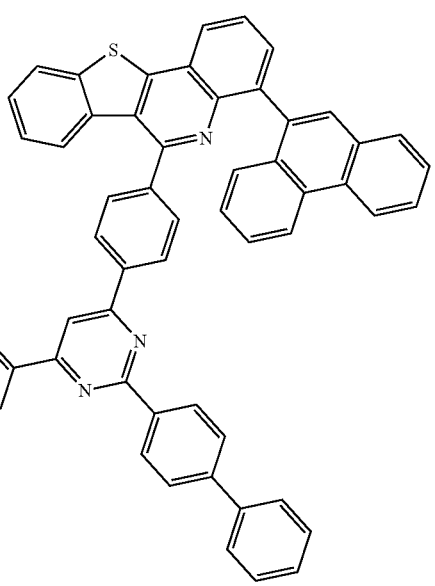

995
-continued
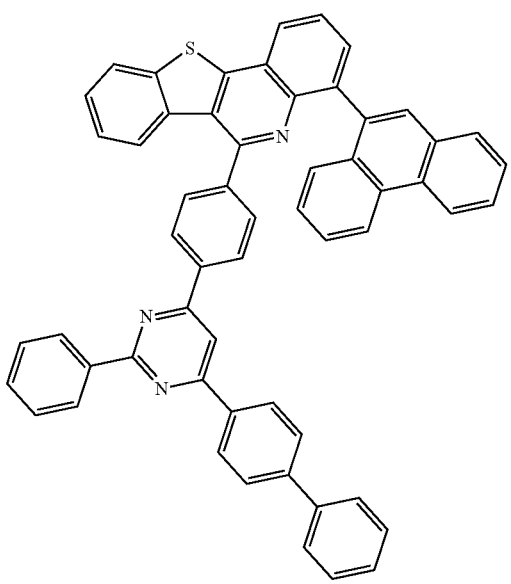
996
-continued
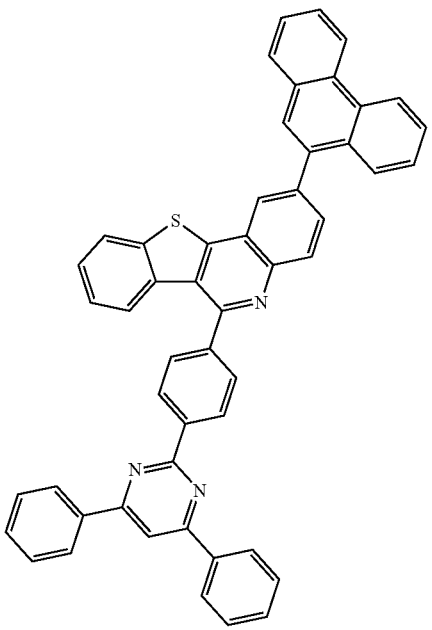
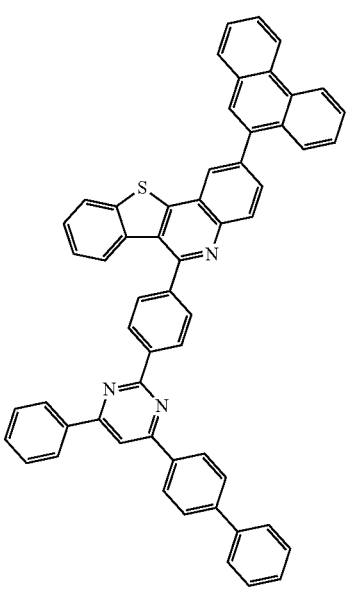

997
-continued
798
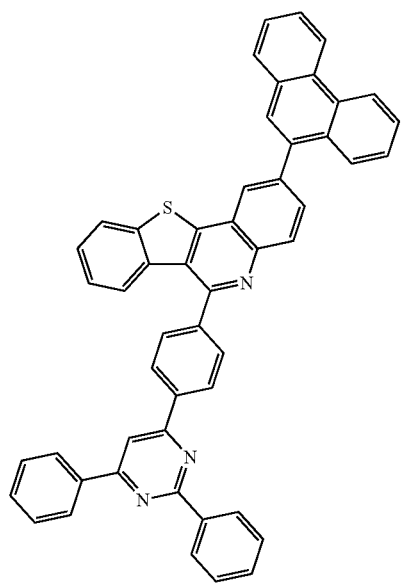
799
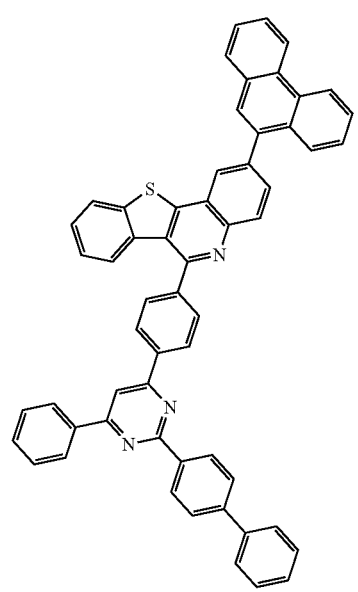
998
-continued
800
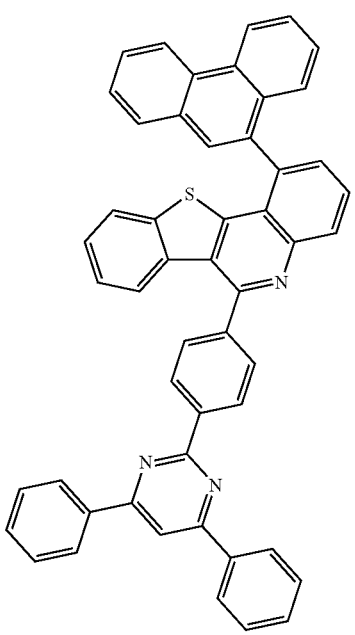
801
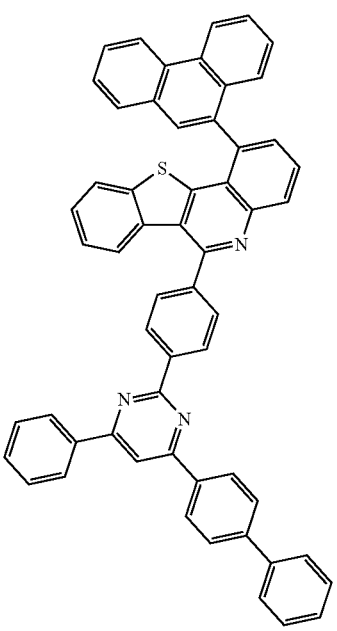

999
-continued
1000
-continued
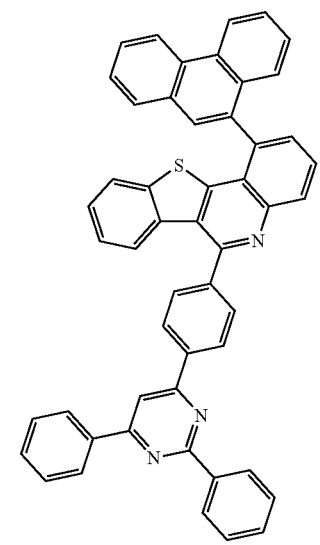
802
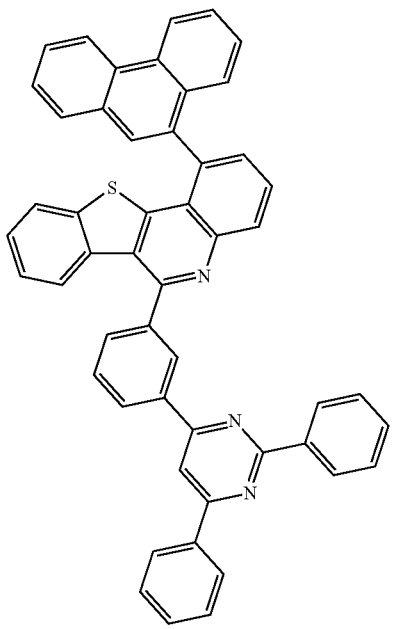
804
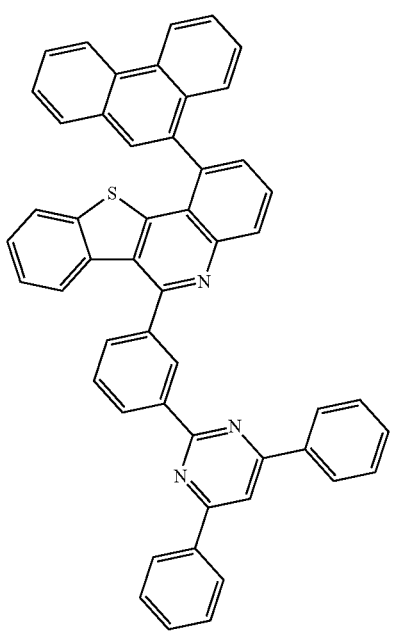
805
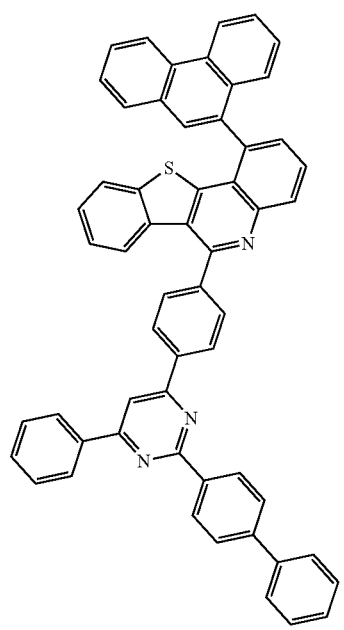
803
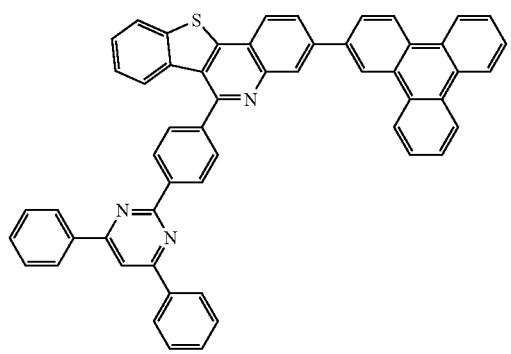
806

1001
-continued
1002
-continued
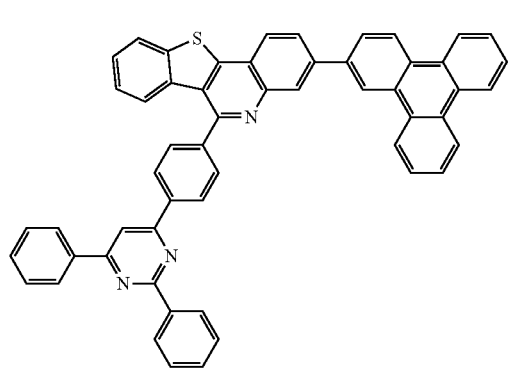
807
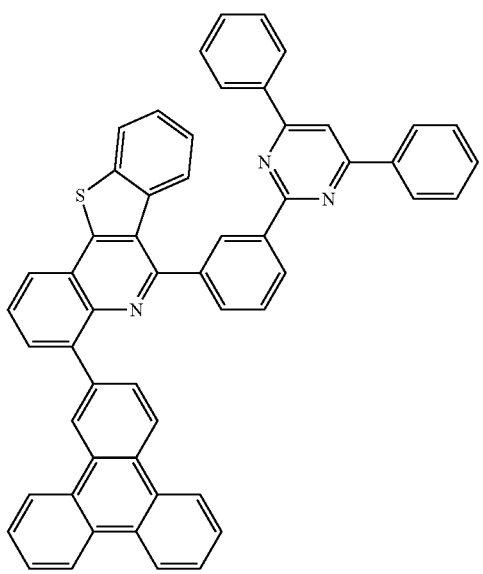
810
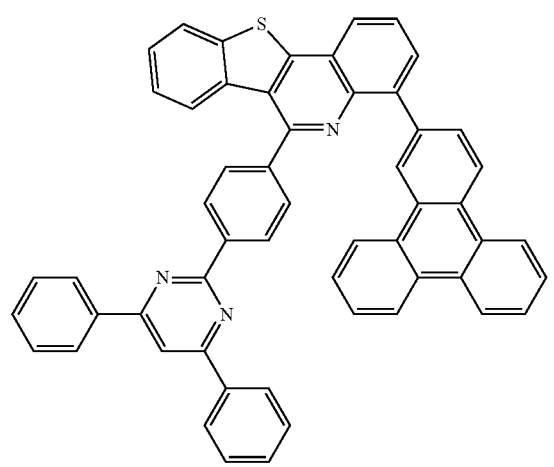
808
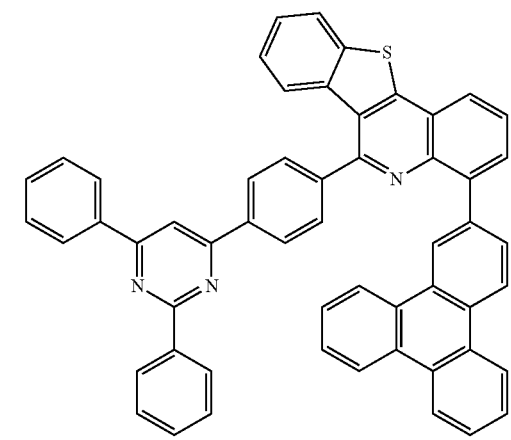
809
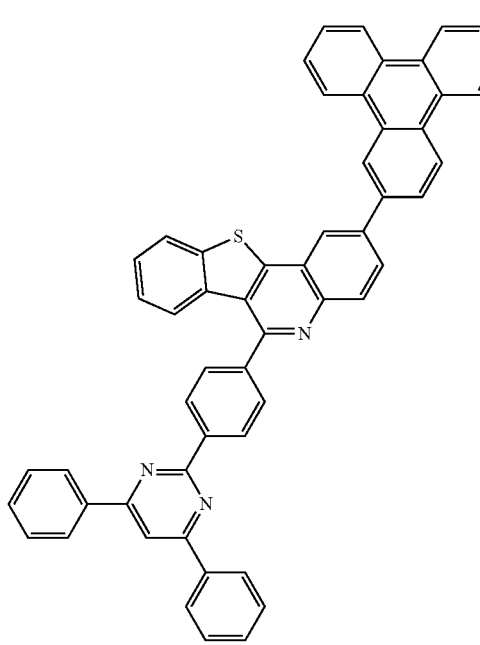
811

1003
-continued
812
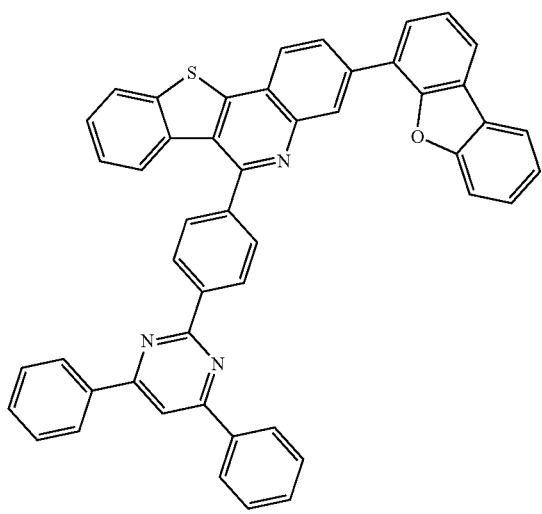
813
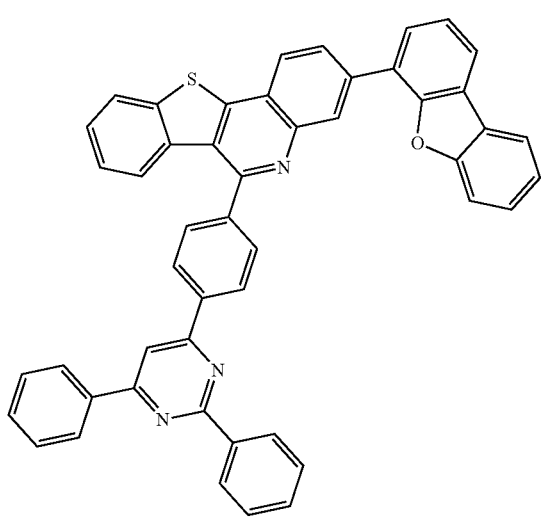
814
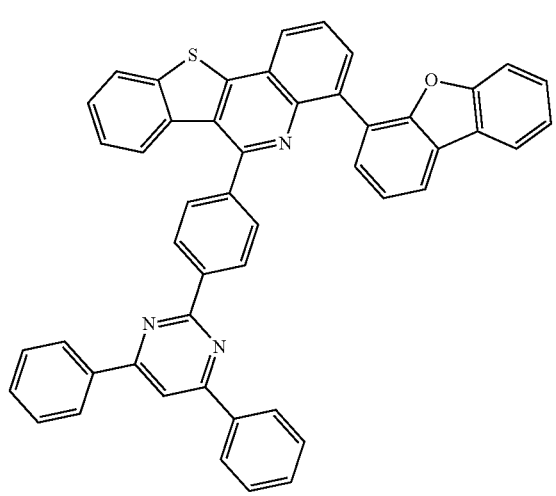
1004
-continued
815
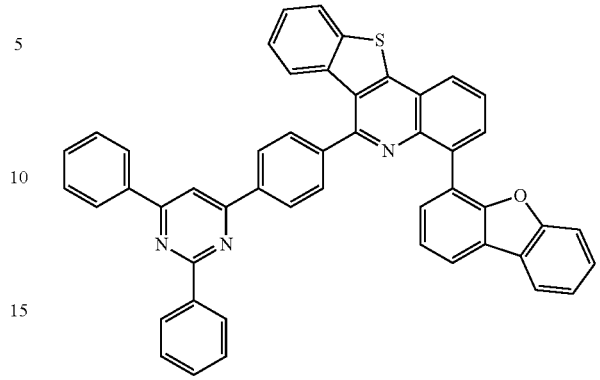
816
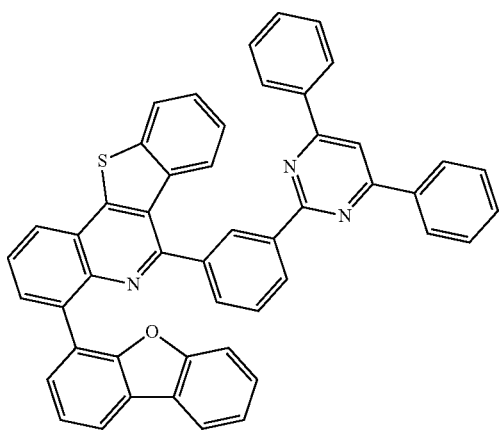
817
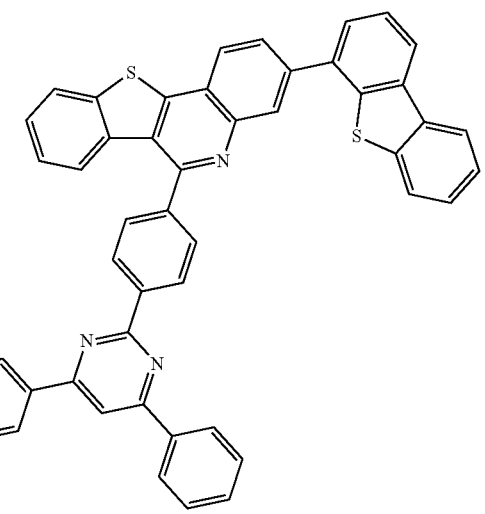

1005
-continued
818
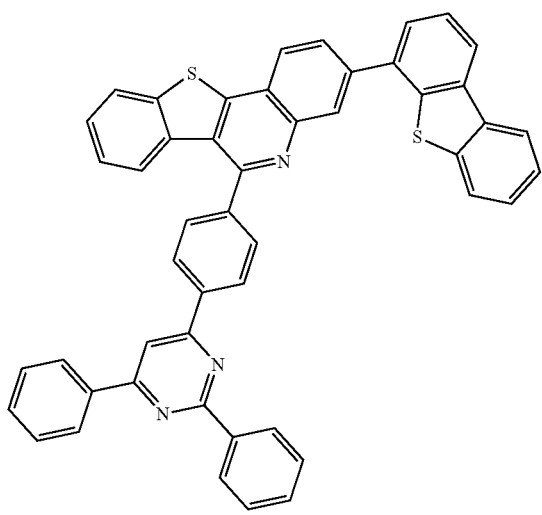
819
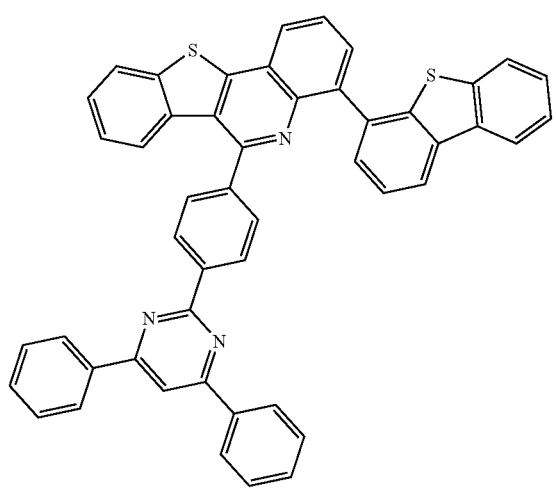
820
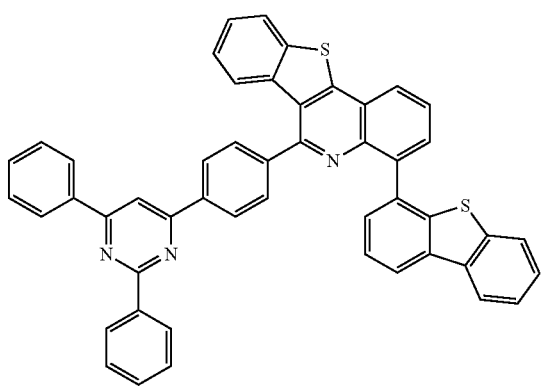
1006
-continued
821
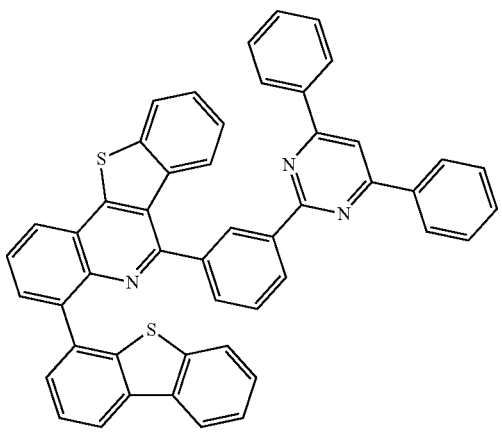
822
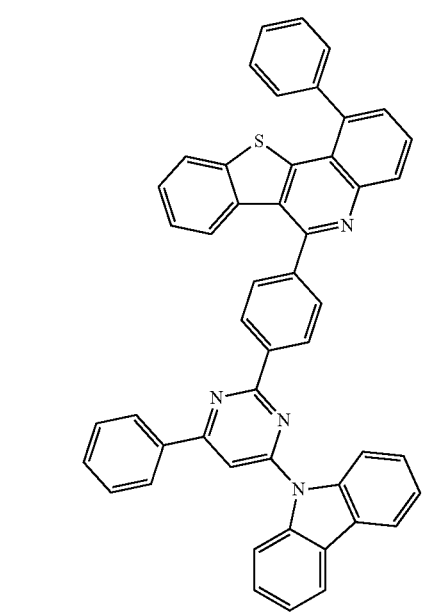

1007
-continued
1008
-continued
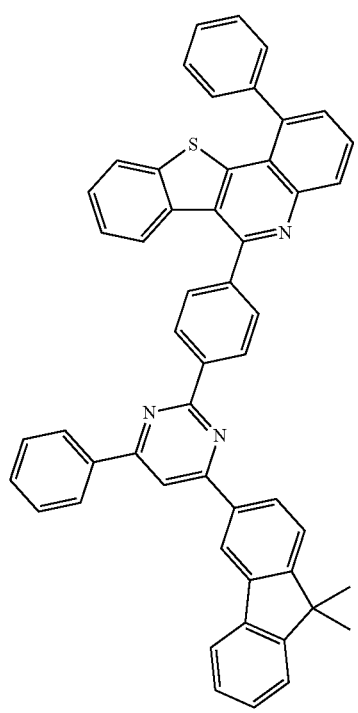
823
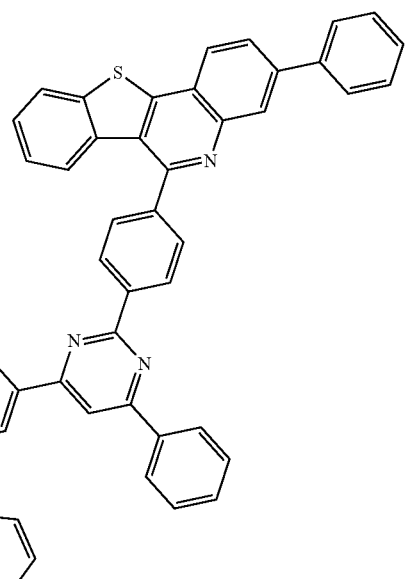
825
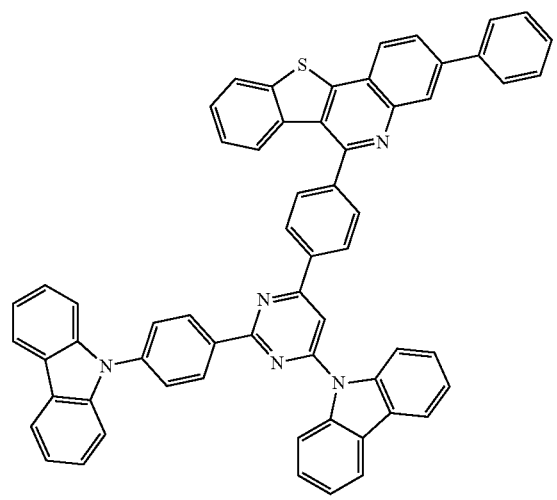
824
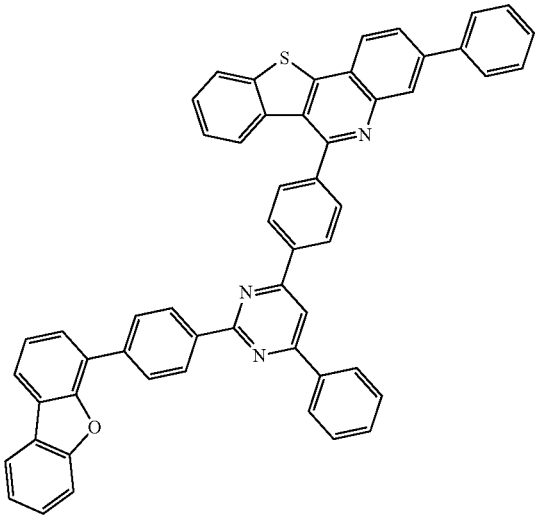
826

1009
-continued
827
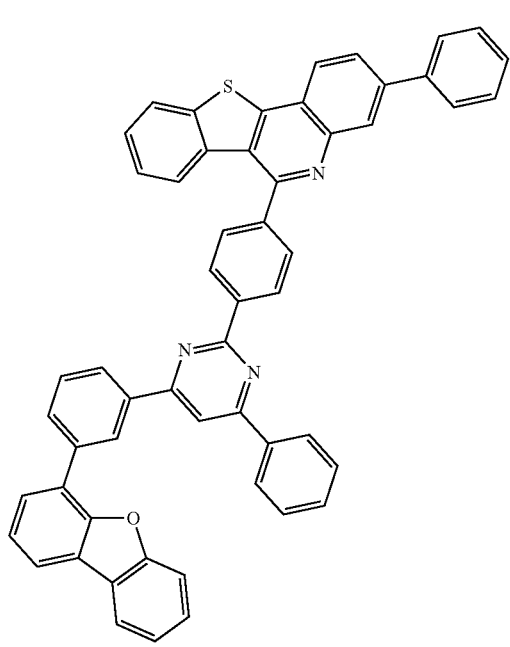
828
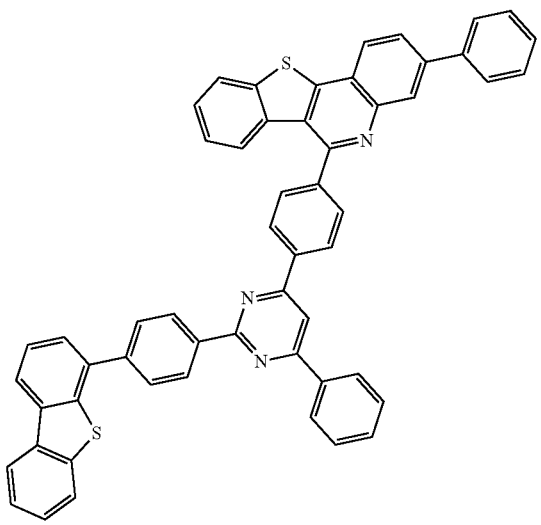
1010
-continued
829
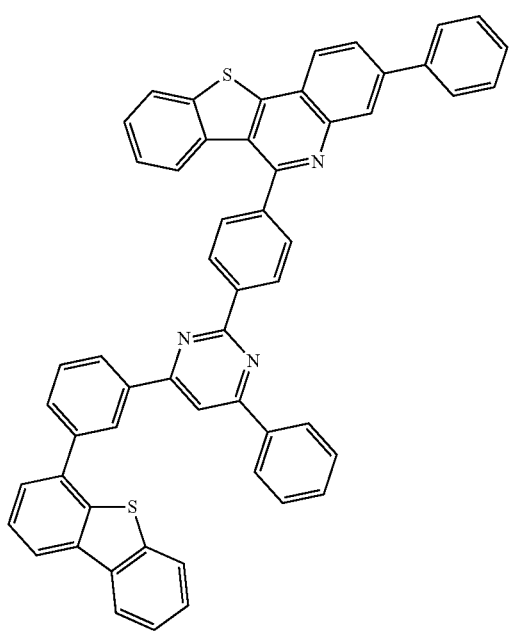
830
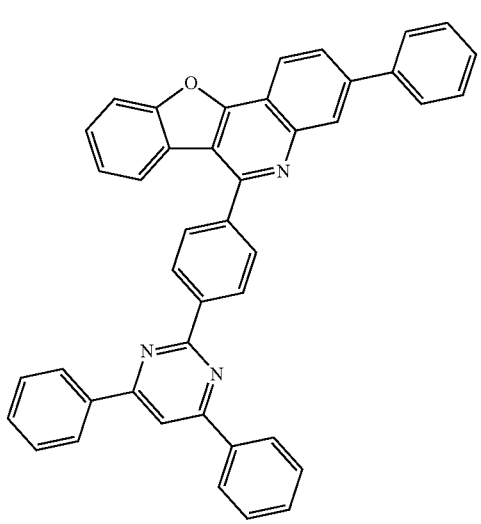

1011
-continued
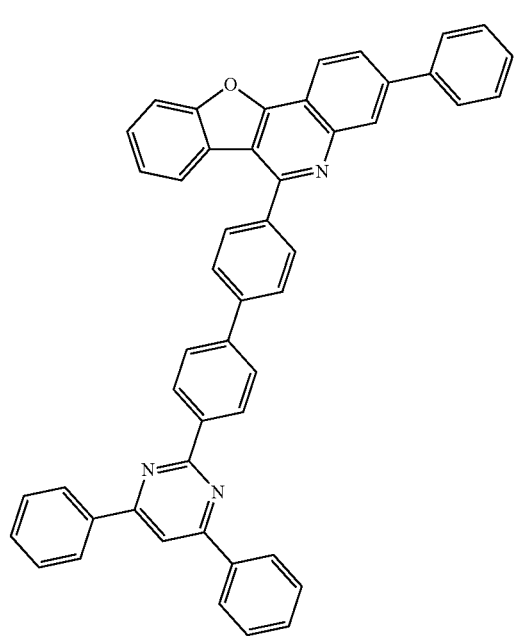
831
1012
-continued
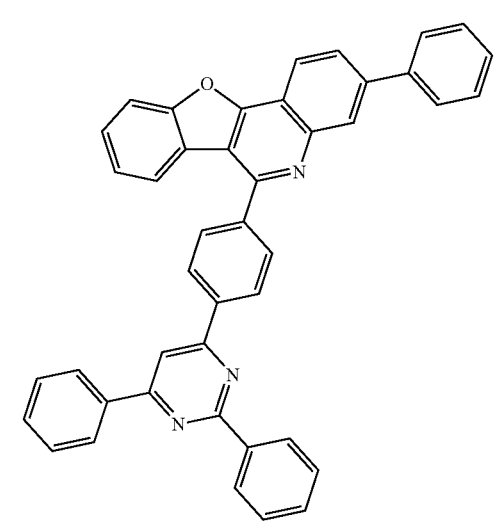
833
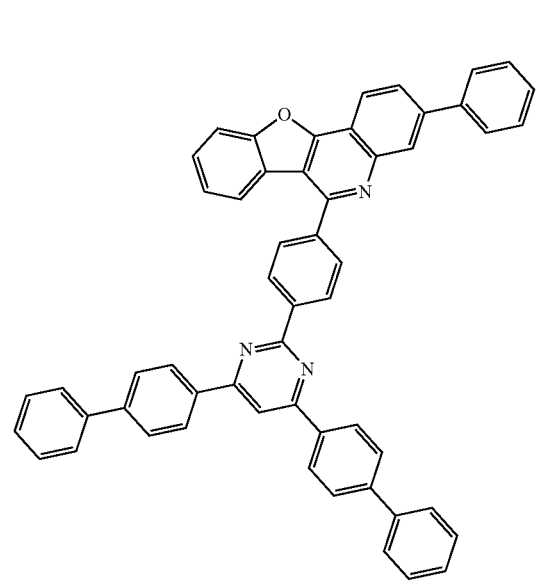
832
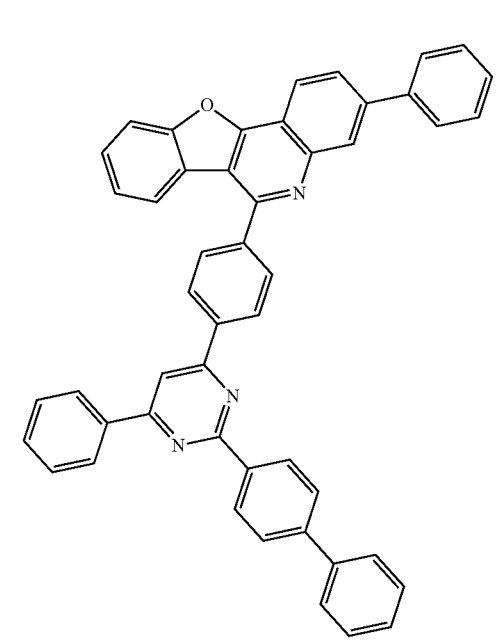
834

1013
-continued
1014
-continued
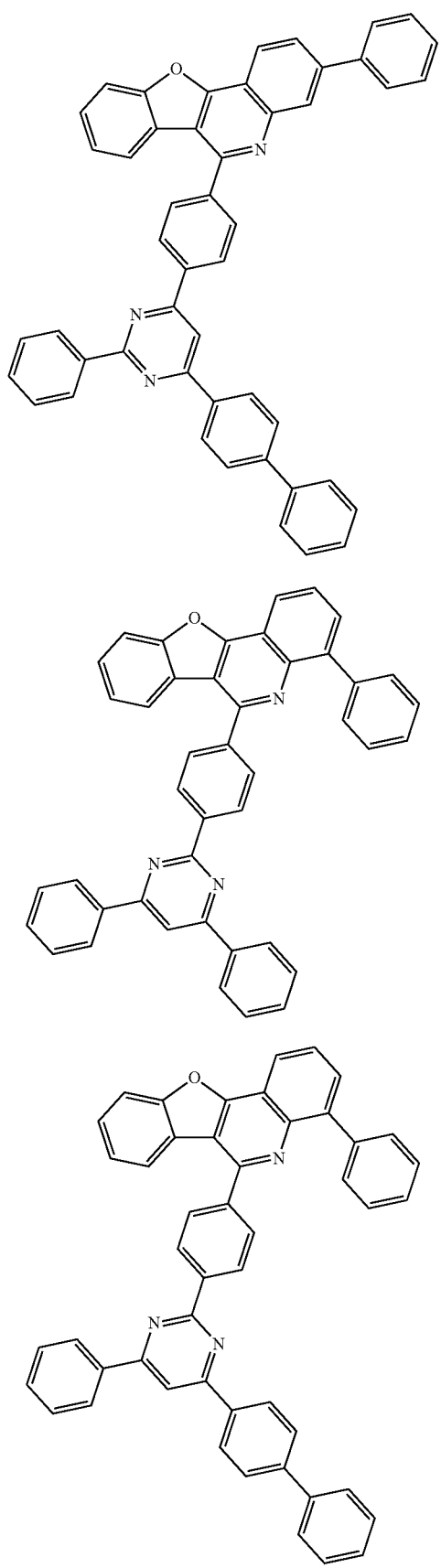
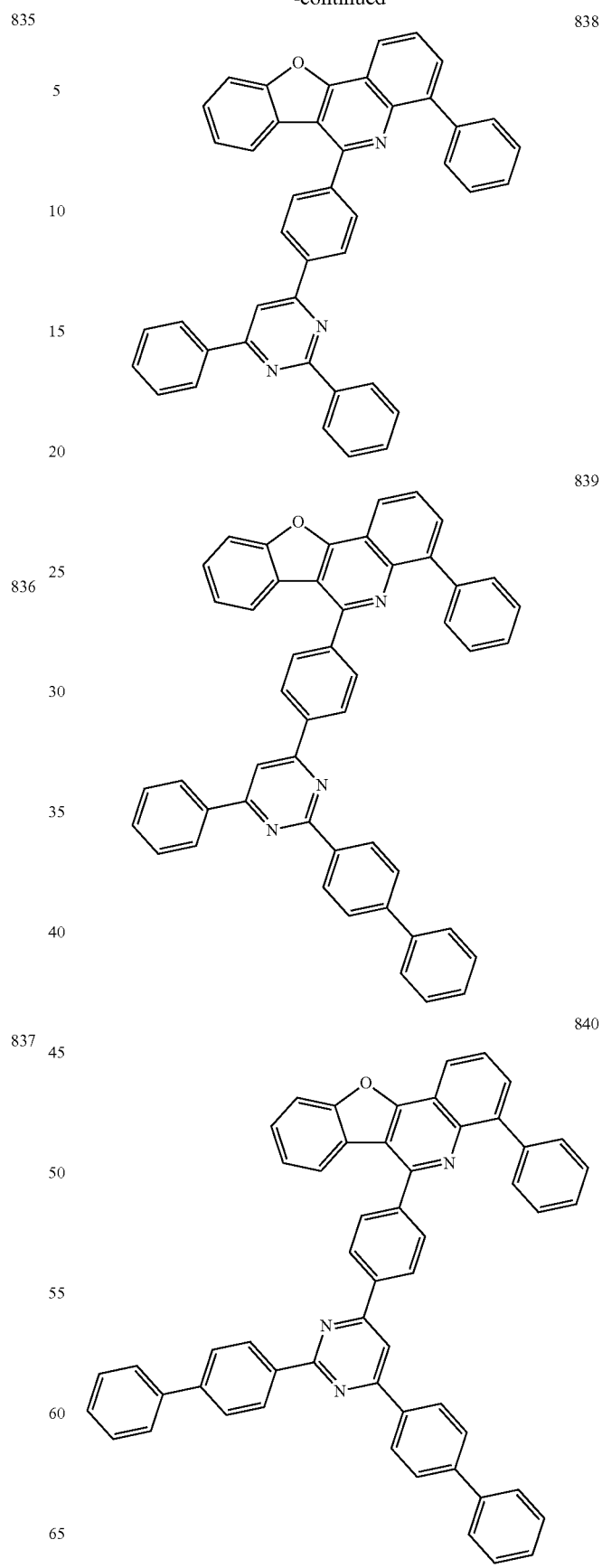

1015
-continued
841
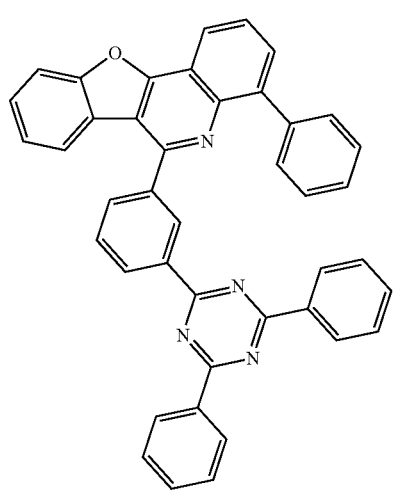
1016
-continued
843
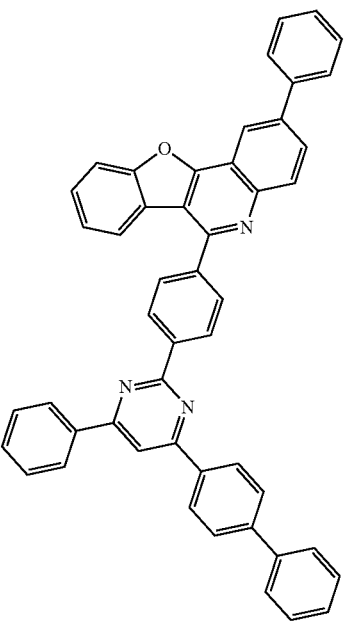
842
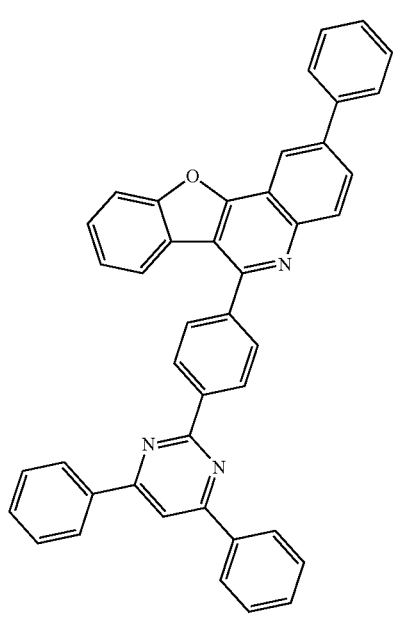
844
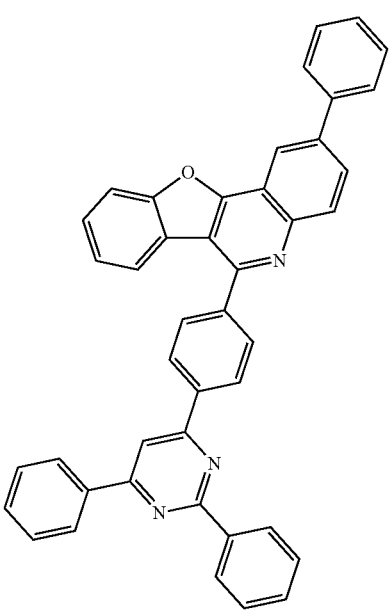

1017
-continued
845
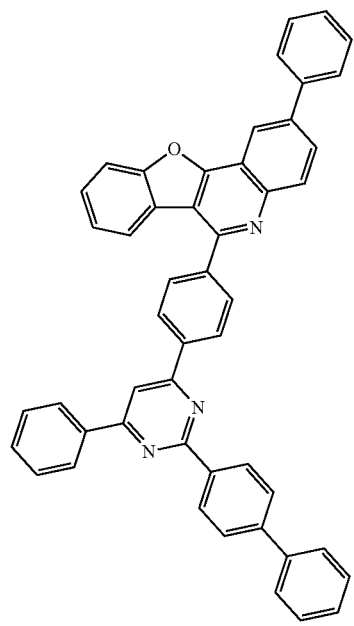
1018
-continued
847
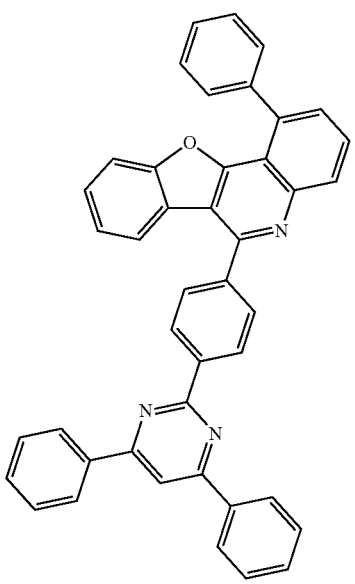
846
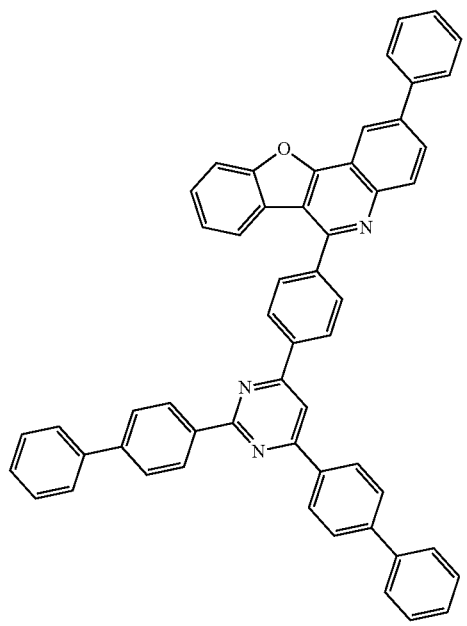
848
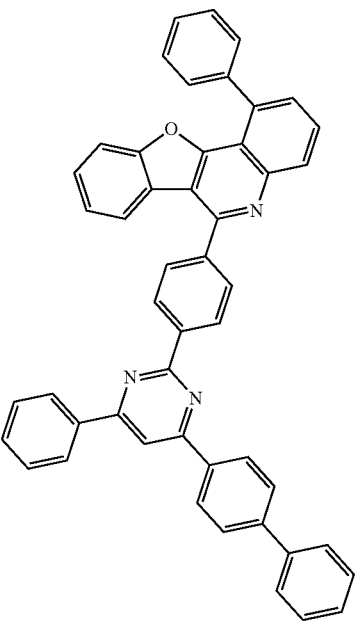

1019
-continued
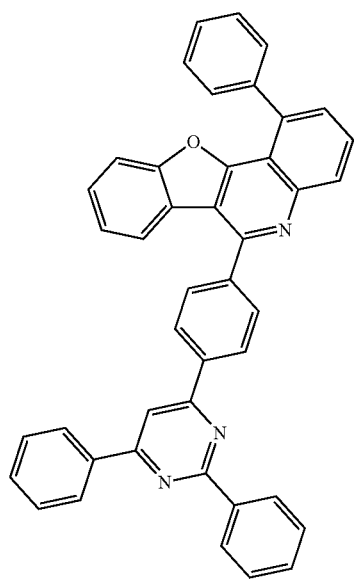
849
1020
-continued
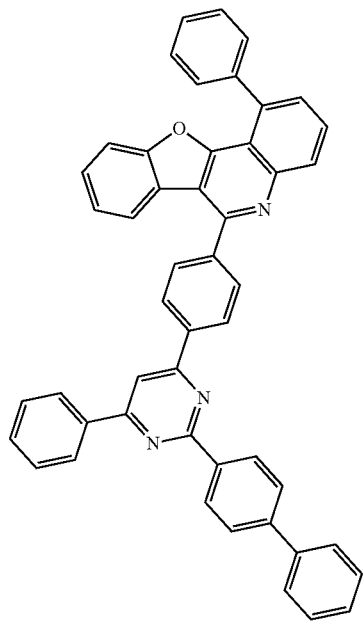
851
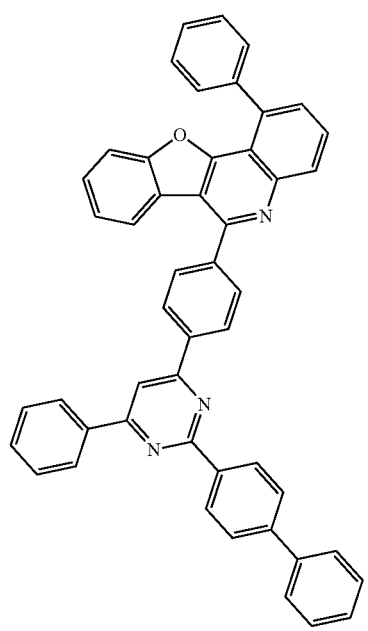
850
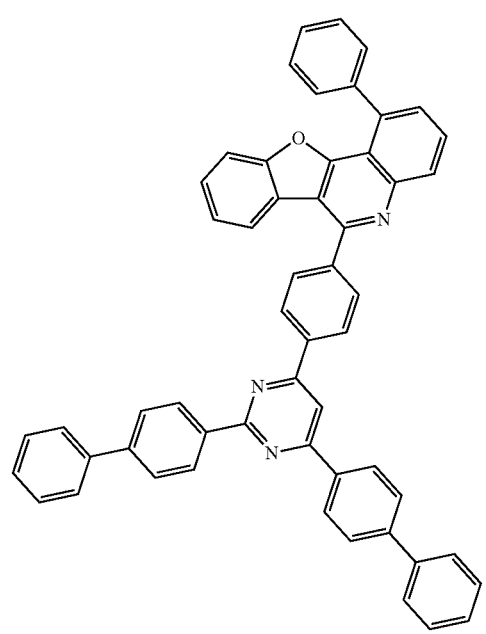
852

1021
-continued
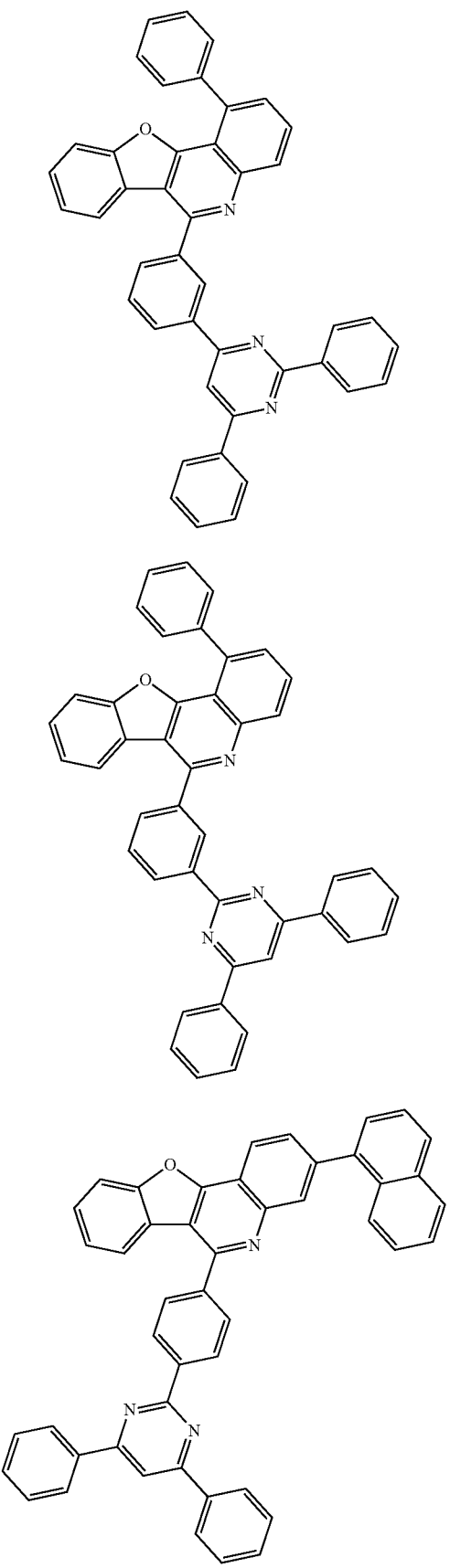
1022
-continued
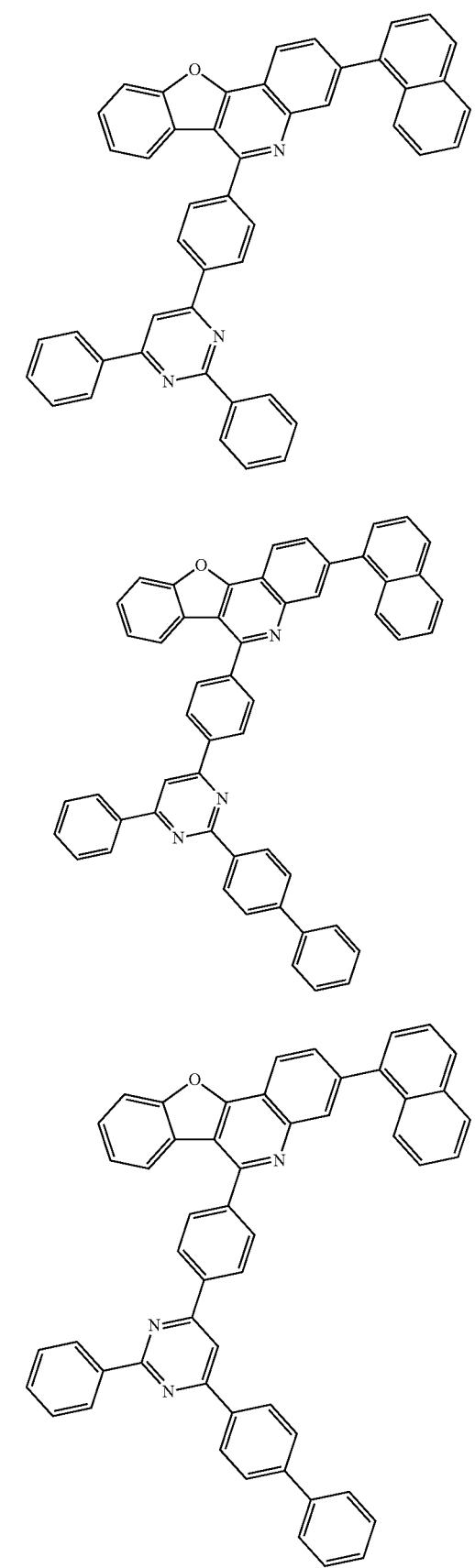

1023
-continued
859
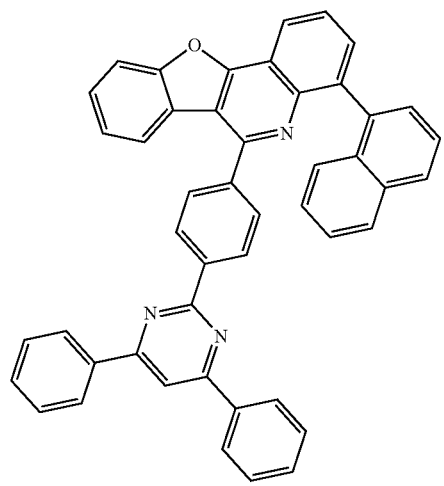
860
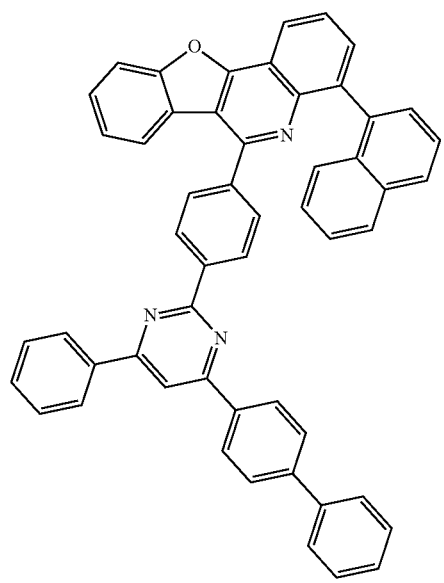
861
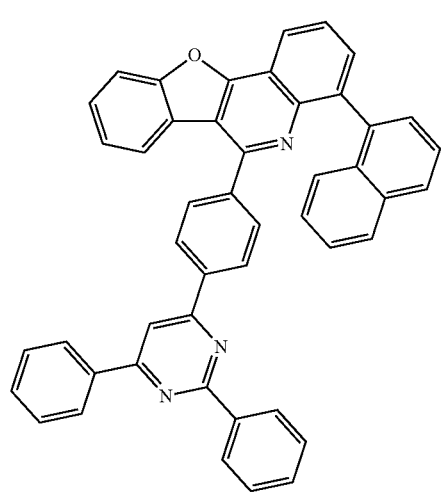
1024
-continued
862
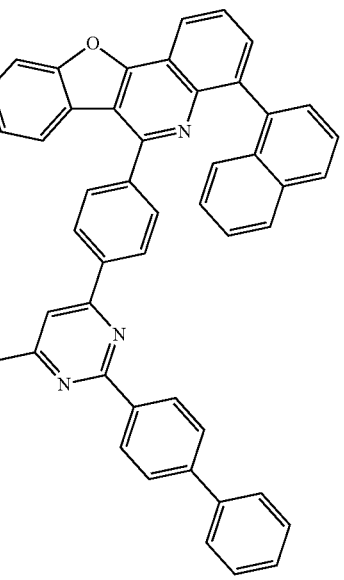
863
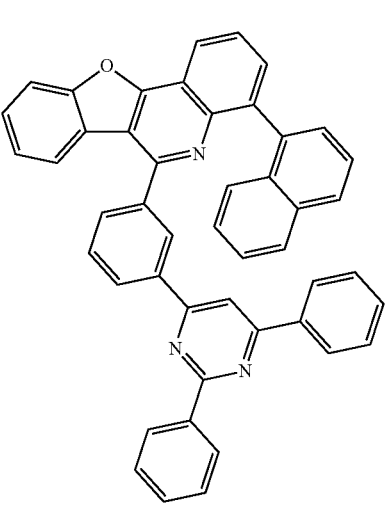
864
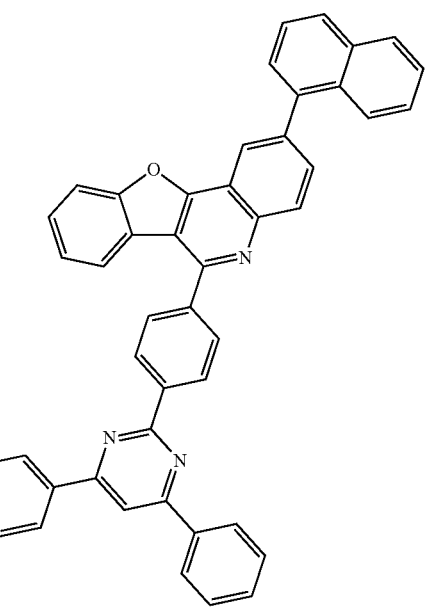

1025
-continued
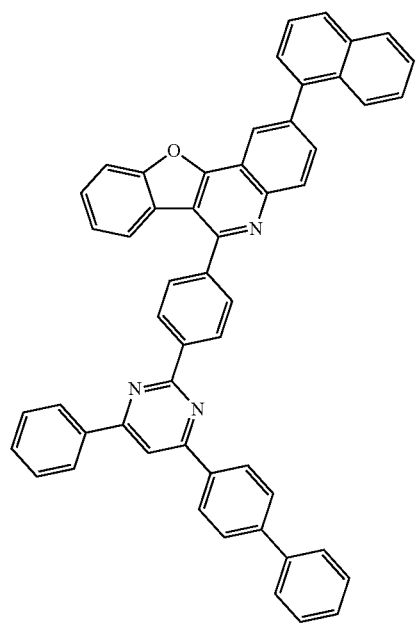
1026
-continued
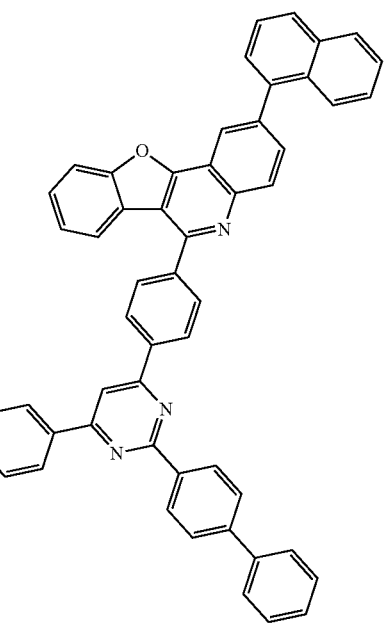
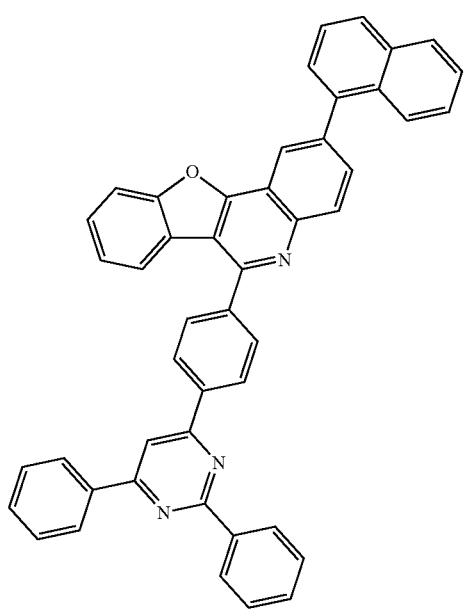
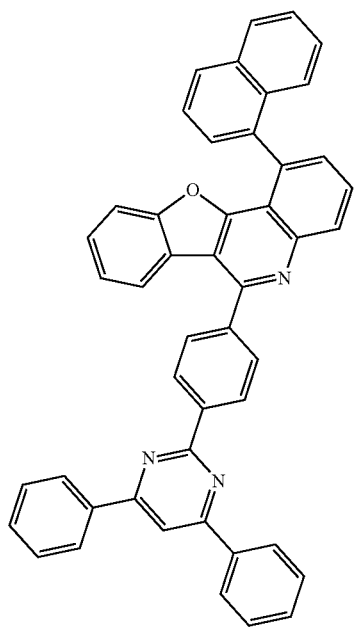

1027
-continued
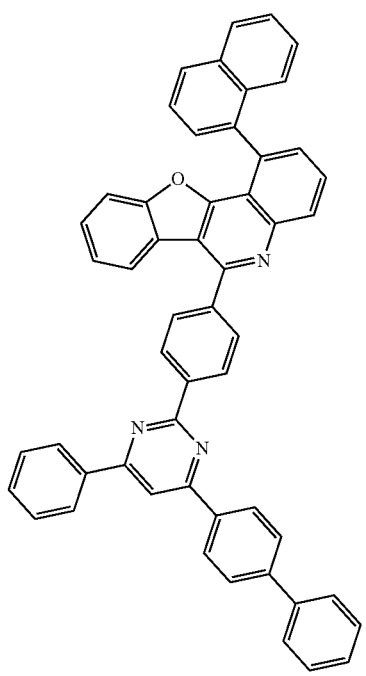
869
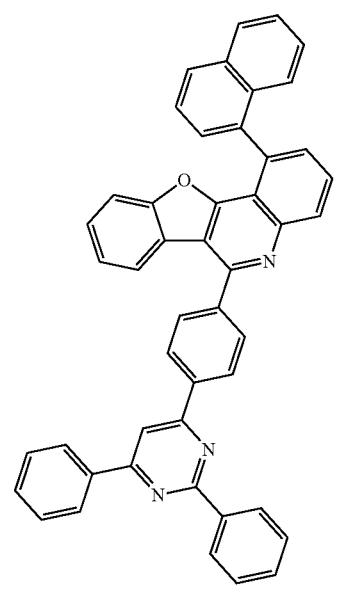
870
1028
-continued
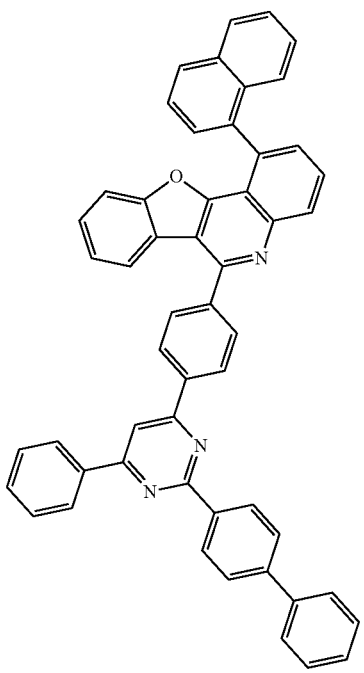
871
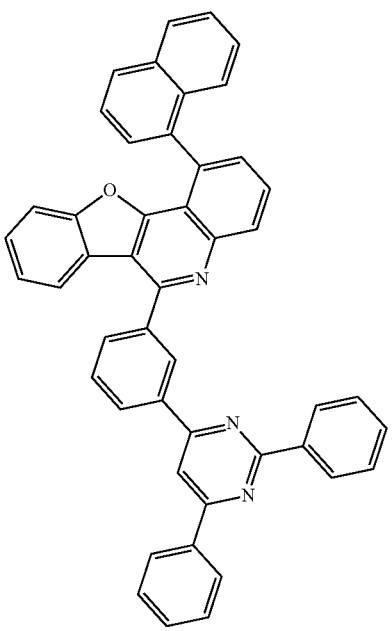
872

1029
-continued
873
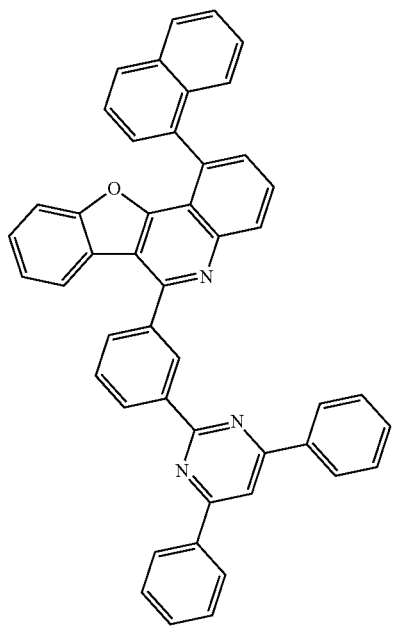
874
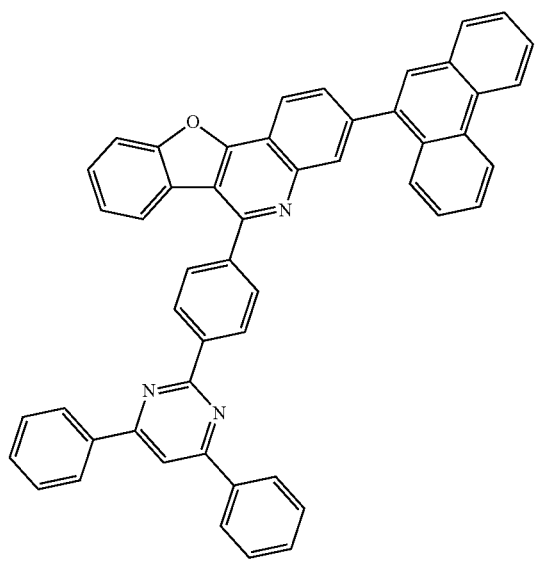
1030
-continued
875
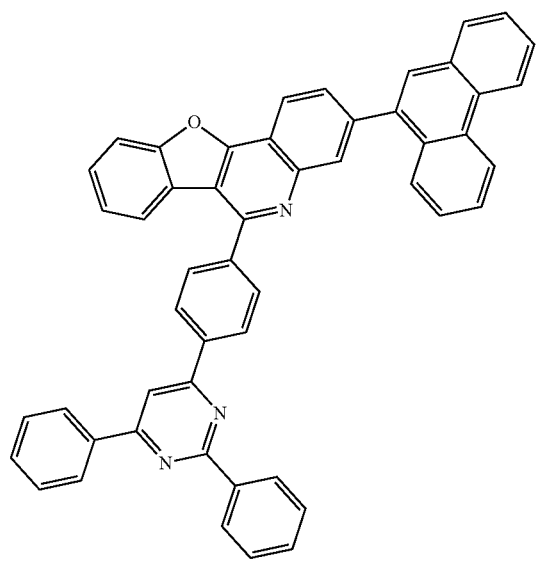
876

1031
-continued
877
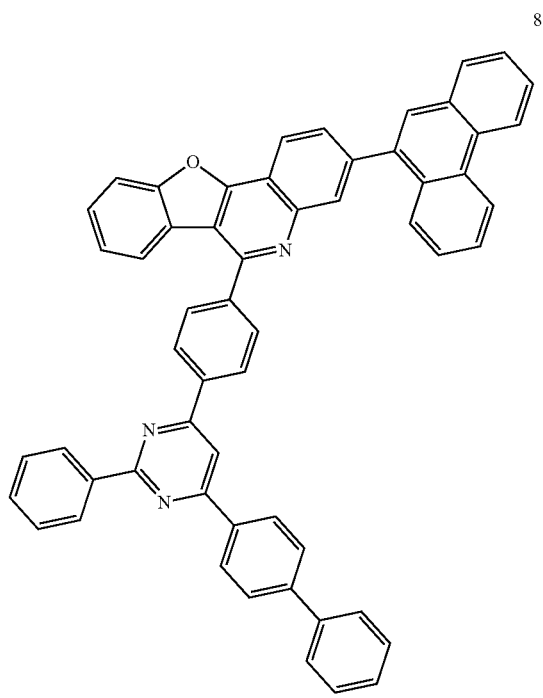
878
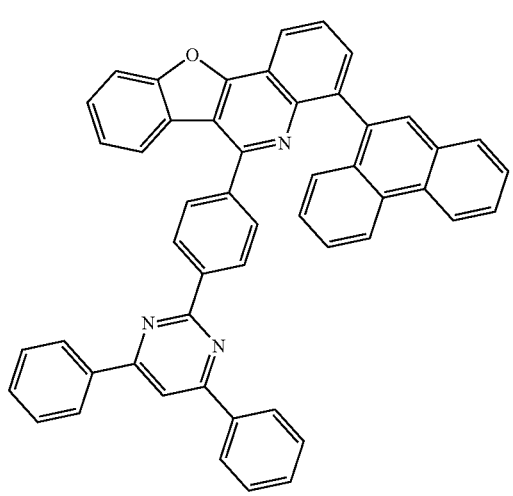
1032
-continued
879
880
881
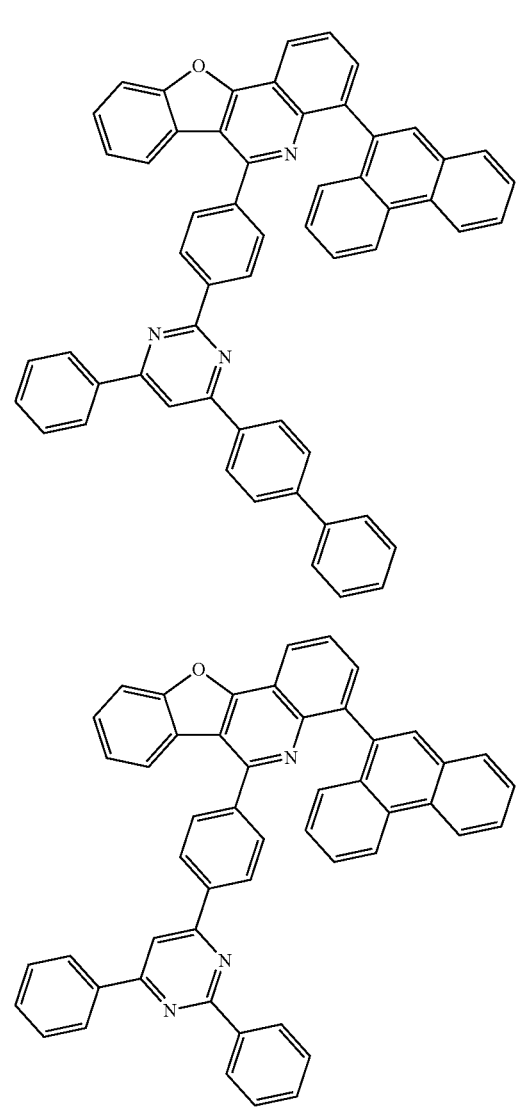

1033
-continued
882
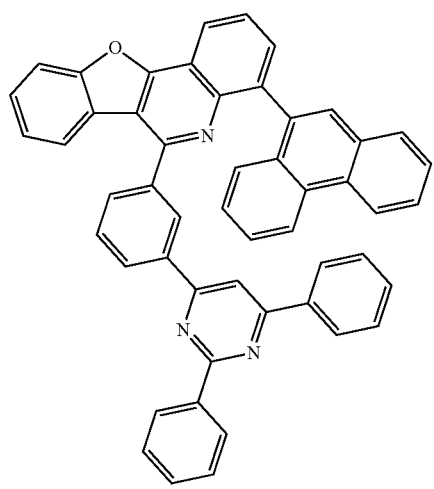
1034
-continued
884
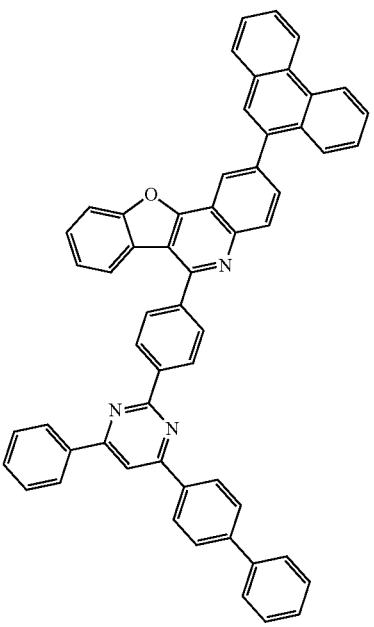
883
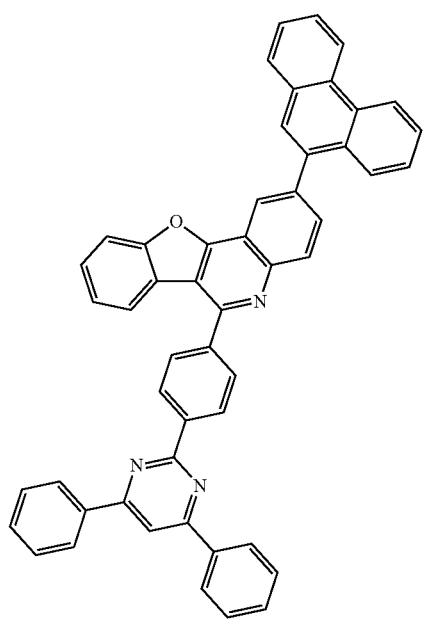
885
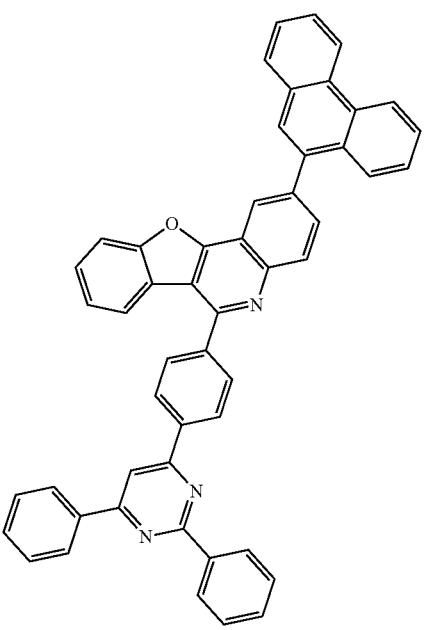

1035
-continued
886
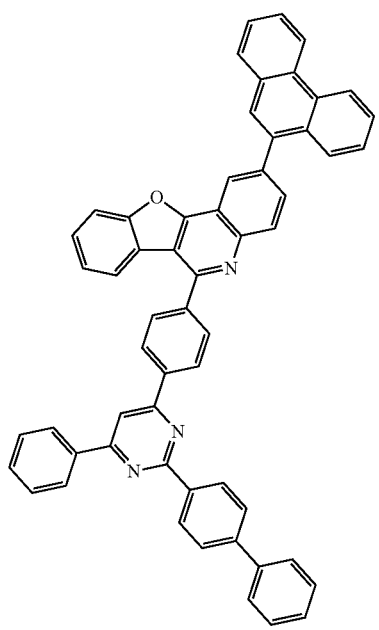
1036
-continued
888
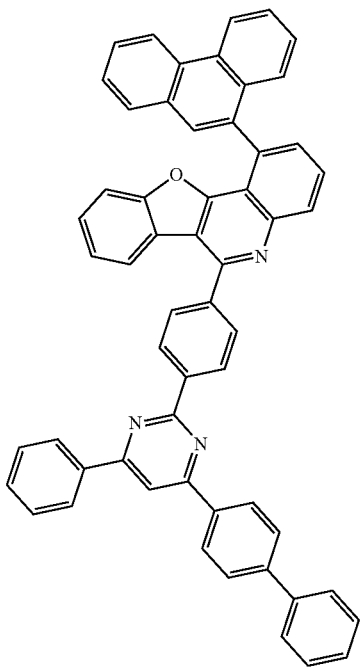
887
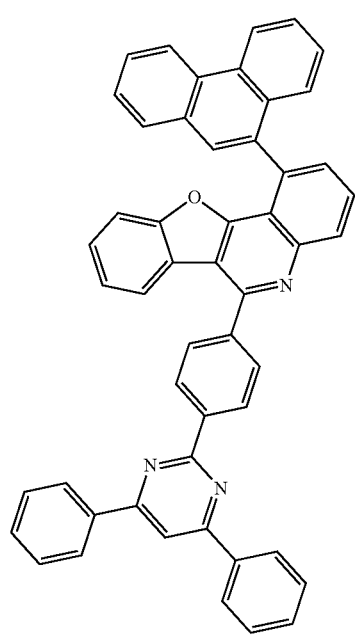
889
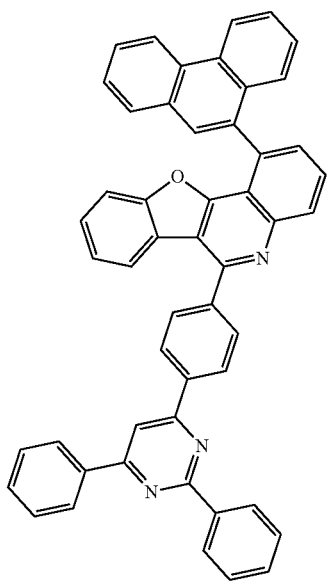

1037
-continued
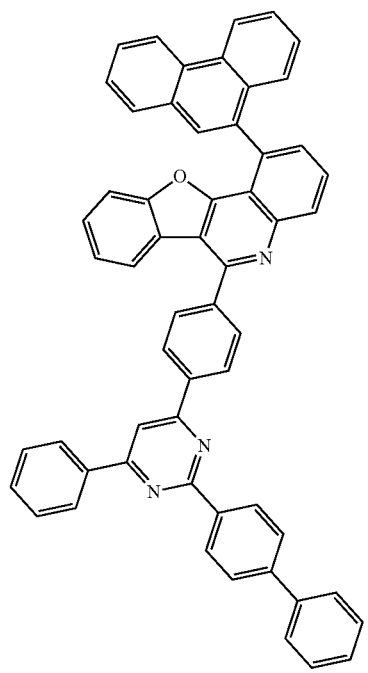
890
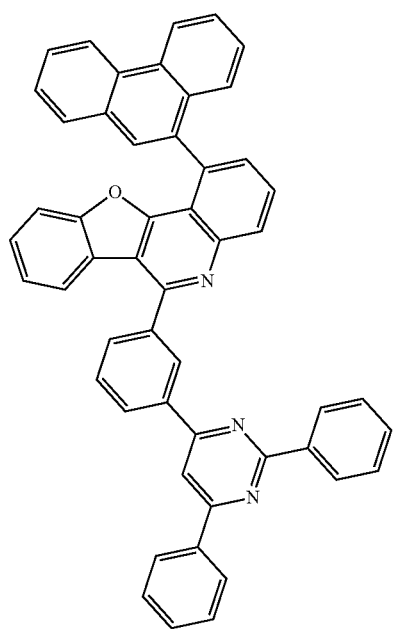
891
1038
-continued
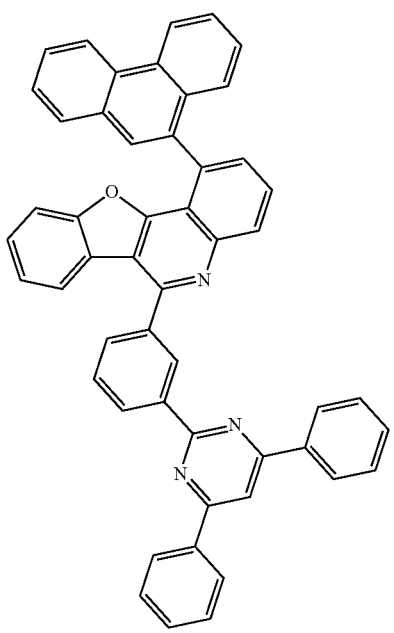
892
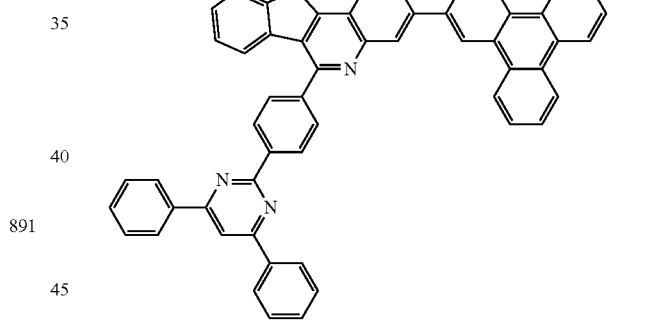
893
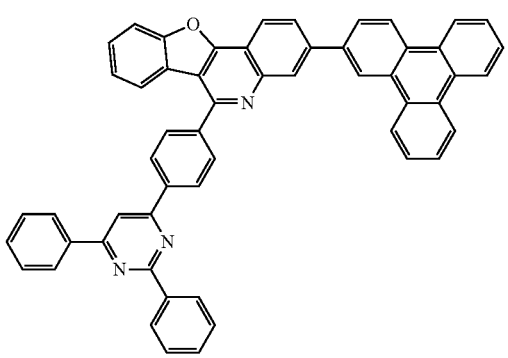
894

1039
-continued
895
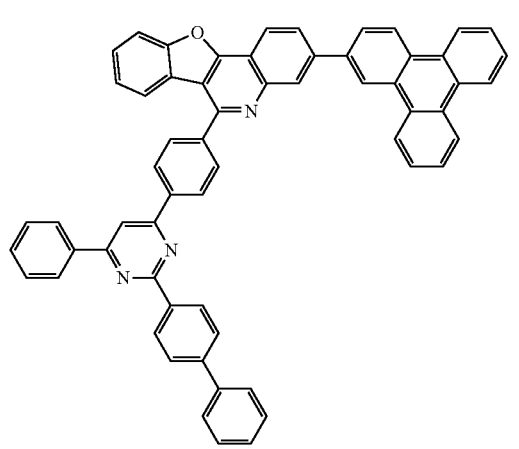
896
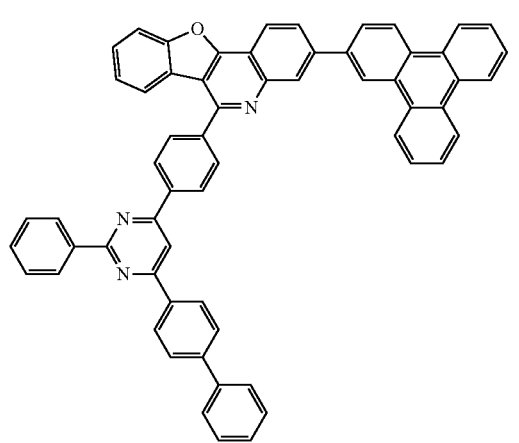
897
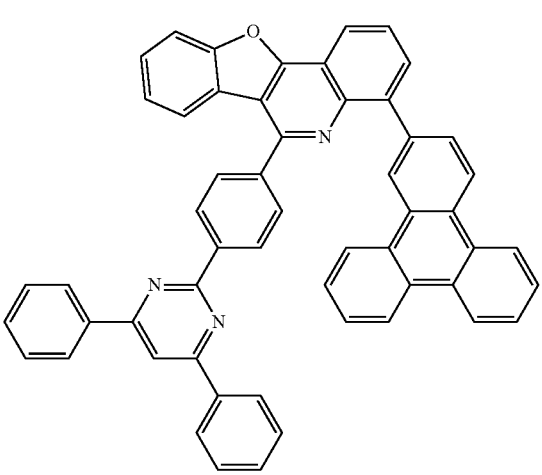
1040
-continued
898
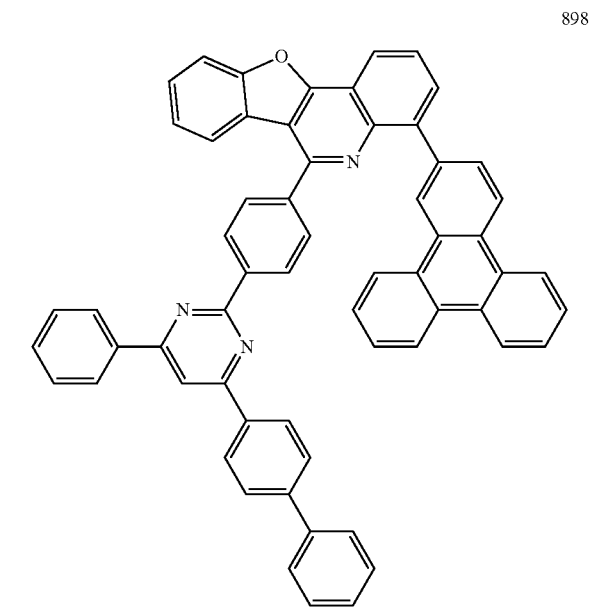
899
900

1041
-continued
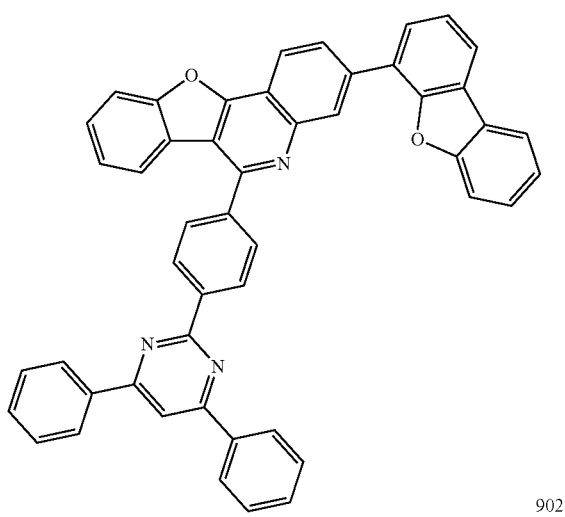
901
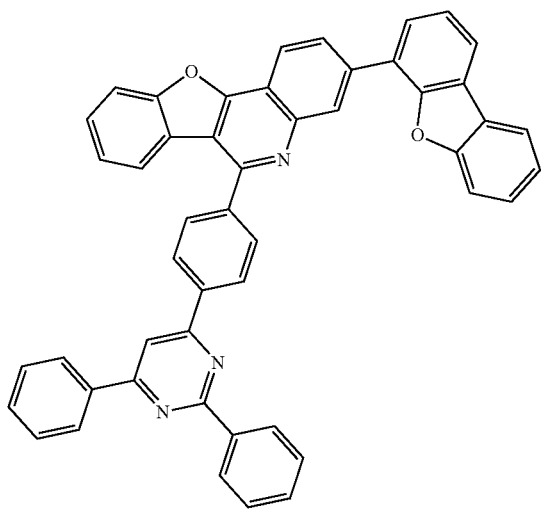
902
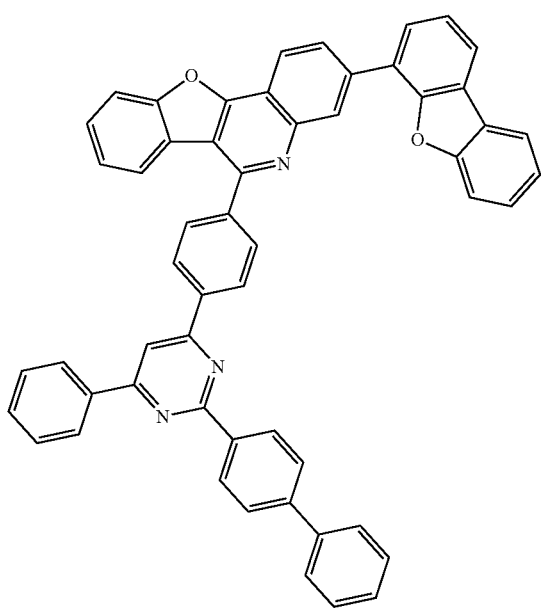
903
1042
-continued
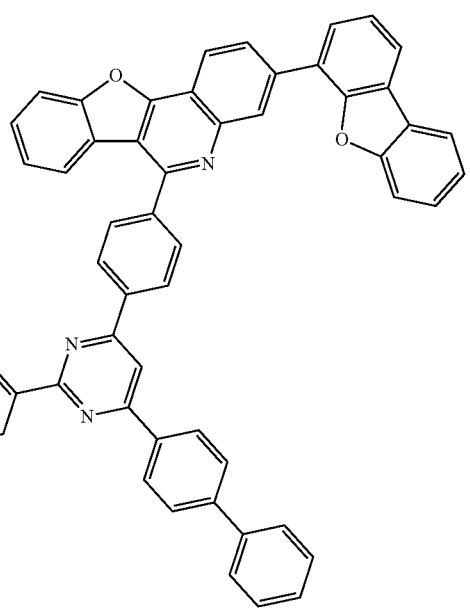
904
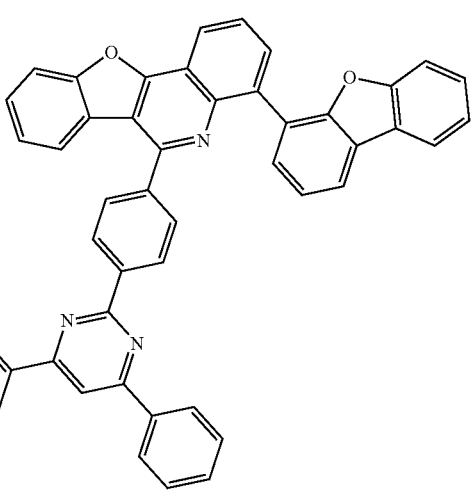
905

906
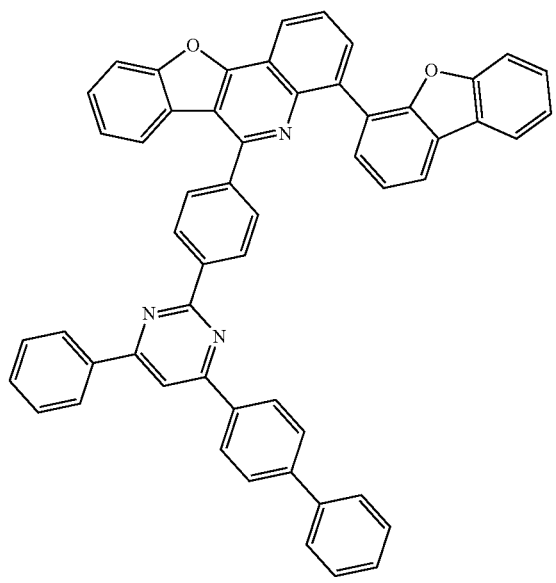
907
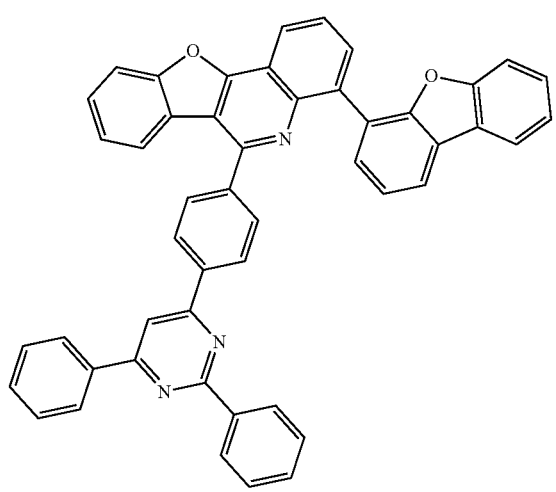
908
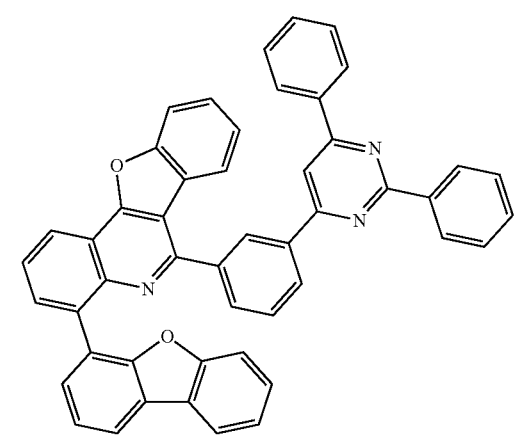
909
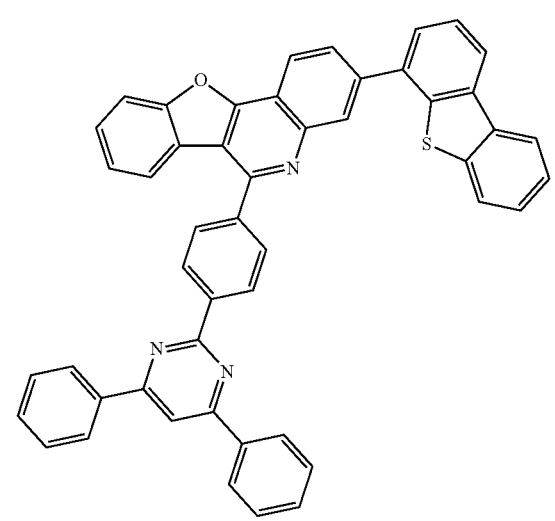
910
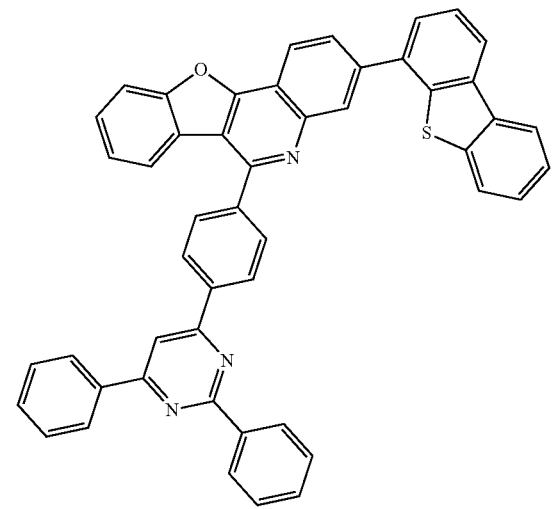

911
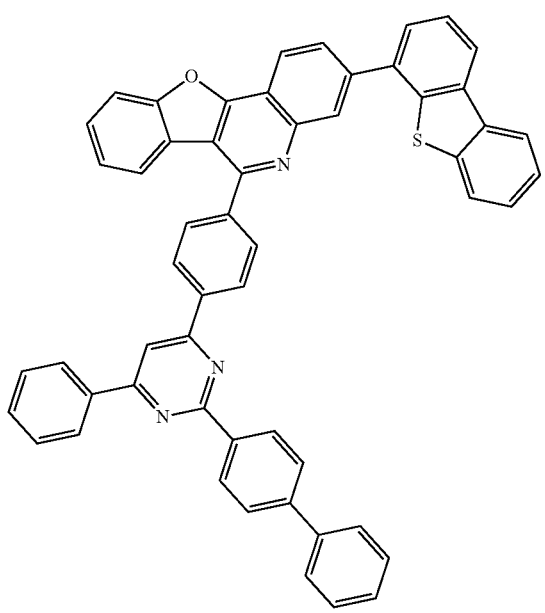
912
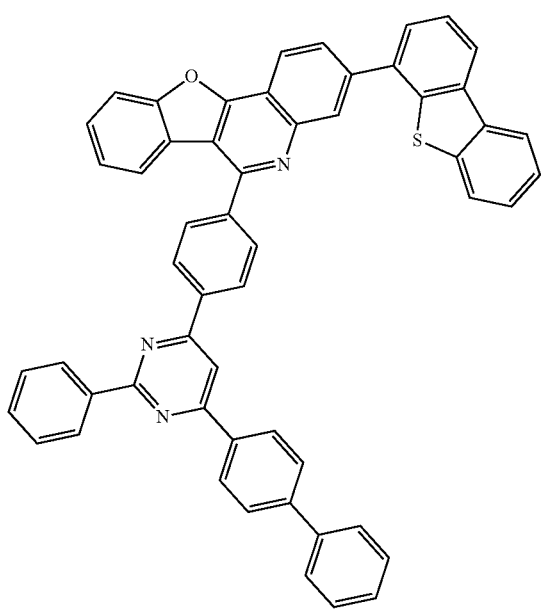
913
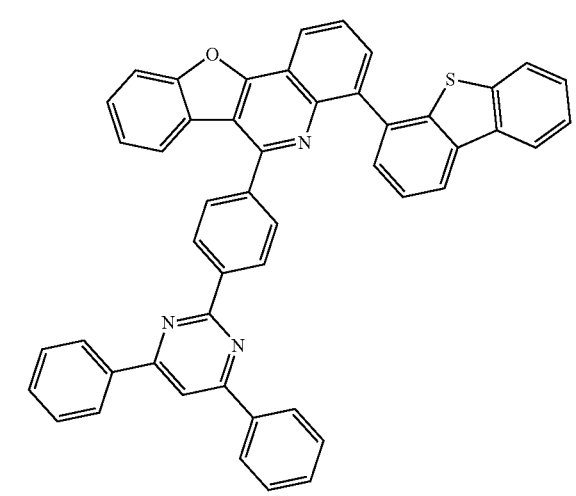
914
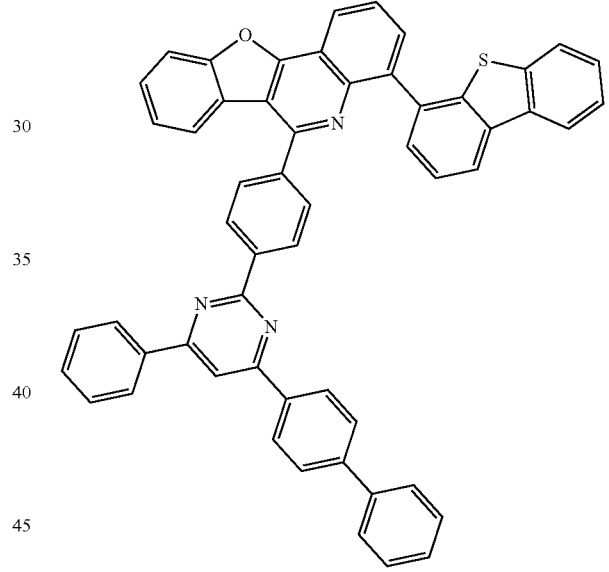
915
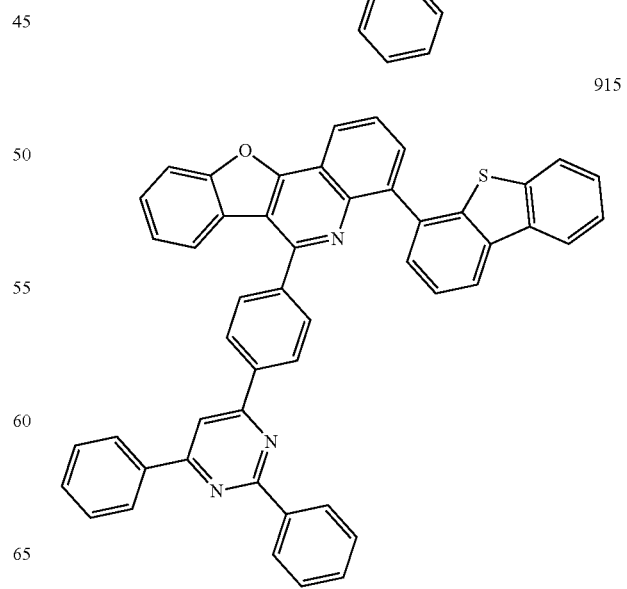

-continued
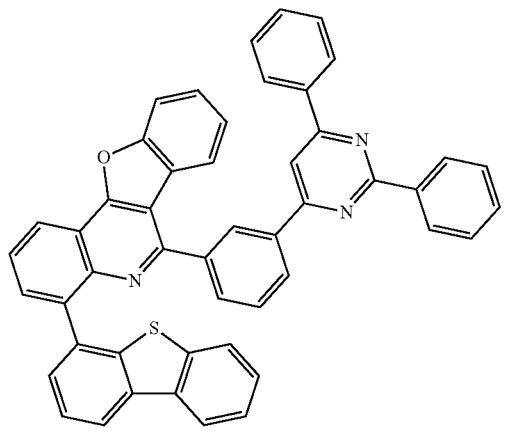
916
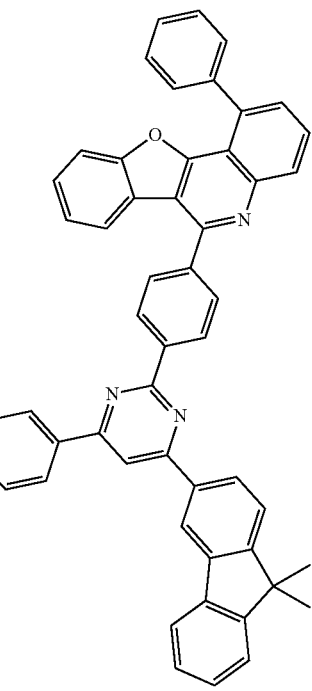
919
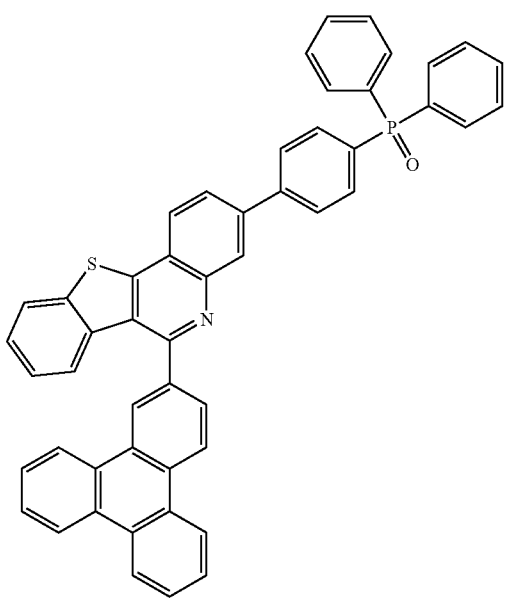
917
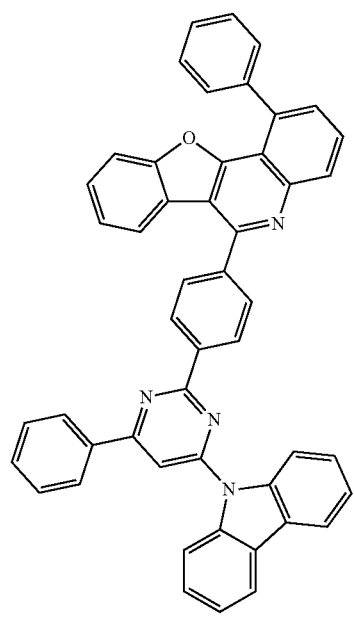
918
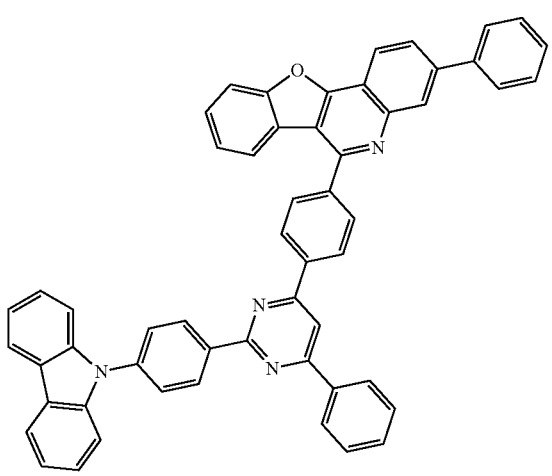
920

1049
-continued
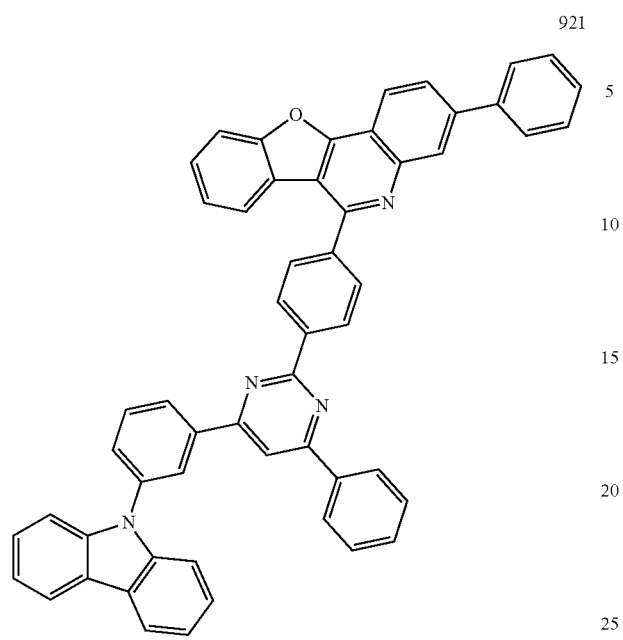
921
1050
-continued
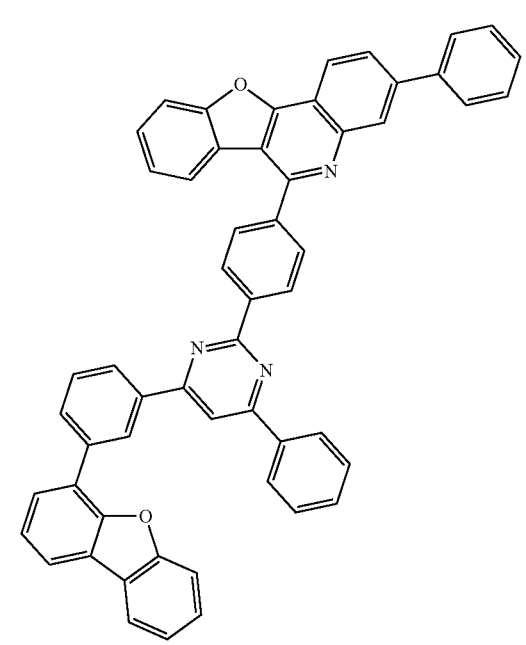
923
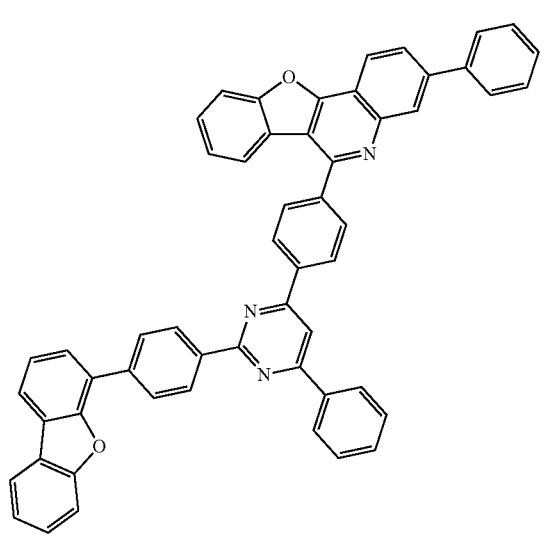
922
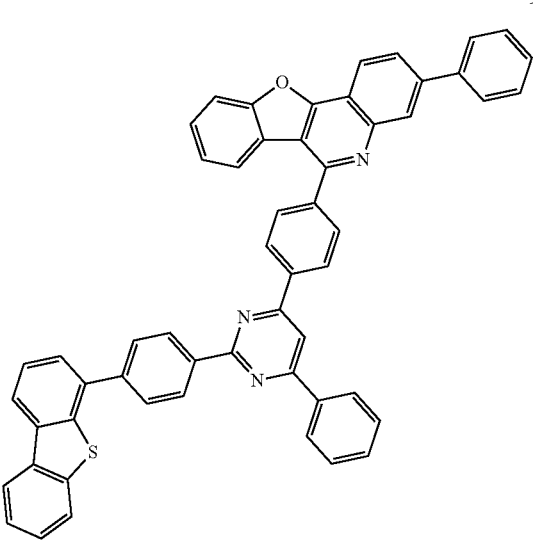
924

1051
-continued
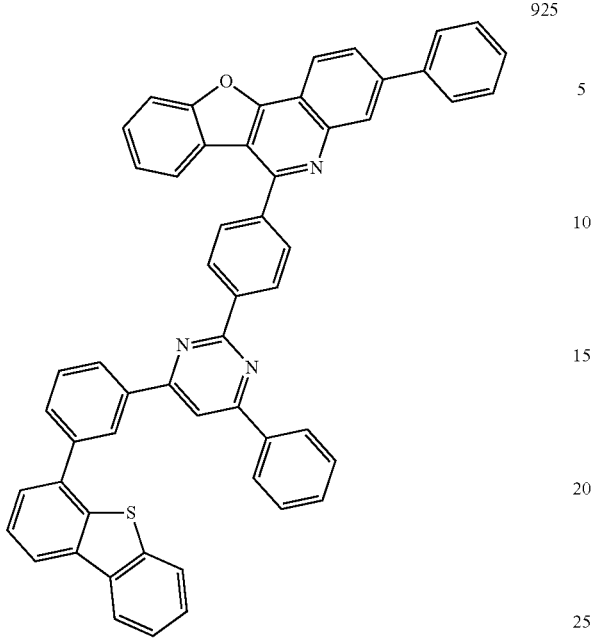
925
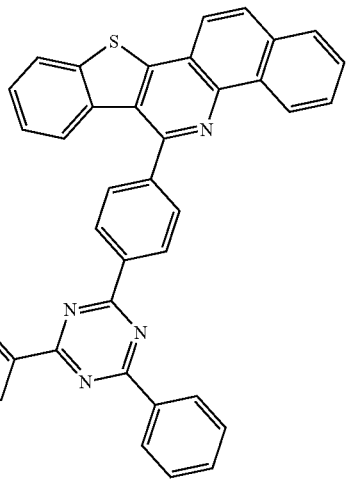
926
1052
-continued
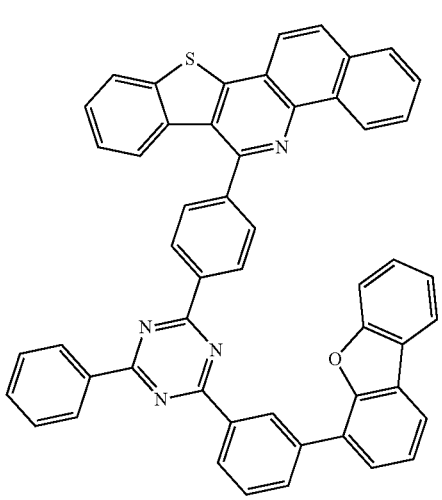
928
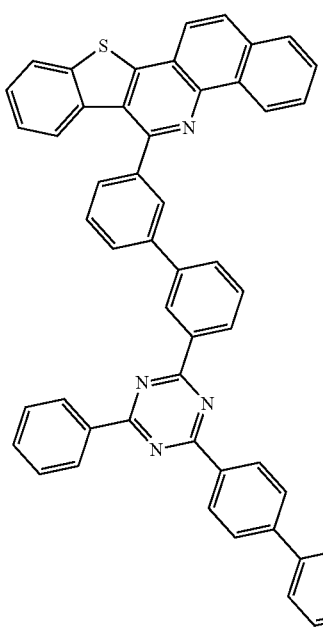
929

1053
-continued
930
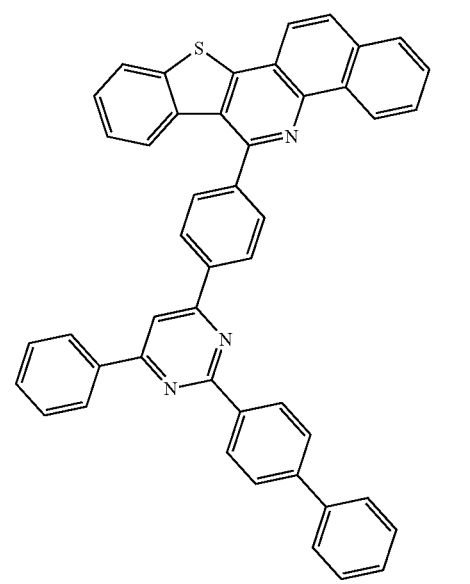
931
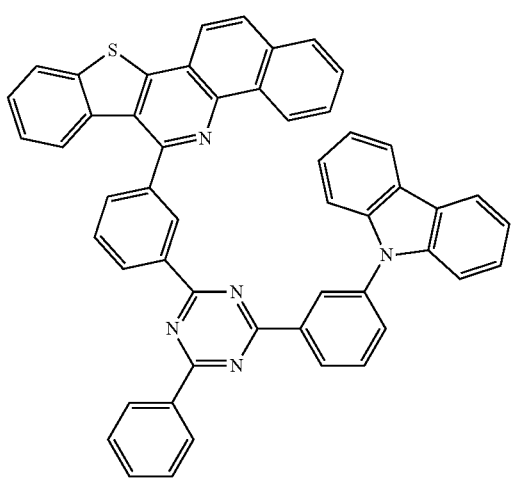
932
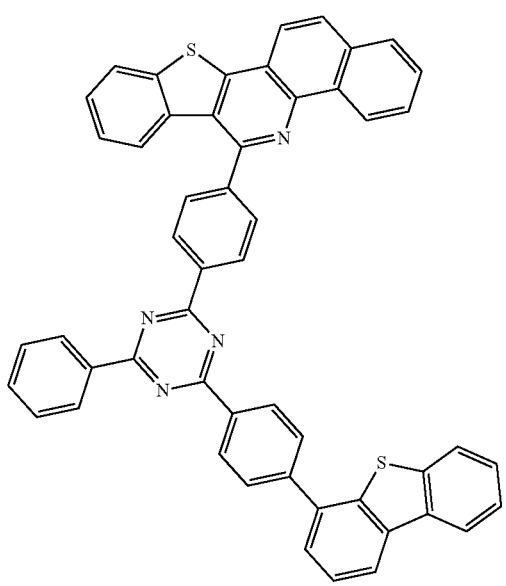
1054
-continued
933
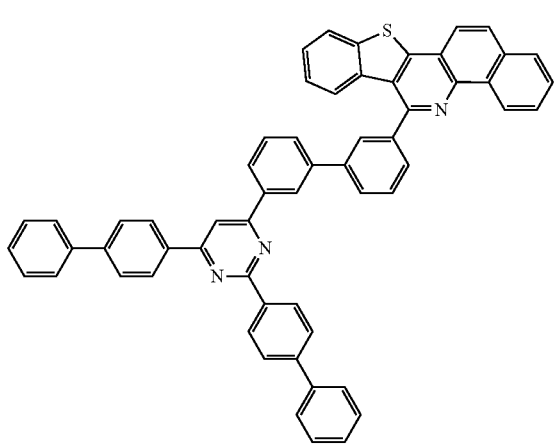
934
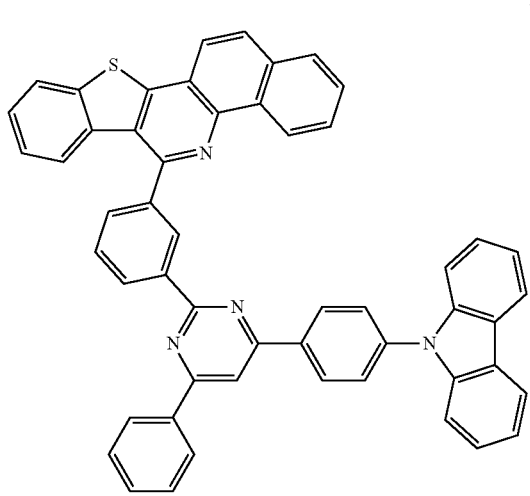
935
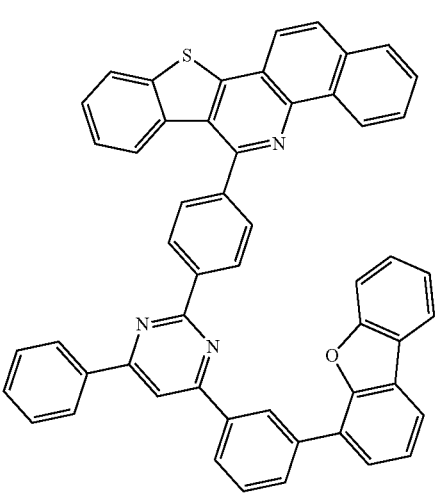

1055
-continued
936
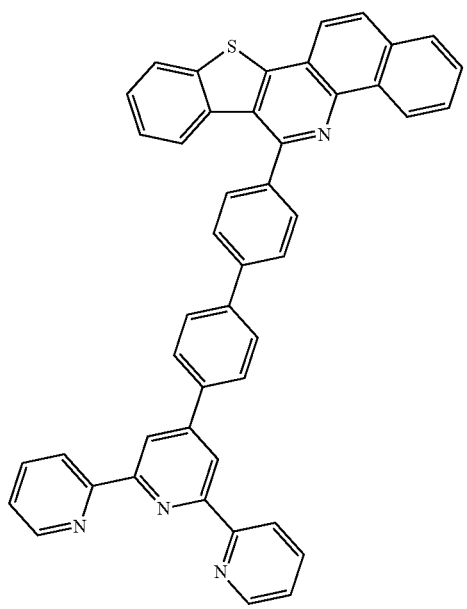
937
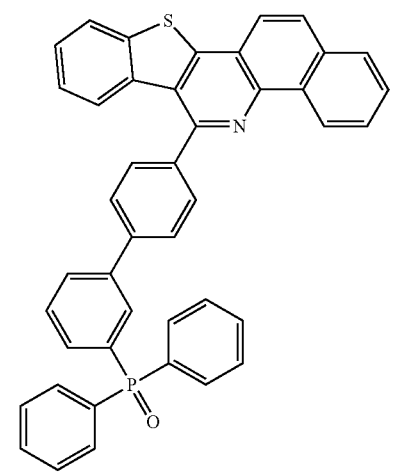
938
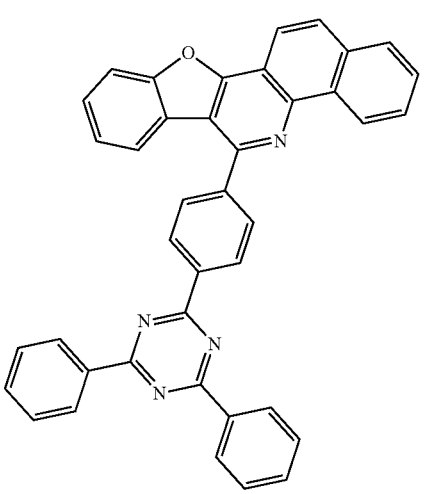 [SMILES: c1ccc(-c2nc(-c3ccccc3)nc(-c3ccc(-c4nc5c6ccccc6ccc5c5sc6ccccc6c45)cc3)n2)cc1]
1056
-continued
939
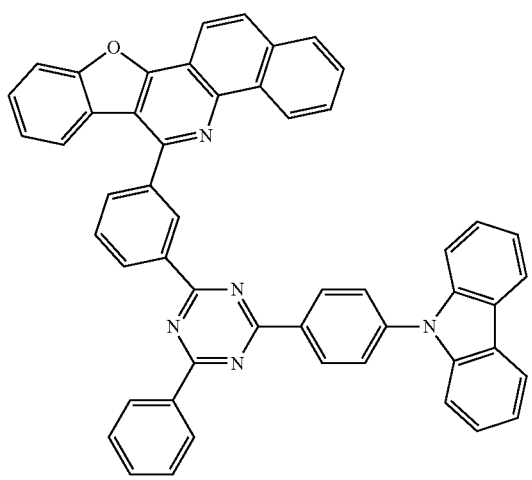
940
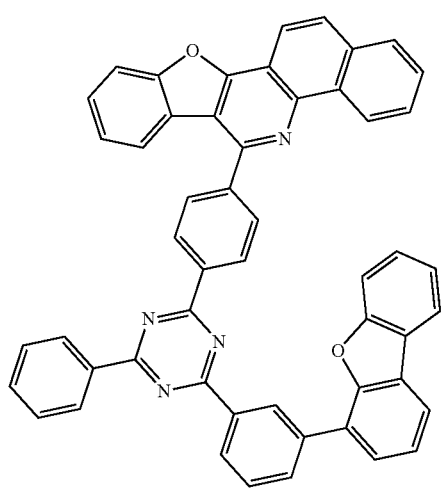 [SMILES: c1ccc(-c2nc(-c3ccc(-c4nc5c6ccccc6ccc5c5sc6ccccc6c45)cc3)nc(-c3cccc(-c4cccc5c4oc4ccccc45)c3)n2)cc1]
941
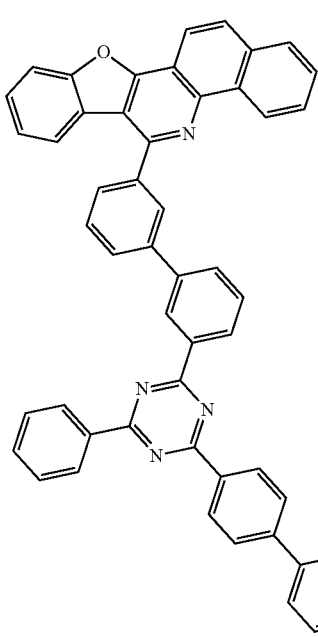

1057
-continued
942
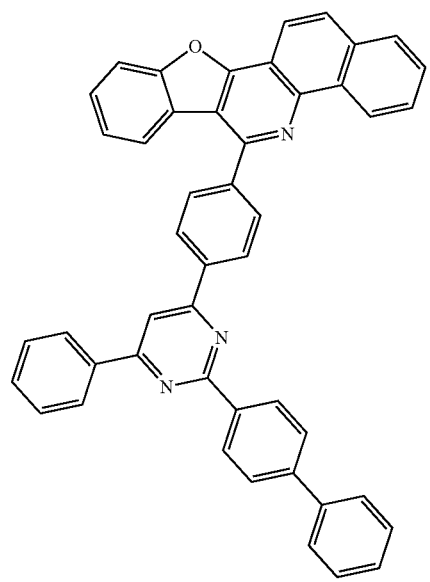
943
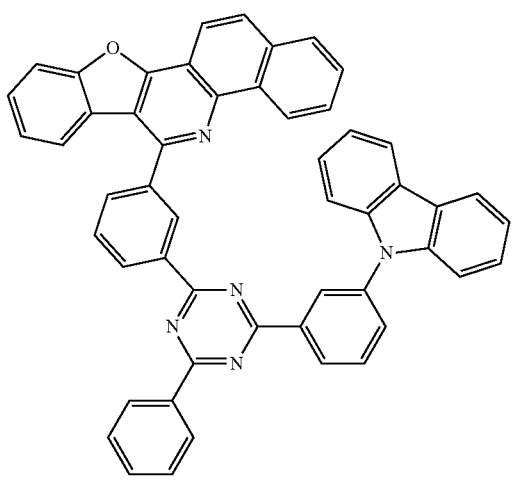
944
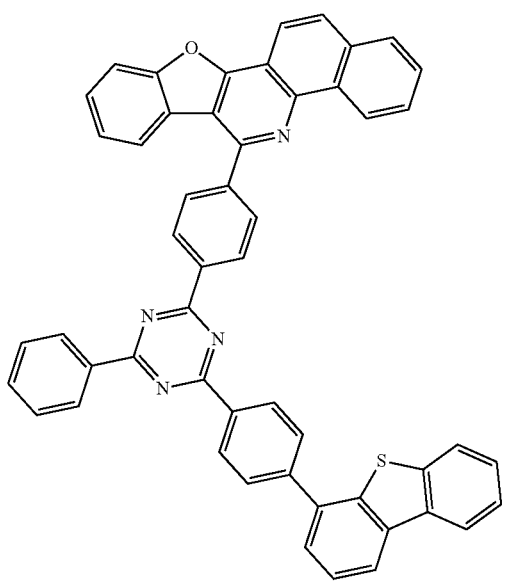 [SMILES: c1ccc(-c2nc(-c3ccc(-c4cccc5c4sc4ccccc45)cc3)nc(-c3ccc(-c4nc5c6ccccc6ccc5c5sc6ccccc6c45)cc3)n2)cc1]
1058
-continued
945
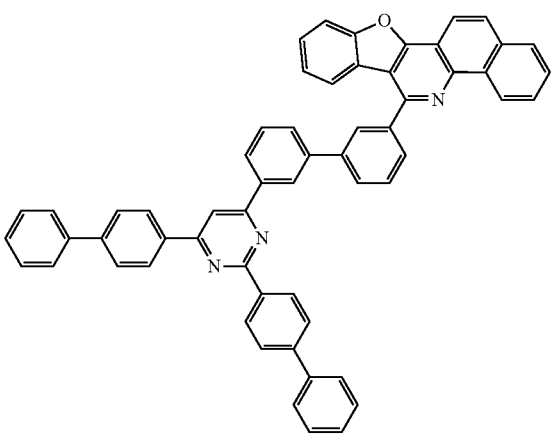
946
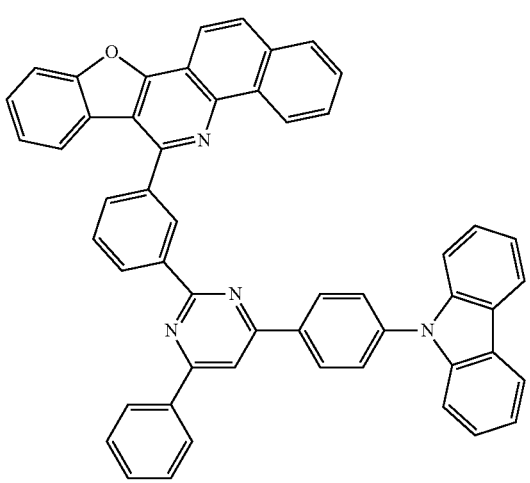
947
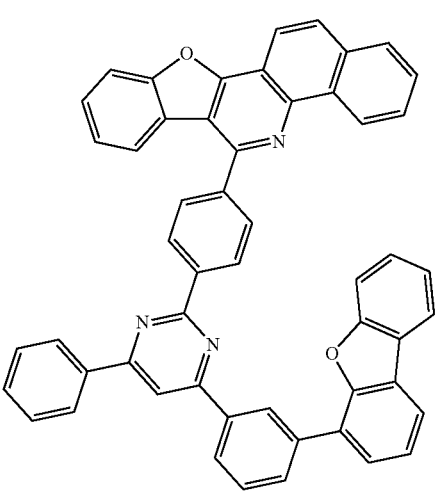

1059
-continued
948
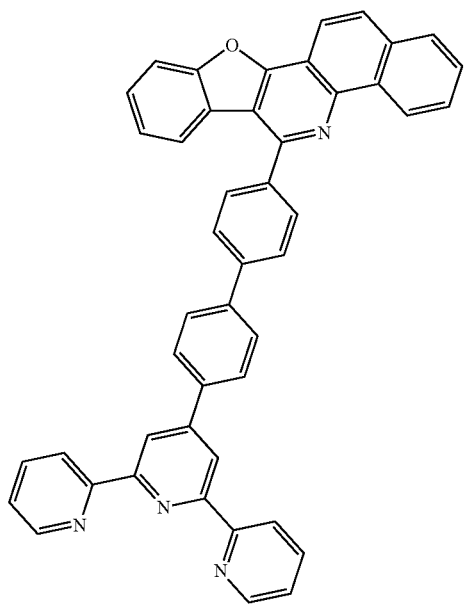 [SMILES: c1ccc(-c2cc(-c3ccc(-c4ccc(-c5nc6c7ccccc7ccc6c6sc7ccccc7c56)cc4)cc3)cc(-c3ccccn3)n2)nc1]
949
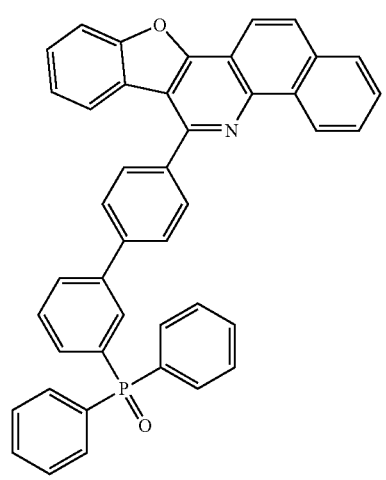 [SMILES: O=P(c1ccccc1)(c1ccccc1)c1cccc(-c2ccc(-c3nc4c5ccccc5ccc4c4sc5ccccc5c34)cc2)c1]
950
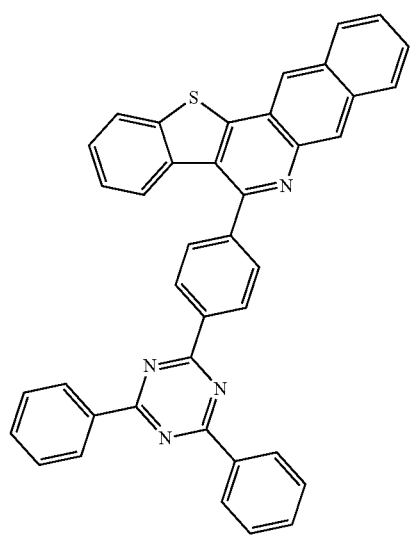 [SMILES: c1ccc(-c2nc(-c3ccccc3)nc(-c3ccc(-c4nc5cc6ccccc6cc5c5sc6ccccc6c45)cc3)n2)cc1]
1060
-continued
951
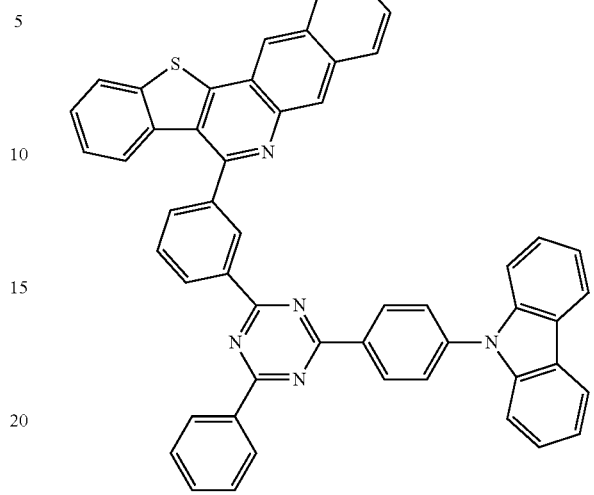
952
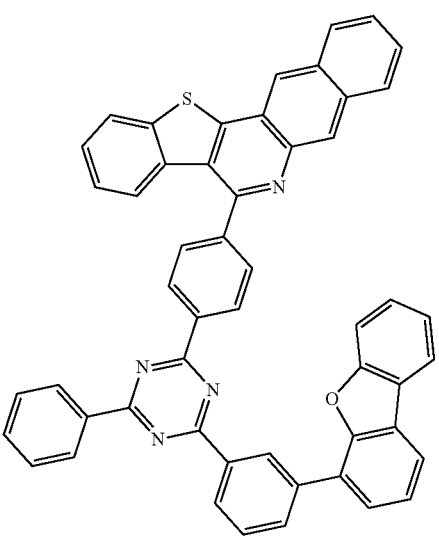 [SMILES: c1ccc(-c2nc(-c3ccc(-c4nc5cc6ccccc6cc5c5sc6ccccc6c45)cc3)nc(-c3cccc(-c4cccc5c4oc4ccccc45)c3)n2)cc1]
953
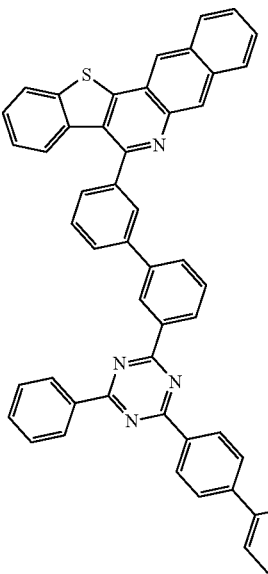

-continued
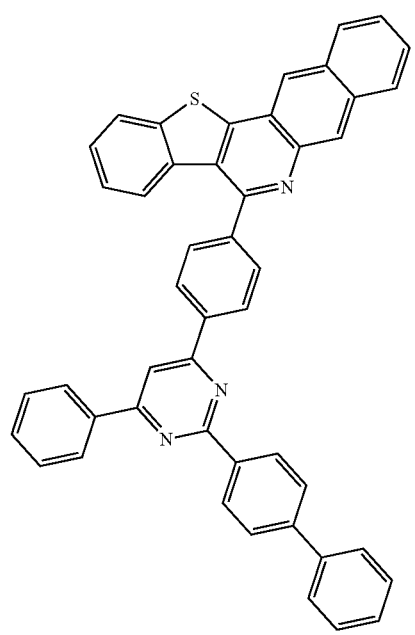 [SMILES: c1ccc(-c2ccc(-c3nc(-c4ccccc4)cc(-c4ccc(-c5nc6cc7ccccc7cc6c6sc7ccccc7c56)cc4)n3)cc2)cc1]
954
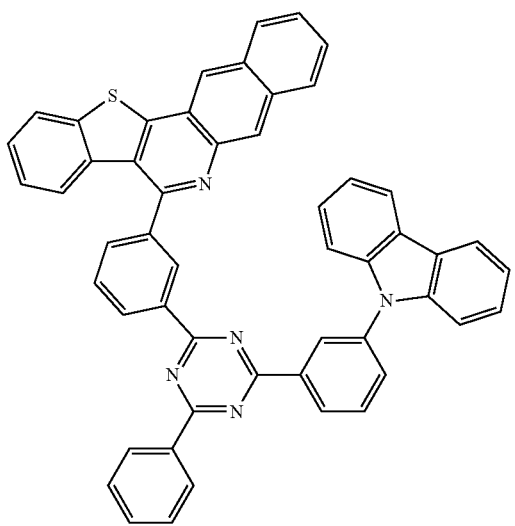
955
-continued
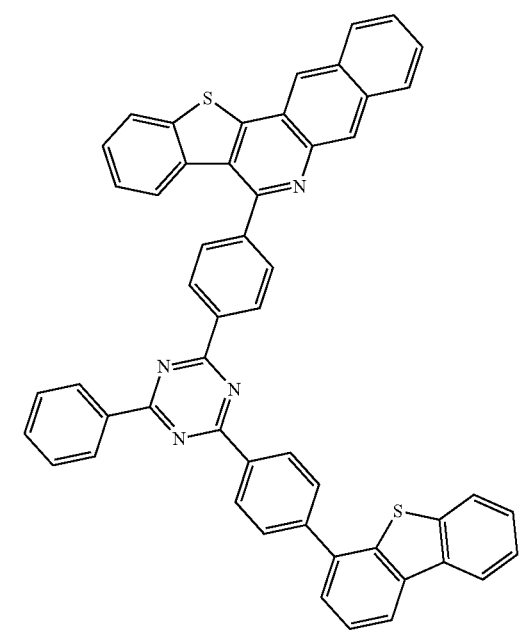 [SMILES: c1ccc(-c2nc(-c3ccc(-c4cccc5c4sc4ccccc45)cc3)nc(-c3ccc(-c4nc5cc6ccccc6cc5c5sc6ccccc6c45)cc3)n2)cc1]
956
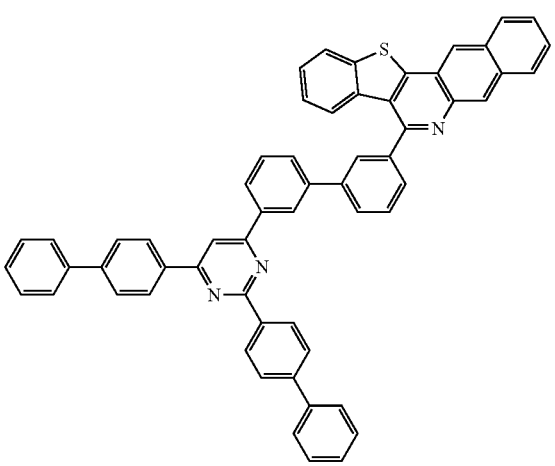
957
958

1063
-continued
959
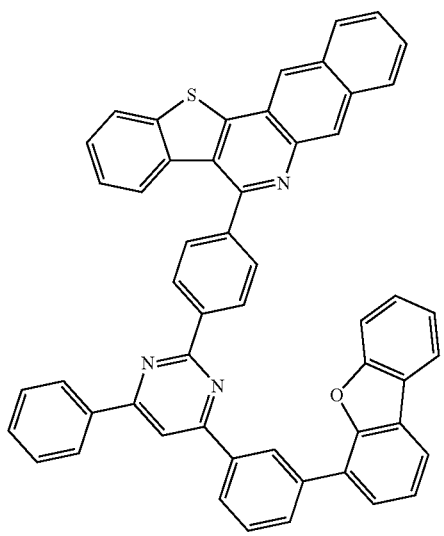 [SMILES: c1ccc(-c2cc(-c3cccc(-c4cccc5c4oc4ccccc45)c3)nc(-c3ccc(-c4nc5cc6ccccc6cc5c5sc6ccccc6c45)cc3)n2)cc1]
960
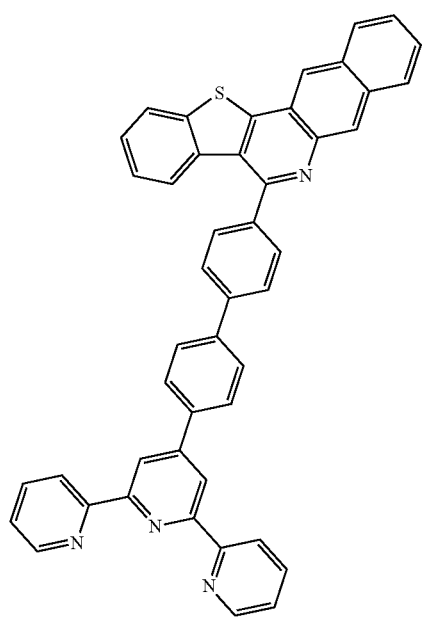
961
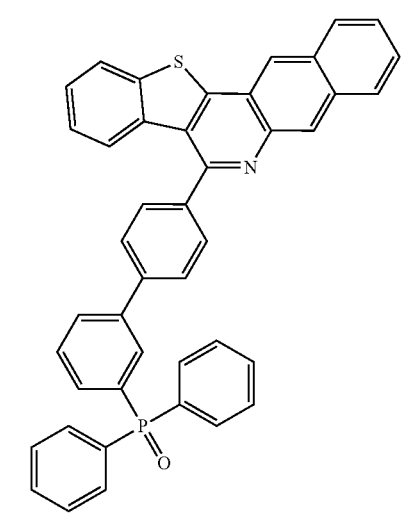 [SMILES: O=P(c1ccccc1)(c1ccccc1)c1cccc(-c2ccc(-c3nc4cc5ccccc5cc4c4sc5ccccc5c34)cc2)c1]
1064
-continued
962
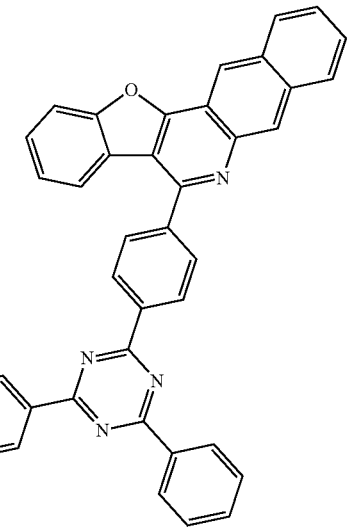
963
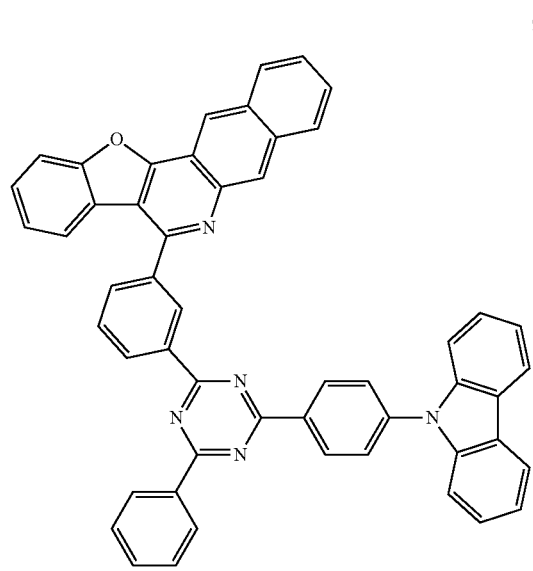
964
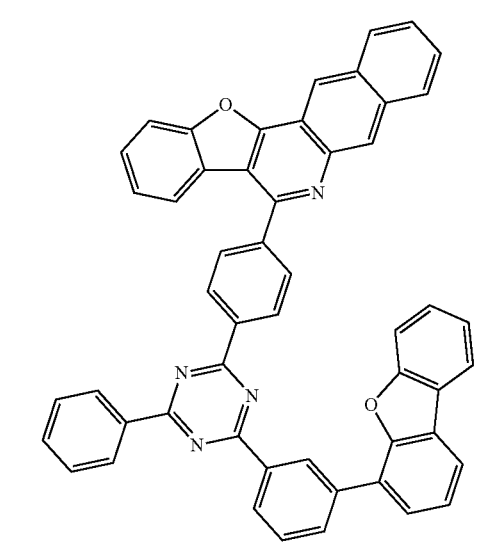

1065
-continued
965
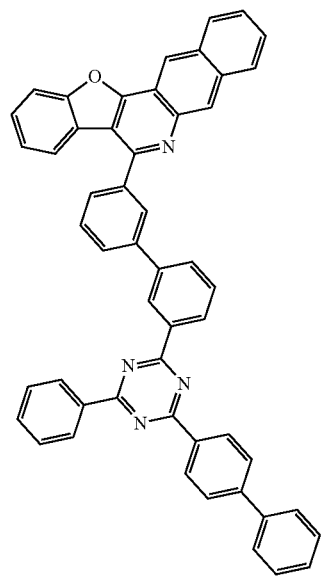
966
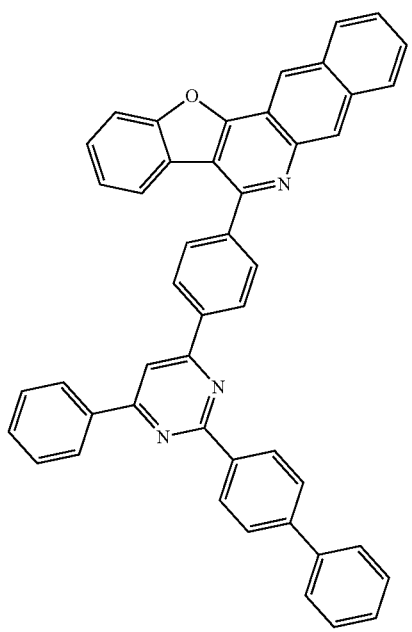
1066
-continued
967
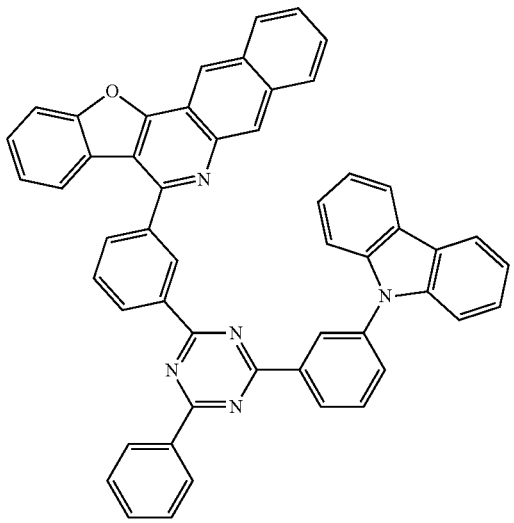
968
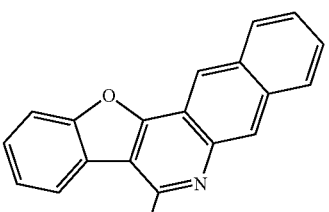
969
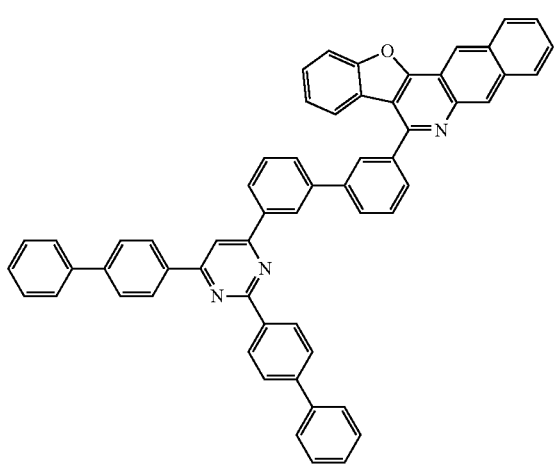 [SMILES: c1ccc(-c2ccc(-c3cc(-c4cccc(-c5cccc(-c6nc7cc8ccccc8cc7c7oc8ccccc8c67)c5)c4)nc(-c4ccc(-c5ccccc5)cc4)n3)cc2)cc1]

1067
-continued
970
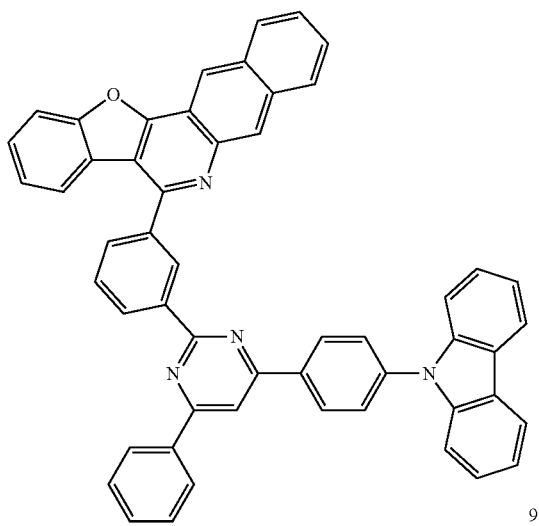
971
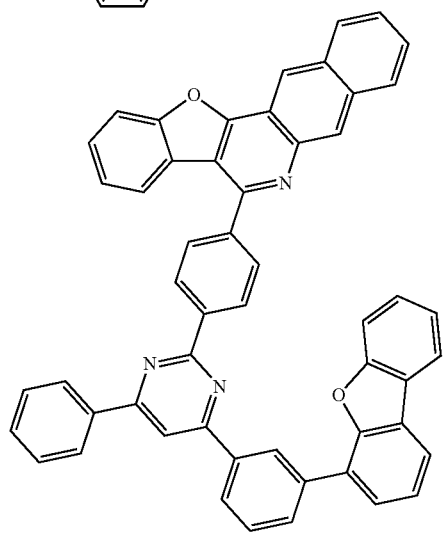
972
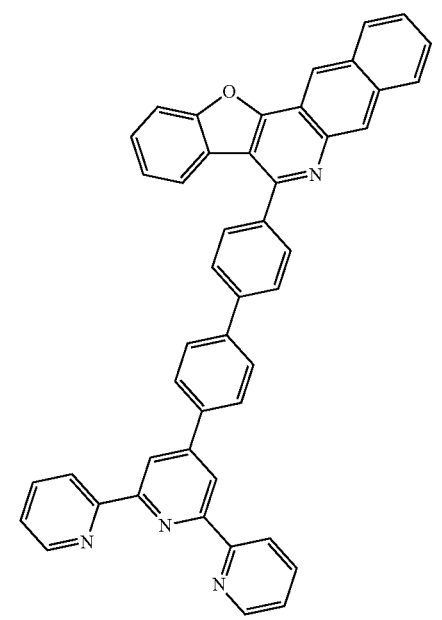
1068
-continued
973
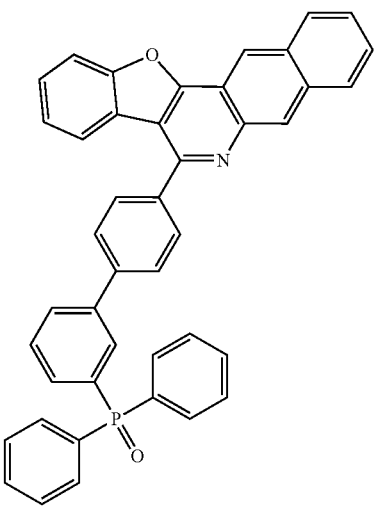
974
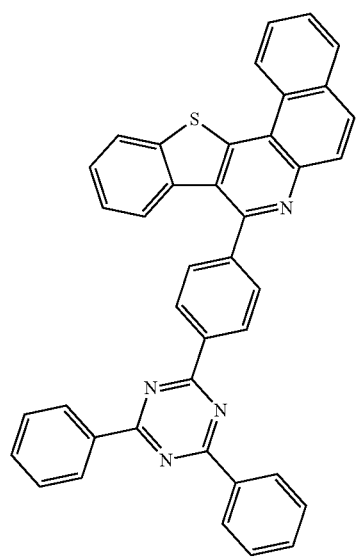
975
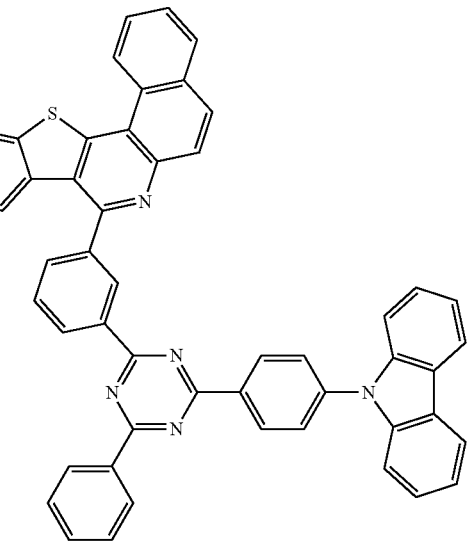

1069
-continued
976
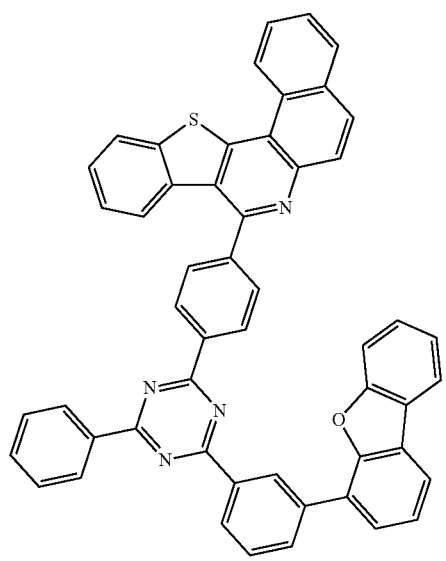
977
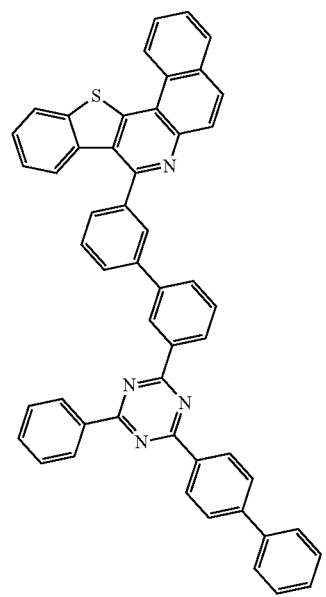
1070
-continued
978
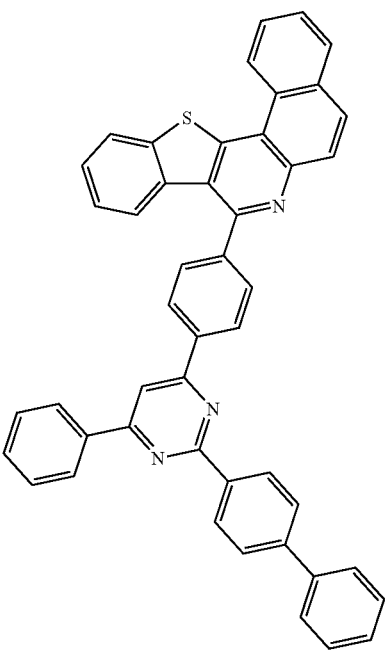 [SMILES: c1ccc(-c2ccc(-c3nc(-c4ccccc4)cc(-c4ccc(-c5nc6ccc7ccccc7c6c6sc7ccccc7c56)cc4)n3)cc2)cc1]
979
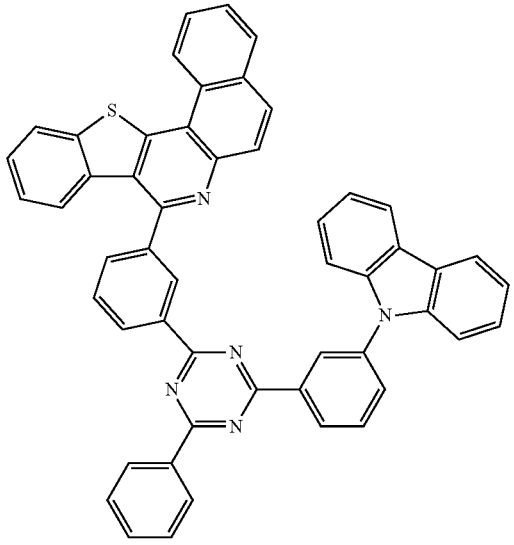

1071
-continued
1072
-continued
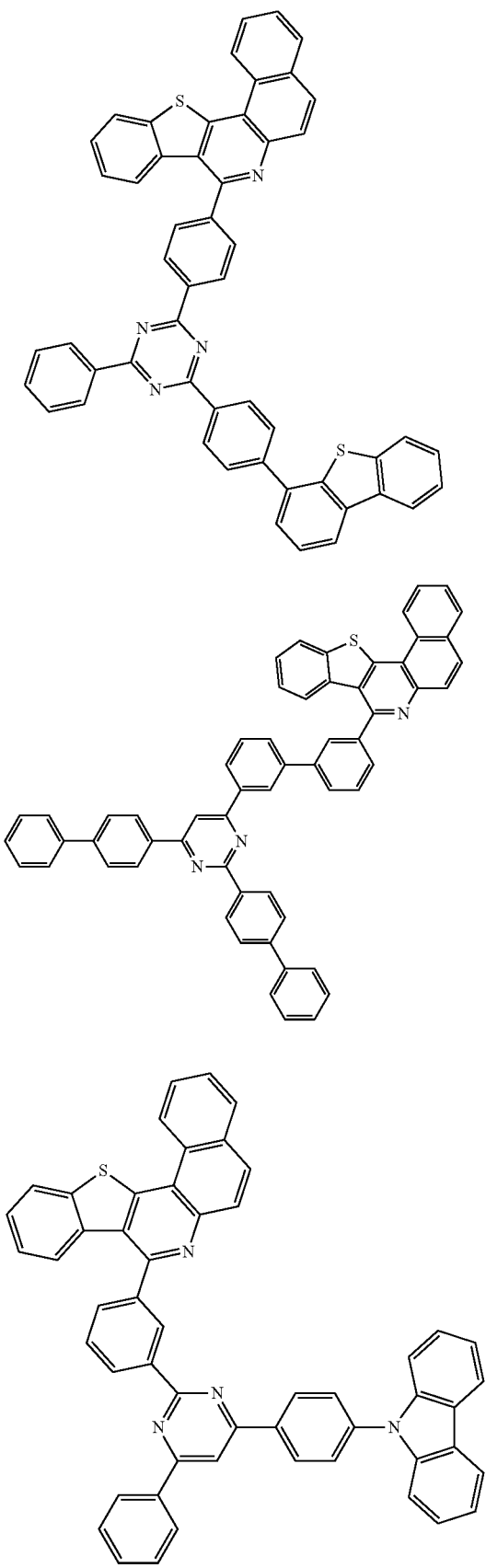

1073
-continued
985
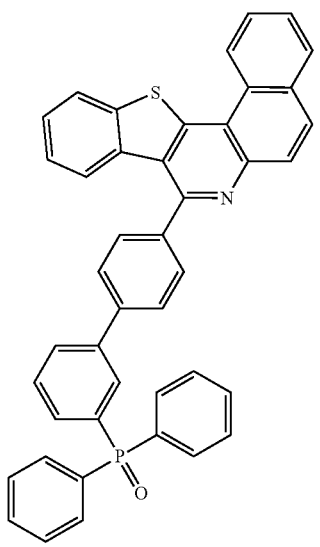
986
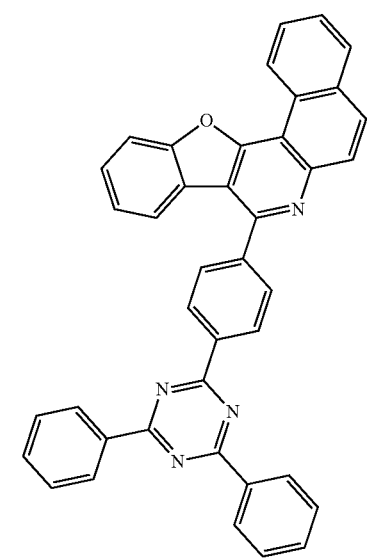
987
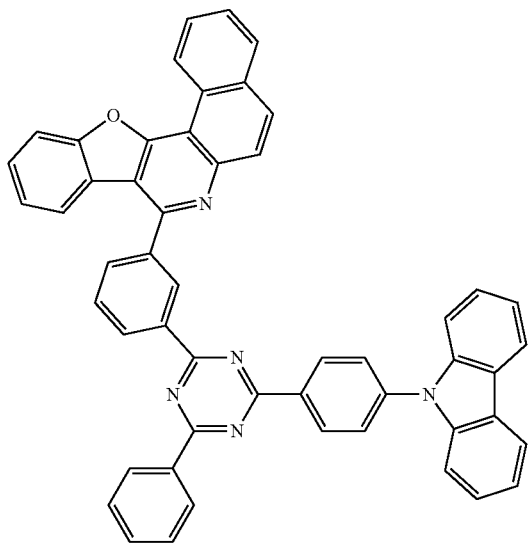
1074
-continued
988
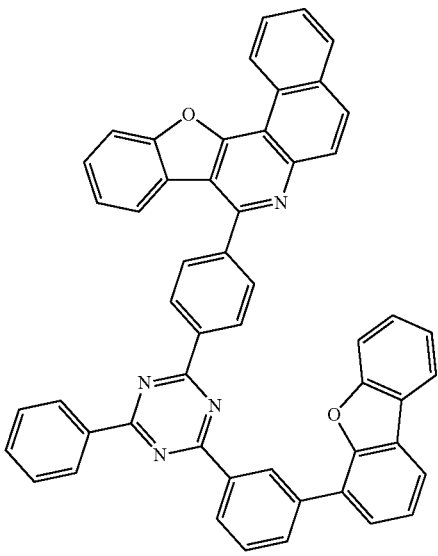
989
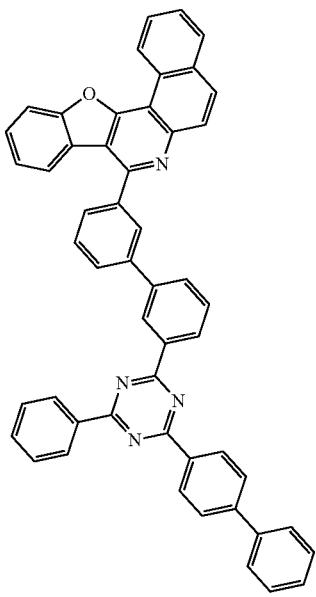 [SMILES: c1ccc(-c2ccc(-c3nc(-c4ccccc4)nc(-c4cccc(-c5cccc(-c6nc7ccc8ccccc8c7c7sc8ccccc8c67)c5)c4)n3)cc2)cc1]

-continued
990
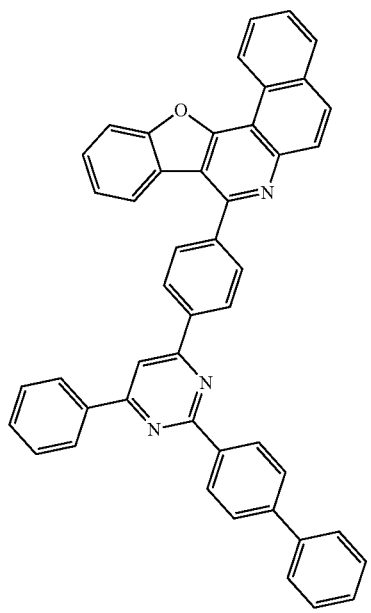 [SMILES: c1ccc(-c2ccc(-c3nc(-c4ccccc4)cc(-c4ccc(-c5nc6ccc7ccccc7c6c6oc7ccccc7c56)cc4)n3)cc2)cc1]
-continued
992
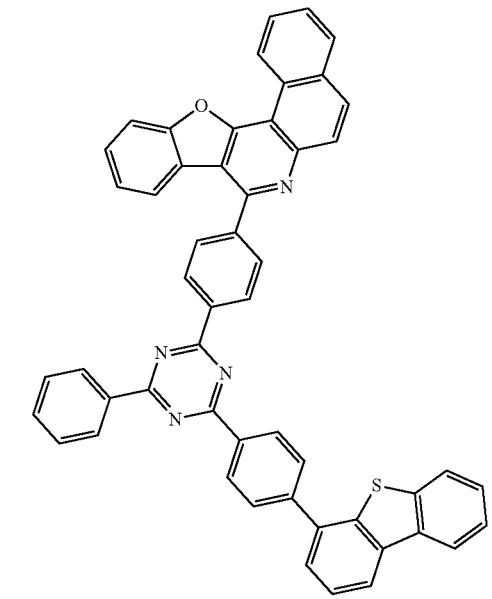
993
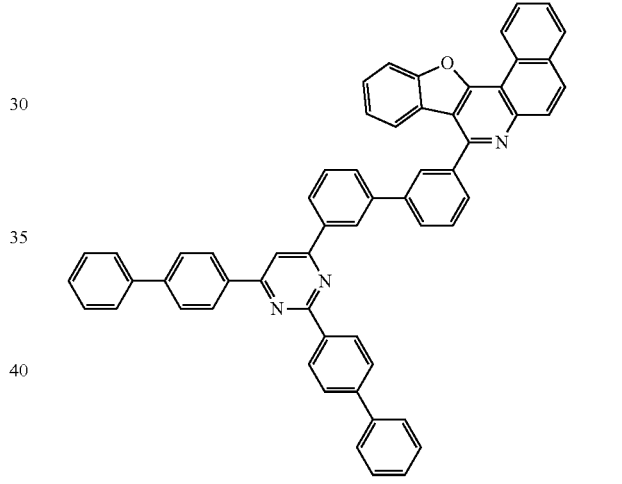
991
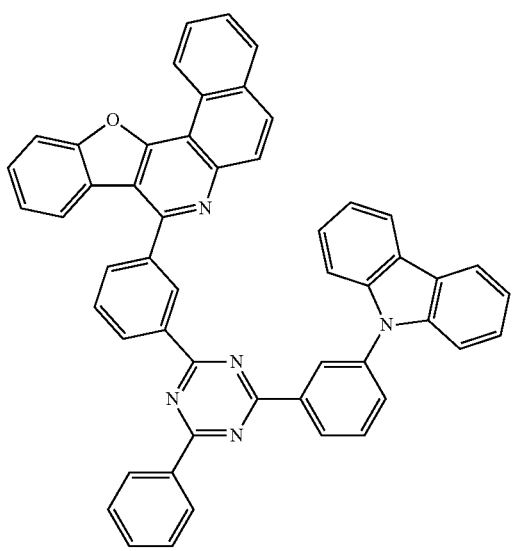
994
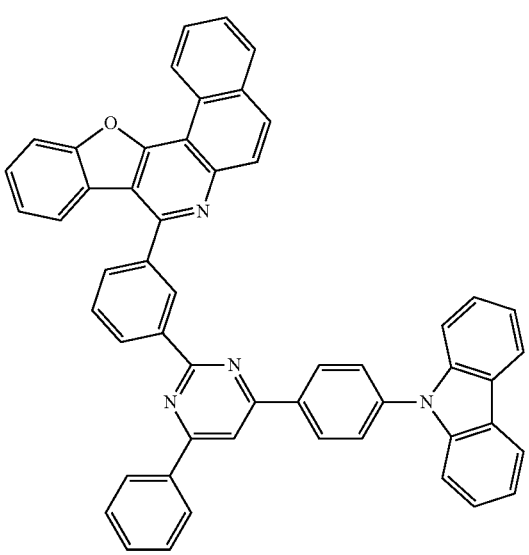

1077  1078
-continued  -continued
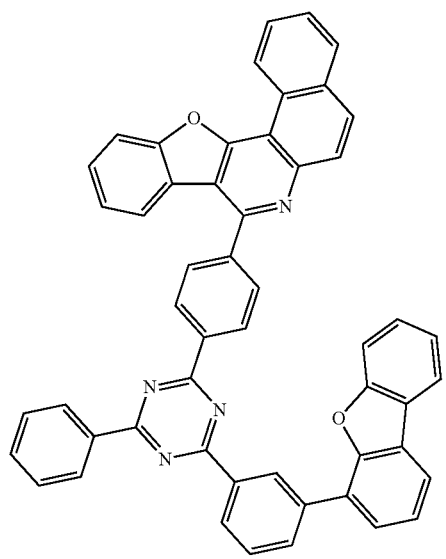
995
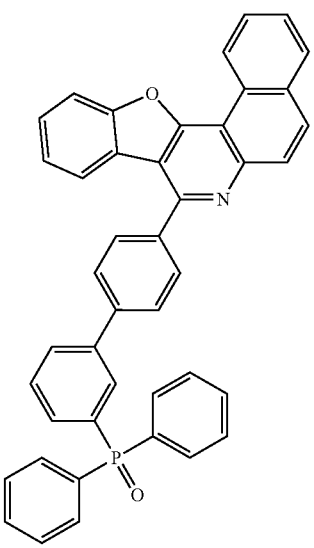
997
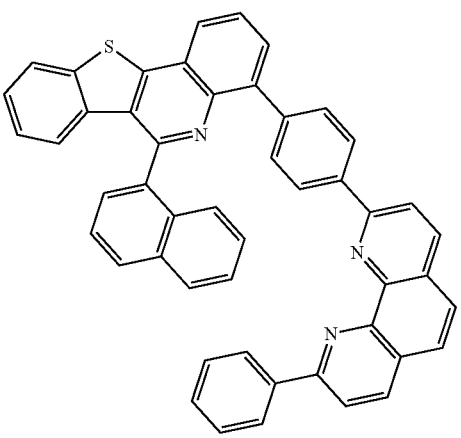
998
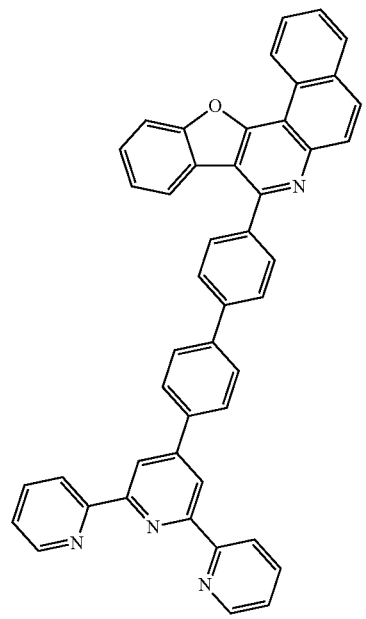 [SMILES: c1ccc(-c2cc(-c3ccc(-c4ccc(-c5nc6ccc7ccccc7c6c6oc7ccccc7c56)cc4)cc3)cc(-c3ccccn3)n2)nc1]
996
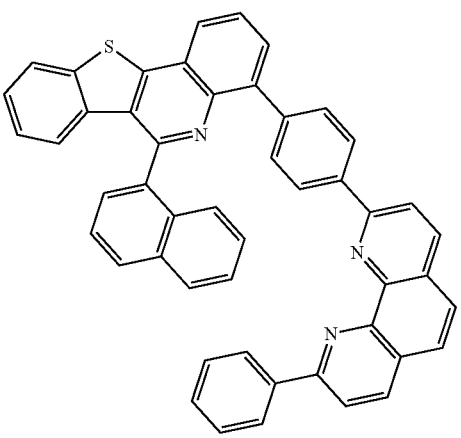
999

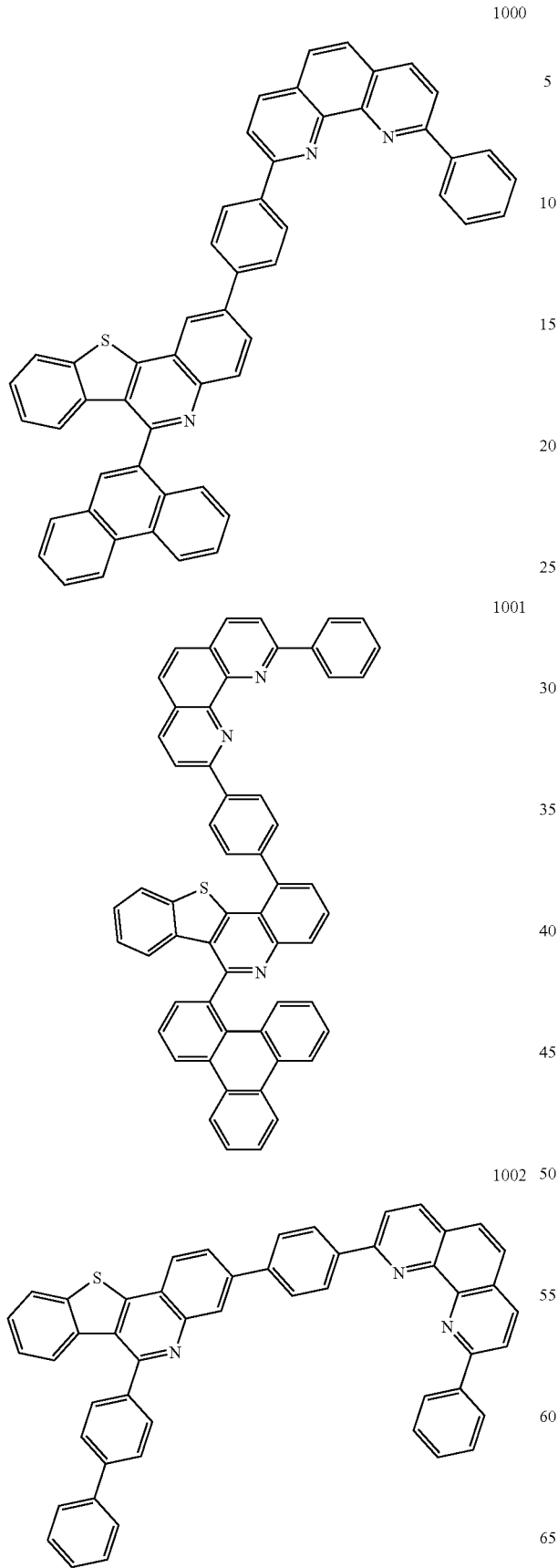
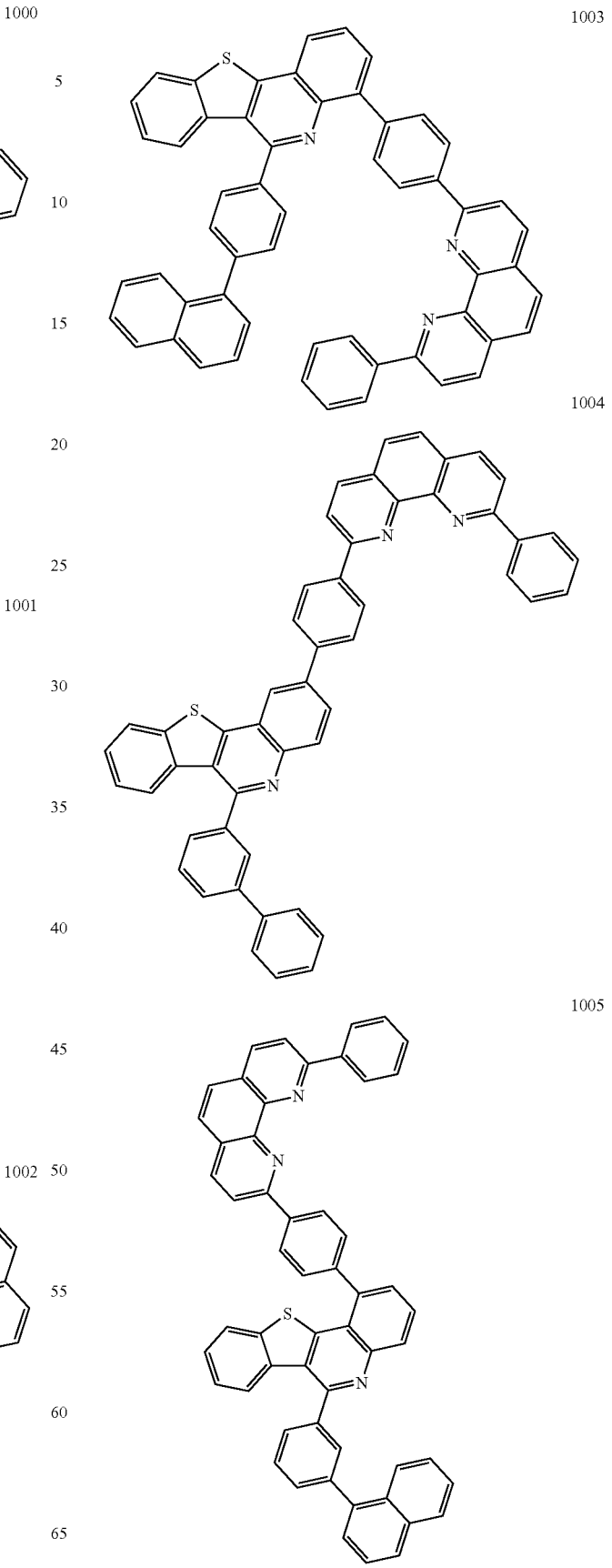

1081
-continued
1082
-continued
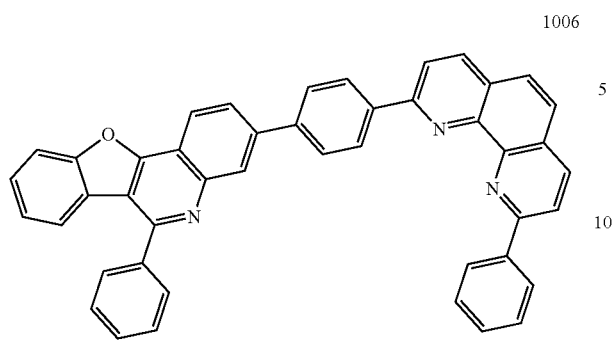
1006
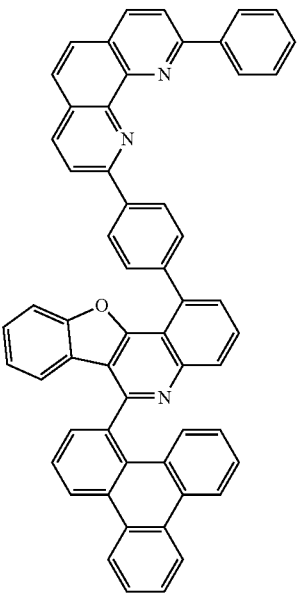
1009
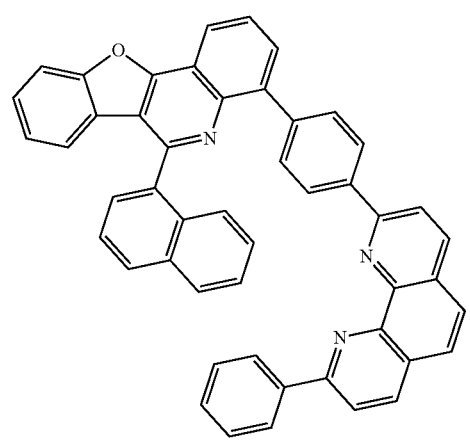
1007
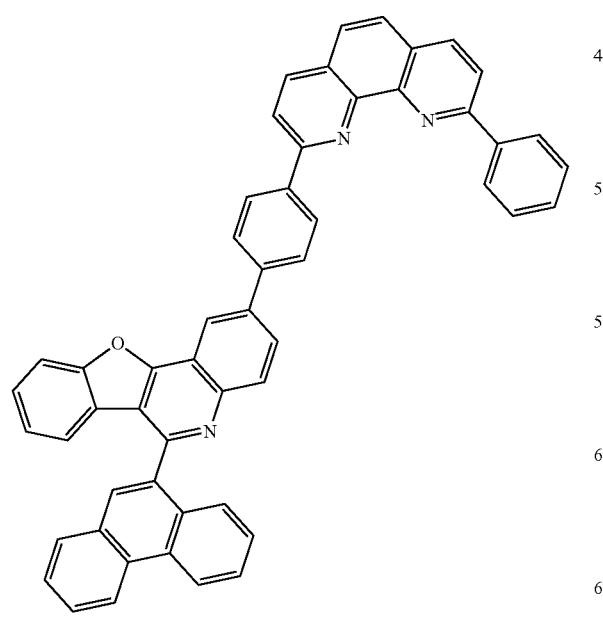
1008
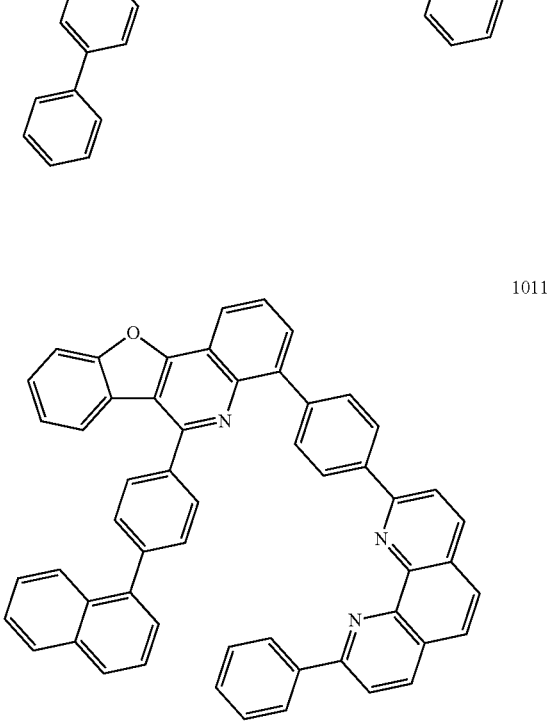
1010
1011

-continued
1012
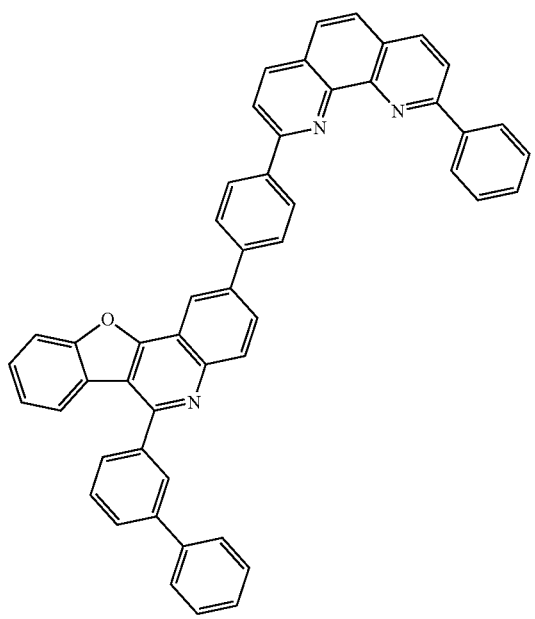
1013
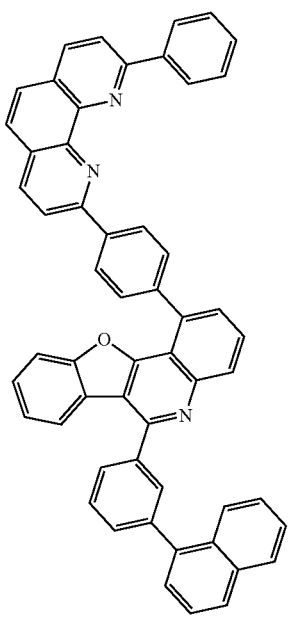
-continued
1014
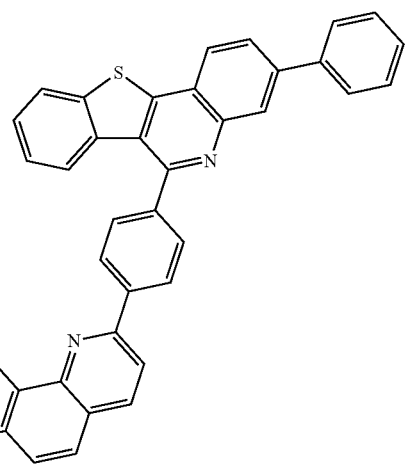
1015
1016
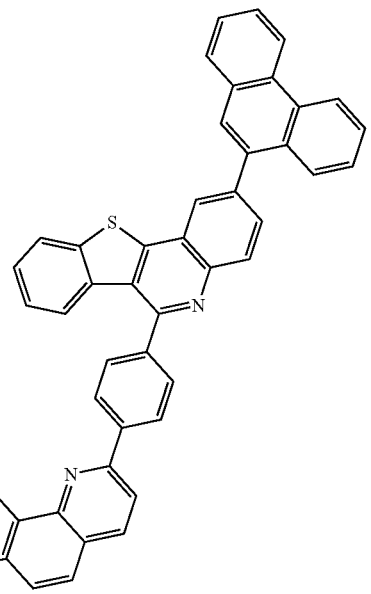

-continued
1017
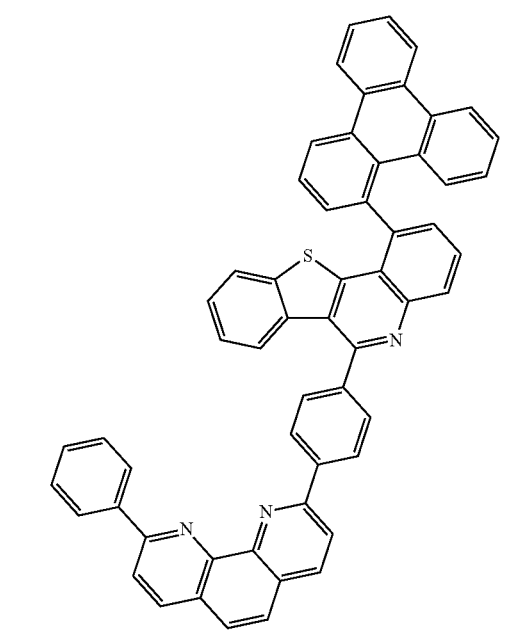
1018
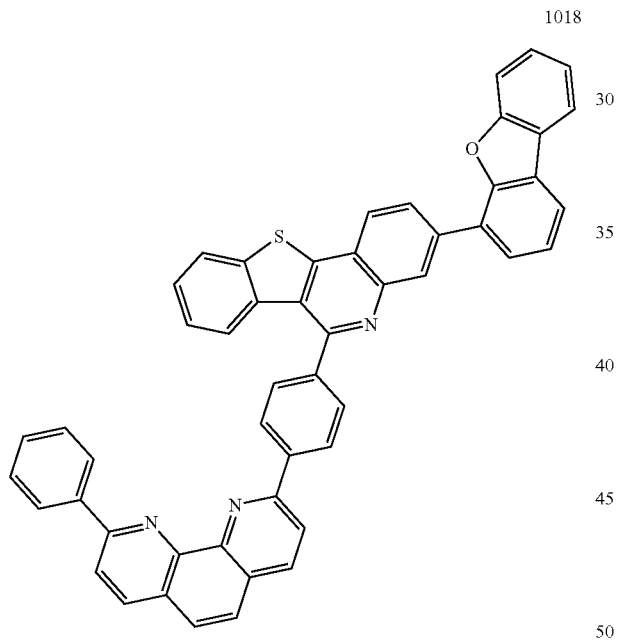
1019
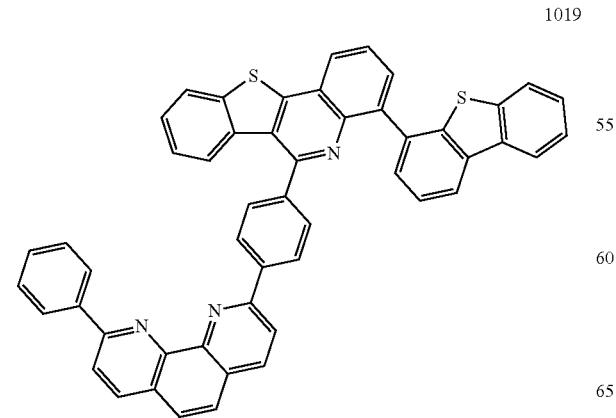
-continued
1020
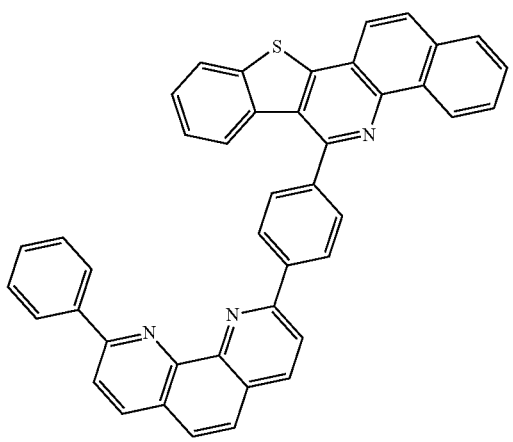
1021
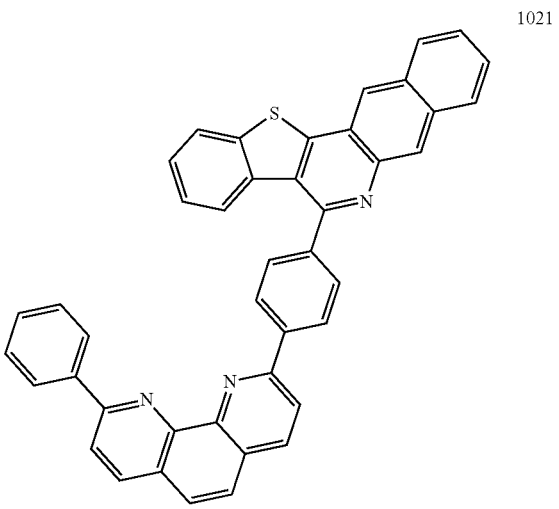
1022
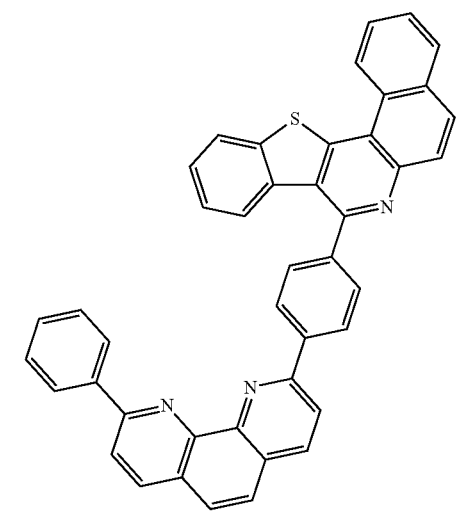

1087
-continued
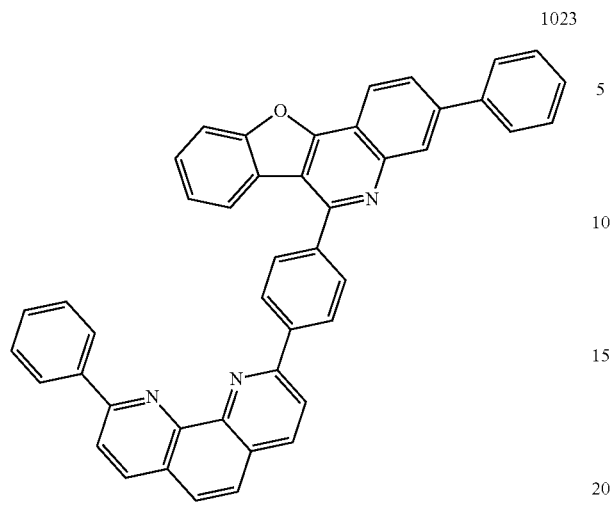
1023
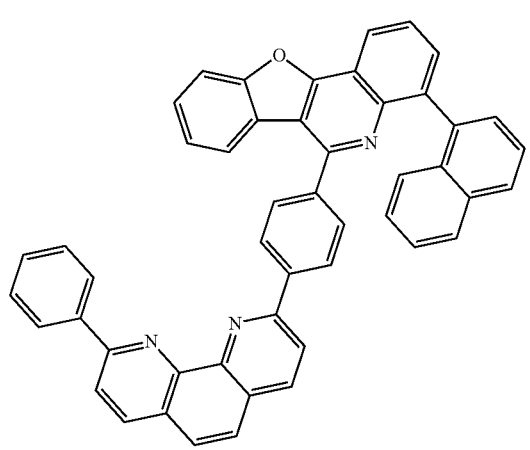
1024
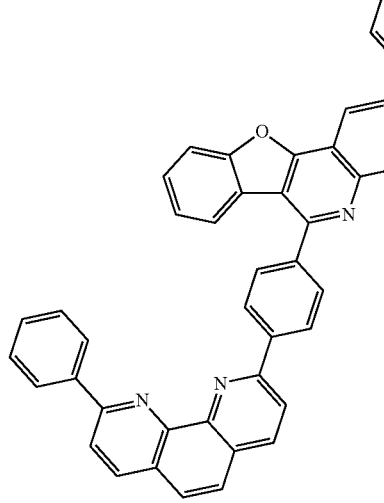
1025
1088
-continued
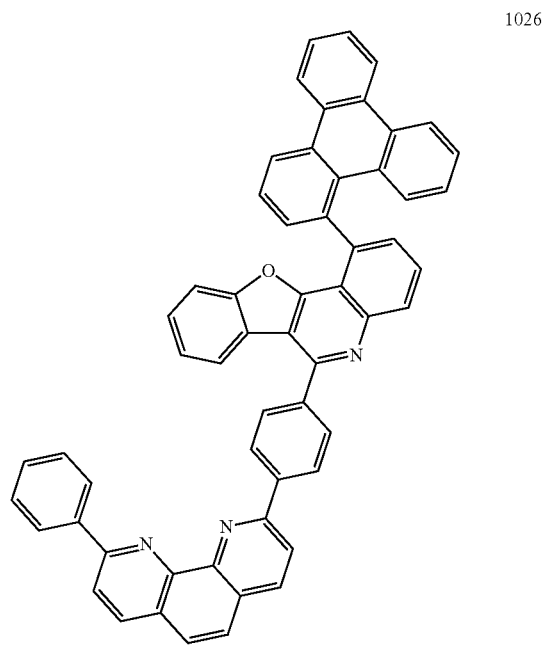 [SMILES: c1ccc(-c2ccc3ccc4ccc(-c5ccc(-c6nc7cccc(-c8cccc9c%10ccccc%10c%10ccccc%10c89)c7c7sc8ccccc8c67)cc5)nc4c3n2)cc1]
1026
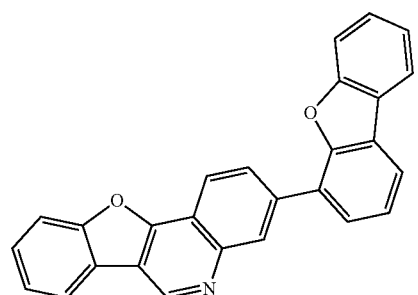
1027
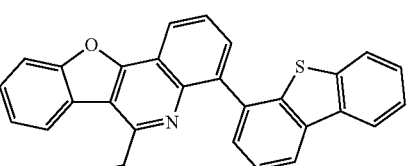
1028

-continued

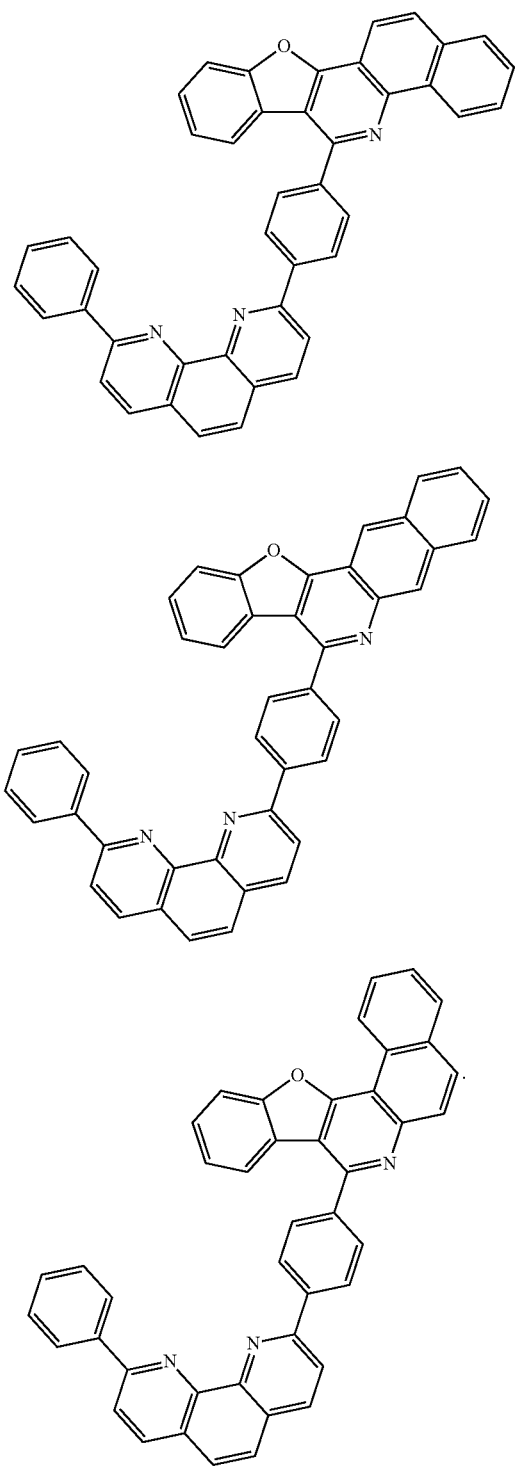

9. An organic light emitting device comprising:
   a first electrode;
   a second electrode provided opposite to the first electrode; and
   one or more organic material layers provided between the first electrode and the second electrode,
   wherein one or more layers of the organic material layers comprise the heterocyclic compound of claim 1.

10. The organic light emitting device of claim 9, wherein the organic material layer comprises a light emitting layer, and the light emitting layer comprises the heterocyclic compound.

11. The organic light emitting device of claim 9, wherein the organic material layer comprises a light emitting layer, the light emitting layer comprises a host material, and the host material comprises the heterocyclic compound.

12. The organic light emitting device of claim 9, wherein the organic material layer comprises an electron injection layer or an electron transfer layer, and the electron injection layer or the electron transfer layer comprises the heterocyclic compound.

13. The organic light emitting device of claim 9, wherein the organic material layer comprises an electron blocking layer or a hole blocking layer, and the electron blocking layer or the hole blocking layer comprises the heterocyclic compound.

14. The organic light emitting device of claim 9, further comprising one, two or more layers selected from the group consisting of a light emitting layer, a hole injection layer, a hole transfer layer, an electron injection layer, an electron transfer layer, an electron blocking layer and a hole blocking layer.

15. The organic light emitting device of claim 9, comprising:
   a first electrode;
   a first stack provided on the first electrode and comprising a first light emitting layer;
   a charge generation layer provided on the first stack;
   a second stack provided on the charge generation layer and comprising a second light emitting layer; and
   a second electrode provided on the second stack.

16. The organic light emitting device of claim 15, wherein the charge generation layer comprises the heterocyclic compound.

* * * * *